United States Patent
Allen et al.

(10) Patent No.: US 11,285,156 B2
(45) Date of Patent: Mar. 29, 2022

(54) SUBSTITUTED PIPERAZINES AS KRAS G12C INHIBITORS

(71) Applicant: Amgen Inc., Thousand Oaks, CA (US)

(72) Inventors: John Gordon Allen, Newbury Park, CA (US); Brian Alan Lanman, Woodland Hills, CA (US); Jian Chen, Camarillo, CA (US); Anthony B. Reed, Newbury Park, CA (US); Victor J. Cee, Thousand Oaks, CA (US); Longbin Liu, Thousand Oaks, CA (US); Patricia Lopez, Woodland Hills, CA (US); Ryan Paul Wurz, Newbury Park, CA (US); Thomas T. Nguyen, Newbury Park, CA (US); Shon Booker, Sherman Oaks, CA (US); Jennifer Rebecca Allen, Newbury Park, CA (US); Margaret Chu-Moyer, Brookline, MA (US); Albert Amegadzie, Moorpark, CA (US); Ning Chen, Thousand Oaks, CA (US); Clifford Goodman, Thousand Oaks, CA (US); Jonathan D. Low, Reseda, CA (US); Vu Van Ma, Oak Park, CA (US); Ana Elena Minatti, Los Angeles, CA (US); Nobuko Nishimura, West Hills, CA (US); Alexander J. Pickrell, Westlake Village, CA (US); Hui-Ling Wang, Thousand Oaks, CA (US); Youngsook Shin, Thousand Oaks, CA (US); Aaron C. Siegmund, Ventura, CA (US); Kevin C. Yang, San Gabriel, CA (US); Nuria A. Tamayo, Newbury Park, CA (US); Mary Walton, Burlingame, CA (US); Qiufen Xue, Thousand Oaks, CA (US)

(73) Assignee: AMGEN INC., Thousand Oaks, CA (US)

(*) Notice: Subject to any disclaimer, the term of this patent is extended or adjusted under 35 U.S.C. 154(b) by 0 days.

(21) Appl. No.: 16/438,349

(22) Filed: Jun. 11, 2019

(65) Prior Publication Data
US 2019/0374542 A1    Dec. 12, 2019

Related U.S. Application Data

(60) Provisional application No. 62/684,117, filed on Jun. 12, 2018.

(51) Int. Cl.
| A61K 31/497 | (2006.01) |
| C07D 241/04 | (2006.01) |
| A61K 31/519 | (2006.01) |
| A61K 31/551 | (2006.01) |
| A61K 39/395 | (2006.01) |
| A61P 35/00  | (2006.01) |

(52) U.S. Cl.
CPC .......... *A61K 31/519* (2013.01); *A61K 31/551* (2013.01); *A61K 39/39558* (2013.01); *A61P 35/00* (2018.01)

(58) Field of Classification Search
CPC ............................ A61K 31/497; C07D 241/04
USPC ...................................... 514/255.06; 544/406
See application file for complete search history.

(56) References Cited

U.S. PATENT DOCUMENTS

| 4,232,027 A | 11/1980 | Turk et al. |
| 5,100,883 A | 3/1992  | Schiehser   |

(Continued)

FOREIGN PATENT DOCUMENTS

| DE | 19629652 A1 | 1/1998  |
| EP | 0090505 A2  | 10/1983 |

(Continued)

OTHER PUBLICATIONS

"A Phase 1, Study Evaluating the Safety, Tolerability, PK, and Efficacy of AMG 510 in Subjects With Solid Tumors With a S Mutation." NCT03600883, comparison of version published Jul. 17, 2018 and Apr. 3, 2019, https://www.clinicaltrials.gov/ct2/history/NCT03600883 (last accessed Apr. 25, 2020), pp. 1-7.

(Continued)

*Primary Examiner* — Douglas M Willis
(74) *Attorney, Agent, or Firm* — Markus Bergauer

(57) ABSTRACT

Provided herein are KRAS G12C inhibitors, such as

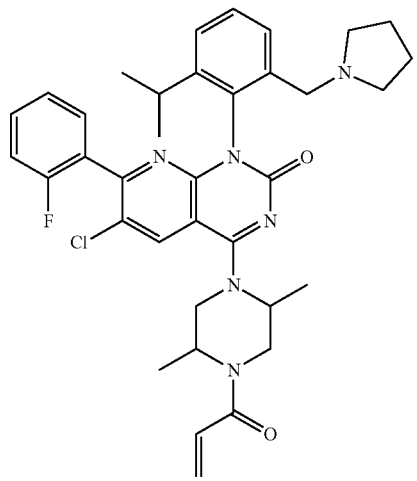

composition of the same, and methods of using the same. These inhibitors are useful for treating a number of disorders, including pancreatic, colorectal, and lung cancers.

4 Claims, No Drawings

Specification includes a Sequence Listing.

(56) References Cited

U.S. PATENT DOCUMENTS

| | | |
|---|---|---|
| 5,118,677 A | 6/1992 | Caufield |
| 5,118,678 A | 6/1992 | Kao et al. |
| 5,120,842 A | 6/1992 | Failli et al. |
| 5,151,413 A | 9/1992 | Caufield et al. |
| 5,256,790 A | 10/1993 | Nelson |
| 5,258,389 A | 11/1993 | Goulet et al. |
| 5,521,184 A | 5/1996 | Zimmerman |
| 5,650,415 A | 7/1997 | Tang et al. |
| 5,656,643 A | 8/1997 | Spada et al. |
| 5,712,291 A | 1/1998 | D'Amato |
| 5,728,813 A | 3/1998 | Lyman et al. |
| 5,747,498 A | 5/1998 | Schnur et al. |
| 5,770,599 A | 6/1998 | Gibson |
| 5,789,427 A | 8/1998 | Chen et al. |
| 5,792,783 A | 8/1998 | Tang et al. |
| 5,861,510 A | 1/1999 | Piscopio et al. |
| 5,863,949 A | 1/1999 | Robinson et al. |
| 5,892,112 A | 4/1999 | Levy et al. |
| 5,969,110 A | 10/1999 | Beckmann et al. |
| 5,981,245 A | 11/1999 | Fox et al. |
| 5,990,141 A | 11/1999 | Hirth et al. |
| 6,057,124 A | 5/2000 | Bartley et al. |
| 6,111,090 A | 8/2000 | Gorman et al. |
| 6,232,447 B1 | 5/2001 | Cerretti |
| 6,235,764 B1 | 5/2001 | Larson et al. |
| 6,258,812 B1 | 7/2001 | Bold et al. |
| 6,413,932 B1 | 7/2002 | Cerretti et al. |
| 6,515,004 B1 | 2/2003 | Misra et al. |
| 6,596,852 B2 | 7/2003 | Cerretti et al. |
| 6,630,500 B2 | 10/2003 | Gingrich et al. |
| 6,656,963 B2 | 12/2003 | Firestone et al. |
| 6,713,485 B2 | 3/2004 | Carter et al. |
| 6,727,225 B2 | 4/2004 | Wiley |
| 7,025,962 B1 | 4/2006 | Gorman et al. |
| 7,361,760 B2 | 4/2008 | Sircar et al. |
| 7,618,632 B2 | 11/2009 | Collins et al. |
| 7,812,135 B2 | 10/2010 | Smith et al. |
| 8,388,967 B2 | 3/2013 | Smith et al. |
| 8,586,023 B2 | 11/2013 | Shiku et al. |
| 8,591,886 B2 | 11/2013 | Ponath et al. |
| 10,519,146 B2 | 12/2019 | Lanman et al. |
| 10,532,042 B2 | 1/2020 | Lanman et al. |
| 10,640,504 B2 | 5/2020 | Lanman et al. |
| 10,988,485 B2 | 4/2021 | Minatti et al. |
| 11,045,484 B2 | 6/2021 | Wurz et al. |
| 11,053,226 B2 | 7/2021 | Shin et al. |
| 11,090,304 B2 | 8/2021 | Allen et al. |
| 11,096,939 B2 | 8/2021 | Booker et al. |
| 11,236,091 B2 | 2/2022 | Chaves et al. |
| 2002/0042368 A1 | 4/2002 | Fanslow, III et al. |
| 2003/0105091 A1 | 6/2003 | Riedl et al. |
| 2003/0162712 A1 | 8/2003 | Cerretti et al. |
| 2009/0012085 A1 | 1/2009 | Baum et al. |
| 2014/0288045 A1 | 9/2014 | Ren et al. |
| 2015/0239900 A1 | 8/2015 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2018/0015087 A1 | 1/2018 | Liu et al. |
| 2018/0072723 A1 | 3/2018 | Blake et al. |
| 2019/0336514 A1 | 11/2019 | Wurz et al. |
| 2019/0343838 A1 | 11/2019 | Allen et al. |
| 2019/0345169 A1 | 11/2019 | Minatti et al. |
| 2019/0375749 A1 | 12/2019 | Chen et al. |
| 2020/0300324 A1 | 1/2020 | Booker et al. |
| 2020/0055845 A1 | 2/2020 | Lanman et al. |
| 2020/0069657 A1 | 3/2020 | Lanman et al. |
| 2020/0165231 A1 | 5/2020 | Shin et al. |
| 2020/0207766 A1 | 7/2020 | Lanman et al. |
| 2020/0216446 A1 | 7/2020 | Parsons et al. |
| 2020/0222407 A1 | 7/2020 | Lipford et al. |
| 2020/0360374 A1 | 11/2020 | Henary et al. |
| 2020/0369662 A1 | 11/2020 | Chaves et al. |
| 2021/0009577 A1 | 1/2021 | Lanman et al. |
| 2022/0002298 A1 | 1/2022 | Chen et al. |

FOREIGN PATENT DOCUMENTS

| | | |
|---|---|---|
| EP | 0520722 A1 | 12/1992 |
| EP | 0566226 A1 | 10/1993 |
| EP | 0606046 A1 | 7/1994 |
| EP | 0682027 A1 | 11/1995 |
| EP | 0407122 A1 | 10/1996 |
| EP | 0770622 A2 | 5/1997 |
| EP | 0780386 A1 | 6/1997 |
| EP | 0787772 A2 | 8/1997 |
| EP | 0818442 A2 | 1/1998 |
| EP | 0837063 A1 | 4/1998 |
| EP | 0931788 A2 | 7/1999 |
| EP | 0970070 B1 | 1/2000 |
| EP | 1004578 A2 | 5/2000 |
| EP | 1181017 B1 | 2/2002 |
| EP | 1786785 B9 | 5/2007 |
| EP | 1866339 B1 | 12/2007 |
| EP | 1947183 A1 | 7/2008 |
| EP | 3401314 A1 | 11/2019 |
| EP | 3055290 B1 | 12/2019 |
| JP | 02233610 A | 9/1990 |
| JP | 2019031476 A | 2/2019 |
| WO | 1990005719 A1 | 5/1990 |
| WO | 1992005179 A1 | 4/1992 |
| WO | 1992020642 A1 | 11/1992 |
| WO | 1993011130 A1 | 6/1993 |
| WO | 1994002485 A1 | 2/1994 |
| WO | 1994002136 A1 | 3/1994 |
| WO | 1994009010 A1 | 4/1994 |
| WO | 1995009847 A1 | 4/1995 |
| WO | 1995014023 A1 | 5/1995 |
| WO | 1995016691 A1 | 6/1995 |
| WO | 1995019774 A1 | 7/1995 |
| WO | 1995019970 A1 | 7/1995 |
| WO | 1996027583 A1 | 9/1996 |
| WO | 1996030347 A1 | 10/1996 |
| WO | 1996031510 A1 | 10/1996 |
| WO | 1996033172 A1 | 10/1996 |
| WO | 1996033980 A1 | 10/1996 |
| WO | 1996041807 A1 | 12/1996 |
| WO | 1997002266 A1 | 1/1997 |
| WO | 1997013771 A1 | 4/1997 |
| WO | 1997019065 A1 | 5/1997 |
| WO | 1997027199 A1 | 7/1997 |
| WO | 1997030034 A1 | 8/1997 |
| WO | 1997030044 A1 | 8/1997 |
| WO | 1997032880 A1 | 9/1997 |
| WO | 1997032881 A1 | 9/1997 |
| WO | 1997034895 A1 | 9/1997 |
| WO | 1997038983 A1 | 10/1997 |
| WO | 1997038994 A1 | 10/1997 |
| WO | 1997049688 A1 | 12/1997 |
| WO | 1998002434 A1 | 1/1998 |
| WO | 1998002437 A1 | 1/1998 |
| WO | 1998002438 A1 | 1/1998 |
| WO | 1998002441 A2 | 1/1998 |
| WO | 1998003516 A1 | 1/1998 |
| WO | 1998007697 A1 | 2/1998 |
| WO | 1998007726 A1 | 2/1998 |
| WO | 1998014449 A1 | 4/1998 |
| WO | 1998014450 A1 | 4/1998 |
| WO | 1998014451 A1 | 4/1998 |
| WO | 1998017662 A1 | 4/1998 |
| WO | 1998030566 A1 | 7/1998 |
| WO | 1998033768 A1 | 8/1998 |
| WO | 1998033798 A2 | 8/1998 |
| WO | 1998034915 A1 | 8/1998 |
| WO | 1998034918 A1 | 8/1998 |
| WO | 1999007675 A1 | 2/1999 |
| WO | 1999007701 A1 | 2/1999 |
| WO | 1999020758 A1 | 4/1999 |
| WO | 1999029667 A1 | 6/1999 |
| WO | 1999035132 A1 | 7/1999 |
| WO | 1999035146 A1 | 7/1999 |
| WO | 1999040196 A1 | 8/1999 |
| WO | 1999045009 A1 | 9/1999 |
| WO | 1999052889 A1 | 10/1999 |
| WO | 1999052910 A1 | 10/1999 |

(56) References Cited

FOREIGN PATENT DOCUMENTS

| | | |
|---|---|---|
| WO | 1999061422 A1 | 12/1999 |
| WO | 2000002871 A1 | 1/2000 |
| WO | 2000012089 A1 | 3/2000 |
| WO | 2000059509 A1 | 10/2000 |
| WO | 2001003720 A2 | 1/2001 |
| WO | 2001014387 A1 | 3/2001 |
| WO | 2001032651 A1 | 5/2001 |
| WO | 2001037820 A2 | 5/2001 |
| WO | 2002055501 A2 | 7/2002 |
| WO | 2002059110 A1 | 8/2002 |
| WO | 2002066470 A1 | 8/2002 |
| WO | 2002068406 A2 | 9/2002 |
| WO | 2004005279 A2 | 1/2004 |
| WO | 2004007458 A1 | 1/2004 |
| WO | 2004007481 A2 | 1/2004 |
| WO | 2004009784 A2 | 1/2004 |
| WO | 2005005434 A1 | 1/2005 |
| WO | 2005007190 A1 | 1/2005 |
| WO | 2005011700 A1 | 2/2005 |
| WO | 2005016252 A2 | 2/2005 |
| WO | 2005021546 A1 | 3/2005 |
| WO | 2005055808 A2 | 6/2005 |
| WO | 2005115451 A2 | 12/2005 |
| WO | 2006044453 A1 | 4/2006 |
| WO | 2006083289 A2 | 8/2006 |
| WO | 2006121168 A1 | 11/2006 |
| WO | 2006122806 A1 | 11/2006 |
| WO | 2007133822 A1 | 11/2007 |
| WO | 2008070740 A1 | 6/2008 |
| WO | 2009036082 A2 | 3/2009 |
| WO | 2009055730 A1 | 4/2009 |
| WO | 2010003118 A1 | 1/2010 |
| WO | 2011028683 A1 | 3/2011 |
| WO | 2011051726 A2 | 5/2011 |
| WO | 2011090754 A1 | 7/2011 |
| WO | 2012142498 A2 | 10/2012 |
| WO | 2013039954 A1 | 3/2013 |
| WO | 2013155223 A1 | 10/2013 |
| WO | 2014143659 A1 | 9/2014 |
| WO | 2014152588 A1 | 9/2014 |
| WO | 2015001076 A1 | 1/2015 |
| WO | 2015054572 A1 | 4/2015 |
| WO | 2015075483 A1 | 5/2015 |
| WO | 2016049524 A1 | 3/2016 |
| WO | 2016049565 A1 | 3/2016 |
| WO | 2016049568 A1 | 3/2016 |
| WO | 2016044772 A1 | 5/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017100546 A1 | 6/2017 |
| WO | 2017172979 A1 | 10/2017 |
| WO | 2017201161 A1 | 11/2017 |
| WO | 2018064510 A1 | 4/2018 |
| WO | 2018068017 A1 | 4/2018 |
| WO | 2018119183 A3 | 6/2018 |
| WO | 2018140598 A1 | 8/2018 |
| WO | 2018217651 A1 | 11/2018 |
| WO | 2018218069 A1 | 11/2018 |
| WO | 2019051291 A1 | 3/2019 |
| WO | 2019213516 A1 | 11/2019 |
| WO | 2019213526 A1 | 11/2019 |
| WO | 2019217691 A1 | 11/2019 |
| WO | 2019232419 A1 | 12/2019 |
| WO | 2019241157 A1 | 12/2019 |
| WO | 2019243533 A1 | 12/2019 |
| WO | 2019243535 A1 | 12/2019 |
| WO | 2020050890 A2 | 3/2020 |
| WO | 2020102730 A1 | 5/2020 |
| WO | 2020106640 A1 | 5/2020 |
| WO | 2020156285 A1 | 8/2020 |
| WO | 2020232130 A1 | 11/2020 |
| WO | 2020236947 A1 | 11/2020 |
| WO | 2020236948 A1 | 11/2020 |
| WO | 2021081212 A1 | 4/2021 |
| WO | 2021126816 A1 | 6/2021 |

OTHER PUBLICATIONS

"Acute Leukemia," *The Merck Manual* (Online Edition), pp. 1-6 (2013).

"KRASG12C Inhibitor," Mirati Therapeutics, retrieved on Nov. 27, 2018, from https://www.mirati.com/mrtx849/, 5 pages.

Ahmadian, et al., "Guanosine triphosphatase stimulation of oncogenic Ras mutants," *PNAS*, 96: 7065-7070, 1999.

Airoldi, et al., "Glucose-Derived Ras Pathway Inhibitors: Evidence of Ras-Ligand Binding and Ras-GEF (Cdc25) Interaction Inhibition," *ChemBioChem*, 8: 1376-1379 (2007).

ATTC "Organism: *Mus musculus* (B cell); *Mus musculus* (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.

Barnett, et al., "Identification and characterization of pleckstrin-holomogy-domain-dependent and isoenzyme specific Akt inhibitors," *Biochem. J.*,385 (2): 399-408 (2005).

Bull, et al., "Isoquino[2,1-c][1,3,2] Benzodiazaphosphorine Derivatives: New Potential Agents for Cancer Chemotherapy," *Phosphorus, Sulfur, and Silicon*, 162:231-243 (2000).

Campillo, et al., "Novel Bronchodilators: Synthesis, Transamination Reactions, and Pharmacology of a Series of Pyrazino[2,3-c][1,2,6]thiadiazine 2,2-Dioxides," *J. Med. Chem.*, 43: 4219-4227 (2000).

Canon, et al., "The clinical KRAS(G12C) inhibitor AMG 510 drives anti-tumour immunity," *Nature*, 575(7781): 217-223 (2019).

Cohen, "The development and therapeutic potential of protein kinase inhibitors," *Current Opinion in Chemical Biology*, 3:459-465 (1999).

Cowen Slide deck—Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).

Dasmahapatra, et al., "In vitro Combination Treatment with Perifosine and UCN-01 Demonstrates Synergism Against Prostate (PC-3) and Lung (A549) Epithelial Adenocarcinoma Cell Lines," *Clin. Cancer Res*. 10(15): 5242-5252 (2004).

Dermer, et al., "Another Anniversary for the War on Cancer," *Bio/Technology*, 12: 320 (1994).

Douelle, et al., "Highly Diastereoselective Synthesis of vicinal Quaternary and Tertiary Stereocenters Using the Iodo-aldol Cyclization," *Org. Lett.*, 9 (10): 1931-1934 (2007).

Erkkilä, et al., "Mild Organocatalytic α-Methylenation of Aldehydes," *J. Org. Chem.*,71 (6), 2538-2541 (2006).

Fakih, et al., "Phase 1 study evaluating the safety, tolerability, pharmacokinetics (PK), and efficacy of AMG 510, a novel small molecule KRASG12C inhibitor, in advanced solid tumors," *Journal of Clinical Oncology*, 37(15 suppl) (May 20, 2019) 3003, published online May 26, 2019.

Final Office Action for U.S. Appl. No. 15/984,855, dated Mar. 28, 2019, 7 pages.

Final Office Action for U.S. Appl. No. 16/661,907, dated Mar. 27, 2020, 29 pages.

Freshney, et al., Culture of Animal Cells, *A Manual of Basic Technique*, Alan R. Liss, Inc, New York, p. 4 (1983).

Gentile, et al., "Discovery and Structural Investigation of Novel Binders to the Ras Switch II Pocket," NCI Initiative Symposium Poster (2015).

Gills and Dennis, "The development of phosphatidylinositol ether lipid analogues as inhibitors of the serine/threonine kinase, Akt," *Expert. Opin. Investig. Drugs*, 13: 787-797 (2004).

(56) References Cited

OTHER PUBLICATIONS

Goldberg, et al., "Role of PD-1 and its ligand, B7-H1, in early fate decisions of CD8 T cells," *Blood*, 110(1): 186-192 (2007).
Goldstein, et al., "Biological efficacy of a chimeric antibody to the epidermal growth factor receptor in a human tumor xenograft model," *Clin. Cancer Res.*, 1: 1311-1318 (1995).
Golub, et al., "Molecular Classification of Cancer: Class Discovery and Class Prediction by Gene Expression Monitoring," *Science*, 286: 531-537 (1999).
Govindan, et al., "Phase 1 Study of AMG 510, a Novel KRAS G12C Inhibitor, in Advanced Solid Tumors with KRAS p.G12C Mutation," Poster, ESMO Congress, Barcelona, Spain, Sep. 27, 2019-Oct. 1, 2019.
Gura, "Cancer Models: Systems for Identifying New Drugs Are Often Faulty," *Science*, 278(5340):1041-1042 (1997).
Hallin, et al., "The KRAS$^{G12C}$ Inhibitor MRTX849 Provides Insight toward Therapeutic Susceptibility of KRAS-Mutant Cancers in Mouse Models and Patients," *Cancer Discov.*, 10: 54-71 (2020).
Hansen, et al., "Abstract 686: Drugging an undruggable pocket: the biochemical mechanism of covalent KRAS$^{G12C}$ inhibitors," Proceedings of the American Association for Cancer Research Annual Meeting 2018; Apr. 14-18, 2018; Chicago, IL; AACR; *Cancer Res.*, 78(13 Suppl): Abstract 686 (2018).
Hichri, et al., "A Convenient Synthesis of 1,3,2-Benzodiazaphophorine-2-Oxide," *Phosphorus, Sulfur, and Silicon*, 190: 29-35 (2015).
Hichri, et al., CAPLUS Abstract, 162:245378 (2015).
Hocker, et al., "Andrographolide derivatives inhibit guanine nucleotide exchange and abrogate oncogenic Ras function," *PNAS*, 110(25): 10201-10206 (2013).
Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).
International Search Report for PCT/US2017/067801, dated Jul. 25, 2018, 6 pages.
International Search Report for PCT/US2018/033714, dated Jul. 17, 2018, 3 pages.
International Search Report for PCT/US2018/050044, dated Oct. 30, 2018, 7 pages.
International Search Report for PCT/US2019/030593, dated Aug. 6, 2019, 4 pages.
International Search Report for PCT/US2019/030606, dated Jul. 23, 2019, 5 pages.
International Search Report for PCT/US2019/031535, dated Jul. 25, 2019, 7 pages.
International Search Report for PCT/US2019/034974, dated Aug. 9, 2019, 5 pages.
International Search Report for PCT/US2019/036397, dated Aug. 26, 2019, 5 pages.
International Search Report for PCT/US2019/061815, dated Mar. 5, 2020, 6 pages.
Janes, et al., "Targeting KRAS Mutant Cancers with a Covalent G12C-Specific Inhibitor," *Cell*, 172: 578-589 (2018).
Janeway et al., "Immunobiology: The Immune System in Health and Disease", Elsevier Science Ltd./Garland Publishing, 4th ed. (1999).
Jarvis, "Notorious KRAS: Taking down cancer researchers' biggest foe," *Chemical & Engineering News*, 97(37), 9 pages (2019).
Jin, et al., "Inhibition of AKT survival pathway by a small molecule inhibitor in human endometrial cancer cells," *Br. J. Cancer*, 91: 1808-1812 (2004).
Johnson et al., "Relationships between drug activity in NCI preclinical in vitro and in vivo models and early clinical trials," *British Journal of Cancer*, 84(10): 1424-1431 (2001).
Lanman, et al., "Discovery of a Covalent Inhibitor of KRAS$^{G12C}$ (AMG 510) for the Treatment of Solid Tumors," *J. Med. Chem.*, 63: 52-65 (2020).
Li, et al., "Targeting Protein-Protein Interaction with Covalent Small-Molecule Inhibitors," *Current Topics in Medicinal Chemistry*, 19(21): 1872-1876 (2019).

Lim, et al., "Therapeutic Targeting of Oncogenic K-Ras by a Covalent Catalytic Site Inhibitor," *Angew. Chem. Int. Ed*, 53: 199-204 (2014).
Liu, Y., "Session SY28—Transformative Small Molecule Therapies— Targeting KRAS mutant cancers with a covalent G12C—specific inhibitor," Presentation on Apr. 4, 2017, AACR Annual Meeting Presentation, Apr. 1-5, 2017, Washington, D.C. (2017).
Lu, et al., "KRAS G12C Drug Development: Discrimination between Switch II Pocket Configurations Using Hydrogen/Deuterium-Exchange Mass Spectrometry," *Structure*, 25: 1-7 (2017).
Maurer, et al., "Small-molecule ligands bind to a distinct pocket in Rad and inhibit SOS-mediated nucleotide exchange activity," *PNAS*, 109(14): 5299-5304 (2012).
McGregor, et al., "Expanding the Scope of Electrophiles Capable of Targeting K-Ras Oncogenes," *ACS Bio. Chem.*, 56: 3179-3183 (2017).
Mirati Therapeutics, "Corporate Presentation Nov. 2017," Slides 1-41 (2017).
Modjtahedi, et al., "The human EGF receptor as a target for cancer therapy: six new rat mAbs AGainst the receptor on the breast carcinoma MDA-MB 468," *Br. J. Cancer*, 67(2): 247-253 (1993).
National Cancer Institute identifier: NSC 154020, retrieved on Nov. 29, 2018, from https://cactus.nci.nih.gov/ncidb2.2/.
NCBI Reference Sequence, "GTPase KRas isoform a [*Homo sapiens*]," GenBank Accession No. NM_203524.1, Retrieved on Nov. 29, 2018 from https://www.ncbi.nlm.nih.gov/protein/15718763?sat=4&satkey=234448549, 4 pages.
Non-Final Office Action (Corrected) for U.S. Appl. No. 16/125,359, dated Apr. 8, 2019, 13 pages.
Non-Final Office Action for U.S. Appl No. 15/849,905, dated Mar. 20, 2019, 18 pages.
Non-Final Office Action for U.S. Appl. No. 15/984,855, dated Sep. 27, 2018, 25 pages.
Non-Final Office Action for U.S. Appl. No. 16/125,359, dated Apr. 5, 2019, 13 pages.
Non-Final Office Action for U.S. Appl. No. 16/402,538, dated Oct. 30, 2019, 12 pages.
Non-Final Office Action for U.S. Appl. No. 16/402,589, dated Mar. 6, 2020, 17 pages.
Non-Final Office Action for U.S. Appl. No. 16/661,907, dated Nov. 18, 2019, 20 pages.
Ostrem, et al., "Development of mutant-specific small molecule inhibitors of K-Ras," Poster, AACR 104th Annual Meeting 2013; Apr. 6-10, 2013; Washington, D.C. (2013).
Ostrem, et al., "K-Ras(G12C) inhibitors allosterically control GTP affinity and effector interactions," *Nature*, 503: 548-551 (2013).
Paez, et al., "EGFR Mutations in Lung Cancer Correlation with Clinical Response to Gefitinib Therapy," *Science*, 304(5676): 1497-500 (2004).
Palmioli, et al., "First experimental identification of Ras-inhibitor binding interface using a water-soluble Ras ligand," *Bioorg. Med. Chem. Lett.*, 19: 4217-4222 (2009).
Patricelli, et al., "Selective Inhibition of Oncogenic KRAS Output with Small Molecules Targeting the Inactive State," *Cancer Discov*, 6 (3): 316-329 (2016).
Pearce, et al., "Failure modes in anticancer drug discovery and development," *Cancer Drug Design and Discovery*, Edited by Stephen Neidle, Chapter 18, pp. 424-435 (2008).
Peri, et al., "Design, Synthesis and Biological Evaluation of Sugar-Derived Ras Inhibitors," *ChemBioChem*, 6: 1839-1848 (2005).
Peri, et al., "Sugar-Derived Ras Inhibitors: Group Epitope Mapping by NMR Spectroscopy and Biological Evaluation," *Eur. J. Org. Chem.*, 16: 3707-3720 (2006).
Peters, et al., "Selective inhibition of K-Ras G12C through allosteric control of GTP affinity and effector interactions," EORTC Poster (2013).
Remington's Pharmaceutical Sciences, 1435-1712 (18th ed., Mack Publishing Co, Easton, Pennsylvania, 1990 (Table of Contents Only).
Rex et al., "KRAS—AACR 2018," Amgen Collection of Information published at Proceedings of the American Association for Cancer Research Annual Meeting 2018; Apr. 14-18, 2018; Chicago, IL; AACR; slides 1-24 (2018).

(56) References Cited

OTHER PUBLICATIONS

Sarkar, et al., "Indole-3-Carbinol and Prostate Cancer[1,2]," *J. Nutr.*, 134(12 Suppl): 3493S-3498S (2004).
Shima, et al., "In silico discovery of small-molecule Ras inhibitors that display antitumor ctivity by blocking the Ras-effector interaction," *PNAS*, 110(20): 8182-8187 (2013).
Simone, "Part XIV Oncology: Introduction," *Cecil Textbook of Medicine*, 20th Edition, 1:1004-1010 (1996).
Singh, et al., "Improving Prospects for Targeting RAS," *J. Clinc. Oncl*, 33(31): 3650-3660 (2015).
Statsyuk, "Let K-Ras activate its own inhibitor," *Nature Structural & Molecular Biology*, 25:435-439 (2018).
Sun, et al., "Discovery of Small Molecules that Bind to K-Ras and Inhibit Sos-Mediated Activation," *Angew. Chem. Int. Ed.*, 51: 6140-6143 (2012).
Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.,*, 5(1): 125-133 (1997).
Teraivioto, et al., 1996, Cancer 77 (4):639-645.
The ASCO Post Staff, "AACR-NCI-EORTC: Investigational KRAS G12C Inhibitor for KRAS-Mutant Solid Tumors," The ASCO Post (2019).
Thompson, et al., "PD-1 Is Expressed by Tumor-Infiltrating Immune Cells and Is Associated with Poor Outcome for Patients with Renal Cell Carcinoma," *Clin. Cancer Res.*, 13(6): 1757-1761 (2007).
Traxler, "Tyrosine kinase inhibitors in cancer treatment (Part II)," *Exp. Opin. Ther. Patents*, 8(12): 1599-1625 (1998).
U.S. Appl. No. 60/528,340, filed Dec. 9, 2003.
Wang, et al., "Ras inhibition via direct Ras binding—is there a path forward?," *Bioorg. Med. Chem. Lett.*, 22: 5766-5776 (2012).
Written Opinion for PCT/US2017/067801, dated Jul. 25, 2018, 10 pages.
Written Opinion for PCT/US2018/033714, dated Jul. 17, 2018, 5 pages.
Written Opinion for PCT/US2018/050044, dated Oct. 30, 2018, 7 pages.
Written Opinion for PCT/US2019/030593, dated Aug. 6, 2019, 5 pages.
Written Opinion for PCT/US2019/030606, dated Jul. 23, 2019, 6 pages.
Written Opinion for PCT/US2019/031535, dated Jul. 25, 2019, 7 pages.
Written Opinion for PCT/US2019/034974, dated Aug. 9, 2019, 5 pages.
Written Opinion for PCT/US2019/036397, dated Aug. 26, 2019, 5 pages.
Written Opinion for PCT/US2019/061815, dated Mar. 5, 2020, 4 pages.
Xiong, et al., "Covalent Guanosine Mimetic Inhibitors of G12C KRAS," *ACS Med. Chem. Lett.*, 8: 61-66 (2017).
Yan, et al., "Pharmacogenetics and pharmacogenomics in oncology therapeutic antibody development," *BioTechniques*, 29(4): 565-568 (2005).
Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).
Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).
Zeng, et al., "Potent and Selective Covalent Quinazoline Inhibitors of KRAS G12C," *Cell Chemical Biology*, 24: 1-12 (2017).
Zimmerman, et al., "Small molecule inhibition of the KRAS—PDEδ interaction impairs oncogenic KRAS signaling," *Nature*, 1-5 (2017).
International Search Report for PCT/US2019/062051, dated Mar. 2, 2020, 3 pages.
Written Opinion for PCT/US2019/062051, dated Mar. 2, 2020, 5 pages.
International Search Report for PCT/US2019/036626, dated Jun. 2, 2020, 5 pages.
Written Opinion for PCT/US2019/036626, dated Jun. 2, 2020, 12 pages.
Morrissey et al., "Immunotherapy and Novel Combinations in Oncology: Current Landscape, Challenges, and Opportunities," *Clin. Transl. Sci.*, 9(2):89-104 (2016).
Cee, et al.,"Discovery of AMG 510, a first-in-humancovalent inhibitor of KRASG12c for the treatment of solid tumors," Abstract and Presentation, ACS Spring Meeting, Orlando, FL, USA, Mar. 31-Apr. 4, 2019.
Extended European Search Report for European Patent Application No. 19208193.2, dated Jun. 3, 2020, pp. 1-8.
Fakih, et al., "Phase 1 study evaluating the safety, tolerability, pharmacokinetics (PK), and efficacy of AMG 510, a novel small molecule KRASG12C inhibitor, in advanced solid tumors," Presentation, ASCO, Chicago, IL, USA, May 31-Jun. 4, 2019.
Govindan, et al., "Safety, Efficacy, and Pharmacokinetics of AMG 510, a Novel KRASG12C Inhibitor, in Patients with Non-Small Cell Lung Cancer," Abstract and Presentation, North American Conference on Lung Cancer (NACLC), Chicago, IL, USA, Oct. 10-12, 2019.
Govindan, et al., "Phase 1 Study of AMG 510, a Novel KRAS G12C Inhibitor, in Advanced Solid Tumors with KRAS p. G12C Mutation," Abstract, ESMO Congress, Barcelona, Spain, Sep. 27-Oct. 1, 2019.
Govindan, et al., "Phase 1 Study of Safety, Tolerability, Pharmacokinetics, and Efficacy of AMG510, a Novel KRASG12C Inhibitor, in Non-Small Cell Lung Cancer," Abstract and Presentation, World Conference on Lung Cancer (WCLC), Barcelona, Spain, Sep. 7-10, 2019.
Halford, "Amgen unveils its Kras covalent inhibitor AMG 510," *Chemical & Engineering News* 97(14):4 (2019).
Lanman, et al., "Abstract 4455: Discovery of AMG 510, a first-in-human covalent inhibitor of KRAS$^{G12c}$ for the treatment of solid tumors," Presentation, American Association for Cancer Research (AACR) Annual Meeting, Atlanta, GA, USA, Mar. 29-Apr. 3, 2019.
Lanman, et al., "Abstract 4455: Discovery of AMG 510, a first-in-human covalent inhibitor of KRAS$^{G12c}$ for the treatment of solid tumors," Proceedings of the American Association for Cancer Research Annual Meeting 2019; Mar 29-Apr 3, 2019; Atlanta, GA. Philadelphia (PA), AACR, *Cancer Res.* 79(13 Suppl): Abstract nr 4455 (2019).
Lipford, et al., "Pre-Clinical Development of AMG 510: The First Inhibitor of KRASG12c in Clinical Testing," Presentation, American Association for Cancer Research (AACR) Annual Meeting, Atlanta, GA, USA, Mar. 29-Apr. 3, 2019.
Lopez, et al.,"Optimization of quinazolinone-based covalent inhibitors of KRAS$^{G12c}$ in the discovery of AMG 510," Abstract and Poster, ACS Fall Meeting, San Diego, CA, USA, Aug. 25-29, 2019.
Rex, et al., "Abstract 3090: in vivo characterization of AMG 510—a potent and selective KRAS$^{G12c}$ covalent small molecule inhibitor in preclinical KRAS$^{G12c}$ cancer models," Poster, American Association for Cancer Research (AACR) Annual Meeting, Atlanta, GA, USA, Mar. 29-Apr. 3, 2019.
Rex, et al., "Abstract 3090: In vivo characterization of AMG 510—a potent and selective KRAS$^{G12c}$ covalent small molecule inhibitor in preclinical KRAS$^{G12c}$ cancer models," Proceedings of the American Association for Cancer Research Annual Meeting 2019; Mar 29-Apr 3, 2019; Atlanta, GA. Philadelphia (PA), AACR, *Cancer Res.* 79(13 Suppl): Abstract nr 3090 (2019).
Saiki, et al., "Abstract 4484: Discovery and in vitro characterization of AMG 510—a potent and selective covalent small-molecule inhibitor of KRAS$^{G12c}$," Presentation, American Association for Cancer Research (AACR) Annual Meeting, Atlanta, GA, USA, Mar. 29-Apr. 3, 2019.
Saiki, et al., "Abstract 4484: Discovery and in vitro characterization of AMG 510—a potent and selective covalent small-molecule inhibitor of KRAS$^{G12c}$," Proceedings of the American Association

(56) References Cited

OTHER PUBLICATIONS for Cancer Research Annual Meeting 2019; Mar. 29-Apr. 3, 2019; Atlanta, GA. Philadelphia (PA), AACR, *Cancer Res.* 79(13 Suppl): Abstract nr 4484 (2019).
International Search Report for PCT/US2020/033831, dated Jul. 9, 2020, 6 pages.
International Search Report for PCT/US2020/033832, dated Jul. 8, 2020, 4 pages.
Non-Final Office Action for U.S. Appl. No. 16/407,889, dated Jul. 1, 2020, 6 pages.
Written Opinion for PCT/US2020/033831, dated Jul. 9, 2020, 7 pages.
Written Opinion for PCT/US2020/033832, dated Jul. 8, 2020, 6 pages.
Bhatia, et al., "A Review on Bioisosterism: A Rational Approach for Drug Design and Molecular Modification," *Pharmacologyonhne*, 1:272-299 (2011).
International Search Report for PCT/US2019/62064, dated Oct. 29, 2020, 9 pages.
International Search Report for PCT/US2020/032686, dated Aug. 14, 2020, 4 pages.
Non-Final Office Action for U.S. Application No. 16/428,163, dated Sep. 15, 2020, 6 pages.
Non-Final Office Action for U.S. Application No. 16/436,647, dated Aug. 7, 2020, 19 pages.
Notice of Allowance dated Jul. 24, 2020 for U.S. Appl. No. 16/402,538, 8 pages.
Notice of Allowance dated Nov. 16, 2020 for U.S. Appl. No. 16/402,538, 8 pages.
Notice of Allowance dated Sep. 16, 2020 for U.S. Appl. No. 16/402,589, 5 pages.
Written Opinion for PCT/US2019/62064, dated Oct. 29, 2020, 13 pages.
Written Opinion for PCT/US2020/032686, dated Aug. 14, 2020, 6 pages.
AMG-510; CS-0081316; Source: AbaChemScene (CS-0081316); Deposit Date: May 13, 2019 Available Date: May 13, 2019; SID: 384060804[CID: 137278711] (available at https://pubchem.ncbi.nlm.nih.gov/substance/384060804/).
AMG-510; HY-114277; Source: MedChemexpress MCE (HY-114277); Deposit Date: May 13, 2019 Available Date: May 13, 2019; SID: 384060569[CID: 137278711] (available at https://pubchem.ncbi.nlm.nih.gov/substance/384060569).
Canon, et al., "The clinical KRAS(G12C) inhibitor AMG 510 drives anti-tumour immunity," Nature, 575(7781): 217-223 (2019) (Supplementary Material, pp. 1-55).
Database Registry [Online], Chemical Abstracts Service, Columbus, Ohio, US; Jul. 31, 2017 (Jul. 31, 2017), XP002801805, retrieved from STN Database accession No. 2105944-09-8.
Final Office Action for U.S. Appl. No. 16/436,647, dated Mar. 24, 2021, 7 pages.
Meanwell, "Synopsis of Some Recent Tactical Application of Bioisosteres in Drug Design," *J. Med. Chem.* 54:2529-2591 (2011).
Non-Final Office Action for U.S. Appl. No. 16/675,121, dated Feb. 2, 2021, 10 pages.
Non-Final Office Action for U.S. Appl. No. 16/817,109, dated Mar. 3, 2021, 12 pages.
Notice of Allowance dated Jan. 14, 2021 for U.S. Appl. No. 16/402,589, 5 pages.
Notice of Allowance, dated Dec. 21, 2020, for U.S. Appl. No. 16/407,889, 5 pages.
Notice of Allowance, dated Feb. 18, 2021, for U.S. Appl. No. 16/687,546, 9 pages.
Notice of Allowance, dated Jan. 27, 2021, for U.S. Appl. No. 16/428,163, 9 pages.
Notice of Allowance, dated Mar. 30, 2021, for U.S. Appl. No. 16/402,538, 8 pages.
Shibata et al., "A Convenient Synthesis of 3-Cyano-2-methylpyridines under Ultrasonic Irradiation," *Bull. Chem. Soc. Jpn.*, 61:2199-2200 (1988).
Stanetty et al., "Synthesis of Aza Analogs of the Herbicide Sindone B," *Monatshefte Fuer Chemie*, 130:441-450 (1999).
Third Party Observation filed for PCT/US2020/033831, submitted Jan. 15, 2021, 2 pages.
4-methyl-2-(1-methylethyl)-3-Pyridinamine, STN Registry, CAS RN 1698293-93-4, STN entry date May 5, 2015 (May 5, 2015).
Hirayama, "Handbook for Making Crystal of Organic Compound,—Principles and Know-how—", Maruzen Co., Ltd., Jul. 25, 2008, pp. 57-84 (incl. English translation).
International Search Report for PCT/US2020/056874, dated Feb. 12, 2021, 7 pages.
International Search Report for PCT/US2020/060415, dated Feb. 3, 2021, 7 pages.
International Search Report for PCT/US2020/065050, dated Mar. 29, 2021, 7 pages.
Kojima, "Aiming to Improve the Efficiency of Crystallization Selection in Drug Development", Pharmaceutics, Sep. 1, 2008, vol. 68, No. 5, pp. 344-349 (incl. English translation).
Noriyuki, "API Form Screening and Selection at the Drug Discovery Stage", Pharm Stage, vol. 6, No. 10, Jan. 15, 2007, pp. 20-25 (incl. English translation).
Notice of Allowance, dated Sep. 9, 2021, for U.S. Appl. No. 16/675,121, 7 pages.
PubChem CID 108190520, 2-isopropyl-4-methylpyridin-3-amine, avaiable at https://pubchem.ncbi.nlm.nih.gov/compound/108190520 (last accessed Aug. 30, 2021).
Written Opinion for PCT/US2020/056874, dated Feb. 12, 2021, 10 pages.
Written Opinion for PCT/US2020/060415, dated Feb. 3, 2021, 9 pages.
Written Opinion for PCT/US2020/065050, dated Mar. 29, 2021, 8 pages.
Notice of Allowance, dated Sep. 22, 2021, for U.S. Appl. No. 16/878,824, 8 pages.
Notice of Allowance, dated Dec. 9, 2021, for U.S. Appl. No. 16/817,109, 9 pages.
Examiner-Initiated Interview Summary, dated Dec. 9, 2021, for U.S. Appl. No. 16/817,109, 1 page.
Notice of Allowance, dated Dec. 9, 2021, for U.S. Appl. No. 16/685,841, 8 pages.
Non-Final Office Action for U.S. Appl. No. 15/930,606, dated Jan. 13, 2022, 4 pages.
Office Communication (Ex Parte Quayle) for U.S. Appl. No. 16/687,563, dated Jan. 14, 2022, 5 pages.

SUBSTITUTED PIPERAZINES AS KRAS G12C INHIBITORS

RELATED APPLICATIONS

This application claims the benefit of U.S. Provisional patent application 62/684,117 filed on Jun. 12, 2018, which specification is hereby incorporated herein by reference in its entirety for all purposes.

The present application is being filed along with a sequence listing in electronic format. The sequence listing is provided as a file entitled A-2263-US-NP_SeqList_061119_ST25.txt, created Jun. 11, 2019, which is 15.5 kb in size. The information in the electronic format of the sequence listing is incorporated herein by reference in its entirety.

FIELD OF THE INVENTION

The present invention relates to compounds that inhibit the KRAS G12C protein; methods of treating diseases or conditions, such as cancer, using the compounds; and pharmaceutical compositions containing the compounds.

BACKGROUND

KRAS gene mutations are common in pancreatic cancer, lung adenocarcinoma, colorectal cancer, gall bladder cancer, thyroid cancer, and bile duct cancer. KRAS mutations are also observed in about 25% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation, and including those who have progressed after chemotherapy.

The compounds disclosed herein can be in the form of a pharmaceutically acceptable salt. The compounds provided can be formulated into a pharmaceutical formulation comprising a compound disclosed herein and a pharmaceutically acceptable excipient.

Also provided is a method of inhibiting KRAS G12C in a cell, comprising contacting the cell with a compound or composition disclosed herein. Further provided is a method of treating cancer in a subject comprising administering to the subject a therapeutically effective amount of a compound or composition disclosed herein. In some embodiments, the cancer is lung cancer, pancreatic cancer, or colorectal cancer.

SUMMARY

In one aspect of the present invention, the invention provides a compound having a structure selected from the formula

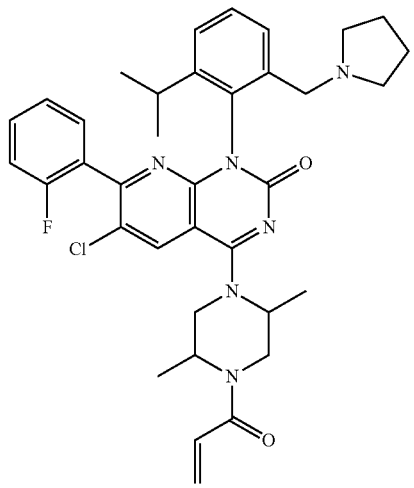

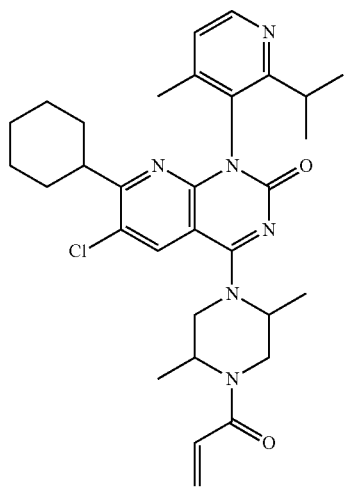

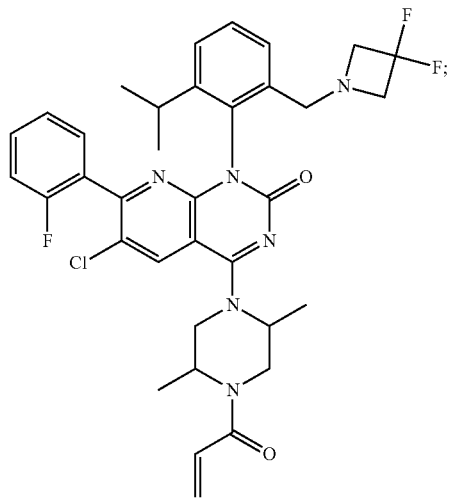

3
-continued
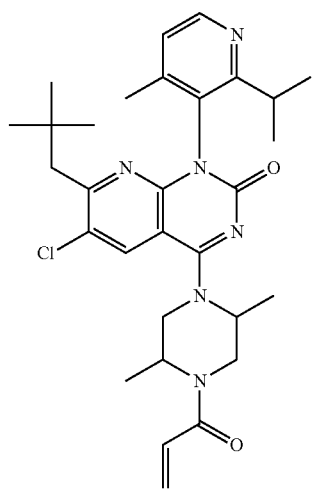
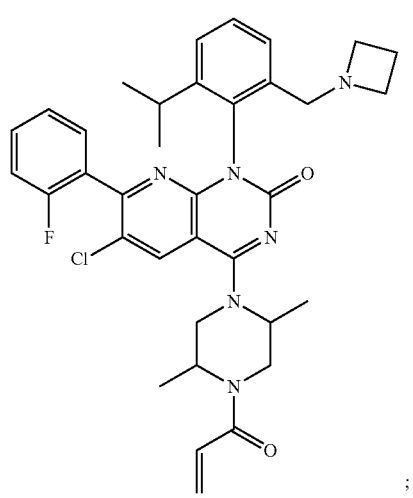
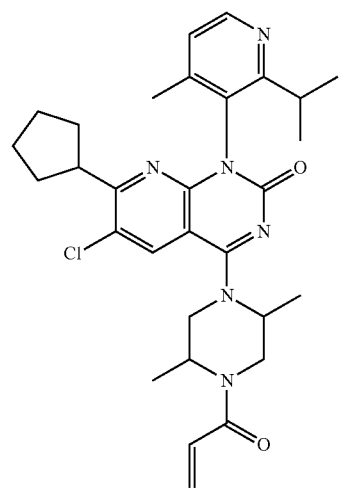
4
-continued
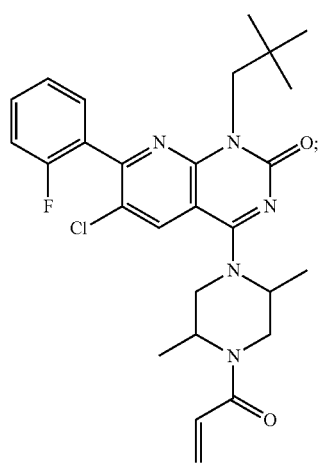
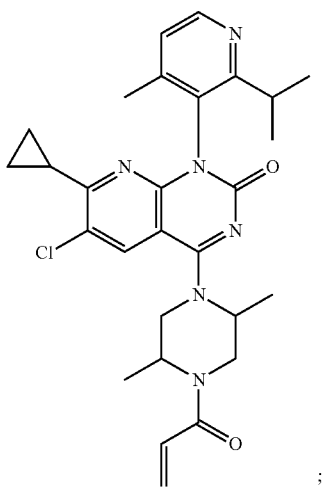
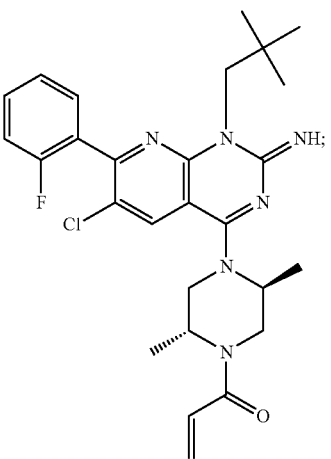

5
-continued
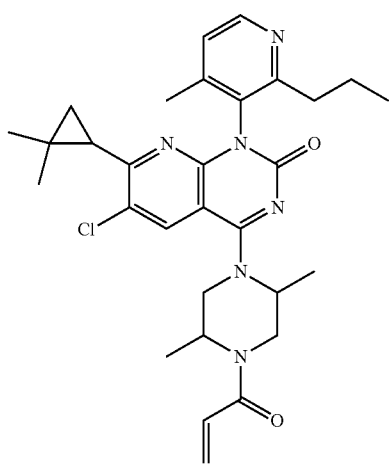
;
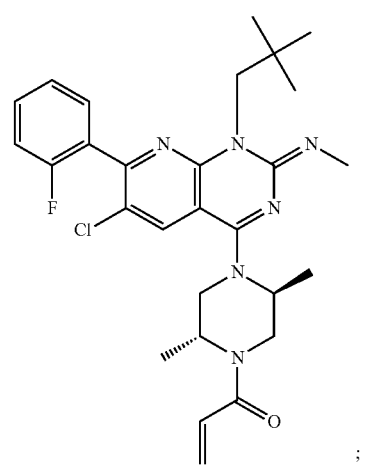
;
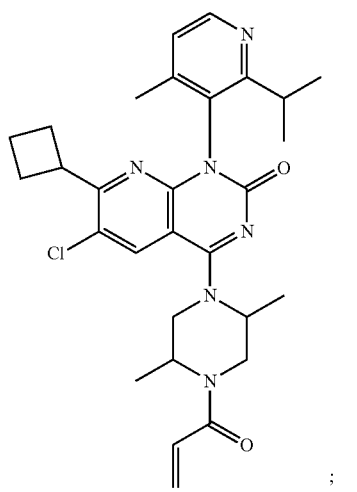
;
6
-continued
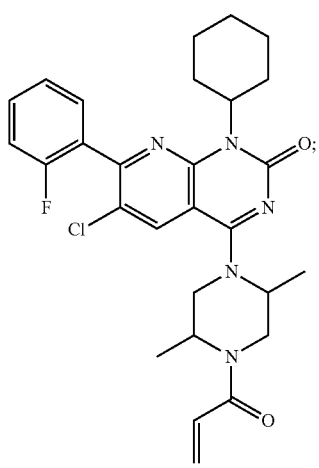
;
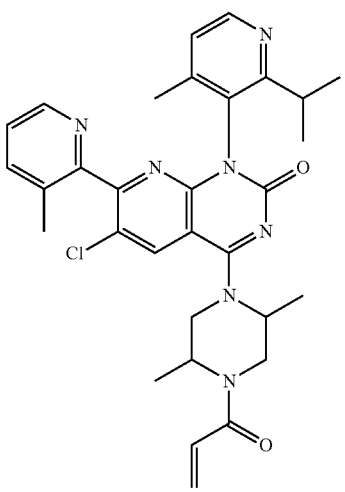
;
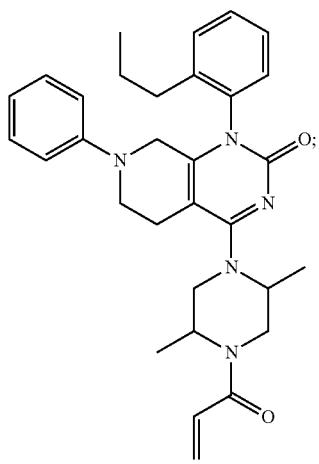
;

7
-continued
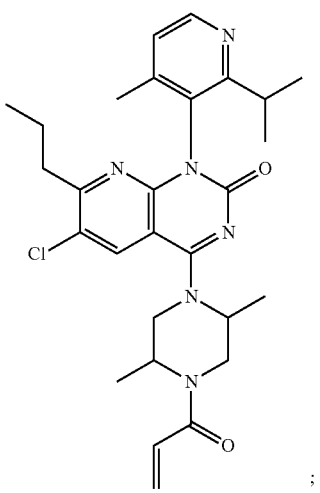
;
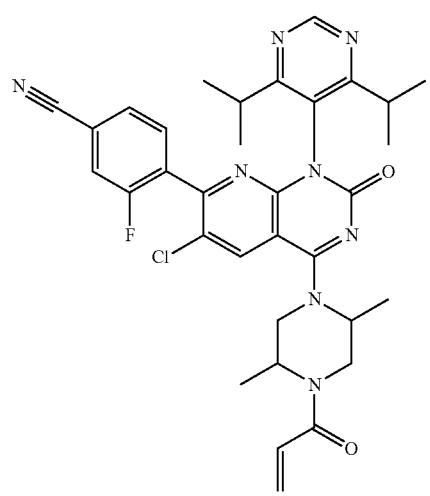
;
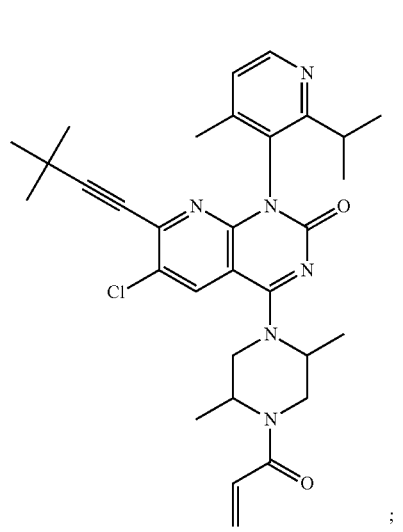
;
8
-continued
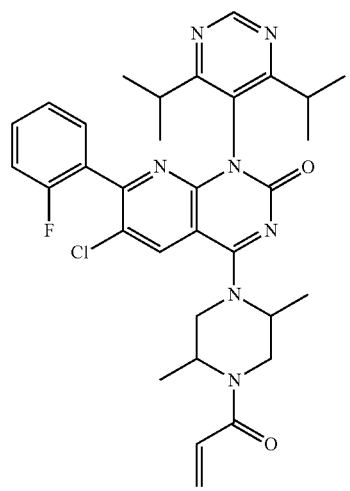
;
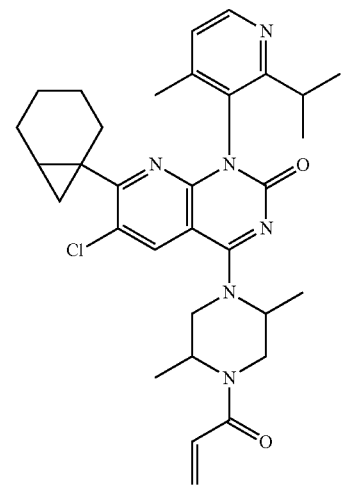
;
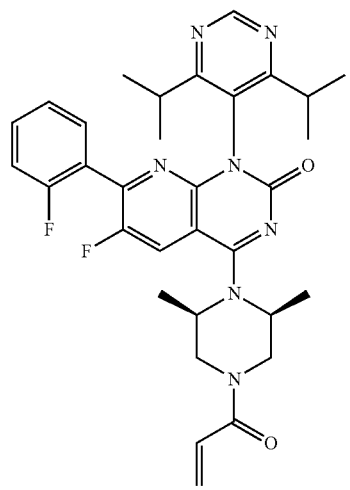
;

9
-continued
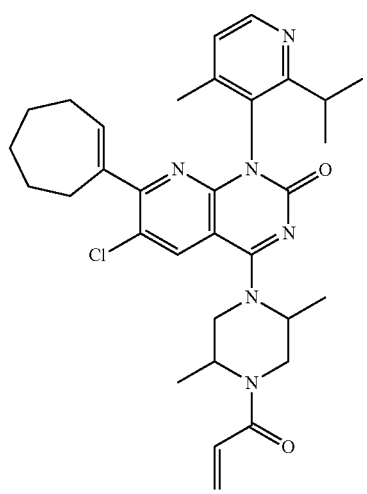
;
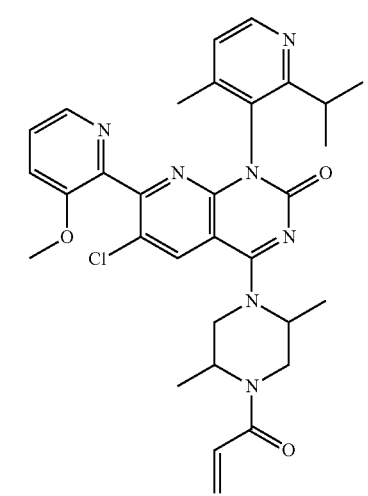
;
10
-continued
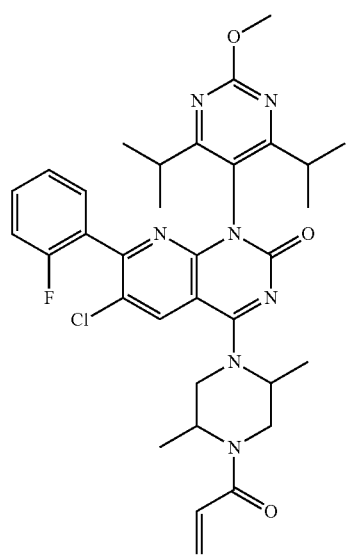
;
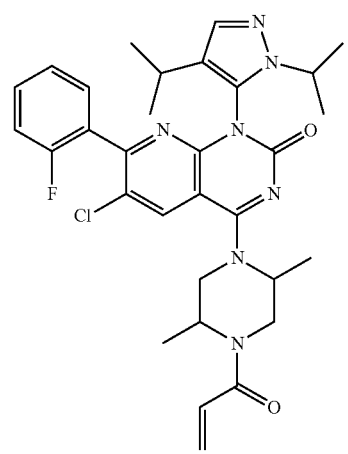
;
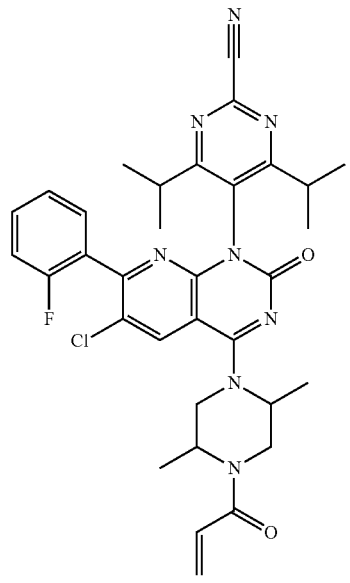
;

-continued
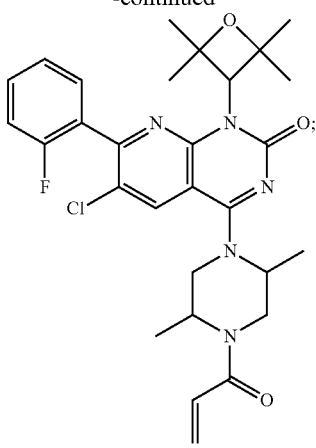
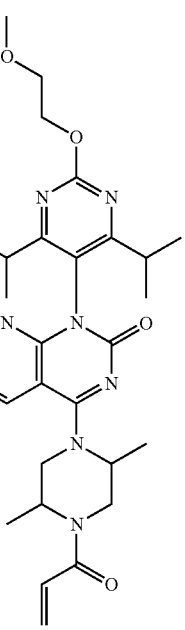
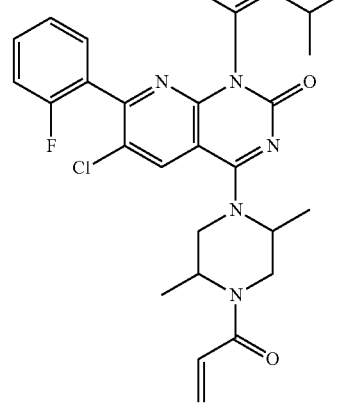
-continued
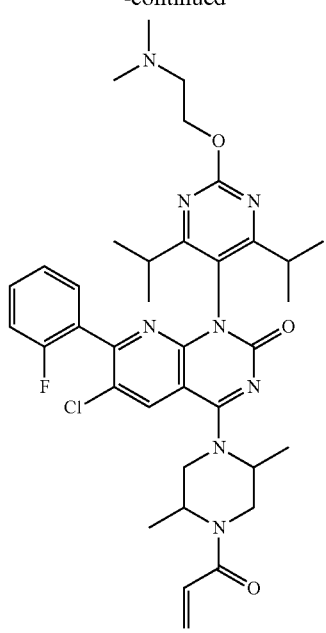
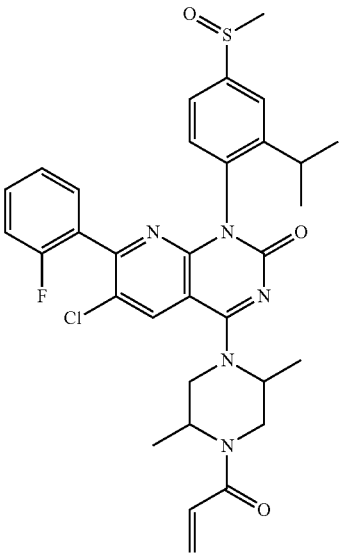

-continued
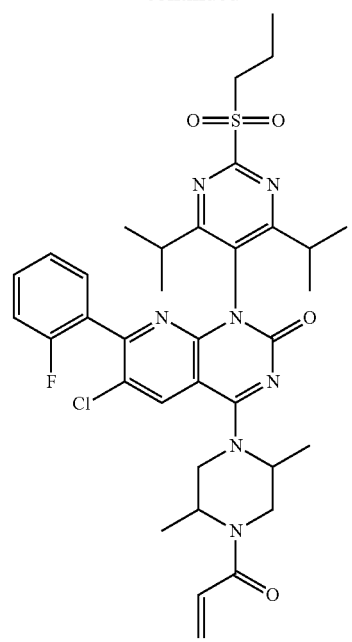
;
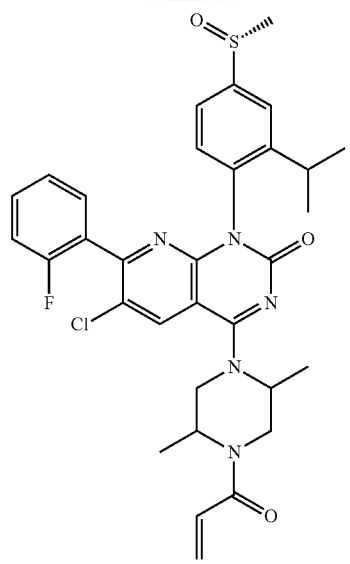
;
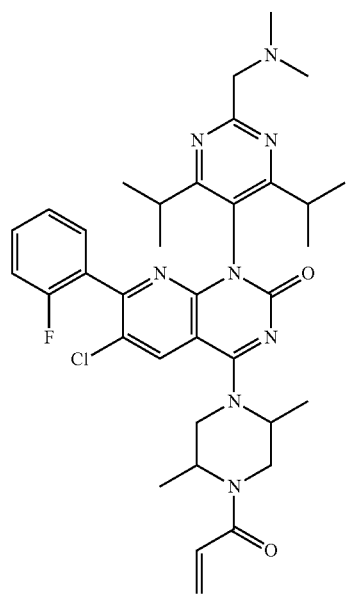
;
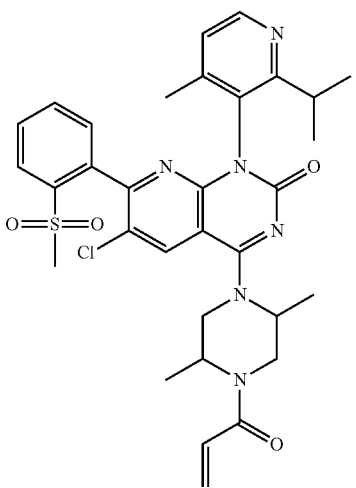
;

15
-continued
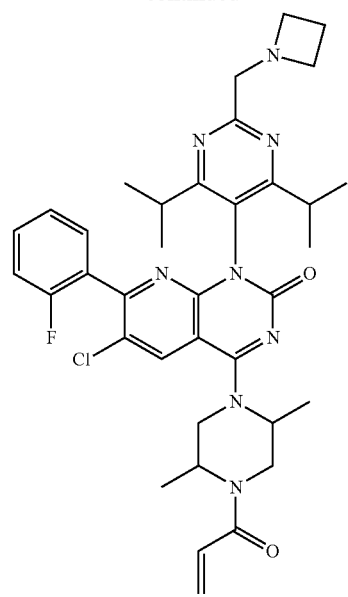
;
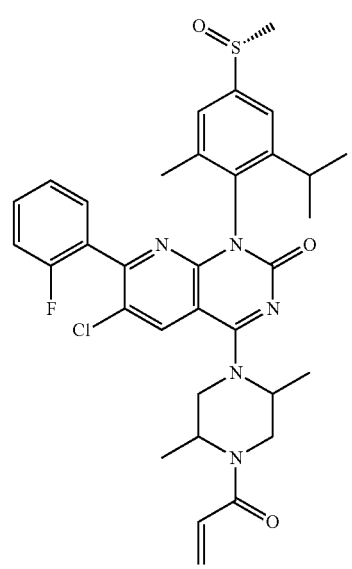
;
16
-continued
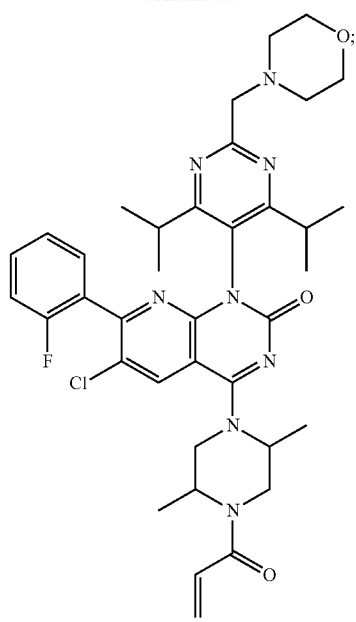
;

17
-continued
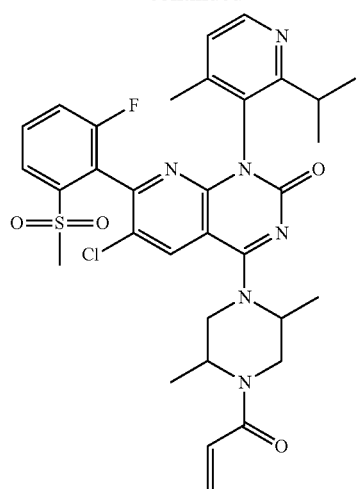
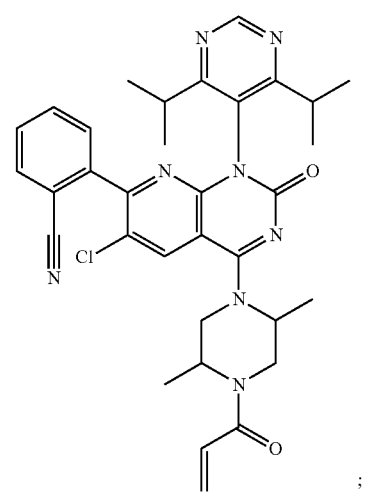
18
-continued
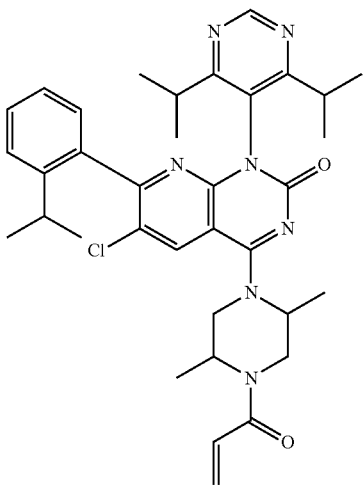

19
-continued
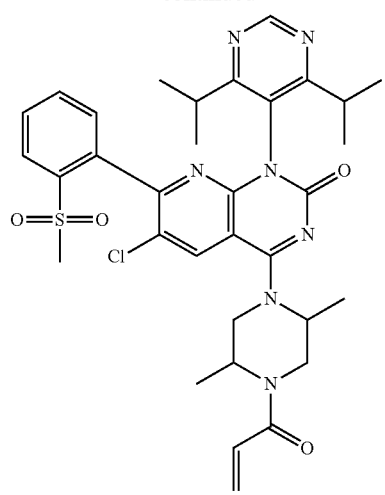
;
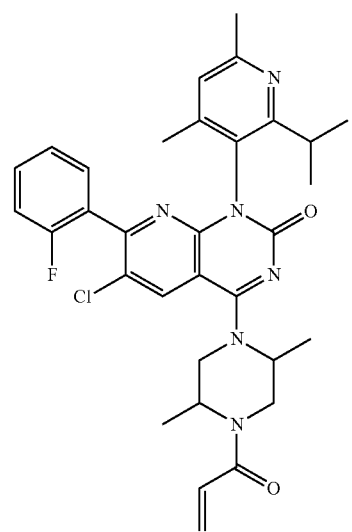
;
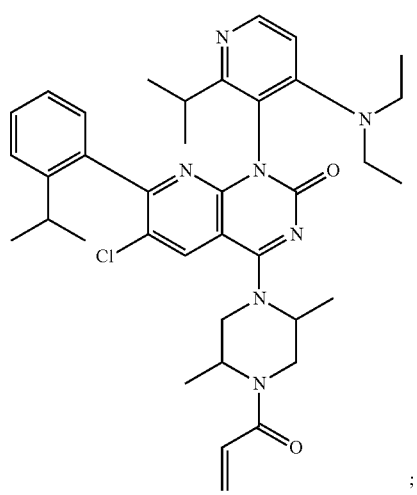
;
20
-continued
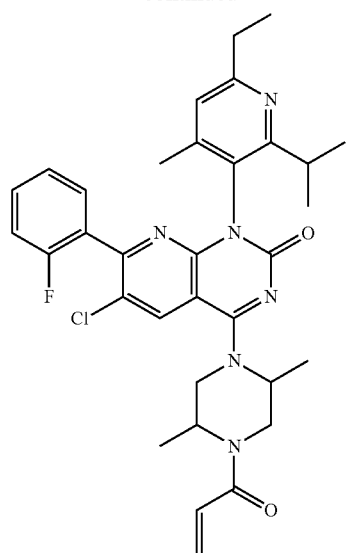
;
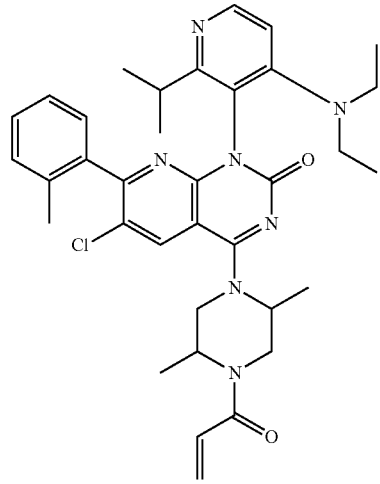
;
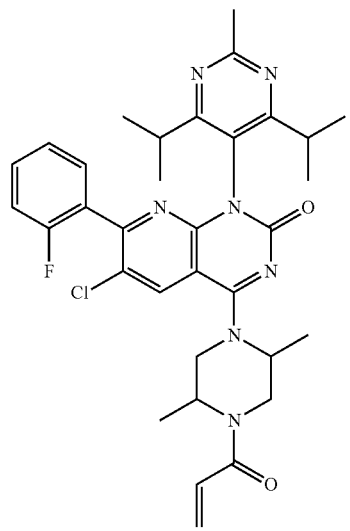
;

21
-continued
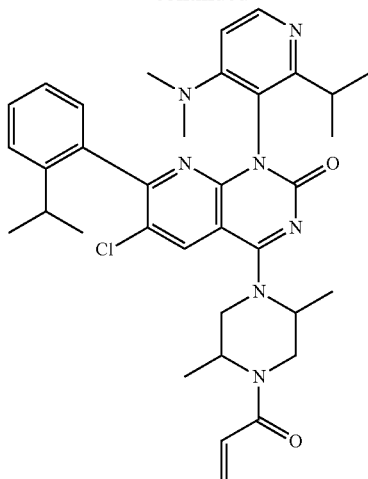
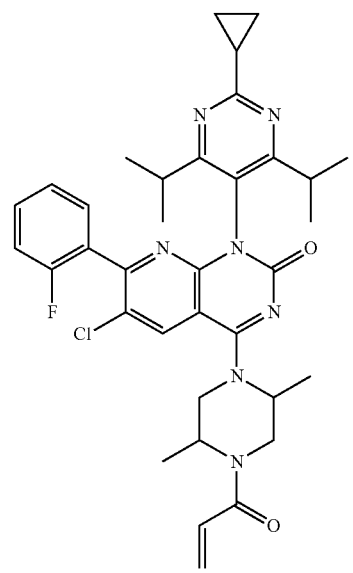
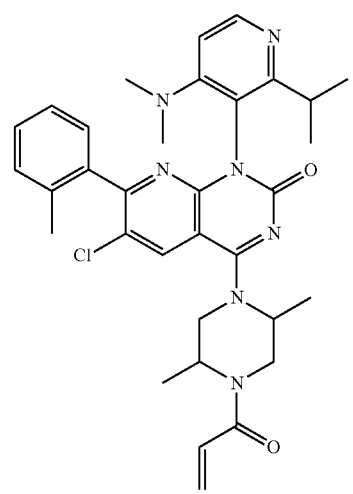
22
-continued
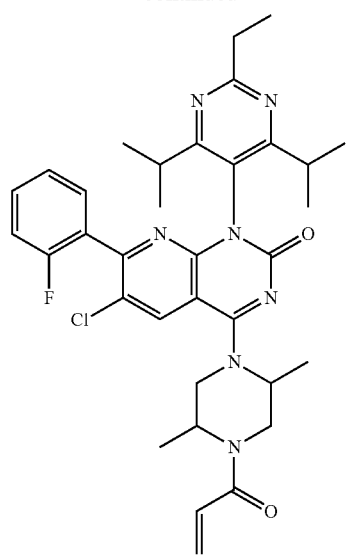
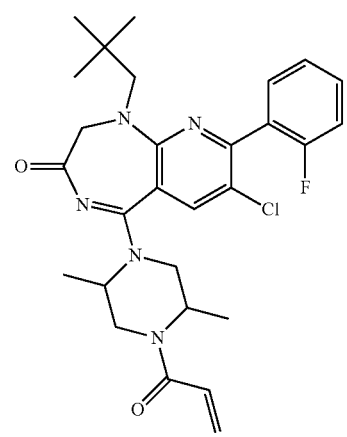
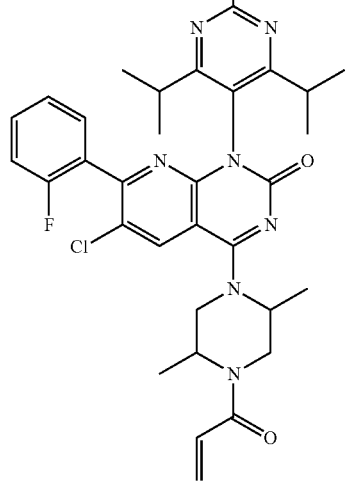

23
-continued
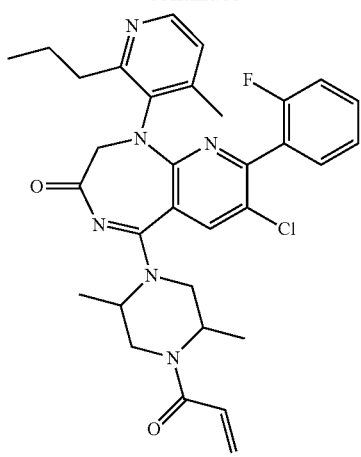
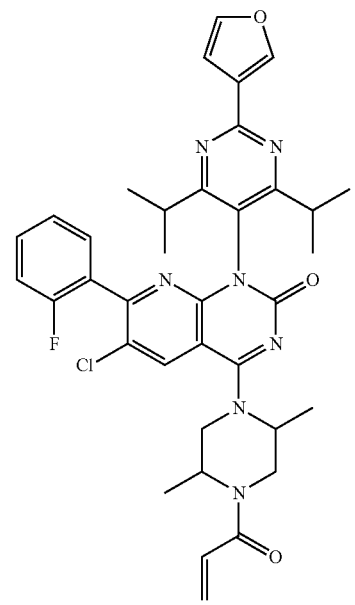
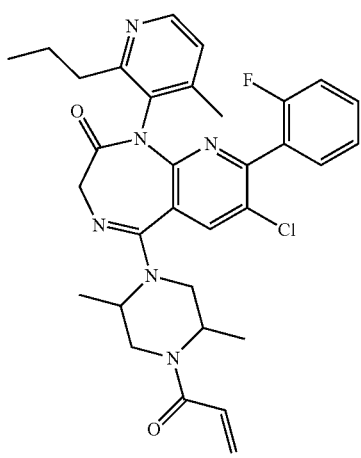
24
-continued
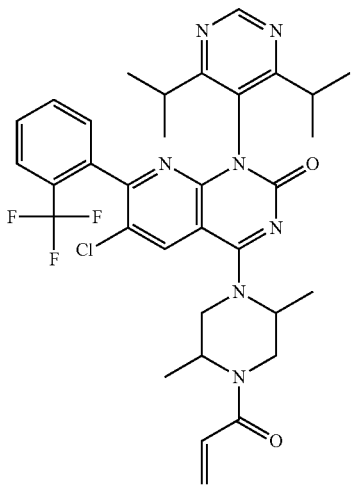
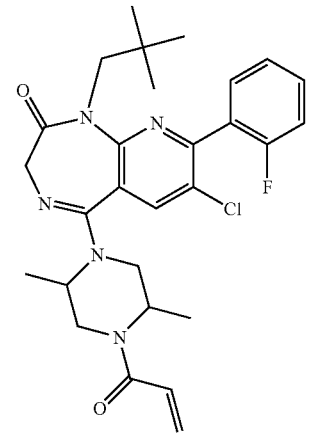
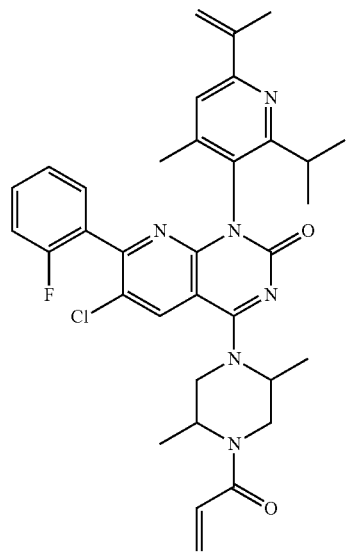

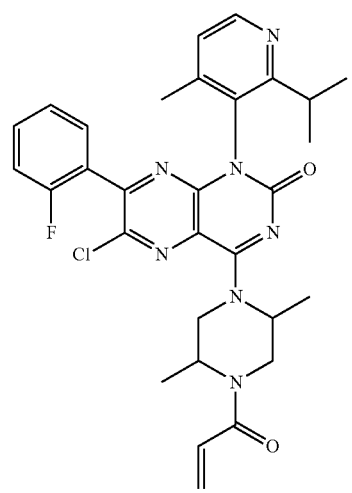
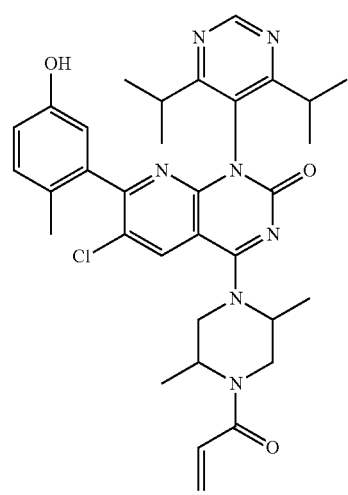
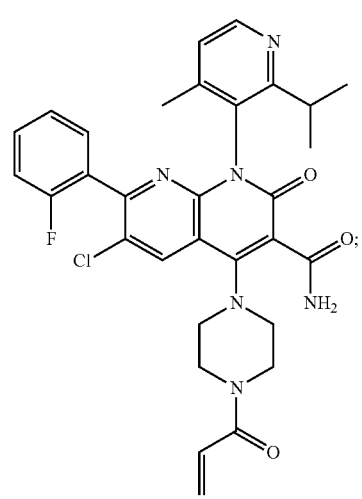
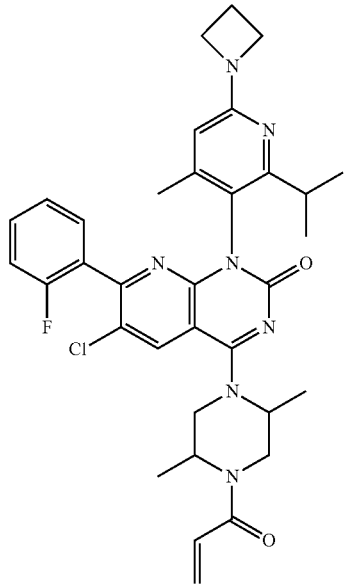
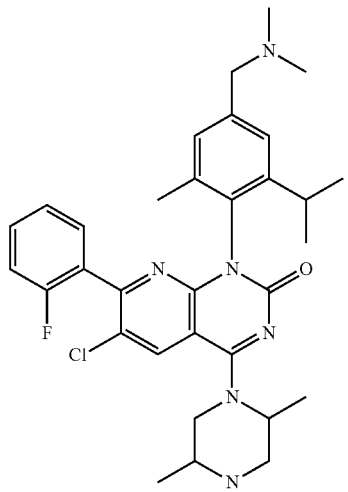
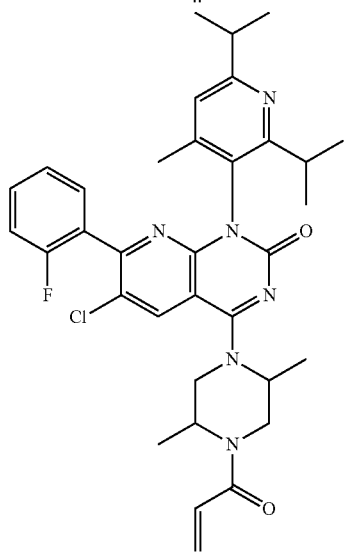

27
-continued
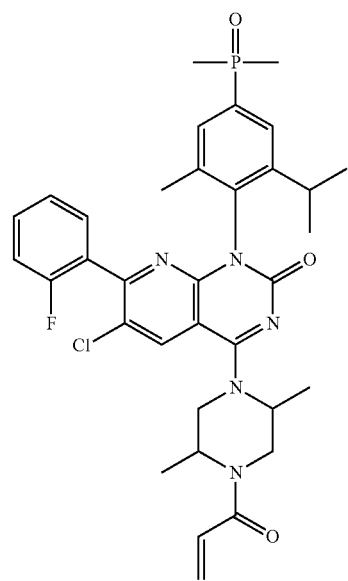
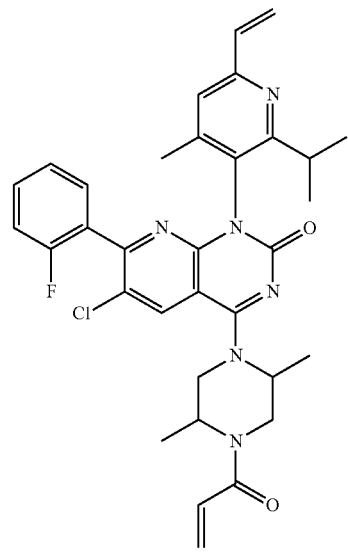
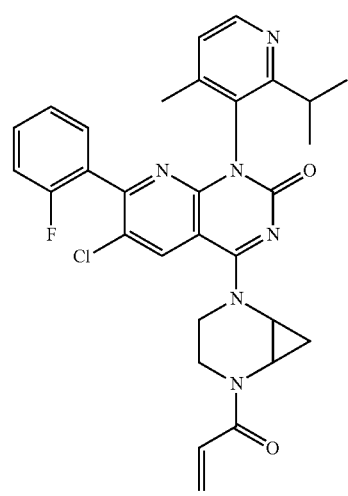
28
-continued
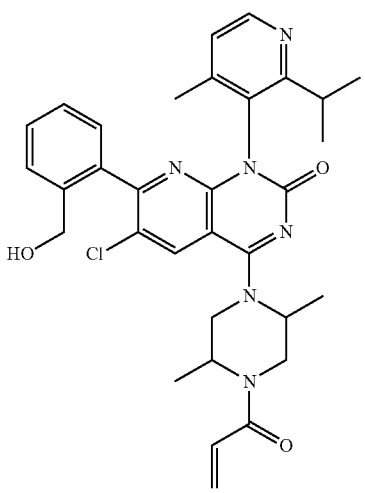
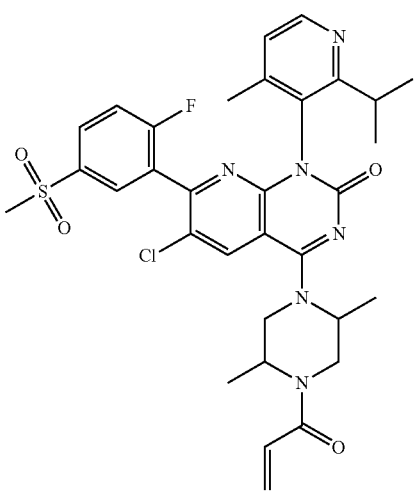
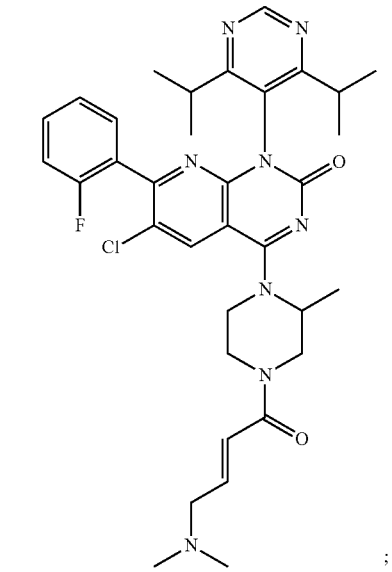

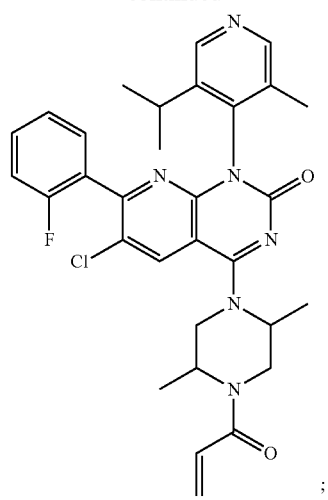
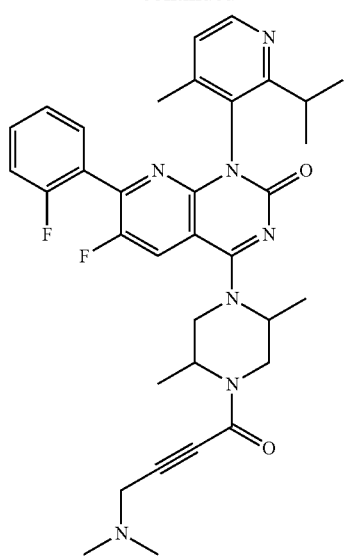
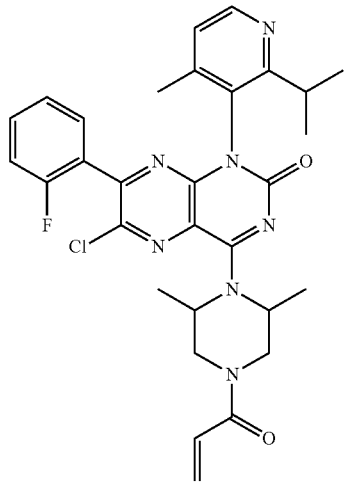
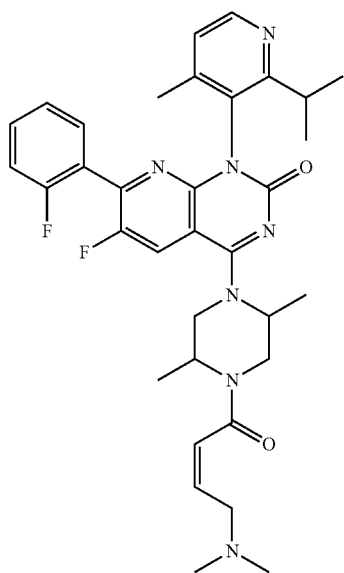

31
-continued
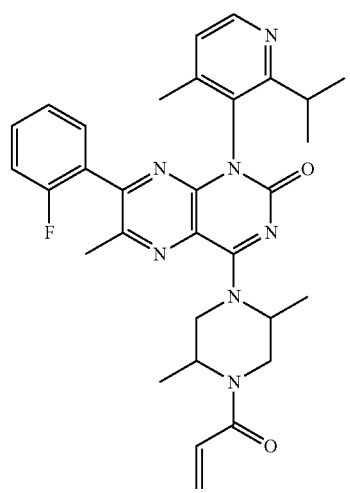
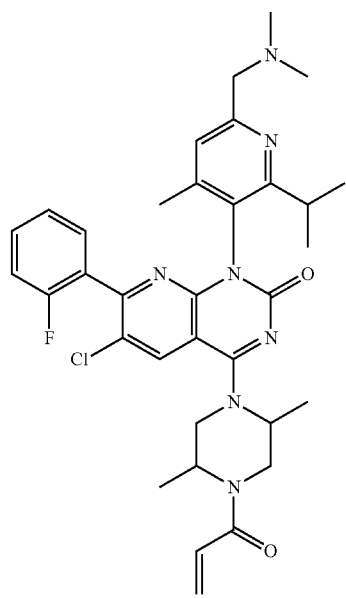
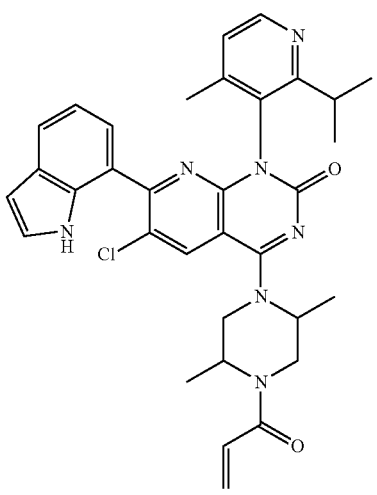
32
-continued
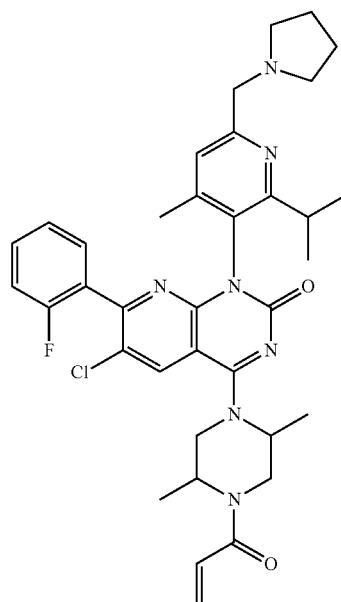
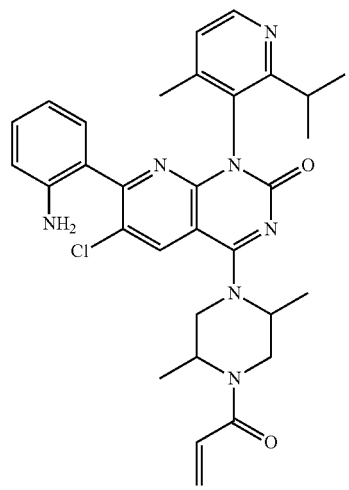
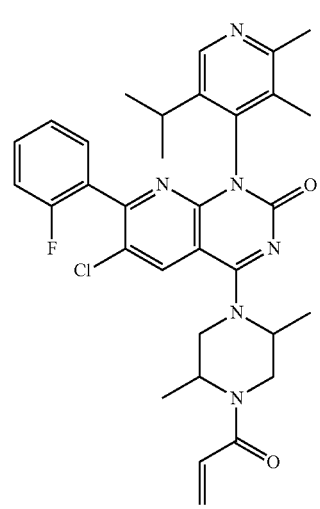

33
-continued
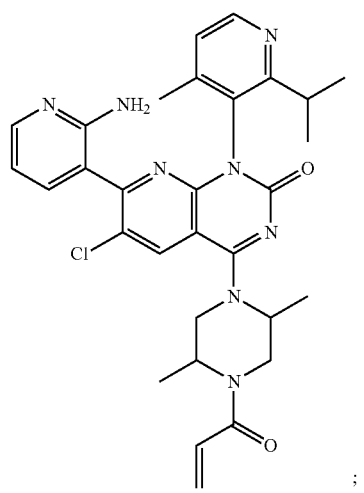
;
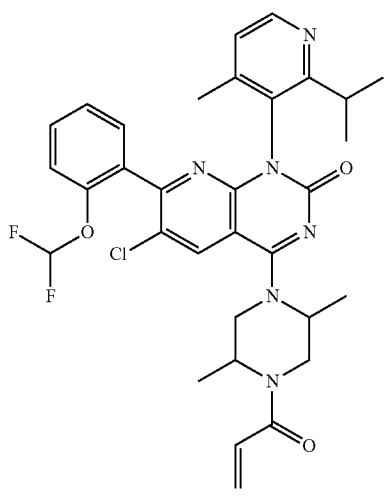
;
34
-continued
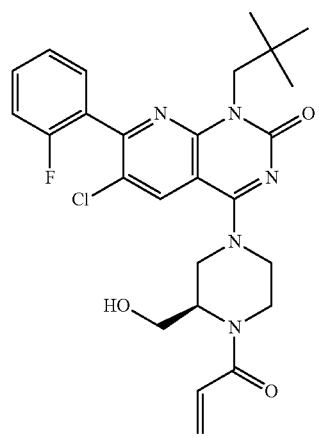
;
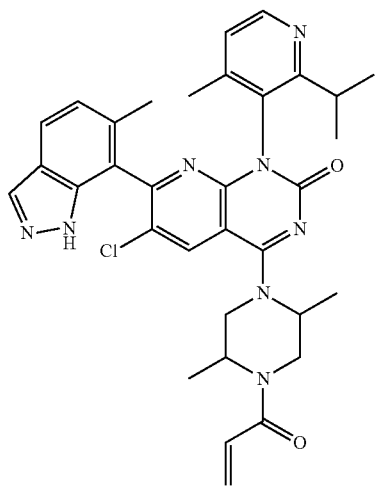
;
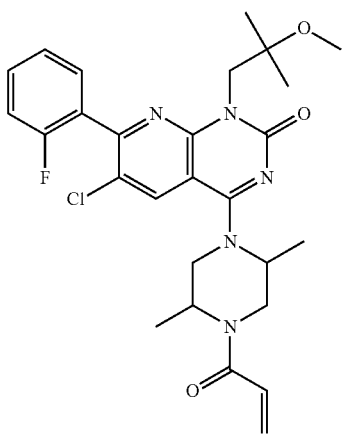
;

35
-continued
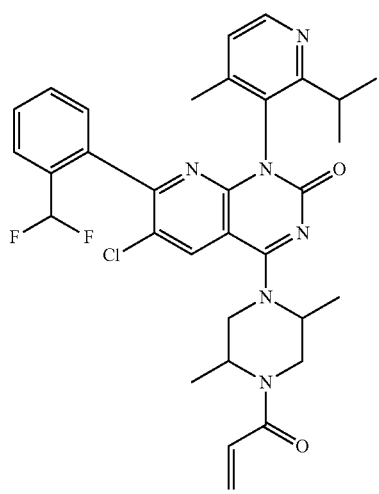
;
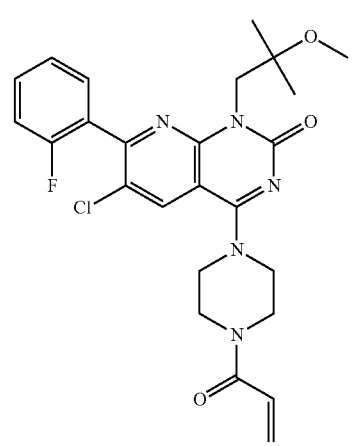
;
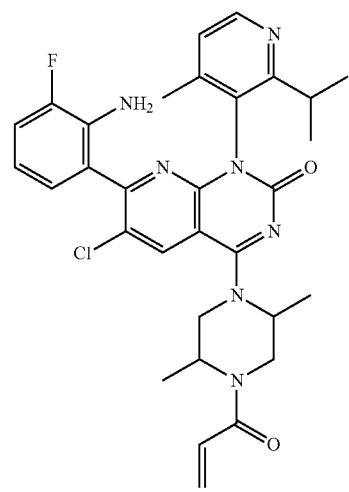
;
36
-continued
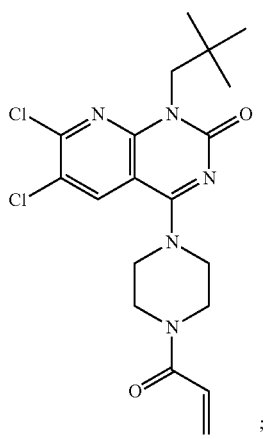
;
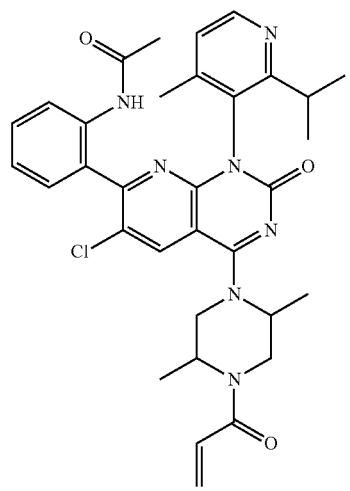
;
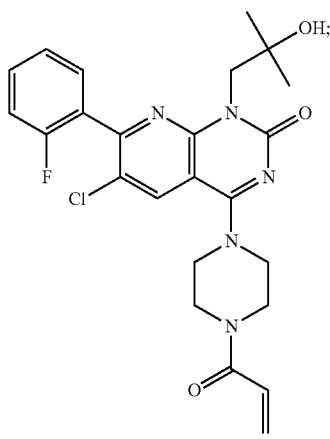

-continued
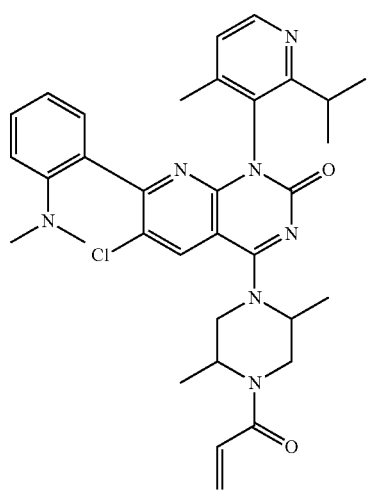
;
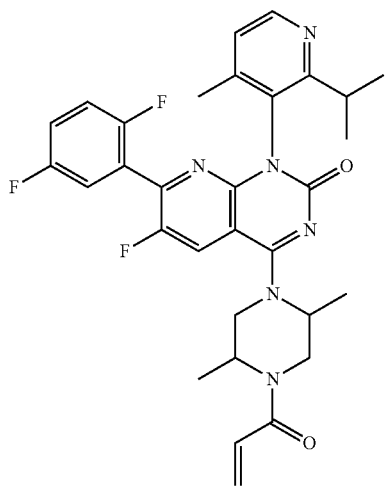
;
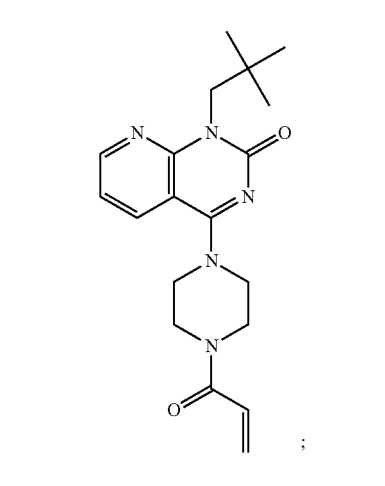
;
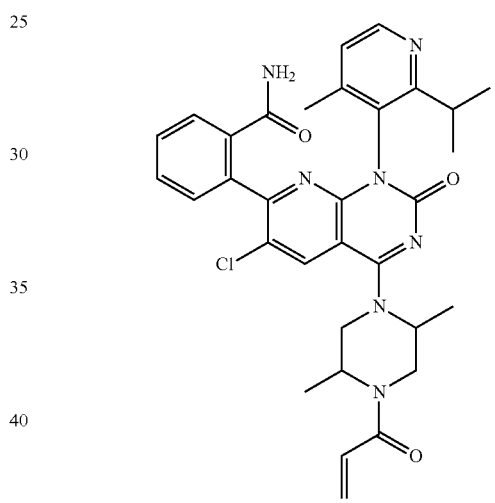
;
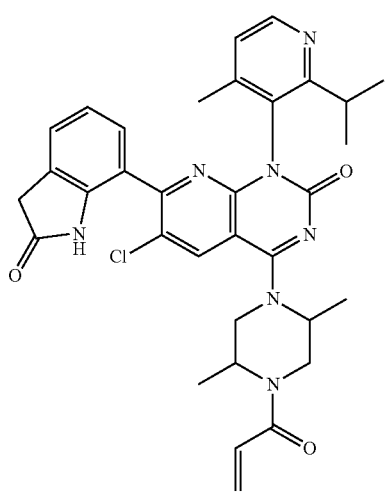
;
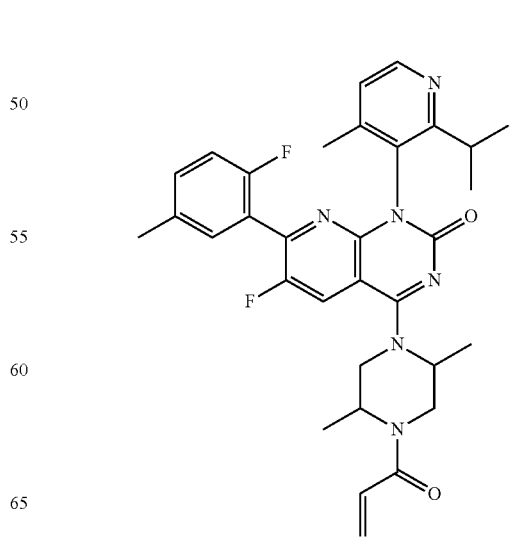
;

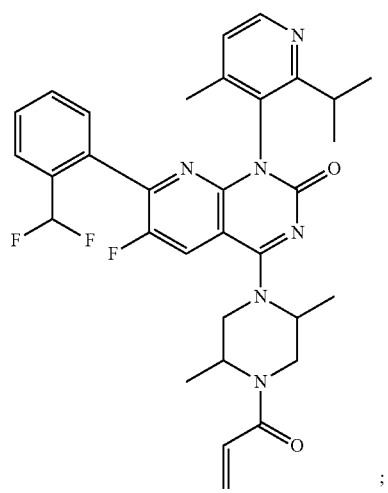
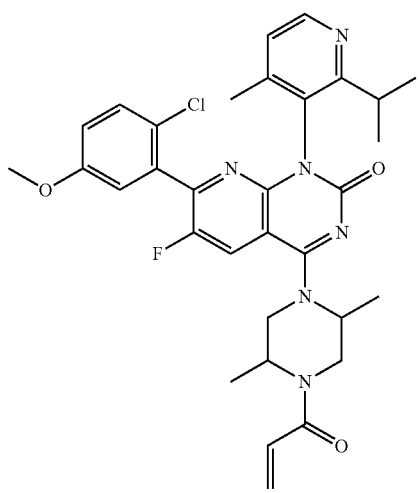
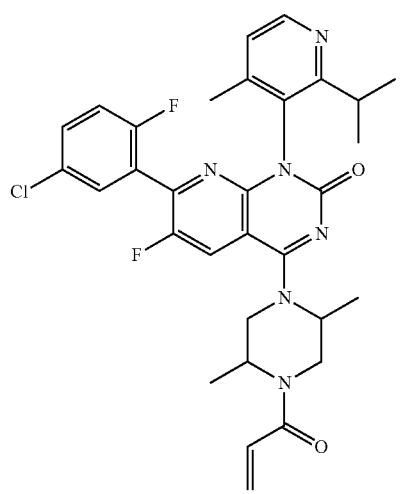
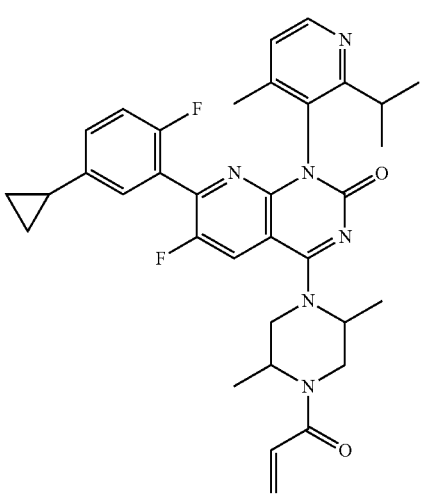
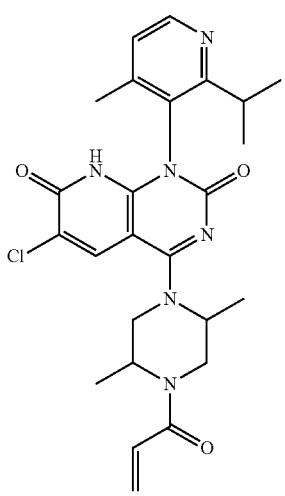

41
-continued
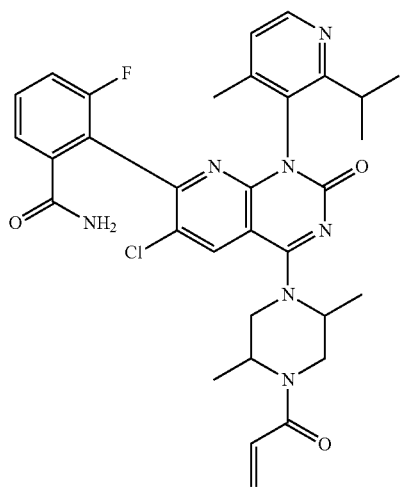
;
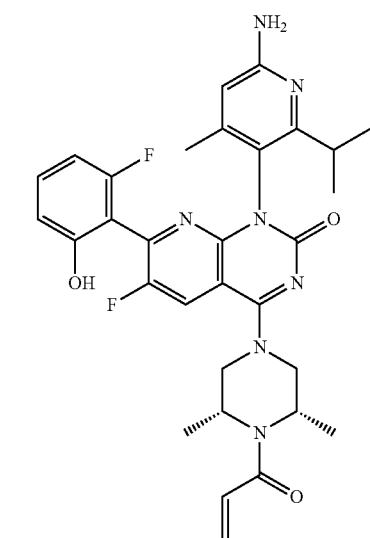
;
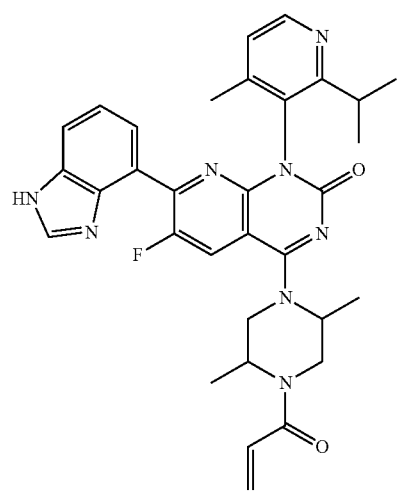
;
42
-continued
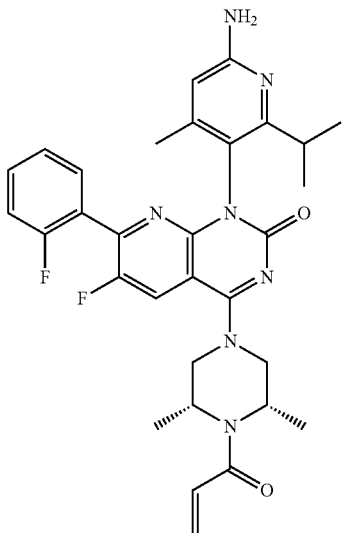
;
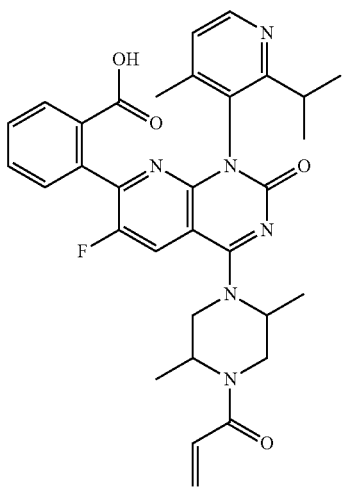
;
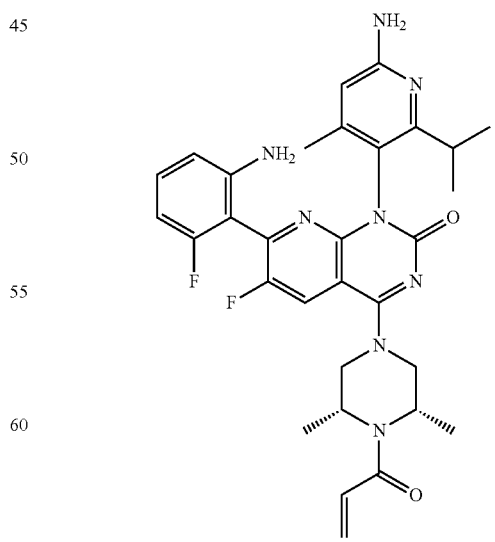
;

43
-continued
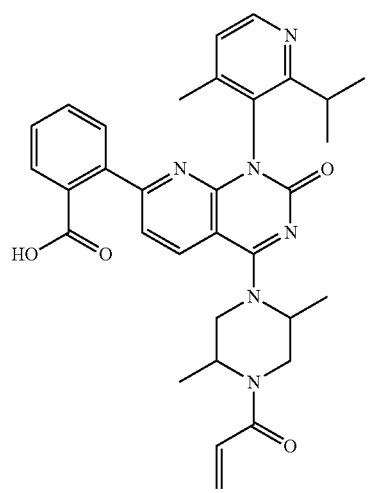
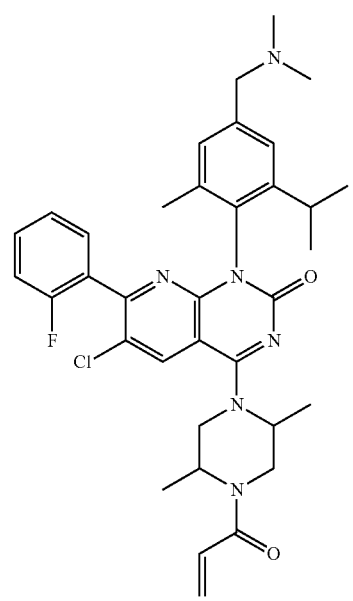
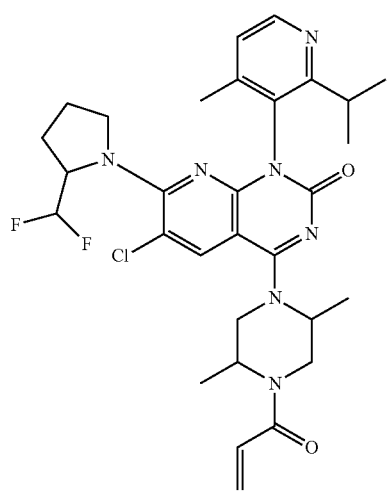
44
-continued
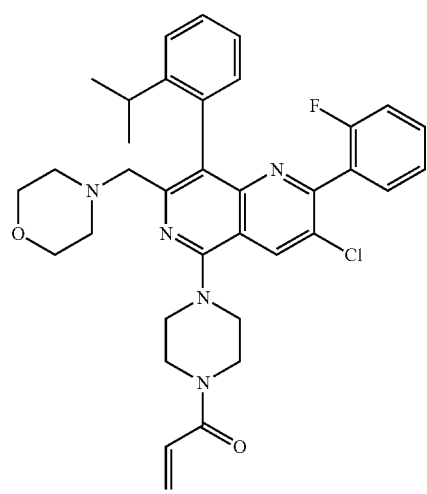
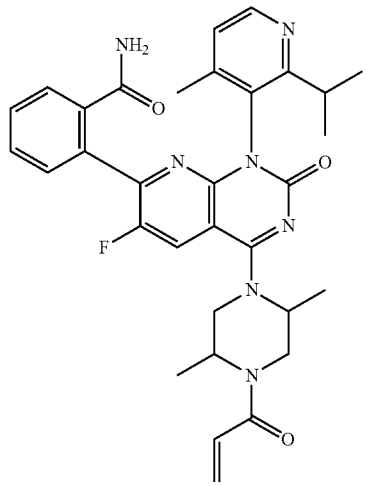
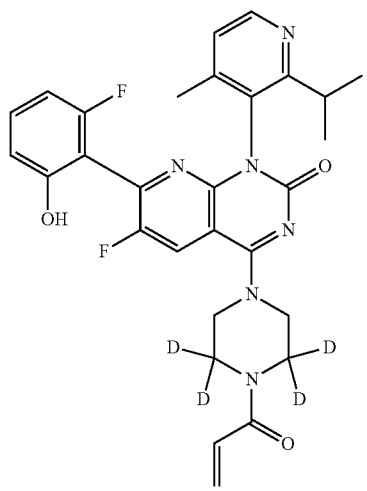

45
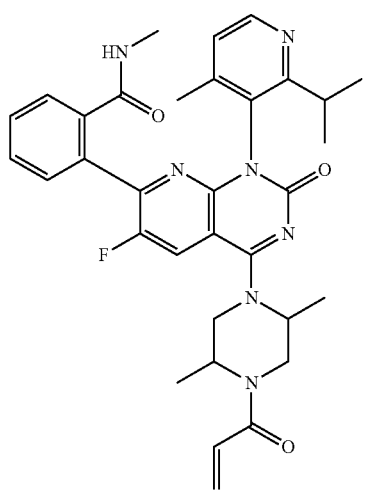
;
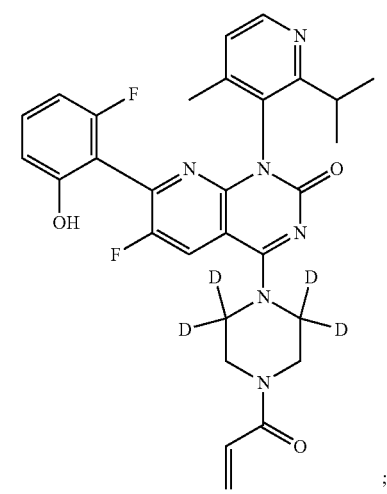
;
46
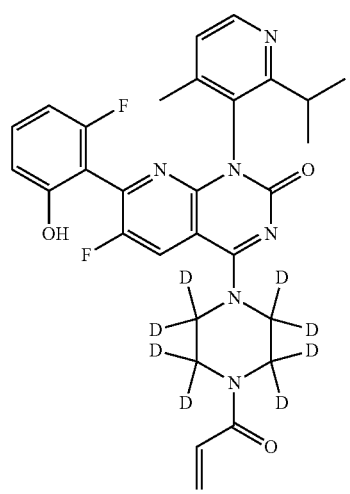
;
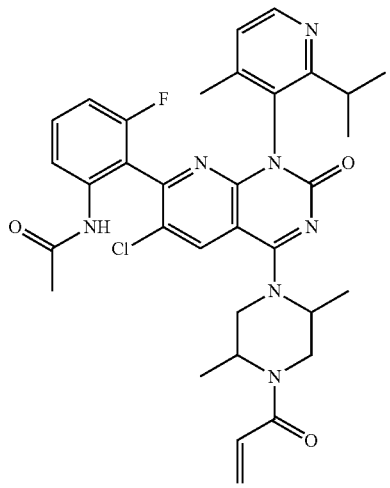
;
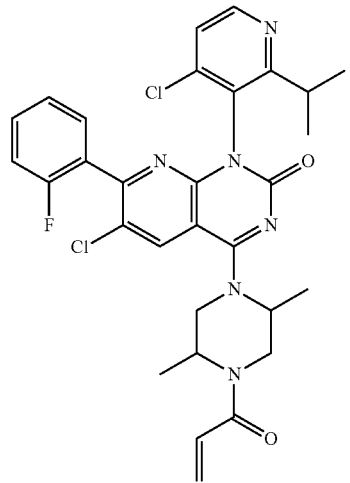
;

47
-continued
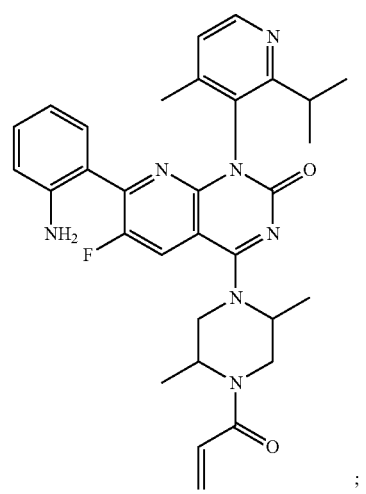
;
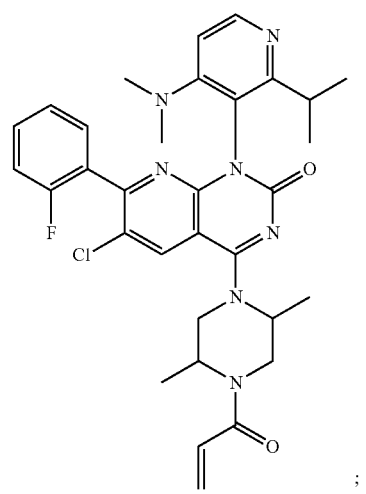
;
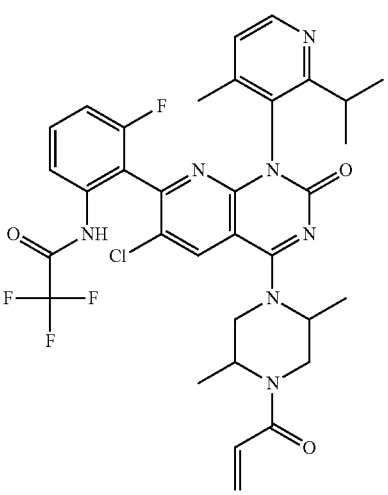
;
48
-continued
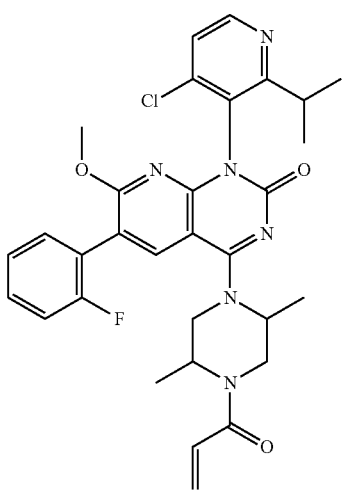
;
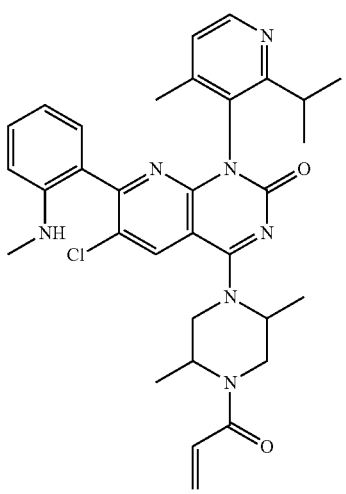
;
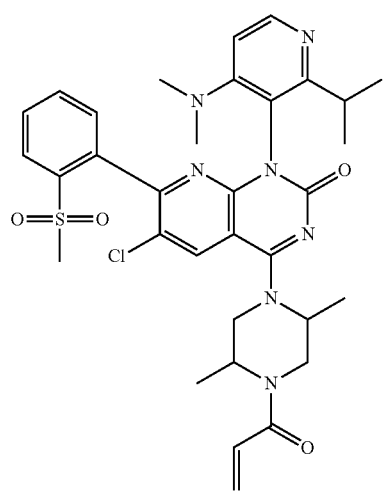
;

49
-continued
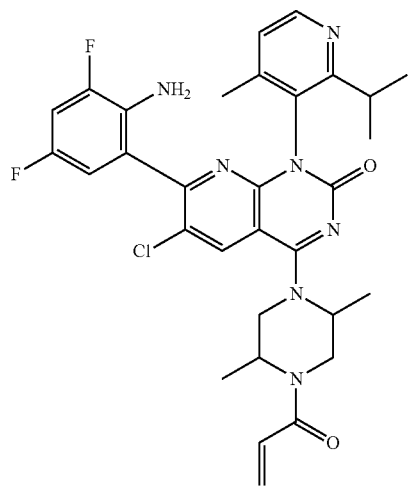
;
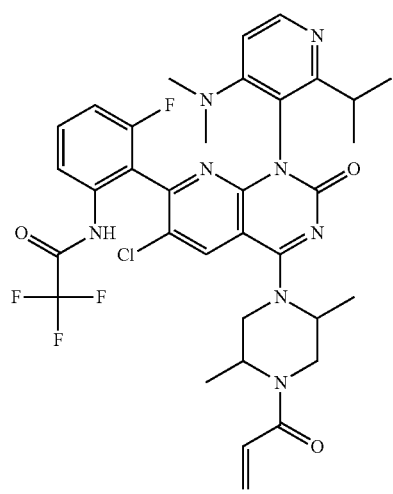
;
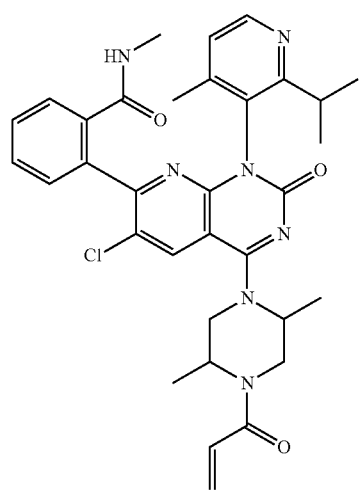
;
50
-continued
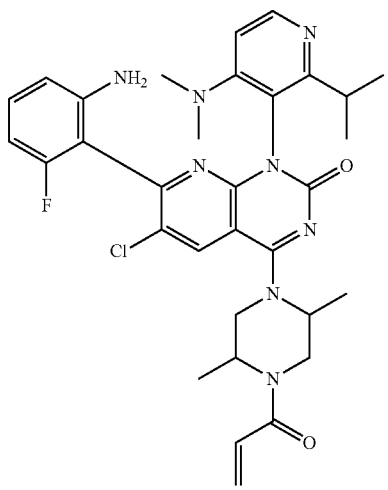
;
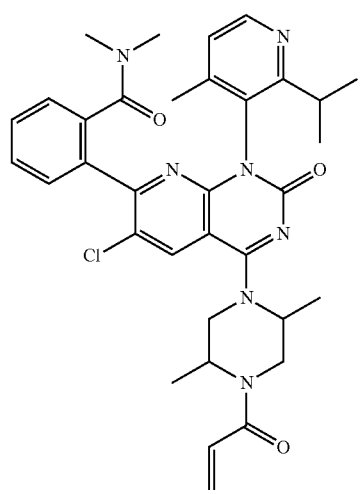
;
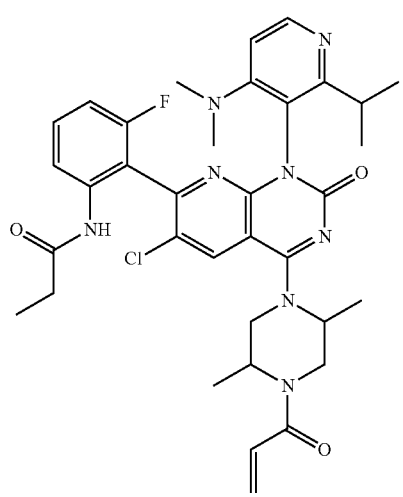
;

51
-continued
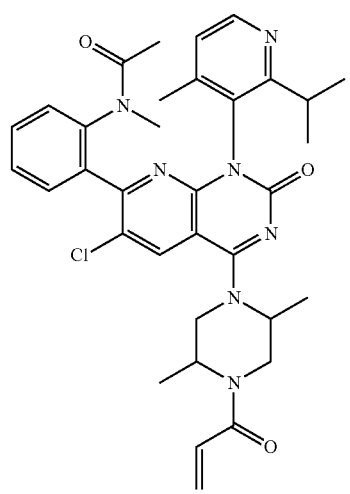
;
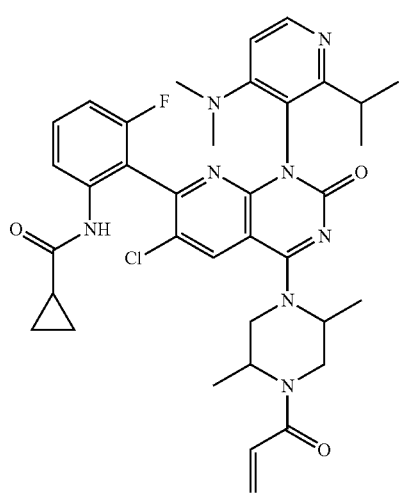
;
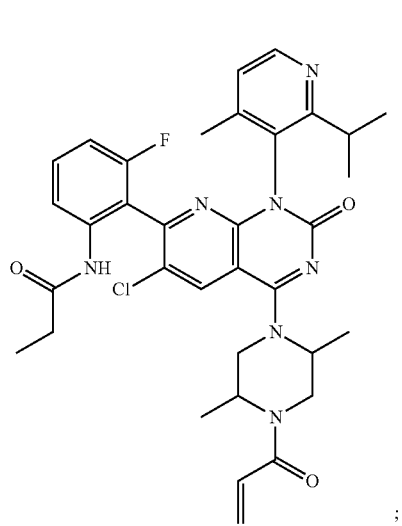
;
52
-continued
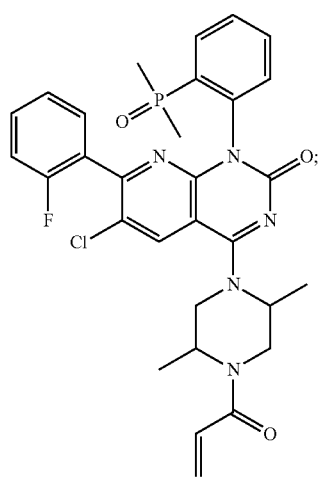
;
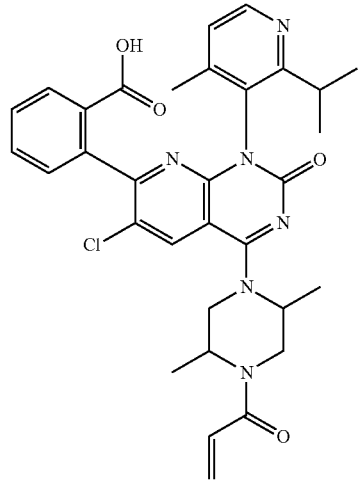
;
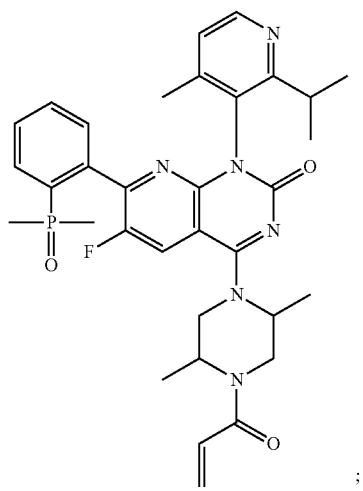
;

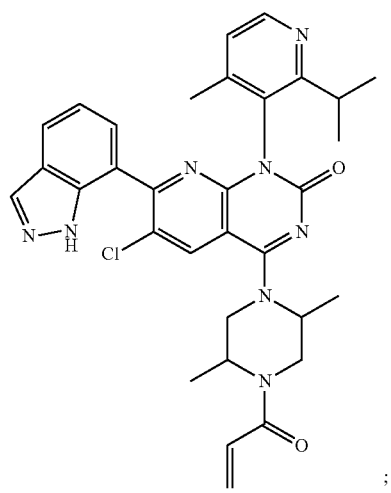
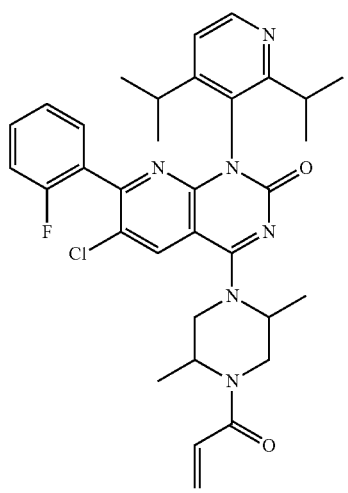
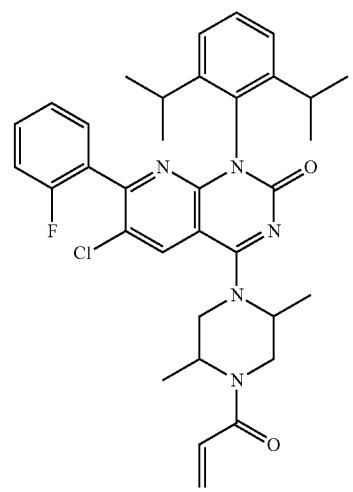
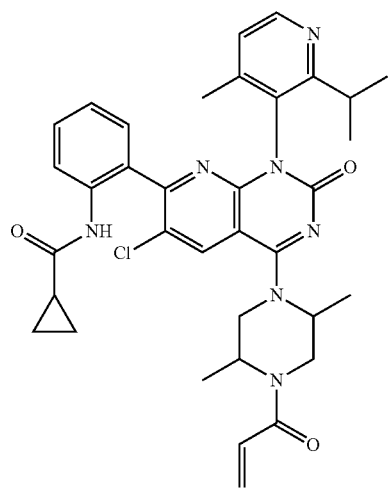
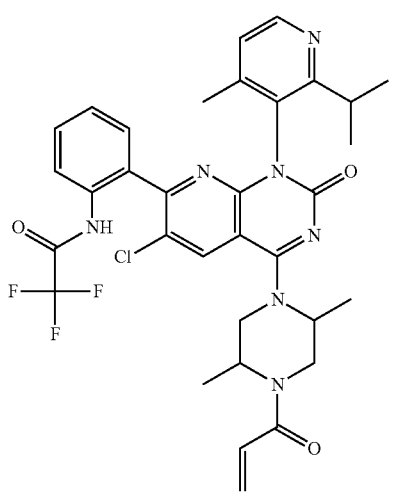
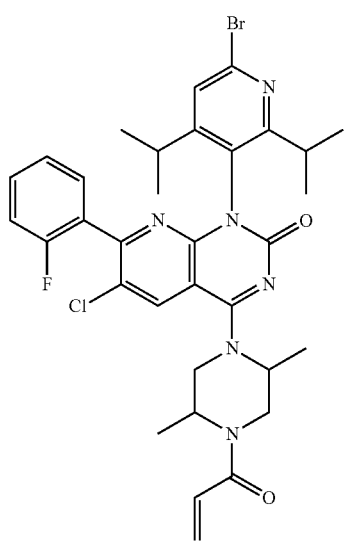

55
-continued
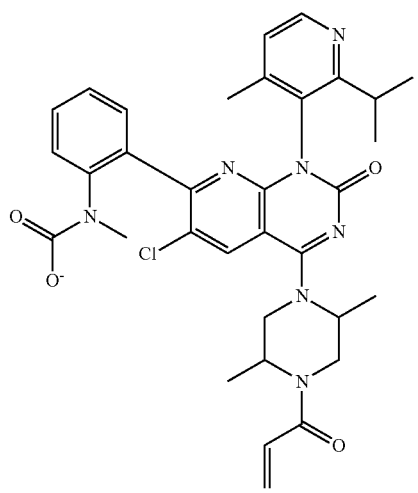
;
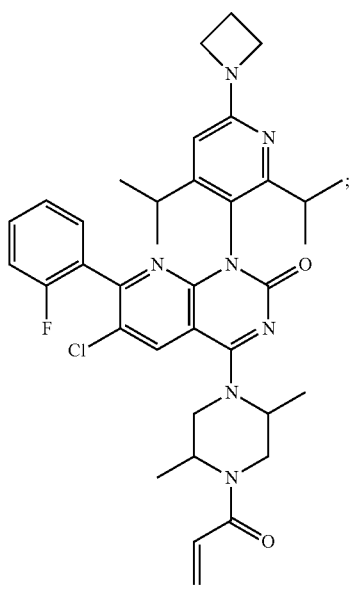
;
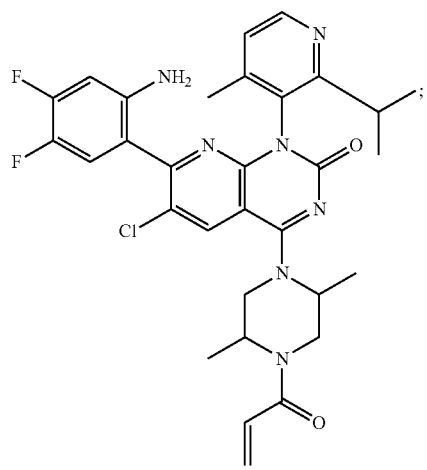
;
56
-continued
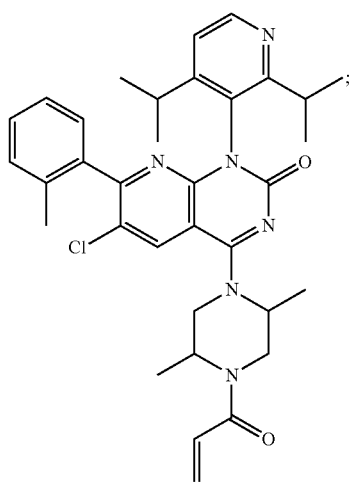
;
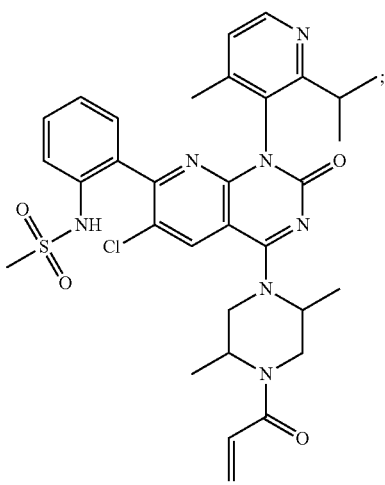
;
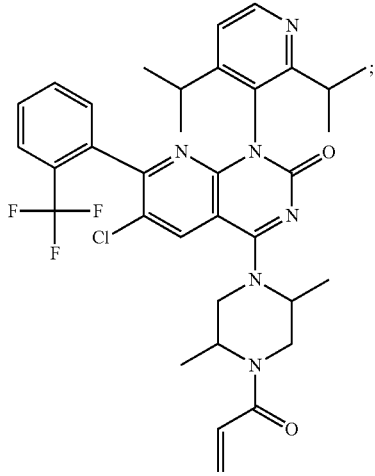
;

57
-continued
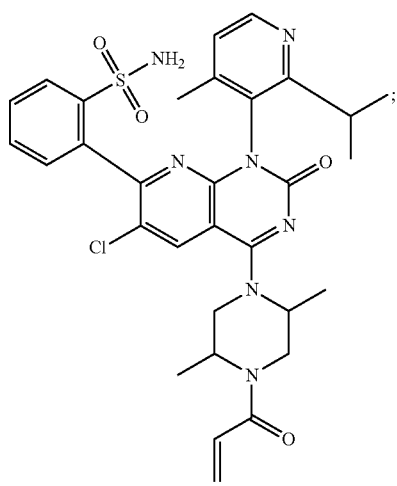
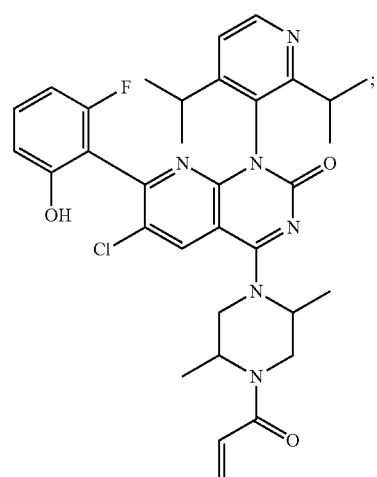
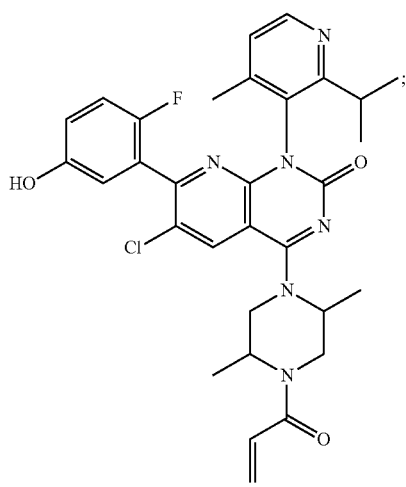
58
-continued
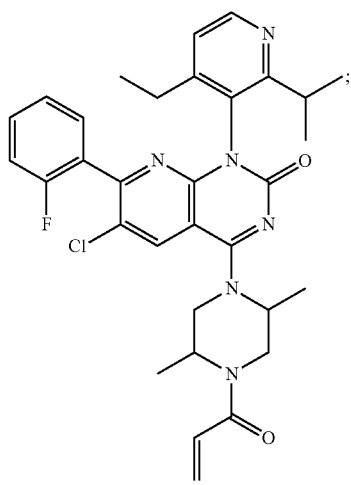
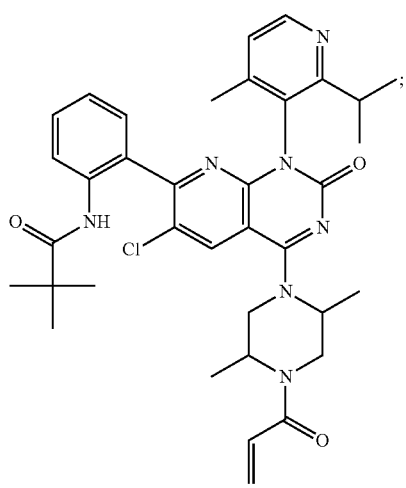
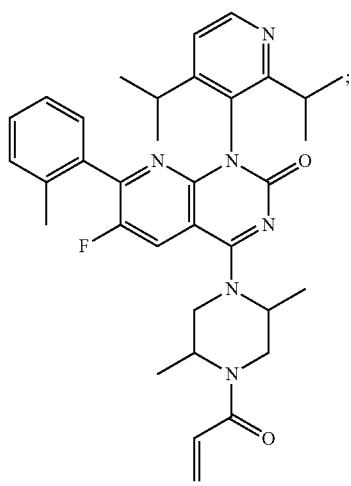

-continued
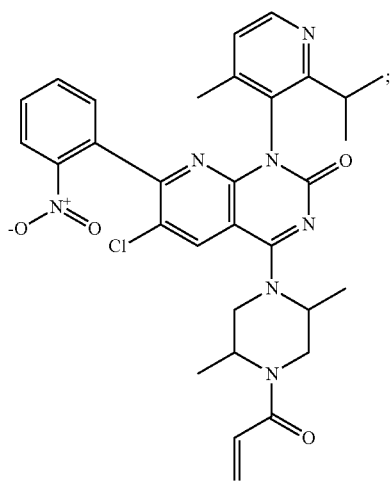
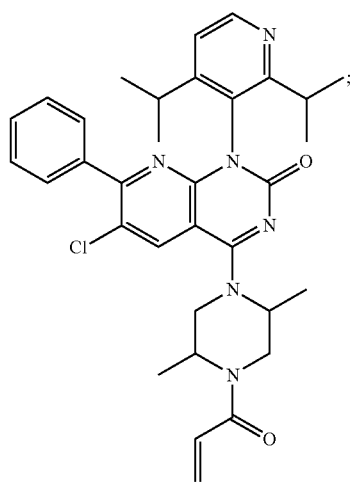
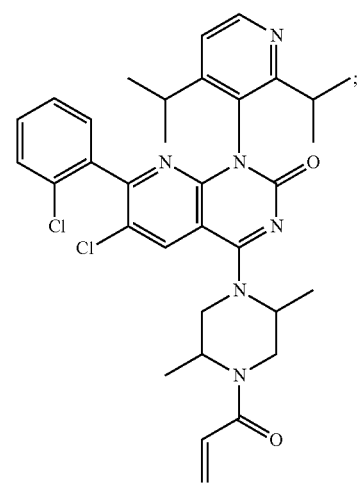
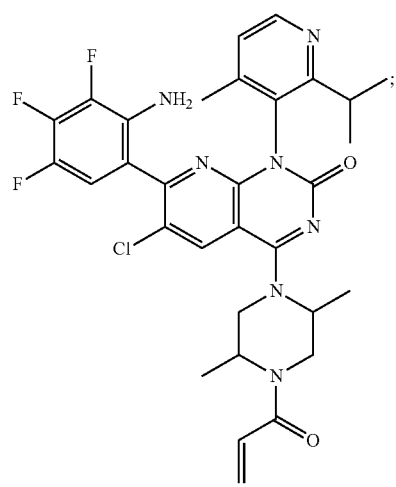
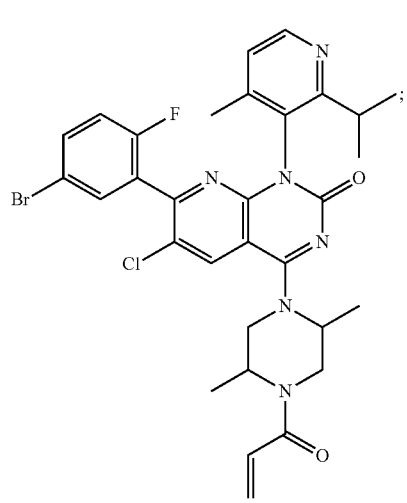
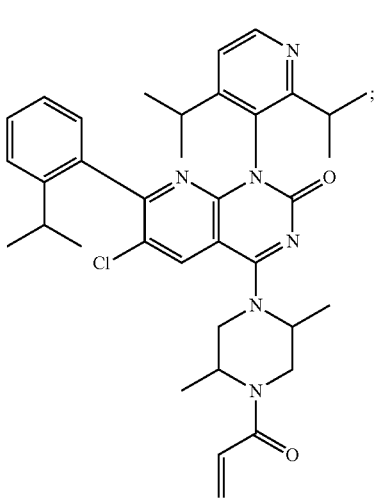

-continued
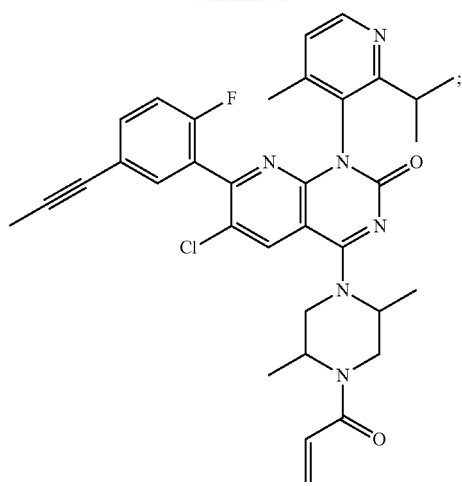
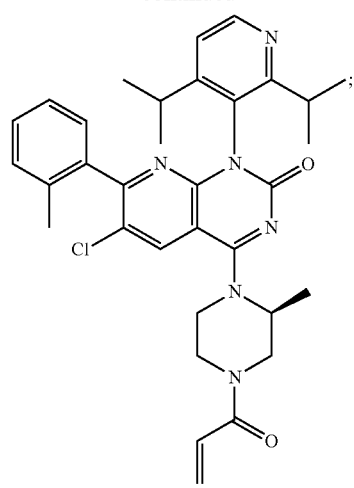
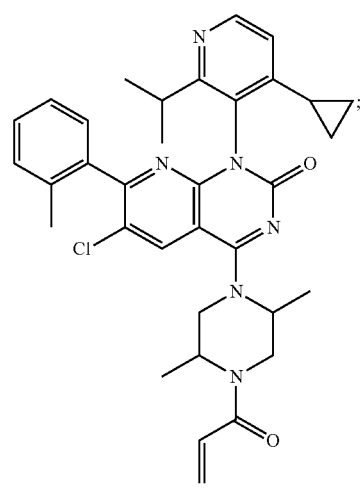
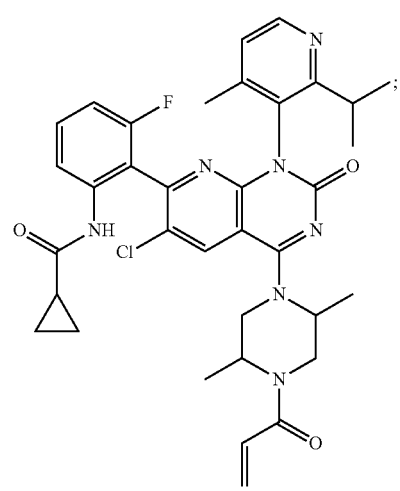
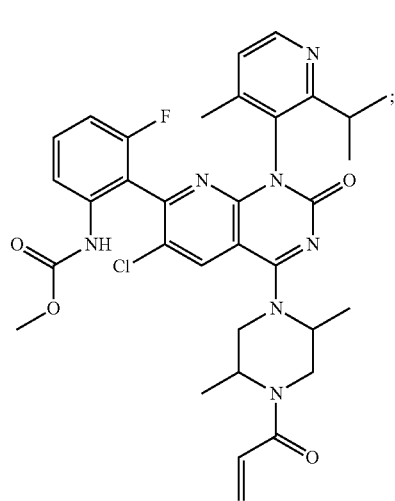
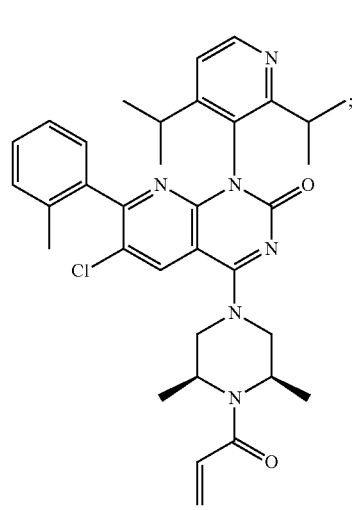

-continued
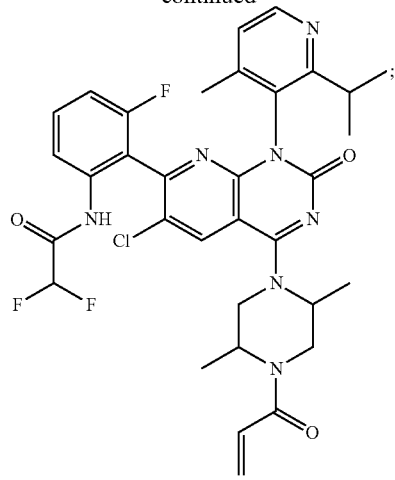
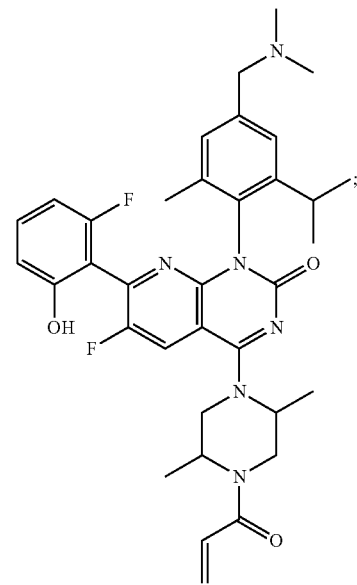
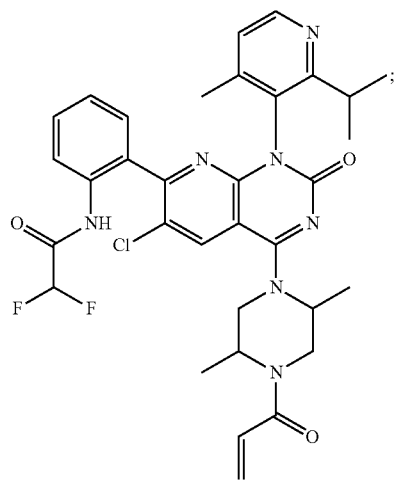
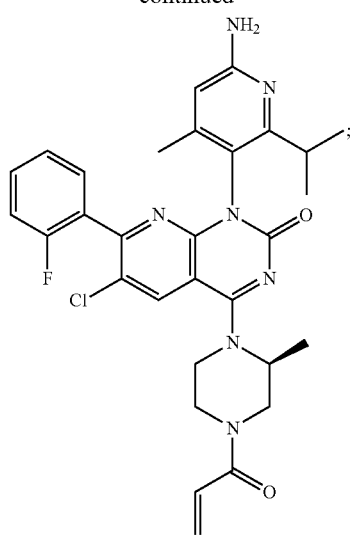
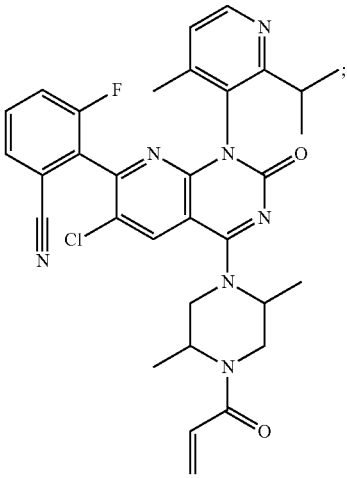
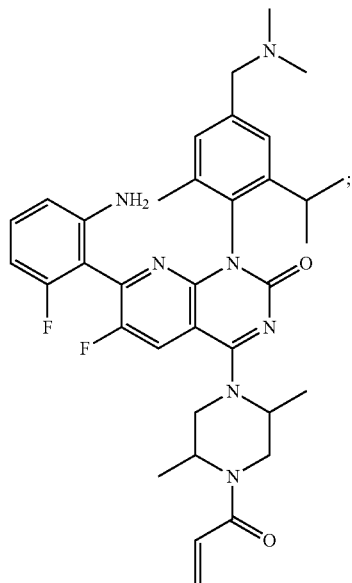

65
-continued
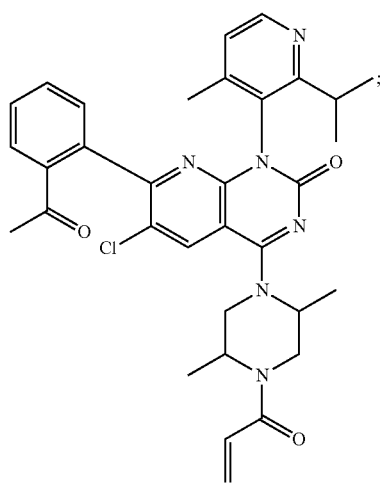
66
-continued
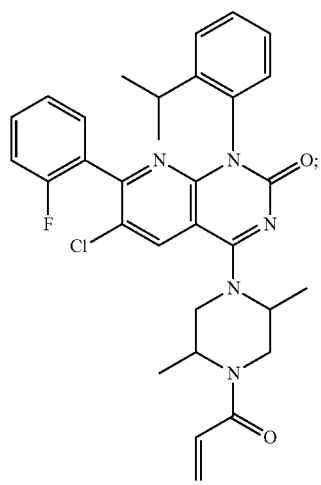
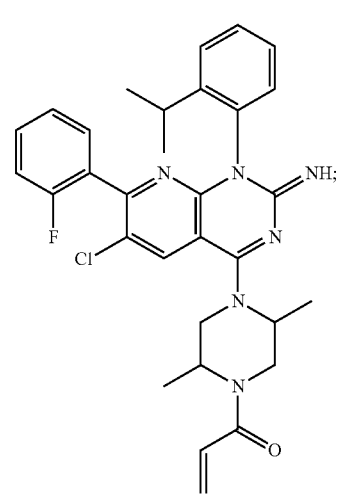
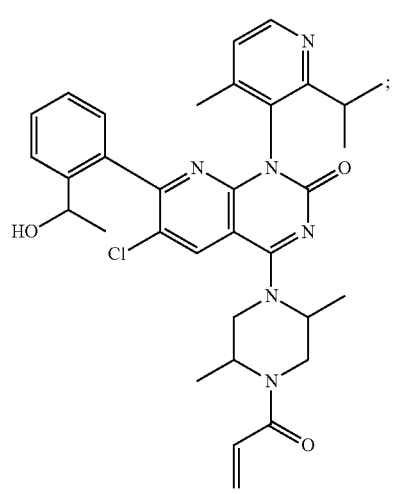
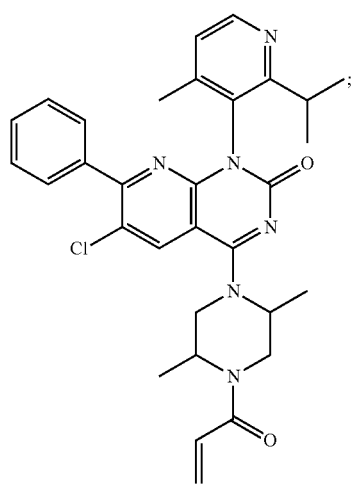
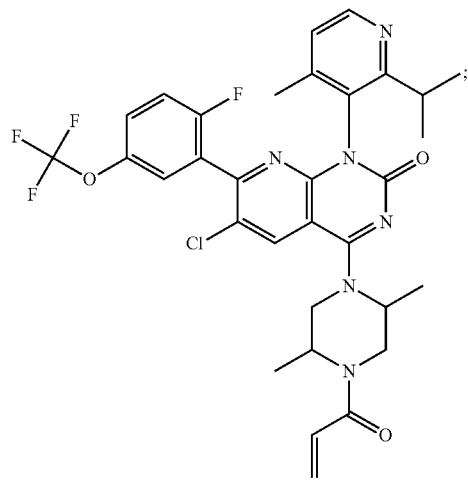

67
-continued
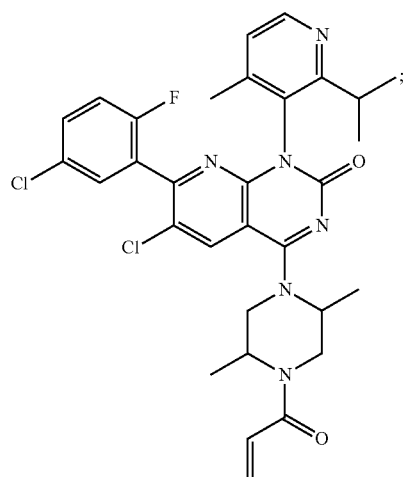
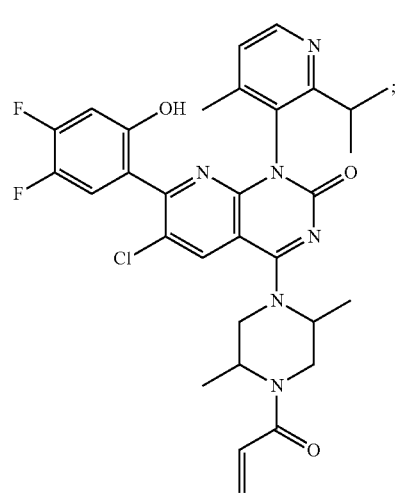
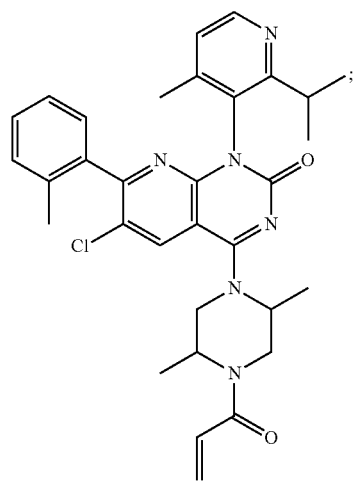
68
-continued
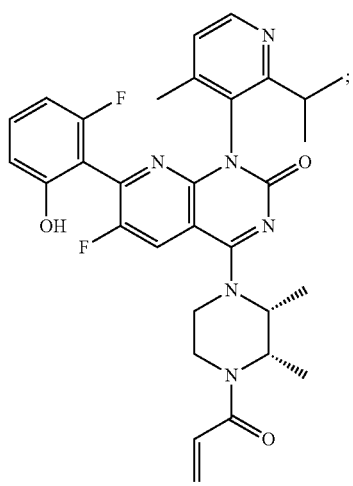
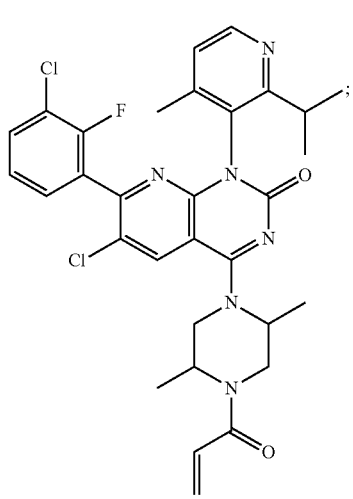
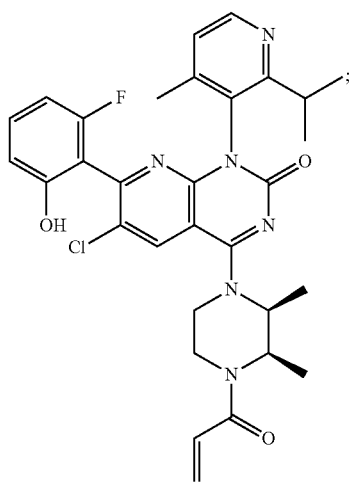

69
-continued
70
-continued
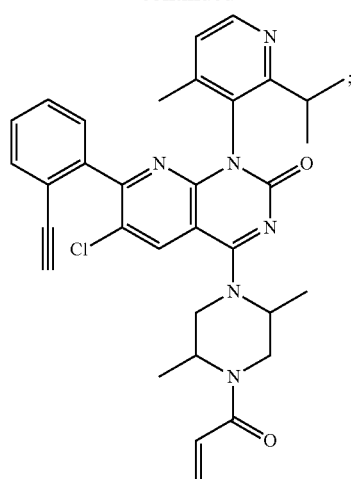
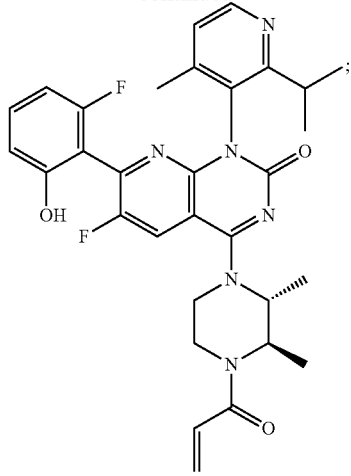
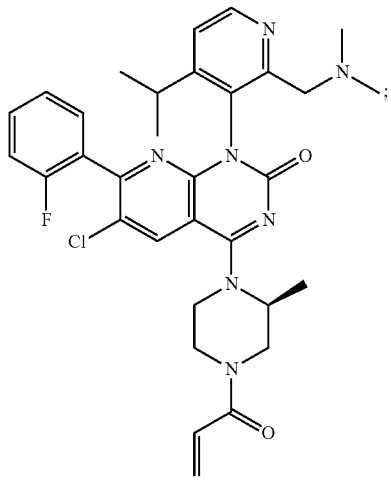

71
-continued
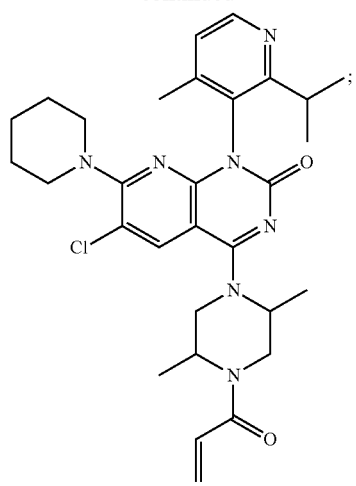
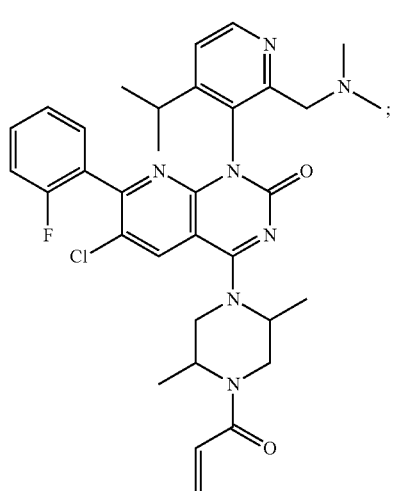
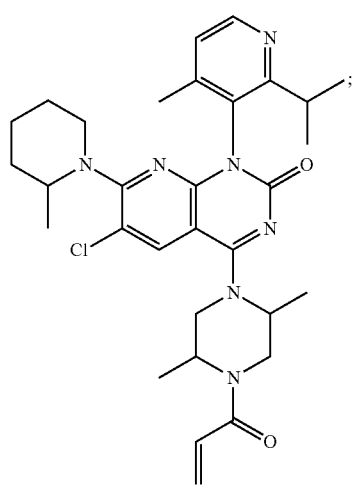
72
-continued
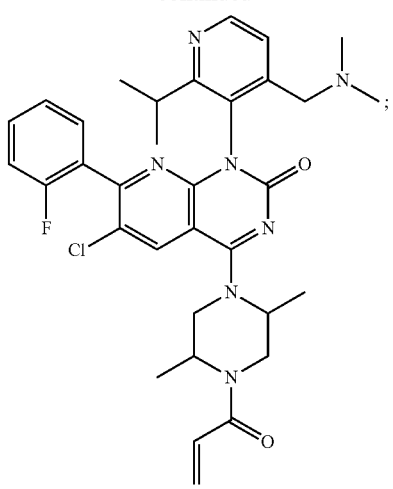
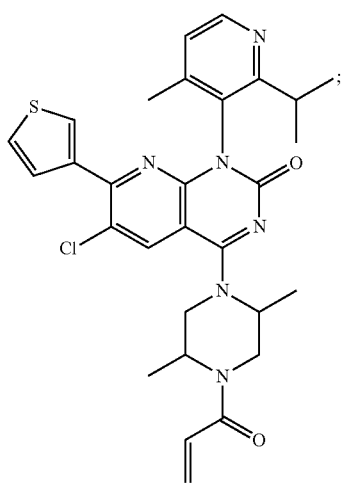
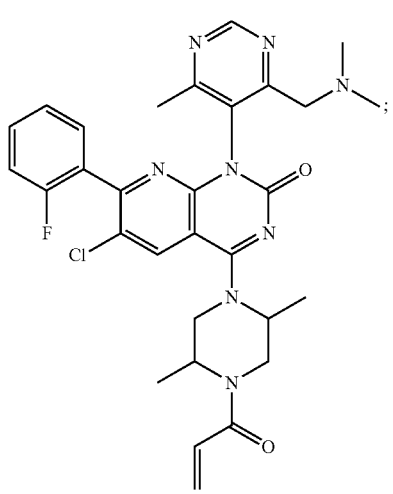

73
-continued
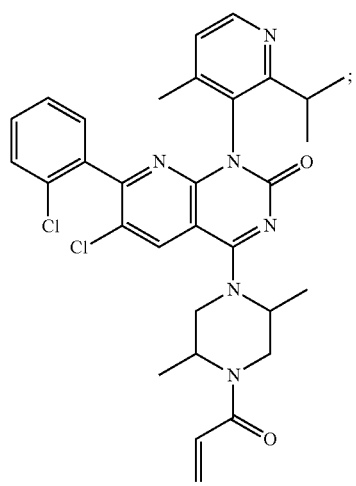
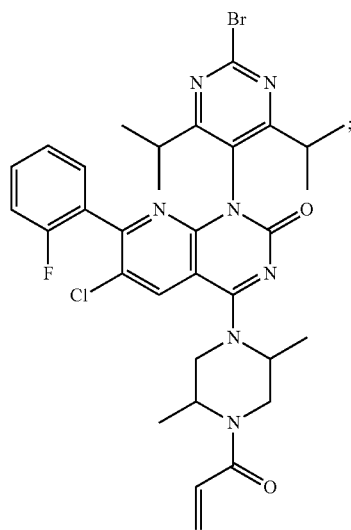
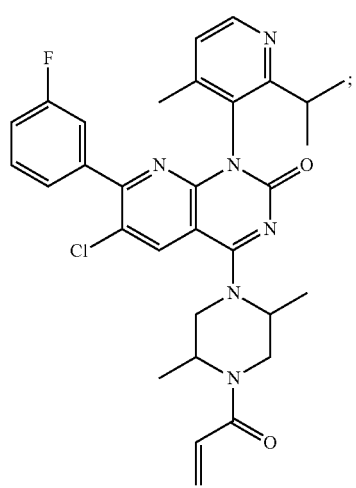
74
-continued
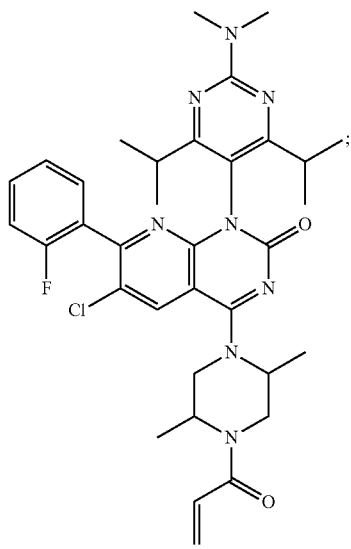
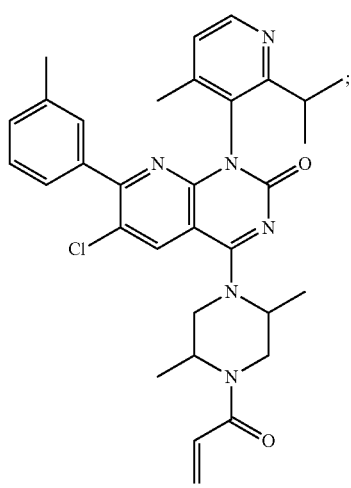
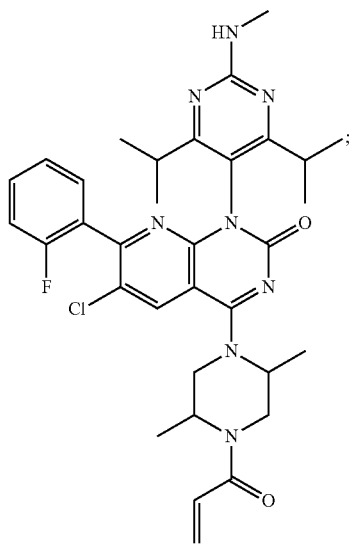

75
-continued
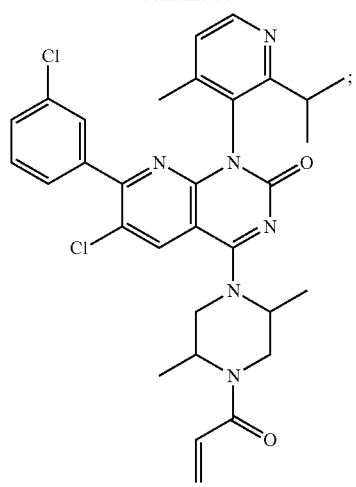
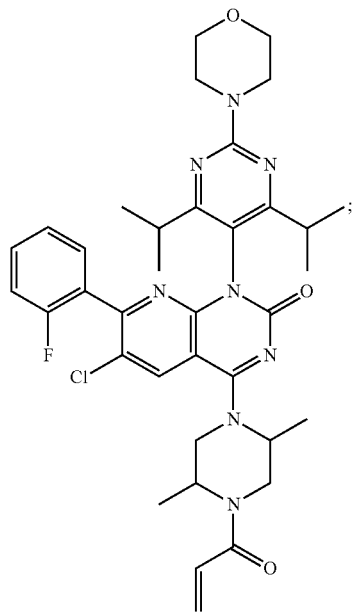
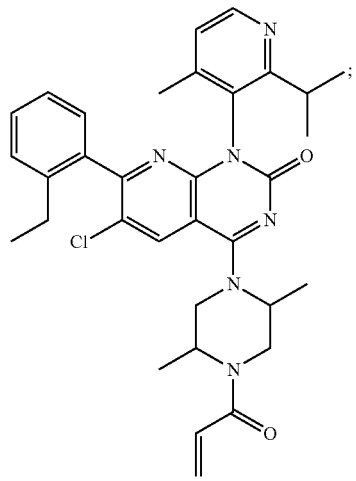
76
-continued
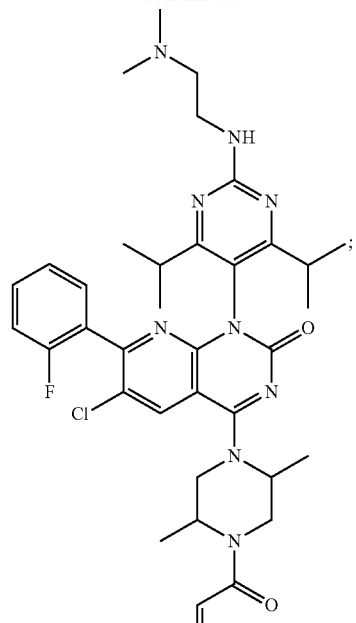
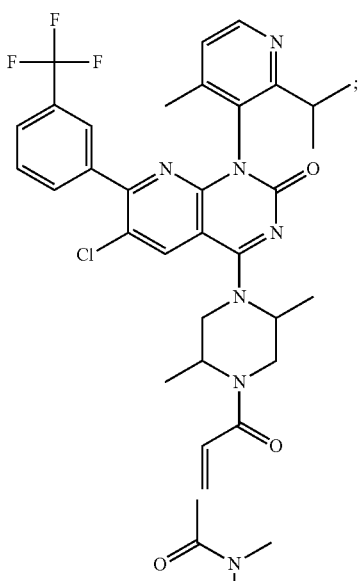
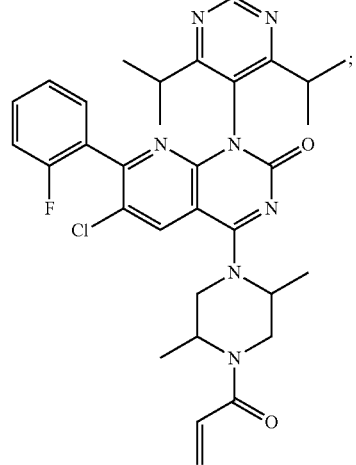

77
-continued
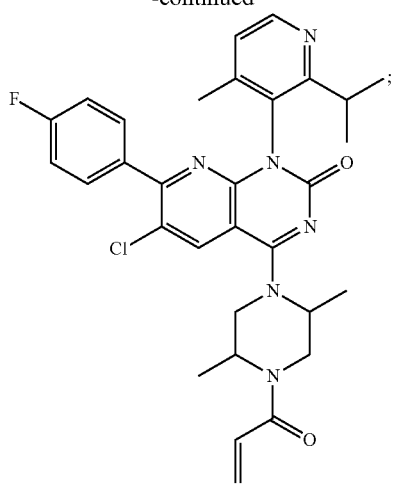
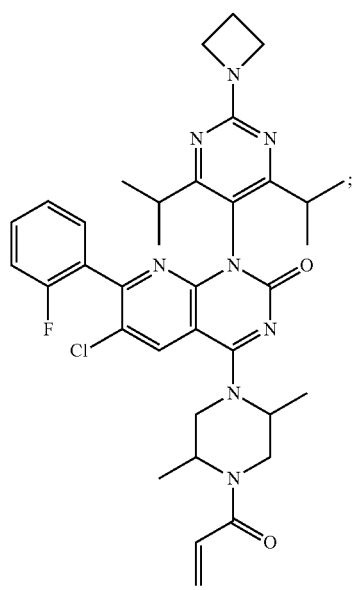
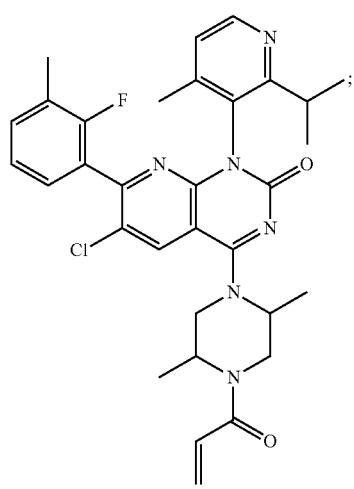
78
-continued
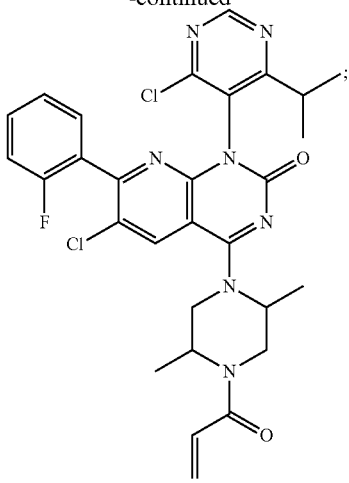
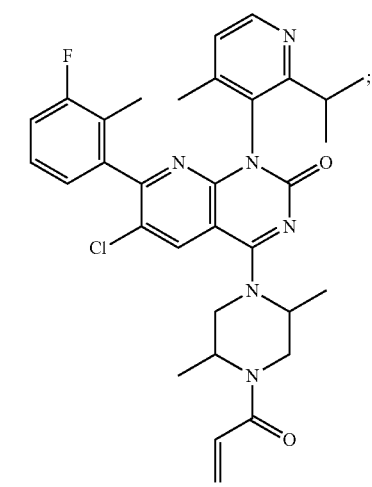
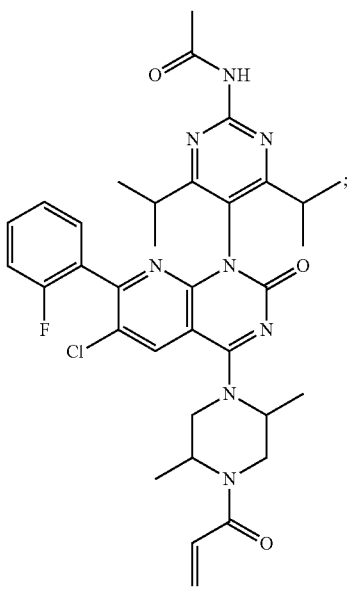

79
-continued
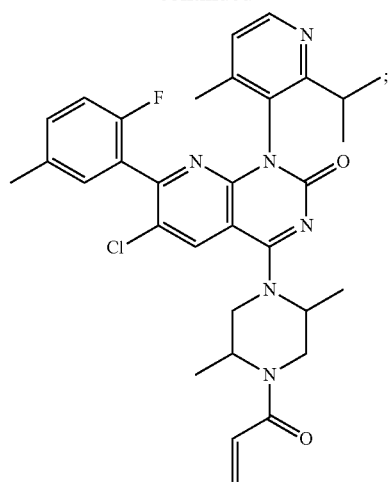
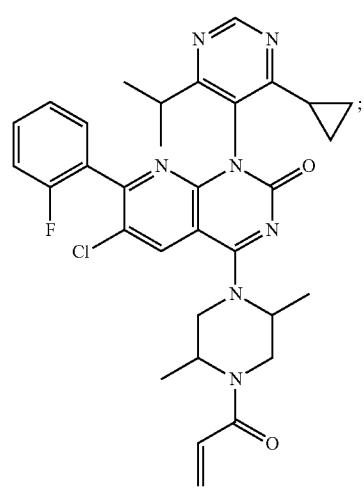
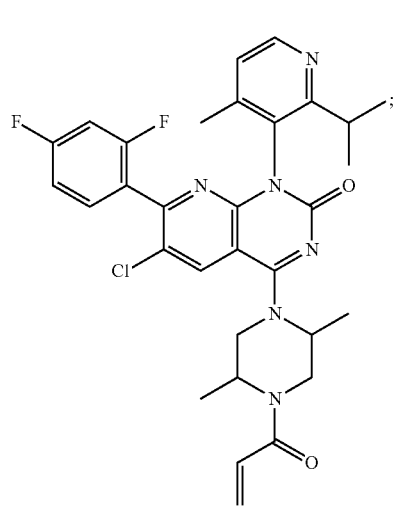
80
-continued
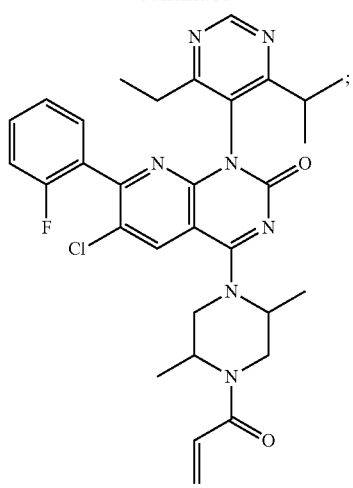
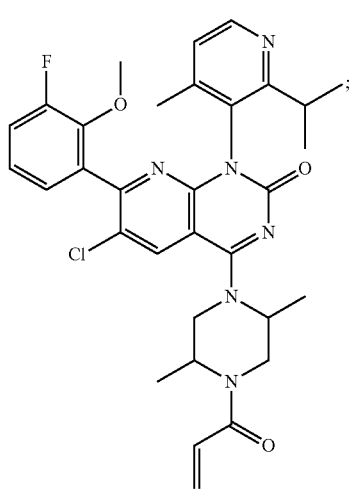
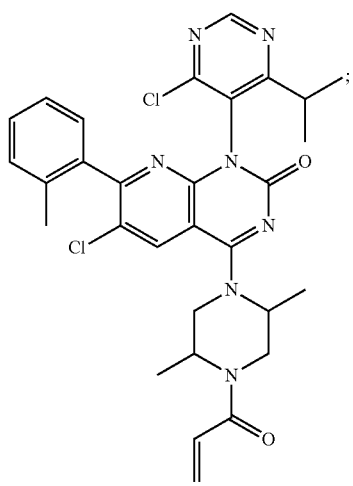

-continued
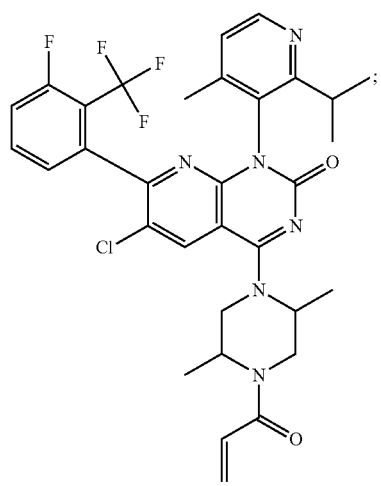
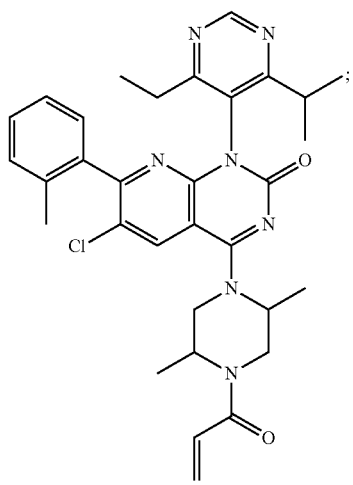
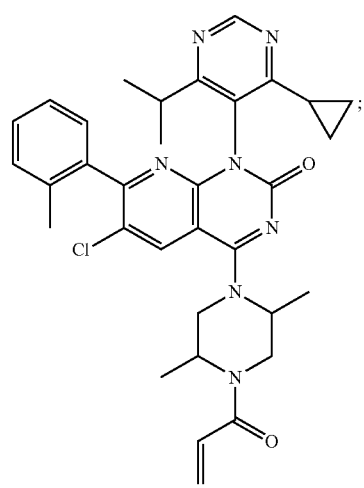
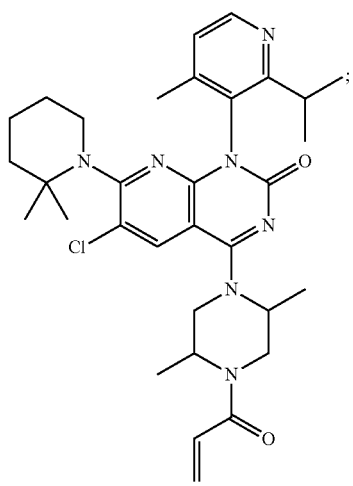
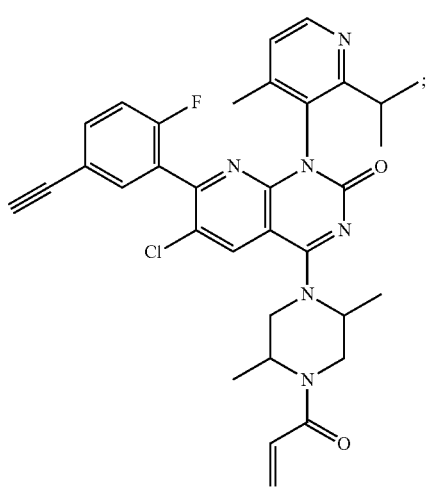
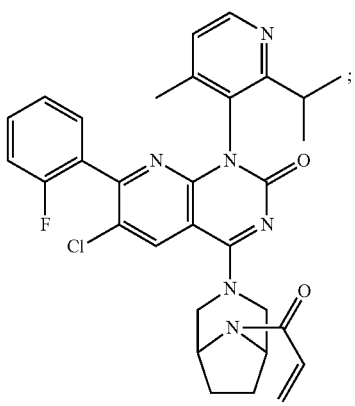

-continued
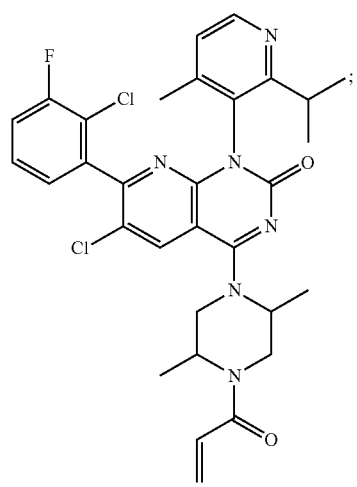
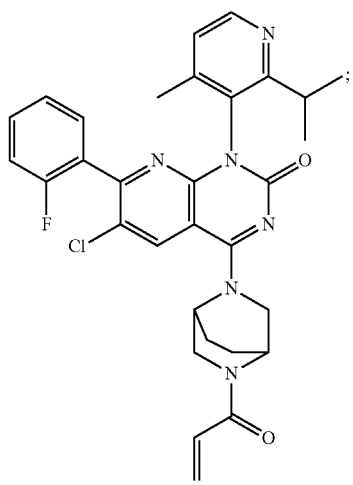
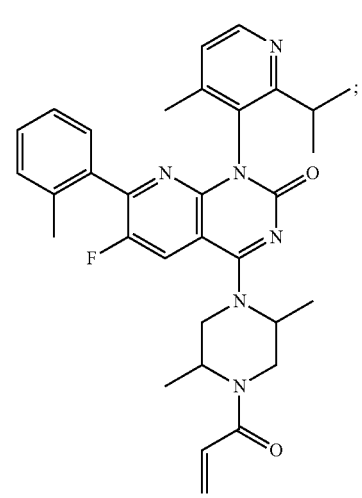
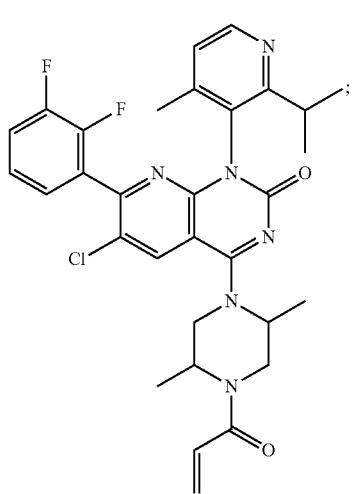
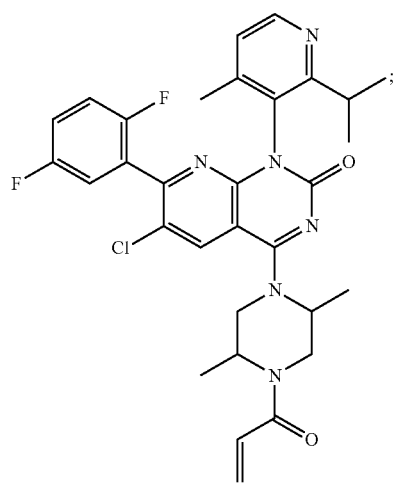

85
-continued
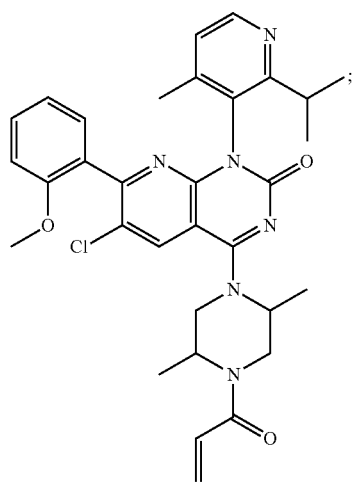
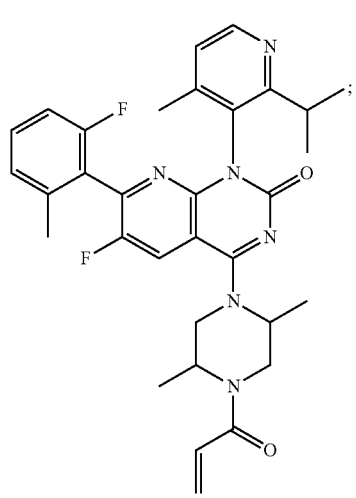
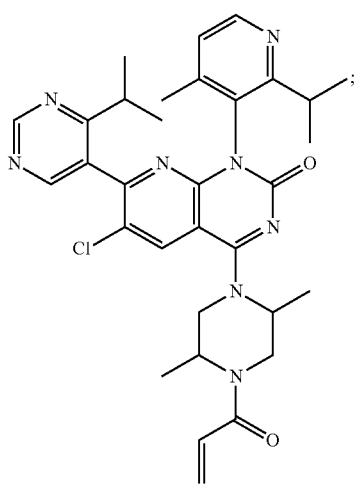
86
-continued
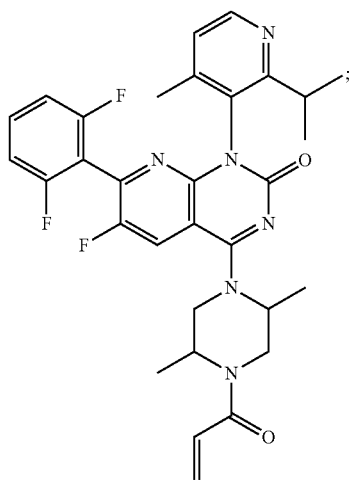
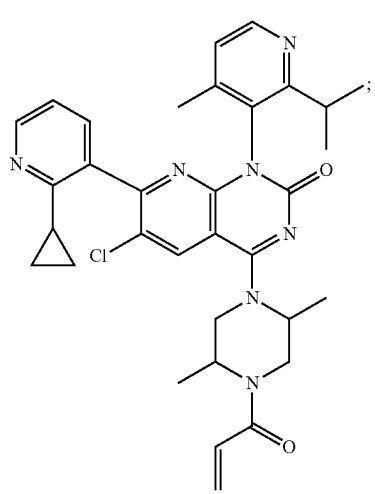
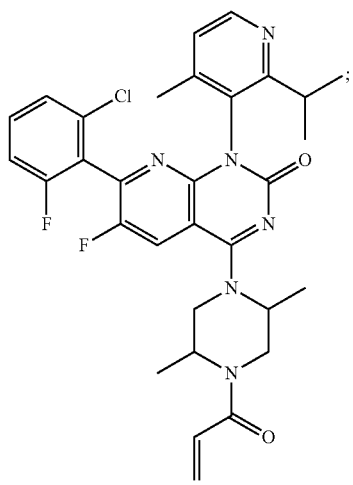

-continued
87
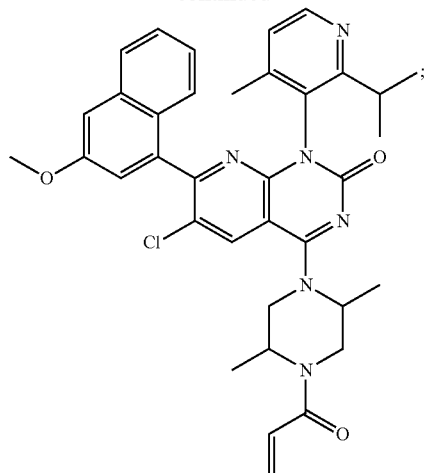
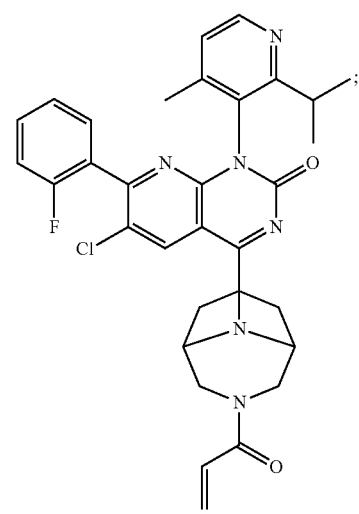
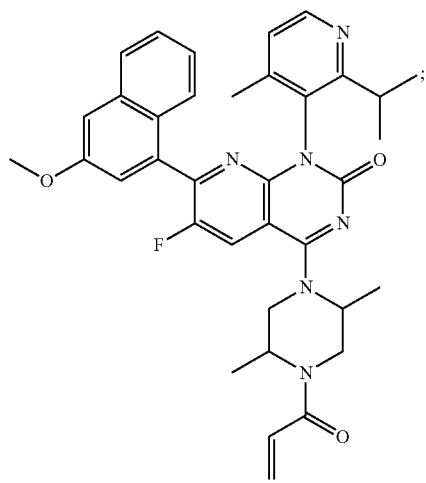
-continued
88
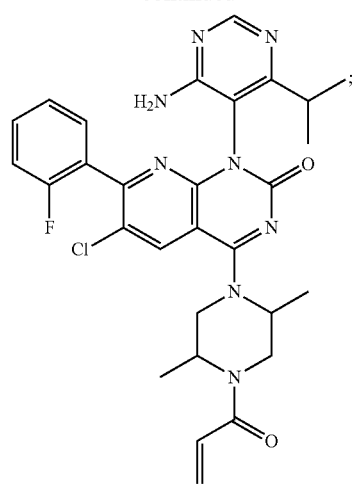
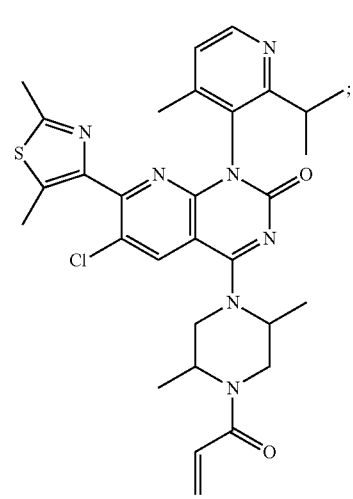
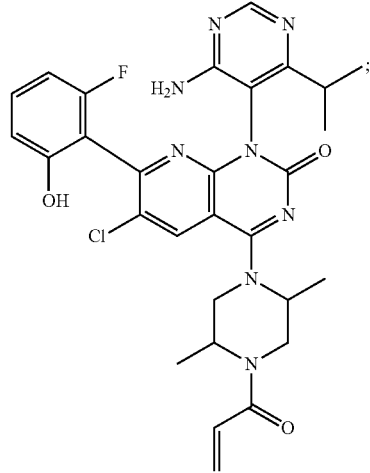

89
-continued
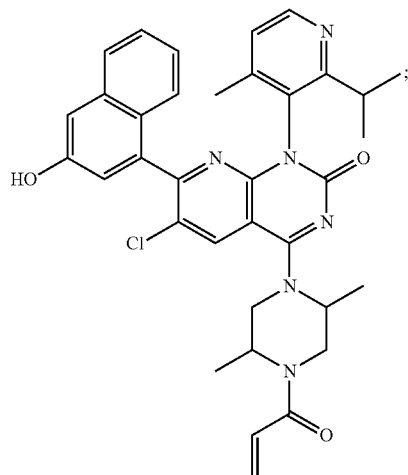
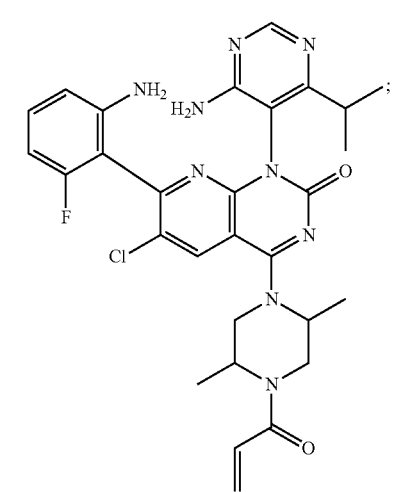
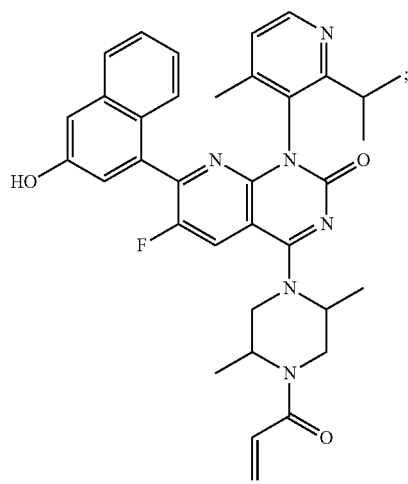
90
-continued
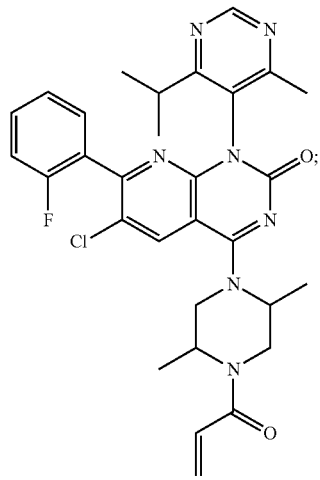
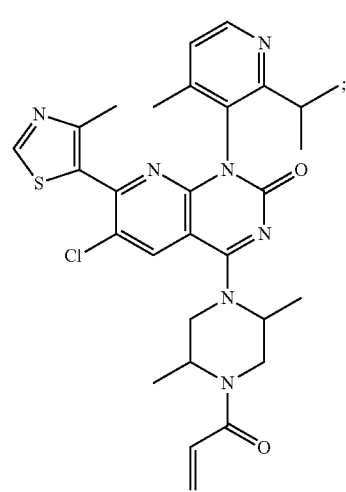
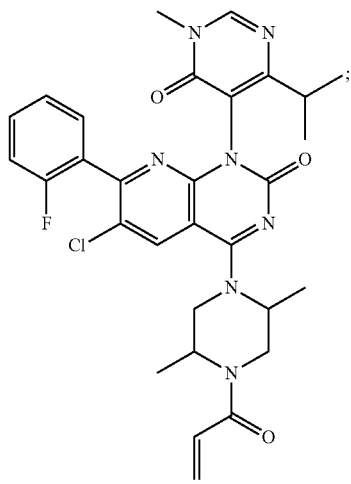

91
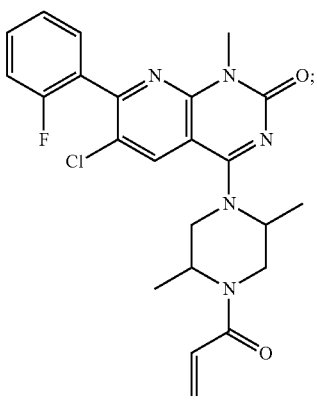
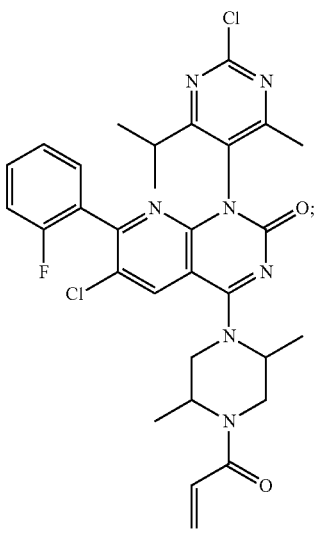
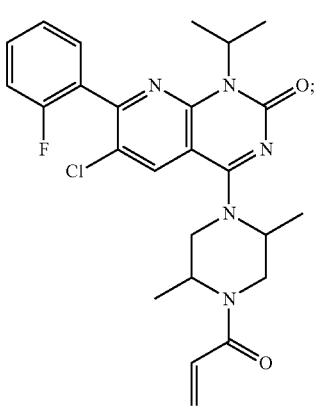
92
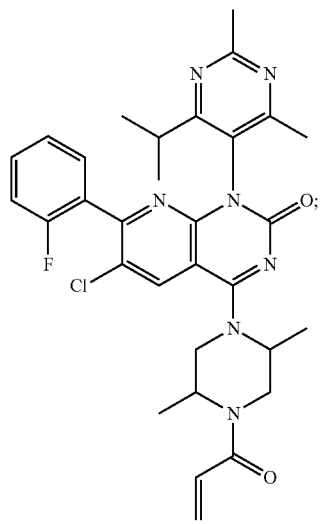
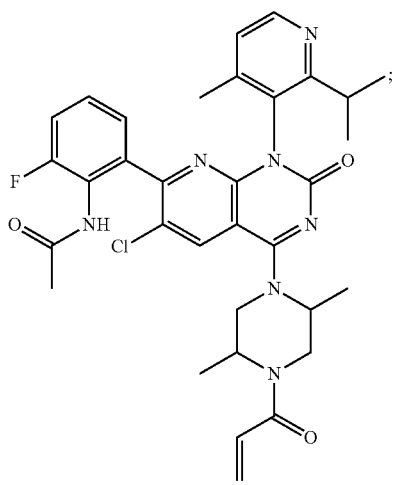
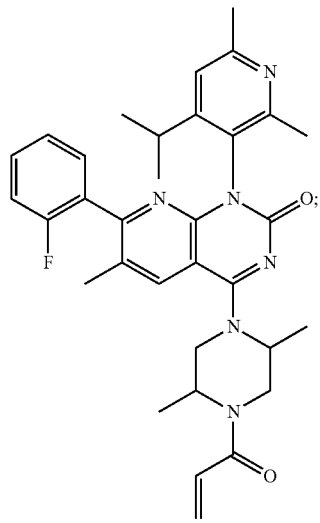

93
-continued
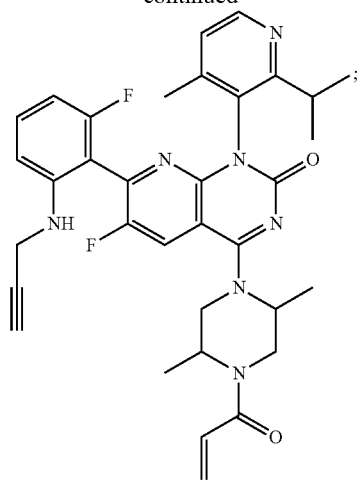
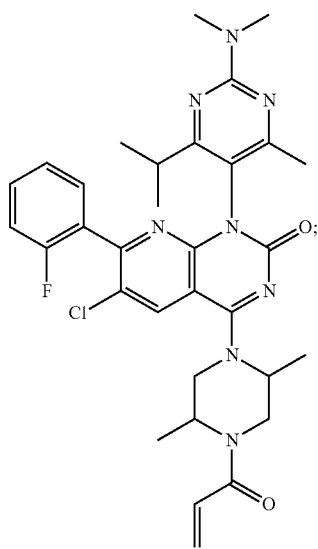
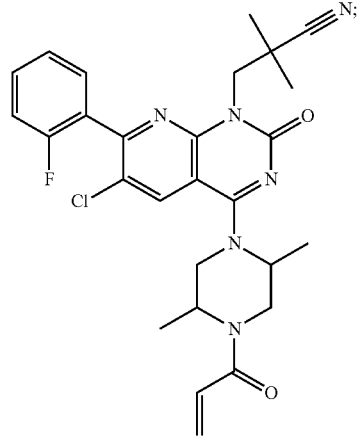
94
-continued
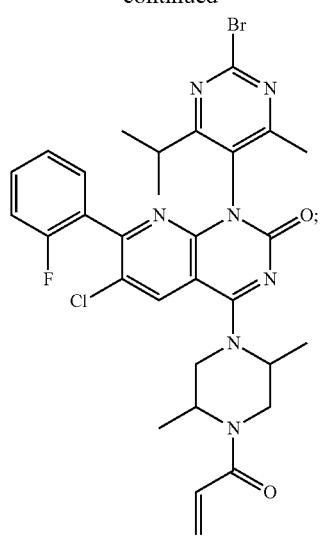
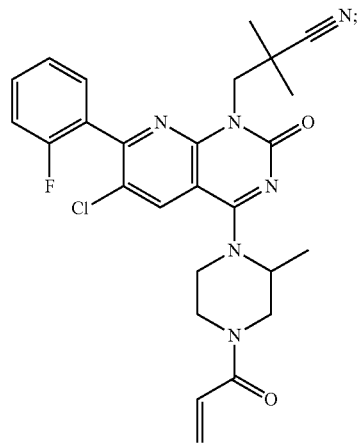
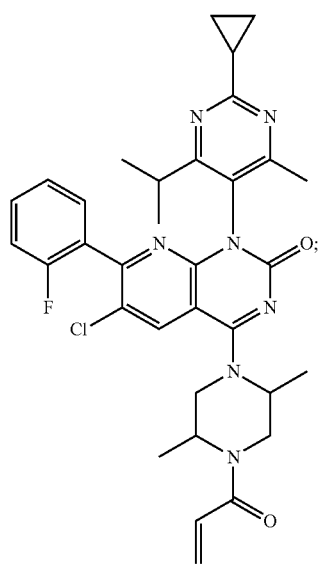

95
-continued
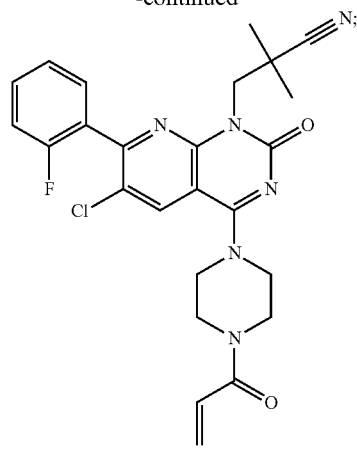
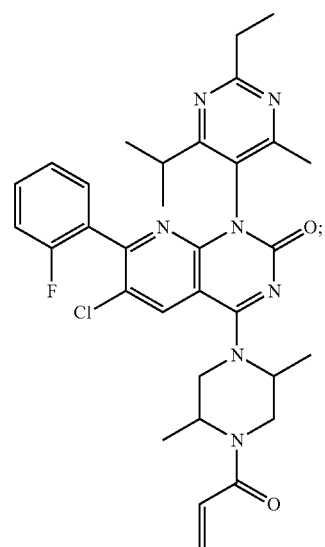
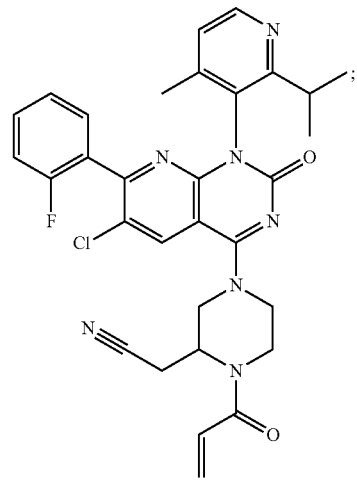
96
-continued
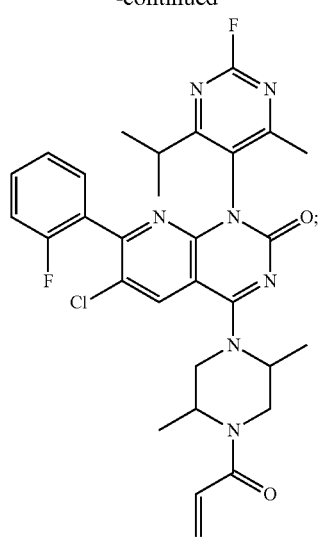
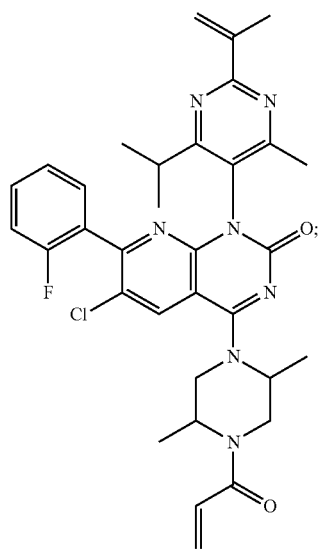

97
-continued
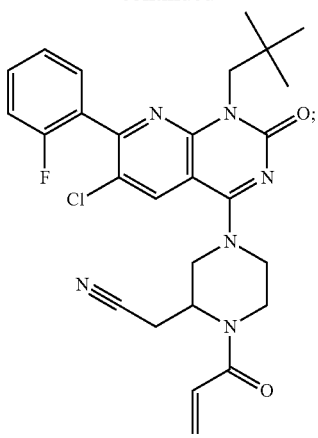
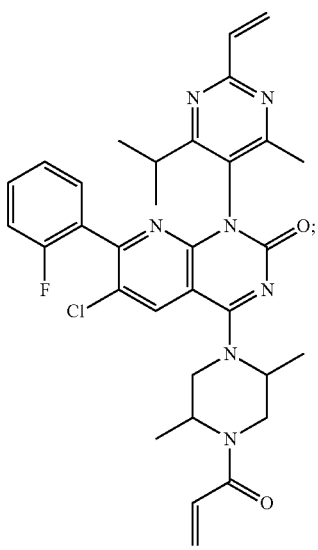
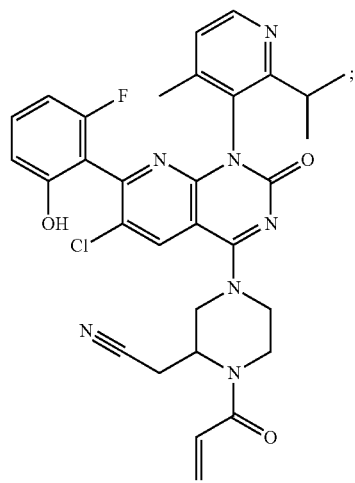
98
-continued
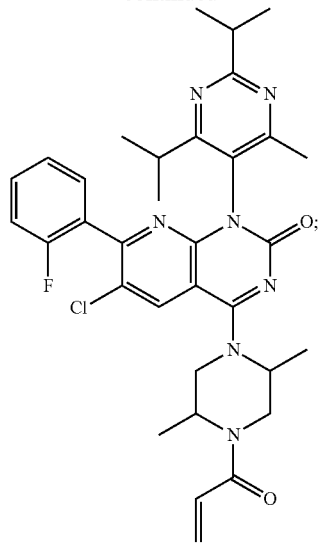
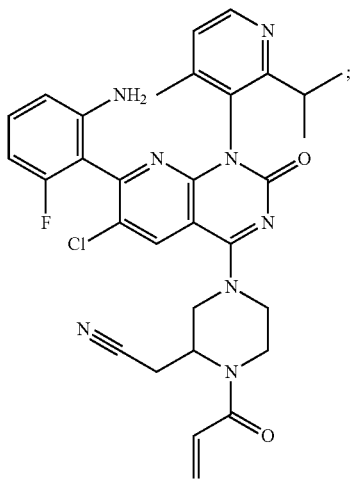

99
-continued
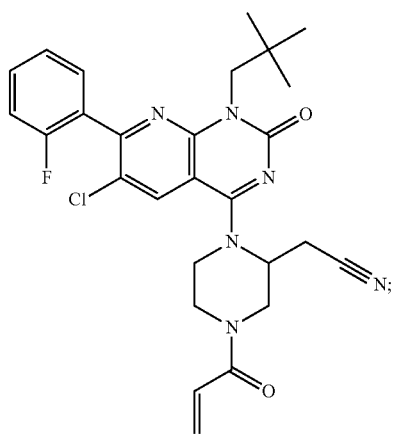
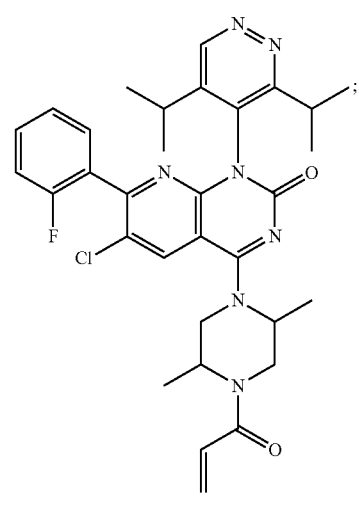
100
-continued
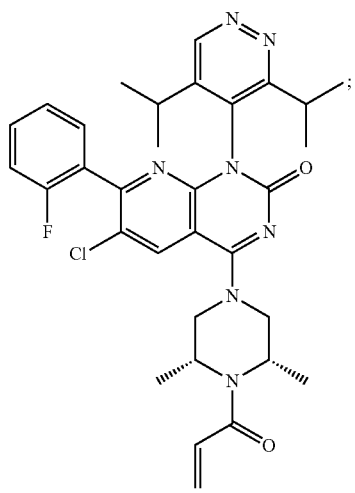
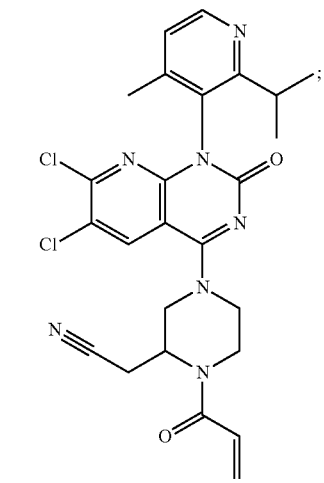
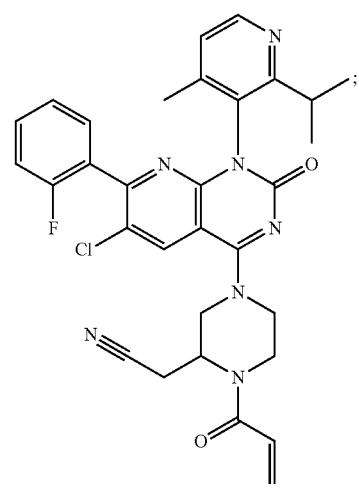

101
-continued
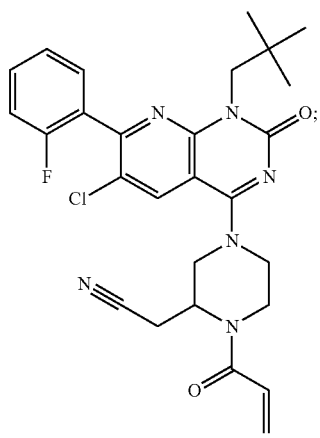
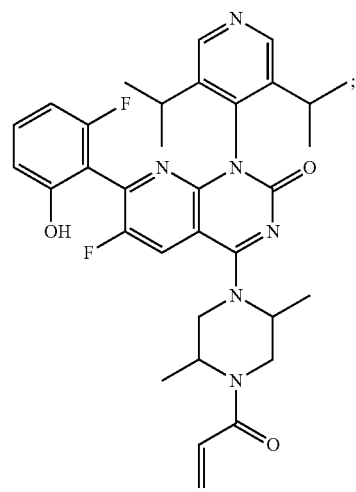
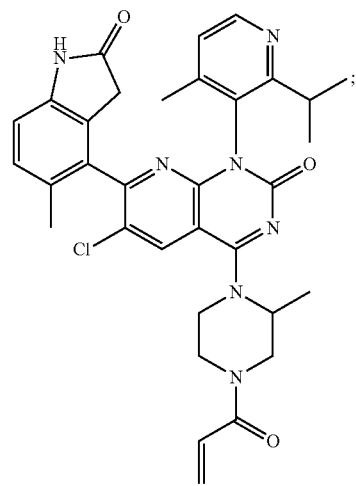
102
-continued
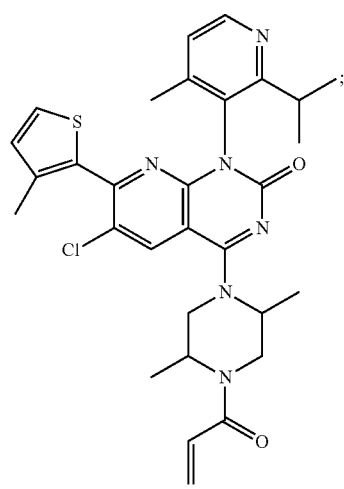
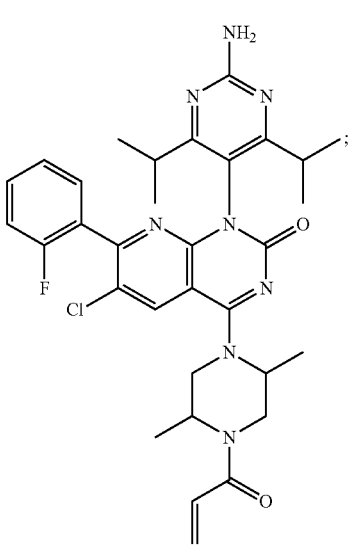
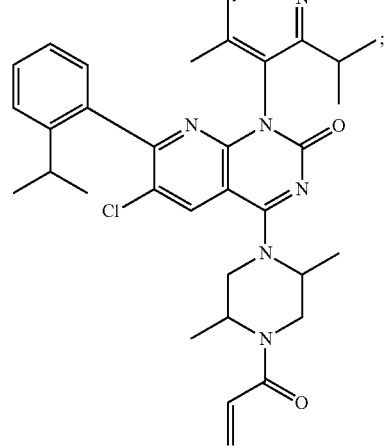

103
-continued
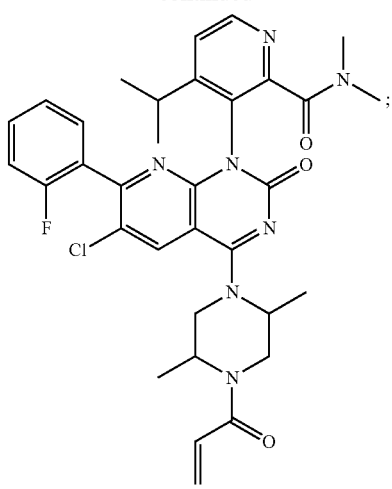
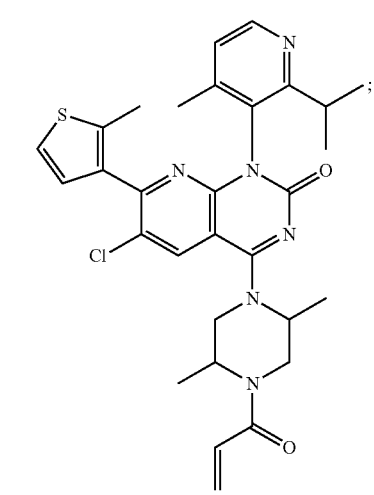
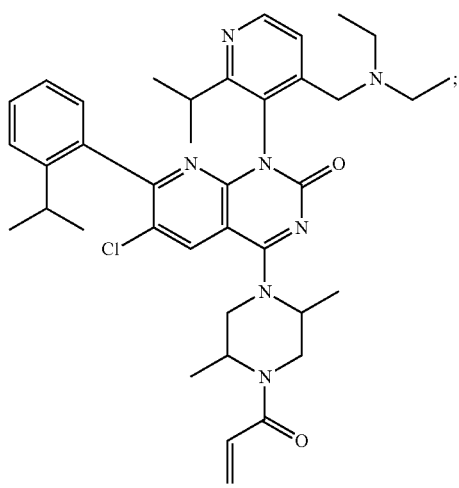
104
-continued
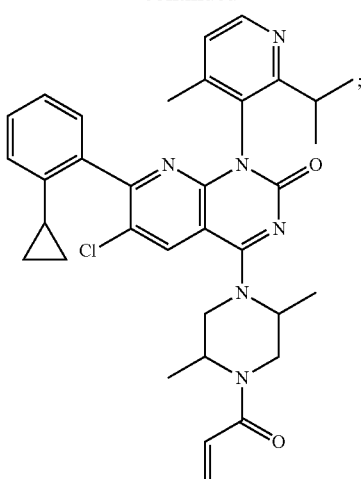
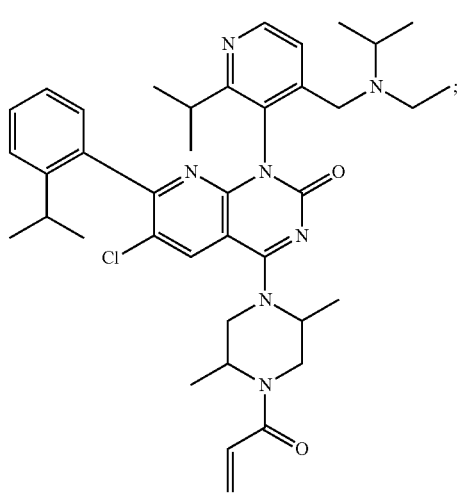
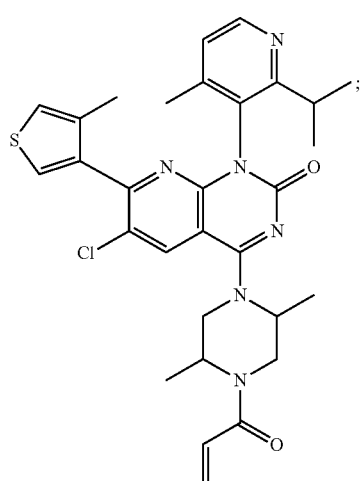

105
-continued
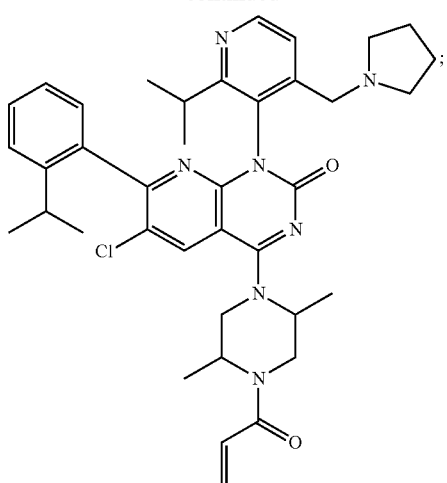
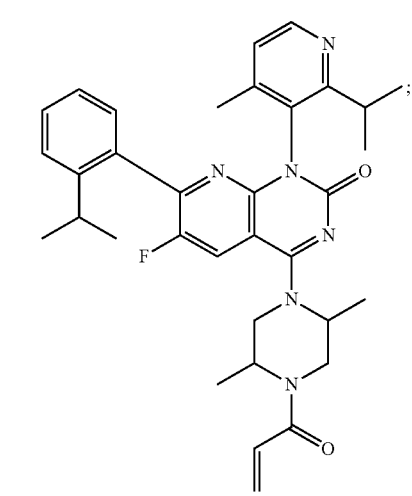
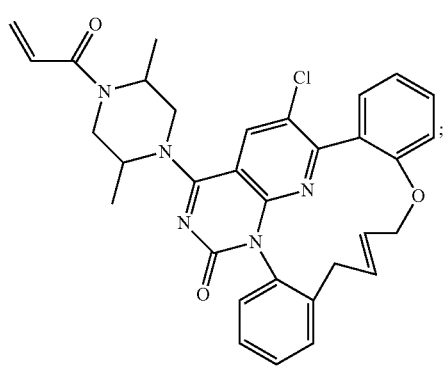
106
-continued
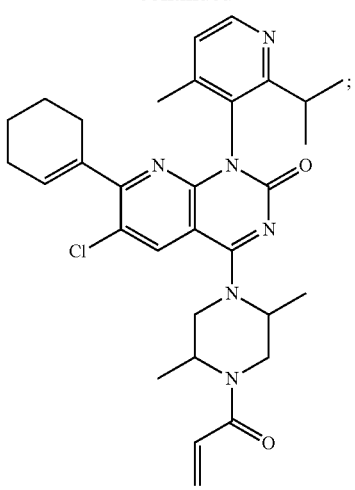
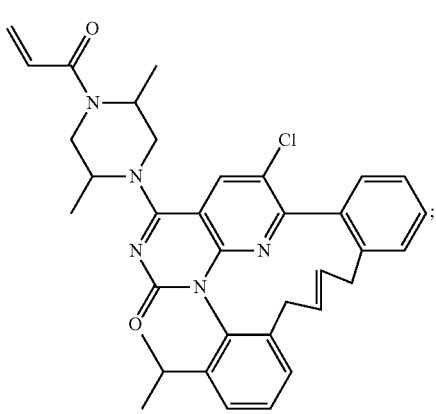
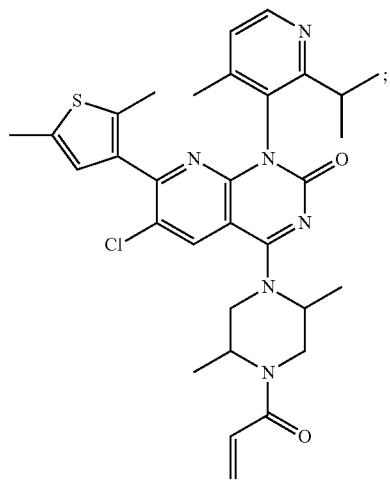

107
-continued
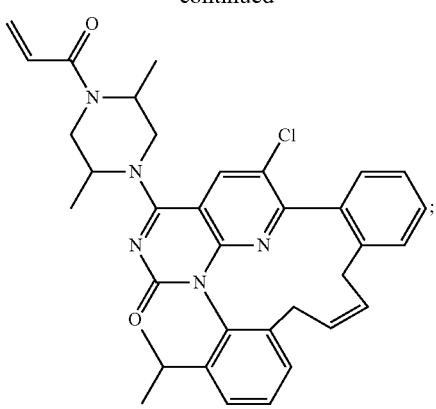
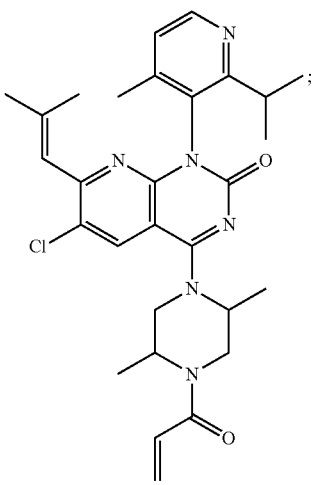
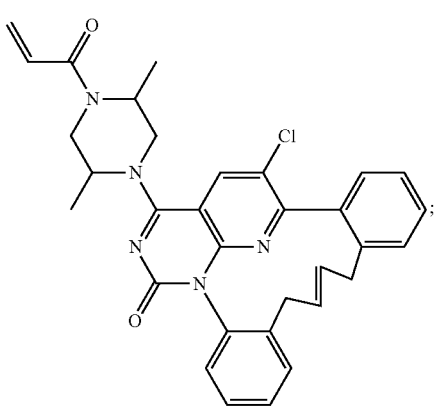
108
-continued
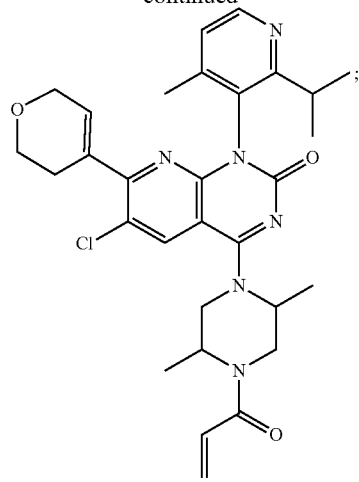
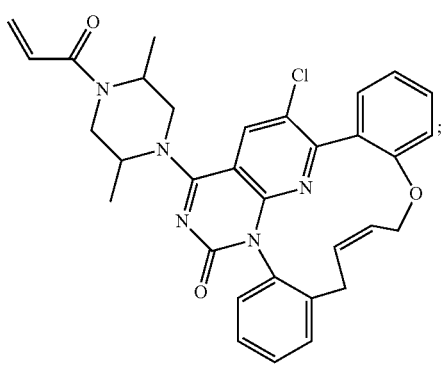 [SMILES: C=CC(=O)N1CC(C)N(c2nc(=O)n3c4nc(c(Cl)cc24)-c2ccccc2OC/C=C\Cc2ccccc2-3)CC1C]
or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.
Another aspect of the present invention provides a compound having a structure selected from the formula

109
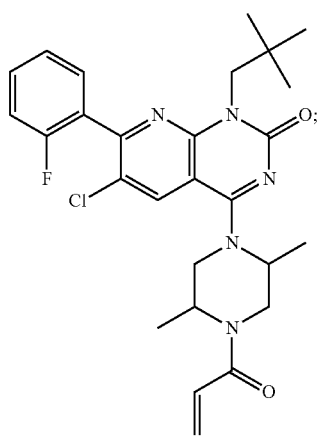
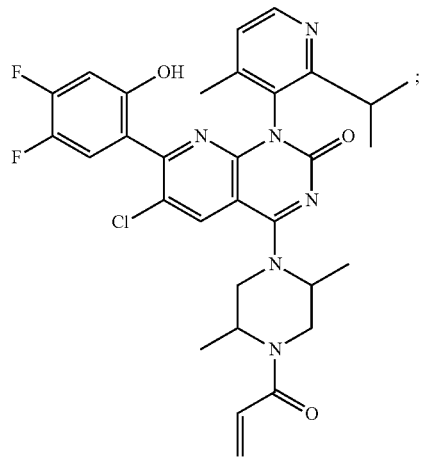
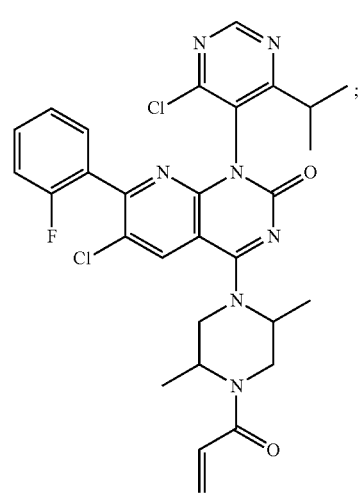
110
-continued
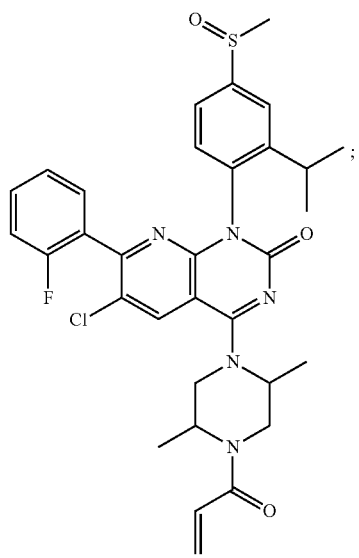
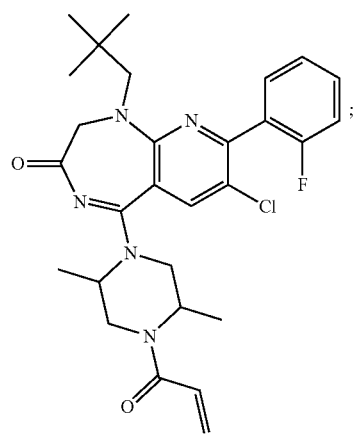

111
-continued
112
-continued
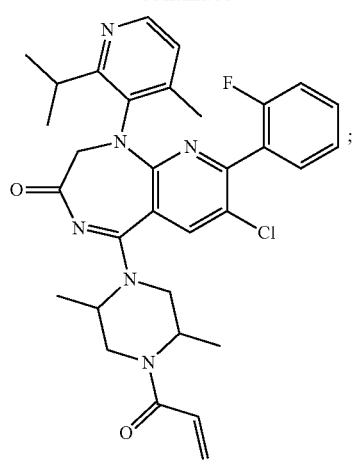
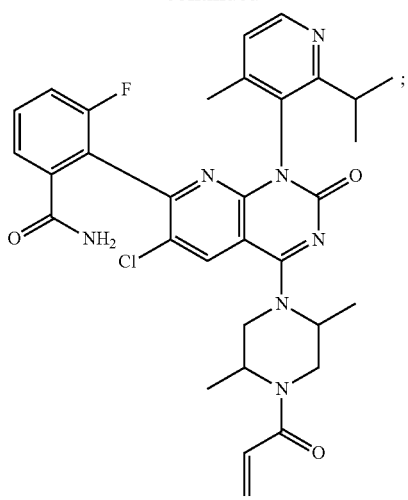
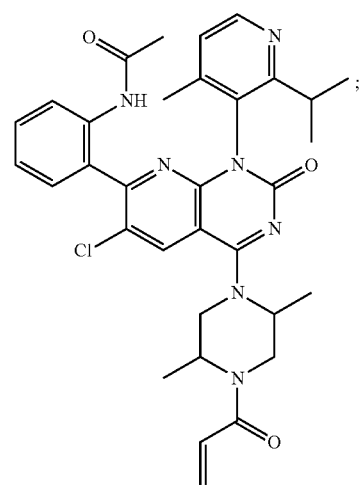
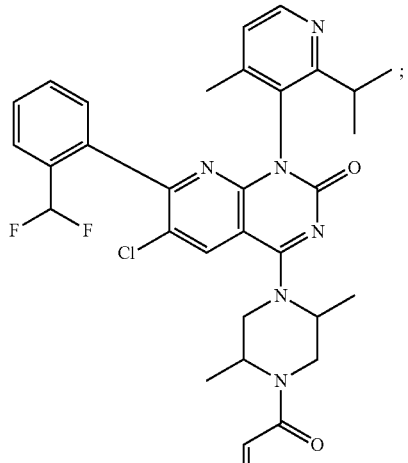
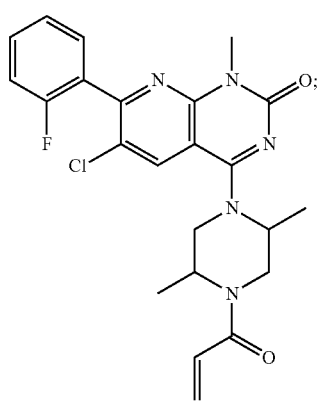
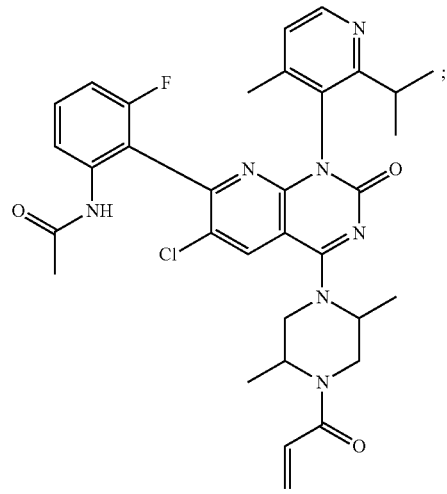

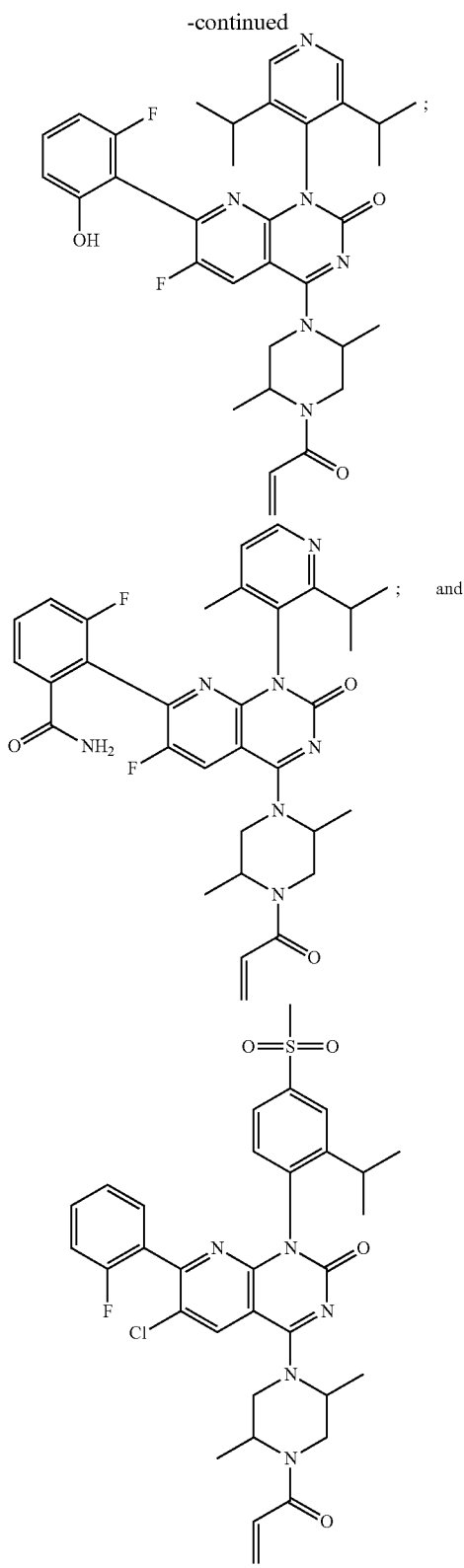

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Another aspect of the present invention provides various compounds, stereoisomers, atropisomers, pharmaceutically acceptable salts, pharmaceutically acceptable salts of the stereoisomers, and pharmaceutically acceptable salts of the atropisomers as described in the embodiments set forth below.

Another aspect of the present invention provides a pharmaceutical composition that includes the compound of any of the embodiments or the pharmaceutically acceptable salt thereof, and a pharmaceutically acceptable carrier or diluent.

Another aspect of the present invention provides a method of treating cancer. Such methods include: administering to a patient in need thereof a therapeutically effective amount of the compound of any of the embodiments or a pharmaceutically acceptable salt thereof. In some such methods, the cancer is a solid tumor. In some such methods, the cancer is selected from the group consisting of breast cancer, colorectal cancer, skin cancer, melanoma, ovarian cancer, kidney cancer, lung cancer, non-small cell lung cancer, cancer of the appendix, lymphoma, non-Hodgkin's lymphoma, myeloma, multiple myeloma, leukemia, and acute myelogenous leukemia. In some other such methods, the cancer is multiple myeloma.

In another aspect, the method further includes administering to a patient in need thereof a therapeutically effective amount of one or more additional pharmaceutically active compounds. For example, in some such methods the one or more additional pharmaceutically active compounds is pembrolizumab. In others, the one or more additional pharmaceutically active compounds is niolumab. In still other such methods, the one or more additional pharmaceutically active compounds is AMG 404. In still other such methods, the one or more additional pharmaceutically active compounds is daratumumab. In still other such methods, the one or more additional pharmaceutically active compound is a MEK inhibitor. In still other such methods, the MEK inhibitor is tremetinib. In still other such methods, the one or more additional pharmaceutically active compounds is an immunomodulatory agent (IMiD).

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the Claims.

DETAILED DESCRIPTION

Definitions

Abbreviations: The following abbreviations may be used herein:

| | |
|---|---|
| AcOH | acetic acid |
| aq or aq. | aqueous |
| BOC or Boc | tert-butyloxycarbonyl |
| CPhos | 2-dicyclohexylphosphino-2',6'-bis(N,N-dimethylamino)biphenyl |

-continued

| | |
|---|---|
| cpme | cyclopentyl methyl ether |
| DCE | 1,2-dichloroethane |
| DABCO | 1,4-diazabicyclo[2.2.2]octane |
| DCM | dichloromethane |
| DMA | N,N-dimethylacetamide |
| DMAP | 4-dimethylaminopyridine |
| DME | 1,2-dimethoxyethane |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | equivalent |
| ESI or ES | electrospray ionization |
| Et | ethyl |
| Et$_2$O | diethyl ether |
| EtOAc | ethyl acetate |
| g | gram(s) |
| h | hour(s) |
| HBTU | N,N,N',N'-tetramethyl-O-(1H-benzotriazol-1-yl)uronium hexafluorophosphate, O-(benzotriazol-1-yl)-N,N,N',N'-tetramethyluronium hexafluorophosphate |
| HPLC | high pressure liquid chromatography |
| iPr | isopropyl |
| iPr$_2$NEt or DIPEA | N-ethyl diisopropylamine (Hünig's base) |
| KHMDS | potassium hexamethyldisilazide |
| KOAc | potassium acetate |
| Lawesson's reagent | 2,4-bis(4-methoxyphenyl)-2,4-dithioxo-1,3,2,4-dithiadiphosphetane, 2,4-bis-(4-methoxyphenyl)-1,3-dithia-2,4-diphosphetane 2,4-disulfide |
| LC MS, LCMS, LC-MS or LC/MS | liquid chromatography mass spectroscopy |
| LG | leaving group (e.g., halogen, mesylate, triflate) |
| LHMDS or LiHMDS | lithium hexamethyldisilazide |
| m/z | mass divided by charge |
| Me | methyl |
| MeCN | acetonitrile |
| MeOH | methanol |
| Met | metal species for cross-coupling (e.g., MgX, ZnX, SnR$_3$, SiR$_3$, B(OR)$_2$) |
| mg | milligrams |
| min | minutes |
| mL | milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| Pd$_2$(dba)$_3$ | tris(dibenzylideneacetone)dipalladium(0) |
| Pd(dppf)Cl$_2$•DCM, Pd(dppf)Cl$_2$ | [1,1'-bis(diphenylphosphino)ferrocene]dichloropalladium(II), complex with dichloromethane |
| Pd(PP$_3$)$_4$ | tetrakis(triphenylphosphine)palladium(0) |
| Ph | phenyl |
| PR or PG or Prot. group | protecting group |
| rbf | round-bottomed flask |
| RP-HPLC | reverse phase high pressure liquid chromatography |
| RT or rt or r.t. | room temperature |
| sat. or satd. | saturated |
| SFC | supercritical fluid chromatography |
| SPhos Pd G3 or SPhos G3 | (2-dicyclohexylphosphino-2',6'-dimethoxybiphenyl) [2-(2'-amino-1,1'-biphenyl)]palladium(II) methanesulfonate |
| TBAF | tetra-n-butylammonium fluoride |
| TBTU | N,N,N',N'-tetramethyl-O-(benzotriazol-1-yl)uronium tetrafluoroborate |
| t-BuOH | tert-butanol |
| TEA or Et$_3$N | trimethylamine |
| TFA | trifluoroacetic acid |
| THF | tetrahydrofuran |
| UV | ultraviolet |

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched C1-C$_8$ hydrocarbon groups, including but not limited to, methyl, ethyl, npropyl, ipropyl, nbutyl, secbutyl, tbutyl, npentyl, 2methylbutyl, 3methylbutyl, 2,2dimethylpropyl, nhexyl, 2methylpentyl, 3-methylpentyl, 4-methylpentyl, 2,2dimethylbutyl, 2,3dimethylbutyl, 3,3dimethylbutyl, and 2ethylbutyl. The term C$_{m-n}$ means the alkyl group has "m" to "n" carbon atoms. The term "alkylene" refers to an alkyl group having a substituent. An alkyl (e.g., methyl), or alkylene (e.g., —CH$_2$—), group can be substituted with one or more, and typically one to three, of independently selected, for example, halo, trifluoromethyl, trifluoromethoxy, hydroxy, alkoxy, nitro, cyano, alkylamino, C$_{1-6}$alkyl, C$_{2-6}$alkenyl, C$_{2-6}$alkynyl, —NC, amino, —CO$_2$H, —CO$_2$C$_1$-C$_6$alkyl, —OCOC$_1$-C$_6$alkyl, C$_3$-C$_{10}$ cycloalkyl, C$_3$-C$_{10}$ heterocycloalkyl, C$_5$-C$_{10}$aryl, and C$_5$-C$_{10}$ heteroaryl. The term "haloalkyl" specifically refers to an alkyl group wherein at least one, e.g., one to six, or all of the hydrogens of the alkyl group are substituted with halo atoms.

The terms "alkenyl" and "alkynyl" indicate an alkyl group that further includes a double bond or a triple bond, respectively.

As used herein, the term "halo" refers to fluoro, chloro, bromo, and iodo. The term "alkoxy" is defined as —OR, wherein R is alkyl.

As used herein, the term "amino" or "amine" interchangeably refers to a —NR$_2$ group, wherein each R is, e.g., H or a substituent. In some embodiments, the amino group is further substituted to form an ammonium ion, e.g., NR$_3$$^+$. Ammonium moieties are specifically included in the definition of "amino" or "amine." Substituents can be, for example, an alkyl, alkoxy, cycloalkyl, heterocycloalkyl, amide, or carboxylate. An R group may be further substituted, for example, with one or more, e.g., one to four, groups selected from halo, cyano, alkenyl, alkynyl, alkyl, cycloalkyl, heterocycloalkyl, aryl, heteroaryl, urea, carbonyl, carboxylate, amine, and amide. An "amide" or "amido" group interchangeably refers to a group similar to an amine or amino group but further including a C(O), e.g., —C(O)NR$_2$. Some contemplated amino or amido groups (some with optional alkylene groups, e.g., alkylene-amino, or alkylene-amido) include CH$_2$NH$_2$, CH(CH$_3$)NH$_2$, CH(CH$_3$)$_2$ NH$_2$, CH$_2$CH$_2$NH$_2$, CH$_2$CH$_2$N(CH$_3$)$_2$, CH$_2$NHCH$_3$, C(O)NHCH$_3$, C(O)N(CH$_3$)$_2$, CH$_2$C(O)NHphenyl, CH$_2$NHC(O)CH$_3$, CH$_2$NHCH$_2$CH$_2$OH, CH$_2$NHCH$_2$CO$_2$H, CH$_2$NH(CH$_3$)CH$_2$CO$_2$CH$_3$, CH$_2$NHCH$_2$CH$_2$OCH$_3$, CH$_2$NH(CH$_3$)CH$_2$CH$_2$OCH$_3$, CH$_2$NH(CH$_3$)CH$_2$C(O)N(CH$_3$)$_2$, CH$_2$NH(CH$_3$)CH$_2$C(O) NHCH$_3$, CH$_2$CH$_2$CCH, CH$_2$NMe$_2$, CH$_2$NH(CH$_3$) CH$_2$CH$_2$OH, CH$_2$NH(CH$_3$)CH$_2$CH$_2$F, CH$_2$N$^+$(CH$_3$)$_3$, CH$_2$NHCH$_2$CHF$_2$, CH$_2$NHCH$_2$CH$_3$,

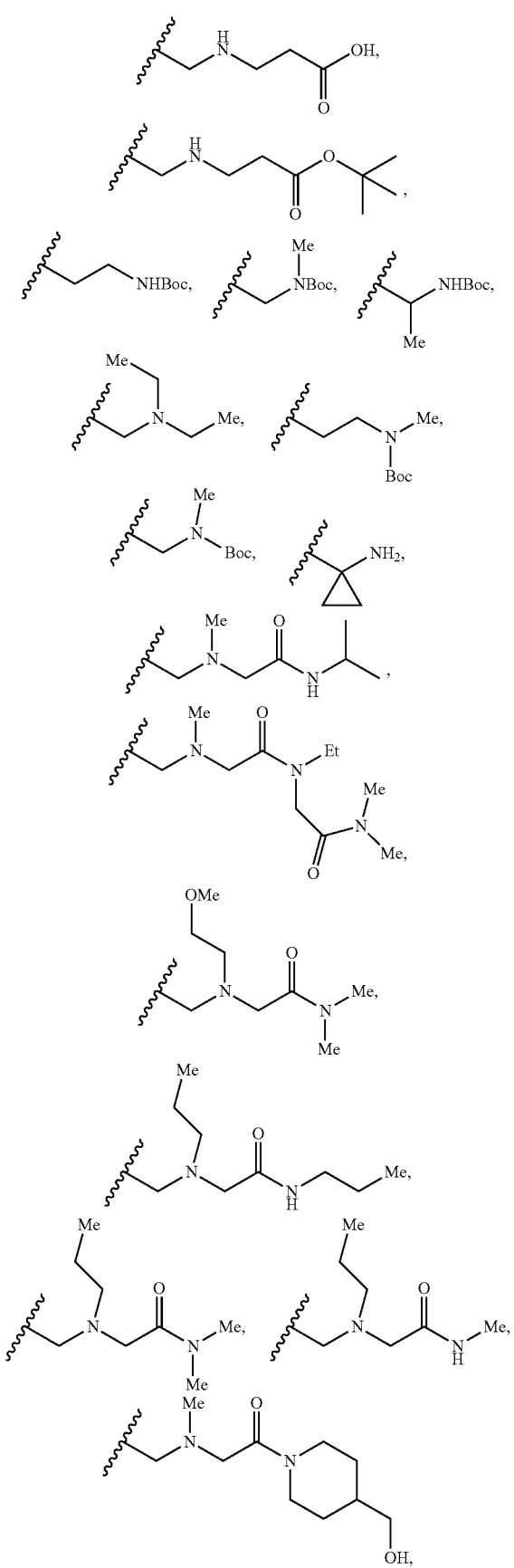

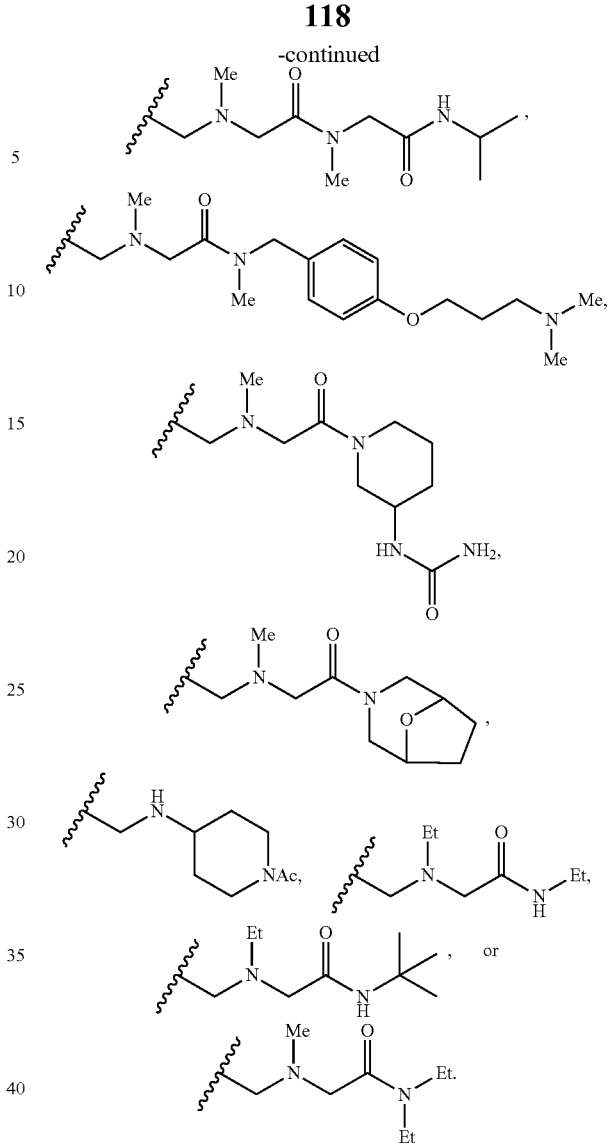

Collectively, antibodies form a family of plasma proteins known as immunoglobulins and comprise of immunoglobulin domains. (Janeway et al., Immunobiology: The Immune System in Health and Disease, 4th ed., Elsevier Science Ltd./Garland Publishing, 1999. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", Immunobiology: The Immune System in Health and Disease, 4$^{th}$ ed. Elsevier Science Ltd./Garland Publishing, (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk. 1987, supra).

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the present disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including any one of IgG1, IgG2, IgG3 or IgG4.

The antibody can be a monoclonal antibody or a polyclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In certain aspects, the antibody is a human antibody. In certain aspects, the antibody is a chimeric antibody or a humanized antibody. The term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also can contain domains of two or more different antibodies within the same species. The term "humanized" when used in relation to antibodies refers to antibodies having at least CDR regions from a non-human source which are engineered to have a structure and immunological function more similar to true human antibodies than the original source antibodies. For example, humanizing can involve grafting a CDR from a non-human antibody, such as a mouse antibody, into a human antibody. Humanizing also can involve select amino acid substitutions to make a non-human sequence more similar to a human sequence.

An antibody can be cleaved into fragments by enzymes, such as, e.g., papain and pepsin. Papain cleaves an antibody to produce two Fab fragments and a single Fc fragment. Pepsin cleaves an antibody to produce a F(ab')2 fragment and a pFc' fragment. As used herein, the term "antigen binding antibody fragment refers to a portion of an antibody molecule that is capable of binding to the antigen of the antibody and is also known as "antigen-binding fragment" or "antigen-binding portion". In exemplary instances, the antigen binding antibody fragment is a Fab fragment or a F(ab')2 fragment.

The architecture of antibodies has been exploited to create a growing range of alternative formats that span a molecular-weight range of at least about 12-150 kDa and has a valency (n) range from monomeric (n=1), to dimeric (n=2), to trimeric (n=3), to tetrameric (n=4), and potentially higher, such alternative formats are referred to herein as "antibody protein products". Antibody protein products include those based on the full antibody structure and those that mimic antibody fragments which retain full antigen-binding capacity, e.g., scFvs, Fabs and VHH/VH (discussed below). The smallest antigen binding antibody fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

As used herein, the term "aryl" refers to a $C_{6-14}$ monocyclic or polycyclic aromatic group, preferably a $C_{6-10}$ monocyclic or bicyclic aromatic group, or $C_{10-14}$ polycyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to $C_{10-14}$ bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, $C_{1-6}$alkyl, $C_{2-6}$alkenyl, $C_{2-6}$alkynyl, —$CF_3$, —$OCF_3$, —$NO_2$, —CN, —NC, —OH, alkoxy, amino, —$CO_2H$, —$CO_2C_1$-$C_6$alkyl, —$OCOC_1$-$C_6$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term "carbocyclic ring" refers to a monocyclic ring which only includes carbon atoms as ring members. Such rings may be fully saturated, partially saturated, or aromatic and may include 3 to 10 carbon atoms.

As used herein, the term "cycloalkyl" refers to a monocyclic or polycyclic non-aromatic carbocyclic ring, where the polycyclic ring can be fused, bridged, or spiro. The carbocyclic ring can have 3 to 10 carbon ring atoms. Contemplated carbocyclic rings include, but are not limited to, cyclopropyl, cyclobutyl, cyclopentyl, cyclohexyl, cycloheptyl, cyclooctyl, and cyclononyl.

As used herein, the term "heterocycloalkyl" means a monocyclic or polycyclic (e.g., bicyclic), saturated or partially unsaturated, ring system containing 3 or more (e.g., 3 to 12, 4 to 10, 4 to 8, or 5 to 7) total atoms, of which one to five (e.g., 1, 2, 3, 4, or 5) of the atoms are independently selected from nitrogen, oxygen, and sulfur. Nonlimiting examples of heterocycloalkyl groups include azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, and diazacycloheptyl.

Unless otherwise indicated, a cycloalkyl or heterocycloalkyl group can be unsubstituted or substituted with one or more, and in particular one to four, groups. Some contemplated substituents include halo, $C_{1-6}$alkyl, $C_{2-6}$alkenyl, $C_{2-6}$alkynyl, —$OCF_3$, —$NO_2$, —CN, —NC, —OH, alkoxy, amino, —$CO_2H$, —$CO_2C_1$-$C_6$alkyl, —$OCOC_1$-$C_8$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term "heteroaryl" refers to a monocyclic or polycyclic ring system (for example, bicyclic) containing one to three aromatic rings and containing one to four (e.g., 1, 2, 3, or 4) heteroatoms selected from nitrogen, oxygen, and sulfur in an aromatic ring. In certain embodiments, the heteroaryl group has from 5 to 20, from 5 to 15, from 5 to 10 ring, or from 5 to 7 atoms. Heteroaryl also refers to $C_{10-14}$ bicyclic and tricyclic rings, where one ring is aromatic and the others are saturated, partially unsaturated, or aromatic. Examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four or one or two, substituents. Contemplated substituents include halo, $C_{1-6}$alkyl, $C_{2-6}$alkenyl, $C_{2-6}$alkynyl, —$OCF_3$, —$NO_2$, —CN, —NC, —OH, alkoxy, amino, —$CO_2H$, —$CO_2C_1$-$C_6$alkyl, —$OCOC_1$-$C_6$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term Boc refers to the structure

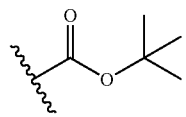

As used herein, the term Cbz refers to the structure

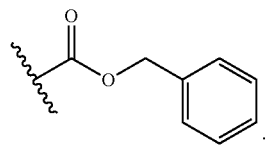 [SMILES: *C(=O)OCc1ccccc1]

As used herein, the term Bn refers to the structure

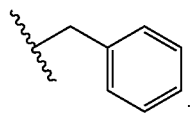

As used herein, the term trifluoroacetamide refers to the structure

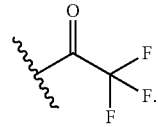 [SMILES: *C(=O)C(F)(F)F]

As used herein, the term trityl refers to the structure

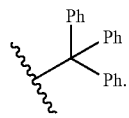

As used herein, the term tosyl refers to the structure

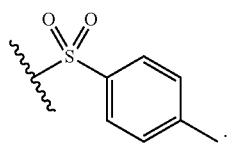 [SMILES: *S(=O)(=O)c1ccc(C)cc1]

As used herein, the term Troc refers to the structure

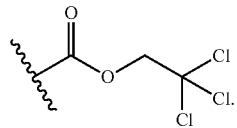 [SMILES: *C(=O)OCC(Cl)(Cl)Cl]

As used herein, the term Teoc refers to the structure

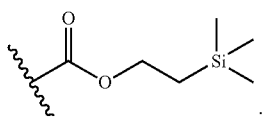 [SMILES: *C(=O)OCC[Si](C)(C)C]

As used herein, the term Alloc refers to the structure

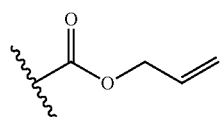

As used herein, the term Fmoc refers to the structure

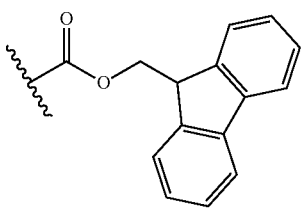

Compounds of the Disclosure

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labeled compounds of the disclosure, for example, those incorporating a radioactive isotope, are useful in drug and/or substrate tissue distribution studies. The radioactive isotopes tritium, i.e. $^{3}H$. and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. For example, groups such as, but not limited to, the following groups

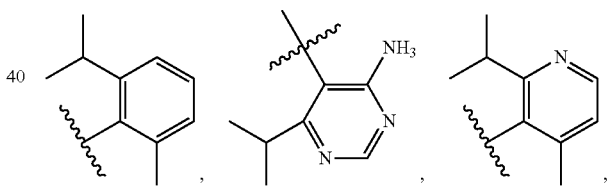

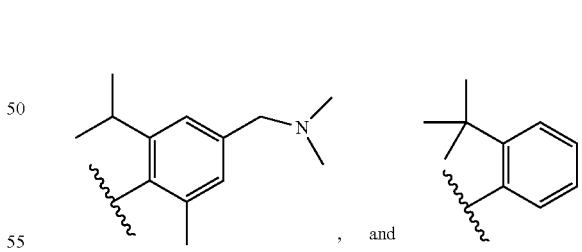

, and may exhibit restricted rotation.

EMBODIMENTS

Embodiment 1

In one embodiment of the present invention, the present invention comprises a compound having a structure selected from the formula 125
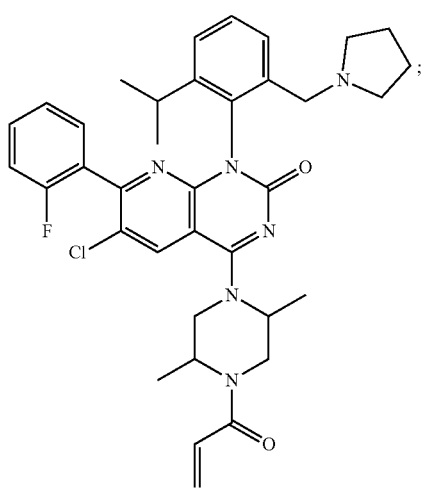
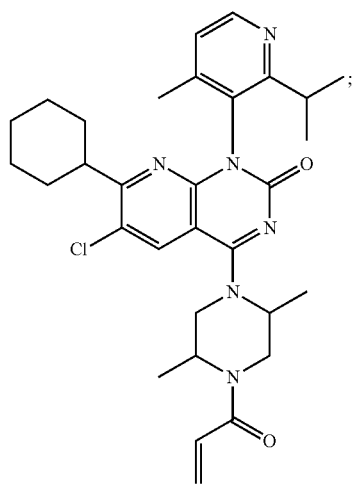
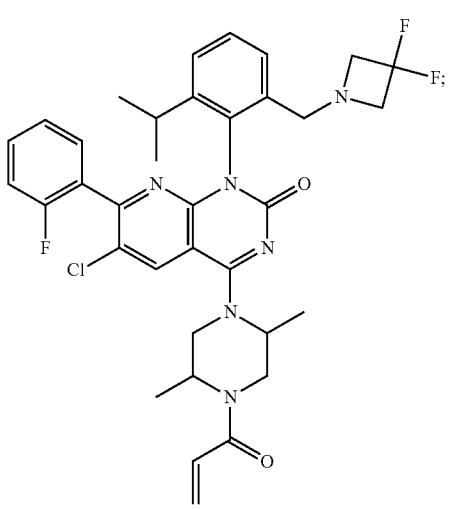
126
-continued
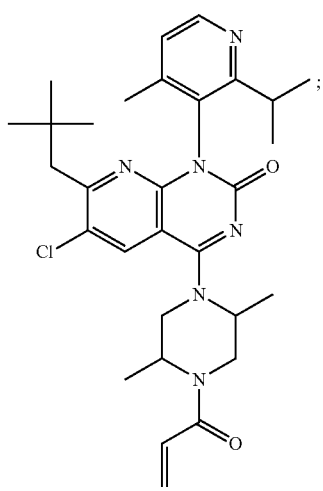
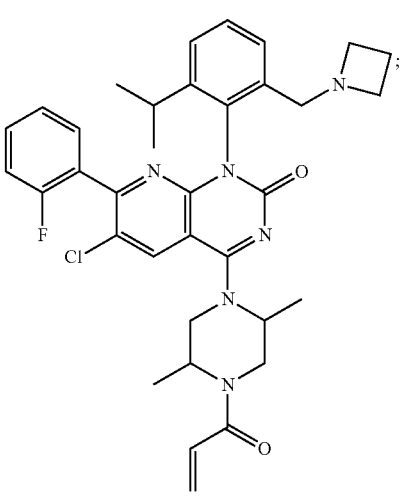
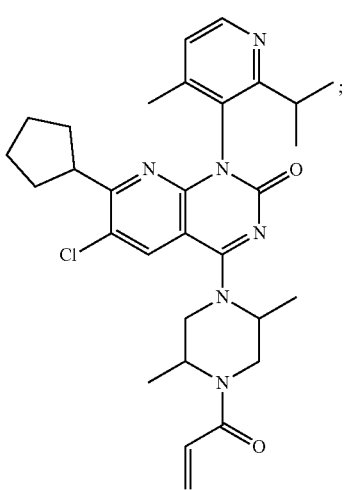

127
-continued
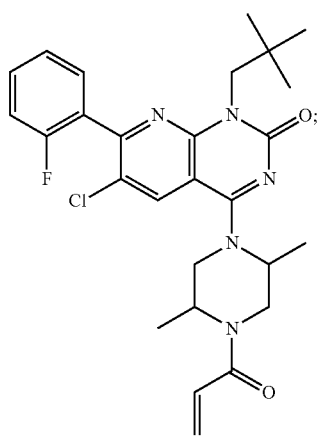
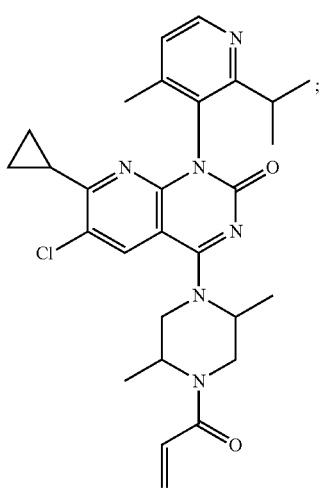
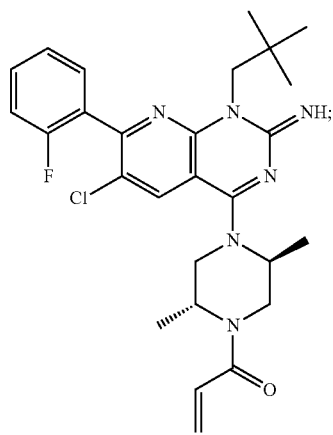
128
-continued
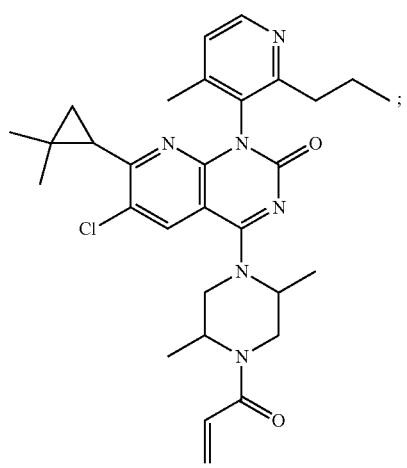
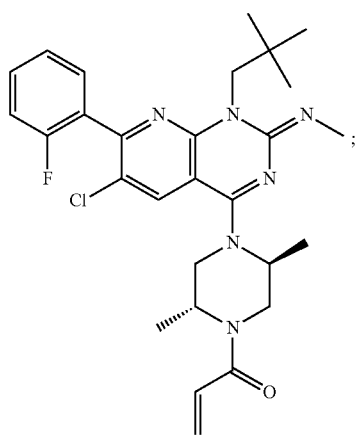
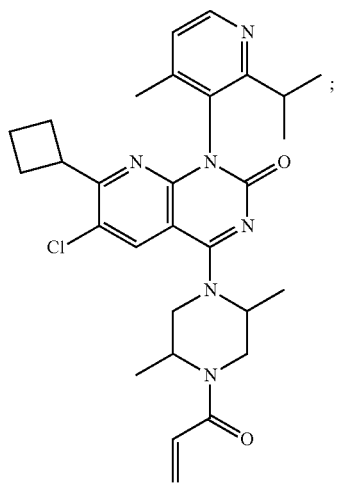

129
-continued
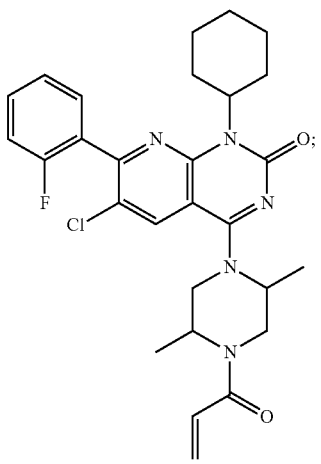
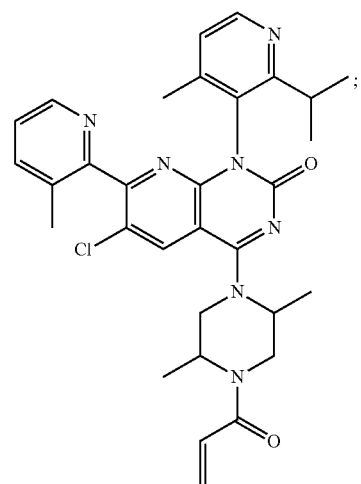
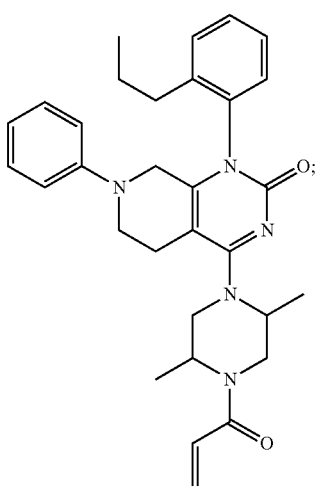
130
-continued
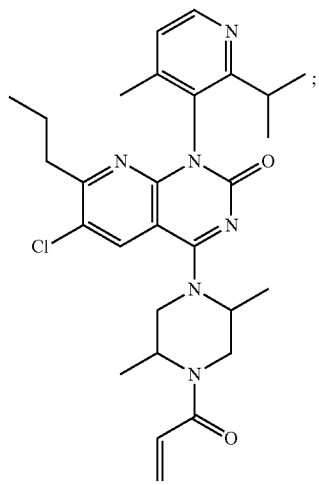
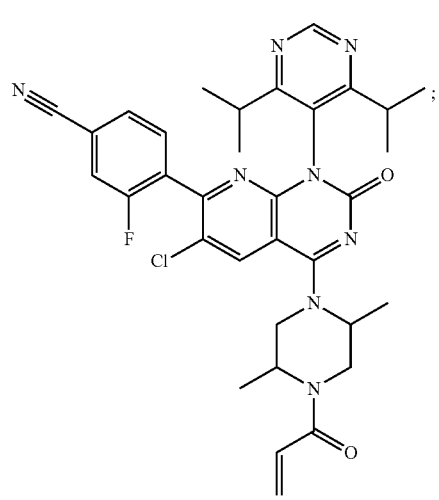
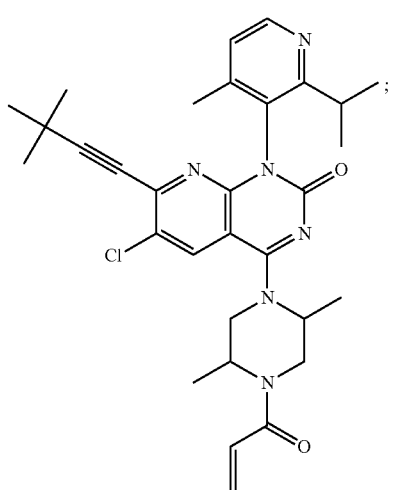

131
-continued
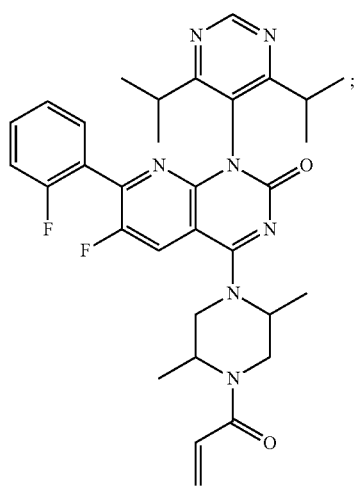
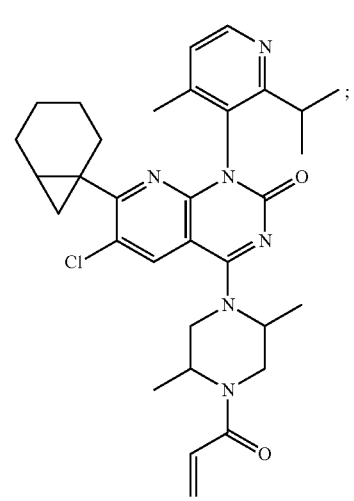
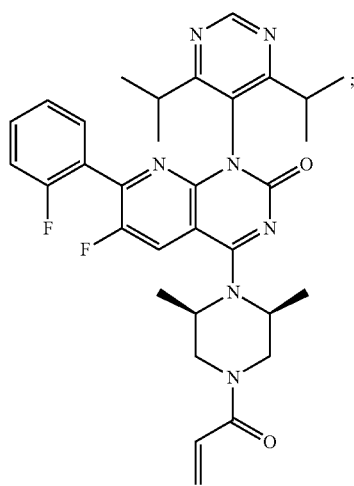
132
-continued
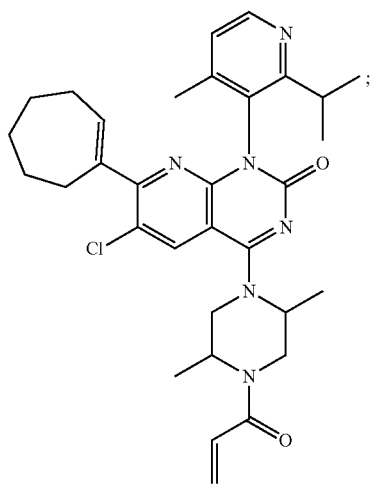
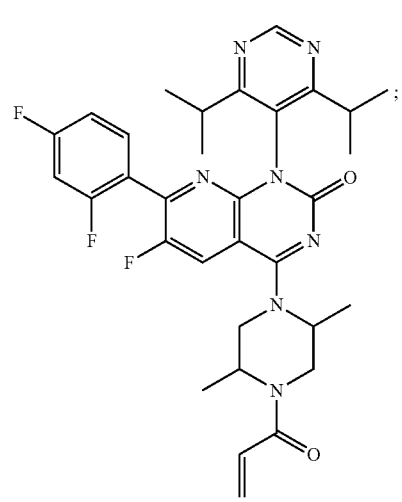
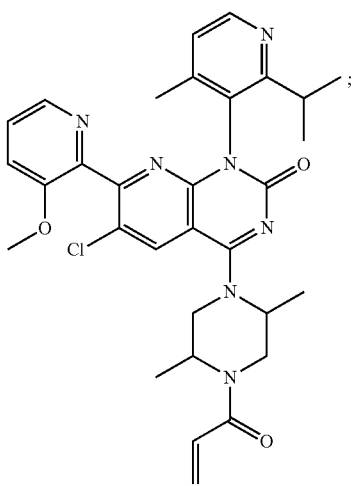

133
-continued
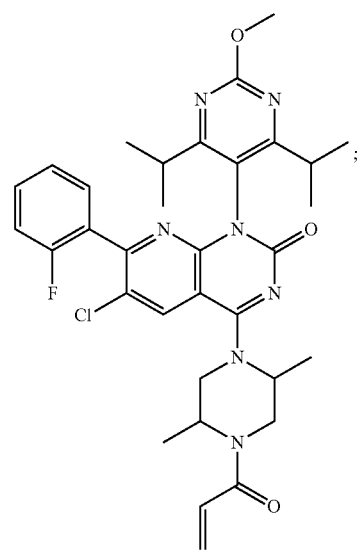
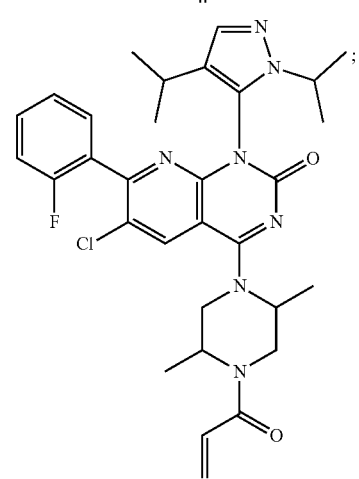
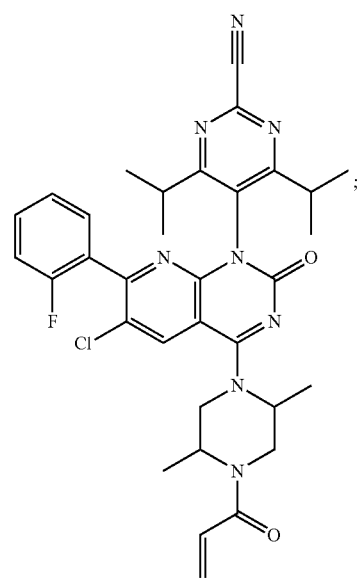
134
-continued
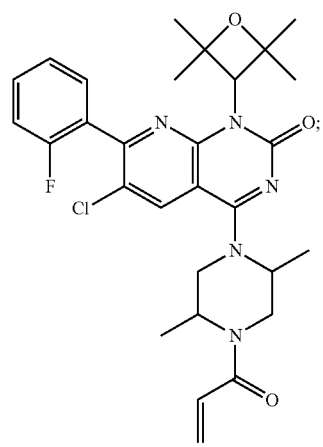
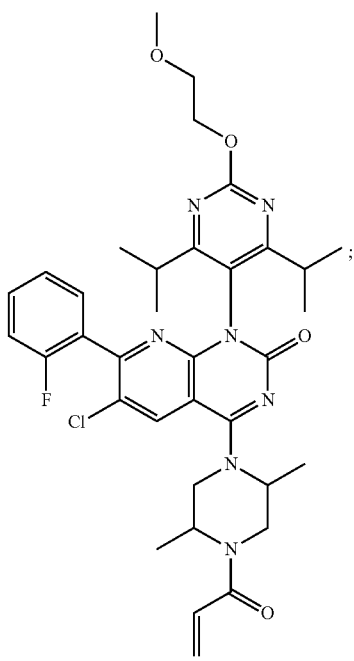
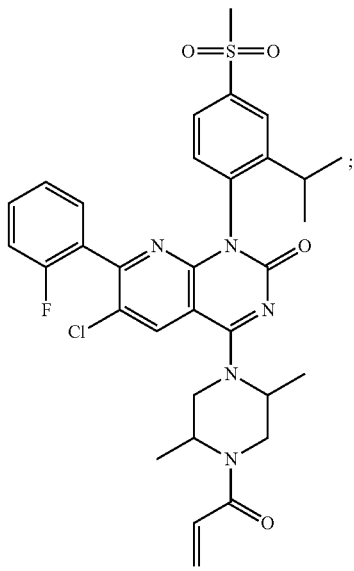

135
-continued
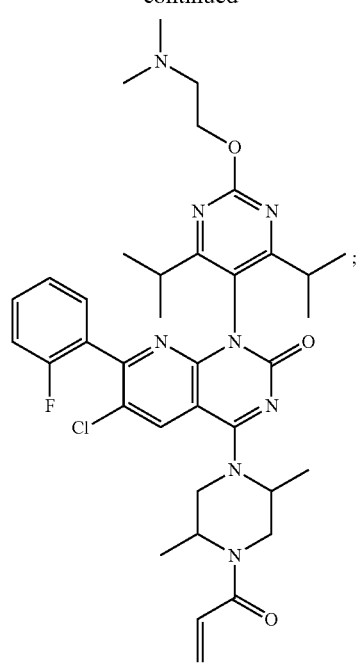
136
-continued
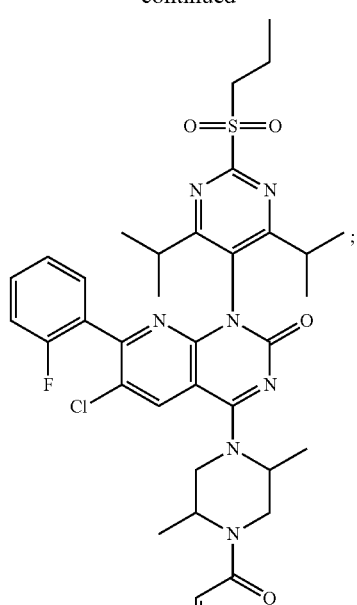
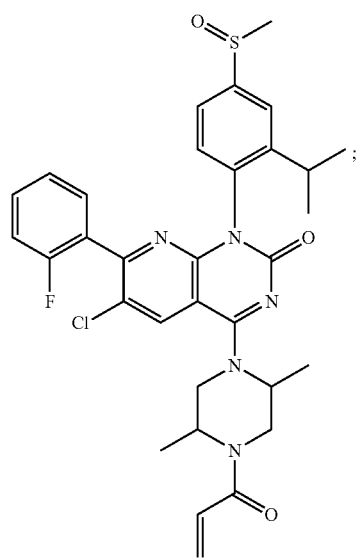

137
-continued
138
-continued
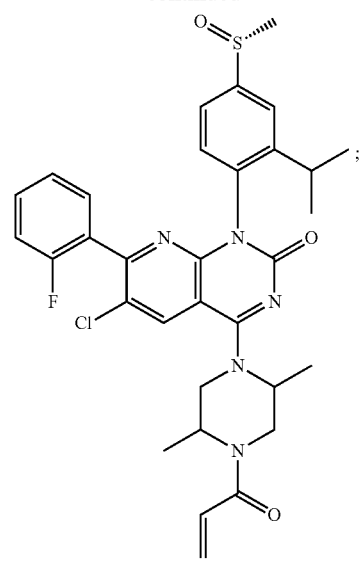
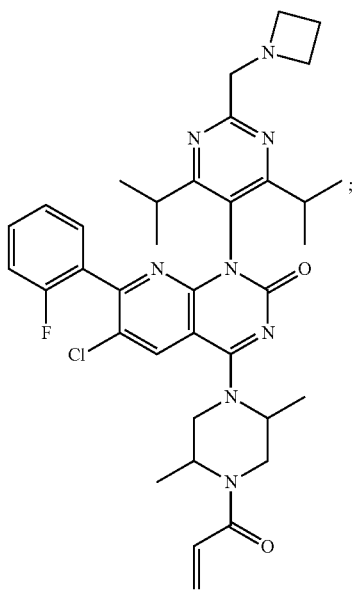
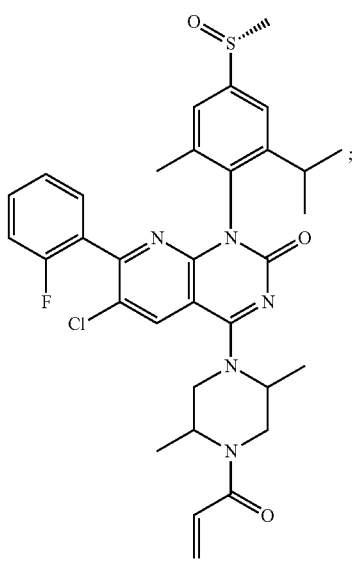

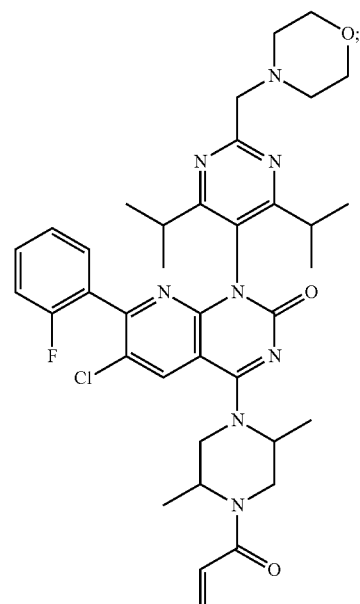
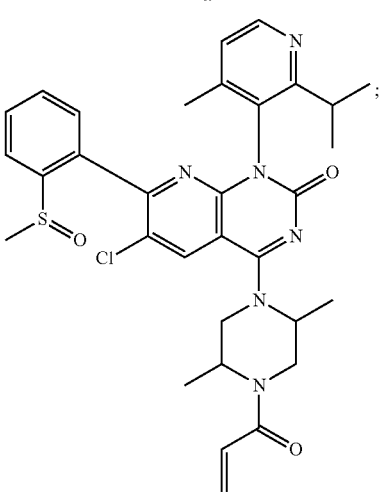
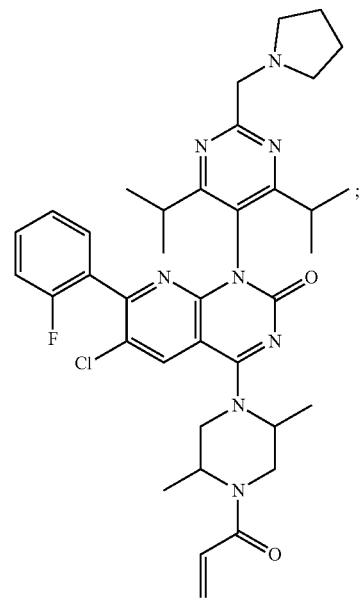
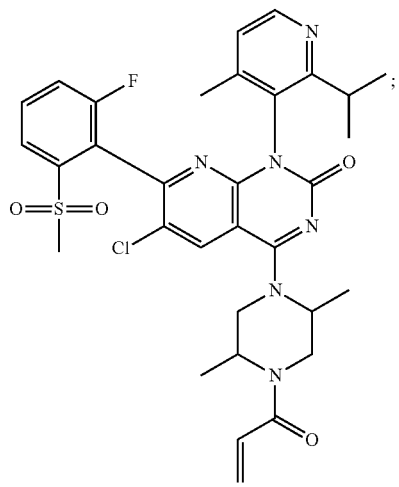
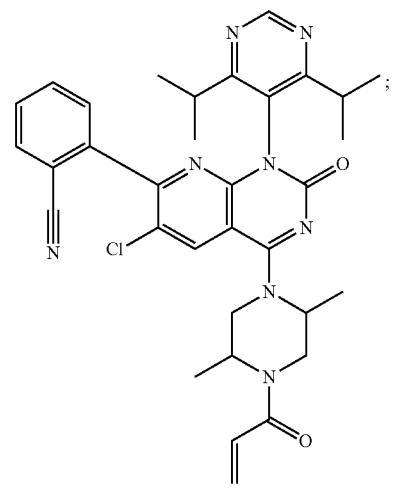
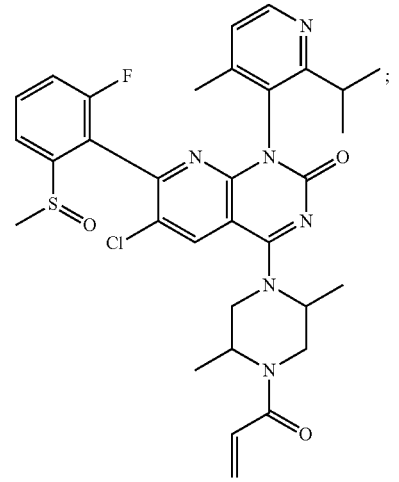

-continued
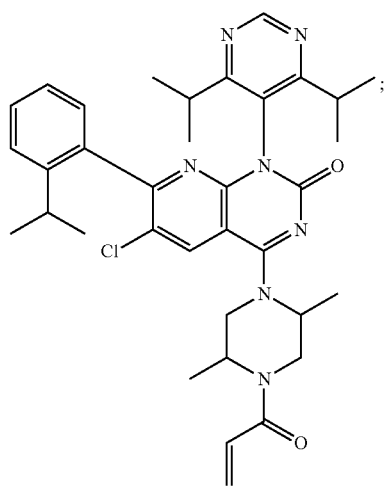
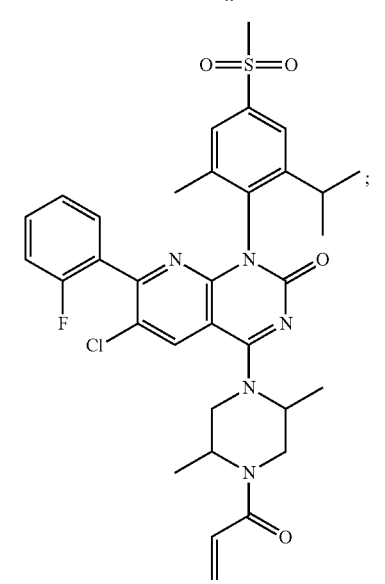
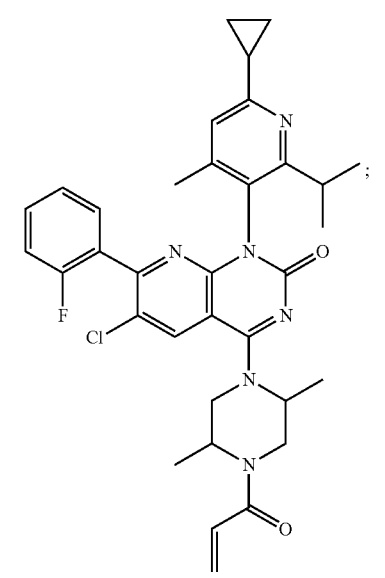
-continued
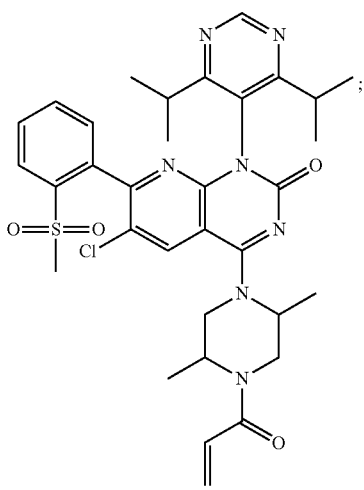
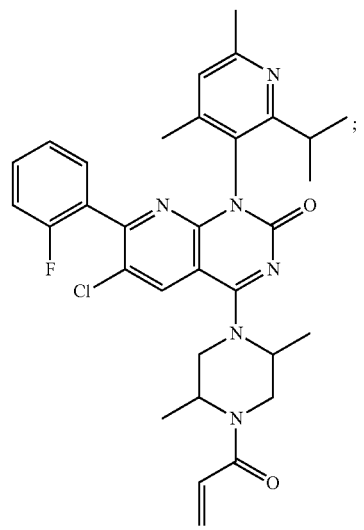
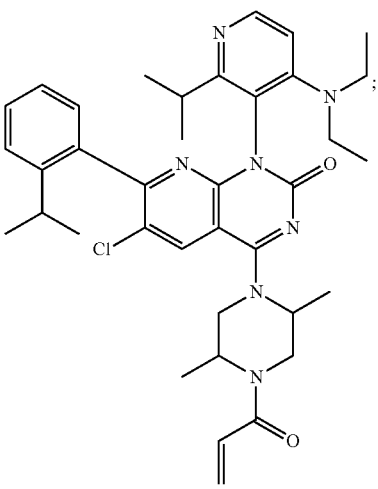

143
-continued
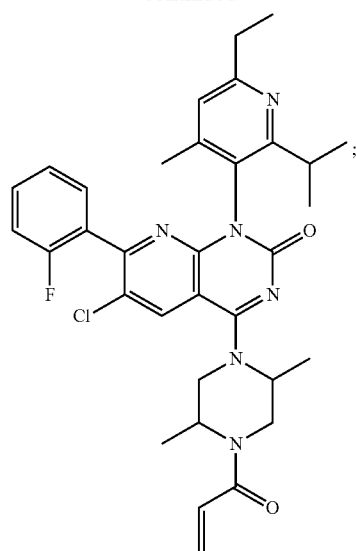
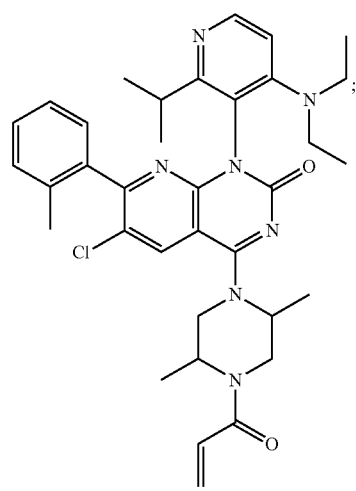
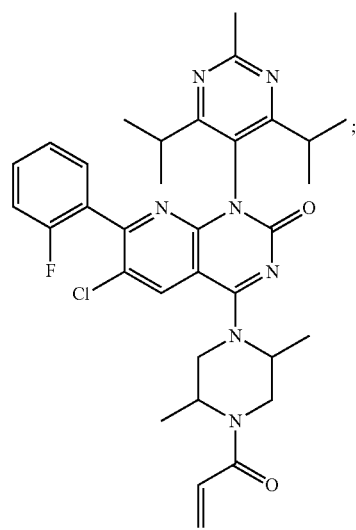
144
-continued
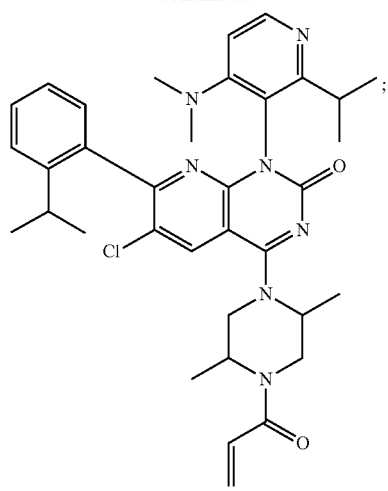
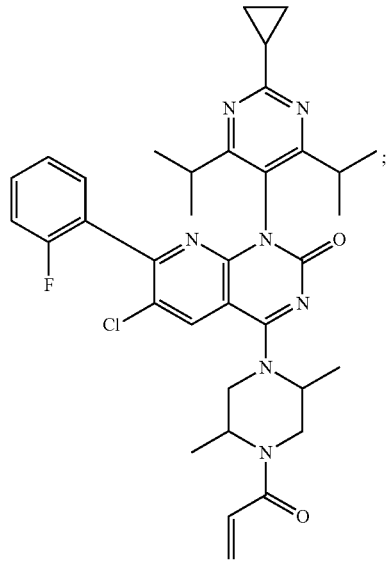
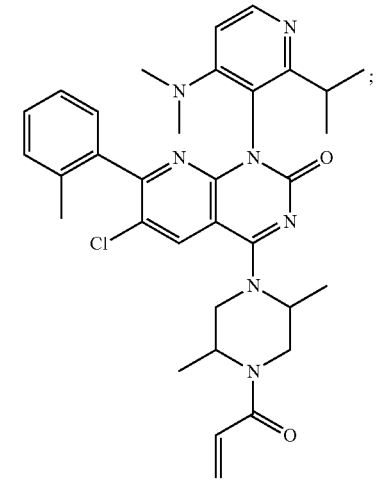

145
-continued
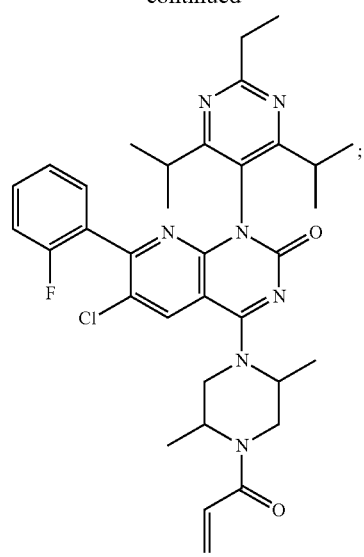
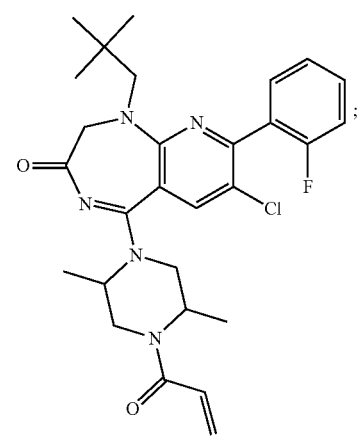
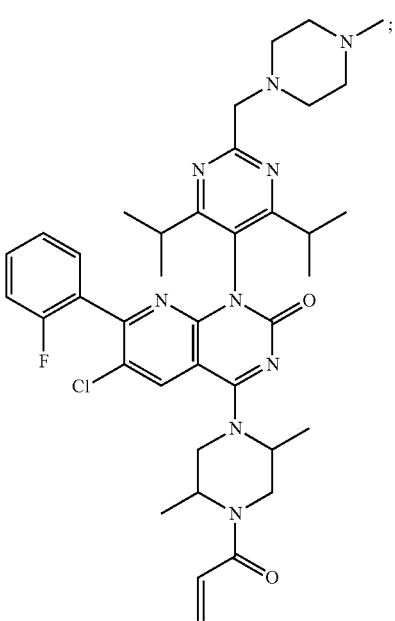
146
-continued
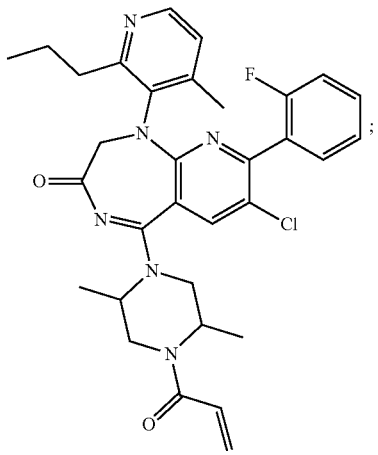
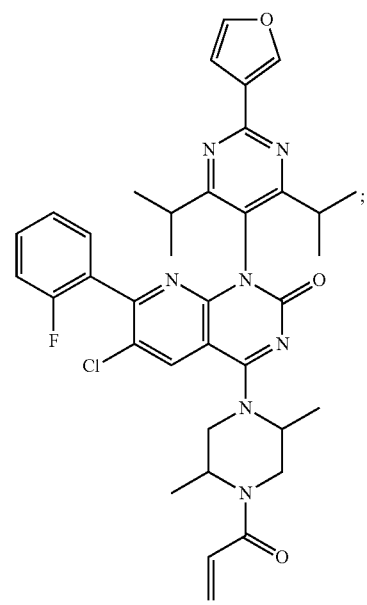
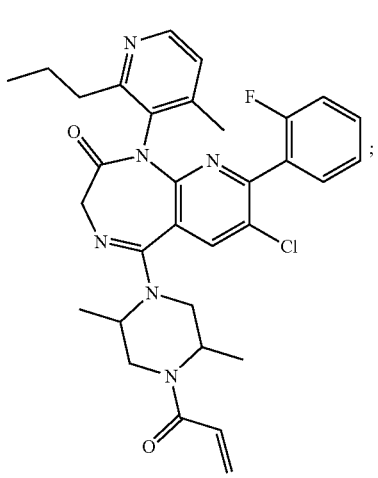

147
-continued
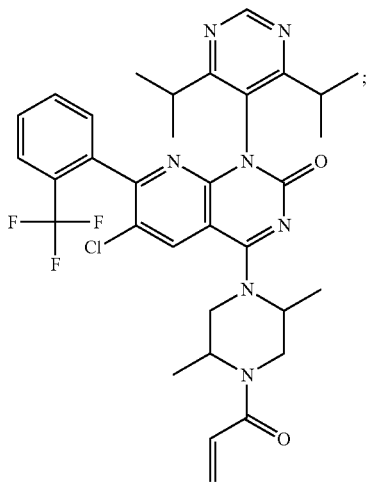
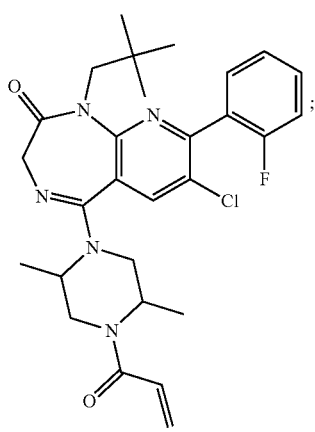
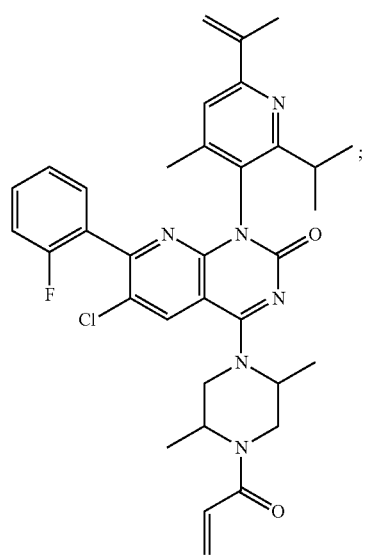
148
-continued
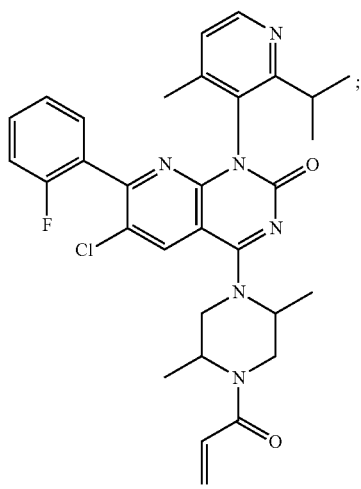
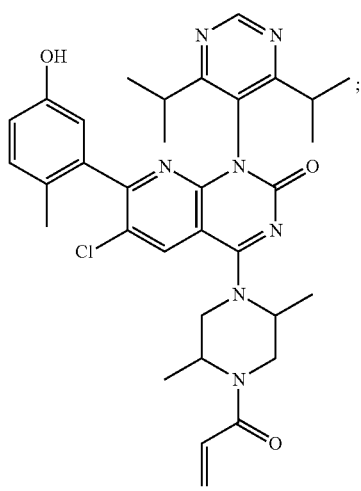
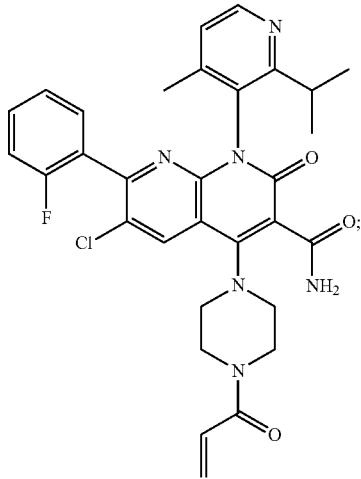

149
-continued
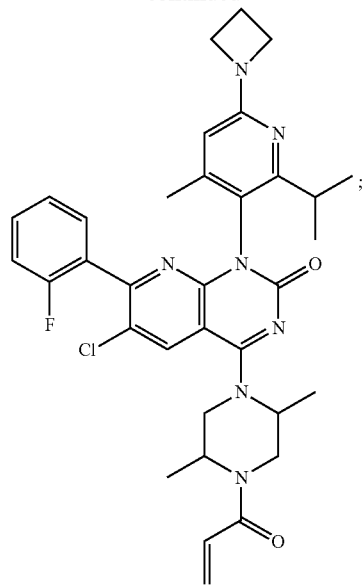
150
-continued
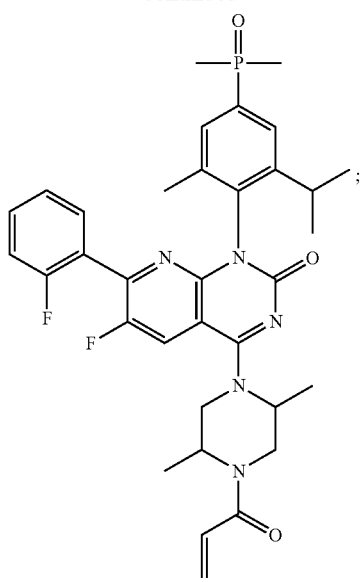
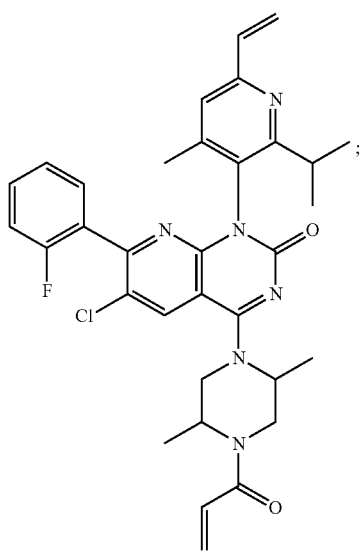
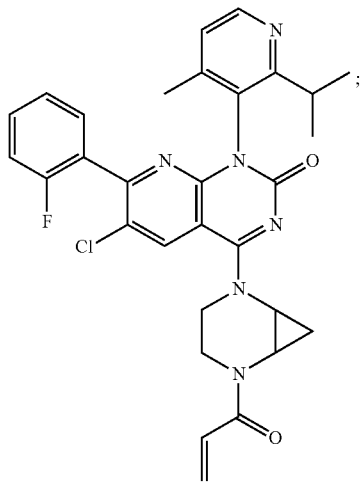

151
-continued
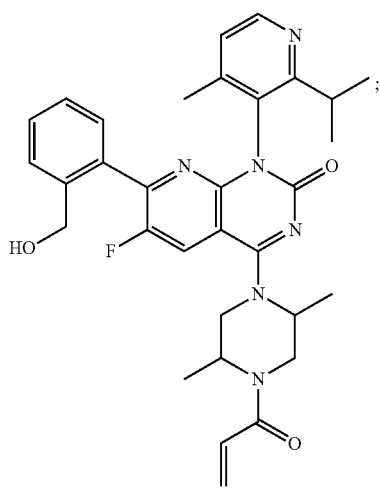
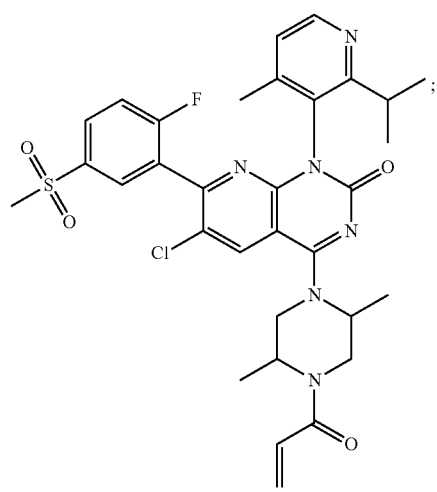
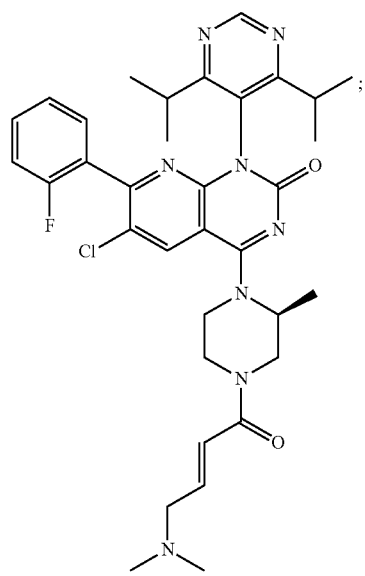
152
-continued
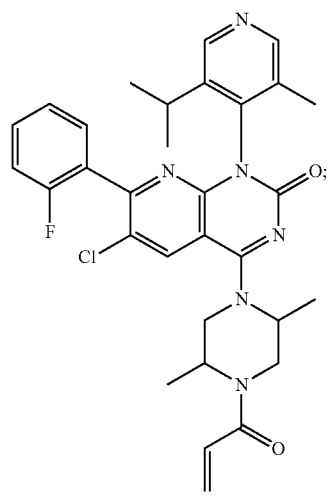
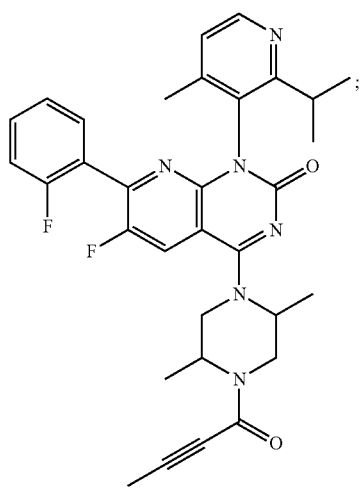
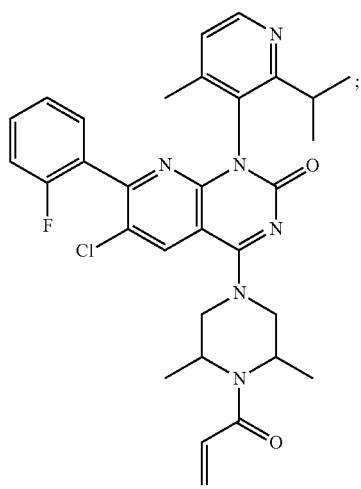

153
-continued
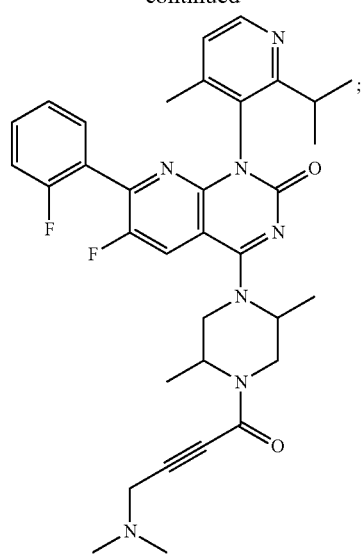
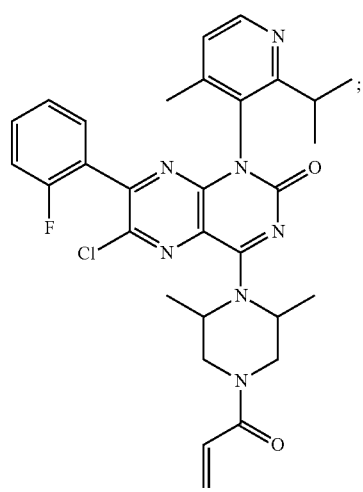
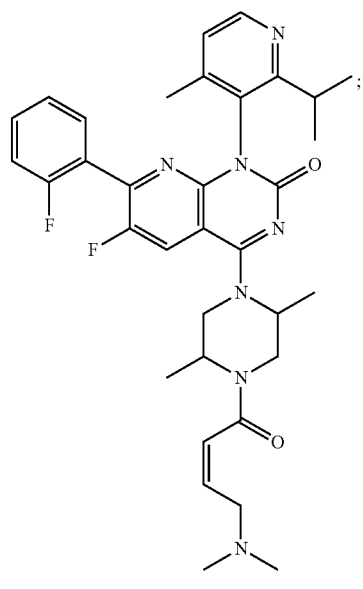
154
-continued
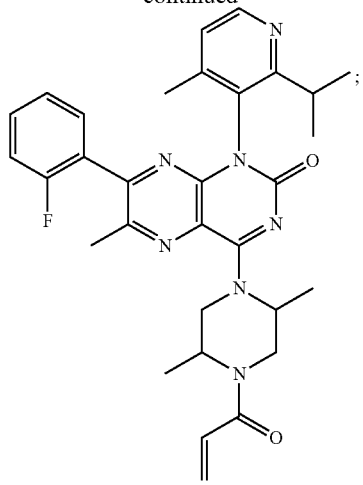
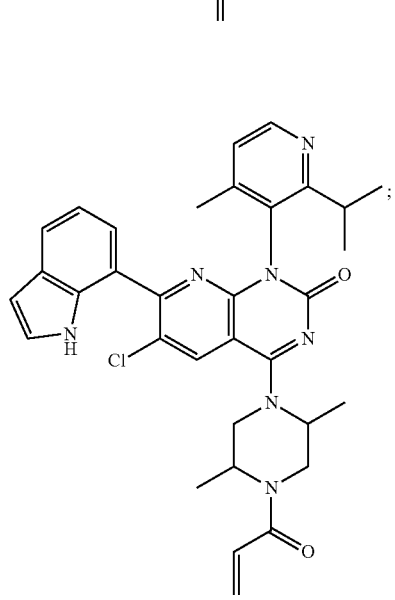

155
-continued
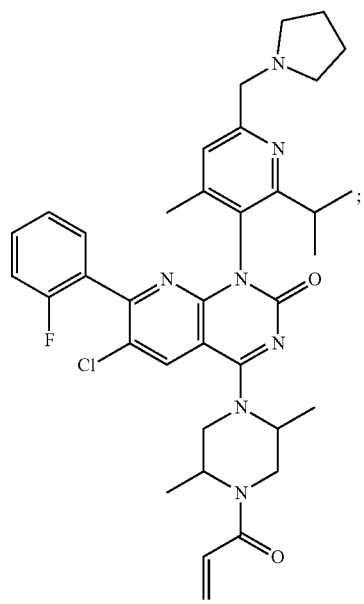
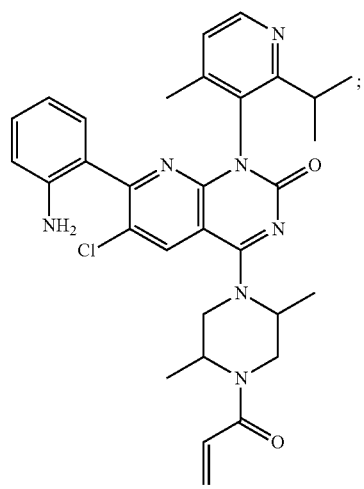
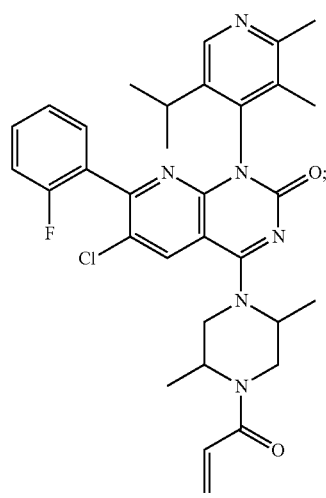
156
-continued
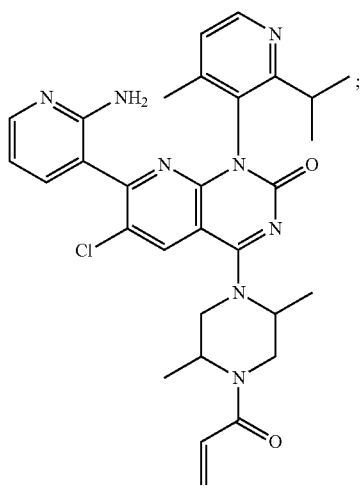
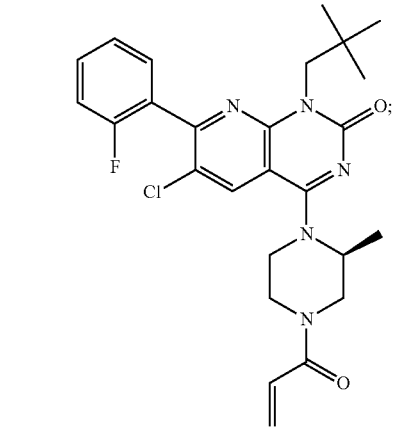
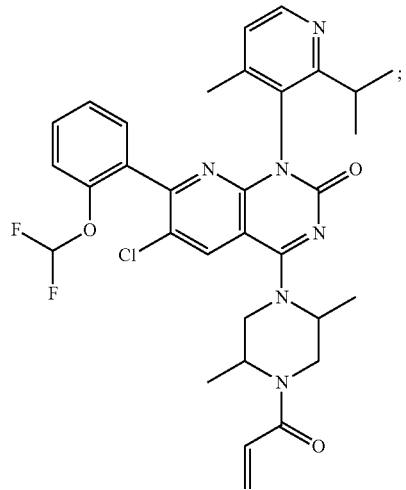

157
-continued
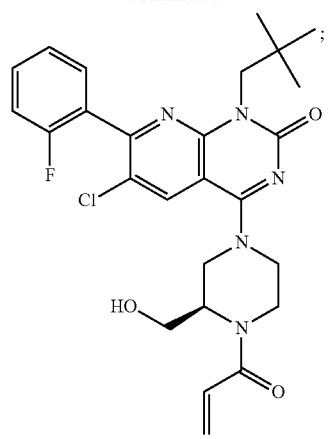
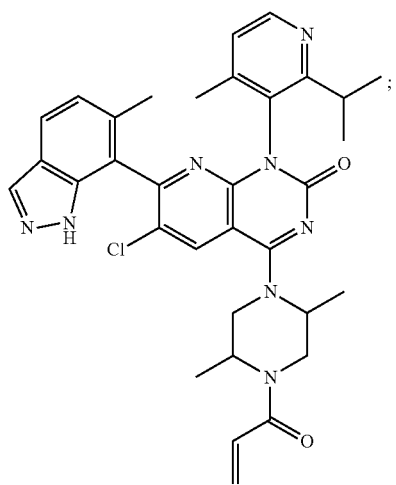
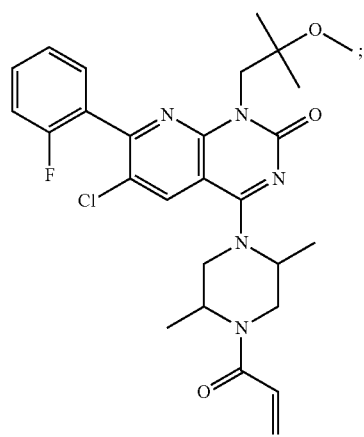
158
-continued
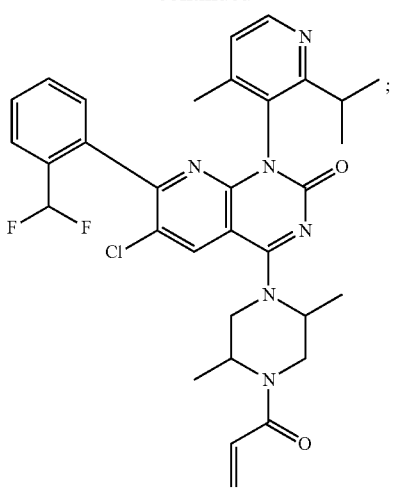
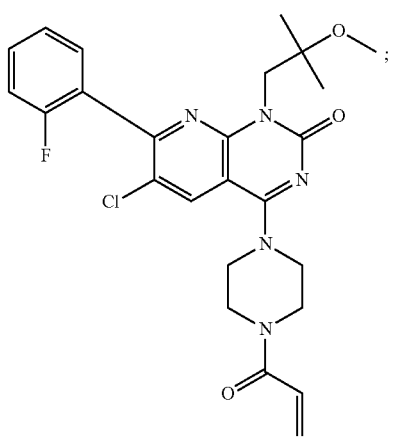
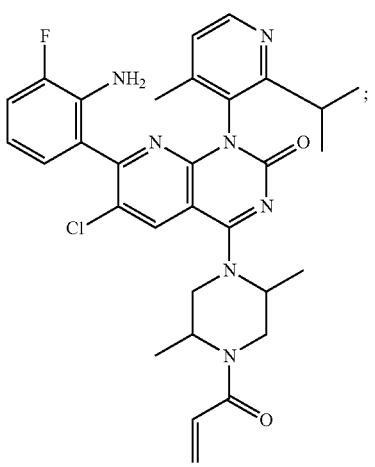

159
-continued
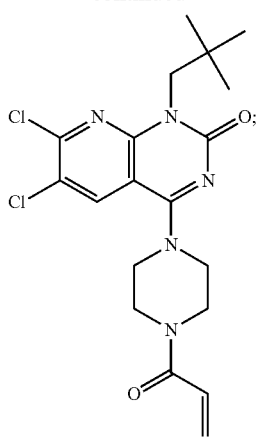
160
-continued
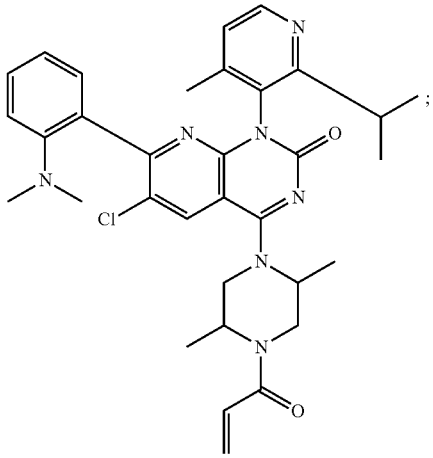
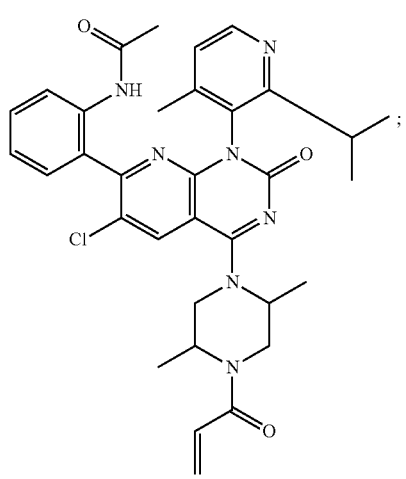
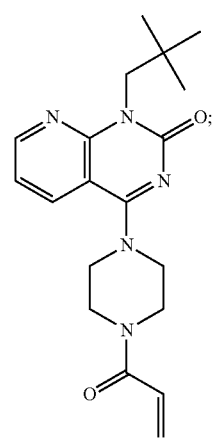
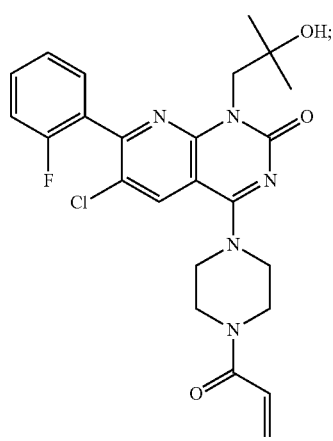
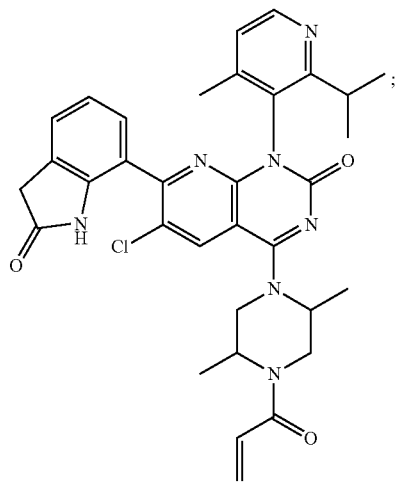

161
-continued
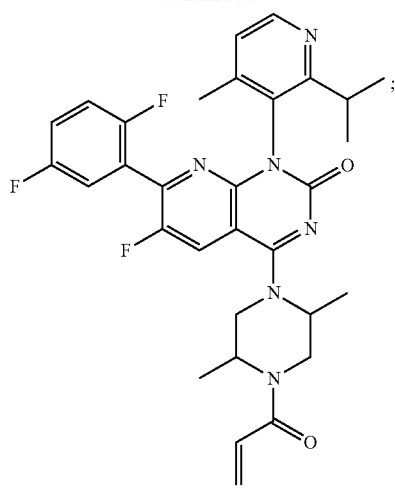
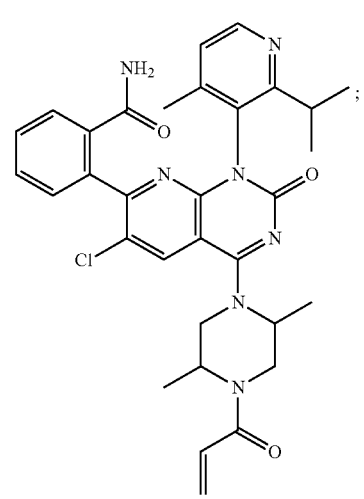
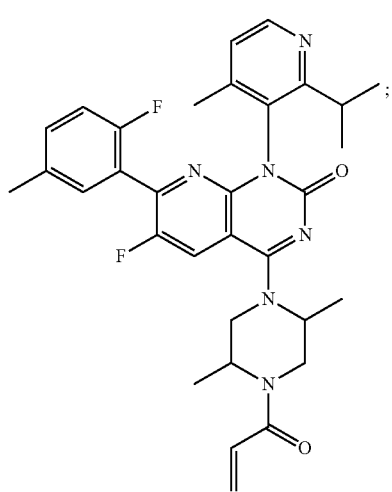
162
-continued
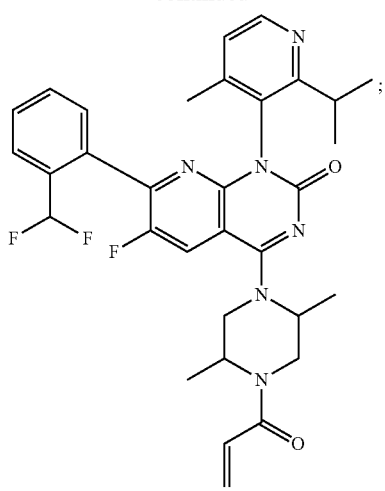
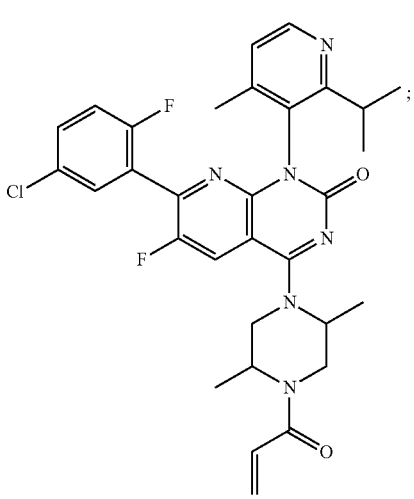
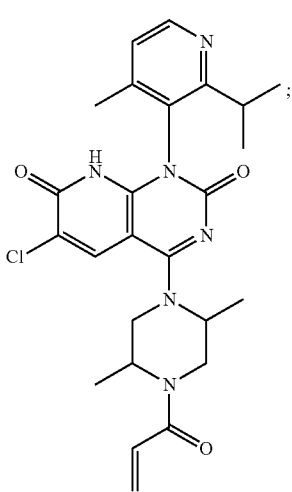

163
-continued
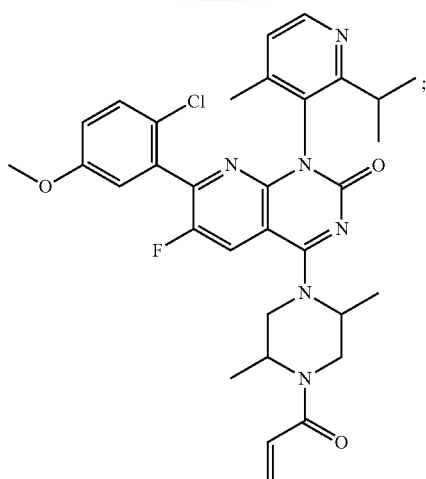
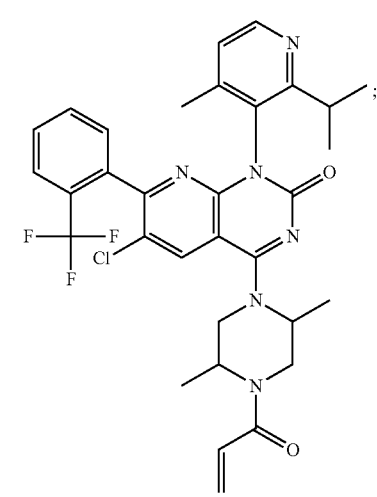
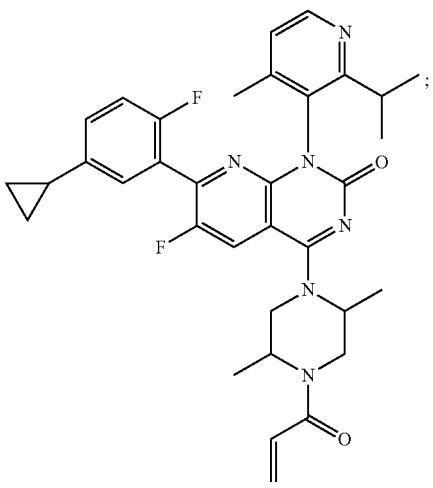
164
-continued
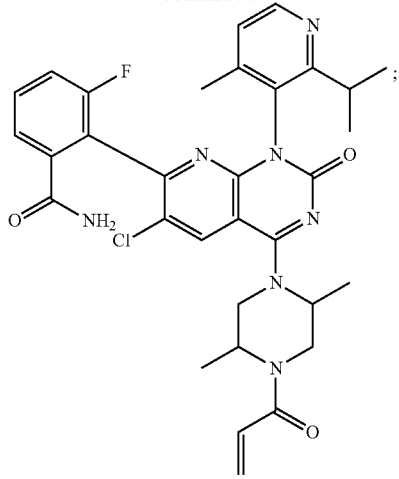
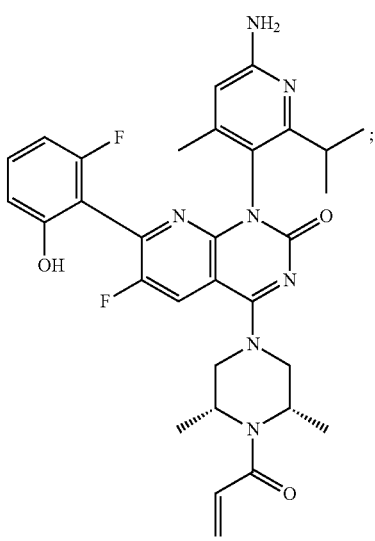
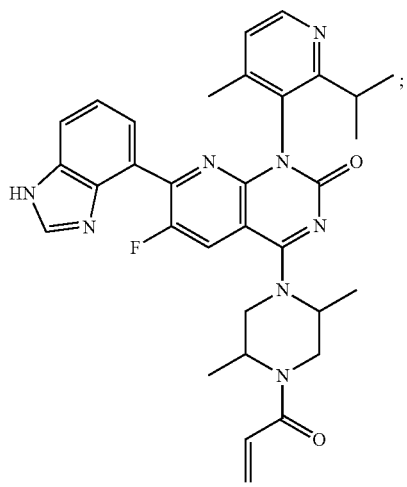

165
-continued
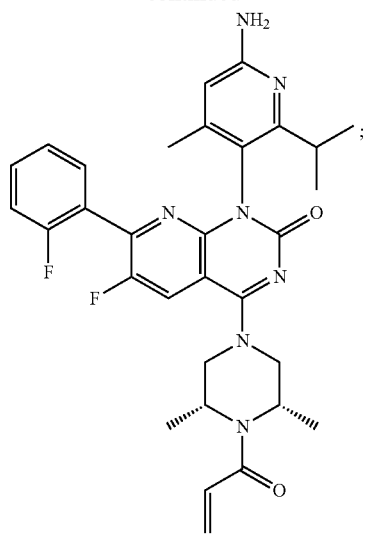
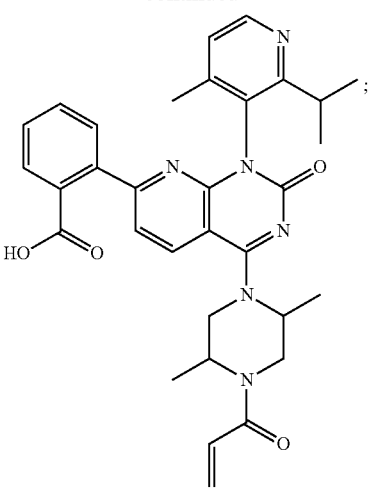
166
-continued
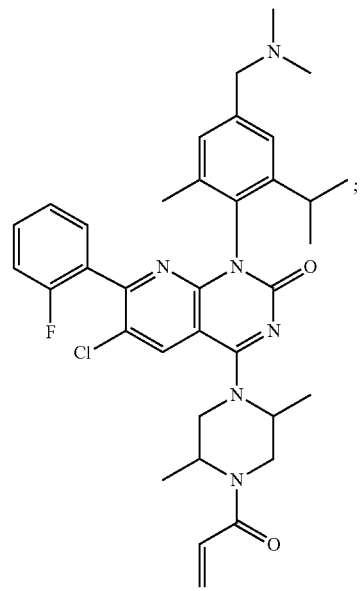
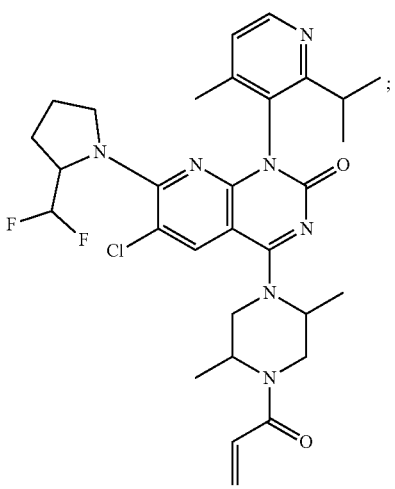

167
-continued
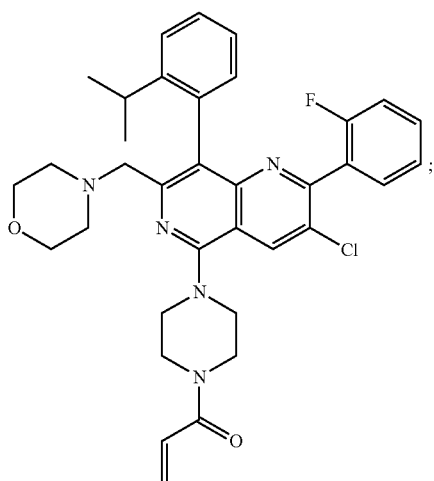
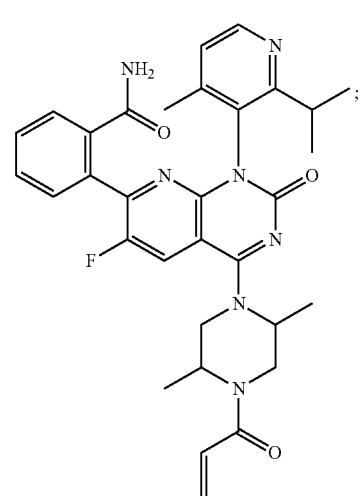
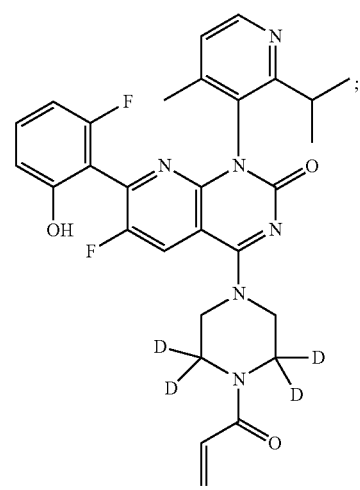
168
-continued
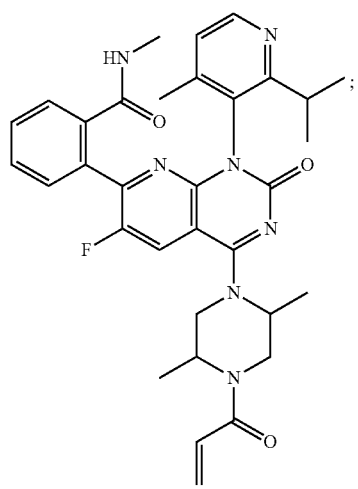
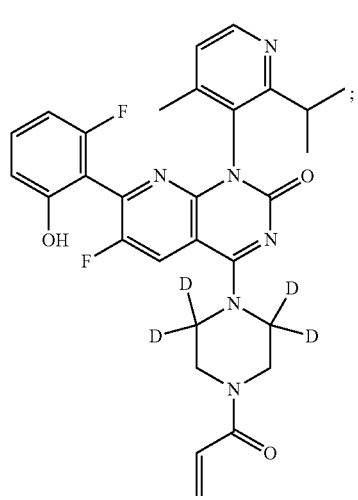
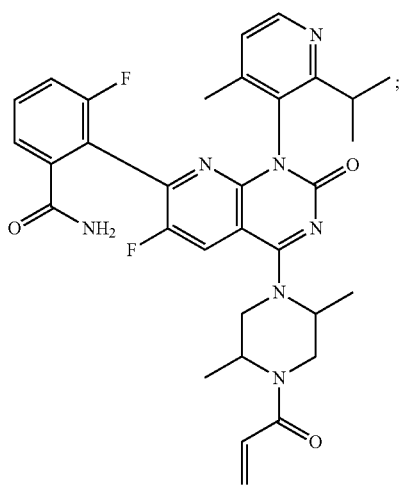

-continued
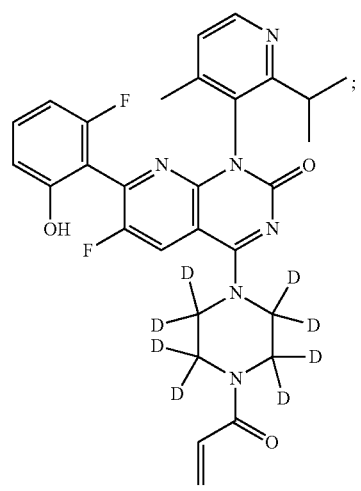
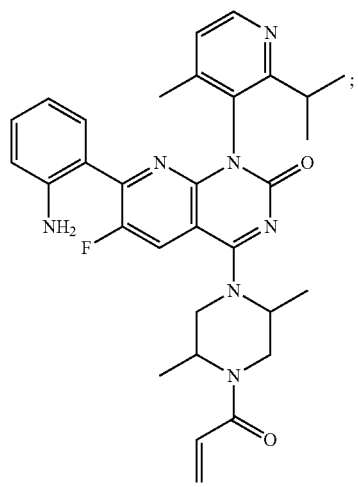
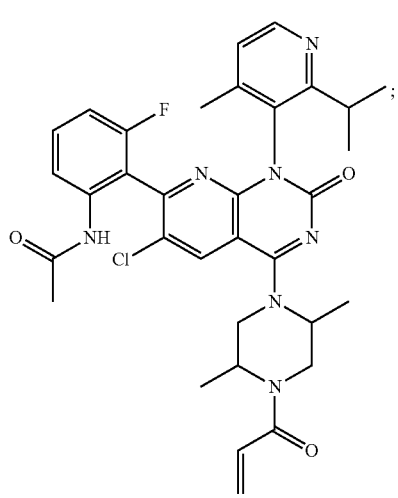
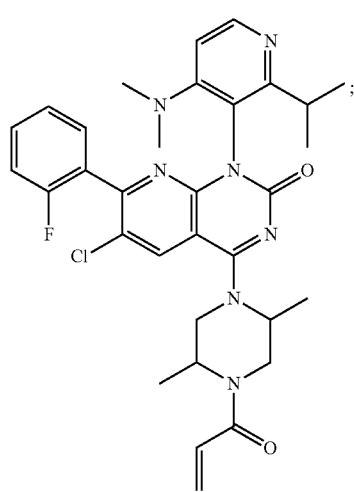
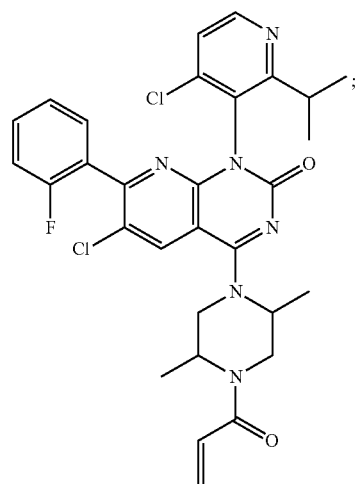
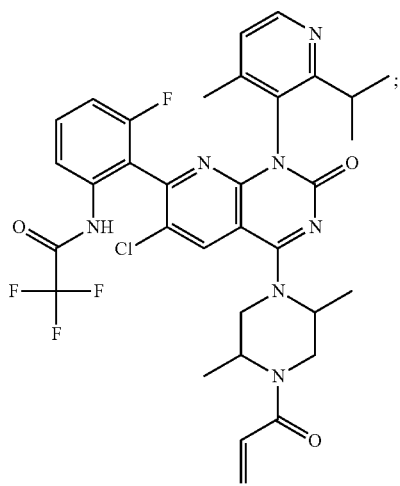

171
-continued
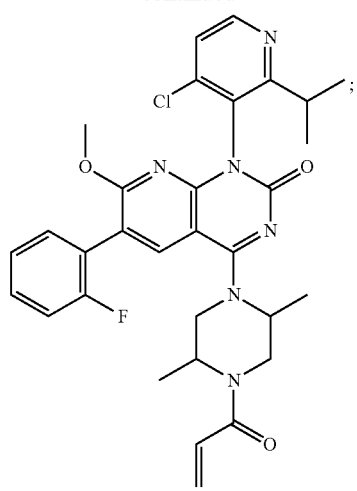
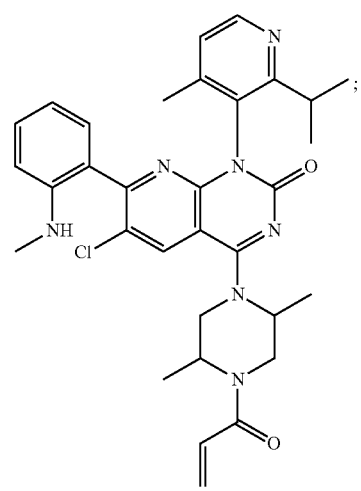
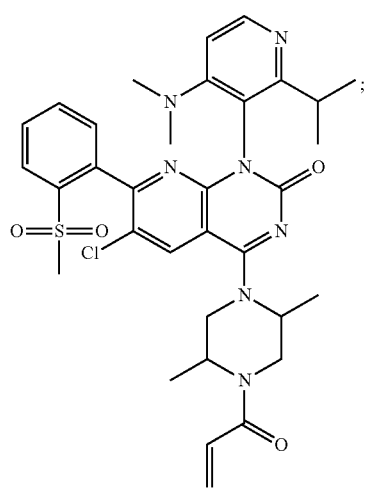
172
-continued
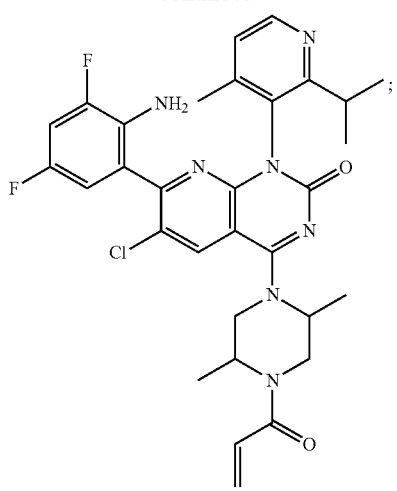
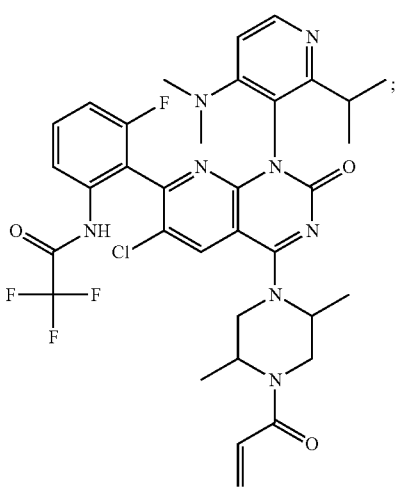
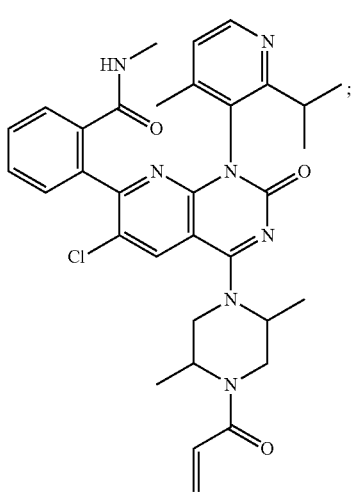

173
-continued
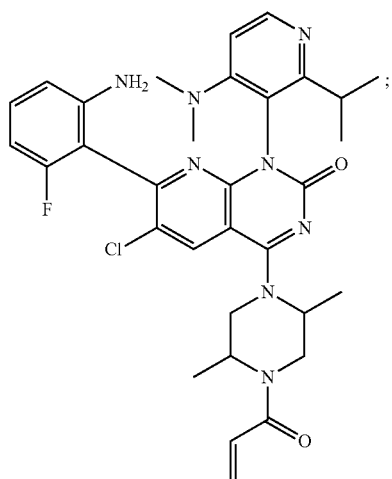
174
-continued
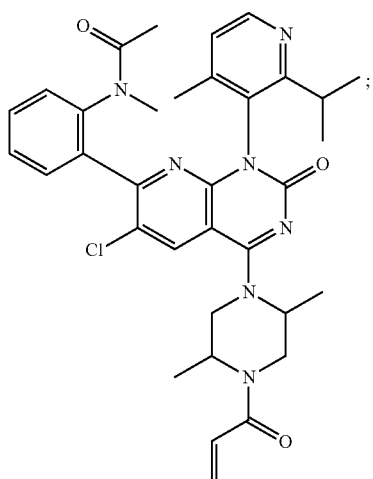
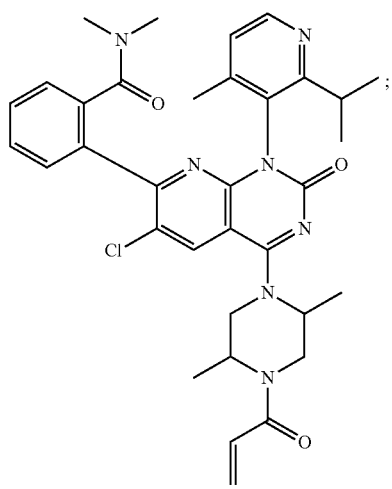
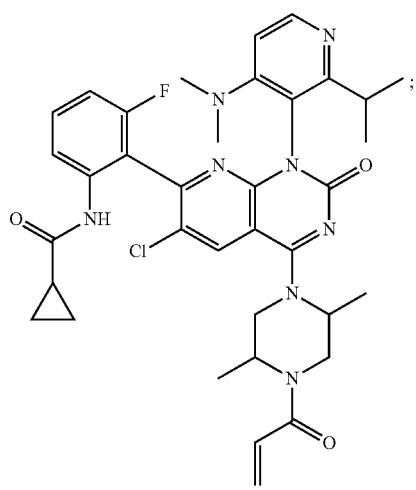
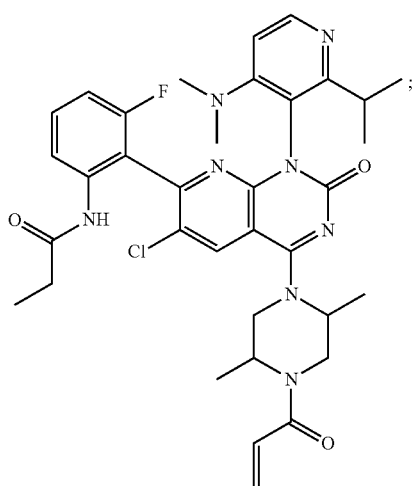
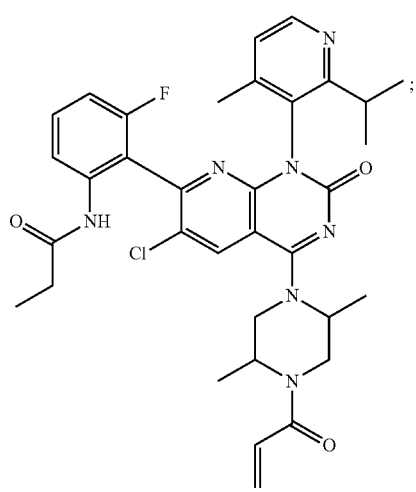

175
-continued
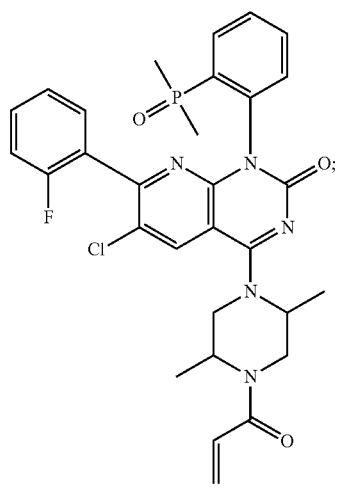
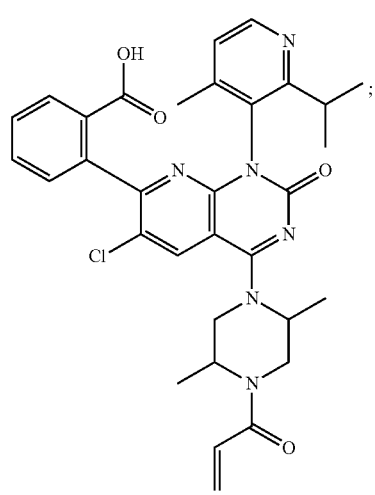 [SMILES: C=CC(=O)N1CC(C)N(c2nc(=O)n(-c3c(C)ccnc3C(C)C)c3nc(-c4ccccc4C(=O)O)c(Cl)cc23)CC1C]
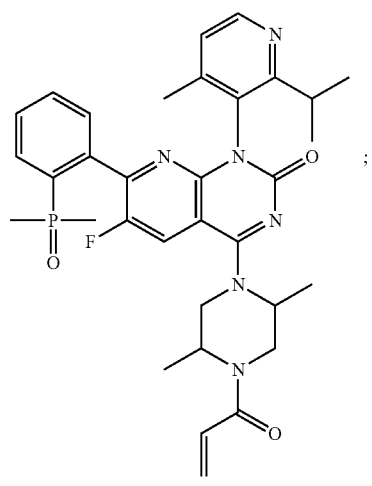
176
-continued
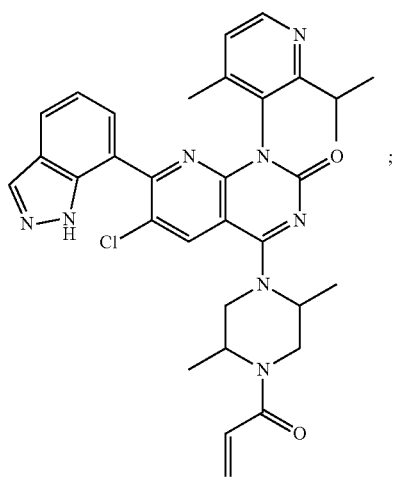
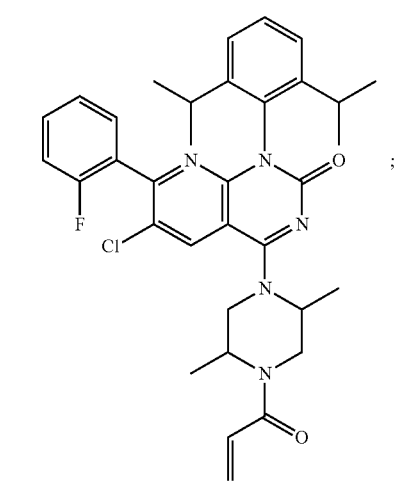
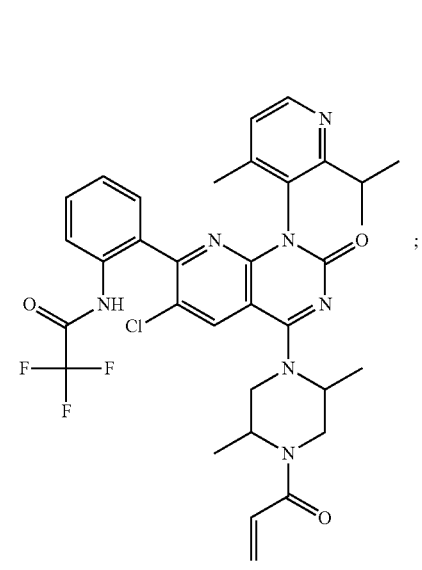

177
-continued
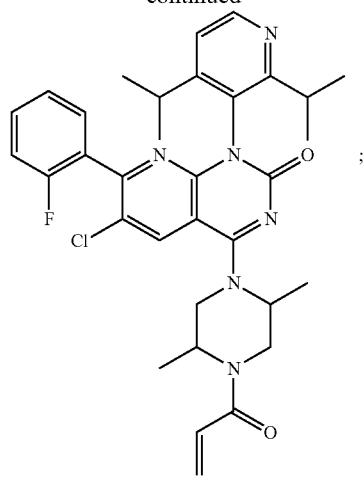
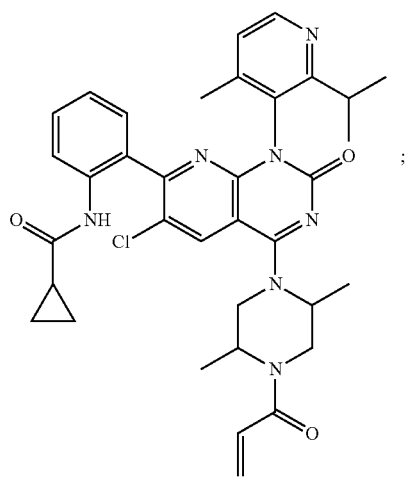
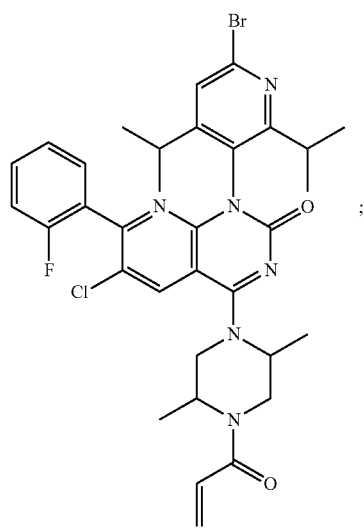
178
-continued
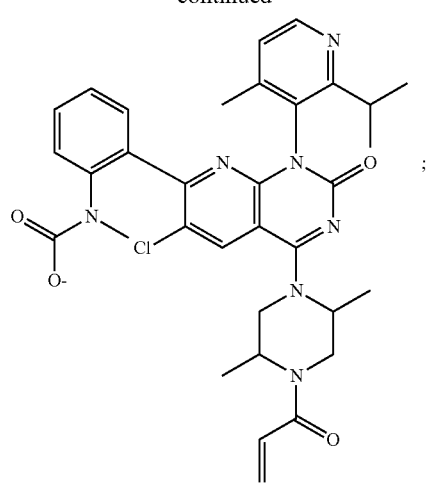
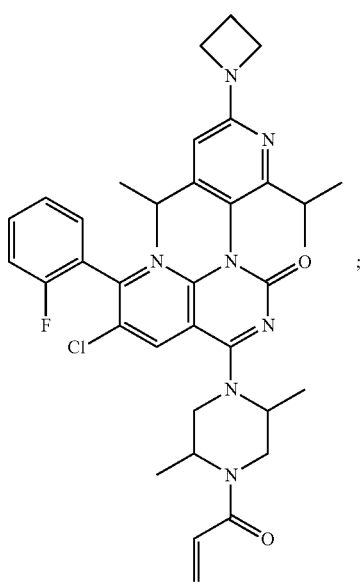
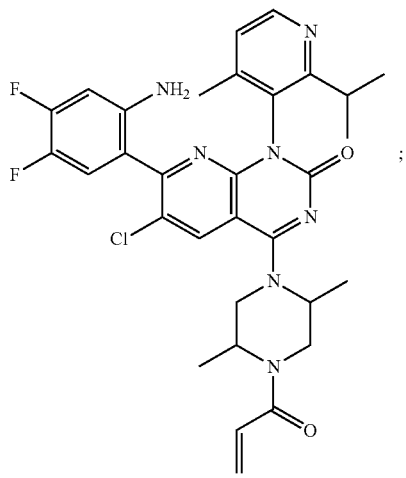

-continued
179
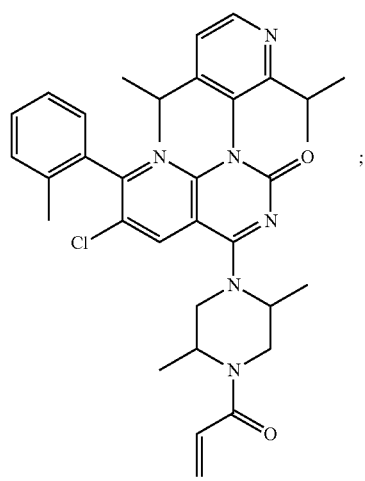
;
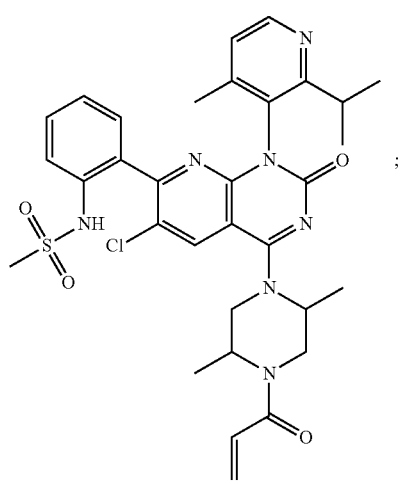
;
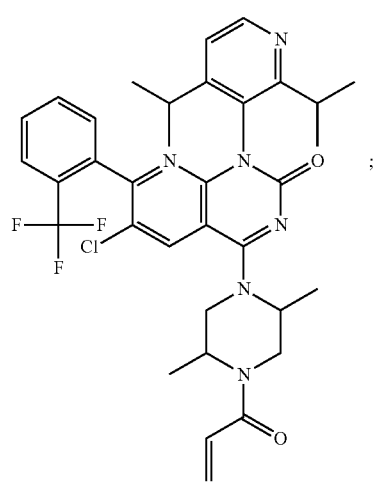
;
180
-continued
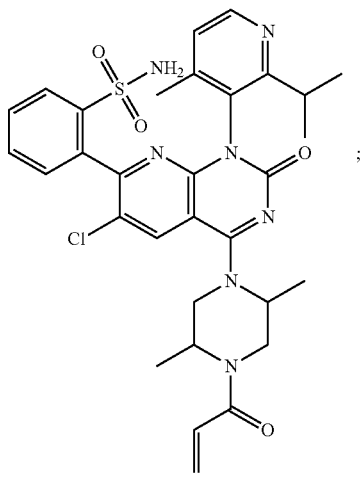
;
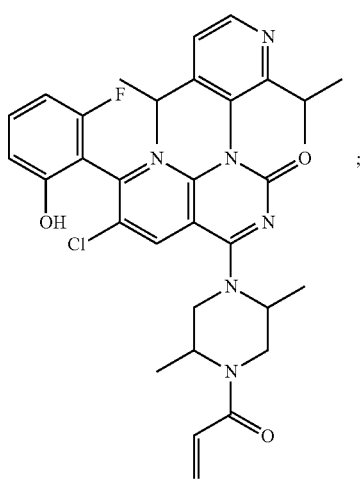
;
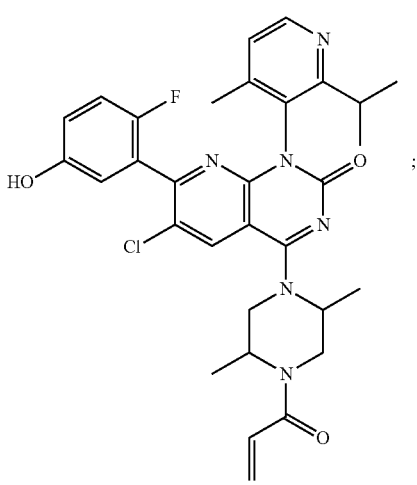
;

181
-continued
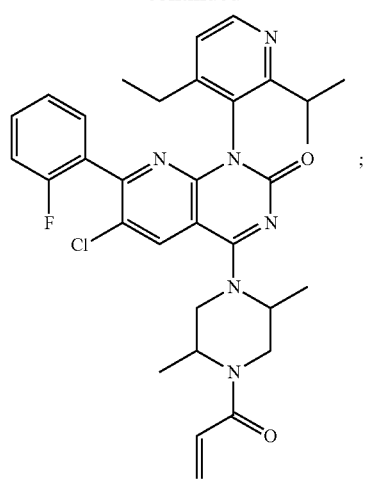
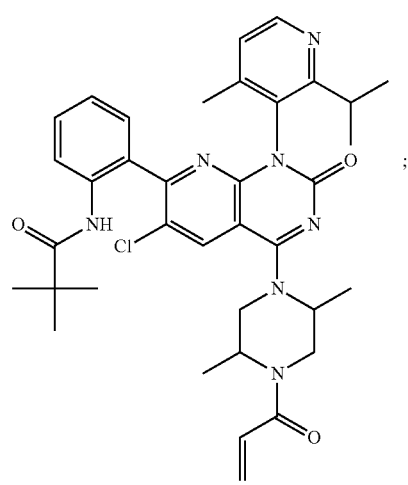
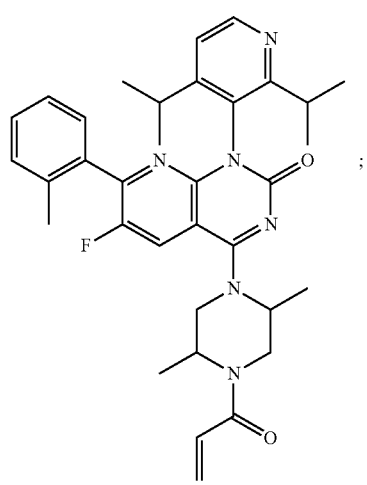
182
-continued
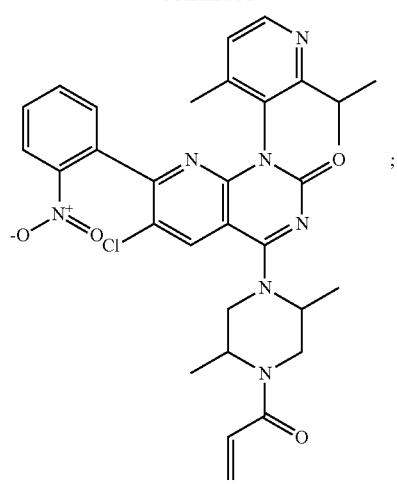
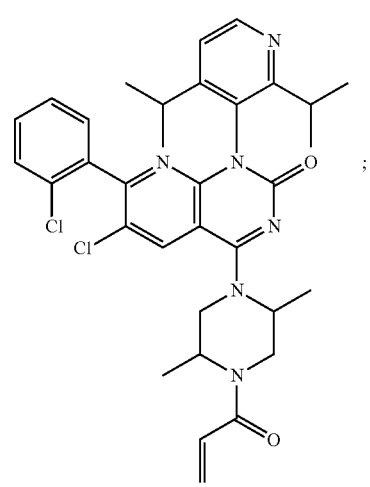
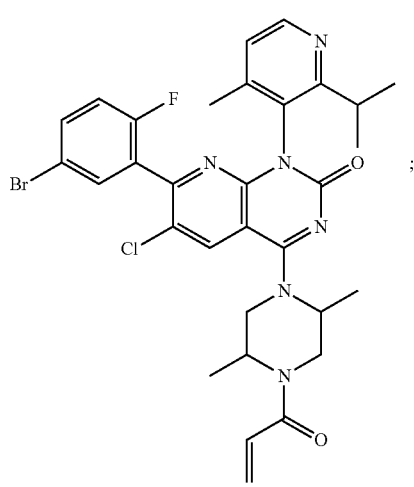

183
-continued
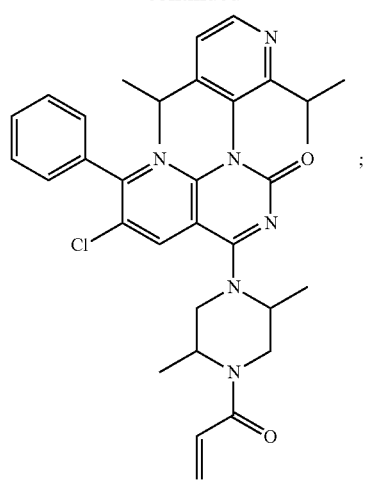
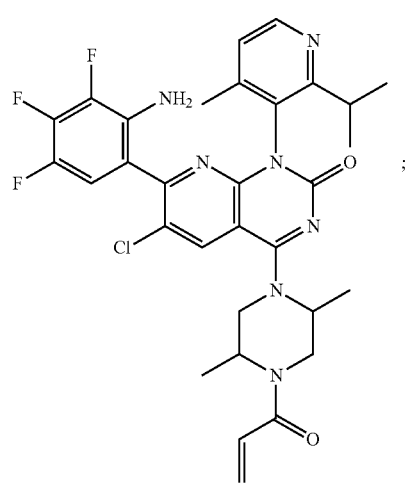
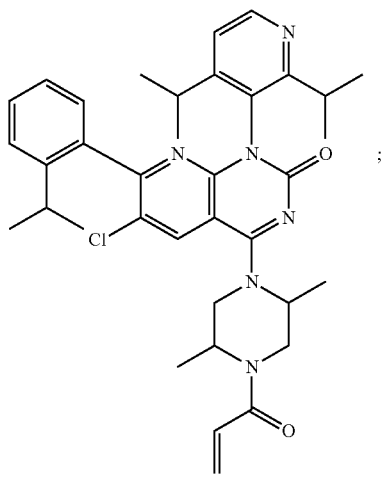
184
-continued
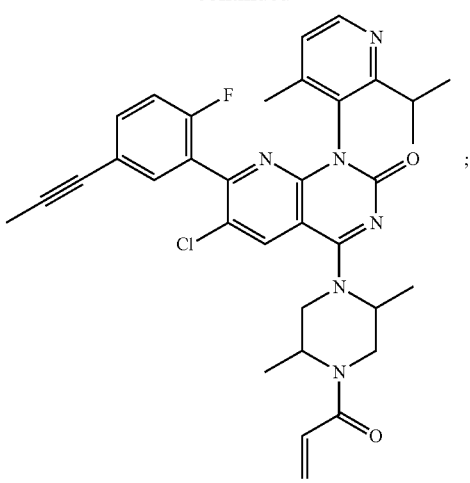
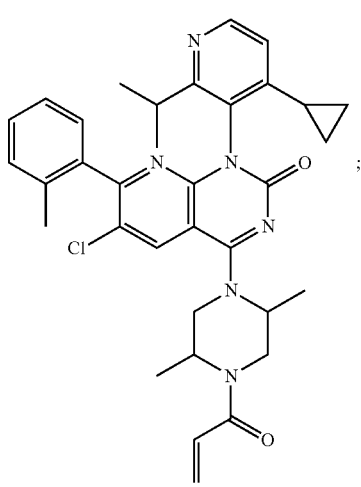
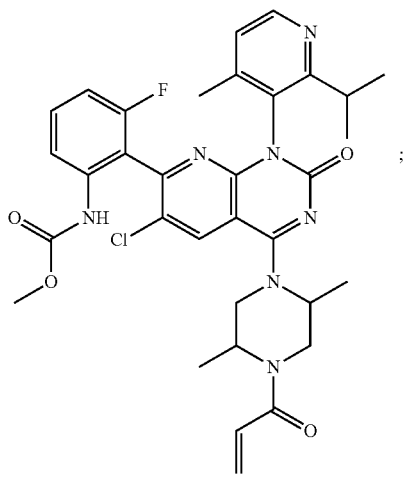

185
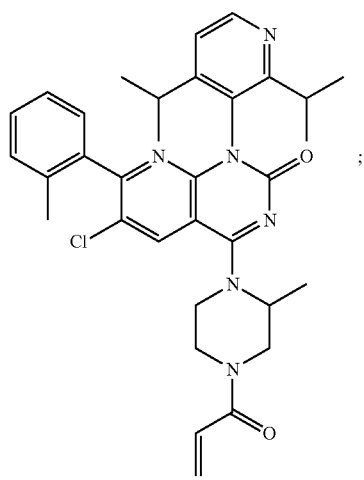
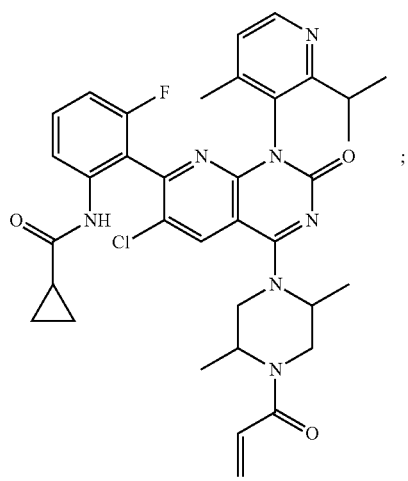
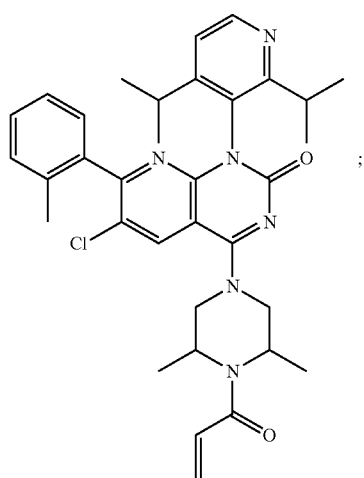
186
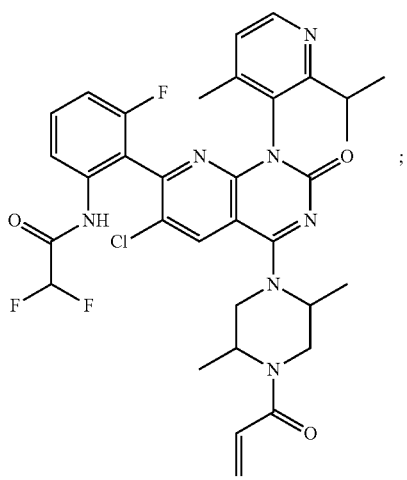
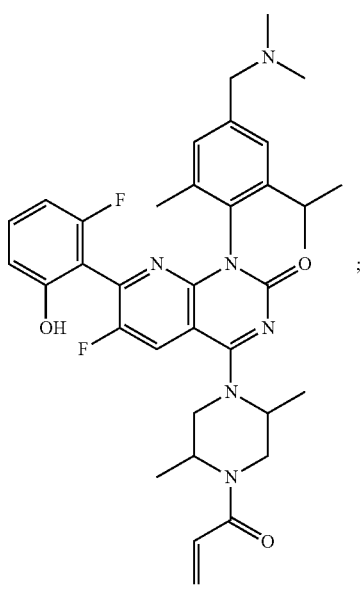
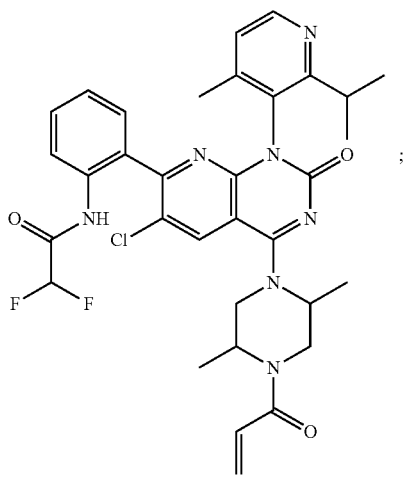

187
-continued
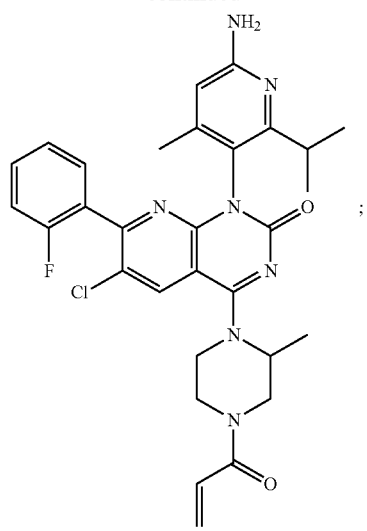
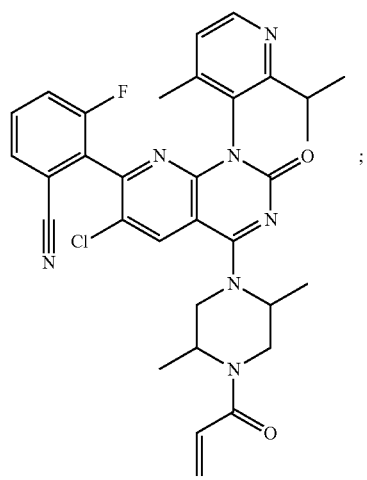
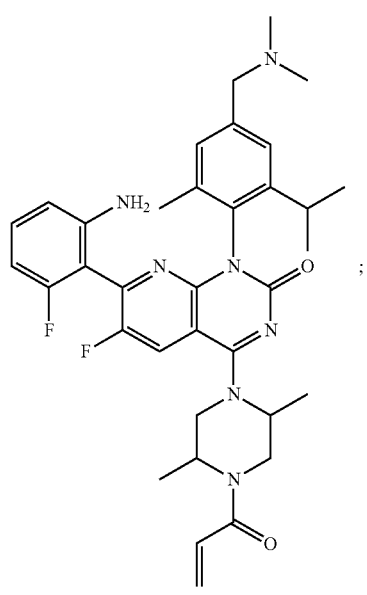
188
-continued
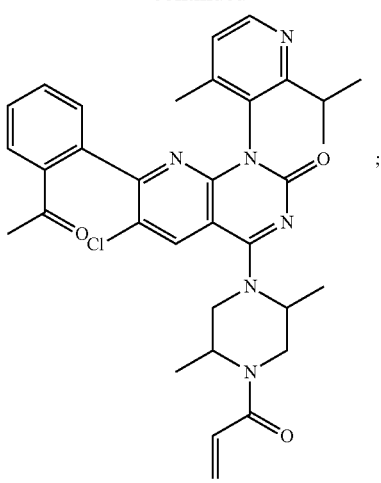
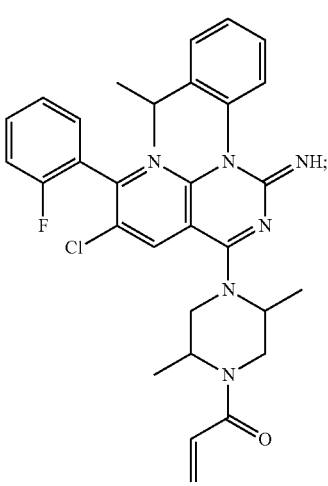
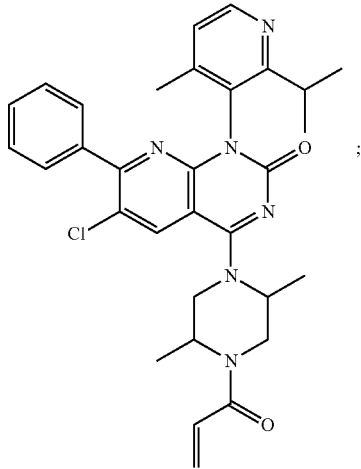

189
-continued
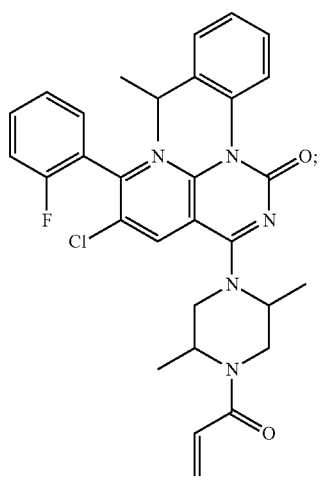
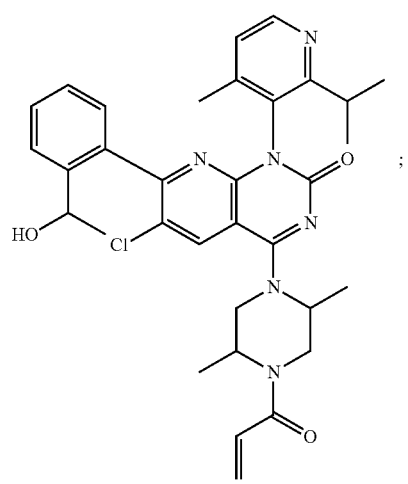
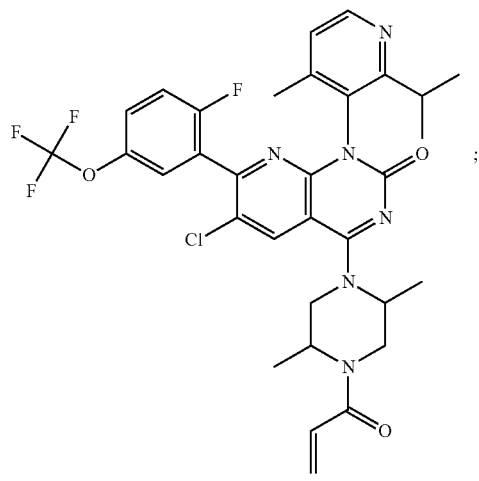
190
-continued
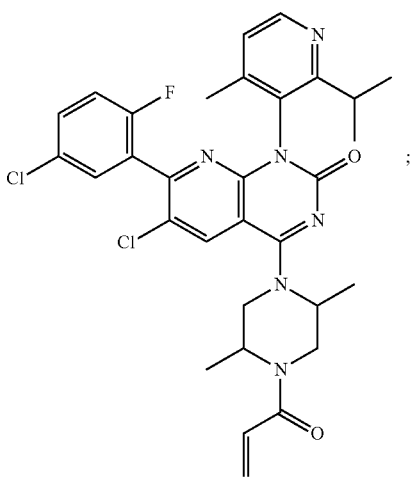
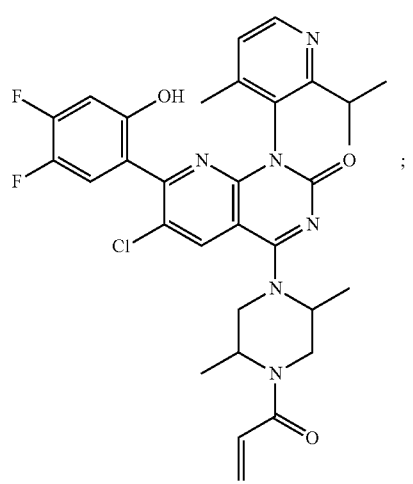
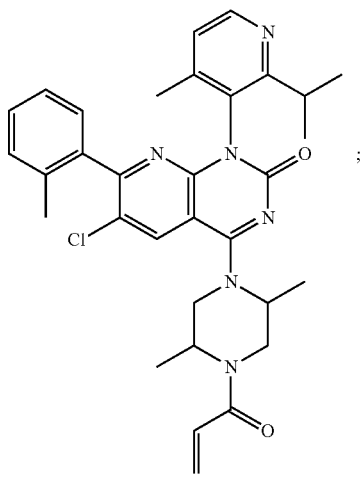

191
-continued
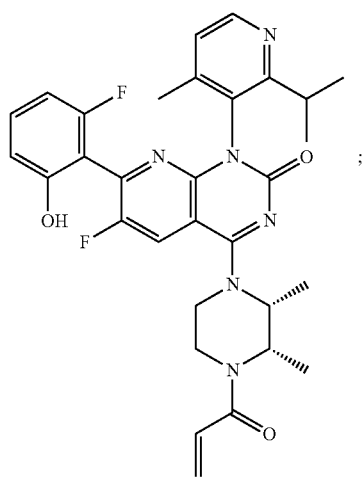
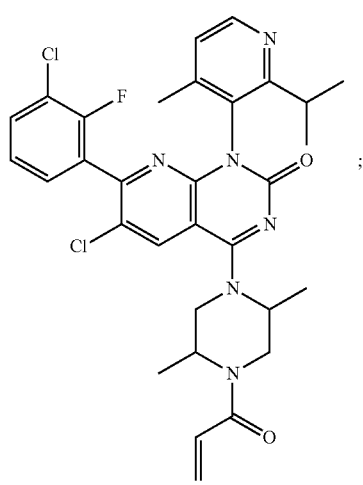
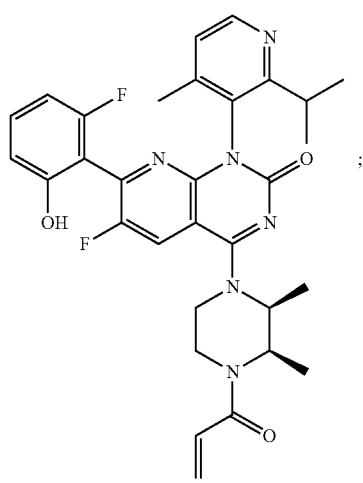
192
-continued
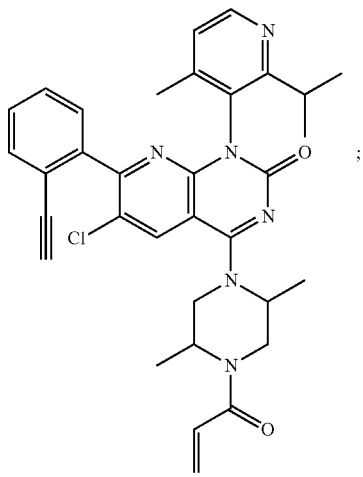
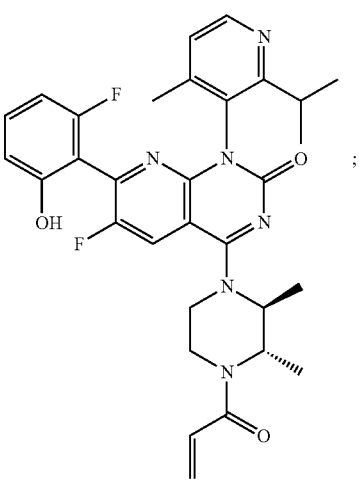
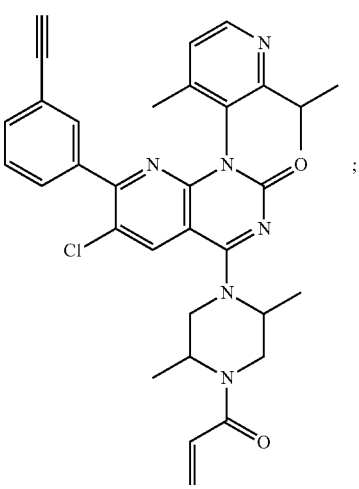

193
-continued
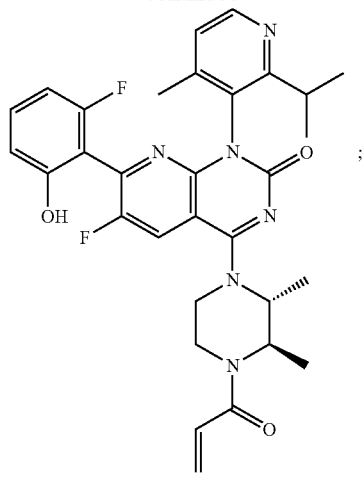
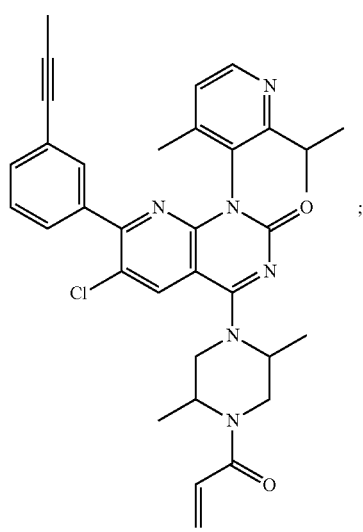
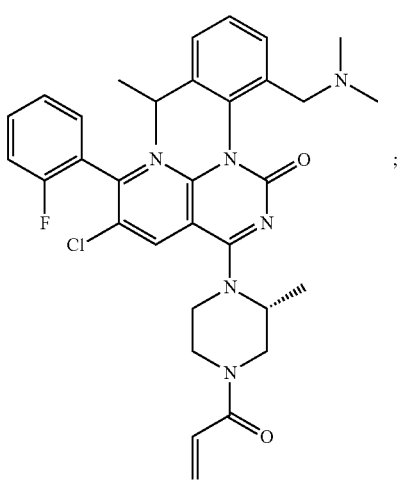
194
-continued
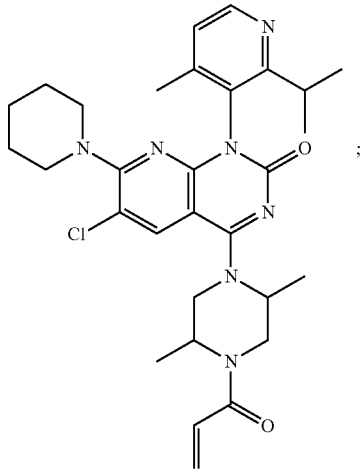
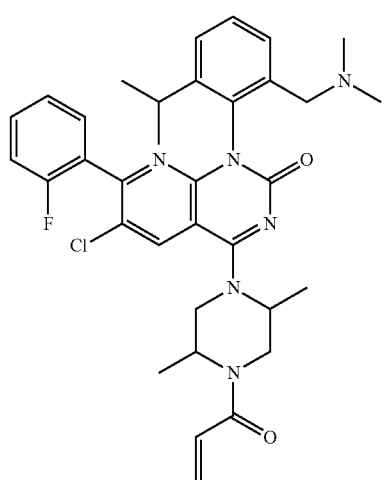
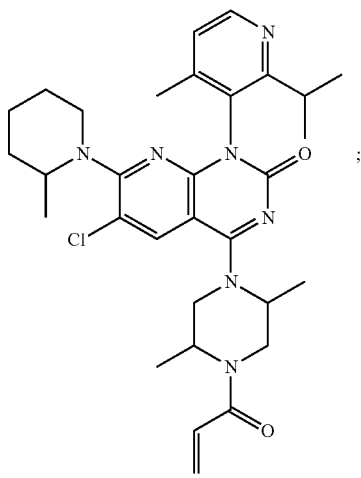

195
-continued
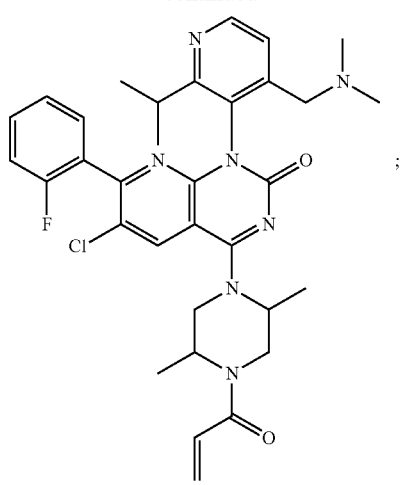
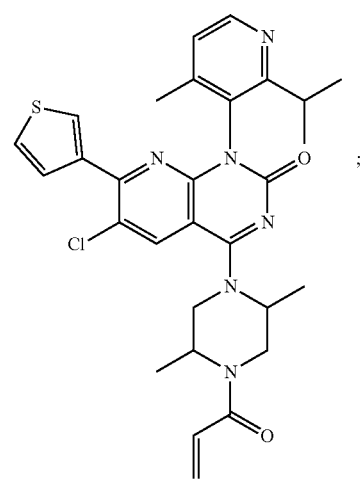
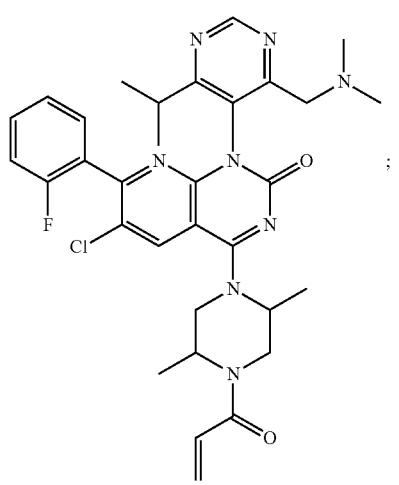
196
-continued
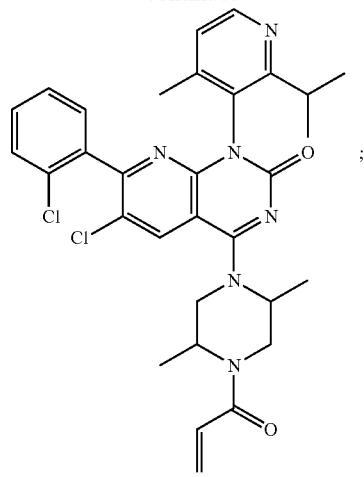
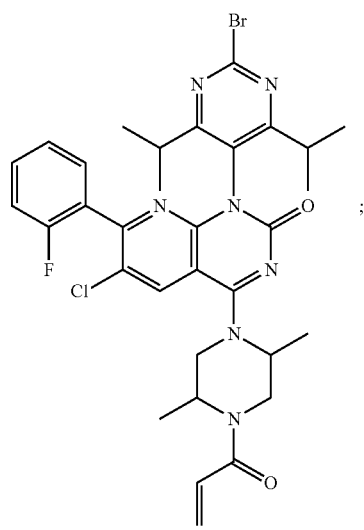
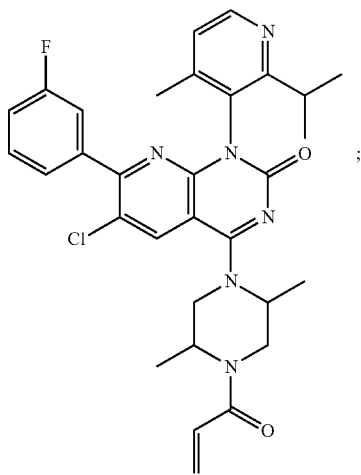

197
-continued
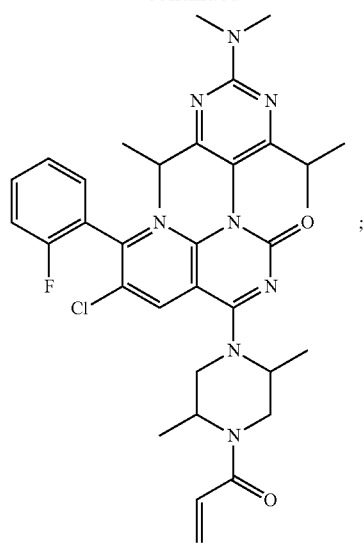
;
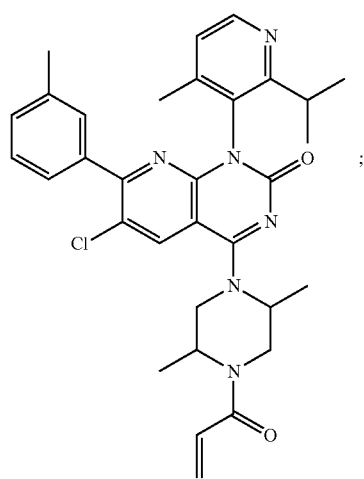
;
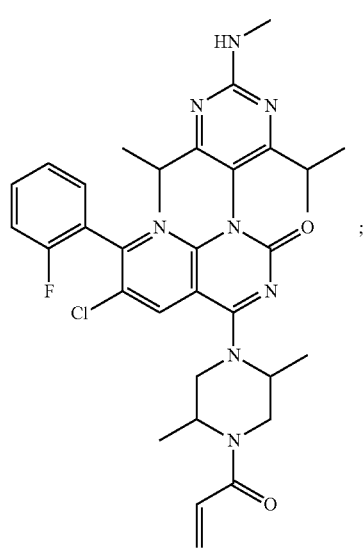
;
198
-continued
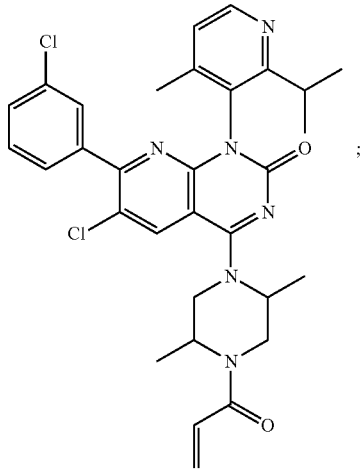
;
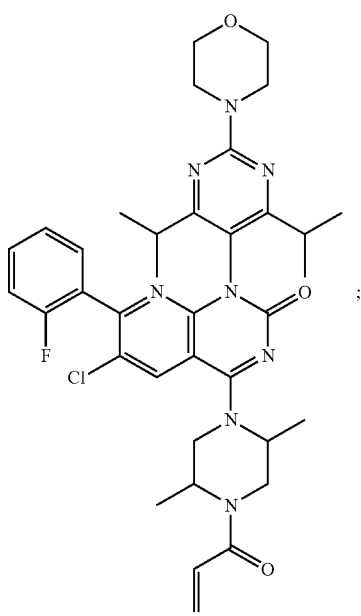
;
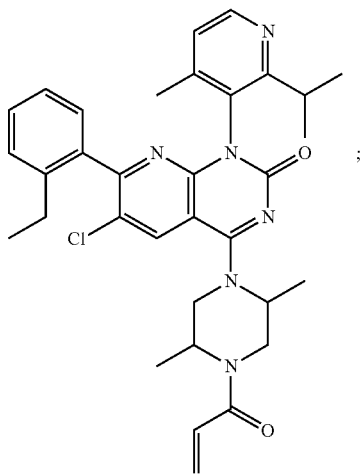
;

199
-continued
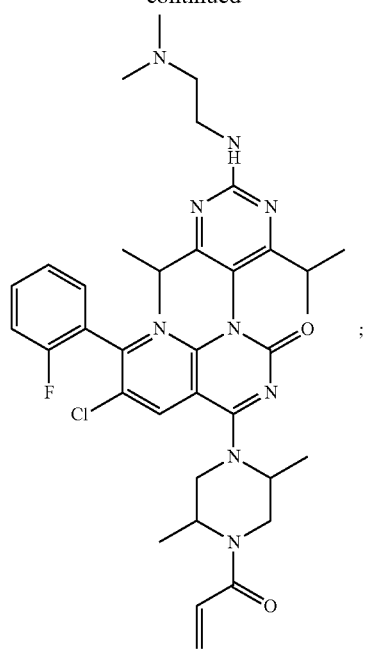
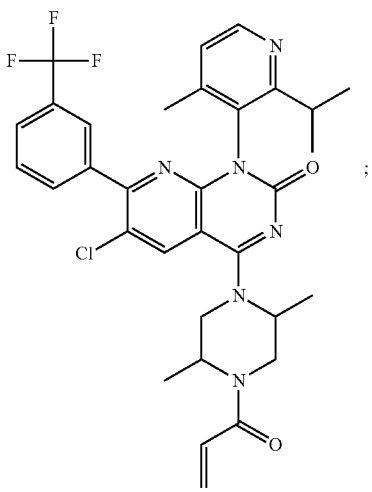
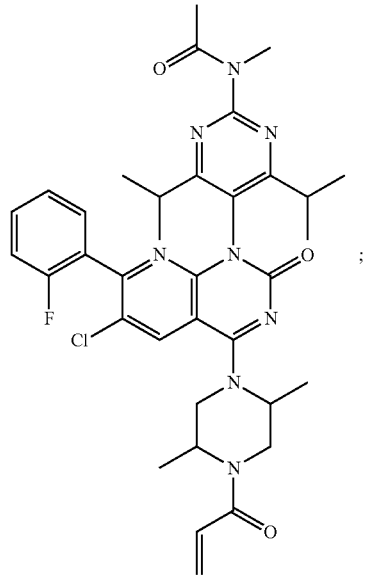
200
-continued
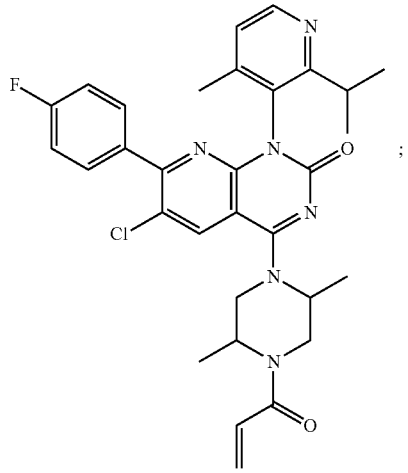
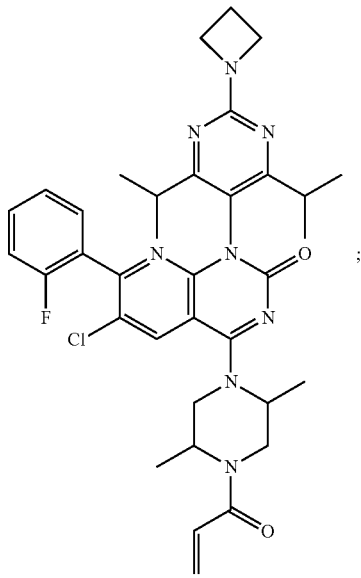
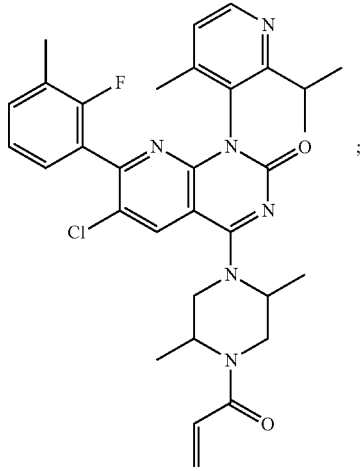

201
-continued
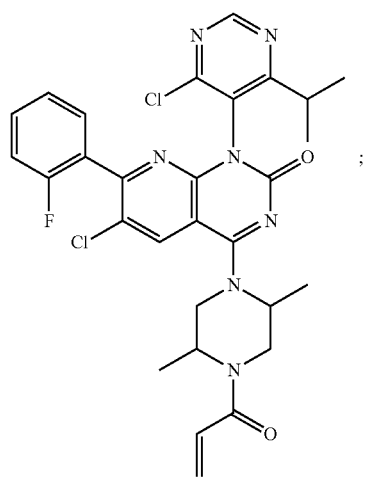
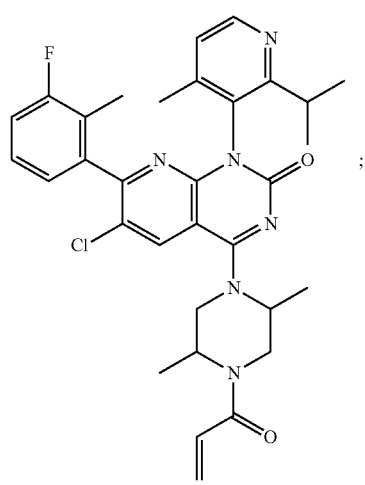

202
-continued
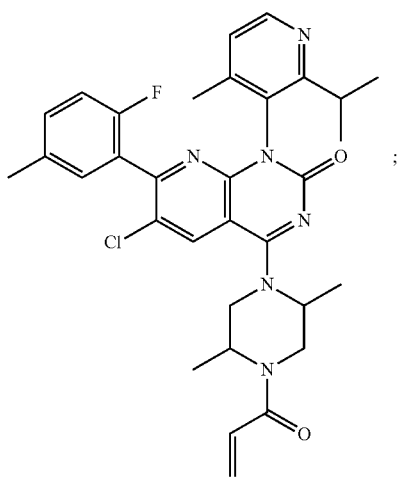
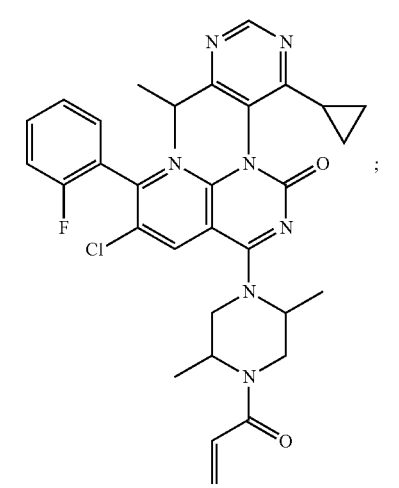
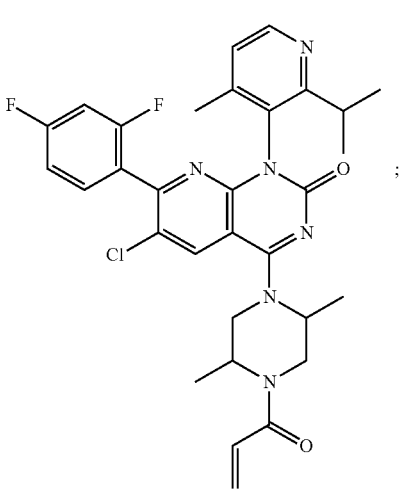

203
-continued

;
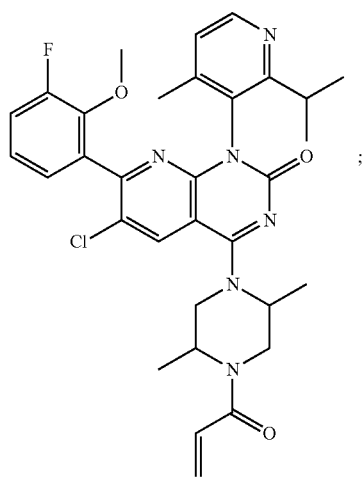
;
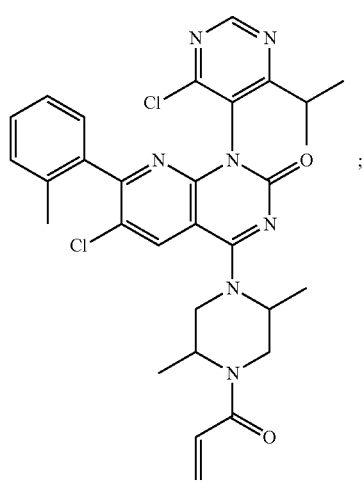
;
204
-continued
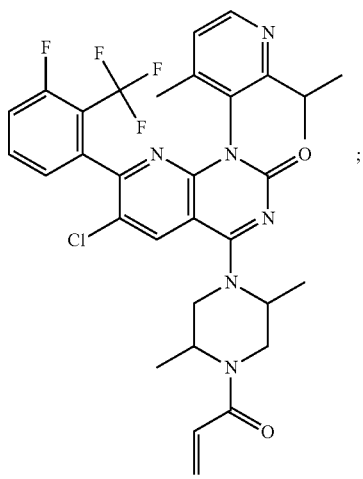
;
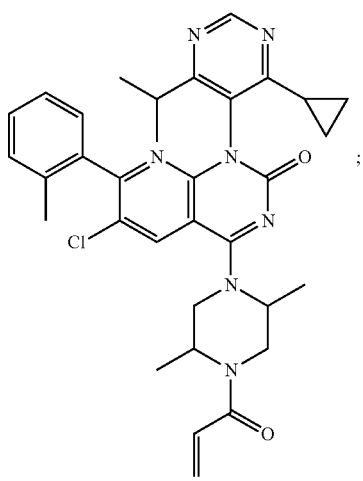
;
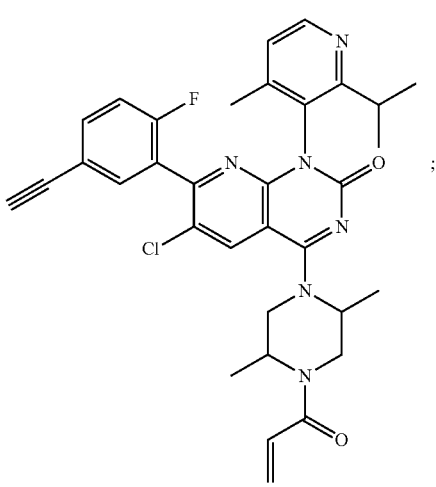
;

205
-continued
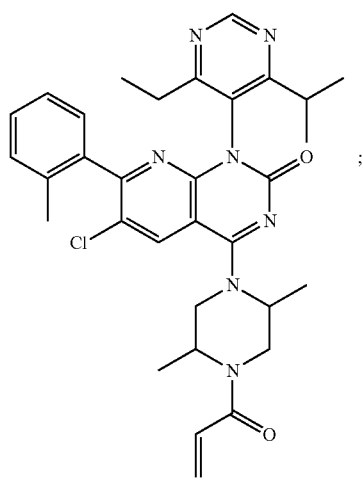
;
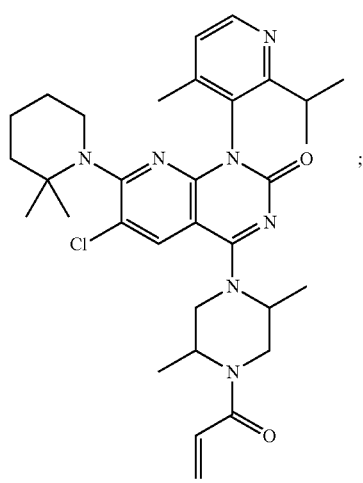
;
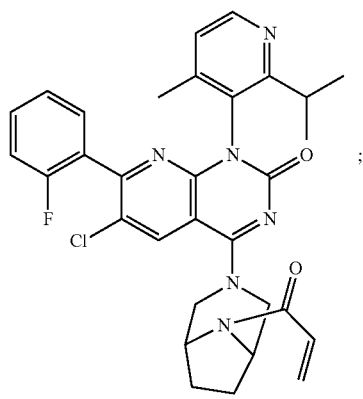
;
206
-continued
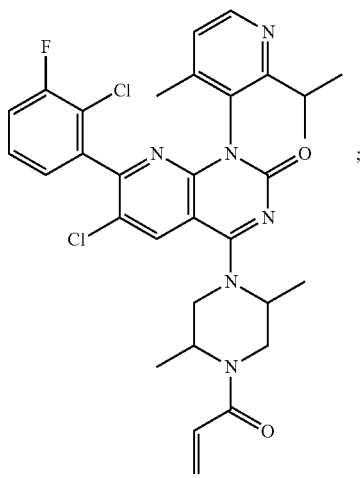
;
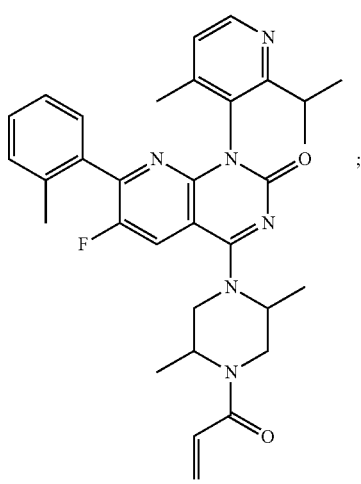
;
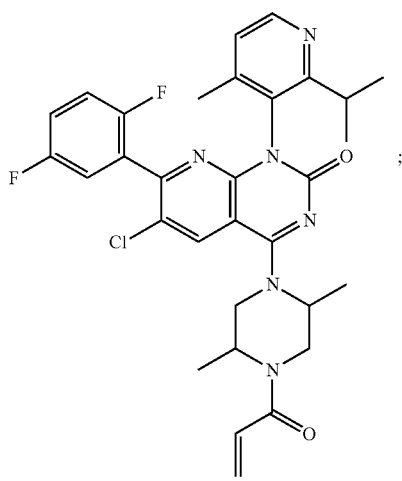
;

207
-continued
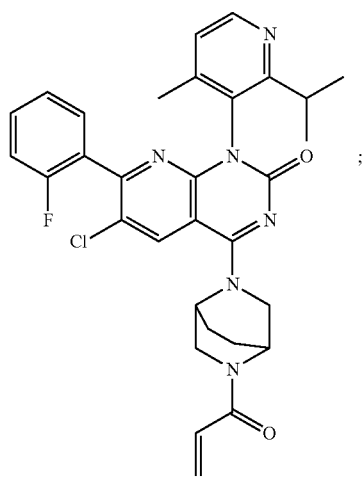
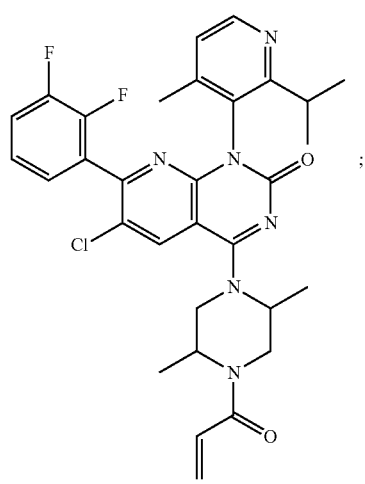
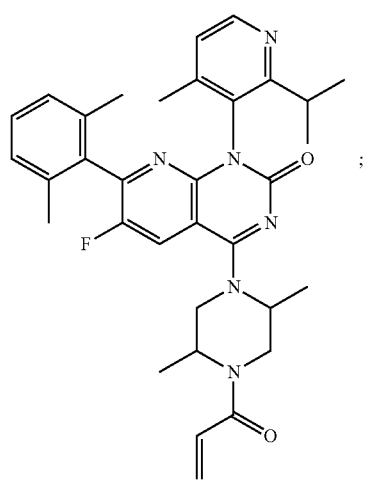
208
-continued
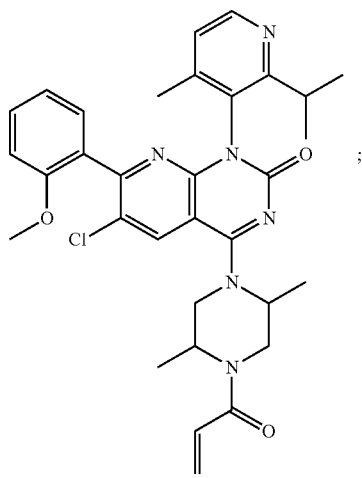
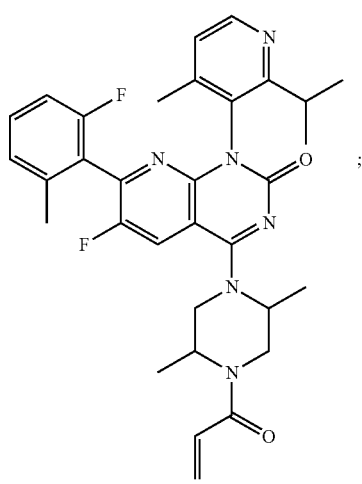
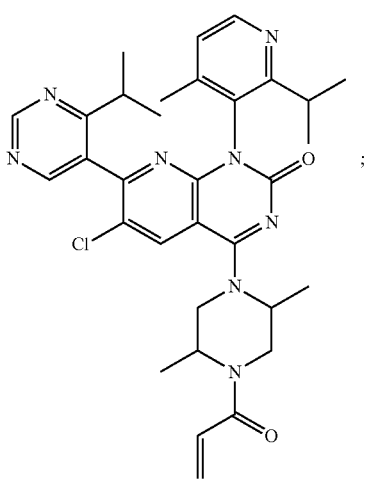

209
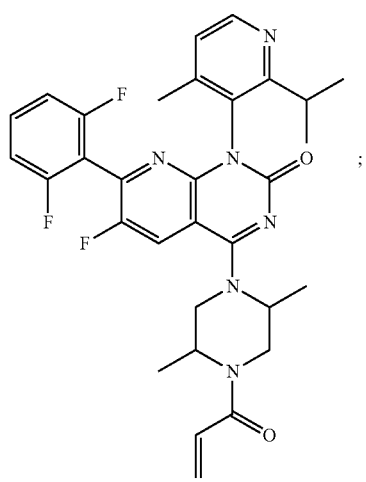
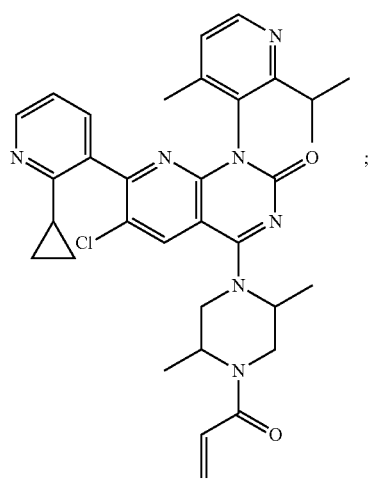
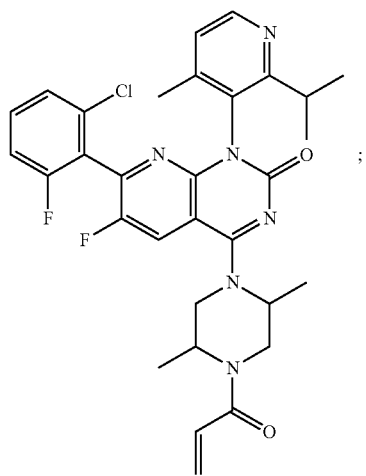
210
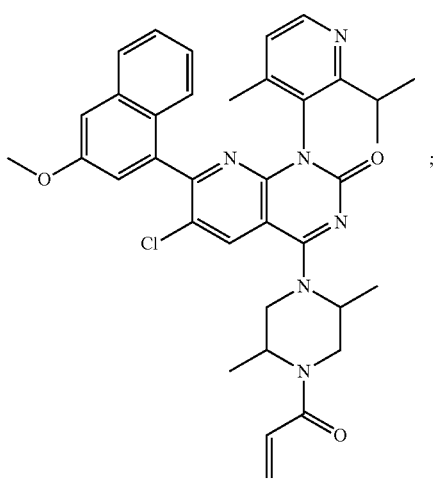
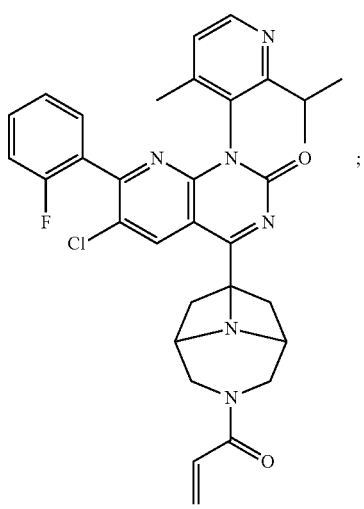
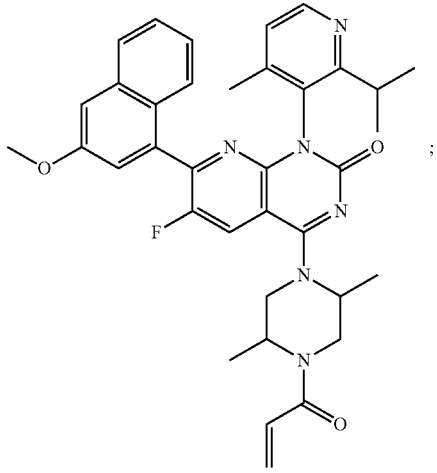

211
-continued
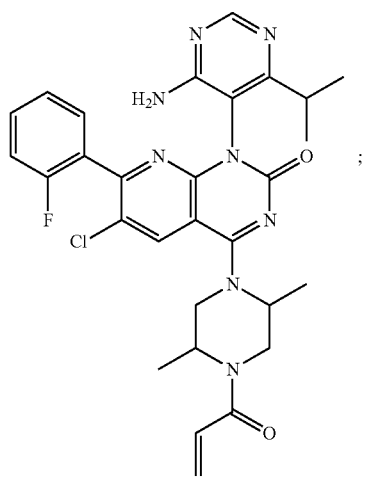
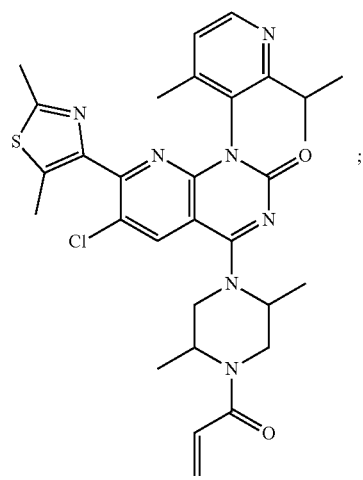
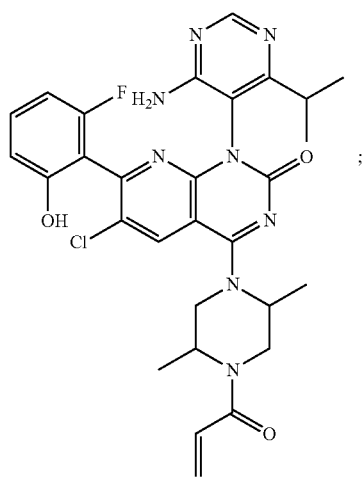
212
-continued
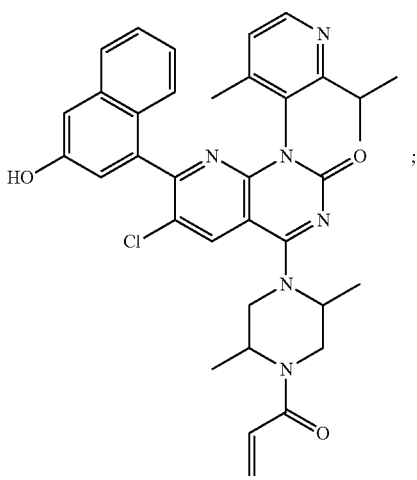
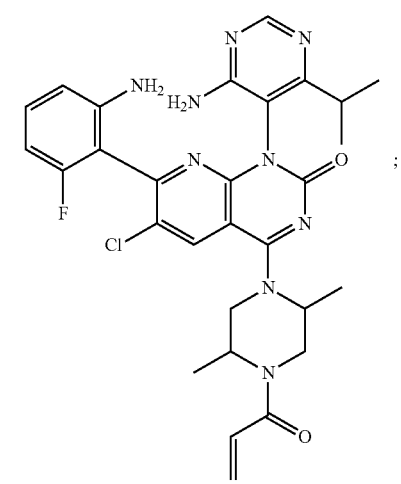
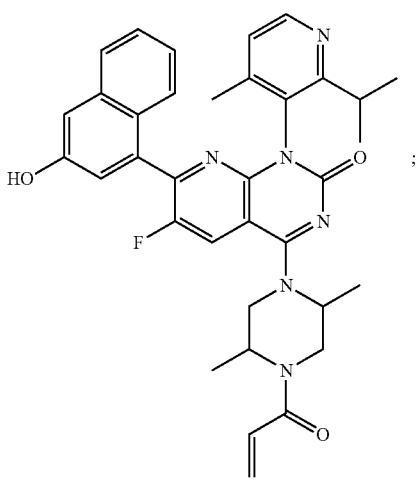

213
-continued
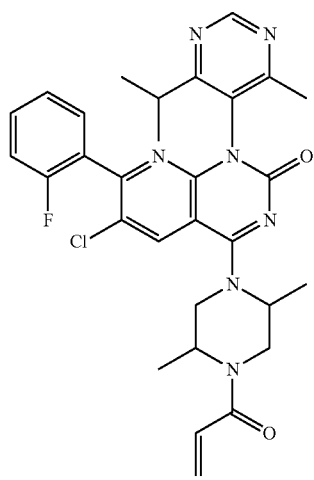
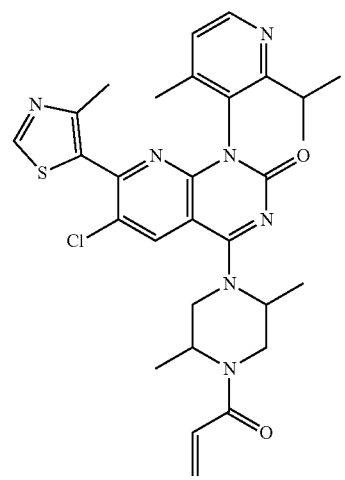
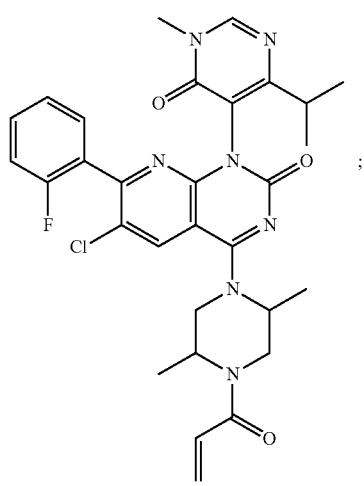
214
-continued
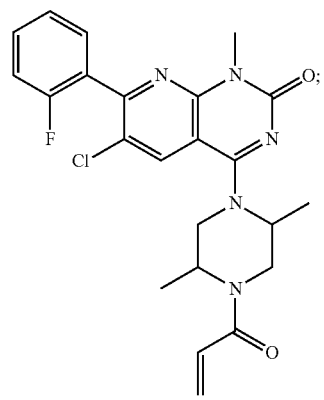
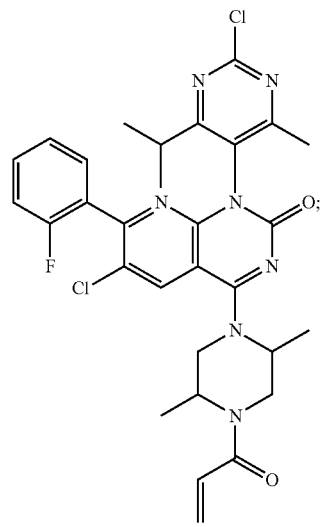
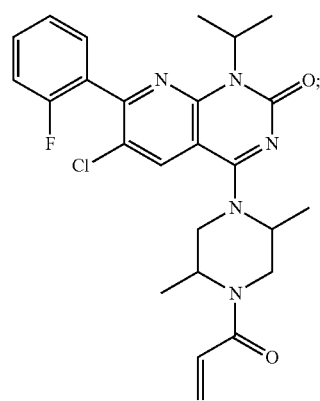

215
-continued
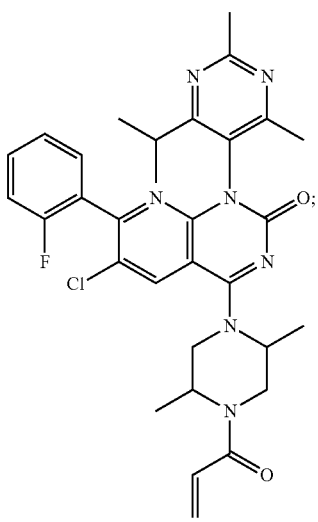
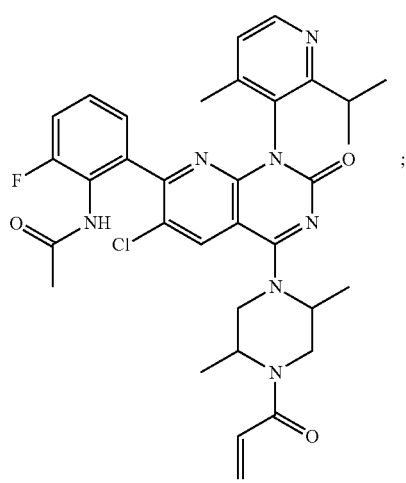
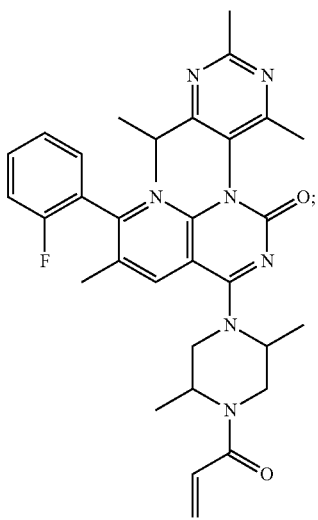
216
-continued
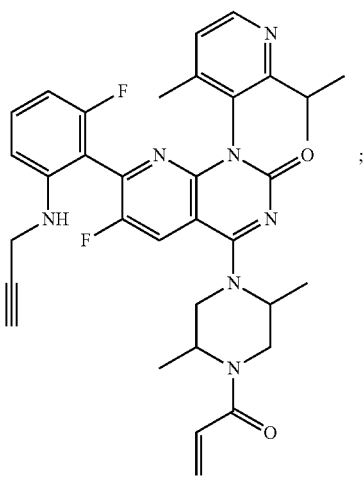
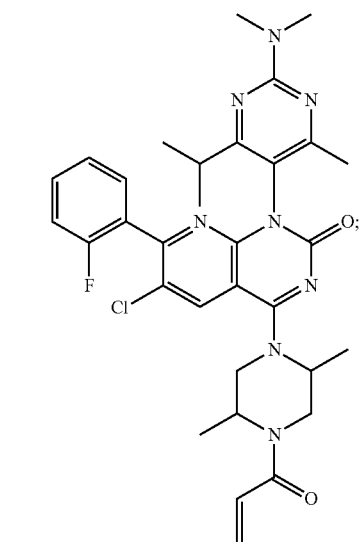

217
-continued
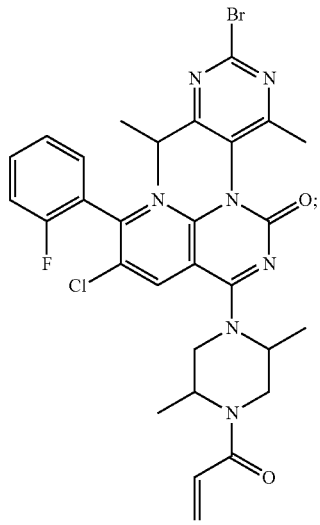
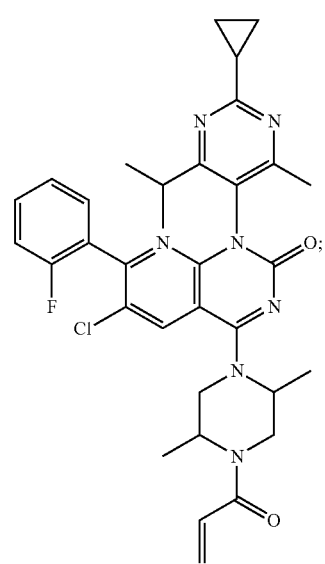
218
-continued
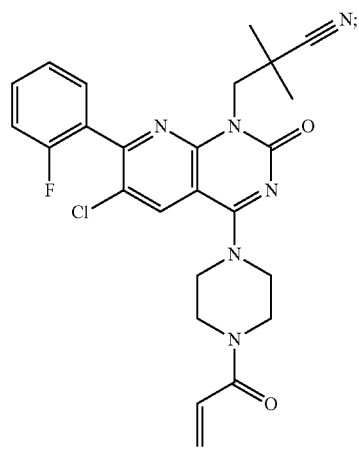
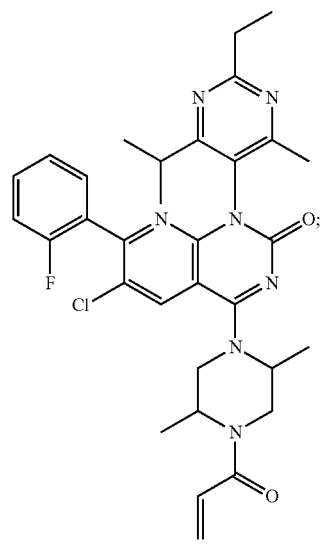
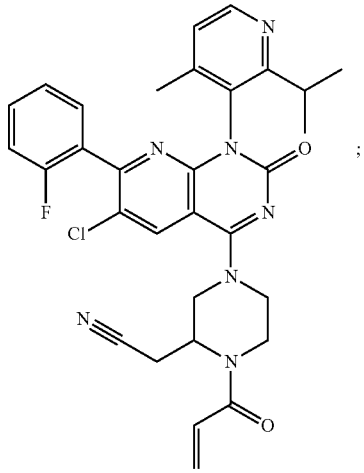

-continued
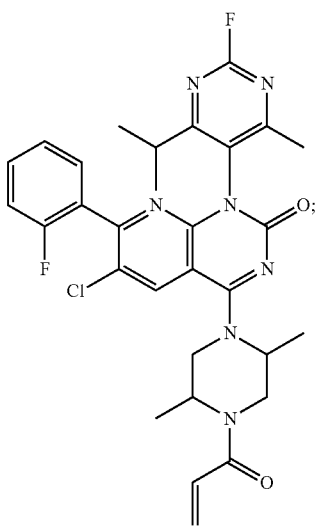
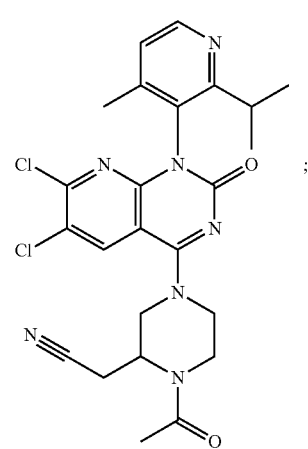
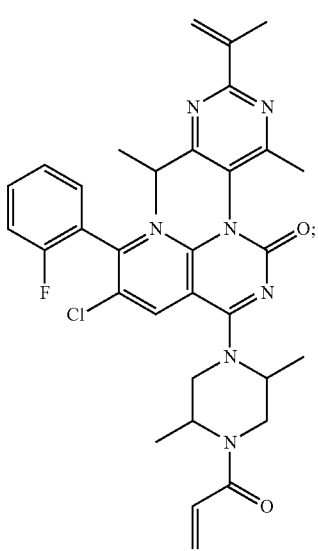
-continued
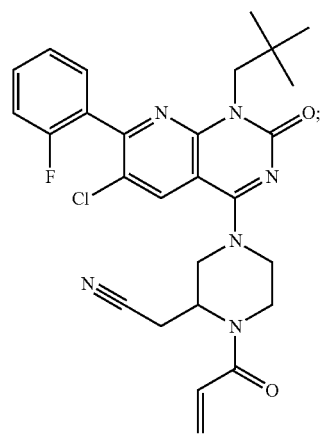
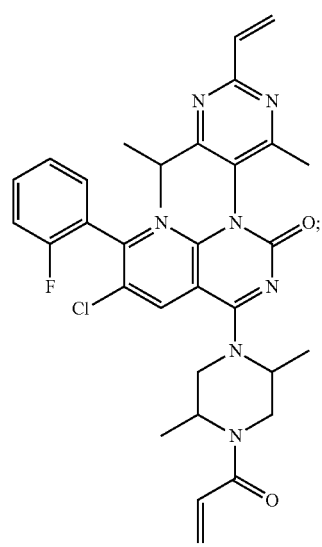
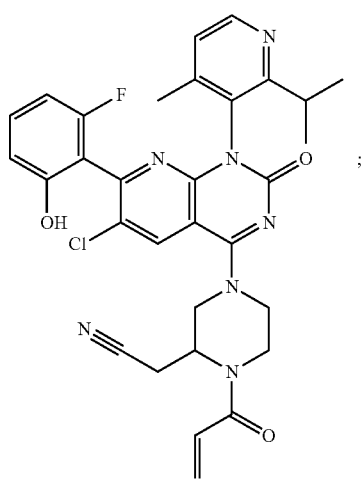

221
-continued
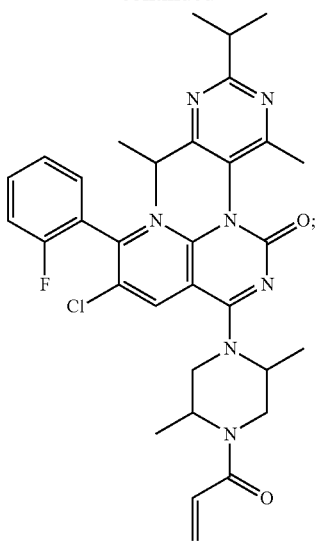
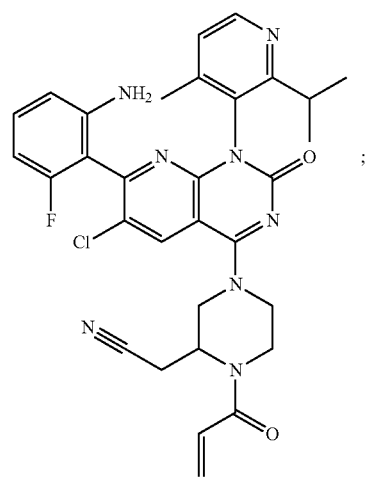
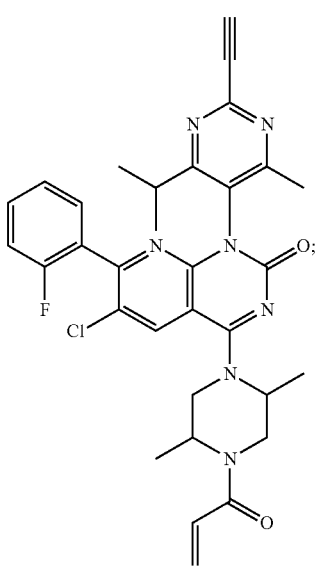
222
-continued
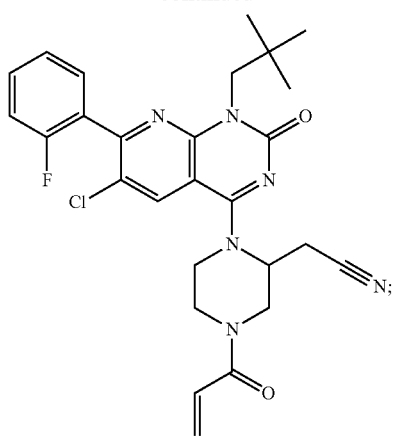
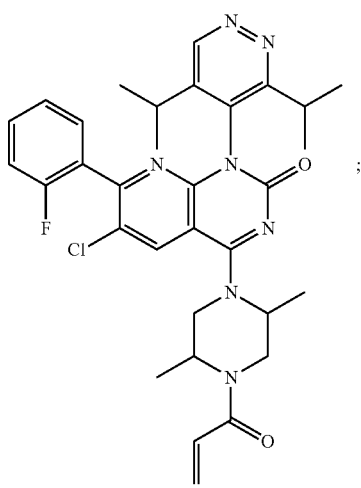

223
-continued
224
-continued
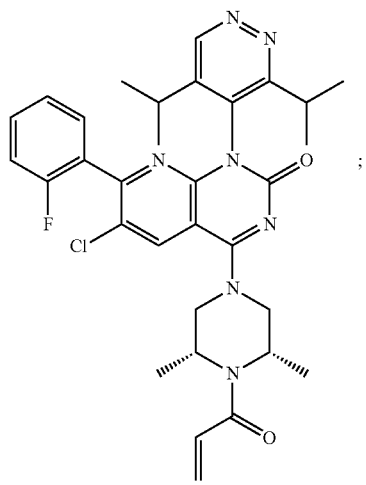
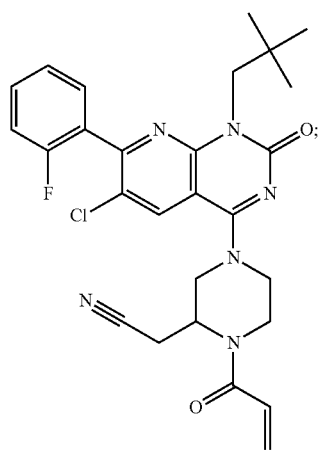
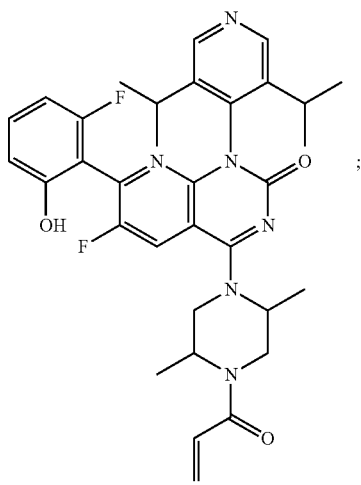
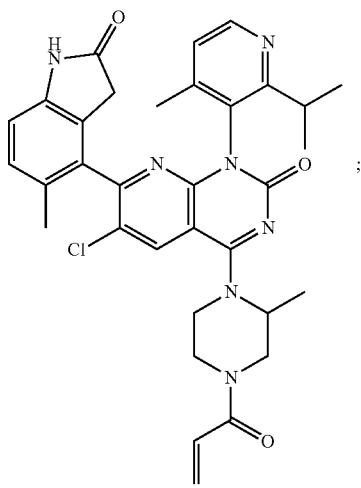

225
-continued
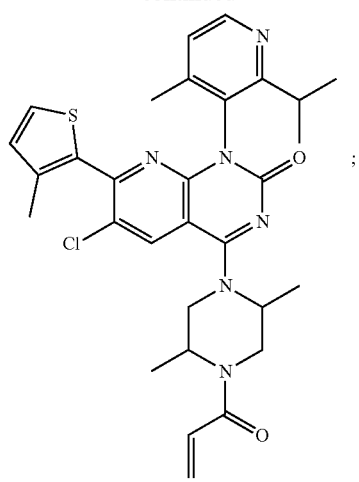
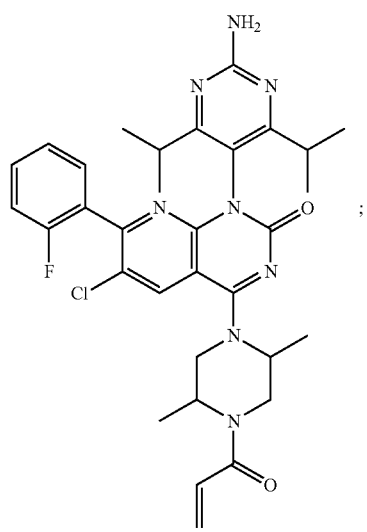
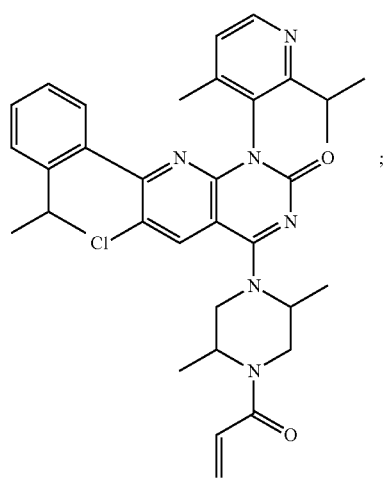
226
-continued
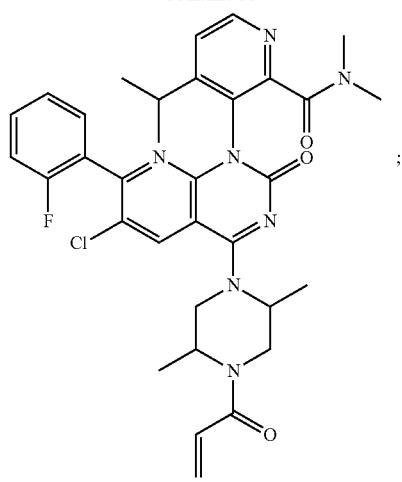
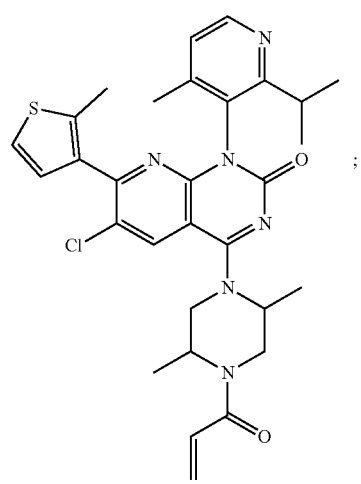
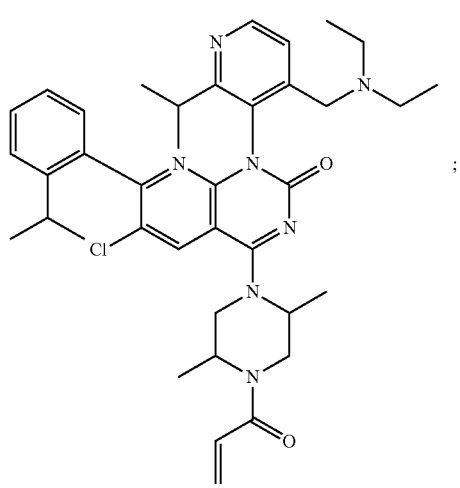

227
-continued
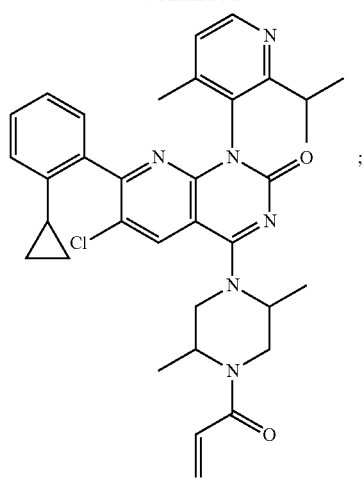
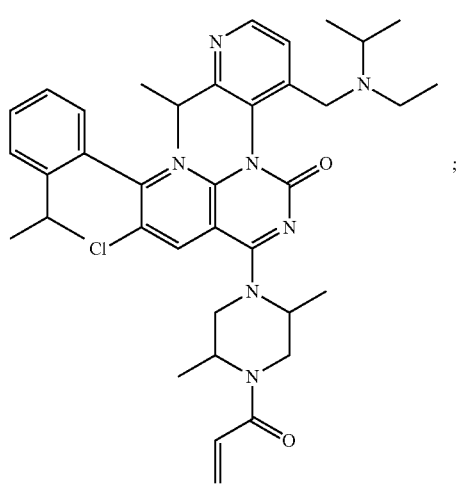
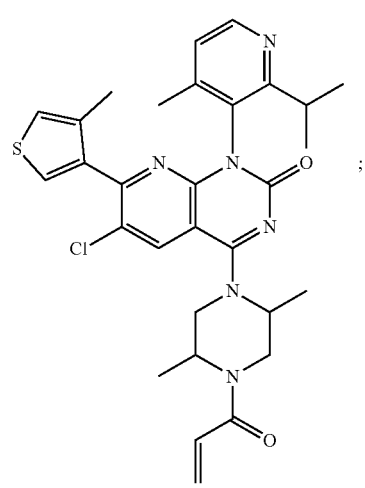
228
-continued
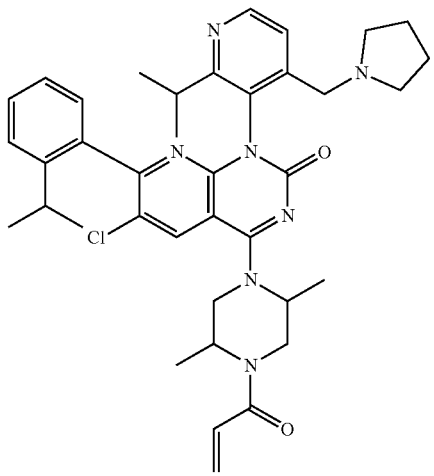
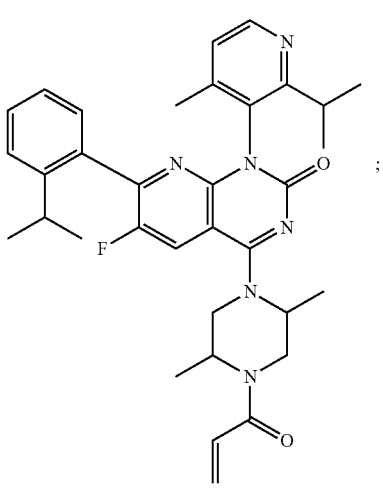
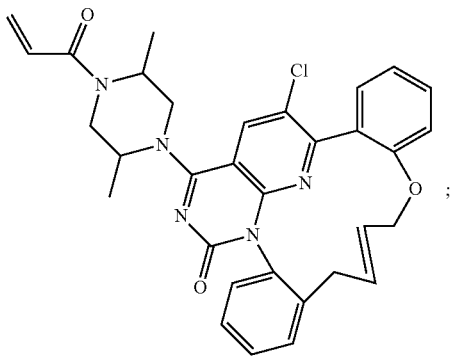

229
-continued
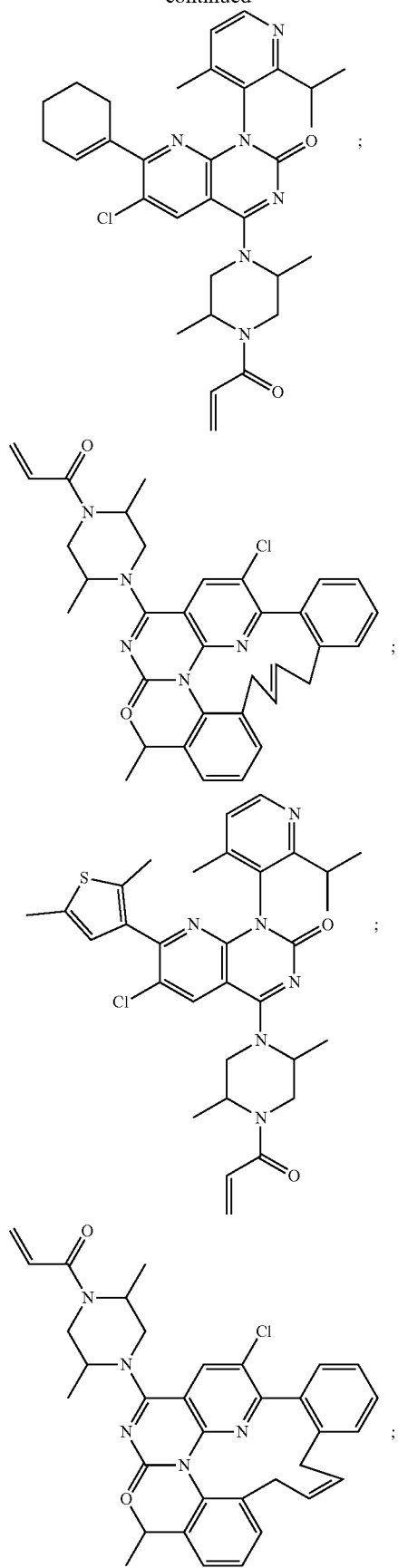
230
-continued
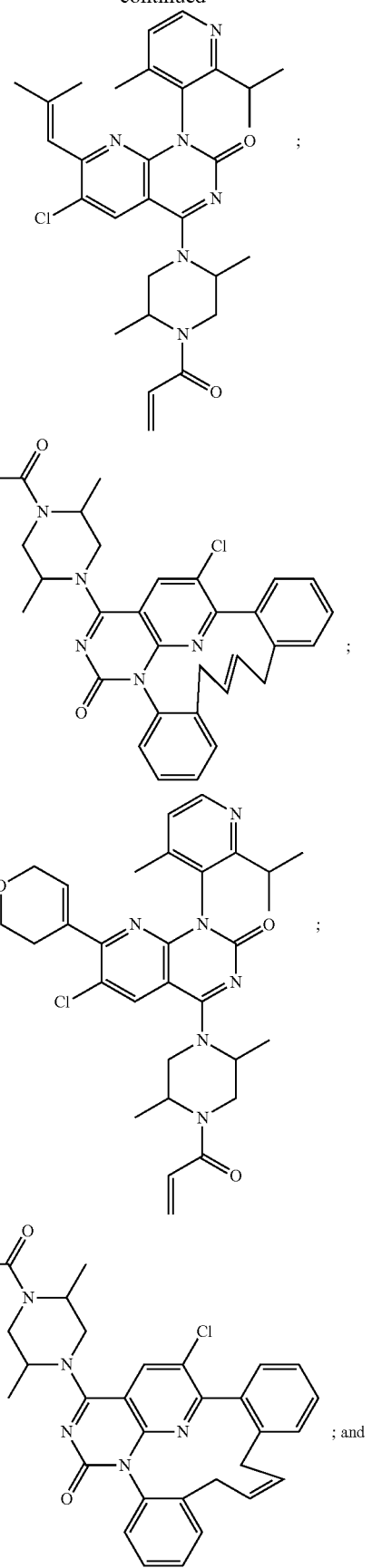
; and

231
-continued

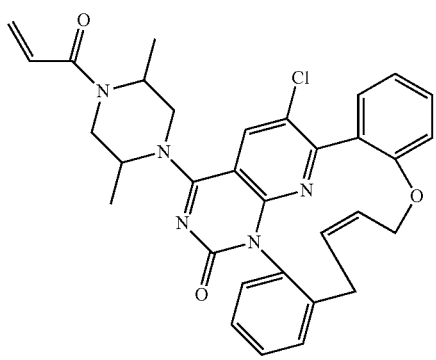

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 2

In another embodiment of the present invention, the present invention comprises a compound having a structure selected from the formula

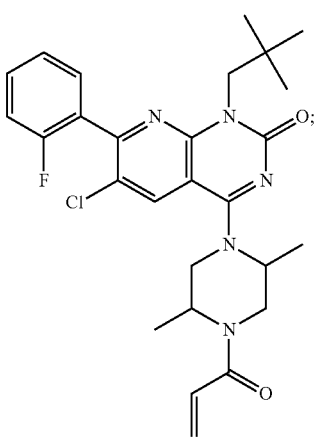

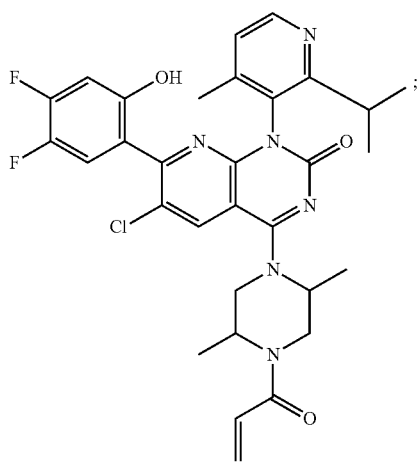

232
-continued

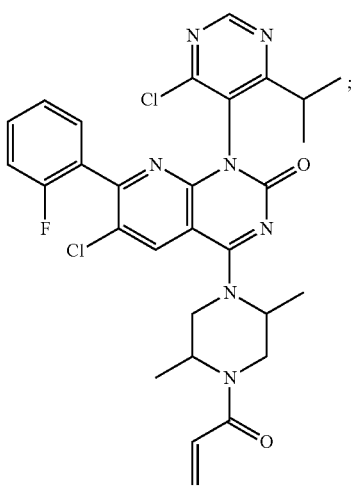

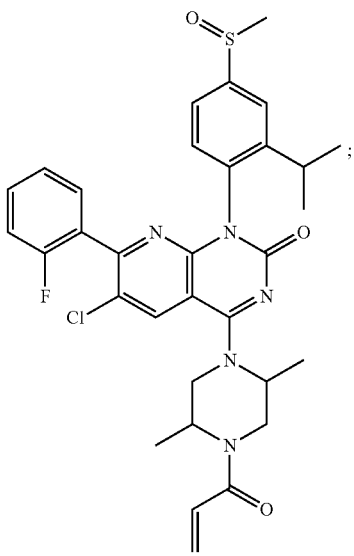

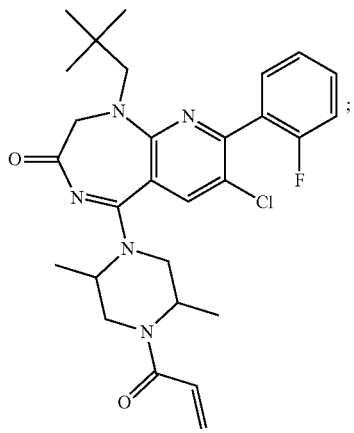

233
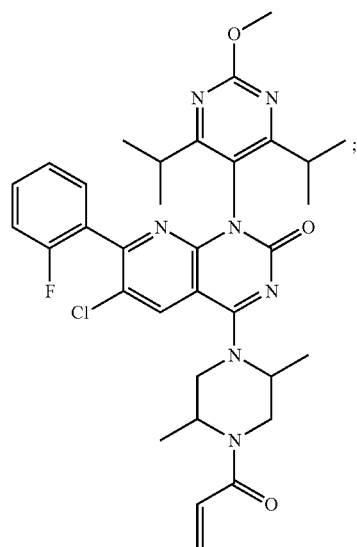
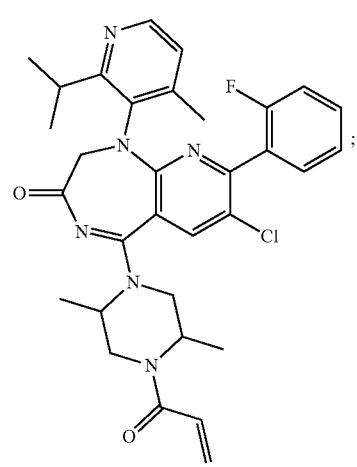
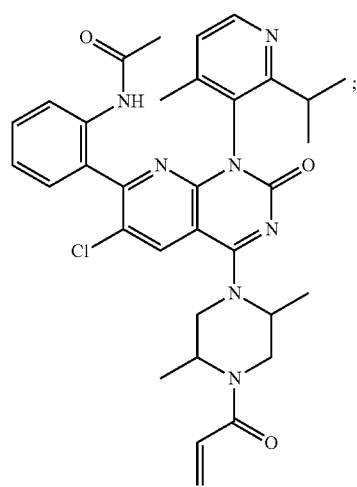
234
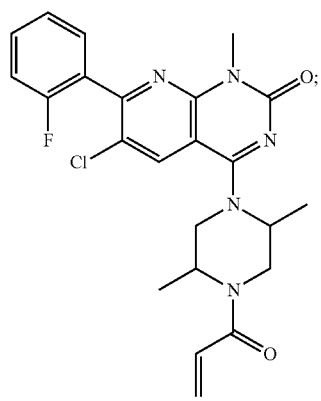
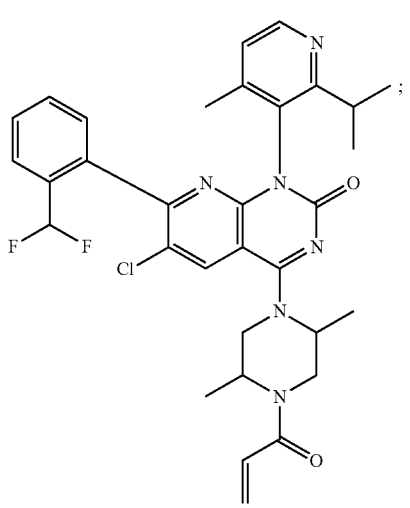

-continued

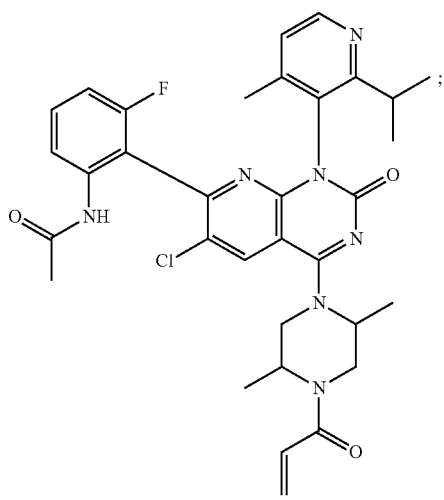

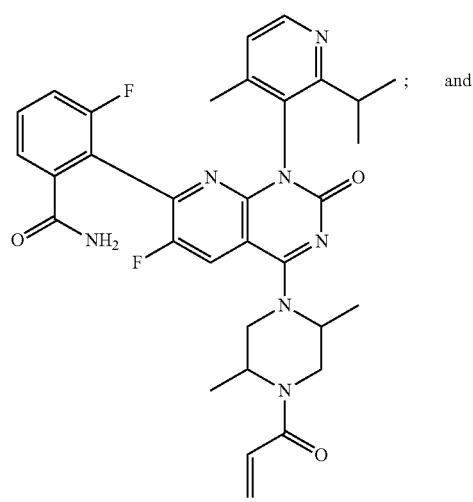

-continued

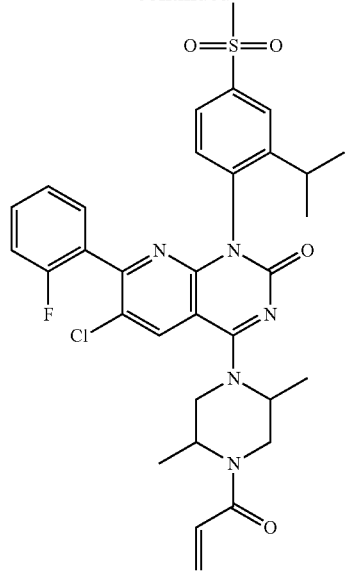

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 3

In another embodiment of the present invention, the present invention comprises the compound of any one of embodiments 1-2 in the form of a pharmaceutically acceptable salt.

Embodiment 4

In another embodiment of the present invention, the present invention comprises a pharmaceutical composition comprising the compound of any one of embodiments 1-3 and a pharmaceutically acceptable excipient.

Embodiment 5

In another embodiment of the present invention, the present invention comprises a method of inhibiting KRAS G12C in a cell, comprising contacting the cell with the compound of any one of embodiments 1-3 or the composition of embodiment 4.

Embodiment 6

In another embodiment of the present invention, the present invention comprises a method of treating cancer in a subject comprising administering to the subject a therapeutically effective amount of the compound of any one of embodiments 1-3 or the composition of embodiment 4.

Embodiment 7

In another embodiment of the present invention, the present invention comprises the method of embodiment 6, wherein the cancer is lung cancer, pancreatic cancer, or colorectal cancer.

Embodiment 8

In another embodiment of the present invention, the present invention comprises the method of embodiment 7, wherein the cancer is lung cancer.

Embodiment 9

In another embodiment of the present invention, the present invention comprises the method of embodiment 7, wherein the cancer is pancreatic cancer.

Embodiment 10

In another embodiment of the present invention, the present invention comprises the method of embodiment 7, wherein the cancer is colorectal cancer.

Embodiment 11

In another embodiment of the present invention, the present invention comprises the method of embodiment 6, further comprising administering to the patient in need thereof a therapeutically effective amount of one or more additional pharmaceutically active compounds.

Embodiment 12

In another embodiment of the present invention, the present invention comprises the method of embodiment 11, wherein the one or more additional pharmaceutically active compounds is an anti-PD-1 antibody

Embodiment 13

In another embodiment of the present invention, the present invention comprises the method of embodiment 12, wherein the anti-PD-1 antibody is pembrolizumab.

Embodiment 14

In another embodiment of the present invention, the present invention comprises the method of embodiment 12 wherein the anti-PD-1 antibody is niolumab.

Embodiment 15

In another embodiment of the present invention, the present invention comprises the method of embodiment 11, wherein the one or more additional pharmaceutically active compounds is an MCl-1 inhibitor.

Embodiment 16

In another embodiment of the present invention, the present invention comprises the method of embodiment 11, wherein the one or more additional pharmaceutically active compounds is a MEK inhibitor.

Embodiment 17

In another embodiment of the present invention, the present invention comprises the method of embodiment 11, wherein the one or more additional pharmaceutically active compounds is daratumumab.

Embodiment 18

In another embodiment of the present invention, the present invention comprises the method of embodiment 11, wherein the one or more additional pharmaceutically active compounds is an immunomodulatory agent.

Embodiment 19

In another embodiment of the present invention, the present invention comprises the use of a compound according to any one of embodiments 1-3 for treating cancer in a subject.

Embodiment 20

In another embodiment of the present invention, the present invention comprises a compound according to any one of embodiments 1-3 in the preparation of a medicament for treating cancer.

Embodiment 21

In another embodiment of the present invention, the present invention comprises the compound according to embodiment 20, wherein the cancer is non-small cell lung cancer.

Synthesis of Disclosed Compounds

Compounds as disclosed herein can be synthesized via a number of specific methods. The examples which outline specific synthetic routes, and the generic schemes below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

Pharmaceutical Compositions, Dosing, and Routes of Administration

Also provided herein are pharmaceutical compositions that include a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine. L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 1500 mg/day, about 5 mg/day to about 1000 mg/day, about 10 mg/day to about 750 mg/day, about 3 mg/day to about 350 mg/day, or about 100 mg/day to about 250 mg/day. Such doses may be administered in a single dose or it may be divided into multiple doses.

Methods of Using KRAS G12C Inhibitors

The present disclosure provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by G12C KRAS, HRAS or NRAS mutation (e.g., cancer).

In some embodiments, a method for treatment of cancer is provided, the method comprising administering an effective amount of any of the foregoing pharmaceutical compositions comprising a compound as disclosed herein to a subject in need thereof. In some embodiments, the cancer is mediated by a KRAS, HRAS or NRAS G12C mutation. In various embodiments, the cancer is pancreatic cancer, colorectal cancer or lung cancer. In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound as disclosed herein or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount a compound disclosed herein.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound as disclosed herein, or a pharmaceutically acceptable salt thereof. In some embodiments, said method relates to the treatment of a subject who suffers from a cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/mycloproliferative neoplasms, multiple myeloma, merkel cell carcinoma, malignant mesothelioma, malignant fibrous histiocytoma of bone and ostcosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C Mutant KRAS, HRAS or NRAS protein activity by contacting the protein with an effective amount of a compound of the disclosure. Modulation can be inhibiting or activating protein activity. In some embodiments, the disclosure provides methods of inhibiting protein activity by contacting the G12C Mutant KRAS, HRAS or NRAS protein with an effective amount of a compound of the disclosure in solution. In some embodiments, the disclosure provides methods of inhibiting the G12C Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of a compound of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS, HRAS or NRAS G12C activity in a cell by contacting said cell with an amount of a compound of the disclosure sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of a compound of the disclosure sufficient to inhibit the activity of KRAS. HRAS or NRAS G12C in said tissue. In some embodiments, the disclosure provides methods of inhibiting KRAS, HRAS or NRAS G12C activity in an organism by contacting said organism with an amount of a compound of the disclosure sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of a compound of the disclosure sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of a compound of the disclosure sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of a compound of the disclosure sufficient to inhibit the activity of KRAS, HRAS or NRAS G12C in said human. The present disclosure provides methods of treating a disease mediated by KRAS, HRAS or NRAS G12C activity in a subject in need of such treatment.

Combination Therapy:

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec®, (Imatinib Mesylate), Kyprolis® (carfilzomib), Velcade® (bortezomib), Casodex (bicalutamide), Iressa® (gefitinib), Venclexta™ (venetoclax) and Adriamycin™, (docorubicin) as well as a host of chemotherapeutic agents. Non-limiting examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, chlorocyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide, mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675. European Patent Publication EP1786785, European Patent Publication No. EP 1181017, United States Publication No. US20090012085. United States Publication U.S. Pat. No. 5,863,949, United States Publication U.S. Pat. No. 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-1, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflomithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-$_{n3}$, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel crythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeternma), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Phanna), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto). EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland. EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-11142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly. USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory. New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca. UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals. USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline. UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda. Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinvaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists (ImClone Systems, USA); Vasostatin, (National Institutes of Health, USA); vaccine, Flk-1, (ImClone Systems, USA); TZ 93, (Tsumura, Japan); TumStatin, (Beth Israel Hospital USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 176; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., clotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zamestra™), anti-CD138

(e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387). PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamcethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds of the present invention may also be used in combination with an additional pharmaceutically active compound that disrupts or inhibits RAS-RAF-ERK or PI3K-AKT-TOR signaling pathways. In other such combinations, the additional pharmaceutically active compound is a PD-1 and PD-L1 antagonist. The compounds or pharmaceutical compositions of the disclosure can also be used in combination with an amount of one or more substances selected from EGFR inhibitors, MEK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., *Pharmacogenetics and Pharmacogenomics In Oncology Therapeutic Antibody Development*, BioTechniques 2005; 39(4): 565-8, and Pacz J G, et. al., *EGFR Mutations In Lung Cancer Correlation With Clinical Response To Gefitinib Therapy*, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12):1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res.

1:1311-1318; Huang, S. M., et al., 1999, Cancer Res. 15:59(8):1935-40; and Yang, X., et al., 1999, Cancer Res. 59:1236-1243, Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) Biochem. J. 385 (Pt. 2), 399-408); Akt-1-1,2 (inhibits Ak1 and 2) (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); and triciribine (TCN or API-2 or NCI identifier: NSC 154020; Yang et al. (2004) Cancer Res. 64, 4394-9).

TOR inhibitors include, but are not limited to, AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573. AP23464, or AP23841; 40-(2-hydroxyethyl)rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883. U.S. Pat. Nos. 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

MCl-1 inhibitors include, but are not limited to, AMG-176, AMG-397, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

SHP inhibitors include, but are not limited to, SHP099.

Proteasome inhibitors include, but are not limited to, Kyprolis® (carfilzomib), Velcade® (bortezomib), and oprozomib.

Immune therapies include, but are not limited to, anti-PD-1 agents, anti-PDL-1 agents, anti-CTLA-4 agents, anti-LAG1 agents, and anti-OX40 agents.

Monoclonal antibodies include, but are not limited to, Darzalex® (daratumumab), Herceptin® (trastuzumab), Avastin® (bevacizumab), Rituxan® (rituximab), Lucentis® (ranibizumab), and Eylea® (aflibercept).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 110(1):186-192 (2007). Thompson et al., Clin. Cancer Res. 13(6):1757-1761 (2007), and Korman et al., International Application No. PCT/JP2006/309606 (publication no. WO 2006/121168 A1), each of which are expressly incorporated by reference herein, include: Keytruda® (pembrolizumab), Opdivo® (niolumab), Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CDI37), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

In a particular embodiment, the compounds of the present invention are used in combination with an anti-PD-1 antibody, such as AMG 404. In a specific embodiment, the anti-PD-1 antibody (or antigen binding antibody fragment thereof) comprises 1, 2, 3, 4, 5, or all 6 the CDR amino acid sequences of SEQ ID NOs: 1-6 (representing HC CDR1, HC CDR2, HC CDR3, LC CDR1, LC CDR2, and LC CDR3, in that order). In specific embodiments, the anti-PD-1 antibody (or antigen binding antibody fragment thereof) comprises all 6 of the CDR amino acid sequences of SEQ ID NOs: 1-6. In other embodiments, the anti-PD-1 antibody (or antigen binding antibody fragment thereof) comprises (a) the heavy chain variable region amino acid sequence in SEQ ID NO: 7, or a variant sequence thereof which differs by only one or two amino acids or which has at least or about 70% sequence identity, or (b) the light chain variable region amino acid sequence in SEQ ID NO: 8 or a variant sequence thereof which differs by only one or two amino acids or which has at least or about 70% sequence identity. In an exemplary embodiment, the anti-PD-1 antibody (or antigen binding antibody fragment thereof) comprises the heavy chain variable region amino acid sequence in SEQ ID NO: 7 and the light chain variable region amino acid sequence in SEQ ID NO: 8. In other embodiments, the anti-PD-1 antibody (or antigen binding antibody fragment thereof) comprises (a) the heavy chain amino acid sequence of SEQ ID NO: 9 or a variant sequence thereof which differs by only one or two amino acids or which has at least or about 70% sequence identity; or (b) the light chain amino acid sequence of SEQ ID NO: 10 or a variant sequence thereof which differs by only one or two amino acids or which has at least or about 70% sequence identity. In an exemplary embodiment, the anti-PD-1 antibody (or antigen binding antibody fragment thereof) comprises the heavy chain amino acid sequence of SEQ ID NO: 9 and the light chain amino acid sequence of SEQ ID NO: 10.

The present disclosure further provides nucleic acid sequences encoding the anti-PD-1 antibody (or an antigen binding portion thereof). In exemplary aspects, the antibody comprises 1, 2, 3, 4, 5, or all 6 CDRs encoded by the nucleic acid(s) of SEQ ID NOs: 11-16 (representing HC CDR1, HC CDR2, HC CDR3, LC CDR1, LC CDR2, and LC CDR3, in that order). In another exemplary aspect, the antibody comprises all 6 CDRs encoded by the nucleic acids of SEQ ID NOs: 11-16. In some embodiments, the anti-PD-1 antibody (or an antigen binding portion thereof) comprises (a) a heavy chain variable region encoded by SEQ ID NO: 17 or a variant sequence thereof which differs by only 1, 2, 3, 4, 5, or 6 nucleic acids or which has at least or about 70%, 85%, 90%, or 95% sequence identity, or (b) a light chain variable region encoded by SEQ ID NO: 18 or a variant sequence thereof which differs by only 1, 2, 3, 4, 5, or 6 nucleic acids or which has at least or about 70%, 85%, 90%, or 95% sequence identity. In an exemplary embodiment, the anti-PD-1 antibody (or an antigen binding portion thereof) comprises a heavy chain variable region encoded by SEQ ID NO: 17 and a light chain variable region encoded by SEQ ID NO: 18. In other embodiments, the anti-PD-1 antibody (or an antigen binding portion thereof) comprises (a) a heavy chain encoded by SEQ ID NO: 19 or a variant sequence thereof which differs by only 1, 2, 3, 4, 5, or 6 nucleic acids or which has at least or about 70%, 85%, 90%, or 95% sequence identity, or (b) a light chain encoded by SEQ ID NO: 20 or a variant sequence thereof which differs by only 1, 2, 3, 4, 5, or 6 nucleic acids or which has at least or about 70%, 85%, 90%, or 95% sequence identity. In an exemplary embodiment, the anti-PD-1 antibody (or an antigen binding portion thereof) comprises a heavy chain encoded by SEQ ID NO: 19 and a light chain encoded by SEQ ID NO: 20.

GITR agonists include, but are not limited to, GITR fusion proteins and anti-GITR antibodies (e.g., bivalent anti-GITR antibodies), such as, a GITR fusion protein described in U.S. Pat. No. 6,111,090box.c, European Patent No.: 090505B1, U.S. Pat. No. 8,586,023. PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683. PCT Publication No.: WO 2013/039954, PCT Publication No.: WO2005/007190, PCT Publication No.: WO 2007/133822, PCT Publication No.: WO2005/055808, PCT Publication No.: WO 99/40196. PCT Publication No.: WO 2001/03720. PCT Publication No.: WO99/20758, PCT Publication No.: WO2006/083289. PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

EXAMPLES

Section 1—Methods and Method Examples

Method 55

6-Chloro-7-(2-fluoro-6-hydroxyphenyl)-1-(3-methyl-5-(2-propanyl)-1,2-oxazol-4-yl)-4-((2S)-2-methyl-4-(2-propenoyl)-1-piperazinyl)pyrido[2,3-d]pyrimidin-2(1H)-one

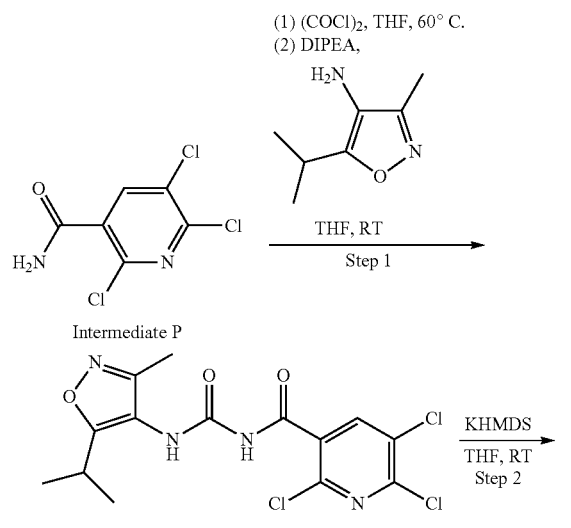

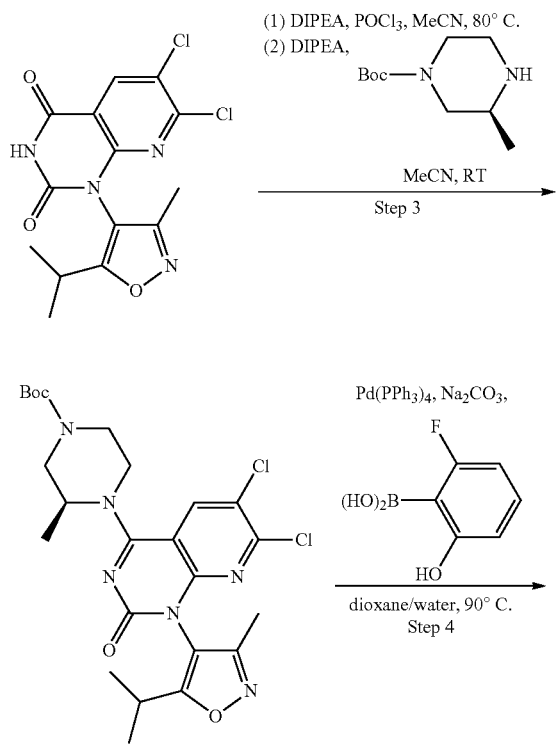

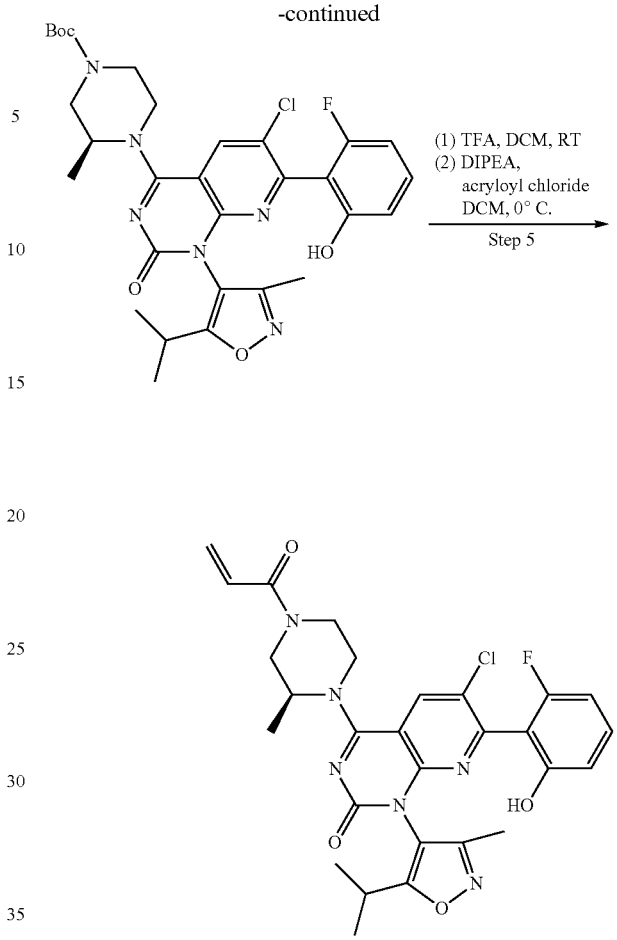

Step 1: 2,5,6-Trichloro-N-((5-isopropyl-3-methyl-isoxazol-4-yl)carbamoyl)nicotinamide To a grey heterogeneous mixture of 2,5,6-trichloronicotinamide (Intermediate P, 2.5 g, 11 mmol) in THF (22 mL) was added oxalyl chloride, 2 M solution in DCM (5.8 mL, 11.6 mmol) at rt. The resulting yellow heterogeneous mixture was stirred and heated at 65° C. After 4 h, the mixture was cooled to 0° C. and treated with a white suspension of 5-isopropyl-3-methylisoxazol-4-amine hydrochloride (1.96 g, 11.08 mmol, Enamine, Monmouth Junction, N.J., USA) and DIPEA (3.9 mL, 22.2 mmol) in THF (5 mL) and the mixture was stirred at 0° C. After 5 min, the cooling bath was removed and the mixture was stirred at rt for 2 h. The mixture was concentrated in vacuo to give the crude product as yellow syrup. The residue was partitioned between EtOAc (100 mL) and saturated $NaHCO_3$ (100 mL) and the organic extract was washed with brine (1×100 mL) and dried over $Na_2SO_4$. The solution was filtered and concentrated in vacuo and the resulting residue was suspended in acetonitrile (20 mL), filtered and the solid was washed with acetonitrile (20 mL), and dried to give 2,5,6-trichloro-N-((5-isopropyl-3-methylisoxazol-4-yl)carbamoyl)nicotinamide (2.84 g, 7.26 mmol, 65.5% yield) as an off-white solid. $^1$H NMR (400 MHz, DMSO-$d_6$) δ 11.31 (br s, 1H), 9.22 (br s, 1H), 8.62 (s, 1H), 3.02-3.16 (m, 1H), 2.11 (s, 3H), 1.23 (d, J=7.0 Hz, 6H). m/z (ESI, +ve ion): 390.8 (M+H)$^+$.

Step 2: 6,7-Dichloro-1-(5-isopropyl-3-methylisoxazol-4-yl)pyrido[2,3-d]pyrimidine-2,4(1H,3H)-dione To a cooled mixture of 2,5,6-trichloro-N-((5-isopropyl-3-methylisoxazol-4-yl)carbamoyl)nicotinamide (2.84 g, 7.24 mmol) in THF (24 mL) at 0° C. was added dropwise KHMDS, 1 M solution in THF (14.5 mL, 14.5 mmol) and the mixture was stirred at 0° C. After 30 min, the cooling bath was removed and the reddish brown homogeneous mixture was stirred at rt for 1 h. The mixture was quenched with satd. ammonium chloride (50 mL) and brine (50 mL) and extracted with EtOAc (2×50 mL). The organic extract was dried over $Na_2SO_4$ and the solution was filtered and concentrated in vacuo. The crude product was purified by silica gel chromatography (eluent: 0-50% EtOAc/heptane) to provide 6,7-dichloro-1-(5-isopropyl-3-methylisoxazol-4-yl)pyrido[2,3-d]pyrimidine-2,4(1H,3H)-dione (1.68 g, 66% yield). This material was used without further purification in the following step. $^1$H NMR (400 MHz, DMSO-$d_6$) δ 12.24 (s, 1H), 8.56 (s, 1H), 3.00-3.13 (m, 1H), 2.04 (s, 3H), 1.15 (dd, J=6.9, 4.3 Hz, 6H). m/z (ESI, +ve ion): 355.0 (M+H)$^+$.

Step 3: tert-Butyl (S)-4-(6,7-dichloro-1-(5-isopropyl-3-methylisoxazol-4-yl)-2-oxo-1,2-dihydropyrido[2,3-d]pyrimidin-4-yl)-3-methylpiperazine-1-carboxylate A solution of 6,7-dichloro-1-(5-isopropyl-3-methylisoxazol-4-yl)pyrido[2,3-d]pyrimidine-2,4(1H,3H)-dione (1.69 g, 4.74 mmol), DIPEA (1.1 mL, 6.2 mmol), and phosphoryl trichloride (0.53 mL, 5.7 mmol) in acetonitrile (2 mL) was stirred at 80° C. for 1 h. The reaction mixture cooled to rt, DIPEA (3.4 mL, 19.4 mmol) and tert-butyl (S)-3-methylpiperazine-1-carboxylate (1.04 g, 5.21 mmol) were added and the reaction was stirred at rt for 30 min. The mixture was poured into cold, satd. $NaHCO_3$ (5 mL) and stirred vigorously for 10 min. The mixture was partitioned between EtOAc (100 mL), and satd. $NaHCO_3$ (75 mL), the organic layer was washed with satd. $NaHCO_3$ (75 mL). The organic extract was dried over $Na_2SO_4$, filtered and concentrated in vacuo. The crude product was purified by silica gel chromatography (eluent: 0-5% MeOH/DCM) to provide tert-butyl (S)-4-(6,7-dichloro-1-(5-isopropyl-3-methylisoxazol-4-yl)-2-oxo-1,2-dihydropyrido[2,3-d]pyrimidin-4-yl)-3-methylpiperazine-1-carboxylate (2.5 g, 98% yield). m/z (ESI, +ve ion): 537.0 (M+H)$^+$.

Step 4: tert-Butyl (3S)-4-(6-chloro-7-(2-fluoro-6-hydroxyphenyl)-1-(5-isopropyl-3-methylisoxazol-4-yl)-2-oxo-1,2-dihydropyrido[2,3-d]pyrimidin-4-yl)-3-methylpiperazine-1-carboxylate A mixture of tert-butyl (S)-4-(6,7-dichloro-1-(5-isopropyl-3-methylisoxazol-4-yl)-2-oxo-1,2-dihydropyrido[2,3-d]pyrimidin-4-yl)-3-methylpiperazine-1-carboxylate (0.6 g, 1.1 mmol), (2-fluoro-5-hydroxyphenyl)boronic acid (261 mg, 1.68 mmol), Pd(PPh$_3$)$_4$ (0.13 g, 0.11 mmol) and sodium carbonate (0.36 g, 3.35 mmol) was purged with N2 followed by the addition of 1,4-dioxane (12 mL) and water (3 mL). The mixture was heated at 80° C. for 1 h then quenched with sat. NaHCO$_3$, extracted with EtOAc, dried over Na$_2$SO$_4$, filtered and concentrated in vacuo. The crude product was purified by silica gel chromatography (eluent: 0-5% MeOH/DCM) to provide tert-butyl (3S)-4-(6-chloro-7-(2-fluoro-6-hydroxyphenyl)-1-(5-isopropyl-3-methylisoxazol-4-yl)-2-oxo-1,2-dihydropyrido[2,3-d]pyrimidin-4-yl)-3-methylpiperazine-1-carboxylate (0.22 g, 0.37 mmol, 33% yield) with some traces of ether byproduct. m/z (ESI, +ve ion): 613.0 (M+H)$^+$.

Step 5: 6-Chloro-7-(2-fluoro-6-hydroxyphenyl)-1-(3-methyl-5-(2-propanyl)-1,2-oxazol-4-yl)-4-((2S)-2-methyl-4-(2-propenoyl)-1-piperazinyl)pyrido[2,3-d]pyrimidin-2(1H)-one To a solution of tert-butyl (3S)-4-(6-chloro-7-(2-fluoro-6-hydroxyphenyl)-1-(5-isopropyl-3-methylisoxazol-4-yl)-2-oxo-1,2-dihydropyrido[2,3-d]pyrimidin-4-yl)-3-methylpiperazine-1-carboxylate (0.22 g, 0.37 mmol) in DCM (5 mL) at rt was added TFA (5 mL, 64.9 mmol) and the mixture was stirred at rt for 30 min. The mixture was concentrated in vacuo to afford 6-chloro-7-(2-fluoro-6-hydroxyphenyl)-1-(5-isopropyl-3-methylisoxazol-4-yl)-4-((S)-2-methylpiperazin-1-yl)pyrido[2,3-d]pyrimidin-2(1H)-one. The crude product was dissolved in DCM (15 mL), treated with DIPEA (0.26 mL, 1.5 mmol) and a solution of acryloyl chloride (0.021 mL, 0.26 mmol) in DCM (1 mL) in small portions. After 30 min. the mixture was diluted with DCM, washed with satd. NaHCO$_3$, with satd. ammonium chloride. The organic extract was dried over Na$_2$SO$_4$, filtered and concentrated in vacuo. The crude product was purified by silica gel chromatography (eluent: 0-5% MeOH/DCM) to provide 6-chloro-7-(2-fluoro-6-hydroxyphenyl)-1-(3-methyl-5-(2-propanyl)-1,2-oxazol-4-yl)-4-((2S)-2-methyl-4-(2-propenoyl)-1-piperazinyl)pyrido[2,3-d]pyrimidin-2(1H)-one (0.16 g, 0.14 mmol, 37.4% yield). $^1$H NMR (400 MHz, DMSO-$d_6$) δ 10.18 (br s, 1H), 8.40 (br d, J=13.1 Hz, 1H), 7.25-7.32 (m, 1H), 6.79-6.91 (m, 1H), 6.68-6.79 (m, 2H), 6.20 (br d, J=16.6 Hz, 1H), 5.74-5.79 (m, 1H), 4.93 (br d, J=27.8 Hz, 1H), 3.97-4.46 (m, 3H), 3.36-3.88 (m, 2H), 2.98-3.28 (m, 1H), 2.85-2.97 (m, 1H), 1.92 (br d, J=6.0 Hz, 3H), 1.33 (dd, J=12.6, 6.6 Hz, 3H), 1.10 (d, J=6.8 Hz, 3H), 1.05 (dd, J=6.9, 2.6 Hz, 3H). $^{19}$F NMR (376 MHz, DMSO-$d_6$) δ −115.73 (br dd, J=82.4, 10.4 Hz, 1F). m/z (ESI, +ve ion): 567.2 (M+H)$^+$.

TABLE 55

Compounds 55-50 to 55-64 were prepared following the procedure described in Method 55, Steps 1-5, above as follows:

| Ex.# | Chemical Structure | Name | Method Changes | Reagent |
|---|---|---|---|---|
| 55-50 | 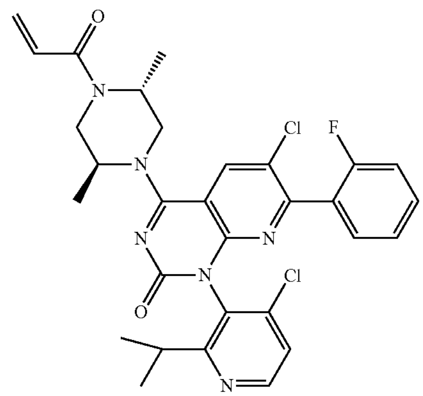 [SMILES: C=CC(=O)N1C[C@H](C)N(c2nc(=O)n(-c3c(Cl)ccnc3C(C)C)c3nc(-c4ccccc4F)c(Cl)cc23)C[C@H]1C] | 6-Chloro-1-(4-chloro-2-isopropyl-3-pyridyl)-4-[(2S,5R)-2,5-dimethyl-4-prop-2-enoyl-piperazin-1-yl]-7-(2-fluorophenyl)pyrido[2,3-d]pyrimidin-2-one | Intermediate 190 in Step 1 | Step 3: (2R,5S)-tert-butyl 2,5-dimethylpiperazine-1-carboxylate, eNovation Chemicals LLC, Step 4: (2-fluorophenyl)borane diol, Combi-Blocks Inc |
| 55-51 | 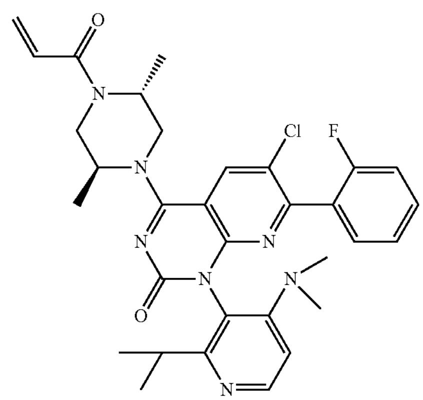 [SMILES: C=CC(=O)N1C[C@H](C)N(c2nc(=O)n(-c3c(N(C)C)ccnc3C(C)C)c3nc(-c4ccccc4F)c(Cl)cc23)C[C@H]1C] | 6-Chloro-1-[4-(dimethylamino)-2-isopropyl-3-pyridyl]-4-[(2S,5R)-2,5-dimethyl-4-prop-2-enoyl-piperazin-1-yl]-7-(2-fluorophenyl)pyrido[2,3-d]pyrimidin-2-one | Intermediate 163 in Step 1 | Step 3: (2R,5S)-tert-butyl 2,5-dimethylpiperazine-1-carboxylate, eNovation Chemicals LLC, Step 4: (2-fluorophenyl)borane diol, Combi-Blocks Inc |
| 55-52 | 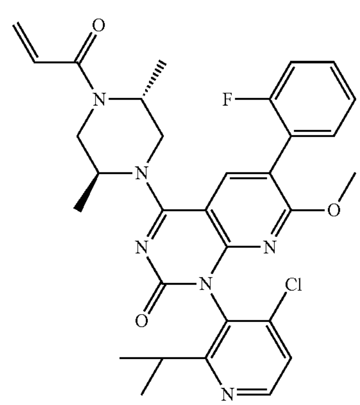 [SMILES: C=CC(=O)N1C[C@H](C)N(c2nc(=O)n(-c3c(Cl)ccnc3C(C)C)c3nc(OC)c(-c4ccccc4F)cc23)C[C@H]1C] | 1-(4-Chloro-2-isopropyl-3-pyridyl)-4-[(2S,5R)-2,5-dimethyl-4-prop-2-enoyl-piperazin-1-yl]-6-(2-fluorophenyl)-7-methoxy-pyrido[2,3-d]pyrimidin-2-one | Intermediate 190 in Step 1 and Intermediate 191 | (2-Step 3: (2R,5S)-tert-butyl 2,5-dimethylpiperazine-1-carboxylate, eNovation Chemicals LLC, Step 4: (2-fluorophenyl)borane diol, Combi-Blocks Inc |

TABLE 55-continued

Compounds 55-50 to 55-64 were prepared following the procedure described in Method 55, Steps 1-5, above as follows:

| Ex.# | Chemical Structure | Name | Method Changes | Reagent |
|---|---|---|---|---|
| 55-53 | 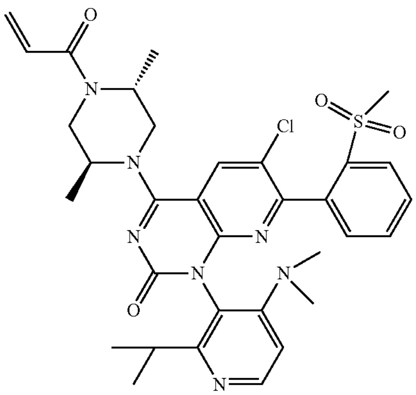 [SMILES: C=CC(=O)N1C[C@H](C)N(c2nc(=O)n(-c3c(N(C)C)ccnc3C(C)C)c3nc(-c4ccccc4S(C)(=O)=O)c(Cl)cc23)C[C@H]1C] | 6-Chloro-1-[4-(dimethylamino)-2-isopropyl-3-pyridyl]-4-[(2S,5R)-2,5-dimethyl-4-prop-2-enoyl-piperazin-1-yl]-7-(2-methylsulfonylphenyl)pyrido[2,3-d]pyrimidin-2-one | Intermediate 163 in Step 1 | Step 3: (2R,5S)-tert-butyl 2,5-dimethylpiperazine-1-carboxylate, eNovation Chemicals LLC, Step 4: (2-methylsulfonylphenyl)boronic acid, Combi-Blocks Inc. |
| 55-54 | 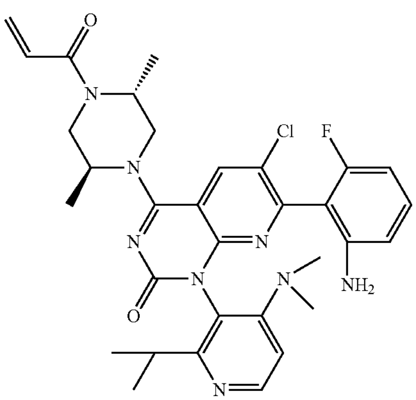 [SMILES: C=CC(=O)N1C[C@H](C)N(c2nc(=O)n(-c3c(N(C)C)ccnc3C(C)C)c3nc(-c4c(N)cccc4F)c(Cl)cc23)C[C@H]1C] | 7-(2-Amino-6-fluoro-phenyl)-6-chloro-1-[4-(dimethylamino)-2-isopropyl-3-pyridyl]-4-[(2S,5R)-2,5-dimethyl-4-prop-2-enoyl-piperazin-1-yl]pyrido[2,3-d]pyrimidin-2-one | Intermediate 163 in Step 1 | Step 3: (2R,5S)-tert-butyl 2,5-dimethylpiperazine-1-carboxylate, eNovation Chemicals LLC Step 4: (2-amino-6-fluorophenyl)boronic acid pinacol ester, CombiPhos Catalysts, Inc. |
| 55-55 | 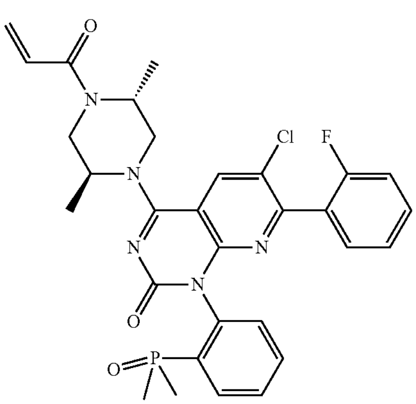 [SMILES: C=CC(=O)N1C[C@H](C)N(c2nc(=O)n(-c3ccccc3P(C)(C)=O)c3nc(-c4ccccc4F)c(Cl)cc23)C[C@H]1C] | 6-Chloro-1-(2-dimethylphosphorylphenyl)-4-[(2S,5R)-2,5-dimethyl-4-prop-2-enoyl-piperazin-1-yl]-7-(2-fluorophenyl)pyrido[2,3-d]pyrimidin-2-one | None | Step 1: (2-aminophenyl)dimethylphosphine oxide, AstaTech, Inc, Step 4: (2-fluorophenyl)borane diol, Combi-Blocks Inc. |

TABLE 55-continued

Compounds 55-50 to 55-64 were prepared following the procedure described in Method 55, Steps 1-5, above as follows:

| Ex.# | Chemical Structure | Name | Method Changes | Reagent |
|---|---|---|---|---|
| 55-56 | 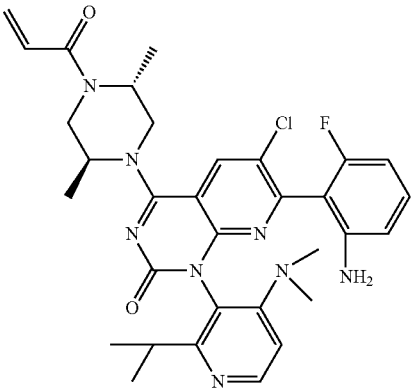<br>Single isomer (M) | 7-(2-Amino-6-fluoro-phenyl)-6-chloro-1-[4-(dimethylamino)-2-isopropyl-3-pyridyl]-4-[(2S,5R)-2,5-dimethyl-4-prop-2-enoyl-piperazin-1-yl]pyrido[2,3-d]pyrimidin-2-one | Intermediate 163 in Step 1 | Step 3: (2R,5S)-tert-butyl 2,5-dimethylpiperazine-1-carboxylate, eNovation Chemicals LLC, Step 4: (2-amino-6-fluorophenyl)boronic acid pinacol ester, CombiPhos Catalysts, Inc. |
| 55-57 | 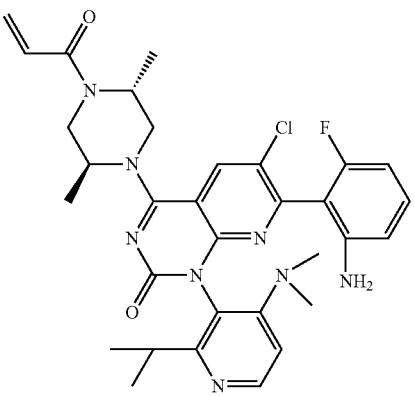<br>Single isomer (P) | 7-(2-Amino-6-fluoro-phenyl)-6-chloro-1-[4-(dimethylamino)-2-isopropyl-3-pyridyl]-4-[(2S,5R)-2,5-dimethyl-4-prop-2-enoyl-piperazin-1-yl]pyrido[2,3-d]pyrimidin-2-one | Intermediate 163 in Step 1 | Step 3: (2R,5S)-tert-butyl 2,5-dimethylpiperazine-1-carboxylate, eNovation Chemicals LLC, Step 4: (2-amino-6-fluorophenyl)boronic acid pinacol ester, CombiPhos Catalysts, Inc. |
| 55-58 | 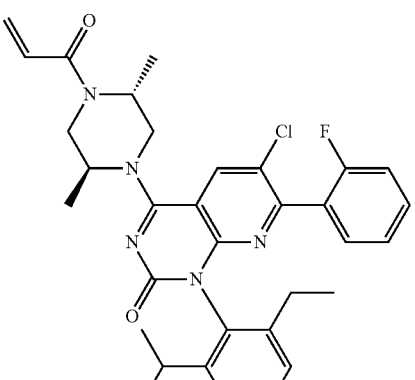 | 6-Chloro-4-[(2S,5R)-2,5-dimethyl-4-prop-2-enoyl-piperazin-1-yl]-1-(4-ethyl-2-isopropyl-3-pyridyl)-7-(2-fluorophenyl)pyrido[2,3-d]pyrimidin-2-one | Intermediate 197 in Step 1 | Step 3: (2R,5S)-tert-butyl 2,5-dimethylpiperazine-1-carboxylate, Astatech, Step 4: 2-Fluorophenyl boronic acid, Combi-Blocks |

TABLE 55-continued

Compounds 55-50 to 55-64 were prepared following the procedure described
in Method 55, Steps 1-5, above as follows:

| Ex.# | Chemical Structure | Name | Method Changes | Reagent |
|---|---|---|---|---|
| 55-59 | 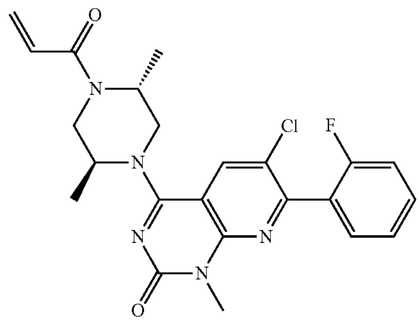 [SMILES: C=CC(=O)N1C[C@H](C)N(c2nc(=O)n(C)c3nc(-c4ccccc4F)c(Cl)cc23)C[C@H]1C] | 6-Chloro-4-[(2S,5R)-2,5-dimethyl-4-prop-2-enoyl-piperazin-1-yl]-7-(2-fluorophenyl)-1-methyl-pyrido[2,3-d]pyrimidin-2-one | None | Step 1: methylamine (Sigma-Aldrich Corporation); Step 3: (2R,5S)-tert-butyl 2,5-dimethylpiperazine-1-carboxylate (AstaTech, Inc.); Step 4: (2-fluorophenyl)boronic acid (Combi-Blocks Inc.) |
| 55-60 | 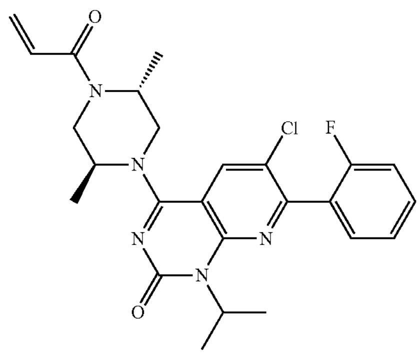 [SMILES: C=CC(=O)N1C[C@H](C)N(c2nc(=O)n(C(C)C)c3nc(-c4ccccc4F)c(Cl)cc23)C[C@H]1C] | 6-Chloro-4-[(2S,5R)-2,5-dimethyl-4-prop-2-enoyl-piperazin-1-yl]-7-(2-fluorophenyl)-1-isopropyl-pyrido[2,3-d]pyrimidin-2-one | None | Step 1: isopropylamine (Sigma-Aldrich Corporation); Step 3: (2R,5S)-tert-butyl 2,5-dimethylpiperazine-1-carboxylate (AstaTech, Inc.); Step 4: (2-fluorophenyl)boronic acid (Combi-Blocks Inc.) |

Method 69

6-Chloro-4-((2S)-2-methyl-4-(2-propenoyl)-1-piperazinyl)-7-(1-piperidinyl)-1-(2-(2-propanyl)phenyl)pyrido[2,3-d]pyrimidin-2(1H)-one

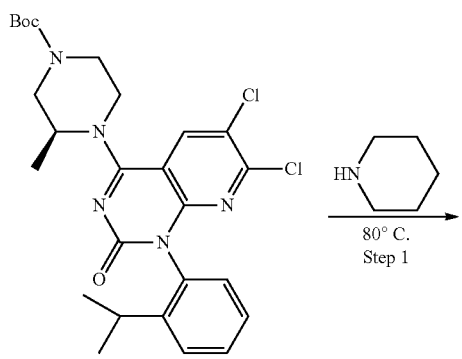

Intermediate 61B

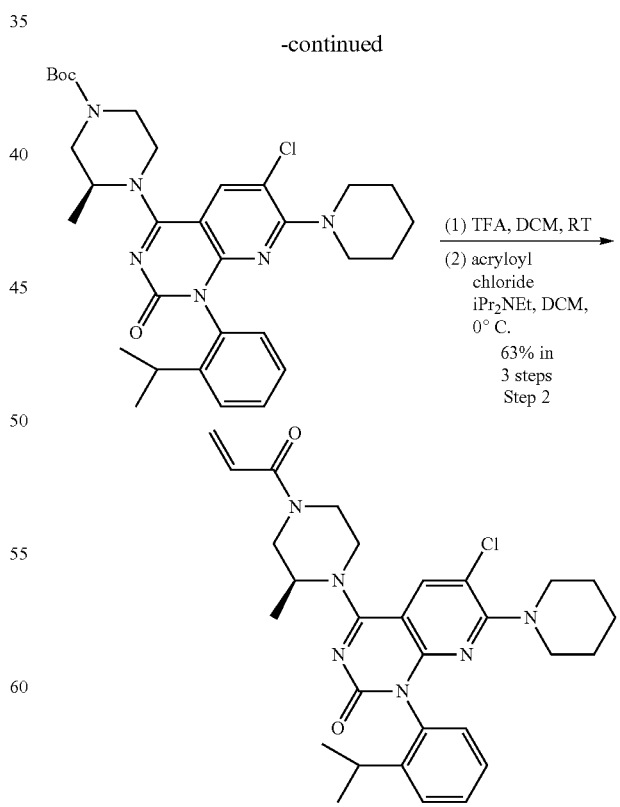

(1) TFA, DCM, RT
(2) acryloyl chloride iPr₂NEt, DCM, 0° C.
63% in 3 steps
Step 2

Step 1: tert-Butyl (S)-4-(6-chloro-1-(2-isopropylphenyl)-2-oxo-7-(piperidin-1-yl)-1,2-dihydropyrido[2,3-d]pyrimidin-4-yl)-3-methylpiperazine-1-carboxylate A 25-mL round-bottomed flask was charged with (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 45 mg, 0.085 mmol) and piperidine (0.1 mL, 1.01 mmol, Spectrum Chemicals & Laboratory Products, Gardena, Calif., USA). The reaction mixture was stirred and heated at 80° C. for 16 h. The reaction mixture was concentrated in vacuo to give crude (S)-tert-butyl 4-(6-chloro-1-(2-isopropylphenyl)-2-oxo-7-(piperidin-1-yl)-1,2-dihydropyrido[2,3-d]pyrimidin-4-yl)-3-methylpiperazine-1-carboxylate (49 mg) as a yellow solid. m/z (ESI, +ve ion): 581.3 (M+H)$^+$. The crude yellow solid was used in next step without purification.

Step 2: 6-Chloro-4-((2S)-2-methyl-4-(2-propenoyl)-1-piperazinyl)-7-(1-piperidinyl)-1-(2-(2-propanyl)phenyl)pyrido[2,3-d]pyrimidin-2(1H)-one To a solution of (S)-tert-butyl 4-(6-chloro-1-(2-isopropylphenyl)-2-oxo-7-(piperidin-1-yl)-1,2-dihydropyrido[2,3-d]pyrimidin-4-yl)-3-methylpiperazine-1-carboxylate (49 mg, 0.084 mmol) in DCM (1 mL) was treated with TFA (1 mL) at rt and stirred for 15 min. The reaction was concentrated in vacuo to afford (S)-6-chloro-1-(2-isopropylphenyl)-4-(2-methylpiperazin-1-yl)-7-(piperidin-1-yl)pyrido[2,3-d]pyrimidin-2(1H)-one. m/z (ESI, +ve ion): 481.3 (M+H)$^+$.

A mixture of (S)-6-chloro-1-(2-isopropylphenyl)-4-(2-methylpiperazin-1-yl)-7-(piperidin-1-yl)pyrido[2,3-d]pyrimidin-2(1H)-one and DIPEA (0.07 mL, 0.42 mmol) in DCM (1.0 mL) was added acryloyl chloride (0.26 M in DCM, 0.33 mL, 0.084 mmol) at 0° C. and stirred for 40 min at 0° C. The resulting mixture was concentrated in vacuo. The crude product was purified by silica gel chromatography (eluent: 0-50% of EtOAc/EtOH(3:1)/heptane) to provide pure (S)-4-(4-acryloyl-2-methylpiperazin-1-yl)-6-chloro-1-(2-isopropylphenyl)-7-(piperidin-1-yl)pyrido[2,3-d]pyrimidin-2(1H)-one (28 mg, 0.053 mmol, 62.5% yield) as a light-yellow solid. $^1$H NMR (400 MHz, DMSO-d$_6$) δ 7.85-8.03 (m, 1H), 7.42-7.50 (m, 1H), 7.34-7.42 (m, 1H), 7.26 (t, J=7.5 Hz, 1H), 7.05 (d, J=7.7 Hz, 1H), 6.74-6.92 (m, 1H), 6.19 (br dd, J=17.5, 4.5 Hz, 1H), 5.71-5.78 (m, 1H), 4.68-4.84 (m, 1H), 4.21-4.45 (m, 1H), 3.93-4.19 (m, 2H), 3.35-3.66 (m, 2H), 3.25 (br s, 4H), 2.89-3.19 (m, 1H), 2.45-2.48 (m, 1H), 1.34 (br d, J=3.9 Hz, 3H), 1.20-1.29 (m, 6H), 1.08 (d, J=6.8 Hz, 3H), 0.98 (br d, J=6.8 Hz, 3H). m/z (ESI, +ve ion): 536.3 (M+H)$^+$.

TABLE 69

Compounds 69-10 to 69-12 were prepared following the procedure described in Method 69, Steps 1-2, above as follows:

| Ex.# | Chemical Structure | Name | Method Changes | Reagent |
|---|---|---|---|---|
| 69-10 | 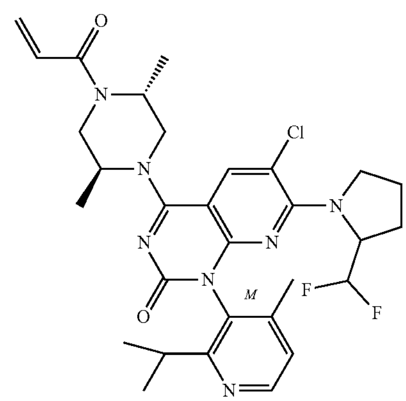 | (M)-6-Chloro-7-[2-(difluoromethyl)pyrrolidin-1-yl]-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 1: 2-(difluoromethyl)pyrrolidine hydrochloride (Advanced ChemBlocks Inc.) |
| 69-11 | 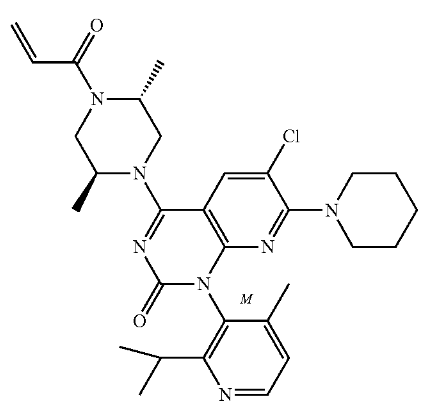 | (M)-6-Chloro-4-[(2S,5R)-2,5-dimethyl-4-prop-2-enoyl-piperazin-1-yl]-1-(2-isopropyl-4-methyl-3-pyridyl)-7-(1-piperidyl)pyrido[2,3-d]pyrimidin-2-one | None | Step 1: [3-(prop-1-yn-1-yl)phenyl]boronic acid (Enamine Ltd.) |

TABLE 69-continued

Compounds 69-10 to 69-12 were prepared following the procedure described in Method 69, Steps 1-2, above as follows:

| Ex.# | Chemical Structure | Name | Method Changes | Reagent |
|---|---|---|---|---|
| 69-12 | 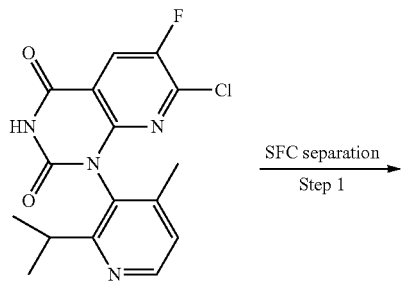 | (M)-6-Chloro-4-[(2S,5R)-2,5-dimethyl-4-prop-2-enoyl-piperazin-1-yl]-1-(2-isopropyl-4-methyl-3-pyridyl)-7-[(2SR)-2-methyl-1-piperidyl]pyrido[2,3-d]pyrimidin-2-one | None | Step 1: piperidine (Spectrum Chemicals & Laboratory Products) |

Method 72

(M)-6-Fluoro-7-(5-fluoro-2-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one

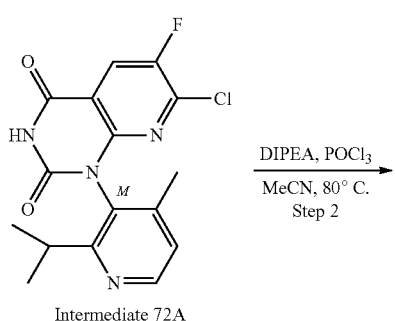

Example 41, Step 3

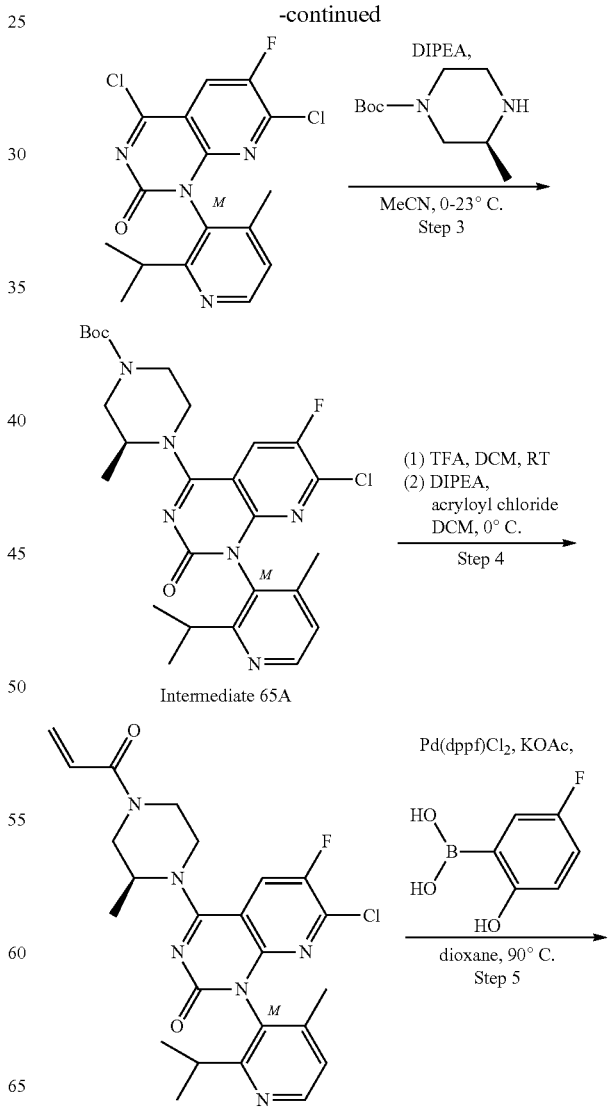

-continued

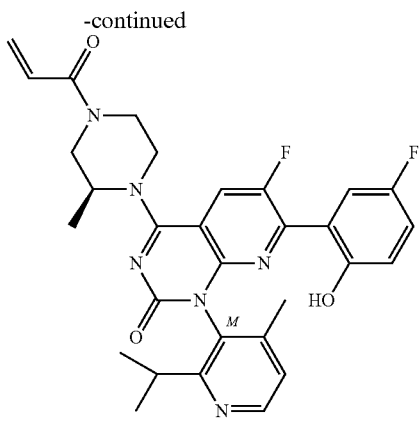

Step 1: (M)-7-Chloro-6-fluoro-1-(2-isopropyl-4-methylpyridin-3-yl)pyrido[2,3-d]pyrimidine-2,4-dione (Intermediate 72A)

A mixture of atropisomers 7-chloro-6-fluoro-1-(2-isopropyl-4-methylpyridin-3-yl)pyrido[2,3-d]pyrimidine-2,4(1H,3H)-dione (Example 41, Step 3, 648 g) was purified by SFC (AD, 150×50 mm, 5 μm, 50% MeOH/CO$_2$, 180 g/min, 102 bar) to obtain two peaks: Peak 1 (P isomer, 230.6 g, >99% ee) and Peak 2 (M isomer, 227.8 g, 97.1% ee, Intermediate 72A).

Step 2: (M)-4,7-Dichloro-6-fluoro-1-(2-isopropyl-4-methylpyridin-3-yl)pyrido[2,3-d]pyrimidin-2(1H)-one To a suspension of (M)-7-chloro-6-fluoro-1-(2-isopropyl-4-methylpyridin-3-yl)pyrido[2,3-d]pyrimidine-2,4(1H,3H)-dione (Intermediate 72A, 2.51 g, 7.19 mmol) in a mixture of acetonitrile (11 mL) and DIPEA (1.9 mL, 11 mmol) was added phosphorous oxychloride (0.87 mL, 9.3 mmol). The mixture was heated at 80° C. for 90 min and then concentrated in vacuo. The crude residue was used without further purification in the following step. m/z (ESI, +ve ion): 367.0 (M+H)$^+$.

Step 3: (M,S)-tert-Butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (Intermediate 65A)

A solution of (M)-4,7-dichloro-6-fluoro-1-(2-isopropyl-4-methylpyridin-3-yl)pyrido[2,3-d]pyrimidin-2(1H)-one (2.64 g, 7.19 mmol) in acetonitrile (11 mL) was cooled in an ice-water bath to 0° C. DIPEA (3.8 mL, 22 mmol) was added, followed by (3S)-1-(tert-butoxycarbonyl)-3-methylpiperazine (1.8 g, 8.7 mmol, Ark Pharm, Inc., Libertyville, Ill., USA). The mixture was allowed to warm to rt and stir for 18 h. The mixture was quenched with satd. NaHCO$_3$ (100 mL). The mixture was diluted with EtOAc (175 mL) and water (75 mL). The aqueous layer was washed with EtOAc (2×100 mL). The combined organic phases were dried over MgSO$_4$ and then concentrated in vacuo. The crude product was purified by silica gel chromatography (eluent: 10-50% EtOAc-EtOH (3:1)/heptane) to provide (MS)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (Intermediate 65A). m/z (ESI, +ve ion): 530.9 (M+H)$^+$.

Step 4: (M,S)-4-(4-Acryloyl-2-methylpiperazin-1-yl)-7-chloro-6-fluoro-1-(2-isopropyl-4-methylpyridin-3-yl)pyrido[2,3-d]pyrimidin-2(1H)-one TFA (10 mL) was added to a solution of (MS)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (Intermediate 65A, 3.0 g, 5.7 mmol) in DCM (20 mL). The mixture was stirred for 20 min at rt and then concentrated in vacuo. The resulting residue was re-dissolved in DCM (40 mL) and cooled to 0° C. DIPEA (5.0 mL, 28 mmol) and acryloyl chloride (0.46 mL, 5.7 mmol) were sequentially added and the mixture was stirred for 80 min. The reaction mixture was quenched at 0° C. by adding satd. NaHCO$_3$ (100 mL) and water (50 mL) and diluted with DCM (150 mL). The aqueous layer was extracted with DCM (2×50 mL). The combined organic extracts were dried over MgSO$_4$ and then concentrated in vacuo to give crude (M,S)-4-(4-acryloyl-2-methylpiperazin-1-yl)-7-chloro-6-fluoro-1-(2-isopropyl-4-methylpyridin-3-yl)pyrido[2,3-d]pyrimidin-2(1H)-one which was used without further purification in the following step. m/z (ESI, +ve ion): 485.0 (M+H)$^+$.

Step 5: (M)-6-Fluoro-7-(5-fluoro-2-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one A mixture of (M,S)-4-(4-acryloyl-2-methylpiperazin-1-yl)-7-chloro-6-fluoro-1-(2-isopropyl-4-methylpyridin-3-yl)pyrido[2,3-d]pyrimidin-2(1H)-one (120 mg, 0.25 mmol), (5-fluoro-2-hydroxy)phenylboronic acid (58 mg, 0.37 mmol, Combi-Blocks, San Diego, Calif., USA), Pd(dppf)Cl$_2$ (18 mg, 0.025 mmol), and potassium acetate (120 mg, 1.2 mmol) in 1,4-dioxane (1.2 mL) and one drop of water was deoxygenated with nitrogen for 10 min. The mixture was stirred at 90° C. for 2 h, then was filtered through a plug of silica gel and then partitioned between water (50 mL) and EtOAc (50 mL). The organic phase was washed with water (50 mL) and then with brine (50 mL), dried over MgSO$_4$, filtered, and concentrated in vacuo. The crude product was purified by silica gel chromatography (eluent: 0-100% EtOAc-EtOH (3:1)/heptane) to provide (M)-6-fluoro-7-(5-fluoro-2-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one. $^1$H NMR (400 MHz, DMSO-d$_6$) δ 0.96 (d, J=6.8 Hz, 3H), 1.08 (d, J=6.8 Hz, 3H), 1.33 (d, J=6.8 Hz, 3H), 1.94 (s, 3H), 2.68-2.78 (m, 0.5H), 3.06-3.19 (m, 0.5H), 3.43-3.55 (m, 0.5H), 3.59-3.80 (m, 1.5H), 3.98-4.07 (m, 0.5H), 4.10-4.19 (m, 0.5H), 4.29 (br d, J=13.5 Hz, 1.5H), 4.40 (br d, J=12.7 Hz, 0.5H), 4.91 (br s, 1H), 5.73-5.81 (m, 1H), 6.21 (br d, J=16.4 Hz, 1H), 6.80-6.93 (m, 2H), 7.09 (dd, J=9.4, 3.2 Hz, 1H), 7.18 (td, J=8.5, 3.1 Hz, 1H), 7.26 (d, J=5.0 Hz, 1H), 8.26-8.37 (m, 1H), 8.48 (d, J=5.0 Hz, 1H), 10.35 (s, 1H). $^{19}$F NMR (376 MHz, DMSO-d$_6$) δ −126.02 (s, 1F), −125.16 (s, 1F). m/z (ESI, +ve ion): 561.0 (M+H)$^+$.

TABLE 72

Compounds 72-20 to 72-23 were prepared following the procedure described in Method 72, Steps 1-5, above as follows:

| Ex.# | Chemical Structure | Name | Method Changes | Reagent |
|---|---|---|---|---|
| 72-20 | Single isomer (M) | (M)-6-Fluoro-7-(2-fluoro-6-hydroxy-phenyl)-1-(2-isopropyl-4-methyl-3-pyridyl)-4-(3,3,5,5-tetradeuterio-4-prop-2-enoyl-piperazin-1-yl)pyrido[2,3-d]pyrimidin-2-one | Tetrakis and sodium carbonate used in Step 5 | Step 3: piperazine-3,3,5,5-$d_4$-N-t-Boc, C/D/N Isotopes Inc. |
| 72-21 | Single isomer (M) | (M)-6-Fluoro-7-(2-fluoro-6-hydroxy-phenyl)-1-(2-isopropyl-4-methyl-3-pyridyl)-4-(2,2,6,6-tetradeuterio-4-prop-2-enoyl-piperazin-1-yl)pyrido[2,3-d]pyrimidin-2-one | Tetrakis and sodium carbonate used in Step 5 | Step 3: piperazine-3,3,5,5-$d_4$-N-t-Boc, C/D/N Isotopes Inc. |
| 72-22 | Single isomer (M) | (M)-6-Fluoro-7-(2-fluoro-6-hydroxy-phenyl)-1-(2-isopropyl-4-methyl-3-pyridyl)-4-(2,2,3,3,5,5,6,6-octadeuterio-4-prop-2-enoyl-piperazin-1-yl)pyrido[2,3-d]pyrimidin-2-one | Tetrakis and sodium carbonate used in Step 5 | Step 3: tert-butyl piperazine-1-carboxylate-2,2,3,3,5,5,6,6-$d_8$, CDN ISOTOPES |

TABLE 72-continued

Compounds 72-20 to 72-23 were prepared following the procedure described in Method 72, Steps 1-5, above as follows:

| Ex.# | Chemical Structure | Name | Method Changes | Reagent |
|---|---|---|---|---|
| 72-23 | Single isomer (M) | (M)-7-(2-Dimethylphosphorylphenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Tetrakis, sodium carbonate and Intermediate 192, used in Step 5 | Step 3: (2R,5S)-tert-butyl 2,5-dimethylpiperazine-1-carboxylate, eNovation Chemicals LLC |

Method 79

(M)-6-Chloro-7-(2-fluorophenyl)-1-(4-methyl-2-(2-propanyl)-3-pyridinyl)-4-((1-(2-propenoyl)-3-azetidinyl)oxy)pyrido[2,3-d]pyrimidin-2(1H)-one

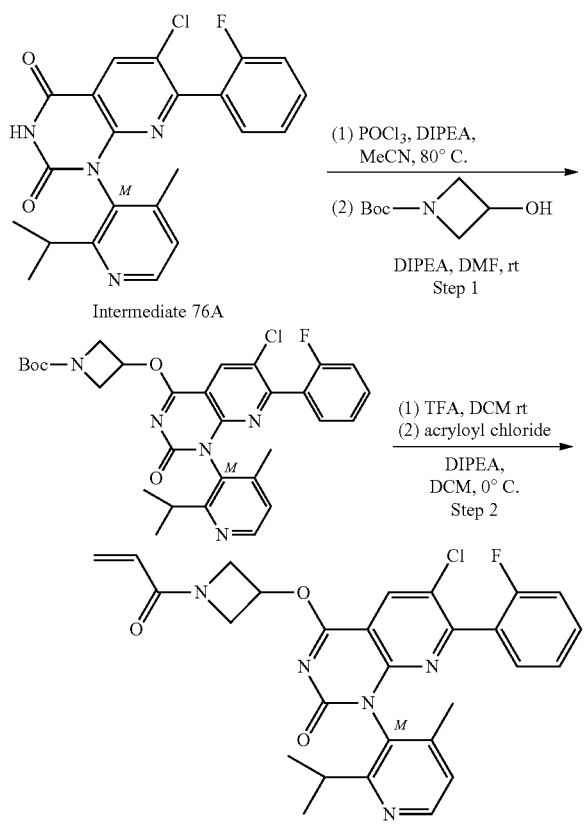

Step 1: (M)-tert-Butyl 3-((6-chloro-7-(2-fluorophenyl)-1-(2-isopropyl-4-methylpyridin-3-yl)-2-oxo-1,2-dihydropyrido[2,3-d]pyrimidin-4-y)oxy)azetidine-1-carboxylate A 50-mL round-bottomed flask was charged with (M)-6-chloro-7-(2-fluorophenyl)-1-(2-isopropyl-4-methylpyridin-3-yl)pyrido[2,3-d]pyrimidine-2,4(1H,3H)-dione (Intermediate 76A, 256 mg, 0.60 mmol) and DIPEA (0.2 mL, 0.90 mmol) in acetonitrile (3 mL) followed by phosphorous oxychloride (0.1 mL, 0.9 mmol). The mixture was stirred and heated at 80° C. for 40 min. The reaction mixture was concentrated in vacuo to give (M)-4,6-dichloro-7-(2-fluorophenyl)-1-(2-isopropyl-4-methylpyridin-3-yl)pyrido[2,3-d]pyrimidin-2(1H)-one as brown solid [m/z (ESI, +ve ion): 443 (M+H)$^+$] which was used in next step without purification.

A mixture of the above crude (M)-4,6-dichloro-7-(2-fluorophenyl)-1-(2-isopropyl-4-methylpyridin-3-yl)pyrido[2,3-d]pyrimidin-2(1H)-one (267 mg, 0.6 mmol) in acetonitrile (3 mL) was treated with DIPEA (0.3 mL, 1.81 mmol) followed by 1-Boc-3-(hydroxy)azetidine (313 mg, 1.81 mmol, CNH Technologies, Inc., Woburn, Mass., USA). The reaction mixture was stirred at rt for 24 h then concentrated in vacuo and purified by silica gel chromatography (eluent: 0-30% 3:1 EtOAc-EtOH/heptane) to provide (M)-tert-butyl 3-((6-chloro-7-(2-fluorophenyl)-1-(2-isopropyl-4-methylpyridin-3-yl)-2-oxo-1,2-dihydropyrido[2,3-d]pyrimidin-4-yl)oxy)azetidine-1-carboxylate (51 mg, 0.09 mmol, 14.6% yield) as a light yellow foam. m/z (ESI, +ve ion) 580.3 (M+H)$^+$.

Step 2: (M)-4-((1-Acryloylazetidin-3-yl)oxy)-6-chloro-7-(2-fluorophenyl)-1-(2-isopropyl-4-methylpyridin-3-yl)pyrido[2,3-d]pyrimidin-2(1H)-one To a solution of (M)-tert-butyl 3-((6-chloro-7-(2-fluorophenyl)-1-(2-isopropyl-4-methylpyridin-3-yl)-2-oxo-1,2-dihydropyrido[2,3-d]pyrimidin-4-yl)oxy)azetidine-1-carboxylate (51 mg, 0.9 mmol) in DCM (1 mL) was treated with TFA (1 mL) at rt and stirred for 1 h. The reaction was concentrated to afford (M)-4-(azetidin-3-yloxy)-6-chloro-7-(2-fluorophenyl)-1-(2-isopropyl-4-methylpyridin-3-yl)pyrido[2,3-d]pyrimidin-2(1H)-one as a yellow gum. m/z (ESI, +ve ion) 480.2 (M+H)+.

A mixture of the above (M)-4-(azetidin-3-yloxy)-6-chloro-7-(2-fluorophenyl)-1-(2-isopropyl-4-methylpyridin-3-yl)pyrido[2,3-d]pyrimidin-2(1H)-one and DIPEA (0.08 mL, 0.44 mmol) in DCM (1 mL) was treated with acryloyl chloride (0.25 M in DCM, 0.3 mL, 0.08 mmol) at 0° C. and stirred for 5 min. The reaction mixture was concentrated in vacuo and the crude product was purified by silica gel chromatography (eluent: 0-50% EtOAc-EtOH (3:1)/heptane) to give (M)-4-((1-acryloylazetidin-3-yl)oxy)-6-chloro-7-(2-fluorophenyl)-1-(2-isopropyl-4-methylpyridin-3-yl)pyrido[2,3-d]pyrimidin-2(1H)-one (22 mg, 0.041 mmol, 46.2% yield) as a white solid. $^1$H NMR (400 MHz, DMSO-$d_6$) δ 8.83 (s, 1H), 8.43 (d, J=4.8 Hz, 1H), 7.47-7.64 (m, 1H), 7.18-7.39 (m, 4H), 6.32-6.51 (m, 1H), 6.16 (dd, J=17.0, 2.1 Hz, 1H), 5.62-5.84 (m, 2H), 4.70-4.85 (m, 1H), 4.54 (td, J=10.4, 3.2 Hz, 1H), 4.44 (br dd, J=11.2, 6.8 Hz, 1H), 4.23-4.37 (m, 1H), 2.76 (dt, J=13.4, 6.8 Hz, 1H), 1.96 (s, 3H), 1.07 (d, J=6.8 Hz, 3H), 0.94 (d, J=6.6 Hz, 3H), 19F NMR (376 MHz, DMSO-d6) δ 114.69 (d, J=4.3 Hz, 1F). m/z (ESI, +ve) 534.1 (M+H)+.

TABLE 79

Compounds 79-10 to 79-12 were prepared following the procedure described in Method 79, Steps 1-2, above as follows:

| Ex. # | Chemical structure | Name | Method Changes | Reagent |
|---|---|---|---|---|
| 79-10 | 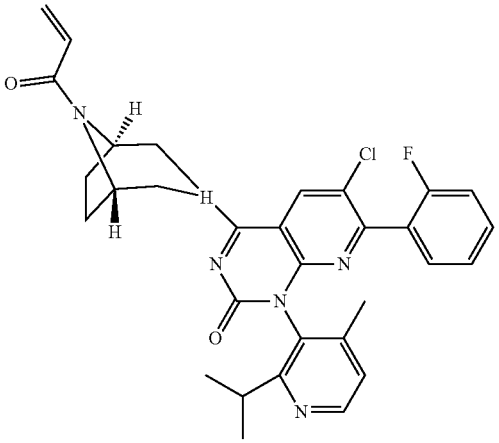<br>Single isomer (M) | (M)-6-Chloro-7-(2-fluorophenyl)-1-(2-isopropyl-4-methyl-3-pyridyl)-4-[(1S,5R)-8-prop-2-enoyl-3,8-diazabicyclo[3.2.1]octan-3-yl]pyrido[2,3-d]pyrimidin-2-one | Omit Step 2 | Step 1.2: Intermediate 213 |
| 79-11 | 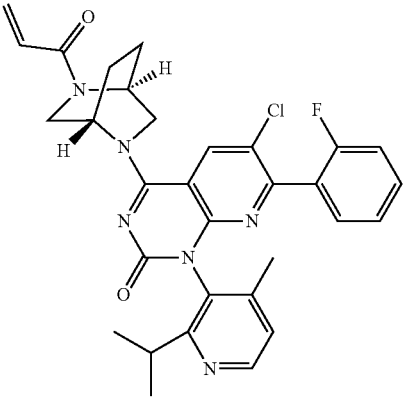<br>Single isomer (M) | (M)-6-Chloro-7-(2-fluorophenyl)-1-(2-isopropyl-4-methyl-3-pyridyl)-4-[(1S,4S)-5-prop-2-enoyl-2,5-diazabicyclo[2.2.2]octan-2-yl]pyrido[2,3-d]pyrimidin-2-one | None | Step 1.2: (1S,4S)-2-Boc-2,5-diazabicyclo(2.2.2)octane; Astatech, Inc., Bristol, PA |

TABLE 79-continued

Compounds 79-10 to 79-12 were prepared following the procedure described in Method 79, Steps 1-2, above as follows:

| Ex. # | Chemical structure | Name | Method Changes | Reagent |
|---|---|---|---|---|
| 79-12 | 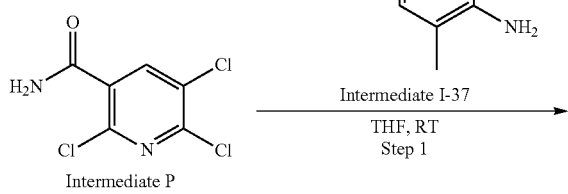  Single isomer (M) | (M)-6-Chloro-7-(2-fluorophenyl)-1-(2-isopropyl-4-methyl-3-pyridyl)-4-[(1S,5R)-3-prop-2-enoyl-3,9-diazabicyclo[3.3.1]nonan-9-yl]pyrido[2,3-d]pyrimidin-2-one | Omit Step 2 | Step 1.2: Intermediate 214 |

Method 80

6-Chloro-1-(4-((dimethylamino)methyl)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one

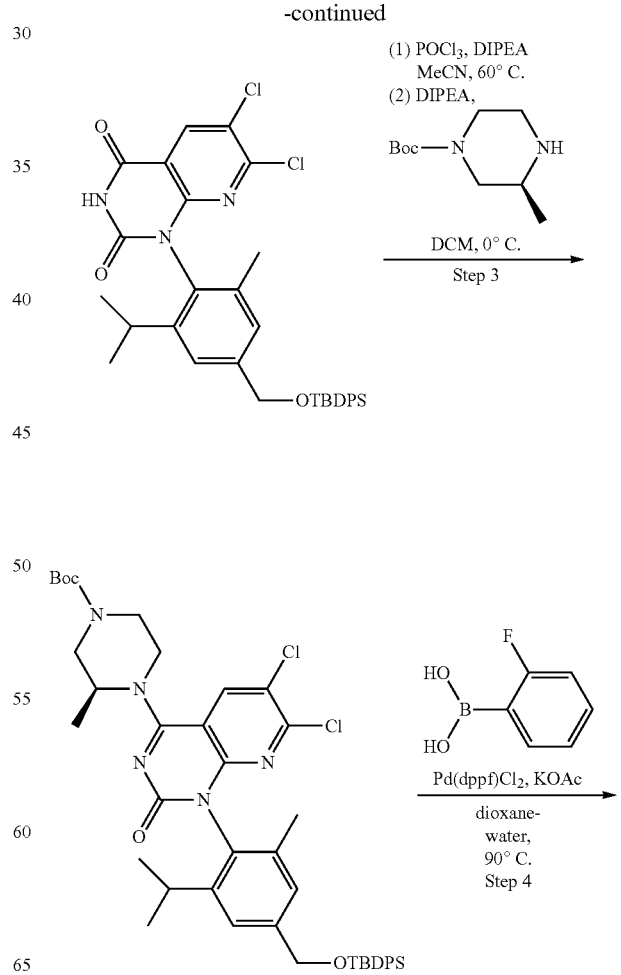

287
-continued

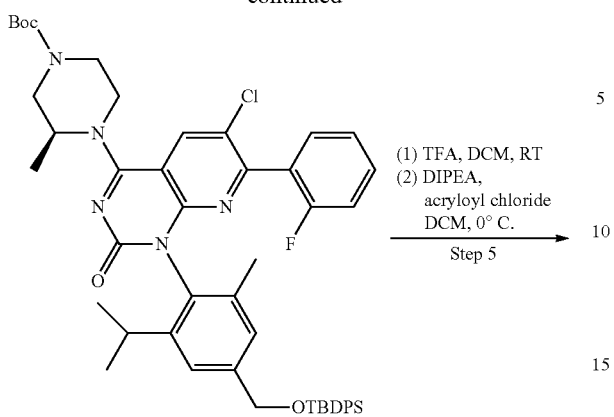

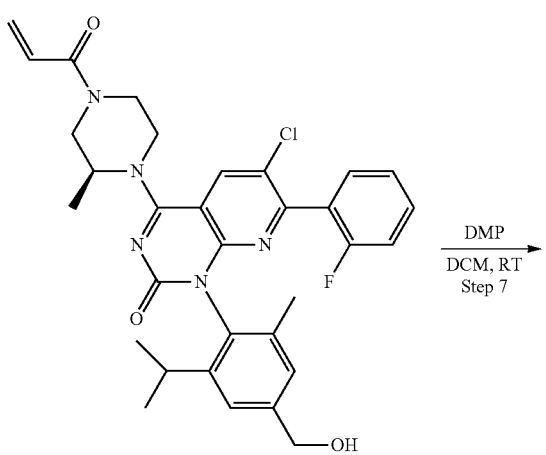

288
-continued

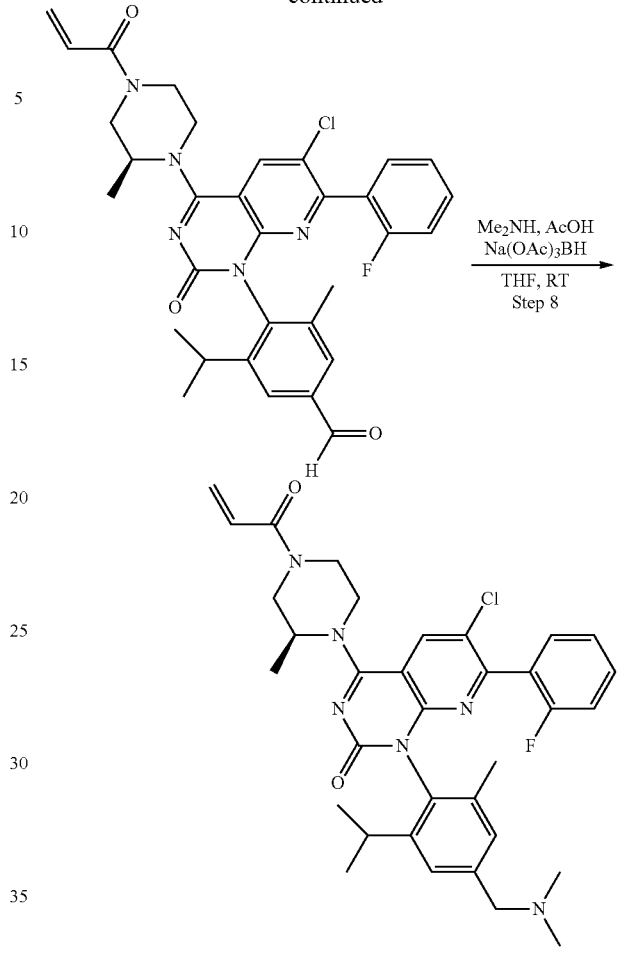

Step 1: N-((4-(((tert-Butyldiphenylsilyl)oxy)methyl)-2-isopropyl-6-methylphenyl)carbamoyl)-2,5,6-trichloronicotinamide To a stirred solution of 2,5,6-trichloronicotinamide (Intermediate P, 1.3 g, 5.5 mmol) in THF (10 mL) was added oxalyl chloride (2 M in DCM, 4.2 mL, 8.4 mmol). After die addition was completed, the reaction mixture was stirred and heated at 65° C. for 2 h. The reaction mixture was cooled, concentrated in vacuo and the crude residue was dissolved in THF (10 mL) and a solution of 4-(((tert-butyldiphenyl-silyl)oxy)methyl)-2-isopropyl-6-methylaniline (Intermediate I-37, 2.3 g, 5.5 mmol) in THF (10 mL) was added. After the addition was completed, the solution was maintained at rt for 2 h. The mixture was concentrated in vacuo to provide crude N-((4-(((tert-butyldiphenylsilyl)oxy)methyl)-2-isopropyl-6-methylphenyl)carbamoyl)-2,5,6-trichloronicotinamide which was carried forward in the next step without purification, m/z (ESI, +ve ion): 668.0 (M+H)⁺.

Step 2: 1-(4-(((tert-Butyldiphenylsilyl)oxy)methyl)-2-isopropyl-6-methylphenyl)-6,7-dichloropyrido[2,3-d]pyrimidine-2,4(1H,3H)-dione To a stirred solution of N-((4-(((tert-butyldiphenylsilyl)oxy)methyl)-2-isopropyl-6-methylphenyl)carbamoyl)-2,5,6-trichloronicotinamide (3.7 g, 5.5 mmol) in THF (20 mL) at 0° C. was added 1 M KHMDS in THF (11 mL, 11 mmol).

After 2 h, the reaction was quenched with satd. ammonium chloride and diluted with EtOAc. The aqueous layer was extracted with EtOAc and the combined organic extracts were dried over $Na_2SO_4$, filtered, and concentrated in vacuo. The crude product was purified by silica gel chromatography (eluent: 0-50% EtOAc/heptane) to provide 1-(4-(((tert-butyldiphenylsilyl)oxy)methyl)-2-isopropyl-6-methylphenyl)-6,7-dichloropyrido[2,3-d]pyrimidine-2,4(1H,3H)-dione. m/z (ESI, +ve ion): 632.0 (M+H)$^+$.

Step 3: tert-Butyl (S)-4-(1-(4-(((tert-butyldiphenylsilyl)oxy)methyl)-2-isopropyl-6-methylphenyl)-6,7-dichloro-2-oxo-1,2-dihydropyrido[2,3-d]pyrimidin-4-yl)-3-methylpiperazine-1-carboxylate To a stirred solution of 1-(4-(((tert-butyldiphenylsilyl)oxy)methyl)-2-isopropyl-6-methylphenyl)-6,7-dichloropyrido[2,3-d]pyrimidine-2,4(1H,3H)-dione (2.8 g, 4.5 mmol) in acetonitrile (20 mL) was added DIPEA (1.2 mL, 6.7 mmol), followed by phosphorus oxychloride (0.63 mL, 6.7 mmol). After the addition was completed, the mixture was stirred and heated at 60° C. for 3 h. The mixture was concentrated in vacuo to provide a crude residue which was dissolved in DCM. The solution was cooled to 0° C. and DIPEA (3.9 mL, 23 mmol) and tert-butyl (S)-3-methylpiperazine-1-carboxylate (0.90 g, 4.5 mmol) were added. After 2 h, the reaction was quenched with water, the aqueous layer was extracted with DCM and the combined organic extracts were dried over $Na_2SO_4$, then concentrated in vacuo. The crude product was purified by silica gel chromatography (eluent: 0-50% EtOAc/heptane) to provide tert-butyl (S)-4-(1-(4-(((tert-butyldiphenylsilyl)oxy)methyl)-2-isopropyl-6-methylphenyl)-6,7-dichloro-2-oxo-1,2-dihydropyrido[2,3-d]pyrimidin-4-yl)-3-methylpiperazine-1-carboxylate. $^1$H NMR (400 MHz, DMSO-d$_6$) δ 0.96 (d, J=6.7 Hz, 3H), 1.02 (d, J=6.8 Hz, 3H), 1.08 (s, 9H), 1.31 (dd, J=8.9, 7.1 Hz, 3H), 1.45 (s, 9H), 1.87 (d, J=2.5 Hz, 3H), 2.39-2.47 (m, 1H), 2.96-3.19 (m, 2H), 3.28 (s, 1H), 3.59-3.74 (m, 1H), 3.82 (br d, J=12.0 Hz, 1H), 3.88-4.00 (m, 1H), 4.09-4.23 (m, 1H), 4.83 (s, 3H), 7.10 (s, 1H), 7.31 (s, 1H), 7.41-7.54 (m, 6H), 7.69 (br d, J=7.7 Hz, 4H), 8.42 (d, J=9.5 Hz, 1H).

Step 4: tert-Butyl (S)-4-(1-(4-(((tert-butyldiphenylsilyl)oxy)methyl)-2-isopropyl-6-methylphenyl)-6-chloro-7-(2-fluorophenyl)-2-oxo-1,2-dihydropyrido[2,3-d]pyrimidin-4-yl)-3-methylpiperazine-1-carboxylate A mixture of tert-butyl (S)-4-(1-(4-(((tert-butyldiphenylsilyl)oxy)methyl)-2-isopropyl-6-methylphenyl)-6,7-dichloro-2-oxo-1,2-dihydropyrido[2,3-d]pyrimidin-4-yl)-3-methylpiperazine-1-carboxylate (2.8 g, 3.4 mmol), (2-fluorophenyl)boronic acid (0.71 g, 5.1 mmol. Combi-Blocks, San Diego, Calif., USA), potassium acetate (1.7 g, 17 mmol), and Pd(dppf)Cl$_2$ (0.25 g, 0.34 mmol) in 1,4-dioxane (20 mL)/water (0.5 mL) was stirred and heated at 90° C. for 3 h. The mixture was cooled to rt and diluted with water. The aqueous mixture was extracted with EtOAc, the combined organic extracts were dried over $Na_2SO_4$ and concentrated in vacuo to provide tert-butyl (S)-4-(1-(4-(((tert-butyldiphenylsilyl)oxy)methyl)-2-isopropyl-6-methylphenyl)-6-chloro-7-(2-fluorophenyl)-2-oxo-1,2-dihydropyrido[2,3-d]pyrimidin-4-yl)-3-methylpiperazine-1-carboxylate which was used in the next step without further purification.

Step 5: (S)-4-(4-Acryloyl-2-methylpiperazin-1-yl)-1-(4-(((tert-butyldiphenylsilyl)oxy)methyl)-2-isopropyl-6-methylphenyl)-6-chloro-7-(2-fluorophenyl)pyrido[2,3-d]pyrimidin-2(1H)-one To a solution of tert-butyl (S)-4-(1-(4-(((tert-butyldiphenylsilyl)oxy)methyl)-2-isopropyl-6-methylphenyl)-6-chloro-7-(2-fluorophenyl)-2-oxo-1,2-dihydropyrido[2,3-d]pyrimidin-4-yl)-3-methylpiperazine-1-carboxylate (2.0 g, 2.3 mmol) in DCM (10 mL) was added TFA (3.5 mL, 46 mmol). The reaction was stirred at rt for 3 h and concentrated in vacuo. The residue was dissolved in DCM (10 mL), cooled to 0° C., then treated with DIPEA (2.0 mL, 11 mmol) and acryloyl chloride (1.1 M in DCM. 2.1 mL, 2.3 mmol). The reaction was stirred at 0° C. for 2 h, the mixture was diluted with water and extracted with DCM. The organic layer was dried over $Na_2SO_4$ and concentrated in vacuo. The crude product was purified by silica gel chromatography (eluent: 0-70% EtOAc/heptane) to provide (S)-4-(4-acryloyl-2-methylpiperazin-1-yl)-1-(4-(((tert-butyldiphenylsilyl)oxy)methyl)-2-isopropyl-6-methylphenyl)-6-chloro-7-(2-fluorophenyl)pyrido[2,3-d]pyrimidin-2(1H)-one. $^1$H NMR (400 MHz, DMSO-d$_6$) δ 0.88-0.94 (m, 3H), 1.03 (s, 9H), 1.24-1.28 (m, 3H), 1.31-1.37 (m, 3H), 1.87 (s, 3H), 3.03-3.33 (m, 2H), 3.58-3.83 (m, 2H), 3.98-4.19 (m, 1H), 4.22-4.48 (m, 2H), 4.76 (s, 2H), 4.93 (br s. 1H), 5.76 (br d, J=10.6 Hz, 1H), 6.13-6.27 (m, 1H), 6.79-6.94 (m, 1H), 7.02 (br s, 1H), 7.17-7.33 (m, 4H), 7.35-7.55 (m, 7H), 7.60-7.68 (m, 4H), 8.44 (br s, 1H). $^{19}$F NMR (377 MHz, DMSO-d$_6$) δ −114.17 (s, 1F).

Step 6: (S)-4-(4-Acryloyl-2-methylpiperazin-1-yl)-6-chloro-7-(2-fluorophenyl)-1-(4-(hydroxymethyl)-2-isopropyl-6-methylphenyl)pyrido[2,3-d]pyrimidin-2(1H)-one (Intermediate 80A)

To a stirred solution of (S)-4-(4-acryloyl-2-methylpiperazin-1-yl)-1-(4-(((tert-butyldiphenylsilyl)oxy)methyl)-2-isopropyl-6-methylphenyl)-6-chloro-7-(2-fluorophenyl)pyrido[2,3-d]pyrimidin-2(1H)-one (270 mg, 0.33 mmol) in THF (5 mL) was added TBAF (1 M in THF, 0.33 mL, 0.33 mmol). The mixture was stirred at rt for 2 h and concentrated in vacuo. The crude product was purified by silica gel chromatography (eluent: 0-50% 3:1 EtOAc-EtOH/heptane) to provide (S)-4-(4-acryloyl-2-methylpiperazin-1-yl)-6-chloro-7-(2-fluorophenyl)-1-(4-(hydroxymethyl)-2-isopropyl-6-methylphenyl)pyrido[2,3-d]pyrimidin-2(1H)-one (Intermediate 80A). $^1$H NMR (400 MHz, DMSO-d$_6$) δ 0.94 (d, J=6.8 Hz, 3H), 1.05 (d, J=6.8 Hz, 3H), 1.33 (d, J=6.8 Hz, 3H), 1.87 (s, 3H), 2.51-2.58 (m, 1H), 3.03-3.28 (m, 1H), 3.41-3.86 (m, 2H), 3.97-4.44 (m, 3H), 4.46 (d, J=5.8 Hz, 2H), 4.92 (br s, 1H), 5.14 (t, J=5.8 Hz, 1H), 5.71-5.81 (m, 1H), 6.20 (br dd, J=16.6, 3.3 Hz, 1H), 6.79-6.94 (m, 1H), 7.05 (s, 1H), 7.16 (s, 1H), 7.18-7.23 (m, 1H), 7.24-7.36 (m, 2H), 7.47-7.56 (m, 1H), 8.43 (br d, J=4.6 Hz, 1H). $^{19}$F NMR (376 MHz, DMSO-d$_6$) δ 114.26 (s, 1F); m/z (ESI, +ve ion): 590.0 (M+H)$^+$.

Step 7: (S)-4-(4-(4-Acryloyl-2-methylpiperazin-1-yl)-6-chloro-7-(2-fluorophenyl)-2-oxopyrido[2,3-d]pyrimidin-1(2H)-yl)-3-isopropyl-5-methylbenzaldehyde To a solution of (S)-4-(4-acryloyl-2-methylpiperazin-1-yl)-6-chloro-7-(2-fluorophenyl)-1-(4-(hydroxymethyl)-2-isopropyl-6-methylphenyl)pyrido[2,3-d]pyrimidin-2(1H)-one (Intermediate 80A, 100 mg, 0.17 mmol) in DCM (3.4 mL) at it was added Dess-Martin periodinane (110 mg, 0.25 mmol). After 20 min, the reaction was quenched by addition of 1 N sodium thiosulfate (10 mL) and diluted with DCM (5 mL). The layers were partitioned and then the aqueous phase was washed with DCM (2×10 mL). The combined organic extracts were dried over anhydrous sodium sulfate, filtered through Celite®, and concentrated under reduced pressure to afford crude (S)-4-(4-(4-acryloyl-2-methylpiperazin-1-yl)-6-chloro-7-(2-fluorophenyl)-2-oxopyrido[2,3-d]pyrimidin-1(2H)-yl)-3-isopropyl-5-methylbenzaldehyde as a light-yellow foam that was carried forward in the following step without purification. m/z (ESI, +ve ion): 588.0 (M+H)+.

Step 8: 6-Chloro-1-(4-((dimethylamino)methyl)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one To a solution of (S)-4-(4-(4-acryloyl-2-methylpiperazin-1-yl)-6-chloro-7-(2-fluorophenyl)-2-oxopyrido[2,3-d]pyrimidin-1(2H)-yl)-3-isopropyl-5-methylbenzaldehyde (100 mg, 0.17 mmol) in THF (1.0 mL) at rt was added dimethyl amine solution (2 M in THF, 95 µL, 0.19 mmol), glacial acetic acid (10 µL, 0.17 mmol), and sodium triacetoxyborohydride (72 mg, 0.34 mmol). The resulting cloudy yellow mixture was stirred at rt. After 18 h, the reaction mixture was diluted with EtOAc (10 mL) and water (5 mL), then saturated aqueous sodium bicarbonate (5 mL) was added until the aqueous phase was neutralized. The layers were partitioned and the aqueous phase was extracted with EtOAc (1×20 mL), then the combined organic extracts were dried over anhydrous magnesium sulfate, filtered, and concentrated to afford a light-yellow oil. The crude product was purified by silica gel chromatography (eluent: 0-20% 2 M NH3 in MeOH/DCM) to afford 6-chloro-1-(4-((dimethylamino)methyl)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one. $^1$H NMR (400 MHz, DMSO-d6) δ 0.92 (d, J=6.8 Hz, 3H), 1.05 (d, J=6.8 Hz, 3H), 1.31-1.36 (m, 3H), 1.87 (s, 3H), 2.14 (s, 6H), 3.02-3.26 (m, 1H), 3.35 (s, 2H), 3.44-3.83 (m, 2H), 3.97-4.47 (m, 3H), 4.93 (br s, 1H), 5.72-5.80 (m, 1H), 6.13-6.28 (m, 1H), 6.79-6.93 (m, 1H), 7.02 (s, 1H), 7.11 (s, 1H), 7.14-7.36 (m, 4H), 7.42-7.56 (m, 1H), 8.43 (br s, 1H). $^{19}$F NMR (376 MHz, DMSO-d$_6$) δ −113.53 (s, 1F). m/z (ESI, +ve ion): 617.2 (M+H)+.

TABLE 80

Compounds 80-10 to 80-21 were prepared following the procedure described in Method 80, Steps 1-8, above as follows:

| Ex. # | Chemical structure | Name | Method Changes | Reagent |
|---|---|---|---|---|
| 80-10 | 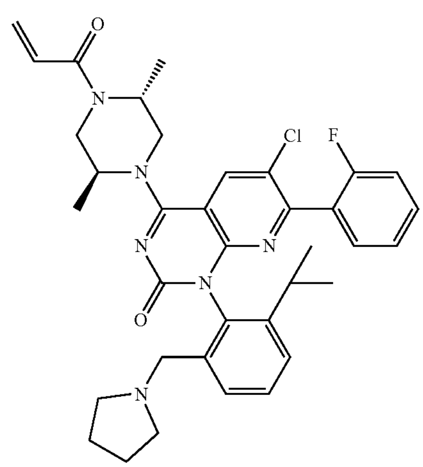 [SMILES: C=CC(=O)N1C[C@H](C)N(c2nc(=O)n(-c3c(CN4CCCC4)cccc3C(C)C)c3nc(-c4ccccc4F)c(Cl)cc23)C[C@H]1C] | 6-Chloro-4-[(2S,5R)-2,5-dimethyl-4-prop-2-enoyl-piperazin-1-yl]-7-(2-fluorophenyl)-1-[2-isopropyl-6-(pyrrolidin-1-ylmethyl)phenyl]pyrido[2,3-d]pyrimidin-2-one | Step 1 (Intermediates 99B and I-40). Omit step 4. Used Pyridine. SO3 instead of DMP in step 7 | Step 8: (pyrrolidine) |
| 80-11 | 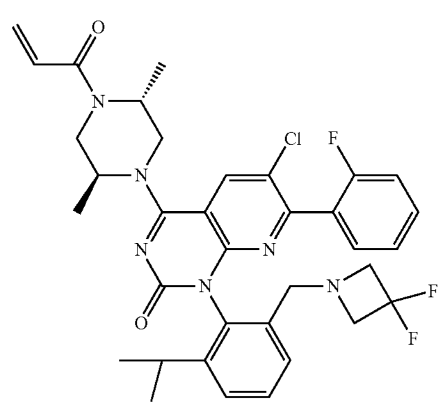 [SMILES: C=CC(=O)N1C[C@H](C)N(c2nc(=O)n(-c3c(CN4CC(F)(F)C4)cccc3C(C)C)c3nc(-c4ccccc4F)c(Cl)cc23)C[C@H]1C] | 6-chloro-1-[2-[(3,3-difluoroazetidin-1-yl)methyl]-6-isopropyl-phenyl]-4-[(2S,5R)-2,5-dimethyl-4-prop-2-enoyl-piperazin-1-yl]-7-(2-fluorophenyl)pyrido[2,3-d]pyrimidin-2-one | Step 1 (Intermediates 99B and I-40). Omit step 4. Used Pyridine. SO3 instead of DMP in step 7 | Step 8: (3,3-difluoroazetidine hydrochloride) |

TABLE 80-continued

Compounds 80-10 to 80-21 were prepared following the procedure described in Method 80, Steps 1-8, above as follows:

| Ex. # | Chemical structure | Name | Method Changes | Reagent |
|---|---|---|---|---|
| 80-12 | 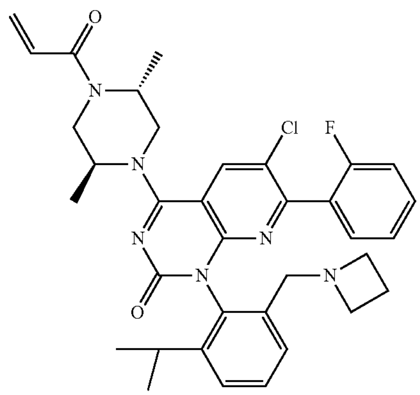 [SMILES: C=CC(=O)N1C[C@H](C)N(c2nc(=O)n(-c3c(CN4CCC4)cccc3C(C)C)c3nc(-c4ccccc4F)c(Cl)cc23)C[C@H]1C] | 1-[2-(azetidin-1-ylmethyl)-6-isopropyl-phenyl]-6-chloro-4-[(2S,5R)-2,5-dimethyl-4-prop-2-enoyl-piperazin-1-yl]-7-(2-fluorophenyl)pyrido[2,3-d]pyrimidin-2-one | Step 1 (Intermediates 99B and I-40). Omit step 4. Used Pyridine. SO3 instead of DMP in step 7 | Step 8: (azetidine) |
| 80-13 | 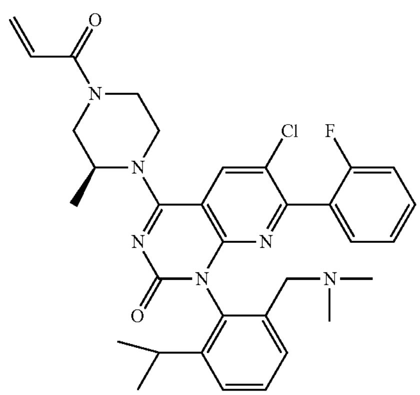 [SMILES: C=CC(=O)N1CCN(c2nc(=O)n(-c3c(CN(C)C)cccc3C(C)C)c3nc(-c4ccccc4F)c(Cl)cc23)[C@@H](C)C1] | 6-Chloro-1-[2-[(dimethylamino)methyl]-6-isopropyl-phenyl]-7-(2-fluorophenyl)-4-[(2S)-2-methyl-4-prop-2-enoyl-piperazin-1-yl]pyrido[2,3-d]pyrimidin-2-one | Step 8: dimethylamine hydrochloride and no acetic acid | Step 7: Intermediate 206 |
| 80-14 | 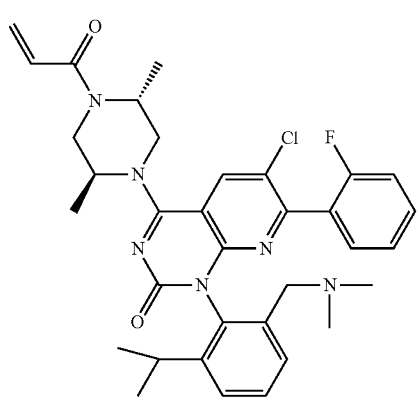 [SMILES: C=CC(=O)N1C[C@H](C)N(c2nc(=O)n(-c3c(CN(C)C)cccc3C(C)C)c3nc(-c4ccccc4F)c(Cl)cc23)C[C@H]1C] | 6-Chloro-1-[2-[(dimethylamino)methyl]-6-isopropyl-phenyl]-4-[(2S,5R)-2,5-dimethyl-4-prop-2-enoyl-piperazin-1-yl]-7-(2-fluorophenyl)pyrido[2,3-d]pyrimidin-2-one | Step 8: dimethylamine hydrochloride and no acetic acid | Step 1: Intermediate I-40; Step 3: (2R,5S)-tert-butyl 2,5-dimethylpiperazine-1-carboxylate (eNovation Chemicals LLC) |

TABLE 80-continued

Compounds 80-10 to 80-21 were prepared following the procedure described in Method 80, Steps 1-8, above as follows:

| Ex. # | Chemical structure | Name | Method Changes | Reagent |
|---|---|---|---|---|
| 80-16 | 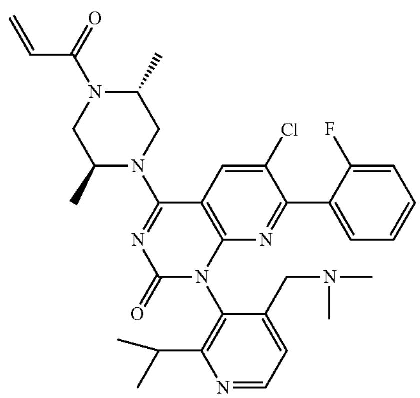 [SMILES: C=CC(=O)N1C[C@H](C)N(c2nc(=O)n(-c3c(CN(C)C)ccnc3C(C)C)c3nc(-c4ccccc4F)c(Cl)cc23)C[C@H]1C] | 6-Chloro-1-[4-[(dimethylamino)methyl]-2-isopropyl-3-pyridyl]-4-[(2S,5R)-2,5-dimethyl-4-prop-2-enoyl-piperazin-1-yl]-7-(2-fluorophenyl)pyrido[2,3-d]pyrimidin-2-one | Step 8: dimethylamine hydrochloride and no acetic acid | Step 1: Intermediate 207; Step 3: (2R,5S)-tert-butyl 2,5-dimethylpiperazine-1-carboxylate (eNovation Chemicals LLC) |
| 80-18 | 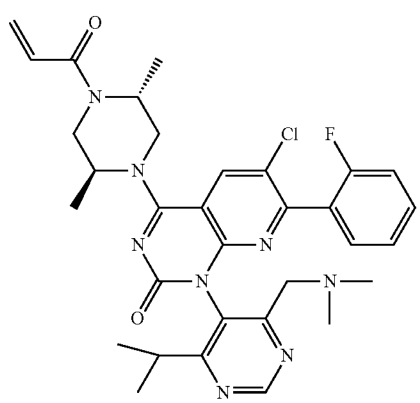 [SMILES: C=CC(=O)N1C[C@H](C)N(c2nc(=O)n(-c3c(CN(C)C)ncnc3C(C)C)c3nc(-c4ccccc4F)c(Cl)cc23)C[C@H]1C] | 6-Chloro-1-[4-[(dimethylamino)methyl]-6-isopropyl-pyrimidin-5-yl]-4-[(2S,5R)-2,5-dimethyl-4-prop-2-enoyl-piperazin-1-yl]-7-(2-fluorophenyl)pyrido[2,3-d]pyrimidin-2-one | Step 8: dimethylamine hydrochloride and no acetic acid | Step 1: Intermediate 208; Step 3: (2R,5S)-tert-butyl 2,5-dimethylpiperazine-1-carboxylate (eNovation Chemicals LLC) |
| 80-20 | 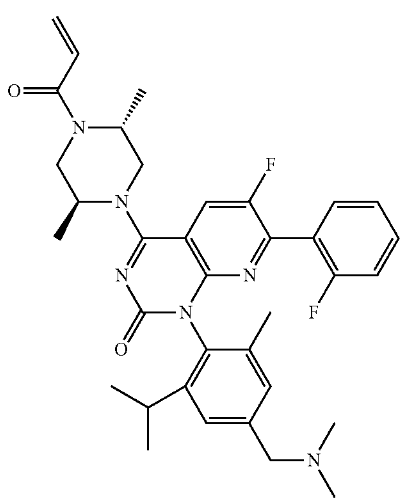 [SMILES: C=CC(=O)N1C[C@H](C)N(c2nc(=O)n(-c3c(C)cc(CN(C)C)cc3C(C)C)c3nc(-c4ccccc4F)c(F)cc23)C[C@H]1C] | 1-[4-[(Dimethylamino)methyl]-2-isopropyl-6-methyl-phenyl]-4-[(2S,5R)-2,5-dimethyl-4-prop-2-enoyl-piperazin-1-yl]-6-fluoro-7-(2-fluorophenyl)pyrido[2,3-d]pyrimidin-2-one | Step 6: 0° C. to room temp | Step 1: Intermediate S; Step 3 (2): tert-butyl (2R,5S)-2,5-dimethylpiperazine-1-carboxylate (eNovation Chemicals LLC, Bridgewater, NJ, USA) |

TABLE 80-continued

Compounds 80-10 to 80-21 were prepared following the procedure described in Method 80, Steps 1-8, above as follows:

| Ex. # | Chemical structure | Name | Method Changes | Reagent |
|---|---|---|---|---|
| 80-21 | 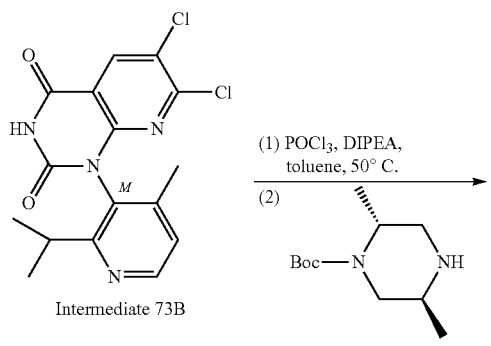 | 1-[4-[(Dimethylamino)methyl]-2-isopropyl-6-methyl-phenyl]-4-[(2S,5R)-2,5-dimethyl-4-prop-2-enoyl-piperazin-1-yl]-6-fluoro-7-(2-fluoro-6-hydroxy-phenyl)pyrido[2,3-d]pyrimidin-2-one | Step 6: 0° C. to room temp | Step 1: Intermediate S; Step 3 (2): tert-butyl (2R,5S)-2,5-dimethylpiperazine-1-carboxylate (eNovation Chemicals LLC, Bridgewater, NJ, USA); Step 4: Intermediate Q |

Method 92

Example 92-1: (M)-6-Chloro-4-[(2S,5R)-2,5-dimethyl-4-prop-2-enoyl-piperazin-1-yl]-1-(2-isopropyl-4-methyl-3-pyridyl)-7-(2-isopropylphenyl)pyrido[2,3-d]pyrimidin-2-one

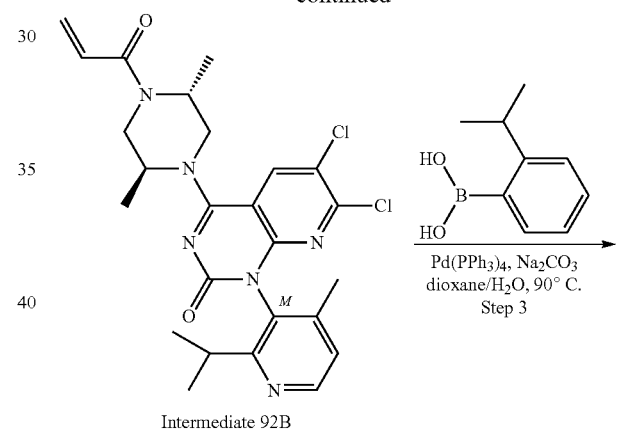

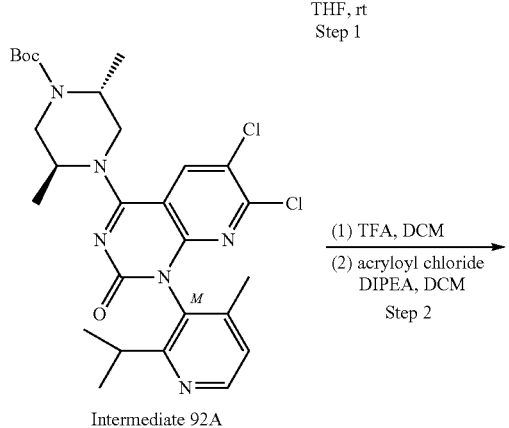

Step 1: (M)-tert-Butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate To a mixture of (M)-6,7-dichloro-1-(2-isopropyl-4-methylpyridin-3-yl)pyrido[2,3-d]pyrimidine-2,4(1H,3H)-dione (Intermediate 73B, 9.96 g, 27.3 mmol) and DIPEA (7.1 mL, 40.9 mmol) in acetonitrile (100 mL) was added phosphorous oxychloride (3.8 mL, 40.9 mmol) and the mixture was stirred at 80° C. for 1.5 h. The reaction mixture was concentrated in vacuo to give brown solid. The crude solid was used in next step without purification. m/z (ESI, +ve ion): 383.0 (M+H)$^+$.

The above crude solid and DIPEA (7.1 mL, 40.9 mmol) in DMF (60 mL) was treated with (2R,5S)-1-(tert-butoxycarbonyl)-2,5-dimethylpiperazine (6.43 g, 30 mmol, AstaTech, Inc.) and stirred at rt for 16 h. The mixture was treated with satd. NaHCO$_3$ (100 mL) and stirred at rt for 15 min. The resulting precipitate was collected by filtration, washed with water, and dried to give (M)-tert-butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 92A, 14.8 g, 26.4 mmol, 97% yield). $^1$H NMR (400 MHz, DMSO-d$_6$) δ 8.46-8.50 (m, 2H), 7.26 (d, J=5.0 Hz, 1H), 4.12-4.87 (m, 2H), 3.94-4.05 (m, 1H), 3.89 (br d, J=7.9 Hz, 1H), 3.67 (dd, J=13.8, 2.6 Hz, 1H), 3.41-3.58 (m, 1H), 2.61 (quin, J=6.7 Hz, 1 H), 1.94 (s, 3H), 1.44 (s, 9H), 1.30 (d, J=6.4 Hz, 3H), 1.09 (br d, J=6.4 Hz, 3H), 1.05 (d, J=6.8 Hz, 3H), 1.02 (d, J=6.6 Hz, 3H). m/z (ESI, +ve ion): 561.2 (M+H)$^+$.

Step 2: (M)-4-((2 S,5R)-4-Acryloyl-2,5-dimethylpiperazin-1-yl)-6,7-dichloro-1-(2-isopropyl-4-methylpyridin-3-yl)pyrido[2,3-d]pyrimidin-2(1H)-one A mixture of (M)-tert-butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 92A, 0.82 g, 1.45 mmol) in DCM (7 mL) and TFA (7 mL) was stirred at rt for 30 min. The reaction was concentrated in vacuo to afford (M)-6,7-dichloro-4-((2S,5R)-2,5-dimethylpiperazin-1-yl)-1-(2-isopropyl-4-methylpyridin-3-yl)pyrido[2,3-d]pyrimidin-2(1H)-one as yellow syrup. m/z (ESI, +ve ion): 461.2 (M+H)$^+$.

A mixture of (M)-6,7-dichloro-4-((2S,5R)-2,5-dimethylpiperazin-1-yl)-1-(2-isopropyl-4-methylpyridin-3-yl)pyrido[2,3-d]pyrimidin-2(1H)-one and DIPEA (1.3 mL, 7.26 mmol) in DCM (7 mL) was treated with acryloyl chloride (0.12 mL, 1.45 mmol) at 0° C. and stirred for 40 min. The reaction mixture was concentrated in vacuo. The crude product was purified by silica gel chromatography (eluent: 0-100% EtOAc-MeOH (9:1)/heptane) to provide pure (M)-4-((2S,5R)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate 92B; 0.53 g, 1.03 mmol, 71% yield) as a light-yellow foam. $^1$H NMR (400 MHz, DMSO-d$_6$) δ 8.46-8.54 (m, 2H), 7.30 (d, J=5.0 Hz, 1H), 6.82 (ddd, J=16.5, 14.0, 10.5 Hz, 1H), 6.18 (dd, J=16.7, 2.2 Hz, 1H), 5.74 (dt, J=10.4, 2.7 Hz, 1H), 4.78-4.91 (m, 1H), 4.39-4.75 (m, 1H), 3.97-4.16 (m, 1H), 3.94 (br s, 1H), 3.83 (br d, J=3.9 Hz, 1H), 3.49 (br dd, J=13.9, 3.7 Hz, 1H), 2.59-2.70 (m, 1H), 1.97 (s, 3H), 1.25-1.32 (m, 3H), 1.09-1.20 (m, 3H), 1.05 (dd, J=11.4, 6.6 Hz, 6H). m/z (ESI, +ve ion): 515.2 (M+H)$^+$.

Step 3: (M)-6-Chloro-4-[(2S,5R)-2,5-dimethyl-4-prop-2-enoyl-piperazin-1-yl]-1-(2-isopropyl-4-methyl-3-pyridyl)-7-(2-isopropylphenyl)pyrido[2,3-d]pyrimidin-2-one A mixture of (M)-4-((2S,5R)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate 92B; 1.01 g, 1.97 mmol), tetrakis(triphenylphosphine)palladium (0) (0.23 g, 0.20 mmol, Sigma-Aldrich Corporation), 2-isopropylphenylboronic acid (0.49 g, 2.95 mmol, CombiBlocks Inc.) and sodium carbonate (0.63 g, 5.9 mmol) in 1,4-dioxane (6 mL) and water (3 mL) was stirred and heated at 90° C. for 2 h. The mixture was treated with water (25 mL), extracted with EtOAc (2×50 mL), dried over MgSO$_4$, filtered, and concentrated in vacuo. The crude product was purified by silica gel chromatography (eluent: 0-70% of EtOAc-EtOH (3:1)/heptane) to provide (M)-6-chloro-4-[(2S,5R)-2,5-dimethyl-4-prop-2-enoyl-piperazin-1-yl]-1-(2-isopropyl-4-methyl-3-pyridyl)-7-(2-isopropylphenyl)pyrido[2,3-d]pyrimidin-2-one (0.52 g, 0.86 mmol, 43.7% yield) as light-yellow solid. $^1$H NMR (400 MHz, DMSO-d$_6$) δ 8.42 (d, J=5.2 Hz, 1H), 8.35 (d, J=5.0 Hz, 1H), 7.37 (d, J=3.9 Hz, 2H), 7.22 (dt, J=8.2, 4.0 Hz, 1H), 7.16 (d, J=5.0 Hz, 1H), 7.00 (d, J=7.5 Hz, 1H), 6.84 (ddd, J=20.3, 16.8, 10.6 Hz, 1H), 6.19 (dd, J=16.7, 2.2 Hz, 1H), 5.72-5.80 (m, 1H), 4.44-4.93 (m, 2H), 3.39-4.32 (m, 4H), 2.74 (br s, 1H), 2.52-2.60 (m, 1H), 1.89 (s, 3H), 1.36 (dd, J=6.3, 3.8 Hz, 3H), 1.26 (br dd, J=24.7, 6.6 Hz, 3H), 0.80-1.10 (m, 12H). m/z (ESI, +ve ion): 599.2 (M+H)$^+$.

TABLE 92

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-2 | 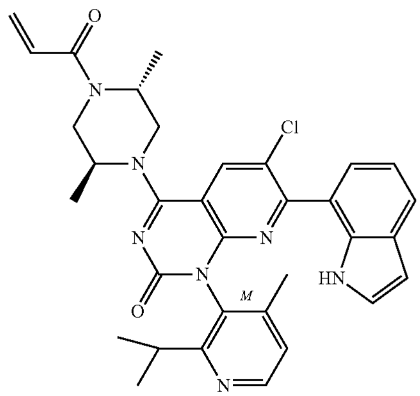 | (M)-7-(2-Amino-6-fluoro-phenyl)-6-chloro-1-(2-isopropyl-4-methyl-3-pyridyl)-4-[(3R)-3-methyl-4-prop-2-enoyl-piperazin-1-yl]pyrido[2,3-d]pyrimidin-2-one | None | Step 1: (R)-1-N-Boc-2-methylpiperazine (Combi-Blocks Inc); Step 3: (2-amino-6-fluorophenyl)boronic acid pinacol ester (CombiPhos Catalysts) |
| 92-3 | 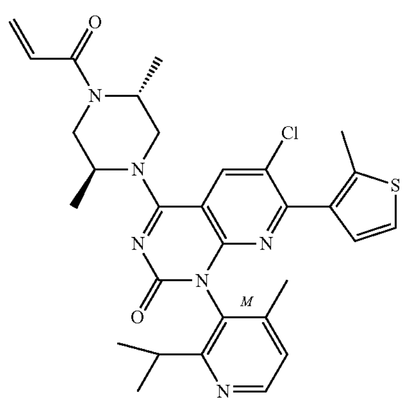 | (M)-6-Chloro-4-[(2S,5R)-2,5-dimethyl-4-prop-2-enoyl-piperazin-1-yl]-1-(2-isopropyl-4-methyl-3-pyridyl)-7-(2-methyl-3-thienyl)pyrido[2,3-d]pyrimidin-2-one | None | Step 3: (2-methylthiophen-3-yl)boronic acid (Combi-Blocks, Inc.) |
| 92-4 | 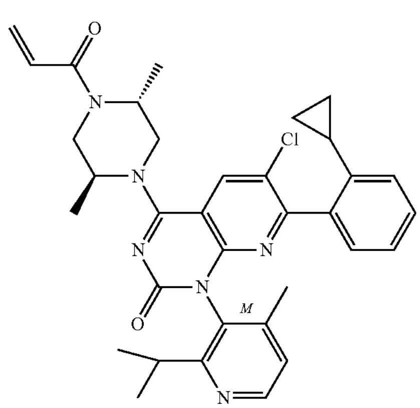 | (M)-6-Chloro-7-(2-cyclopropylphenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2-cyclopropylphenylboronic acid (CombiPhos Catalysts, Inc.) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-5 | 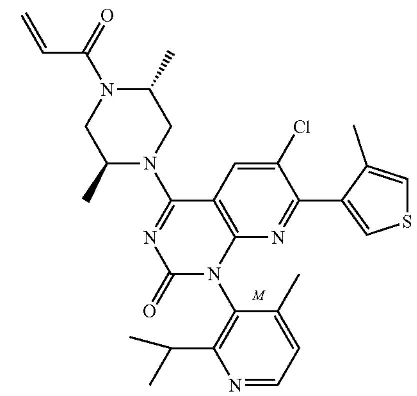 | (M)-6-Chloro-4-[(2S,5R)-2,5-dimethyl-4-prop-2-enoyl-piperazin-1-yl]-1-(2-isopropyl-4-methyl-3-pyridyl)-7-(4-methyl-3-thienyl)pyrido[2,3-d]pyrimidin-2-one | None | Step 3: 4-methyl-3-thiopheneboronic acid (Combi-Blocks, Inc.) |
| 92-6 | 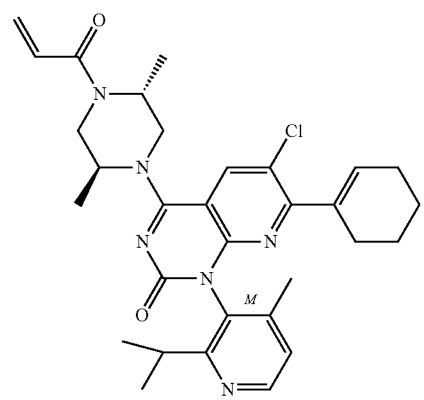 | (M)-6-Chloro-7-(cyclohexen-1-yl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: cyclohexen-1-ylboronic acid (Combi-Blocks Inc.) |
| 92-7 | 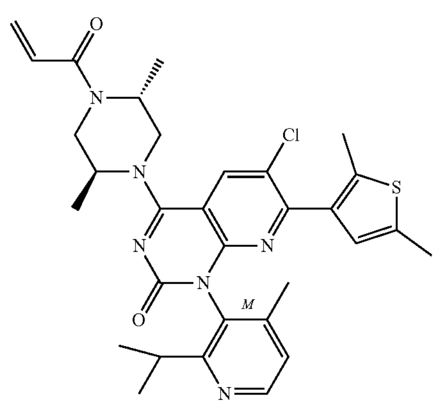 | (M)-6-Chloro-4-[(2S,5R)-2,5-dimethyl-4-prop-2-enoyl-piperazin-1-yl]-7-(2,5-dimethyl-3-thienyl)-1-(2-isopropyl-4-methyl-3-pyridyl)pyrido[2,3-d]pyrimidin-2-one | None | Step 3: 2,5-dimethylthiophene-3-boronic acid (Combi-Blocks Inc.) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-8 | 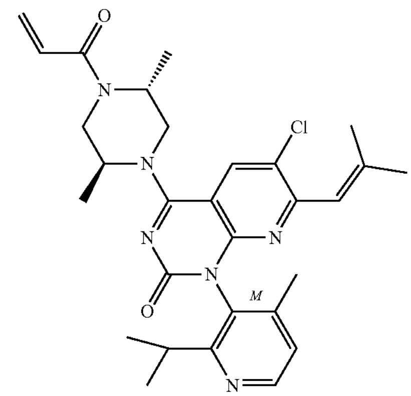 | (M)-6-Chloro-4-[(2S,5R)-2,5-dimethyl-4-prop-2-enoyl-piperazin-1-yl]-1-(2-isopropyl-4-methyl-3-pyridyl)-7-(2-methylprop-1-enyl)pyrido[2,3-d]pyrimidin-2-one | None | Step 3: 2,2-dimethylethenylboronic acid (Synthonix Inc.) |
| 92-9 | 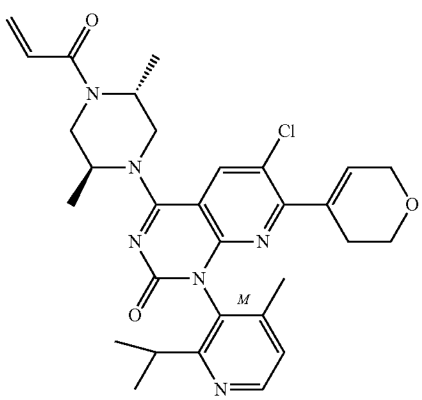 | (M)-6-Chloro-7-(3,6-dihydro-2H-pyran-4-yl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 3,6-dihydro-2H-pyran-4-boronic acid pinacol ester (Synthonix Inc.) |
| 92-10 | 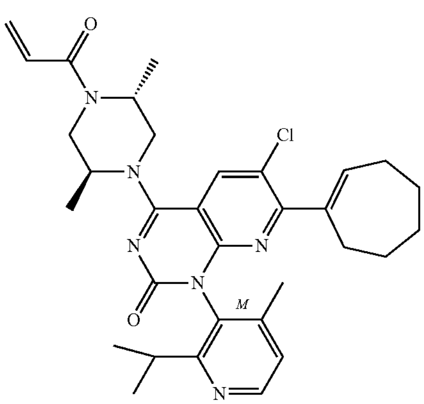 | (M)-6-Chloro-7-(cyclohepten-1-yl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 1-cycloheptenylboronic acid pinacol ester (Combi-Blocks Inc.) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-11 | 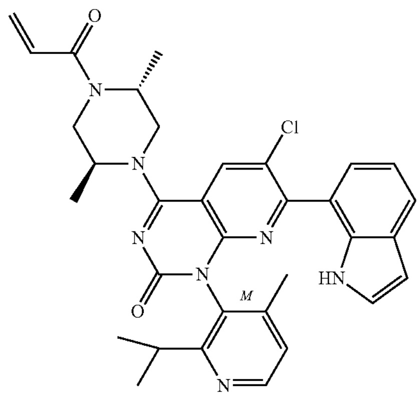 | (M)-6-Chloro-4-[(2S,5R)-2,5-dimethyl-4-prop-2-enoyl-piperazin-1-yl]-7-(1H-indol-7-yl)-1-(2-isopropyl-4-methyl-3-pyridyl)pyrido[2,3-d]pyrimidin-2-one | None | Step 3: 1H-Indol-7-ylboronic acid pinacol ester (Combi-Blocks, San Diego, CA, USA) |
| 92-12 | 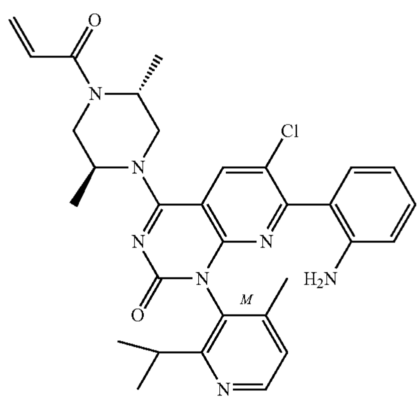 | (M)-7-(2-Aminophenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2-(4,4,5,5-Tetramethyl-1,3,2-dioxaborolan-2-yl)-aniline (Oakwood Products, Inc.) |
| 92-13 | 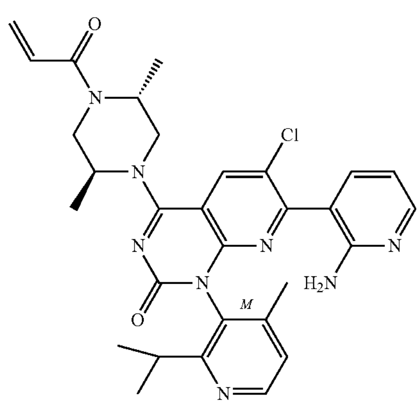 | (M)-7-(2-Amino-3-pyridyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: (2-AminopyridiN-3-yl)boronic acid pinacol ester(Combi-Blocks, San Diego, CA, USA) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-14 | 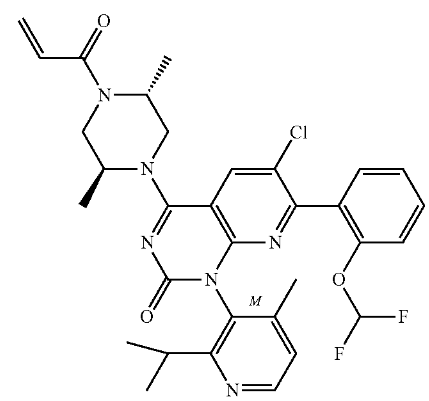 | (M)-6-Chloro-7-[2-(difluoromethoxy)phenyl]-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: (2-(Difluoromethoxy)phenyl)boronic acid (Oxchem Corporation) |
| 92-15 | 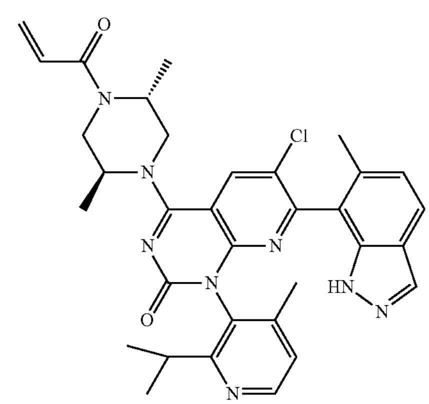 [SMILES: C=CC(=O)N1C[C@H](C)N(c2nc(=O)n(-c3c(C)ccnc3C(C)C)c3nc(-c4c(C)ccc5cn[nH]c45)c(Cl)cc23)C[C@H]1C] | (M)-6-Chloro-4-[(2S,5R)-2,5-dimethyl-4-prop-2-enoyl-piperazin-1-yl]-1-(2-isopropyl-4-methyl-3-pyridyl)-7-(6-methyl-1H-indazol-7-yl)pyrido[2,3-d]pyrimidin-2-one | None | Step 3: 6-Methyl-1h-indazole-7-boronic acid pinacol ester (J & W Pharmlab, LLC) |
| 92-16 | 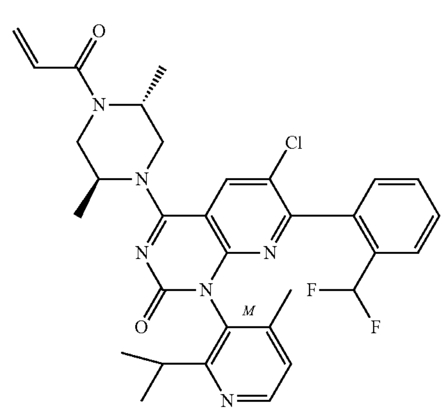 | (M)-6-Chloro-7-[2-(difluoromethyl)phenyl]-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2-[2-(Difluoromethyl)phenyl]-4,4,5,5-tetramethyl-1,3,2-dioxaborolane (Enamine) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-17 | 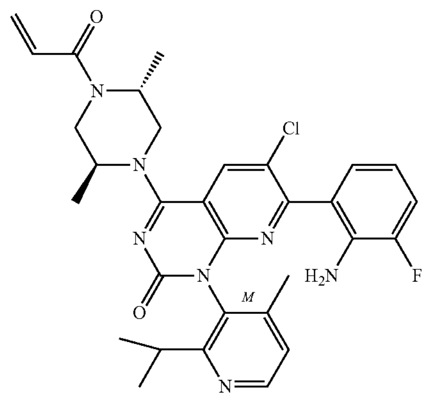 | (M)-7-(2-Amino-3-fluoro-phenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2-Fluoro-6-(4,4,5,5-tetramethyl-1,3,2-dioxaborolan-2-yl)aniline (HDH Pharma) |
| 92-18 | 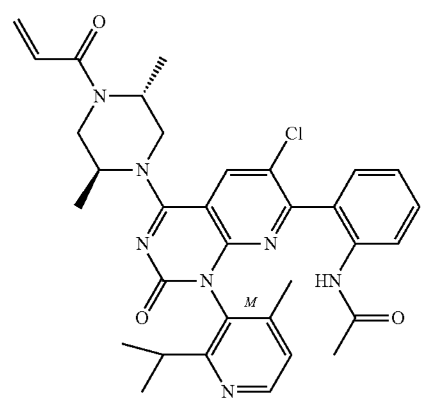 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]phenyl]acetamide | None | Step 3: (2-Acetylaminophenyl) boronic acid (Combi-Blocks, San Diego, CA, USA) |
| 92-19 | 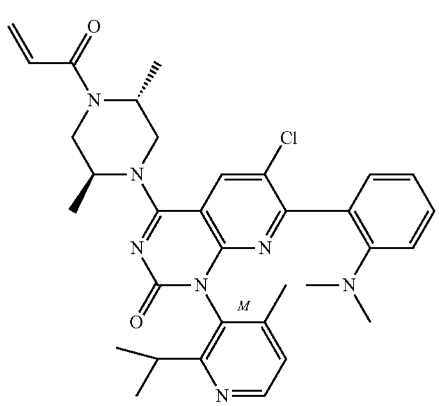 | (M)-6-Chloro-7-[2-(dimethylamino)phenyl]-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: Dimethyl[2-(4,4,5,5-tetramethyl-1,3,2-dioxaborlan-2-yl)-phenyl]amine (Fluorochem Limited) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-20 | 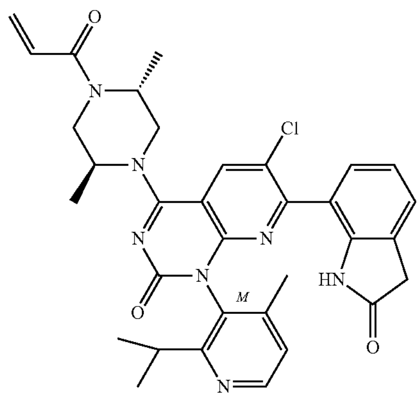 | (M)-6-Chloro-4-[(2S,5R)-2,5-dimethyl-4-prop-2-enoyl-piperazin-1-yl]-1-(2-isopropyl-4-methyl-3-pyridyl)-7-(2-oxoindolin-7-yl)pyrido[2,3-d]pyrimidin-2-one | None | Step 3: 7-(4,4,5,5-tetramethyl-1,3,2-dioxaborolan-2-yl)-1,3-dihydroindol-2-one (Combi-Blocks, San Diego, CA, USA) |
| 92-21 | 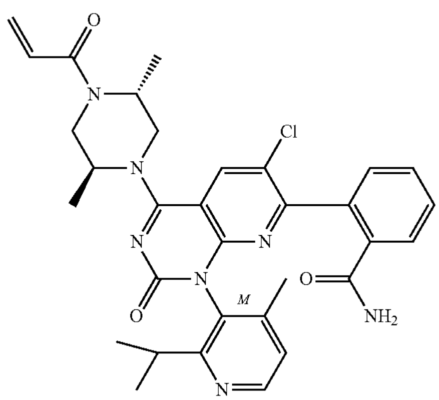 | (M)-2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]benzamide | None | Step 3: 2-aminocarbonylphenyl-boronic acid (Combi-Blocks, San Diego, CA, USA) |
| 92-22 | 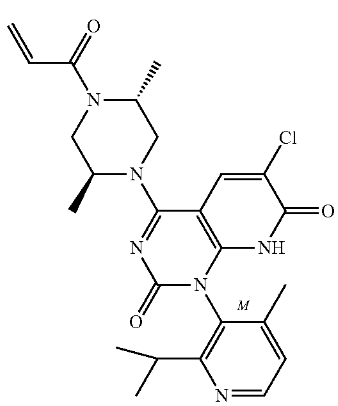 | (M)-6-Chloro-4-[(2S,5R)-2,5-dimethyl-4-prop-2-enoyl-piperazin-1-yl]-1-(2-isopropyl-4-methyl-3-pyridyl)-8H-pyrido[2,3-d]pyrimidine-2,7-dione | None | side product when using 2-aminocarbonylphenyl-boronic acid (Combi-Blocks, San Diego, CA, USA) |

TABLE 92-continued

Compounds 92-2 to 92-73 were prepared following the procedure described in
Method 92, Steps 1-3, above as follows:

| Ex. # | Chemical structure | Name | Method Changes | Reagent |
|---|---|---|---|---|
| 92-23 | 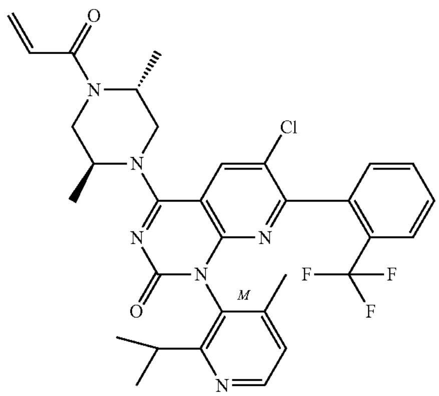 | (M)-6-Chloro-4-[(2S,5R)-2,5-dimethyl-4-prop-2-enoyl-piperazin-1-yl]-1-(2-isopropyl-4-methyl-3-pyridyl)-7-[2-(trifluoromethyl)phenyl]pyrido[2,3-d]pyrimidin-2-one | None | Step 3: 2-(trifluoromethyl)phenylboronic acid (Combi-Blocks San Diego, CA, USA) |
| 92-24 | 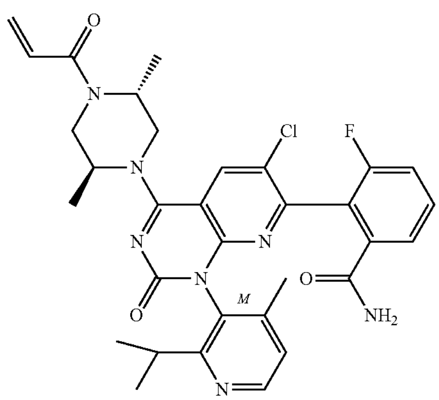 | (M)-2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-benzamide | None | Step 3: 2-carbamoyl-6-fluorophenylboronic acid pinacol ester (Combi-Blocks, San Diego, CA, USA) |
| 92-25 | 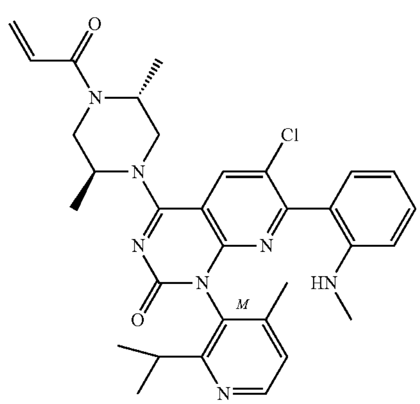 | (M)-6-Chloro-4-[(2S,5R)-2,5-dimethyl-4-prop-2-enoyl-piperazin-1-yl]-1-(2-isopropyl-4-methyl-3-pyridyl)-7-[2-(methylamino)phenyl]pyrido[2,3-d]pyrimidin-2-one | Step 3: Pd(dppf)Cl$_2$ KOAc | Step 3: 2-(methylamino)phenylboronic acid (Matrix Scientific) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-26 | 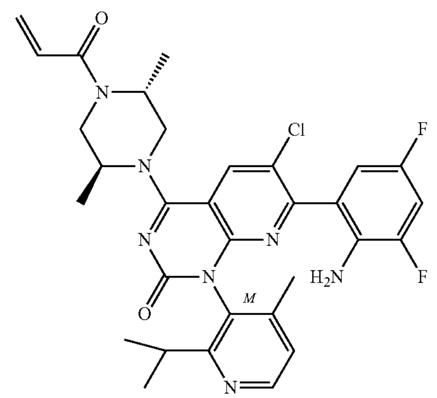 | (M)-7-(2-Amino-3,5-difluorophenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | Step 3: Pd(dppf)Cl$_2$ KOAc | Step 3: (2-amino-3,5-difluorophenyl)boronic acid pinacol ester (AstaTech, Inc) |
| 92-27 | 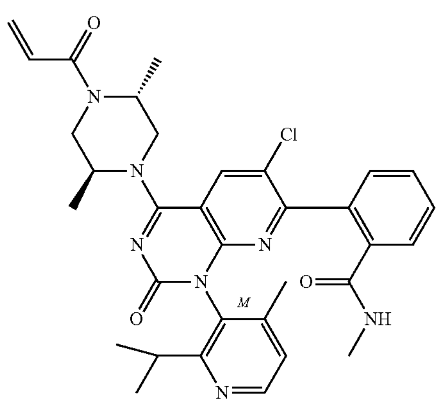 | (M)-2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-N-methyl-benzamide | Step 3: Pd(dppf)Cl$_2$ KOAc | Step 3: 2-(methylcarbamoyl)benzeneboronic acid (Combi-Blocks, San Diego, CA, USA) |
| 92-28 | 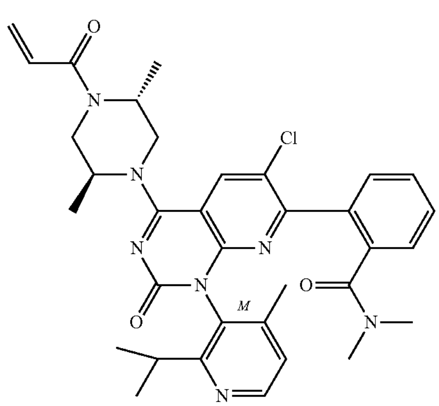 | (M)-2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-N,N-dimethyl-benzamide | Step 3: Pd(dppf)Cl$_2$ KOAc | Step 3: 2-(N,N-dimethylaminocarbonyl)phenylboronic acid, pinacol ester (Combi-Blocks, San Diego, CA, USA) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-29 | 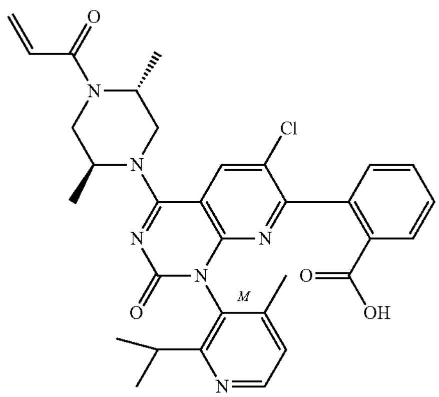 | (M)-2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]benzoic acid | Step 3: Pd(dppf)Cl$_2$ KOAc | Step 3: (2-carboxyphenyl)boronic acid (Combi-Blocks, San Diego, CA, USA) |
| 92-30 | 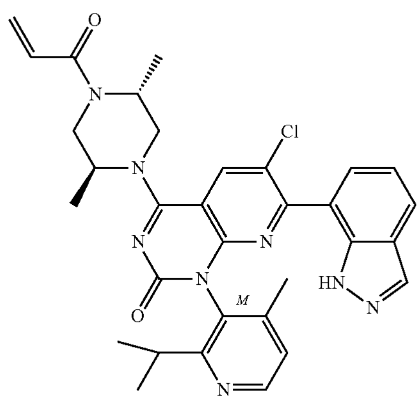 | (M)-6-Chloro-4-[(2S,5R)-2,5-dimethyl-4-prop-2-enoyl-piperazin-1-yl]-7-(1H-indazol-7-yl)-1-(2-isopropyl-4-methyl-3-pyridyl)pyrido[2,3-d]pyrimidin-2-one | Step 3: Pd(dppf)Cl$_2$ KOAc | Step 3: 1H-benzimidazol-4-ylboronic acid (Combi-Blocks, San Diego, CA, USA) |
| 92-31 | 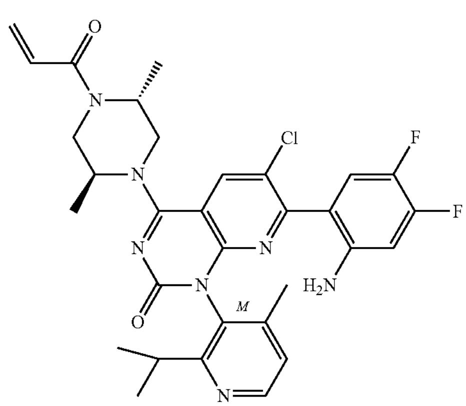 | (M)-7-(2-Amino-4,5-difluoro-phenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | Step 3: Pd(dppf)Cl$_2$ KOAc | Step 3: 2-amino-4,5-difluorophenylboronic acid (Combi-Blocks, San Diego, CA, USA) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-32 | 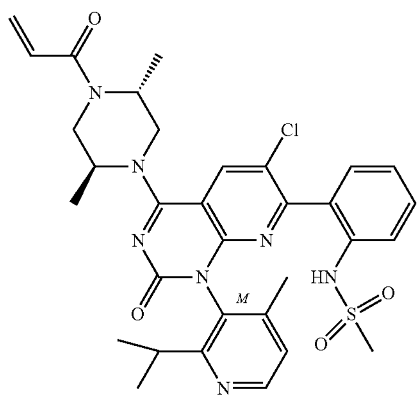 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]phenyl] methanesulfonamide | Step 3: Pd(dppf)Cl$_2$ KOAc | Step 3: (2-(methylsufonamido) phenyl)boronic acid (Combi-Blocks, San Diego, CA, USA) |
| 92-33 | 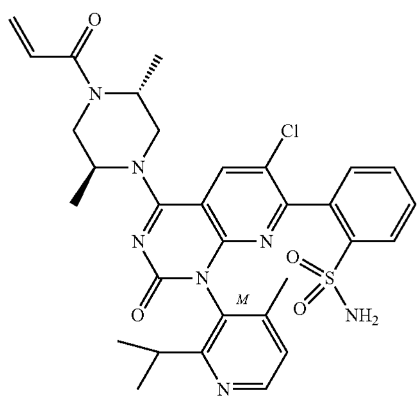 | (M)-2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl] benzenesulfonamide | Step 3: Pd(dppf)Cl$_2$ KOAc | Step 3: (2-sulfamoylphenyl) boronic acid (Combi-Blocks, San Diego, CA, USA) |
| 92-34 | 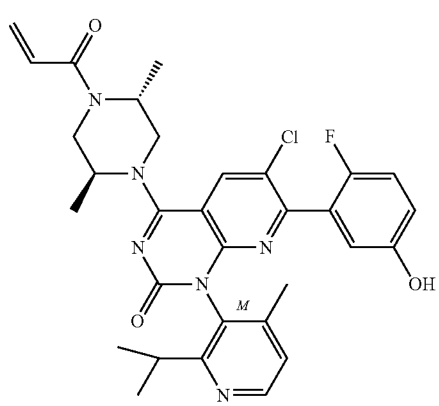 | (M)-6-Chloro-4-[(2S,5R)-2,5-dimethyl-4-prop-2-enoyl-piperazin-1-yl]-7-(2-fluoro-5-hydroxy-phenyl)-1-(2-isopropyl-4-methyl-3-pyridyl)pyrido[2,3-d]pyrimidin-2-one | Step 3: Pd(dppf)Cl$_2$ KOAc | Step 3: 2-fluoro-5-hydroxyphenylboronic acid (Combi-Blocks, San Diego, CA, USA) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-35 | 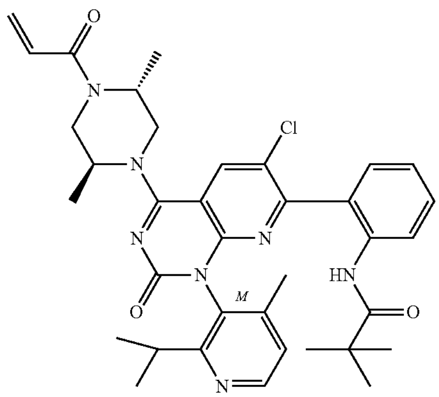 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]phenyl]-2,2-dimethyl-propanamide | Step 3: PdCl$_2$(dppf), KOAc | Step 3: 2-(2,2-dimethyl-propionylamino)phenylboronic acid (Boron Molecular Inc.) |
| 92-36 | 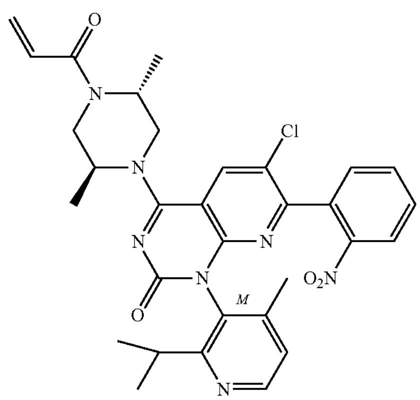 | (M)-6-Chloro-4-[(2S,5R)-2,5-dimethyl-4-prop-2-enoyl-piperazin-1-yl]-1-(2-isopropyl-4-methyl-3-pyridyl)-7-(2-nitrophenyl)pyrido[2,3-d]pyrimidin-2-one | None | Step 3: 4,4,5,5-tetramethyl-2-(2-nitrophenyl)-1,3,2-dioxaborolane (Combi-Blocks, San Diego, CA, USA) |
| 92-37 | 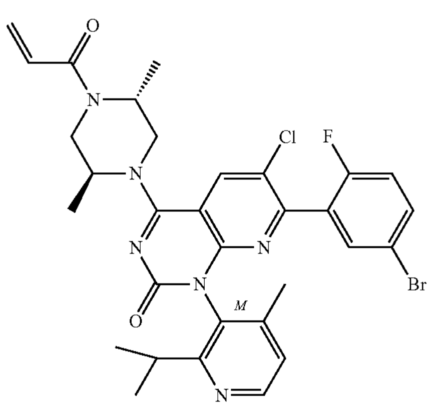 | (M)-7-(5-Bromo-2-fluoro-phenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2-(5-bromo-2-fluorophenyl)-4,4,5,5-tetramethyl-1,3,2-dioxaborolane (Combi-Blocks, San Diego, CA, USA) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-38 | 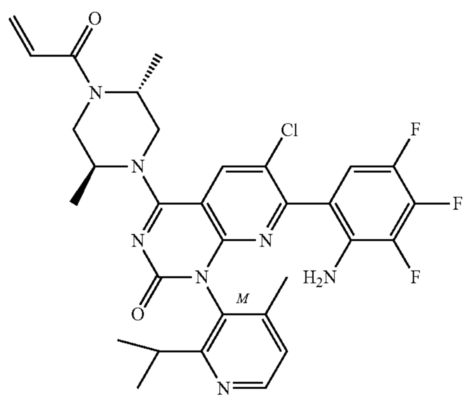 | (M)-7-(2-Amino-3,4,5-trifluoro-phenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: (2-amino-3,4,5-trifluorophenyl) boronic acid pinacol ester (Aurum Pharmatech LLC) |
| 92-39 | 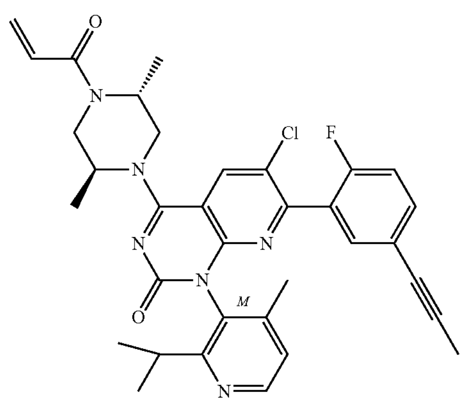 | (M)-6-Chloro-4-[(2S,5R)-2,5-dimethyl-4-prop-2-enoyl-piperazin-1-yl]-7-(2-fluoro-5-prop-1-ynyl-phenyl)-1-(2-isopropyl-4-methyl-3-pyridyl)pyrido[2,3-d]pyrimidin-2-one | None | Step 3: (2-fluoro-5-(prop-1-yn-1-yl)phenyl)boronic acid (ChemShuttle) |
| 92-40 | 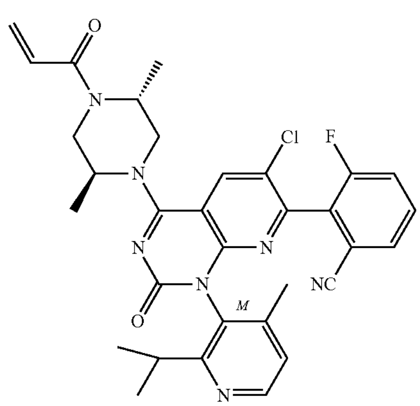 | (M)-2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-benzonitrile | Step 3: Pd(dppf)Cl$_2$ KOAc | Step 3: 3-fluoro-2-(4,4,5,5-tetramethyl-1,3,2-dioxaborolan-2-yl)benzonitrile (Combi-Blocks, San Diego, CA, USA) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-41 | 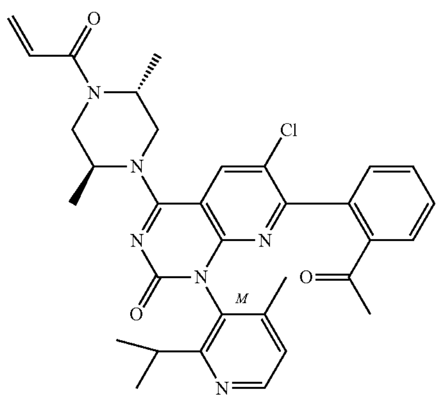 | (M)-7-(2-Acetylphenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: (2-acetylphenyl)boronic acid (Aurum Pharmatech Inc.) |
| 92-42 | 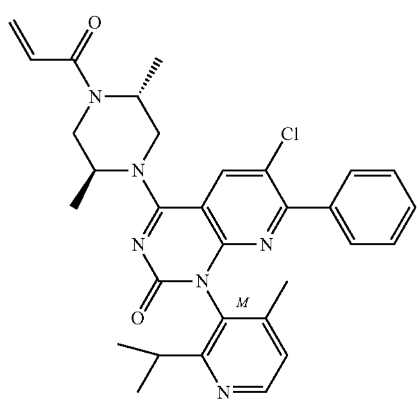 | (M)-6-Chloro-4-[(2S,5R)-2,5-dimethyl-4-prop-2-enoyl-piperazin-1-yl]-1-(2-isopropyl-4-methyl-3-pyridyl)-7-phenyl-pyrido[2,3-d]pyrimidin-2-one | None | Step 3: phenylboronic acid (Sigma-Aldrich Corporation) |
| 92-43 | 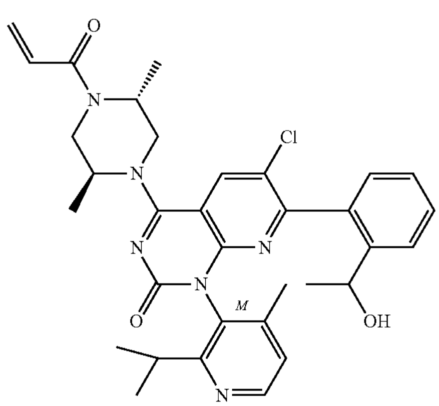 | (M)-6-Chloro-4-[(2S,5R)-2,5-dimethyl-4-prop-2-enoyl-piperazin-1-yl]-7-[2-[(1RS)-1-hydroxyethyl]phenyl]-1-(2-isopropyl-4-methyl-3-pyridyl)pyrido[2,3-d]pyrimidin-2-one | None | Step 3: (2-(1-hydroxyethyl)phenyl)boronic acid (HDH Pharma, Inc.) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-44 | 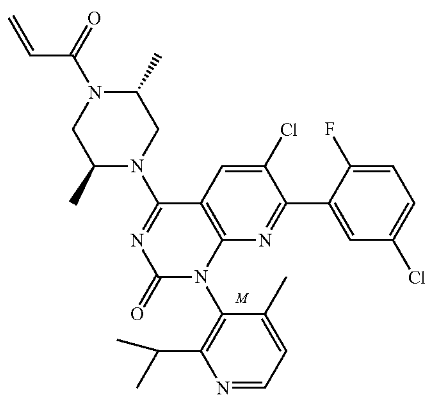 | (M)-6-Chloro-7-(5-chloro-2-fluoro-phenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 5-chloro-2-fluorophenylboronic acid (Sigma-Aldrich Corporation) |
| 92-45 | 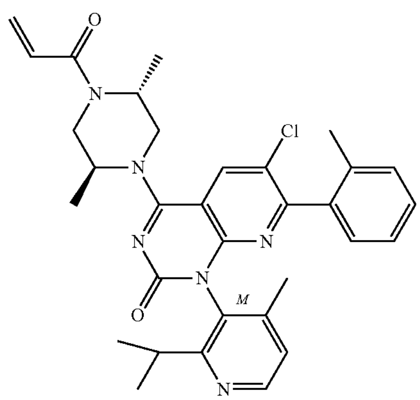 | (M)-6-Chloro-4-[(2S,5R)-2,5-dimethyl-4-prop-2-enoyl-piperazin-1-yl]-1-(2-isopropyl-4-methyl-3-pyridyl)-7-(o-tolyl)pyrido[2,3-d]pyrimidin-2-one | None | Step 3: o-tolylboronic acid (Sigma-Aldrich Corporation) |
| 92-46 | 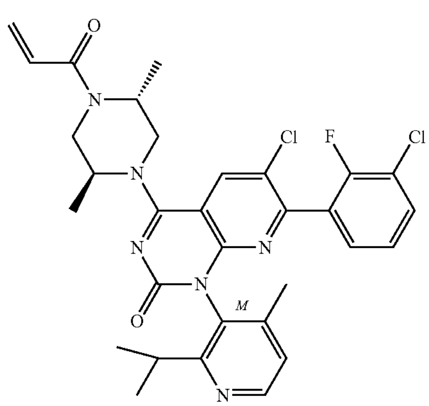 | (M)-6-Chloro-7-(3-chloro-2-fluoro-phenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2-fluoro-3-chlorophenylboronic acid (Combi-Blocks Inc.) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-47 | 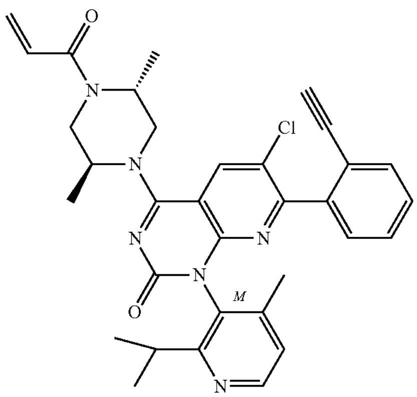 | (M)-6-Chloro-4-[(2S,5R)-2,5-dimethyl-4-prop-2-enoyl-piperazin-1-yl]-7-(2-ethynylphenyl)-1-(2-isopropyl-4-methyl-3-pyridyl)pyrido[2,3-d]pyrimidin-2-one | None | Step 3: (2-ethynylphenyl)boronic acid (Combi-Blocks Inc.) |
| 92-48 | 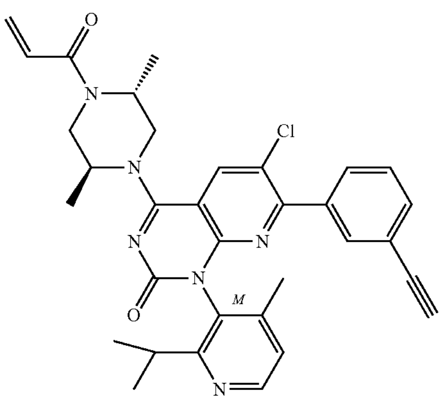 | (M)-6-Chloro-4-[(2S,5R)-2,5-dimethyl-4-prop-2-enoyl-piperazin-1-yl]-7-(3-ethynylphenyl)-1-(2-isopropyl-4-methyl-3-pyridyl)pyrido[2,3-d]pyrimidin-2-one | None | Step 3: (3-ethynylphenyl)boronic acid pinacol ester (Combi-Blocks Inc.) |
| 92-49 | 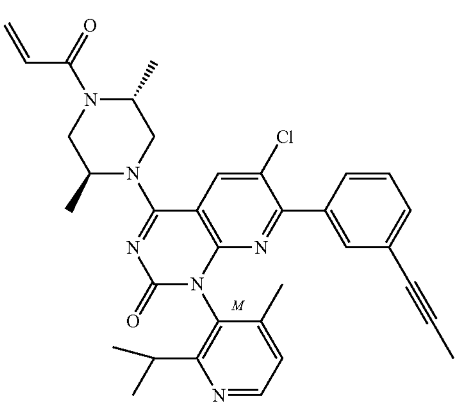 | (M)-6-Chloro-4-[(2S,5R)-2,5-dimethyl-4-prop-2-enoyl-piperazin-1-yl]-1-(2-isopropyl-4-methyl-3-pyridyl)-7-(3-prop-1-ynylphenyl)pyrido[2,3-d]pyrimidin-2-one | None | Step 3: [3-(prop-1-yn-1-yl)phenyl]boronic acid (Enamine) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-50 | 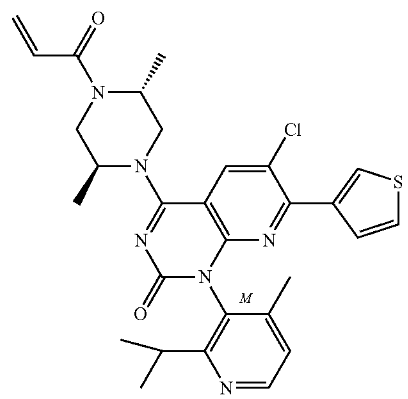 | (M)-6-Chloro-4-[(2S,5R)-2,5-dimethyl-4-prop-2-enoyl-piperazin-1-yl]-1-(2-isopropyl-4-methyl-3-pyridyl)-7-(3-thienyl)pyrido[2,3-d]pyrimidin-2-one | None | Step 3: 3-thienylboronic acid (Maybridge Chemical Co., Ltd.) |
| 92-51 | 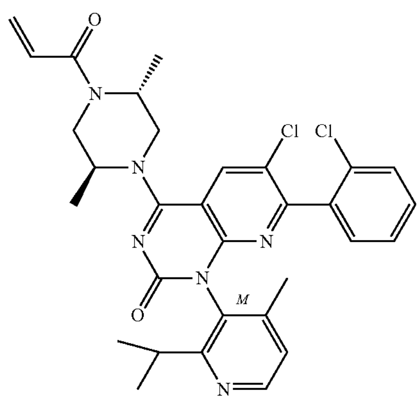 | (M)-6-Chloro-7-(2-chlorophenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2-chlorophenylboronic acid (Matrix Scientific) |
| 92-52 | 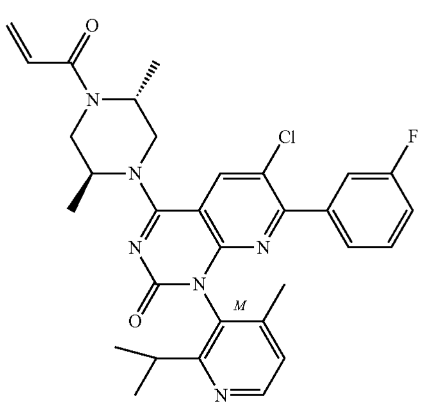 | (M)-6-Chloro-4-[(2S,5R)-2,5-dimethyl-4-prop-2-enoyl-piperazin-1-yl]-7-(3-fluorophenyl)-1-(2-isopropyl-4-methyl-3-pyridyl)pyrido[2,3-d]pyrimidin-2-one | None | Step 3: 3-fluorophenylboronic acid (Steris Corporation) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-53 | 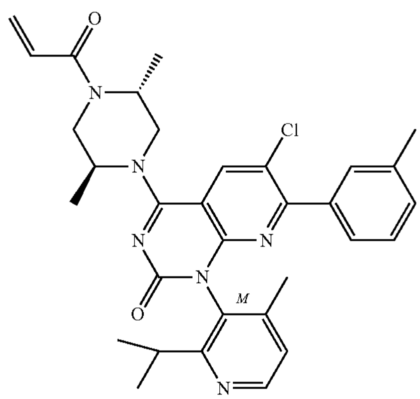 | (M)-6-Chloro-4-[(2S,5R)-2,5-dimethyl-4-prop-2-enoyl-piperazin-1-yl]-1-(2-isopropyl-4-methyl-3-pyridyl)-7-(m-tolyl)pyrido[2,3-d]pyrimidin-2-one | None | Step 3: (3-methylphenyl)boranediol (Sigma-Aldrich Corporation) |
| 92-54 | 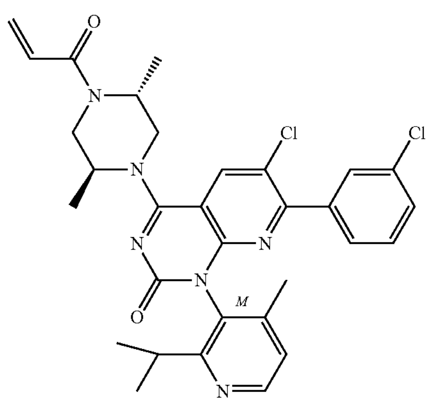 | (M)-6-Chloro-7-(3-chlorophenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 3-chlorophenylboronic acid (AstaTech, Inc) |
| 92-55 | 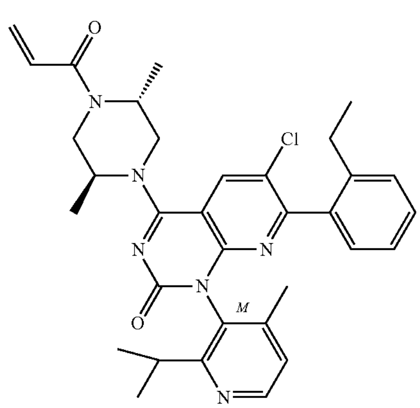 | (M)-6-Chloro-4-[(2S,5R)-2,5-dimethyl-4-prop-2-enoyl-piperazin-1-yl]-7-(2-ethylphenyl)-1-(2-isopropyl-4-methyl-3-pyridyl)pyrido[2,3-d]pyrimidin-2-one | None | Step 3: (2-ethylphenyl)boronic acid (Combi-Block Inc.) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-56 | 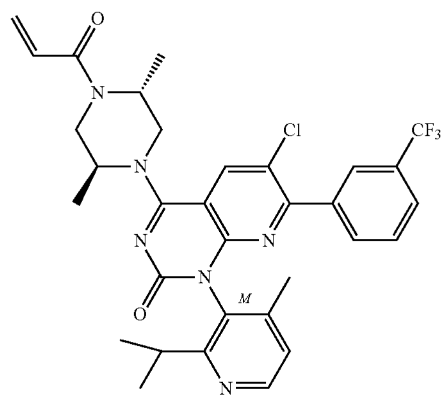 | (M)-6-Chloro-4-[(2S,5R)-2,5-dimethyl-4-prop-2-enoyl-piperazin-1-yl]-1-(2-isopropyl-4-methyl-3-pyridyl)-7-[3-(trifluoromethyl)phenyl]pyrido[2,3-d]pyrimidin-2-one | None | Step 3: 3-(trifluoromethyl)phenylboronic acid (Sigma-Aldrich Corporation) |
| 92-57 | 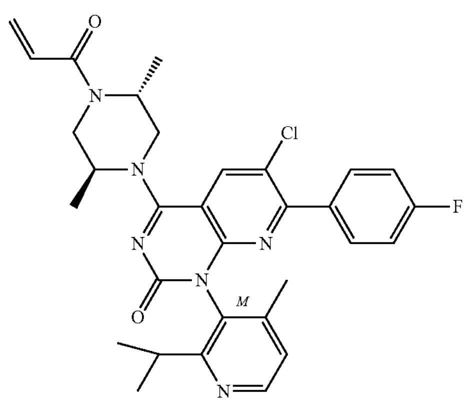 | (M)-6-Chloro-4-[(2S,5R)-2,5-dimethyl-4-prop-2-enoyl-piperazin-1-yl]-7-(4-fluorophenyl)-1-(2-isopropyl-4-methyl-3-pyridyl)pyrido[2,3-d]pyrimidin-2-one | None | Step 3: 4-fluorobenzeneboronic acid (Sigma-Aldrich Corporation) |
| 92-58 | 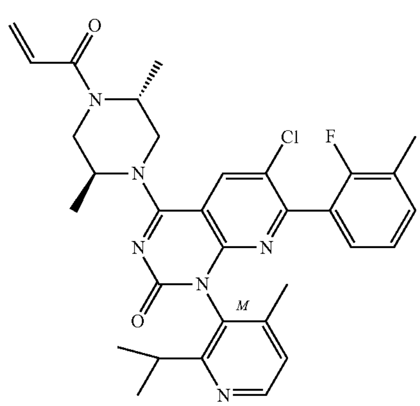 | (M)-6-Chloro-4-[(2S,5R)-2,5-dimethyl-4-prop-2-enoyl-piperazin-1-yl]-7-(2-fluoro-3-methyl-phenyl)-1-(2-isopropyl-4-methyl-3-pyridyl)pyrido[2,3-d]pyrimidin-2-one | None | Step 3: 2-fluoro-3-methylphenylboronic acid (Combi-Blocks Inc.) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-59 | 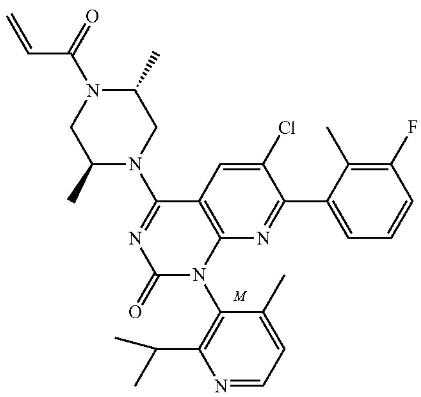 | (M)-6-Chloro-4-[(2S,5R)-2,5-dimethyl-4-prop-2-enoyl-piperazin-1-yl]-7-(3-fluoro-2-methyl-phenyl)-1-(2-isopropyl-4-methyl-3-pyridyl)pyrido[2,3-d]pyrimidin-2-one | None | Step 3: 3-fluoro-2-methylphenylboronic acid (Combi-Blocks Inc.) |
| 92-60 | 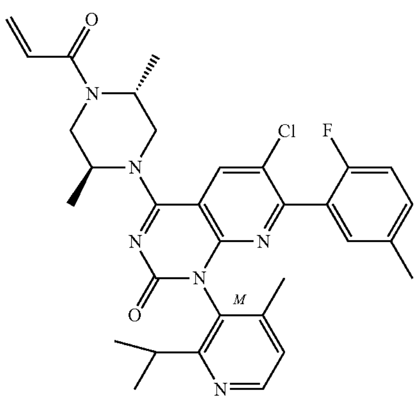 | (M)-6-Chloro-4-[(2S,5R)-2,5-dimethyl-4-prop-2-enoyl-piperazin-1-yl]-7-(2-fluoro-5-methyl-phenyl)-1-(2-isopropyl-4-methyl-3-pyridyl)pyrido[2,3-d]pyrimidin-2-one | None | Step 3: (2-fluoro-5-methylphenyl)boranediol (Sigma-Aldrich Corporation) |
| 92-61 | 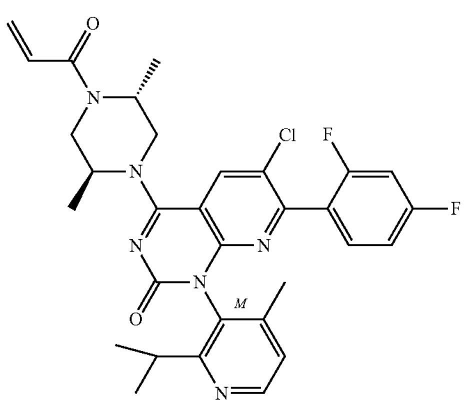 | (M)-6-Chloro-7-(2,4-difluorophenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2,4-difluorophenylboronic acid pinacol ester (Sigma-Aldrich Corporation) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-62 | 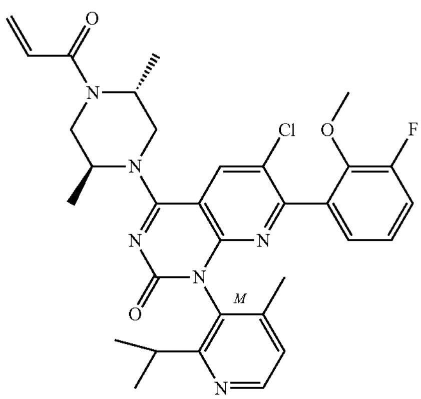 | (M)-6-Chloro-4-[(2S,5R)-2,5-dimethyl-4-prop-2-enoyl-piperazin-1-yl]-7-(3-fluoro-2-methoxy-phenyl)-1-(2-isopropyl-4-methyl-3-pyridyl)pyrido[2,3-d]pyrimidin-2-one | None | Step 3: 3-fluoro-2-methoxyphenylboronic acid (Asymchem Laboratories, Inc.) |
| 92-63 | 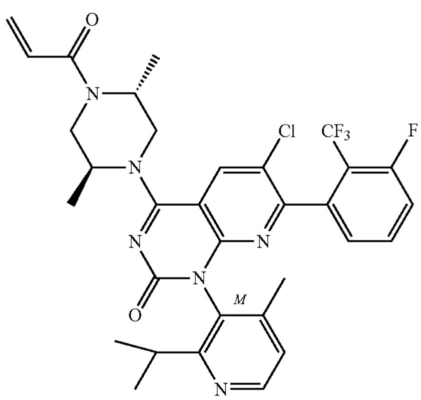 | (M)-6-Chloro-4-[(2S,5R)-2,5-dimethyl-4-prop-2-enoyl-piperazin-1-yl]-7-[3-fluoro-2-(trifluoromethyl)phenyl]-1-(2-isopropyl-4-methyl-3-pyridyl)pyrido[2,3-d]pyrimidin-2-one | None | Step 3: (3-fluro-2-trifluoromethyl)phenyl)boronic acid (Combi-Blocks) |
| 92-64 | 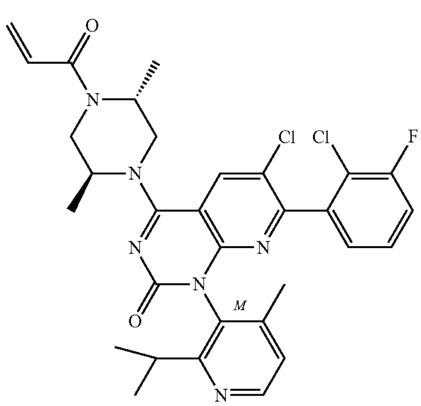 | (M)-6-Chloro-7-(2-chloro-3-fluoro-phenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2-chloro-3-fluorophenylboronic acid (Combi-Blocks Inc.) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-65 | 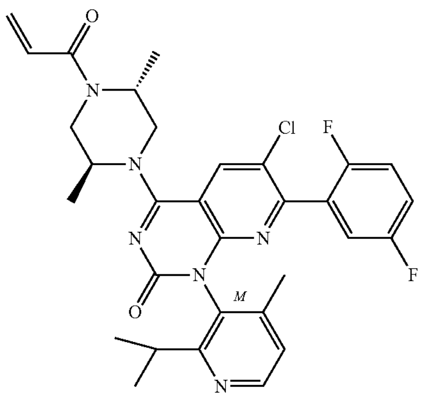 | (M)-6-Chloro-7-(2,5-difluorophenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2,5-difluorophenylboronic acid pinacol ester (Combi-Blocks Inc.) |
| 92-66 | 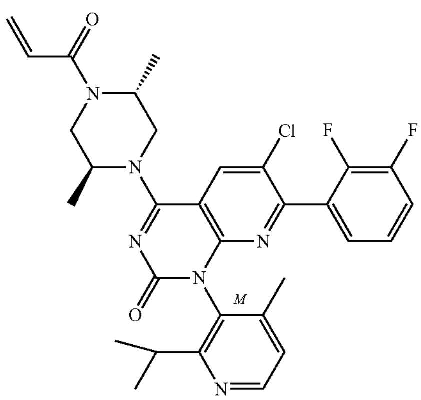 | (M)-6-Chloro-7-(2,3-difluorophenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: 2,3-difluorophenylboronic acid pinacol ester (Combi-Blocks Inc.) |
| 92-67 | 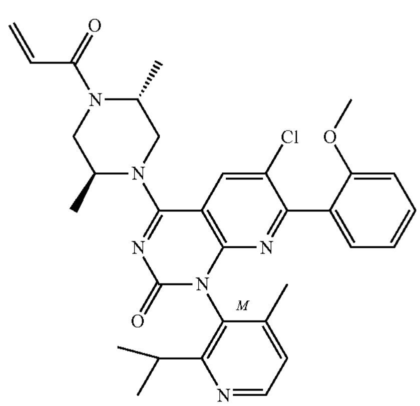 | (M)-6-Chloro-4-[(2S,5R)-2,5-dimethyl-4-prop-2-enoyl-piperazin-1-yl]-1-(2-isopropyl-4-methyl-3-pyridyl)-7-(2-methoxyphenyl)pyrido[2,3-d]pyrimidin-2-one | None | Step 3: 2-methoxyphenylboronic acid (TCI America) |

TABLE 92-continued

Compounds 92-2 to 92-73 were prepared following the procedure described in Method 92, Steps 1-3, above as follows:

| Ex. # | Chemical structure | Name | Method Changes | Reagent |
|---|---|---|---|---|
| 92-68 | 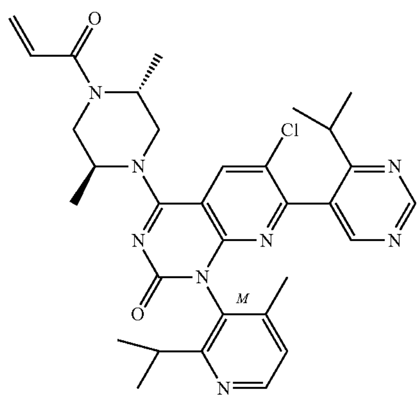 | (M)-6-Chloro-4-[(2S,5R)-2,5-dimethyl-4-prop-2-enoyl-piperazin-1-yl]-1-(2-isopropyl-4-methyl-3-pyridyl)-7-(4-isopropylpyrimidin-5-yl)pyrido[2,3-d]pyrimidin-2-one | None | Step 3: 4-isopropylpyrimidine-5-boronic acid (Combi-Blocks Inc.) |
| 92-69 | 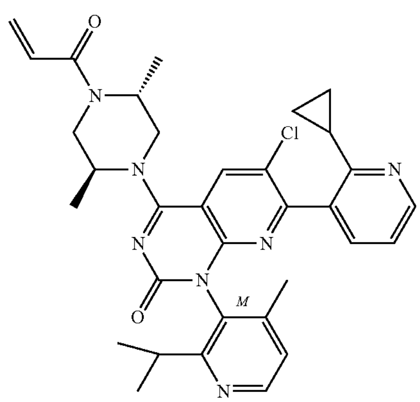 | (M)-6-Chloro-7-(2-cyclopropyl-3-pyridyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 3: (2-cyclopropylpyridin-3-yl)boronic acid (Activate Scientific) |
| 92-70 | 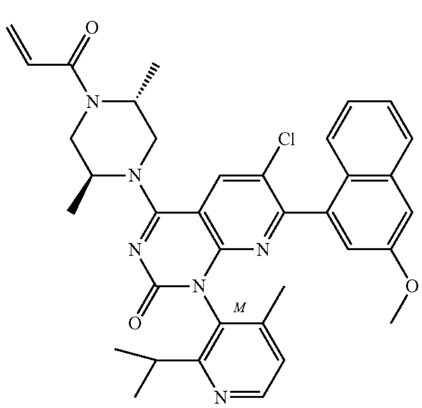 | (M)-6-Chloro-4-[(2S,5R)-2,5-dimethyl-4-prop-2-enoyl-piperazin-1-yl]-1-(2-isopropyl-4-methyl-3-pyridyl)-7-(3-methoxy-1-naphthyl)pyrido[2,3-d]pyrimidin-2-one | None | Step 3: (3-methoxynaphthalen-1-yl)boronic acid (Ark Pharm, Inc.) |

TABLE 92-continued

Compounds 92-2 to 92-73 were prepared following the procedure described in
Method 92, Steps 1-3, above as follows:

| Ex. # | Chemical structure | Name | Method Changes | Reagent |
|---|---|---|---|---|
| 92-71 | 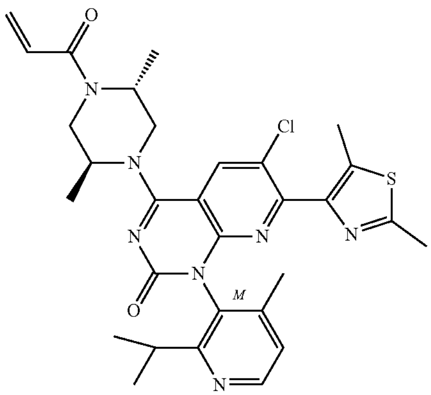 | (M)-6-Chloro-4-[(2S,5R)-2,5-dimethyl-4-prop-2-enoyl-piperazin-1-yl]-7-(2,5-dimethylthiazol-4-yl)-1-(2-isopropyl-4-methyl-3-pyridyl)pyrido[2,3-d]pyrimidin-2-one | None | Step 3: 2,5-dimethylthiazole-4-boronic acid pinacol ester (CombiPhos Catalysts, Inc.) |
| 92-72 | 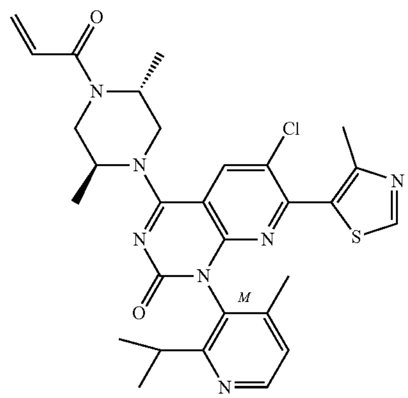 | (M)-6-Chloro-4-[(2S,5R)-2,5-dimethyl-4-prop-2-enoyl-piperazin-1-yl]-1-(2-isopropyl-4-methyl-3-pyridyl)-7-(4-methylthiazol-5-yl)pyrido[2,3-d]pyrimidin-2-one | None | Step 3: 4-methyl-5-(4,4,5,5-tetramethyl-1,3,2-dioxaborolan-2-yl)-1,3-thiazole (CombiPhos Catalysts, Inc.) |

Method 93

Example 93-1: (M)-6-Chloro-4-[(2S,5R)-2,5-dimethyl-4-prop-2-enoyl-piperazin-1-yl]-1-(2-isopropyl-4-methyl-3-pyridyl)-7-(3-methyl-2-thienyl)pyrido[2,3-d]pyrimidin-2-one

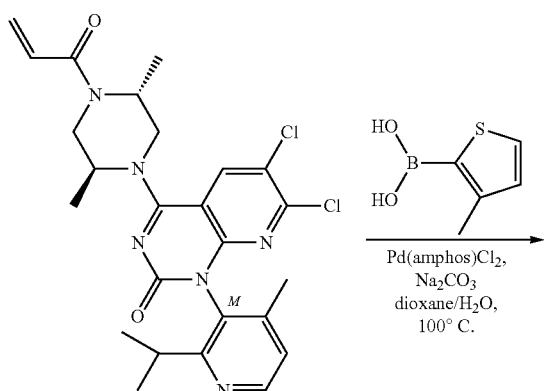

Intermediate 92B

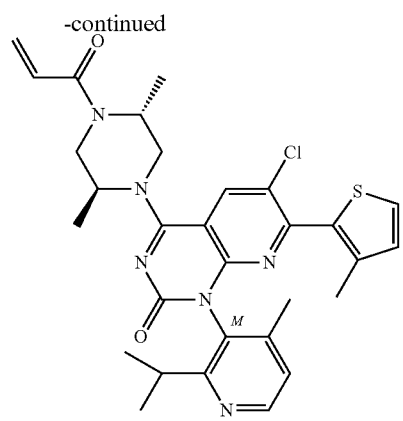

(M)-6-Chloro-4-[(2S,5R)-2,5-dimethyl-4-prop-2-enoyl-piperazin-1-yl]-1-(2-isopropyl-4-methyl-3-pyridyl)-7-(3-methyl-2-thienyl)pyrido[2,3-d]pyrimidin-2-one A mixture of (M)-4-((2S,5R)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate 92B; 0.15 g, 0.29 mmol), 3-methylthiophene-2-boronic acid (0.06 g, 0.44 mmol, Combi-Blocks Inc.), sodium carbonate (0.094 g, 0.89 mmol), and Pd(AmPhos)Cl$_2$ (0.013 g, 0.018 mmol, Sigma-Aldrich Corporation) in 1,4-dioxane (1 mL) and water (0.5 mL) was stirred and heated at 100° C. for 16 h. The crude material was purified by silica gel chromatography (eluent: 0-60% EtOAc-EtOH (3:1)/heptane) to provide (M)-6-chloro-4-[(2S,5R)-2,5-dimethyl-4-prop-2-enoyl-piperazin-1-yl]-1-(2-isopropyl-4-methyl-3-pyridyl)-7-(3-methyl-2-thienyl)pyrido[2,3-d]pyrimidin-2-one (0.010 g, 0.018 mmol, 6.1% yield) as yellow solid. $^1$H NMR (400 MHz, DMSO-d$_6$) δ 8.45 (d, J=4.8 Hz, 1H), 8.39 (d, J=3.9 Hz, 1H), 7.66 (d, J=5.0 Hz, 1H), 7.23 (d, J=5.0 Hz, 1H), 6.94 (d, J=5.2 Hz, 1H), 6.83 (td, J=17.2, 10.7 Hz, 1H), 6.19 (dd, J=16.7, 1.3 Hz, 1H), 5.71-5.78 (m, 1H), 4.41-4.94 (m, 2H), 3.42-4.23 (m, 4H), 2.63-2.74 (m, 1H), 1.94 (s, 3H), 1.83 (s, 3H), 1.33 (t, J=6.5 Hz, 3H), 1.21 (br dd, J=27.7, 6.5 Hz, 3H), 1.06 (d, J=6.8 Hz, 3H), 0.94 (d, J=6.6 Hz, 3H). m/z (ESI, +ve ion): 577.3 (M+H)$^+$.

TABLE 93

Compound 93-2 was prepared following the procedure described in Method 93 above as follows:

| Ex. # | Chemical structure | Name | Method Changes | Reagent |
|---|---|---|---|---|
| 93-2 | 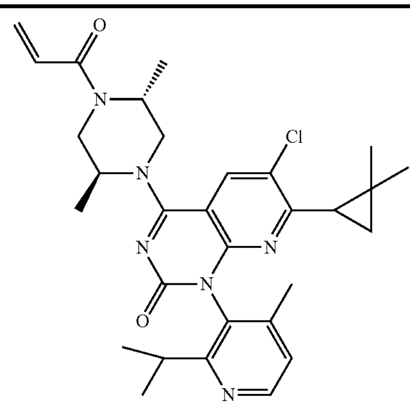 | (M)-6-chloro-7-[(1SR)-2,2-dimethylcyclopropyl]-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | 1,1-dimethyl cyclopropyl-2-boronic acid pinacol ester (Aurum Pharmatech LLC) |

Method 94

Example 94-1: (M)-4-[(2S,5R)-2,5-Dimethyl-4-prop-2-enoyl-piperazin-1-yl]-6-fluoro-1-(2-isopropyl-4-methyl-3-pyridyl)-7-(2-isopropylphenyl)pyrido[2,3-d]pyrimidin-2-one

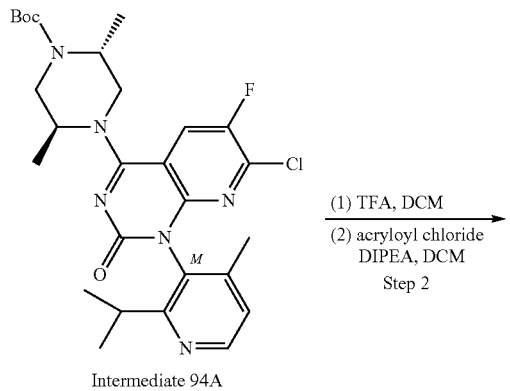

Intermediate 94A (1) TFA, DCM
(2) acryloyl chloride
DIPEA, DCM
Step 2

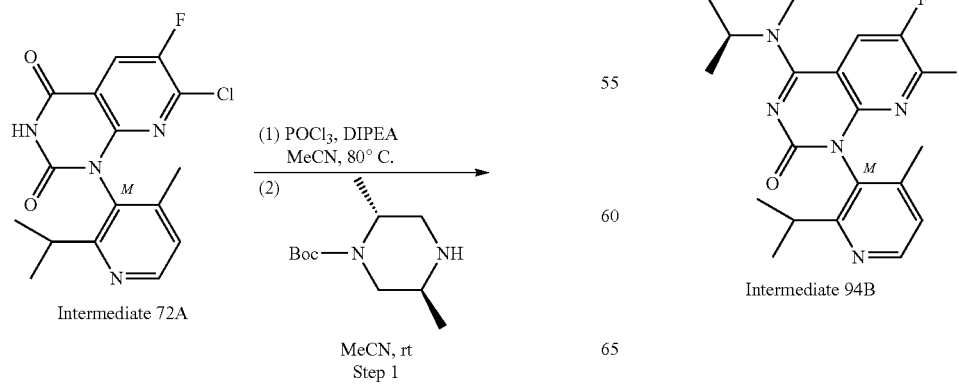

Intermediate 94B

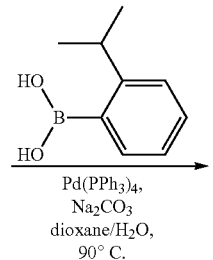

Pd(PPh$_3$)$_4$,
Na$_2$CO$_3$
dioxane/H$_2$O,
90° C.

-continued

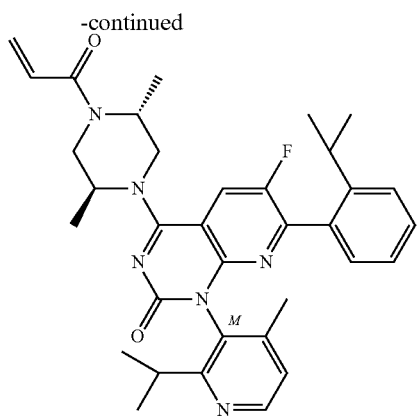

Step 1: (M)-tert-Butyl (2R,5S)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate A solution of (M)-7-chloro-6-fluoro-1-(2-isopropyl-4-methylpyridin-3-yl)pyrido[2,3-d]pyrimidine-2,4(1H,3H)-dione (Intermediate 72A; 3.35 g, 9.61 mmol), phosphorous oxychloride (1.07 mL, 11.53 mmol), and DIPEA (5.02 mL, 28.8 mmol) in acetonitrile (24 mL) was stirred at 80° C. for 30 min. The reaction mixture was cooled to rt and added (2R,5S)-tert-butyl 2,5-dimethylpiperazine-1-carboxylate (2.26 g, 10.6 mmol). The reaction mixture was stirred at rt for 15 min. The reaction mixture was diluted with EtOAc (200 mL), washed with satd. NaHCO$_3$ (3×75 mL), dried over Na$_2$SO$_4$, filtered, and concentrated in vacuo. The crude product was purified by silica gel chromatography (eluent: 0-100% EtOAc/heptane) to provide (M)-tert-butyl (2R,5S)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 94A; 2.2 g, 4.04 mmol, 42.0% yield) as yellow-orange solid. $^1$H NMR (400 MHz, CHLOROFORM-d) δ 8.57 (d, J=5.0 Hz, 1H), 7.79 (br d, J=7.5 Hz, 1H), 7.13-7.16 (m, 1H), 4.80-5.04 (m, 1H), 4.32-4.64 (m, 1H), 3.73-4.08 (m, 3H), 3.43-3.66 (m, 1H), 2.58 (dt, J=13.4, 6.6 Hz, 1H), 2.04 (s, 3H), 1.59 (s, 9H), 1.39-1.48 (m, 3H), 1.11-1.25 (m, 9H). $^{19}$F NMR (377 MHz, CHLOROFORM-d) δ −126.30 (br s, 1F) −126.34 (br s, 1F). m/z (ESI, +ve ion): 544.8 (M+H)$^+$.

Step 2: (M)-4-((2S,5R)-4-Acryloyl-2,5-dimethylpiperazin-1-yl)-7-chloro-6-fluoro-1-(2-isopropyl-4-methylpyridin-3-yl)pyrido[2,3-d]pyrimidin-2(1H)-one A mixture of (M)-tert-butyl (2R,5S)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 94A; 8.16 g, 14.97 mmol) in DCM (30 mL) and TFA (30 mL) was stirred at it for 30 min. The reaction mixture was concentrated in vacuo to provide (A)-7-chloro-4-((2S,5R)-2,5-dimethylpiperazin-1-yl)-6-fluoro-1-(2-isopropyl-4-methylpyridin-3-yl)pyrido[2,3-d]pyrimidin-2(1H)-one. The crude product was used in next step without purification. m/z (ESI, +ve ion) 445.1 (M+H)$^+$.

A mixture of (M) 7-chloro-4-((2S,5R)-2,5-dimethylpiperazin-1-yl)-6-fluoro-1-(2-isopropyl-4-methylpyridin-3-yl)pyrido[2,3-d]pyrimidin-2(1H)-one and DIPEA (13.1 mL, 74.9 mmol) in DCM (20 mL) was cooled to 0° C. To the cooled mixture was added acryloyl chloride (1.22 mL, 14.97 mmol) and stirred for 1 h. The reaction mixture was quenched with satd. NH$_4$Cl (50 mL), extracted with DCM (2:50 mL)), dried over MgSO$_4$, filtered, and concentrated in vacuo. The crude product was purified by silica gel chromatography (eluent: 0-100% EtOAc-MeOH (9:1)/heptane) to provide (M)-4-((2S,5R)-4-acryloyl-2,5-dimethylpiperazin-1-yl)-7-chloro-6-fluoro-1-(2-isopropyl-4-methylpyridin-3-yl)pyrido[2,3-d]pyrimidin-2(1H)-one (Intermediate 94B; 5.62 g, 11.3 mmol, 75% yield) as light-yellow foam. $^1$H NMR (400 MHz, DMSO-d$_6$) δ 8.53 (d, J=5.0 Hz, 1H), 8.44 (d, J=8.5 Hz, 1H), 7.35 (br d, J=3.7 Hz, 1H), 6.83 (td, J=16.9, 10.6 Hz, 1H), 6.18 (dd, J=16.6, 2.3 Hz, 1H), 5.69-5.80 (m, 1H), 4.65-4.92 (m, 2H), 3.79-4.15 (m, 3H), 3.07-3.69 (m, 1H), 2.60-2.72 (m, 1H), 1.98 (s, 3H), 1.20-1.33 (m, 6H), 1.06 (dd, J=13.1, 6.8 Hz, 6H). m/z (ESI, +ve ion): 499.2 (M+H)$^+$.

Step 3: (M)-4-[(2S,5R)-2,5-Dimethyl-4-prop-2-enoyl-piperazin-1-yl]-6-fluoro-1-(2-isopropyl-4-methyl-3-pyridyl)-7-(2-isopropylphenyl)pyrido[2,3-d]pyrimidin-2-one A mixture of (M)-4-((2S,5R)-4-acryloyl-2,5-dimethylpiperazin-1-yl)-7-chloro-6-fluoro-1-(2-isopropyl-4-methylpyridin-3-yl)pyrido[2,3-d]pyrimidin-2(1H)-one (Intermediate 94B, 0.21 g, 0.42 mmol), 2-isopropylphenylboronic acid (0.10 g, 0.62 mmol, Combi-Blocks Inc.), sodium carbonate (0.13 g, 1.25 mmol), and tetrakis(triphenylphosphine)palladium(0) (0.048 g, 0.042 mmol, Sigma-Aldrich Corporation) in 1,4-dioxane (1.2 mL) and water (0.6 mL) was stirred and heated at 90° C. The crude material was purified by silica gel chromatography (eluent: 0-50% of EtOAc-EtOH (3:1)/heptane) to provide (M)-4-[(2S,5R)-2,5-dimethyl-4-prop-2-enoyl-piperazin-1-yl]-6-fluoro-1-(2-isopropyl-4-methyl-3-pyridyl)-7-(2-isopropylphenyl)pyrido[2,3-d]pyrimidin-2-one (0.037 g, 0.063 mmol, 15% yield) as off-white solid. $^1$H NMR (400 MHz, DMSO-d$_6$) δ 8.37 (d, J=4.8 Hz, 1H), 8.30 (dd, J=9.4, 3.2 Hz, 1H), 7.38-7.44 (m, 2H), 7.21-7.27 (m, 1H), 7.18 (d, J=5.0 Hz, 1H), 7.12 (d, J=7.7 Hz, 1H), 6.77-6.92 (m, 1H), 6.19 (dd, J=16.7, 2.2 Hz, 1H), 5.73-5.78 (m, 1H), 4.82-4.93 (m, 1H), 4.43-4.81 (m, 1H), 3.44-4.27 (m, 4H), 2.69 (quin, J=6.4 Hz, 2H), 1.92 (s, 3H), 1.33 (t, J=6.3 Hz, 3H), 1.18-1.30 (m, 3H), 0.87-1.09 (m, 12H). $^{19}$F NMR (376 MHz, DMSO-d$_6$) δ −129.20 (d, J=10.4 Hz, 1F). m/z (ESI, +ve ion): 582.8 (M+H)$^+$.

TABLE 94

Compounds 94-2 to 94-20 were prepared following the procedure described in Method 94, Steps 1-3, above as follows:

| Ex. # | Chemical structure | Name | Method Changes | Reagent |
|---|---|---|---|---|
| 94-2 | 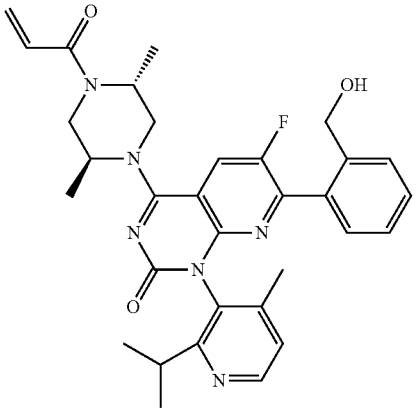<br>Single Isomer<br>(M) | (M)-4-[(2S,5R)-2,5-dimethyl-4-prop-2-enoyl-piperazin-1-yl]-6-fluoro-7-[2-(hydroxymethyl)phenyl]-1-(2-isopropyl-4-methyl-3-pyridyl)pyrido[2,3-d]pyrimidin-2-one | None | Step 3: 1,3-dihydro-1-hydroxy-2,1-benzoxaborole |
| 94-3 | 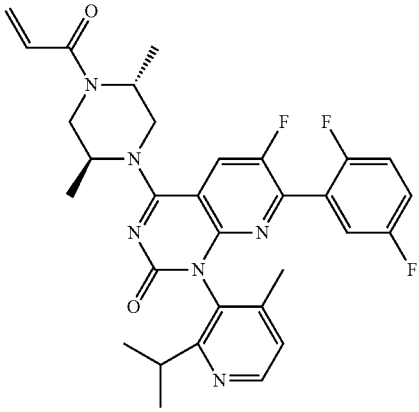<br>Single Isomer<br>(M) | (M)-7-(2,5-difluorophenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Step 3: Pd(dppf)Cl$_2$ KOAc | Step 3: (2,5-difluorophenyl)boronic acid (Combi-Blocks) |
| 94-4 | 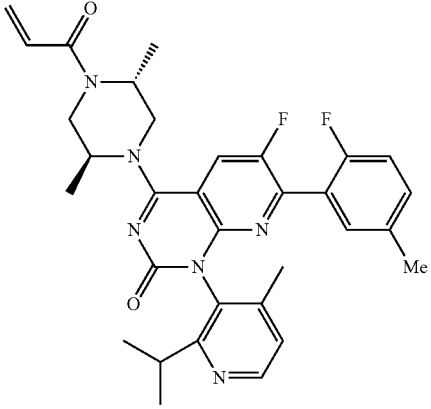<br>Single Isomer<br>(M) | (M)-4-[(2S,5R)-2,5-dimethyl-4-prop-2-enoyl-piperazin-1-yl]-6-fluoro-7-(2-fluoro-5-methyl-phenyl)-1-(2-isopropyl-4-methyl-3-pyridyl)pyrido[2,3-d]pyrimidin-2-one | Step 3: Pd(dppf)Cl$_2$ KOAc | Step 3: (2-fluoro-5-methylphenyl)boranediol |

TABLE 94-continued

Compounds 94-2 to 94-20 were prepared following the procedure described in Method 94, Steps 1-3, above as follows:

| Ex. # | Chemical structure | Name | Method Changes | Reagent |
|---|---|---|---|---|
| 94-5 | Single Isomer (M) | (M)-7-(5-chloro-2-fluoro-phenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Step 3: Pd(dppf)Cl$_2$ KOAc | Step 3: 5-chloro-2-fluorophenyl boronic acid |
| 94-6 | Single Isomer (M) | (M)-7-(2-chloro-5-methoxy-phenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Step 3: Pd(dppf)Cl$_2$ KOAc | Step 3: 2-chloro-5-methoxyphenyl boronic acid (Combi Blocks) |
| 94-7 | 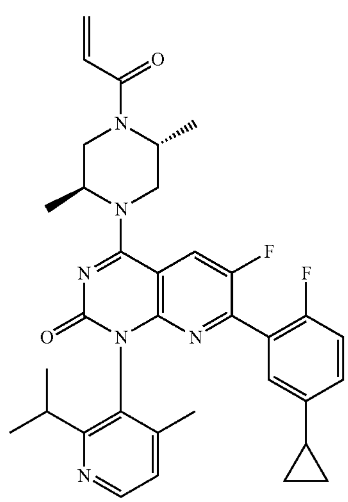 [SMILES: C=CC(=O)N1C[C@H](C)N(c2nc(=O)n(-c3c(C)ccnc3C(C)C)c3nc(-c4cc(C5CC5)ccc4F)c(F)cc23)C[C@H]1C] | (M)-7-(5-cyclopropyl-2-fluoro-phenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Step 3: Pd(dppf)Cl$_2$ KOAc | Step 3: 5-cyclopropyl-2-fluorophenyl boronic acid (Combi-Blocks) |

TABLE 94-continued

Compounds 94-2 to 94-20 were prepared following the procedure described in Method 94, Steps 1-3, above as follows:

| Ex. # | Chemical structure | Name | Method Changes | Reagent |
|---|---|---|---|---|
| 94-8 | Single Isomer (M) | (M)-4-[(2S,5R)-2,5-Dimethyl-4-prop-2-enoyl-piperazin-1-yl]-6-fluoro-1-(2-isopropyl-4-methyl-3-pyridyl)-7-(o-tolyl)pyrido[2,3-d]pyrimidin-2-one | Step 3: PdCl$_2$(dppf), KOAc, 100° C. | Step 3: o-tolylboronic acid; Sigma-Aldrich, St. Louis, MO |
| 94-9 | Single Isomer (M) | (M)-7-(2,6-Dimethylphenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Switch Step 2 & Step 3; Step 3: PdCl$_2$(dppf), KOAc, 100° C. | Step 3: 2,6-dimethylphenyl boronic acid; Sigma-Aldrich, St, Louis, MO |
| 94-10 | Single Isomer (M) | (M)-4-[(2S,5R)-2,5-Dimethyl-4-prop-2-enoyl-piperazin-1-yl]-6-fluoro-7-(2-fluoro-6-methyl-phenyl)-1-(2-isopropyl-4-methyl-3-pyridyl)pyrido[2,3-d]pyrimidin-2- | Switch Step 2 & Step 3; Step 3: PdCh$_2$(dppf), KOAc, 100° C. | Step 3: 2-fluoro-6-dimethylphenyl boronic acid; Combi-Blocks, Inc., San Diego, CA |

TABLE 94-continued

Compounds 94-2 to 94-20 were prepared following the procedure described in Method 94, Steps 1-3, above as follows:

| Ex. # | Chemical structure | Name | Method Changes | Reagent |
|---|---|---|---|---|
| 94-11 | Single Isomer (M) | (M)-7-(2,6-Difluorophenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Switch Step 2 & Step 3; Step 3: PdCl₂(dppf), KOAc, 100° C. | Step 3: 2,6-difluorophenyl boronic acid; Sigma-Aldrich, St. Louis, MO |
| 94-12 | Single Isomer (M) | (M)-7-(2-Chloro-6-fluoro-phenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Switch Step 2 & Step 3; Step 3: PdCl₂(dppf), KOAc, 100° C. | Step 3: 2-chloro-6-fluorophenyl boronic acid; Sigma-Aldrich, St. Louis, MO |
| 94-13 | 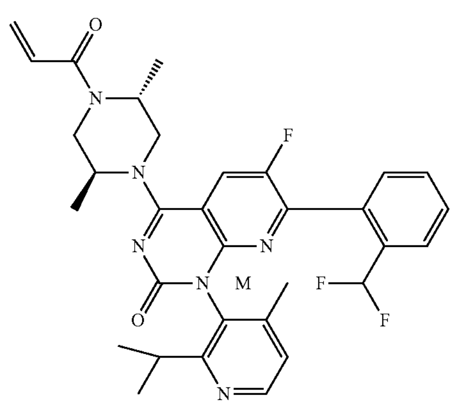 | (M)-7-[2-(Difluoromethyl)phenyl]-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | None | Step 3: 2-[2-(difluoromethyl)phenyl]-4,4,5,5-tetramethyl-1,3,2-dioxaborolane (Enamine Ltd.) |

TABLE 94-continued

Compounds 94-2 to 94-20 were prepared following the procedure described in Method 94, Steps 1-3, above as follows:

| Ex. # | Chemical structure | Name | Method Changes | Reagent |
|---|---|---|---|---|
| 94-14 | 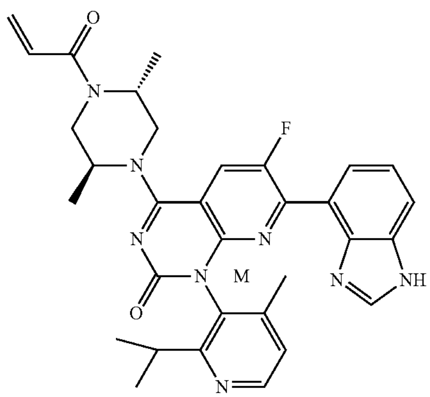 | (M)-7-(1H-Benzimidazol-4-yl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | Step 3: Pd(dppf)Cl$_2$ KOAc | Step 3: 1H-benzimidazol-4-ylboronic acid (Combi-Blocks, San Diego, CA, USA) |
| 94-15 | 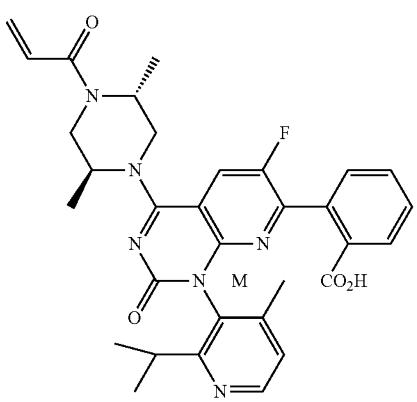 | (M)-2-[4-[(2S,5R)-2,5-Dimethyl-4-prop-2-enoyl-piperazin-1-yl]-6-fluoro-1-(2-isopropyl-4-methyl-3-pyridyl)-2-oxo-pyrido[2,3-a]pyrimidin-7-yl]benzoic acid | Step 3: Pd(dppf)Cl$_2$ KOAc | Step 3: (2-carboxyphenyl)boronic acid (Combi-Blocks, San Diego, CA, USA |
| 94-16 | 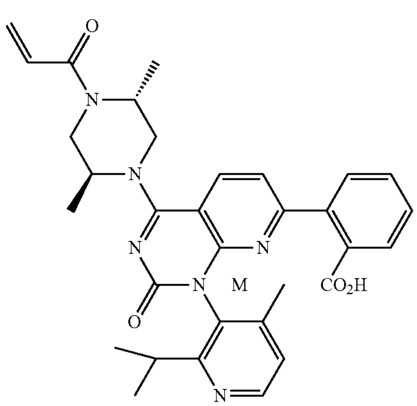 | (M)-2-[4-[(2S,5R)-2,5-Dimethyl-4-prop-2-enoyl-piperazin-1-yl]-1-(2-isopropyl-4-methyl-3-pyridyl)-2-oxo-pyrido[2,3-d]pyrimidin-7-yl]benzoic acid | Step 3: Pd(dppf)Cl$_2$ KOAc | Step 3: (2-carboxyphenyl)boronic acid (Combi-Blocks, San Diego, CA, USA |

TABLE 94-continued

Compounds 94-2 to 94-20 were prepared following the procedure described in Method 94, Steps 1-3, above as follows:

| Ex. # | Chemical structure | Name | Method Changes | Reagent |
|---|---|---|---|---|
| 94-17 | 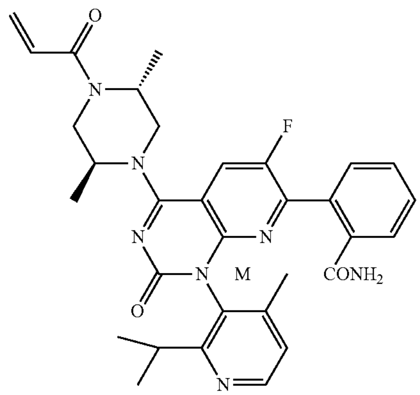 | (M)-2-[4-[(2S,5R)-2,5-Dimethyl-4-prop-2-enoyl-piperazin-1-yl]-6-fluoro-1-(2-isopropyl-4-methyl-3-pyridyl)-2-oxo-pyrido[2,3-d]pyrimidin-7-yl]benzamide | Step 3: Pd(dppf)Cl$_2$ KOAc | Step 3: 2-aminocarbonyl-phenylboronic acid (Combi-Blocks, San Diego, CA, USA) |
| 94-18 | 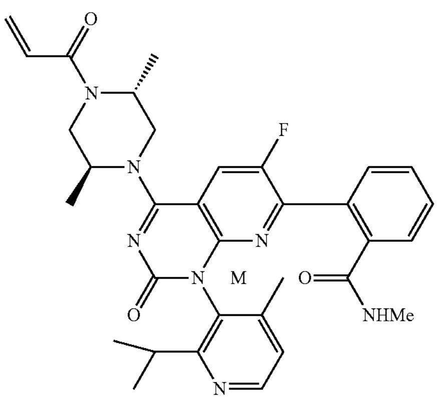 | (M)-2-[4-[(2S,5R-2,5-Dimethyl-4-prop-2-enoyl-piperazin-1-yl]-6-fluoro-1-(2-isopropyl-4-methyl-3-pyridyl)-2-oxo-pyrido[2,3-d]pyrimidin-7-yl]-N-methyl-benzamide | Step 3: Pd(dppf)Cl$_2$ KOAc | Step 3: 2-(methyl-carbamoyl) benzene-boronic acid (Combi-Blocks, San Diego, CA, USA) |
| 94-19 | 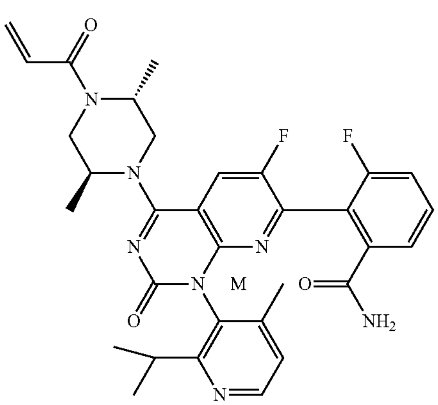 | (M)-2-[4-[(2S,5R)-2,5-Dimethyl-4-prop-2-enoyl-piperazin-1-yl]-6-fluoro-1-(2-isopropyl-4-methyl-3-pyridyl)-2-oxo-pyrido[2,3-d]pyrimidin-7-yl]-3-fluoro-benzamide | None | Step 3: 2-carbamoyl-6-fluorophenyl boronic acid pinacol ester (Combi-Blocks, San Diego, CA, USA) |

TABLE 94-continued

Compounds 94-2 to 94-20 were prepared following the procedure described in Method 94, Steps 1-3, above as follows:

| Ex. # | Chemical structure | Name | Method Changes | Reagent |
|---|---|---|---|---|
| 94-20 | 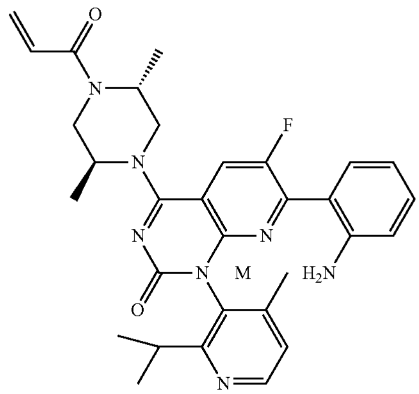 | (M)-7-(2-Aminophenyl)-4-[(2S,5R)-2,5-dimethyl-4-prop-2-enoyl-piperazin-1-yl]-6-fluoro-1-(2-isopropyl-4-methyl-3-pyridyl)pyrido[2,3-d]pyrimidin-2-one | None | Step 3: 2-(4,4,5,5-tetramethyl-1,3,2-dioxaborolan-2-yl)-aniline (Oakwood Products, Inc.) |
| 94-21 | 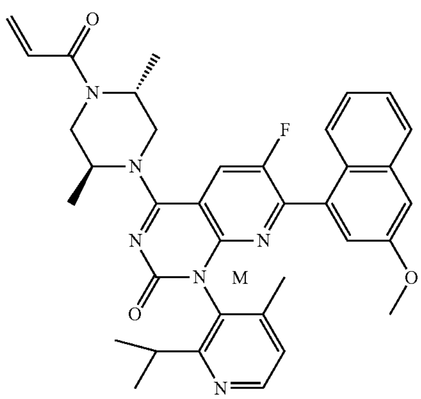 | (M)-4-[(2S,5R)-2,5-Dimethyl-4-prop-2-enoyl-piperazin-1-yl]-6-fluoro-1-(2-isopropyl-4-methyl-3-pyridyl)-7-(3-methoxy-1-naphthyl)pyrido[2,3-d]pyrimidin-2-one | None | Step 3: (3-methoxy naphthalen-1-yl)boronic acid (Ark Pharm, Inc.) |

Method 95

Example 95-1: (M)-6-Chloro-7-cyclohexyl-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one

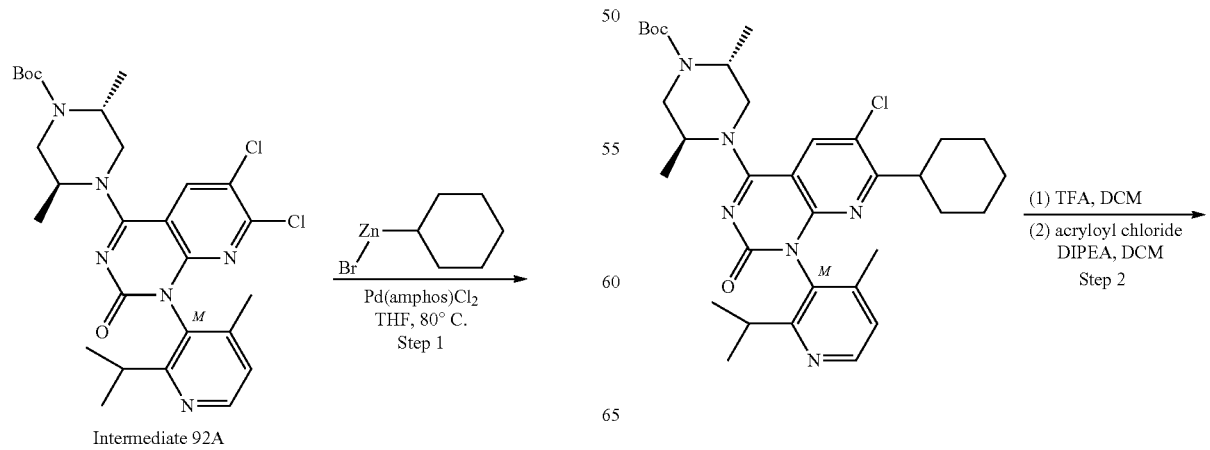

-continued

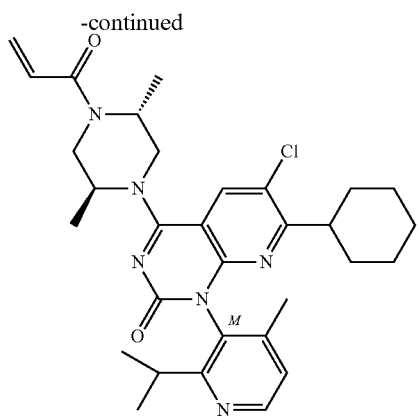

Step 1: (M)-tert-Butyl (2R,5S)-4-(6-chloro-7-cyclohexyl-1-(2-isopropyl-4-methylpyridin-3-yl)-2-oxo-1,2-dihydropyrido[2,3-d]pyrimidin-4-yl)-2,5-dimethylpiperazine-1-carboxylate A mixture of (M)-tert-butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 92A; 0.31 g, 0.55 mmol), Pd(AmPhos)Cl$_2$ (0.020 g, 0.028 mmol, Sigma-Aldrich Corporation), and cyclohexylzinc bromide, 0.5 M in THF (2.20 mL, 1.10 mmol, Ricke Metals, Inc.) in THF (1 mL) was stirred and heated at 80° C. for 4 h. The reaction mixture was purified by silica gel chromatography (eluent: 0-50% of EtOAc-EtOH (3:1)/heptane) to provide (M)-tert-butyl (2R,5S)-4-(6-chloro-7-cyclohexyl-1-(2-isopropyl-4-methylpyridin-3-yl)-2-oxo-1,2-dihydropyrido[2,3-d]pyrimidin-4-yl)-2,5-dimethylpiperazine-1-carboxylate (0.13 g, 0.22 mmol, 39.7% yield) as light-yellow syrupy solid. $^1$H NMR (400 MHz, DMSO-d$_6$) δ 8.48 (d, J=5.0 Hz, 1H), 8.22 (s, 1H), 7.25 (d, J=5.0 Hz, 1H), 4.76 (br d, J=1.5 Hz, 1H), 4.30 (br d, J=38.8 Hz, 1H), 4.09 (br d, J=13.7 Hz, 1H), 3.76 (br dd, J=9.7, 2.5 Hz, 1H), 3.68 (br d, J=13.5 Hz, 1H), 3.34-3.56 (m, 1H), 3.01 (tt, J=1.1, 3.0 Hz, 1H), 2.67 (quin, J=6.7 Hz, 1H), 1.85 (s, 3H), 1.50-1.75 (m, 6H), 1.44 (s, 9H), 1.31 (d, J=6.6 Hz, 3H), 1.19-1.29 (m, 4H), 1.15 (br d, J=6.4 Hz, 3H), 1.09 (d, J=6.6 Hz, 3H), 0.97 (d, J=6.8 Hz, 3H). m/z (ESI, +ve ion): 609.3 (M+H)$^+$.

Step 2: (M)-6-Chloro-7-cyclohexyl-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one A mixture of (M)-tert-butyl (2R,5S)-4-(6-chloro-7-cyclohexyl-1-(2-isopropyl-4-methylpyridin-3-yl)-2-oxo-1,2-dihydropyrido[2,3-d]pyrimidin-4-yl)-2,5-dimethylpiperazine-1-carboxylate (0.13 g, 0.22 mmol) in DCM (2 mL) and TFA (2 mL) was stirred at rt for 20 min. The mixture was concentrated in vacuo to give (M)-6-chloro-7-cyclohexyl-4-((2S,5R)-2,5-dimethylpiperazin-1-yl)-1-(2-isopropyl-4-methylpyridin-3-yl)pyrido[2,3-d]pyrimidin-2(1H)-one as orange syrup. m/z (ESI, +ve ion): 509.1 (M+H)$^+$.

A mixture of (M)-6-chloro-7-cyclohexyl-4-((2S,5R)-2,5-dimethylpiperazin-1-yl)-1-(2-isopropyl-4-methylpyridin-3-yl)pyrido[2,3-d]pyrimidin-2(1H)-one and DIPEA (0.57 mL, 3.3 mmol) in DCM (2 mL) was treated with acryloyl chloride, 0.2 M solution in DCM (1.19 mL, 0.24 mmol) at 0° C. and stirred for 30 min. The reaction mixture was quenched with satd. NH$_4$Cl (50 mL), extracted with EtOAc (2×50 mL), dried over Na$_2$SO$_4$, filtered, and concentrated in vacuo. The crude product was purified by silica gel chromatography (eluent: 0-60% EtOAc-EtOH (3:1)/heptane) to provide (M)-6-chloro-7-cyclohexyl-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one (0.05 g, 0.089 mmol, 41% yield) as white solid. $^1$H NMR (400 MHz, DMSO-d$_6$) δ 8.48 (d, J=4.8 Hz, 1H), 8.25 (d, J=4.1 Hz, 1H), 7.25 (d, J=4.8 Hz, 1H), 6.82 (td, J=17.5, 10.5 Hz, 1H), 6.18 (dd, J=16.6, 1.9 Hz, 1H), 5.71-5.77 (m, 1H), 4.40-4.89 (m, 2H), 3.37-4.19 (m, 4H), 3.02 (tt, J=11.0, 2.9 Hz, 1H), 2.63-2.72 (m, 1H), 1.86 (s, 3H), 1.50-1.68 (m, 5H), 1.13-1.34 (m, 9H), 1.03 (dd, J=45.3, 6.7 Hz, 8H). m/z (ESI, +ve ion): 563.3 (M+H)$^+$.

TABLE 95

Compounds 95-2 to 95-7 were prepared following the procedure described in Method 95, Steps 1-2, above as follows:

| Ex. # | Chemical structure | Name | Method Changes | Reagent |
|---|---|---|---|---|
| 95-2 | 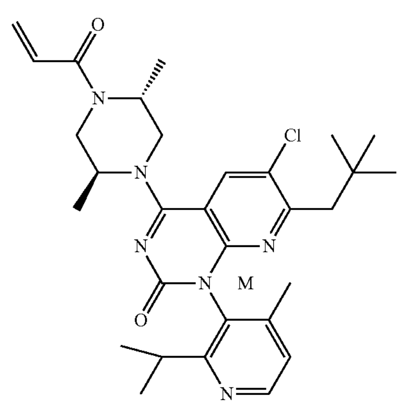 | (M)-6-chloro-4-[(2S,5R)-2,5-dimethyl-4-prop-2-enoyl-piperazin-1-yl]-7-(2,2-dimethylpropyl)-1-(2-isopropyl-4-methyl-3-pyridyl)pyrido[2,3-d]pyrimidin-2-one | None | Step 1: neopentyl-zinc bromide, 0.5M in THF (Rieke) |

TABLE 95-continued

Compounds 95-2 to 95-7 were prepared following the procedure described in Method 95, Steps 1-2, above as follows:

| Ex. # | Chemical structure | Name | Method Changes | Reagent |
|---|---|---|---|---|
| 95-3 | 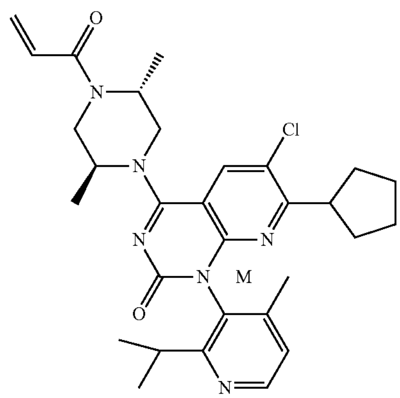 | (M)-6-chloro-7-cyclopentyl-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 1: cyclopentyl zinc bromide, 0.5M in THF (Sigma-Aldrich Corporation) |
| 95-4 | 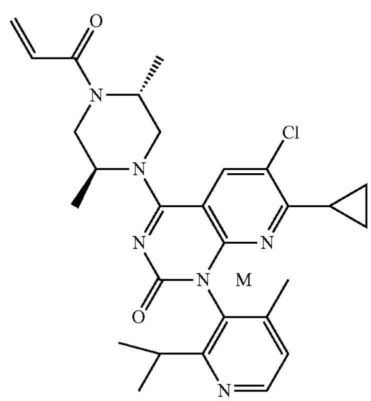 | (M)-6-chloro-7-cyclopropyl-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 1: cyclopropyl zinc bromide, 0.5M in THF (Sigma-Aldrich Corporation) |
| 95-5 | 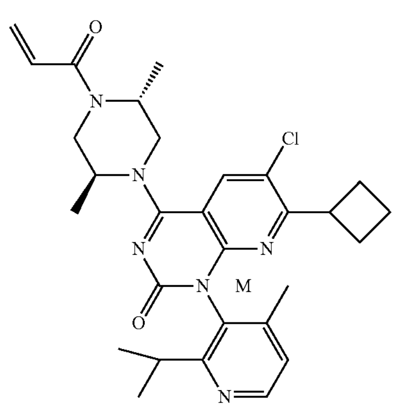 | (M)-6-chloro-7-cyclobutyl-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 1: 1,1-dimethyl-cyclopropyl-2-boronic acid pinacol ester (Aurum Pharmatech LLC) |

TABLE 95-continued

Compounds 95-2 to 95-7 were prepared following the procedure described in Method 95, Steps 1-2, above as follows:

| Ex. # | Chemical structure | Name | Method Changes | Reagent |
|---|---|---|---|---|
| 95-6 | 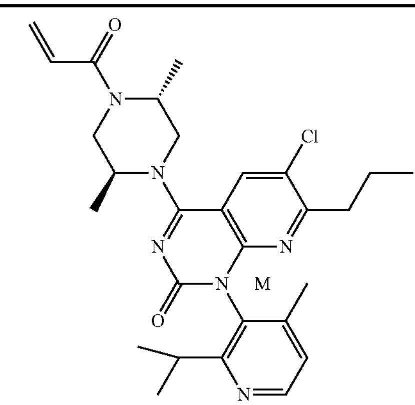 | (M)-6-chloro-4-[(2S,5R)-2,5-dimethyl-4-prop-2-enoyl-piperazin-1-yl]-1-(2-isopropyl-4-methyl-3-pyridyl)-7-propyl-pyrido[2,3-d]pyrimidin-2-one | None | Step 1: n-propylzinc bromide, 0.5M in THF (Sigma-Aldrich Corporation) |
| 95-7 | 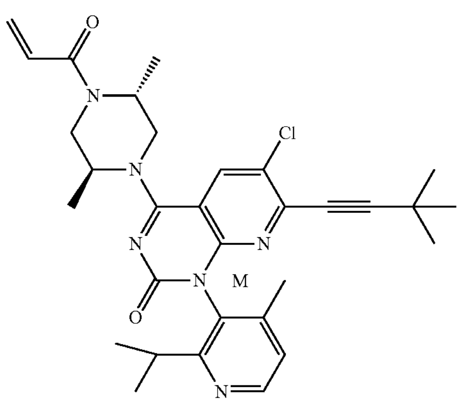 | (M)-6-chloro-7-(3,3-dimethylbut-1-ynyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 1: 3,3-dimethyl-1-butyne (Enamine) |

Method 96

Example 96-1: (M)-6-Chloro-4-[(2S,5R)-2,5-dimethyl-4-prop-2-enoyl-piperazin-1-yl]-1-(2-isopropyl-4-methyl-3-pyridyl)-7-(3-methyl-2-pyridyl)pyrido[2,3-d]pyrimidin-2-one

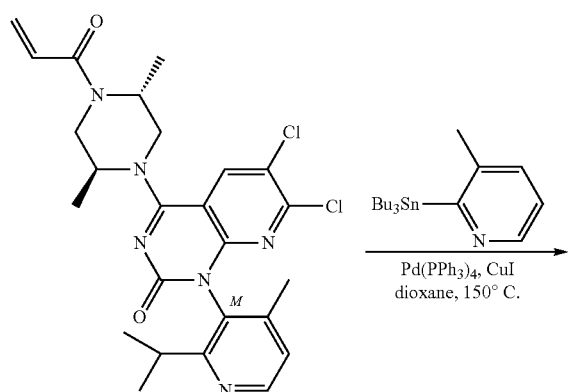

Intermediate 92B

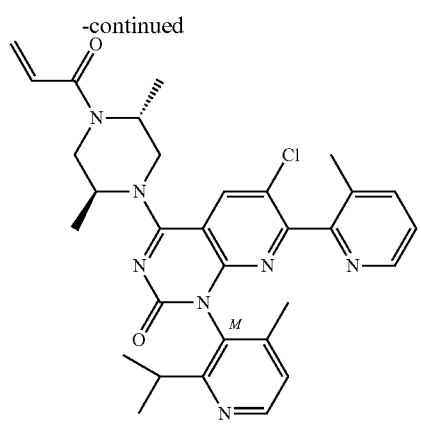

(M)-6-Chloro-4-[(2S,5R)-2,5-dimethyl-4-prop-2-enoyl-piperazin-1-yl]-1-(2-isopropyl-4-methyl-3-pyridyl)-7-(3-methyl-2-pyridyl)pyrido[2,3-d]pyrimidin-2-one A mixture of (M)-4-((2S,5R)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate 92B; 0.2 g, 0.39 mmol), 3-methyl-2-(tributylstannyl)pyridine (0.17 g, 0.44 mmol, Indofine Chemical Company, Inc), copper iodide (7.4 mg, 0.039 mmol, Sigma-Aldrich Corporation), and tetrakis(triphenylphosphine)palladium(0) (0.022 g, 0.019 mmol, Sigma-Aldrich Corporation) in 1,4-dioxane (2 mL) was stirred and heated in a Initiator microwave reactor (Personal Chemistry, Biotage AB, Inc., Upssala, Sweden) at 150° C. for 30 min. The crude material was purified by silica gel chromatography (eluent: 0-50% DCM-MeOH (4:1)/DCM) to provide (M)-6-chloro-4-[(2S,5R)-2,5-dimethyl-4-prop-2-enoyl-piperazin-1-yl]-1-(2-isopropyl-4-methyl-3-pyridyl)-7-(3-methyl-2-pyridyl)pyrido[2,3-d]pyrimidin-2-one (0.031 g, 0.054 mmol, 14% yield) as yellow solid. $^1$H NMR (400 MHz, DMSO-$d_6$) δ 8.47 (d, J=4.8 Hz, 1H), 8.41 (d, J=3.9 Hz, 1H), 8.38 (d, J=5.0 Hz, 1H), 7.70 (d, J=7.7 Hz, 1H), 7.35 (dd, J=7.9, 4.8 Hz, 1H), 7.19 (d, J=4.8 Hz, 1H), 6.84 (td, J=17.1, 10.5 Hz, 1H), 6.19 (dd, J=16.6, 2.1 Hz, 1H), 5.73-5.78 (m, 1H), 4.43-4.96 (m, 2H), 4.13-4.27 (m, 1H), 3.43-3.93 (m, 3H), 2.72 (tt, J=6.6, 3.2 Hz, 1H), 1.95 (s, 3H), 1.91 (s, 3H), 1.35 (t, J=6.2 Hz, 3H), 1.18-1.28 (m, 3H), 1.06 (d, J=6.6 Hz, 3H), 0.92 (d, J=6.6 Hz, 3H). m/z (ESI, +ve ion): 572.2 (M+H)$^+$.

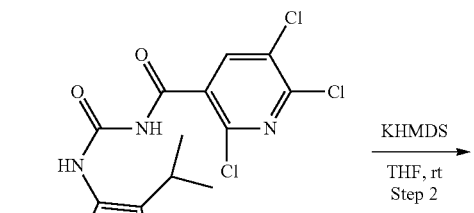

KHMDS
THF, rt
Step 2

TABLE 96

Compound 96-2 was prepared following the procedure described in Method 96 above as follows:

| Ex. # | Chemical structure | Name | Method Changes | Reagent |
|---|---|---|---|---|
| 96-2 | 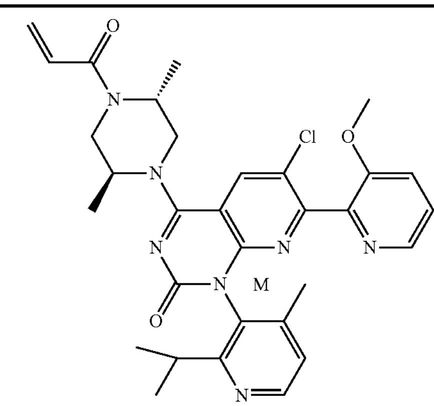 | (M)-6-Chloro-4-[(2S,5R-2,5-dimethyl-4-prop-2-enoyl-piperazin-1-yl]-1-(2-isopropyl-4-methyl-3-pyridyl)-7-(3-methoxy-2-pyridyl)pyrido[2,3-d]pyrimidin-2-one | None | 3-methoxy-2-(tributylstannyl)pyridine (Combi-Blocks Inc.) |

Method 100

Example 100-1: 6-Chloro-1-(2,4-diisopropylpyrazol-3-yl)-4-[(2S,5R)-2,5-dimethyl-4-prop-2-enoyl-piperazin-1-yl]-7-(2-fluorophenyl)pyrido[2,3-d]pyrimidin-2-one

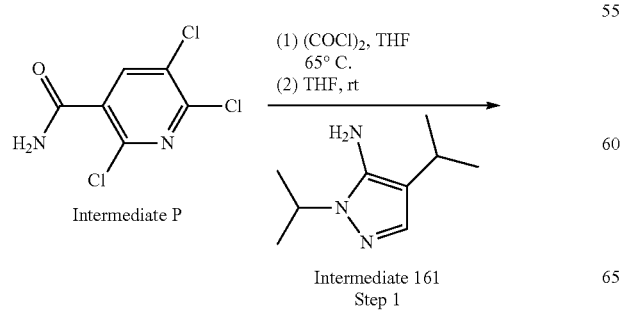

Intermediate P (1) (COCl)$_2$, THF 65° C.
(2) THF, rt

Intermediate 161
Step 1

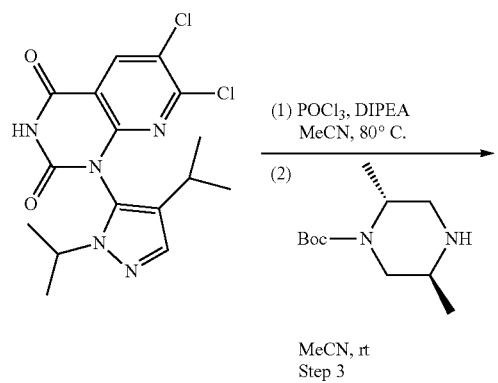

(1) POCl$_3$, DIPEA MeCN, 80° C.
(2)

Boc—N⏑NH

MeCN, rt
Step 3

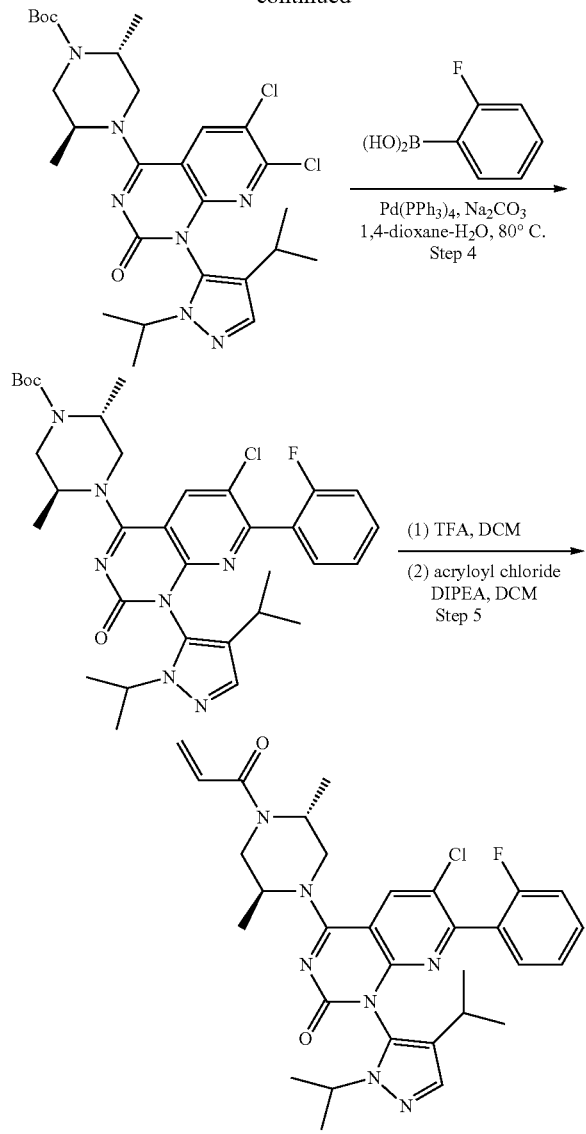

Step 1: 2,5,6-Trichloro-N-((1,4-diisopropyl-1H-pyrazol-5-yl)carbamoyl)nicotinamide To a mixture of 2,5,6-trichloronicotinamide (Intermediate P; 1.4 g, 6.1 mmol) in THF (12 mL) was added oxalyl chloride, 2 M solution in DCM (3.3 mL, 6.5 mmol) at rt and the mixture was stirred and heated at 65° C. for 3 h. The mixture was cooled to 0° C. To the cooled mixture was added a solution of 1,4-diisopropyl-1H-pyrazol-5-amine (Intermediate 161; 1.03 g, 6.13 mmol) in THF (5 mL) and the mixture was stirred at rt for 15 h. The reaction mixture was quenched with satd NaHCO$_3$ (100 mL), extracted with EtOAc (2×50 mL), washed with brine (1×50 mL), dried over Na$_2$SO$_4$, filtered, and concentrated in vacuo. The crude material was purified by silica gel chromatography (eluent: 0-50% EtOAc-EtOH (3:1)/heptane) to provide 2,5,6-trichloro-N-((1,4-diisopropyl-1H-pyrazol-5-yl)carbamoyl)nicotinamide (2.43 g, 5.79 mmol, 94% yield) as orange syrup. $^1$H NMR (400 MHz, DMSO-d$_6$) δ 11.36 (br s, 1H), 9.39 (br s, 1H), 8.63 (s, 1H), 7.33 (s, 1H), 4.37 (dt, J=13.3, 6.6 Hz, 1H), 2.64-2.75 (m, 1H), 1.33 (d, J=6.4 Hz, 6H), 1.13 (d, J=7.0 Hz, 6H), m/z (ESI, +ve ion): 417.6 (M+H)$^+$.

Step 2: 6,7-Dichloro-1-(1,4-diisopropyl-1H-pyrazol-5-yl)pyrido[2,3-d]pyrimidine-2,4(1H,3H)-dione To a cooled mixture of 2,5,6-trichloro-N-((1,4-diisopropyl-1H-pyrazol-5-yl)carbamoyl)nicotinamide (2.42 g, 5.78 mmol) in THF (19 mL) at 0° C. was added 1 M KHMDS in THF (14.5 mL, 14.5 mmol) dropwise and the mixture was stirred at 0° C. for 30 min. The mixture was quenched with satd. NH$_4$Cl (50 mL) and brine (50 mL), extracted with EtOAc (2×50 mL), dried over Na$_2$SO$_4$, filtered, and concentrated in vacuo. The crude material was purified by silica gel chromatography (eluent: 0-50% EtOAc/heptane) to provide 6,7-dichloro-1-(1,4-diisopropyl-1H-pyrazol-5-yl)pyrido[2,3-d]pyrimidine-2,4(1H,3H)-dione (0.16 g, 0.41 mmol, 7% yield) as yellow syrupy solid. $^1$H NMR (400 MHz, DMSO-d$_6$) δ 12.26 (br s, 1H), 8.57 (s, 1H), 7.52 (s, 1H), 4.32 (spt, J=6.6 Hz, 1H), 2.53-2.61 (m, 1H), 1.27 (d, J=6.6 Hz, 3H), 1.22 (d, J=6.4 Hz, 3H), 1.04 (d, J=6.8 Hz, 3H), 0.99 (d, J=6.8 Hz, 3H). m/z (ESI, +ve ion): 381.6 (M+H)$^+$.

Step 3: tert-Butyl (2R,5S)-4-(6,7-dichloro-1-(1,4-diisopropyl-1H-pyrazol-5-yl)-2-oxo-1,2-dihydropyrido[2,3-d]pyrimidin-4-yl)-2,5-dimethylpiperazine-1-carboxylate To a mixture of 6,7-dichloro-1-(1,4-diisopropyl-1H-pyrazol-5-yl)pyrido[2,3-d]pyrimidine-2,4(1H,3H)-dione (0.15 g, 0.39 mmol) and DIPEA (0.34 mL, 2.0 mmol) in acetonitrile (2.0 mL) was added phosphorus oxychloride (0.070 mL, 0.79 mmol) and the mixture was stirred and heated at 80° C. for 1 h. The mixture was cooled to 0° C. To the cooled mixture was added DIPEA (0.34 mL, 1.96 mmol) followed by (2R,5S)-tert-butyl 2,5-dimethylpiperazine-1-carboxylate (0.13 g, 0.59 mmol, AstaTech Inc.) and the mixture was stirred at 0° C. for 1 h. The reaction mixture was quenched with satd NaHCO$_3$ (50 mL), extracted with EtOAc (2×50 mL), dried over Na$_2$SO$_4$, filtered, and concentrated in vacuo. The crude material was purified by silica gel chromatography (eluent: 0-25% EtOAc-EtOH(3:1)/heptane) to provide tert-butyl (2R,5S)-4-(6,7-dichloro-1-(1,4-diisopropyl-1H-pyrazol-5-yl)-2-oxo-1,2-dihydropyrido[2,3-d]pyrimidin-4-yl)-2,5-dimethylpiperazine-1-carboxylate (0.15 g, 0.26 mmol, 66.7% yield) as orange solid. $^1$H NMR (400 MHz, DMSO-d$_6$) δ 8.44 (d, J=45.0 Hz, 1H), 7.47 (d, J=7.3 Hz, 1H), 3.33-4.89 (m, 7H), 2.38-2.47 (m, 1H), 0.94-1.47 (m, 27H). m/z (ESI, +ve ion): 577.7 (M+H)$^+$.

Step 4: tert-Butyl (2R,5S)-4-(6-chloro-1-(1,4-diisopropyl-1H-pyrazol-5-yl)-7-(2-fluorophenyl)-2-oxo-1,2-dihydropyrido[2,3-d]pyrimidin-4-yl)-2,5-dimethylpiperazine-1-carboxylate A mixture of tert-butyl (2R,5S)-4-(6,7-dichloro-1-(1,4-diisopropyl-1H-pyrazol-5-yl)-2-oxo-1,2-dihydropyrido[2,3-d]pyrimidin-4-yl)-2,5-dimethylpiperazine-1-carboxylate (0.15 g, 0.25 mmol). 2-fluorophenylboronic acid (0.053 g, 0.38 mmol, Combi-Blocks Inc.), sodium carbonate (0.080 g, 0.76 mmol), tetrakis(triphenylphosphine)palladium(0) (0.029 g, 0.025 mmol, Sigma-Aldrich Corporation) in 1,4-dioxane (1 mL) and water (0.25 mL) was stirred and heated at 80° C. for 2 h. The crude material was purified by silica gel chromatography (eluent: 0-25% EtOAc-EtOH (3:1)/heptane) to provide tert-butyl (2R,5S)-4-(6-chloro-1-(1,4- diisopropyl-1H-pyrazol-5-yl)-7-(2-fluorophenyl)-2-oxo-1,2-dihydropyrido[2,3-d]pyrimidin-4-yl)-2,5-dimethylpiperazine-1-carboxylate (0.16 g, 0.25 mmol, quantitative yield) as yellow syrup. $^1$H NMR (400 MHz, DMSO-$d_6$) δ 8.42 (d, J=25.9 Hz, 1H), 7.49-7.66 (m, 1H), 7.21-7.41 (m, 4H), 3.35-4.90 (m, 7H), 2.39-2.47 (m, 1H), 1.45 (s, 9H), 1.09-1.39 (m, 12H), 0.98 (dd, J=9.2, 6.9 Hz, 3H), 0.93 (dd, J=6.8, 3.1 Hz, 3H). $^{19}$F NMR (376 MHz, DMSO-$d_6$) δ −114.44−−114.14 (m, 1F). m/z (ESI, +ve ion): 638.2 (M+H)$^+$.

Step 5: 6-Chloro-1-(2,4-diisopropylpyrazol-3-yl)-4-[(2S,5R)-2,5-dimethyl-4-prop-2-enoyl-piperazin-1-yl]-7-(2-fluorophenyl)pyrido[2,3-d]pyrimidin-2-one A mixture of tert-butyl (2R,5S)-4-(6-chloro-1-(1,4-diisopropyl-1H-pyrazol-5-yl)-7-(2-fluorophenyl)-2-oxo-1,2-dihydropyrido[2,3-d]pyrimidin-4-yl)-2,5-dimethylpiperazine-1-carboxylate (0.16 g, 0.25 mmol) in DCM (2.5 mL) and TFA (2.5 mL) was stirred at rt for 1 h. The mixture was concentrated in vacuo to afford 6-chloro-1-(1,4-diisopropyl-1H-pyrazol-5-yl)-4-((2S,5R)-2,5-dimethylpiperazin-1-yl)-7-(2-fluorophenyl)pyrido[2,3-d]pyrimidin-2(1H)-one as yellow syrup. The crude product was used in next step without purification. m/z (ESI, +ve ion): 539.3 (M+H)$^+$.

A mixture of 6-chloro-1-(1,4-diisopropyl-1H-pyrazol-5-yl)-4-((2S,5R)-2,5-dimethylpiperazin-1-yl)-7-(2-fluorophenyl)pyrido[2,3-d]pyrimidin-2(1H)-one and DIPEA (0.66 mL, 3.78 mmol) in DCM (2.5 mL) was cooled to 0° C. To the cooled mixture was added acryloyl chloride (0.020 mL, 0.25 mmol) dropwise and the mixture was stirred at 0° C. for 10 min. The reaction mixture was quenched with satd. NH$_4$Cl (50 mL), extracted with EtOAc (2×50 mL), washed with satd NaHCO$_3$ (1×50 mL), dried over Na$_2$SO$_4$, filtered, and concentrated in vacuo. The crude material was purified by silica gel chromatography (eluent: 0-50% DCM-EtOH (4:1)/DCM) to provide 6-chloro-1-(2,4-diisopropylpyrazol-3-yl)-4-[(2S,5R)-2,5-dimethyl-4-prop-2-enoyl-piperazin-1-yl]-7-(2-fluorophenyl)pyrido[2,3-d]pyrimidin-2-one (0.093 g, 0.16 mmol, 63% yield) as yellow solid. $^1$H NMR (400 MHz, DMSO-$d_6$) δ 8.38-8.50 (m, 1H), 7.50-7.59 (m, 1H), 7.22-7.42 (m, 4H), 6.75-6.91 (m, 1H), 6.19 (dd, J=16.8, 2.1 Hz, 1H), 5.71-5.79 (m, 1H), 4.41-4.97 (m, 2H), 3.38-4.33 (m, 5H), 2.39-2.48 (m, 1H), 1.11-1.37 (m, 12H), 0.99 (dd, J=9.4, 6.9 Hz, 3H), 0.93 (dd, J=6.9, 2.8 Hz, 3H). $^{19}$F NMR (376 MHz, DMSO-$d_6$) δ −114.42−−114.15 (m, 1F). m/z (ESI, +ve ion): 592.3 (M+H)$^+$.

TABLE 100

Compounds 100-2 to 100-9 were prepared following the procedure described in Method 100, Steps 1-5, above as follows:

| Ex. # | Chemical structure | Name | Method Changes | Reagent |
|---|---|---|---|---|
| 100-2 | 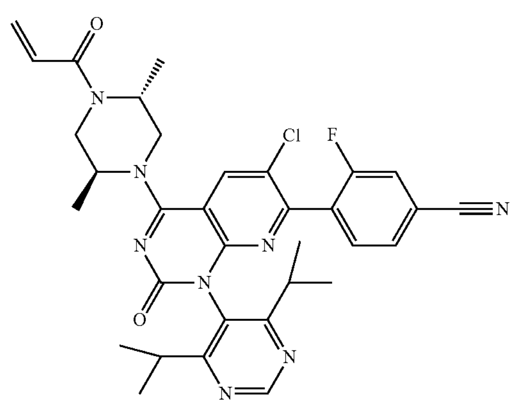 [SMILES: C=CC(=O)N1C[C@H](C)N(c2nc(=O)n(-c3c(C(C)C)ncnc3C(C)C)c3nc(-c4ccc(C#N)cc4F)c(Cl)cc23)C[C@H]1C] | 4-[6-Chloro-1-(4,6-diisopropylpyrimidin-5-yl)-4-[(2S,5R)-2,5-dimethyl-4-prop-2-enoyl-piperazin-1-yl]-2-oxo-pyrido[2,3-d]pyrimidin-7-yl]-3-fluoro-benzonitrile | None | Step 1: Intermediate U<br>Step 4: 4-Cyano-2-fluorophenylboronic acid pinacol ester, Combi-Blocks, San Diego, CA, USA |
| 100-3 | 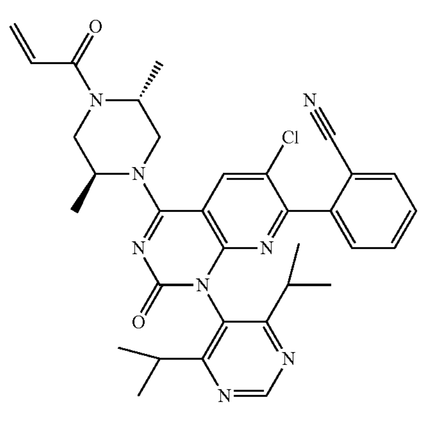 [SMILES: C=CC(=O)N1C[C@H](C)N(c2nc(=O)n(-c3c(C(C)C)ncnc3C(C)C)c3nc(-c4ccccc4C#N)c(Cl)cc23)C[C@H]1C] | 2-[6-Chloro-1-(4,6-diisopropylpyrimidin-5-yl)-4-[(2S,5R)-2,5-dimethyl-4-prop-2-enoyl-piperazin-1-yl]-2-oxo-pyrido[2,3-d]pyrimidin-7-yl]benzonitrile | None | Step 1: Intermediate U<br>Step 4: 2-cyanophenylboronic acid, pinacol ester, Combi-Blocks, San Diego, CA, USA |

TABLE 100-continued

Compounds 100-2 to 100-9 were prepared following the procedure described in Method 100, Steps 1-5, above as follows:

| Ex. # | Chemical structure | Name | Method Changes | Reagent |
|---|---|---|---|---|
| 100-4 | 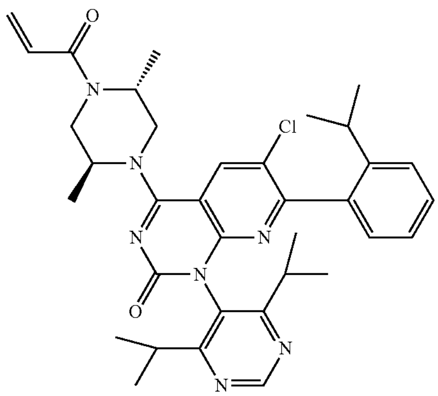 [SMILES: C=CC(=O)N1C[C@H](C)N(c2nc(=O)n(-c3c(C(C)C)ncnc3C(C)C)c3nc(-c4ccccc4C(C)C)c(Cl)cc23)C[C@H]1C] | 6-Chloro-1-(4,6-diisopropylpyrimidin-5-yl)-4-[(2S,5R)-2,5-dimethyl-4-prop-2-enoyl-piperazin-1-yl]-7-(2-isopropylphenyl)pyrido[2,3-d]pyrimidin-2-one | None | Step 1: Intermediate U<br>Step 4: 2-isopropylphenyl boronic acid, Combi-Blocks, San Diego, CA, USA |
| 100-5 | 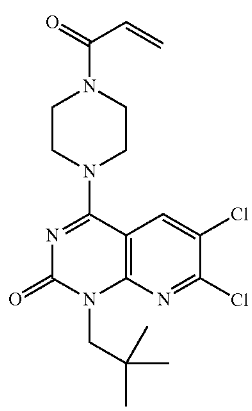 [SMILES: C=CC(=O)N1CCN(c2nc(=O)n(CC(C)(C)C)c3nc(Cl)c(Cl)cc23)CC1] | 6,7-Dichloro-1-(2,2-dimethylpropyl)-4-(4-prop-2-enoylpiperazin-1-yl)pyrido[2,3-d]pyrimidin-2-one | Omit step 4&5 | Step 1: Neopentylamine (TCI America)<br>Step 3: 1-Boc-piperazine, (Sigma-Aldrich Corporation) |
| 100-6 | 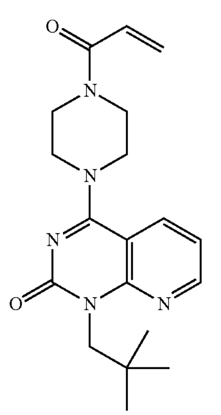 [SMILES: C=CC(=O)N1CCN(c2nc(=O)n(CC(C)(C)C)c3ncccc23)CC1] | 1-(2,2-dimethylpropyl)-4-(4-prop-2-enoylpiperazin-1-yl)pyrido[2,3-d]pyrimidin-2-one | Add a reduction step ($H_2$, Pd/C, NaOMe, THF/MeOH, 55 psi, RT) before Step 3, Omit step 4&5 | Step 1: Neopentylamine (TCI America)<br>Step 3: 1-Boc-piperazine, (Sigma-Aldrich Corporation) |

TABLE 100-continued

Compounds 100-2 to 100-9 were prepared following the procedure described in Method 100, Steps 1-5, above as follows:

| Ex. # | Chemical structure | Name | Method Changes | Reagent |
|---|---|---|---|---|
| 100-7 | 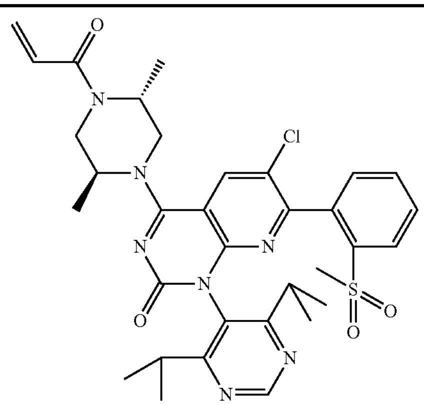 | 6-Chloro-1-(4,6-diisopropylpyrimidin-5-yl)-4-[(2S,5R)-2,5-dimethyl-4-prop-2-enoyl-piperazin-1-yl]-7-(2-methylsulfonylphenyl)pyrido[2,3-d]pyrimidin-2-one | Step 4: 95° C. | Step 1: Intermediate U Step 4: (2-methylsulfonylphenyl)boronic acid (Sigma-Aldrich Corporation) |
| 100-8 | First-eluting isomer | 6-Chloro-4-[(2S,5R)-2,5-dimethyl-4-prop-2-enoyl-piperazin-1-yl]-7-(2-fluorophenyl)-1-(3-isopropyl-5-methyl-4-pyridyl)pyrido[2,3-d]pyrimidin-2-one | Step 3 (1): Toluene, 50° C.; Step 4: Pd(dppf)Cl$_2$, KOAc; Chiral separation after Step 5 | Step 1: Intermediate 222 |
| 100-9 | Second-eluting Isomer | 6-Chloro-4-[(2S,5R-2,5-dimethyl-prop-2-enoyl-piperazin-1-yl]-7-(2-fluorophenyl)-1-(3-isopropyl-5-methyl-4-pyridyl)pyrido[2,3-d]pyrimidin-2-one | Step 3 (1): Toluene, 50° C.; Step 4: Pd(dppf)Cl$_2$, KOAc; Chiral separation after Step 5 | Step 1: Intermediate 222 |

Method 101

Example 101-1: 1-(3,5-Diisopropyl-4-pyridyl)-4-[(2S,5R)-2,5-dimethyl-4-prop-2-enoyl-piperazin-1-yl]-6-fluoro-7-(2-fluoro-6-hydroxy-phenyl)pyrido[2,3-d]pyrimidin-2-one

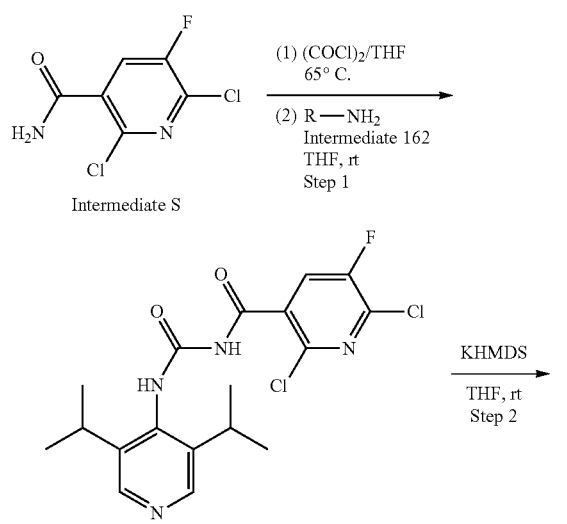

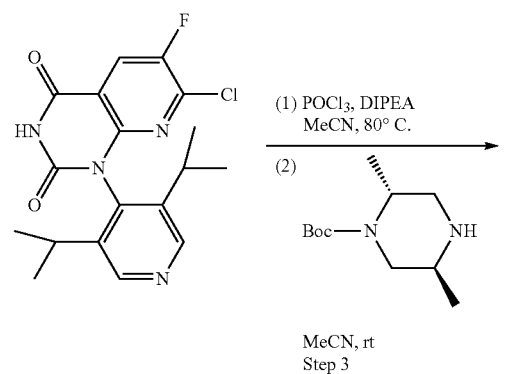

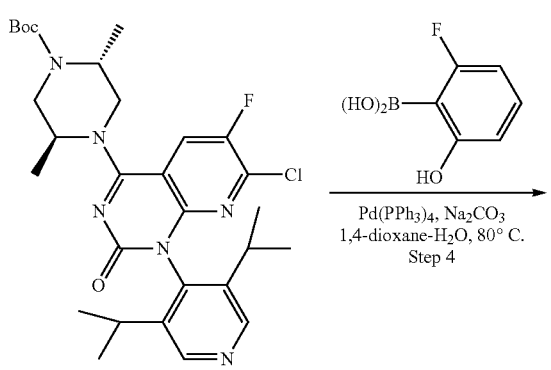

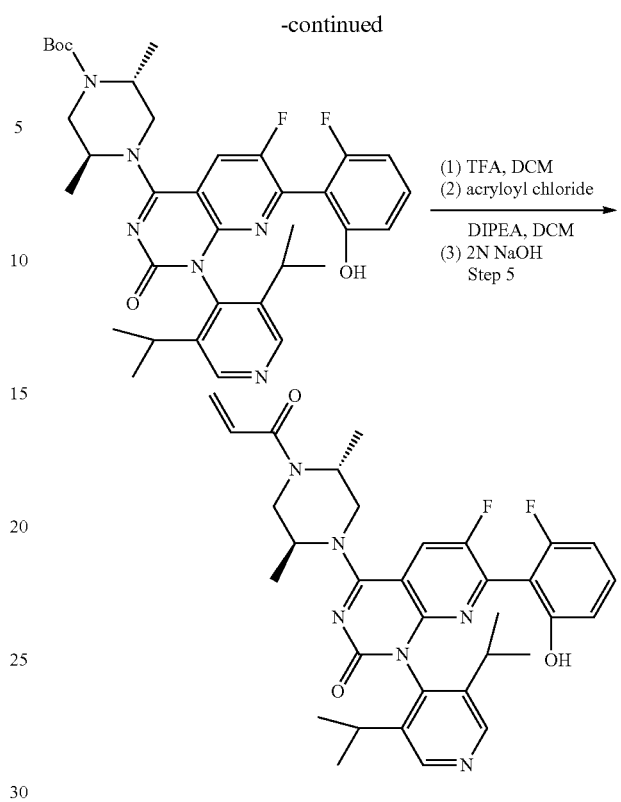

Step 1: 2,6-Dichloro-N-((3,5-diisopropylpyridin-4-yl)carbamoyl)-5-fluoronicotinamide To a mixture of 2,6-dichloro-5-fluoronicotinamide (Intermediate S; 1.58 g, 7.57 mmol) in THF (15 mL) was added oxalyl chloride, 2 M solution in DCM (3.99 mL, 7.97 mmol) at rt and the mixture was stirred and heated at 65° C. for 1 h. The mixture was cooled to it. To the mixture was added a solution of 3,5-diisopropylpyridin-4-amine (Intermediate 162; 1.35 g, 7.57 mmol) in THF (8 mL) and the mixture was stirred at rt for 1 h. The mixture was quenched with satd NaHCO$_3$ (100 mL), extracted with EtOAc (3×50 mL), dried over Na$_2$SO$_4$, filtered, and concentrated in vacuo. The crude material was purified by silica gel chromatography (eluent: 0-40% EtOAc-EtOH(3:1)/heptane) to provide 2,6-dichloro-N-((3,5-diisopropylpyridin-4-yl)carbamoyl)-5-fluoronicotinamide (0.54 g, 1.3 mmol, 17% yield) as light-yellow solid. $^1$H NMR (400 MHz, DMSO-d$_6$) δ 11.39 (br s, 1H), 9.40-9.81 (m, 1H), 8.54 (br d, J=7.9 Hz, 1H), 8.45 (s, 2H), 3.09 (spt, J=6.7 Hz, 2H), 1.22 (d, J=6.8 Hz, 12H). $^{19}$F NMR (376 MHz, DMSO-d$_6$) δ −122.48−−121.38 (m, 1F). m/z (ESI, +ve ion): 413.0 (M+H)$^+$.

Step 2: 7-Chloro-1-(3,5-diisopropylpyridin-4-yl)-6-fluoropyrido[2,3-d]pyrimidine-2,4(1H,3H)-dione To a cooled mixture of 2,6-dichloro-N-((3,5-diisopropylpyridin-4-yl)carbamoyl)-5-fluoronicotinamide (0.54 g, 1.3 mmol) in THF (6 mL) at 0° C. was added 1 M KHMDS in THF (2.58 mL, 2.58 mmol) dropwise and the mixture was stirred at rt for 3 h. The mixture was quenched with satd NH$_4$Cl (50 mL), extracted with EtOAc (3×50 mL), dried over Na$_2$SO$_4$, filtered, and concentrated in vacuo. The crude material was purified by silica gel chromatography (eluent: 0-25% EtOAc-EtOH(3:1)/heptane) to provide 7-chloro-1-

(3,5-diisopropylpyridin-4-yl)-6-fluoropyrido[2,3-d]pyrimidine-2,4(1H,3H)-dione (0.23 g, 0.62 mmol, 48% yield) as light-yellow solid. $^1$H NMR (400 MHz, DMSO-$d_6$) δ 12.28 (s, 1H), 8.62 (s, 2H), 8.50 (d, J=7.5 Hz, 1H), 2.65-2.78 (m, 2H), 1.15 (d, J=7.0 Hz, 6H), 1.03 (d, J=6.8 Hz, 6H). $^{19}$F NMR (377 MHz, DMSO-$d_6$) δ −126.68 (s, 1F). m/z (ESI, +ve ion): 377.0 (M+H)$^+$.

Step 3: tert-Butyl (2R,5S)-4-(7-chloro-1-(3,5-diisopropylpyridin-4-yl)-6-fluoro-2-oxo-1,2-dihydropyrido[2,3-d]pyrimidin-4-yl)-2,5-dimethylpiperazine-1-carboxylate To a mixture of 7-chloro-1-(3,5-diisopropylpyridin-4-yl)-6-fluoropyrido[2,3-d]pyrimidine-2,4(1H,3H)-dione (0.23 g, 0.61 mmol) and DIPEA (0.53 mL, 3.05 mmol) in acetonitrile (4 mL) was added phosphorus oxychloride (0.11 mL, 1.22 mmol) and the mixture was stirred and heated at 80° C. for 30 min. The reaction mixture was cooled to 0° C. To the cooled mixture was added DIPEA (0.53 mL, 3.05 mmol) followed by (2R,5S)-tert-butyl 2,5-dimethylpiperazine-1-carboxylate (0.2 g, 0.92 mmol, eNovation Chemicals LLC) and the mixture was stirred at rt for 2 h. The reaction mixture was quenched with satd. NaHCO$_3$ (100 mL), extracted with EtOAc (3×50 mL), dried over Na$_2$SO$_4$, filtered, and concentrated in vacuo. The crude material was purified by silica gel chromatography (eluent: 0-25% EtOAc-EtOH(3:1)/heptane) to provide tert-butyl (2R,5S)-4-(7-chloro-1-(3,5-diisopropylpyridin-4-yl)-6-fluoro-2-oxo-1,2-dihydropyrido[2,3-d]pyrimidin-4-yl)-2,5-dimethylpiperazine-1-carboxylate (0.14 g, 0.25 mmol, 40.7% yield) as orange solid. $^1$H NMR (400 MHz, DMSO-$d_6$) δ 8.59 (d, J=12.6 Hz, 2H), 8.38 (d, J=8.5 Hz, 1H), 4.80 (br s, 1H), 4.14-4.40 (m, 1H), 4.03 (br d, J=13.5 Hz, 1H), 3.84 (br d, J=12.4 Hz, 1H), 3.66 (br d, J=13.3 Hz, 1H), 3.50 (br dd, J=31.9, 13.5 Hz, 1H), 2.40-2.49 (m, 2H), 1.44 (s, 9H), 1.30 (d, J=6.6 Hz, 3H), 1.08-1.15 (m, 9H), 1.04 (dd, J=17.2, 6.8 Hz, 6H). $^{19}$F NMR (376 MHz, DMSO-$d_6$) δ −127.96 (s, 1F). m/z (ESI, +ve ion): 573.0 (M+H)$^+$.

Step 4: tert-Butyl (2R,5S)-4-(1-(3,5-diisopropylpyridin-4-yl)-6-fluoro-7-(2-fluoro-6-hydroxyphenyl)-2-oxo-1,2-dihydropyrido[2,3-d]pyrimidin-4-yl)-2,5-dimethylpiperazine-1-carboxylate A mixture of tert-butyl (2R,5S)-4-(7-chloro-1-(3,5-diisopropylpyridin-4-yl)-6-fluoro-2-oxo-1,2-dihydropyrido[2,3-d]pyrimidin-4-yl)-2,5-dimethylpiperazine-1-carboxylate (0.13 g, 0.23 mmol), (2-fluoro-6-hydroxyphenyl)boronic acid (0.073 g, 0.47 mmol, Wuxi), potassium acetate (0.115 g, 1.17 mmol), (1,1'-bis(diphenylphosphino)ferrocene)dichloropalladium-dichloromethane (1:1) (0.019 g, 0.023 mmol, Oakwood Products, Inc.) in 1,4-dioxane (2 mL) and water (0.01 mL) was stirred and heated at 90° C. for 14 h. The crude material was purified by silica gel chromatography (eluent: 0-50% EtOAc-EtOH (3:1)/heptane) to provide tert-butyl (2R,5S)-4-(1-(3,5-diisopropylpyridin-4-yl)-6-fluoro-7-(2-fluoro-6-hydroxyphenyl)-2-oxo-1,2-dihydropyrido[2,3-d]pyrimidin-4-yl)-2,5-dimethylpiperazine-1-carboxylate (0.054 g, 0.083 mmol, 35.5% yield) as yellow solid. $^1$H NMR (400 MHz, DMSO-$d_6$) δ 10.17 (br s, 1H), 8.49 (d, J=2.9 Hz, 2H), 8.27 (d, J=9.1 Hz, 1H), 7.21-7.29 (m, 1H), 6.60-6.76 (m, 2H), 4.72-4.91 (m, 1H), 4.18-4.42 (m, 1H), 4.10 (br d, J=13.9 Hz, 1H), 3.77-3.88 (m, 1H), 3.43-3.73 (m, 2H), 2.42-2.49 (m, 2H), 1.45 (s, 9H), 0.93-1.36 (m, 18H). $^{19}$F NMR (377 MHz, DMSO-$d_6$) δ −115.75 (br d, J=4.3 Hz, 1F), −128.53 (br s, 1F). m/z (ESI, +ve ion): 649.1 (M+H)$^+$.

Step 5: 1-(3,5-Diisopropyl-4-pyridyl)-4-[(2S,5R)-2,5-dimethyl-4-prop-2-enoyl-piperazin-1-yl]-6-fluoro-7-(2-fluoro-6-hydroxy-phenyl)pyrido[2,3-d]pyrimidin-2-one A mixture of tert-butyl (2R,5S)-4-(1-(3,5-diisopropylpyridin-4-yl)-6-fluoro-7-(2-fluoro-6-hydroxyphenyl)-2-oxo-1,2-dihydropyrido[2,3-d]pyrimidin-4-yl)-2,5-dimethylpiperazine-1-carboxylate (0.052 g, 0.077 mmol) in DCM (2 mL) and TFA (2 mL) was stirred at rt for 10 min. The mixture was concentrated in vacuo to afford 1-(3,5-diisopropylpyridin-4-yl)-4-((2S,5R)-2,5-dimethylpiperazin-1-yl)-6-fluoro-7-(2-fluoro-6-hydroxyphenyl)pyrido[2,3-d]pyrimidin-2(1H)-one as orange syrup. The crude product was used in next step without purification. m/z (ESI, +ve ion): 549.0 (M+H)$^+$.

A mixture of 1-(3,5-diisopropylpyridin-4-yl)-4-((2S,5R)-2,5-dimethylpiperazin-1-yl)-6-fluoro-7-(2-fluoro-6-hydroxyphenyl)pyrido[2,3-d]pyrimidin-2(1H)-one and DIPEA (0.2 mL, 1.16 mmol) in DCM (2 mL) was cooled to −20° C. To the cooled mixture at −20° C. was added acryloyl chloride, 0.2 M solution in DCM (0.39 mL, 0.077 mmol) dropwise and the mixture was stirred at −20° C. for 30 min. The mixture was concentrated in vacuo to afford the crude material as a yellow solid. The residue was dissolved in THF (3 mL), treated with 2 N NaOH (0.4 mL, 0.8 mmol), and stirred at it for 1 h. The reaction mixture was diluted with satd. NH$_4$Cl (50 mL), extracted with EtOAc (3×50 mL), dried over Na$_2$SO$_4$, filtered, and concentrated in vacuo. The crude material was purified by silica gel chromatography (eluent 0-25% DCM-MeOH (4:1)/DCM) to provide 1-(3,5-diisopropyl-4-pyridyl)-4-[(2S,5R)-2,5-dimethyl-4-prop-2-enoyl-piperazin-1-yl]-6-fluoro-7-(2-fluoro-6-hydroxy-phenyl)pyrido[2,3-d]pyrimidin-2-one (0.024 g, 0.040 mmol, 51.7% yield) as yellow solid. $^1$H NMR (400 MHz, DMSO-$d_6$) δ 10.19 (br s, 1H), 8.49 (d, J=3.1 Hz, 2H), 8.30 (d, J=9.1 Hz, 1H), 7.25 (q, J=8.1 Hz, 1H), 6.62-6.90 (m, 3H), 6.18 (dd, J=16.6, 2.3 Hz, 1H), 5.74-5.79 (m, 1H), 4.42-4.93 (m, 2H), 3.79-4.23 (m, 4H), 2.41-2.48 (m, 2H), 1.16-1.33 (m, 6H), 1.11 (dd, J=6.7, 4.5 Hz, 6H), 0.97 (br d, J=6.6 Hz, 6H). $^{19}$F NMR (377 MHz, DMSO-$d_6$) δ −115.75 (br s, 1F), −128.46 (br s, 1F). m/z (ESI, +ve ion): 603.0 (M+H)$^+$.

TABLE 101

Compounds 101-2 to 101-3 were prepared following the procedure described in Method 101, Steps 1-5, above as follows:

| Ex. # | Chemical structure | Name | Method Changes | Reagent |
|---|---|---|---|---|
| 101-2 | 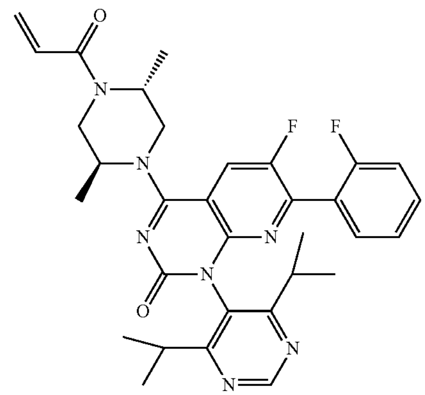 [SMILES: C=CC(=O)N1C[C@H](C)N(c2nc(=O)n(-c3c(C(C)C)ncnc3C(C)C)c3nc(-c4ccccc4F)c(F)cc23)C[C@H]1C] | 1-(4,6-Diisopropylpyrimidin-5-yl)-4-[(2S,5R)-2,5-dimethyl-4-prop-2-enoyl-piperazin-1-yl]-6-fluoro-7-(2-fluorophenyl)pyrido[2,3-d]pyrimidin-2-one | None | Step 1: Intermediate U Step 4: 2-fluorophenylboronic acid, Combi-Blocks, San Diego, CA, USA |
| 101-3 | 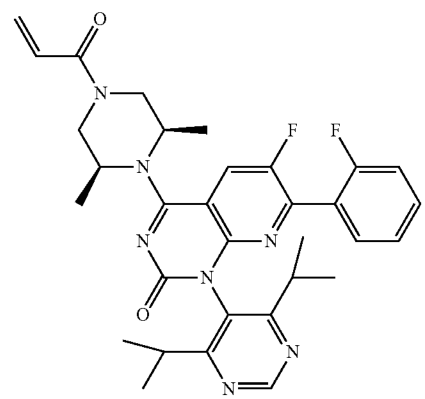 [SMILES: C=CC(=O)N1C[C@@H](C)N(c2nc(=O)n(-c3c(C(C)C)ncnc3C(C)C)c3nc(-c4ccccc4F)c(F)cc23)[C@@H](C)C1] | 1-(4,6-Diisopropylpyrimidin-5-yl)-4-[(2R,6S)-2,6-dimethyl-4-prop-2-enoyl-piperazin-1-yl]-6-fluoro-7-(2-fluorophenyl)pyrido[2,3-d]pyrimidin-2-one | None | Step 1: Intermediate U Step 3: tert-butyl cis-3,5-dimethylpiperazine-1-carboxylate, Combi-Blocks, San Diego, CA, USA) Step 4: 2-fluorophenylboronic acid, Combi-Blocks, San Diego, CA, USA |

Method 102

Example 102-1: 4-((2S,5R)-4-Acryloyl-2,5-dimethylpiperazin-1-yl)-6-chloro-1-(2,6-diisopropylphenyl)-7-(2-fluorophenyl)pyrido[2,3-d]pyrimidin-2 (1H)-one

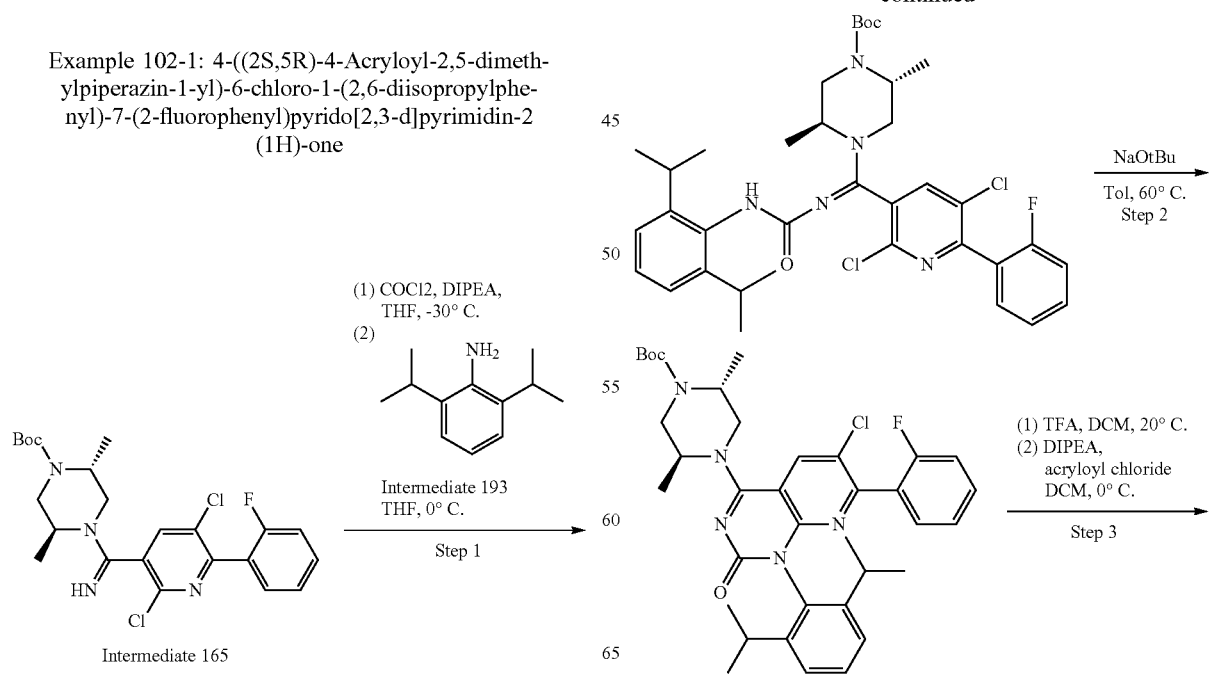

-continued

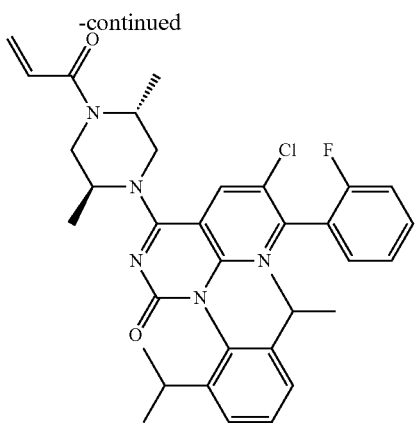

Step 1: tert-Butyl (2R,5S)-4-(6-chloro-1-(2,6-diisopropylphenyl)-7-(2-fluorophenyl)-2-oxo-1,2-dihydropyrido[2,3-d]pyrimidin-4-yl)-2,5-dimethylpiperazine-1-carboxylate To a solution of tert-butyl (2R,5S)-4-((2,5-dichloro-6-(2-fluorophenyl)pyridin-3-yl)(imino)methyl)-2,5-dimethylpiperazine-1-carboxylate (0.050 g, 0.10 mmol, Intermediate 165) and DIEA (0.038 mL, 0.22 mmol) in TH-F (5 mL) was added phosgene solution, 150/0 in toluene (0.078 mL, 0.11 mmol) at 0° C. This solution was stirred for 10 min followed by addition of 2,6-diisopropylaniline (0.022 g, 0.13 mmol, Intermediate 193) in THF (1 mL) at 0° C. The resulting mixture was stirred at room temp for 15 min at which point LC-MS analysis indicated consumption of starting material and the presence of tert-butyl (2R,5S)-4-((2,5-dichloro-6-(2-fluorophenyl)pyridin-3-yl)(((2,6-diisopropylphenyl)carbamoyl)imino)methyl)-2,5-dimethylpiperazine-1-carboxylate. The reaction was diluted with EtOAc (20 mL) and quenched with saturated aqueous NaHCO$_3$. The layers were partitioned and the organic phase was dried over anhydrous MgSO$_4$, filtered, and concentrated under reduced pressure. m/z (ESI, +ve ion): 683.6 (M+H)$^+$.

Step 2: tert-Butyl (2R,5S)-4-(6-chloro-1-(2,6-diisopropylphenyl)-7-(2-fluorophenyl)-2-oxo-1,2-dihydropyrido[2,3-d]pyrimidin-4-yl)-2,5-dimethylpiperazine-1-carboxylate tert-Butyl (2R,5S)-4-((2,5-dichloro-6-(2-fluorophenyl)pyridin-3-yl)(((2,6-diisopropylphenyl)carbamoyl)imino)methyl)-2,5-dimethylpiperazine-1-carboxylate was re-dissolved in THF (3 mL) and toluene (3 mL). The resulting solution was cooled to 0° C. followed by addition of sodium tert-butoxide (0.015 mg, 0.156 µmol). The reaction was stirred at this temperature for 40 min, diluted with EtOAc, and washed with sat. aqueous NaHCO$_3$. The combined organics were purified by chromatography on silica gel using 0-40% EtOAc in heptane to afford tert-butyl (2R,5S)-4-(6-chloro-1-(2,6-diisopropylphenyl)-7-(2-fluorophenyl)-2-oxo-12-dihydropyrido[2,3-d]pyrimidin-4-yl)-2,5-dimethylpiperazine-1-carboxylate (0.029 g, 0.045 mmol, 43.3% yield) as a yellow solid. m/z (ESI, +ve ion): 648.2 (M+H)$^+$.

Step 3: 4-((2S,5R)-4-Acryloyl-2,5-dimethylpiperazin-1-yl)-6-chloro-1-(2,6-diisopropylphenyl)-7-(2-fluorophenyl)pyrido[2,3-d]pyrimidin-2(1H)-one To a solution of tert-butyl (2R,5S)-4-(6-chloro-1-(2,6-diisopropylphenyl)-7-(2-fluorophenyl)-2-oxo-1,2-dihydropyrido[2,3-d]pyrimidin-4-yl)-2,5-dimethylpiperazine-1-carboxylate (0.029 g, 0.045 mmol) in DCM (3 mL) was added tfa (2.0 mL, 26.0 mmol) and the resulting mixture was stirred at rt for 30 min. The reaction went to completion and concentrated to afford 6-chloro-1-(2,6-diisopropylphenyl)-4-((2S,5R)-2,5-dimethylpiperazin-1-yl)-7-(2-fluorophenyl)pyrido[2,3-d]pyrimidin-2(1H)-one which was dissolved in DCM (3 mL) then acryloyl chloride (3.27 µl, 0.040 mmol) was added at rt. The reaction was stirred at it for 15 min, washed with sat. NaHCO$_3$ and extracted with DCM. The combined organics were purified by HPLC to afford 4-((2S,5R)-4-acryloyl-2,5-dimethylpiperazin-1-yl)-6-chloro-1-(2,6-diisopropylphenyl)-7-(2-fluorophenyl)pyrido[2,3-d]pyrimidin-2(1H)-one (0.010 g, 8.30 µmol, 18.56% yield) as a light yellow solid. $^1$H NMR (400 MHz, DMSO-d$_6$) δ 8.46 (s, 1H), 7.43-7.57 (m, 1H), 7.12-7.36 (m, 6H), 6.75-6.94 (m, 1H), 6.19 (dd, J=16.7, 2.4 Hz, 1H), 5.67-5.85 (m, 1H), 4.69-4.96 (m, 2H), 4.39-4.52 (m, 1H), 4.14 (br t, J=11.9 Hz, 1H), 3.78-3.99 (m, 2H), 3.44-3.62 (m, 1H), 1.30-1.37 (m, 3H), 1.25 (br d, J=6.4 Hz, 2H), 1.17 (d, J=6.8 Hz, 2H), 1.03-1.10 (m, 6H), 0.92 (dd, J=10.0, 6.8 Hz, 6H), 601.6 (M+H)$^+$.

TABLE 102

Compounds 102-2 to 102-7 were prepared following the procedure described in Method 102, Steps 1-3, above as follows:

| Ex. # | Chemical structure | Name | Method Changes | Reagent |
|---|---|---|---|---|
| 102-2 | 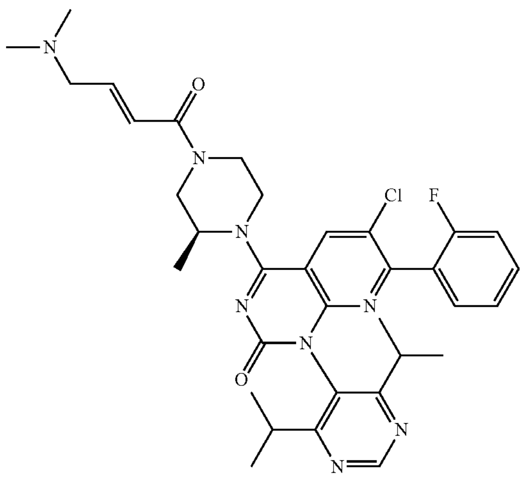 [SMILES: CC(C)c1ncnc(C(C)C)c1-n1c(=O)nc(N2CCN(C(=O)/C=C/CN(C)C)C[C@@H]2C)c2cc(Cl)c(-c3ccccc3F)nc21] | 6-Chloro-1-(4,6-diisopropylpyrimidin-5-yl)-4-[(2S)-4-[(E)-4-(dimethylamino)but-2-enoyl]-2-methylpiperazin-1-yl]-7-(2-fluorophenyl)pyrido[2,3-d]pyrimidin-2-one | Step 1: 4,6-Diisopropylpyrimidin-5-amine and tert-butyl (S)-4-((2,5-dichloro-6-(2-fluorophenyl)pyridin-3-yl)(imino)methyl)-3-methylpiperazine-1-carboxylate | Step 3: ([(1-Cyano-2-ethoxy-2-oxoethylidene)amino]oxy)dimethylamino(morpholin-4-yl)carbenium hexafluorophosphate and trans-4-dimethylaminocrotonic acid hydrochloride |
| 102-3 | 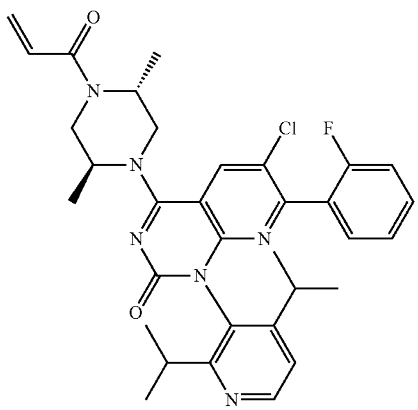 [SMILES: C=CC(=O)N1C[C@H](C)N(c2nc(=O)n(-c3c(C(C)C)ccnc3C(C)C)c3nc(-c4ccccc4F)c(Cl)cc23)C[C@H]1C] | 6-Chloro-1-(2,4-diisopropyl-3-pyridyl)-4-[(2S,5R)-2,5-dimethyl-4-prop-2-enoyl-piperazin-1-yl]-7-(2-fluorophenyl)pyrido[2,3-d]pyrimidin-2-one | Intermediate 194 in Step 1 | No change |
| 102-4 | 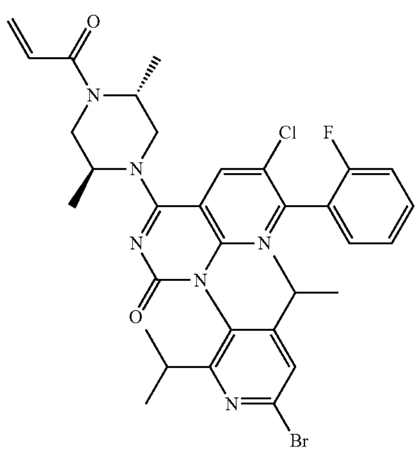 [SMILES: C=CC(=O)N1C[C@H](C)N(c2nc(=O)n(-c3c(C(C)C)cc(Br)nc3C(C)C)c3nc(-c4ccccc4F)c(Cl)cc23)C[C@H]1C] | 1-(6-Bromo-2,4-diisopropyl-3-pyridyl)-6-chloro-4-[(2S,5R)-2,5-dimethyl-4-prop-2-enoyl-piperazin-1-yl]-7-(2-fluorophenyl)pyrido[2,3-d]pyrimidin-2-one | Intermediate 196 used in Step 1 | No change |

TABLE 102-continued

Compounds 102-2 to 102-7 were prepared following the procedure described in Method 102, Steps 1-3, above as follows:

| Ex. # | Chemical structure | Name | Method Changes | Reagent |
|---|---|---|---|---|
| 102-5 | 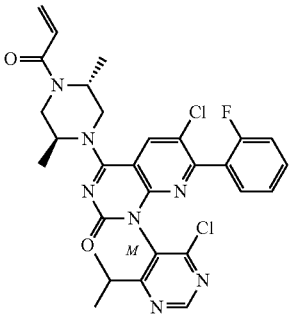 | 6-Chloro-1-(4-chloro-6-isopropyl-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one | Step 2: Performed in Toluene | Step 1: Intermediate 177 |
| 102-6 | 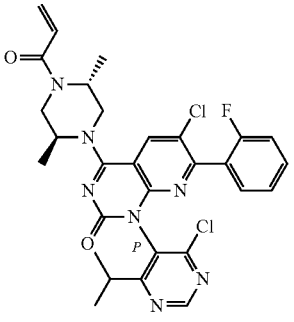 | 6-Chloro-1-(4-chloro-6-isopropyl-pyrimidin-5-yl)-4-[(2S,5R)-2,5-dimethyl-4-prop-2-enoyl-piperazin-1-yl]-7-(o-tolyl)pyrido[2,3-d]pyrimidin-2-one | Step 2: Performed in Toluene | Step 1: Intermediate 168 and Intermediate 177 |
| 102-7 | 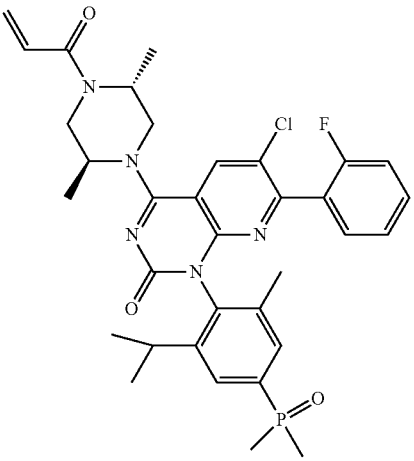 [SMILES: C=CC(=O)N1C[C@H](C)N(c2nc(=O)n(-c3c(C)cc(P(C)(C)=O)cc3C(C)C)c3nc(-c4ccccc4F)c(Cl)cc23)C[C@H]1C] | 6-Chloro-1-(4-dimethylphosphoryl-2-isopropyl-6-methyl-phenyl)-4-[(2S,5R)-2,5-dimethyl-4-prop-2-enoyl-piperazin-1-yl]-7-(2-fluorophenyl)pyrido[2,3-d]pyrimidin-2-one | Step 1 (1): 0° C.; Step 2: 1:1 THF-toluene, 0° C. | Step 1 (2): Intermediate 221 |

TABLE 102-continued

Compounds 102-2 to 102-7 were prepared following the procedure described in Method 102, Steps 1-3, above as follows:

| Ex. # | Chemical structure | Name | Method Changes | Reagent |
|---|---|---|---|---|
| 102-8 | 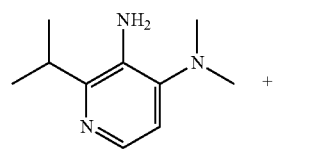 | 3-[6-Chloro-4-[(2S,5R)-2,5-dimethyl-4-prop-2-enoyl-piperazin-1-yl]-7-(2-fluorophenyl)-2-oxo-pyrido[2,3-d]pyrimidin-1-yl]-4-isopropyl-N,N-dimethyl-pyridine-2-carboxamide | None | Step 1: Intermediate 210 |

Method 103

Example 103-1

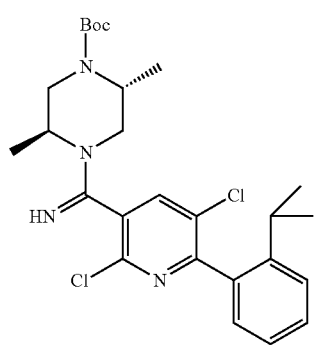

Intermediate 163

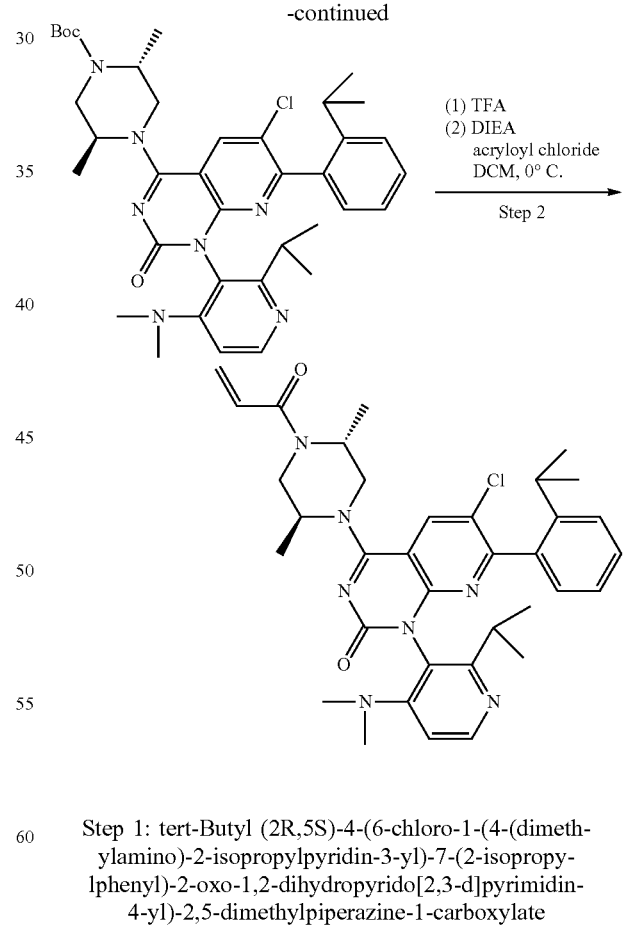

Step 1: tert-Butyl (2R,5S)-4-(6-chloro-1-(4-(dimethylamino)-2-isopropylpyridin-3-yl)-7-(2-isopropylphenyl)-2-oxo-1,2-dihydropyrido[2,3-d]pyrimidin-4-yl)-2,5-dimethylpiperazine-1-carboxylate To a stirring solution of 3-isopropyl-N1,N1-dimethylbenzene-1,2-diamine (282 mg, 1.583 mmol, Intermediate 163) and DIEA (580 μl, 3.32 mmol) in THF (6 mL; 20:1 mL) at 20° C. was added a phosgene solution. 15% in toluene (1248 µl, 1.741 mmol) dropwise. A precipitate formed and the resulting mixture was stirred at 20° C. for 15 min then chilled to 0° C. Once chilled, solid tert-butyl (2R,5S)-4-((2,5-dichloro-6-(2-isopropylphenyl)pyridin-3-yl)(imino)methyl)-2,5-dimethylpiperazine-1-carboxylate (800 mg, 1.583 mmol, Intermediate 170) was added in one portion. The ice bath was removed and stirred for a total of 45 min at 20° C. The reaction was returned to 0° C., a sodium tert-butoxide solution, 2.0 M in THF (2374 µl, 4.75 mmol) was added, and then the ice bath removed. After 30 min, the reaction was partitioned between EtOAc (60 mL) and sat. NaHCO3 (20 mL). The organic was further washed with sat. NaCl (10 mL), dried over MgSO$_4$, concentrated under reduced pressure, then purified by silica gel chromatography (40 g) eluting products with a gradient of 10>35% EtOAc/EtOH (3:1 blend)/heptane to afford tert-butyl (2R,5S)-4-(6-chloro-1-(4-(dimethylamino)-2-isopropylpyridin-3-yl)-7-(2-isopropylphenyl)-2-oxo-1,2-dihydropyrido[2,3-d]pyrimidin-4-yl)-2,5-dimethylpiperazine-1-carboxylate as white foam. m/z (ESI, +ve ion): 674.5 (M+H)$^+$. 124611-28

Step 2: 4-((2S,5R)-4-Acryloyl-2,5-dimethylpiperazin-1-yl)-6-chloro-1-(4-(dimethylamino)-2-isopropylpyridin-3-yl)-7-(2-isopropylphenyl)pyrido[2,3-d]pyrimidin-2(1H)-one A solution of tert-butyl (2R,5S)-4-(6-chloro-1-(4-(dimethylamino)-2-isopropylpyridin-3-yl)-7-(2-isopropylphenyl)-2-oxo-1,2-dihydropyrido[2,3-d]pyrimidin-4-yl)-2,5-dimethylpiperazine-1-carboxylate (760 mg, 1.127 mmol) was stirred in TFA (3 mL) at 20° C. for 30 min. The solvent was then removed under reduced pressure followed by an azeotrope with heptane (30 mL). The residue was then partitioned between EtOAc (30 mL) and 5% Na$_2$CO$_3$ (20 mL). The separated organic was washed with sat. NaCl (10 mL), dried over MgSO$_4$, then concentrated under reduced pressure to afford the intermediate. To the material was added DCM (10 mL) and DIEA (394 µl, 2.254 mmol), and the solution was chilled to 0° C. To this solution was added a second solution of acryloyl chloride (92 µl, 1.127 mmol) in DCM (3 mL) was dropwise over a period of 1 min. The reaction was then directly purified by silica gel chromatography (40 g) eluting products with a gradient of 0>70% EtOAc/EtOH (3:1 blend)/heptane to afford 4-((2S,5R)-4-acryloyl-2,5-dimethylpiperazin-1-yl)-6-chloro-1-(4-(dimethylamino)-2-isopropylpyridin-3-yl)-7-(2-isopropylphenyl)pyrido[2,3-d]pyrimidin-2(1H)-one as white foam. m/z (ESI, +ve ion): 628.3 (M+H)$^+$.

TABLE 103

Compounds 103-2 to 103-7 were prepared following the procedure described in Method 103, Steps x-x, above as follows:

| Ex. # | Chemical structure | Name | Method Changes | Reagent |
|---|---|---|---|---|
| 103-2 | 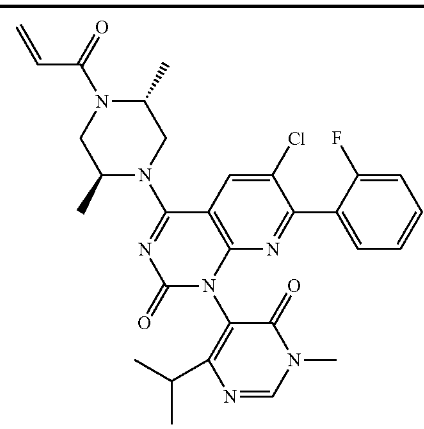 | 6-Chloro-4-[(2S,5R)-2,5-dimethyl-4-prop-2-enoyl-piperazin-1-yl]-7-(2-fluorophenyl)-1-(4-isopropyl-1-methyl-6-oxo-pyrimidin-5-yl)pyrido[2,3-d]pyrimidin-2-one | Step 1-1 & 1-2: 0° C., phosgene added to Intermediate 165; Step 1-4; Intermediate 234 added as a THF solution; Step 1-4: aqueous workup performed; Step 1-5: THF/toluene (1:1); Step 2-1: omit DCM; Step 2-2: RT. | Intermediate 234 & intermediate 165 |
| 103-3 Chiral | | 6-Chloro-4-[(2S,5R)-2,5-dimethyl-4-prop-2-enoyl-piperazin-1-yl]-7-(2-fluorophenyl)-1-[2-isopropyl-4-[(S)-methylsulfinyl]phenyl]pyrido[2,3-d]pyrimidin-2-one | None | Intermediate 173 and Intermediate 165 |

TABLE 103-continued

Compounds 103-2 to 103-7 were prepared following the procedure described in Method 103, Steps x-x, above as follows:

| Ex. # | Chemical structure | Name | Method Changes | Reagent |
|---|---|---|---|---|
| 103-4 | 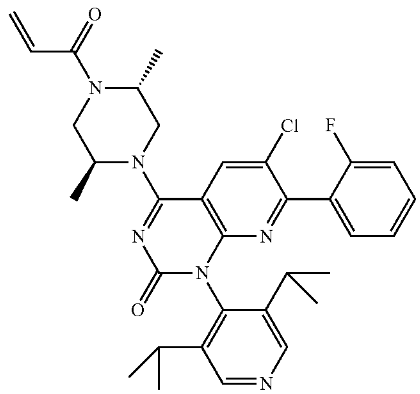 [SMILES: C=CC(=O)N1C[C@H](C)N(c2nc(=O)n(-c3c(C(C)C)cncc3C(C)C)c3nc(-c4ccccc4F)c(Cl)cc23)C[C@H]1C] | 6-Chloro-1-(3,5-diisopropyl-4-pyridyl)-4-[(2S,5R)-2,5-dimethyl-4-prop-2-enoyl-piperazin-1-yl]-7-(2-fluorophenyl)pyrido[2,3-d]pyrimidin-2-one | None | Intermediate 162 and Intermediate 165 |
| 103-5 | 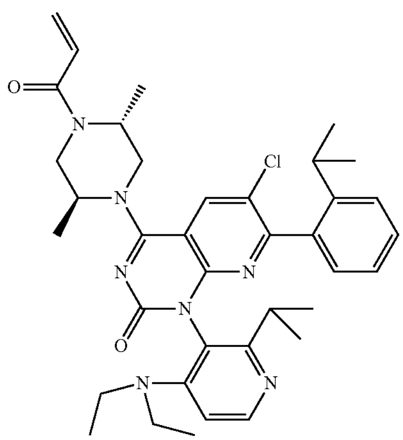 [SMILES: C=CC(=O)N1C[C@H](C)N(c2nc(=O)n(-c3c(N(CC)CC)ccnc3C(C)C)c3nc(-c4ccccc4C(C)C)c(Cl)cc23)C[C@H]1C] | 6-Chloro-1-[4-(diethylamino)-2-isopropyl-3-pyridyl]-4-[(2S,5R)-2,5-dimethyl-4-prop-2-enoyl-piperazin-1-yl]-7-(2-isopropylphenyl)pyrido[2,3-d]pyrimidin-2-one | None | Intermediate 170 and Intermediate 164 |
| 103-6 | 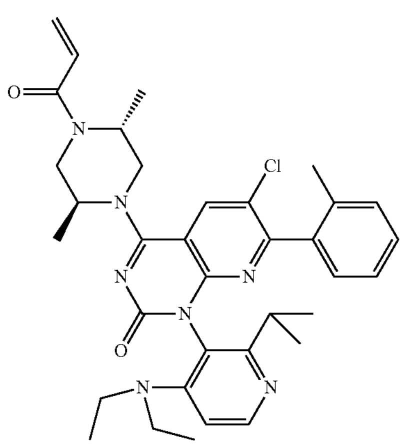 [SMILES: C=CC(=O)N1C[C@H](C)N(c2nc(=O)n(-c3c(N(CC)CC)ccnc3C(C)C)c3nc(-c4ccccc4C)c(Cl)cc23)C[C@H]1C] | 6-chloro-1-[4-(diethylamino)-2-isopropyl-3-pyridyl]-4-[(2S,5R)-2,5-dimethyl-4-prop-2-enoyl-piperazin-1-yl]-7-(o-tolyl)pyrido[2,3-d]pyrimidin-2-one | None | Intermediate 168 and Intermediate 164 |

TABLE 103-continued

Compounds 103-2 to 103-7 were prepared following the procedure described in Method 103, Steps x-x, above as follows:

| Ex. # | Chemical structure | Name | Method Changes | Reagent |
|---|---|---|---|---|
| 103-7 | 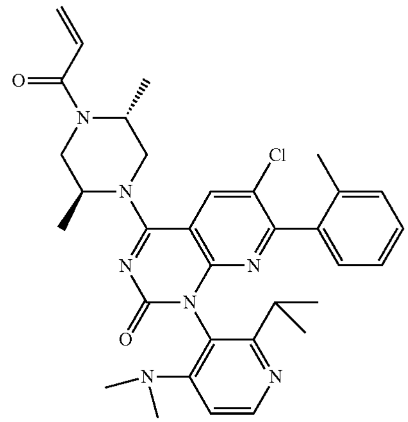 [SMILES: C=CC(=O)N1C[C@H](C)N(c2nc(=O)n(-c3c(N(C)C)ccnc3C(C)C)c3nc(-c4ccccc4C)c(Cl)cc23)C[C@H]1C] | 6-Chloro-1-[4-(dimethylamino)-2-isopropyl-3-pyridyl]-4-[(2S,5R)-2,5-dimethyl-4-prop-2-enoyl-piperazin-1-yl]-7-(o-tolyl)pyrido[2,3-d]pyrimidin-2-one | None | Intermediate 168 and Intermediate 163 |

Method 106

Example 106-1: 4-((2S,5R)-4-Acryloyl-2,5-dimethylpiperazin-1-yl)-1-(2-bromo-4,6-diisopropylpyrimidin-5-yl)-6-chloro-7-(2-fluorophenyl)pyrido[2,3-d]pyrimidin-2(1H)-one

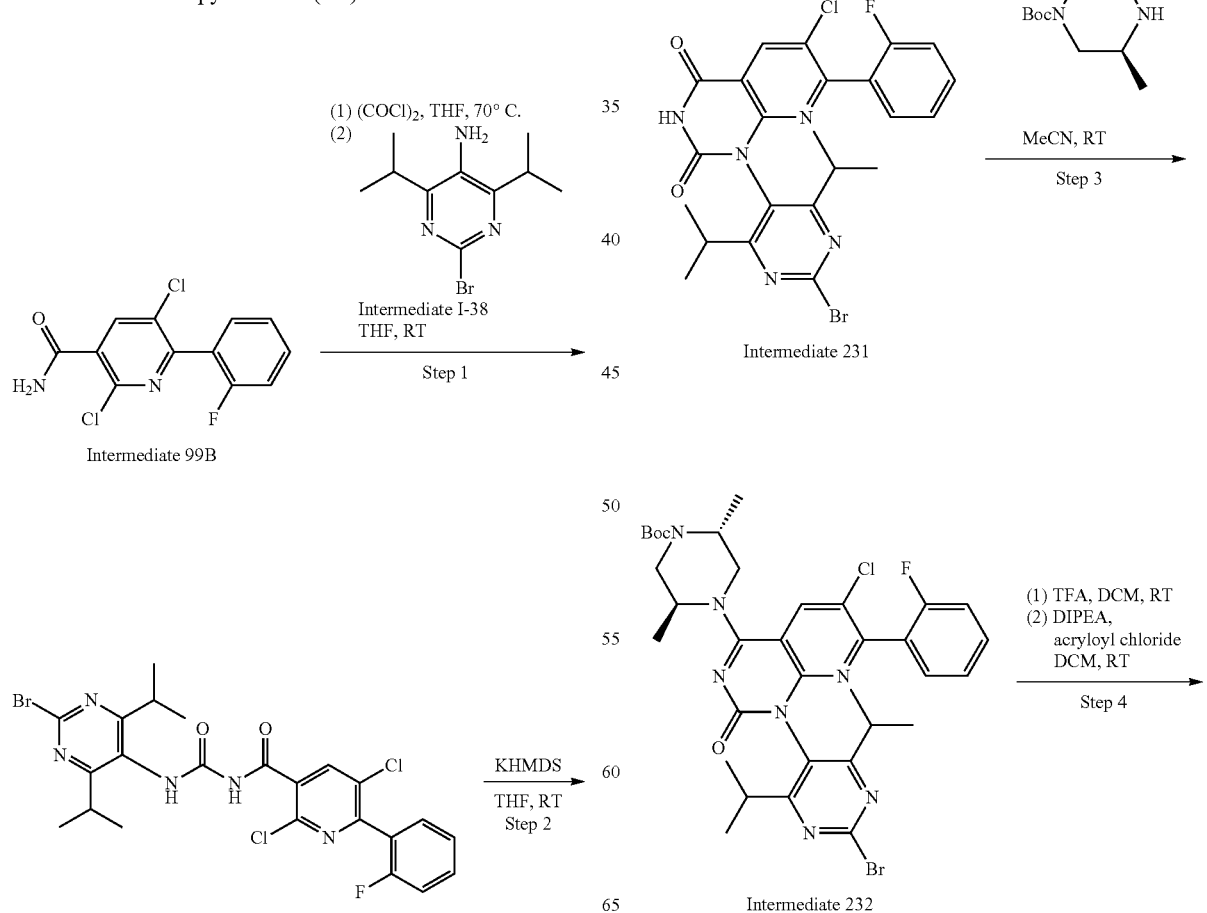

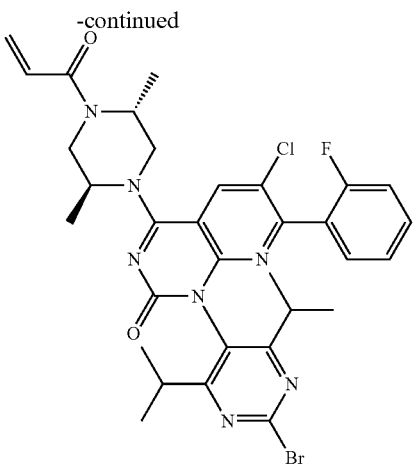

Step 1: N-((2-Bromo-4,6-diisopropylpyrimidin-5-yl)carbamoyl)-2,5-dichloro-6-(2-fluorophenyl)nicotinamide To a 250-mL round-bottomed flask was added 2,5-dichloro-6-(2-fluorophenyl)nicotinamide (2.95 g, 9.73 mmol, Intermediate 99B) and oxalyl chloride (7.29 mL, 14.59 mmol) in tetrahydrofuran (32.4 mL). The flask was fitted with a reflux condensor, and the mixture was stirred and heated at 80° C. for 45 min. The reaction mixture was concentrated in vacuo. The crude mixture was carried on without further purification.

To a 150-mL round-bottomed flask was added the crude (2,5-dichloro-6-(2-fluorophenyl)nicotinoyl)carbamoyl isocyanate from above in tetrahydrofuran (32.4 mL). The mixture was cooled to −10° C. before a solution of 2-bromo-4,6-diisopropylpyrimidin-5-amine (2.89 g, 11.19 mmol, Intermediate I-38) in THF (3 mL) was added. The reaction mixture was allowed to stir under an inert (N2) atmosphere for 1 h. The reaction mixture was concentrated in vacuo. The crude material was triturated with EtOAc and heptane, and the solids were collected by filtration. The solids were washed with heptane to afford N-((2-bromo-4,6-diisopropylpyrimidin-5-yl)carbamoyl)-2,5-dichloro-6-(2-fluorophenyl)nicotinamide as a tan solid (4.500 g, 7.91 mmol, 81% yield). $^1$H NMR (400 MHz, DMSO-$d_6$) δ 11.48 (s, 1H) 9.74 (br s, 1H) 8.62 (s, 1H) 7.55-7.64 (m, 2H) 7.37-7.42 (m, 2H) 3.21-3.30 (m, 2H) 1.16-1.19 (m, 12H). m/z (ESI, +ve ion): 568.0 (M+H)$^+$.

Step 2: 1-(2-Bromo-4,6-diisopropylpyrimidin-5-yl)-6-chloro-7-(2-fluorophenyl)pyrido[2,3-d]pyrimidine-2,4(1H,3H)-dione (Intermediate 231)

To a 250-mL round-bottomed flask was added N-((2-bromo-4,6-diisopropylpyrimidin-5-yl)carbamoyl)-2,5-dichloro-6-(2-fluorophenyl)nicotinamide (4.790 g, 8.41 mmol) in tetrahydrofuran (42.1 mL). Potassium bis(trimethylsilyl)amide (1.0 M solution in tetrahydrofuran, 10.52 mL, 10.52 mmol) was added dropwise via addition funnel into the reaction mixture over 5 min. The reaction mixture was allowed to stir under an inert (N2) atmosphere for 10 min. Additional potassium bis(trimethylsilyl)amide (0.5 eq; 5.5 mL) was added dropwise into the reaction mixture. The reaction mixture was quenched with sat. aq. NH$_4$Cl (50 mL), then the mixture was diluted with 3:1 EtOAc/MeOH and brine solution. The layers were separated and the aqueous layer was extracted with EtOAc. The combined organic extracts were dried over MgSO4, filtered and concentrated in vacuo. The crude was triturated with EtOAc and heptane. The solids were washed with heptane and allowed to dry in a reduced-pressure oven (40° C.) for 1 h to afford 1-(2-bromo-4,6-diisopropylpyrimidin-5-yl)-6-chloro-7-(2-fluorophenyl)pyrido[2,3-d]pyrimidine-2,4(1H,3H)-dione as a tan solid (4.26 g, 7.99 mmol, 95% yield, Intermediate 231). $^1$H NMR (400 MHz, DMSO-d6) δ 11.83-12.28 (m, 1H) 8.57 (s, 1H) 7.50-7.56 (m, 1H) 7.31 (d, J=7.88 Hz, 2H) 7.18-7.23 (m, 1H) 2.94-3.02 (m, 2H) 1.08 (d, J=6.63 Hz, 6H) 0.91 (d, J=6.63 Hz, 6H). m/z (ESI, +ve ion): 532.0 (M+H)$^+$.

Step 3: tert-Butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (Intermediate 232)

Phosphorus(V) oxychloride (0.237 mL, 2.54 mmol) was added to a stirred mixture of 1-(2-bromo-4,6-diisopropylpyrimidin-5-yl)-6-chloro-7-(2-fluorophenyl)pyrido[2,3-d]pyrimidine-2,4(1H,3H)-dione (1.04 g, 1.952 mmol, Intermediate 231) and N,N-diisopropylethylamine (0.477 mL, 2.73 mmol) in acetonitrile (8 mL). The reaction mixture was stirred at 80° C. for 40 min before being cooled to room temperature. Additional N,N-diisopropylethylamine (0.477 mL, 2.73 mmol) was added followed by (2R,5S)-tert-butyl 2,5-dimethylpiperazine-1-carboxylate (0.418 mL, 1.952 mmol). The reaction mixture was stirred at room temperature for 25 min. The reaction was quenched with water (150 mL) and extracted with EtOAc (200 mL). The organic layer was separated, washed with saturated sodium chloride (150 mL), dried over MgSO$_4$, filtered, and concentrated in vacuo. The crude product was purified by silica gel chromatography (eluent 0-30% [(3:1) EtOAc/EtOH]/heptane) to provide tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate as a white solid (1.10 g, 1.509 mmol, 77% yield, Intermediate 232). $^1$H NMR (400 MHz, CHLOROFORM-d) δ 8.17 (1H, s) 7.48-7.54 (1H, m) 7.15-7.28 (3H, m) 3.49-5.08 (6H, m) 2.62-2.72 (2H, m) 1.56 (9H, s) 1.50-1.55 (3H, m) 1.30-1.36 (3H, m) 1.26 (6H, dd, J=6.63, 3.32 Hz) 1.06 (6H, t, J=6.84 Hz). m/z (ESI, +ve ion): 728.0 (M+H)$^+$.

Step 4: 4-((2S,5R)-4-Acryloyl-2,5-dimethylpiperazin-1-yl)-1-(2-bromo-4,6-diisopropylpyrimidin-5-yl)-6-chloro-7-(2-fluorophenyl)pyrido[2,3-d]pyrimidin-2(1H)-one Trifluoroacetic acid (1.00 mL, 13.42 mmol) was added to a stirred solution of tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (300 mg, 0.411 mmol) in dichloromethane (2 mL). The reaction mixture was stirred at room temperature for 20 min. The reaction mixture was concentrated in vacuo to provide crude 1-(2-bromo-4,6-diisopropylpyrimidin-5-yl)-6-chloro-4-((2S,5R)-2,5-dimethylpiperazin-1-yl)-7-(2-fluorophenyl)pyrido[2,3-d]pyrimidin-2(1H)-one that was used without purification assuming 100% yield.

Acryloyl chloride (1.1 M in DCM, 0.487 mL, 0.535 mmol) was added to a stirred mixture of the crude 1-(2-bromo-4,6-diisopropylpyrimidin-5-yl)-6-chloro-4-((2S,5R)-2,5-dimethylpiperazin-1-yl)-7-(2-fluorophenyl)pyrido[2,3- d]pyrimidin-2(1H)-one (259 mg, 0.412 mmol) and N,N-diisopropylethylamine (0.360 mL, 2.059 mmol) in dichloromethane (2 mL). The reaction mixture was stirred at room temperature for 30 min. The reaction mixture was diluted with DCM (60 mL) and washed with saturated aqueous NH$_4$Cl (50 mL). The organic layer was separated, dried over MgSO$_4$, filtered, and concentrated in vacuo. The crude product was purified by silica gel chromatography (eluent 0-50% [(3:1) EtOAc/EtOH]/heptane) to provide 4-((2S,5R)-4-acryloyl-2,5-dimethylpiperazin-1-yl)-1-(2-bromo-4,6-diisopropylpyrimidin-5-yl)-6-chloro-7-(2-fluorophenyl)pyrido[2,3-d]pyrimidin-2(1H)-one as a white solid (241 mg, 0.353 mmol, 86% yield). $^1$H NMR (400 MHz, CHLOROFORM-d) δ 8.17 (1H, s) 7.48-7.54 (1H, m) 7.16-7.28 (3H, m) 6.56-6.74 (1H, m) 6.40-6.49 (1H, m) 5.82-5.88 (1H, m) 3.49-5.23 (6H, m) 2.60-2.72 (2H, m) 1.44-1.56 (3H, m) 1.29-1.40 (3H, m) 1.23-1.29 (6H, m) 1.03-1.09 (6H, m). m/z (ESI, +ve ion): 682.0 (M+H)$^+$.

TABLE 106

Compounds 106-2 to 106-10 were prepared following the procedure described in Method 106, Steps 1-4, above as follows:

| Ex. # | Chemical structure | Name | Method Changes | Reagent |
|---|---|---|---|---|
| 106-2 | 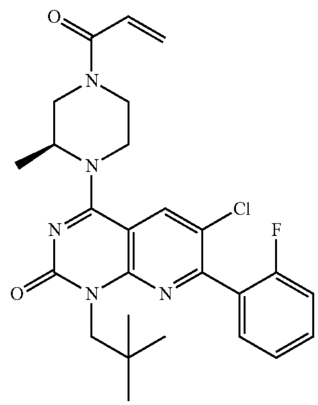 [SMILES: C=CC(=O)N1CCN(c2nc(=O)n(CC(C)(C)C)c3nc(-c4ccccc4F)c(Cl)cc23)[C@@H](C)C1] | 6-Chloro-1-(2,2-dimethylpropyl)-7-(2-fluorophenyl)-4-[(2S)-2-methyl-4-prop-2-enoyl-piperazin-1-yl]pyrido[2,3-d]pyrimidin-2-one | Step 1: RT | Step 1: neopentylamine (TCI America) Step 3: (3S)-1-(tert-butoxycarbonyl)-3-methylpiperazine (Combi-Blocks Inc.) |
| 106-3 | 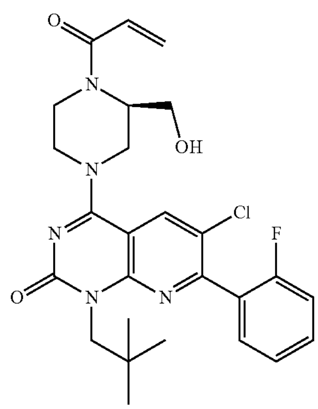 [SMILES: C=CC(=O)N1CCN(c2nc(=O)n(CC(C)(C)C)c3nc(-c4ccccc4F)c(Cl)cc23)C[C@@H]1CO] | 6-Chloro-1-(2,2-dimethylpropyl)-7-(2-fluorophenyl)-4-[(3R)-3-(hydroxymethyl)-4-prop-2-enoyl-piperazin-1-yl]pyrido[2,3-d]pyrimidin-2-one | Step 1: RT | Step 1: neopentylamine (TCI America) Step 3: (R)-1-N-Boc-2-hydroxymethyl-piperazine, (Sigma-Aldrich Corporation) |
| 106-4 | 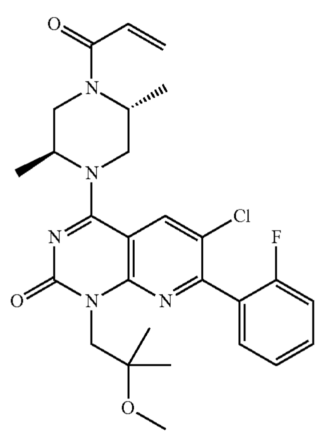 [SMILES: C=CC(=O)N1C[C@H](C)N(c2nc(=O)n(CC(C)(C)OC)c3nc(-c4ccccc4F)c(Cl)cc23)C[C@H]1C] | 6-Chloro-4-[(2S,5R)-2,5-dimethyl-4-prop-2-enoyl-piperazin-1-yl]-7-(2-fluorophenyl)-1-(2-methoxy-2-methyl-propyl)pyrido[2,3-d]pyrimidin-2-one | None | Step 1: 2-methoxy-2-methylpropan-1-amine, (Aurum Pharmatech) |

TABLE 106-continued

Compounds 106-2 to 106-10 were prepared following the procedure described in Method 106, Steps 1-4, above as follows:

| Ex. # | Chemical structure | Name | Method Changes | Reagent |
|---|---|---|---|---|
| 106-5 | 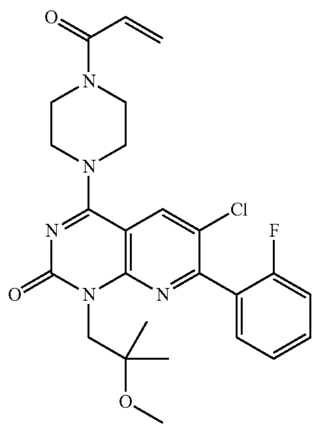 [SMILES: C=CC(=O)N1CCN(c2nc(=O)n(CC(C)(C)OC)c3nc(-c4ccccc4F)c(Cl)cc23)CC1] | 6-Chloro-7-(2-fluorophenyl)-1-(2-methoxy-2-methyl-propyl)-4-(4-prop-2-enoylpiperazin-1-yl)pyrido[2,3-d]pyrimidin-2-one | None | Step 1: 2-methoxy-2-methylpropan-1-amine, (Aurum Pharmatech) Step 3: 1-Boc-piperazine, (Sigma-Aldrich Corporation) |
| 106-6 | 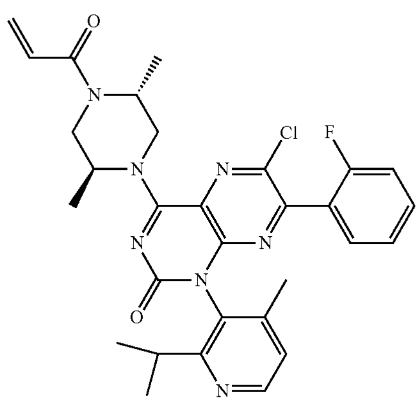 [SMILES: C=CC(=O)N1C[C@H](C)N(c2nc(=O)n(-c3c(C)ccnc3C(C)C)c3nc(-c4ccccc4F)c(Cl)nc23)C[C@H]1C] | 6-Chloro-4-[(2S,5R)-2,5-dimethyl-4-prop-2-enoyl-piperazin-1-yl]-7-(2-fluorophenyl)-1-(2-isopropyl-4-methyl-3-pyridyl)pteridin-2-one | Step 1 (1): 80° C.; Step 1 (2): 0° C. to rt; Step 2: 0° C. to rt; Step 3: 0° C.; Step 4: 0° C. | Step 1 (1): Example 50, step 3; Step 1 (2): Intermediate R; Step 3 (2): (2R,5S)-tert-butyl 2,5-dimethylpiperazine-1-carboxylate (eNovation Chemicals LLC) |
| 106-7 | 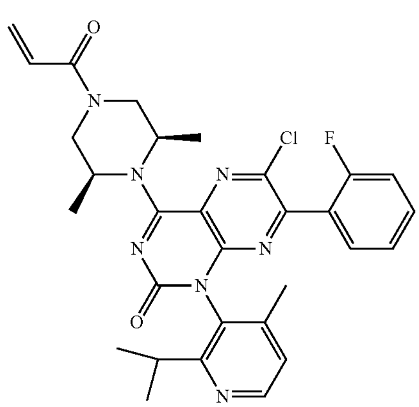 [SMILES: C=CC(=O)N1C[C@@H](C)N(c2nc(=O)n(-c3c(C)ccnc3C(C)C)c3nc(-c4ccccc4F)c(Cl)nc23)[C@@H](C)C1] | 6-Chloro-4-[(2R,6S)-2,6-dimethyl-4-prop-2-enoyl-piperazin-1-yl]-7-(2-fluorophenyl)-1-(2-isopropyl-4-methyl-3-pyridyl)pteridin-2-one | Step 1 (1): 80° C.; Step 1 (2): 0° C.; Step 2: 0° C. to rt; Step 3: 0° C.; Step 4: 0° C. | Step 1 (1): Example 50, step 3; Step 1 (2): Intermediate R; Step 3 (2): cis-3,5-dimethyl-piperazine-1-carboxylic acid tert-butyl ester (Combi-Blocks Inc, San Diego, CA, USA) |

TABLE 106-continued

Compounds 106-2 to 106-10 were prepared following the procedure described in Method 106, Steps 1-4, above as follows:

| Ex. # | Chemical structure | Name | Method Changes | Reagent |
|---|---|---|---|---|
| 106-8 | 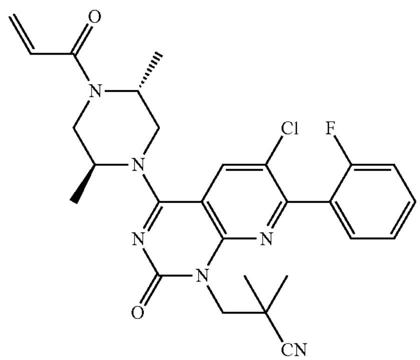 [SMILES: C=CC(=O)N1C[C@H](C)N(c2nc(=O)n(CC(C)(C)C#N)c3nc(-c4ccccc4F)c(Cl)cc23)C[C@H]1C] | 3-[6-Chloro-4-[(2S,5R)-2,5-dimethyl-4-prop-2-enoyl-piperazin-1-yl]-7-(2-fluorophenyl)-2-oxo-pyrido[2,3-d]pyrimidin-1-yl]-2,2-dimethyl-propanenitrile | None | Step 1: 3-Amino-2,2-dimethylpropane-nitrile hydrochloride salt and DIPEA |
| 106-9 | 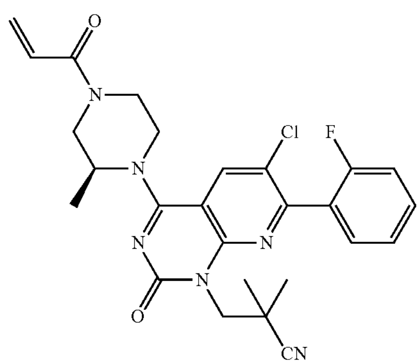 [SMILES: C=CC(=O)N1CCN(c2nc(=O)n(CC(C)(C)C#N)c3nc(-c4ccccc4F)c(Cl)cc23)[C@@H](C)C1] | 3-[6-Chloro-7-(2-fluorophenyl)-4-[(2S)-2-methyl-4-prop-2-enoyl-piperazin-1-yl]-2-oxo-pyrido[2,3-d]pyrimidin-1-yl]-2,2-dimethyl-propanenitrile | None | Step 1: 3-Amino-2,2-dimethylpropane-nitrile hydrochloride salt and DIPEA; Step 3: (3S)-1-(tert-Butoxycarbonyl)-3-methylpiperazine |
| 106-10 | 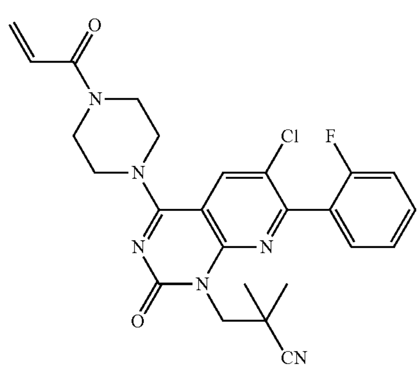 [SMILES: C=CC(=O)N1CCN(c2nc(=O)n(CC(C)(C)C#N)c3nc(-c4ccccc4F)c(Cl)cc23)CC1] | 3-[6-Chloro-7-(2-fluorophenyl)-2-oxo-4-(4-prop-2-enoylpiperazin-1-yl)pyrido[2,3-d]pyrimidin-1-yl]-2,2-dimethyl-propanenitrile | None | Step 1: 3-Amino-2,2-dimethylpropane-nitrile hydrochloride salt and DIPEA; Step 3: tert-butyl piperazine-1-carboxylate |

Method 107

Example 107-1: 4-((2S,5R)-4-Acryloyl-2,5-dimethylpiperazin-1-yl)-6-chloro-1-(4,6-diisopropyl-2-(methylamino)pyrimidin-5-yl)-7-(2-fluorophenyl)pyrido[2,3-d]pyrimidin-2(1H)-one

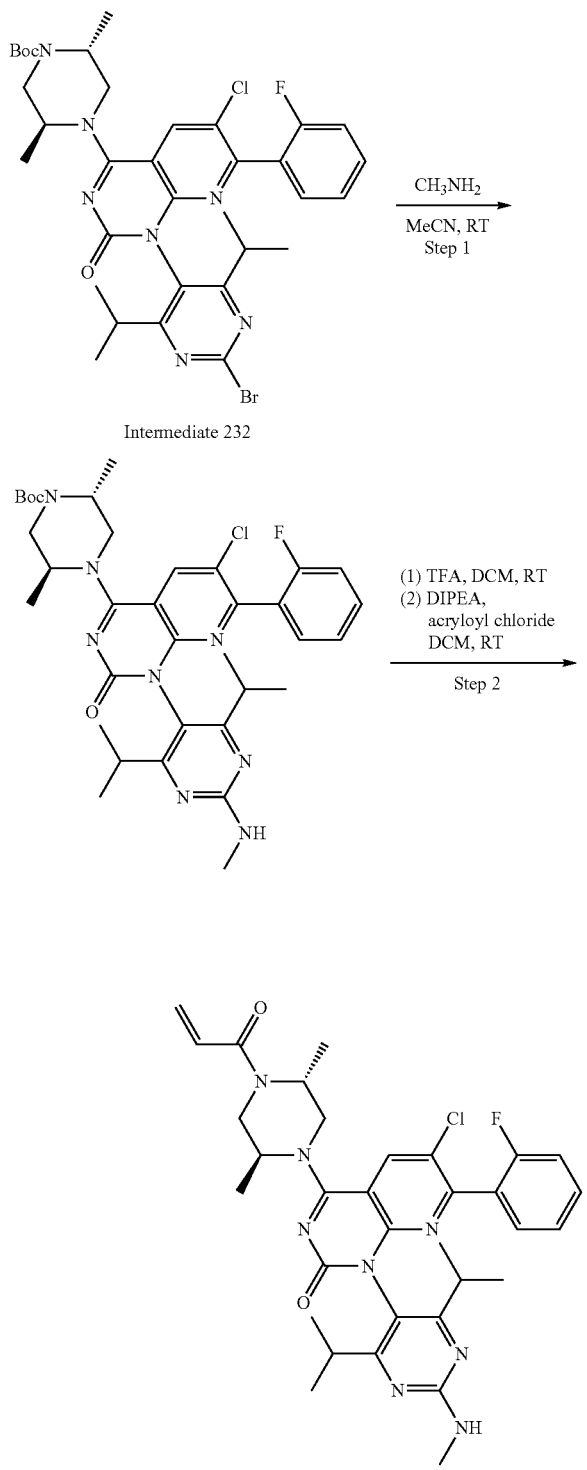

Step 1: tert-Butyl (2R,5S)-4-(6-chloro-1-(4,6-diisopropyl-2-(methylamino)pyrimidin-5-yl)-7-(2-fluorophenyl)-2-oxo-1,2-dihydropyrido[2,3-d]pyrimidin-4-yl)-2,5-dimethylpiperazine-1-carboxylate Methylamine (2.0 M in tetrahydrofuran, 0.312 mL, 0.624 mmol) was added to a stirred solution of tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (91 mg, 0.125 mmol, Intermediate 232) in acetonitrile (0.5 mL). The reaction mixture was stirred at room temperature for 9 h. The reaction mixture was concentrated in vacuo. The crude product was purified by silica gel chromatography (eluent 0-50% [(3:1) EtOAc/EtOH]/heptane) to provide tert-butyl (2R,5S)-4-(6-chloro-1-(4,6-diisopropyl-2-(methylamino)pyrimidin-5-yl)-7-(2-fluorophenyl)-2-oxo-,2-dihydropyrido[2,3-d]pyrimidin-4-yl)-2,5-methylpiperazine-1-carboxylate as a yellow solid (45 mg, 0.066 mmol, 53.1% yield). $^1$H NMR (400 MHz, CHLOROFORM-d) δ 8.13 (1H, s) 7.45-7.52 (1H, m) 7.21-7.29 (2H, m) 7.14-7.20 (1H, m) 3.53-5.12 (7H, m) 3.05 (3H, d, J=4.98 Hz) 2.49-2.61 (2H, m) 1.57 (9H, s) 1.44-1.54 (3H, m) 1.30-1.36 (3H, m) 1.21 (3H, dd, J=6.34, 4.25 Hz) 1.01 (6H, br t, J=7.26 Hz). m/z (ESI, +ve ion): 679.1 (M+H)$^+$.

Step 2: 4-((2S,5R)-4-Acryloyl-2,5-dimethylpiperazin-1-yl)-6-chloro-1-(4,6-diisopropyl-2-(methylamino)pyrimidin-5-y)-7-(2-fluorophenyl)pyrido[2,3-d]pyrimidin-2(1H)-one Trifluoroacetic acid (0.5 mL, 6.71 mmol) was added to a stirred solution of tert-butyl (2R,5S)-4-(6-chloro-1-(4,6-diisopropyl-2-(methylamino)pyrimidin-5-yl)-7-(2-fluorophenyl)-2-oxo-1,2-dihydropyrido[2,3-d]pyrimidin-4-yl)-2,5-dimethylpiperazine-1-carboxylate (45 mg, 0.066 mmol) in dichloromethane (1 mL). The reaction mixture was stirred at room temperature for 25 min. The reaction mixture was concentrated in vacuo to give crude 6-chloro-1-(4,6-diisopropyl-2-(methylamino)pyrimidin-5-yl)-4-((2S,5R)-2,5-dimethylpiperazin-1-yl)-7-(2-fluorophenyl)pyrido[2,3-d]pyrimidin-2(1H)-one that was used without purification assuming 100% yield.

Acryloyl chloride (1.1 M in DCM, 0.072 mL, 0.079 mmol) was added to a stirred mixture of the crude 6-chloro-1-(4,6-diisopropyl-2-(methylamino)pyrimidin-5-yl)-4-((2S,5R)-2,5-dimethylpiperazin-1-yl)-7-(2-fluorophenyl)pyrido[2,3-d]pyrimidin-2(1H)-one (38 mg, 0.066 mmol) and N,N-diisopropylethylamine (0.046 mL, 0.262 mmol) in dichloromethane (0.5 mL). The reaction mixture was stirred at room temperature for 1 h. The reaction mixture was diluted with DCM (40 mL) and washed with saturated aqueous NH$_4$Cl (30 mL). The organic layer was separated, dried over MgSO$_4$, filtered, and concentrated in vacuo. The crude product was purified by silica gel chromatography (eluent 0-50% [(3:1) EtOAc/EtOH]/heptane) to provide 4-((2S,5R)-4-acryloyl-2,5-dimethylpiperazin-1-yl)-6-chloro-1-(4,6-diisopropyl-2-(methylamino)pyrimidin-5-yl)-7-(2-fluorophenyl)pyrido[2,3-d]pyrimidin-2(1H)-one as a light yellow solid (33 mg, 0.052 mmol, 79% yield). $^1$H NMR (400 MHz, CHLOROFORM-d) δ 8.15 (1H, br s) 7.47-7.54 (1H, m) 7.16-7.29 (3H, m) 6.59-6.76 (1H, m) 6.42-6.51 (1H, m) 5.84-5.90 (1H, m) 3.53-5.24 (6H, m) 3.07 (3H, d, J=4.80 Hz) 2.50-2.63 (2H, m) 1.46-1.54 (3H, m) 1.32-1.42 (3H, m) 1.19-1.28 (6H, m) 0.98-1.09 (6H, m). m/z (ESI, +ve ion): 633.2 (M+H)$^+$.

TABLE 107

Compounds 107-2 to 107-5 were prepared following the procedure described in Method 107, Steps 1-2, abovt as follows:

| Ex. # | Chemical structure | Name | Method Changes | Reagent |
|---|---|---|---|---|
| 107-2 | 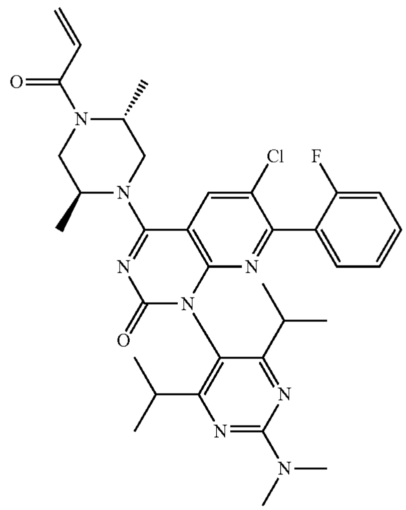 [SMILES: C=CC(=O)N1C[C@H](C)N(c2nc(=O)n(-c3c(C(C)C)nc(N(C)C)nc3C(C)C)c3nc(-c4ccccc4F)c(Cl)cc23)C[C@H]1C] | 6-Chloro-1-[2-(dimethylamino)-4,6-diisopropyl-pyrimidin-5-yl]-4-[(2S,5R)-2,5-dimethyl-4-prop-2-enoyl-piperazin-1-yl]-7-(2-fluorophenyl)pyrido[2,3-d]pyrimidin-2-one | Step 1: Performed at 40° C. | Step 1: dimethylamine, 2.0 M in THF (Sigma-Aldrich Corporation) |
| 107-3 | 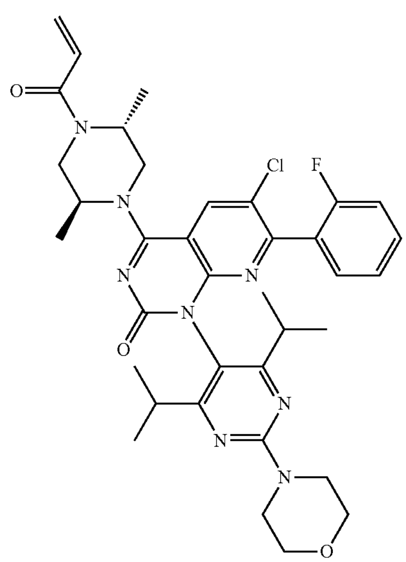 [SMILES: C=CC(=O)N1C[C@H](C)N(c2nc(=O)n(-c3c(C(C)C)nc(N4CCOCC4)nc3C(C)C)c3nc(-c4ccccc4F)c(Cl)cc23)C[C@H]1C] | 6-Chloro-1-(4,6-diisopropyl-2-morpholino-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one | None | Step 1: morpholine (Sigma-Aldrich Corporation) |

TABLE 107-continued

Compounds 107-2 to 107-5 were prepared following the procedure described in Method 107, Steps 1-2, abovt as follows:

| Ex. # | Chemical structure | Name | Method Changes | Reagent |
|---|---|---|---|---|
| 107-4 | 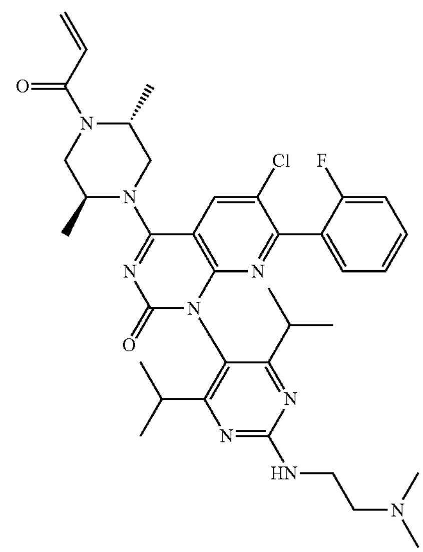 [SMILES: C=CC(=O)N1C[C@H](C)N(c2nc(=O)n(-c3c(C(C)C)nc(NCCN(C)C)nc3C(C)C)c3nc(-c4ccccc4F)c(Cl)cc23)C[C@H]1C] | 6-Chloro-1-[2-[2-(dimethylamino)ethylamino]-4,6-diisopropyl-pyrimidin-5-yl]-4-[(2S,5R)-2,5-dimethyl-4-prop-2-enoyl-piperazin-1-yl]-7-(2-fluorophenyl)pyrido[2,3-d]pyrimidin-2-one | None | Step 1: N,N-dimethylethylene-diamine (Sigma-Aldrich Corporation) |
| 107-5 | 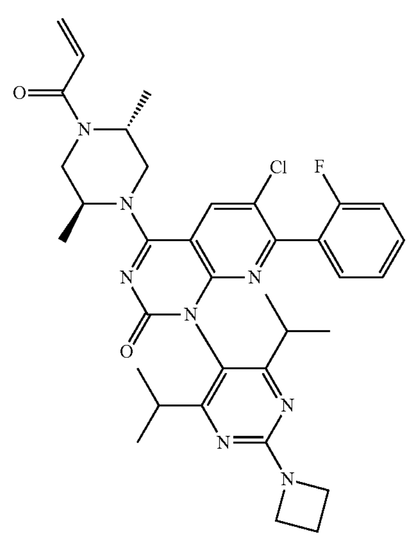 [SMILES: C=CC(=O)N1C[C@H](C)N(c2nc(=O)n(-c3c(C(C)C)nc(N4CCC4)nc3C(C)C)c3nc(-c4ccccc4F)c(Cl)cc23)C[C@H]1C] | 1-[2-(Azetidin-1-yl)-4,6-diisopropyl-pyrimidin-5-yl]-6-chloro-4-[(2S,5R)-2,5-dimethyl-4-prop-2-enoyl-piperazin-1-yl]-7-(2-fluorophenyl)pyrido[2,3-d]pyrimidin-2-one | None | Step 1: azetidine (Combi-Blocks Inc.) |

Method 108

Example 108-1: 4-((2S,5R)-4-Acryloyl-2,5-dimethylpiperazin-1-yl)-6-chloro-1-(4-cyclopropyl-6-isopropylpyrimidin-5-yl)-7-(2-fluorophenyl)pyrido[2,3-d]pyrimidin-2(1H)-one

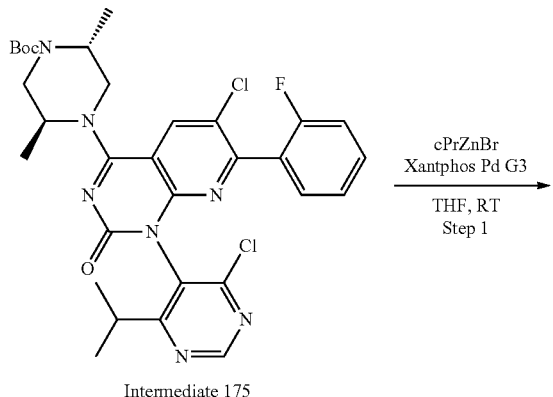

Intermediate 175

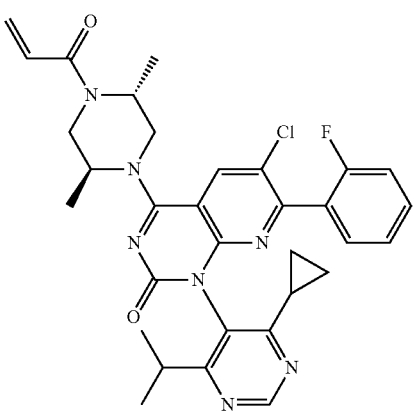

Step 1: tert-Butyl (2R,5S)-4-(6-chloro-1-(4-cyclopropyl-6-isopropylpyrimidin-5-yl)-7-(2-fluorophenyl)-2-oxo-1,2-dihydropyrido[2,3-d]pyrimidin-4-yl)-2,5-dimethylpiperazine-1-carboxylate Cyclopropylzinc bromide (0.5 M in THF, 3.819 mL, 1.910 mmol) was added to a flask charged with tert-butyl (2R,5S)-4-(6-chloro-1-(4-chloro-1-isopropylpyrimidin-5-yl)-7-(2-fluorophenyl)-2-oxo-1,2-dihydropyrido[2,3-d]pyrimidin-4-yl)-2,5-dimethylpiperazine-1-carboxylate (409 mg, 0.637 mmol, Intermediate 175) and Xantphos Pd G3 (60.4 mg, 0.064 mmol) under an argon atmosphere. The reaction mixture was stirred at room temperature for 2 h. The reaction mixture was quenched with saturated aqueous $NH_4Cl$ (75 mL) and extracted with EtOAc (125 ml). The organic layer was separated, washed with saturated aqueous sodium chloride (75 mL), dried over $MgSO_4$, filtered, and concentrated in vacuo. The crude product was purified by silica gel chromatography (eluent 0-50% [(3:1) EtOAc/EtOH]/heptane) to provide tert-butyl (2R,5S)-4-(6-chloro-1-(4-cyclopropyl-6-isopropylpyrimidin-5-yl)-7-(2-fluorophenyl)-2-oxo-1,2-dihydropyrido[2,3-d]pyrimidin-4-yl)-2,5-dimethylpiperazine-1-carboxylate as an off-white solid (297 mg, 0.458 mmol, 72.0% yield). $^1$H NMR (400 MHz, CHLOROFORM-d) δ 8.96 (1H, s) 8.10-8.14 (1H, m) 7.40-7.47 (1H, m) 7.09-7.25 (3H, m) 3.45-5.09 (6H, m) 2.71-2.81 (1H, m) 1.42-1.60 (13H, m) 1.22-1.32 (6H, m) 1.02-1.14 (4H, m) 0.91-1.00 (1H, m) 0.78-0.86 (1H, m). m/z (ESI, +ve ion): 648.0 $(M+H)^+$.

Step 2: 4-((2S,5R)-4-Acryloyl-2,5-dimethylpiperazin-1-yl)-6-chloro-1-(4-cyclopropyl-6-isopropylpyrimidin-5-yl)-7-(2-fluorophenyl)pyrido[2,3-d]pyrimidin-2(1H)-one Trifluoroacetic acid (1.00 mL, 13.42 mmol) was added to a stirred solution of tert-butyl (2R,5S)-4-(6-chloro-1-(4-cyclopropyl-6-isopropylpyrimidin-5-yl)-7-(2-fluorophenyl)-2-oxo-1,2-dihydropyrido[2,3-d]pyrimidin-4-yl)-2,5-dimethylpiperazine-1-carboxylate (297 mg, 0.458 mmol) in dichloromethane (1 mL). The reaction mixture was stirred at room temperature for 40 min. The reaction mixture was concentrated in vacuo to give crude 6-chloro-1-(4-cyclopropyl-6-isopropylpyrimidin-5-yl)-4-((2S,5R)-2,5-dimethylpiperazin-1-yl)-7-(2-fluorophenyl)pyrido[2,3-d]pyrimidin-2(1H)-one that was used without purification assuming 100% yield.

Acryloyl chloride (1.1 M in DCM, 0.500 mL, 0.550 mmol) was added to a stirred mixture of the crude 6-chloro-1-(4-cyclopropyl-6-isopropylpyrimidin-5-yl)-4-((2S,5R)-2,5-dimethylpiperazin-1-yl)-7-(2-fluorophenyl)pyrido[2,3-d]pyrimidin-2(1H)-one (251 mg, 0.458 mmol) and N,N-diisopropylethylamine (0.400 mL, 2.290 mmol) in dichloromethane (2 mL). The reaction mixture was stirred at room temperature for 30 min. The reaction mixture was diluted with DCM (100 mL) and washed with saturated aqueous NaHCO3 (75 mL). The organic layer was separated, dried over MgSO4, filtered, and concentrated in vacuo. The crude product was purified by silica gel chromatography (eluent 0-50% [(3:1) EtOAc/EtOH]/heptane) to provide 4-((2S,5R)-4-acryloyl-2,5-dimethylpiperazin-1-yl)-6-chloro-1-(4-cyclopropyl-6-isopropylpyrimidin-5-yl)-7-(2-fluorophenyl)pyrido[2,3-d]pyrimidin-2(1H)-one as an off-white solid (220 mg, 0.183 mmol, 80% yield). $^1$H NMR (400 MHz, CHLOROFORM-d) δ 9.01-9.03 (1H, m) 8.16-8.19 (1H, m) 7.46-7.52 (1H, m) 7.14-7.30 (3H, m) 6.58-6.74 (1H, m) 6.46 (1H, br t, J=15.03 Hz) 5.83-5.89 (1H, m) 3.49-5.27 (6H, m) 2.75-2.86 (1H, m) 1.44-1.63 (5H, m) 1.27-1.41 (6H, m) 1.07-1.20 (4H, m) 0.96-1.06 (1H, m) 0.84-0.95 (1H, m). m/z (ESI, +ve ion): 602.0 $(M+H)^+$.

TABLE 108

Compound 108-2 was prepared following the procedure described in Method 108, Steps 1-2, above as follows:

| Ex. # | Chemical structure | Name | Method Changes | Reagent |
|---|---|---|---|---|
| 108-2 | 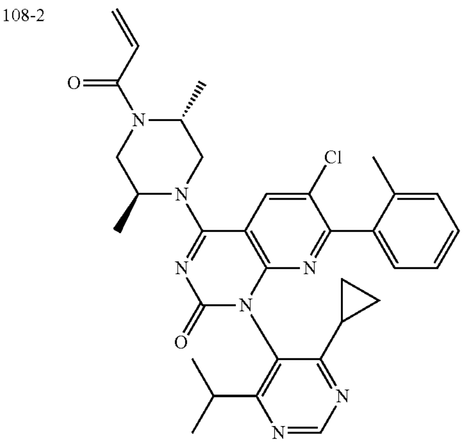 | 6-Chloro-1-(4-cyclopropyl-6-isopropyl-pyrimidin-5-yl)-4-[(2S,5R)-2,5-dimethyl-4-prop-2-enoyl-piperazin-1-yl]-7-(o-tolyl)pyrido[2,3-d]pyrimidin-2-one | None | Step 1: Intermediate 176 |

Method 109

Example 109-1: 4-((2S,5R)-4-Acryloyl-2,5-dimethylpiperazin-1-yl)-6-chloro-1-(4-ethyl-6-isopropylpyrimidin-5-yl)-7-(2-fluorophenyl)pyrido[2,3-d]pyrimidin-2(1H)-one

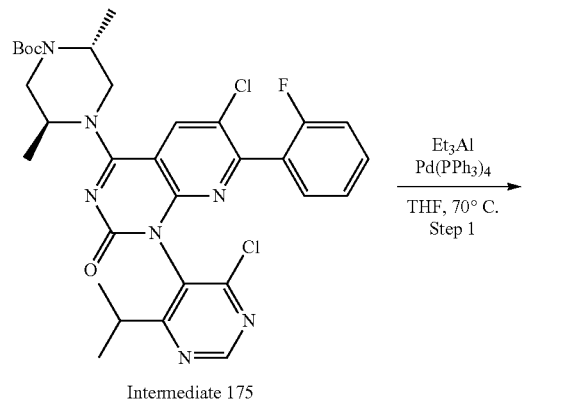

Intermediate 175

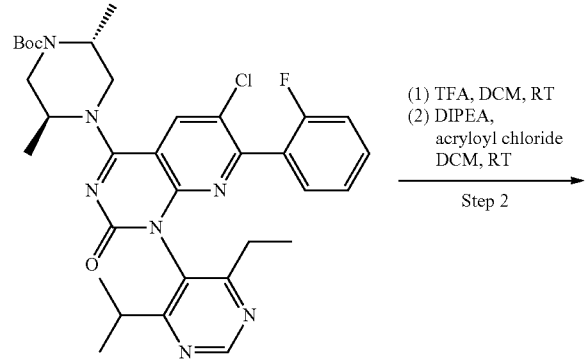

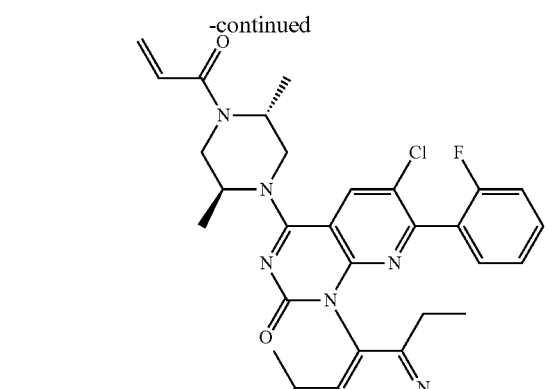

Step 1: tert-Butyl (2R,5S)-4-(6-chloro-1-(4-ethyl-6-isopropylpyrimidin-5-yl)-7-(2-fluorophenyl)-2-oxo-1,2-dihydropyrido[2,3-d]pyrimidin-4-yl)-2,5-dimethylpiperazine-1-carboxylate Triethylaluminum (1.0 M in heptane, 0.934 mL, 0.934 mmol) was added to a stirred mixture of tert-butyl (2R,5S)-4-(6-chloro-1-(4-chloro-6-isopropylpyrimidin-5-yl)-7-(2-fluorophenyl)-2-oxo-1,2-dihydropyrido[2,3-d]pyrimidin-4-yl)-2,5-dimethylpiperazine-1-carboxylate (400 mg, 0.623 mmol, Intermediate 175) and tetrakis(triphenylphosphine)palladium (71.9 mg, 0.062 mmol) in tetrahydrofuran (3 mL) under an argon atmosphere. The reaction mixture was stirred at 70° C. for 22 h. The reaction mixture was quenched with saturated aqueous $NaHCO_3$ (50 mL) and extracted with EtOAc (75 mL). The organic layer was separated, washed with saturated aqueous sodium chloride (50 mL), dried over $MgSO_4$, filtered, and concentrated in vacuo to provide crude tert-butyl (2R,5S)-4-(6-chloro-1-(4-ethyl-6-isopropylpyrimidin-5-yl)-7-(2-fluorophenyl)-2-oxo-1,2-dihydropyrido

[2,3-d]pyrimidin-4-yl)-2,5-dimethylpiperazine-1-carboxylate as a brown solid. m/z (ESI, +ve ion): 636.1 (M+H)⁺. The crude product contained a large amount of the des-Boc product and was used without purification assuming 100% yield.

Step 2: 4-((2S,5R)-4-Acryloyl-2,5-dimethylpiperazin-1-yl)-6-chloro-1-(4-ethyl-6-isopropylpyrimidin-5-yl)-7-(2-fluorophenyl)pyrido[2,3-d]pyrimidin-2(1H)-one Trifluoroacetic acid (2 mL, 26.8 mmol) was added to a stirred solution of the crude tert-butyl (2R,5S)-4-(6-chloro-1-(4-ethyl-6-isopropylpyrimidin-5-yl)-7-(2-fluorophenyl)-2-oxo-1,2-dihydropyrido[2,3-d]pyrimidin-4-yl)-2,5-dimethylpiperazine-1-carboxylate (396 mg, 0.622 mmol) in dichloromethane (2 mL). The reaction mixture was stirred at room temperature for 25 min. The reaction mixture was concentrated in vacuo to provide crude 6-chloro-4-((2S,5R)-2,5-dimethylpiperazin-1-yl)-1-(4-ethyl-6-isopropylpyrimidin-5-yl)-7-(2-fluorophenyl)pyrido[2,3-d]pyrimidin-2(1H)-one (124607-19-1) that was used without purification assuming 100% yield.

Acryloyl chloride (1.1 M in DCM, 0.680 mL, 0.748 mmol) was added to a stirred mixture of the crude 6-chloro-4-((2S,5R)-2,5-dimethylpiperazin-1-yl)-1-(4-ethyl-6-isopropylpyrimidin-5-yl)-7-(2-fluorophenyl)pyrido[2,3-d]pyrimidin-2(1H)-one (334 mg, 0.623 mmol) and N,N-diisopropylethylamine (0.544 mL, 3.12 mmol) in dichloromethane (2 mL). The reaction mixture was stirred at room temperature for 30 min. The reaction mixture was diluted with DCM (75 mL) and washed with saturated aqueous NH₄Cl (50 mL). The organic layer was separated, dried over MgSO₄, filtered, and concentrated in vacuo. The crude product was purified by silica gel chromatography (eluent 0-70% [(3:1) EtOAc/EtOH]/heptane) to provide 4-((2S,5R)-4-acryloyl-2,5-dimethylpiperazin-1-yl)-6-chloro-1-(4-ethyl-6-isopropylpyrimidin-5-yl)-7-(2-fluorophenyl)pyrido[2,3-d]pyrimidin-2(1H)-one as a light yellow solid (231 mg, 0.196 mmol, 62.8% yield). ¹H NMR (400 MHz, CHLOROFORM-d) δ 9.11 (1H, s) 8.10-8.14 (1H, m) 7.40-7.47 (1H, m) 7.08-7.20 (3H, m) 6.51-6.70 (1H, m) 6.41 (1H, br t, J=14.93 Hz) 5.77-5.85 (1H, m) 3.44-5.21 (6H, m) 2.65-2.77 (1H, m) 2.48-2.59 (1H, m) 2.36-2.49 (1H, m) 1.40-1.52 (4H, m) 1.30-1.36 (2H, m) 1.14-1.28 (6H, m) 1.02-1.09 (3H, m). m/z (ESI, +ve ion): 590.2 (M+H)⁺.

TABLE 109

Compound 109-2 was prepared following the procedure described in Method 109, Steps 1-2, above as follows:

| Ex. # | Chemical structure | Name | Method Changes | Reagent |
|---|---|---|---|---|
| 109-2 | 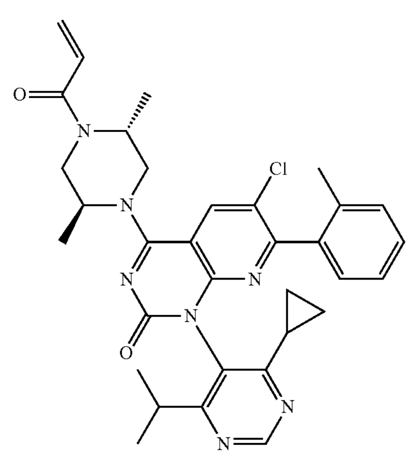 [SMILES: C=CC(=O)N1C[C@H](C)N(c2nc(=O)n(-c3c(C(C)C)ncnc3C3CC3)c3nc(-c4ccccc4C)c(Cl)cc23)C[C@H]1C] | 6-Chloro-4-[(2S,5R)-2,5-dimethyl-4-prop-2-enoyl-piperazin-1-yl]-1-(4-ethyl-6-isopropyl-pyrimidin-5-yl)-7-(o-tolyl)pyrido[2,3-d]pyrimidin-2-one | None | Step 1: Intermediate 176 |

Method 110

Example 110-1: 4-((2S,5R)-4-Acryloyl-2,5-dimethylpiperazin-1-yl)-6-chloro-7-(2-fluorophenyl)-1-neopentylpyrido[2,3-d]pyrimidin-2(1H)-one

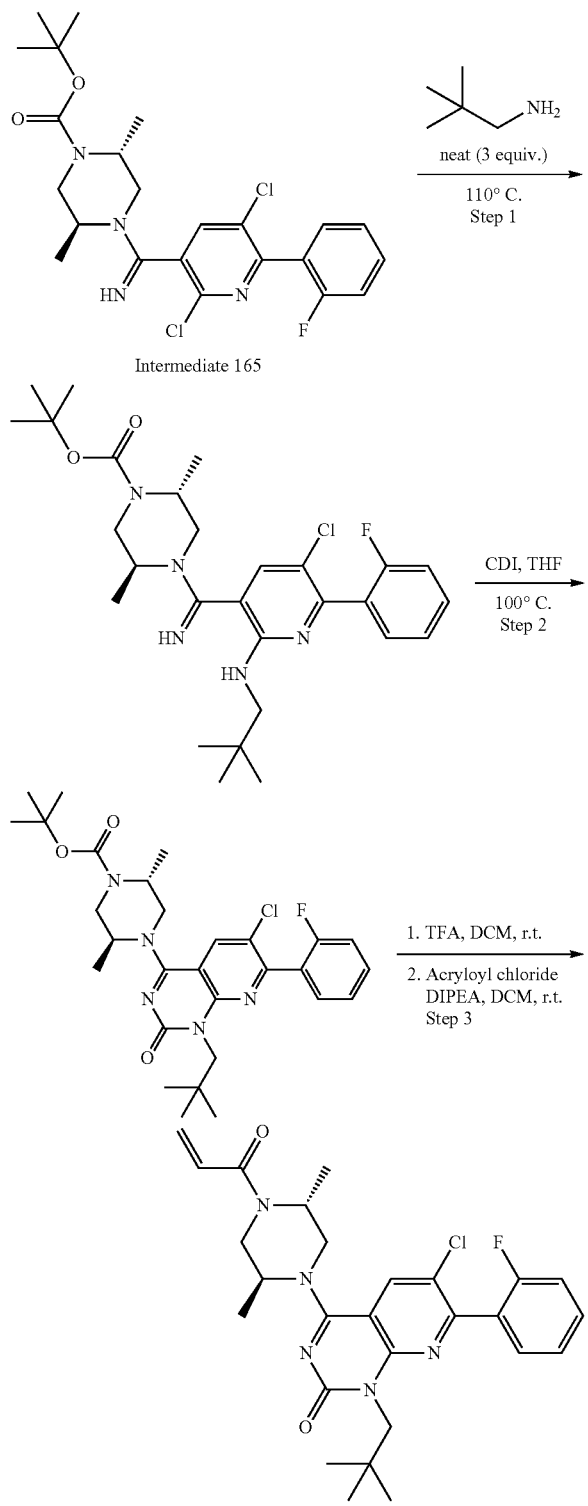

Step 1: tert-Butyl (2R,5S)-4-((5-chloro-6-(2-fluorophenyl)-2-(neopentylamino)pyridin-3-yl)(imino)methyl)-2,5-dimethylpiperazine-1-carboxylate A mixture of tert-butyl (2R,5S)-4-((2,5-dichloro-6-(2-fluorophenyl)pyridin-3-yl)(imino)methyl)-2,5-dimethylpiperazine-1-carboxylate (Intermediate 165, 1.30 g, 2.70 mmol) and neopentylamine (1.27 mL, 10.80 mmol) was heated at 110° C. for 3 days. The reaction mixture was purified on silica gel chromatography using 0-5% MeOH in DCM to afford tert-butyl (2R,5S)-4-((5-chloro-6-(2-fluorophenyl)-2-(neopentylamino)pyridin-3-yl)(imino)methyl)-2,5-dimethylpiperazine-1-carboxylate (1.10 g, 2.07 mmol, 77.0% yield). m/z (ESI, +ve ion): 532.3 (M+H)$^+$.

Step 2: tert-Butyl (2R,5S)-4-(6-chloro-7-(2-fluorophenyl)-1-neopentyl-2-oxo-1,2-dihydropyrido[2,3-d]pyrimidin-4-yl)-2,5-dimethylpiperazine-1-carboxylate A solution of tert-butyl (2R,5S)-4-((5-chloro-6-(2-fluorophenyl)-2-(neopentylamino)pyridin-3-yl)(imino)methyl)-2,5-dimethylpiperazine-1-carboxylate (0.065 g, 0.122 mmol) and 1,1'-carbonyldiimidazole (0.040 g, 0.244 mmol) in THF (1.0 mL) was stirred at 100° C. for 2 hours. The reaction was concentrated and residue purified on silica gel chromatography using 0-60% EtOAc/EtOH (3:1) in heptane to afford tert-butyl (2R,5S)-4-(6-chloro-7-(2-fluorophenyl)-1-neopentyl-2-oxo-1,2-dihydropyrido[2,3-d]pyrimidin-4-yl)-2,5-dimethylpiperazine-1-carboxylate (0.064 g, 0.115 mmol, 94% yield). m/z (ESI, +ve ion): 558.4 (M+H)$^+$.

Step 3: 4-((2S,5R)-4Acryloyl-2,5-dimethylpiperazin-1-yl)-6-chloro-7-(2-fluorophenyl)-1-neopentylpyrido[2,3-d]pyrimidin-2(1H)-one TFA (0.160 mL, 2.150 mmol) was added to a solution of tert-butyl (2R,5S)-4-(6-chloro-7-(2-fluorophenyl)-1-neopentyl-2-oxo-1,2-dihydropyrido[2,3-d]pyrimidin-4-yl)-2,5-dimethylpiperazine-1-carboxylate (0.060 g, 0.108 mmol) in DCM (4 mL). The resulting mixture was stirred at r.t. for 1 h and then concentrated under reduced pressure. The residue was suspended in DCM (4 mL), cooled to 0° C., and treated with DIPEA (0.056 mL, 0.323 mmol) followed by acryloyl chloride (0.013 mL, 0.161 mmol). The reaction was warmed to r.t. and stirred for 10 min. The mixture was quenched with sat'd aqueous NaHCO$_3$ and extracted with DCM (2×). The combined organic layers were concentrated and the residue purified on silica gel using 0-50% EtOAc/EtOH (3:1) in heptane to provide 4-((2S,5R)-4-acryloyl-2,5-dimethylpiperazin-1-yl)-6-chloro-7-(2-fluorophenyl)-1-neopentylpyrido[2,3-d]pyrimidin-2(1H)-one (0.048 g, 0.094 mmol, 87% yield). $^1$H NMR (400 MHz, DMSO-d6) δ 8.33 (s, 1H), 7.53-7.65 (m, 2H), 7.37-7.46 (m, 2H), 6.76-6.87 (m, 1H), 6.09-6.25 (m, 1H), 5.76 (s, 1H), 4.37-4.88 (m, 2H), 4.19-4.30 (m, 1H), 4.03-4.18 (m, 2H), 3.72-3.93 (m, 2H), 3.45 (br d, J=12.02 Hz, 1H), 1.23-1.31 (m, 3H), 1.08-1.21 (m, 3H), 0.88 (s, 9H). $^{19}$F NMR (376 MHz, DMSO-d6) δ 113.60 (s, 1F). m/z (ESI, +ve ion): 512.3 (M+H)$^+$.

TABLE 110

Compound 110-2 was prepared following the procedure described in Method 110, Steps 1-3, above as follows:

| Ex. # | Chemical structure | Name | Method Changes | Reagent |
|---|---|---|---|---|
| 110-2 | 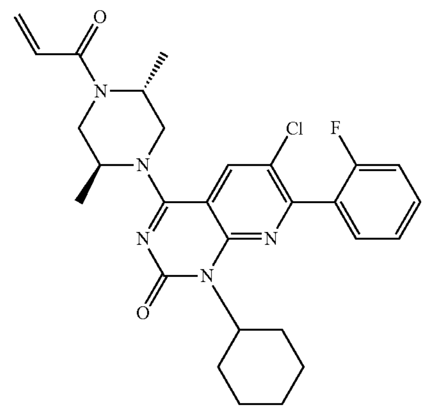 [SMILES: C=CC(=O)N1C[C@H](C)N(c2nc(=O)n(C3CCCCC3)c3nc(-c4ccccc4F)c(Cl)cc23)C[C@H]1C] | 6-Chloro-1-cyclohexyl-4-[(2S,5R)-2,5-dimethyl-4-prop-2-enoyl-piperazin-1-yl]-7-(2-fluorophenyl)pyrido[2,3-d]pyrimidin-2-one | None | 1-amino cyclohexane |

Method 119

Example 119-1: 4-((2S,5R)-4(But-2-ynoyl)-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one

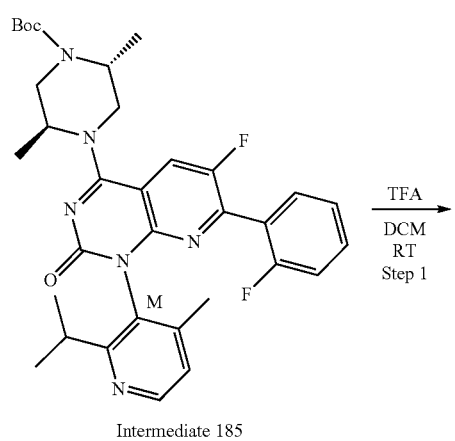

Intermediate 185

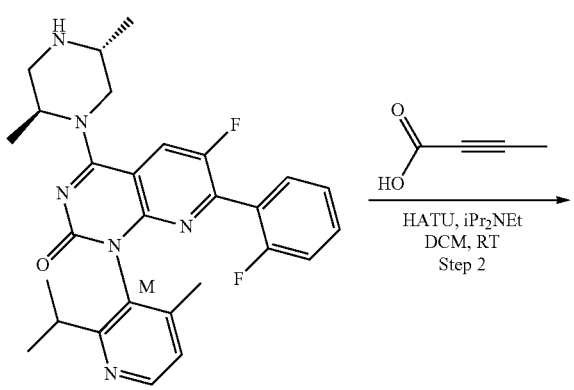

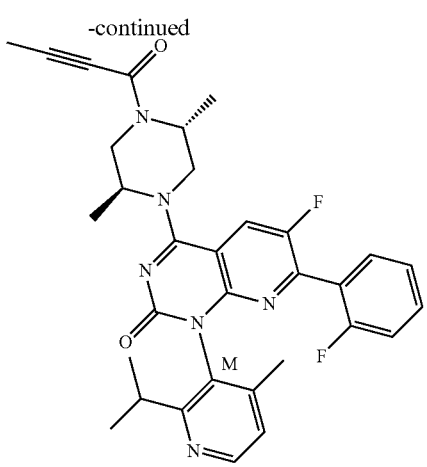

Steps 1&2. 4-((2S,5R)-4-(But-2-ynoyl)-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one 4-((2S,5R)-4-(But-2-ynoyl)-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one. To tert-butyl (2R,5S)-4-(6-fluoro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 185, 0.12 g, 0.2 mmol) dissolved in dichloromethane (0.9 mL) was added trifluoroacetic acid (0.3 mL, 4.0 mmol). The reaction mixture was stirred at RT for 30 min. The solvent was removed in vacuo and to the residue was added DCM (1 mL), 1,1'-dimethyltriethylamine (0.13 mL, 0.73 mmol), [(dimethylamino)(([1,2,3]triazolo[4,5-b]pyridin-3-yloxy))methylidene]dimethylazanium hexafluorophosphate (0.12 mL, 0.30 mmol), and 2-butynoic acid (20 mg, 0.24 mmol). The reaction mixture was stirred at RT for 3 h. The reaction mixture was partitioned between DCM and brine. The aqueous layer was extracted with DCM (2×). The organic layer was dried over anhydrous sodium sulfate, filtered and concentrated. The crude material was purified by chromatography through an ISCO 12 Gold column, eluting with a gradient of 0% to 45% 3:1 EtOAc/EtOH in heptane, to provide 4-((2S,5S)-4-(but-2-ynoyl)-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one (44 mg, 0.077 mmol, 38% yield) as off-white solid, m/z (ESI, +ve ion): 571.3 (M+H)$^+$. $^1$H NMR (400 MHz, CHLOROFORM-d) δ 8.57 (d, J=4.98 Hz, 1H), 7.84 (dd, J=4.15, 8.91 Hz, 1H), 7.40-7.51 (m, 1H), 7.27-7.30 (m, 1H), 7.08-7.23 (m, 3H), 4.79-5.12 (m, 2H), 4.06-4.41 (m, 2H), 3.41-3.92 (m, 2H), 2.76 (dt, J=5.08, 6.58 Hz, 1H), 2.08-2.10 (m, 3H), 2.04-2.06 (m, 3H), 1.42 (t, J=7.26 Hz, 3H), 1.24-1.3 (m, 6H), 1.11 (dd, J=2.07, 6.84 Hz, 3H). $^{19}$F NMR (376 MHz, CHLOROFORM-d) δ −112.58 (dd, J=16.04, 40.31 Hz, 1F), −126.38 (br dd, J=26.44, 40.31 Hz, 1F).

TABLE 119

Compounds 119-2 was prepared following the procedure described in Method 119, Steps 1-2, above as follows:

| Ex. # | Chemical structure | Name | Method Changes | Reagent |
|---|---|---|---|---|
| 119-2 | 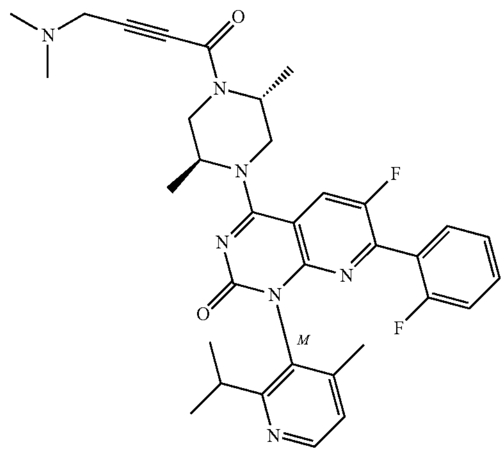 | 4-[(2S,5R)-4-[4-(Dimethylamino)but-2-ynoyl]-2,5-dimethyl-piperazin-1-yl]-6-fluoro-7-(2-fluorophenyl)-1-(2-isopropyl-4-methyl-3-pyridyl)pyrido[2,3-d]pyrimidin-2-one | No | Step 2: Intermediate 186 |

Method 121

Example 121-1: 4-((2S,5R)-4-Acryloyl-2,5-dimethylpiperazin-1-yl)-6-chloro-1-(6-((dimethylamino)methyl)-2-isopropyl-4-methylpyridin-3-yl)-7-(2-fluorophenyl)pyrido[2,3-d]pyrimidin-2(1H)-one

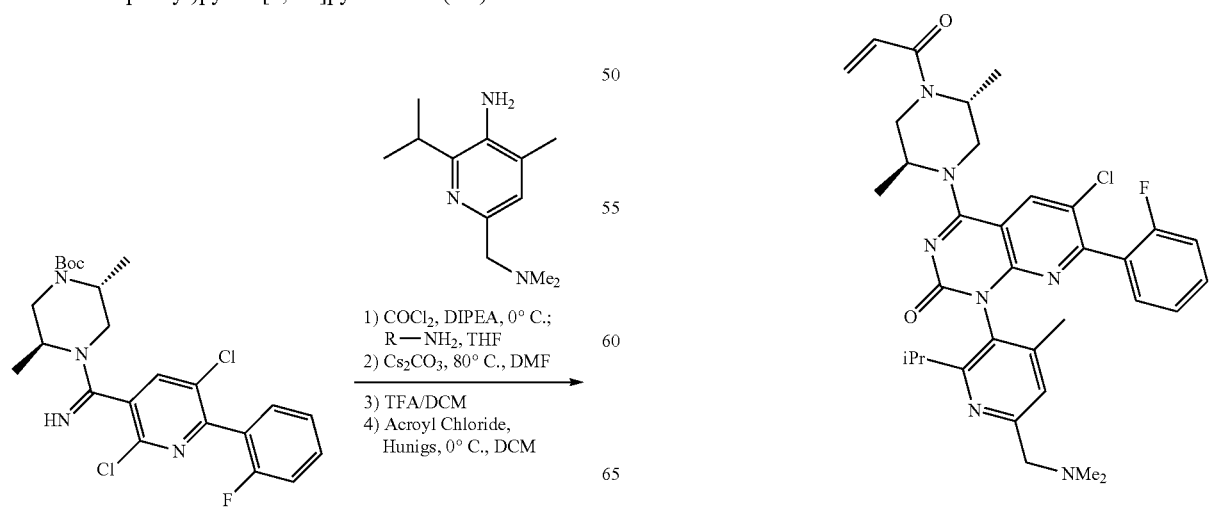

1) COCl$_2$, DIPEA, 0° C.; R—NH$_2$, THF
2) Cs$_2$CO$_3$, 80° C., DMF
3) TFA/DCM
4) Acroyl Chloride, Hunigs, 0° C., DCM -continued

Steps 1&2. tert-Butyl (2R,5S)-4-(6-chloro-1-(6-((dimethylamino)methyl)-2-isopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate To a solution of tert-butyl (2R,5S)-4-((2,5-dichloro-6-(2-fluorophenyl)pyridin-3-yl)(imino)methyl)-2,5-dimethylpiperazine-1-carboxylate (Intermediate 165, 460 mg, 0.96 mmol) and DIEA (350 μl, 2.01 mmol) in THF (2 mL) cooled to 0° C. was added phosgene solution, 15% in toluene (716 μl, 1.00 mmol) dropwise. This solution was stirred for 10 min followed by addition of a solution of 6-((dimethylamino)methyl)-2-isopropyl-4-methylpyridin-3-amine (Intermediate 187, 238 mg, 1.15 mmol) in THF (2 mL) at 0° C. The resulting mixture was stirred at it for 15 min.

The reaction mixture was partitioned between EtOAc and sat. NaHCO$_3$. The organic was dried over Na$_2$SO$_4$, concentrated then re-dissolved in DMF (4 mL) and treated with cesium carbonate (311 mg, 0.956 mmol). The reaction mixture was heated in a 80° C. oil bath for 30 min. The reaction mixture was then partitioned between EtOAc and brine, the organic was dried over Na$_2$SO$_4$, and concentrated under reduced pressure. The crude material was purified by chromatography through a Biotage pre-packed silica gel column (40S), eluting with a gradient of 0% to 100% 3:1 EtOAc/EtOH, then with 20% MeOH in DCM to give tert-butyl (2R,5S)-4-(6-chloro-1-(6-((dimethylamino)methyl)-2-isopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate (62 mg, 0.092 mmol, 9.6% yield) as off-white solid. m/z (ESI, +ve ion): 678.3 (M+H)$^+$.

Step 3&4. 4-((2S,5R)-4-Acryloyl-2,5-dimethylpiperazin-1-yl)-6-chloro-1-(6-((dimethylamino)methyl)-2-isopropyl-4-methylpyridin-3-yl)-7-(2-fluorophenyl)pyrido[2,3-d]pyrimidin-2(1H)-one A RBF was loaded with crude tert-butyl (2R,5S)-4-(6-chloro-1-(6-((dimethylamino)methyl)-2-isopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate (62 mg, 0.091 mmol) and dichloromethane (0.5 ml). Trifluoroacetic acid (136 μl, 1.83 mmol) was added dropwise. After stirring at rt 30 min, the reaction mixture was concentrated in vacuo and the residue was re-dissolved in dichloromethane (0.5 ml). 1,1'-Dimethyltriethylamine (80 μl, 0.46 mmol) was added followed by dropwise addition of acryloyl chloride (100 μl, 0.11 mmol) at 0° C. The reaction was stirred at 0° C. for 30 min and the reaction mixture was purified using a RediSep Gold (12 g) column and an eluent gradient of 0-20% 5% 2N NH3 in MeOH/MeOH in DCM to give 4-((2S,5R)-4-acryloyl-2,5-dimethylpiperazin-1-yl)-6-chloro-1-(6-((dimethylamino)methyl)-2-isopropyl-4-methylpyridin-3-yl)-7-(2-fluorophenyl)pyrido[2,3-d]pyrimidin-2(1H)-one (9.5 mg, 16%) as white solid. m/z (ESI, +ve ion): 632.4 (M+H)$^+$. $^1$H NMR (400 MHz, CHLOROFORM-d) δ 8.15 (s, 1H), 7.79-8.04 (m, 1H), 7.40-7.49 (m, 1H), 7.08-7.22 (m, 3H), 6.32-6.72 (m, 2H), 5.72-5.94 (m, 1H), 4.96-5.19 (m, 1H), 4.56-4.76 (m, 1H), 3.58-4.49 (m, 4H), 3.09 (dq, J=4.35, 7.39 Hz, 1H), 2.76-3.01 (m, 6H), 2.16 (br s, 2H), 1.53-1.55 (m, 3H), 1.44-1.48 (m, 3H), 1.33 (br d, J=6.84 Hz, 6H), 1.14-1.21 (m, 3H), $^{19}$F NMR (376 MHz, CHLOROFORM-d) δ −112.77 (br dd, J=7.37, 11.70 Hz, 1F).

TABLE 121

Compounds 121-2 to 121-4 were prepared following the procedure described in Method 121, Steps 1-4, above as follows:

| Ex. # | Chemical structure | Name | Method Changes | Reagent |
|---|---|---|---|---|
| 121-2 | 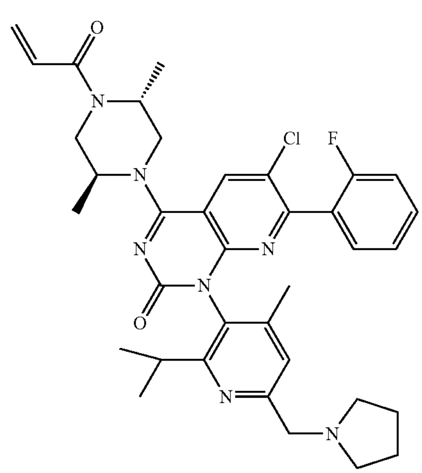 [SMILES: C=CC(=O)N1C[C@H](C)N(c2nc(=O)n(-c3c(C)cc(CN4CCCC4)nc3C(C)C)c3nc(-c4ccccc4F)c(Cl)cc23)C[C@H]1C] | 6-Chloro-4-[(2S,5R)-2,5-dimethyl-4-prop-2-enoyl-piperazin-1-yl]-7-(2-fluorophenyl)-1-[2-isopropyl-4-methyl-6-(pyrrolidin-1-ylmethyl)-3-pyridyl]pyrido[2,3-d]pyrimidin-2-one | No | Step 1: Intermediate 188 |

TABLE 121-continued

Compounds 121-2 to 121-4 were prepared following the procedure described in Method 121, Steps 1-4, above as follows:

| Ex. # | Chemical structure | Name | Method Changes | Reagent |
|---|---|---|---|---|
| 121-3 | 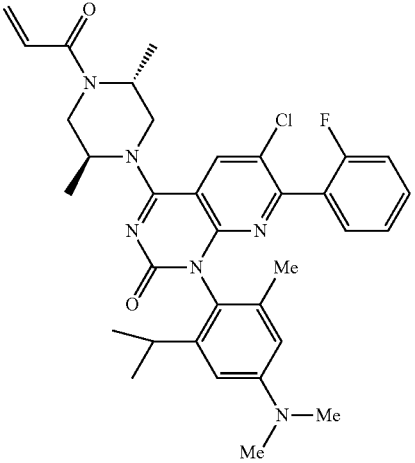 Single Isomer | 6-Chloro-1-[4-[(dimethylamino)methyl]-2-isopropyl-6-methyl-phenyl]-4-[(2S,5R)-2,5-dimethyl-4-prop-2-enoyl-piperazin-1-yl]-7-(2-fluorophenyl)pyrido[2,3-d]pyrimidin-2-one | Step 2: tBuOK in toluene | Step 1: I-8 |
| 121-4 | 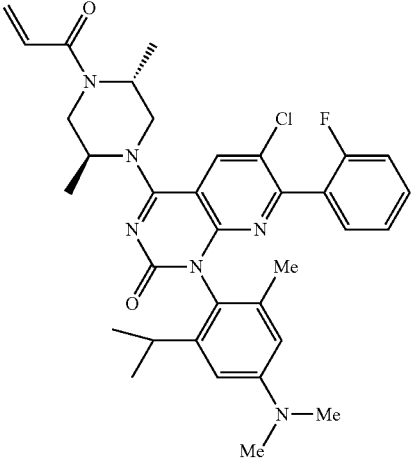 Single Isomer | 6-Chloro-1-[4-[(dimethylamino)methyl]-2-isopropyl-6-methyl-phenyl]-4-[(2S,5R)-2,5-dimethyl-4-prop-2-enoyl-piperazin-1-yl]-7-(2-fluorophenyl)pyrido[2,3-d]pyrimidin-2-one | Step 2: tBuOK in toluene | Step 1: I-8 |

Method 122

Example 122-1: N-(2-(4-((2S,5R)-4-Acryloyl-2,5-dimethylpiperazin-1-yl)-6-chloro-1-(4-(dimethylamino)-2-isopropylpyridin-3-yl)-2-oxo-1,2-dihydropyrido[2,3-d]pyrimidin-7-yl)-3-fluorophenyl)-2,2,2-trifluoroacetamide

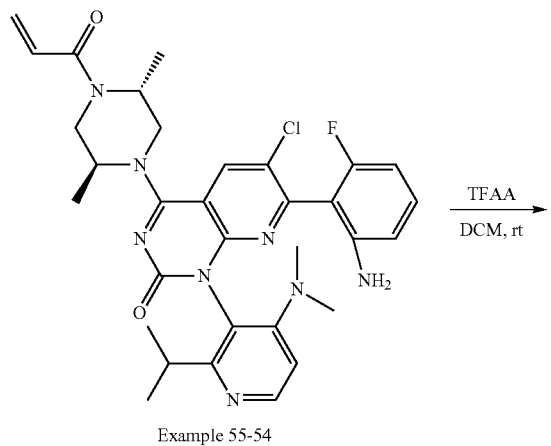

Example 55-54

TFAA
DCM, rt

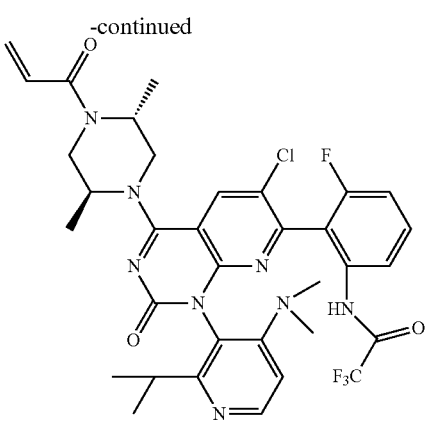

To a solution of 4-((2S,5R)-4-acryloyl-2,5-dimethylpiperazin-1-yl)-7-(2-amino-6-fluorophenyl)-6-chloro-1-(4-(dimethylamino)-2-isopropylpyridin-3-yl)pyrido[2,3-d]pyrimidin-2(1H)-one (0.050 g, 0.081 mmol, Example 55-54) in DCM (3 mL) was added trifluoroacetic anhydride (10.27 μl, 0.073 mmol) and the resulting mixture was stirred at rt for 15 min. The reaction went to completion, concentrated and purified by HPLC to afford N-(2-(4-((2S,5R)-4-acryloyl-2,5-dimethylpiperazin-1-yl)-6-chloro-1-(4-(dimethylamino)-2-isopropylpyridin-3-yl)-2-oxo-1,2-dihydropyrido[2,3-d]pyrimidin-7-yl)-3-fluorophenyl)-2,2,2-trifluoroacetamide (0.0432 g, 0.030 mmol, 37.4% yield) as a yellow solid. $^1$H NMR (400 MHz, DMSO-$d_6$) δ 8.59 (s, 1H), 8.07-8.18 (m, 1H), 7.59 (br dd, J=7.8, 6.5 Hz, 1H), 7.37 (br d, J=8.9 Hz, 1H), 7.17-7.30 (m, 1H), 6.84 (dt, J=16.7, 10.7 Hz, 1H), 6.57-6.72 (m, 1H), 6.19 (dd, J=16.5, 2.2 Hz, 1H), 5.74 (br d, J=2.3 Hz, 1H), 4.81-5.05 (m, 1H), 4.66-4.76 (m, 1H), 4.45-4.57 (m, 1H), 4.04-4.29 (m, 2H), 3.67-3.79 (m, 1H), 2.72 (s, 7H), 1.21-1.31 (m, 4H), 1.00-1.12 (m, 3H), 0.92 (br dd, J=6.6, 2.5 Hz, 3H), 0.78 (br d, J=6.6 Hz, 3H). m/z (ESI, +ve ion): 714.4 (M+H)$^+$.

TABLE 122

Compounds 122-2 to 122-3 were prepared following the procedure described in Method 122 above as follows:

| Ex. # | Chemical structure | Name | Method Changes | Reagent |
|---|---|---|---|---|
| 122-2 | 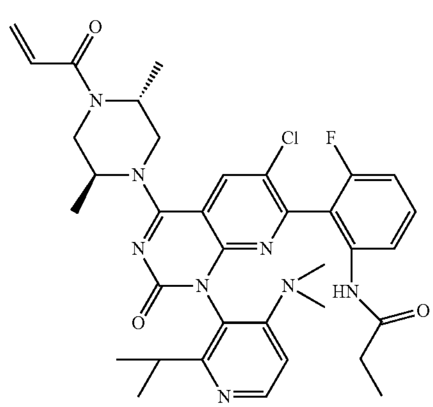 [SMILES: C=CC(=O)N1C[C@H](C)N(c2nc(=O)n(-c3c(N(C)C)ccnc3C(C)C)c3nc(-c4c(F)cccc4NC(=O)CC)c(Cl)cc23)C[C@H]1C] | N-[2-[6-Chloro-1-[4-(dimethylamino)-2-isopropyl-3-pyridyl]-4-[(2S,5R)-2,5-dimethyl-4-prop-2-enoyl-piperazin-1-yl]-2-oxo-pyrido[2,3-d]pyrimidin-7-yl]-3-fluorophenyl]propanamide | propionyl chloride was used in Step 1 | No change |

TABLE 122-continued

Compounds 122-2 to 122-3 were prepared following the procedure described in Method 122 above as follows:

| Ex. # | Chemical structure | Name | Method Changes | Reagent |
|---|---|---|---|---|
| 122-3 | 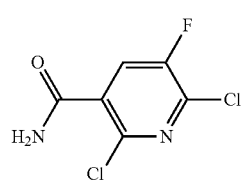 | N-[2-[6-Chloro-1-[4-(dimethylamino)-2-isopropyl-3-pyridyl]-4-[(2S,5R)-2,5-dimethyl-4-prop-2-enoyl-piperazin-1-yl]-2-oxo-pyrido[2,3-d]pyrimidin-7-yl]-3-fluoro-phenyl]cyclopropane-carboxamide | cyclopropane carbonyl chloride was used in Step 1 | No change |

Method 123

4-((3S,5R)-4-Acryloyl-3,5-dimethylpiperazin-1-yl)-1-(6-amino-2-isopropyl-4-methylpyridin-3-yl)-6-chloro-7-(2-fluoro-6-hydroxyphenyl)pyrido[2,3-d]pyrimidin-2(1H)-one 2,2,2-trifluoroacetate

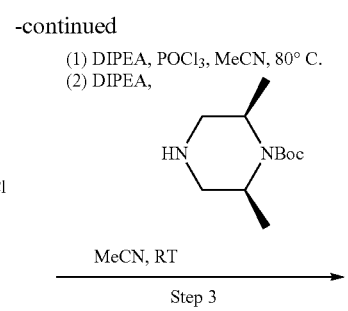

(1) DIPEA, POCl$_3$, MeCN, 80° C.
(2) DIPEA,

MeCN, RT
Step 3

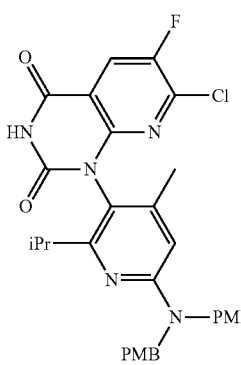

(1) (COCl)$_2$, THF, 60° C.
(2)

THF, RT
Step 1

Intermediate P

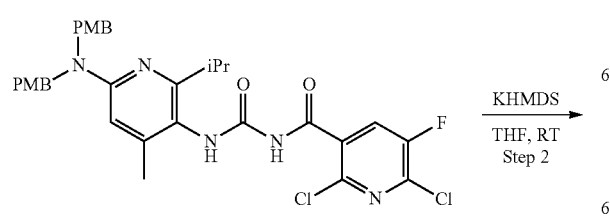

KHMDS
THF, RT
Step 2

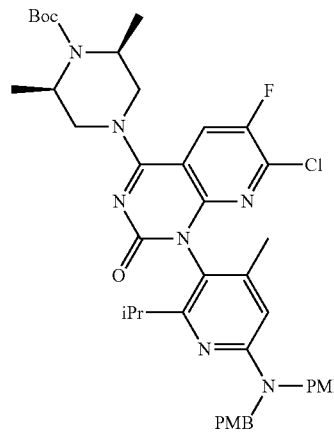

(1) TFA, DCM, RT
(2) NEt$_3$, acryloyl chloride DCM, 0° C.

Step 4

-continued

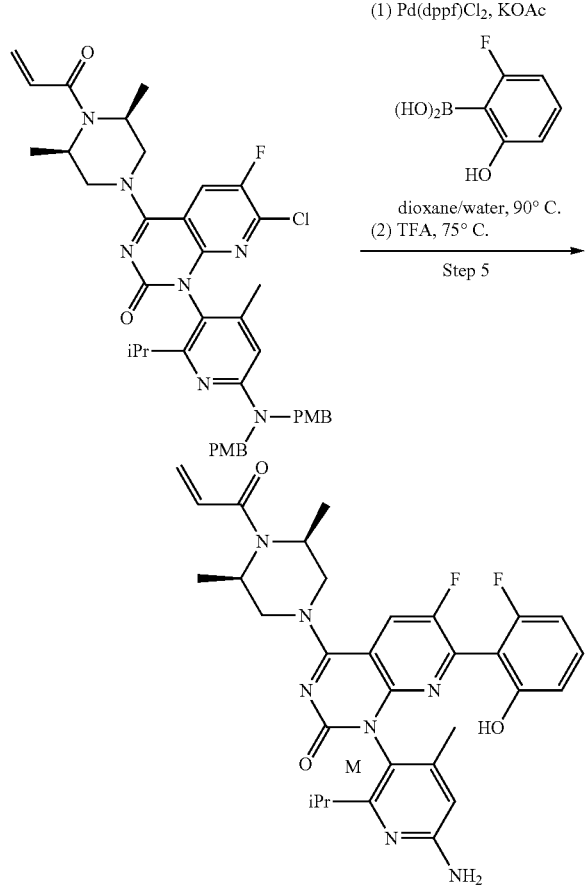

Step 1: N-((6-(bis(4-Methoxybenzyl)amino)-2-isopropyl-4-methylpyridin-3-yl)carbamoyl)-2,6-dichloro-5-fluoronicotinamide To a stirred solution of 2,6-dichloro-5-fluoronicotinamide (0.34 g, 1.62 mmol, Intermediate P) in tetrahydrofuran (5.4 ml) was added oxalyl chloride (2M in DCM) (0.97 ml, 1.94 mmol) dropwise. The reaction mixture was heated to 70° C. for 1 h, cooled to rt, concentrated in vacuo, then redissolved in 5 mL acetonitrile. To this was added a stirred solution of 6-isopropyl-$N^2,N^2$-bis(4-methoxybenzyl)-4-methylpyridine-2,5-diamine (0.66 g, 1.62 mmol, Intermediate I-33) in 3 mL acetonitrile at 0° C. for 20 min at rt. The mixture was partitioned between EtOAc and 4:1 brine:water, backextracted with EtOAc (1x), dried over MgSO4, filtered, and concentrated to provide N-((6-(bis(4-methoxybenzyl)amino)-2-isopropyl-4-methylpyridin-3-yl)carbamoyl)-2,6-dichloro-5-fluoronicotinamide as a tan solid which was used without purification. m/z (ESI, +ve ion): 640.1 (M+H)$^+$.

Step 2: 1-(6-(bis(4-Methoxybenzyl)amino)-2-isopropyl-4-methylpyridin-3-yl)-7-chloro-6-fluoropyrido[2,3-d]pyrimidine-2,4(1H,3H)-dione To a stirred solution of N-((6-(bis(4-methoxybenzyl)amino)-2-isopropyl-4-methylpyridin-3-yl)carbamoyl)-2,6-dichloro-5-fluoronicotinamide (1.04 g, 1.62 mmol) in THF at 0° C. was added potassium bis(trimethylsilyl)amide (1M in THF) (4.06 ml, 4.06 mmol). The solution was warmed slowly to rt and stirred for 20 min, then the reaction was quenched with ammonium chloride (aq), and partitioned between EtOAc and brine. The aqueous was backextracted with EtOAc (2x) and the combined organics were dried over MgSO4, filtered, and concentrated. The crude was purified using silica gel chromatography (eluent: 0-40% 3:1 [EtOAc/EtOH] in heptane to provide 1-(6-(bis(4-methoxybenzyl)amino)-2-isopropyl-4-methylpyridin-3-yl)-7-chloro-6-fluoropyrido[2,3-d]pyrimidine-2,4(1H,3H)-dione (0.61 g, 1.01 mmol, 62% yield) as an off white solid. m/z (ESI, +ve ion): 604.6 (M+H)$^+$.

Step 3: tert-Butyl (2S,6R)-4-(1-(6-(bis(4-Methoxybenzyl)amino)-2-isopropyl-4-methylpyridin-3-yl)-7-chloro-6-fluoro-2-oxo-1,2-dihydropyrido[2,3-d]pyrimidin-4-yl)-2,6-dimethylpiperazine-1-carboxylate Phosphorous oxychloride (0.11 ml, 1.22 mmol) was added dropwise to a solution of 1-(6-(bis(4-methoxybenzyl)amino)-2-isopropyl-4-methylpyridin-3-yl)-7-chloro-6-fluoropyrido[2,3-d]pyrimidine-2,4(1H,3H)-dione (0.61 g, 1.01 mmol) and 1,1'-dimethyltriethylamine (0.23 ml, 1.32 mmol) in acetonitrile (1 ml). The mixture was heated to 80° C. for 1 h. The reaction mixture was cooled to 0° C. and N-ethyl-N-isopropylpropan-2-amine (0.53 ml, 3.0 mmol) was added followed by (2R,6S)-tert-butyl 2,6-dimethylpiperazine-1-carboxylate (0.228 ml, 1.064 mmol). This mixture was warmed to RT and stirred for 1 h then was partitioned between EtOAc/NaHCO$_3$(aq) and the resulting biphasic mixture was separated. The aqueous layer was back-extracted with EtOAc (2x) and the organic extracts were dried over MgSO4, filtered, and concentrated in vacuo. The crude material was purified via silica gel chromatography (eluent: 0-60% 3:1 [EtOAc:EtOH] in heptane to provide tert-butyl (2S,6R)-4-(1-(6-(bis(4-methoxybenzyl)amino)-2-isopropyl-4-methylpyridin-3-yl)-7-chloro-6-fluoro-2-oxo-1,2-dihydropyrido[2,3-d]pyrimidin-4-yl)-2,6-dimethylpiperazine-1-carboxylate (0.66 g, 0.83 mmol, 82% yield) as a white solid, containing residual impurities but which will be used as-is without further purification. m/z (ESI, +ve ion): 800.4 (M+H)$^+$.

Step 4: 4((3S,5R)-4-Acryloyl-3,5-dimethylpiperazin-1-yl)-1-(6-(bis(4-methoxybenzyl)amino)-2-isopropyl-4-methylpyridin-3-yl)-7-chloro-6-fluoropyrido[2,3-d]pyrimidin-2(1H)-one To a vial loaded with tert-butyl (2S,6R)-4-(1-(6-(bis(4-methoxybenzyl)amino)-2-isopropyl-4-methylpyridin-3-yl)-7-chloro-6-fluoro-2-oxo-1,2-dihydropyrido[2,3-d]pyrimidin-4-yl)-2,6-dimethylpiperazine-1-carboxylate (0.66 g, 0.83 mmol), was added dichloromethane (4.1 ml), and trifluoroacetic acid (1.2 ml, 16.5 mmol). After stirring at rt 1 h the reaction mixture was concentrated in vacuo, and the residue was re-dissolved in dichloromethane (4.1 ml) and triethylamine (0.58 ml, 4.1 mmol) followed by dropwise addition of acryloyl chloride (1.12 ml, 1.2 mmol). The reaction was stirred at rt for 30 min, was partitioned between EtOAc/NaHCO$_3$, washed with NaHCO$_3$ (2x), brine (1x), dried over MgSO4 then purified using silica gel chromatography (eluent: 0-60% 3:1 [EtOAc:EtOH] in heptane to provide 4-((3S,5R)-4-acryloyl-3,5-dimethylpiperazin-1-yl)-1-(6-(bis(4-methoxybenzyl)amino)-2-isopropyl-4-methylpyridin-3-yl)-7-chloro-6-fluoropyrido[2,3-d]pyrimidin-2(1H)-one (0.30 g, 0.39 mmol, 47% yield) as a white solid m/z (ESI, +ve ion): 754.0 (M+H)$^+$.

Step 5: 4-((3S,5R)-4-Acryloyl-3,5-dimethylpiperazin-1-yl)-1-(6-amino-2-isopropyl-4-methylpyridin-3-yl)-6-fluoro-7-(2-fluoro-6-hydroxyphenyl)pyrido[2,3-d]pyrimidin-2(1H)-one A vial was charged with 4-((3S,5R)-4-acryloyl-3,5-dimethylpiperazin-1-yl)-1-(6-(bis(4-methoxybenzyl)amino)-2-isopropyl-4-methylpyridin-3-yl)-7-chloro-6-fluoropyrido[2,3-d]pyrimidin-2(1H)-one (0.1 g, 0.13 mmol), potassium trifluoro(2-fluoro-6-hydroxyphenyl)borate (0.04 g, 0.16 mmol, Intermediate Q), dichloro[1,1'-bis(diphenylphosphino)ferrocene]palladium (ii) dichloromethane adduct (9.7 mg, 0.013 mmol), and potassium acetate (0.065 g, 0.66 mmol). The flask was evacuated and backfilled with N2 (3×) followed by addition of 1,4-dioxane (1 ml) and water (0.2 ml). The mixture was stirred at 90° C. for 18 h. The reaction mixture was cooled to rt, then filtered through a short plug of SiO2 (eluent: 3:1 EtOAc:EtOH). The filtrate was concentrated, redissolved in trifluoroacetic acid (290 μl, 4 mmol) and heated to 75° C. for 10 min, the solvent was concentrated in vacuo, the remaining residue was taken up with EtOAc, washed with NaHCO$_3$, dried over MgSO$_4$, adsorbed directly onto silica gel and purified via chromatography (eluent: 60% 3:1 [EtOAc/EtOH] in heptane followed by SFC purification to provide 4-((3S,5R)-4-acryloyl-3,5-dimethylpiperazin-1-yl)-1-(6-amino-2-isopropyl-4-methylpyridin-3-yl)-6-fluoro-7-(2-fluoro-6-hydroxyphenyl)pyrido[2,3-d]pyrimidin-2(1H)-. $^1$H NMR (CDCl3, 400 MHz): δ=9.79 (br s, 1H), 8.05 (d, J=9.7 Hz, 1H), 7.25-7.32 (m, 1H), 6.57-6.76 (m, 3H), 6.34-6.43 (m, 2H), 5.78 (dd, J=10.5, 1.8 Hz, 1H), 4.68 (br s, 2H), 4.50 (s, 2H), 4.29 (br d, J=13.5 Hz, 2H), 3.60 (br dd, J=13.5, 4.1 Hz, 2H), 2.56 (dt, J=13.3, 6.7 Hz, 1H), 1.90 (s, 3H), 1.46-1.61 (m, 6H), 1.14 (d, J=6.6 Hz, 3H), 0.97 (d, J=6.8 Hz, 3H). $^{19}$F NMR (CDCl3, 376 MHz): δ=−107.30 (d, J=82.4 Hz, 1F), −121.70 (d, J=83.2 Hz, 1F). m/z (ESI, +ve ion): 590.2 (M+H)$^+$.

TABLE 123

Compounds 123-2 to 123-6 were prepared following the procedure described in Method 123, Steps 1-5, above as follows:

| Ex. # | Chemical structure | Name | Method Changes | Reagent |
|---|---|---|---|---|
| 123-2 | 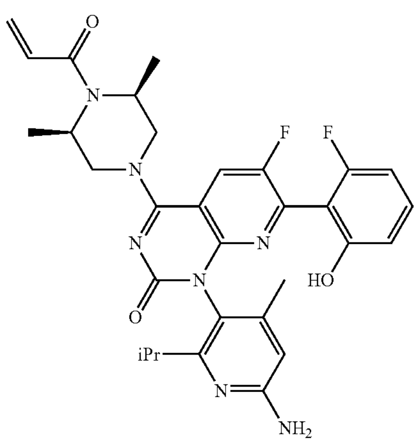 | 1-(6-Amino-2-isopropyl-4-methyl-3-pyridyl)-4-[(3S,5R)-3,5-dimethyl-4-prop-2-enoyl-piperazin-1-yl]-6-fluoro-7-(2-fluoro-6-hydroxy-phenyl)pyrido[2,3-d]pyrimidin-2-one Single Isomer (P) | None | Step 1: I-33 |
| 123-3 | 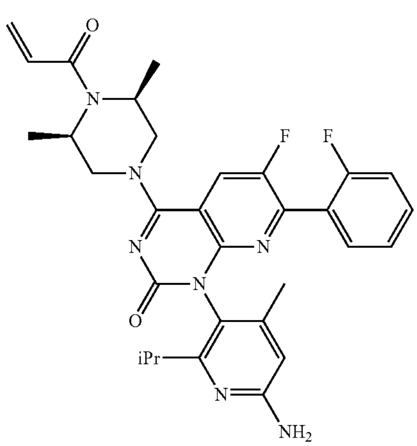 | 1-(6-Amino-2-isopropyl-4-methyl-3-pyridyl)-4-[(3S,5R)-3,5-dimethyl-4-prop-2-enoyl-piperazin-1-yl]-6-fluoro-7-(2-fluorophenyl)pyrido[2,3-d]pyrimidin-2-one Single Isomer (P) | None | Step 1: I-33 Step 3: (2R,6S)-tert-butyl 2,6-dimethyl-piperazine-1-carboxylate (ArkPharm) Step 5: (2-fluorophenyl)boranediol (Combi-Blocks) |

TABLE 123-continued

Compounds 123-2 to 123-6 were prepared following the procedure described
in Method 123, Steps 1-5, above as follows:

| Ex. # | Chemical structure | Name | Method Changes | Reagent |
|---|---|---|---|---|
| 123-4 | Single Isomer (M) | 1-(6-Amino-2-isopropyl-4-methyl-3-pyridyl)-4-[(3S,5R)-3,5-dimethyl-4-prop-2-enoyl-piperazin-1-yl]-6-fluoro-7-(2-fluorophenyl)pyrido[2,3-d]pyrimidin-2-one | None | Step 1: I-33 Step 3: (2R,6S)-tert-butyl 2,6-dimethyl-piperazine-1-carboxylate (ArkPharm) Step 5: (2-fluorophenyl)boranediol (Combi-Blocks) |
| 123-5 | Single Isomer (P) | 7-(2-Amino-6-fluoro-phenyl)-1-(6-amino-2-isopropyl-4-methyl-3-pyridyl)-4-[(3S,5R)-3,5-dimethyl-4-prop-2-enoyl-piperazin-1-yl]-6-fluoro-pyrido[2,3-d]pyrimidin-2-one | None | Step 1: I-33 Step 3: (2R,6S)-tert-butyl 2,6-dimethyl-piperazine-1-carboxylate (ArkPharm) Step 5: (2-amino-6-fluorophenyl)boronic acid pinacol ester (CombiPhos) |
| 123-6 | Single Isomer (M) | 7-(2-Amino-6-fluoro-phenyl)-1-(6-amino-2-isopropyl-4-methyl-3-pyridyl)-4-[(3S,5R)-3,5-dimethyl-4-prop-2-enoyl-piperazin-1-yl]-6-fluoro-pyrido[2,3-d]pyrimidin-2-one | None | Step 1: I-33 Step 3: (2R,6S)-tert-butyl 2,6-dimethyl-piperazine-1-carboxylate (ArkPharm) Step 5: (2-amino-6-fluorophenyl)boronic acid pinacol ester (CombiPhos) |

Method 124

Example 124-1: 6-Chloro-1-(2,4-diisopropyl-3-pyridyl)-4-[(2S,5R)-2,5-dimethyl-4-prop-2-enoyl-piperazin-1-yl]-7-(2-fluorophenyl)pyrido[2,3-d]pyrimidin-2-one

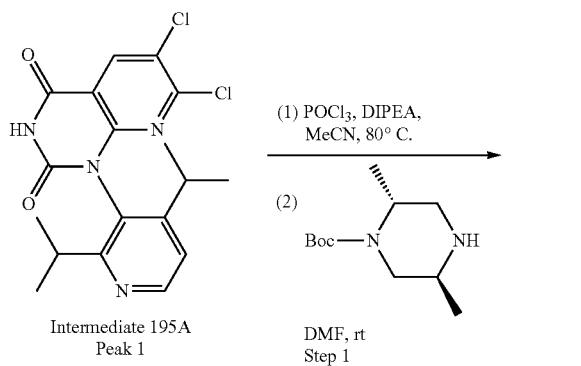

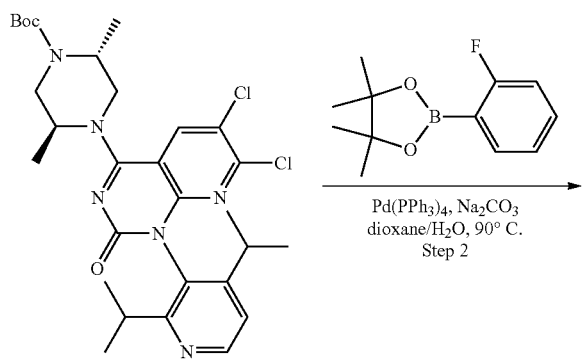

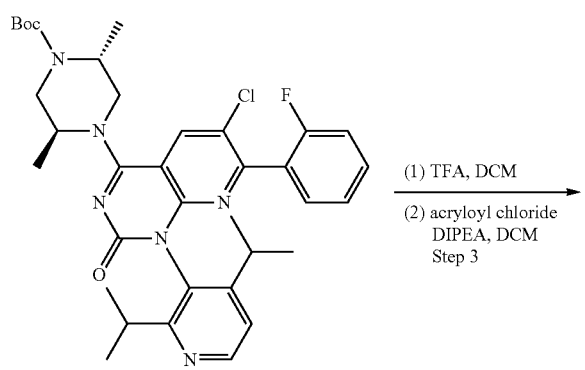

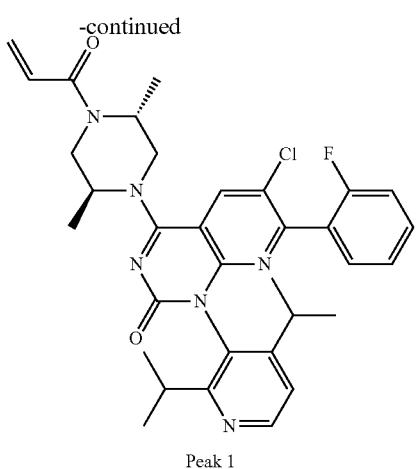

Peak 1

Step 1. tert-Butyl (2R,5S)-4-(6,7-dichloro-1-(2,4-diisopropylpyridin-3-yl)-2-oxo-1,2-dihydropyrido[2,3-d]pyrimidin-4-yl)-2,5-dimethylpiperazine-1-carboxylate Phosphorous oxychloride (0.016 mL, 0.168 mmol) was added dropwise to a solution of 6,7-dichloro-1-(2,4-diisopropylpyridin-3-yl)pyrido[2,3-d]pyrimidine-2,4(1H,3H)-dione (0.055 g, 0.140 mmol, Intermediate 195A) and 1,1'-dimethyltriethylamine (0.032 mL, 0.182 mmol) in $CH_3CN$ (20 mL) under N2. This mixture was then heated to 80° C. for 30 min. LCMS showed chlorination completed. The reaction mixture was cooled to 0° C. and 3 equiv DIPEA were added followed by (2R,5S)-tert-butyl 2,5-dimethylpiperazine-1-carboxylate (0.033 mL, 0.154 mmol, AstaTech). This mixture was stirred with warming to rt over 30 min at which time LCMS showed conversion to desired product. The mixture was poured into cold satd. $NaHCO_3$ solution and stirred vigorously for 10 min. The mixture was extracted with EtOAc, the combined organics were dried over $Na_2SO_4$, filtered, concentrated and purified by chromatography on silica gel using 0-70% EtOAc in heptane to afford a light yellow solid as tert-butyl (2R,5S)-4-(6,7-dichloro-1-(2,4-diisopropylpyridin-3-yl)-2-oxo-1,2-dihydropyrido[2,3-d]pyrimidin-4-yl)-2,5-dimethylpiperazine-1-carboxylate (0.051 g, 0.087 mmol, 61.9% yield). m/z (ESI, +ve ion): 588.6 $(M+H)^+$.

Step 2. tert-Butyl (2R,5S)-4-(6-chloro-1-(2,4-diisopropylpyridin-3-yl)-7-(2-fluorophenyl)-2-oxo-1,2-dihydropyrido[2,3-d]pyrimidin-4-yl)-2,5-dimethylpiperazine-1-carboxylate A mixture of tert-butyl (2R,5S)-4-(6,7-dichloro-1-(2,4-diisopropylpyridin-3-yl)-2-oxo-1,2-dihydropyrido[2,3-d]pyrimidin-4-yl)-2,5-dimethylpiperazine-1-carboxylate (0.051 g, 0.087 mmol), 2-fluorophenylboronic acid (0.015 ml, 0.104 mmol, CombiBlocks), sodium carbonate (0.028 g, 0.260 mmol) and tetrakis (10.00 mg, 8.65 µmol) in 1,4-dioxane/water (6/1.5 mL) was heated at 90 C for 1 h. The reaction went to completion, quenched with sat. $NaHCO_3$ and extracted with EtOAc. The combined organics were purified by chromatography on silica gel using 0-50% 3:1 (EtOAc/EtOH) in heptane to afford tert-butyl (2R,5S)-4-(6-chloro-1-(2,4-diisopropylpyridin-3-yl)-7-(2-fluorophenyl)-2-oxo-1,2-dihydropyrido[2,3-d]pyrimidin-4-yl)-2,5-dimethylpiperazine-1-carboxylate as a light solid. Theoretical yield considered. m/z (ESI, +ve ion): 648.6 (M+H)+.

Step 3. 4-((2S,5R)-4-Acryloyl-2,5-dimethylpiperazin-1-yl)-6-chloro-1-(2,4-diisopropylpyridin-3-yl)-7-(2-fluorophenyl)pyrido[2,3-d]pyrimidin-2(1H)-one To a solution of tert-butyl (2R,5S)-4-(6-chloro-1-(2,4-diisopropylpyridin-3-yl)-7-(2-fluorophenyl)-2-oxo-1,2-dihydropyrido[2,3-d]pyrimidin-4-yl)-2,5-dimethylpiperazine-1-carboxylate (0.056 g, 0.086 mmol) in DCM (5 mL) was added TFA (2.0 mL, 26.0 mmol) and the resulting mixture was stirred at rt for 30 min. The reaction went to completion and concentrated to afford 6-chloro-1-(2,4-diisopropylpyridin-3-yl)-4-((2S,5R)-2,5-dimethylpiperazin-1-yl)-7-(2-fluorophenyl)pyrido[2,3-d]pyrimidin-2(1H)-one. m/z (ESI, +ve ion): 548.6 (M+H)+.

6-chloro-1-(2,4-diisopropylpyridin-3-yl)-4-((2S,5R)-2,5-dimethylpiperazin-1-yl)-7-(2-fluorophenyl)pyrido[2,3-d]pyrimidin-2(1H)-one was dissolved in DCM (5 mL) then acryloyl chloride (7.01 µl, 0.086 mmol) was added at rt. The reaction was stirred at rt for 15 min, washed with sat. NaHCO₃ and extracted with DCM. The combined organics were purified by HPLC to afford 4-((2S,5R)-4-acryloyl-2,5-dimethylpiperazin-1-yl)-6-chloro-1-(2,4-diisopropylpyridin-3-yl)-7-(2-fluorophenyl)pyrido[2,3-d]pyrimidin-2(1H)-one (0.023 g, 0.038 mmol, 44.2% yield) as a white solid. ¹H NMR (400 MHz, DMSO-d₆) δ 8.42-8.51 (m, 2H), 7.45-7.58 (m, 1H), 7.21-7.38 (m, 3H), 7.18 (td, J=7.4, 1.6 Hz, 1H), 6.84 (td, J=15.8, 10.5 Hz, 1H), 6.20 (dd, J=16.7, 2.2 Hz, 1H), 5.72-5.82 (m, 1H), 4.73-4.97 (m, 2H), 4.47 (br dd, J=6.1, 3.4 Hz, 1H), 4.12-4.23 (m, 1H), 3.83-3.96 (m, 2H), 3.51 (br dd, J=13.6, 3.6 Hz, 1H), 1.31-1.40 (m, 3H), 1.26 (br d, J=6.6 Hz, 2H), 1.18 (d, J=6.6 Hz, 2H), 1.07 (dd, J=6.6, 4.4 Hz, 6H), 0.93 (t, J=7.7 Hz, 6H). m/z (ESI, +ve ion): 602.6 (M+H)+.

TABLE 124

Compounds 124-2 to 124-17 were prepared following the procedure described in Method 124, Steps 1-3, above as follows:

| Ex, # | Chemical structure | Name | Method Changes | Reagent |
|---|---|---|---|---|
| 124-2 | 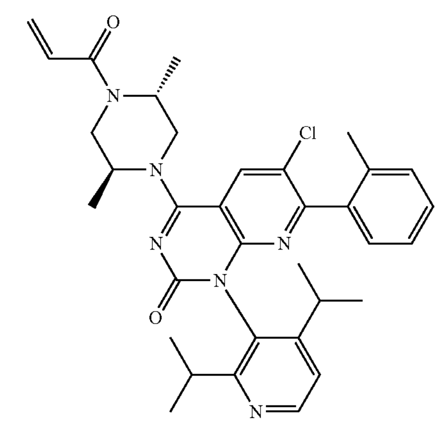 | 6-Chloro-1-(2,4-diisopropyl-3-pyridyl)-4-[(2S,5R)-2,5-dimethyl-4-prop-2-enoyl-piperazin-1-yl]-7-(o-tolyl)pyrido[2,3-d]pyrimidin-2-one Single Isomer Peak 1 | None | Step 1: (2R,5S)-tert-butyl 2,5-dimethylpiperazine-1-carboxylate, eNovation Chemicals LLC, Step 2: o-tolylboronic acid, Sigma-Aldrich Corporation |
| 124-3 | 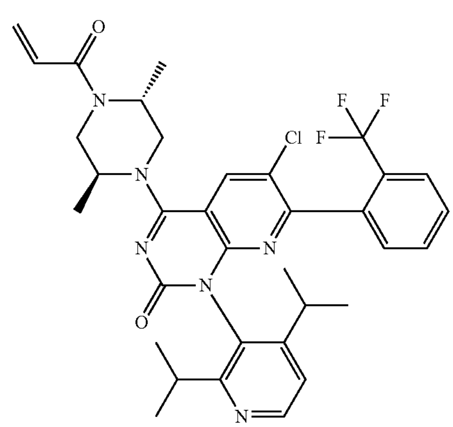 [SMILES: C=CC(=O)N1C[C@H](C)N(c2nc(=O)n(-c3c(C(C)C)ccnc3C(C)C)c3nc(-c4ccccc4C)c(F)cc23)C[C@H]1C] | 6-Chloro-1-(2,4-diisopropyl-3-pyridyl)-4-[(2S,5R)-2,5-dimethyl-4-prop-2-enoyl-piperazin-1-yl]-7-[2-(trifluoromethyl)phenyl]pyrido[2,3-d]pyrimidin-2-one Single Isomer Peak 1 | None | Step 1: (2R,5S)-tert-butyl 2,5-dimethylpiperazine-1-carboxylate, eNovation Chemicals LLC, Step 2: 2-(trifluoromethyl)phenylboronic acid, Combi-Blocks Inc. |

TABLE 124-continued

Compounds 124-2 to 124-17 were prepared following the procedure described in Method 124, Steps 1-3, above as follows:

| Ex, # | Chemical structure | Name | Method Changes | Reagent |
|---|---|---|---|---|
| 124-4 | *(structure shown) Single Isomer Peak 1* | 6-Chloro-1-(2,4-diisopropyl-3-pyridyl)-4-[(2S,5R)-2,5-dimethyl-4-prop-2-enoyl-piperazin-1-yl]-7-(2-fluoro-6-hydroxyphenyl)pyrido[2,3-d]pyrimidin-2-one | None | Step 1: (2R,5S)-tert-butyl 2,5-dimethylpiperazine-1-carboxylate, Astatech, Step 2: (2-fluoro-6-hydroxyphenyl) boronic acid, WuXi |
| 124-5 | *(structure shown)* | 1-(2,4-Diisopropyl-3-pyridyl)-4-[(2S,5R)-2,5-dimethyl-4-prop-2-enoyl-piperazin-1-yl]-6-fluoro-7-(o-tolyl)pyrido[2,3-d]pyrimidin-2-one | 2,6-dichloro-5-fluoro-nicotinamide, Intermediate S | Step 1: (2R,5S)-tert-butyl 2,5-dimethylpiperazine-1-carboxylate, Astatech, Step 2: o-tolylboronic acid, Sigma-Aldrich Corporation |
| 124-6 | *(structure shown) Single Isomer Peak 2* | 6-Chloro-7-(2-chlorophenyl)-1-(2,4-diisopropyl-3-pyridyl)-4-[(2S,5R)-2,5-dimethyl-4-prop-2-enoyl-piperazin-1-yl]pyrido[2,3-d]pyrimidin-2-one | None | Step 1: (2R,5S)-tert-butyl 2,5-dimethylpiperazine-1-carboxylate, Astatech, Step 2: 2-chlorophenylboronic acid, Matrix Scientific |

TABLE 124-continued

Compounds 124-2 to 124-17 were prepared following the procedure described in Method 124, Steps 1-3, above as follows:

| Ex, # | Chemical structure | Name | Method Changes | Reagent |
|---|---|---|---|---|
| 124-7 | 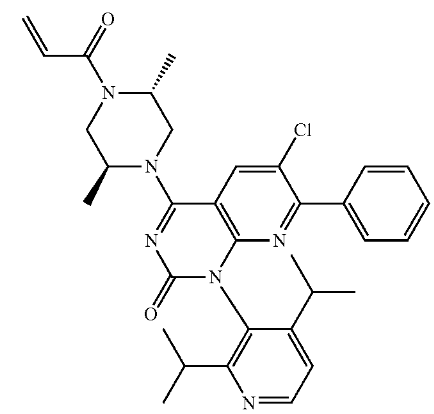 [SMILES: C=CC(=O)N1C[C@H](C)N(c2nc(=O)n(-c3c(C(C)C)ccnc3C(C)C)c3nc(-c4ccccc4)c(Cl)cc23)C[C@H]1C] | 6-Chloro-1-(2,4-diisopropyl-3-pyridyl)-4-[(2S,5R)-2,5-dimethyl-4-prop-2-enoyl-piperazin-1-yl]-7-phenyl-pyrido[2,3-d]pyrimidin-2-one | None | Step 1: (2R,5S)-tert-butyl 2,5-dimethylpiperazine-1-carboxylate, Astatech, Step 2: phenylboronic acid, Sigma-Aldrich Corporation |
| 124-8 | 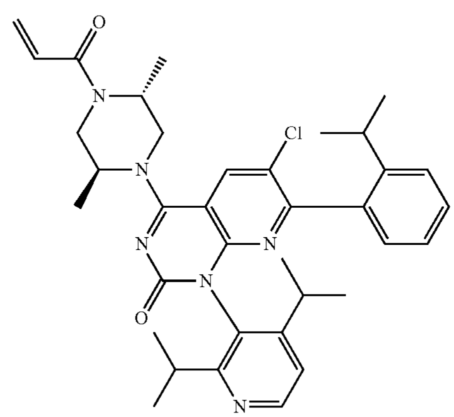 [SMILES: C=CC(=O)N1C[C@H](C)N(c2nc(=O)n(-c3c(C(C)C)ccnc3C(C)C)c3nc(-c4ccccc4C(C)C)c(Cl)cc23)C[C@H]1C] | 6-Chloro-1-(2,4-diisopropyl-3-pyridyl)-4-[(2S,5R)-2,5-dimethyl-4-prop-2-enoyl-piperazin-1-yl]-7-(2-isopropylphenyl)pyrido[2,3-d]pyrimidin-2-one | None | Step 1: (2R,5S)-tert-butyl 2,5-dimethylpiperazine-1-carboxylate, Astatech, Step 2: [2-(1-methylethyl)phenyl]boronic acid, Combi-Blocks Inc. |
| 124-9 Single Isomer Peak 1 | | 6-Chloro-1-(4-cyclopropyl-2-isopropyl-3-pyridyl)-4-[(2S,5R)-2,5-dimethyl-4-prop-2-enoyl-piperazin-1-yl]-7-(o-tolyl)pyrido[2,3-d]pyrimidin-2-one | Intermediate 199A/ Peak 1 in Step 1 | Step 1: (2R,5S)-tert-butyl 2,5-dimethylpiperazine-1-carboxylate, Astatech |

TABLE 124-continued

Compounds 124-2 to 124-17 were prepared following the procedure described in Method 124, Steps 1-3, above as follows:

| Ex, # | Chemical structure | Name | Method Changes | Reagent |
|---|---|---|---|---|
| 124-10 | Single Isomer Peak 2 | 6-Chloro-1-(2,4-diisopropyl-3-pyridyl)-4-[(2S)-2-methyl-4-prop-2-enoyl-piperazin-1-yl]-7-(o-tolyl)pyrido[2,3-d]pyrimidin-2-one | (s)-4-N-Boc-2-methyl piperazine in Step 1 | Step 1: (s)-4-N-Boc-2-methyl piperazine, Sigma-Aidrich Corporation, Step 2: o-tolylboronic acid, Sigma-Aldrich Corporation |
| 124-11 | 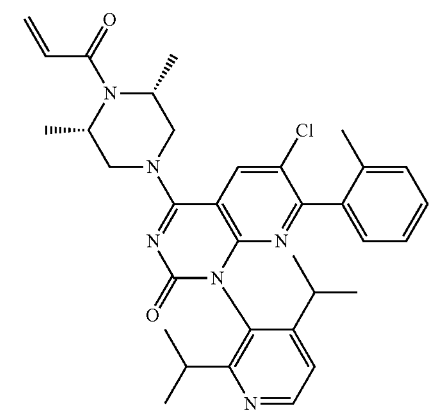 [SMILES: C=CC(=O)N1[C@H](C)CN(c2nc(=O)n(-c3c(C(C)C)ccnc3C(C)C)c3nc(-c4ccccc4C)c(Cl)cc23)C[C@@H]1C] | 6-Chloro-1-(2,4-diisopropyl-3-pyridyl)-4-[(3R,5S)-3,5-dimethyl-4-prop-2-enoyl-piperazin-1-yl]-7-(o-tolyl)pyrido[2,3-d]pyrimidin-2-one | 1-((2R,6S)-2,6-dimethyl piperazin-1-yl)prop-2-en-1-one, Intermediate 223 Step 3: Omit | Step 1:1-((2R,6S)-2,6-dimethylpiperazin-1-yl)prop-2-en-1-one, Syngene, Step 2: o-tolylboronic acid, Sigma-Aldrich Corporation |
| 124-12 | 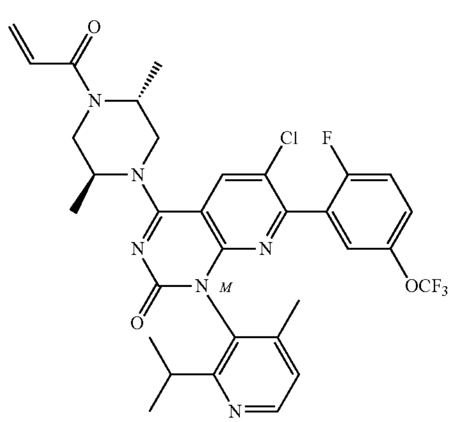 | (M)-6-Chloro-4-[(2S,5R)-2,5-dimethyl-4-prop-2-enoyl-piperazin-1-yl]-7-[2-fluoro-5-(trifluoromethoxy)phenyl]-1-(2-isopropyl-4-methyl-3-pyridyl)pyrido[2,3-d]pyrimidin-2-one | None | Step 1: Intermediate 73B; Step 2: 2-fluoro-5-(trifluoromethoxy)benzeneboronic acid (Combi-Blocks, Inc.) |

TABLE 124-continued

Compounds 124-2 to 124-17 were prepared following the procedure described in Method 124, Steps 1-3, above as follows:

| Ex, # | Chemical structure | Name | Method Changes | Reagent |
|---|---|---|---|---|
| 124-13 | 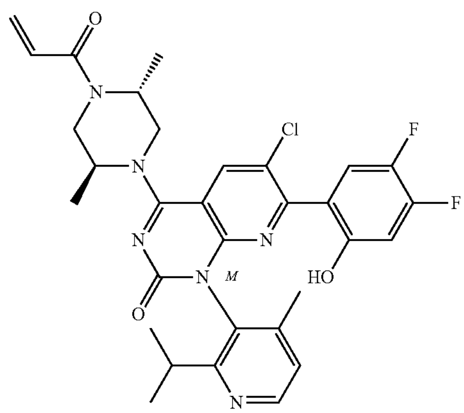 | (M)-6-Chloro-7-(4,5-difluoro-2-hydroxyphenyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one | None | Step 1: Intermediate 73B; Step 2: 4,5-difluoro-2-hydroxyphenyl-boronic acid (Combi-Blocks, Inc., San Diego, CA) |
| 124-14 | 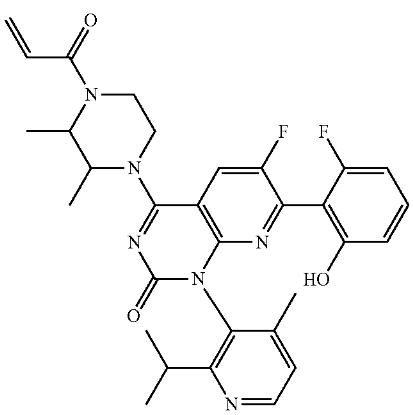 [SMILES: C=CC(=O)N1CCN(c2nc(=O)n(-c3c(C)ccnc3C(C)C)c3nc(-c4c(O)cccc4F)c(F)cc23)C(C)C1C] | (M)-4-[cis-2,3-Dimethyl-4-prop-2-enoyl-piperazin-1-yl]-6-fluoro-7-(2-fluoro-6-hydroxy-phenyl)-1-(2-isopropyl-4-methyl-3-pyridyl)pyrido[2,3-d]pyrimidin-2-one | None | Step 1: Intermediate 72A and 2,3-dimethyl-piperazine-1-carboxylic acid tert-butyl ester (Enamine, Monmouth Jct., NJ); Step 2: (2-fluoro-6-hydroxyphenyl) boronic acid (Wuxi) |
| 124-16 | 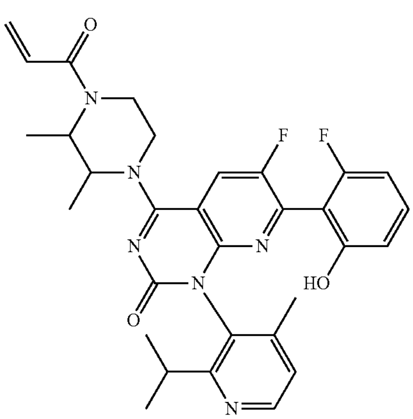 [SMILES: C=CC(=O)N1CCN(c2nc(=O)n(-c3c(C)ccnc3C(C)C)c3nc(-c4c(O)cccc4F)c(F)cc23)C(C)C1C] | (M)-4-[trans-2,3-Dimethyl-4-prop-2-enoyl-piperazin-1-yl]-6-fluoro-7-(2-fluoro-6-hydroxy-phenyl)-1-(2-isopropyl-4-methyl-3-pyridyl)pyrido[2,3-d]pyrimidin-2-one | None | Step 1: Intermediate 72A and 2,3-dimethyl-piperazine-1-carboxylic acid tert-butyl ester (Enamine, Monmouth Jct., NJ); Step 2: 2,3-dimethyl-piperazine-1-carboxylic acid (Alchem Pharmtech, Inc.) |

Method 125

Example 125-1: 4-((2S,5R)-4-Acryloyl-2,5-dimethylpiperazin-1-yl)-6-chloro-1-(2,4-diisopropylpyridin-3-yl)-7-(2-fluorophenyl)pyrido[2,3-d]pyrimidin-2(1H)-one

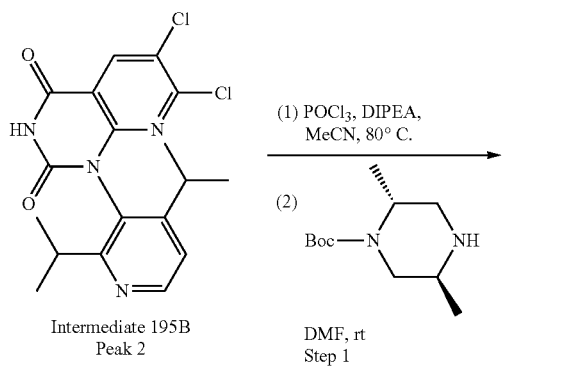

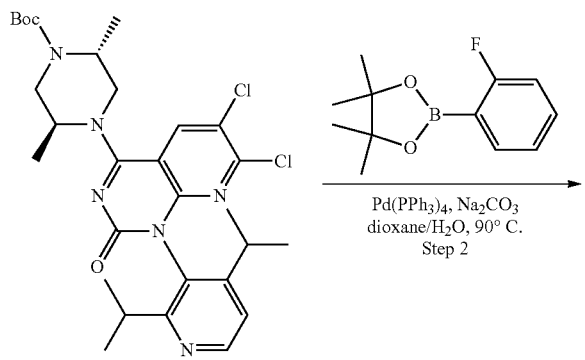

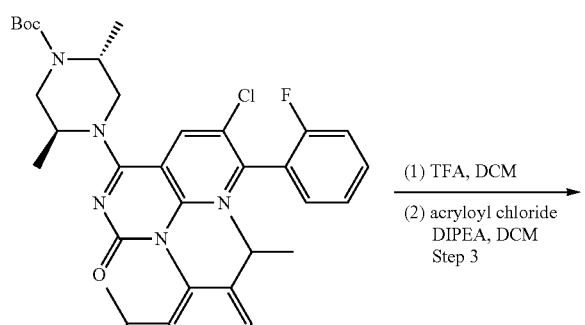

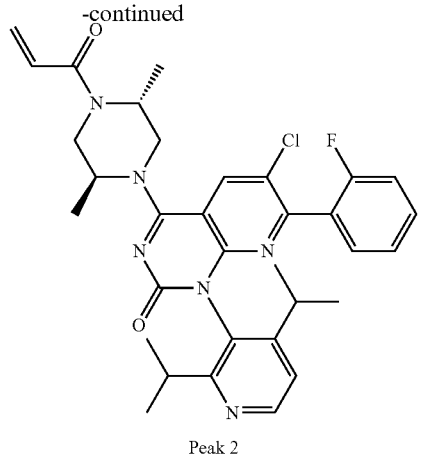

Peak 2

Step 1. tert-Butyl (2R,5S)-4-(6,7-dichloro-1-(2,4-diisopropylpyridin-3-yl)-2-oxo-1,2-dihydropyrido[2,3-d]pyrimidin-4-yl)-2,5-dimethylpiperazine-1-carboxylate Phosphorous oxychloride (0.206 mL, 2.206 mmol) was added dropwise to a solution of 6,7-dichloro-1-(2,4-diisopropylpyridin-3-yl)pyrido[2,3-d]pyrimidine-2,4(1H,3H)-dione (0.723 g, 1.838 mmol, Intermediate 195B) and 1,1'-dimethyltriethylamine (0.417 mL, 2.390 mmol) in CH3CN (5 mL) under $N_2$. This mixture was then heated to 80° C. for 30 min. LCMS showed chlorination completed. The reaction mixture was cooled to 0° C. and 3 equiv DIPEA were added followed by (2R,5S)-tert-butyl 2,5-dimethylpiperazine-1-carboxylate (0.433 mL, 2.022 mmol, AstaTech). This mixture was stirred with warming to rt over 30 min at which time LCMS showed conversion to desired product. The mixture was poured into cold satd. NaHCO3 solution and stirred vigorously for 10 min. The mixture was extracted with EtOAc, the combined organics were dried over Na2SO4, filtered, concentrated and purified by chromatography on silica gel using 0-70% EtOAc in heptane to afford a light yellow solid as tert-butyl (2R,5S)-4-(6,7-dichloro-1-(2,4-diisopropylpyridin-3-yl)-2-oxo-1,2-dihydropyrido[2,3-d]pyrimidin-4-yl)-2,5-dimethylpiperazine-1-carboxylate (0.83 g, 1.408 mmol, 77% yield). m/z (ESI, +ve ion): 588.6 $(M+H)^+$.

Step 2. tert-Butyl (2R,5S)-4-(6-chloro-1-(2,4-diisopropylpyridin-3-yl)-7-(2-fluorophenyl)-2-oxo-1,2-dihydropyrido[2,3-d]pyrimidin-4-yl)-2,5-dimethylpiperazine-1-carboxylate A mixture of tert-butyl (2R,5S)-4-(6,7-dichloro-1-(2,4-diisopropylpyridin-3-yl)-2-oxo-1,2-dihydropyrido[2,3-d]pyrimidin-4-yl)-2,5-dimethylpiperazine-1-carboxylate (0.280 g, 0.475 mmol), 2-fluorophenylboronic acid (0.080 ml, 0.570 mmol, CombiBlocks), sodium carbonate (0.151 g, 1.425 mmol) and tetrakis (0.055 g, 0.047 mmol) in 1,4-dioxane/water (6/1.5 mL) was heated at 90 C for 1 h. The reaction went to completion, quenched with sat. NaHCO3 and extracted with EtOAc. The combined organics were purified by chromatography on silica gel using 0-50% 3:1 (EtOAc/EtOH) inheptane to afford tert-butyl (2R,5S)-4-(6-chloro-1-(2,4-diisopropylpyridin-3-yl)-7-(2-fluorophenyl)-2-oxo-1,2-dihydropyrido[2,3-d]pyrimidin-4-yl)-2,5-dimethylpiperazine-1-carboxylate (0.200 g, 0.308 mmol, 64.9% yield). m/z (ESI, +ve ion): 648.6 (M+H)⁺.

Step 3. 4-((2S,5R)-4-Acryloyl-2,5-dimethylpiperazin-1-yl)-6-chloro-1-(2,4-diisopropylpyridin-3-yl)-7-(2-fluorophenyl)pyrido[2,3-d]pyrimidin-2(1H)-one To a solution of tert-butyl (2R,5S)-4-(6-chloro-1-(2,4-diisopropylpyridin-3-yl)-7-(2-fluorophenyl)-2-oxo-1,2-dihydropyrido[2,3-d]pyrimidin-4-yl)-2,5-dimethylpiperazine-1-carboxylate (0.200 g, 0.308 mmol) in DCM (3 mL) was added TFA (2.0 mL, 26.0 mmol) and the resulting mixture was stirred at rt for 30 min. The reaction went to completion, concentrated to afford 6-chloro-1-(2,4-diisopropylpyridin-3-yl)-4-((2S,5R)-2,5-dimethylpiperazin-1-yl)-7-(2-fluorophenyl)pyrido[2,3-d]pyrimidin-2(1H)-one to be used as is. m/z (ESI, +ve ion): 548.6 (M+H)⁺.

6-chloro-1-(2,4-diisopropylpyridin-3-yl)-4-((2S,5R)-2,5-dimethylpiperazin-1-yl)-7-(2-fluorophenyl)pyrido[2,3-d]pyrimidin-2(1H)-one was dissolved in DCM (6 mL) then acryloyl chloride (0.025 mL, 0.308 mmol) was added at it. The reaction was stirred at it for 15 min, washed with sat. NaHCO₃ and extracted with DCM. The combined organics were purified by HPLC to afford 4-((2S,5R)-4-acryloyl-2,5-dimethylpiperazin-1-yl)-6-chloro-1-(2,4-diisopropylpyridin-3-yl)-7-(2-fluorophenyl)pyrido[2,3-d]pyrimidin-2(1H)-one (0.130 g, 0.216 mmol, 70.0% yield) as a white solid. ¹H NMR (400 MHz, DMSO-d₆) δ 8.20-8.61 (m, 2H), 7.44-7.59 (m, 1H), 7.23-7.37 (m, 3H), 7.10-7.22 (m, 1H), 6.84 (td, J=16.1, 10.4 Hz, 1H), 6.20 (dd, J=16.7, 2.2 Hz, 1H), 5.76 (ddd, J=10.3, 4.5, 2.3 Hz, 1H), 4.72-4.97 (m, 2H), 4.43-4.55 (m, 1H), 4.10-4.24 (m, 2H), 3.83-3.97 (m, 2H), 1.31-1.40 (m, 3H), 1.26 (br d, J=6.6 Hz, 2H), 1.18 (br d, J=6.8 Hz, 2H), 1.08 (br d, J=5.6 Hz, 6H), 0.94 (t, J=6.5 Hz, 6H). m/z (ESI, +ve ion): 602.6 (M+H)⁺.

TABLE 125

Compounds 125-2 to 125-11 were prepared following the procedure described in Method 125, Steps 1-3, above as follows:

| Ex. # | Chemical structure | Name | Method Changes | Reagent |
|---|---|---|---|---|
| 125-2 | 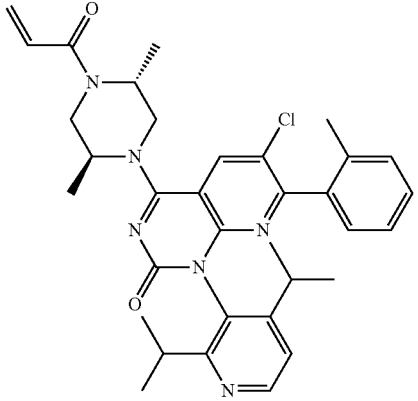<br>Single isomer<br>Peak 2 | 6-Chloro-1-(2,4-diisopropyl-3-pyridyl)-4-[(2S,5R)-2,5-dimethyl-4-prop-2-enoyl-piperazin-1-yl]-7-(o-tolyl)pyrido[2,3-d]pyrimidin-2-one | None | Step 1: (2R,5S)-tert-butyl 2,5-dimethylpiperazine-1-carboxylate, eNovation Chemicals LLC, Step 2: o-tolylboronic acid, Sigma-Aldrich Corporation |
| 125-3 | 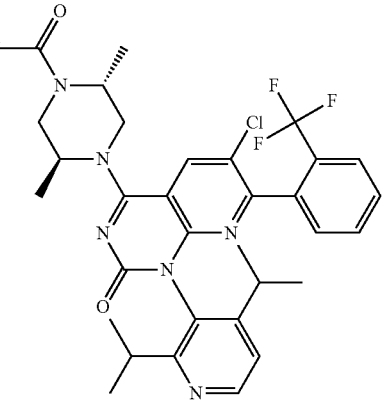<br>Single isomer<br>Peak 2 | 6-Chloro-1-(2,4-diisopropyl-3-pyridyl)-4-[(2S,5R)-2,5-dimethyl-4-prop-2-enoyl-piperazin-1-yl]-7-[2-(trifluoromethyl)phenyl]pyrido[2,3-d]pyrimidin-2-one | None | Step 1: (2R,5S)-tert-butyl 2,5-dimethylpiperazine-1-carboxylate, eNovation Chemicals LLC, Step 2: 2-(trifluoromethyl)phenylboronic acid, Combi-Blocks Inc. |

TABLE 125-continued

Compounds 125-2 to 125-11 were prepared following the procedure described in Method 125, Steps 1-3, above as follows:

| Ex. # | Chemical structure | Name | Method Changes | Reagent |
|---|---|---|---|---|
| 125-4 | Single isomer Peak 2 | 6-Chloro-1-(2,4-diisopropyl-3-pyridyl)-4-[(2S,5R)-2,5-dimethyl-4-prop-2-enoyl-piperazin-1-yl]-7-(2-fluoro-6-hydroxy-phenyl)pyrido[2,3-d]pyrimidin-2-one | None | Step 1: (2R,5S)-tert-butyl 2,5-dimethylpiperazine-1-carboxylate, Astatech, Step 2: (2-fluoro-6-hydroxyphenyl)boronic acid, WuXi |
| 125-5 | Single isomer Peak 2 | 1-(2,4-Diisopropyl-3-pyridyl)-4-[(2S,5R)-2,5-dimethyl-4-prop-2-enoyl-piperazin-1-yl]-6-fluoro-7-(o-tolyl)pyrido[2,3-d]pyrimidin-2-one | Step 1: 7-chloro-1-(2,4-diisopropyl pyridin-3-yl)-6-fluoropyrido[2,3-d]pyrimidine-2,4(1H,3H)-dione | Step 1: (2R,5S)-tert-butyl 2,5-dimethylpiperazine-1-carboxylate, Astatech, Step 2: o-tolylboronic acid, Sigma-Aldrich Corporation |
| 125-6 | Single isomer Peak 1 | 6-Chloro-7-(2-chlorophenyl)-1-(2,4-diisopropyl-3-pyridyl)-4-[(2S,5R)-2,5-dimethyl-4-prop-2-enoyl-piperazin-1-yl]pyrido[2,3-d]pyrimidin-2-one | None | Step 1: (2R,5S)-tert-butyl 2,5-dimethylpiperazine-1-carboxylate, Astatech, Step 2: 2-chlorophenylboronic acid, Matrix Scientific |

TABLE 125-continued

Compounds 125-2 to 125-11 were prepared following the procedure described in Method 125,
Steps 1-3, above as follows:

| Ex. # | Chemical structure | Name | Method Changes | Reagent |
|---|---|---|---|---|
| 125-7 | Single isomer Peak 1 | 6-Chloro-1-(2,4-diisopropyl-3-pyridyl)-4-[(2S,5R)-2,5-dimethyl-4-prop-2-enoyl-piperazin-1-yl]-7-phenyl-pyrido[2,3-d]pyrimidin-2-one | None | Step 1: (2R,5S)-tert-butyl 2,5-dimethylpiperazine-1-carboxylate, Astatech, Step 2: phenylboronic acid, Sigma-Aldrich Corporation |
| 125-8 | Single isomer Peak 1 | 6-Chloro-1-(2,4-diisopropyl-3-pyridyl)-4-[(2S,5R)-2,5-dimethyl-4-prop-2-enoyl-piperazin-1-yl]-7-(2-isopropylphenyl)pyrido[2,3-d]pyrimidin-2-one | None | Step 1: (2R,5S)-tert-butyl 2,5-dimethylpiperazine-1-carboxylate, Astatech, Step 2: 2-isopropylphenyboronic acid, Combi-Blocks Inc. |
| 125-9 | Single isomer Peak 2 | 6-Chloro-1-(4-cyclopropyl-2-isopropyl-3-pyridyl)-4-[(2S,5R)-2,5-dimethyl-4-prop-2-enoyl-piperazin-1-yl]-7-(o-tolyl)pyrido[2,3-d]pyrimidin-2-one | Intermediate 199B/ Peak 2 In Step 1 | Step 1: (2R,5S)-tert-butyl 2,5-dimethylpiperazine-1-carboxylate, Astatech, Step 2: o-tolylboronic acid, Sigma-Aldrich Corporation |

TABLE 125-continued

Compounds 125-2 to 125-11 were prepared following the procedure described in Method 125, Steps 1-3, above as follows:

| Ex. # | Chemical structure | Name | Method Changes | Reagent |
|---|---|---|---|---|
| 125-10 | 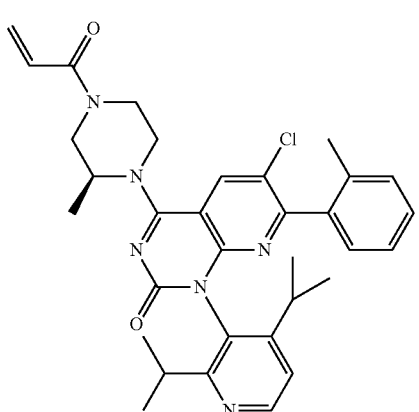<br>Single isomer<br>Peak 1 | 6-Chloro-1-(2,4-diisopropyl-3-pyridyl)-4-[(2S)-2-methyl-4-prop-2-enoyl-piperazin-1-yl]-7-(o-tolyl)pyrido[2,3-d]pyrimidin-2-one | None | Step 1: (s)-4-N-Boc-2-methyl piperazine, Sigma-Aldrich Corporation, Step 2: o-tolylboronic acid, Sigma-Aldrich Corporation |
| 125-11 | 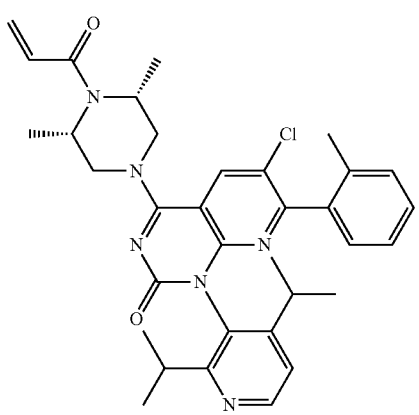<br>Single isomer<br>Peak 1 | 6-Chloro-1-(2,4-diisopropyl-3-pyridyl)-4-[(3R,5S)-3,5-dimethyl-4-prop-2-enoyl-piperazin-1-yl]-7-(o-tolyl)pyrido[2,3-d]pyrimidin-2-one | 1-((2R,6S)-2,6-dimethylpiperazin-1-yl)prop-2-en-1-one, Intermediate 223 in Step 1 Omit Step 3 | Step 2: o-tolylboronic acid, Sigma-Aldrich Corporation |

Method 12

Example 129-1: (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-phenyl]acetamide

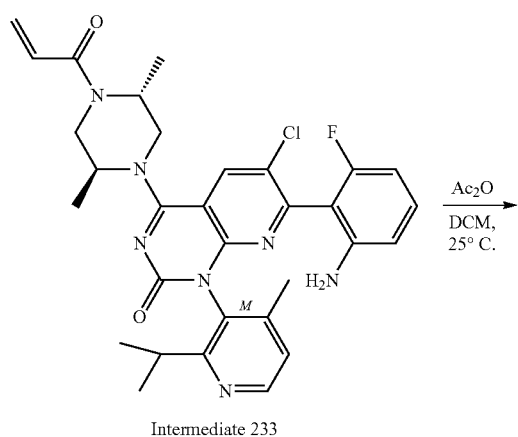

Intermediate 233

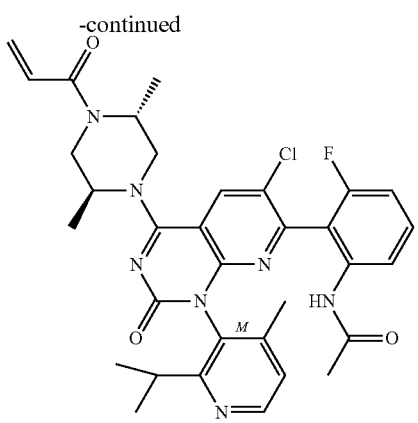

-continued

A mixture of 4-((2S,5R,M)-4-Acryloyl-2,5-dimethylpiperazin-1-yl)-7-(2-amino-6-fluorophenyl)-6-chloro-1-(2-isopropyl-4-methylpyridin-3-yl)pyrido[2,3-d]pyrimidin-2(1H)-one (0.11 g, 0.18 mmol, Intermediate 233) in dichloromethane (0.2 mL) was added acetic acid anhydride (0.1 mL, 0.98 mmol) and stirred at room temperature for 1 h. The resulting mixture was diluted with EtOAc (10 mL) and washed with saturated sodium bicarbonate solution (10 mL). The aqueous layer was extracted with EtOAc (10 mL×2). The combined organic extracts were washed with saturated NaCl solution (20 mL) and dried over MgSO4. The solution was filtered and concentrated in vacuo to give (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-phenyl]acetamide (0.10 mg, 0.17 mmol, 91% yield) as a light-yellow solid. $^1$H NMR (400 MHz, DMSO-$d_6$) δ 8.73-9.11 (m, 1H), 8.43-8.51 (m, 1H), 8.37 (d, J=5.0 Hz, 1H), 7.36-7.81 (m, 2H), 7.14-7.22 (m, 1H), 6.94-7.10 (m, 1H), 6.73-6.92 (m, 1H), 6.14-6.26 (m, 1H), 5.76 (dt, J=10.2, 3.0 Hz, 1H), 4.44-4.96 (m, 2H), 3.76-4.25 (m, 4H), 2.56-2.63 (m, 1H), 2.22 (s, 3H), 1.89-2.04 (m, 3H), 1.34 (br t, J=7.2 Hz, 3H), 1.15-1.27 (m, 3H), 1.01-1.13 (m, 3H), 0.79-0.99 (m, 3H). $^{19}$F NMR (376 MHz, DMSO-$d_6$) δ -116.97-112.40 (m, 1F). m/z (ESI, +ve ion): 632.2 (M+H)$^+$.

TABLE 129

Compounds 129-2 to 129-13 were prepared following the procedure described in Method 129 above as follows:

| Ex. # | Chemical structure | Name | Method Changes | Reagent |
|---|---|---|---|---|
| 129-2 | 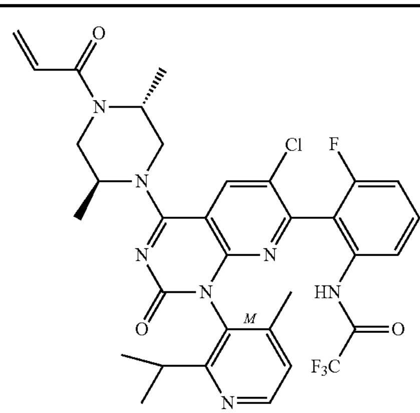 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-phenyl]-2,2,2-trifluoro-acetamide | None | 2,2,2-trifluoroacetic anhydride (Sigma-Aldrich Corporation) |

TABLE 129-continued

Compounds 129-2 to 129-13 were prepared following the procedure described in Method 129 above as follows:

| Ex. # | Chemical structure | Name | Method Changes | Reagent |
|---|---|---|---|---|
| 129-3 | 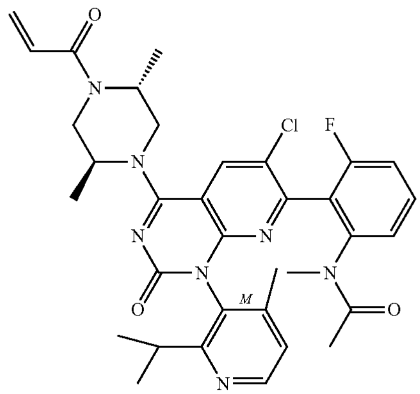 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]phenyl]-N-methyl-acetamide | None | (M)-6-Chloro-4-[(2S,5R)-2,5-dimethyl-4-prop-2-enoyl-piperazin-1-yl]-1-(2-isopropyl-4-methyl-3-pyridyl)-7-[2-(methylamino)phenyl]pyrido[2,3-d]pyrimidin-2-one (Ex. 92-25) |
| 129-4 | 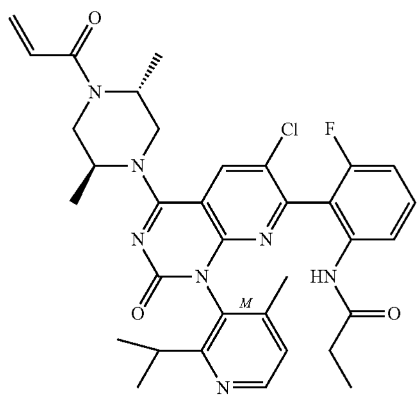 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-phenyl]propanamide | None | propionyl chloride (Sigma-Aldrich Corporation) |
| 129-5 | 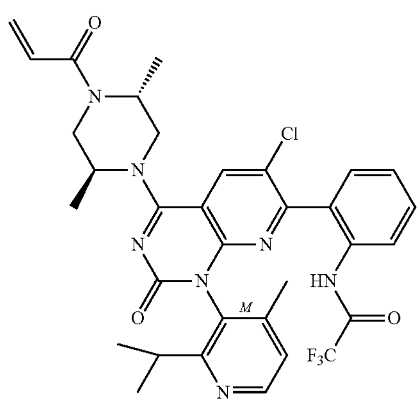 | (M)-N-2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]phenyl]-2,2,2-trifluoro-acetamide | None | (M)-7-(2-Aminophenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one (Ex. 92-12) and 2,2,2-trifluoroacetic anhydride (Sigma-Aldrich Corporation) |

TABLE 129-continued

Compounds 129-2 to 129-13 were prepared following the procedure described in Method 129 above as follows:

| Ex. # | Chemical structure | Name | Method Changes | Reagent |
|---|---|---|---|---|
| 129-6 | 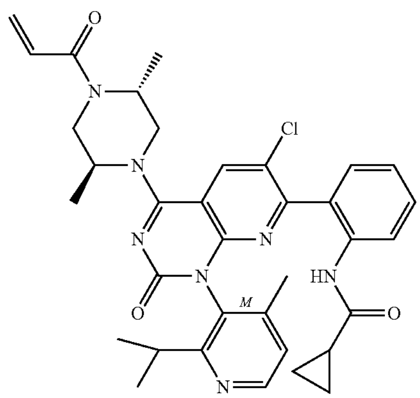 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]phenyl]cyclo-propane-carboxamide | None | (M)-7-(2-Aminophenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one (Ex. 92-12) and cyclopropane carbonyl chloride (Sigma-Aldrich Corporation) |
| 129-7 | 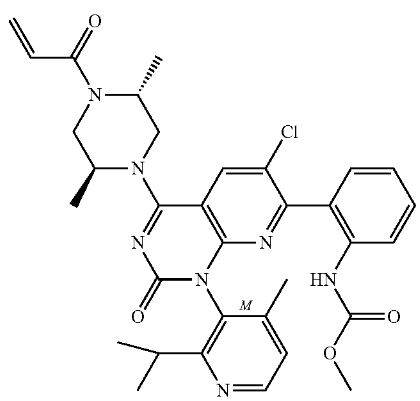 | (M)-Methyl-N-[2-[6-chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]phenyl] carbamate | None | (M)-7-(2-Aminophenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one (Ex. 92-12) and methyl chloroformate (Sigma-Aldrich Corporation) |
| 129-8 | 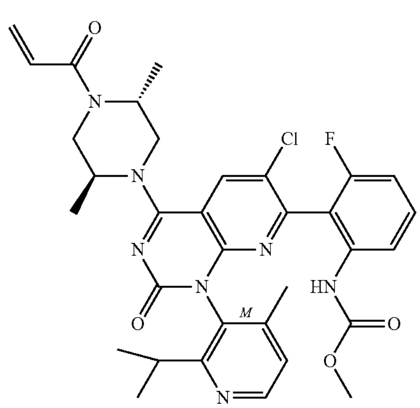 | (M)-Methyl N-[2-[6-chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-phenyl] carbamate | None | methyl chloroformate (Sigma-Aldrich Corporation) |

TABLE 129-continued

Compounds 129-2 to 129-13 were prepared following the procedure described in Method 129 above as follows:

| Ex. # | Chemical structure | Name | Method Changes | Reagent |
|---|---|---|---|---|
| 129-9 | 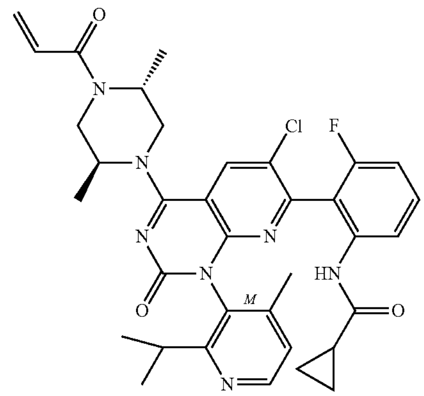 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-phenyl]cyclopropanecarboxamide | None | cyclopropane carbonyl chloride (Sigma-Aldrich Corporation) |
| 129-10 | 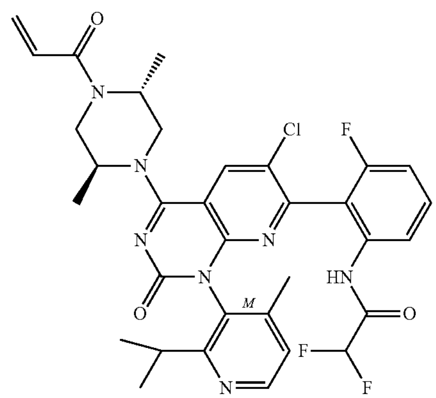 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-3-fluoro-phenyl]-2,2-difluoro-acetamide | None | difluoroacetic anhydride (Matrix Scientific) |
| 129-11 | 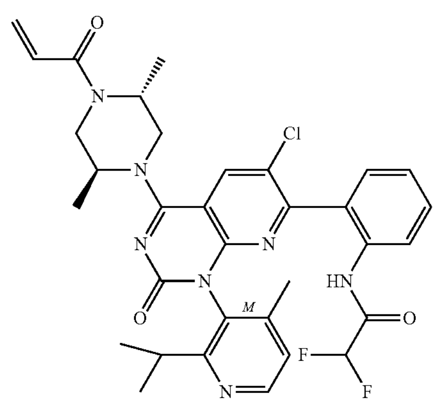 | (M)-N-[2-[6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]phenyl]-2,2-difluoro-acetamide | None | (M)-7-(2-Aminophenyl)-6-chloro-4-[2S,5R)-2,5-dimethyl-4-prop-2-enoyl-piperazin-1-yl]-1-(2-isopropyl-4-methyl-3-pyridyl)pyrido[2,3-d]pyrimidin-2-one (Ex. 92-12) and difluoroacetic anhydride (Matrix Scientific) |

TABLE 129-continued

Compounds 129-2 to 129-13 were prepared following the procedure described in Method 129 above as follows:

| Ex. # | Chemical structure | Name | Method Changes | Reagent |
|---|---|---|---|---|
| 129-12 | 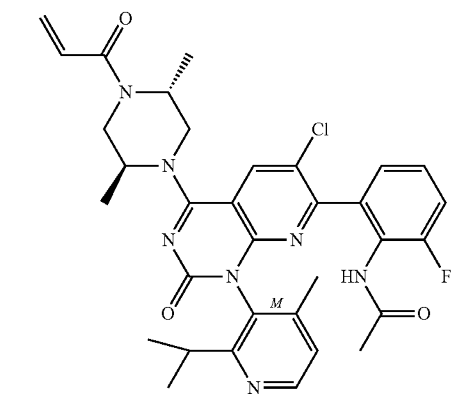 | N[2-(6-Chloro-4-[(2S,5R)-2,5-dimethyl-4-prop-2-enoyl-piperazin-1-yl]-1-(2-isopropyl-4-methyl-3-pyridyl)-2-oxo-pyrido[2,3-d]pyrimidin-7-yl]-6-fluoro-phenyl]acetamide | None | (M)-7-(2-Amino-3-fluoro-phenyl)-6-chloro-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one (Ex. 92-17) |
| 129-13 | 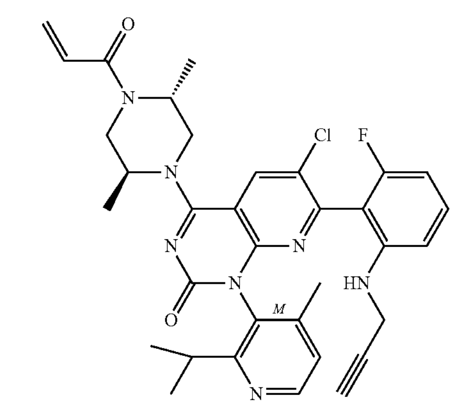 | 4-[(2S,5R)-2,5-Dimethyl-4-prop-2-enoyl-piperazin-1-yl]-6-fluoro-7-[2-fluoro-6-(prop-2-ynylamino)phenyl]-1-(2-isopropyl-4-methyl-3-pyridyl)pyrido[2,3-d]pyrimidin-2-one | None | Propargyl bromide, (Sigma-Aldrich Corporation), $K_2CO_3$ and DMF |

Method 132

Example 132-1: (M)-6-Chloro-4-[(2S,5R)-2,5-dimethyl-4-prop-2-enoyl-piperazin-1-yl]-7-(3-hydroxy-1-naphthyl)-1-(2-isopropyl-4-methyl-3-pyridyl)pyrido[2,3-d]pyrimidin-2-one

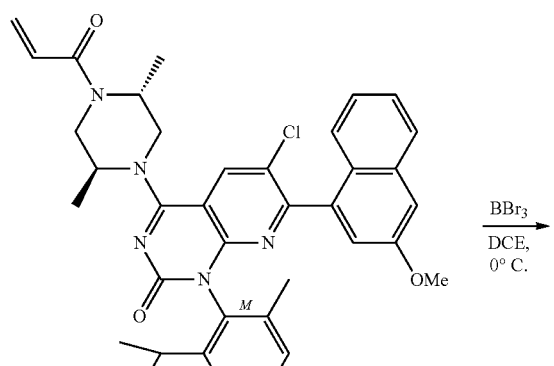

Example 92-70

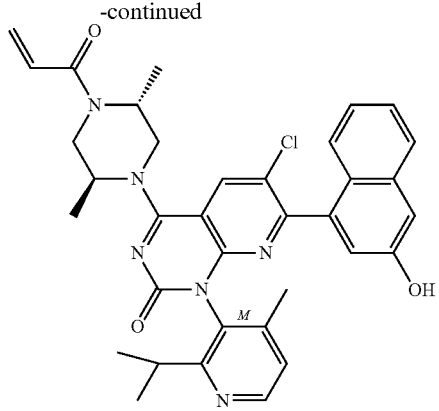

A mixture of (M)-6-chloro-4-[(2S,5R)-2,5-dimethyl-4-prop-2-enoyl-piperazin-1-yl]-1-(2-isopropyl-4-methyl-3-pyridyl)-7-(2-methoxyphenyl)pyrido[2,3-d]pyrimidin-2-one (0.31 g, 0.49 mmol) in 1,2-dichloroethane (10 mL) was treated with boron tribromide solution (1.0 M in hexanes, 2.5 mL, 2.5 mmol) 0° C. and stirred for 1 h. The reaction mixture was added saturated sodium bicarbonate solution (10 mL) and extracted with EtOAc (10 mL×2). The combined organic extracts were dried over Na2SO4. The solution was filtered and concentrated in vacuo to give the crude material. The crude material was purified by silica gel chromatography (eluent: 0-100% of EtOAc-MeOH (4:1)/heptane) to provide (M)-6-Chloro-4-[(2S,5R)-2,5-dimethyl-4-prop-2-enoyl-piperazin-1-yl]-7-(3-hydroxy-1-naphthyl)-1-(2-isopropyl-4-methyl-3-pyridyl)pyrido[2,3-d]pyrimidin-2-one (0.26 g, 0.42 mmol, 85% yield) as an yellow solid. $^1$H NMR (400 MHz, DMSO-d$_6$) δ 9.96 (s, 1H), 8.49 (d, J=3.1 Hz, 1H), 8.30 (d, J=4.8 Hz, 1H), 7.73 (d, J=8.3 Hz, 1H), 7.39 (ddd, J=8.1, 6.2, 1.9 Hz, 1H), 7.15-7.25 (m, 3H), 7.12 (d, J=4.8 Hz, 1H), 6.78-6.95 (m, 2H), 6.20 (dd, J=16.6, 2.3 Hz, 1H), 5.71-5.82 (m, 1H), 4.89 (br s, 1H), 4.46-4.84 (m, 1H), 3.47-4.30 (m, 4H), 2.70-2.80 (m, 1H), 1.94 (s, 3H), 1.32-1.41 (m, 3H), 1.18-1.32 (m, 3H), 1.06 (d, J=6.6 Hz, 3H), 0.92 (d, J=6.6 Hz, 3H). m/z (ESI, +ve ion): 632.2 (M+H)$^+$.

TABLE 132

Compound 132-2 was prepared following the procedure described in Method 132 above as follows:

| Ex. # | Chemical structure | Name | Method Changes | Reagent |
|---|---|---|---|---|
| 132-2 | (structure) | (M)-4-[(2S,5R)-2,5-dimethyl-4-prop-2-enoyl-piperazin-1-yl]-6-fluoro-7-(3-hydroxy-1-naphthyl)-1-(2-isopropyl-4-methyl-3-pyridyl)pyrido[2,3-d]pyrimidin-2-one | None | (M)-4-[(2S,5R)-2,5-Dimethyl-4-prop-2-enoyl-piperazin-1-yl]-6-fluoro-1-(2-isopropyl-4-methyl-3-pyridyl)-7-(3-methoxy-1-naphthyl)pyrido[2,3-d]pyrimidin-2-one (Ex. 94-21) |

477

Method 141

Example 141-1

4-((2S,5R)-4-Acryloyl-2,5-dimethylpiperazin-1-yl)-6-chloro-1-(4-(((diethylamino)methyl)-2-isopropylpyridin-3-yl)-7-(2-isopropylphenyl)pyrido[2,3-d]pyrimidin-2(1H)-one

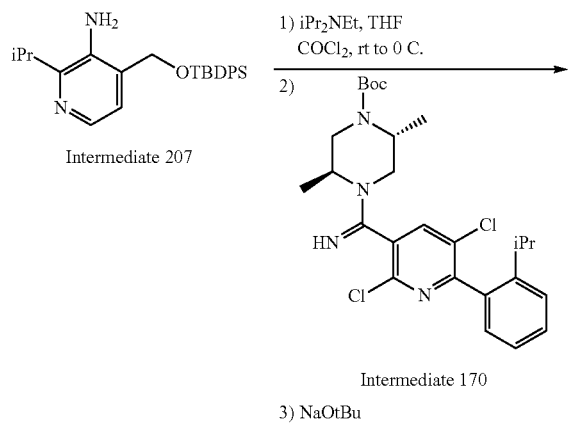

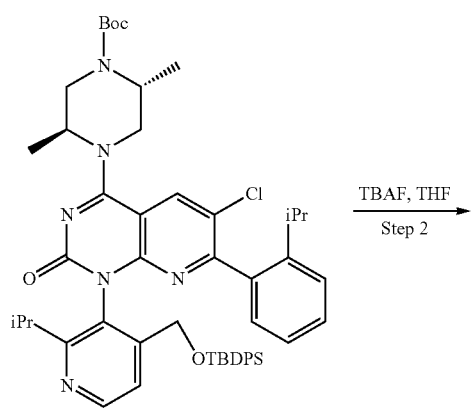

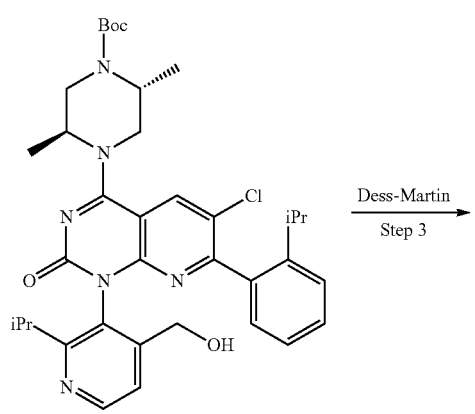

478

-continued

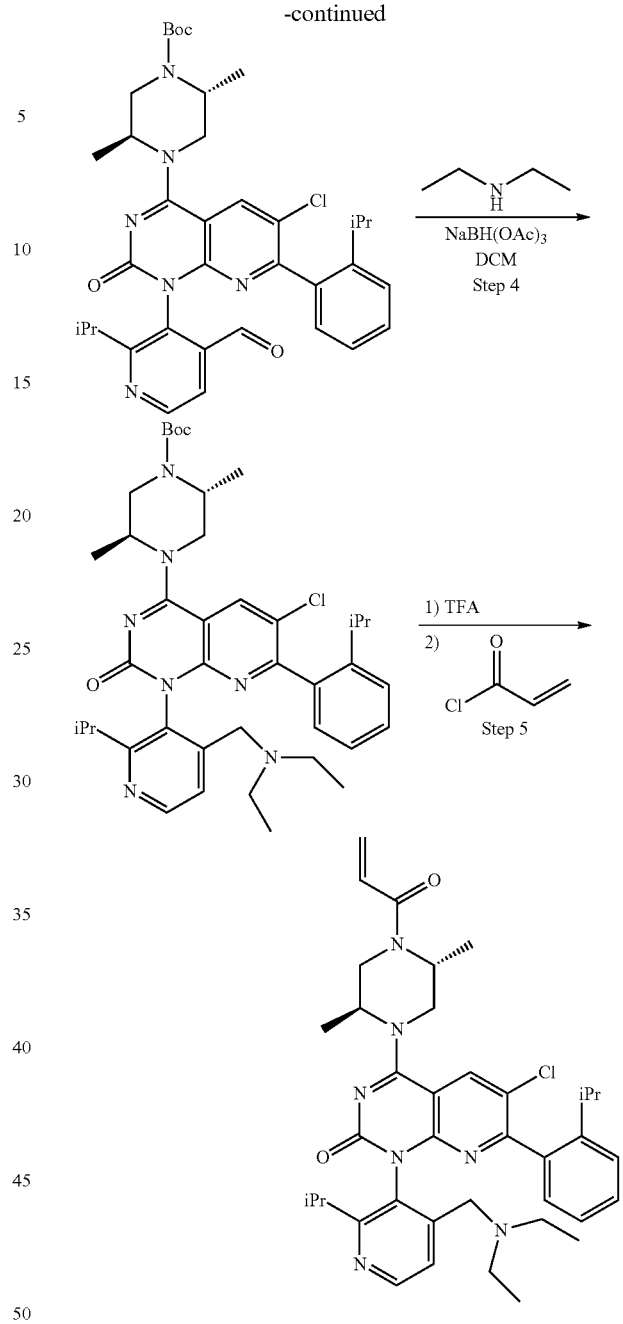

Step 1. (2R,5S)-tert-Butyl 4-(1-(2-(((tert-butyldiphenylsilyl)oxy)methyl)-6-isopropylphenyl)-6-chloro-7-(2-isopropylphenyl)-2-oxo-1,2-dihydropyrido[2,3-d]pyrimidin-4-yl)-2,5-dimethylpiperazine-1-carboxylate To a solution of 4-(((tert-butyldiphenylsilyl)oxy)methyl)-2-isopropylpyridin-3-amine (1.0 g, 2.47 mmol, Intermediate 207) and N,N-diisopropylethylamine (0.950 ml, 5.44 mmol, Aldrich, St. Louis, Mo.) in tetrahydrofuran (25 mL) was added phosgene solution, 15% in toluene (1.30 ml, 2.74 mmol, Aldrich, St. Louis, Mo.) dropwise via syringe. After stirring for 10 min at rt, the resulting mixture was cooled to 0° C. and (2R,5S)-tert-butyl 4-((2,5-dichloro-6-(2-isopropylphenyl)pyridin-3-yl)(imino)methyl)-2,5-dimethylpiperazine-1-carboxylate (1.50 g, 2.97 mmol, Intermediate 170) was added as a solid. After the addition, the ice bath was removed and the reaction was warmed to rt and stirred for 1 h. To this mixture was added sodium tert-butoxide solution, 2.0 M in tetrahydrofuran (3.71 ml, 7.41 mmol, Aldrich, St. Louis, Mo.) dropwise via syringe and the mixture was stirred for 30 min. The reaction was quenched with water (3 mL) and partitioned between EtOAc (40 mL) and water (20 mL). The aqueous layer was extracted with EtOAc (30 mL). The combined organic layers were dried over $MgSO_4$, filtered, and concentrated. The crude product was purified by silica gel chromatography (eluent: 5-40% acetone/heptane) to provide (2R,5S)-tert-butyl 4-(1-(2-(((tert-butyldiphenylsilyl)oxy)methyl)-6-isopropylphenyl)-6-chloro-7-(2-isopropylphenyl)-2-oxo-1,2-dihydropyrido[2,3-d]pyrimidin-4-yl)-2,5-dimethylpiperazine-1-carboxylate as a brown foam (1.6 g). $^1H$ NMR (400 MHz, CHLOROFORM-d) δ 8.63-8.68 (m, 1H), 8.01 (d, J=3.32 Hz, 1H), 7.61 (s, 1H), 7.49-7.59 (m, 4H), 7.29-7.43 (m, 7H), 7.24 (d, J=6.84 Hz, 2H), 7.09-7.17 (m, 1H), 4.78-4.93 (m, 1H), 4.60-4.73 (m, 1H), 4.44-4.59 (m, 1H), 4.22-4.37 (m, 1H), 4.13 (d, J=7.26 Hz, 1H), 3.73-3.92 (m, 2H), 3.34-3.60 (m, 1H), 2.60-2.75 (m, 1H), 2.39-2.55 (m, 1H), 1.54 (d, J=14.31 Hz, 15H), 1.38 (s, 3H), 1.18-1.27 (m, 5H), 0.99-1.09 (m, 13H). m/z (ESI) M+H: 899.4.

Step 2. (2R,5S)-tert-Butyl 4-(6-chloro-1-(2-(hydroxymethyl)-6-isopropylphenyl)-7-(2-isopropylphenyl)-2-oxo-1,2-dihydropyrido[2,3-d]pyrimidin-4-yl)-2,5-dimethylpiperazine-1-carboxylate To a solution of (2R,5S)-tert-butyl 4-(1-(2-(((tert-butyldiphenylsilyl)oxy)methyl)-6-isopropylphenyl)-6-chloro-7-(2-isopropylphenyl)-2-oxo-1,2-dihydropyrido[2,3-d]pyrimidin-4-yl)-2,5-dimethylpiperazine-1-carboxylate (1.3 g, 1.44 mmol) in tetrahydrofuran (15 mL) was added tetrabutylammonium fluoride, 1.0 M in THF (1.60 mL, 1.60 mmol, Aldrich, St. Louis, Mo.). The resulting mixture was stirred at rt under N2 for 2 h. The reaction was concentrated. The crude product was purified by silica gel chromatography (eluent: 0-40% acetone/heptane) to provide (2R,5S)-tert-butyl 4-(6-chloro-1-(2-(hydroxymethyl)-6-isopropylphenyl)-7-(2-isopropylphenyl)-2-oxo-1,2-dihydropyrido[2,3-d]pyrimidin-4-yl)-2,5-dimethylpiperazine-1-carboxylate as light yellow foam (0.740 g). $^1H$ NMR (400 MHz, CHLOROFORM-d) δ 8.61 (d, J=4.98 Hz, 1H), 8.16 (s, 1H), 8.07-8.13 (m, 1H), 7.38 (s, 1H), 7.30-7.34 (m, 2H), 7.19 (s, 1H), 6.95-7.03 (m, 1H), 4.78-4.97 (m, 1H), 4.52-4.73 (m, 1H), 4.34-4.42 (m, 1H), 4.21-4.33 (m, 1H), 3.94-4.10 (m, 1H), 3.73-3.88 (m, 1H), 3.49-3.69 (m, 1H), 2.68-2.80 (m, 1H), 2.37-2.58 (m, 2H), 1.56 (s, 6H), 1.53 (s, 9H), 1.26-1.30 (m, 3H), 1.18-1.24 (m, 3H), 0.97-1.09 (m, 6H). m/z (ESI) M+H: 661.2.

Step 3. (2R,5S)-tert-Butyl 4-(6-chloro-1-(2-formyl-6-isopropylphenyl)-7-(2-isopropylphenyl)-2-oxo-1,2-dihydropyrido[2,3-d]pyrimidin-4-yl)-2,5-dimethylpiperazine-1-carboxylate To a solution of (2R,5S)-tert-butyl 4-(6-chloro-1-(2-(hydroxymethyl)-6-isopropylphenyl)-7-(2-isopropylphenyl)-2-oxo-1,2-dihydropyrido[2,3-d]pyrimidin-4-yl)-2,5-dimethylpiperazine-1-carboxylate (0.845 g, 1.28 mmol) in dichloromethane (12 mL) was added Dess-Martin periodinane (0.813 g, 1.92 mmol, Aldrich, St. Louis, Mo.). The resulting mixture was stirred at rt under $N_2$ for 2 h. The reaction was quenched with sat. $Na_2S_2O_3$ (10 mL) and stirred for 30 min. The aqueous layer was extracted with DCM (2×20 mL). The combined organic layers were dried over $MgSO_4$, filtered, and concentrated. The crude product was purified by silica gel chromatography (eluent: 5-40% acetone/heptane) to provide (2R,5S)-tert-butyl 4-(6-chloro-1-(2-formyl-6-isopropylphenyl)-7-(2-isopropylphenyl)-2-oxo-1,2-dihydropyrido[2,3-d]pyrimidin-4-yl)-2,5-dimethylpiperazine-1-carboxylate as a white solid (0.150 g). $^1H$ NMR (400 MHz, CHLOROFORM-d) δ 9.86 (d, J=3.11 Hz, 1H), 8.82-8.89 (m, 1H), 8.16 (s, 1H), 7.55 (s, 1H), 7.35-7.40 (m, 1H), 7.31 (s, 1H), 7.17 (s, 1H), 6.89-7.03 (m, 1H), 4.88-5.12 (m, 1H), 4.54-4.70 (m, 1H), 4.33-4.53 (m, 1H), 4.02-4.24 (m, 1H), 3.84-3.96 (m, 1H), 3.46-3.70 (m, 1H), 2.90-3.06 (m, 1H), 2.35-2.53 (m, 1H), 1.55 (s, 6H), 1.53 (s, 9H), 1.25-1.30 (m, 6H), 1.04-1.10 (m, 3H), 0.94-1.03 (m, 3H). m/z (ESI) M+H: 659.2.

Step 4. (2R,5S)-tert-Butyl 4-(6-chloro-1-(4-((diethylamino)methyl)-2-isopropylpyridin-3-yl)-7-(2-isopropylphenyl)-2-oxo-1,2-dihydropyrido[2,3-d]pyrimidin-4-yl)-2,5-dimethylpiperazine-1-carboxylate To a solution of (2R,5S)-tert-butyl 4-(6-chloro-1-(2-formyl-6-isopropylphenyl)-7-(2-isopropylphenyl)-2-oxo-1,2-dihydropyrido[2,3-d]pyrimidin-4-yl)-2,5-dimethylpiperazine-1-carboxylate (0.150 g, 0.228 mmol) in dichloromethane (3 mL) was added diethylamine (0.100 mL, 0.943 mmol, Aldrich, St. Louis, Mo.) and 2 drops of AcOH. After stirred for 10 min, sodium triacetoxyborohydride (0.145 g, 0.683 mmol, Aldrich, St. Louis, Mo.) was added and the resulting mixture was continued to stir at rt under $N_2$ for 1 h. Reaction was quenched with sat. $NaHCO_3$ (2 mL) and partitioned between DCM (30 mL) and sat. $NaHCO_3$ (10 mL). The aqueous layer was extracted with DCM (30 mL). The combined organic layers were dried over $MgSO_4$, filtered, and concentrated. The crude product was purified by silica gel chromatography (eluent: 3-5% 2M $NH_3$ MeOH/DCM) to provide (2R,5S)-tert-butyl 4-(6-chloro-1-(4-((diethylamino)methyl)-2-isopropylpyridin-3-yl)-7-(2-isopropylphenyl)-2-oxo-1,2-dihydropyrido[2,3-d]pyrimidin-4-yl)-2,5-dimethylpiperazine-1-carboxylate as white foam (0.120 g). $^1H$ NMR (400 MHz, CHLOROFORM-d) δ 8.49-8.56 (m, 1H), 8.07-8.16 (m, 1H), 7.39-7.45 (m, 1H), 7.37 (s, 1H), 7.33 (s, 1H), 7.17 (s, 1H), 6.95-7.03 (m, 1H), 4.87-5.08 (m, 1H), 4.37-4.66 (m, 1H), 4.01-4.22 (m, 1H), 3.85-3.98 (m, 1H), 3.75-3.85 (m, 1H), 3.49-3.68 (m, 1H), 3.34-3.46 (m, 1H), 2.99-3.13 (m, 1H), 2.68-2.82 (m, 1H), 2.50-2.63 (m, 1H), 2.29-2.42 (m, 2H), 2.18-2.29 (m, 2H), 1.53 (s, 9H), 1.42-1.49 (m, 3H), 1.28 (br s, 6H), 1.23 (d, J=6.84 Hz, 3H), 1.04 (s, 3H), 0.89 (s, 3H), 0.83 (br d, J=4.35 Hz, 6H). m/z (ESI) M+H: 716.4.

Step 5. 4-((2S,5R)-4-Acryloyl-2,5-dimethylpiperazin-1-yl)-6-chloro-1-(4-((diethylamino)methyl)-2-isopropylpyridin-3-yl)-7-(2-isopropylphenyl)pyrido[2,3-d]pyrimidin-2(1H)-one To a solution of (2R,5S)-tert-butyl 4-(6-chloro-1-(4-((diethylamino)methyl)-2-isopropylpyridin-3-yl)-7-(2-isopropylphenyl)-2-oxo-1,2-dihydropyrido[2,3-d]pyrimidin-4-yl)-2,5-dimethylpiperazine-1-carboxylate (0.120 g, 0.168 mmol) in dichloromethane (3 mL) was added trifluoroacetic acid (0.262 mL, 3.52 mmol. Aldrich, St. Louis, Mo.). The resulting mixture was stirred at rt for 2 h. The mixture was concentrated, redissolved in DCM (3 mL) and treated with N,N-diisopropylethylamine (0.120 mL, 0.687 mmol. Aldrich, St. Louis, Mo.). The mixture was cooled to 0° C.

and treated with acryloyl chloride (0.170 mL, 0.187 mmol, 1.1 M. Aldrich, St. Louis, Mo.). After the addition, the ice bath was removed and the reaction was warmed up to rt and continued to stir for 30 min. The reaction was quenched with sat. NaHCO$_3$ (3 mL) and extracted with DCM (2×10 mL). The combined organic layers were dried over MgSO$_4$, filtered, and concentrated. The crude product was purified by silica gel chromatography (eluent: 3-5% 2M NH$_3$ MeOH/DCM) to provide 4-((2S,5R)-4-acrloyl-2,5-dimethylpiperazin-1-yl)-6-chloro-1-(4-((diethylamino)methyl)-2-isopropylpyridin-3-yl)-7-(2-isopropylphenyl)pyrido[2,3-d]pyrimidin-2(1H)-one as a white solid (0.100 g, Example 141-1). $^1$H NMR (400 MHz, CHLOROFORM-d) δ 8.49-8.56 (m, 1H), 8.09-8.17 (m, 1H), 7.35-7.47 (m, 2H), 7.30-7.35 (m, 1H), 7.14-7.22 (m, 1H), 6.96-7.04 (m, 1H), 6.52-6.72 (m, 1H), 6.34-6.47 (m, 1H), 5.75-5.85 (m, 1H), 5.03-5.19 (m, 1H), 4.33-4.55 (m, 1H), 3.88-4.12 (m, 2H), 3.67-3.82 (m, 1H), 3.35-3.47 (m, 1H), 3.00-3.12 (m, 1H), 2.67-2.82 (m, 1H), 2.52-2.64 (m, 1H), 2.30-2.41 (m, 2H), 2.21-2.29 (m, 2H), 1.46 (br d, J=6.43 Hz, 4H), 1.28 (br s, 6H), 1.23 (br d, J=6.63 Hz, 3H), 1.03 (br d, J=6.63 Hz, 6H), 0.83 (br d, J=3.73 Hz, 6H). m/z (ESI) M+H: 670.2.

TABLE 141

Compounds 141-2 to 141-3 were prepared following the procedure described in Method 141, Steps 1-5, above as follows:

| Ex. # | Chemical structure | Name | Method Changes | Reagent |
|---|---|---|---|---|
| 141-2 | 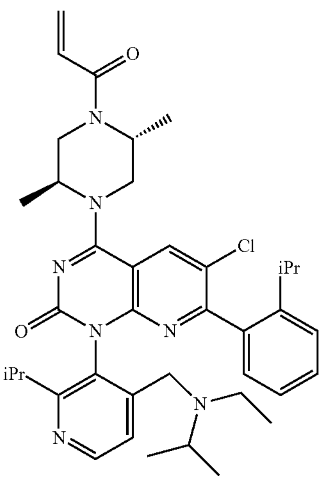 [SMILES: C=CC(=O)N1C[C@H](C)N(c2nc(=O)n(-c3c(CN(CC)C(C)C)ccnc3C(C)C)c3nc(-c4ccccc4C(C)C)c(Cl)cc23)C[C@H]1C] | 6-Chloro-4-[(2S,5R)-2,5-dimethyl-4-prop-2-enoyl-piperazin-1-yl]-1-[4-[[ethyl(isopropyl)amino]methyl]-2-isopropyl-3-pyridyl]-7-(2-isopropylphenyl)pyrido[2,3-d]pyrimidin-2-one | None | N-Ethylisopropylamine (Aldrich, St. Louis, MO) instead of diethylamine in Step 4 |
| 141-3 | 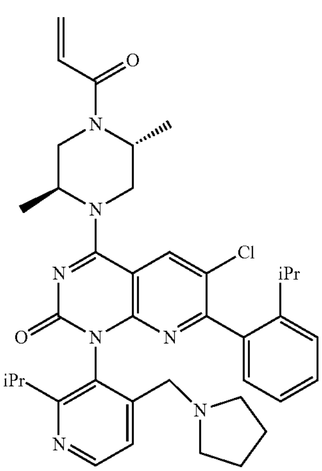 [SMILES: C=CC(=O)N1C[C@H](C)N(c2nc(=O)n(-c3c(CN4CCCC4)ccnc3C(C)C)c3nc(-c4ccccc4C(C)C)c(Cl)cc23)C[C@H]1C] | 6-Chloro-4-[(2S,5R)-2,5-dimethyl-4-prop-2-enoyl-piperazin-1-yl]-7-(2-isopropylphenyl)-1-[2-isopropyl-4-(pyrrolidin-1-ylmethyl)-3-pyridyl]pyrido[2,3-d]pyrimidin-2-one | None | Pyrrolidine (Aldrich, St. Louis, MO) instead of diethylamine in Step 4 |

Method 144

Example 144-1: (M)-2-[4-[7-(2-Amino-6-fluoro-phenyl)-6-chloro-1-(2-isopropyl-4-methyl-3-pyridyl)-2-oxo-pyrido[2,3-d]pyrimidin-4-yl]-1-prop-2-enoyl-piperazin-2-yl]acetonitrile

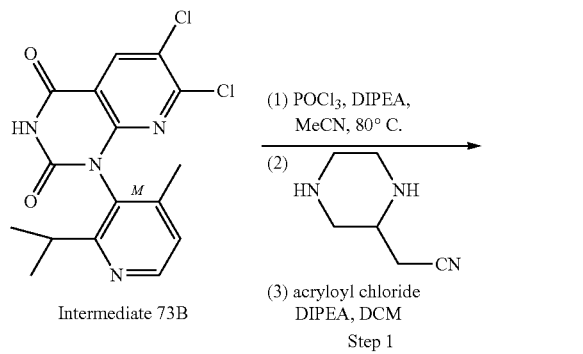

Intermediate 73B (1) POCl₃, DIPEA, MeCN, 80° C.
(2) HN⟩NH ⟩CN
(3) acryloyl chloride DIPEA, DCM
Step 1

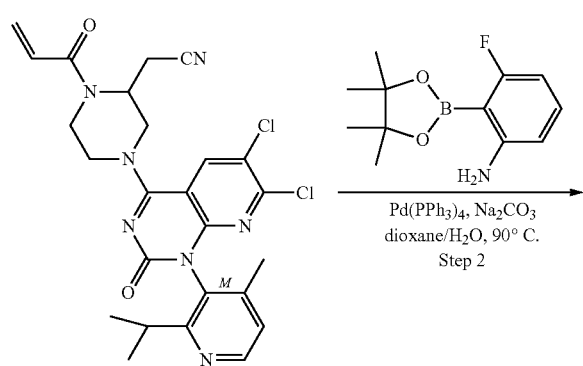

Pd(PPh₃)₄, Na₂CO₃
dioxane/H₂O, 90° C.
Step 2

Step 1: (M)-2-[4-[6,7-Dichloro-1-(2-isopropyl-4-methyl-3-pyridyl)-2-oxo-pyrido[2,3-d]pyrimidin-4-yl]-1-prop-2-enoyl-piperazin-2-yl]acetonitrile A mixture of (M)-6,7-dichloro-1-(2-isopropyl-4-methylpyridin-3-yl)pyrido[2,3-d]pyrimidine-2,4(1H,3H)-dione (Intermediate 73B, 0.43 g, 1.16 mmol) and DIPEA (1.0 mL, 5.82 mmol) in acetonitrile (5.0 mL) was treated with phosphorous oxychloride (0.3 mL, 3.49 mmol) at room temperature. The mixture was stirred at 80° C. for 30 min. The reaction mixture was evaporated to dryness to give 4,6,7-trichloro-1-(2-isopropyl-4-methylpyridin-3-yl)pyrido[2,3-d]pyrimidin-2(1H)-one as a orange oil. LC/MS purity: >95% (215 nm); >95% (254 nm). m/z (ESI, +ve ion): 383.1 (M+H)⁺. The resulting brown solid was used in next step without purification.

To a mixture of the above crude 4,6,7-trichloro-1-(2-isopropyl-4-methylpyridin-3-yl)pyrido[2,3-d]pyrimidin-2(1H)-one in acetonitrile (5.0 mL) was added a solution of 2-(piperazin-2-yl)acetonitrile dihydrochloride (0.35 g, 1.75 mmol) and DIPEA (1.0 mL, 5.82 mmol) in acetonitrile (2.0 mL). The resulting mixture was stirred at room temperature for 10 min and then treated with acryloyl chloride (1.1 M solution in DCM 1.6 mL, 1.75 mmol). The resulting mixture was stirred at room temperature for 10 min and evaporated to dryness. The resulting crude product was purified by silica gel chromatography (eluent: 0-100% of EtOAc-MeOH (9:1)/heptane) to provide (M)-2-[4-[6,7-dichloro-1-(2-isopropyl-4-methyl-3-pyridyl)-2-oxo-pyrido[2,3-d]pyrimidin-4-yl]-1-prop-2-enoyl-piperazin-2-yl]acetonitrile (0.36 g, 0.68 mmol, 58.5% yield) as an yellow solid. ¹H NMR (400 MHz, DMSO-$d_6$) δ 8.66 (s, 1H), 8.52 (d, J=5.0 Hz, 1H), 7.34 (br s, 1H), 6.73-7.00 (m, 1H), 6.22 (dd, J=16.6, 1.9 Hz, 1H), 5.73-5.89 (m, 1H), 4.81-5.02 (m, 1H), 4.26-4.41 (m, 2H), 3.79-4.09 (m, 3H), 3.57 (d, J=11.0 Hz, 2H), 2.97-3.07 (m, 1H), 2.59-2.82 (m, 1H), 1.91-2.04 (m, 3H), 1.08 (dd, J=6.6, 3.5 Hz, 3H), 1.02 (dd, J=6.6, 2.7 Hz, 3H). m/z (ESI, +ve ion): 526.1 (M+H)⁺.

Step 2: (M)-2-[4-[7-(2-Amino-6-fluoro-phenyl)-6-chloro-1-(2-isopropyl-4-methyl-3-pyridyl)-2-oxo-pyrido[2,3-d]pyrimidin-4-yl]-1-prop-2-enoyl-piperazin-2-yl]acetonitrile A mixture of (M)-2-[4-[6,7-dichloro-1-(2-isopropyl-4-methyl-3-pyridyl)-2-oxo-pyrido[2,3-d]pyrimidin-4-yl]-1-prop-2-enoyl-piperazin-2-yl]acetonitrile (0.11 g, 0.21 mmol), tetrakis(triphenylphosphine)palladium (0.02 g, 0.02 mmol), 2-fluoro-6-aminophenylboronic acid pinacol ester (0.07 g, 0.31 mmol, CombiPhos Catalysts, Inc.) and sodium carbonate (0.11 g, 1.04 mmol) in 1,4-dioxane (1.0 mL)/water (0.5 mL) was stirred at 90° for 30 min. The resulting mixture was evaporated to dryness. The resulting crude product was purified by silica gel chromatography (eluent: 0-100% of EtOAc/heptane) to provide (M)-2-[4-[7-(2-amino-6-fluoro-phenyl)-6-chloro-1-(2-isopropyl-4-methyl-3-pyridyl)-2-oxo-pyrido[2,3-d]pyrimidin-4-yl]-1-prop-2-enoyl-piperazin-2-yl]acetonitrile (0.06 g, 0.10 mmol, 48.1% yield) as an yellow solid. ¹H NMR (400 MHz, DMSO-$d_6$) δ 8.59-8.65 (m, 1H), 8.36-8.44 (m, 1H), 7.19 (d, J=5.0 Hz, 1H), 7.06 (q, J=7.9 Hz, 1H), 6.77-6.98 (m, 1H), 6.41-6.49 (m, 1H), 6.32 (br t, J=8.3 Hz, 1H), 6.23 (dd, J=16.6, 1.7 Hz, 1H), 5.81 (br d, J=1.8 Hz, 1H), 5.10-5.18 (m, 1H), 5.05 (br s, 1H), 4.83-5.01 (m, 1H), 4.02-4.48 (m, 3H), 3.45-4.00 (m, 3H), 3.13-3.21 (m, 1H), 2.98-3.13 (m, 1H), 2.63-2.93 (m, 1H), 1.81-2.02 (m, 3H), 1.03-1.12 (m, 3H), 0.86-1.01 (m, 3H). ¹⁹F NMR (376 MHz, DMSO-$d_6$) δ -116.31--115.08 (m, 1F). m/z (ESI, +ve ion): 601.2 (M+H)⁺.

TABLE 144

Compounds 144-2 to 144-3 were prepared following the procedure described
in Method 144, Steps 1-2 above, as follows:

| Ex. # | Chemical structure | Name | Method Changes | Reagent |
|---|---|---|---|---|
| 144-2 | 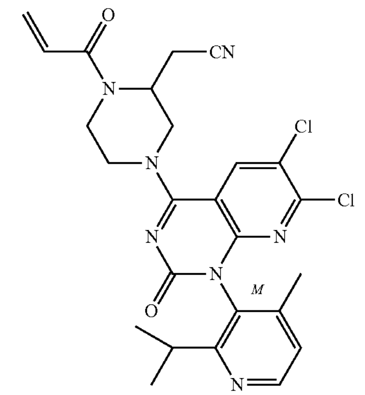 | (M)-2-[4-[6,7-Dichloro-1-(2-isopropyl-4-methyl-3-pyridyl)-2-oxo-pyrido[2,3-d]pyrimidin-4-yl]-1-prop-2-enoyl-piperazin-2-yl]acetonitrile | Omit step 2 | No change |
| 144-3 | 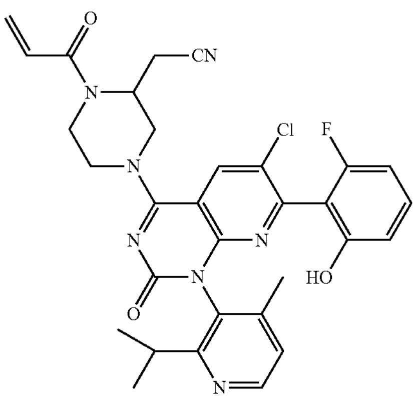 [SMILES: C=CC(=O)N1CCN(c2nc(=O)n(-c3c(C)ccnc3C(C)C)c3nc(-c4c(O)cccc4F)c(Cl)cc23)CC1CC#N] | (M)-2-[4-[6-Chloro-7-(2-fluoro-6-hydroxy-phenyl)-1-(2-isopropyl-4-methyl-3-pyridyl)-2-oxo-pyrido[2,3-d]pyrimidin-4-yl]-1-prop-2-enoyl-piperazin-2-yl]acetonitrile | Step 4: Pd(dppf)2Cl2 and KOAc | Step 2: (2-fluoro-6-hydroxyphenyl) boronic acid (WuXi) |

Method 145

Example 145-1: 2-[4-[6-Chloro-1-(2,2-dimethylpropyl)-7-(2-fluorophenyl)-2-oxo-pyrido[2,3-d]pyrimidin-4-yl]-1-prop-2-enoyl-piperazin-2-yl]acetonitrile

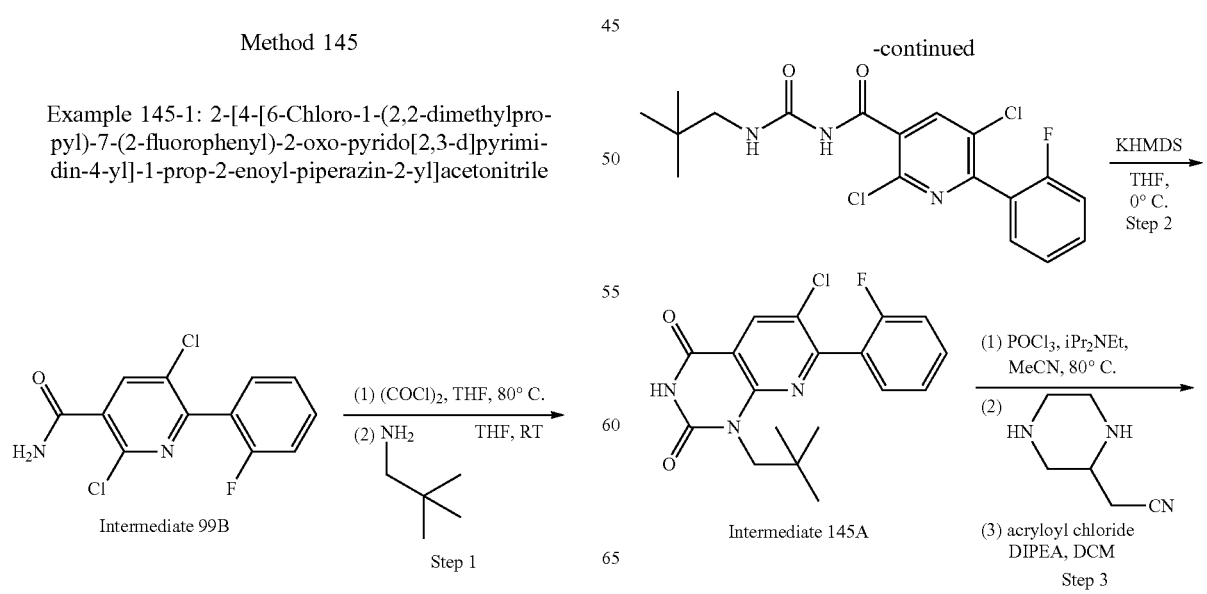

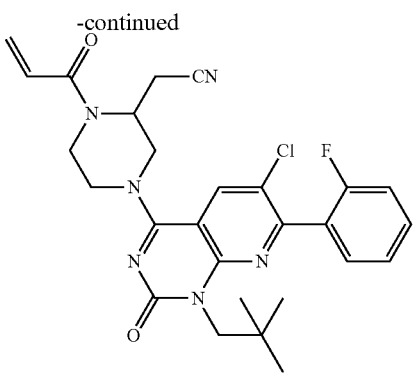

Step 1: 2,5-Dichloro-6-(2-fluorophenyl)-N-(neopentylcarbamoyl)-nicotinamide

A solution of 2,5-dichloro-6-(2-fluorophenyl)nicotinamide (Intermediate 99B, 2.75 g, 9.65 mmol) in THF (20 mL) was treated with oxalyl chloride (2.0 M solution in DCM, 5.8 mL, 11.57 mmol). The mixture was stirred at 75° C. for 60 min. The mixture was cooled to room temperature and concentrated in vacuo. The above crude material was redissolved into THF (20 mL) and a mixture of neopentylamine (1.1 mL, 9.65 mmol) and huenigs base (3.4 mL, 19.29 mmol) in THF (10 mL) was added. The resulting mixture was stirred at room temperature for 3 days. The reaction mixture was then partitioned between water (50 mL) and EtOAc (50 mL). The aqueous phase was extracted with EtOAc (50 mL). The combined organic phases were dried over Na2SO4 and concentrated to give a crude material, which was purified by silica gel chromatography (eluent: 0-50% of EtOAc/heptane) to provide 2,5-dichloro-6-(2-fluorophenyl)-N-(neopentylcarbamoyl)nicotinamide (1.09 g, 2.74 mmol, 28.4% yield) as a light yellow solid. m/z (ESI, +ve ion): 398.0 (M+H)$^+$.

Step 2: 6-Chloro-7-(2-fluorophenyl)-1-neopentylpyrido[2,3-d]pyrimidine-2,4(1H,3H)-dione A mixture of 2,5-dichloro-6-(2-fluorophenyl)-N-(neopentylcarbamoyl)-nicotinamide (1.09 g, 2.74 mmol) in THF (10 mL) at 0° C. was treated with potassium bis(trimethylsilyl)amide (1.0 M in THF, 5.5 mL, 5.50 mmol) and stirred at 0° C. for 15 min. The reaction mixture was quenched with saturated aqueous NH4Cl (10 mL) and extracted with EtOAc (20 mL×2). The combined organic layers were washed with brine (50 mL), dried over Na2SO4, filtered, and concentrated in vacuo. The resulting crude product was sonicated in EtOAc (3 mL). The resulting solid was collected by filtration, washed with EtOAc and dried to give pure 6-chloro-7-(2-fluorophenyl)-1-neopentylpyrido[2,3-d]pyrimidine-2,4(1H,3H)-dione (0.75 g, 2.06 mmol, 75% yield) as a light yellow solid. $^1$H NMR (400 MHz, DMSO-d6) δ 11.88 (s, 1H), 8.44 (s, 1H), 7.56-7.66 (m, 1H), 7.45-7.53 (m, 1H), 7.35-7.44 (m, 2H), 4.07 (s, 2H), 0.90 (s, 9H). $^{19}$F NMR (376 MHz, DMSO-d$_6$) δ 114.02 (s, 1F). m/z (ESI, +ve ion): 362.2 (M+H)$^+$.

Step 3: 2-[4-[6-Chloro-1-(2,2-dimethylpropyl)-7-(2-fluorophenyl)-2-oxo-pyrido[2,3-d]pyrimidin-4-yl]-1-prop-2-enoyl-piperazin-2-yl]acetonitrile A mixture of 6-chloro-7-(2-fluorophenyl)-1-neopentylpyrido[2,3-d]pyrimidine-2,4(1H,3H)-dione (0.35 g, 0.97 mmol) and n,n'-diisopropylethylamine (0.8 mL, 4.84 mmol) in acetonitrile (5.0 mL) was treated with phosphorous oxychloride (0.3 mL, 2.90 mmol) at room temperature. The mixture was stirred at 80° C. for 1 h. The reaction mixture was evaporated to dryness to give 4,6-dichloro-7-(2-fluorophenyl)-1-neopentylpyrido[2,3-d]pyrimidin-2(1H)-one as a brown oil. m/z (ESI, +ve ion): 380.0 (M+H)$^+$. The resulting brown oil was used in next step without purification.

To the mixture of 4,6-dichloro-7-(2-fluorophenyl)-1-neopentylpyrido[2,3-d]pyrimidin-2(1H)-one in acetonitrile (5.0 mL) was added a solution of 2-(piperazin-2-yl)acetonitrile dihydrochloride (0.29 g, 1.45 mmol, Enamine Ltd.) and n,n'-diisopropylethylamine (0.8 mL, 4.84 mmol) in acetonitrile (2.0 mL) and stirred at rt for 10 min. The resulting mixture was then treated with acryloyl chloride (1.1 M in DCM, 1.3 mL, 1.45 mmol) and stirred at rt for 10 min. The reaction mixture was evaporated to dryness. The resulting crude product was purified by silica gel chromatography (0-100% of EtOAc-MeOH (9:1)/heptane) to provide 2-[4-[6-chloro-1-(2,2-dimethylpropyl)-7-(2-fluorophenyl)-2-oxo-pyrido[2,3-d]pyrimidin-4-yl]-1-prop-2-enoyl-piperazin-2-yl]acetonitrile (0.23 g, 0.43 mmol, 44.7% yield) as an yellow solid. $^1$H NMR (400 MHz, DMSO-d$_6$) δ 8.49 (s, 1H), 7.49-7.70 (m, 2H), 7.33-7.46 (m, 2H), 6.73-7.01 (m, 1H), 6.20 (dd, J=16.6, 2.1 Hz, 1H), 5.79 (br d, J=11.8 Hz, 1H), 4.75-5.01 (m, 1H), 4.03-4.37 (m, 5H), 3.42-4.01 (m, 3H), 2.90-3.20 (m, 2H), 0.88 (s, 9H). $^{19}$F NMR (376 MHz, DMSO-d6) δ 113.65 (s, 1F). m/z (ESI, +ve ion): 523.3 (M+H)$^+$.

TABLE 145

Compounds 145-2 to 145-3 were prepared following the procedure described in Method 145, Steps 1-3, above as follows:

| Ex. # | Chemical structure | Name | Method Changes | Reagent |
|---|---|---|---|---|
| 145-2 | 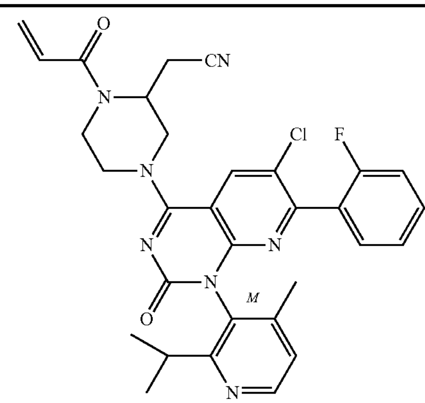 | (M)-2-[4-[6-Chloro-7-(2-fluorophenyl)-1-(2-isopropyl-4-methyl-3-pyridyl)-2-oxo-pyrido[2,3-d]pyrimidin-4-yl]-1-prop-2-enoyl-piperazin-2-yl]acetonitrile | Omit Step 1 and Step 2 | Step 3: (M)-6-Chloro-7-(2-fluorophenyl)-1-(2-isopropyl-4-methylpyridin-3-yl)pyrido[2,3-d]pyrimidine-2,4(1H,3H)-dione (Intermediate 76A) |
| 145-3 | 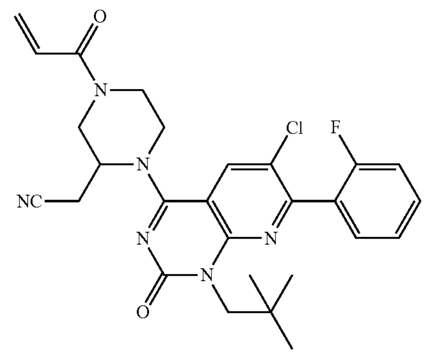 [SMILES: C=CC(=O)N1CCN(c2nc(=O)n(CC(C)(C)C)c3nc(-c4ccccc4F)c(Cl)cc23)C(CC#N)C1] | 2-[1-[6-Chloro-1-(2,2-dimethypropyl)-7-(2-fluorophenyl)-2-oxo-pyrido[2,3-d]pyrimidin-4-yl]-4-prop-2-enoyl-piperazin-2-yl]acetonitrile | None | Step 3: 2-(4-Acryloyl-piperazin-2-yl)acetonitrile (Intermediate 218) |

Method 146

Example 146-1: (F)-(9Z)-19-Chloro-22-((2S,5R)-2,5-dimethyl-4-(2-propenoyl)-1-piperazinyl)-3-(2-propanyl)-1,23,26-triazapentacyclo[16.6.2.0~2,7~.0~12,17~0~21,25-]hexacosa-2,4,6,9,12,14,16,18,20,22,25-undecaen-24-one and (F)-19-chloro-22-((2S,5R)-2,5-dimethyl-4-(2-propenoyl)-1-piperazinyl)-3-(2-propanyl)-1,23,26-triazapentacyclo[6.6.2.0~2,7~.0~12,17~.0~21,25~]hexacosa-2,4,6,9,12,14,16,18,20,22,25-undecaen-24-one

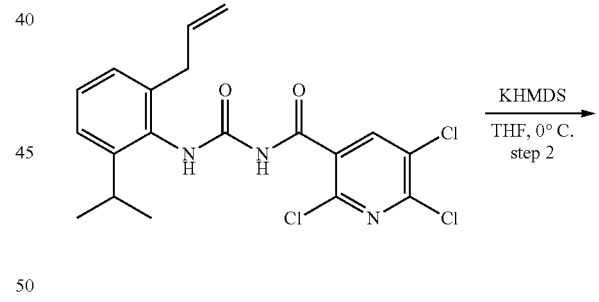

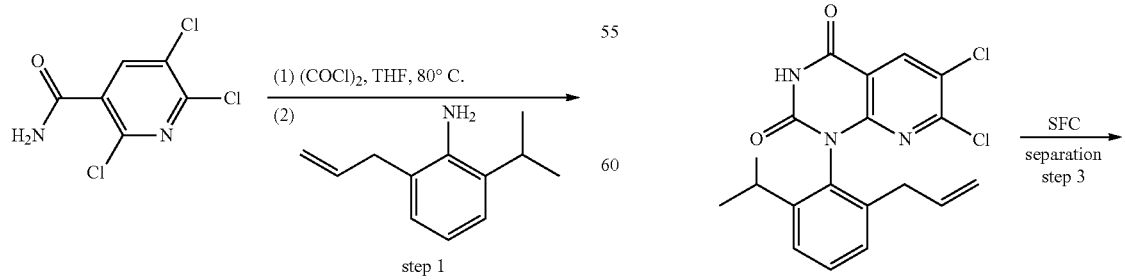

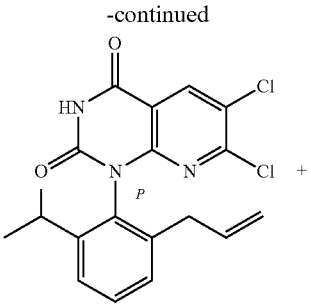
Peak #1
Intermediate 146A
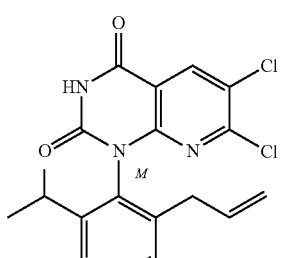
Peak #2
Intermediate 146B
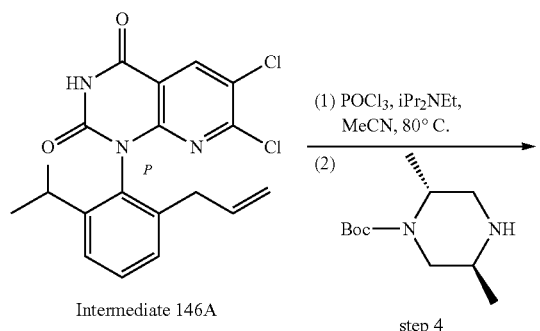
Intermediate 146A
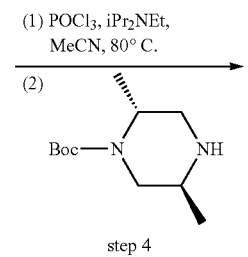
step 4
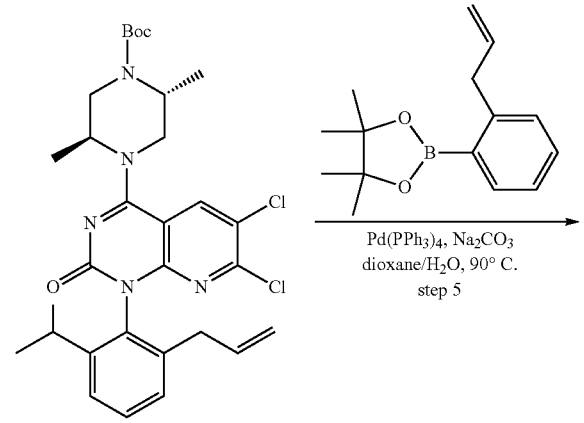
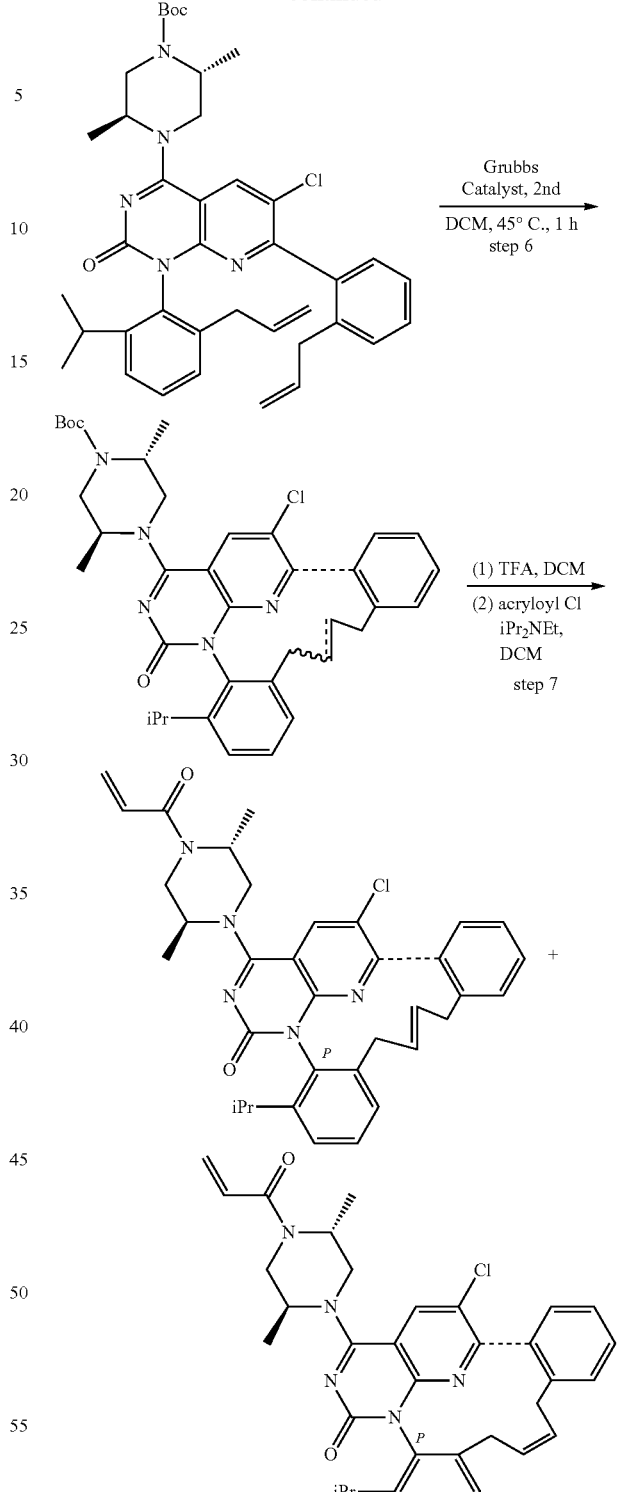
Step 1: N-((2-Allyl-6-isopropylphenyl)carbamoyl)-2,5,6-trichloronicotinamide
A 100-mL round-bottomed flask was charged with 2,5,6-trichloronicotinamide (1.89 g, 8.38 mmol, WuXi) and tetrahydrofuran (32 ml). Oxalyl chloride (2.0 M solution in DCM, 5.0 mL, 10.06 mmol) was added to the reaction mixture and stirred at 75° C. for 1.5 h. The mixture was allowed to cool to rt and concentrated in vacuo.

The resulting residue was redissolved into tetrahydrofuran (32 mL) and treated with 2-(prop-2-en-1-yl)-6-(propan-2-yl)aniline (1.5 mL, 8.38 mmol, Enamine Ltd.). The mixture was stirred at 0 for 10 min. The reaction mixture was partitioned between water (50 mL) and EtOAc (50 mL). The aqueous phase was extracted with EtOAc (50 mL). The aqueous phase was then saturated with solid NaCl and further extracted with EtOAc (200 mL). The combined organic phases were dried over $Na_2SO_4$ and concentrated to give N-((2-allyl-6-isopropylphenyl)carbamoyl)-2,5,6-trichloronicotinamide (3.81 g, 8.94 mmol, 100% yield) as a tan foam. m/z (ESI, +ve ion): 426.0 $(M+H)^+$.

Step 2: 1-(2-Allyl-6-isopropylphenyl)-6,7-dichloropyrido[2,3-d]pyrimidine-2,4(1H,3H)-dione A mixture of N-((2-allyl-6-isopropylphenyl)carbamoyl)-2,5,6-trichloronicotinamide (3.58 g, 8.38 mmol) in tetrahydrofuran (27.9 mL) at 0° C. was treated with potassium bis(trimethylsilyl)amide (1.0 M in THF, 16.8 mL, 16.76 mmol) The resulting mixture was stirred at 0° C. for 10 min. The reaction mixture was quenched with saturated aqueous $NH_4Cl$ (30 mL) and extracted with EtOAc (30 mL×2). The organic layers were combined, washed with brine (50 mL), dried over $Na_2SO_4$, filtered, and concentrated in vacuo. The resulting crude product was sonicated in MeOH (20 mL). The resulting solid was collected by filtration, washed with MeOH and dried to give pure 1-(2-allyl-6-isopropylphenyl)-6,7-dichloropyrido[2,3-d]pyrimidine-2,4(1H,3H)-dione (2.636 g, 6.75 mmol, 81% yield) as a tan solid. LC/MS purity: 99% (215 nm); 99% (254 nm). $^1$H NMR (400 MHz, DMSO-$d_6$) δ 12.18 (s, 1H), 8.56 (s, 1H), 7.32-7.49 (m, 2H), 7.20 (dd, J=7.3, 1.5 Hz, 1H), 5.66 (ddt, J=16.9, 10.1, 6.8, 6.8 Hz, 1H), 4.80-4.90 (m, 2H), 3.10 (d, J=6.6 Hz, 2H), 2.64-2.74 (m, 1H), 1.08 (d, J=6.8 Hz, 3H), 0.99 (d, J=6.6 Hz, 3H). m/z (ESI, +ve ion): 390.0 $(M+H)^+$.

Step 3: (P)-1-(2-Allyl-6-isopropylphenyl)-6,7-dichloropyrido[2,3-d]pyrimidine-2,4(1H,3H)-dione and (M)-1-(2-Allyl-6-isopropylphenyl)-6,7-dichloropyrido[2,3-d]pyrimidine-2,4(1H,3H)-dione A mixture of atropisomers 1-(2-allyl-6-isopropylphenyl)-6,7-dichloropyrido[2,3-d]pyrimidine-2,4(1H,3H)-dione (2.15 g) was purified by SFC (WelkoSS, 5 µm, 21×250 mm two in series, total 50 cm, 15% MeOH/CO2, 80 mL/min, 90 bar) to obtain two peaks: Peak 1 (Intermediate 146A, (P)-isomer, 780 mg, >99% ee) and Peak 2 (Intermediate 146B, (M)-isomer, 850 mg, 95.3% ee).

Step 4: (P)-tert-Butyl (2R,5S)-4-(1-(2-allyl-6-isopropylphenyl)-6,7-dichloro-2-oxo-1,2-dihydropyrido[2,3-d]pyrimidin-4-yl)-2,5-dimethylpiperazine-1-carboxylate A mixture of (P)-1-(2-allyl-6-isopropylphenyl)-6,7-dichloropyrido[2,3-d]pyrimidine-2,4(1H,3H)-dione (Peak 1) (780 mg, 2.00 mmol) and DIPEA (1.75 mL, 9.99 mmol) in acetonitrile (10 mL) was treated with phosphorous oxychloride (0.56 mL, 6.00 mmol) at room temperature. The mixture was stirred at 80° C. for 30 min. The reaction mixture was evaporated to dryness to give (P)-1-(2-allyl-6-isopropylphenyl)-4,6,7-trichloropyrido[2,3-d]pyrimidin-2(1H)-one as a brown oil. m/z (ESI, +ve ion): 408.0 $(M+H)^+$. The resulting brown solid was used in next step without purification.

The mixture of (P)-1-(2-allyl-6-isopropylphenyl)-4,6,7-trichloropyrido[2,3-d]pyrimidin-2(1H)-one and DIPEA (1.75 mL, 9.99 mmol) in acetonitrile (10 mL) was added tert-butyl (2R,5S)-2,5-dimethylpiperazine-1-carboxylate (578 mg, 2.70 mmol, AstaTech) and stirred at rt for 15 min. The resulting mixture was diluted with water (15 mL) and extracted with EtOAc (3×15 mL). The organic extract was dried over $MgSO_4$. The solution was filtered and concentrated in vacuo to give the crude material as a brown solid. The crude material brown solid which was purified by silica gel chromatography (0-50% of EtOAc/heptane) to provide (P)-tert-butyl (2R,5S)-4-(1-(2-allyl-6-isopropylphenyl)-6,7-dichloro-2-oxo-1,2-dihydropyrido[2,3-d]pyrimidin-4-yl)-2,5-dimethylpiperazine-1-carboxylate (696 mg, 1.19 mmol, 59.4% yield) as a light yellow solid. $^1$H NMR (400 MHz, DMSO-$d_6$) δ 8.38 (s, 1H), 7.29-7.46 (m, 2H), 7.18 (dd, J=7.3, 1.2 Hz, 1H), 5.66 (ddt, J=17.8, 9.2, 6.8, 6.8 Hz, 1H), 4.82-4.86 (m, 1H), 4.81 (s, 1H), 4.75 (br s, 1H), 4.16-4.42 (m, 1H), 4.08 (br d, J=13.7 Hz, 1H), 3.79 (br s, 1H), 3.67 (br d, J=12.9 Hz, 1H), 3.34-3.51 (m, 1H), 2.93-3.11 (m, 2H), 2.42 (dt, J=13.7, 6.8 Hz, 1H), 1.44 (s, 9H), 1.32 (d, J=6.6 Hz, 3H), 1.13 (br d, J=6.6 Hz, 3H), 1.04 (d, J=6.8 Hz, 3H), 0.97 (d, J=6.8 Hz, 3H). m/z (ESI, +ve ion): 526.2 $(M+H)^+$.

Step 5: (P)-tert-Butyl (2R,5S)-4-(1-(2-allyl-6-isopropylphenyl)-7-(2-allylphenyl)-6-chloro-2-oxo-1,2-dihydropyrido[2,3-d]pyrimidin-4-yl)-2,5-dimethylpiperazine-1-carboxylate A mixture of (P)-tert-butyl (2R,5S)-4-(1-(2-allyl-6-isopropylphenyl)-6,7-dichloro-2-oxo-1,2-dihydropyrido[2,3-d]pyrimidin-4-yl)-2,5-dimethylpiperazine-1-carboxylate (250 mg, 0.43 mmol), 2-(2-allylphenyl)-4,4,5,5-tetramethyl-1,3,2-dioxaborolane (156 mg, 0.64 mmol), tetrakis(triphenylphosphine)palladium (49.3 mg, 0.04 mmol), and sodium carbonate (226 mg, 2.13 mmol) in 1,4-dioxane (1.5 mL)/water (0.8 mL) was stirred at 90° for 1 h. The resulting mixture was evaporated to dryness. The resulting crude product was purified by silica gel chromatography (0-50% of EtOAc/heptane) to provide (P)-tert-butyl (2R,5S)-4-(1-(2-allyl-6-isopropylphenyl)-7-(2-allylphenyl)-6-chloro-2-oxo-1,2-dihydropyrido[2,3-d]pyrimidin-4-yl)-2,5-dimethylpiperazine-1-carboxylate (169 mg, 0.25 mmol, 59.5% yield) a light yellow solid. $^1$H NMR (400 MHz, DMSO-$d_6$) δ 8.38 (s, 1H), 7.31-7.40 (m, 1H), 7.19-7.31 (m, 4H), 7.06-7.14 (m, 2H), 5.60-5.75 (m, 1H), 5.49 (ddt, J=16.9, 10.1, 6.7, 6.7 Hz, 1H), 4.74-4.91 (m, 5H), 4.22-4.43 (m, 1H), 4.09 (br d, J=13.9 Hz, 1H), 3.81-3.90 (m, 1H), 3.70 (dd, J=13.5, 2.3 Hz, 1H), 3.38-3.58 (m, 1H), 2.90-3.14 (m, 4H), 2.43-2.47 (m, 1H), 1.45 (s, 9H), 1.34 (d, J=6.4 Hz, 3H), 1.16 (br d, J=6.4 Hz, 3H), 1.03 (d, J=6.8 Hz, 3H), 0.90 (d, J=6.8 Hz, 3H). m/z (ESI, +ve ion): 668.2 $(M+H)^+$.

Step 6: (P)-tert-Butyl (2R,5S)-4-(26-chloro-16-isopropyl-22-oxo-21,22-dihydro-2(1,7)-pyrido[2,3-d]pyrimidin-1,3(1,2)-dibenzenacycloheptaphan-5-en-24-yl)-2,5-dimethylpiperazine-1-carboxylate A mixture of Grubbs Catalyst, $2^{nd}$ generation (tricyclohexylphosphine[1,3-bis(2,4,6-trimethylphenyl)-4,5-dihydroimidazol-2-ylidene][benzylidine]rut) (43 mg, 0.05 mmol, Sigma-Aldrich Corporation), (P)-tert-butyl (2R,5S)-4-(1-(2-allyl-6-isopropylphenyl)-7-(2-allylphenyl)-6-chloro-2-oxo-1,2-dihydropyrido[2,3-d]pyrimidin-4-yl)-2,5-dimethylpiperazine-1-carboxylate (168 mg, 0.25 mmol) in dichloromethane (14 mL) was stirred at 450 for 1 h. The resulting mixture was evaporated to dryness. The resulting crude product was purified by silica gel chromatography (0-50% of EtOAc/heptane) to provide (P)-tert-butyl (2R, 5S)-4-(26-chloro-16-isopropyl-22-oxo-21,22-dihydro-2(1, 7)-pyrido[2,3-d]pyrimidina-1,3(1,2)-dibenzenacycloheptaphan-5-en-24-yl)-2,5-dimethylpiperazine-1-carboxylate (120 mg, 0.19 mmol, 74.6% yield) as a light yellow solid. $^1$H NMR (400 MHz, DMSO-$d_6$) δ 8.41-8.48 (m, 1H), 7.22-7.40 (m, 5H), 7.04-7.14 (m, 2H), 4.86-4.95 (m, 1H), 4.80-4.84 (m, 1H), 4.17-4.36 (m, 1H), 3.93-4.04 (m, 1H), 3.85-3.91 (m, 1H), 3.50-3.75 (m, 2H), 3.22-3.29 (m, 1H), 3.02 (br dd, J=15.8, 3.3 Hz, 1H), 2.86 (br dd, J=15.0, 9.0 Hz, 1H), 2.61-2.80 (m, 2H), 2.52-2.57 (m, 1H), 1.45 (s, 9H), 1.27 (br d, J=5.0 Hz, 3H), 1.07 (br d, J=6.8 Hz, 6H), 0.93 (d, J=6.8 Hz, 3H). m/z (ESI, +ve ion): 640.2 (M+H)$^+$.

Step 7: A mixture of (P)-(9Z)-19-Chloro-22-((2S, 5R)-2,5-dimethyl-4-(2-propenoyl)-1-piperazinyl)-3-(2-propanyl)-1,23,26-triazapentacyclo[16.6.2.0~2, 7~.0~12,17~.0~21,25~]hexacosa-2,4,6,9,12,14,16, 18,20,22,25-undecaen-24-one and (P)-19-chloro-22-((2S,5R)-2,5-dimethyl-4-(2-propenoyl)-1-piperazinyl)-3-(2-propanyl)-1,23,26-triazapentacyclo [6.6.2.0~2,7~.0~12,17~.0~21,25-]hexacosa-2,4,6,9, 12,14,16,18,20,22,25-undecaen-24-one To a solution of (P)-tert-butyl (2R,5S)-4-(26-chloro-16-isopropyl-22-oxo-21,22-dihydro-2(1,7)-pyrido[2,3-d]pyrimidina-1,3(1,2)-dibenzenacycloheptaphan-5-en-24-yl)-2, 5-dimethylpiperazine-1-carboxylate (120 mg, 0.19 mmol) in dichloromethane (2.0 mL) was treated with 2,2,2-trifluoroacetic acid (2.0 mL, 0.19 mmol) at rt and stirred for 1.5 h. The reaction went to completion and the resulting mixture was concentrated to afford (P)-26-chloro-24-((2S,5R)-2,5-dimethylpiperazin-1-yl)-16-isopropyl-21,22-dihydro-2(1, 7)-pyrido[2,3-d]pyrimidina-1,3(1,2)-dibenzenacycloheptaphan-5-en-22-one, m/z (ESI, +ve ion): 540.2 (M+H)$^+$.

A mixture of the above crude product and DIPEA (0.2 mL, 0.94 mmol) in dichloromethane (2.0 mL) was added acryloyl chloride (1.1 M in DCM, 0.2 mL, 0.19 mmol) at 0° C. and stirred for 5 min. The resulting mixture was evaporated to dryness. The resulting crude product was purified by silica gel chromatography (0-100% of EtOAc/heptane) to provide a mixture of (P)-(9Z)-19-chloro-22-((2S,5R)-2,5-dimethyl-4-(2-propenoyl)-1-piperazinyl)-3-(2-propanyl)-1, 23,26-triazapentacyclo[16.6.2.0~2,7~.0~12,17~.0~21,25~] hexacosa-2,4,6,9,12,14,16,18,20,22,25-undecaen-24-one and (P)-19-chloro-22-((2S,5R)-2,5-dimethyl-4-(2-propenoyl)-1-piperazinyl)-3-(2-propanyl)-1,23,26-triazapentacyclo[16.6.2.0·2,7~.0~12,17~.0~21,25~]hexacosa-2,4,6,9,12, 14,16,18,20,22,25-undecaen-24-one (1:6 ratio, 94 mg, 0.16 mmol, 84% yield) as a light yellow foam. $^1$H NMR (400 MHz, DMSO-$d_6$) δ 8.48 (br d, J=8.7 Hz, 1H), 7.22-7.37 (m, 5H), 7.05-7.17 (m, 2H), 6.76-6.93 (m, 1H), 6.19 (dd, J=16.7, 2.2 Hz, 1H), 5.72-5.80 (m, 1H), 4.95 (br s, 1H), 4.84 (br d, J=4.6 Hz, 1H), 4.40-4.77 (m, 1H), 3.56-4.18 (m, 4H), 3.23-3.29 (m, 1H), 3.03 (br dd, J=15.4, 3.2 Hz, 1H), 2.83-2.93 (m, 1H), 2.74-2.82 (m, 1H), 2.64-2.73 (m, 1H), 2.54-2.60 (m, 1H), 1.27 (br dd, J=18.1, 6.5 Hz, 3H), 1.05-1.21 (m, 6H), 0.94 (d, J=6.8 Hz, 3H). m/z (ESI, +ve ion): 594.2 (M+H)$^+$.

TABLE 146

Compounds 146-2 to 146-3 were prepared following the procedure described in Method 146, Steps 1-7, above as follows:

| Ex. # | Chemical structure | Name | Method Changes | Reagent |
|---|---|---|---|---|
| 146-2 | 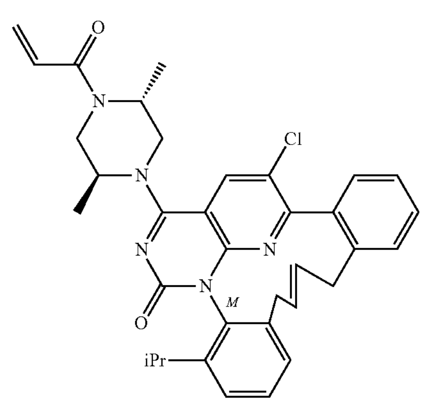 | (M)-(9Z)-19-Chloro-22-((2S,5R)-2,5-dimethyl-4-(2-propenoyl)-1-piperazinyl)-3-(2-propanyl)-1,23,26-triazapentacyclo[16.6.2.0~2,7~.0~12,17~.0~21,25~]hexacosa-2,4,6,9,12,14,16,18,20,22,25-undecaen-24-one, (M)-19-chloro-22-((2S,5R)-2,5-dimethyl-4-(2-propenoyl)-1-piperazinyl)-3-(2-propanyl)-1,23,26-triazapentacyclo[16.6.2.0~2,7~.0~12,17~.0~21,25~]hexacosa-2,4,6,9,12,14,16,18,20,22,25-undecaen-24-one | None | Step 3: Intermediate 146B |

TABLE 146-continued

Compounds 146-2 to 146-3 were prepared following the procedure described in Method 146, Steps 1-7, above as follows:

| Ex. # | Chemical structure | Name | Method Changes | Reagent |
|---|---|---|---|---|
| 146-3 | 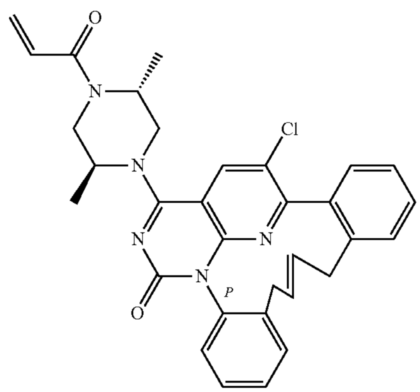 | (P)-19-Chloro-22-((2S,5R)-2,5-dimethyl-4-(2-propenoyl)-1-piperazinyl)-1,23,26-triazapentacyclo[16.6.2.0~2,7~.0~12,17~.0~21,25~]hexacosa-2,4,6,9,12,14,16,18,20,22,25-undecaen-24-one, (P)-(9Z)-19-chloro-22-((2S,5R)-2,5-dimethyl-4-(2-propenoyl)-1-piperazinyl)-1,23,26-triazapentacyclo[16.6.2.0~2,7~.0~12,17~.0~21,25~]hexacosa-2,4,6,9,12,14,16,18,20,22,25-undecaen-24-one, (M)-19-chloro-22-((2S,5R)-2,5-dimethyl-4-(2-propenoyl)-1-piperazinyl)-1,23,26-triazapentacyclo[16.6.2.0~2,7~.0~12,17~.0~21,25~]hexacosa-2,4,6,9,12,14,16,18,20,22,25-undecaen-24-one, (M)-(9Z)-19-chloro-22-((2S,5R)-2,5-dimethyl-4-(2-propenoyl)-1-piperazinyl)-1,23,26-triazapentacyclo[16.6.2.0~2,7~.0~12,17~.0~21,25~]hexacosa-2,4,6,9,12,14,16,18,20,22,25-undecaen-24-one | Omit Step 3 | Step 1: 2-allylaniline hydrochloride salt (TCI America) |

TABLE 146-continued

Compounds 146-2 to 146-3 were prepared following the procedure described in Method 146, Steps 1-7, above as follows:

| Ex. # | Chemical structure | Name | Method Changes | Reagent |
|---|---|---|---|---|
| 146-4 | 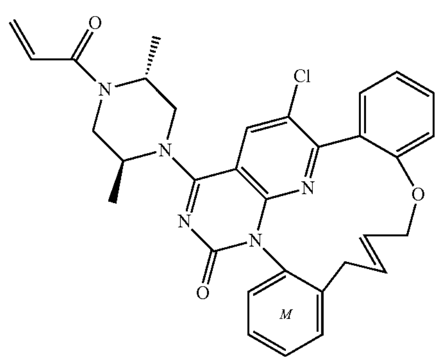 | 20-chloro-23-((2S,5R)-2,5-dimethyl-4-(2-propenoyl)-1-piperazinyl)-12-oxa-1,24,27-triazapentacyclo[17.6.2.0~2,7~.0~13,18~.0~22,26~]heptacosa-2,4,6,9,13,15,17,19,21,23,26-undecaen-25-one | After Step 5, added an alkylation step (allyl chloride, $K_2CO_3$, $CH_3CN$, RT) | Step 5: 2-allyloxyphenyl-boronic acid (Combi-Blocks Inc.) |

TABLE 147

Separated Compound Examples From Methods

| Ex. # | Chemical Structure | Name | Separation conditions |
|---|---|---|---|
| 55-51-1 | 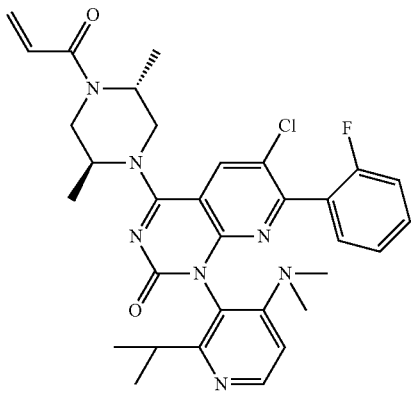<br>1st-eluting isomer | 6-Chloro-1-[4-(dimethylamino)-2-isopropyl-3-pyridyl]-4-[(2S,5R)-2,5-dimethyl-4-prop-2-enoyl-piperazin-1-yl]-7-(2-fluorophenyl)pyrido[2,3-d]pyrimidin-2-one | SFC: (R,R) Whelk-01 (150 × 4.6 mm, 5 μm); Mobile Phase: 70:30 B: methanol with 0.2% TEA Flow Rate: 4.0 mL/min Oven/Column Temp.: 23 C. Outlet Pressure: 100 bar |
| 55-51-2 | 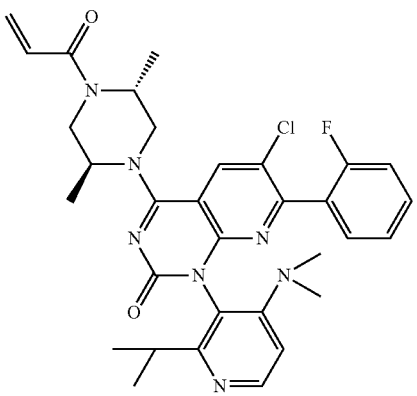<br>2nd-eluting isomer | 6-Chloro-1-[4-(dimethylamino)-2-isopropyl-3-pyridyl]-4-[(2S,5R)-2,5-dimethyl-4-prop-2-enoyl-piperazin-1-yl]-7-(2-fluorophenyl)pyrido[2,3-d]pyrimidin-2-one | SFC: (R,R) Whelk-01 (150 × 4.6 mm, 5 μm) Mobile Phase: 70:30 B: methanol with 0.2% TEA Flow Rate: 4.0 mL/min Oven/Column Temp.: 23 C. Outlet Pressure: 100 bar |
| 55-58-1 | 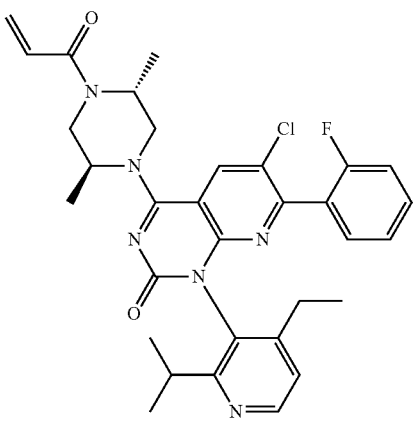<br>1st-eluting isomer | 6-Chloro-4-[(2S,5R)-2,5-dimethyl-4-prop-2-enoyl-piperazin-1-yl]-1-(4-ethyl-2-isopropyl-3-pyridyl)-7-(2-fluorophenyl)pyrido[2,3-d]pyrimidin-2-one | SFC: IA (150 × 4.6 mm, 5 μm) Mobile Phase: 80:20 B: ethanol Flow Rate: 4.0 mL/min Oven/Column Temp.: 23 C. Outlet Pressure: 100 bar |

TABLE 147-continued

Separated Compound Examples From Methods

| Ex. # | Chemical Structure | Name | Separation conditions |
|---|---|---|---|
| 55-58-2 | 2nd-eluting isomer | 6-Chloro-4-[(2S,5R)-2,5-dimethyl-4-prop-2-enoyl-piperazin-1-yl]-1-(4-ethyl-2-isopropyl-3-pyridyl)-7-(2-fluorophenyl)pyrido[2,3-d]pyrimidin-2-one | SFC: IA (150 × 4.6 mm, 5 μm) Mobile Phase: 80:20 B: ethanol Flow Rate: 4.0 mL/min Oven/Column Temp.: 23 C. Outlet Pressure: 100 bar |
| 80-10-1 | 1st-eluting isomer | 6-chloro-4-[(2S,5R)-2,5-dimethyl-4-prop-2-enoyl-piperazin-1-yl]-7-(2-fluorophenyl)-1-[2-isopropyl-6-(pyrrolidin-1-ylmethyl)phenyl]pyrido[2,3-d]pyrimidin-2-one | SFC Whelk-01 (250 × 21 mm, 5 μm), 45:55 methanol with 0.2% TEA:CO2, 50 g/min, 102 bar |
| 80-10-2 | 2nd-eluting isomer | 6-chloro-4-[(2S,5R)-2,5-dimethyl-4-prop-2-enoyl-piperazin-1-yl]-7-(2-fluorophenyl)-1-[2-isopropyl-6-(pyrrolidin-1-ylmethyl)phenyl]pyrido[2,3-d]pyrimidin-2-one | SFC Whelk-01 (250 × 21 mm, 5 μm), 45:55 methanol with 0.2% TEA:CO2, 50 g/min, 102 bar |

TABLE 147-continued

Separated Compound Examples From Methods

| Ex. # | Chemical Structure | Name | Separation conditions |
|---|---|---|---|
| 80-14-1 | 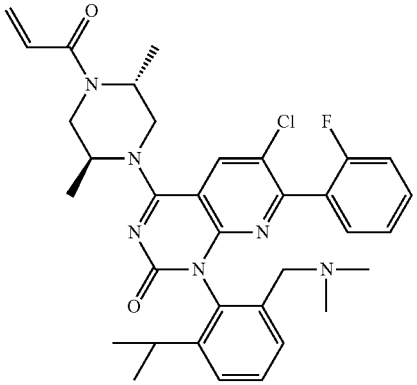<br>1st-eluting isomer | 6-chloro-1-[2-[(dimethylamino)methyl]-6-isopropyl-phenyl]-4-[(2S,5R)-2,5-dimethyl-4-prop-2-enoyl-piperazin-1-yl]-7-(2-fluorophenyl)pyrido[2,3-d]pyrimidin-2-one | SFC Chiralpak ID (250 × 20 mm, 220-nm), 45:55 methanol with 0.2% TEA:$CO_2$, 80 ml/min, 207 bar |
| 80-14-2 | 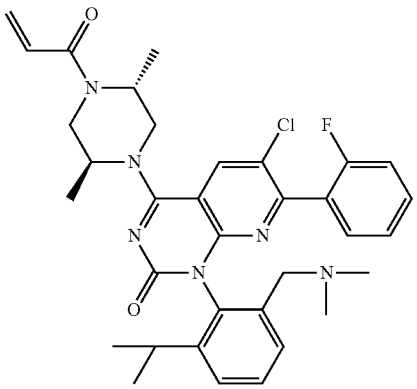<br>2nd-eluting isomer | 6-chloro-1-[2-[(dimethylamino)methyl]-6-isopropyl-phenyl]-4-[(2S,5R)-2,5-dimethyl-4-prop-2-enoyl-piperazin-1-yl]-7-(2-fluorophenyl)pyrido[2,3-d]pyrimidin-2-one | SFC Chiralpak ID (250 × 20 mm, 220-nm), 45:55 methanol with 0.2% TEA:$CO_2$, 80 ml/min, 207 bar |
| 80-16-1 | 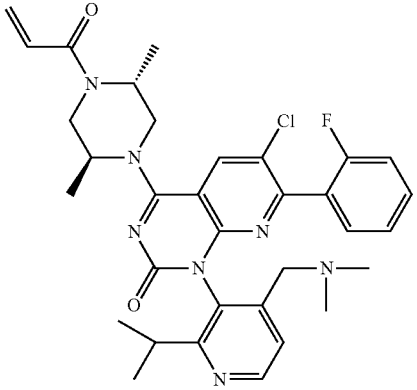<br>1st-eluting isomer | 6-chloro-1-[4-[(dimethylamino)methyl]-2-isopropyl-3-pyridyl]-4-[(2S,5R)-2,5-dimethyl-4-prop-2-enoyl-piperazin-1-yl]-7-(2-fluorophenyl)pyrido[2,3-d]pyrimidin-2-one | SFC OX-H (150 × 21 mm, 5 μm), 30:70 methanol with 0.2% TEA:$CO_2$, 70 ml/min |

TABLE 147-continued

Separated Compound Examples From Methods

| Ex. # | Chemical Structure | Name | Separation conditions |
|---|---|---|---|
| 80-16-2 | 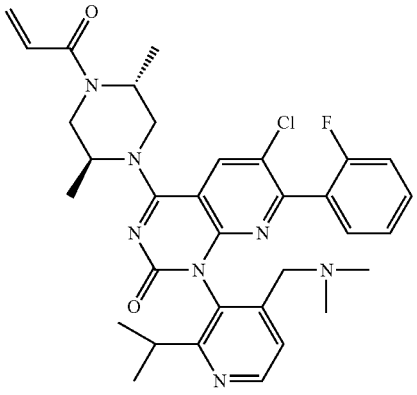 2<sup>nd</sup>-eluting isomer | 6-chloro-1-[4-[(dimethylamino)methyl]-2-isopropyl-3-pyridyl]-4-[(2S,5R)-2,5-dimethyl-4-prop-2-enoyl-piperazin-1-yl]-7-(2-fluorophenyl)pyrido[2,3-d]pyrimidin-2-one | SFC OX-H (150 × 21 mm, 5 µm), 30:70 methanol with 0.2% TEA:CO$_2$, 70 ml/min |
| 80-18-1 | 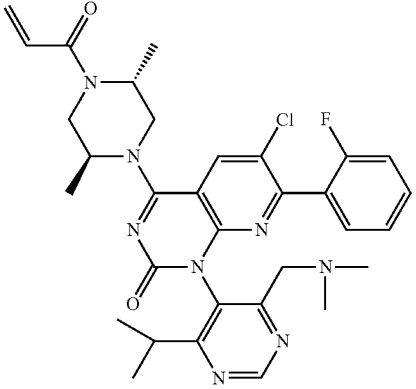 1<sup>st</sup>-eluting isomer | 6-chloro-1-[4-[(dimethylamino)methyl]-6-isopropyl-pyrimidin-5-yl]-4-[(2S,5R)-2,5-dimethyl-4-prop-2-enoyl-piperazin-1-yl]-7-(2-fluorophenyl)pyrido[2,3-d]pyrimidin-2-one | SFC OD (250 × 21 mm, 5 µm), 15:85 methanol with 0.2% TEA:CO$_2$, 80 ml/min, 102 bar followed by SFC OZ (250 × 21 mm, 5 µm), 30:70 methanol with 0.2% TEA:CO$_2$, 65 ml/min, 102 bar |
| 80-18-2 | 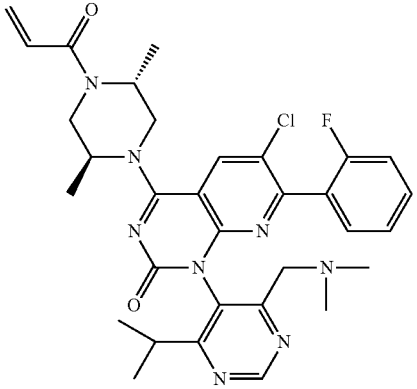 2<sup>nd</sup>-eluting isomer | 6-chloro-1-[4-[(dimethylamino)methyl]-6-isopropyl-pyrimidin-5-yl]-4-[(2S,5R)-2,5-dimethyl-4-prop-2-enoyl-piperazin-1-yl]-7-(2-fluorophenyl)pyrido[2,3-d]pyrimidin-2-one | SFC OD (250 × 21 mm, 5 µm), 15:85 methanol with 0.2% TEA:CO$_2$, 80 ml/min, 102 bar |

TABLE 147-continued

Separated Compound Examples From Methods

| Ex. # | Chemical Structure | Name | Separation conditions |
|---|---|---|---|
| 80-20-1 | 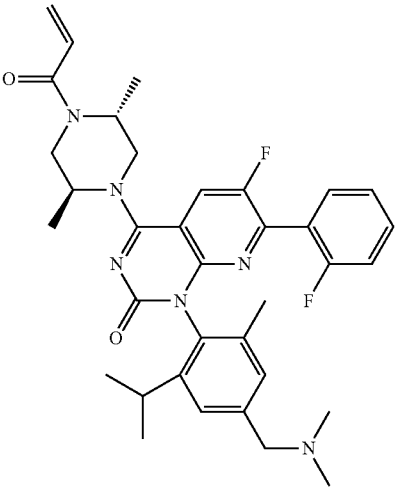<br>1st-eluting isomer | 1-[4-[(Dimethylamino)methyl]-2-isopropyl-6-methyl-phenyl]-4-[(2S,5R)-2-dimethyl-4-prop-2-enoyl-piperazin-1-yl]-6-fluoro-7-(2-fluorophenyl)pyrido[2,3-d]pyrimidin-2-one | Preparative Thar 200 SFC method:<br>Column: (R,R) whelk-01 (250 × 21 mm, 5 u)<br>Mobile Phase: 75:25 (A:B)<br>A: Liquid CO2<br>B: methanol with 0.2% TEA<br>Flow Rate: 60 g/min<br>Column/Oven temp.: ambient temperature<br>220 nm<br>BPR = 102 bar |
| 80-20-2 | 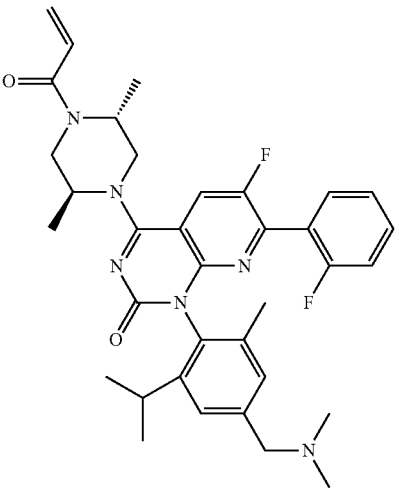<br>2nd-eluting isomer | 1-[4-[(Dimethylamino)methyl]-2-isopropyl-6-methyl-phenyl]-4-[(2S,5R)-2,5-dimethyl-4-prop-2-enoyl-piperazin-1-yl]-6-fluoro-7-(2-fluorophenyl)pyrido[2,3-d]pyrimidin-2-one | Preparative Thar 200 SFC method:<br>Column: (R,R) whelk-01 (250 × 21 mm, 5 u)<br>Mobile Phase: 75:25 (A:B)<br>A: Liquid CO2<br>B: methanol with 0.2% TEA<br>Flow Rate: 60 g/min<br>Column/Oven temp.: ambient temperature<br>220 nm<br>BPR = 102 bar |

TABLE 147-continued

Separated Compound Examples From Methods

| Ex. # | Chemical Structure | Name | Separation conditions |
|---|---|---|---|
| 80-21-1 | 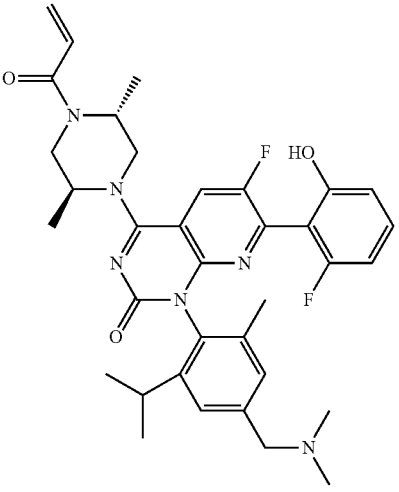<br>1<sup>st</sup>-eluting isomer | 1-[4-[(Dimethylamino)methyl]-2-isopropyl-6-methyl-phenyl]-4-[(2S,5R)-2,5-dimethyl-4-prop-2-enoyl-piperazin-1-yl]-6-fluoro-7-(2-fluoro-6-hydroxy-phenyl)pyrido[2,3-d]pyrimidin-2-one | SFC Whelk-01 (R,R) (250 × 30 mm, 5 μm) 30% MeOH (with 20 mM $NH_3$)/$CO_2$, 180 g/min, 102 bar |
| 80-21-2 | 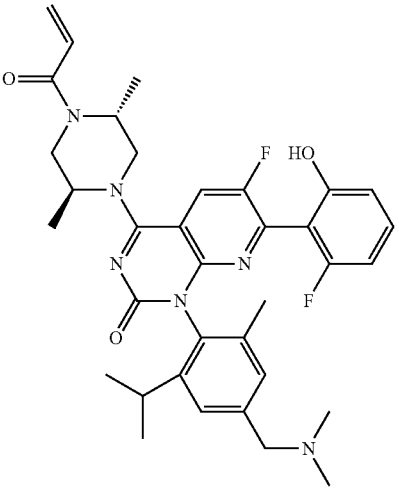<br>2<sup>nd</sup>-eluting isomer | 1-[4-[(Dimethylamino)methyl]-2-isopropyl-6-methyl-phenyl]-4-[(2S,5R)-2,5-dimethyl-4-prop-2-enoyl-piperazin-1-yl]-6-fluoro-7-(2-fluoro-6-hydroxy-phenyl)pyrido[2,3-d]pyrimidin-2-one | SFC Whelk-01 (R,R) (250 × 30 mm, 5 μm) 30% MeOH (with 20 mM $NH_3$)/$CO_2$, 180 g/min, 102 bar |
| 100-1-1 | 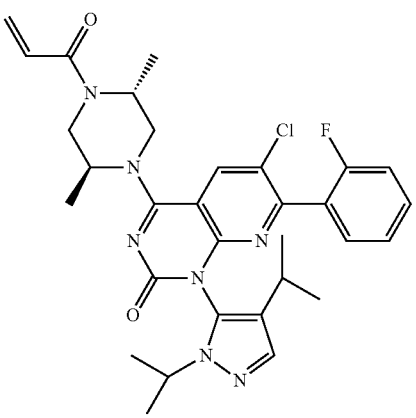<br>1<sup>st</sup>-eluting isomer | 6-Chloro-1-(2,4-diisopropylpyrazol-3-yl)-4-[(2S,5R)-2,5-dimethyl-4-prop-2-enoyl-piperazin-1-yl]-7-(2-fluorophenyl)pyrido[2,3-d]pyrimidin-2-one | SFC OD-H column (5 μm, 2 × 21 × 250 mm, two columns in series, total length 50 cm) F = 80 ml, 20% Methanol, 80% carbon dioxide, Back pressure = 90 bars |

US 11,285,156 B2

TABLE 147-continued

Separated Compound Examples From Methods

| Ex. # | Chemical Structure | Name | Separation conditions |
|---|---|---|---|
| 100-1-2 | 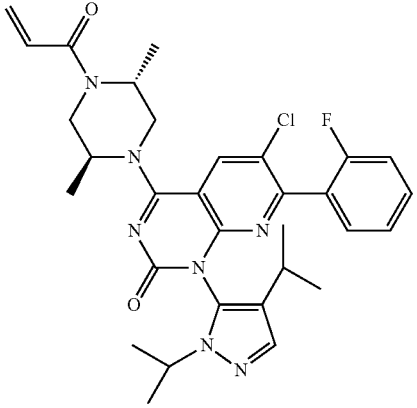<br>2^{nd}-eluting isomer | 6-Chloro-1-(2,4-diisopropylpyrazol-3-yl)-4-[(2S,5R)-2,5-dimethyl-4-prop-2-enoyl-piperazin-1-yl]-7-(2-fluorophenyl)pyrido[2,3-d]pyrimidin-2-one | SFC OD-H column (5 μm, 2 × 21 × 250 mm, two columns in series, total length 50 cm) F = 80 ml, 20% Methanol, 80% carbon dioxide, Back pressure = 90 bars |
| 102-5-1 | 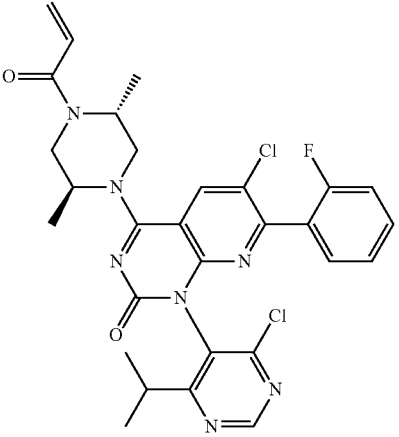<br>1^{st}-eluting isomer | 6-Chloro-1-(4-chloro-6-isopropyl-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one | SFC ID, 21 × 250 mm, 5 μm, 30% MeOH/CO$_2$, 80 g/min, 102 bar |
| 102-5-2 | 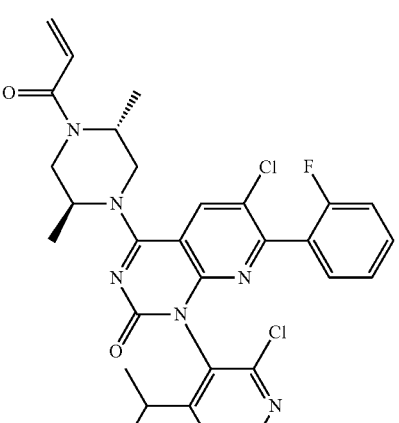<br>2^{nd}-eluting isomer | 6-Chloro-1-(4-chloro-6-isopropyl-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one | SFC ID, 21 × 250 mm, 5 μm, 30% MeOH/CO$_2$, 80 g/min, 102 bar |

TABLE 147-continued

Separated Compound Examples From Methods

| Ex. # | Chemical Structure | Name | Separation conditions |
|---|---|---|---|
| 102-6-1 | 1st-eluting isomer | 6-Chloro-1-(4-chloro-6-isopropyl-pyrimidin-5-yl)-4-[(2S,5R)-2,5-dimethyl-4-prop-2-enoyl-piperazin-1-yl]-7-(o-tolyl)pyrido[2,3-d]pyrimidin-2-one | SFC IF, 21 × 250 mm, 5 μm, 35% MeOH/$CO_2$, 80 mL/min, 90 bar |
| 102-6-2 | 2nd-eluting isomer | 6-Chloro-1-(4-chloro-6-isopropyl-pyrimidin-5-yl)-4-[(2S,5R)-2,5-dimethyl-4-prop-2-enoyl-piperazin-1-yl]-7-(o-tolyl)pyrido[2,3-d]pyrimidin-2-one | SFC IF, 21 × 250 mm, 5 μm, 35% MeOH/$CO_2$, 80 mL/min, 90 bar |
| 102-7-1 | 1st-eluting isomer | 6-Chloro-1-(4-dimethylphosphoryl-2-isopropyl-6-methyl-phenyl)-4-[(2S,5R)-2,5-dimethyl-4-prop-2-enoyl-piperazin-1-yl]-7-(2-fluorophenyl)pyrido[2,3-d]pyrimidin-2-one | SFC: Chiralcel ID (5 μm, 21 × 250 mm) F = 70 ml, 30% Ethanol, 70% carbon dioxide, bpr = 102 bars |

TABLE 147-continued

Separated Compound Examples From Methods

| Ex. # | Chemical Structure | Name | Separation conditions |
|---|---|---|---|
| 102-7-2 | 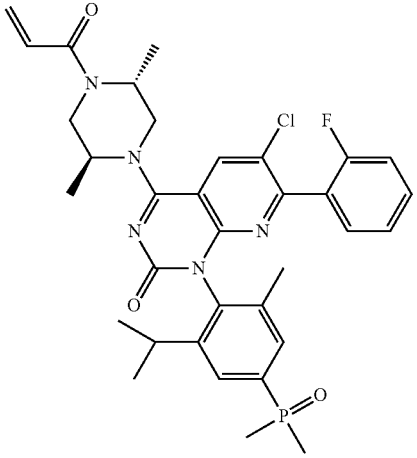<br>2<sup>nd</sup>-eluting isomer | 6-Chloro-1-(4-dimethylphosphoryl-2-isopropyl-6-methyl-phenyl)-4-[(2S,5R)-2,5-dimethyl-4-prop-2-enoyl-piperazin-1-yl]-7-(2-fluorophenyl)pyrido[2,3-d]pyrimidin-2-one | SFC: Chiralcel ID (5 μm, 21 × 250 mm) F = 70 ml, 30% Ethanol, 70% carbon dioxide, bpr = 102 bars |
| 103-1-1 | 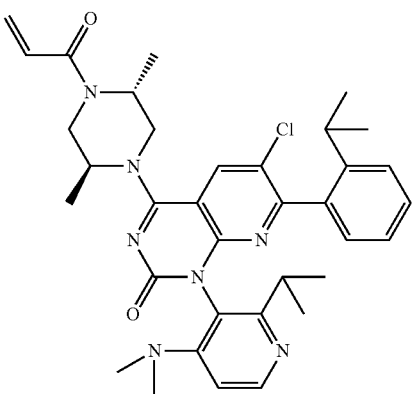<br>1<sup>st</sup>-Eluting Isomer | 6-Chloro-1-[4-(dimethylamino)-2-isopropyl-3-pyridyl]-4-[(2S,5R)-2,5-dimethyl-4-prop-2-enoyl-piperazin-1-yl]-7-(2-isopropylphenyl)pyrido[2,3-d]pyrimidin-2-one | SFC Welko (RR) (5 μm, 21 × 250 mm), 80 ml/min, 50% MeOH (0.2% triethylamine), 50% carbon dioxide, bpr = 90 bars |
| 103-1-2 | 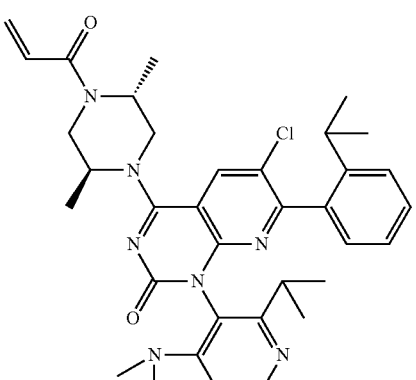<br>2<sup>nd</sup> Eluting Isomer | 6-Chloro-1-[4-(dimethylamino)-2-isopropyl-3-pyridyl]-4-[(2S,5R)-2,5-dimethyl-4-prop-2-enoyl-piperazin-1-yl]-7-(2-isopropylphenyl)pyrido[2,3-d]pyrimidin-2-one | SFC Welko (RR) (5 μm, 21 × 250 mm), 80 ml/min, 50% MeOH (0.2% triethylamine), 50% carbon dioxide, bpr = 90 bars |

TABLE 147-continued

Separated Compound Examples From Methods

| Ex. # | Chemical Structure | Name | Separation conditions |
|---|---|---|---|
| 103-6-1 | 1st Eluting Peak | 6-Chloro-1-[4-(diethylamino)-2-isopropyl-3-pyridyl]-4-[(2S,5R)-2,5-dimethyl-4-prop-2-enoyl-piperazin-1-yl]-7-(2-isopropylphenyl)pyrido[2,3-d]pyrimidin-2-one | SFC OD-H (21 × 250 mm, 5 μm), 80 ml/min, 15% MeOH, 85% carbon dioxide, bpr = 90 bars |
| 103-6-2 | 2nd Eluting Peak | 6-Chloro-1-[4-(diethylamino)-2-isopropyl-3-pyridyl]-4-[(2S,5R)-2,5-dimethyl-4-prop-2-enoyl-piperazin-1-yl]-7-(2-isopropylphenyl)pyrido[2,3-d]pyrimidin-2-one | SFC OD-H (21 × 250 mm, 5 μm), 80 ml/min, 15% MeOH, 85% carbon dioxide, bpr = 90 bars |
| 103-7-1 | 1st Eluting Peak | 6-Chloro-1-[4-(dimethylamino)-2-isopropyl-3-pyridyl]-4-[(2S,5R)-2,5-dimethyl-4-prop-2-enoyl-piperazin-1-yl]-7-(o-tolyl)pyrido[2,3-d]pyrimidin-2-one | SFC (R,R) Whelk-01 (21 × 250 mm, 5 μm), 80 ml/min, 35% MeOH (0.2% TEA), 65% carbon dioxide, bpr = 102 bars |

TABLE 147-continued

Separated Compound Examples From Methods

| Ex. # | Chemical Structure | Name | Separation conditions |
|---|---|---|---|
| 103-7-2 | 2nd Eluting Peak | 6-Chloro-1-[4-(dimethylamino)-2-isopropyl-3-pyridyl]-4-[(2S,5R)-2,5-dimethyl-4-prop-2-enoyl-piperazin-1-yl]-1-(o-tolyl)pyrido[2,3-d]pyrimidin-2-one | SFC (R,R) Whelk-01 (21 × 250 mm, 5 μm), 80 ml/min, 35% MeOH (0.2% TEA), 65% carbon dioxide, bpr = 102 bars |
| 103-8-1 | 1st Eluting Peak | 4-((2S,5R)-4-acryloyl-2,5-dimethylpiperazin-1-yl)-6-chloro-1-(4-(diethylamino)-2-isopropylpyridin-3-yl)-7-(o-tolyl)pyrido[2,3-d]pyrimidin-2(1H)-one | SFC OD (21 × 150 mm, 5 μm), 80 ml/min, 20% MeOH (0.2% TEA), 80% carbon dioxide, bpr = 102 bars |
| 103-8-2 | 2nd Eluting Peak | 4-((2S,5R)-4-acryloyl-2,5-dimethylpiperazin-1-yl)-6-chloro-1-(4-(diethylamino)-2-isopropylpyridin-3-yl)-7-(o-tolyl)pyrido[2,3-d]pyrimidin-2(1H)-one | SFC OD (21 × 150 mm, 5 μm), 80 ml/min, 20% MeOH (0.2% TEA), 80% carbon dioxide, bpr = 102 bars |

TABLE 147-continued

Separated Compound Examples From Methods

| Ex. # | Chemical Structure | Name | Separation conditions |
|---|---|---|---|
| 106-6-1 | 1st-eluting isomer | 6-Chloro-4-[(2S,5R)-2,5-dimethyl-4-prop-2-enoyl-piperazin-1-yl]-7-(2-fluorophenyl)-1-(2-isopropyl-4-methyl-3-pyridyl)pteridin-2-one | SFC: Column: ID (250 × 21 mm, 5 μm) Mobile Phase: 70:30 (A:B) A: Liquid CO2 B: MeOH Flow Rate: 80 g/min Column/Oven temp.: ambient temperature BPR = 187 bar |
| 106-6-2 | 2nd-eluting isomer | 6-Chloro-4-[(2S,5R)-2,5-dimethyl-4-prop-2-enoyl-piperazin-1-yl]-7-(2-fluorophenyl)-1-(2-isopropyl-4-methyl-3-pyridyl)pteridin-2-one | SFC: Column: ID (250 × 21 mm, 5 μm) Mobile Phase: 70:30 (A:B) A: Liquid CO2 B: MeOH Flow Rate: 80 g/min Column/Oven temp.: ambient temperature BPR = 187 bar |
| 106-7-1 | 1st-eluting isomer | 6-Chloro-4-[(2R,6S)-2,6-dimethyl-4-prop-2-enoyl-piperazin-1-yl]-7-(2-fluorophenyl)-1-(2-isopropyl-4-methyl-3-pyridyl)pteridin-2-one | SFC: Chiralcel AS-H (5 um, 21 × 250 mm) F = 80 ml, 15% methanol, 85% carbon dioxide, back pressure = 90 bars |

TABLE 147-continued

Separated Compound Examples From Methods

| Ex. # | Chemical Structure | Name | Separation conditions |
|---|---|---|---|
| 106-7-2 | 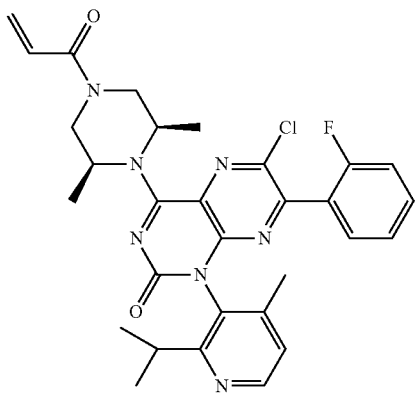<br>2<sup>nd</sup>-eluting isomer | 6-Chloro-4-[(2R,6S)-2,6-dimethyl-4-prop-2-enoyl-piperazin-1-yl]-7-(2-fluorophenyl)-1-(2-isopropyl-4-methyl-3-pyridyl)pteridin-2-one | SFC: Chiralcel AS-H (5 um, 21 × 250 mm) F = 80 ml, 15% methanol, 85% carbon dioxide, back pressure = 90 bars |
| 108-1-1 | 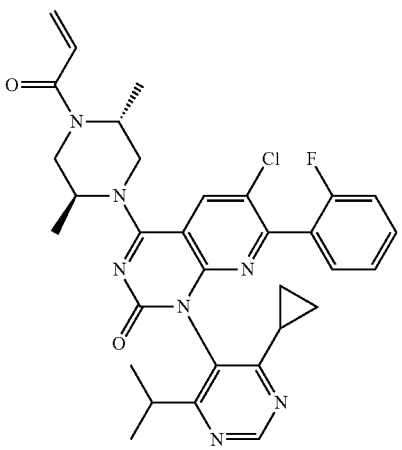<br>1<sup>st</sup>-eluting isomer | 6-Chloro-1-(4-cyclopropyl-6-isopropyl-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one | SFC IC, 21 × 250 mm, 5 μm, 45% MeOH/CO$_2$, 70 g/min, 102 bar |
| 108-1-2 | 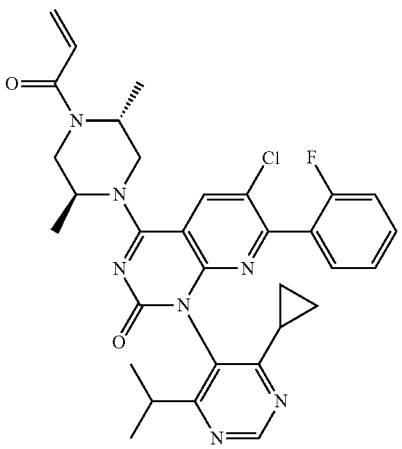<br>2<sup>nd</sup>-eluting isomer | 6-Chloro-1-(4-cyclopropyl-6-isopropyl-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one | SFC IC, 21 × 250 mm, 5 μm, 45% MeOH/CO$_2$, 70 g/min, 102 bar |

TABLE 147-continued

Separated Compound Examples From Methods

| Ex. # | Chemical Structure | Name | Separation conditions |
|---|---|---|---|
| 108-2-1 | 1st-eluting isomer | 6-Chloro-1-(4-cyclopropyl-6-isopropyl-pyrimidin-5-yl)-4-[(2S,5R)-2,5-dimethyl-4-prop-2-enoyl-piperazin-1-yl]-7-(o-tolyl)pyrido[2,3-d]pyrimidin-2-one | SFC IA, 21 × 250 mm, 5 μm, 20% EtOH/CO$_2$, 80 mL/min, 90 bar |
| 108-2-2 | 2nd-eluting isomer | 6-Chloro-1-(4-cyclopropyl-6-isopropyl-pyrimidin-5-yl)-4-[(2S,5R)-2,5-dimethyl-4-prop-2-enoyl-piperazin-1-yl]-7-(o-tolyl)pyrido[2,3-d]pyrimidin-2-one | SFC IA, 21 × 250 mm, 5 μm, 20% EtOH/CO$_2$, 80 mL/min, 90 bar |
| 109-1-1 | 1st-eluting isomer | 6-Chloro-4-[(2S,5R)-2,5-dimethyl-4-prop-2-enoyl-piperazin-1-yl]-1-(4-ethyl-6-isopropyl-pyrimidin-5-yl)-7-(2-fluorophenyl)pyrido[2,3-d]pyrimidin-2-one | SFC IC, 21 × 250 mm, 5 μm, 40% MeOH/CO$_2$, 80 g/min, 102 bar |

TABLE 147-continued

Separated Compound Examples From Methods

| Ex. # | Chemical Structure | Name | Separation conditions |
|---|---|---|---|
| 109-1-2 | 2nd-eluting isomer | 6-Chloro-4-[(2S,5R)-2,5-dimethyl-4-prop-2-enoyl-piperazin-1-yl]-1-(4-ethyl-6-isopropyl-pyrimidin-5-yl)-7-(2-fluorophenyl)pyrido[2,3-d]pyrimidin-2-one | SFC IC 21 × 250 mm, 5 μm, 40% MeOH/CO$_2$, 80 g/min, 102 bar |
| 109-2-1 | 1st-eluting isomer | 6-Chloro-4-[(2S,5R)-2,5-dimethyl-4-prop-2-enoyl-piperazin-1-yl]-1-(4-ethyl-6-isopropyl-pyrimidin-5-yl)-7-(o-tolyl)pyrido[2,3-d]pyrimidin-2-one | SFC IF, 30 × 150 mm, 5 μm, 40% isopropanol/CO$_2$, 100 g/min, 102 bar |
| 109-2-2 | 2nd-eluting isomer | 6-Chloro-4-[(2S,5R)-2,5-dimethyl-4-prop-2-enoyl-piperazin-1-yl]-1-(4-ethyl-6-isopropyl-pyrimidin-5-yl)-7-(o-tolyl)pyrido[2,3-d]pyrimidin-2-one | SFC IF, 30 × 150 mm, 5 μm, 40% isopropanol/CO$_2$, 100 g/min, 102 bar |

TABLE 147-continued

Separated Compound Examples From Methods

| Ex. # | Chemical Structure | Name | Separation conditions |
|---|---|---|---|
| 122-2-1 | 1st-eluting isomer | N-[2-[6-Chloro-1-[4-(dimethylamino)-2-isopropyl-3-pyridyl]-4-[(2S,5R)-2,5-dimethyl-4-prop-2-enoyl-piperazin-1-yl]-2-oxo-pyrido[2,3-d]pyrimidin-7-yl]-3-fluoro-phenyl]propanamide | SFC: DIOL (3 um, 2.1 × 100 mm) Mobile Phase: A – CO2, B Methanol with 0.2% triethylamine, Isocratic B: 15%, Flow Rate: 0.8 ml/min, BPR = 120 bar |
| 122-2-2 | 2nd-eluting isomer | N-[2-[6-Chloro-1-[4-(dimethylamino)-2-isopropyl-3-pyridyl]-4-[(2S,5R)-2,5-dimethyl-4-prop-2-enoyl-piperazin-1-yl]-2-oxo-pyrido[2,3-d]pyrimidin-7-yl]-3-fluoro-phenyl]propanamide | SFC: DIOL (3 um, 2.1 × 100 mm) Mobile Phase: A – CO2, B Methanol with 0.2% triethylamine, Isocratic B: 15%, Flow Rate: 0.8 ml/min, BPR = 120 bar |
| 122-3-1 | 1st-eluting isomer | N-[2-[6-Chloro-1-[4-(dimethylamino)-2-isopropyl-3-pyridyl]-4-[(2S,5R)-2,5-dimethyl-4-prop-2-enoyl-piperazin-1-yl]-2-oxo-pyrido[2,3-d]pyrimidin-7-yl]-3-fluoro-phenyl]cyclopropane-carboxamide | SFC: WElko-1 RR (5 um, 21 × 150 mm), F = 80 ml, 35% MeOH with 0.2% triethylamine, 65% carbon dioxide, 120 BAR |

TABLE 147-continued

Separated Compound Examples From Methods

| Ex. # | Chemical Structure | Name | Separation conditions |
|---|---|---|---|
| 122-3-2 | 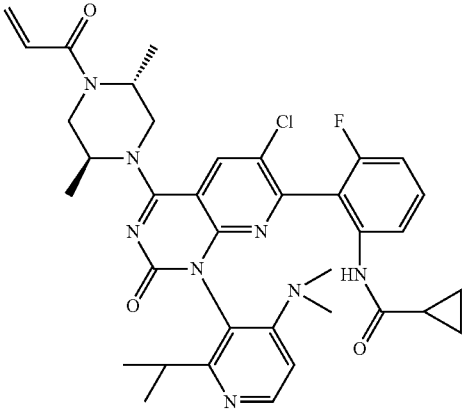 2nd-eluting isomer | N-[2-[6-Chloro-1-[4-(dimethylamino)-2-isopropyl-3-pyridyl]-4-[(2S,5R)-2,5-dimethyl-4-prop-2-enoyl-piperazin-1-yl]-2-oxo-pyrido[2,3-d]pyrimidin-7-yl]-3-fluoro-phenyl]cyclopropane-carboxamide | SFC: WElko-1 RR (5 um, 21 × 150 mm), F = 80 ml, 35% MeOH with 0.2% triethylamine, 65% carbon dioxide, 120 BAR |
| 124-14-1 | 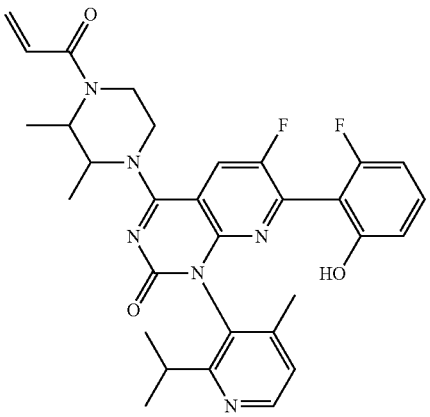 1st-eluting isomer | 4-[cis-2,3-dimethyl-4-prop-2-enoyl-piperazin-1-yl]-6-fluoro-7-(2-fluoro-6-hydroxy-phenyl)-1-(2-isopropyl-4-methyl-3-pyridyl)pyrido[2,3-d]pyrimidin-2-one | SFC: ID (250 × 20 mm, 5 μm), 75:25 $CO_2$ and iPrOH, 85 g/min, 103 bar |
| 124-14-2 | 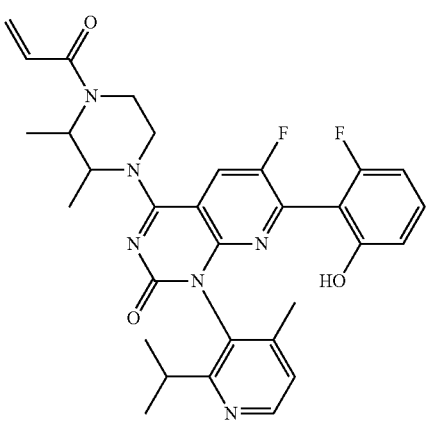 2nd-eluting isomer | 4-[cis-2,3-dimethyl-4-prop-2-enoyl-piperazin-1-yl]-6-fluoro-7-(2-fluoro-6-hydroxy-phenyl)-1-(2-isopropyl-4-methyl-3-pyridyl)pyrido[2,3-d]pyrimidin-2-one | SFC: ID (250 × 20 mm, 5 μm), 75:25 $CO_2$ and iPrOH, 85 g/min, 103 bar |

TABLE 147-continued

Separated Compound Examples From Methods

| Ex. # | Chemical Structure | Name | Separation conditions |
|---|---|---|---|
| 124-16-1 | 1st-eluting isomer | 4-[trans-2,3-dimethyl-4-prop-2-enoyl-piperazin-1-yl]-6-fluoro-7-(2-fluoro-6-hydroxy-phenyl)-1-(2-isopropyl-4-methyl-3-pyridyl)pyrido[2,3-d]pyrimidin-2-one | SFC: IF (250 × 20 mm, 5 μm), 60:40 $CO_2$ and iPrOH, 75 g/min, 103 bar; then SFC: ID (250 × 20 mm, 5 μm), 75:25 $CO_2$ and iPrOH, 85 g/min, 103 bar |
| 124-16-2 | 2nd-eluting isomer | 4-[trans-2,3-dimethyl-4-prop-2-enoyl-piperazin-1-yl]-6-fluoro-7-(2-fluoro-6-hydroxy-phenyl)-1-(2-isopropyl-4-methyl-3-pyridyl)pyrido[2,3-d]pyrimidin-2-one | SFC: IF (250 × 20 mm, 5 μm), 60:40 $CO_2$ and iPrOH, 75 g/min 103 bar |
| 144-2-1 | 1st-eluting isomer | (M)-2-[4-[6,7-Dichloro-1-(2-isopropyl-4-methyl-3-pyridyl)-2-oxo-pyrido[2,3-d]pyrimidin-4-yl]-1-prop-2-enoyl-piperazin-2-yl]acetonitrile | SFC OD × 2 (250 × 21 mm, 5 μm and 150 × 21, 5 μm) with a mobile phase of 60% Liquid CO2 and 40% MeOH, flowrate of 50 mL/min, 102 bar |

TABLE 147-continued

Separated Compound Examples From Methods

| Ex. # | Chemical Structure | Name | Separation conditions |
|---|---|---|---|
| 144-2-2 | 2nd-eluting isomer | (M)-2-[4-[6,7-Dichloro-1-(2-isopropyl-4-methyl-3-pyridyl)-2-oxo-pyrido[2,3-d]pyrimidin-4-yl]-1-prop-2-enoyl-piperazin-2-yl]acetonitrile | SFC OD × 2 (250 × 21 mm, 5 μm and 150 × 21, 5 μm) with a mobile phase of 60% Liquid CO2 and 40% MeOH, flowrate of 50 mL/min, 102 bar |
| 145-1-1 | 1st-eluting isomer | 2-[4-[6-Chloro-1-(2,2-dimethylpropyl)-7-(2-fluorophenyl)-2-oxo-pyrido[2,3-d]pyrimidin-4-yl]-1-prop-2-enoyl-piperazin-2-yl]acetonitrile | SFC AS (250 × 21 mm, 5 μm) with a mobile phase of 80% Liquid CO2 and 20% MeOH, flowrate of 80 mL/min, 102 bar |
| 145-1-2 | 2nd-eluting isomer | 2-[4-[6-Chloro-1-(2,2-dimethylpropyl)-7-(2-fluorophenyl)-2-oxo-pyrido[2,3-d]pyrimidin-4-yl]-1-prop-2-enoyl-piperazin-2-yl]acetonitrile | SFC AS (250 × 21 mm, 5 μm) with a mobile phase of 80% Liquid CO2 and 20% MeOH, flowrate of 80 mL/min, 102 bar |

TABLE 147-continued

Separated Compound Examples From Methods

| Ex. # | Chemical Structure | Name | Separation conditions |
|---|---|---|---|
| 145-2-1 | 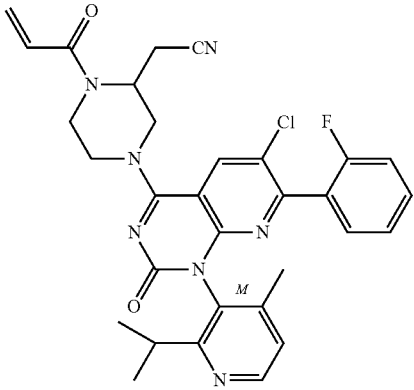<br>1st-eluting isomer | (M)-2-[4-[6-Chloro-7-(2-fluorophenyl)-1-(2-isopropyl-4-methyl-3-pyridyl)-2-oxo-pyrido[2,3-d]pyrimidin-4-yl]-1-prop-2-enoyl-piperazin-2-yl]acetonitrile | SFC OJ (250 × 21 mm, 5 μm) with a mobile phase of 90% Liquid CO2 and 10% MeOH, flowrate of 90 mL/min, 102 bar |
| 145-2-2 | 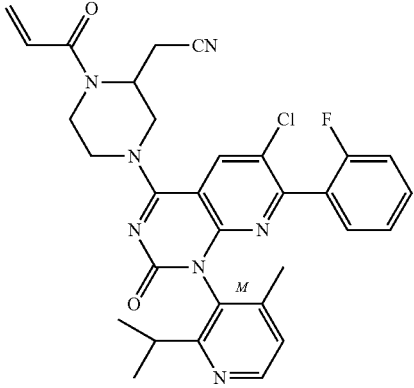<br>2nd-eluting isomer | (M)-2-[4-[6-Chloro-7-(2-fluorophenyl)-1-(2-isopropyl-4-methyl-3-pyridyl)-2-oxo-pyrido[2,3-d]pyrimidin-4-yl]-1-prop-2-enoyl-piperazin-2-yl]acetonitrile | SFC OJ (250 × 21 mm, 5 μm) with a mobile phase of 90% Liquid CO2 and 10% MeOH, flowrate of 90 mL/min, 102 bar |
| 146-1-1 | 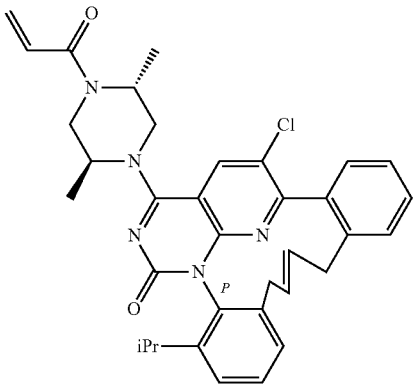<br>1st-eluting isomer | 19-chloro-22-((2S,5R)-2,5-dimethyl-4-(2-propenoyl)-1-piperazinyl)-3-(2-propanyl)-1,23,26-triazapentacyclo[16.6.2.0~2,7~.0~12,17~.0~21,25~]hexacosa-2,4,6,9,12,14,16,18,20,22,25-undecaen-24-one | SFC Welko SS (5 μm, 21 × 250 mm) F = 80 ml, 35% Methanol, 65% carbon dioxide, Back pressure = 90 bar |

TABLE 147-continued

Separated Compound Examples From Methods

| Ex. # | Chemical Structure | Name | Separation conditions |
|---|---|---|---|
| 146-1-2 | 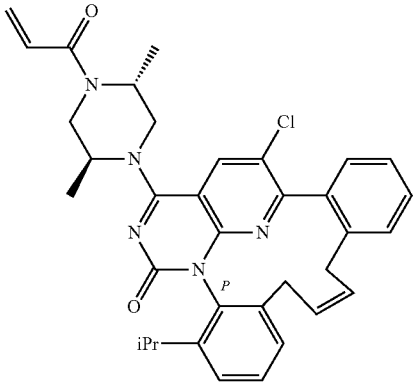<br>2$^{nd}$-eluting isomer | (9Z)-19-chloro-22-((2S,5R)-2,5-dimethyl-4-(2-propenoyl)-1-piperazinyl)-3-(2-propanyl)-1,23,26-triazapentacyclo[16.6.2.0~2,7~.0~12,17~.0~21,25~]hexacosa-2,4,6,9,12,14,16,18,20,22,25-undecaen-24-one | SFC Welko SS (5 μm, 21 × 250 mm) F = 80 ml, 35% Methanol, 65% carbon dioxide, Back pressure = 90 bar |
| 146-2-1 | 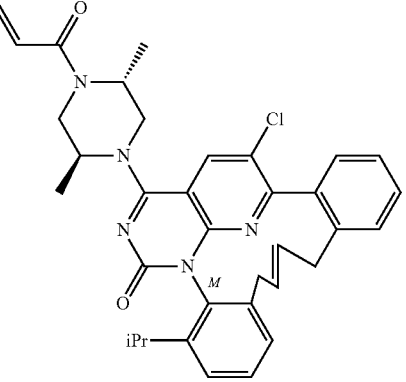<br>1$^{st}$-eluting isomer | 19-chloro-22-((2S,5R)-2,5-dimethyl-4-(2-propenoyl)-1-piperazinyl)-3-(2-propanyl)-1,23,26-triazapentacyclo[16.6.2.0~2,7~.0~12,17~.0~21,25~]hexacosa-2,4,6,9,12,14,16,18,20,22,25-undecaen-24-one | SFC Welko SS (5 μm, 21 × 250 mm) F = 80 ml, 35% Methanol, 65% carbon dioxide, Back pressure = 90 bar |
| 146-2-2 | 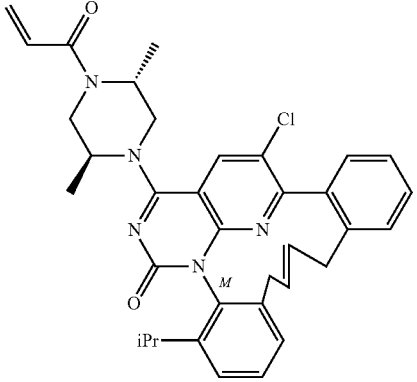<br>2$^{nd}$-eluting isomer | (9Z)-19-chloro-22-((2S,5R)-2,5-dimethyl-4-(2-propenoyl)-1-piperazinyl)-3-(2-propanyl)-1,23,26-triazapentacyclo[16.6.2.0~2,7~.0~12,17~.0~21,25~]hexacosa-2,4,6,9,12,14,16,18,20,22,25-undecaen-24-one | SFC Welko SS (5 μm, 21 × 250 mm) F = 80 ml, 35% Methanol, 65% carbon dioxide, Back pressure = 90 bar |

TABLE 147-continued

Separated Compound Examples From Methods

| Ex. # | Chemical Structure | Name | Separation conditions |
|---|---|---|---|
| 146-3-1 | 1st-eluting isomer | 19-chloro-22-((2S,5R)-2,5-dimethyl-4-(2-propenoyl)-1-piperazinyl)-1,23,26-triazapentacyclo[16.6.2.0~2,7~.0~12,17~.0~21,25~]hexacosa-2,4,6,9,12,14,16,18,20,22,25-undecaen-24-one | SFC (R,R) Whelk-01 (250 × 21 mm, 5 μm) with a mobile phase of 60% Liquid CO2 and 40% MeOH using a flowrate of 80 mL/min, 102 bar |
| 146-3-2 | 2nd-eluting isomer | 19-chloro-22-((2S,5R)-2,5-dimethyl-4-(2-propenoyl)-1-piperazinyl)-1,23,26-triazapentacyclo[16.6.2.0~2,7~.0~12,17~.0~21,25~]hexacosa-2,4,6,9,12,14,16,18,20,22,25-undecaen-24-one | SFC (R,R) Whelk-01 (250 × 21 mm, 5 μm) with a mobile phase of 60% Liquid CO2 and 40% MeOH using a flowrate of 80 mL/min, 102 bar |
| 146-3-3 | 3rd-eluting isomer | (9Z)-19-chloro-22-((2S,5R)-2,5-dimethyl-4-(2-propenoyl)-1-piperazinyl)-1,23,26-triazapentacyclo[16.6.2.0~2,7~.0~12,17~.0~21,25~]hexacosa-2,4,6,9,12,14,16,18,20,22,25-undecaen-24-one | SFC (R,R) Whelk-01 (250 × 21 mm, 5 μm) with a mobile phase of 60% Liquid CO2 and 40% MeOH using a flowrate of 80 mL/min, 102 bar |

TABLE 147-continued

Separated Compound Examples From Methods

| Ex. # | Chemical Structure | Name | Separation conditions |
|---|---|---|---|
| 146-3-4 | [chemical structure] 4th-eluting isomer | (9Z)-19-chloro-22-((2S,5R)-2,5-dimethyl-4-(2-propenoyl)-1-piperazinyl)-1,23,26-triazapentacyclo[16.6.2.0~2,7~.0~12,17~.0~21,25~]hexacosa-2,4,6,9,12,14,16,18,20,22,25-undecaen-24-one | SFC (R,R) Whelk-01 (250 × 21 mm, 5 μm) with a mobile phase of 60% Liquid CO2 and 40% MeOH using a flowrate of 80 mL/min, 102 bar |

TABLE 148

Analytical Data for Method Table Examples

| Ex. # | LRMS: m/z (ESI, +ve ion): (M + H)+ | NMR |
|---|---|---|
| 55-50 | 594.4 | $^1$H NMR (DMSO-$d_6$) δ 8.45-8.59 (m, 2H), 7.48-7.59 (m, 2H), 7.19-7.39 (m, 3H), 6.75-6.93 (m, 1H), 6.11-6.25 (m, 1H), 5.72-5.80 (m, 1H), 4.83-5.00 (m, 1H), 4.72-4.83 (m, 1H), 4.44-4.53 (m, 1H), 4.11-4.29 (m, 1H), 3.78-3.98 (m, 2H), 2.80-2.94 (m, 1H), 1.32-1.38 (m, 2H), 1.22-1.29 (m, 2H), 1.16-1.22 (m, 2H), 1.09-1.14 (m, 3H), 0.96-1.04 (m, 3H) |
| 55-51 | 604.2 | $^1$H NMR (400 MHz, DMSO-$d_6$) δ 8.49 (s, 1 H), 8.16 (dd, J = 9.4, 5.7 Hz, 1 H), 7.48-7.59 (m, 1 H), 7.19-7.38 (m, 3 H), 6.74-6.90 (m, 1 H), 6.68 (dd, J = 5.7, 3.2 Hz, 1 H), 6.19 (dd, J = 16.7, 2.2 Hz, 1 H), 5.71-5.81 (m, 1 H), 4.68-4.95 (m, 2 H), 4.46 (br dd, J = 8.8, 3.6 Hz, 1 H), 3.94-4.30 (m, 2 H), 3.79-3.91 (m, 1 H), 2.68 (d, J = 4.1 Hz, 6 H), 1.31-1.38 (m, 3 H), 1.10-1.22 (m, 3 H), 1.09-1.10 (m, 1 H), 1.03 (dd, J = 6.6, 3.1 Hz, 3 H), 0.81-0.92 (m, 3 H) |
| 55-51-1 | 604.2 | $^1$H NMR (400 MHz, DMSO-$d_6$) δ 8.44 (d, J = 5.4 Hz, 1 H), 8.15 (d, J = 5.8 Hz, 1 H), 7.55 (br d, J = 8.3 Hz, 1 H), 7.29-7.37 (m, 2 H), 7.22-7.28 (m, 1 H), 6.81 (br dd, J = 16.4, 10.4 Hz, 1 H), 6.67 (d, J = 5.8 Hz, 1 H), 6.19 (br d, J = 16.8 Hz, 1 H), 5.68-5.84 (m, 1 H), 4.68-4.94 (m, 2 H), 4.42-4.54 (m, 1 H), 4.09-4.33 (m, 1 H), 3.70-3.97 (m, 2 H), 2.68 (s, 7 H), 1.32-1.38 (m, 2 H), 1.20-1.26 (m, 2 H), 1.15 (br d, J = 6.8 Hz, 2 H), 1.04 (d, J = 6.6 Hz, 3 H), 0.84 (d, J = 6.6 Hz, 3 H) |
| 55-51-2 | 604.2 | $^1$H NMR (400 MHz, DMSO-$d_6$) δ 8.49 (s, 1 H), 8.17 (d, J = 5.8 Hz, 1 H), 7.49-7.62 (m, 1 H), 7.17-7.38 (m, 3 H), 6.73-6.91 (m, 1 H), 6.68 (d, J = 5.8 Hz, 1 H), 6.19 (dd, J = 16.7, 2.4 Hz, 1 H), 5.75 (br dd, J = 10.3, 2.6 Hz, 1 H), 4.90 (br d, J = 4.6 Hz, 1 H), 4.73 (dd, J = 4.0, 1.6 Hz, 1 H), 4.44 (br d, J = 3.5 Hz, 1 H), 3.92-4.18 (m, 3 H), 3.86 (br d, J = 3.1 Hz, 1 H), 2.67 (s, 6 H), 1.30 (dd, J = 12.4, 6.6 Hz, 3 H), 1.20 (br d, J = 6.6 Hz, 1 H), 1.11 (br d, J = 6.6 Hz, 2 H), 1.03 (d, J = 6.6 Hz, 3 H), 0.87 (d, J = 6.4 Hz, 3 H) |
| 55-52 | 591.2 | $^1$H NMR (400 MHz, DMSO-$d_6$) δ 8.63 (d, J = 5.4 Hz, 1 H), 8.18 (d, J = 5.6 Hz, 1 H), 7.56-7.67 (m, 2 H), 7.44-7.52 (m, 1 H), 7.26-7.35 (m, 2 H), 6.83 (td, J = 15.8, 10.4 Hz, 1 H), 6.13-6.22 (m, 1 H), 5.71-5.79 (m, 1 H), 4.75-4.94 (m, 1 H), 4.05-4.19 (m, 1 H), 3.96-4.05 (m, 1 H), 3.74-3.92 (m, 2 H), 3.47 (s, 3 H), 2.77-2.94 (m, 1 H), 1.26-1.32 (m, 3 H), 1.23 (br d, J = 6.6 Hz, 2 H), 1.16 (d, J = 6.6 Hz, 5 H), 1.09 (br d, J = 6.4 Hz, 3 H) |
| 55-53 | 664.2 | $^1$H NMR (400 MHz, DMSO-$d_6$) δ 8.56 (dd, J = 8.4, 4.7 Hz, 1 H), 8.44 (d, J = 3.9 Hz, 1 H), 7.97-8.11 (m, 2 H), |

TABLE 148-continued

Analytical Data for Method Table Examples

| Ex. # | LRMS: m/z (ESI, +ve ion): (M + H)+ | NMR |
|---|---|---|
| | | 7.81-7.88 (m, 1 H), 7.70-7.81 (m, 1 H), 7.39 (d, J = 7.9 Hz, 1 H), 6.55 (dd, J = 9.7, 5.8 Hz, 1 H), 6.20 (dd, J = 16.7, 2.2 Hz, 1 H), 5.70-5.82 (m, 1 H), 4.72-4.98 (m, 2 H), 4.47-4.53 (m, 1 H), 4.08-4.26 (m, 1 H), 3.84-3.93 (m, 2 H), 2.87 (s, 3 H), 2.74 (s, 6 H), 2.66-2.70 (m, 1 H), 1.25-1.37 (m, 5 H), 1.23-1.25 (m, 1 H), 0.94 (d, J = 6.8 Hz, 3 H), 0.74-0.80 (m, 3 H) |
| 55-54 | 618.6 | $^1$H NMR (400 MHz, DMSO-$d_6$) δ 8.43-8.50 (m, 1 H), 8.18 (d, J = 5.6 Hz, 1 H), 7.03-7.17 (m, 1 H), 6.77-6.91 (m, 1 H), 6.69 (br d, J = 3.9 Hz, 1 H), 6.45-6.55 (m, 1 H), 6.38 (br t, J = 9.1 Hz, 1 H), 6.20 (dd, J = 16.5, 2.0 Hz, 1 H), 5.73-5.80 (m, 1 H), 5.13-5.19 (m, 1 H), 4.71-4.92 (m, 2 H), 4.43-4.51 (m, 1 H), 4.03-4.19 (m, 1 H), 3.82-3.99 (m, 2 H) 2.69 (br d, J = 7.0 Hz, 6 H), 2.62 (br s, 1 H), 1.27-1.36 (m, 3 H), 1.22 (br d, J = 5.0 Hz, 2 H), 1.14 (br d, J = 6.6 Hz, 2 H), 1.02-1.06 (m, 3 H), 0.80 (br dd, J = 10.7, 6.9 Hz, 3 H) |
| 55-55 | 594.2 | $^1$H NMR (400 MHz, CHLOROFORM-d) δ 7.97-8.09 (m, 1 H), 7.64 (br t, J = 7.7 Hz, 2 H), 7.46-7.55 (m, 1 H), 7.39 (br d, J = 7.7 Hz, 2 H), 7.22 (s, 1 H), 7.03-7.17 (m, 2 H), 6.49-6.70 (m, 1 H), 6.32-6.44 (m, 1 H), 5.71-5.84 (m, 1 H), 5.05 (br d, J = 1.7 Hz, 1 H), 4.29-4.50 (m, 1 H), 4.05-4.19 (m, 1 H), 3.61-3.95 (m, 2 H), 3.41-3.48 (m, 1 H), 1.58-1.72 (m, 6 H), 1.40-1.50 (m, 4 H), 1.28-1.39 (m, 2 H) |
| 55-56 | 618.6 | $^1$H NMR (400 MHz, DMSO-$d_6$) δ 8.45 (s, 1 H), 8.18 (d, J = 5.6 Hz, 1 H), 7.03-7.19 (m, 1 H), 6.83 (br dd, J = 16.4, 10.6 Hz, 1 H), 6.68 (d, J = 5.6 Hz, 1 H), 6.44-6.53 (m, 1 H), 6.28-6.41 (m, 1 H), 6.20 (dd, J = 1.67, 2.2 Hz, 1 H), 5.72-5.81 (m, 1 H), 5.16 (br s, 2 H), 4.62-4.96 (m, 2 H), 4.40-4.52 (m, 1 H), 3.84-4.18 (m, 3 H), 2.58-2.74 (m, 7 H), 1.32 (br dd, J = 10.3, 6.5 Hz, 3 H), 1.08-1.24 (m, 3 H), 1.03 (br d, J = 6.4 Hz, 3 H), 0.81 (br d, J = 6.8 Hz, 3 H) |
| 55-57 | 618.6 | $^1$H NMR (400 MHz, DMSO-$d_6$) δ 8.36-8.49 (m, 1 H), 8.18 (d, J = 5.8 Hz, 1 H), 7.03-7.16 (m, 1 H), 6.82 (br dd, J = 16.9, 9.8 Hz, 1 H), 6.68 (br d, J = 5.8 Hz, 1 H), 6.53 (d, J = 8.1 Hz, 1 H), 6.38 (br t, J = 9.3 Hz, 1 H), 6.19 (dd, J = 16.7, 2.4 Hz, 1 H), 5.72-5.80 (m, 1 H), 5.29 (br s, 1 H), 5.13 (br s, 1 H), 4.72-4.95 (m, 2 H), 4.44-4.54 (m, 1 H), 4.07-4.22 (m, 1 H), 3.82-3.98 (m, 2 H), 2.60-2.72 (m, 7 H), 1.33 (br s, 3 H), 1.12-1.25 (m, 3 H), 0.97-1.07 (m, 3 H), 0.78 (d, J = 6.8 Hz, 3 H) |
| 55-58 | 588.6 | $^1$H NMR (400 MHz, DMSO-$d_6$) δ 8.44-8.53 (m, 2 H), 7.52 (br d, J = 7.0 Hz, 1 H), 7.16-7.35 (m, 4 H), 6.75-6.93 (m, 1 H), 6.20 (dd, J = 16.7, 1.6 Hz, 1 H), 5.76 (s, 1 H), 4.72-4.97 (m, 2 H), 4.48 (br d, J = 2.5 Hz, 1 H), 4.08-4.27 (m, 1 H), 3.80-3.98 (m, 2 H), 2.19-2.32 (m, 2 H), 1.31-1.39 (m, 3 H), 1.25 (br t, J = 5.7 Hz, 1 H), 1.21-1.23 (m, 1 H), 1.18 (br t, J = 7.2 Hz, 2 H), 1.07 (dd, J = 6.5, 4.0 Hz, 3 H), 0.91-1.04 (m, 6 H) |
| 55-58-1 | 589.2 | $^1$H NMR (400 MHz, DMSO-$d_6$) δ 8.49 (s, 1 H), 8.45 (d, J = 5.0 Hz, 1 H), 7.48-7.59 (m, 1 H), 7.25-7.35 (m, 2 H), 7.22 (br d, J = 5.0 Hz, 2 H), 6.76-6.92 (m, 1 H), 6.15-6.25 (m, 1 H), 5.76-5.80 (m, 1 H), 4.74-4.95 (m, 2 H), 4.43-4.53 (m, 1 H), 4.10-4.21 (m, 1 H), 3.84-3.99 (m, 2 H), 2.21-2.30 (m, 2 H), 1.34 (br t, J = 7.2 Hz, 3 H), 1.22-1.27 (m, 2 H), 1.17 (br d, J = 8.9 Hz, 2 H), 1.05-1.10 (m, 4 H), 0.94-1.01 (m, 5 H) |
| 55-58-2 | 589.3 | $^1$H NMR (400 MHz, DMSO-$d_6$) δ 8.42-8.50 (m, 2 H), 7.48-7.58 (m, 1 H), 7.17-7.36 (m, 4 H), 6.75-6.92 (m, 1 H), 6.20 (dd, J = 16.8, 1.9 Hz, 1 H), 5.75-5.80 (m, 1 H), 4.93 (s, 2 H), 4.44-4.53 (m, 1 H), 4.13-4.28 (m, 1 H), 3.78-3.97 (m, 2 H), 2.22-2.33 (m, 2 H), 1.33-1.38 (m, 3 H), 1.26 (br d, J = 6.8 Hz, 2 H), 1.17-1.21 (m, 2 H), 1.04-1.09 (m, 4 H), 0.98-1.04 (m, 2 H), 0.91-0.96 (m, 3 H) |
| 55-59 | 456.2 | $^1$H NMR (400 MHz, DMSO-$d_6$) δ 8.33 (d, J = 2.7 Hz, 1 H), 7.56-7.68 (m, 2 H), 7.34-7.46 (m, 2 H), 6.81 (td, J = 16.8, 10.6 Hz, 1 H), 6.17 (dd, J = 16.7, 1.6 Hz, 1 H), 5.74 (br dd, J = 10.6, 1.9 Hz, 1 H), 4.37-4.79 (m, 2 H), 3.69-4.13 (m, 4 H), 3.48 (s, 3 H), 1.27 (br t, J = 5.7 Hz, 3 H), 1.10-1.23 (m, 3 H) |
| 55-60 | 484.2 | $^1$H NMR (400 MHz, DMSO-$d_6$) δ 8.30 (s, 1 H), 7.56-7.67 (m, 2 H), 7.37-7.47 (m, 2 H), 6.81 (td, J = 17.5, 10.6 Hz, 1 H), 6.17 (dd, J = 16.6, 1.9 Hz, 1 H), 5.69-5.75 (m, 1 |

TABLE 148-continued

Analytical Data for Method Table Examples

| Ex. # | LRMS: m/z (ESI, +ve ion): (M + H)+ | NMR |
|---|---|---|
| | | H), 5.35 (quin, J = 6.9 Hz, 1 H), 4.37-4.80 (m, 2 H), 3.38-4.19 (m, 4 H), 1.46 (dd, J = 6.8, 3.9 Hz, 6 H), 1.25 (t, J = 6.4 Hz, 3 H), 1.10-1.22 (m, 3 H) |
| 69-10 | 600.2 | $^1$H NMR (400 MHz, DMSO-$d_6$) δ 8.45 (1 H, dd, J = 6.3, 4.9 Hz), 7.90-8.13 (1 H, m), 7.24 (1 H, dd, J = 17.9, 5.1 Hz), 6.69-6.94 (1 H, m), 6.17 (1 H, dd, J = 16.7, 2.0 Hz), 5.68-5.79 (1 H, m), 5.02-5.62 (1 H, m), 4.36-4.89 (2 H, m), 4.03-4.23 (1 H, m), 3.42-4.00 (6 H, m), 2.70-2.96 (2 H, m), 2.54 (1 H, m), 2.04 (2 H, m), 1.86 (3 H, s), 1.10-1.35 (6 H, m), 0.84-1.09 (6 H, m) |
| 69-11 | 564.2 | $^1$H NMR (400 MHz, DMSO-$d_6$) δ 8.46 (d, J = 4.8 Hz, 1 H), 8.02 (s, 1 H), 7.27 (d, J = 5.0 Hz, 1 H), 6.82 (td, J = 17.5, 10.4 Hz, 1 H), 6.17 (dd, J = 16.7, 2.2 Hz, 1 H), 5.67-5.83 (m, 1 H), 4.36-4.87 (m, 2 H), 3.36-4.17 (m, 4 H), 3.27 (br t, J = 5.3 Hz, 4 H), 2.58-2.72 (m, 1 H), 1.94 (s, 3 H), 1.44-1.54 (m, 2 H), 1.30-1.41 (m, 4 H), 1.11-1.29 (m, 6 H), 1.08 (d, J = 6.8 Hz, 3 H), 0.98 (d, J = 6.6 Hz, 3 H) |
| 69-12 | 578.3 | $^1$H NMR (400 MHz, DMSO-$d_6$) δ 8.36-8.52 (m, 1 H), 7.90-8.08 (m, 1 H), 7.23 (d, J = 4.8 Hz, 1 H), 6.71-6.96 (m, 1 H), 6.17 (dd, J = 16.6, 1.9 Hz, 1 H), 5.60-5.86 (m, 1 H), 4.31-4.86 (m, 2 H), 3.50-4.25 (m, 6 H), 2.84-2.98 (m, 1 H), 2.65-2.77 (m, 1 H), 2.52-2.62 (m, 1 H), 1.83-2.01 (m, 3 H), 1.34-1.64 (m, 5 H), 1.16-1.33 (m, 6 H), 1.07 (br d, J = 6.6 Hz, 3 H), 0.89-1.04 (m, 6 H) |
| 72-20 | 550.6 | $^1$H NMR (DMSO-$d_6$) δ 10.04-10.46 (m, 1H), 8.35-8.44 (m, 2H), 7.21-7.33 (m, 1H), 7.13-7.21 (m, 1H), 6.78-6.93 (m, 1H), 6.64-6.76 (m, 2H), 6.14-6.26 (m, 1H), 5.77-5.82 (m, 1H), 3.93-4.07 (m, 4H), 2.67-2.78 (m, 1H), 1.86-1.93 (m, 3H), 1.04-1.12 (m, 3H), 0.89-0.97 (m, 3H) |
| 72-21 | 550.6 | $^1$H NMR (DMSO-$d_6$) δ 9.96-10.32 (m, 1H), 8.23-8.48 (m, 2H), 7.24-7.33 (m, 1H), 7.15-7.20 (m, 1H), 6.79-6.90 (m, 1H), 6.66-6.76 (m, 2H), 6.16-6.23 (m, 1H), 5.74-5.79 (m, 1H), 3.70-3.93 (m, 4H), 2.65-2.78 (m, 1H), 1.85-1.94 (m, 3H), 1.07-1.11 (m, 3H), 0.86-0.98 (m, 3H) |
| 72-22 | 555.4 | $^1$H NMR (DMSO-$d_6$) δ 9.98-10.30 (m, 1H), 8.35-8.45 (m, 2H), 7.22-7.34 (m, 1H), 7.14-7.21 (m, 1H), 6.78-6.90 (m, 1H), 6.63-6.76 (m, 2H), 6.15-6.26 (m, 1H), 5.71-5.81 (m, 1H), 2.65-2.80 (m, 1H), 1.85-1.94 (m, 3H), 1.05-1.12 (m, 3H), 0.89-0.97 (m, 3H) |
| 72-23 | 617.2 | $^1$H NMR (400 MHz, DMSO-$d_6$) δ 8.37 (d, J = 4.8 Hz, 1 H), 8.24-8.31 (m, 1 H), 7.76 (br dd, J = 11.9, 7.4 Hz, 1 H), 7.59 (br dd, J = 9.2, 7.6 Hz, 2 H), 7.30 (br d, J = 2.5 Hz, 1 H), 7.18 (d, J = 4.8 Hz, 1 H), 6.71-6.96 (m, 1 H), 6.20 (dd, J = 16.7, 2.2 Hz, 1 H), 5.66-5.82 (m, 1 H), 4.71-4.97 (m, 2 H), 4.50 (br s, 1 H), 3.87 (br s, 4 H), 1.97 (s, 3 H), 1.57 (br d, J = 10.6 Hz, 3 H), 1.26-1.35 (m, 3 H), 1.09-1.26 (m, 6 H), 1.05 (br d, J = 6.6 Hz, 3 H), 0.81-0.91 (m, 3 H) |
| 79-10 | 573.2 | $^1$H NMR (500 MHz, DMSO-$d_6$) δ 8.50 (s, 1 H) 8.39 (d, J = 4.8 Hz, 1 H) 7.46-7.54 (m, 1 H) 7.18-7.33 (m, 4 H) 6.83 (dd, J = 16.7, 10.4 Hz, 1 H) 6.27 (dd, J = 16.7, 2.3 Hz, 1 H) 5.77-5.82 (m, 1 H) 4.72 (br s, 2 H) 4.51-4.61 (m, 2 H) 4.10-4.17 (m, 2 H) 3.55-3.67 (m, 2 H) 2.69 (tt, J = 12.9, 6.6 Hz, 1 H) 1.95 (d, J = 5.2 Hz, 3 H) 1.75-1.84 (m, 2 H) 1.05 (d, J = 6.7 Hz, 3 H) 0.96 (d, J = 6.6 Hz, 3 H). $^{19}$F NMR (377 MHz, CDCl$_3$) δ −112.45−−112.58 (m, 1 F). |
| 79-11 | 573.2 | $^1$H NMR (400 MHz, CDCl$_3$) δ 8.47 (d, J = 5.0 Hz, 1 H) 8.23-8.37 (m, 1 H) 7.35-7.45 (m, 1 H) 7.03-7.18 (m, 4 H) 6.38-6.61 (m, 2 H) 5.74-5.85 (m, 1 H) 3.74-5.56 (m, 6 H) 2.66-2.81 (m, 1 H) 2.13-2.47 (m, 2 H) 1.98-2.10 (m, 5 H) 1.19-1.26 (m, 3 H) 1.00-1.07 (m, 3 H). $^{19}$F NMR (376 MHz, CDCl$_3$) δ −112.71−−112.43 (m, 1 F). |
| 79-12 | 586.8 | $^1$H NMR (400 MHz, CDCl$_3$) δ 8.49 (d, J = 5.0 Hz, 1 H) 8.03 (s, 1 H) 7.37-7.45 (m, 1 H) 7.04-7.21 (m, 4 H) 6.57-6.69 (m, 1 H) 6.39 (dd, J = 16.8, 1.7 Hz, 1 H) 5.80 (dd, J = 10.6, 1.7 Hz, 1 H) 4.54-5.07 (m, 3 H) 3.57-4.40 (m, 2 H) 3.28 (br d, J = 12.6 Hz, 1 H) 2.63-2.80 (m, 1 H) 2.08-2.37 (m, 4 H) 2.01-2.06 (m, 3 H) 1.72-1.99 (m, 2 H) 1.23 (d, J = 6.6 Hz, 3 H) 1.06 (d, J = 6.8 Hz, 3 H). $^{19}$F NMR (377 MHz, CDCl$_3$) δ −112.54−−112.44 (m, 1 F) −112.60 (s, 1 F). |
| 80-10 | 643.3 | $^1$H NMR (400 MHz, CHLOROFORM-d) δ 8.02-8.08 (m, 1H), 7.22-7.41 (m, 4H), 7.03-7.20 (m, 3H), 6.52-6.70 (m, 1H), 6.39 (br t, J = 14.82 Hz, 1H), 5.75-5.83 (m, 1H), |

TABLE 148-continued

Analytical Data for Method Table Examples

| Ex. # | LRMS: m/z (ESI, +ve ion): (M + H)+ | NMR |
|---|---|---|
| | | 5.00-5.26 (m, 1H), 4.31-4.49 (m, 1H), 3.85-4.06 (m, 2H), 3.35-3.81 (m, 2H), 3.07-3.17 (m, 1H), 2.50-2.73 (m, 1H), 2.15 (br s, 4H), 1.34-1.50 (m, 9H), 1.25 (br t, J = 7.15 Hz, 2H), 1.18 (d, J = 6.63 Hz, 3H), 1.01-1.08 (m, 3H). $^{19}$F NMR (376 MHz, CHLOROFORM-d) δ −112.37 (m, 1F). |
| 80-10-1 | 643.4 | $^1$H NMR (400 MHz, DICHLOROMETHANE-d$_2$) δ 8.03 (s, 1H), 7.17-7.37 (m, 4H), 7.00-7.14 (m, 3H), 6.46-6.63 (m, 1H), 6.22 (br t, J = 15.13 Hz, 1H), 5.67 (br t, J = 8.71 Hz, 1H), 5.23-5.26 (m, 1H), 4.64-5.01 (m, 2H), 4.14-4.35 (m, 2H), 3.91-4.07 (m, 1H), 3.62-3.83 (m, 2H), 3.29-3.48 (m, 1H), 3.04 (br, d, J = 13.48 Hz, 1H), 2.52-2.66 (m, 1H), 1.99-2.00 (m, 1H), 1.97-2.11 (m, 3H), 1.36 (br dd, J = 6.53, 11.51 Hz, 8H), 1.05 (d, J = 6.84 Hz, 3H), 0.97 (d, J = 6.84 Hz, 3H). $^{19}$F NMR (376 MHz, DICHLOROMETHANE-d$_2$) δ −113.32 (s, 1F). |
| 80-10-2 | 643.4 | $^1$H NMR (400 MHz, DICHLOROMETHANE-d$_2$) δ 8.02 (s, 1H), 7.16-7.37 (m, 4H), 7.00-7.13 (m, 3H), 6.46-6.63 (m, 1H), 6.22 (br t, J = 14.82 Hz, 1H), 5.67 (br t, J = 8.40 Hz, 1H), 5.24 (br s, 1H), 5.00 (br s, 1H), 4.87 (br s, 1H), 4.28 (br d, J = 11.61 Hz, 1H), 3.78-4.04 (m, 3H), 3.44 (d, J = 13.27 Hz, 2H), 3.03 (br d, J = 13.27 Hz, 1H), 2.44-2.60 (m, 1H), 2.06 (br s, 4H), 1.32 (br s, 8H), 1.05 (d, J = 6.84 Hz, 3H), 0.98 (br d, J = 6.84 Hz, 3H). $^{19}$F NMR (376 MHz, DIHLOROMETHANE-d$_2$) δ −113.35 (s, 1F). |
| 80-11 | 665.3 | $^1$H NMR (400 MHz, CHLOROFORM-d) δ 8.01 (br d, J = 4.98 Hz, 1H), 7.27 (br s, 3H), 7.15-7.22 (m, 2H), 6.99-7.11 (m, 3H), 6.44-6.62 (m, 1H), 6.27-6.37 (m, 1H), 5.68-5.76 (m, 1H), 4.77-5.23 (m, 2H), 4.25-4.44 (m, 1H), 3.73-3.97 (m, 2H), 3.40-3.70 (m, 2H), 3.04-3.38 (m, 4H), 2.34-2.64 (m, 1H), 1.31-1.37 (m, 3H), 1.24 (br dd, J = 3.63, 6.12 Hz, 3H), 1.09 (d, J = 6.84 Hz, 3H), 0.94 (br dd, J = 6.84, 11.61 Hz, 3H). $^{19}$F NMR (376 MHz, CHLOROFORM-d) δ −99.38 (m, 2F), −112.89 (s, 1F). |
| 80-12 | 629.3 | $^1$H NMR (400 MHz, CHLOROFORM-d) δ 8.06-8.13 (m, 1H), 7.22-7.42 (m, 5H), 7.05-7.19 (m, 3H), 6.53-6.71 (m, 1H), 6.35-6.46 (m, 1H), 5.76-5.85 (m, 1H), 4.21-5.31 (m, 3H), 3.47-4.08 (m, 1H), 3.25-3.44 (m, 2H), 2.98-3.08 (m, 3H), 2.48-2.58 (m, 1H), 2.37 (br s, 2H), 1.86-1.98 (m, 2H), 1.31-1.47 (m, 6H), 1.19 (d, J = 6.84 Hz, 3H), 0.98-1.05 (m, 3H). $^{19}$F NMR (376 MHz, CHLOROFORM-d) δ −112.80 (s, 1F). |
| 80-13 | 603.2 | $^1$H NMR (400 MHz, CHLOROFORM-d) δ 8.06 (s, 1H), 7.32-7.42 (m, 4H), 7.12-7.17 (m, 2H), 7.05-7.11 (m, 1H), 6.54-6.72 (m, 1H), 6.37-6.46 (m, 1H), 5.81 (dd, J = 1.76, 10.47 Hz, 1H), 4.80-5.22 (m, 1H), 4.39-4.79 (m, 1H), 3.97-4.37 (m, 1H), 3.51-3.95 (m, 3H), 3.26-3.50 (m, 1H), 2.97-3.24 (m, 2H), 2.59 (br s, 1H), 2.00-2.07 (m, 6H), 1.48 (br d, J = 7.67 Hz, 3H), 1.19 (d, J = 6.84 Hz, 3H), 1.02 (d, J = 6.84 Hz, 3H). |
| 80-14 | 617.2 | $^1$H NMR (400 MHz, CHLOROFORM-d) δ 8.04-8.11 (1 H, m), 7.32-7.45 (4 H, m), 7.05-7.18 (3 H, m), 6.50-6.73 (1 H, m), 6.35-6.46 (1 H, m), 5.81 (1 H, br t, J = 8.4 Hz), 4.85-5.25 (2 H, m), 4.32-4.51 (1 H, m), 3.84-4.26 (2 H, m), 3.38-3.83 (2 H, m), 3.07-3.35 (2 H, m), 2.47-2.63 (1 H, m), 2.13 (2 H, br d, J = 8.1 Hz), 2.03 (3 H, s), 1.28-1.50 (6 H, m), 1.19 (3 H, d, J = 6.8 Hz), 1.01 (3 H, br t, J = 6.4 Hz) |
| 80-14-1 | 617.2 | $^1$H NMR (400 MHz, DMSO-d$_6$) δ 8.40 (1 H, d, J = 4.6 Hz), 7.44-7.54 (1 H, m), 7.22-7.34 (5 H, m), 7.16 (1 H, td, J = 7.4, 1.7 Hz), 6.83 (1 H, td, J = 16.3, 10.5 Hz), 6.19 (1 H, dd, J = 16.6, 2.3 Hz), 5.71-5.80 (1 H, m), 4.41-4.93 (2 H, m), 3.39-4.26 (4 H, m), 2.91-3.10 (2 H, m), 2.56-2.62 (1 H, m), 1.85 (6 H, s), 1.34 (3 H, dd, J = 6.1, 4.3 Hz), 1.17-1.29 (3 H, m), 1.06 (3 H, d, J = 6.8 Hz), 0.96 (3 H, d, J = 6.8 Hz). |
| 80-14-2 | 617.2 | $^1$H NMR (400 MHz, DMSO-d$_6$) δ 8.45 (1 H, d, J = 1.7 Hz), 7.44-7.53 (1 H, m), 7.21-7.35 (5 H, m), 7.11-7.19 (1 H, m), 6.83 (1 H, dt, J = 16.7, 11.0 Hz), 6.19 (1 H, dd, J = 16.7, 2.4 Hz), 5.71-5.79 (1 H, m), 4.86-4.96 (1 H, m), 4.40-4.80 (1 H, m), 3.83-4.18 (4 H, m), 2.95-3.13 (2 H, m), 2.53-2.56 (1 H, m), 1.81-1.92 (6 H, m), 1.29 (3 H, br dd, J = 12.0, 6.6 Hz), 1.14-1.24 (3 H, m), 1.06 (3 H, d, J = 6.8 Hz), 0.96 (3 H, d, J = 6.8 Hz) |

TABLE 148-continued

Analytical Data for Method Table Examples

| Ex. # | LRMS: m/z (ESI, +ve ion): (M + H)+ | NMR |
|---|---|---|
| 80-16 | 618.2 | $^1$H NMR (400 MHz, CHLOROFORM-d) δ 8.58 (1 H, d, J = 5.0 Hz), 8.08-8.13 (1 H, m), 7.38-7.47 (1 H, m), 7.29 (1 H, d, J = 4.8 Hz), 7.05-7.17 (3 H, m), 6.55 (1 H, br d, J = 10.6 Hz), 6.41 (1 H, br t, J = 14.9 Hz), 5.77-5.86 (1 H, m), 4.89-5.24 (2 H, m), 4.31-4.53 (1 H, m), 3.85-4.08 (2 H, m), 3.68-3.77 (1 H, m), 3.08-3.27 (2 H, m), 2.66-2.83 (1 H, m), 1.98-2.03 (6 H, m), 1.30-1.48 (6 H, m), 1.21-1.24 (3 H, m), 1.06-1.13 (3 H, m) |
| 80-16-1 | 618.2 | $^1$H NMR (400 MHz, DMSO-$d_6$) δ 8.44-8.52 (2 H, m), 7.45-7.55 (1 H, m), 7.23-7.34 (3 H, m), 7.17 (1 H, td, J = 7.4, 1.5 Hz), 6.76-6.91 (1 H, m), 6.19 (1 H, dd, J = 16.6, 2.3 Hz), 5.71-5.80 (1 H, m), 4.85-4.99 (1 H, m), 4.40-4.80 (1 H, m), 3.46-4.18 (4 H, m), 3.04 (2 H, s), 2.65-2.76 (1 H, m), 1.90 (6 H, s), 1.28-1.37 (3 H, m), 1.14-1.27 (3 H, m), 1.07 (3 H, d, J = 6.6 Hz), 0.96 (3 H, d, J = 6.6 Hz) |
| 80-16-2 | 618.2 | $^1$H NMR (400 MHz, DMSO-$d_6$) δ 8.42-8.52 (2 H, m), 7.45-7.54 (1 H, m), 7.24-7.39 (3 H, m), 7.14-7.22 (1 H, m), 6.83 (1 H, td, J = 15.9, 10.5 Hz), 6.19 (1 H, dd, J = 16.6, 2.3 Hz), 5.70-5.80 (1 H, m), 4.83-4.95 (1 H, m), 4.77 (1 H, br d, J = 1.9 Hz), 3.43-4.26 (4 H, m), 3.00-3.13 (2 H, m), 2.73 (1 H, dt, J = 13.3, 6.5 Hz), 1.92 (6 H, s), 1.31-1.39 (3 H, m), 1.15-1.28 (3 H, m), 1.07 (3 H, d, J = 6.6 Hz), 0.96 (3 H, d, J = 6.8 Hz) |
| 80-18 | 619.3 | $^1$H NMR (400 MHz, CHLOROFORM-d) δ 9.11-9.17 (1 H, m), 8.12 (1 H, br d, J = 5.6 Hz), 7.38-7.47 (1 H, m), 7.06-7.20 (3 H, m), 6.52-6.69 (1 H, m), 6.35-6.47 (1 H, m), 5.76-5.86 (1 H, m), 4.81-5.26 (2 H, m), 3.59-3.96 (6 H, m), 2.76 (1 H, td, J = 12.8, 6.6 Hz), 2.13-2.33 (6 H, m), 1.42-1.51 (3 H, m), 1.28-1.41 (3 H, m), 1.24 (3 H, d, J = 6.6 Hz), 1.08 (3 H, br d, J = 6.6 Hz) |
| 80-18-1 | 619.3 | $^1$H NMR (400 MHz, DMSO-$d_6$) δ 9.03 (1 H, s), 8.43 (1 H, d, J = 8.5 Hz), 7.47-7.56 (1 H, m), 7.25-7.35 (2 H, m), 7.16-7.24 (1 H, m), 6.83 (1 H, td, J = 17.5, 10.6 Hz), 6.19 (1 H, dd, J = 16.8, 2.3 Hz), 5.72-5.80 (1 H, m), 4.45-4.96 (2 H, m), 3.42-4.37 (4 H, m), 3.39 (1 H, d, J = 13.7 Hz), 3.15 (1 H, d, J = 13.7 Hz), 2.82-2.95 (1 H, m), 1.83 (6 H, s), 1.37 (3 H, d, J = 6.6 Hz), 1.19-1.29 (3 H, m), 1.10 (3 H, d, J = 6.6 Hz), 1.01 (3 H, d, J = 6.6 Hz) |
| 80-18-2 | 619.3 | $^1$H NMR (400 MHz, DMSO-$d_6$) δ 9.03 (1 H, s), 8.51 (1 H, s), 7.46-7.56 (1 H, m), 7.25-7.35 (2 H, m), 7.15-7.23 (1 H, m), 6.84 (1 H, dt, J = 16.6, 11.0 Hz), 6.19 (1 H, dd, J = 16.6, 2.3 Hz), 5.71-5.82 (1 H, m), 4.95 (1 H, br s), 4.40-4.82 (1 H, m), 3.51-4.20 (4 H, m), 3.38 (1 H, br d, J = 13.3 Hz), 3.15 (1 H, d, J = 13.3 Hz), 2.72-2.85 (1 H, m), 1.85 (6 H, s), 1.31 (3 H, br dd, J = 10.8, 6.6 Hz), 1.13-1.24 (3 H, m), 1.08 (3 H, d, J = 6.6 Hz), 0.98 (3 H, d, J = 6.6 Hz) |
| 80-20 | 615.0 | $^1$H NMR (400 MHz, DMSO-$d_6$) δ 0.93 (dd, J = 15.6, 6.84 Hz, 3 H), 1.05 (dd, J = 6.6, 4.6 Hz, 3 H) 1.23-1.34 (m, 6 H), 1.88 (d, J = 3.5 Hz, 3 H), 2.16 (s, 6 H), 2.52-2.57 (m, 1H), 3.39 (s, 2 H), 3.47-3.56 (m, 0.5 H), 3.80-3.90 (m, 2 H), 4.05-4.21 (m, 1.5 H), 4.38-4.96 (m, 2 H), 5.70-5.81 (m, 1 H), 6.18 (dd, J = 16.6, 2.1 Hz, 1 H), 6.76-6.92 (m, 1 H), 7.06 (br d, J = 8.7 Hz, 1 H), 7.15 (br d, J = 10.4 Hz, 1 H), 7.19-7.28 (m, 2 H), 7.29-7.38 (m, 1 H), 7.48-7.60 (m, 1 H), 8.32 (dd, J = 9.6, 1.4 Hz, 1 H); $^{19}\{^1H\}$ NMR (376 MHz, DMSO-$d_6$) δ -129.38--129.36 (m, 1F), -129.29--129.26 (m, 1 F), -113.36 (dd, J = 34.7, 2.6 Hz, 1 F), -113.22 (dd, J = 35.6, 4.4 Hz, 1 F) |
| 80-20-1 | 615.2 | $^1$H NMR (400 MHz, DMSO-$d_6$) δ 0.91 (d, J = 6.8 Hz, 3 H), 1.05 (d, J = 6.8 Hz, 3 H), 1.25 (br s, 3 H), 1.28-1.33 (m, 3 H), 1.88 (s, 3 H), 2.16 (s, 6 H), 2.52-2.58 (m, 1 H), 3.38 (s, 2 H), 3.45-4.21 (m, 4 H), 4.40-4.79 (m, 1 H), 4.86 (br s, 1 H), 5.69-5.81 (m, 1 H), 6.18 (dd, J = 16.7, 2.2 Hz, 1 H), 6.83 (td, J = 17.0, 10.5 Hz, 1 H), 7.07 (s, 1 H), 7.13 (s, 1 H), 7.20-7.28 (m, 2 H), 7.29-7.37 (m, 1 H), 7.49-7.60 (m, 1 H), 8.32 (d, J = 9.7 Hz, 1 H); $^{19}F\{^1H\}$ NMR (376 MHz, DMSO-$d_6$) δ -129.32 (dd, J = 30.1, 3.8 Hz, 1 F), -113.36 (dd, J = 30.1, 3.8 Hz, 1 F) |
| 80-20-2 | 615.2 | $^1$H NMR (400 MHz, DMSO-$d_6$) δ 0.95 (d, J = 6.8 Hz, 3 H), 1.05 (dd, J = 6.4, 2.9 Hz, 3 H), 1.13 (d, J = 15.1 Hz, 3 H), 1.29 (br dd, J = 10.5, 6.7 Hz, 3 H), 1.87 (s, 3 H), 2.16 (s, 6 H), 2.45-2.49 (m, 1 H), 3.38 (s, 2 H), 3.80-4.21 (m, 4 H), 4.47 (br d, J = 4.8 Hz, 0.5 H), 4.72-4.90 (m, 1.5 H), 5.72-5.78 (m, 1 H), 6.19 (dd, J = 16.6, 2.3 Hz, 1 H), |

TABLE 148-continued

Analytical Data for Method Table Examples

| Ex. # | LRMS: m/z (ESI, +ve ion): (M + H)+ | NMR |
|---|---|---|
| | | 6.76-6.91 (m, 1 H), 7.05 (s, 1 H), 7.16 (s, 1 H), 7.20-7.28 (m, 2 H), 7.29-7.36 (m, 1 H), 7.49-7.59 (m, 1 H), 8.33 (d, J = 9.7 Hz, 1 H); $^{19}$F{$^{1}$H} NMR (376 MHz, DMSO-$d_6$) δ −129.32 (dd, J = 36.0, 3.9 Hz, 1 F), −113.22 (dd, J = 36.0, 3.9 Hz, 1 F) |
| 80-21 | 631.1 | $^{1}$H NMR (400 MHz, DMSO-$d_6$) δ 0.88-0.96 (m, 3 H), 1.04 (dd, J = 6.7, 2.6 Hz, 3 H), 1.11-1.22 (m, 3 H), 1.27-1.32 (m, 3 H), 1.85 (d, J = 1.9 Hz, 3 H), 2.16 (s, 6 H), 3.35 (s, 2 H), 3.78-3.92 (m, 2 H), 3.97-4.21 (m, 2 H), 4.42-4.94 (m, 2 H), 5.66-5.82 (m, 1 H), 6.18 (dd, 16.6, 2.3 Hz, 1 H), 6.60-6.72 (m, 2 H), 6.76-6.91 (m, 1 H), 7.02 (br s, 1 H), 7.10 (br s, 1 H), 7.20-7.31 (m, 2 H), 8.24-8.30 (m, 1 H), 10.26 (br s, 1 H); $^{19}$F{$^{1}$H} NMR (376 MHz, DMSO-$d_6$) δ −128.74 (s, 0.5 F), −128.57 (s, 0.5 F), −115.38 (s, 0.5 F), −115.22 (s, 0.5 F) |
| 80-21-1 | 630.6 | $^{1}$H NMR (400 MHz, CHLOROFORM-d) δ 9.30-9.81 (br s, 1 H) 7.84-7.93 (m, 1 H) 7.24-7.29 (m, 1 H) 7.22 (s, 1 H) 6.51-6.71 (m, 3 H) 6.40 (br t, J = 14.82 Hz, 1 H) 5.73-5.88 (m, 1 H) 4.80-5.22 (m, 2 H) 4.28-4.50 (m, 1 H) 3.89-4.08 (m, 2 H) 3.67-3.87 (m, 1 H) 3.43-3.54 (m, 3 H) 2.54-2.68 (m, 1 H) 2.32 (s, 6 H) 1.94-2.03 (m, 3 H) 1.41-1.48 (m, 3 H) 1.25-1.32 (m, 3 H) 1.19 (d, J = 6.63 Hz, 3 H) 1.00 (br d, J = 6.84 Hz, 3 H) |
| 80-21-2 | 630.6 | $^{1}$H NMR (400 MHz, CHLOROFORM-d) δ 9.56 (br s, 1 H) 7.85-7.95 (m, 1 H) 7.28 (s, 1 H) 7.20-7.25 (m, 1 H) 6.52-6.70 (m, 3 H) 6.34-6.45 (m, 1 H) 5.76-5.85 (m, 1 H) 4.86-5.19 (m, 2 H) 4.33-4.51 (m, 1 H) 3.87-4.09 (m, 2 H) 3.68-3.84 (m, 1 H) 3.48 (s, 3 H) 2.48-2.61 (m, 1 H) 2.32 (s, 6 H) 2.00 (br d, J = 7.05 Hz, 3 H) 1.44 (br d, J = 6.43 Hz, 3 H) 1.33 (br d, J = 7.05 Hz, 3 H) 1.20 (d, J = 6.84 Hz, 3 H) 1.01 (m, J = 6.40 Hz, 3 H) |
| 92-1 | 599.2 | $^{1}$H NMR (400 MHz, DMSO-$d_6$) δ 8.42 (d, J = 5.2 Hz, 1 H), 8.35 (d, J = 5.0 Hz, 1 H), 7.37 (d, J = 3.9 Hz, 2 H), 7.22 (dt, J = 8.2, 4.0 Hz, 1 H), 7.16 (d, J = 5.0 Hz, 1 H), 7.00 (d, J = 7.5 Hz, 1 H), 6.84 (ddd, J = 20.3, 16.8, 10.6 Hz, 1 H), 6.19 (dd, J = 16.7, 2.2 Hz, 1 H), 5.72-5.80 (m, 1 H), 4.44-4.93 (m, 2 H), 3.39-4.32 (m, 4 H), 2.74 (br s, 1 H), 2.52-2.60 (m, 1 H), 1.89 (s, 3 H), 1.36 (dd, J = 6.3, 3.8 Hz, 3 H), 1.26 (br dd, J = 24.7, 6.6 Hz, 3 H), 0.80-1.10 (m, 12 H). |
| 92-2 | 576.0 | $^{1}$H NMR (400 MHz, DMSO-$d_6$) δ 8.56 (s, 1 H), 8.36-8.41 (m, 1 H), 7.18 (br d, J = 4.6 Hz, 1 H), 7.05 (q, J = 7.9 Hz, 1 H), 6.82 (dd, J = 16.7, 10.5 Hz, 1 H), 6.41-6.48 (m, 1 H), 6.32 (t, J = 8.8 Hz, 1 H), 6.19 (br d, J = 16.4 Hz, 1 H), 5.71-5.79 (m, 1 H), 5.04-5.17 (m, 2 H), 4.47-4.81 (m, 1 H), 4.39 (br d, J = 9.3 Hz, 1 H), 4.15-4.26 (m, 1 H), 3.97-4.13 (m, 1 H), 3.56-3.93 (m, 3 H), 2.54-2.83 (m, 1 H), 1.84-2.04 (m, 3 H), 1.29 (br s, 3 H), 0.82-1.12 (m, 6 H) |
| 92-3 | 577.3 | $^{1}$H NMR (400 MHz, DMSO-$d_6$) δ 8.44 (d, J = 4.8 Hz, 1 H), 8.34-8.41 (m, 1 H), 7.31 (d, J = 5.4 Hz, 1 H), 7.22 (dd, J = 8.5, 5.2 Hz, 2 H), 6.75-6.92 (m, 1 H), 6.19 (br d, J = 16.6 Hz, 1 H), 5.70-5.80 (m, 1 H), 4.44-4.90 (m, 2 H), 3.41-4.25 (m, 4 H), 2.65-2.77 (m, 1 H), 1.99 (s, 3 H), 1.93 (s, 3 H), 1.34 (t, J = 5.8 Hz, 3 H), 1.23 (br dd, J = 25.8, 6.9 Hz, 3 H), 1.06 (d, J = 6.6 Hz, 3 H), 0.91 (d, J = 6.6 Hz, 3 H) |
| 92-4 | 597.2 | $^{1}$H NMR (400 MHz, DMSO-$d_6$) δ 8.44 (d, J = 2.7 Hz, 1 H), 8.37 (d, J = 4.8 Hz, 1 H), 7.30 (td, J = 7.6, 0.9 Hz, 1 H), 7.15-7.22 (m, 2 H), 6.99-7.04 (m, 1 H), 6.94 (d, J = 7.7 Hz, 1 H), 6.84 (td, J = 16.5, 10.5 Hz, 1 H), 6.19 (dd, J = 16.7, 2.4 Hz, 1 H), 5.72-5.79 (m, 1 H), 4.82-4.94 (m, 1 H), 4.44-4.81 (m, 1 H), 3.43-4.24 (m, 4 H), 2.68-2.76 (m, 1 H), 1.91 (s, 3 H), 1.43-1.52 (m, 1 H), 1.31-1.38 (m, 3 H), 1.17-1.29 (m, 3 H), 1.07 (d, J = 6.6 Hz, 3 H), 0.94 (d, J = 6.6 Hz, 3 H), 0.61-0.73 (m, 2 H), 0.52-0.59 (m, 1 H), 0.47 (br s, 1 H) |
| 92-5 | 576.6 | $^{1}$H NMR (400 MHz, DMSO-$d_6$) δ 8.43 (d, J = 5.0 Hz, 1 H), 8.40 (d, J = 5.2 Hz, 1 H), 7.90 (d, J = 3.1 Hz, 1 H), 7.22 (d, J = 4.8 Hz, 1 H), 7.16 (dd, J = 3.1, 0.8 Hz, 1 H), 6.75-6.92 (m, 1 H), 6.19 (br d, J = 16.6 Hz, 1 H), 5.71-5.79 (m, 1 H), 4.43-4.93 (m, 2 H), 3.41-4.25 (m, 4 H), 2.65-2.75 (m, 1 H), 1.92 (s, 3 H), 1.70 (s, 3 H), 1.34 (br t, J = 5.8 Hz, 3 H), 1.17-1.27 (m, 3 H), 1.06 (d, J = 6.8 Hz, 3 H), 0.89 (br d, J = 6.6 Hz, 3 H) |

TABLE 148-continued

Analytical Data for Method Table Examples

| Ex. # | LRMS: m/z (ESI, +ve ion): (M + H)+ | NMR |
|---|---|---|
| 92-6 | 560.6 | $^1$H NMR (400 MHz, DMSO-d$_6$) δ 8.46 (d, J = 4.8 Hz, 1 H), 8.30 (d, J = 2.1 Hz, 1 H), 7.24 (d, J = 5.0 Hz, 1 H), 6.82 (td, J = 16.0, 10.5 Hz, 1 H), 6.33 (dt, J = 3.6, 2.0 Hz, 1 H) 6.18 (dd, J = 16.7, 2.2 Hz, 1 H), 5.71-5.79 (m, 1 H), 4.78-4.90 (m, 1 H), 4.40-4.78 (m, 1 H), 3.41-4.18 (m, 4 H), 2.58-2.69 (m, 1 H), 2.13 (br d, J = 1.5 Hz, 2 H), 1.93-2.07 (m, 2 H), 1.90 (s, 3 H), 1.45-1.58 (m, 4 H), 1.30 (t, J = 7.4 Hz, 3 H), 1.18 (br dd, J = 29.0, 6.6 Hz, 3 H), 1.06 (d, J = 6.6 Hz, 3 H), 0.97 (d, J = 6.6 Hz, 3 H) |
| 92-7 | 590.6 | $^1$H NMR (400 MHz, DMSO-d$_6$) δ 8.44 (d, J = 4.8 Hz, 1 H), 8.36 (d, J = 5.4 Hz, 1 H), 7.22 (d, J = 5.0 Hz, 1 H), 6.89 (s, 1 H), 6.76-6.88 (m, 1 H), 6.19 (dd, J = 16.6, 1.7 Hz, 1 H), 5.72-5.78 (m, 1 H), 4.41-4.89 (m, 2 H), 3.40-4.25 (m, 4 H), 2.65-2.77 (m, 1 H), 2.35 (s, 3 H), 1.91 (d, J = 7.0 Hz, 6 H), 1.34 (br t, J = 5.8 Hz, 3 H), 1.18-1.27 (m, 3 H), 1.06 (d, J = 6.8 Hz, 3 H), 0.92 (d, J = 6.6 Hz, 3 H) |
| 92-8 | 534.8 | $^1$H NMR (400 MHz, DMSO-d$_6$) δ 8.45 (d, J = 5.0 Hz, 1 H), 8.25 (d, J = 2.3 Hz, 1 H), 7.24 (d, J = 4.8 Hz, 1 H), 6.82 (td, J = 16.2, 10.6 Hz, 1 H), 6.56 (s, 1 H), 6.18 (br d, J = 16.6 Hz, 1 H), 5.70-5.78 (m, 1 H), 4.78-4.89 (m, 1 H), 4.39-4.77 (m, 1 H), 3.41-4.18 (m, 4 H), 2.61-2.70 (m, 1 H), 1.92 (s, 3 H), 1.88 (s, 3 H), 1.37 (s, 3 H), 1.30 (br t, J = 7.6 Hz, 3 H), 1.12-1.22 (m, 3 H), 1.07 (d, J = 6.8 Hz, 3 H), 0.93 (d, J = 6.4 Hz, 3 H) |
| 92-9 | 563.2 | $^1$H NMR (400 MHz, DMSO-d$_6$) δ 8.47 (d, J = 4.8 Hz, 1 H), 8.33 (d, J = 2.7 Hz, 1 H), 7.24 (d, J = 4.8 Hz, 1 H), 6.83 (td, J = 16.1, 10.5 Hz, 1 H), 6.54-6.59 (m, 1 H), 6.18 (dd, J = 16.5, 2.0 Hz, 1 H), 5.72-5.77 (m, 1 H), 4.79-4.91 (m, 1 H), 4.39-4.78 (m, 1 H), 3.39-4.23 (m, 8 H), 2.59-2.69 (m, 1 H), 1.95-2.13 (m, 2 H), 1.90 (s, 3 H), 1.30 (t, J = 7.3 Hz, 3 H), 1.13-1.23 (m, 3 H), 1.06 (d, J = 6.6 Hz, 3 H), 0.96 (d, J = 6.6 Hz, 3 H) |
| 92-10 | 575.3 | $^1$H NMR (400 MHz, DMSO-d$_6$) δ 8.45 (d, J = 4.8 Hz, 1 H), 8.28 (d, J = 2.9 Hz, 1 H), 7.23 (d, J = 5.0 Hz, 1 H), 6.83 (td, J = 16.5, 10.6 Hz, 1 H), 6.37 (t, J = 6.7 Hz, 1 H), 6.14-6.22 (m, 1 H), 5.71-5.78 (m, 1 H), 4.82 (dt, J = 6.7, 3.5 Hz, 1 H), 4.40-4.78 (m, 1 H), 3.40-4.18 (m, 4 H), 2.58-2.68 (m, 1 H), 2.17-2.28 (m, 4 H), 1.90 (s, 3 H), 1.67 (quin, J = 5.8 Hz, 2 H), 1.35-1.43 (m, 2 H), 1.30 (t, J = 7.3 Hz, 3 H), 1.13-1.26 (m, 5 H), 1.06 (d, J = 6.6 Hz, 3 H), 0.97 (d, J = 6.6 Hz, 3 H) |
| 92-11 | 596.2 | $^1$H NMR (400 MHz, DMSO-d$_6$) δ 10.04 (br s, 1 H), 8.49 (br s, 2 H), 7.66 (br d, J = 7.7 Hz, 1 H), 7.42-7.50 (m, 1 H), 7.26 (br d, J = 4.4 Hz, 1 H), 7.15 (br s, 1 H), 7.07 (t, J = 7.6 Hz, 1 H), 6.86 (td, J = 17.0, 10.6 Hz, 1 H), 6.48 (br s, 1 H), 6.20 (br d, J = 16.4 Hz, 1 H), 5.76 (br d, J = 9.5 Hz, 1 H), 4.89 (br s, 1 H), 4.44-4.83 (m, 1 H), 3.44-4.26 (m, 4 H), 2.70-2.86 (m, 1 H), 1.98 (s, 3 H), 1.35 (br t, J = 6.9 Hz, 3 H) 1.16-1.30 (m, 3 H), 1.09 (br d, J = 6.6 Hz, 3 H), 0.92 (br d, J = 6.6 Hz, 3 H) |
| 92-12 | 572.2 | $^1$H NMR (400 MHz, DMSO-d$_6$) δ 8.44 (br d, J = 4.8 Hz, 1 H), 8.39 (br s, 1 H), 7.22 (br d, J = 4.6 Hz, 1 H), 7.03-7.13 (m, 2 H), 6.76-6.93 (m, 1 H), 6.65 (br d, J = 8.1 Hz, 1 H), 6.54 (br t, J = 7.2 Hz, 1 H), 6.19 (br d, J = 16.8 Hz, 1 H), 5.75 (br d, J = 7.7 Hz, 1 H), 5.09 (br s, 2H), 4.43-4.94 (m, 2 H), 3.43-4.21 (m, 4 H), 2.65-2.80 (m, 1 H), 1.93 (s, 3 H), 1.33 (br t, J = 6.3 Hz, 3 H), 1.16-1.28 (m, 3 H), 1.07 (br d, J = 6.4 Hz, 3 H), 0.98 (br d, J = 6.4 Hz, 3 H) |
| 92-13 | 573.2 | $^1$H NMR (400 MHz, DMSO-d$_6$) δ 8.38-8.47 (m, 2 H), 7.98 (br d, J = 3.5 Hz, 1 H), 7.36 (br d, J = 7.0 Hz, 1 H), 7.20 (d, J = 4.8 Hz, 1 H), 6.76-6.94 (m, 1 H), 6.58 (dd, J = 7.0, 5.0 Hz, 1 H), 6.14-6.28 (m, 1 H), 5.83 (s, 2 H), 5.75 (br d, J = 9.7 Hz, 1 H), 4.44-4.92 (m, 2 H), 3.45-4.25 (m, 4 H), 2.63-2.77 (m, 1 H), 1.94 (s, 3 H), 1.29-1.39 (m, 3 H), 1.13-1.28 (m, 3 H), 1.06 (br d, J = 6.6 Hz, 3 H), 0.97 (br d, J = 6.6 Hz, 3 H) |
| 92-14 | 623.2 | $^1$H NMR (400 MHz, DMSO-d$_6$) δ 8.46 (br s, 1 H), 8.38 (br d, J = 4.1 Hz, 1 H), 7.47-7.38 (m, 1 H), 7.23-7.35 (m, 2 H), 7.18 (br d, J = 3.7 Hz, 2 H), 6.76-7.09 (m, 2 H), 6.19 (br d, J = 16.6 Hz, 1 H), 5.75 (br d, J = 8.5 Hz, 1 H), 4.42-4.94 (m, 2 H), 3.44-4.24 (m, 4 H), 2.69 (br d, J = 8.3 Hz, 1 H), 1.92 (br s, 3 H), 1.33 (br s, 3 H), 1.16-1.28 (m, 3 H), 1.06 (br d, J = 6.2 Hz, 3 H), 0.93 (br d, J = 4.1 Hz, 3 H) |

TABLE 148-continued

Analytical Data for Method Table Examples

| Ex. # | LRMS: m/z (ESI, +ve ion): (M + H)+ | NMR |
|---|---|---|
| 92-15 | 611.2 | $^1$H NMR (400 MHz, DMSO-d$_6$) δ 12.44-12.72 (m, 1 H), 8.51-8.61 (m, 1 H), 8.31 (dd, J = 8.3, 4.8 Hz, 1 H), 8.02 (d, J = 14.7 Hz, 1 H), 7.69 (dd, J = 8.1, 5.6 Hz, 1 H), 7.07-7.21 (m, 1 H), 7.01 (dd, J = 11.2, 8.3 Hz, 1 H), 6.78-6.95 (m, 1 H), 6.21 (br d, J = 16.6 Hz, 1 H), 5.74-5.83 (m, 1 H), 4.47-4.99 (m, 2 H), 3.83-4.25 (m, 4 H), 2.63-2.86 (m, 1 H), 2.03-2.11 (m, 3 H), 1.90-1.98 (m, 3 H), 1.32-1.41 (m, 3 H), 1.21-1.31 (m, 3 H), 1.07 (dd, J = 6.5, 4.3 Hz, 3 H), 0.73-0.99 (m, 3 H) |
| 92-16 | 607.1 | $^1$H NMR (400 MHz, DMSO-d$_6$) δ 8.46 (d, J = 4.4 Hz, 1 H), 8.37 (d, J = 4.8 Hz, 1 H), 7.55-7.70 (m, 3 H), 7.36 (br d, J = 6.6 Hz, 1 H), 7.18 (d, J = 5.0 Hz, 1 H), 6.76-6.93 (m, 1 H), 6.38-6.72 (m, 1 H), 6.19 (dd, J = 16.7, 2.2 Hz, 1 H), 5.76 (ddd, J = 10.2, 5.1, 2.5 Hz, 1 H), 4.46-4.94 (m, 2 H), 3.76-4.24 (m, 4 H), 2.72 (dt, J = 6.8, 3.2 Hz, 1 H), 1.91 (s, 3 H), 1.31-1.39 (m, 3 H), 1.16-1.29 (m, 3 H), 1.06 (d, J = 6.8 Hz, 3 H), 0.90 (d, J = 6.6 Hz, 3 H) |
| 92-17 | 590.2 | $^1$H NMR (400 MHz, DMSO-d$_6$) δ 8.36-8.45 (m, 2 H), 7.20 (d, J = 4.8 Hz, 1 H), 7.05 (dd, J = 10.7, 8.0 Hz, 1 H), 6.75-6.92 (m, 2 H), 6.54 (td, J = 7.8, 5.1 Hz, 1 H), 6.19 (dd, J = 16.7, 2.2 Hz, 1 H), 5.69-5.83 (m, 1 H), 5.02 (s, 2 H), 4.81-4.92 (m, 1 H), 4.46-4.80 (m, 1 H), 3.45-4.23 (m, 4 H), 2.63-2.78 (m, 1 H), 1.94 (s, 3 H), 1.33 (br t, J = 6.9 Hz, 3 H), 1.15-1.29 (m, 3 H), 1.06 (d, J = 6.6 Hz, 3 H), 0.98 (d, J = 6.6 Hz, 3 H) |
| 92-18 | 614.2 | $^1$H NMR (400 MHz, DMSO-d$_6$) δ 8.98-9.29 (m, 1 H), 8.42 (br s, 1 H), 8.39 (br d, J = 4.1 Hz, 1 H), 7.62 (br s, 1 H), 7.38 (br t, J = 7.3 Hz, 1 H), 7.03-7.24 (m, 3 H), 6.72-6.97 (m, 1 H), 6.19 (br d, J = 16.8 Hz, 1 H), 5.63-5.88 (m, 1 H), 4.46-3.00 (m, 2 H), 3.73-4.27 (m, 4 H), 2.66-2.81 (m, 1 H), 1.97 (br s, 3 H), 1.85 (br s, 3 H), 1.33 (br d, J = 6.0 Hz, 3 H), 1.14-1.25 (m, 3 H), 1.06 (br d, J = 6.2 Hz, 3 H), 0.93 (br d, J = 5.8 Hz, 3 H) |
| 92-19 | 600.2 | $^1$H NMR (400 MHz, DMSO-d$_6$) δ 8.38 (br d, J = 4.8 Hz, 2 H), 7.32 (br t, J = 6.9 Hz, 1 H), 7.19 (br s, 1 H), 7.06 (br d, J = 8.1 Hz, 1 H), 6.70-6.98 (m, 3 H), 6.19 (dd, J = 16.7, 2.0 Hz, 1 H), 5.67-5.84 (m, 1 H), 4.41-4.93 (m, 2 H), 3.38-4.33 (m, 4 H), 2.72-2.88 (m, 1 H), 2.44 (s, 6 H), 1.90 (br s, 3 H), 1.35 (br d, J = 6.0 Hz, 3 H), 1.14-1.29 (m, 3 H), 1.05-1.14 (m, 3 H), 0.98 (br d, J = 3.5 Hz, 3 H) |
| 92-20 | 612.2 | $^1$H NMR (400 MHz, DMSO-d$_6$) δ 9.97 (br d, J = 7.5 Hz, 1 H), 8.45 (s, 1 H), 8.39 (d, J = 4.8 Hz, 1 H), 7.25 (br d, J = 6.8 Hz, 1 H), 7.18 (d, J = 5.0 Hz, 1 H), 6.94-7.03 (m, 2 H), 6.85 (td, J = 16.1, 10.4 Hz, 1 H), 6.20 (dd, J = 16.6, 2.1 Hz, 1 H), 5.72-5.81 (m, 1 H), 4.87 (br s, 1 H), 4.43-4.82 (m, 1 H), 3.79-4.24 (m, 4 H), 3.52 (br s, 2 H), 2.64-2.75 (m, 1 H), 1.95 (s, 3 H), 1.29-1.38 (m, 3 H), 1.13-1.27 (m, 3 H), 1.06 (d, J = 6.6 Hz, 3 H), 0.98 (d, J = 6.6 Hz, 3 H) |
| 92-21 | 600.2 | $^1$H NMR (400 MHz, DMSO-d$_6$) δ 8.35 (d, J = 4.8 Hz, 1 H), 8.32 (d, J = 3.1 Hz, 1 H), 7.81 (br s, 1 H), 7.68 (br d, J = 7.3 Hz, 1 H), 7.50 (quin, J = 7.5 Hz, 2 H), 7.10-7.20 (m, 3 H), 6.75-6.92 (m, 1 H), 6.19 (dd, J = 16.7, 2.2 Hz, 1 H), 5.75 (ddd, J = 10.1, 5.5, 2.0 Hz, 1 H), 4.47-4.90 (m, 2 H), 3.75-4.22 (m, 4 H), 2.65-2.77 (m, 1 H), 1.92 (s, 3 H), 1.34 (br t, J = 5.5 Hz, 3 H), 1.18-1.29 (m, 3 H), 1.07 (d, J = 6.6 Hz, 3 H), 0.90 (br d, J = 6.6 Hz, 3 H) |
| 92-22 | 497.2 | $^1$H NMR (400 MHz, DMSO-d$_6$) δ 11.53-11.97 (br s, 1 H), 8.39 (d, J = 4.8 Hz, 1 H), 7.81 (br s, 1 H), 7.18 (d, J = 4.8 Hz, 1 H), 6.81 (td, J = 16.5, 10.7 Hz, 1 H), 6.16 (dd, J = 16.7, 2.4 Hz, 1 H), 5.67-5.80 (m, 1 H), 4.28-4.79 (m, 2 H), 3.42-4.15 (m, 4 H), 2.56-2.66 (m, 1 H), 1.91 (s, 3 H), 1.15-1.30 (m, 6 H), 1.04 (dd, J = 9.7, 6.8 Hz, 6 H) |
| 92-23 | 625 | $^1$H NMR (400 MHz, DMSO-d$_6$) δ 8.50 (br s, 1 H), 8.35 (d, J = 4.8 Hz, 1 H), 7.80 (d, J = 7.9 Hz, 1 H), 7.72-7.77 (m, 1 H), 7.62-7.71 (m, 1 H), 7.36 (d, J = 7.5 Hz, 1 H), 7.16 (d, J = 4.8 Hz, 1 H), 6.75-6.92 (m, 1H), 6.19 (dd, J = 16.7, 2.2 Hz, 1 H), 5.76 (ddd, J = 10.4, 5.3, 2.2 Hz, 1 H), 4.46-4.94 (m, 2 H), 3.41-4.28 (m, 4 H), 2.69 (br dd, J = 16.1, 1.3 Hz, 1 H), 1.88 (s, 3 H), 1.32-1.40 (m, 3 H), 1.15-1.30 (m, 3 H), 1.06 (d, J = 6.6 Hz, 3 H), 0.89 (br d, J = 1.2 Hz, 3 H) |
| 92-24 | 618.2 | $^1$H NMR (400 MHz, DMSO-d$_6$) δ 8.29-8.43 (m, 2 H), 7.80-7.98 (m, 1 H), 7.37-7.61 (m, 3 H), 7.17-7.33 (m, 1 H), 7.07-7.16 (m, 1 H), 6.71-6.94 (m, 1 H), 6.19 (dd, J = 16.7, 2.0 Hz, 1 H), 5.75 (dt, J = 10.3, 2.6 Hz, 1 H), |

TABLE 148-continued

Analytical Data for Method Table Examples

| Ex. # | LRMS: m/z (ESI, +ve ion): (M + H)+ | NMR |
|---|---|---|
| | | 4.44-4.93 (m, 2 H), 3.40-4.30 (m, 4 H), 2.64-2.84 (m, 1 H), 1.79-1.95 (m, 3 H), 1.35 (br d, J = 4.4 Hz, 3 H), 1.17-1.29 (m, 3 H), 1.04-1.12 (m, 3 H), 0.79-0.98 (m, 3 H) |
| 92-25 | 586.2 | $^1$H NMR (400 MHz, DMSO-d$_6$) δ 8.31-8.50 (m, 2 H), 7.17-7.29 (m, 2 H), 7.14 (br d, J = 7.5 Hz, 1 H), 6.85 (td, J = 17.3, 10.5 Hz, 1 H), 6.52-6.65 (m, 2 H), 6.19 dd, J = 16.6, 2.3 Hz, 1 H), 5.68-5.82 (m, 1 H), 5.32 (br d, J = 4.4 Hz, 1 H), 4.42-4.94 (m, 2 H), 3.45-4.24 (m, 4 H) 2.62-2.79 (m, 1 H), 2.47 (br s, 3 H), 1.95 (s, 3 H), 1.33 (t, J = 6.9 Hz, 3 H), 1.15-1.28 (m, 3 H), 1.07 (d, J = 6.6 Hz, 3 H), 0.96 (d, J = 6.6 Hz, 3 H) |
| 92-26 | 608.2 | $^1$H NMR (400 MHz, DMSO-d$_6$) δ 8.38-8.47 (m, 2 H), 7.54-7.60 (m, 1 H), 7.43-7.52 (m, 1 H), 7.19-7.23 (m, 1 H), 7.11-7.19 (m, 1 H), 6.85 (td, J = 16.6, 10.6 Hz, 1 H), 6.69 (br d, J = 7.9 Hz, 1 H), 6.19 (dd, J = 16.6, 2.3 Hz, 1 H), 5.70-5.82 (m, 1 H), 4.73-4.86 (m, 1 H), 4.50 (br d, J = 1.7 Hz, 1 H), 4.06-4.26 (m, 2 H), 3.83-3.98 (m, 2 H), 2.63-2.79 (m, 1 H), 1.94 (s, 3 H), 1.29-1.38 (m, 3 H), 1.14-1.26 (m, 3 H), 1.06 (d, J = 6.8 Hz, 3 H), 0.98 (d, J = 6.6 Hz, 3 H |
| 92-27 | 614.2 | $^1$H NMR (400 MHz, DMSO-d$_6$) δ 8.18-8.42 (m, 3 H), 7.55-7.73 (m, 1 H), 7.39-7.54 (m, 2 H), 7.16 (d, J = 5.0 Hz, 2 H), 6.72-6.93 (m, 1 H), 6.19 (dd, J = 2.3 Hz, 1 H), 5.68-5.82 (m, 1 H), 4.44-4.99 (m, 2 H), 3.73-4.26 (m, 4 H), 2.65-2.78 (m, 1 H), 2.60 (d, J = 4.4 Hz, 3 H), 1.84-1.92 (m, 3 H), 1.35 (br d, J = 6.4 Hz, 3 H), 1.20-1.31 (m, 3 H), 1.06 (d, J = 6.6 Hz, 3 H), 0.88 (br d, J = 5.2 Hz, 3 H) |
| 92-28 | 628.2 | $^1$H NMR (400 MHz, DMSO-d$_6$) δ 8.33-8.47 (m, 2 H), 7.42-7.51 (m, 2 H), 7.20-7.41 (m, 3 H), 6.73-6.92 (m, 1 H), 6.19 (dd, J = 16.7, 2.4 Hz, 1 H), 5.66-5.84 (m, 1 H), 4.41-4.93 (m, 2 H), 3.67-4.20 (m, 4 H), 2.70 (s, 3 H), 2.58 (br d, J = 5.6 Hz, 1 H), 2.32 (br dd, J = 4.3, 2.4 Hz, 3 H), 1.92 (s, 3 H), 1.32 (br t, J = 6.8 Hz, 3 H), 1.14-1.27 (m, 3 H), 1.01 (d, J = 6.6 Hz, 3 H), 0.80 (br d, J = 6.0 Hz, 3 H) |
| 92-29 | 601.2 | $^1$H NMR (400 MHz, DMSO-d$_6$) δ 12.12 (br s, 1 H), 8.24-8.45 (m, 2 H), 7.93 (br d, J = 7.5 Hz, 1 H), 7.39-7.68 (m, 2 H), 7.05-7.21 (m, 2 H), 6.83 (td, J = 16.0, 10.5 Hz, 1 H), 6.19 (dd, J = 16.7, 2.2 Hz, 1 H), 5.62-5.87 (m, 1 H), 4.40-5.00 (m, 2 H), 3.45-4.28 (m, 4 H), 2.62-2.77 (m, 1 H), 1.91 (s, 3 H), 1.33 (br t, J = 6.9 Hz, 3 H), 1.16-1.27 (m, 3 H), 1.07 (br d, J = 6.6 Hz, 3 H), 0.91 (br s, 3 H) |
| 92-30 | 597.2 | $^1$H NMR (400 MHz, DMSO-d$_6$) δ 12.24 (br s, 1 H), 8.54 (s, 1 H), 8.42 (d, J = 4.8 Hz, 1 H), 8.13 (s, 1 H), 7.88 (d, J = 8.1 Hz, 1 H), 7.48 (br dd, J = 7.2, 3.8 Hz, 1 H), 7.14-7.26 (m, 2 H), 6.86 (td, J = 16.4, 10.6 Hz, 1 H), 6.20 (dd, J = 16.7, 2.2 Hz, 1 H), 5.71-5.83 (m, 1 H), 4.45-5.02 (m, 2 H) 3.73-4.31 (m, 4 H), 2.73 (td, J = 6.6, 3.1 Hz, 1H) 1.97 (s, 3 H), 1.35 (br t, J = 7.6 Hz, 3 H), 1.16-1.28 (m, 3 H), 1.07 (d, J = 6.6 Hz, 3 H), 0.92 (d, J = 6.6 Hz, 3 H) |
| 92-31 | 608.2 | $^1$H NMR (400 MHz, DMSO-d$_6$) δ 8.45 (d, J = 5.0 Hz, 1 H), 8.42 (d, J = 2.1 Hz, 1 H), 7.23 (d, J = 5.0 Hz, 1 H), 7.13 (ddd, J = 11.6, 9.0, 3.1 Hz, 1 H), 6.84 (td, J = 17.0, 10.4 Hz, 1 H), 6.60 (dd, J = 13.2, 7.4 Hz, 1 H), 6.19 (dd, J = 16.6, 2.3 Hz, 1 H), 5.69-5.83 (m, 1 H), 5.29 (s, 2 H), 4.44-4.94 (m, 2 H), 3.45-4.22 (m, 4 H), 2.65-2.77 (m, 1 H), 1.93 (s, 3 H), 1.32 (br t, J = 6.8 Hz, 3 H), 1.16-1.26 (m, 3 H), 1.06 (d, J = 6.6 Hz, 3 H), 0.98 (d, J = 6.6 Hz, 3 H) |
| 92-32 | 650.2 | $^1$H NMR (400 MHz, DMSO-d$_6$) δ 8.92 (br s, 1 H), 8.44 (s, 1 H), 8.37 (d, J = 5.0 Hz, 1 H), 7.44 (br d, J = 2.9 Hz, 2 H), 7.23 (br s, 1 H), 7.17 (d, J = 5.0 Hz, 1 H), 7.14 (br d, J = 6.6 Hz, 1 H), 6.82 (br dd, J = 16.8, 10.6 Hz, 1 H), 6.19 (dd, J = 16.6, 2.3 Hz, 1 H), 5.62-5.87 (m, 1 H), 4.46-4.92 (m, 2 H), 3.78-4.21 (m, 4 H), 2.66-2.74 (m, 1 H), 2.63 (s, 3 H), 1.96 (s, 3 H), 1.32 (br t, 17.3 Hz, 3 H), 1.14-1.25 (m, 3 H), 1.05 (d, J = 6.8 Hz, 3 H), 0.95 (d, J = 6.6 Hz, 3 H) |
| 92-33 | 636.2 | $^1$H NMR (400 MHz, DMSO-d$_6$) δ 8.48 (s, 1 H), 8.36 (d, J = 4.8 Hz, 1 H), 7.91-7.98 (m, 1 H), 7.62-7.72 (m, 2 H), 7.21-7.33 (m, 1 H), 7.15 (d, J = 5.0 Hz, 1 H), 6.79-6.90 (m, 1 H), 6.73 (s, 2 H), 6.19 (dd, J = 16.7, 2.0 Hz, 1 H), 5.71-5.81 (m, 1 H), 4.45-4.99 (m, 2 H), 3.82-4.30 (m, 4 H), 2.63-2.74 (m, 1 H), 1.95 (s, 3 H), 1.33 (s, 3 H), |

TABLE 148-continued

Analytical Data for Method Table Examples

| Ex. # | LRMS: m/z (ESI, +ve ion): (M + H)+ | NMR |
|---|---|---|
| | | 1.13-1.22 (m, 3 H), 1.05 (br d, J = 6.4 Hz, 3 H), 0.88 (br d, J = 6.4 Hz, 3 H) |
| 92-34 | 591.0 | $^1$H NMR (400 MHz, DMSO-d$_6$) δ 9.66 (br s, 1 H), 8.43 (d, J = 3.7 Hz, 1 H), 8.41 (d, J = 4.8 Hz, 1 H), 7.20 (d, J = 4.8 Hz, 1 H), 7.08 (t, J = 9.2 Hz, 1 H), 6.70-6.93 (m, 2 H), 6.53 (dd, J = 5.7, 3.0 Hz, 1 H), 6.19 (dd, J = 16.7, 2.0 Hz, 1 H), 5.68-5.81 (m, 1 H), 4.42-4.95 (m, 2 H), 4.11-4.24 (m, 1 H), 3.43-3.94 (m, 3 H), 2.63-2.75 (m, 1 H), 1.93 (s, 3 H), 1.29-1.40 (m, 3 H), 1.17-1.27 (m, 3 H), 1.06 (d, J = 6.6 Hz, 3 H), 0.97 (d, J = 6.6 Hz, 3 H) |
| 92-35 | 656.2 | $^1$H NMR (400 MHz, DMSO-d$_6$) δ 9.11 (br s, 1 H), 8.34-8.50 (m, 2 H), 7.36-7.52 (m, 1 H), 7.17-7.30 (m, 3 H), 7.11 (br d, J = 7.5 Hz, 1 H), 6.74-6.95 (m, 1 H), 6.19 (br d, J = 16.0 Hz, 1 H), 5.66-5.82 (m, 1 H), 4.41-5.02 (m, 2 H), 3.50-4.27 (m, 4 H), 2.61-2.72 (m, 1 H), 2.00 (br s, 3 H), 1.23-1.34 (m, 3 H), 1.01-1.10 (m, 9 H), 0.97 (br s, 9 H) |
| 92-36 | 602.2 | $^1$H NMR (400 MHz, DMSO-d$_6$) δ 8.48 (d, J = 3.5 Hz, 1 H), 8.36 (d, J = 4.8 Hz, 1 H), 8.14 (d, J = 8.1 Hz, 1 H), 7.81-7.90 (m, 1 H), 7.68-7.77 (m, 1 H), 7.41-7.49 (m, 1 H), 7.17 (d, J = 5.0 Hz, 1 H), 6.84 (td, J = 17.5, 10.6 Hz, 1 H), 6.19 (dd, J = 16.6, 2.3 Hz, 1H), 5.69-5.82 (m, 1 H), 4.44-4.95 (m, 2 H), 3.45-4.23 (m, 4 H), 2.63-2.78 (m, 1 H), 1.90 (s, 3 H), 1.35 (br t, J = 5.7 Hz, 3 H), 1.16-1.28 (m, 3 H), 1.06 (d, J = 6.8 Hz, 3H), 0.88 (br d, J = 6.6 Hz, 3 H) |
| 92-37 | 653.2 | $^1$H NMR (400 MHz, DMSO-d$_6$) δ 8.49 (d, J = 2.5 Hz, 1 H), 8.41 (d, J = 5.0 Hz, 1 H), 7.72 (ddd, J = 8.9, 4.6, 2.7 Hz, 1 H), 7.42 (dd, J = 6.3, 2.6 Hz, 1 H), 7.33 (t, J = 9.3 Hz, 1 H), 7.21 (d, J = 4.8 Hz, 1 H), 6.72-6.90 (m, 1 H), 6.19 (dd J = 16.7, 2.4 Hz, 1 H), 5.69-5.82 (m, 1 H), 4.41-4.94 (m, 2 H), 3.45-4.22 (m, 4 H), 2.67-2.77 (m, 1 H), 1.94 (s, 3 H), 1.32 (br t, J = 7.0 Hz, 3 H), 1.13-1.27 (m, 3 H), 1.06 (d, J = 6.6 Hz, 3 H), 0.99 (d, J = 6.6 Hz, 3 H) |
| 92-38 | 676.2 | $^1$H NMR (400 MHz, DMSO-d$_6$) δ 8.36-8.50 (m, 2 H), 7.20 (d, J = 5.0 Hz, 1 H), 6.68-6.98 (m, 2 H), 6.19 (dd, J = 16.7, 2.2 Hz, 1 H), 5.75 (ddd, J = 10.3, 5.1, 2.0 Hz, 1 H), 5.28 (s, 2 H), 4.45-4.92 (m, 2 H), 3.43-4.25 (m, 4 H), 2.60-2.73 (m, 1 H), 1.93 (s, 3 H), 1.29-1.36 (m, 3 H), 1.13-1.26 (m, 3 H), 1.06 (d, J = 6.6 Hz, 3 H), 0.98 (d, J = 6.6 Hz, 3 H) |
| 92-39 | 613.2 | $^1$H NMR (400 MHz, DMSO-d$_6$) δ 8.48 (d, J = 2.7 Hz, 1 H), 8.41 (d, J = 5.0 Hz, 1 H), 7.51 (ddd, J = 8.5, 5.1, 2.2 Hz, 1 H), 7.30 (t, J = 9.2 Hz, 1 H), 7.24 (dd, J = 6.8, 2.1 Hz, 1 H), 7.20 (d, J = 4.8 Hz, 1 H), 6.83 (td, J = 16.4, 10.8 Hz, 1 H), 6.19 (dd, J = 16.6, 2.3 Hz, 1 H), 5.71-5.80 (m, 1 H), 4.40-4.98 (m, 2 H), 3.46-4.22 (m, 4 H), 2.65-2.76 (m, 1 H), 2.01 (s, 3 H), 1.93 (s, 3 H), 1.32 (br t, J = 6.9 Hz, 3 H), 1.13-1.26 (m, 3 H), 1.06 (d, J = 6.8 Hz, 3 H), 0.97 (d, J = 6.6 Hz, 3 H) |
| 92-40 | 600.1 | $^1$H NMR (400 MHz, DMSO-d$_6$) δ 8.50-8.64 (m, 1 H), 8.34-8.42 (m, 1 H), 7.80-7.92 (m, 1 H), 7.65-7.79 (m, 2 H), 7.12-7.25 (m, 1 H), 6.83 (td, J = 17.7, 10.4 Hz, 1 H), 6.12-6.27 (m, 1 H), 5.75 (br dd, J = 10.6, 2.3 Hz, 1 H), 4.41-4.98 (m, 2 H), 3.43-4.37 (m, 4 H), 2.63-2.83 (m, 1 H), 1.95 (s, 3 H), 1.36 (br d, J = 6.4 Hz, 3 H), 1.19-1.30 (m, 3 H), 1.03-1.14 (m, 3 H), 0.80-1.00 (m, 3 H) |
| 92-41 | 599.2 | $^1$H NMR (400 MHz, DMSO-d$_6$) δ 8.36 (d, J = 5.0 Hz, 2 H), 7.94 (dd, J = 7.6, 0.9 Hz, 1 H), 7.53-7.68 (m, 2 H), 7.23 (dd, J = 7.4, 0.9 Hz, 1 H), 7.17 (d, J = 4.8 Hz, 1 H), 6.83 (td, J = 17.3, 10.6 Hz, 1 H), 6.19 (dd, J = 16.7, 2.2 Hz, 1H) 5.68-5.84 (m, 1 H), 4.41-4.93 (m, 2 H), 3.41-4.26 (m, 4 H), 2.62-2.78 (m, 1 H), 2.35 (s, 3 H), 1.89 (s, 3 H), 1.31-1.37 (m, 3 H), 1.18-1.29 (m, 3 H), 1.06 (d, J = 6.6 Hz, 3 H), 0.88 (br d, J = 6.4 Hz, 3 H) |
| 92-42 | 557.2 | $^1$H NMR (400 MHz, DMSO-d$_6$) δ 8.37-8.51 (m, 2 H), 7.38-7.56 (m, 5 H), 7.22 (d, J = 4.8 Hz, 1 H), 6.84 (td, J = 16.4, 10.5 Hz, 1H), 6.19 (dd, J = 46.5, 2.0 Hz, 1 H), 5.72-5.81 (m, 1 H), 4.41-4.95 (m, 2 H), 3.39-4.35 (m, 4 H), 2.63-2.84 (m, 1 H), 1.94 (s, 3 H), 1.33 (t, J = 7.0 Hz, 3 H), 1.14-1.26 (m, 3 H), 1.08 (d, J = 6.6 Hz, 3 H), 0.98 (d, J = 6.6 Hz, 3H) |
| 92-43 | 601.2 | $^1$H NMR (400 MHz, DMSO-d$_6$) δ 8.39-8.47 (m, 1 H), 8.35 (dd, J = 6.4, 5.0 Hz, 1 H), 7.56 (d, J = 8.1 Hz, 1 H), 7.41 (t, J = 7.7 Hz, 1 H), 7.23-7.31 (m, 1 H), 7.16 (dd, J = 4.9, |

TABLE 148-continued

Analytical Data for Method Table Examples

| Ex. # | LRMS: m/z (ESI, +ve ion): (M + H)+ | NMR |
|---|---|---|
| | | 2.0 Hz, 1 H), 7.04 (d, J = 7.7 Hz, 1 H), 6.71-6.93 (m, 1 H), 6.19 (dd, J = 16.6, 2.3 Hz, 1 H), 5.69-5.81 (m, 1 H), 4.95 (br d, J = 4.1 Hz, 1 H), 4.42-4.88 (m, 2 H), 3.34-4.38 (m, 5 H), 2.63-2.79 (m, 1 H), 1.91 (d, J = 3.9 Hz, 3 H), 1.30-1.38 (m, 3 H), 1.14-1.30 (m, 3 H), 1.05 (dd, J = 10.2, 6.6 Hz, 3 H), 0.78-0.97 (m, 6 H) |
| 92-44 | 609.2 | $^1$H NMR (400 MHz, DMSO-$d_6$) δ 8.50 (d, J = 2.7 Hz, 1 H), 8.41 (d, J = 4.8 Hz, 1 H), 7.60 (ddd, J = 8.9, 4.3, 2.8 Hz, 1 H), 7.39 (t, J = 9.2 Hz, 1 H), 7.31 (dd, J = 6.0, 2.7 Hz, 1 H), 7.21 (d, J = 5.0 Hz, 1 H), 6.84 (td, J = 16.5, 10.6 Hz, 1 H), 6.19 (dd, J = 16.7, 2.2 Hz, 1 H), 5.70-5.81 (m, 1 H), 4.81-4.95 (m, 1 H), 4.43-4.80 (m, 1 H), 3.47-4.20 (m, 4 H), 2.63-2.78 (m, 1 H), 1.94 (s, 3 H), 1.33 (br t, J = 6.9 Hz, 3 H), 1.13-1.25 (m, 3 H), 1.06 (d, J = 6.6 Hz, 3 H), 0.98 (d, J = 6.6 Hz, 3 H) |
| 92-45 | 571.3 | $^1$H NMR (400 MHz, DMSO-$d_6$) δ 8.44 (d, J = 3.9 Hz, 1 H), 8.37 (d, J = 4.8 Hz, 1 H), 7.14-7.37 (m, 4 H), 7.08 (d, J = 7.3 Hz, 1 H), 6.84 (td, J = 17.3, 10.4 Hz, 1 H), 6.19 (dd, J = 16.7, 2.2 Hz, 1 H), 5.69-5.82 (m, 1 H), 4.42-4.97 (m, 2 H), 3.42-4.27 (m, 4 H), 2.72 (td, J = 6.6, 3.2 Hz, 1 H), 1.96 (s, 3 H), 1.92 (s, 3 H), 1.34 (t, J = 6.1 Hz, 3 H), 1.16-1.30 (m, 3 H), 1.06 (d, J = 6.6 Hz, 3 H), 0.93 (d, J = 6.8 Hz, 3H) |
| 92-46 | 609.2 | $^1$H NMR (400 MHz, DMSO-$d_6$) δ 8.50 (br s, 1 H), 8.40 (br d, J = 4.6 Hz, 1 H), 7.71 (br t, J = 7.3 Hz, 1 H), 7.32 (br t, J = 7.8 Hz, 1 H), 7.16-7.25 (m, 2 H), 6.74-6.93 (m, 1 H), 6.19 (br d, J = 16.4 Hz, 1 H), 5.75 (br d, J = 8.9 Hz, 1 H), 4.43-4.96 (m, 2 H), 3.44-4.26 (m, 4 H), 2.70 (br s, 1 H), 1.93 (s, 3 H), 1.33 (br t, J = 5.8 Hz, 3 H), 1.14-1.29 (m, 3 H), 1.06 (br d, J = 6.4 Hz, 3 H), 0.96 (br d, J = 6.2 Hz, 3 H) |
| 92-47 | 581.2 | $^1$H NMR (400 MHz, DMSO-$d_6$) δ 8.47 (d, J = 2.3 Hz, 1 H), 8.36 (d, J = 5.0 Hz, 1 H), 7.50-7.60 (m, 1 H), 7.40-7.49 (m, 2 H), 7.18 (d, J = 5.2 Hz, 2 H), 6.83 (td, J = 16.4, 10.5 Hz, 1 H), 6.19 (dd, J = 16.7, 2.2 Hz, 1 H), 5.66-5.86 (m, 1 H), 4.42-4.96 (m, 2 H), 3.74-4.22 (m, 5 H), 2.63-2.77 (m, 1 H), 1.93 (s, 3 H), 1.34 (br t, J = 6.8 Hz, 3 H), 1.15-1.29 (m, 3 H), 1.06 (d, J = 6.6 Hz, 3 H), 0.93 (d, J = 6.6 Hz, 3 H) |
| 92-48 | 581.2 | $^1$H NMR (400 MHz, DMSO-$d_6$) δ 8.42-8.49 (m, 2 H), 7.53-7.74 (m, 3 H), 7.40-7.49 (m, 1 H), 7.22 (d, J = 4.8 Hz, 1 H), 6.84 (td, J = 16.4, 10.8 Hz, 1 H), 6.19 (dd, J = 16.7, 2.2 Hz, 1 H), 5.68-5.82 (m, 1 H), 4.82-4.95 (m, 1 H), 4.44-4.80 (m, 1 H), 4.25 (s, 1 H), 3.46-4.18 (m, 4 H), 2.65-2.78 (m, 1 H), 1.93 (s, 3 H), 1.33 (br t, J = 7.2 Hz, 3 H), 1.13-1.27 (m, 3 H), 1.08 (d, J = 5.8 Hz, 3 H), 1.00 (d, J = 6.6 Hz, 3 H) |
| 92-49 | 595.3 | $^1$H NMR (400 MHz, DMSO-$d_6$) δ 8.42-8.49 (m, 2 H), 7.34-7.54 (m, 4 H), 7.22 (d, J = 5.0 Hz, 1 H), 6.84 (td, J = 16.5, 10.6 Hz, 1 H), 6.19 (dd, J = 16.6, 2.3 Hz, 1 H), 5.70-5.80 (m, 1 H), 4.81-4.95 (m, 1 H), 4.41-4.80 (m, 1 H), 3.45-4.20 (m, 4 H), 2.64-2.77 (m, 1 H), 2.04 (s, 3 H), 1.93 (s, 3H), 1.33 (t, J = 7.0 Hz, 3 H), 1.14-1.27 (m, 3 H), 1.07 (d, J = 6.6 Hz, 3 H), 0.99 (d, J = 6.6 Hz, 3 H) |
| 92-50 | 563.2 | $^1$H NMR (400 MHz, DMSO-$d_6$) δ 8.53 (d, J = 4.8 Hz, 1 H), 8.40 (d, J = 2.3 Hz, 1 H), 8.30 (dd, J = 2.9, 1.2 Hz, 1 H), 7.56 (dd, J = 5.0, 2.9 Hz, 1 H), 7.30 (br d, J = 4.6 Hz, 1 H), 7.16 (dd, J = 5.1, 1.1 Hz, 1 H), 6.83 (td, J = 15.8, 10.5 Hz, 1 H), 6.18 (br d, J = 16.6 Hz, 1 H), 5.70-5.82 (m, 1 H), 4.81-4.95 (m, 1 H), 4.39-4.78 (m, 1 H), 3.77-4.22 (m, 4 H), 2.64-2.75 (m, 1 H), 1.95 (s, 3 H), 1.32 (t, J = 7.3 Hz, 3 H), 1.13-1.26 (m, 3 H), 1.09 (d, J = 6.8 Hz, 3 H), 0.96 (d, J = 6.6 Hz, 3 H) |
| 92-51 | 591.2 | $^1$H NMR (400 MHz, DMSO-$d_6$) δ 8.48 (d, J = 3.3 Hz, 1 H), 8.37 (d, J = 4.8 Hz, 1 H), 7.51-7.56 (m, 1 H), 7.37-7.50 (m, 2 H), 7.23 (dd, J = 7.5, 1.7 Hz, 1 H), 7.18 (d, J = 5.0 Hz, 1 H), 6.83 (td, J = 17.1, 10.5 Hz, 1 H), 6.19 (dd, J = 16.7, 2.4 Hz, 1 H), 5.70-5.83 (m, 1 H), 4.44-4.96 (m, 2 H), 3.72-4.23 (m, 4 H), 2.65-2.74 (m, 1 H), 1.92 (s, 3 H), 1.30-1.37 (ro, 3 H), 1.25 (br dd, J = 6.3, 3.0 Hz, 3 H), 1.06 (d, J = 6.8 Hz, 3 H), 0.95 (d, J = 6.4 Hz, 3 H) |
| 92-52 | 575.2 | $^1$H NMR (400 MHz, DMSO-$d_6$) δ 8.36-8.56 (m, 2 H), 7.44-7.55 (m, 1 H), 7.39 (d, J = 7.9 Hz, 1 H), 7.16-7.36 (m, 3 H), 6.84 (td, J = 16.5, 10.6 Hz, 1 H), 6.19 (dd, J = 16.6, 2.1 Hz, 1 H), 5.69-5.83 (m, 1 H), 4.82-4.95 (m, 1 H), |

TABLE 148-continued

Analytical Data for Method Table Examples

| Ex. # | LRMS: m/z (ESI, +ve ion): (M + H)+ | NMR |
|---|---|---|
| | | 4.44-4.81 (m, 1 H), 3.45-4.20 (m, 4 H), 2.65-2.75 (m, 1 H), 1.94 (s, 3 H), 1.33 (t, J = 6.9 Hz, 3 H), 1.12-1.26 (m, 3 H), 1.08 (d, J = 6.6 Hz, 3 H), 0.98 (d, J = 6.6 Hz, 3 H) |
| 92-53 | 571.2 | $^1$H NMR (400 MHz, DMSO-d$_6$) δ 8.40-8.49 (m, 2 H), 7.25-7.34 (m, 4 H), 7.22 (d, J = 5.0 Hz, 1 H), 6.84 (td, J = 16.3, 10.5 Hz, 1 H), 6.19 (dd, J = 16.5, 2.0 Hz, 1 H), 5.70-5.81 (m, 1 H), 4.81-4.96 (m, 1 H), 4.40-4.79 (m, 1 H), 3.43-4.25 (m, 4 H), 2.64-2.78 (m, 1 H), 2.27 (s, 3 H), 1.93 (s, 3 H), 1.33 (t, J = 7.2 Hz, 3 H), 1.13-1.26 (m, 3 H), 1.08 (d, J = 6.6 Hz, 3 H), 1.01 (d, J = 6.6 Hz, 3 H) |
| 92-54 | 591.2 | $^1$H NMR (400 MHz, DMSO-d$_6$) δ 8.37-8.51 (m, 2 H), 7.40-7.57 (m, 4 H), 7.23 (d, J = 5.0 Hz, 1 H), 6.84 (td, J = 16.3, 10.6 Hz, 1 H), 6.19 (dd, J = 16.6, 1.9 Hz, 1 H), 5.66-5.82 (m, 1 H), 4.82-4.97 (m, 1 H), 4.42-4.81 (m, 1 H), 3.45-4.22 (m, 4 H), 2.64-2.78 (m, 1 H), 1.93 (s, 3 H), 1.32 (br t, J = 7.0 Hz, 3 H), 1.14-1.25 (m, 3 H), 1.07 (d, J = 6.6 Hz, 3 H), 1.00 (d, J = 6.8 Hz, 3 H) |
| 92-55 | 585.2 | $^1$H NMR (400 MHz, DMSO-d$_6$) δ 8.43 (d, J = 4.1 Hz, 1 H), 8.36 (d, J = 4.8 Hz, 1 H), 7.31-7.41 (m, 1 H), 7.20-7.30 (m, 2 H), 7.17 (d, J = 5.0 Hz, 1 H), 7.06 (d, J = 6.8 Hz, 1 H), 6.84 (td, J = 17.4, 10.5 Hz, 1 H), 6.19 (dd, J = 16.7, 2.2 Hz, 1 H), 5.69-5.83 (m, 1 H), 4.43-4.97 (m, 2 H), 3.41-4.31 (m, 4 H), 2.64-2.79 (m, 1 H), 2.17-2.38 (m, 2 H), 1.90 (s, 3 H), 1.35 (br t, J = 5.8 Hz, 3 H), 1.17-1.29 (m, 3 H), 1.06 (d, J = 6.6 Hz, 3 H), 0.92 (d, J = 6.6 Hz, 3 H), 0.82 (t, J = 7.5 Hz, 3 H) |
| 92-56 | 625.2 | $^1$H NMR (400 MHz, DMSO-d$_6$) δ 8.50 (d, J = 2.5 Hz, 1 H), 8.45 (d, J = 5.0 Hz, 1 H), 7.92 (d, J = 7.9 Hz, 1 H), 7.83 (d, J = 7.9 Hz, 1 H), 7.76 (s, 1 H), 7.65-7.74 (m, 1 H), 7.22 (d, J = 5.0 Hz, 1 H), 6.84 (td, J = 16.4, 10.5 Hz, 1 H), 6.19 (dd, J = 16.6, 2.1 Hz, 1 H), 5.70-5.80 (m, 1 H), 4.83-4.98 (m, 1 H), 4.40-4.81 (m, 1 H), 3.43-4.20 (m, 4 H), 2.72 (td, J = 6.6, 2.4 Hz, 1 H), 1.93 (s, 3 H), 1.28-1.38 (m, 3 H), 1.13-1.26 (m, 3 H), 1.08 (d, J = 6.6 Hz, 3 H), 1.00 (d, J = 6.6 Hz, 3 H) |
| 92-57 | 575.2 | $^1$H NMR (400 MHz, DMSO-d$_6$) δ 8.42-8.48 (m, 2 H), 7.57 (dd, J = 8.7, 5.4 Hz, 2 H), 7.28 (t, J = 8.9 Hz, 2 H), 7.23 (d, J = 4.8 Hz, 1 H), 6.84 (td, J = 16.3, 10.7 Hz, 1 H), 6.19 (dd, J = 16.6, 1.7 Hz, 1 H), 5.66-5.83 (m, 1 H), 4.82-4.99 (m, 1 H), 4.38-4.80 (m, 1 H), 3.69-4.22 (m, 4 H), 2.66-2.76 (m, 1 H), 1.94 (s, 3 H), 1.33 (br t, J = 7.0 Hz, 3 H), 1.14-1.26 (m, 3 H), 1.07 (d, J = 6.6 Hz, 3 H), 0.97 (d, J = 6.6 Hz, 3 H) |
| 92-58 | 589.3 | $^1$H NMR (400 MHz, DMSO-d$_6$) δ 8.46 (d, J = 3.3 Hz, 1 H), 8.39 (d, J = 4.8 Hz, 1 H), 7.38 (br t, J = 7.3 Hz, 1 H), 7.19 (d, J = 5.0 Hz, 1 H), 7.15 (t, J = 7.6 Hz, 1 H), 7.01 (br t, J = 6.6 Hz, 1 H), 6.84 (td, J = 16.7, 10.6 Hz, 1 H), 6.19 (dd, J = 16.6, 1.9 Hz, 1 H), 5.70-5.81 (m, 1 H), 4.81-4.93 (m, 1 H), 4.42-4.81 (m, 1 H), 3.44-4.23 (m, 4 H), 2.63-2.76 (m, 1 H), 2.24 (s, 3 H), 1.93 (s, 3 H), 1.33 (t, J = 6.6 Hz, 3 H), 1.14-1.27 (m, 3 H), 1.06 (d, J = 6.6 Hz, 3 H), 0.97 (d, J = 6.8 Hz, 3 H) |
| 92-59 | 589.2 | $^1$H NMR (400 MHz, DMSO-d$_6$) δ 8.46 (d, J = 3.7 Hz, 1 H), 8.38 (d, J = 4.8 Hz, 1 H), 7.20-7.33 (m, 2 H), 7.19 (d, J = 5.2 Hz, 1 H), 6.95 (d, J = 7.5 Hz, 1 H), 6.84 (td, J = 16.9, 10.5 Hz, 1 H), 6.19 (dd, J = 16.7, 2.2 Hz, 1 H), 5.68-5.83 (m, 1 H), 4.82-4.93 (m, 1 H), 4.44-4.80 (m, 1 H), 3.44-4.26 (m, 4 H), 2.68-2.78 (m, 1 H), 1.92 (s, 3 H), 1.87 (s, 3 H), 1.34 (br t, J = 6.1 Hz, 3 H), 1.16-1.29 (m, 3 H), 1.06 (d, J = 6.6 Hz, 3 H), 0.93 (d, J = 6.6 Hz, 3 H) |
| 92-60 | 589.2 | $^1$H NMR (400 MHz, DMSO-d$_6$) δ 8.46 (d, J = 2.5 Hz, 1 H), 8.40 (d, J = 4.8 Hz, 1 H), 7.26-7.39 (m, 1 H), 7.12-7.25 (m, 2 H), 7.00 (br d, J = 6.6 Hz, 1 H), 6.83 (td, J = 16.3, 10.6 Hz, 1 H), 6.18 (dd, J = 16.6, 1.9 Hz, 1 H), 5.65-5.82 (m, 1 H), 4.85 (br d, J = 6.2 Hz, 1 H), 4.42-4.79 (m, 1 H), 3.53-4.22 (m, 4 H), 2.62-2.77 (m, 1 H), 2.24 (s, 3 H), 1.93 (s, 3 H), 1.32 (br t, J = 6.8 Hz, 3 H), 1.14-1.25 (m, 3 H), 1.06 (d, J = 6.6 Hz, 3 H), 0.99 (br d, J = 6.6 Hz, 3 H) |
| 92-61 | 593.2 | $^1$H NMR (400 MHz, DMSO-d$_6$) δ 8.47 (d, J = 3.7 Hz, 1 H), 8.41 (d, J = 5.0 Hz, 1 H), 7.34-7.42 (m, 1 H), 7.30 (td, J = 8.3, 6.5 Hz, 1 H), 7.13-7.24 (m, 2 H), 6.83 (td, J = 16.9, 10.4 Hz, 1 H), 6.19 (dd, J = 16.7, 2.2 Hz, 1 H), 5.69-5.81 (m, 1 H), 4.42-4.94 (m, 2 H), 3.42-4.27 (m, 4 H), 2.65-2.77 (m, 1 H), 1.93 (s, 3 H), 1.33 (br t, J = 6.4 Hz, 3 H), |

TABLE 148-continued

Analytical Data for Method Table Examples

| Ex. # | LRMS: m/z (ESI, +ve ion): (M + H)+ | NMR |
|---|---|---|
| | | 1.15-1.28 (m, 3 H), 1.04-1.09 (m, 3 H), 0.96 (d, J = 6.6 Hz, 3 H) |
| 92-62 | 605.2 | $^1$H NMR (400 MHz, DMSO-d$_6$) δ 8.44 (d, J = 3.5 Hz, 1 H), 8.38 (d, J = 4.8 Hz, 1 H), 7.35 (ddd, J = 11.9, 8.3, 1.3 Hz, 1 H), 7.18 (d, J = 5.0 Hz, 1 H), 7.14 (td, J = 8.0, 5.0 Hz, 1 H), 6.92 (d, J = 7.7 Hz, 1 H), 6.84 (td, J = 16.9, 10.5 Hz, 1 H), 6.19 (dd, J = 16.7, 2.2 Hz, 1 H), 5.71-5.80 (m, 1 H), 4.45-4.94 (m, 2 H), 3.76-4.26 (m, 4 H), 3.55 (s, 3 H), 2.65-2.74 (m, 1 H), 1.93 (s, 3 H), 1.34 (t, J = 6.5 Hz, 3 H), 1.16-1.2.8 (m, 3 H), 1.06 (d, J = 6.8 Hz, 3 H), 0.93 (d, J = 6.6 Hz, 3 H) |
| 92-63 | 643.2 | $^1$H NMR (400 MHz, DMSO-d$_6$) δ 8.45-8.54 (m, 1 H), 8.37 (d, J = 5.0 Hz, 1 H), 7.76-7.88 (m, 1 H), 7.56-7.68 (m, 1 H), 7.12-7.22 (m, 2 H), 6.75-6.91 (m, 1 H), 6.19 (dd, J = 16.6, 2.3 Hz, 1 H), 5.76 (ddd, J = 10.3, 5.4, 2.2 Hz, 1 H), 4.44-4.95 (m, 2 H), 3.74-4.26 (m, 4 H), 2.64-2.79 (m, 1 H), 1.82-1.95 (m, 3 H), 1.30-1.39 (m, 3 H), 1.18-1.28 (m, 3 H), 1.07 (d, J = 6.0 Hz, 3 H), 0.86-0.93 (m, 3 H) |
| 92-64 | 609.2 | $^1$H NMR (400 MHz, DMSO-d$_6$) δ 8.51 (d, J = 3.3 Hz, 1 H), 8.38 (d, J = 4.8 Hz, 1 H), 7.43-7.56 (m, 2 H), 7.19 (d, J = 4.8 Hz, 1 H), 7.11 (br d, J = 7.0 Hz, 1 H), 6.74-6.93 (m, 1 H), 6.19 (dd, J = 16.7, 2.2 Hz, 1 H), 5.70-5.80 (m, 1 H), 4.45-4.93 (m, 2 H), 3.44-4.23 (m, 4 H), 2.64-2.82 (m, 1 H), 1.92 (s, 3 H), 1.34 (br t, J = 6.2 Hz, 3 H), 1.17-1.28 (m, 3 H), 1.07 (d, J = 6.6 Hz, 3 H), 0.94 (br d, J = 6.6 Hz, 3 H) |
| 92-65 | 593.2 | $^1$H NMR (400 MHz, DMSO-d$_6$) δ 8.49 (d, J = 3.5 Hz, 1 H), 8.41 (d, J = 5.0 Hz, 1 H), 7.34-7.44 (m, 2 H), 7.21 (d, J = 5.0 Hz, 1 H), 7.03-7.14 (m, 1 H), 6.83 (td, J = 16.8, 10.7 Hz, 1 H), 6.19 (dd, J = 16.7, 2.2 Hz, 1 H), 5.66-5.84 (m, 1 H), 4.40-4.96 (m, 2 H), 3.43-4.24 (m, 4 H), 2.64-2.76 (m, 1 H), 1.94 (s, 3 H), 1.33 (t, J = 6.6 Hz, 3 H), 1.15-1.27 (m, 3 H), 1.06 (d, J = 6.4 Hz, 3 H), 0.96 (d, J = 6.6 Hz, 3 H) |
| 92-66 | 593.2 | $^1$H NMR (400 MHz, DMSO-d$_6$) δ 8.50 (d, J = 3.9 Hz, 1 H), 8.41 (d, J = 4.8 Hz, 1 H), 7.49-7.64 (m, 1 H), 7.27-7.36 (m, 1 H), 7.21 (d, J = 4.8 Hz, 1 H), 7.07 (br t, J = 6.8 Hz, 1 H), 6.84 (td, J = 17.0, 10.6 Hz, 1 H), 6.20 (dd, J = 16.6, 1.9 Hz, 1 H), 5.69-5.84 (m, 1 H), 4.88 (br dd, J = 15.2, 6.5 Hz, 1 H), 4.43-4.81 (m, 1 H), 3.46-4.25 (m, 4 H), 2.65-2.79 (m, 1 H), 1.94 (s, 3 H), 1.34 (br t, J = 6.4 Hz, 3 H), 1.14-1.29 (m, 3 H), 1.07 (d, J = 6.0 Hz, 3 H), 0.97 (d, J = 6.6 Hz, 3 H) |
| 92-67 | 587.2 | $^1$H NMR (400 MHz, DMSO-d$_6$) δ 8.39 (d, J = 4.6 Hz, 2 H), 7.37-7.50 (m, 1 H), 7.19 (d, J = 5.0 Hz, 1 H), 7.10 (d, J = 8.3 Hz, 1 H), 6.93-7.05 (m, 2 H), 6.84 (td, J = 17.2, 10.6 Hz, 1 H), 6.20 (dd, J = 16.7, 1.6 Hz, 1 H), 5.68-5.83 (m, 1 H), 4.44-4.94 (m, 2 H), 3.80-4.23 (m, 4 H), 3.70 (s, 3 H), 2.64-2.78 (m, 1 H), 1.94 (s, 3 H), 1.34 (br t, J = 6.5 Hz, 3 H), 1.16-1.30 (m, 3 H), 1.07 (d, J = 6.6 Hz, 3 H), 0.97 (br d, J = 6.2 Hz, 3 H) |
| 92-68 | 601.3 | $^1$H NMR (400 MHz, DMSO-d$_6$) δ 9.18 (s, 1 H), 8.58 (s, 1 H), 8.50 (d, J = 6.2 Hz, 1 H), 8.38 (d, J = 5.0 Hz, 1 H), 7.18 (d, J = 5.0 Hz, 1 H), 6.72-6.94 (m, 1 H), 6.19 (dd, J = 16.7, 2.2 Hz, 1 H), 5.69-5.84 (m, 1 H), 4.43-4.92 (m, 2 H), 3.42-4.34 (m, 4 H), 2.63-2.80 (m, 2 H), 1.91 (s, 3 H), 1.36 (dd, J = 6.3, 3.4 Hz, 3 H), 1.19-1.31 (m, 3 H), 1.07 (d, J = 6.6 Hz, 3 H), 0.97 (br d, J = 6.4 Hz, 3 H), 0.90 (br d, J = 4.6 Hz, 6H) |
| 92-69 | 598.2 | $^1$H NMR (400 MHz, DMSO-d$_6$) δ 8.48 (d, J = 3.1 Hz, 1 H), 8.42-8.46 (m, 1 H), 8.38 (d, J = 4.8 Hz, 1 H), 7.44 (dd, J = 7.7, 1.5 Hz, 1 H), 7.12-7.25 (m, 2 H), 6.84 (td, J = 17.1, 10.4 Hz, 1 H), 6.19 (dd, J = 16.6, 2.1 Hz, 1 H), 5.76 (br dd, J = 10.6, 2.7 Hz, 1 H), 4.82-4.96 (m, 1 H), 4.43-4.81 (m, 1 H), 3.77-4.25 (m, 4 H), 2.62-2.78 (m, 1 H), 1.93 (s, 3 H), 1.55-1.66 (m, 1 H), 1.34 (br t, J = 6.3 Hz, 3 H), 1.17-1.28 (m, 3 H), 1.06 (d, J = 6.6 Hz, 3 H), 0.92 (br d, J = 6.6 Hz, 3 H), 0.89 (br s, 2 H), 0.67-0.79 (m, 2 H) |
| 92-70 | 637.2 | $^1$H NMR (400 MHz, DMSO-d$_6$) δ 8.49 (d, J = 2.5 Hz, 1 H), 8.30 (d, J = 4.8 Hz, 1 H), 7.87 (d, J = 8.3 Hz, 1 H), 7.46 (dt, J = 8.2, 4.1 Hz, 1 H), 7.42 (d, J = 2.5 Hz, 1 H), 7.26 (d, J = 3.7 Hz, 2 H), 7.11 (d, J = 5.0 Hz, 1 H), 6.96 (d, J = 2.7 Hz, 1 H), 6.85 (td, J = 17.2, 10.6 Hz, 1 H), 6.20 (dd, J = 16.7, 2.2 Hz, 1 H), 5.72.-5.80 (m, 1 H), 4.84-5.00 (m, 1 H), |

TABLE 148-continued

Analytical Data for Method Table Examples

| Ex. # | LRMS: m/z (ESI, +ve ion): (M + H)+ | NMR |
|---|---|---|
| | | 4.44-4.83 (m, 1 H), 3.97-4.29 (m, 2 H), 3.87-3.96 (m, 2 H), 3.86 (s, 3 H), 2.69-2.80 (m, 1 H), 1.93 (s, 3 H), 1.32-1.39 (m, 3 H), 1.19-1.31 (m, 3 H), 1.06 (d, J = 6.8 Hz, 3 H), 0.91 (d, J = 6.6 Hz, 3 H) |
| 92-71 | 592.2 | $^1$H NMR (400 MHz, DMSO-d$_6$) δ 8.44 (d, J = 5.0 Hz, 1 H), 8.38 (d, J = 5.2 Hz, 1 H), 7.23 (d, J = 5.0 Hz, 1 H), 6.84 (td, J = 17.4, 10.5 Hz, 1 H), 6.19 (br d, J = 17.0 Hz, 1 H), 5.71-5.81 (m, 1 H), 4.42-4.96 (m, 2 H), 3.38-4.30 (m, 4 H), 2.65-2.78 (m, 1 H), 2.57 (s, 3 H), 1.92 (s, 6 H), 1.34 (t, J = 6.1 Hz, 3 H), 1.14-1.30 (m, 3 H), 1.06 (d, J = 6.6 Hz, 3 H), 0.92 (d, J = 6.6 Hz, 3 H) |
| 92-72 | 578.2 | $^1$H NMR (400 MHz, DMSO-d$_6$) δ 9.11 (s, 1 H), 8.41-8.48 (m, 2 H), 7.25 (d, J = 5.0 Hz, 1 H), 6.84 (td, J = 17.1, 10.8 Hz, 1 H), 6.18 (br d, J = 16.6 Hz, 1 H), 5.68-5.81 (m, 1 H), 4.80-4.95 (m, 1 H), 4.39-4.80 (m, 1 H), 3.42-4.24 (m, 4 H), 2.63-2.76 (m, 1 H), 2.01 (s, 3 H), 1.95 (s, 3 H), 1.33 (t, J = 6.4 Hz, 3 H), 1.13-1.28 (m, 3 H), 1.06 (d, J = 6.2 Hz, 3 H), 0.92 (d, J = 6.6 Hz, 3 H) |
| 93-1 | 577.3 | $^1$H NMR (400 MHz, DMSO-d$_6$) δ 8.45 (d, J = 4.8 Hz, 1 H), 8.39 (d, J = 3.9 Hz, 1 H), 7.66 (d, J = 5.0 Hz, 1 H), 7.23 (d, J = 5.0 Hz, 1 H), 6.94 (d, J = 5.2 Hz, 1 H), 6.83 (td, J = 17.2, 10.7 Hz, 1 H), 6.19 (dd, J = 16.7, 1.3 Hz, 1 H), 5.71-5.78 (m, 1 H), 4.41-4.94 (m, 2 H), 3.42-4.23 (m, 4 H), 2.63-2.74 (m, 1 H), 1.94 (s, 3 H), 1.83 (s, 3 H), 1.33 (t, J = 6.5 Hz, 3 H), 1.21 (br dd, J = 27.7, 6.5 Hz, 3 H), 1.06 (d, J = 6.8 Hz, 3 H), 0.94 (d, J = 6.6 Hz, 3 H) |
| 93-2 | 549.2 | $^1$H NMR (400 MHz, DMSO-d$_6$) δ 8.52-8.57 (m, 1 H), 8.21-8.27 (m, 1 H), 7.34-7.43 (m, 1 H), 6.75-6.90 (m, 1 H), 6.18 (dd, J = 16.6, 2.3 Hz, 1 H), 5.71-5.78 (m, 1 H), 3.34-4.91 (m, 6 H), 2.70-2.83 (m, 1 H), 2.13-2.35 (m, 1 H), 1.81-1.97 (m, 3 H), 1.28-1.35 (m, 3 H), 1.14-1.27 (m, 6H), 1.07-1.13 (m, 3 H), 1.01 (dd, J = 11.8, 6.6 Hz, 3 H), 0.79-0.90 (m, 1 H), 0.65-0.72 (m, 1 H), 0.62 (s, 3 H) |
| 94-1 | 582.8 | $^1$H NMR (400 MHz, DMSO-d$_6$) δ 8.37 (d, J = 4.8 Hz, 1 H), 8.30 (dd, J = 9.4, 3.2 Hz, 1 H), 7.38-7.44 (m, 2 H), 7.21-7.27 (m, 1 H), 7.18 (d, J = 5.0 Hz, 1 H), 7.12 (d, J = 7.7 Hz, 1 H), 6.77-6.92 (m, 1 H), 6.19 (dd, J = 16.7, 2.2 Hz, 1 H), 5.73-5.78 (m, 1 H), 4.82-4.93 (m, 1H), 4.43-4.81 (m, 1 H), 3.44-4.27 (m, 4 H), 2.69 (quin, J = 6.4 Hz, 2 H), 1.92 (s, 3 H), 1.33 (t, J = 6.3 Hz, 3 H), 1.18-1.30 (m, 3 H), 0.87-1.09 (m, 12 H) |
| 94-2 | 571.0 | $^1$H NMR (400 MHz, DMSO-d6) δ 0.88-0.99 (m, 3 H) 1.03-1.10 (m, 3H) 1.18-1.29 (m, 3 H) 1.30-1.37 (m, 3 H) 1.90-1.96 (m, 3 H) 2.64-2.77 (m, 1 H) 3.72-4.25 (m, 6 H) 4.39-4.89 (m, 2 H) 4.90-4.96 (m, 1 H) 5.70-5.85 (m, 1 H) 6.14-6.25 (m, 1 H) 6.74-6.93 (m, 1H) 7.16-7.23 (m, 1 H) 7.24-7.36 (m, 2 H) 7.41-7.49 (m, 1 H) 7.51-7.57 (m, 1 H) 8.21-8.33 (m, 1 H) 8.36-8.46 (m, 1 H) <br> $^{19}$F NMR (376 MHz, DMSO-d6) δ −129.76 (br d, J = 6.07 Hz, 1 F) |
| 94-3 | 577.1 | $^1$H NMR (400 MHz, DMSO-d$_6$) δ = 8.52-8.36 (m, 2H), 7.60-7.38 (m, 3H), 7.23 (d, J = 4.8 Hz, 1H), 7.13-7.03 (m, 1H), 6.90-6.77 (m, 1H), 6.19 (dd, J = 2.2, 16.5 Hz, 1H), 5.79-5.71 (m, 1H), 4.87 (br s, 1H), 4.25-4.08 (m, 2H), 3.85 (br s, 2H), 1.99-1.92 (m, 4H), 1.31 (br t, J = 7.4 Hz, 3H), 1.27-1.14 (m, 3H), 1.07 (d, J = 6.8 Hz, 3H), 0.97 (d, J = 6.6 Hz, 3H); $^{19}$F NMR (376 MHz, DMSO-d6) δ = −118.05 (dd, J = 3.0, 17.8 Hz, 1F), −118.95 (br dd, J = 18.2, 32.9 Hz, 1F), −128.78 (d, 1F) |
| 94-4 | 573.0 | $^1$H NMR (400 MHz, DMSO-d6) δ 8.44 (d, J = 5.0 Hz, 1H), 8.34 (br d, J = 9.5 Hz, 1H), 7.37-7.32 (m, 1H), 7.26-7.19 (m, 2H), 7.06 (br d, J = 5.0 Hz, 1H), 6.81 (br dd, J = 10.4, 17.0 Hz, 1H), 6.21 (s, 1H), 5.75 (s, 2H), 4.93-4.39 (m, 2H), 4.14 (br t, J = 12.4 Hz, 1H), 3.85 (br s, 2H), 2.26-2.20 (m, 3H), 1.94 (s, 3H), 1.34-1.21 (m, 5H), 1.17 (br d, J = 6.8 Hz, 2H), 1.08 (d, J = 6.8 Hz, 3H), 1.01 (d, J = 6.6 Hz, 3H); $^{19}$F NMR (376 MHz, DMSO-d6) δ = −118.76 (s, 1F, −128.99 s, 1F) |
| 94-5 | 593.0 | $^1$H NMR (400 MHz, DMSO-d6) δ = 8.46-8.37 (m, 2H), 7.63 (ddd, J = 2.9, 4.3, 8.8 Hz, 1H), 7.43 (t J = 9.3 Hz, 1H), 7.30 (dd, J = 2.7, 5.8 Hz, 1H), 7.23 (d, J = 5.0 Hz, 1H), 6.90-6.77 (m, 1H), 6.19 (dd, J = 2.3, 16.6 Hz, 1H), |

TABLE 148-continued

Analytical Data for Method Table Examples

| Ex. # | LRMS: m/z (ESI, +ve ion): (M + H)+ | NMR |
|---|---|---|
| | | 5.78-5.73 (m, 2H), 4.94-4.78 (m, 1H), 4.13 (m, 2H), 3.91-3.82 (m, 2H), 2.75-2.68 (m, 1H), 1.94 (s, 3H), 1.34-1.28 (m, 3H), 1.24 (br d, J = 6.6 Hz, 3H), 1.07 (d, J = 6.6 Hz, 3H), 1.00 (d, J = 6.6 Hz, 3H); $^{19}$F NMR (376 MHz, DMSO-d6) δ = −115.61 (s, 1F), −128.78 (s, 1F) |
| 94-6 | 605.0 | $^1$H NMR (400 MHz, CHLOROFORM-d) δ = 8.49 (d, J = 5.0 Hz, 1H), 7.81 (br d, J = 8.5 Hz, 1H), 7.28 (d, J = 8.7 Hz, 1H), 7.08 (br d, J = 5.0 Hz, 1H), 6.88 (dd, J = 2.9, 8.9 Hz, 1H), 6.72-6.50 (m, 2H), 6.43-6.33 (m, 1H), 5.82-5.74 (m, 1H), 5.19-4.83 (m, 2H), 4.55-4.25 (m, 1H), 4.08-3.75 (m, 3H), 3.68 (s, 3H), 2.82-2.61 (m, 1H), 2.03 (br s, 3H), 1.33-1.25 (m, 3H), 1.25-1.18 (m, 6H), 1.13-1.00 (m, 3H); $^{19}$F NMR (376 MHz, CDCl3) δ = −125.80 (s, 1F) |
| 94-7 | 598.6 | $^1$H NMR (400 MHz, DMSO-d$_6$) δ = 8.46 (d, J = 4.8 Hz, 1H), 8.34 (br d, J = 9.7 Hz, 1H), 7.33-7.17 (m, 3H), 6.90-6.77 (m, 2H), 6.19 (dd, J = 2.1, 16.6 Hz, 1H), 5.78-5.73 (m, 1H), 4.98-4.42 (m, 2H), 4.14 (br t, J = 13.1 Hz, 2H), 3.92-3.81 (m, 2H), 2.75-2.61 (m, 1H), 1.94 (s, 3H), 1.91-1.82 (m, 1H), 1.37-1.13 (m, 8H), 1.08 (d, J = 6.6 Hz, 3H), 1.01 (d, J = 6.6 Hz, 3H), 0.93 (dd, J = 1.8, 8.2 Hz, 2H); $^{19}$F NMR (376 MHz, DMSO-d$_6$) δ = −117.96 (s, 1F), −128.53 (s, 1F) |
| 94-8 | 555.4 | $^1$H NMR (400 MHz, CDCl$_3$) δ 8.49 (d, J = 5.0 Hz, 1 H) 7.84 (br d, J = 9.3 Hz, 1 H) 7.29-7.35 (m, 1 H) 7.18-7.26 (m, 3 H) 7.08 (d, J = 5.0 Hz, 1 H) 6.51-6.71 (m, 1 H) 6.40 (br t, J = 15.1 Hz, 1 H) 5.76-5.84 (m, 1 H) 4.86-5.19 (m, 2 H) 4.35-4.53 (m, 1 H) 3.88-4.13 (m, 2 H) 3.68-3.83 (m, 1 H) 2.64-2.77 (m, 1 H) 2.01-2.05 (m, 6 H) 1.32-1.50 (m, 6 H) 1.22 (d, J = 6.6 Hz, 3 H) 0.98-1.05 (m, 3 H). $^{19}$F NMR (377 MHz, CDCl$_3$) δ −127.82--127-.88 (m, 1 F) |
| 94-9 | 569.4 | $^1$H NMR (400 MHz, CDCl$_3$) δ 8.46 (d, J = 5.0 Hz, 1H) 7.86 (d, J = 8.5 Hz, 1H) 7.16-7.23 (m, 1 H) 6.99-7.08 (m, 3H) 6.51-6.72 (m, 1 H) 6.40 (br t, J = 15.1 Hz, 1 H) 5.76-5.86 (m, 1 H) 3.67-5.17 (m, 6H) 2.66-2.80 (m, 1 H) 1.96-2.02 (m, 6 H) 1.89 (s, 3 H) 1.46 (br d, J = 6.6 Hz, 3 H) 1.33-1.52 (m, 3 H) 1.23 (d, J = 6.8 Hz, 3 H) 0.98-1.06 (m, 3 H). $^{19}$F NMR (376 MHz, CDCl$_3$) δ −128.31 (s, 1 F) |
| 94-10 | 573.4 | $^1$H NMR (400 MHz, CDCl$_3$) δ 8.48 (d, J = 4.8 Hz, 1 H) 7.87 (d, J = 8.5 Hz, 1 H) 7.27-7.32 (m, 1 H) 7.08 (d, J = 5.0 Hz, 1 H) 6.99 (d, J = 7.5 Hz, 1 H) 6.94 (t, J = 8.8 Hz, 1 H) 6.52-6.72 (m, 1H) 6.40 (br t, J = 14.9 Hz, 1H) 5.76-5.85 (m, 1 H) 3.67-5.18 (m, 6 H) 2.67-2.79 (m, 1 H) 1.99-2.03 (m, 3 H) 1.97 (br s, 3 H) 1.46 (br d, J = 6.6 Hz, 3 H) 1.34-1.53 (m, 3 H) 1.22 (d, J = 6.8 Hz, 3 H) 1.01 (br s, 3 H). $^{19}$F NMR (376 MHz, CDCl$_3$) δ −115.74--115.69 (m, 1 F) −127.11--127.73 (m, 1 F) |
| 94-11 | 577.4 | $^1$H NMR (400 MHz, CDCl$_3$) δ 8.40 (d, J = 4.8 Hz, 1 H) 7.79 (d, J = 8.3 Hz, 1 H) 7.25-7.36 (m, 1 H) 6.99 (d, J = 5.0 Hz, 1 H) 6.85 (t, J = 8.3 Hz, 2 H) 6.42-6.62 (m, 1 H) 6.31 (br t, J = 14.9 Hz, 1 H) 5.66-5.76 (m, 1 H) 3.56-5.08 (m, 6 H) 2.55-2.70 (m, 1 H) 1.90-1.94 (m, 3 H) 1.24-1.43 (m, 6 H) 1.14 (d, J = 6.8 Hz, 3 H) 0.93-0.99 (m, 3 H). $^{19}$F NMR (377 MHz, CDCl$_3$) δ −112.48 (br s, 1 F) −127.51 (q, J = 11.3 Hz, 1 F) |
| 94-12 | 593.2 | $^1$H NMR (400 MHz, CDCl$_3$) δ 8.48 (d, J = 5.0 Hz, 1 H) 7.89 (d, J = 8.3 Hz, 1H) 7.35 (td, J = 8.3, 6.0 Hz, 1 H) 7.23 (d, J = 8.1 Hz, 1 H) 7.00-7.11 (m, 2 H) 6.51-6.72 (m, 1 H) 6.40 (br t, J = 15.0 Hz, 1 H) 5.76-5.85 (m, 1 H) 4.45-5.18 (m, 2 H) 3.68-4.45 (m, 4 H) 2.66-2.79 (m, 1 H) 2.01 (br s, 3 H) 1.46 (br d, J = 6.4 Hz, 3 H) 1.33-1.52 (m, 3 H) 1.23 (d, J = 6.8 Hz, 3 H) 1.03 (br d, J = 5.2 Hz, 3 H). $^{19}$F NMR (377 MHz, CDCl$_3$) δ −111.80 (br d, J = 221.9 Hz, 1 F) −128.23--127.28 (m, 1 F) |
| 94-13 | 591.2 | $^1$H NMR (400 MHz, DMSO-d$_6$) δ 8.41 (d, J = 4.8 Hz, 1 H), 8.36 (dd, J = 9.7, 3.9 Hz, 1 H), 7.58-7.71 (m, 3 H), 7.52 (br d, J = 6.0 Hz, 1 H), 7.22 (d, J = 5.0 Hz, 1 H), 6.78-6.94 (m, 1 H), 6.44-6.77 (m, 1H), 6.19 (dd, J = 16.7, 2.4 Hz, 1 H), 5.71-5.81 (m, 1H), 4.85 (dt, J = 6.4, 3.4 Hz, 1 H), 4.44-4.81 (m, 1 H), 3.43-4.28 (m, 4 H), 2.64-2.77 (m, 1 H), 1.93 (s, 3 H), 1.33 (t, J = 5.9 Hz, 3 H), 1.17-1.30 (m, 3 H), 1.06 (d, J = 6.6 Hz, 3 H), 0.89 (br d, J = 6.6 Hz, 3 H) |

TABLE 148-continued

Analytical Data for Method Table Examples

| Ex. # | LRMS: m/z (ESI, +ve ion): (M + H)+ | NMR |
|---|---|---|
| 94-14 | 580.6 | $^1$H NMR (400 MHz, DMSO-d$_6$) δ 10.19 (s, 1H), 8.75 (d, J = 4.8 Hz, 1 H), 8.27-8.48 (m, 1 H), 7.79-8.02 (m, 2 H), 6.99-7.70 (m, 3 H), 6.73-6.95 (m, 1 H), 6.11-6.27 (m, 1 H), 5.70-5.80 (m, 1 H), 4.91 (br s, 1 H), 4.43-4.84 (m, 1 H), 3.46-4.29 (m, 4 H), 2.70-2.85 (m, 1 H), 1.92-2.08 (m, 3 H), 1.34 (br t, J = 7.0 Hz, 3 H), 1.16-1.28 (m, 3 H), 1.06-1.15 (m, 3H), 0.80-1.05 (m, 3 H) |
| 94-15 | 585.2 | $^1$H NMR (400 MHz, DMSO-d$_6$) δ 12.94 (br s, 1 H), 8.37 (d, J = 5.0 Hz, 1 H), 8.22 (br d, J = 9.5 Hz, 1 H), 7.91 (d, J = 7.3 Hz, 1 H), 7.50-7.69 (m, 2 H), 7.14-7.32 (m, 2 H), 6.84 (ddd, J = 19.0, 17.0, 10.5 Hz, 1 H), 6.19 (dd, J = 16.7, 2.2 Hz, 1 H), 5.67-5.81 (m, 1 H), 4.40-4.95 (m, 2 H), 4.02-4.23 (m, 1 H), 3.77-3.93 (m, 2 H), 3.51 (br dd, J = 13.4, 2.4 Hz, 1 H), 2.62-2.75 (m, 1 H), 1.92 (d, J = 12.9 Hz, 3 H), 1.30 (br dd, J = 9.3, 6.8 Hz, 3 H), 1.14-1.26 (m, 3 H), 1.07 (d, J = 6.6 Hz, 3 H), 0.91 (br d, J = 6.6 Hz, 3 H) |
| 94-16 | 566.2 | $^1$H NMR (400 MHz, DMSO-d$_6$) δ 8.53-8.62 (m, 1 H), 8.40 (s, 1 H), 8.27 (d, J = 7.7 Hz, 1 H), 7.90-8.01 (m, 1 H), 7.80-7.87 (m, 1 H), 7.74 (d, J = 7.9 Hz, 1 H), 7.47-7.56 (m, 2 H), 7.33 (d, J = 5.0 Hz, 1 H), 6.70-6.97 (m, 1 H), 6.19 (dd, J = 16.7, 2.2 Hz, 1 H), 5.65-5.82 (m, 1 H), 4.64-4.99 (m, 2 H), 3.79-4.32 (m, 4 H), 2.62-2.79 (m, 1 H), 1.97 (s, 3 H), 1.32 (dd, J = 10.6, 6.6 Hz, 3 H), 1.13-1.25 (m, 3 H), 1.08 (d, J = 6.6 Hz, 3 H), 0.94 (d, J = 6.6 Hz, 3 H) |
| 94-17 | 584.2 | $^1$H NMR (400 MHz, DMSO-d$_6$) δ 8.38 (d, J = 4.8 Hz, 1 H), 8.17 (d, J = 9.5 Hz, 1 H), 7.86 (s, 1 H), 7.62-7.69 (m, 1 H), 7.47-7.55 (m, 2 H), 7.20-7.28 (m, 1 H), 7.10-7.20 (m, 2 H), 6.73-6.93 (m, 1H), 6.18 (dd, J = 16.7, 2.4 Hz, 1 H), 5.71-5.79 (m, 1 H), 4.44-4.92 (m, 2H), 3.43-4.25 (m, 4 H), 2.68 (td J = 6.3, 3.8 Hz, 1 H), 1.94 (s, 3 H), 1.31 (t, J = 6.7 Hz, 3 H), 1.17-1.27 (m, 3 H), 1.07 (d, J = 6.6 Hz, 3 H), 0.92 (br d, J = 6.6 Hz, 3 H) |
| 94-18 | 598.2 | $^1$H NMR (400 MHz, DMSO-d$_6$) δ 8.38 (d, J = 4.8 Hz, 1 H), 8.32 (br d, J = 4.6 Hz, 1 H), 8.19 (d J = 9.5 Hz, 1 H), 7.56-7.64 (m, 1 H), 7.47-7.55 (m, 2 H), 7.16-7.25 (m, 2 H), 6.73-6.94 (m, 1 H), 6.19 (dd, J = 16.7, 2.2 Hz, 1 H), 5.69-5.82 (m, 1 H), 4.41-4.93 (m, 2H), 3.43-4.23 (m, 4 H), 2.60-2.74 (m, 4 H), 1.93 (s, 3 H), 1.31 (br t, J = 7.4 Hz, 3 H), 1.16-1.28 (m, 3 H), 1.06 (d, J = 6.6 Hz, 3 H), 0.89 (br d, J = 6.4 Hz, 3 H) |
| 94-19 | 602.2 | $^1$H NMR (400 MHz, DMSO-d$_6$) δ 8.36 (d, J = 4.8 Hz, 1 H), 8.25 (br s, 1 H), 7.87 (br s, 1 H), 7.53-7.65 (m, 1 H), 7.36-7.53 (m, 2 H), 7.27 (br s, 1 H), 7.16 (br d, J = 4.8 Hz, 1 H), 6.71-6.98 (m, 1 H), 6.19 (dd, J = 16.7, 1.8 Hz, 1 H), 5.69-5.84 (m, 1 H), 4.40-4.91 (m, 2 H), 3.71-4.32 (m, 4 H), 2.64-2.78 (m, 1 H), 1.87-1.97 (m, 3 H), 1.34 (br d, J = 6.0 Hz, 3 H), 1.18-1.29 (m, 3 H), 1.07 (br d, J = 6.4 Hz, 3 H), 0.82 (br d, J = 6.0 Hz, 3 H) |
| 94-20 | 556.4 | $^1$H NMR (400 MHz, DMSO-d$_6$) δ 8.51 (d, J = 5.0 Hz, 1 H), 8.24 (dd, J = 11.8, 3.1 Hz, 1 H), 7.51 (dd, J = 8.1, 1.7 Hz, 1 H), 7.28 (d, J = 5.0 Hz, 1 H), 7.05-7.13 (m, 1 H), 6.77-6.92 (m, 1 H) 6.68 (d, J = 7.9 Hz, 1H) 6.56 (t, J = 7.6 Hz, 1 H), 6.19 (br d, J = 16.8 Hz, 1 H), 5.76 (s, 3 H), 4.43-4.94 (m, 2 H), 4.09-4.20 (m, 1 H), 3.43-3.92 (m, 3 H), 2.64-2.77 (m, 1 H), 1.95 (s, 3 H), 1.32 (t, J = 6.9 Hz, 3 H), 1.17-1.27 (m, 3 H), 1.08 (d, J = 6.8 Hz, 3 H), 0.97 (d, J = 6.6 Hz, 3 H) |
| 94-21 | 621.2 | $^1$H NMR (400 MHz, DMSO-d$_6$) δ 8.31-8.44 (m, 2 H), 7.88 (br d, J = 8.3 Hz, 1H), 7.45-7.56 (m, 3 H), 7.27 (br t, J = 7.7 Hz, 1H), 7.16 (br d, J = 4.8 Hz, 1 H), 7.09 (s, 1 H), 6.75-6.94 (m, 1 H), 6.20 (br d, J = 16.8 Hz, 1 H), 5.69-5.80 (m, 1 H), 4.92 (br dd, J = 6.7, 4.0 Hz, 1 H), 4.46-4.84 (m, 1 H), 4.1.4-4.26 (m, 1 H), 3.87 (s, 6 H), 2.74 (br d, J = 6.0 Hz, 1 H), 1.96 (s, 3 H), 1.34 (br t, J = 6.8 Hz, 3 H), 1.18-1.31 (m, 3 H), 1.07 (br d, J = 6.6 Hz, 3 H), 0.95 (br d, J = 6.4 Hz, 3 H) |
| 95-1 | 563.3 | $^1$H NMR (400 MHz, DMSO-d$_6$) δ 8.48 (d, J = 4.8 Hz, 1 H), 8.25 (d, J = 4.1 Hz, 1 H), 7.25 (d, J = 4.8 Hz, 1 H), 6.82 (td, J = 17.5, 10.5 Hz, 1 H), 6.18 (dd, J = 16.6, 1.9 Hz, 1 H), 5.71-5.77 (m, 1 H), 4.40-4.89 (m, 2 H), 3.37-4.19 (m, 4 H), 3.02 (tt, J = 11.0, 2.9 Hz, 1 H), 2.63-2.72 (m, 1 H), 1.86 (s, 3 H), 1.50-1.68 (m, 5 H), 1.13-1.34 (m, 9 H), 1.03 (dd, J = 45.3, 6.7 Hz, 8 H) |

TABLE 148-continued

Analytical Data for Method Table Examples

| Ex. # | LRMS: m/z (ESI, +ve ion): (M + H)+ | NMR |
|---|---|---|
| 95-2 | 551.3 | $^1$H NMR (400 MHz, CHLOROFORM-d) δ 8.55 (br d, J = 3.9 Hz, 1 H), 7.99 (s, 1 H), 7.15 (br s, 1 H), 6.51-6.72 (m, 1H), 6.40 (br t, J = 15.1 Hz, 1 H), 5.75-5.86 (m, 1 H), 4.78-5.18 (m, 2 H), 3.36-4.54 (m, 4 H), 2.47-2.93 (m, 3 H), 2.03 (br s, 3 H), 1.40-1.50 (m, 3 H), 1.24-1.36 (m, 6 H), 1.12 (br s, 3 H), 0.78 (s, 9H) |
| 95-3 | 549.2 | $^1$H NMR (400 MHz, DMSO-d$_6$) δ 8.47 (d, J = 4.8 Hz, 1 H), 8.24 (d, J = 4.1 Hz, 1 H), 7.24 (d, J = 4.8 Hz, 1 H), 6.82 (td, J = 17.3, 10.6 Hz, 1 H), 6.13-6.22 (m, 1 H), 5.70-5.78 (m, 1 H), 4.38-4.89 (m, 2 H), 3.37-4.19 (m, 5 H), 2.60-2.72 (m, 1 H), 1.87 (s, 3 H), 1.69-1.84 (m, 2 H), 1.27-1.48 (m, 7 H), 1.23 (br d, J = 6.4 Hz, 3 H), 1.16 (d, J = 6.6 Hz, 2 H), 1.08 (d, J = 6.6 Hz, 3 H), 0.95 (d, J = 6.6 Hz, 3 H) |
| 95-4 | 521.2 | $^1$H NMR (400 MHz, DMSO d$_6$) δ 8.47 (d, J = 4.8 Hz, 1 H), 8.23 (d, J = 3.1 Hz, 1 H), 7.24 (d, J = 5.0 Hz, 1 H), 6.82 (td, J = 16.8, 10.6 Hz, 1 H), 6.12-6.22 (m, 1 H), 5.69-5.79 (m, 1H), 4.39-4.89 (m, 2 H), 3.38-4.17 (m, 4H), 2.59 (ddd, J = 13.3, 6.7, 3.0 Hz, 1H), 2.37-2.45 (m, 1H), 1.85 (s, 3 H), 1.26-1.33 (m, 3 H), 1.18 (dd, J = 28.4, 6.6 Hz, 3 H), 1.07 (d, J = 6.8 Hz, 3H), 0.91-0.99 (m, 5 H), 0.39-0.49 (m, 2 H) |
| 95-5 | 535.3 | $^1$H NMR (400 MHz, DMSO-d$_6$) δ 8.48 (d, J = 5.0 Hz, 1H), 8.25 (d, J = 1.7 Hz, 1 H), 7.26 (d, J = 4.8 Hz, 1 H), 6.75-6.89 (m, 1 H), 6.18 (dd, J = 16.7, 2.0 Hz, 1 H), 5.71-5.77 (m, 1 H), 4.77-4.89 (m, 1 H), 4.39-4.77 (m, 1 H), 3.41-4.16 (m, 5 H), 2.61-2.70 (m, 1 H), 2.02-2.22 (m, 2 H), 1.91 (s, 3 H), 1.74-1.89 (m, 3 H), 1.52 (ddt, J = 12.0, 7.7, 3.9, 3.9 Hz, 1 H), 1.25-1.33 (m, 3 H), 1.17 (br dd, J = 30.0, 6.5 Hz, 3 H), 1.08 (d, J = 6.6 Hz, 3 H), 0.99 (d, J = 6.8 Hz, 3 H) |
| 95-6 | 523.3 | $^1$H NMR (400 MHz, DMSO-d$_6$) δ 8.47 (d, J = 5.0 Hz, 1 H), 8.27 (d, J = 2.5 Hz, 1 H), 7.24 (d, J = 5.0 Hz, 1 H), 6.75-6.89 (m, 1H), 6.18 (dd, J = 16.7, 1.8 Hz, 1 H), 5.71-5.78 (m, 1H), 4.81 (dt, J = 6.5, 3.4 Hz, 1 H), 4.39-4.77 (m, 1 H), 3.40-4.18 (m, 4 H), 2.60-2.74 (m, 3 H), 1.89 (s, 3 H), 1.39 (sxt, J = 7.3 Hz, 2 H), 1.26-1.33 (m, 3 H), 1.12-1.23 (m, 3 H) 1.07 (d, J = 6.6 Hz, 3 H), 0.97 (d, J = 6.4 Hz, 3 H), 0.72 (t, J = 7.4 Hz, 3 H) |
| 95-7 | 561.2 | $^1$H NMR (400 MHz, DMSO-d$_6$) δ 8.48 (d, J = 4.8 Hz, 1H), 8.39 (s, 1 H), 7.26 (d, J = 4.8 Hz, 1 H), 6.82 (td, J = 16.6, 11.2 Hz, 1 H), 6.18 (dd, J = 16.7, 2.0 Hz, 1 H), 5.71-5.77 (m, 1 H), 4.83 (dt, J = 6.2, 3.2 Hz, 1 H), 4.34-4.75 (m, 1 H), 3.44-4.16 (m, 4 H), 2.53-2.60 (m, 1 H), 1.94 (s, 3 H), 1.22-1.31 (m, 12 H), 1.07-1.18 (m, 3 H), 1.04 (d, J = 6.6 Hz, 6 H) |
| 96-1 | 572.2 | $^1$H NMR (400 MHz, DMSO-d$_6$) δ 8.47 (d, J = 4.8 Hz, 1 H), 8.41 (d, J = 3.9 Hz, 1 H), 8.38 (d, J = 5.0 Hz, 1 H), 7.70 (d, J = 7.7 Hz, 1 H), 7.35 (dd, J = 7.9, 4.8 Hz, 1H), 7.19 (d, J = 4.8 Hz, 1 H), 6.84 (td, J = 17.1, 10.5 Hz, 1H), 6.19 (dd, J = 16.6, 2.1 Hz, 1H), 5.73-5.78 (m, 1 H), 4.43-4.96 (m, 2 H), 4.13-4.27 (m, 1 H), 3.43-3.93 (m, 3 H), 2.72 (tt, J = 6.6, 3.2 Hz, 1 H), 1.95 (s, 3 H), 1.91 (s, 3 H), 1.35 (t, J = 6.2 Hz, 3 H), 1.18-1.28 (m, 3 H), 1.06 (d, J = 6.6 Hz, 3 H), 0.92 (d, J = 6.6 Hz, 3 H) |
| 96-2 | 587.6 | $^1$H NMR (400 MHz, DMSO-d$_6$) δ 8.43 (d, J = 2.7 Hz, 1H), 8.36 (d, J = 4.8 Hz, 1 H), 8.15 (dd, J = 4.6, 0.8 Hz, 1 H), 7.54-7.59 (m, 1 H), 7.44 (dd, J = 8.5, 4.6 Hz, 1 H), 7.17 (d, J = 5.0 Hz, 1 H), 6.83 (td, J = 16.3, 10.6 Hz, 1 H), 6.19 (dd, J = 16.7, 1.6 Hz, 1 H), 5.72-5.78 (m, 1 H), 4.82-4.94 (m, 1 H), 4.42-4.81 (m, 1 H), 3.78-4.21 (m, 4 H), 3.69 (s, 3 H), 2.62-2.70 (m, 1 H), 1.93 (s, 3 H), 1.33 (t, J = 7.0 Hz, 3 H), 1.21 (br dd, J = 29.1, 6.7 Hz, 3 H), 1.05 (d, J = 6.6 Hz, 3 H), 0.95 (d, J = 6.6 Hz, 3 H) |
| 100-1 | 592.3 | $^1$H NMR (400 MHz, DMSO-d$_6$) δ 8.38-8.50 (m, 1 H), 7.50-7.59 (m, 1 H), 7.22-7.42 (m, 4 H), 6.75-6.91 (m, 1 H), 6.19 (dd, J = 16.8, 2.1 Hz, 1 H), 5.71-5.79 (m, 1 H), 4.41-4.97 (m, 2 H), 3.38-4.33 (m, 5 H), 2.39-2.48 (m, 1 H), 1.11-1.37 (m, 12 H), 0.99 (dd, J = 9.4, 6.9 Hz, 3 H), 0.93 (dd, J = 6.9, 2.8 Hz, 3 H) |
| 100-1-1 | 592.3 | $^1$H NMR (400 MHz, DMSO-d$_6$) δ 8.41 (d, J = 8.1 Hz, 1 H), 7.51-7.58 (m, 1 H), 7.39 (s, 1 H), 7.29-7.37 (m, 2 H), 7.23-7.28 (m, 1H), 6.83 (ddd, J = 24.3, 16.6, 10.6 Hz, 1 H), 6.19 (br d, J = 16.8 Hz, 1 H), 5.75 (ddd, J = 10.3, 4.9, 2.3 Hz, 1 H), 4.46-4.93 (m, 2 H), 3.38-4.32 (m, 5 H), |

TABLE 148-continued

Analytical Data for Method Table Examples

| Ex. # | LRMS: m/z (ESI, +ve ion): (M + H)+ | NMR |
|---|---|---|
| | | 2.44 (td, J = 6.9, 2.3 Hz, 1 H), 1.35 (br d, J = 6.4 Hz, 3 H), 1.19-1.29 (m, 6 H), 1.14 (d, J = 6.4 Hz, 3 H), 1.00 (d, J = 6.8 Hz, 3 H), 0.93 (d, J = 7.0 Hz, 3 H) |
| 100-1-2 | 592.3 | $^1$H NMR (400 MHz, DMSO-$d_6$) δ 8.48 (s, 1 H), 7.50-7.58 (m, 1 H), 7.38 (s, 1 H), 7.29-7.37 (m, 2 H), 7.23-7.29 (m, 1 H), 6.82 (dt, J = 16.6, 11.0 Hz, 1 H), 6.19 (dd, J = 16.6, 2.3 Hz, 1 H), 5.72-5.78 (m, 1 H), 4.40-4.95 (m, 2 H), 3.48-4.17 (m, 5 H), 2.41-2.48 (m, 1 H), 1.29-1.35 (m, 3 H), 1.26 (d, J = 6.4 Hz, 3 H), 1.11-1.23 (m, 6 H), 0.97 (d, J = 6.8 Hz, 3 H), 0.93 (d, J = 6.8 Hz, 3 H) |
| 100-2 | 629.4 | $^1$H NMR (500 MHz, DMSO-$d_6$) δ 9.06 (s, 1 H) 8.49 (d, J = 7.01 Hz, 1H) 7.52 (q, J = 6.62 Hz, 1 H) 7.26-7.33 (m, 2 H) 7.17-7.20 (m, 1 H) 6.19 (br d, J = 16.87 Hz, 1 H) 5.74-5.78 (m, 1 H) 4.88 (br d, J = 13.62 Hz, 1 H) 4.46-4.52 (m, 1 H) 4.13-4.26 (m, 2 H) 3.75-3.94 (m, 4 H) 2.65-2.81 (m, 1 H) 1.34 (t, J = 5.84 Hz, 3 H) 1.17-1.20 (m, 2 H) 1.07 (dd, J = 6.55, 3.05 Hz, 6H) 0.93 (br d, J = 6.62 Hz, 6H) |
| 100-3 | 611.4 | $^1$H NMR (500 MHz, DMSO-$d_6$) δ 9.09 (s, 1 H) 8.63 (d, J = 4.80 Hz, 1 H) 8.00 (d, J = 7.79 Hz, 1 H) 7.85 (t, J = 7.72 Hz, 1 H) 7.71 (t, J = 7.72 Hz, 1 H) 7.47 (d, J = 7.79 Hz, 1 H) 6.83-6.94 (m, 1 H) 6.24 (dd, J = 16.61, 2.08 Hz, 1 H) 5.80 (ddd, J = 10.25, 5.97, 2.08 Hz, 1 H) 4.90-5.00 (m, 1 H) 4.83 (br s, 1H) 4.24 (q, J = 13.75 Hz, 1 H) 3.85-4.02 (m, 2 H) 3.49-3.60 (m, 1 H) 2.71-2.82 (m, 2 H) 1.37-1.43 (m, 3 H) 1.22-1.32 (m, 3 H) 1.12 (d, J = 6.62 Hz, 6 H) 0.95-1.02 (m, 6 H) |
| 100-4 | 628.4 | $^1$H NMR (500 MHz, DMSO-$d_6$) δ 9.02 (s, 1 H) 8.47 (br s, 1 H) 7.39 (d, J = 4.02 Hz, 2 H) 7.20-7.26 (m, 1 H) 7.00 (br d, J = 7.53 Hz, 1 H) 6.79-6.89 (m, 1 H) 6.19 (dd, J = 16.61, 2.34 Hz, 1 H) 5.74-5.78 (m, 1 H) 4.90 (br s, 1 H) 4.79 (br s, 1 H) 4.49 (br s, 1 H) 4.17 (br d, J = 12.59 Hz, 1 H) 3.77-3.98 (m, 2 H) 2.64-2.85 (m, 2 H) 1.17-1.39 (m, 7 H) 1.02-1.12 (m, 9 H) 0.87-0.99 (m, 9 H) |
| 100-5 | 424.1 | $^1$H NMR (400 MHz, CHLOROFORM-d) δ 7.96 (s, 1H), 6.51-6.67 (m, 1H), 6.31-6.45 (m, 1H), 5.79 (dd, J = 1.87, 10.57 Hz, 1H), 4.30 (s, 2H), 3.81-3.88 (m, 8H), 1.00 (s, 9H). |
| 100-6 | 356.3 | $^1$H NMR (400 MHz, CHLOROFORM-d) δ 8.61 (dd, J = 1.87, 4.56 Hz, 1H), 7.94 (dd, J = 1.76, 7.98 Hz, 1H), 7.08 (dd, J = 4.56, 8.09 Hz, 1H), 6.60 (dd, J = 10.57, 16.79 Hz, 1H), 6.37 (dd, J = 1.87, 16.79 Hz, 1H), 5.78 (dd, J = 1.76, 10.47 Hz, 1H), 4.41 (br s, 2H), 3.74-3.96 (m, 8H), 1.00 (s, 9H). |
| 100-7 | 664.2 | $^1$H NMR (400 MHz, CDCl$_3$) δ 9.07 (d, J = 2.28 Hz, 1H), 8.01-8.19 (m, 2H), 7.63-7.74 (m, 2H), 7.18-7.25 (m, 1H), 6.50-6.74 (m, 1H), 6.40 (t, J = 29.90 Hz, 1H), 5.76-5.86 (m, 1H), 3.57-5.30 (m, 6H), 2.82-2.96 (m, 1H), 2.53-2.66 (m, 4H), 0.91-1.61 (m, 18H). |
| 100-8 | 574.6 | $^1$H NMR (400 MHz, DMSO-$d_6$) δ 1.03 (d, J = 6.8 Hz, 3 H), 1.12 (d, J = 6.8 Hz, 3 H), 1.16-1.27 (m, 3 H), 1.33 (t, J = 6.1 Hz, 3 H), 1.90 (s, 3 H), 2.56-2.65 (m, 1 H), 3.44-4.96 (m, 6 H), 5.67-5.82 (m, 1 H), 6.19 (dd, J = 16.7, 2.0 Hz, 1 H), 6.83 (td, J = 16.9, 10.6 Hz, 1 H), 7.18-7.37 (m, 3 H), 7.43-7.62 (m, 1 H), 8.38 (s, 1 H), 8.47 (d, J = 4.4 Hz, 1 H), 8.52 (s, 1 H); $^{19}$F{$^1$H} NMR (376 MHz, DMSO-$d_6$) δ −113.93 (s, 1 F) |
| 100-9 | 574.6 | $^1$H NMR (400 MHz, DMSO-$d_6$) δ 1.00 (d, J = 6.8 Hz, 3 H), 1.11 (d, J = 6.8 Hz, 3 H), 1.13-1.27 (m, 3 H), 1.29-1.38 (m, 3 H), 1.93 (s, 3 H), 2.55-2.63 (m, 1 H), 3.44-4.97 (m, 6 H), 5.70-5.80 (m, 1 H), 6.19 (dd, J = 16.7, 2.0 Hz, 1 H), 6.83 (td, J = 15.9, 10.5 Hz, 1 H), 7.17-7.37 (m, 3 H), 7.47-7.57 (m, 1 H), 8.39 (s, 1 H), 8.48 (d, J = 3.5 Hz, 1 H), 8.50 (s, 1 H); $^{19}$F NMR (376 MHz, DMSO-$d_6$) δ −114.03 (s, 1 F) |
| 101-1 | 603.0 | $^1$H NMR (400 MHz, DMSO-$d_6$) δ 10.19 (br s, 1 H), 8.49 (d, J = 3.1 Hz, 2 H), 8.30 (d, J = 9.1 Hz, 1 H), 7.25 (q, J = 8.1 Hz, 1 H), 6.62-6.90 (m, 3 H), 6.18 (dd, J = 16,6, 2.3 Hz, 1 H), 5.74-5.79 (m, 1 H), 4.42-4.93 (m, 2 H), 3.79-4.23 (m, 4 H), 2.41-2.48 (m, 2H), 1.16-1.33 (m, 6 H), 1.11 (dd, J = 6.7, 4.5 Hz, 6 H), 0.97 (br d, J = 6.6 Hz, 6 H); $^{19}$F NMR (377 MHz, DMSO-$d_6$) δ −115.75 (br s, 1 F), −128.46 (br s, 1 F) |
| 101-2 | 588.2 | $^1$H NMR (400 MHz, DMSO-$d_6$) δ 9.03 (s, 1 H) 8.30 (dd, J = 9.43, 4.87 Hz, 1 H) 7.48 (q, J = 6.98 Hz, 1 H) |

TABLE 148-continued

Analytical Data for Method Table Examples

| Ex. # | LRMS: m/z (ESI, +ve ion): (M + H)+ | NMR |
|---|---|---|
| | | 7.16-7.30 (m, 3 H) 6.71-6.84 (m, 1 H) 6.12 (br d, J = 17.00 Hz, 1 H) 5.69 (br d, J = 10.16 Hz, 1 H) 4.67-4.89 (m, 2 H) 4.06-4.19 (m, 1 H) 3.74-3.85 (m, 2 H) 2.65 (dq, J = 12.75, 6.39 Hz, 2 H) 1.27 (t, J = 5.91 Hz, 3 H) 1.19 (br d, J = 6.63 Hz, 2 H) 1.12 (d, J = 6.63 Hz, 2 H) 1.02 (dd, J = 6.63, 1.87 Hz, 6 H) 0.87 (d, J = 6.63 Hz, 6 H) |
| 101-3 | 588.2 | $^1$H NMR (400 MHz, DMSO-d$_6$) δ 9.15 (s, 1 H) 8.27 (d, J = 10.16 Hz, 1 H) 7.61 (q, J = 7.19 Hz, 1 H) 7.27-7.43 (m, 3 H) 6.96 (dd, J = 16.59, 10.37 Hz, 1 H) 6.32 (dd, J = 16.69, 2.18 Hz, 1 H) 5.86 (dd, J = 10.26, 1.97 Hz, 1 H) 5.12 (br s, 2 H) 4.39 (br d, J = 13.06 Hz, 1 H) 4.12 (br d, J = 13.48 Hz, 1 H) 3.66 (br d, J = 12.23 Hz, 1 H) 3.19-3.31 (m, 1 H) 2.72-2.85 (m, 2 H) 1.54 (d, J = 6.84 Hz, 6 H) 1.16 (d, J = 6.63 Hz, 6 H) 0.99 (d, J = 6.63 Hz, 6 H) |
| 102-1 | 601.6 | $^1$H NMR (400 MHz, DMSO-d$_6$) δ 8.46 (s, 1 H), 7.43-7.57 (m, 1 H), 7.12-7.36 (m, 6 H), 6.75-6.94 (m, 1 H), 6.19 (dd, J = 16.7, 2.4 Hz, 1 H), 5.67-5.85 (m, 1 H), 4.69-4.96 (m, 2 H), 4.39-4.52 (m, 1 H), 4.14 (br t, J = 11.9 Hz, 1 H), 3.78-3.99 (m, 2 H), 3.44-3.62 (m, 1 H), 1.30-1.37 (m, 3 H), 1.25 (br d, J = 6.4 Hz, 2 H), 1.17 (d, J = 6.8 Hz, 2 H), 1.03-1.10 (m, 6 H), 0.92 (dd, J = 10.0, 6.8 Hz, 6 H) |
| 102-2 | 646.8 | $^1$H NMR (400 MHz, DMSO-d$_6$) δ 0.88-1.00 (m, 6 H) 1.04-1.18 (m, 6 H) 1.31-1.42 (m, 3 H) 2.06-2.28 (m, 6 H) 2.65-2.82 (m, 2 H) 3.02-3.17 (m, 2 H) 3.37-3.89 (m, 3 H) 3.95-4.19 (m, 1 H) 4.22-4.45 (m, 2 H) 4.85-5.18 (m, 1 H) 6.53-6.83 (m, 2 H) 7.07-7.24 (m, 1 H) 7.26-7.40 (m, 2 H) 7.43-7.62 (m, 1 H) 8.32-8.69 (m, 1 H) 8.88-9.20 (m, 1 H) <br> $^{19}$F NMR (376 MHz, DMSO-d6) δ −113.35 (s, 1 F) |
| 102-3 | 602.6 | $^1$H NMR (400 MHz, DMSO-d$_6$) δ 8.44-8.51 (m, 2 H), 7.46-7.56 (m, 1 H), 7.25-7.35 (m, 3 H), 7.14-7.21 (m, 1 H), 6.78-6.91 (m, 1 H), 6.20 (dd, J = 16.5, 2.2 Hz, 1 H), 5.74-5.80 (m, 1 H), 4.73-4.94 (m, 2 H), 4.44 (s, 1 H), 4.11-4.24 (m, 1 H), 3.84-3.96 (m, 2 H), 2.61-2.70 (m, 2 H), 1.34 (t, J = 6.6 Hz, 3 H), 1.26 (br d, J = 7.0 Hz, 1 H), 1.18 (d, J = 6.8 Hz, 2 H), 1.07 (dd, J = 6.5, 3.8 Hz, 6 H), 0.93 (td, J = 6.2, 2.9 Hz, 6 H) |
| 102-4 | 682.4 | $^1$H NMR (400 MHz, DMSO-d$_6$) δ 8.49 (d, J = 3.1 Hz, 1 H), 7.53 (d, J = 4.8 Hz, 2 H), 7.26-7.39 (m, 2 H), 7.14-7.24 (m, 1 H), 6.74-6.91 (m, 1 H), 6.20 (dd, J = 16.9, 2.2 Hz, 1 H), 5.72-5.80 (m, 1 H), 4.73-4.95 (m, 1 H) 4.44-4.53 (m, 1 H), 4.11-4.28 (m, 1 H), 3.78-3.96 (m, 2 H), 3.49 (br dd, J = 14.1, 2.3 Hz, 1 H), 1.34 (br t, J = 5.8 Hz, 3 H), 1.22-1.28 (m, 3 H), 1.18 (br d, J = 6.8 Hz, 2 H), 1.06 (td, J = 7.3, 3.8 Hz, 6 H), 0.86-0.98 (m, 6 H) |
| 102-5 | 596.2 | $^1$H NMR (400 MHz, CHLOROFORM-d) δ 8.96 (1 H, s) 8.15 (1 H, s) 7.44-7.51 (1 H, m) 7.13-7.28 (3 H, m) 6.55-6.71 (1 H, m) 6.38-6.48 (1 H, m) 5.80-5.87 (1 H, m) 3.45-5.24 (6 H, m) 2.86-2.97 (1 H, m) 1.41-1.56 (4 H, m) 1.36 (2 H, br d, J = 6.84 Hz) 1.25-1.34 (3 H, m) 1.12 (3 H, dd, J = 8.71, 6.84 Hz) |
| 102-5-1 | 596.0 | $^1$H NMR (400 MHz, CHLOROFORM-d) δ 8.96 (1 H, s) 8.15 (1 H, s) 7.44-7.51 (1 H, m) 7.13-7.28 (3 H, m) 6.55-6.71 (1 H, m) 6.38-6.48 (1 H, m) 5.80-5.87 (1 H, m) 3.49-5.24 (6 H, m) 2.87-2.97 (1 H, m) 1.42-1.55 (4 H, m) 1.36 (2 H, d, J = 6.84 Hz) 1.31 (3 H, d, J = 6.84 Hz) 1.14 (3 H, d, J = 6.63 Hz) |
| 102-5-2 | 596.0 | $^1$H NMR (400 MHz, CHLOROFORM-d) δ 8.96 (1 H, s) 8.14 (1 H, s) 7.44-7.51 (1 H, m) 7.13-7.28 (3 H, m) 6.55-6.71 (1 H, m) 6.38-6.48 (1 H, m) 5.80-5.87 (1 H, m) 3.45-5.24 (6 H, m) 2.86-2.97 (1 H, m) 1.49 (4 H, td, J = 15.76, 6.63 Hz) 1.35 (2 H, d, J = 6.63 Hz) 1.30 (3, H, d, J = 6.63 Hz) 1.11 (3 H, d, J = 6.84 Hz) |
| 102-6 | 592.1 | $^1$H NMR (400 MHz, CHLOROFORM-d) δ 8.87 (1 H, s) 8.10 (1 H, s) 7.25-7.32 (1 H, m) 7.14-7.21 (2 H, m) 7.03-7.08 (1 H, m) 6.49-6.66 (1 H, m) 6.32-6.42 (1 H, m) 5.74-5.81 (1 H, m) 3.41-5.19 (6 H, m) 2.78-2.92 (1 H, m) 1.99-2.04 (3 H, m) 1.38-1.50 (4 H, m) 1.28-1.34 (2 H, m) 1.20-1.26 (3 H, m) 1.02 (3 H, br d, J = 6.63 Hz) |
| 102-6-1 | 592.1 | $^1$H NMR (400 MHz, CHLOROFORM-d) δ 8.91 (1 H, s) 8.14 (1 H, s) 7.29-7.35 (1 H, m) 7.19-7.24 (2 H, m) 7.08 (1 H, d, J = 7.46 Hz) 6.52-6.69 (1 H, m) 6.40 (1 H, br t, |

TABLE 148-continued

Analytical Data for Method Table Examples

| Ex. # | LRMS: m/z (ESI, +ve ion): (M + H)+ | NMR |
|---|---|---|
| | | J = 15.13 Hz) 5.78-5.84 (1 H, m) 3.44-5.20 (6 H, m) 2.84-2.95 (1 H, m) 2.05 (3 H, s) 1.41-1.53 (4H, m) 1.33-1.37 (2 H, m) 1.25-1.30 (3 H, m) 1.03-1.08 (3 H, m) |
| 102-6-2 | 592.1 | $^1$H NMR (400 MHz, CHLOROFORM-d) δ 8.91 (1 H, s) 8.13 (1 H, s) 7.29-7.35 (1 H, m) 7.19-7.25 (2 H, m) 7.10 (1 H, br d, J = 7.46 Hz) 6.52-6.69 (1 H, m) 6.36-6.45 (1 H, m) 5.78-5.84 (1 H, m) 3.44-5.22 (6 H, m) 2.82-2.94 (1 H, m) 2.06 (3 H, s) 1.40-1.53 (4 H, m) 1.30-1.36 (2 H, m) 1.27 (3 H, d, J = 6.84 Hz) 1.05 (3 H, d, J = 6.84 Hz) |
| 102-7 | 650.2 | $^1$H NMR (400 MHz, DMSO-$d_6$) δ 0.95-1.06 (m, 3 H), 1.06-1.11 (m, 3 H), 1.15-1.20 (m, 3 H), 1.28-1.35 (m, 3 H) 1.66 (d, J = 13.3 Hz, 6 H), 1.92-2.01 (m, 3 H), 2.56-2.64 (m, 1 H), 3.45-4.96 (m, 6 H), 5.71-5.79 (m, 1 H), 6.19 (dd, J = 16.7, 2.2 Hz, 1 H), 6.76-6.91 (m, 1 H), 7.16-7.36 (m, 3 H), 7.44-7.57 (m, 2 H), 7.57-7.67 (m, 1 H), 8.47 (s, 1 H); $^{19}$F{$^1$H} NMR (376 MHz, DMSO-$d_6$) δ −113.91 (s 1 F), −113.81 (s, 1 F); $^{31}$P{$^1$H} NMR (162 MHz, DMSO-$d_6$) δ 32.40 (s, 1 P) |
| 102-7-1 | 649.6 | $^1$H NMR (400 MHz, DMSO-$d_6$) δ 1.01 (d, J = 6.8 Hz, 3 H), 1.05 (d, J = 6.2 Hz, 3 H), 1.08 (d, J = 6.8 Hz, 3 H), 1.17 (br d, J = 6.8 Hz, 3 H), 1.66 (d, J = 13.3 Hz, 6 H), 1.95 (s, 3 H), 2.55-2.64 (m, 1 H), 3.51 (dd, J = 14.2, 3.4 Hz, 0.5 H), 3.83-3.97 (m, 2 H), 4.07-4.22 (m, 1.5 H), 4.40-4.52 (m, 0.5 H), 4.72-4.97 (m, 1.5 H), 5.70-5.81 (m, 1 H), 6.19 (dd, J = 16.7, 2.4 Hz, 1 H), 6.83 (td, J = 16.0, 10.6 Hz, 1 H), 7.19-7.35 (m, 3 H), 7.46-7.57 (m, 2 H), 7.62 (d, J = 11.8 Hz, 1 H), 8.47 (d, J = 1.87 Hz, 1 H); $^{19}$F{$^1$H} NMR (377 MHz, DMSO-$d_6$) δ 113.82 (s, 1 F), $^{31}$P{$^1$H} NMR (162 MHz, DMSO-$d_6$) δ 32.41 (s, 1 P) |
| 102-7-2 | 649.6 | $^1$H NMR (400 MHz, DMSO-$d_6$) δ 0.97 (d, J = 6.8 Hz, 3 H), 1.03-1.08 (m, 6 H), 1.40-1.46 (m, 3 H), 1.66 (d, J = 13.3 Hz, 6 H), 1.98 (s, 3 H), 2.55-263 (m, 1 H), 3.44-3.55 (m, 0.5 H), 3.76-4.00 (m, 2 H), 4.10-4.22 (m, 1.5 H), 4.42-4.51 (m, 0.5 H), 4.72-4.95 (m, 1.5 H), 5.69-5.81 (m, 1 H), 6.19 (dd, J = 16.6, 2.1 Hz, 1 H), 6.75-6.92 (m, 1 H), 7.20-7.36 (m, 3 H), 7.47-7.63 (m, 3 H), 8.47 (s, 1 H); $^{19}$F{$^1$H} NMR (376 MHz, DMSO-$d_6$) δ −113.92 (s, 1 F); $^{31}$P{$^1$H} NMR (162 MHz, DMSO-$d_6$) δ 32.43 (s, 1 P) |
| 102-8 | 632.2 | $^1$H NMR (400 MHz, CHLOROFORM-d) δ 8.30 (br dd, J = 4.77, 12.44 Hz, 1H), 7.50 (s, 1H), 7.33-7.43 (m, 1H), 7.20 (br s, 2H), 7.04-7.17 (m, 2H), 6.26-6.38 (m, 1H), 5.65-5.80 (m, 1H), 5.01-5.14 (m, 1H), 4.27-4.47 (m, 1H), 3.76-3.94 (m, 1H), 3.54-3.74 (m, 1H), 3.23-3.41 (m, 1H), 2.93-3.00 (m, 1H), 2.66-2.83 (m, 2H), 1.33 (br s, 6H), 1.23-1.30 (m, 6H), 1.11-1.22 (m, 6H) |
| 103-1 | 628.3 | |
| 103-1-1 | 628.4 | $^1$H NMR (400 MHz, CDCl$_3$) δ 8.26 (br d, J = 5.60 Hz, 1H), 8.08 (s, 1 H), 7.30-7.42 (m, 2H), 7.16-7.22 (m, 1H), 7.00 (d, J = 7.67 Hz, 1H), 6.52-6.68 (m, 2H), 6.40 (br t, J = 14.82 Hz, 1H), 5.77-5.84 (m, 1H), 3.40-5.23 (m, 6H), 2.69 (s, 6H), 2.49-2.65 (m, 2H), 0.88-1.52 (m, 18H) |
| 103-1-2 | 628.4 | $^1$H NMR (400 MHz, CDCl$_3$) δ 8.29 (d, J = 5.60 Hz, 1H), 8.06-8.12 (m, 1H), 7.30-7.41 (m, 2H), 7.19 (t, J = 7.26 Hz, 1H), 7.00 (d, J = 7.67 Hz, 1H), 6.52-6.69 (m, 2H), 6.40 (br t, J = 15.45 Hz, 1H), 5.77-5.84 (m, 1H), 3.43-5.26 (m, 6H), 2.69 (br s, 6H), 2.51-2.63 (m, 2H), 0.94-1.45 (m, 18H) |
| 103-2 | 591.8 | $^1$H NMR (400 MHz, CDCl$_3$) δ 8.14 (s, 1 H) 8.06 (s, 1 H) 7.40-7.48 (m, 1 H) 7.30 (td, J = 7.4, 1.9 Hz, 1 H) 7.16-7.23 (m, 1 H) 7.13 (t, J = 9.1 Hz, 1 H) 6.51-6.69 (m, 1 H) 6.32-6.44 (m, 1 H) 5.74-5.83 (m, 1 H) 4.83-5.16 (m, 2 H) 4.25-4.48 (m, 1 H), 3.79-4.07 (m, 2 H) 3.48-3.51 (m, 3 H) 3.44-3.71 (m, 1 H) 2.65-2.79 (m, 1 H) 1.33-1.48 (m, 6 H) 1.22 (d, J = 6.6 Hz, 3 H) 1.06 (d, J = 6.6 Hz, 3 H). $^{19}$F NMR (376 MHz, CDCl$_3$) δ −112.44--112.19 (m, 1 F) |
| 103-3 | 622.1 | $^1$H NMR (400 MHz, CDCl3) δ 8.09 (s, 1H), 7.21-7.91 (m, 4H), 7.13-7.19 (m, 2H), 7.09 (t, J = 18.20 Hz, 1H), 6.50-6.71 (m, 1H), 6.40 (t, J = 29.60 Hz, 1H), 5.80 (t, J = 18.00 Hz, 1H), 4.19-5.25 (m, 3H), 3.35-4.11 (m, 3H), 2.76-2.81 (m, 3H), 2.58-2.76 (m, 1H), 1.31-1.55 (m, 6H), 1.19-1.27 (m, 3H), 1.02-1.09 (m, 3H). $^{19}$F NMR (376 MHz, CDCl3) δ −112.37 (s, 1F), −112.42 (s, 1F), −112.40 (br dd, J = 16.91, 23.84 Hz, 1F) |

TABLE 148-continued

Analytical Data for Method Table Examples

| Ex. # | LRMS: m/z (ESI, +ve ion): (M + H)+ | NMR |
|---|---|---|
| 103-4 | 603.2 | $^1$H NMR (400 MHz, CDCl3) δ 8.53 (s, 1H), 8.52 (s, 1H), 8.10-8.14 (m, 1H), 7.38-7.46 (m, 1H), 7.07-7.18 (m, 3H), 6.52-6.70 (m, 1H), 6.40 (t, J = 29.90 Hz, 1H), 5.80 (t, J = 18.00 Hz, 1H), 4.26-5.22 (m, 3H), 3.44-4.08 (m, 3H), 2.45-2.68 (m, 2H), 1.31-1.50 (m, 6H), 1.25 (dd, J = 2.28, 6.43 Hz, 6H), 1.01-1.07 (m, 6H). $^{19}$F NMR (376 MHz, CDCl3) δ −113.19 (s, 1F), −113.21 (s, 1F) |
| 103-5 | 656.2 | $^1$H NMR (400 MHz, CDCl3) δ 8.27-8.36 (m, 1H), 8.04-8.14 (m, 1H), 7.29-7.42 (m, 2H), 7.17 (t, J = 7.26 Hz, 1H), 7.04 (t, J = 6.74 Hz, 1H), 6.52-6.71 (m, 2H), 6.35-6.45 (m, 1H), 5.77-5.84 (m, 1H), 3.27-5.33 (m, 6H), 2.98 (br s, 4H), 2.57 (br s, 2H), 1.32-1.62 (m, 6H), 1.23-1.31 (m, 7H), 0.91-1.05 (m, 7H), 0.86-0.91 (m, 3H), 0.67-0.84 (m, 6H) |
| 103-6 | 628.3 | $^1$H NMR (400 MHz, CDCl3) δ 8.32-8.38 (m, 1H), 8.03-8.12 (m, 1H), 7.27-7.32 (m, 1H), 7.14-7.21 (m, 2H), 7.05-7.11 (m, 1H), 6.51-6.73 (m, 2H), 6.40 (br t, J = 15.03 Hz, 1H), 5.76-5.83 (m, 1H), 4.16-5.32 (m, 3H), 3.27-4.10 (m, 3H), 2.90-3.05 (m, 4H), 2.52-2.67 (m, 1H), 1.99 (s, 3H), 1.35-1.67 (m, 6H), 1.15-1.35 (m, 6H), 0.86-0.99 (m, 4H), 0.68-0.85 (m, 6H) |
| 103-6-1 | 656.2 | $^1$H NMR (400 MHz, CDCl3) δ 8.30 (br d, J = 4.98 Hz, 1H), 8.10 (br d, J = 4.56 Hz, 1H), 7.29-7.40 (m, 2H), 7.17 (t, J = 6.74 Hz, 1H), 7.04 (br d, J = 7.88 Hz, 1H), 6.49-6.73 (m, 2H), 6.40 (br t, J = 15.13 Hz, 1H), 5.80 (br t, J = 8.91 Hz, 1H), 4.25-5.23 (m, 3H), 3.25-4.22 (m, 3H), 2.88-3.08 (m, 4H), 2.49-2.74 (m, 2H), 1.36-1.59 (m, 6H), 1.21-1.29 (m, 3H), 0.62-1.11 (m, 15H) |
| 103-6-2 | 656.2 | $^1$H NMR (400 MHz, CDCl3) δ 8.33 (d, J = 5.60 Hz, 1H), 8.04-8.11 (m, 1H), 7.29-7.41 (m, 2H), 7.17 (t, J = 7.36 Hz, 1H), 7.03 (d, J = 7.46 Hz, 1H), 6.53-6.70 (m, 2H), 6.40 (br t, J = 14.93 Hz, 1H), 5.77-5.83 (m, 1H), 3.54-5.33 (m, 6H), 2.98 (br s, 4H), 2.58 (br s, 2H), 1.23-1.44 (m, 9H), 0.67-1.05 (m, 15H) |
| 103-7 | 600.3 | |
| 103-7-1 | 600.3 | $^1$H NMR (400 MHz, CDCl3) δ 8.29 (br d, J = 5.80 Hz, 1H), 8.08 (s, 1H), 7.28-7.34 (m, 1H), 7.17-7.23 (m, 2H), 7.10 (d, J = 7.26 Hz, 1H), 6.50-6.70 (m, 2H), 6.40 (br t, J = 14.82 Hz, 1H), 5.77-5.83 (m, 1H), 3.42-5.21 (m, 6H), 2.63-2.76 (m, 7H), 2.04 (s, 3H), 1.27-1.50 (m, 6H), 1.20-1.27 (m, 3H), 0.93 (br d, J = 6.63 Hz, 3H) |
| 103-7-2 | 600.2 | $^1$H NMR (400 MHz, CDCl3) δ 8.32 (d, J = 5.81 Hz, 1H), 8.06-8.11 (m, 1H), 7.27-7.34 (m, 1H), 7.16-7.23 (m, 2H), 7.08-7.12 (m, 1H), 6.52-6.70 (m, 2H), 6.40 (br t, J = 15.34 Hz, 1H), 5.77-5.83 (m, 1H), 3.44-5.26 (m, 6H), 2.70 (s, 6H), 2.52-2.66 (m, 1H), 2.02 (s, 3H), 1.26-1.47 (m, 6H), 1.23 (d, J = 6.63 Hz, 3H), 0.94 (br d, J = 6.22 Hz, 3H) |
| 103-8-1 | 628.4 | $^1$H NMR (400 MHz, CHLOROFORM-d) δ 8.26-8.38 (m, 1H), 8.10 (br d, J = 6.84 Hz, 1H), 7.28-7.33 (m, 1H), 7.07-7.22 (m, 3H), 6.52-6.71 (m, 2H), 6.34-6.52 (m, 1H), 5.80 (br t J = 9.02 Hz, 1H), 3.64-5.17 (m, 6H), 2.90-3.06 (m, 4H), 2.61 (tdd, J = 6.45, 13.09, 19.62 Hz, 1H), 1.99 (s, 3H), 1.34-1.59 (m, 6H), 1.25 (d, J = 6.63 Hz, 3H), 0.93 (d, J = 6.84 Hz, 3H), 0.70-0.85 (m, 6H) |
| 103.8-2 | 628.4 | $^1$H NMR (400 MHz, CHLOROFORM-d) δ 8.36 (d, J = 5.60 Hz, 1H), 8.02-8.14 (m, 1H), 7.27-7.34 (m, 1H), 7.14-7.22 (m, 2H), 7.00-7.14 (m, 1H), 6.71 (d, J = 5.60 Hz, 1H), 6.51-6.67 (m, 1H), 6.34-6.51 (m, 1H), 5.73-5.83 (m, 1H), 3.46-5.31 (m, 6H), 2.99 (br d, J = 6.63 Hz, 4H), 2.50-2.60 (m, 1H), 1.99 (s, 3H), 1.18-1.45 (m, 9H), 0.96 (br d, J = 6.43 Hz, 3H), 0.69-0.89 (m, 6H) |
| 106-1 | 682.0 | $^1$H NMR (400 MHz, CHLOROFORM-d) δ 8.17 (1 H, s) 7.48-7.54 (1 H, m) 7.16-7.28 (3 H, m) 6.56-6.74 (1 H, m) 6.40-6.49 (1 H, m) 5.82-5.88 (1 H, m) 3.49-5.23 (6 H, m) 2.60-2.72 (2 H, m) 1.44-1.56 (3 H, m) 1.29-1.40 (3 H, m) 1.23-1.29 (6 H, m) 1.03-1.09 (6 H, m) |
| 106-2 | 498.2 | $^1$H NMR (400 MHz, CHLOROFORM-d) δ 7.93 (s, 1H), 7.44-7.53 (m. 2H), 7.27-7.34 (m, 1H), 7.14-7.19 (m, 1H), 6.46-6.71 (m, 1H), 6.30-6.43 (m, 1H), 5.71-5.82 (m, 1H), 4.39-4.74 (m, 2H), 4.34 (br s, 2H), 3.53-4.19 (m, 4H), 2.97-3.20 (m, 1H), 1.24 (s, 3H), 0.95 (s, 9H). $^{19}$F NMR (376 MHz, CHLOROFORM-d) δ −112.58 (s, 1F) |
| 106-3 | 514.3 | $^1$H NMR (400 MHz, CHLOROFORM-d) δ 8.04-8.38 (m, 1H), 7.38-7.56 (m, 2H), 7.26-7.32 (m, 1H), 7.18 (t, J = 9.12 Hz, |

TABLE 148-continued

Analytical Data for Method Table Examples

| Ex. # | LRMS: m/z (ESI, +ve ion): (M + H)+ | NMR |
|---|---|---|
| | | 1H), 6.47-6.73 (m, 1H), 6.37 (br d, J = 16.38 Hz, 1H), 5.68-5.84 (m, 1H), 4.45-4.87 (m, 2H), 4.28 (br d, J = 8.50 Hz, 2H), 3.57-3.89 (m, 4H), 3.31-3.49 (m, 1H), 3.07 (tt, J = 3.63, 7.36 Hz, 1H), 1.39 (d, J = 6.63 Hz, 2H), 0.90-0.98 (m, 9H). $^{19}$F NMR (376 MHz, CHLOROFORM-d) δ −112.40 (br s, 1F) |
| 106-4 | 528.2 | $^1$H NMR (400 MHz, CHLOROFORM-d) δ 7.94 (s, 1H), 7.40-7.56 (m, 2H), 7.26-7.32 (m, 1H), 7.18 (t, J = 9.12 Hz, 1H), 6.48-6.60 (m, 1H), 6.25-6.41 (m, 1H), 5.69-5.80 (m, 1H), 4.80-4.99 (m, 2H), 3.59-4.62 (m, 6H), 3.11 (s, 3H), 1.35-1.37 (m, 3H), 1.23-1.26 (m, 3H), 1.19 (s, 6H). $^{19}$F NMR (376 MHz, CHLOROFORM-d) δ −112.72 (br d, J = 9.54 Hz, 1F) |
| 106-5 | 500.1 | $^1$H NMR (400 MHz, CHLOROFORM-d) δ 8.00 (s, 1H), 7.46-7.58 (m, 2H), 7.28-7.36 (m, 1H), 7.21 (t, J = 9.12 Hz, 1H), 6.61 (dd, J = 10.47, 16.69 Hz, 1H), 6.39 (dd, J = 1.87, 16.79 Hz, 1H), 5.80 (dd, J = 1.76, 10.47 Hz, 1H), 4.57 (br s, 2H), 3.75-4.08 (m, 8H), 3.15 (s, 3H), 1.23 (s, 6H). $^{19}$F NMR (376 MHz, CHLOROFORM-d) δ −112.74 (s, 1F) |
| 106-6 | 576.0 | $^1$H NMR (400 MHz, DMSO-d$_6$) 8..42 (d, J = 4.77 Hz, 1 H), 7.50-7.63 (m, 1 H), 7.29-7.41 (m, 3 H), 7.20 (dd, J = 4.46, 3.42 Hz, 1 H), 6.77-7.04 (m, 1 H), 6.13-6.31 (m, 1 H), 5.69-6.02 (m, 1 H), 5.10-5.66 (m, 1 H), 4.54-4.97 (m, 2 H), 4.30 (br d, J = 13.48 Hz, 1 H), 3.54-3.99 (m, 2 H), 2.73-2.96 (m, 1 H), 1.92-2.05 (m, 3 H), 1.24-1.52 (m, 6 H), 1.08 (br d, J = 6.63 Hz, 3 H), 0.98 (br d, J = 6.63 Hz, 3 H) |
| 106-6-1 | 576.0 | $^1$H NMR (400 MHz, DMSO-d$_6$) δ 8.42 (d, J = 4.77 Hz, 1 H), 7.51-7.66 (m, 1 H), 7.27-7.42 (m, 3 H), 7.20 (d, J = 4.98 Hz, 1 H), 6.77-7.00 (m, 1 H), 6.21 (br d, J = 16.59 Hz, 1 H), 5.43-6.01 (m, 2 H), 4.21-5.33 (m, 3 H), 3.41-4.10 (m, 2 H), 2.71-2.89 (m, 1 H), 2.01 (br s, 3 H), 1.18-1.53 (m, 6 H), 1.07 (br s, 3 H), 0.98 (d, J = 6.63 Hz, 3 H); $^{19}$F{$^1$H} NMR (376 MHz, DMSO-d$_6$) δ −113.62 (s, 1 F) |
| 106-6-2 | 576.0 | $^1$H NMR (400 MHz, DMSO-d$_6$) δ 8.42 (d, J = 4.77 Hz, 1 H), 7.52-7.62 (m, 1 H), 7.28-7.42 (m, 3 H), 7.20 (d, J = 4.98 Hz, 1 H), 6.76-7.01 (m, 1 H), 6.12-6.30 (m, 1 H), 5.42-5.96 (m, 2 H), 4.20-5.30 (m, 3 H), 3.39-4.11 (m, 2 H), 2.81-2.96 (m, 1 H), 1.97 (br s, 3 H), 1.20-1.53 (m, 6 H), 1.08 (d, J = 6.63 Hz, 3 H), 0.96 (br s, 3 H); $^{19}$F{$^1$H} NMR (376 MHz, DMSO-d$_6$) δ −113.80 (s, 1 F) |
| 106-7 | 576.2 | $^1$H NMR (400 MHz, DMSO-d$_6$) δ 0.96 (br s, 3 H), 1.04-1.12 (m, 3 H), 1.28-1.42 (m, 3 H), 1.52 (br s, 3 H), 1.90-2.09 (m, 3 H), 2.77-2.90 (m, 1 H), 3.09-3.23 (m, 1 H), 3.51-3.62 (m, 1 H), 4.13-4.27 (m, 1 H), 4.36-4.50 (m, 1 H), 5.33-5.53 (m, 1 H), 5.63-5.75 (m, 1 H), 5.77-5.85 (m, 1 H), 6.27 (br d, J = 17.8 Hz, 1 H), 6.95 (dd, J = 16.5, 10.5 Hz, 1 H), 7.20 (d, J = 4.8 Hz, 1 H), 7.26-7.39 (m, 3 H), 7.52-7.62 (m, 1 H), 8.41 (d, J = 5.0 Hz, 1 H); $^{19}$F{$^1$H} NMR (376 MHz, DMSO-d$_6$) δ −113.77 (s, 1 F), −113.56 (s, 1 F) |
| 106-7-1 | 576.2 | $^1$H NMR (400 MHz, DMSO-d$_6$) δ 0.96 (br s, 3 H), 1.07 (d, J = 6.6 Hz, 3 H), 1.33 (br s, 3 H), 1.52 (br s, 3 H), 1.98 (s, 3 H), 2.72-2.96 (m, 1 H), 3.09-3.23 (m, 1 H), 3.47-3.65 (m, 1 H), 4.07-4.28 (m, 1 H), 4.31-4.52 (m, 1 H), 5.33-5.56 (m, 1 H), 5.61-5.75 (m, 1 H), 5.77-5.85 (m, 1 H), 6.27 (br d, J = 16.6 Hz, 1 H), 6.95 (dd, J = 16.6, 10.4 Hz, 1 H), 7.20 (d, J = 4.8 Hz, 1 H), 7.25-7.42 (m, 3 H), 7.51-7.63 (m, 1 H), 8.41 (d, J = 5.0 Hz, 1 H); $^{19}$F{$^1$H} NMR (376 MHz, DMSO-d$_6$) δ −113.78 (s, 1 F), −113.56 (s, 1 F) |
| 106-7-2 | 576.2 | $^1$H NMR (400 MHz, DMSO-d$_6$) δ 0.95 (br s, 3 H), 1.07 (br d, J = 6.6 Hz, 3 H), 1.33 (br s, 3 H), 1.52 (br s, 3 H), 1.98 (s, 3 H), 2.74-2.93 (m, 1 H), 3.09-3.25 (m, 1 H), 3.56 (br dd, J = 9.6, 2.8 Hz, 1 H), 4.12-4.26 (m, 1 H), 4.33-4.50 (m, 1 H), 5.34-5.53 (m, 1 H), 5.61-5.74 (m, 1 H), 5.79 (dd, J = 10.4, 2.1 Hz, 1 H), 6.27 (br d, J = 16.6 Hz, 1 H), 6.95 (br dd, J = 16.6, 10.4 Hz, 1 H), 7.19 (br d, J = 5.0 Hz, 1 H), 7.26-7.40 (m, 3 H), 7.52-7.61 (m, 1 H), 8.41 (d, J = 5.0 Hz, 1 H); $^{19}$F{$^1$H} NMR (376 MHz, DMSO-d$_6$) δ −113.78 (s, 1 F), −113.57 (s, 1 F) |
| 106-8 | 523.1 | $^1$H NMR (400 MHz, DMSO-d$_6$) δ 8.37 (br s, 1 H), 7.55-7.72 (m, 2 H), 7.34-7.46 (m, 2 H), 6.81 (td, J = 16.0, 10.6 Hz, 1 H), 6.17 (br d, J = 16.4 Hz, 1 H), 5.74 (br d, J = 9.5 Hz, |

TABLE 148-continued

Analytical Data for Method Table Examples

| Ex. # | LRMS: m/z (ESI, +ve ion): (M + H)+ | NMR |
|---|---|---|
| | | 1 H), 4.77 (br d, J = 16.4 Hz, 2 H), 4.33-4.52 (m, 2 H), 4.01-4.19 (m, 2 H), 3.73-3.91 (m, 2 H), 1.36 (s, 6 H), 1.29 (br t, J = 5.7 Hz, 3 H), 1.07-1.23 (m, 3 H) |
| 106-9 | 509.1 | $^1$H NMR (400 MHz, DMSO-d$_6$) δ 8.37 (br s, 1 H), 7.57-7.71 (m, 2 H), 7.34-7.46 (m, 2 H), 6.76-6.93 (m, 1 H), 6.19 (br d, J = 16.4 Hz, 1 H), 5.75 (br d, J = 10.8 Hz, 1 H), 4.88 (br s, 1 H), 4.44 (s, 2 H), 4.18-4.40 (m, 2 H), 3.94-4.16 (m, 1 H), 3.36-3.78 (m, 2 H), 2.99-3.25 (m, 1 H), 1.37 (s, 6 H), 1.29 (br d, J = 6.4 Hz, 3 H) |
| 106-10 | 495.2 | $^1$H NMR (400 MHz, DMSO-d$_6$) δ 8.47 (s, 1 H), 7.55-7.72 (m, 2 H), 7.34-7.49 (m, 2 H), 6.83 (dd, J = 16.7, 10.5 Hz, 1 H), 6.10-6.27 (m, 1 H), 5.70-5.81 (m, 1 H), 4.45 (s, 2 H), 3.97 (br d, J = 5.2 Hz, 4 H), 3.71-3.89 (m, 4 H), 1.37 (s, 6 H) |
| 107-1 | 633.2 | $^1$H NMR (400 MHz, CHLOROFORM-d) δ 8.13 (1 H, s) 7.42-7.53 (1 H, m) 7.15-7.29 (3 H, m) 6.57-6.74 (1 H, m) 6.39-6.49 (1 H, m) 5.81-5.88 (1 H, m) 3.51-5.23 (7 H, m) 3.05 (3 H, d, J = 4.77 Hz) 2.48-2.61 (2 H, m) 1.44-1.52 (3 H, m) 1.28-1.39 (3 H, m) 1.21 (6 H, dd, J = 6.53, 4.66 Hz) 0.98-1.05 (6 H, m) |
| 107-2 | 647.2 | $^1$H NMR (400 MHz, CHLOROFORM-d) δ 8.05-8.09 (1 H, m) 7.40-7.47 (1 H, m) 7.15-7.23 (2 H, m) 7.12 (1 H, t, J = 9.12 Hz) 6.51-6.69 (1 H, m) 6.34-6.44 (1 H, m) 5.76-5.83 (1 H, m) 3.47-5.17 (6 H, m) 3.21 (6 H, s) 2.44-2.60 (2 H, m) 1.39-1.46 (3 H, m) 1.25-1.33 (3 H, m) 1.14-1.19 (6 H, m) 0.95-1.01 (6 H, m) |
| 107-3 | 689.2 | $^1$H NMR (400 MHz, CHLOROFORM-d) δ 8.11-8.15 (1 H, m) 7.46-7.53 (1 H, m) 7.22-7.28 (2 H, m) 7.15-7.21 (1 H, m) 6.56-6.74 (1 H, m) 6.39-6.49 (1 H, m) 5.81-5.88 (1 H, m) 3.80-3.94 (8 H, m) 3.51-5.24 (6 H, m) 2.51-2.69 (2 H, m) 1.43-1.52 (3 H, m) 1.29-1.38 (3 H, m) 1.20 (6 H, dd, J = 6.63, 4.77 Hz) 0.99-1.05 (6 H, m) |
| 107-4 | 690.2 | $^1$H NMR (400 MHz, CHLOROFORM-d) δ 8.12-8.18 (1 H, m) 7.45-7.55 (1 H, m) 7.15-7.30 (3 H, m) 6.58-6.76 (1 H, m) 6.41-6.51 (1 H, m) 5.83-5.90 (1 H, m) 3.53-5.59 (9 H, m) 2.37-2.85 (10 H, m) 1.45-1.53 (3 H, m) 1.31-1.41 (3 H, m) 1.21 (6 H, dd, J = 6.63, 3.94 Hz) 0.97-1.04 (6 H, m) |
| 107-5 | 659.5 | $^1$H NMR (400 MHz, CHLOROFORM-d) δ 8.15 (1 H, br s) 7.47-7.55 (1 H, m) 7.23-7.29 (2 H, m) 7.19 (1 H, t, J = 9.12 Hz) 6.58-6.77 (1 H, m) 6.42-6.52 (1 H, m) 5.84-5.91 (1 H, m) 3.53-5.25 (10 H, m) 2.49-2.71 (2 H, m) 2.35-2.44 (2 H, m) 1.31-1.54 (6 H, m) 1.20-1.27 (6 H, m) 0.99-1.07 (6H, m) |
| 108-1 | 602.0 | $^1$H NMR (400 MHz, CHLOROFORM-d) δ 9.01-9.03 (1 H, m) 8.16-8.19 (1 H, m) 7.46-7.52 (1 H, m) 7.14-7.30 (3 H, m) 6.58-6.74 (1 H, m) 6.46 (1 H, br t, J = 15.03 Hz) 5.83-5.89 (1 H, m) 3.49-5.27 (6 H, m) 2.75-2.86 (1 H, m) 1.44-1.63 (5 H, m) 1.27-1.41 (6 H, m) 1.07-1.20 (4 H, m) 0.96-1.06 (1 H, m) 0.84-0.95 (1 H, m) |
| 108-1-1 | 602.0 | $^1$H NMR (400 MHz, CHLOROFORM-d) δ 9.01 (1 H, s) 8.18 (1 H, s) 7.45-7.52 (1 H, m) 7.14-7.29 (3 H, m) 6.57-6.74 (1 H, m) 6.45 (1 H, br t, J = 14.72 Hz) 5.83-5.89 (1 H, m) 3.48-5.25 (6 H, m) 2.73-2.84 (1 H, m) 1.46-1.63 (5 H, m) 1.36-1.42 (2 H, m) 1.26-1.33 (4 H, m) 1.08-1.17 (4 H, m) 0.93-1.03 (1 H, m) 0.81-0.89 (1 H, m) |
| 108-1-2 | 602.2 | $^1$H NMR (400 MHz, CHLOROFORM-d) δ 8.99 (1 H, s) 8.13-8.17 (1 H, m) 7.45-7.51 (1 H, m) 7.13-7.28 (3 H, m) 6.56-6.72 (1 H, m) 6.44 (1 H, br t, J = 15.03 Hz) 5.81-5.87 (1 H, m) 3.50-5.27 (6 H, m) 2.75-2.86 (1 H, m) 1.53-1.61 (1 H, m) 1.43-1.53 (4 H, m) 1.26-1.38 (6 H, m) 1.11-1.18 (1 H, m) 1.08 (3 H, d, J = 6.84 Hz) 0.96-1.05 (1 H, m) 0.84-0.92 (1 H, m) |
| 108-2 | 598.2 | $^1$H NMR (400 MHz, CHLOROFORM-d) δ 8.91 (1 H, s) 8.09-8.14 (1 H, m) 7.26-7.31 (1 H, m) 7.15-7.21 (2 H, m) 7.04-7.09 (1 H, m) 6.50-6.67 (1 H, m) 6.38 (1 H, br t, J = 14.93 Hz) 5.75-5.81 (1 H, m) 3.37-5.21 (6 H, m) 2.67-2.78 (1 H, m) 2.00 (3 H, s) 1.38-1.55 (5 H, m) 1.19-1.36 (6 H, m) 0.70-1.09 (6 H, m) |
| 108-2-1 | 598.1 | $^1$H NMR (400 MHz, CHLOROFORM-d) δ 8.91 (1 H, s) 8.13 (1 H, s) 7.26-7.31 (1 H, m) 7.16-7.21 (2 H, m) 7.06 (1 H, br d, J = 7.88 Hz) 6.50-6.67 (1 H, m) 6.38 (1 H, br t, J = 15.45 Hz) 5.75-5.82 (1 H, m) 3.38-5.15 (6 H, m) 2.67-2.78 (1 H, m) 2.00 (3 H, s) 1.40-1.53 (5 H, m) |

TABLE 148-continued

Analytical Data for Method Table Examples

| Ex. # | LRMS: m/z (ESI, +ve ion): (M + H)+ | NMR |
|---|---|---|
| | | 1.31-1.37 (2 H, m) 1.15-1.27 (4 H, m) 0.88-1.07 (5 H, m) 0.71-0.79 (1 H, m) |
| 108-2-2 | 598.3 | $^1$H NMR (400 MHz, CHLOROFORM-d) δ 8.93 (1 H, s) 8.11-8.15 (1 H, m) 7.29-7.34 (1 H, m) 7.19-7.24 (2 H, m) 7.10 (1 H, d, J = 7.67 Hz) 6.53-6.69 (1 H, m) 6.41 (1 H, br t, J = 14.93 Hz) 5.78-5.84 (1 H, m) 3.48-5.25 (6 H, m) 2.68-2.82 (1 H, m) 2.03 (3 H, s) 1.39-1.57 (5 H, m) 1.30-1.35 (2 H, m) 1.17-1.28 (4 H, m) 0.91-1.11 (5 H, m) 0.74-0.84 (1 H, m) |
| 109-1 | 590.2 | $^1$H NMR (400 MHz, CHLOROFORM-d) δ 9.11 (1 H, s) 8.10-8.14 (1 H, m) 7.40-7.47 (1 H, m) 7.08-7.20 (3 H, m) 6.51-6.70 (1 H, m) 6.41 (1 H, br t, J = 14.93 Hz) 5.77-5.85 (1 H, m) 3.44-5.21 (6 H, m) 2.65-2.77 (1 H, m) 2.48-2.59 (1 H, m) 2.36-2.49 (1 H, m) 1.40-1.52 (4 H, m) 1.30-1.36 (2 H, m) 1.14-1.28 (6 H, m) 1.02-1.09 (3 H, m) |
| 109-1-1 | 590.2 | $^1$H NMR (400 MHz, CHLOROFORM-d) δ 9.19 (1 H, s) 8.20 (1 H, s) 7.47-7.56 (1 H, m) 7.17-7.28 (3 H, m) 6.61-6.77 (1 H, m) 6.49 (1 H, br t, J = 15.03 Hz) 5.86-5.93 (1 H, m) 3.54-5.30 (6 H, m) 2.72-2.85 (1 H, m) 2.44-2.69 (2 H, m) 1.48-1.60 (4 H, m) 1.41 (2 H, br d, J = 6.84 Hz) 1.32 (3 H, d, J = 6.84 Hz) 1.25 (3 H, t, J = 7.57 Hz) 1.14 (3 H, d, J = 6.63 Hz) |
| 109-1-2 | 590.2 | $^1$H NMR (400 MHz, CHLOROFORM-d) δ 9.19 (1 H, s) 8.20 (1 H, s) 7.48-7.55 (1 H, m) 7.16-7.28 (3 H, m) 6.59-6.77 (1 H, m) 6.49 (1 H, br t, J = 14.82 Hz) 5.85-5.93 (1 H, m) 3.51-5.28 (6 H, m) 2.74-2.85 (1 H, m) 2.44-2.69 (2 H, m) 1.49-1.61 (4 H, m) 1.42 (2 H, d, J = 6.84 Hz) 1.31 (3 H, d, J = 6.63 Hz) 1.27 (3 H, t, J = 7.57 Hz) 1.12 (3 H, d, J = 6.84 Hz) |
| 109-2 | 586.2 | $^1$H NMR (400 MHz, CHLOROFORM-d) δ 9.06 (1 H, s) 8.11 (1 H, s) 7.26-7.32 (1 H, m) 7.15-7.21 (2 H, m) 6.99-7.05 (1 H, m) 6.50-6.67 (1 H, m) 6.38 (1 H, br t, J = 14.93 Hz) 5.75-5.82 (1H, m) 3.43-5.17 (6 H, m) 2.62-2.75 (1 H, m) 2.45-2.58 (1 H, m) 2.30-2.45 (1 H, m) 1.98 (3 H, s) 1.39-1.50 (4 H, m) 1.29-1.35 (2 H, m) 1.11-1.26 (6 H, m) 0.97-1.04 (3 H, m) |
| 109-2-1 | 586.1 | $^1$H NMR (400 MHz, CHLOROFORM-d) δ 9.06 (1 H, s) 8.11 (1 H, s) 7.26-7.32 (1 H, m) 7.15-7.21 (2 H, m) 7.00-7.04 (1 H, m) 6.50-6.67 (1 H, m) 6.33-6.43 (1 H, m) 5.76-5.82 (1 H, m) 3.43-5.17 (6 H, m) 2.63-2.74 (1 H, m) 2.45-2.57 (1 H, m) 2.31-2.45 (1 H, m) 1.98 (3 H, s) 1.39-1.50 (4 H, m) 1.32 (2 H, br d, J = 6.84 Hz) 1.21 (3 H, d, J = 6.63 Hz) 1.13 (3 H, t, J = 7.57 Hz) 0.98-1.03 (3 H, m) |
| 109-2-2 | 586.3 | $^1$H NMR (400 MHz, CHLOROFORM-d) δ 9.06 (1 H, s) 8.11 (1 H, s) 7.26-7.32 (1 H, m) 7.14-7.21 (2H, m) 7.03 (1 H, d, J = 7.05 Hz) 6.50-6.67 (1 H, m) 6.38 (1 H, br t, J = 15.24 Hz) 5.75-5.82 (1 H, m) 3.43-5.17 (6 H, m) 2.63-2.74 (1 H, m) 2.45-2.57 (1 H, m) 2.28-2.43 (1 H, m) 1.98 (3 H, s) 1.37-1.50 (4 H, m) 1.31 (2 H, br d, J = 6.84 Hz) 1.20 (3 H, d, J = 6.84 Hz) 1.16 (3 H, t, J = 7.46 Hz) 0.99 (3 H, d, J = 6.84 Hz) |
| 110-1 | 512.3 | $^1$H NMR (400 MHz, DMSO-d$_6$) δ 8.33 (s, 1H), 7.53-7.65 (m, 2H), 7.37-7.46 (m, 2H), 6.76-6.87 (m, 1H), 6.09-6.25 (m, 1H), 5.76 (s, 1H), 4.37-4.88 (m, 2H), 4.19-4.30 (m, 1H), 4.03-4.18 (m, 2H), 3.72-3.93 (m, 2H), 3.45 (br d, J = 12.02 Hz, 1H), 1.23-1.31 (m, 3H), 1.08-1.21 (m, 3H), 0.88 (s, 9H). $^{19}$F NMR (376 MHz, DMSO-d$_6$) δ −113.60 (s, 1F) |
| 110-2 | 524.3 | $^1$H NMR (400 MHz, CHLOROFORM-d) δ 7.97 (s, 1H), 7.49-7.60 (m, 2H), 7.20-7.36 (m, 2H), 6.49-6.69 (m, 1H), 6.31-6.43 (m, 1H), 5.73-5.81 (m, 1H), 5.03-5.15 (m, 1H), 4.99 (br s, 1H), 4.79 (br s, 0.5H), 4.26-4.50 (m, 1H), 4.07-4.23 (m, 0.5H), 3.33-4.01 (m, 3H), 2.54-2.70 (m, 2H), 1.83 (br d, J = 12.44 Hz, 2H), 1.60-1.77 (m, 3H), 1.32-1.45 (m, 6H), 1.24-1.32 (m, 3H). $^{19}$F NMR (376 MHz, CHLOROFORM-d) δ −112.30 (s, 1F) |
| 119-1 | 571.3 | $^1$H NMR (400 MHz, CHLOROFORM-d) δ 8.57 (d, J = 4.98 Hz, 1H), 7.84 (dd, J = 4.15, 8.91 Hz, 1H), 7.40-7.51 (m, 1H), 7.27-7.30 (m, 1H), 7.08-7.23 (m, 3H), 4.79-5.12 (m, 2H), 4.06-4.41 (m, 2H), 3.41-3.92 (m, 2H), 2.76 (dt, J = 5.08, 6.58 Hz, 1H), 2.08-2.10 (m, 3H), 2.04-2.06 (m, 3H), 1.42 (t, J = 7.26 Hz, 3H), 1.24-1.3 (m, 6H), 1.11 (dd, J = 2.07, 6.84 Hz, 3H). $^{19}$F NMR (376 MHz, |

TABLE 148-continued

Analytical Data for Method Table Examples

| Ex. # | LRMS: m/z (ESI, +ve ion): (M + H)+ | NMR |
|---|---|---|
| 119-2 | 614.2 | CHLOROFORM-d) δ −112.58 (dd, J = 16.04, 40.31 Hz, 1F), −126.38 (br dd, J = 26.44, 40.31 Hz, 1F) <br> $^1$H NMR (400 MHz, CHLOROFORM-d) δ 8.52 (d, J = 4.77 Hz, 1H), 7.82 (dd, J = 4.46, 9.02 Hz, 1H), 7.39-7.49 (m, 1H), 7.26-7.30 (m, 1H), 7.05-7.22 (m, 3H), 4.75-5.20 (m, 2H), 4.23-4.46 (m, 1H), 4.18 (br d, J = 14.31 Hz, 1H), 4.06 (br d, J = 14.10 Hz, 1H), 3.83-3.99 (m, 2H), 3.50 (d, J = 3.11 Hz, 1H), 2.64-2.75 (m, 1H), 2.36 (d, J = 3.94 Hz, 6H), 2.04 (d, J = 2.70 Hz, 3H), 1.43 (dd, J = 1.45, 6.84 Hz, 3H), 1.31 (d, J = 6.84 Hz, 3H), 1.24 (d, J = 6.84 Hz, 3H), 1.08 (dd, J = 2.07, 6.63 Hz, 3H). $^{19}$F NMR (376 MHz, CHLOROFORM-d) δ −112.45 (dd, J = 19.07, 41.61 Hz, 1F), −126.70 (dd, J = 28.61, 41.62 Hz, 1F) |
| 121-1 | 632.4 | $^1$H NMR (400 MHz, CHLOROFORM-d) δ 8.15 (s, 1H), 7.79-8.04 (m, 1H), 7.40-7.49 (m, 1H), 7.08-7.22 (m, 3H), 6.32-6.72 (m, 2H), 5.72-5.94 (m, 1H), 4.96-5.19 (m, 1H), 4.56-4.76 (m, 1H), 3.58-4.49 (m, 4H), 3.09 (dq, J = 4.35, 7.39 Hz, 1H), 2.76-3.01 (m, 6H), 2.16 (br s, 2H), 1.53-1.55 (m, 3H), 1.44-1.48 (m, 3H), 1.33 (br d, J = 6.84 Hz, 6H), 1.14-1.21 (m, 3H). $^{19}$F NMR (376 MHz, CHLOROFORM-d) δ −112.77 (br dd, J = 7.37, 11.70 Hz, 1F) |
| 121-2 | 658.3 | $^1$H NMR (400 MHz, CHLOROFORM-d) δ 7.94-8.10 (m, 1H), 7.28-7.40 (m, 1H), 6.97-7.16 (m, 4H), 6.42-6.65 (m, 1H), 6.27-6.40 (m, 1H), 5.73 (br t, J = 8.60 Hz, 1H), 4.80-5.14 (m, 2H), 4.16-4.43 (m, 1H), 3.58-4.00 (m, 5H), 2.44-2.67 (m, 5H), 1.93 (s, 3H), 1.74 (br d, J = 2.70 Hz, 3H), 1.54 (br s, 3H), 1.31-1.42 (m, 3H), 1.13 (dd, J = 4.35, 6.43 Hz, 3H), 0.89-1.01 (m, 4H). $^{19}$F NMR (376 MHz, CHLOROFORM-d) δ −112.71--111.79 (m, 1F) |
| 121-3 | 631.6 | $^1$H NMR (400 MHz, CDCl3) δ = 8.07 (br s, 1H), 7.48-7.28 (m, 1H), 7.22-7.02 (m, 5H), 6.71-6.50 (m, 1H), 6.47-6.33 (m, 1H), 5.79 (br d, J = 9.3 Hz, 1H), 5.28-4.85 (m, 2H), 4.56-4.17 (m, 1H), 4.08-3.62 (m, 3H), 3.58-3.28 (m, 2H), 2.60-2.38 (m, 1H), 2.25 (s, 6H), 1.98 (br s, 3H), 1.43 (br d, J = 5.8 Hz, 3H), 1.37-1.23 (m, 3H), 1.19 (br d, J = 6.6 Hz, 3H), 1.01 (br d, J = 6.6 Hz, 3H); $^{19}$F NMR (376 MHz, CDCl3) δ = −111.70 (s, 1F) |
| 121-4 | 631.6 | $^1$H NMR (400 MHz, CDCl3) δ 8.17-8.11 (m, 1H), 7.60-7.38 (m, 1H), 7.29-7.12 (m, 5H), 6.78-6.59 (m, 1H), 6.54-6.42 (m, 1H), 5.92-5.83 (m, 1H), 5.34-4.89 (m, 2H), 4.60-4.30 (m, 1H), 4.17-3.70 (m, 3H), 3.70-3.36 (m, 2H), 2.66 (td, J = 6.8, 13.6 Hz, 1H), 2.34 (s, 6H), 2.05 (s, 3H), 1.55-1.47 (m, 3H), 1.42-1.33 (m, 3H), 1.25 (br d, J = 6.8 Hz, 3H), 1.05 (br d, J = 6.8 Hz, 3H); $^{19}$F NMR (376 MHz, CDCl3) δ = −111.77 (s, 1F) |
| 122-1 | 714.4 | $^1$H NMR (400 MHz, DMSO-d$_6$) δ 8.59 (s, 1 H), 8.07-8.18 (m, 1 H), 7.59 (br d, J = 7.8, 6.5 Hz, 1 H), 7.37 (br d, J = 8.9 Hz, 1 H), 7.17-7.30 (m, 1 H), 6.84 (dt, J = 16.7, 10.7 Hz, 1 H), 6.57-6.72 (m, 1 H), 6.19 (dd, J = 16.5, 2.2 Hz, 1 H), 5.74 (br d, J = 2.3 Hz, 1 H), 4.81-5.05 (m, 1 H), 4.66-4.76 (m, 1 H), 4.45-4.57 (m, 1 H), 4.04-4.29 (m, 2 H), 3.67-3.79 (m, 1 H), 2.72 (s, 7 H), 1.21-1.31 (m, 4 H), 1.00-1.12 (m, 3 H), 0.92 (br dd, J = 6.6, 2.5 Hz, 3 H), 0.78 (br d, J = 6.6 Hz, 3 H) |
| 122-2 | 675.4 | $^1$H NMR (400 MHz, DMSO-d$_6$) δ 8.98-9.25 (m, 1 H), 8.36-8.59 (m, 1 H), 8.04-8.16 (m, 1 H), 7.37-7.49 (m, 1 H), 7.03-7.17 (m, 1 H), 6.78-6.93 (m, 1 H), 6.63 (dd, J = 15.3, 6.0 Hz, 1 H), 6.20 (br d, J = 16.6 Hz, 1H) 5.76 (br dd, J = 10.0, 2.1 Hz, 1H), 4.72-4.98 (m, 2 H), 4.44-4.54 (m, 1 H), 4.01-4.21 (m, 2 H), 3.79-3.95 (m, 2H), 2.70-2.77 (m, 6 H), 2.12-2.27 (m, 1 H), 1.91-2.11 (m, 2H), 1.18-1.41 (m, 4 H), 1.01-1.17 (m, 3 H), 0.86-0.99 (m, 4 H), 0.78-0.85 (m, 2 H), 0.75 (br d, J = 6.4 Hz, 2 H) |
| 122-2-1 | 674.6 | $^1$H NMR (400 MHz, DMSO-d$_6$) δ 8.99-9.13 (m, 1 H), 8.38-8.56 (m, 1 H), 8.10 (dd, J = 10.8, 5.8 Hz, 1 H), 7.35-7.48 (m, 2 H), 7.08 (q, J = 8.6 Hz, 1 H), 6.73-6.92 (m, 1 H), 6.59-6.66 (m, 1 H), 6.20 (dd, J = 16.7, 2.2 Hz, 1 H), 5.71-5.81 (m, 1 H), 4.72-4.99 (m, 2 H), 4.12-4.24 (m, 1 H), 3.83-3.97 (m, 3 H), 2.75 (s, 6 H), 1.98-2.12 (m, 1 H), 1.23-1.39 (m, 3 H), 1.12-1.23 (m, 3 H), 1.06 (d, J = 6.6 Hz, 3 H), 0.86-0.94 (m, 3 H), 0.82 (t, J = 7.5 Hz, 2 H), 0.75 (d, J = 6.6 Hz, 3 H) |

TABLE 148-continued

Analytical Data for Method Table Examples

| Ex. # | LRMS: m/z (ESI, +ve ion): (M + H)+ | NMR |
|---|---|---|
| 122-2-2 | 675.2 | $^1$H NMR (400 MHz, DMSO-$d_6$) δ 9.19 (br d, J = 11.6 Hz, 1 H), 8.53 (br d, J = 5.2 Hz, 1 H), 8.12 (d, J = 5.8 Hz, 1 H), 7.37-7.52 (m, 1 H), 7.31-7.36 (m, 1 H), 7.12 (t, J = 8.9 Hz, 1 H), 6.79-6.91 (m, 1 H), 6.65 (d, J = 5.8 Hz, 1 H), 6.20 (br d, J = 16.4 Hz, 1 H), 5.72-5.83 (m, 1 H), 4.72-4.99 (m, 1 H), 4.43-4.54 (m, 1 H), 4.02-4.19 (m, 1 H), 3.89 (br s, 1 H), 3.81 (br d, J = 14.7 Hz, 1 H), 2.73 (s, 6 H), 2.19 (dt, J = 15.7, 7.0 Hz, 2 H), 1.95-2.02 (m, 2 H), 1.27 (br dd, J = 14.8, 6.7 Hz, 3 H), 1.13 (br dd, J = 11.7, 6.5 Hz, 2 H), 1.03-1.07 (m, 2 H), 0.92 (d, J = 6.6 Hz, 3 H), 0.71-0.88 (m, 5 H) |
| 122-3 | 687.2 | $^1$H NMR (400 MHz, DMSO-$d_6$) δ 9.18-9.70 (m, 1 H), 8.50 (d, J = 10.4 Hz, 1 H), 8.03-8.14 (m, 1H), 7.26-7.50 (m, 2 H), 7.03-7.17 (m, 1 H), 6.83 (br dd, J = 16.1, 10.3 Hz, 1 H), 6.59-6.72 (m, 1 H), 6.20 (dd, J = 16.7, 2.2 Hz, 1 H), 5.71-5.83 (m, 1 H), 4.73-4.98 (m, 2 H), 4.47-4.56 (m, 1 H), 4.00-4.25 (m, 2 H), 3.79 (br d, J = 13.1 Hz, 1 H), 2.72-2.78 (m, 6 H), 2.68 (br d, J = 1.7 Hz, 1 H), 1.37 (br dd, J = 5.9, 3.4 Hz, 1 H), 1.19-1.34 (m, 4 H), 1.11-1.17 (m, 2 H), 1.02-1.11 (m, 3 H), 0.91 (br d, J = 6.4 Hz, 4 H), 0.74 (dd, J = 6.6, 2.3 Hz, 3 H) |
| 122-3-1 | 687.2 | $^1$H NMR (400 MHz, DMSO-$d_6$) δ 9.27-9.46 (m, 1 H), 8.49 (s, 1 H), 8.40 (d, J = 4.8 Hz, 1 H), 8.10 (dd, J = 11.8, 5.8 Hz, 1 H), 7.40-7.50 (m, 1 H), 7.01-7.13 (m, 1 H), 6.78-6.91 (m, 1 H), 6.63 (dd, J = 5.8, 3.5 Hz, 1 H), 6.20 (dd, J = 16.8, 2.3 Hz, 1 H), 5.71-5.83 (m, 1H), 4.71-4.99 (m, 2H), 4.11-4.26 (m, 1 H), 4.00-4.09 (m, 1 H), 3.81-3.97 (m, 2 H), 3.68-3.79 (m, 1 H), 2.77 (s, 7 H), 1.18-1.42 (m, 5 H) 1.02-1.12 (m, 2 H), 0.89-0.97 (m, 3 H), 0.74 (d, J = 6.4 Hz, 3 H), 0.60-0.71 (m, 2H), 0.40-0.56 (m, 1 H) |
| 122-3-2 | 687.4 | $^1$H NMR (400 MHz, DMSO-$d_6$) δ 9.59 (br d, J = 13.9 Hz, 1 H), 8.51 (s, 1 H), 8.12 (d, J = 5.8 Hz, 1 H), 7.40-7.50 (m, 1 H), 7.27-7.35 (m, 1 H), 7.12 (t, J = 8.8 Hz, 1 H), 6.77-6.92 (m, 1 H), 6.66 (d, J = 5.6 Hz, 1 H), 6.20 (br d, J = 16.0 Hz, 1 H), 5.66-5.82 (m, 1 H), 4.72-4.98 (m, 2 H), 4.01-4.18 (m, 2 H), 3.91 (br s, 1 H), 3.79 (br d, J = 13.7 Hz, 1 H), 2.74 (s, 7 H), 1.27 (br dd, J = 12.6, 6.4 Hz, 5 H), 1.03-1.19 (m, 3 H), 0.91 (d, J = 6.6 Hz, 3 H), 0.73 (d, J = 6.6 Hz, 3 H), 0.51-0.68 (m, 2 H), 0.30-0.41 (m, 1 H) |
| 123-1 | 590.2 | $^1$H NMR (CDCl3, 400 MHz): δ = 9.79 (br s, 1H), 8.05 (d, J = 9.7 Hz, 1H), 7.25-7.32 (m, 1H), 6.57-6.76 (m, 3H), 6.34-6.43 (m, 2H), 5.78 (dd, J = 10.5, 1.8 Hz, 1H), 4.68 (br s, 2H), 4.50 (s, 2H), 4.29 (br d, J = 13.5 Hz, 2H), 3.60 (br dd, J = 13.5, 4.1 Hz, 2H), 2.56 (dt, J = 13.3, 6.7 Hz, 1H), 1.90 (s, 3H), 1.46-1.61 (m, 6H), 1.14 (d, J = 6.6 Hz, 3H), 0.97 (d, J = 6.8 Hz, 3H). $^{19}$F NMR (CDCl3, 376 MHz): δ = –107.30 (d, J = 82.4 Hz, 1F), –121.70 (d, J = 83.2 Hz, 1F) |
| 123-2 | 590.2 | $^1$H NMR (400 MHz, CDCl3) δ 9.79 (br s, 1H), 8.05 (d, J = 9.7 Hz, 1H), 7.32-7.25 (m, 1H), 6.76-6.57 (m, 3H), 6.43-6.34 (m, 2H), 5.78 (dd, J = 1.8, 10.5 Hz, 1H), 4.68 (br s, 2H), 4.50 (s, 2H), 4.29 (br d, J = 13.5 Hz, 2H), 3.60 (br dd, J = 4.1, 13.5 Hz, 2H), 2.56 (td, J = 6.7, 13.3 Hz, 1H), 1.90 (s, 3H), 1.58 (d, J = 7.0 Hz, 3H), 1.52 (d, J = 7.0 Hz, 3H), 1.14 (d, J = 6.6 Hz, 3H), 0.97 (d, J = 6.8 Hz, 3H); $^{19}$F NMR (376 MHz, CDCl3) δ = –107.30 (d, J = 82.4 Hz, 1F), –121.70 (d, J = 83.2 Hz, 1F) |
| 123-3 | 574.1 | $^1$H NMR (400 MHz, CDCl3) δ = 7.99 (d, J = 9.1 Hz, 1H), 7.52-7.40 (m, 1H), 7.34 (dt, J = 1.7, 7.4 Hz, 1H), 7.23-7.11 (m, 2H), 6.69-6.60 (m, 1H), 6.52 (s, 1H), 6.32 (s, 1H), 5.79 (dd, J = 1.9, 10.4 Hz, 1H), 4.84-4.39 (m, 4H), 4.30 (br d, J = 13.5 Hz, 2H), 3.57 (ddd, J = 4.3, 4.4, 13.4 Hz, 2H), 2.63-2.52 (m, 1H), 1.91 (s, 3H), 1.64-1.50 (m, 6H) 1.17 (d, J = 6.8 Hz, 3H), 1.00 (d, J = 6.6 Hz, 3H); $^{19}$F NMR (376 MHz, CDCl3) δ = –112.60 (d, J = 40.7 Hz, 1F), –125.87--127.76 (m, 1F) |
| 123-4 | 574.1 | $^1$H NMR (400 MHz, CDCl3) δ = 7.99 (d, J = 9.1 Hz, 1H), 7.50-7.29 (m, 2H), 7.24-7.10 (m, 2H), 6.71-6.57 (m, 1H), 6.43 (dd, J = 2.0, 16.7 Hz, 1H), 6.31 (s, 1H), 5.80 (dd, J = 1.9, 10.4 Hz, 1H), 4.71 (br s, 2H), 4.45 (br s, 2H), 4.30 (br d, J = 13.3 Hz, 2H), 3.57 (td, J = 4.2, 13.3 Hz, 2H), 2.57 (s, 1H), 1.90 (s, 3H), 1.57 (t, J = 6.7 Hz, 6H), 1.16 (d, J = 6.6 Hz, 3H), 0.99 (d, J = 6.8 Hz, 3H); $^{19}$F NMR (376 MHz, |

TABLE 148-continued

Analytical Data for Method Table Examples

| Ex. # | LRMS: m/z (ESI, +ve ion): (M + H)+ | NMR |
|---|---|---|
| | | CDCl3) δ = −112.60 (d, J = 41.6 Hz, 1F), −127.13 (d, J = 41.6 Hz, 1F) |
| 123-5 | 589.1 | $^1$H NMR (400 MHz, CDCl3) δ = 8.00 (d, J = 9.3 Hz, 1H), 7.14 (br d, J = 6.4 Hz, 1H), 6.64 (dd, J = 10.5, 16.7 Hz, 1H), 6.51-6.39 (m, 3H), 6.34 (s, 1H), 5.79 (dd, J = 1.7, 10.4 Hz, 1H), 4.83-4.40 (m, 6H), 4.31 (br d, J = 12.9 Hz, 2H), 3.59 (ddd, J = 3.9, 4.0, 13.4 Hz, 2H), 2.68-2.55 (m, 1H), 1.92 (s, 3H), 1.60 (br d, J = 6.8 Hz, 3H), 1.55 (d, J = 6.8 Hz, 3H), 1.17 (br d, J = 6.6 Hz, 3H), 0.99 (br d, J = 6.6 Hz, 3H); $^{19}$F NMR (376 MHz, CDCl3) δ = −110.99 (d, J = 56.4 Hz, 1F), −123.22 (br d, J = 56.4 Hz, 1F) |
| 123-6 | 589.1 | $^1$H NMR (400 MHz, CDCl3) δ = 8.00 (d, J = 9.3 Hz, 1H), 7.14 (dt, J = 6.4, 8.1 Hz, 1H), 6.68-6.60 (m, 1H), 6.51-6.39 (m, 3H), 6.33 (s, 1H), 5.79 (dd, J = 1.9, 10.6 Hz, 1H), 4.84-4.45 (m, 6H), 4.31 (br d, J = 13.1 Hz, 2H), 3.59 (ddd, J = 4.0, 4.1, 13.4 Hz, 2H), 2.70-2.52 (m, 1H), 1.91 (s, 3H), 1.60 (d, J = 6.8 Hz, 3H), 1.55 (d, J = 6.8 Hz, 3H), 1.16 (d, J = 6.8 Hz, 3H), 0.98 (d, J = 6.6 Hz, 3H); $^{19}$F NMR (376 MHz, CDCl3) δ = −110.99 (d, J = 56.4 Hz, 1F), −123.22 (br d, J = 56.4 Hz, 1F) |
| 124-1 | 602.6 | $^1$H NMR (400 MHz, DMSO-d$_6$) δ 8.42-8.51 (m, 2 H), 7.45-7.58 (m, 1 H), 7.21-7.38 (m, 3 H), 7.18 (td, J = 7.4, 1.6 Hz, 1 H), 6.84 (td, J = 15.8, 10.5 Hz, 1 H), 6.20 (dd, J = 16.7, 2.2 Hz, 1 H), 5.72-5.82 (m, 1 H), 4.73-4.97 (m, 2 H), 4.47 (br dd, J = 6.1, 3.4 Hz, 1H), 4.12-4.23 (m, 1 H), 3.83-3.96 (m, 2 H), 3.51 (br dd, J = 13.6, 3.6 Hz, 1 H), 1.31-1.40 (m, 3 H), 1.26 (br d, J = 6.6 Hz, 2 H), 1.18 (d, J = 6.6 Hz, 2 H), 1.07 (dd, J = 6.6, 4.4 Hz, 6 H), 0.93 (t, J = 7.7 Hz, 6 H) |
| 124-2 | 599.2 | $^1$H NMR (400 MHz, DMSO-d$_6$) δ 8.33-8.60 (m, 2 H), 7.18-7.37 (m, 4 H), 7.02 (d, J = 7.3 Hz, 1 H), 6.76-6.93 (m, 1 H), 6.20 (dd, J = 16.6, 2.3 Hz, 1 H), 5.76 (ddd, J = 10.3, 5.7, 2.3 Hz, 1 H), 4.72-4.96 (m, 2 H), 4.48 (dd, J = 5.1, 1.3 Hz, 1 H), 4.11-4.24 (m, 1 H), 3.83-3.99 (m, 2 H), 3.46-3.57 (m, 1 H), 1.95 (s, 3 H), 1.30-1.38 (m, 3 H), 1.25 (br d, J = 6.3 Hz, 2 H), 1.18 (d, J = 6.6 Hz, 2 H), 1.07 (t, J = 6.3 Hz, 6 H), 0.93 (t, J = 6.5 Hz, 6 H) |
| 124-3 | 653.2 | $^1$H NMR (400 MHz, DMSO-d$_6$) δ 8.59 (br d, J = 4.6 Hz, 1 H), 8.43 (d, J = 5.2 Hz, 1H), 7.78 (br dd, J = 19.3, 7.7 Hz, 2 H), 7.64-7.71 (m, 1 H), 7.34 (br d, J = 8.1 Hz, 1 H), 7.24 (d, J = 5.0 Hz, 1 H), 6.72-6.90 (m, 1 H), 6.14-6.25 (m, 1 H), 5.76 (ddd, J = 10.4, 5.9, 2.0 Hz, 1H), 4.72-5.01 (m, 2 H), 4.43-4.55 (m, 1 H), 4.09-4.34 (m, 1 H), 3.94-4.09 (m, 1 H), 3.76-3.93 (m, 2 H), 3.39-3.64 (m, 1 H), 1.28-1.41 (m, 3 H), 1.13-1.28 (m, 2 H), 1.06 (br d, J = 5.8 Hz, 7 H), 0.92 (br d, J = 6.6 Hz, 6 H) |
| 124-4 | 619.2 | $^1$H NMR (400 MHz, DMSO-d$_6$) δ 9.92-10.32 (m, 1 H), 8.45 (d, J = 5.0 Hz, 2 H), 7.19-7.29 (m, 2 H), 6.84 (td, J = 15.7, 10.9 Hz, 1 H), 6.60-6.72 (m, 2 H), 6.20 (dd, J = 16.8, 2.3 Hz, 1 H), 5.71-5.80 (m, 1 H), 4.73-4.96 (m, 2 H), 4.43-4.55 (m, 1H), 4.08-4.24 (m, 2 H), 3.84-3.97 (m, 2 H), 1.30-1.37 (m, 3H), 1.27 (br d, J = 6.4 Hz, 2 H), 1.19 (br d, J = 6.6 Hz, 2 H), 1.07 (dd, J = 6.6, 4.8 Hz, 6 H), 0.93 (br s, 6 H) |
| 124-5 | 583.2 | $^1$H NMR (400 MHz, DMSO-d$_6$) δ 8.48 (d, J = 5.2 Hz, 1 H), 8.33 (d, J = 9.5 Hz, 1 H), 7.31-7.39 (m, 1 H), 7.22-7.29 (m, 3 H), 7.12-7.19 (m, 1 H), 6.78-6.95 (m, 1 H), 6.20 (dd, J = 16.6, 2.3 Hz, 1 H), 5.72-5.81 (m, 1 H), 4.72-4.96 (m, 2 H), 4.48 (br dd, J = 5.0, 2.3 Hz, 1 H), 4.11-4.23 (m, 1 H), 3.82-3.94 (m, 2 H), 2.60-2.67 (m, 1 H), 1.98 (s, 3 H), 1.29-1.37 (m, 3 H), 1.26 (br d, J = 6.8 Hz, 2 H), 1.18 (d, J = 6.8 Hz, 2 H), 1.07 (d, J = 6.8 Hz, 6 H), 0.91 (br t, J = 7.7 Hz, 6H) |
| 124-6 | 618.6 | $^1$H NMR (400 MHz, DMSO-d$_6$) δ 8.51 (s, 1 H), 8.45 (d, J = 5.0 Hz, 1 H), 7.51-7.59 (m, 1 H), 7.36-7.49 (m, 2 H), 7.27 (d, J = 5.2 Hz, 1 H), 7.17 (dd, J = 7.5, 1.7 Hz, 1 H), 6.71-6.94 (m, 1 H), 6.20 (dd, J = 16.6, 2.3 Hz, 1 H), 5.72-5.80 (m, 1 H), 4.73-4.97 (m, 2 H), 4.42-4.54 (m, 1 H), 4.10-4.21 (m, 1 H), 3.80-3.98 (m, 2 H), 2.60-2.67 (m, 1 H), 1.34 (t, J = 6.8 Hz, 3 H), 1.25 (br d, J = 6.6 Hz, 2 H), 1.18 (br d, J = 6.6 Hz, 2 H), 1.07 (t, J = 6.1 Hz, 6 H), 0.95 (t, J = 7.6 Hz, 6H) |
| 124-7 | 584.6 | $^1$H NMR (400 MHz, DMSO-d$_6$) δ 8.52 (d, J = 5.2 Hz, 1 H), 8.45 (d, J = 1.5 Hz, 1 H), 7.47-7.52 (m, 2 H), |

TABLE 148-continued

Analytical Data for Method Table Examples

| Ex. # | LRMS: m/z (ESI, +ve ion): (M + H)+ | NMR |
|---|---|---|
| | | 7.39-7.46 (m, 3 H), 7.33 (d, J = 5.0 Hz, 1 H), 6.67-6.98 (m, 1 H), 6.20 (dd, J = 16.6, 1.9 Hz, 1 H), 5.64-5.83 (m, 1 H), 4.71-4.97 (m, 2 H), 4.40-4.55 (m, 1 H), 4.11-4.24 (m, 1 H), 3.80-3.97 (m, 2 H), 2.62-2.72 (m, 2 H), 1.34 (t, J = 6.5 Hz, 3 H), 1.25 (br d, J = 6.6 Hz, 1 H), 1.18 (d, J = 6.8 Hz, 2 H), 1.08 (t, J = 6.4 Hz, 6 H), 0.94 (d, J = 6.8 Hz, 3 H), 0.90 (d, J = 6.8 Hz, 3 H) |
| 124-8 | 626.6 | $^1$H NMR (400 MHz, DMSO-$d_6$) δ 8.43 (d, J = 5.0 Hz, 2 H), 7.38 (d, J = 3.9 Hz, 2 H), 7.17-7.29 (m, 2 H), 6.95-7.04 (m, 1 H), 6.76-6.92 (m, 1 H), 6.20 (dd, J = 16.7, 2.2 Hz, 1 H), 5.74-5.82 (m, 1 H), 4.72-4.97 (m, 2 H), 4.44-4.55 (m, 1 H), 4.11-4.28 (m, 1 H), 3.78-3.98 (m, 2 H), 1.35 (br d, J = 6.8 Hz, 3 H), 1.14-1.30 (m, 4 H), 1.01-1.13 (m, 10 H), 0.87-0.99 (m, 10H) |
| 124-9 | 596.6 | $^1$H NMR (400 MHz, DMSO-$d_6$) δ 8.47 (s, 1 H), 8.35 (d, J = 5.2 Hz, 1 H), 7.29-7.36 (m, 1 H), 7.18-7.28 (m, 2 H), 7.10 (d, J = 7.7 Hz, 1 H), 6.81-6.92 (m, 1 H), 6.78 (d, J = 5.2 Hz, 1 H), 6.20 (dd, J = 16.8, 2.3 Hz, 1 H), 5.73-5.80 (m, 1 H), 4.71-4.96 (m, 2 H), 4.43-4.54 (m, 1 H), 4.15 (br dd, J = 13.2, 8.4 Hz, 1 H), 3.82-3.98 (m, 2 H), 2.66-2.77 (m, 1 H), 1.98 (s, 3 H), 1.43-1.53 (m, 1 H), 1.33 (t, J = 6.5 Hz, 3 H), 1.25 (br d, J = 6.4 Hz, 2 H), 1.18 (d, J = 6.8 Hz, 2 H), 1.07 (d, J = 6.6 Hz, 3 H), 0.91 (d, J = 6.6 Hz, 3 H), 0.78-0.87 (m, 1 H), 0.69-0.77 (m, 2 H) |
| 124-10 | 584.6 | $^1$H NMR (400 MHz, DMSO-$d_6$) δ 8.39-8.50 (m, 2 H), 7.29-7.34 (m, 1 H), 7.20-7.27 (m, 3 H), 6.99 (d, J = 7.7 Hz, 1 H), 6.81-6.96 (m, 1 H), 6.22 (br d, J = 17.0 Hz, 1 H), 5.74-5.82 (m, 1 H), 4.98 (br d, J = 3.1 Hz, 1 H), 4.26-4.46 (m, 2 H), 4.01-4.22 (m, 1 H), 3.63-3.88 (m, 2 H), 3.46-3.59 (m, 1 H), 3.08-3.21 (m, 1 H), 2.62-2.71 (m, 1 H), 1.95 (s, 3 H), 1.35 (d, J = 6.6 Hz, 3 H), 1.07 (d, J = 6.6 Hz, 6 H), 0.93 (d, J = 6.6 Hz, 6 H) |
| 124-11 | 598.6 | $^1$H NMR (400 MHz, DMSO-$d_6$) δ 8.54 (s, 1 H), 8.45 (d, J = 5.0 Hz, 1 H), 7.29-7.34 (m, 1 H), 7.22-7.25 (m, 1 H), 7.12-7.22 (m, 2 H), 7.01 (d, J = 6.8 Hz, 1 H), 6.77-6.88 (m, 1 H), 6.21 (dd, J = 16.6, 2.5 Hz, 1 H), 5.72-5.80 (m, 1 H), 4.55-4.66 (m, 2 H), 4.35 (br d, J = 13.1 Hz, 2 H), 3.66 (br dd, J = 13.8, 3.2 Hz, 2 H), 2.63-2.73 (m, 2 H), 1.95 (s, 3 H), 1.41 (br d, J = 5.0 Hz, 6 H), 1.07 (d, J = 6.6 Hz, 6 H), 0.93 (d, J = 6.4 Hz, 6 H) |
| 124-12 | 659.2 | $^1$H NMR (400 MHz, DMSO-$d_6$) δ 8.50 (1 H, d, J = 3.5 Hz), 8.41 (1 H, d, J = 4.8 Hz), 7.54-7.61 (1 H, m), 7.46-7.53 (1 H, m), 7.25 (1 H, br s), 7.20 (1 H, d, J = 4.8 Hz), 6.84 (1 H, td, J = 16.7, 10.6 Hz), 6.19 (1 H, dd, J = 16.7, 2.0 Hz), 5.72-5.80 (1 H, m), 4.83-4.94 (1 H, m), 4.43-4.81 (1 H, m), 4.11-4.21 (1 H, m), 3.83-3.95 (2 H, m), 3.50 (1 H, br dd, J = 13.8, 3.4 Hz), 2.65-2.78 (1 H, m), 1.94 (3 H, s), 1.33 (3 H, t, J = 6.7 Hz), 1.15-1.27 (3 H, m), 1.06 (3 H, d, J = 6.6 Hz), 0.96 (3 H, d, J = 6.6 Hz) |
| 124-13 | 609.2 | $^1$H NMR (400 MHz, DMSO-$d_6$) δ 8.41 (d, J = 4.98 Hz, 1H), 8.37 (s, 1H). 7.20 (d, J = 4.98 Hz, 1H), 6.94 (br t, J = 10.06 Hz, 1H), 6.79-6.89 (m, 1H), 6.68-6.79 (m, 1H), 6.19 (dd, J = 2.18, 16.69 Hz, 1H), 5.71-5.79 (m, 1H), 4.42-4.91 (m, 2H), 3.75-4.21 (m, 4H), 3.47 (br d, J = 3.73 Hz, 1H), 2.64-2.75 (m, 1H), 1.92 (s, 3H), 1.31 (br t, J = 7.36 Hz, 3H), 1.14-1.27 (m, 3H), 1.06 (d, J = 6.63 Hz, 3H), 0.99 (d, J = 6.63 Hz, 3H) |
| 124-14 | 575.2 | $^1$H NMR (400 MHz, DMSO-$d_6$) δ 10.20 (br s, 1H), 8.46 (dd, J = 4.35, 9.12 Hz, 1H), 8.39 (dd, J = 1.87, 4.56 Hz, 1H), 7.27 (q, J = 7.88 Hz, 1H), 7.18 (d, J = 4.56 Hz, 1H), 6.64-6.81 (m, 3H), 6.17 (br d, J = 16.59 Hz, 1H), 5.72 (br d, J = 11.61 Hz, 1H), 4.59-4.70 (m, 1H), 4.47-4.57 (m, 1H), 4.20-4.37 (m, 1H), 4.07-4.14 (m, 1H), 3.79-3.90 (m, 1H), 3.69-3.78 (m, 1H), 2.55-2.87 (m, 1H), 1.83-1.97 (m, 3H), 1.42 (br dd, J = 2.90, 6.43 Hz, 3H), 1.24-1.29 (m, 3H), 1.06 (t, J = 6.63 Hz, 3H), 0.93 (dd, J = 6.63, 13.68 Hz, 3H) |
| 124-14-1 | 575.2 | $^1$H NMR (400 MHz, DMSO-$d_6$) δ 10.19 (1 H, br s), 8.46 (1 H, d, J = 9.1 Hz), 8.39 (1 H, d, J = 4.8 Hz), 7.23-7.32 (1 H, m), 7.18 (1 H, d, J = 5.0 Hz), 6.64-6.81 (3 H, m), 6.17 (1 H, dd, J = 16.7, 2.2 Hz), 5.72 (1 H, dd, J = 10.4, 2.3 Hz), 4.65 (1 H, quin, J = 6.2 Hz), 4.52 (1 H, quin, J = 6.4 Hz), 4.29 (1 H, ddd, J = 12.5, 8.3, 3.8 Hz), 4.05-4.15 (1 H, m), 3.79-3.89 (1 H, m), 3.68-3.78 (1 H, m), 2.81 (1 H, quin, |

TABLE 148-continued

Analytical Data for Method Table Examples

| Ex. # | LRMS: m/z (ESI, +ve ion): (M + H)+ | NMR |
|---|---|---|
| | | J = 6.7 Hz), 1.85 (3 H, s), 1.40 (6 H, dd, J = 11.0, 6.6 Hz), 1.07 (3 H, d, J = 6.6 Hz), 0.95 (3 H, d, J = 6.8 Hz) |
| 124-14-2 | 575.2 | $^1$H NMR (400 MHz, DMSO-d$_6$) δ 10.17 (1 H, s), 8.45 (1 H, d, J = 9.1 Hz), 8.38 (1 H, d, J = 4.8 Hz), 7.22-7.32 (1 H, m), 7.18 (1 H, d, J = 4.8 Hz), 6.62-6.82 (3 H, m), 6.16 (1 H, dd, J = 16.6, 2.3 Hz), 5.72 (1 H, dd, J = 10.4, 2.3 Hz), 4.57-4.68 (1 H, m), 4.46-4.56 (1 H, m), 4.26 (1 H, ddd, J = 12.4, 8.2, 3.8 Hz), 4.02-4.13 (1 H, m), 3.79-3.90 (1 H, m), 3.67-3.78 (1 H, m), 2.53-2.61 (1 H, m), 1.95 (3 H, s), 1.41 (6 H, dd, J = 13.1, 6.6 Hz), 1.05 (3 H, d, J = 6.6 Hz), 0.91 (3 H, d, J = 6.6 Hz) |
| 124-16 | 575.2 | $^1$H NMR (400 MHz, DMSO-d$_6$) δ 10.20 (br d, J = 3.73 Hz, 1H), 8.38 (d, J = 4.77 Hz, 1H), 8.18-8.34 (m, 1H), 7.27 (q, J = 7.81 Hz, 1H), 7.19 (br d, J = 4.56 Hz, 1H), 6.77-6.90 (m, 1H), 6.64-6.75 (m, 2H). 6.18 (ddd, J = 1.97, 6.38, 16.74 Hz, 1H), 5.76 (br d, J = 10.99 Hz, 1H), 4.59-4.75 (m, 1H), 4.24-4.40 (m, 2H), 3.57-3.76 (m, 2H), 3.35-3.45 (m, 1H), 2.63-2.77 (m, 1H), 1.91 (br s, 3H), 1.36-1.44 (m, 3H), 1.22-1.34 (m, 3H), 1.07 (d, J = 6.63 Hz, 3H), 0.93 (br d, J = 6.63 Hz, 3H) |
| 124-16-1 | 575.2 | $^1$H NMR (400 MHz, DMSO-d$_6$) δ 10.20 (br s, 1H), 8.39 (d, J = 4.98 Hz, 1H), 8.18-8.33 (m, 1H), 7.23-7.32 (m, 1H), 7.19 (d, J = 4.77 Hz, 1H), 6.77-6.91 (m, 1H), 6.65-6.76 (m, 2H), 6.18 (ddd, J = 1.97, 6.27, 16.64 Hz, 1H), 5.76 (br d, J = 11.82 Hz, 1H), 3.99-4.77 (m, 4H), 3.61-3.71 (m, 1H), 3.35-3.47 (m, 1H), 2.72 (td, J = 6.66, 13.42 Hz, 1H), 1.91 (s, 3H), 1.41 (d, J = 6.43 Hz, 3H), 1.16-1.34 (m, 3H), 1.07 (d, J = 6.84 Hz, 3H), 0.93 (d, J = 6.84 Hz, 3H) |
| 124-16-2 | 575.2 | $^1$H NMR (400 MHz, DMSO-d$_6$) δ 10.19 (br s, 1H), 8.38 (d, J = 4.77 Hz, 1H). 8.20-8.34 (m, 1H), 7.23-7.33 (m, 1H), 7.18 (d, J = 4.77 Hz, 1H), 6.84 (dt, J = 10.57, 17.00 Hz, 1H), 6.63-6.76 (m, 2H), 6.18 (ddd, J = 2.18, 6.17, 16.74 Hz, 1H), 5.76 (br d, J = 11.61 Hz, 1H), 4.42-4.93 (m, 2H), 4.23-4.38 (m, 2H), 3.58-4.13 (m, 2H), 2.62-2.75 (m, 1H), 1.92 (d, J = 2.07 Hz, 3H), 1.37 (dd, J = 2.28, 6.63 Hz, 3H), 1.20-1.35 (m, 3H), 1.04-1.12 (m, 3H), 0.94 (dd, J = 2.49, 6.63 Hz, 3H) |
| 125-1 | 603.2 | $^1$H NMR (400 MHz, DMSO-d$_6$) δ 8.40-8.52 (m, 2 H), 7.50 (br s, 1 H), 7.25-7.36 (m, 3 H), 7.14-7.20 (m, 1 H), 6.84 (td, J = 16.5, 10.6 Hz, 1 H), 6.20 (dd, J = 16.6, 2.3 Hz, 1 H), 5.71-5.81 (m, 1 H), 4.74-4.96 (m, 2 H), 4.44-4.54 (m, 1 H), 4.17 (br d, J = 14.3 Hz, 1 H), 3.82-3.95 (m, 2 H), 3.50 (dd, J = 13.9, 2.9 Hz, 1 H), 1.31-1.38 (m, 3 H), 1.26 (br d, J = 6.6 Hz, 2 H), 1.18 (d, J = 6.6 Hz, 2 H), 1.07 (dd, J = 6.7, 3.0 Hz, 6 H), 0.93 (dd, J = 6.6, 2.9 Hz, 6 H) |
| 125-2 | 598.6 | $^1$H NMR (400 MHz, DMSO-d$_6$) δ 8.39-8.50 (m, 2 H), 7.18-7.37 (m, 4 H), 7.02 (d, J = 7.0 Hz, 1 H), 6.72-6.91 (m, 1 H), 6.20 (dd, J = 16.8, 2.3 Hz, 1 H), 5.76 (ddd, J = 10.3, 5.5, 2.3 Hz, 1 H), 4.72-4.97 (m, 2 H), 4.43-4.54 (m, 1 H), 4.12-4.25 (m, 1 H), 3.79-3.98 (m, 2 H), 3.46-3.56 (m, 1 H), 1.95 (s, 3 H), 1.30-1.38 (m, 3 H), 1.26 (br d, J = 6.6 Hz, 2 H), 1.18 (d, J = 6.8 Hz, 2 H), 1.07 (dd, J = 6.6, 4.4 Hz, 6 H), 0.93 (t, J = 5.8 Hz, 6 H) |
| 125-3 | 652.6 | $^1$H NMR (400 MHz, DMSO-d$_6$) δ 8.58 (br d, J = 1.5 Hz, 1 H), 8.43 (d, J = 5.2 Hz, 1 H), 7.73-7.83 (m, 2 H), 7.65-7.71 (m, 1 H), 7.28-7.40 (m, 1 H), 7.23 (d, J = 5.2 Hz, 1 H), 6.82 (br dd, J = 16.7, 10.3 Hz, 1 H), 6.20 (dd, J = 16.4, 1.7 Hz, 1 H), 5.71-5.81 (m, 1 H), 4.71-5.01 (m, 2 H), 4.46-4.57 (m, 1 H), 4.10-4.35 (m, 1 H), 3.96-4.08 (m, 1 H), 3.75-3.93 (m, 2 H), 3.40-3.64 (m, 1 H), 1.34 (br d, J = 17.4 Hz, 4 H), 1.13-1.27 (m, 2 H), 1.06 (br d, J = 5.2 Hz, 6 H), 0.92 (br d, J = 6.6 Hz, 6 H) |
| 125-4 | 618.6 | $^1$H NMR (400 MHz, DMSO-d$_6$) δ 9.91-10.30 (m, 1 H), 8.46 (d, J = 5.0 Hz, 2 H), 7.18-7.29 (m, 2 H), 6.76-6.92 (m, 1 H), 6.61-6.75 (m, 2 H), 6.20 (dd, J = 16.6, 2.3 Hz, 1 H), 5.75-5.81 (m, 1 H), 4.74-4.97 (m, 2 H), 4.45-4.52 (m, 1 H), 4.10-4.26 (m, 1 H), 3.80-3.95 (m, 2 H), 3.45-3.56 (m, 1 H), 1.31-1.39 (m, 3 H), 1.27 (br d, J = 6.6 Hz, 2 H), 1.20 (br d, J = 6.6 Hz, 2 H), 1.07 (dd, J = 6.7, 4.0 Hz, 6 H), 0.93 (br s, 6 H) |
| 125-5 | 583.2 | $^1$H NMR (400 MHz, DMSO-d$_6$) δ 8.47 (d, J = 5.2 Hz, 1 H), 8.33 (d, J = 9.5 Hz, 1 H), 7.30-7.38 (m, 1 H), 7.21-7.30 (m, 3 H), 7.11-7.19 (m, 1 H), 6.85 (br d, J = 10.8 Hz, 1 H), 6.20 (dd, J = 16.6, 2.3 Hz, 1 H), 5.76 (ddd, J = 7.8, 4.9, 2.6 Hz, |

TABLE 148-continued

Analytical Data for Method Table Examples

| Ex. # | LRMS: m/z (ESI, +ve ion): (M + H)+ | NMR |
|---|---|---|
| | | 1 H), 4.72-4.95 (m, 2 H), 4.43-4.54 (m, 1 H), 4.16 (br dd, J = 13.6, 5.9 Hz, 1 H), 3.83-3.94 (m, 2 H), 2.61-2.67 (m, 1 H), 1.98 (s, 3 H), 1.32 (br t, J = 7.5 Hz, 3 H), 1.26 (br d, J = 6.8 Hz, 2 H), 1.18 (d, J = 6.6 Hz, 2 H), 1.07 (dd, J = 6.7, 2.4 Hz, 6 H), 0.91 (br t, J = 5.3 Hz, 6 H) |
| 125-6 | 618.6 | $^1$H NMR (400 MHz, DMSO-$d_6$) δ 8.51 (s, 1 H), 8.45 (d, J = 5.0 Hz, 1 H), 7.51-7.58 (m, 1 H), 7.37-7.51 (m, 2 H), 7.26 (d, J = 5.0 Hz, 1 H), 7.17 (dd, J = 7.4, 1.6 Hz, 1 H), 6.83 (s, 1 H), 6.20 (dd, J = 16.5, 2.4 Hz, 1 H), 5.75-5.79 (m, 1 H), 4.74-4.97 (m, 2 H), 4.44-4.53 (m, 1 H), 4.11-4.22 (m, 2 H), 3.81-3.98 (m, 2 H), 1.34 (t, J = 6.8 Hz, 3 H), 1.26 (br d, J = 6.4 Hz, 2 H), 1.18 (br d, J = 6.8 Hz, 2 H), 1.07 (dd, J = 6.6, 4.6 Hz, 6 H), 0.95 (t, J = 6.7 Hz, 6 H) |
| 125-7 | 584.6 | $^1$H NMR (400 MHz, DMSO-$d_6$) δ 8 8.53 (d, J = 5.0 Hz, 1 H), 8.45 (d, J = 2.1 Hz, 1 H), 7.47-7.52 (m, 2 H), 7.40-7.46 (m, 3 H), 7.31 (d, J = 5.2 Hz, 1 H), 6.77-6.95 (m, 1 H), 6.20 (dd, J = 16.7, 2.4 Hz, 1 H), 5.72-5.80 (m, 1 H), 4.74-4.95 (m, 2 H), 4.48 (br dd, J = 5.1, 1.6 Hz, 1 H), 4.08-4.25 (m, 2 H), 3.79-3.96 (m, 2 H), 1.34 (t, J = 6.7 Hz, 3 H), 1.25 (br d, J = 6.6 Hz, 2 H), 1.18 (d, J = 6.8 Hz, 2 H), 1.08 (dd, J = 6.5, 5.3 Hz, 6 H), 0.92 (dd, J = 10.6, 6.8 Hz, 6 H |
| 125-8 | 627.2 | $^1$H NMR (400 MHz, DMSO-$d_6$) δ 8.45 (br d, J = 4.8 Hz, 2 H), 7.38 (d, J = 3.9 Hz, 2 H), 7.28 (br d, J = 4.6 Hz, 1 H), 7.20-7.26 (m, 1 H), 6.99 (br d, J = 7.9 Hz, 1 H), 6.77-6.91 (m, 1 H), 6.20 (dd, J = 16.7, 2.2 Hz, 1 H), 5.72-5.80 (m, 1 H), 4.73-4.96 (m, 2 H), 4.45-4.57 (m, 1 H), 4.11-4.31 (m, 1 H), 3.78-3.99 (m, 2 H), 3.46-3.59 (m, 1 H), 2.63-2.81 (m, 1 H), 1.31-1.39 (m, 3 H), 1.14-1.30 (m, 4 H), 1.07 (br t, J = 6.7 Hz, 9 H), 0.91-0.99 (m, 9 H) |
| 125-9 | 596.6 | $^1$H NMR (400 MHz, DMSO-$d_6$) δ 8.45 (s, 1 H), 8.36 (d, J = 5.0 Hz, 1 H), 7.29-7.35 (m, 1 H), 7.25 (br d, J = 9.5 Hz, 2 H), 7.07 (d, J = 7.5 Hz, 1 H), 6.78-6.87 (m, 2 H), 6.20 (dd, J = 16.5, 2.4 Hz, 1 H), 5.72-5.81 (m, 1 H), 4.72-4.95 (m, 2 H), 4.45-4.54 (m, 1 H), 4.12-4.24 (m, 1 H), 3.80-3.94 (m, 2 H), 2.69-2.80 (m, 1 H), 1.98 (s, 3 H), 1.38-1.46 (m, 1 H), 1.34 (br t, J = 7.2 Hz, 3 H), 1.26 (br d, J = 6.6 Hz, 2 H), 1.18 (br d, J = 6.8 Hz, 2 H), 1.09 (d, J = 6.6 Hz, 3 H), 0.94 (d, J = 6.6 Hz, 3 H), 0.74-0.84 (m, 1 H), 0.63-0.73 (m, 2 H) |
| 125-10 | 585.2 | $^1$H NMR (400 MHz, DMSO-$d_6$) δ 8.45 (d, J = 5.2 Hz, 2 H), 7.19-7.35 (m, 4 H), 6.99 (d, J = 7.5 Hz, 1 H), 6.80-6.94 (m, 1 H), 6.16-6.27 (m, 1 H), 5.76-5.81 (m, 1 H), 4.97 (br s, 1 H), 4.26-4.46 (m, 2 H), 4.00-4.22 (m, 1 H), 3.62-3.87 (m, 2 H), 3.45-3.58 (m, 1 H), 3.07-3.21 (m, 1 H), 2.62-2.72 (m, 1 H), 1.95 (s, 3 H), 1.36 (d, J = 6.6 Hz, 3 H), 1.08 (d, J = 6.6 Hz, 6 H), 0.93 (d, J = 6.6 Hz, 6 H) |
| 125-11 | 598.6 | $^1$H NMR (400 MHz, DMSO-$d_6$) δ 8.54 (s, 1 H), 8.45 (d, J = 5.2 Hz, 1 H), 7.29-7.35 (m, 1 H), 7.22-7.25 (m, 1 H), 7.11-7.22 (m, 2 H), 7.01 (d, J = 6.8 Hz, 1 H), 6.82 (dd, J = 16.6, 10.6 Hz, 1 H), 6.21 (dd, J = 16.6, 2.3 Hz, 1 H), 5.72-5.79 (m, 1 H), 4.53-4.67 (m, 2 H), 4.35 (br d, J = 13.3 Hz, 2 H), 3.66 (br dd, J = 13.9, 2.9 Hz, 2 H), 2.63-2.72 (m, 1 H), 1.95 (s, 3H), 1.41 (br d, J = 5.2 Hz, 6 H), 1.07 (d, J = 6.6 Hz, 7 H), 0.93 (d, J = 6.6 Hz, 6 H) |
| 129-1 | 632.2 | $^1$H NMR (400 MHz, DMSO-$d_6$) δ 8.73-9.11 (m, 1 H), 8.43-8.51 (m, 1 H), 8.37 (d, J = 5.0 Hz, 1 H), 7.36-7.81 (m, 2 H), 7.14-7.22 (m, 1 H), 6.94-7.10 (m, 1 H), 6.73-6.92 (m, 1 H), 6.14-6.26 (m, 1 H), 5.76 (dt, J = 10.2, 3.0 Hz, 1 H), 4.44-4.96 (m, 2 H), 3.76-4.25 (m, 4 H), 2.56-2.63 (m, 1 H), 2.22 (s, 3 H), 1.89-2.04 (m, 3 H), 1.34 (br t, J = 7.2 Hz, 3 H), 1.15-1.27 (m, 3 H), 1.01-1.13 (m, 3 H), 0.79-0.99 (m, 3 H) |
| 129-2 | 686.2 | $^1$H NMR (400 MHz, DMSO-$d_6$) δ 11.15 (br s, 1 H), 8.57 (s, 1 H), 8.38 (d, J = 4.8 Hz, 1 H), 7.50-7.63 (m, 1 H), 7.34 (br t, J = 8.8 Hz, 1 H), 7.14-7.23 (m, 2 H), 6.75-6.92 (m, 1 H), 6.19 (br d, J = 16.6 Hz, 1 H), 5.75 (br d, J = 10.4 Hz, 1 H), 4.44-5.04 (m, 2 H), 3.46-4.29 (m, 4 H), 2.39-2.47 (m, 1 H), 1.73-2.00 (m, 3 H), 1.29 (br t, J = 7.3 Hz, 3 H), 0.95-1.12 (m, 6 H), 0.83 (d, J = 6.6 Hz, 3 H) |
| 129-3 | 628.2 | $^1$H NMR (400 MHz, DMSO-$d_6$) δ 8.55 (br s, 1 H), 8.35 (br s, 1 H), 7.43-7.57 (m, 2 H), 7.37 (br s, 2 H), 7.20 (br d, J = 3.3 Hz, 1 H), 6.68-6.95 (m, 1 H), 6.19 (br d, J = 16.6 Hz, 1 H), 5.67-5.86 (m, 1 H), 4.36-5.03 (m, 2 H), 3.49-4.31 (m, 4 H), 2.66-2.84 (m, 1 H), 2.61 (br s, 3 H), |

TABLE 148-continued

Analytical Data for Method Table Examples

| Ex. # | LRMS: m/z (ESI, +ve ion): (M + H)+ | NMR |
|---|---|---|
| | | 2.41 (br s, 3 H), 1.90 (br s, 3 H), 1.32 (br d, J = 5.4 Hz, 3 H), 1.08-1.23 (m, 3 H), 1.02 (br d, J = 11.8 Hz, 3 H), 0.83 (br s, 3 H) |
| 129-4 | 646.2 | $^1$H NMR (400 MHz, DMSO-$d_6$) δ 9.11 (br d, J = 2.5 Hz, 1 H), 8.42-8.54 (m, 1 H), 8.37 (d, J = 5.0 Hz, 1 H), 7.31-7.81 (m, 2 H), 7.17 (d, J = 4.8 Hz, 1 H), 6.94-7.11 (m, 1 H), 6.72-6.93 (m, 1 H), 6.19 (br d, J = 16.8 Hz, 1 H), 5.67-5.83 (m, 1 H), 4.45-5.05 (m, 2 H), 3.44-4.26 (m, 4 H), 2.54-2.94 (m, 1 H), 2.01-2.24 (m, 2 H), 1.81-2.00 (m, 3 H), 1.25-1.37 (m, 3 H), 1.11-1.24 (m, 3 H), 0.99-1.11 (m, 3 H), 0.80-0.99 (m, 6 H) |
| 129-5 | 668.2 | $^1$H NMR (400 MHz, DMSO-$d_6$) δ 8.52 (s, 1 H), 8.40 (d, J = 4.8 Hz, 1 H), 7.48-7.60 (m, 2 H), 7.42 (br t, J = 7.5 Hz, 1 H), 7.35 (br d, J = 7.9 Hz, 1 H), 7.26 (br d, J = 7.7 Hz, 1 H), 7.18 (br d, J = 5.0 Hz, 1 H), 6.75-6.92 (m, 1 H), 6.19 (dd, J = 16.7, 2.2 Hz, 1 H), 5.75 (br d, J = 10.6 Hz, 1 H), 4.44-5.02 (m, 2 H), 3.75-4.29 (m, 4 H), 2.55-2.61 (m, 1 H), 1.96 (s, 3 H), 1.23-1.34 (m, 3 H), 1.00-1.15 (m, 6 H), 0.96 (br d, J = 6.4 Hz, 3 H) |
| 129-6 | 640.2 | $^1$H NMR (400 MHz, DMSO-$d_6$) δ 9.49 (br s, 1 H), 8.44 (s, 1 H), 8.39 (d, J = 5.0 Hz, 1 H), 7.58 (br d, J = 5.2 Hz, 1 H), 7.30-7.43 (m, 1 H), 7.08-7.24 (m, 3 H), 6.85 (td, J = 16.5, 10.6 Hz, 1 H), 6.20 (dd, J = 16.7, 2.0 Hz, 1 H), 5.68-5.83 (m, 1 H), 4.45-4.95 (m, 2 H), 3.79-4.23 (m, 4 H), 2.67 (br s, 1 H), 1.98 (s, 3 H), 1.64 (br d, J = 2.1 Hz, 1 H), 1.27-1.37 (m, 3 H), 1.12-1.26 (m, 3 H), 1.06 (d, J = 6.8 Hz, 3 H), 0.92 (d, J = 6.6 Hz, 3 H), 0.60-0.76 (m, 2 H), 0.54 (br s, 2 H) |
| 129-7 | 630.2 | $^1$H NMR (400 MHz, DMSO-$d_6$) δ 8.84 (s, 1 H), 8.42 (s, 1 H), 8.38 (d, J = 5.0 Hz, 1 H), 7.61 (br d, J = 8.1 Hz, 1 H), 7.34-7.43 (m, 1 H), 7.08-7.30 (m, 3 H), 6.72-6.99 (m, 1 H), 6.19 (br dd, J = 16.7, 2.0 Hz, 1 H), 5.69-5.82 (m, 1 H), 4.42-4.92 (m, 2 H), 3.72-4.27 (m, 4 H), 3.55 (s, 3 H), 2.70 (br dd, J = 13.8, 7.2 Hz, 1 H), 1.96 (s, 3 H), 1.32 (br t, J = 6.7 Hz, 3 H), 1.16-1.26 (m, 3 H), 1.06 (br d, J = 6.6 Hz, 3 H), 0.80-0.97 (m, 3 H) |
| 129-8 | 648.2 | $^1$H NMR (400 MHz, DMSO-$d_6$) δ 8.78-8.87 (m, 1H), 8.42-8.47 (m, 1 H), 8.36 (d, J = 4.8 Hz, 1 H), 7.35-7.48 (m, 2 H), 7.16 (d, J = 4.8 Hz, 1 H), 6.75-7.07 (m, 2 H), 6.19 (dd, J = 16.7, 2.2 Hz, 1 H), 5.69-5.83 (m, 1 H), 4.44-4.92 (m, 2 H), 3.76-4.27 (m, 4 H), 3.54 (s, 3 H), 2.59-2.70 (m, 1 H), 1.96 (s, 3 H), 1.30-1.37 (m, 3 H), 1.16-1.29 (m, 3 H), 1.01-1.12 (m, 3 H), 0.80-0.97 (m, 3 H) |
| 129-9 | 658.3 | $^1$H NMR (400 MHz, DMSO-$d_6$) δ 9.46 (br d, J = 6.0 Hz, 1 H), 8.48 (s, 1 H), 8.37 (d, J = 4.8 Hz, 1 H), 7.42 (br d, J = 1.5 Hz, 2 H), 7.17 (d, J = 4.8 Hz, 1 H), 6.98-7.11 (m, 1 H), 6.70-6.92 (m, 1 H), 6.20 (br d, J = 16.8 Hz, 1 H), 5.69-5.83 (m, 1 H), 4.40-5.03 (m, 2 H), 3.80-4.23 (m, 4 H), 2.55 (br d, J = 6.8 Hz, 1 H), 2.01 (s, 3 H), 1.51-1.61 (m, 1 H), 1.28-1.38 (m, 3 H), 1.14-1.23 (m, 3 H), 1.03 (br d, J = 6.6 Hz, 3 H), 0.79 (br d, J = 6.6 Hz, 3 H), 0.58-0.74 (m, 3 H), 0.45 (br d, J = 4.1 Hz, 1 H) |
| 129-10 | 668.2 | $^1$H NMR (400 MHz, DMSO-$d_6$) δ 10.29 (br s, 1 H), 8.52 (s, 1 H), 8.31-8.41 (m, 1 H), 7.48-7.60 (m, 1 H), 7.21-7.33 (m, 2 H), 7.11-7.19 (m, 1 H), 6.84 (td, J = 16.2, 10.5 Hz, 1 H), 5.94-6.43 (m, 2 H), 5.75 (br d, J = 10.4 Hz, 1 H), 4.42-5.03 (m, 2 H), 3.41-4.31 (m, 4 H), 2.52-2.58 (m, 1 H), 1.96 (s, 3 H), 1.27-1.41 (m, 3 H), 0.99-1.26 (m, 6 H), 0.80-0.96 (m, 3 H) |
| 129-11 | 650.2 | $^1$H NMR (400 MHz, DMSO-$d_6$) δ 10.24-10.54 (m, 1 H), 8.39 (d, J = 4.8 Hz, 2 H), 7.40-7.58 (m, 2 H), 7.28-7.38 (m, 1 H), 7.17 (br d, J = 4.6 Hz, 2 H), 6.73-6.94 (m, 1 H), 5.84-6.43 (m, 2 H), 5.75 (br dd, J = 10.4, 2.3 Hz, 1 H), 4.39-5.11 (m, 2 H), 3.66-4.26 (m, 4 H), 2.56-2.73 (m, 1 H), 1.96 (s, 3 H), 1.26-1.42 (m, 3 H), 1.07 (br d, J = 6.6 Hz, 6 H), 0.95 (br d, J = 6.2 Hz, 3 H) |
| 129-12 | 631.6 | $^1$H NMR (400 MHz, DMSO-$d_6$) δ 9.50 (br s, 1 H), 8.42-8.50 (m, 1 H), 8.39 (d, J = 4.8 Hz, 1 H), 7.26-7.41 (m, 2 H), 7.18 (br d, J = 4.8 Hz, 1 H), 6.95 (br d, J = 0.8 Hz, 1 H), 6.84 (td, J = 16.2, 10.6 Hz, 1 H), 6.19 (dd, J = 16.7, 2.2 Hz, 1 H), 5.75 (br dd, J = 10.4, 2.3 Hz, 1 H), 4.46-5.01 (m, 2 H), 3.41-4.23 (m, 4 H), 2.67 (br s, 1 H), 1.94 (br s, 3 H), 1.80 (br s, 3 H), 1.32 (br d, J = 6.6 Hz, 3 H), 1.10-1.25 (m, 3 H), 1.07 (br d, J = 6.6 Hz, 3 H), 0.96 (br d, J = 6.0 Hz, 3 H) |

TABLE 148-continued

Analytical Data for Method Table Examples

| Ex. # | LRMS: m/z (ESI, +ve ion): (M + H)+ | NMR |
|---|---|---|
| 129-13 | 612.2 | $^1$H NMR (400 MHz, DMSO-$d_6$) δ 8.42 (d, J = 5.0 Hz, 1 H), 8.33 (dd, J = 9.3, 2.5 Hz, 1 H), 7.25-7.34 (m, 1 H), 7.23 (d, J = 5.0 Hz, 1 H), 6.76-6.92 (m, 1 H), 6.57 (d, J = 8.5 Hz, 1 H), 6.52 (t, J = 8.9 Hz, 1 H), 6.19 (dd, J = 16.7, 2.2 Hz, 1 H), 5.72-5.81 (m, 1 H), 5.65 (br s, 1 H), 4.43-4.91 (m, 2 H), 4.16 (br t, J = 12.8 Hz, 1 H), 3.79-3.93 (m, 2 H), 3.71 (dd, J = 6.0, 2.1 Hz, 2 H), 3.51 (br dd, J = 13.6, 3.4 Hz, 1 H), 3.04 (t, J = 2.2 Hz, 1 H), 2.63-2.76 (m, 1 H), 1.96 (s, 3 H), 1.32 (t, J = 6.8 Hz, 3 H), 1.18-1.29 (m, 3 H), 1.06 (d J = 6.6 Hz, 3 H), 0.93 (d, J = 6.4 Hz, 3 H) |
| 132-1 | 623.2 | $^1$H NMR (400 MHz, DMSO-$d_6$) δ 9.96 (s, 1 H), 8.49 (d, J = 3.1 Hz, 1 H), 8.30 (d, J = 4.8 Hz, 1 H), 7.73 (d, J = 8.3 Hz, 1 H), 7.39 (ddd, J = 8.1, 6.2, 1.9 Hz, 1 H), 7.15-7.25 (m, 3 H), 7.12 (d, J = 4.8 Hz, 1 H), 6.78-6.95 (m, 2 H), 6.20 (dd, J = 16.6, 2.3 Hz, 1 H), 5.71-5.82 (m, 1 H), 4.89 (br s, 1 H), 4.46-4.84 (m, 1 H), 3.47-4.30 (m, 4 H), 2.70-2.80 (m, 1 H), 1.94 (s, 3 H), 1.32-1.41 (m, 3 H), 1.18-1.32 (m, 3 H), 1.06 (d, J = 6.6 Hz, 3 H), 0.92 (d, J = 6.6 Hz, 3 H) |
| 132-2 | 607.2 | $^1$H NMR (400 MHz, DMSO-$d_6$) δ 10.01 (br s, 1 H), 8.28-8.42 (m, 2 H), 7.74 (br d, J = 7.9 Hz, 1 H), 7.34-7.51 (m, 2 H), 7.25 (br s, 1 H), 7.11-7.21 (m, 2 H), 7.02 (br s, 1 H), 6.74-6.95 (m, 1 H), 6.20 (br d, J = 16.6 Hz, 1 H), 5.67-5.86 (m, 1 H), 4.85-4.97 (m, 1 H), 4.42-4.84 (m, 1 H), 3.49-4.28 (m, 4 H), 2.71-2.86 (m, 1 H), 1.96 (br s, 3 H), 1.35 (br s, 3 H), 1.19-1.31 (m, 3 H), 1.07 (br d, J = 6.0 Hz, 3 H), 0.94 (br d, J = 5.6 Hz, 3 H) |
| 141-1 | 632.2 | $^1$H NMR (400 MHz, CHLOROFORM-d) δ 8.49-8.56 (m, 1H), 8.09-8.17 (m, 1H), 7.35-7.47 (m, 2H), 7.30-7.35 (m, 1H), 7.14-7.22 (m, 1H), 6.96-7.04 (m, 1H), 6.52-6.72 (m, 1H), 6.34-6.47 (m, 1H), 5.75-5.85 (m, 1H), 5.03-5.19 (m, 1H), 4.33-4.55 (m, 1H), 3.88-4.12 (m, 2H), 3.67-3.82 (m, 1H), 3.35-3.47 (m, 1H), 3.00-3.12 (m, 1H), 2.67-2.82 (m, 1H), 2.52-2.64 (m, 1H), 2.30-2.41 (m, 2H), 2.21-2.29 (m, 2H), 1.46 (br d, J = 6.43 Hz, 4H), 1.28 (br s, 6H), 1.23 (br d, J = 6.63 Hz, 3H), 1.03 (br d, J = 6.63 Hz, 6H), 0.83 (br d, J = 3.73 Hz, 6H) |
| 141-2 | 684.2 | $^1$H NMR (400 MHz, CHLOROFORM-d) δ 8.50-8.59 (m, 1H), 8.13 (br s, 1H), 7.47-7.58 (m, 1H), 7.37 (d, J = 7.46 Hz, 1H), 7.33 (s, 1H), 7.14-7.21 (m, 1H), 6.95-7.05 (m, 1H), 6.51-6.72 (m, 1H), 6.35-6.47 (m, 1H), 5.76-5.86 (m, 1H), 4.95-5.21 (m, 1H), 4.32-4.54 (m, 1H), 3.90-4.12 (m, 2H), 3.69-3.86 (m, 1H), 3.38-3.55 (m, 1H), 3.01-3.15 (m, 1H), 2.78-2.92 (m, 1H), 2.67-2.75 (m, 1H), 2.57 (br d, J = 1.45 Hz, 1H), 2.20-2.38 (m, 2H), 1.55-1.65 (m, 3H), 1.47 (br d, J = 6.63 Hz, 7H), 1.31-1.37 (m, 2H), 1.17-1.29 (m, 6H), 1.00-1.07 (m, 6H), 0.86-0.92 (m, 4H) |
| 141-3 | 668.2 | $^1$H NMR (400 MHz, CHLOROFORM-d) δ 8.51-8.57 (m, 1H), 8.12 (br s, 1H), 7.35-7.41 (m, 1H), 7.34 (s, 2H), 7.14-7.22 (m, 1H), 6.96-7.02 (m, 1H), 6.53-6.72 (m, 1H), 6.35-6.47 (m, 1H), 5.76-5.87 (m, 1H), 5.00-5.19 (m, 1H), 4.32-4.57 (m, 1H), 3.85-4.12 (m, 2H), 3.68-3.78 (m, 1H), 3.23-3.42 (m, 2H), 2.68-2.85 (m, 1H), 2.51-2.63 (m, 1H), 2.31 (br d, J = 5.18 Hz, 3H), 1.61 (br d, J = 5.60 Hz, 3H), 1.46 (br d, J = 6.43 Hz, 3H), 1.31 (br s, 3H), 1.28 (br s, 6H), 1.23 (br d, J = 6.63 Hz, 3H), 1.04 (br d, J = 6.84 Hz, 6H) |
| 144-1 | 601.2 | $^1$H NMR (400 MHz, DMSO-$d_6$) δ 8.59-8.65 (m, 1 H), 8.36-8.44 (m, 1 H), 7.19 (d, J = 5.0 Hz, 1 H), 7.06 (q, J = 7.9 Hz, 1 H), 6.77-6.98 (m, 1 H), 6.41-6.49 (m, 1 H), 6.32 (br t, J = 8.3 Hz, 1 H), 6.23 (dd, J = 16.6, 1.7 Hz, 1 H), 5.81 (br d, J = 11.8 Hz, 1 H), 5.10-5.18 (m, 1 H), 5.05 (br s, 1 H), 4.83-5.01 (m, 1 H), 4.02-4.48 (m, 3 H), 3.45-4.00 (m, 3 H), 3.13-3.21 (m, 1 H), 2.98-3.13 (m, 1 H), 2.63-2.93 (m, 1 H), 1.81-2.02 (m, 3 H), 1.03-1.12 (m, 3 H), 0.86-1.01 (m, 3 H) |
| 144-2 | 526.1 | $^1$H NMR (400 MHz, DMSO-$d_6$) δ 8.66 (s, 1 H), 8.52 (d, J = 5.0 Hz, 1 H), 7.34 (br s, 1 H), 6.73-7.00 (m, 1 H), 6.22 (dd, J = 16.6, 1.9 Hz, 1 H), 5.73-5.89 (m, 1 H), 4.81-5.02 (m, 1 H), 4.26-4.41 (m, 2 H), 3.79-4.09 (m, 3 H), 3.57 (d, J = 11.0 Hz, 2 H), 2.97-3.07 (m, 1 H), 2.59-2.82 (m, 1 H), 1.91-2.04 (m, 3 H), 1.08 (dd, J = 6.6, 3.5 Hz, 3 H), 1.02 (dd, J = 6.6, 2.7 Hz, 3 H) |
| 144-2-1 | 526.0 | $^1$H NMR (400 MHz, DMSO-$d_6$) δ 8.65 (s, 1 H), 8.48 (d, J = 4.8 Hz, 1 H), 7.26 (d, J = 5.0 Hz, 1 H), 6.87 (br s, 1 H), 6.22 (dd, J = 16.7, 2.2 Hz, 1 H), 5.80 (br d, J = 12.0 Hz, 1 |

TABLE 148-continued

Analytical Data for Method Table Examples

| Ex. # | LRMS: m/z (ESI, +ve ion): (M + H)+ | NMR |
|---|---|---|
| | | H), 4.90 (br s, 1 H), 4.23-4.39 (m, 2 H), 3.46-4.10 (m, 4 H), 3.28 (br s, 1 H), 2.98-3.09 (m, 1 H), 2.65-2.77 (m, 1 H), 1.91 (s, 3 H), 1.06 (d, J = 6.6 Hz, 3 H), 1.01 (d, J = 6.6 Hz, 3 H) |
| 144-2-2 | 526.0 | $^1$H NMR (400 MHz, DMSO-$d_6$) δ 8.65 (s, 1 H), 8.49 (d, J = 4.8 Hz, 1 H), 7.26 (d, J = 4.8 Hz, 1 H), 6.73-6.98 (m, 1 H), 6.22 (dd, J = 16.7, 2.0 Hz, 1 H), 5.80 (br d, J = 10.8 Hz, 1 H), 4.82-5.00 (m, 1 H), 4.20-4.40 (m, 2 H), 3.71-4.16 (m, 2 H), 3.36-3.70 (m, 2 H), 3.20-3.29 (m, 1 H), 2.97-3.11 (m, 1 H), 2.54-2.60 (m, 1 H), 1.98 (s, 3 H), 1.05 (d, J = 6.6 Hz, 3 H), 1.00 (d, J = 6.6 Hz, 3 H) |
| 144-3 | 602.2 | $^1$H NMR (400 MHz, DMSO-$d_6$) δ 10.03-10.16 (m, 1 H), 8.59 (s, 1 H), 8.38 (d, J = 4.6 Hz, 1 H), 7.43-7.61 (m, 1 H), 7.20-7.27 (m, 1 H), 7.17 (br d, J = 4.6 Hz, 1 H), 6.77-6.99 (m, 1 H), 6.59-6.74 (m, 2 H), 6.22 (dd, J = 16.7, 1.6 Hz, 1 H), 5.81 (br d, J = 11.8 Hz, 1 H), 4.82-5.01 (m, 1 H), 4.17-4.57 (m, 3 H), 3.87-4.12 (m, 1 H), 3.46-3.82 (m, 2 H), 2.99-3.14 (m, 1 H), 2.59-2.86 (m, 1 H), 1.85-1.96 (m, 3 H), 1.06 (dd, J = 6.4, 3.5 Hz, 3 H), 0.92 (br d, J = 6.4 Hz, 3 H) |
| 145-1 | 523.3 | $^1$H NMR (400 MHz, DMSO-$d_6$) δ 8.49 (s, 1 H), 7.49-7.70 (m, 2 H), 7.33-7.46 (m, 2 H), 6.73-7.01 (m, 1 H), 6.20 (dd, J = 16.6. 2.1 Hz, 1 H), 5.79 (br d, J = 11.8 Hz, 1 H), 4.75-5.01 (m, 1 H), 4.03-4.37 (m, 5 H), 3.42-4.01 (m, 3 H), 2.90-3.20 (m, 2 H), 0.88 (s, 9 H) |
| 145-1-1 | 523.2 | $^1$H NMR (400 MHz, DMSO-$d_6$) δ 8.48 (s, 1 H), 7.50-7.68 (m, 2 H), 7.32-7.45 (m, 2 H), 6.85 (br d, J = 11.0 Hz, 1 H), 6.20 (dd, J = 16.6, 1.9 Hz, 1 H), 5.79 (br d, J = 11.0 Hz, 1 H), 4.75-5.00 (m, 1 H), 4.09-4.33 (m, 5 H), 3.37-3.99 (m, 3 H), 2.91-3.13 (m, 2 H), 0.88 (s, 9 H) |
| 145-1-2 | 523.2 | $^1$H NMR (400 MHz, DMSO-$d_6$) δ 8.49 (s, 1 H), 7.52-7.68 (m, 2 H), 7.35-7.46 (m, 2 H), 6.74-6.95 (m, 1 H), 6.20 (dd, J = 16.7, 2.2 Hz, 1 H), 5.74-5.86 (m, 1 H), 4.76-5.02 (m, 1 H), 3.99-4.41 (m, 5 H), 3.36-3.91 (m, 3 H), 2.88-3.12 (m, 2 H), 0.88 (s, 9 H) |
| 145-2 | 586.3 | $^1$H NMR (400 MHz, DMSO-$d_6$) δ 8.61-8.70 (m, 1 H), 8.50 (br d, J = 4.8 Hz, 1 H), 7.48-7.58 (m, 1 H), 7.42 (br s, 1 H), 7.17-7.36 (m, 3 H), 6.76-7.01 (m, 1 H), 6.23 (dd, J = 16.5, 2.0 Hz, 1 H), 5.81 (br d, J = 12.0 Hz, 1 H), 4.84-5.03 (m, 1 H), 4.26-4.50 (m, 3 H), 3.71-4.17 (m, 3 H), 3.57 (d, J = 11.2 Hz, 3 H), 2.02 (br d, J = 19.5 Hz, 3 H), 1.12 (br d, J = 6.6 Hz, 3 H), 0.95-1.02 (m, 3 H) |
| 145-2-1 | 586.1 | $^1$H NMR (400 MHz, DMSO-$d_6$) δ 8.63 (s, 1 H), 8.40 (d, J = 5.0 Hz, 1 H), 7.45-7.59 (m, 1 H), 7.14-7.35 (m, 4 H), 6.73-7.01 (m, 1 H), 6.23 (dd, J = 16.6, 2.1 Hz, 1 H), 5.71-5.87 (m, 1 H), 4.94 (br d, J = 2.7 Hz, 1 H), 4.28-4.48 (m, 2 H), 3.47-4.15 (m, 4 H), 3.07 (br d, J = 8.1 Hz, 2 H), 2.70-2.82 (m, 1 H), 1.91 (s, 3 H), 1.06 (d, J = 6.8 Hz, 3 H), 0.93 (d, J = 6.8 Hz, 3 H) |
| 145-2-2 | 586.3 | $^1$H NMR (400 MHz, DMSO-$d_6$) δ 8.63 (s, 1 H), 8.39 (d, J = 4.8 Hz, 1 H), 7.46-7.59 (m, 1 H), 7.14-7.36 (m, 4 H), 6.75-7.01 (m, 1 H), 6.23 (dd, J = 16.6, 1.9 Hz, 1 H), 5.81 (br d, J = 10.4 Hz, 1 H), 4.82-5.01 (m, 1 H), 4.28-4.47 (m, 2 H), 3.43-4.18 (m, 4 H), 3.00-3.17 (m, 2 H), 2.61-2.73 (m, 1 H), 1.96 (s, 3 H), 1.06 (br d, J = 6.6 Hz, 3 H), 0.95 (br d, J = 6.6 Hz, 3 H) |
| 145-3 | 523.2 | $^1$H NMR (400 MHz, DMSO-$d_6$) δ 8.38 (s, 1 H), 7.51-7.67 (m, 2 H), 7.34-7.46 (m, 2 H), 6.70-6.91 (m, 1 H), 6.18 (dd, J = 16.7, 2.2 Hz, 1 H), 5.77 (dd, J = 10.5, 2.0 Hz, 1 H), 5.07-5.23 (m, 1 H), 4.32-4.48 (m, 1 H), 4.20-4.28 (m, 1 H), 4.13 (br d, J = 12.6 Hz, 3 H), 3.56-3.90 (m, 2 H), 3.33-3.44 (m, 1 H), 3.05-3.20 (m, 1 H), 2.79-3.02 (m, 1 H), 0.88 (s, 9 H) |
| 146-1 | 594.2 | $^1$H NMR (400 MHz, DMSO-$d_6$) δ 8.48 (br d, J = 8.7 Hz, 1 H), 7.22-7.37 (m, 5 H), 7.05-7.17 (m, 2 H), 6.76-6.93 (m, 1 H), 6.19 (dd, J = 16.7, 2.2 Hz, 1 H), 5.72-5.80 (m, 1 H), 4.95 (br s, 1 H), 4.84 (br d, J = 4.6 Hz, 1 H), 4.40-4.77 (m, 1 H), 3.56-4.18 (m, 4 H), 3.23-3.29 (m, 1 H), 3.03 (br dd, J = 15.4, 3.2 Hz, 1 H), 2.83-2.93 (m, 1 H), 2.74-2.82 (m, 1 H), 2.64-2.73 (m, 1 H), 2.54-2.60 (m, 1H), 1.27 (br dd, J = 18.1, 6.5 Hz, 3 H), 1.05-1.21 (m, 6 H), 0.94 (d, J = 6.8 Hz, 3 H) |
| 146-1-1 | 594.2 | $^1$H NMR (400 MHz, CHLOROFORM-d) δ 7.91-8.05 (m, 1 H), 7.17-7.35 (m, 5 H), 7.03-7.14 (m, 2 H), |

TABLE 148-continued

Analytical Data for Method Table Examples

| Ex. # | LRMS: m/z (ESI, +ve ion): (M + H)+ | NMR |
|---|---|---|
| | | 6.52-6.71 (m, 1 H), 6.33-6.47 (m, 1 H), 5.75-5.87 (m, 1 H), 5.06-5.38 (m, 1 H), 5.02 (br d, J = 7.5 Hz, 1 H), 4.80-4.91 (m, 1 H), 4.31-4.50 (m, 1 H), 3.83-4.14 (m, 3 H), 3.60-3.73 (m, 1 H), 3.18-3.32 (m, 1 H), 3.05-3.16 (m, 1 H), 2.88-3.05 (m, 2 H), 2.76 (dt, J = 13.6, 6.7 Hz, 1 H), 1.42 (br d, J = 6.6 Hz, 2 H), 1.36 (br t, J = 6.2 Hz, 2 H), 1.20 (d, J = 6.8 Hz, 5 H), 1.00 (d, J = 6.8 Hz, 3 H) |
| 146-1-2 | 594.2 | $^1$H NMR (400 MHz, CHLOROFORM-d) δ 7.90-8.01 (m, 1 H), 7.53 (br d, J = 6.2 Hz, 1 H), 7.13-7.38 (m, 6 H), 6.49-6.68 (m, 1 H), 6.29-6.47 (m, 1 H), 5.70-5.82 (m, 1 H), 5.33 (br s, 1 H), 5.02-5.22 (m, 2 H), 4.91-5.02 (m, 1 H), 4.25-4.50 (m, 1 H), 3.83-4.14 (m, 3 H), 3.57-3.70 (m, 1 H), 3.20 (br d, J = 18.2 Hz, 1 H), 2.77-2.98 (m, 2 H), 2.59-2.75 (m, 1 H), 1.30-1.44 (m, 4 H), 1.12-1.26 (m, 5 H), 0.94 (d, J = 6.8 Hz, 3 H) |
| 146-2 | 594.2 | $^1$H NMR (400 MHz, DMSO-d$_6$) δ 8.21 (d, J = 14.3 Hz, 1 H), 7.22-7.36 (m, 5 H), 7.10 (dd, J = 6.2, 2.7 Hz, 1 H), 7.04 (d, J = 7.5 Hz, 1 H), 6.74-6.92 (m, 1 H), 6.19 (dd, J = 16.6, 2.3 Hz, 1 H), 5.70-5.82 (m, 1 H), 4.86 (br d, J = 3.9 Hz, 1 H), 4.77-4.80 (m, 1 H), 4.72 (br d, J = 19.3 Hz, 1 H), 4.40-4.58 (m, 1 H), 4.14-4.25 (m, 1 H), 3.55-3.91 (m, 2 H), 3.26 (br dd, J = 14.4, 3.4 Hz, 1 H), 3.01 (br dd, J = 15.9, 3.2 Hz, 1 H), 2.85-2.95 (m, 1 H), 2.79 (dq, J = 12.6, 6.5 Hz, 1 H), 2.62-2.71 (m, 1 H), 2.51-2.57 (m, 1 H), 1.42 (br t, J = 5.9 Hz, 3 H), 1.34 (br dd, J = 10.9, 6.7 Hz, 3 H), 1.08 (d, J = 6.8 Hz, 3 H), 0.96 (br dd, J = 6.7, 3.8 Hz, 3 H) |
| 146-2-1 | 594.2 | $^1$H NMR (400 MHz, CHLOROFORM-d) δ 8.03-8.18 (m, 1 H), 7.23-7.34 (m, 4 H), 7.19 (d, J = 7.5 Hz, 1 H), 7.09 (dd, J = 7.2, 1.6 Hz, 1 H), 7.03 (br d, J = 7.5 Hz, 1 H), 6.52-6.74 (m, 1 H), 6.31-6.46 (m, 1 H), 5.81 (br t, J = 9.2 Hz, 1 H), 4.89-5.21 (m, 2 H), 4.69-4.87 (m, 2 H), 3.95-4.66 (m, 2 H), 3.56-3.87 (m, 2 H), 3.24 (br dd, J = 15.3, 2.5 Hz, 1 H), 2.94-3.12 (m, 2 H), 2.76-2.92 (m, 2 H), 1.46-1.57 (m, 6 H), 1.22 (br d, J = 6.8 Hz, 3 H), 0.97-1.05 (m, 3 H) |
| 146-2-2 | 594.2 | $^1$H NMR (400 MHz, CHLOROFORM-d) δ 7.98-8.13 (m, 1 H), 7.45-7.61 (m, 1 H), 7.13-7.39 (m, 6 H), 6.48-6.71 (m, 1 H), 6.30-6.45 (m, 1 H), 5.79 (br t, J = 9.4 Hz, 1 H), 4.98-5.24 (m, 2 H), 4.70-4.96 (m, 2 H), 4.18-4.57 (m, 2 H), 3.50-3.79 (m, 3 H), 3.22 (br d, J = 14.9 Hz, 1 H), 2.79-2.95 (m, 2 H), 2.56-2.76 (m, 1 H), 1.42-1.64 (m, 6 H), 1.23 (br d, J = 6.8 Hz, 3 H), 0.99 (br t, J = 6.2 Hz, 3 H) |
| 146-3 | 552.2 | $^1$H NMR (400 MHz, DMSO-d$_6$) δ 8.10-8.30 (m, 1 H), 7.00-7.58 (m, 8 H), 6.75-6.96 (m, 1 H), 6.03-6.29 (m, 2 H), 5.75 (br d, J = 8.9 Hz, 2 H), 4.81-4.88 (m, 1 H), 4.40-4.78 (m, 2 H), 3.44-4.06 (m, 4 H), 2.71-3.13 (m, 2 H), 2.71-2.72 (m, 1 H), 1.31-1.48 (m, 3 H), 1.09-1.30 (m, 3H) |
| 146-3-1 | 552.2 | $^1$H NMR (400 MHz, CHLOROFORM-d) δ 7.90-7.99 (m, 1 H), 7.24-7.32 (m, 6 H), 7.17 (br d, J = 7.5 Hz, 1 H), 7.01-7.09 (m, 1 H), 6.48-6.67 (m, 1 H), 6.28-6.42 (m, 1 H), 5.71-5.81 (m, 1 H), 4.78-5.38 (m, 4 H), 3.49-4.10 (m, 4 H), 3.24 (br d, J = 13.3 Hz, 1 H), 3.03-3.16 (m, 1 H), 2.89-3.03 (m, 2 H), 1.30-1.39 (m, 4 H), 1.18 (br d, J = 6.8 Hz, 2 H) |
| 146-3-2 | 552.2 | $^1$H NMR (400 MHz, CHLOROFORM-d) δ 8.04 (d, J = 19.3 Hz, 1 H), 7.26-7.32 (m, 4 H), 7.21-7.24 (m, 2 H), 7.18 (d, J = 7.5 Hz, 1 H), 7.04 (dd, J = 7.3, 1.0 Hz, 1 H), 6.49-6.70 (m, 1 H), 6.32-6.44 (m, 1 H), 5.78 (br t, J = 8.9 Hz, 1 H), 4.61-5.16 (m, 4 H), 4.24-4.54 (m, 1 H), 3.72 (br d, J = 1.7 Hz, 1 H), 3.50-3.69 (m, 1 H), 3.17-3.30 (m, 1 H), 3.05-3.15 (m, 1 H), 2.90-3.04 (m, 2 H), 1.60 (br d, J = 6.6 Hz, 1 H), 1.46-1.55 (m, 6 H) |
| 146-3-3 | 552.2 | $^1$H NMR (400 MHz, CHLOROFORM-d) δ 7.91-8.03 (m, 1 H), 7.48 (br d, J = 7.3 Hz, 2 H), 7.24-7.38 (m, 4 H), 7.05-7.22 (m, 2 H), 6.47-6.67 (m, 1 H), 6.30-6.43 (m, 1 H), 5.70-5.82 (m, 1 H), 5.32 (br s, 1 H), 4.91-5.25 (m, 2 H), 4.26-4.47 (m, 1 H), 3.35-4.11 (m, 5 H), 3.19 (br d, J = 16.8 Hz, 1 H), 2.91-3.05 (m, 1 H), 2.75 (br d, J = 14.3 Hz, 1 H), 1.31-1.38 (m, 3 H), 1.13-1.26 (m, 3 H) |
| 146-3-4 | 552.2 | $^1$H NMR (400 MHz, CHLOROFORM-d) δ 7.98-8.13 (m, 1 H), 7.43-7.52 (m, 2 H), 7.26-7.38 (m, 4 H), 7.14-7.22 (m, 2 H), 6.48-6.69 (m, 1 H), 6.31-6.44 (m, 1 H), |

TABLE 148-continued

Analytical Data for Method Table Examples

| Ex. # | LRMS: m/z (ESI, +ve ion): (M + H)+ | NMR |
|---|---|---|
| | | 5.78 (br t, J = 9.1 Hz, 1 H), 5.07-5.29 (m, 2 H), 4.76-4.92 (m, 1 H), 4.44-4.76 (m, 1 H), 4.27-4.41 (m, 1 H), 3.71 (br s, 1 H), 3.50-3.68 (m, 2 H), 3.20 (br d, J = 17.0 Hz, 1 H), 2.90-3.07 (m, 1 H), 2.73 (br dd, J = 13.8, 2.0 Hz, 1 H), 1.60 (br d, J = 6.6 Hz, 2 H), 1.46-1.55 (m, 5 H) |
| 146-4 | 568.3 | $^1$H NMR (400 MHz, CHLOROFORM-d) δ 7.89-8.04 (m, 1H), 7.25-7.41 (m, 4H), 7.17 (br s, 1H), 6.99-7.13 (m, 3H), 6.26-6.65 (m, 2H), 5.70-5.81 (m, 1H), 5.37-5.54 (m, 1H), 4.73-5.11 (m, 3H), 4.27-4.46 (m, 2H), 3.59-4.24 (m, 4H), 2.92-3.24 (m, 2H), 1.32-1.46 (m, 6H) |

Section 2—Individual Examples

Example 150

1-((2R,5S)-4-(6-Chloro-7-(2-fluorophenyl)-2-imino-1-neopentyl-1,2-dihydropyrido[2,3-d]pyrimidin-4-yl)-2,5-dimethylpiperazin-1-yl)prop-2-en-1-one

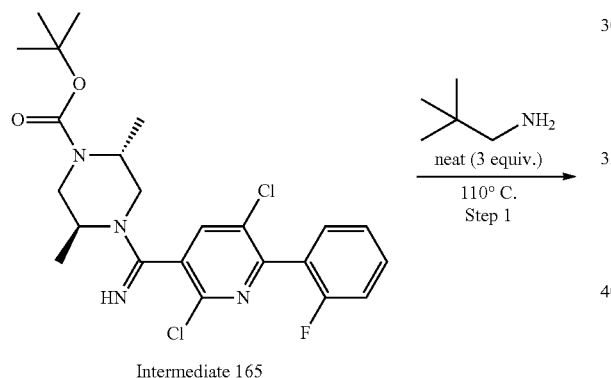

Intermediate 165

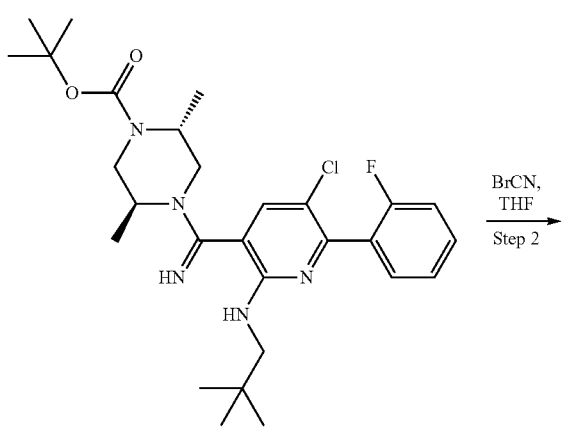

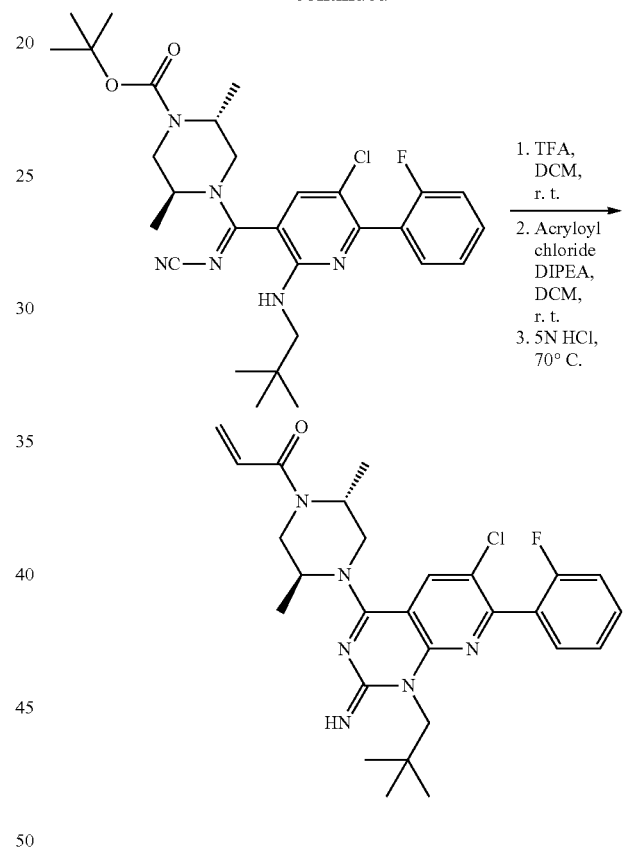

Step 1: tert-Butyl (2R,5S)-4-((5-chloro-6-(2-fluorophenyl)-2-(neopentylamino)pyridin-3-yl)(imino)methyl)-2,5-dimethylpiperazine-1-carboxylate A mixture of tert-butyl (2R,5S)-4-((2,5-dichloro-6-(2-fluorophenyl)pyridin-3-yl)(imino)methyl)-2,5-dimethylpiperazine-1-carboxylate (Intermediate 165, 1.30 g, 2.70 mmol) and neopentylamine (1.27 mL, 10.80 mmol) was heated at 110° C. for 3 days. The reaction mixture was purified on silica gel chromatography using 0-5% MeOH in DCM to afford tert-butyl (2R,5S)-4-((5-chloro-6-(2-fluorophenyl)-2-(neopentylamino)pyridin-3-yl)(imino)methyl)-2,5-dimethylpiperazine-1-carboxylate (1.10 g, 2.07 mmol, 77.0% yield). m/z (ESI, +ve ion): 532.3 (M+H)$^+$.

Step 2: tert-Butyl (2R,5S)-4-((E)-(5-chloro-6-(2-fluorophenyl)-2-(neopentylamino)pyridin-3-yl)(cyanoimino)methyl)-2,5-dimethylpiperazine-1-carboxylate To a solution of tert-butyl (2R,5S)-4-((5-chloro-6-(2-fluorophenyl)-2-(neopentylamino)pyridin-3-yl)(imino)methyl)-2,5-dimethylpiperazine-1-carboxylate (0.600 g, 1.128 mmol) and triethylamine (0.792 mL, 5.64 mmol) in THF (3 mL) at r.t. was added cyanogen bromide solution (1.503 mL, 4.51 mmol) dropwise. The reaction mixture was stirred at r.t. for 30 min. The reaction was diluted with water and extracted with EtOAc (3×). The combined organics were dried (Na$_2$SO$_4$) and concentrated to afford crude tert-butyl (2R,5S)-4-((E)-(5-chloro-6-(2-fluorophenyl)-2-(neopentylamino)pyridin-3-yl)(cyanoimino)methyl)-2,5-dimethylpiperazine-1-carboxylate (0.170 g, 0.305 mmol, 27.1% yield). The crude was used in the next step without further purification. m/z (ESI, +ve ion): 557.3 (M+H)$^+$.

Step 3: 1-((2R,5S)-4-(6-Chloro-7-(2-fluorophenyl)-2-imino-1-neopentyl-1,2-dihydropyrido[2,3-d]pyrimidin-4-yl)-2,5-dimethylpiperazin-1-yl)prop-2-en-1-one TFA (0.803 mL, 10.77 mmol) was added to a solution of tert-butyl (2R,5S)-4-((E)-(5-chloro-6-(2-fluorophenyl)-2-(neopentylamino)pyridin-3-yl)(cyanoimino)methyl)-2,5-dimethylpiperazine-1-carboxylate (0.30 g, 0.538 mmol) in dichloromethane (5 mL). The reaction was stirred at rt for 1 hour and concentrated under reduced pressure. The residue was suspended in DCM (5 mL), cooled to 0° C., and treated with TEA (0.078 mL, 0.538 mmol) followed by acryloyl chloride (0.044 mL, 0.538 mmol). The reaction was warmed to r.t. and stirred for 10 min. The mixture was quenched with sat'd aqueous NaHCO$_3$ and extracted with DCM (2×). The combined organic layers were concentrated and the residue purified on silica gel using 0-100% EtOAc/EtOH (3:1) in heptane to afford the intermediate N-((E)-((2S,5R)-4-acryloyl-2,5-dimethylpiperazin-1-yl)(5-chloro-6-(2-fluorophenyl)-2-(neopentylamino)pyridin-3-yl)methylene)cyanamide (0.160 g, 0.313 mmol, 58.1% yield). To this intermediate was added MeOH (4 mL) and 5N HCl (1.077 mL, 5.38 mmol) and reaction stirred at 70° C. for 1 hour. The reaction was cool to r.t., pH adjusted to 10 with 2N NaOH solution and extracted with EtOAc (2×). The organic was dried and the crude product was purified with ISCO reverse phase hplc eluting with 10-70% CH3CN (0.1% TFA) in water (0.1% TFA) to afford 1-((2R,5S)-4-(6-chloro-7-(2-fluorophenyl)-2-imino-1-neopentyl-1,2-dihydropyrido[2,3-d]pyrimidin-4-yl)-2,5-dimethylpiperazin-1-yl)prop-2-en-1-one (0.102 g, 0.200 mmol, 37.1% yield). m/z (ESI, +ve ion): 511.3 (M+H)$^+$. $^1$H NMR (400 MHz, DICHLOROMETHANE-d$_2$) δ 7.72 (s, 1H), 7.32-7.51 (m, 2H), 7.22 (t, J=7.12 Hz, 1H), 7.12 (t, J=9.13 Hz, 1H), 6.40-6.63 (m, 1H), 6.11-6.28 (m, 1H), 5.63 (br d, J=9.12 Hz, 1H), 5.25-5.35 (m, 1H), 4.80 (br s, 1H), 4.50 (br s, 1H), 4.32 (s, 2H), 4.12-4.24 (m, 1H), 3.50-3.78 (m, 3H), 1.11-1.27 (m, 6H), 0.84-0.94 (m, 9H). $^{19}$F NMR (376 MHz, DICHLOROMETHANE-d$_2$) δ −112.65 (s, 1F).

Example 151

1-((2R,5S)-4-((Z)-6-Chloro-7-(2-fluorophenyl)-2-(methylimino)-1-neopentyl-1,2-dihydropyrido[2,3-d]pyrimidin-4-yl)-2,5-dimethylpiperazin-1-yl)prop-2-en-1-one 2,2,2-trifluoroacetate

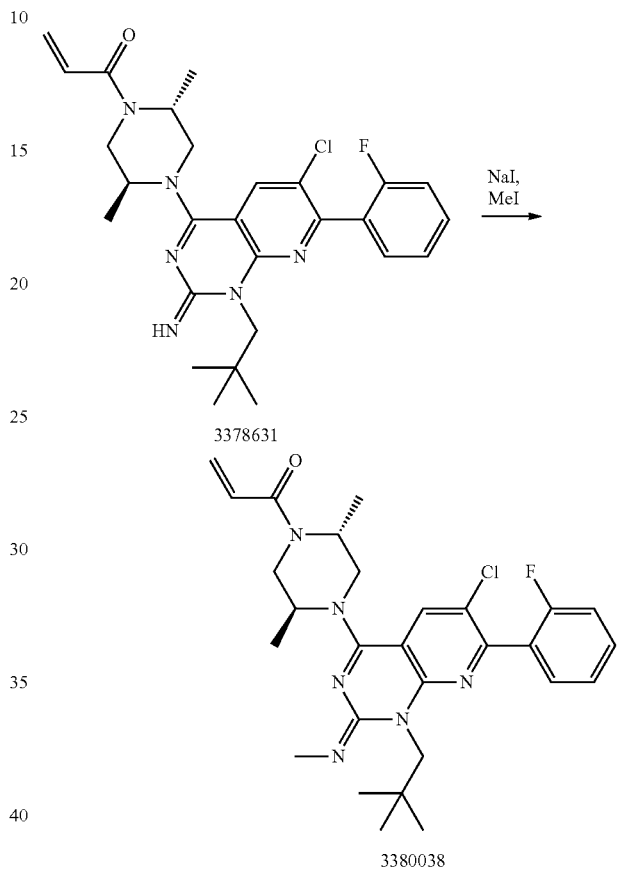

To a solution of 1-((2R,5S)-4-(6-chloro-7-(2-fluorophenyl)-2-imino-1-neopentyl-1,2-dihydropyrido[2,3-d]pyrimidin-4-yl)-2,5-dimethylpiperazin-1-yl)prop-2-en-1-one, Example 150, (0.050 g, 0.098 mmol) in THF (4 mL) was added sodium hydride (0.012 ml, 0.294 mmol). After evolution of hydrogen gas, iodomethane (0.056 ml, 0.391 mmol) was added and the reaction stirred at r.t. for 1 hour and at 50° C. for 4 hours. The reaction was cooled, diluted with water and extracted with EtOAc (3×). The organic was concentrated and the residue purified by a reverse phase HPLC eluting with 10-70% CH3CN (0.1% TFA) in water (0.1% TFA) to afford 1-((2R,5S)-4-((Z)-6-chloro-7-(2-fluorophenyl)-2-(methylimino)-1-neopentyl-1,2-dihydropyrido[2,3-d]pyrimidin-4-yl)-2,5-dimethylpiperazin-1-yl)prop-2-en-1-one 2,2,2-trifluoroacetate, as TFA salt. m/z (ESI, +ve ion): 525.4 (M+H)$^+$. $^1$H NMR (400 MHz, CHLOROFORM-d) δ 10.18-10.34 (m, 1H), 8.09 (s, 1H), 7.50-7.60 (m, 2H), 7.35 (t, J=7.17 Hz, 1H), 7.21-7.25 (m, 1H), 6.49-6.67 (m, 1H), 6.37-6.47 (m, 1H), 5.80-5.88 (m, 1H), 5.53-5.75 (m, 1H), 4.92-5.17 (m, 2H), 4.30-4.59 (m, 2H), 3.63-3.85 (m, 2H), 3.16 (br s, 3H), 1.50-1.71 (m, 3H), 1.12-1.40 (m, 3H), 0.93 (s, 9H). $^{19}$F NMR (376 MHz, CHLOROFORM-d) δ −112.23 (s, 1F).

Example 152
4-((2S,5R)-4-Acryloyl-2,5-dimethylpiperazin-1-yl)-1-(2-isopropylphenyl)-7-phenyl-5,6,7,8-tetrahydropyrido[3,4-d]pyrimidin-2(1H)-one
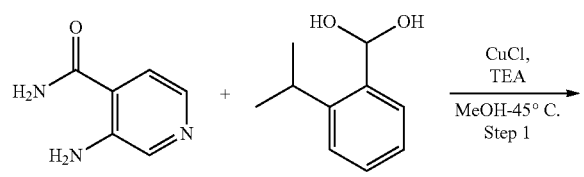
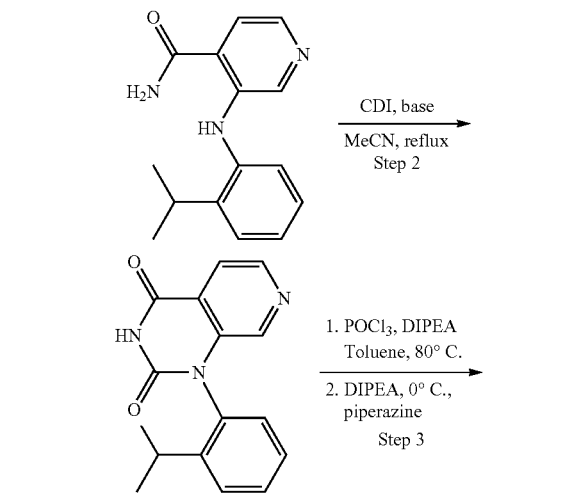
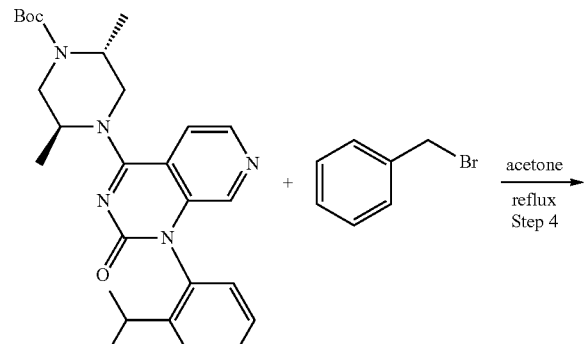
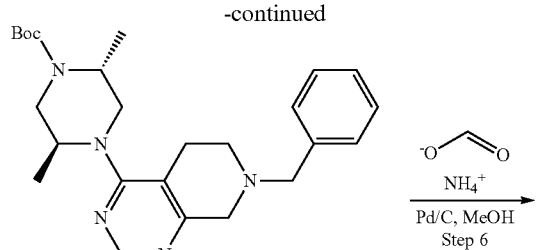
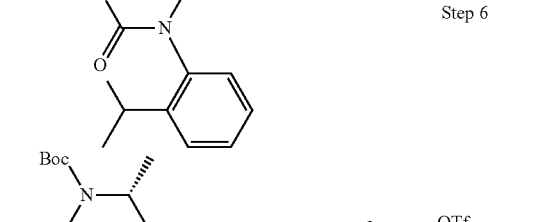
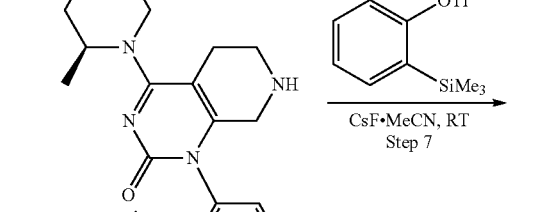
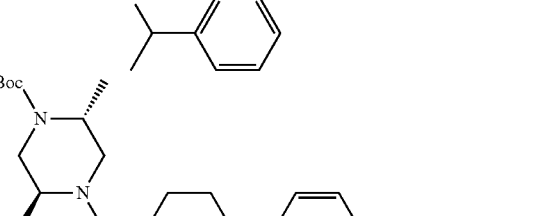
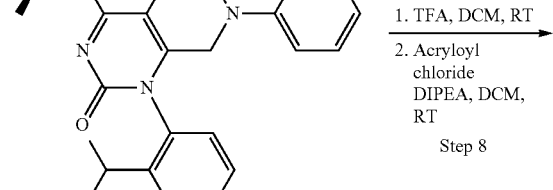
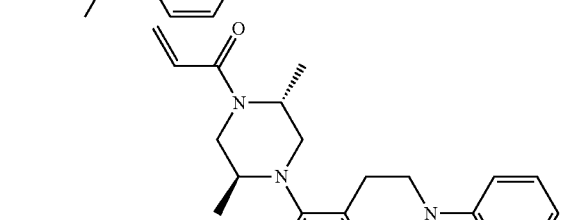
mixture of Atropisomers
Step 1: 3-((2-Isopropylphenyl)amino)isonicotinamide
A mixture of [2-(1-methylethyl)phenyl]-boronic acid (8.97 g, 54.7 mmol), [2-(1-methylethyl)phenyl]-boronic acid (8.97 g, 54.7 mmol), copper chloride (0.541 g, 5.47 mmol) and TEA (2.54 ml, 18.23 mmol) was purged with $N_2$ followed by the addition of MeOH (100 mL) and the resulting mixture was stirred at r.t. overnight. The reaction was quenched with a 9:1 sat. NH$_4$Cl/NH$_4$OH, and extracted with DCM. The combined organics were dried over Na2SO4, filtered, concentrated and purified by chromatography on silica gel using 0-5% MeOH in DCM to afford 3-((2-isopropylphenyl)amino)isonicotinamide (0.97 g, 3.80 mmol, 10.42% yield) as a yellow solid, m/z (ESI, +ve ion): 256 (M+H)$^+$. $^1$H NMR (400 MHz, DMSO-d$_6$) δ 9.65 (s, 1H), 8.32-8.38 (m, 1H), 8.20 (s, 1H), 7.96 (d, J=5.2 Hz, 1H), 7.78 (br s, 1H), 7.60 (d, J=5.2 Hz, 1H), 7.39 (dd, J=7.6, 1.6 Hz, 1H), 7.28-7.32 (m, 1H), 7.15-7.25 (m, 2H), 3.04-3.19 (m, 1H), 1.19 (d, J=6.8 Hz, 6H).

Step 2: 1-(2-Isopropylphenyl)pyrido[3,4-d]pyrimidine-2,4(1H,3H)-dione

A mixture of 3-((2-isopropylphenyl)amino)isonicotinamide (1.51 g, 5.91 mmol), pyridine (1.435 ml, 17.74 mmol) and CDI (2.88 g, 17.74 mmol) in MeCN (100 mL) was heated at 85° C. overnight. The mixture was quenched with sat. NaHCO$_3$, and extracted with EtOAc. The combined organics were dried over Na$_2$SO$_4$, filtered, concentrated and purified by chromatography on silica gel using 0-50% EtOAc in heptane to afford 1-(2-isopropylphenyl)pyrido[3,4-d]pyrimidine-2,4(1H,3H)-dione (1.3 g, 4.62 mmol, 78% yield) as a white solid. m/z (ESI, +ve ion): 281.8 (M+H)$^+$. $^1$H NMR (400 MHz, DMSO-d$_6$) δ 12.03 (s, 1H), 8.48 (d, J=5.2 Hz, 1H), 7.92 (d, J=5.0 Hz, 1H), 7.70 (s, 1H), 7.54-7.66 (m, 2H), 7.42-7.47 (m, 1H), 7.32-7.41 (m, 1H), 2.71-2.85 (m, 1H), 1.13 (d, J=6.8 Hz, 3H), 1.05 (d, J=6.8 Hz, 3H).

Step 3: tert-Butyl (2R,5S)-4-(1-(2-isopropylphenyl)-2-oxo-1,2-dihydropyrido[3,4-d]pyrimidin-4-yl)-2,5-dimethylpiperazine-1-carboxylate A suspension of 1-(2-isopropylphenyl)pyrido[3,4-d]pyrimidine-2,4(1H,3H)-dione (0.186 g, 0.661 mmol) in toluene (3 mL) was added 1,1'-dimethyltriethylamine (1.155 mL, 6.61 mmol) and phosphorous oxychloride (0.308 mL, 3.31 mmol) and the resulting mixture was heated at 80° C. After 5 min, the mixture went into solution and the heating continued for 30 min. LCMS showed complete conversion to desired intermediate. The reaction mixture was cooled to 0° C. and 10 equiv DIEA was added followed by (2R,5S)-tert-butyl 2,5-dimethylpiperazine-1-carboxylate (0.213 mL, 0.992 mmol). This mixture was stirred with warming to r.t. over 1 h at which time LCMS showed conversion to desired product. The mixture was poured into cold satd. NaHCO$_3$ solution and stirred vigorously for 10 min. The mixture was extracted with EtOAc, the combined organics were dried over Na$_2$SO$_4$, filtered, concentrated and purified by chromatography on silica gel using 0-40% EtOAc in heptane to afford tert-butyl (2R,5S)-4-(1-(2-isopropylphenyl)-2-oxo-1,2-dihydropyrido[3,4-d]pyrimidin-4-yl)-2,5-dimethylpiperazine-1-carboxylate (0.281 g, 0.588 mmol, 89% yield) as a light yellow foam. m/z (ESI, +ve ion): 477.8 (M+H)$^+$. $^1$H NMR (400 MHz, DMSO-d$_6$) δ 8.39 (dd, J=5.4, 2.9 Hz, 1H), 7.72-7.80 (m, 2H), 7.50-7.65 (m, 2H), 7.38-7.47 (m, 1H), 7.21-7.31 (m, 1H), 4.72-4.85 (m, 1H), 4.23-4.43 (m, 1H), 4.00-4.14 (m, 2H), 3.67-3.81 (m, 2H), 3.40-3.60 (m, 1H), 1.45 (s, 9H), 1.31 (dd, J=9.1, 6.6 Hz, 3H), 1.15-1.21 (m, 3H), 1.11 (dd, J=6.6, 4.8 Hz, 3H), 1.00 (dd, J=6.8, 4.8 Hz, 3H).

Step 4: 7-Benzyl-4-((2S,5R)-4-(tert-butoxycarbonyl)-2,5-dimethylpiperazin-1-yl)-1-(2-isopropylphenyl)-2-oxo-1,2-dihydropyrido[3,4-d]pyrimidin-7-ium A mixture of tert-butyl (2R,5S)-4-(1-(2-isopropylphenyl)-2-oxo-1,2-dihydropyrido[3,4-d]pyrimidin-4-yl)-2,5-dimethylpiperazine-1-carboxylate (0.36 g, 0.754 mmol) and (bromomethyl)benzene (0.193 mL, 1.131 mmol) in acetone (20 mL) was heated to reflux for 1 h. Some product was observed, mostly starting material. More (bromomethyl)benzene (0.193 mL, 1.131 mmol) was added and the resulting mixture was heated to reflux overnight. The mixture was brought to r.t., concentrated and purified by chromatography on a small amount of silica gel using 0-10% MeOH in DCM to afford 7-benzyl-4-((2S,5R)-4-(tert-butoxycarbonyl)-2,5-dimethylpiperazin-1-yl)-1-(2-isopropylphenyl)-2-oxo-1,2-dihydropyrido[3,4-d]pyrimidin-7-ium (0.401 g, 0.705 mmol, 94% yield) as a yellow solid. m/z (ESI, +ve ion): 567.8 (M+H)$^+$. $^1$H NMR (400 MHz, DMSO-d$_6$) δ 8.84 (br d, J=6.8 Hz, 1H), 8.30-8.40 (m, 2H), 7.56-7.65 (m, 2H), 7.34-7.48 (m, 6H), 7.25 (d, J=8.1 Hz, 1H), 5.87-5.90 (m, 2H), 4.66-4.76 (m, 1H), 4.24-4.46 (m, 1H), 4.01-4.15 (m, 1H), 3.66-3.87 (m, 2H), 3.41-3.61 (m, 1H), 2.58-2.66 (m, 1H), 1.45 (s, 9H), 1.34 (t, J=5.5 Hz, 3H), 1.18 (dd, J=14.5, 6.8 Hz, 3H), 1.08 (d, J=6.8 Hz, 3H), 0.95 (dd, J=10.8, 6.8 Hz, 3H).

Step 5: tert-Butyl (2R,5S)-4-(7-benzyl-1-(2-isopropylphenyl)-2-oxo-1,2,5,6,7,8-hexahydropyrido[3,4-d]pyrimidin-4-yl)-2,5-dimethylpiperazine-1-carboxylate 7-benzyl-4-((2S,5R)-4-(tert-butoxycarbonyl)-2,5-dimethylpiperazin-1-yl)-1-(2-isopropylphenyl)-2-oxo-1,2-dihydropyrido[3,4-d]pyrimidin-7-ium was dissolved in 80% aq. MeOH (20 mL) and brought to 0° C. Then, NaBH$_4$ (0.570 g, 15.08 mmol) was added and the resulting mixture was heated to reflux for 20 min. The reaction went to completion, brought to r.t., carefully quenched with sat. NaHCO$_3$ and extracted with DCM. The combined organics were dried over Na2SO4, filtered and concentrated to afford tert-butyl (2R,5S)-4-(7-benzyl-1-(2-isopropylphenyl)-2-oxo-1,2,5,6,7,8-hexahydropyrido[3,4-d]pyrimidin-4-yl)-2,5-dimethylpiperazine-1-carboxylate. m/z (ESI, +ve ion): 571.8 (M+H)$^+$.

Step 6: tert-Butyl (2R,5S)-4-(1-(2-isopropylphenyl)-2-oxo-1,2,5,6,7,8-hexahydropyrido[3,4-d]pyrimidin-4-yl)-2,5-dimethylpiperazine-1-carboxylate To a solution of tert-butyl (2R,5S)-4-(7-benzyl-1-(2-isopropylphenyl)-2-oxo-1,2,5,6,7,8-hexahydropyrido[3,4-d]pyrimidin-4-yl)-2,5-dimethylpiperazine-1-carboxylate (0.280 g, 0.490 mmol) in MeOH (15 mL) was added palladium 10 wt. % on activated carbon (0.365 g, 0.343 mmol) and ammonium formate (0.309 g, 4.90 mmol) and the resulting mixture was heated to reflux. After 20 min the starting material was consumed and desired mass was observed. The mixture was brought to r.t., filtered through celite, concentrated and purified by chromatography on silica gel using 0-100% 3:1EtOAc/EtOH in heptane to afford tert-butyl (2R,5S)-4-(1-(2-isopropylphenyl)-2-oxo-1,2,5,6,7,8-hexahydropyrido[3,4-d]pyrimidin-4-yl)-2,5-dimethylpiperazine-1-carboxylate (0.105 g, 0.218 mmol, 44.5% yield) as a white solid. m/z (ESI, +ve ion): 481.8 (M+H)$^+$. $^1$H NMR (400 MHz, DMSO-d$_6$) δ 7.39-7.51 (m, 2H), 7.25-7.34 (m, 1H), 7.13-7.18 (m, 1H), 7.03-7.11 (m, 1H), 4.38-4.53 (m, 1H), 4.12-4.38 (m, 1H), 3.93-4.06 (m, 1H), 3.58-3.74 (m, 2H), 3.40-3.49 (m, 2H), 2.98-3.16 (m, 2H), 2.73-2.94 (m, 2H), 2.36-2.46 (m, 2H), 1.41-1.47 (m, 9H), 1.10-1.19 (m, 8H), 1.03-1.10 (m, 4H).

Steps 7 & 8: 4-((2S,5R)-4-Acryloyl-2,5-dimethylpiperazin-1-yl)-1-(2-isopropylphenyl)-7-phenyl-5,6,7,8-tetrahydropyrido[3,4-d]pyrimidin-2(1H)-one, 3386982

A solution of tert-butyl (2R,5S)-4-(1-(2-isopropylphenyl)-2-oxo-1,2,5,6,7,8-hexahydropyrido[3,4-d]pyrimidin-4-yl)-2,5-dimethylpiperazin-1-carboxylate (0.060 g, 0.125 mmol) in acetonitrile (2 mL) was added to a stirring mixture of 2-(trimethylsilyl)phenyl triflate (0.056 g, 0.187 mmol) and cesium fluoride (0.057 g, 0.374 mmol) in acetonitrile (2 mL). The reaction mixture was stirred at r.t. for 1 hour, concentrated, diluted with water and extracted with EtOAc. The organic was concentrated to give a crude tert-butyl (2R,5S)-4-(1-(2-isopropylphenyl)-2-oxo-7-phenyl-1,2,5,6,7,8-hexahydropyrido[3,4-d]pyrimidin-4-yl)-2,5-dimethylpiperazine-1-carboxylate. m/z (ESI, +ve ion): 558.3 (M+H)$^+$. This crude intermediate was dissolved in DCM (2 mL) and treated with TFA (0.288 mL, 3.74 mmol). The resulting mixture was stirred at r.t. for 1 hour and then concentrated in vacuo. The residue was suspended in DCM (2 mL) and treated with TEA (0.087 mL, 0.623 mmol) followed by acryloyl chloride (0.020 mL, 0.249 mmol). The reaction was stirred at r.t. for 10 minutes, quenched with water, and extracted with DCM. The organic was concentrated and the residue purified with ISCO using 0-100% EtOAc/EtOH (3:1) in heptane to afford 4-((2S,5R)-4-acryloyl-2,5-dimethylpiperazin-1-yl)-1-(2-isopropylphenyl)-7-phenyl-5,6,7,8-tetrahydropyrido[3,4-d]pyrimidin-2(1H)-one (0.008 g, 7.82 μmol, 6.28% yield) as a mixture of atropisomers. m/z (ESI, +ve ion): 512.4 (M+H)$^+$. $^1$H NMR (400 MHz, CHLOROFORM-d) δ 7.44-7.50 (m, 2H), 7.28-7.36 (m, 1H), 7.22 (t, J=7.88 Hz, 2H), 7.10-7.16 (m, 1H), 6.86 (t, J=7.26 Hz, 1H), 6.68 (br d, J=7.67 Hz, 2H), 6.35 (br t, J=15.96 Hz, 1H), 5.75 (br t, J=10.26 Hz, 1H), 4.85-5.02 (m, 1H), 4.19-4.44 (m, 1H), 3.89-4.05 (m, 1H), 3.75-3.89 (m, 1H), 3.49-3.74 (m, 4H), 3.30-3.46 (m, 1H), 3.03-3.28 (m, 1H), 2.80-2.93 (m, 1H), 2.54-2.80 (m, 2H), 1.77 (td, J=6.63, 13.27 Hz, 1H), 1.17-1.31 (m, 12H).

Example 153

7-(2,4-Difluorophenyl)-1-(4,6-diisopropylpyrimidin-5-yl)-4-[(2S,5R)-2,5-dimethyl-4-prop-2-enoyl-piperazin-1-yl]-6-fluoro-pyrido[2,3-d]pyrimidin-2-one

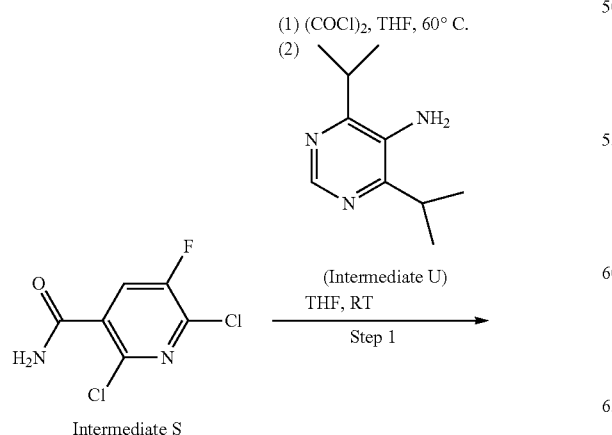

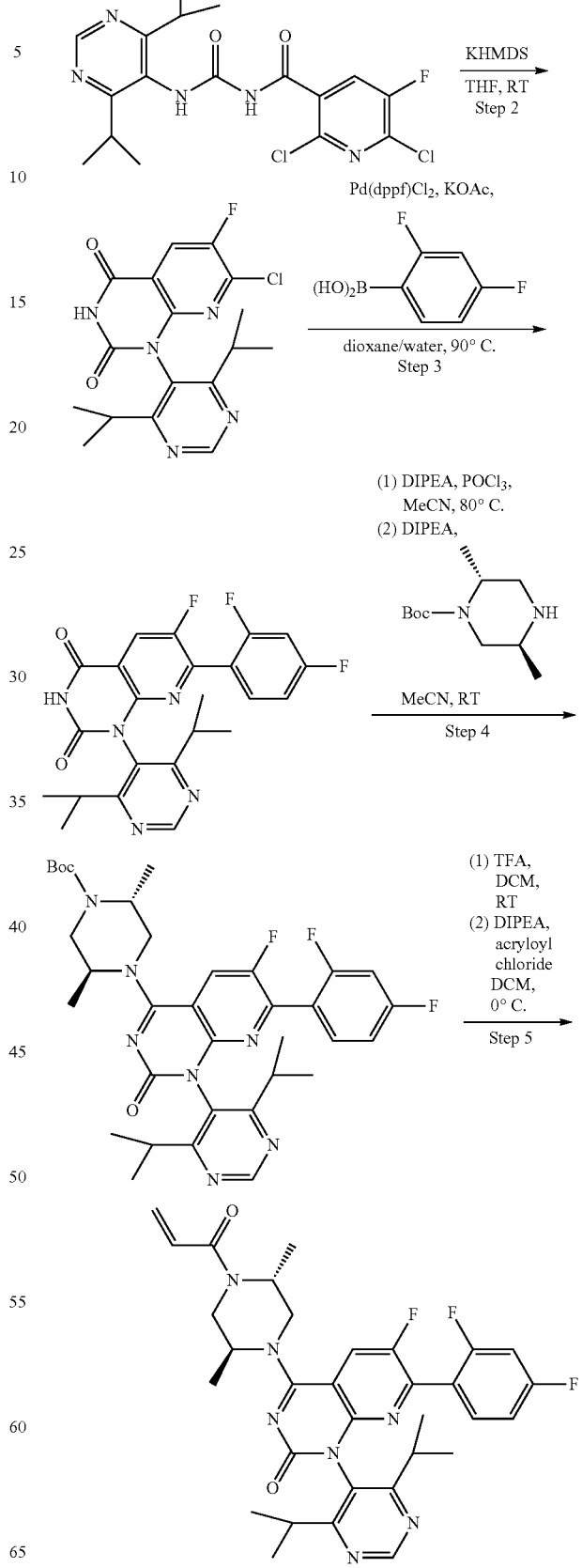

Step 1. 2,6-Dichloro-N-((4,6-diisopropylpyrimidin-5-yl)carbamoyl)-5-fluoronicotinamide To a 250-ml, round-bottomed flask was added 2,6-dichloro-5-fluoronicotinamide (Intermediate S, 3.55 g, 16.7 mmol) and oxalyl chloride (12.5 mL, 25.1 mmol) in tetrahydrofuran (33.5 mL). The flask was fitted with a Findenser, and the mixture was stirred and heated at 80° C. for 1 h. The reaction mixture was concentrated in vacuo. The crude mixture was carried into the next step of the synthesis, without further purification to prevent decomposition.

To a 250-mL round-bottomed flask was added (2,6-dichloro-5-fluoronicotinoyl)carbamoyl isocyanate (crude material from previous step) in tetrahydrofuran (33.5 mL). Then a solution of 4,6-diisopropylpyrimidin-5-amine (Intermediate U, 3.1 g, 17.5 mmol) in THF (10 mL) was added dropwise into the reaction mixture. The mixture was allowed to stir under an inert (N2) atmosphere for 1.5 h. The reaction mixture was concentrated in vacuo. The crude material was absorbed onto a plug of silica gel and purified by chromatography through a Interchim (25 micron) silica-gel column (220 grams), eluting with a gradient of 0-40% EtOAc/heptane, to afford 2,6-dichloro-N-((4,6-diisopropylpyrimidin-5-yl)carbamoyl)-5-fluoronicotinamide (4.2 g, 10.3 mmol, 61.7% yield) as light-yellow solid. $^1$H NMR (400 MHz, DMSO-d6) δ 11.41 (br s, 1H) 9.66 (br s, 1H) 8.99 (s, 1H) 8.55 (br d, J=7.88 Hz, 1H) 3.21-3.28 (m, 2H) 1.17 (d, J=6.63 Hz, 12H). m/z (ESI, +ve ion): 414.0 (M+H)$^+$.

Step 2. 7-Chloro-1-(4,6-diisopropylpyrimidin-5-yl)-6-fluoropyrido[2,3-d]pyrimidine-2,4(1H,3H)-dione To a 250-mL round-bottomed flask was added 2,6-dichloro-N-((4,6-diisopropylpyrimidin-5-yl)carbamoyl)-5-fluoronicotinamide (4.0 g, 9.6 mmol) in tetrahydrofuran (48.3 mL). The reaction mixture was cooled to 0° C. with a wet ice/water bath. Then potassium bis(trimethylsilyl)amide, 1M solution in tetrahydrofuran (12.0 mL, 12.0 mmol) was added via an addition funnel dropwise to the reaction mixture over 5 min. The ice bath was removed and the reaction mixture was allowed to slowly warm to ambient temperature, while stirred under an inert (N$_2$) atmosphere for 1 h. More KHMDS (0.5 eq; 6 mL) was added dropwise to the reaction mixture. The reaction mixture was quenched with sat. aq. NH$_4$Cl (50 mL), then the mixture was diluted with 3:1 EtOAc/MeOH and brine solution. The layers were separated and the aqueous layer was extracted with EtOAc. The combined organic extracts were dried over MgSO$_4$, filtered and concentrated in vacuo. This afforded 7-chloro-1-(4,6-diisopropylpyrimidin-5-yl)-6-fluoropyrido[2,3-d]pyrimidine-2,4(1H,3H)-dione (2.5 g, 6.8 mmol, 70.9% yield) as a tan solid. $^1$H NMR (400 MHz, DMSO-d$_6$) δ 12.03-12.52 (m, 1H) 8.97-9.23 (m, 1H) 8.25-8.58 (m, 1H) 2.80 (dt, J=13.22, 6.56 Hz, 2H) 0.96 (d, J=6.63 Hz, 6H) 0.85 (d, J=6.63 Hz, 6H). m/z (ESI, +ve ion): 378.0 (M+H)$^+$.

Step 3. 7-(2,4-Difluorophenyl)-1-(4,6-diisopropylpyrimidin-5-yl)-6-fluoropyrido[2,3-d]pyrimidine-2,4(1H,3H)-dione To a 100-mL round-bottomed flask was added 7-chloro-1-(4,6-diisopropylpyrimidin-5-yl)-6-fluoropyrido[2,3-d]pyrimidine-2,4(1H,3H)-dione (0.2 g, 0.6 mmol) and potassium acetate (0.195 g, 1.985 mmol) in 1,4-dioxane (3.3 mL). The reaction mixture was deoxygenated by bubbling (N$_2$) gas into the mixture for 5 min. Then (1,1'-bis(diphenylphosphino) ferrocene) dichloropalladium (0.048 g, 0.066 mmol) was added to the reaction mixture. The mixture was stirred and heated at 95° C. for 10 min. Then 2,4-difluorobenzeneboronic acid (0.136 g, 0.860 mmol), followed by water (0.05 mL) was added to the reaction mixture. The reaction mixture was allowed to stir at 95° C. for 16 h. The reaction mixture was diluted with sat. aq. NH$_4$Cl and EtOAc. The layers were separated and the aqueous layer was extracted with EtOAc. The combined organic extracts were dried over MgSO$_4$, filtered and concentrated in vacuo. The crude material was absorbed onto a plug of silica gel and purified by chromatography through a Interchim (15 micron) silica-gel column (40 grams), eluting with a gradient of 0-90% EtOAc/heptane, to afford 7-(2,4-difluorophenyl)-1-(4,6-diisopropylpyrimidin-5-yl)-6-fluoropyrido[2,3-d]pyrimidine-2,4(1H,3H)-dione (0.2 g, 0.4 mmol, 74.7% yield) as light-yellow solid. $^1$H NMR (400 MHz, DMSO-d$_6$) δ 12.27 (s, 1H) 9.13 (s, 1H) 8.47 (d, J=8.50 Hz, 1H) 7.37-7.45 (m, 1H) 7.19-7.33 (m, 2H) 2.97 (spt, J=6.57 Hz, 2H) 1.10 (d, J=6.63 Hz, 6H) 0.93 (d, J=6.63 Hz, 6H). m/z (ESI, +ve ion): 456.0 (M+H)$^+$.

Step 4. tert-Butyl (2R,5S)-4-(7-(2,4-difluorophenyl)-1-(4,6-diisopropylpyrimidin-5-yl)-6-fluoro-2-oxo-1,2-dihydropyrido[2,3-d]pyrimidin-4-yl)-2,5-dimethylpiperazine-1-carboxylate To a 100-mL round-bottomed flask was added 7-(2,4-difluorophenyl)-1-(4,6-diisopropylpyrimidin-5-yl)-6-fluoropyrido[2,3-d]pyrimidine-2,4(1H,3H)-dione (0.2 g, 0.4 mmol) and n,n'-diisopropylethylamine (0.1 mL, 0.5 mmol) in acetonitrile (7.9 mL). Then phosphorous oxychloride (0.1 mL, 0.5 mmol) was added slowly to the reaction mixture. The flask was fitted with a Findenser, then the mixture was stirred and heated at 80° C., while under an inert (N2) atmosphere for 45 min. The reaction mixture was removed from the heat bath and allowed to cool to ambient temperature.

The reaction mixture was cooled to 0° C. with a wet ice/water bath, while stirred. Then DIPEA (0.3 mL) was added slowly to the reaction mixture. Then a mixture of (2R,5S)-1-Boc-2,5-dimethylpiperazine (0.1 g, 0.5 mmol, Astatech, San Diego, Calif., USA) in MeCN (3 mL) was added slowly to the reaction mixture. The ice bath was removed and the reaction mixture was allowed to slowly warm to ambient temperature over 1 h. The mixture was diluted with EtOAc and sat. aq. NH$_4$Cl, then the layers were separated. The aqueous layer was extracted with EtOAc and brine. The combined organic extracts were dried over MgSO4, filtered and concentrated in vacuo. The crude material was absorbed onto a plug of silica gel and purified by chromatography through an Interchim (25 micron) silica-gel column (120 grams), eluting with a gradient of 0-100% EtOAc/heptane, to afford tert-butyl (2R,5S)-4-(7-(2,4-difluorophenyl)-1-(4,6-diisopropylpyrimidin-5-yl)-6-fluoro-2-oxo-1,2-dihydropyrido[2,3-d]pyrimidin-4-yl)-2,5-dimethylpiperazine-1-carboxylate (0.2 g, 0.3 mmol, 83% yield) as tan solid. m/z (ESI, +ve ion): 652.1 (M+H)$^+$.

Step 5. 4-((2S,5R)-4-Acryloyl-2,5-dimethylpiperazin-1-yl)-7-(2,4-difluorophenyl)-1-(4,6-diisopropylpyrimidin-5-yl)-6-fluoropyrido[2,3-d]pyrimidin-2(1H)-one To a 100-mL round-bottomed flask was added tert-butyl (2R,5S)-4-(7-(2,4-difluorophenyl)-1-(4,6-diisopropylpyrimidin-5-yl)-6-fluoro-2-oxo-1,2-dihydropyrido[2,3-d]pyrimidin-4-yl)-2,5-dimethylpiperazine-1-carboxylate (0.2 g, 0.3 mmol) and trifluoroacetic acid (0.1 mL, 1.918 mmol) in dichloromethane (1.9 mL). The reaction mixture was stirred and heated at 38° C. for 2.5 h, while under an inert ($N_2$) atmosphere. The reaction mixture was concentrated in vacuo. This material was carried directly into the next step of the synthesis, without further purification.

The previous residue was diluted with dichloromethane (1.9 mL), then the mixture was cooled to 0° C. with a wet ice bath. Then n,n'-diisopropylethylamine (0.8 mL, 4.6 mmol) was added to the reaction mixture and allowed the mixture to stir 2 min. Then acryloyl chloride (0.1 mL, 0.3 mmol) was added to the mixture dropwise. The mixture was diluted with DCM and sat. aq. $NaHCO_3$, then the layers were separated. The aqueous layer was extracted with DCM. The combined organic extracts were dried over $MgSO_4$, filtered and concentrated in vacuo. The crude material was absorbed onto a plug of silica gel and purified by chromatography through a Interchim (15 micron) silica-gel column (40 grams), eluting with a gradient of 0-5% MeOH/DCM. This afforded 4-((2S,5R)-4-acryloyl-2,5-dimethylpiperazin-1-yl)-7-(2,4-difluorophenyl)-1-(4,6-diisopropylpyrimidin-5-yl)-6-fluoropyrido[2,3-d]pyrimidin-2(1H)-one (0.1 g, 0.2 mmol, 60.3% yield) as light-yellow solid. $^1$H NMR (400 MHz, DMSO-$d_6$) δ 9.10 (s, 1H) 8.38 (dd, J=9.64, 5.29 Hz, 1H) 7.21-7.45 (m, 3H) 6.77-6.91 (m, 1H) 6.19 (br d, J=18.24 Hz, 1H) 5.72-5.79 (m, 1H) 4.72-4.98 (m, 2H) 4.13-4.25 (m, 1H) 3.85 (br s, 2H) 2.66-2.77 (m, 2H) 1.33 (t, J=6.01 Hz, 3H) 1.25 (br d, J=6.63 Hz, 2H) 1.18 (br d, J=6.63 Hz, 2H) 1.09 (dd, J=6.63, 2.28 Hz, 6H) 0.94 (d, J=6.43 Hz, 6H). m/z (ESI, +ve ion): 606.4 $(M+H)^+$.

Example 154

6-Chloro-1-(4,6-diisopropyl-2-methoxy-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one

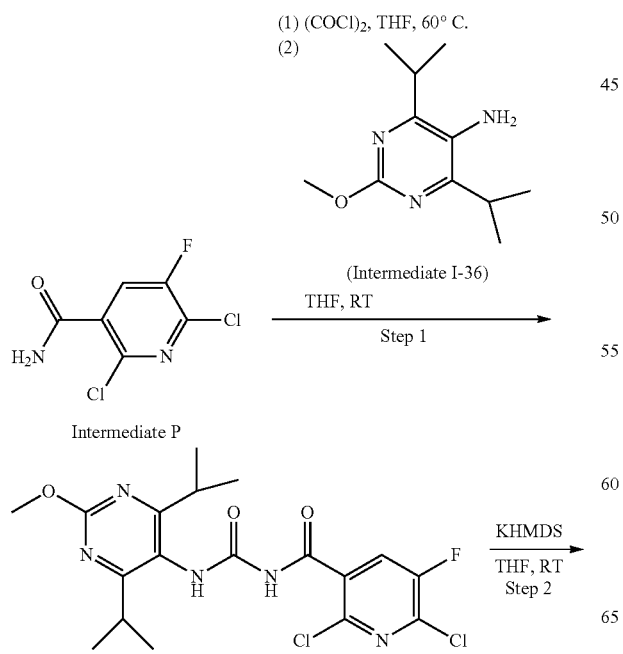

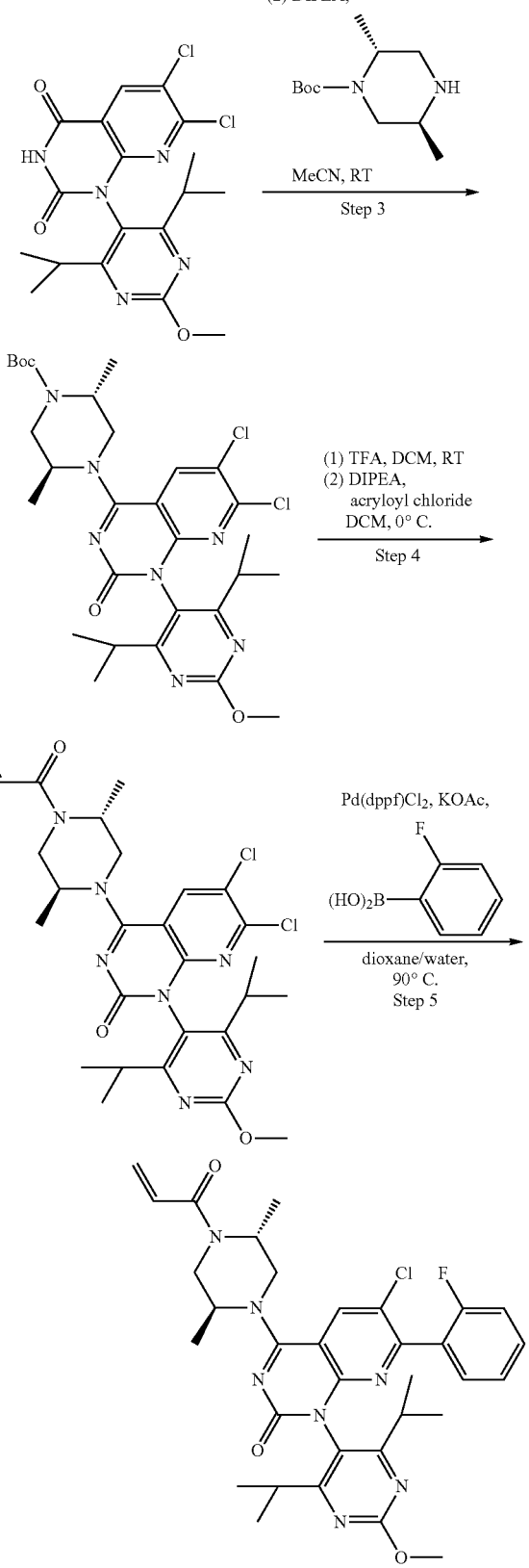

Step 1. 2,5,6-Trichloro-N-((4,6-diisopropyl-2-methoxypyrimidin-5-yl)carbamoyl)nicotinamide To a 150-mL round-bottomed flask was added 2,5,6-trichloronicotinamide (Intermediate P, 0.7 g, 3.1 mmol) and oxalyl chloride (2.3 mL, 4.6 mmol) in tetrahydrofuran (6.2 mL). The flask was fitted with a Findenser, and the mixture was stirred and heated at 80° C. for 45 min. The reaction mixture was concentrated in vacuo. The crude mixture was carried into the next step of the synthesis, without further purification to prevent decomposition.

To a 100-mL round-bottomed flask was added (2,5,6-trichloronicotinoyl)carbamoyl isocyanate (crude material from previous step) in tetrahydrofuran (6.2 mL). The reaction it mixture was cooled to −10° C. with a dilute acetone/dry ice bath, then a solution of 4,6-diisopropyl-2-methoxypyrimidin-5-amine (Intermediate I-36, 0.6 g, 3.2 mmol) in THF (5 mL) was added to the reaction mixture. The mixture was allowed to stir under an inert ($N_2$) atmosphere for 1 h. The reaction mixture was concentrated in vacuo. The crude material was absorbed onto a plug of silica gel and purified by chromatography through a Interchim (25 micron) silica-gel column (220 grams), eluting with a gradient of 0-40% EtOAc/heptane, to provide 2,5,6-trichloro-N-((4,6-diisopropyl-2-methoxypyrimidin-5-yl)carbamoyl)nicotinamide as off-white solid. m/z (ESI, +ve ion): 460.1 (M+H)$^+$.

Step 2. 6,7-Dichloro-1-(4,6-diisopropyl-2-methoxypyrimidin-5-yl)pyrido[2,3-d]pyrimidine-2,4(1H,3H)-dione To a 250-mL round-bottomed flask was added 2,5,6-trichloro-N-((4,6-diisopropyl-2-methoxypyrimidin-5-yl)carbamoyl)nicotinamide (1.0 g, 2.2 mmol) in tetrahydrofuran (11.4 mL). Then potassium bis(trimethylsilyl)amide, 1M solution in tetrahydrofuran (2.8 mL, 2.8 mmol) was added via syringe dropwise to the reaction mixture. The reaction mixture was allowed to stir under an inert ($N_2$) atmosphere for 30 min. The reaction mixture was quenched with sat. aq. $NH_4Cl$ (10 mL), then the mixture was diluted with 3:1 EtOAc/MeOH and brine solution. The layers were separated and the aqueous layer was extracted with EtOAc. The combined organic extracts were dried over $MgSO_4$, filtered and concentrated m vacuo. The crude material was absorbed onto a plug of silica gel and purified by chromatography through an Interchim (25 micron) silica-gel column (80 grams), eluting with a gradient of 0-40% EtOAc/heptane This afforded 6,7-dichloro-1-(4,6-diisopropyl-2-methoxypyrimidin-5-yl)pyrido[2,3-d]pyrimidine-2,4(1H,3H)-dione (0.2 g, 0.5 mmol) as tan solid. $^1$H NMR (400 MHz, DMSO-$d_6$) δ 12.17-12.42 (m, 1H) 8.49-8.74 (m, 1H) 3.98 (s, 3H) 2.82-2.92 (m, 2H) 1.08 (d, J=6.63 Hz, 6H) 0.98 (d, J=6.63 Hz, 6H). m/z (ESI, +ve ion): 424.1 (M+H)$^+$.

Step 3. tert-Butyl (2R,5S)-4-(6,7-dichloro-1-(4,6-diisopropyl-2-methoxypyrimidin-5-yl)-2-oxo-1,2-dihydropyrido[2,3-d]pyrimidin-4-yl)-2,5-dimethylpiperazine-1-carboxylate To a 100-mL round-bottomed flask was added 6,7-dichloro-1-(4,6-diisopropyl-2-methoxypyrimidin-5-yl)pyrido[2,3-d]pyrimidine-2,4(1H,3H)-dione (0.2 g, 0.5 mmol) and n,n'-diisopropylethylamine (0.1 mL, 0.7 mmol) in acetonitrile (7.9 mL). Then phosphorous oxychloride (0.1 mL, 0.7 mmol) was added slowly to the reaction mixture. The flask was fitted with a Findenser, then the mixture was stirred and heated at 80° C. while under an inert ($N_2$) atmosphere for 45 min. The reaction mixture was removed from the heat bath and allowed to cool to ambient temperature. Then set aside for later use.

The previous reaction mixture was cooled to 0° C. with a wet ice/water bath, while stirred. Then DIPEA (1.5 mL) was added slowly to the reaction mixture. Then a mixture of (2R,5S)-1-Boc-2,5-dimethylpiperazine (0.1 g, 0.7 mmol, Astatech, San Diego, Calif., USA) in MeCN (3 mL) was added slowly to the reaction mixture. The ice bath was removed and the overall mixture was allowed to slowly warm to ambient temperature over 1 h. The mixture was diluted with EtOAc and sat. aq. $NH_4Cl$, then the layers were separated. The aqueous layer was extracted with EtOAc and brine. The combined organic extracts were dried over $MgSO4$, filtered and concentrated in vacuo. The crude material was absorbed onto a plug of silica gel and purified by chromatography through a Interchim (25 micron) silica-gel column (120 grams), eluting with a gradient of 0-100% EtOAc/heptane to afford tert-butyl (2R,5S)-4-(6,7-dichloro-1-(4,6-diisopropyl-2-methoxypyrimidin-5-yl)-2-oxo-1,2-dihydropyrido[2,3-d]pyrimidin-4-yl)-2,5-dimethylpiperazine-1-carboxylate (0.1 g, 0.2 mmol, 37.5% yield) as tan solid. m/z (ESI, +ve ion): 620.1 (M+H)$^3$.

Step 4. 4-((2S,5R)-4-Acryloyl-2,5-dimethylpiperazin-1-yl)-6,7-dichloro-1-(4,6-diisopropyl-2-methoxypyrimidin-5-yl)pyrido[2,3-d]pyrimidin-2(1H)-one To a 100-mL round-bottomed flask was added tert-butyl (2R,5S)-4-(6,7-dichloro-1-(4,6-diisopropyl-2-methoxypyrimidin-5-yl)-2-oxo-1,2-dihydropyrido[2,3-d]pyrimidin-4-yl)-2,5-dimethylpiperazine-1-carboxylate (0.1 g, 0.2 mmol) and trifluoroacetic acid (0.1 mL, 2.1 mmol) in 1,2-dichloroethane (4.0 mL). The reaction mixture was stirred and heated at 70° C. for 1 h, while under an inert ($N_2$) atmosphere. The reaction mixture was concentrated in vacuo. This material was carried directly into the next step of the synthesis, without further purification The previous residue was diluted with DCM (4 mL), then the reaction mixture was cooled to 0° C. with a wet ice/water bath. Then N,N'-diisopropylethylamine (0.4 mL, 2.6 mmol) was added to the reaction mixture and allowed the mixture to stir 2 min. Then acryloyl chloride (0.1 mL, 0.2 mmol) was added to the mixture dropwise. The mixture was diluted with DCM and sat. aq. $NaHCO_3$, then the layers were separated. The aqueous layer was extracted with DCM. The combined organic extracts were dried over $MgSO_4$, filtered and concentrated in vacuo. The crude material was absorbed onto a plug of silica gel and purified by chromatography through a Interchim (25 micron) silica-gel column (40 grams), eluting with a gradient of 0-5% MeOH/DCM. This afforded 4-((2S,5R)-4-acryloyl-2,5-dimethylpiperazin-1-yl)-6,7-dichloro-1-(4,6-diisopropyl-2-methoxypyrimidin-5-yl)pyrido[2,3-d]pyrimidin-2(1H)-one (0.1 g, 0.2 mmol, 92% yield) as tan solid. m/z (ESI, +ve ion): 574.1 (M+H)$^+$.

Step 5. 4-((2S,5R)-4-Acryloyl-2,5-dimethylpiperazin-1-yl)-6-chloro-1-(4,6-diisopropyl-2-methoxypyrimidin-5-yl)-7-(2-fluorophenyl)pyrido[2,3-d]pyrimidin-2(1H)-one To a 100-mL round-bottomed flask was added 4-((2S,5R)-4-acryloyl-2,5-dimethylpiperazin-1-yl)-6,7-dichloro-1-(4,6-diisopropyl-2-methoxypyrimidin-5-yl)pyrido[2,3-d]pyrimidin-2(1H)-one (0.1 g, 0.191 mmol) and potassium acetate (0.1 g, 0.5 mmol) in 1,4-dioxane (3.3 mL). The reaction mixture was deoxygenated by bubbling (N2) gas into the mixture for 5 min. Then (1,1'-bis(diphenylphosphino) ferrocene) dichloropalladium (0.1 g, 0.1 mmol) was added to the reaction mixture. The mixture was stirred and heated at 95° C. for 10 min. Then 2-fluorophenylboronic acid (0.1 g, 0.2 mmol), followed by water (0.1 mL) was added to the reaction mixture. The overall reaction mixture was allowed to stir at 95° C. for 16 h. The reaction mixture was diluted with sat. aq. NH4Cl and EtOAc. The layers were separated and the aqueous layer was extracted with EtOAc. The combined organic extracts were dried over MgSO$_4$, filtered and concentrated in vacuo. The crude material was absorbed onto a plug of silica gel and purified by chromatography through an Interchim (15 micron) silica-gel column, eluting with a gradient of 0-4% MeOH/DCM, to afford 4-((2S,5R)-4-acryloyl-2,5-dimethylpiperazin-1-yl)-6-chloro-1-(4,6-diisopropyl-2-methoxypyrimidin-5-yl)-7-(2-fluorophenyl)pyrido[2,3-d]pyrimidin-2(1H)-one (0.1 g, 0.1 mmol, 24.71% yield) as white solid. $^1$H NMR (400 MHz, DMSO-d$_6$) δ 8.47 (d, J=3.94 Hz, 1H) 7.50-7.56 (m, 1H) 7.28-7.35 (m, 2H) 7.19-7.24 (m, 1H) 6.83 (td, J=17.00, 10.57 Hz, 1H) 6.19 (dd, J=16.79, 1.87 Hz, 1H) 5.73-5.78 (m, 1H) 4.72-4.94 (m, 2H) 4.13-4.24 (m, 1H) 3.91 (s, 3H) 3.83-3.88 (m, 1H) 3.17 (d, J=5.18 Hz 1H) 2.58-2.71 (m, 2H) 1.34 (t, J=5.80 Hz, 3H) 1.25 (br d, J=6.63 Hz, 2H) 1.18 (d, J=6.84 Hz, 2H) 1.06 (dd, J=6.53, 3.84 Hz, 6H) 0.92 (dd, J=6.53, 2.80 Hz, 6H). m/z (ESI, +ve ion): 634.4 (M+H)$^+$.

Example 155

5-[6-Chloro-4-[(2S,5R)-2,5-dimethyl-4-prop-2-enoyl-piperazin-1-yl]-7-(2-fluorophenyl)-2-oxo-pyrido[2,3-d]pyrimidin-1-yl]-4,6-diisopropyl-pyrimidine-2-carbonitrile

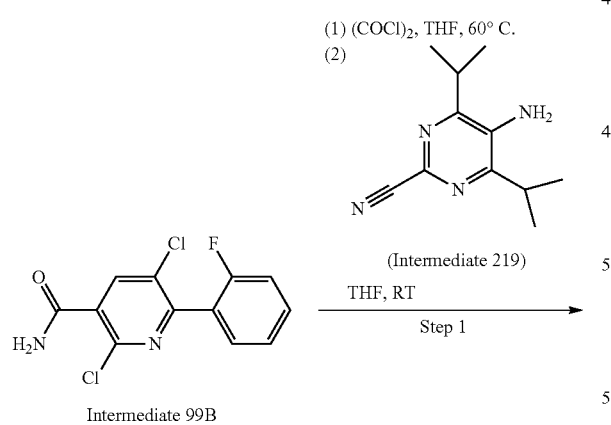

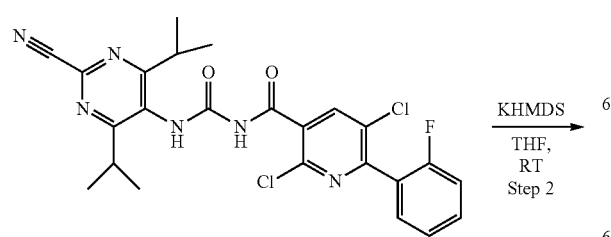

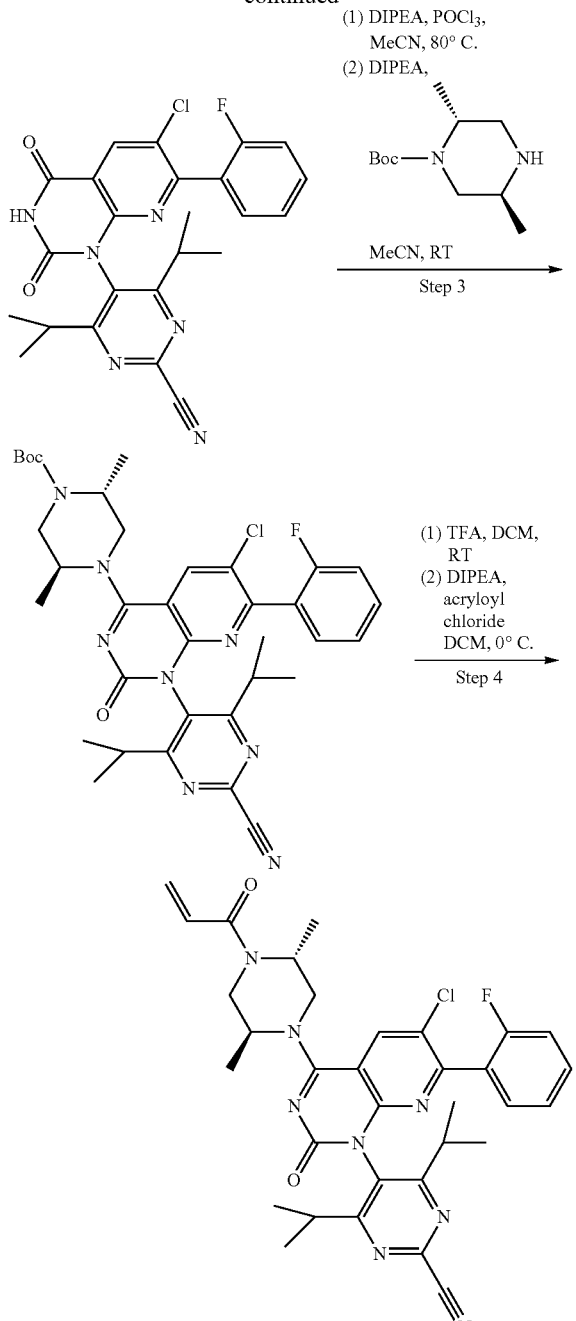

Step 1. 2,5-Dichloro-N-((2-cyano-4,6-diisopropylpyrimidin-5-yl)carbamoyl)-6-(2-fluorophenyl)nicotinamide To a 100-mL round-bottomed flask was added 2,5-dichloro-6-(2-fluorophenyl)nicotinamide (Intermediate 99B, 0.55 g, 1.81 mmol) and oxalyl chloride (1.36 mL, 2.72 mmol) in tetrahydrofuran (9.07 mL). The flask was fitted with a Findenser, and mixture was stirred and heated at 80° C. for 45 min. The reaction mixture was concentrated in vacuo. The crude mixture was carried into the next step of the synthesis, without further purification to prevent decomposition.

To a 150-mL round-bottomed flask was added (2,5-Dichloro-6-(2-fluorophenyl)nicotinoyl)carbamoyl isocyanate (crude material from previous step) in tetrahydrofuran (9.07 mL). The reaction mixture was cooled to −10° C. with a dilute acetone/dry ice bath, then a solution of 5-amino-4,6-diisopropylpyrimidine-2-carbonitrile (Intermediate 219, 0.38 g, 1.90 mmol) in THF (3 mL) was added to the reaction mixture. The mixture was allowed to stir under an inert (N2) atmosphere for 1 h. The reaction mixture was concentrated in vacuo. The crude material was triturated from EtOAc and heptane, then the solids were collected by filtration. The solids were washed with heptane. This afforded 2,5-dichloro-N-((2-cyano-4,6-diisopropylpyrimidin-5-yl)carbamoyl)-6-(2-fluorophenyl)nicotinamide (0.75 g, 1.45 mmol, 80% yield) as tan solid. $^1$H NMR (400 MHz, DMSO-$d_6$) δ 11.57 (br s, 1H) 9.96 (br s, 1H) 8.63 (s, 1H) 7.52-7.64 (m, 2H) 7.37-7.43 (m, 2H) 1.20 (br d, J=6.63 Hz, 14H). m/z (ESI, +ve ion): 515.0 (M+H)$^+$.

Step 2. 5-(6-Chloro-7-(2-fluorophenyl)-2,4-dioxo-3,4-dihydropyrido[2,3-d]pyrimidin-1(2H)-yl)-4,6-diisopropylpyrimidine-2-carbonitrile To a 100-mL round-bottomed flask was added 2,5-dichloro-N-((2-cyano-4,6-diisopropylpyrimidin-5-yl)carbamoyl)-6-(2-fluorophenyl)nicotinamide (0.72 g, 1.39 mmol) in tetrahydrofuran (6.9 mL). Then potassium bis(trimethylsilyl)amide, 1M solution in tetrahydrofuran (1.7 mL, 1.74 mmol) was added via an addition funnel dropwise to the reaction mixture over 5 min. The reaction mixture was allowed to stir under an inert (N$_2$) atmosphere for 1 h. More KHMDS (0.5 eq; 0.6 mL) was added dropwise to the reaction mixture, until SM was mostly consumed. The reaction mixture was quenched with sat. aq. NH$_4$Cl (50 mL), then the mixture was diluted with 3:1 EtOAc/MeOH and brine solution. The layers were separated and the aqueous layer was extracted with EtOAc. The combined organic extracts were dried over MgSO$_4$, filtered and concentrated in vacuo. This afforded 5-(6-chloro-7-(2-fluorophenyl)-2,4-dioxo-3,4-dihydropyrido[2,3-d]pyrimidin-1(2H)-yl)-4,6-diisopropylpyrimidine-2-carbonitrile (0.65 g, 1.35 mmol, 97% yield) as tan solid. $^1$H NMR (400 MHz, DMSO-$d_6$) δ 12.24 (br s, 1H) 8.59 (s, 1H) 7.49-7.54 (m, 1H) 7.25-7.34 (m, 2H) 7.16-7.25 (m, 1H) 3.00-3.21 (m, 2H) 1.09-1.15 (m, 6H) 0.94 (d, J=6.63 Hz, 6H). m/z (ESI, +ve ion): 479.0 (M+H)$^+$.

Step 3. tert-Butyl (2R,5S)-4-(6-chloro-1-(2-cyano-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added 5-(6-chloro-7-(2-fluorophenyl)-2,4-dioxo-3,4-dihydropyrido[2,3-d]pyrimidin-1(2H)-yl)-4,6-diisopropylpyrimidine-2-carbonitrile (0.60 g, 1.25 mmol) and N,N'-diisopropylethylamine (0.28 mL, 1.62 mmol) in acetonitrile (6.26 mL). Then phosphorous oxychloride (0.14 mL, 1.50 mmol) was added slowly to the reaction mixture. The flask was fitted with a Findenser, then the mixture was stirred and heated at 80° C., while under an inert (N2) atmosphere for 45 min. Another aliquot of N,N'-diisopropylethylamine (0.28 mL, 1.62 mmol) and phosphorous oxychloride (0.14 mL, 1.50 mmol) was added to the reaction mixture, then allowed the mixture to stir 10 min. The reaction mixture was removed from the heat bath and allowed to cool to ambient temperature.

The previous reaction mixture was cooled to 0° C. with a wet ice/water bath, while stirred. Then DIPEA (2.4 mL) was added slowly to the mixture. Then a mixture of (2R,5S)-1-Boc-2,5-dimethylpiperazine (0.33 g, 1.56 mmol, Astatech, San Diego, Calif., USA) in MeCN (3 mL) was added slowly to the reaction mixture. The ice bath was removed and the overall mixture was allowed to slowly warm to ambient temperature over 1 h. Another aliquot of DIPEA (0.6 mL) and (2R,5S)-1-Boc-2,5-dimethylpiperazine (0.33 g, 1.56 mmol) in MeCN (2 mL) was added to the mixture, then allowed the mixture to stir an additional 10 min. The mixture was diluted with EtOAc and sat. aq. NH$_4$Cl, then the layers were separated. The aqueous layer was extracted with EtOAc. The combined organic extracts were dried over MgSO4, filtered and concentrated in vacuo. The crude material was absorbed onto a plug of silica gel and purified by chromatography through a Interchim (25 micron) silica-gel column (40 grams), eluting with a gradient of 0-50% EtOAc/heptane, to afford tert-butyl (2R,5S)-4-(6-chloro-1-(2-cyano-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.53 g, 0.79 mmol, 63.7% yield) as a light yellow solid. $^1$H NMR (400 MHz, DMSO-$d_6$) δ 8.49 (s, 1H) 7.50-7.56 (m, 1H) 7.27-7.35 (m, 2H) 7.17-7.24 (m, 1H) 4.86 (br s, 1H) 4.26-4.43 (m, 1H) 4.22 (br d, J=13.48 Hz, 1H) 3.86 (br d, J=13.68 Hz, 1H) 3.72 (br d, J=13.06 Hz, 1H) 3.43-3.61 (m, 1H) 2.75-2.93 (m, 2H) 1.45 (s, 9H) 1.35-1.39 (m, 3H) 1.18 (br d, J=6.63 Hz, 3H) 1.10 (dd, J=6.63, 2.70 Hz, 6H) 0.95 (dd, J=6.63, 2.49 Hz, 6H). m/z (ESI, +ve ion): 675.1 (M+H)$^+$.

Step 4. 5-(4-((2S,5R)-4-Acryloyl-2,5-dimethylpiperazin-1-yl)-6-chloro-7-(2-fluorophenyl)-2-oxopyrido[2,3-d]pyrimidin-1(2H)-yl)-4,6-diisopropylpyrimidine-2-carbonitrile To a 100-mL round-bottomed flask was added tert-butyl (2R,5S)-4-(6-chloro-1-(2-cyano-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.53 g, 0.78 mmol) and trifluoroacetic acid (0.58 mL, 7.85 mmol) in 1,2-dichloroethane (3.9 mL). The reaction mixture was stirred and heated at 30° C. for 1 h, while under an inert (N2) atmosphere. The reaction mixture was concentrated in vacuo. This material was carried directly into the next step of the synthesis, without further purification.

The previous residue was diluted with DCM (4 mL), then the reaction mixture was cooled to 0° C. with a wet ice bath. Then N,N'-diisopropylethylamine (1.64 mL, 9.42 mmol) was added to the reaction mixture and allowed the mixture to stir 2 min. Then acryloyl chloride (0.06 mL, 0.785 mmol) was added to the mixture dropwise. The mixture was diluted with DCM and sat. aq. NaHCO$_3$, then the layers were separated. The aqueous layer was extracted with DCM. The combined organic extracts were dried over MgSO$_4$, filtered and concentrated in vacuo. The crude material was absorbed onto a plug of silica gel and purified by chromatography through a Interchim (25 micron) silica-gel column (40 grams), eluting with a gradient of 0-5% MeOH/CHCl$_3$. This afforded 5-(4-((2S,5R)-4-acryloyl-2,5-dimethylpiperazin-1-yl)-6-chloro-7-(2-fluorophenyl)-2-oxopyrido[2,3-d]pyrimidin-1(2H)-yl)-4,6-diisopropylpyrimidine-2-carbonitrile (0.28 g, 0.44 mmol, 56.7% yield) as white solid. $^1$H NMR (400 MHz, DMSO-$d_6$) δ 8.51 (d, J=6.66 Hz, 1H) 7.48-7.55 (m, 1H) 7.18-7.33 (m, 3H) 6.77-6.90 (m, 1H) 6.19 (br d, J=16.79 Hz, 1H) 5.72-5.78 (m, 1H) 4.75-4.99 (m, 2H) 4.19-4.36 (m, 1H) 3.79-3.96 (m, 2H) 2.76-2.93 (m, 2H)

1.33-1.40 (m, 3H) 1.23-1.29 (m, 2H) 1.20 (br d, J=6.84 Hz, 2H) 1.07-1.13 (m, 6H) 0.93-0.99 (m, 6H). m/z (ESI, +ve ion): 629.1 (M+H)⁺.

Example 156

4-((2S,5R)-4-Acryloyl-2,5-dimethylpiperazin-1-yl)-6-chloro-1-(4,6-diisopropyl-2-(2-methoxyethoxy)pyrimidin-5-yl)-7-(2-fluorophenyl)pyrido[2,3-d]pyrimidin-2(1H)-one

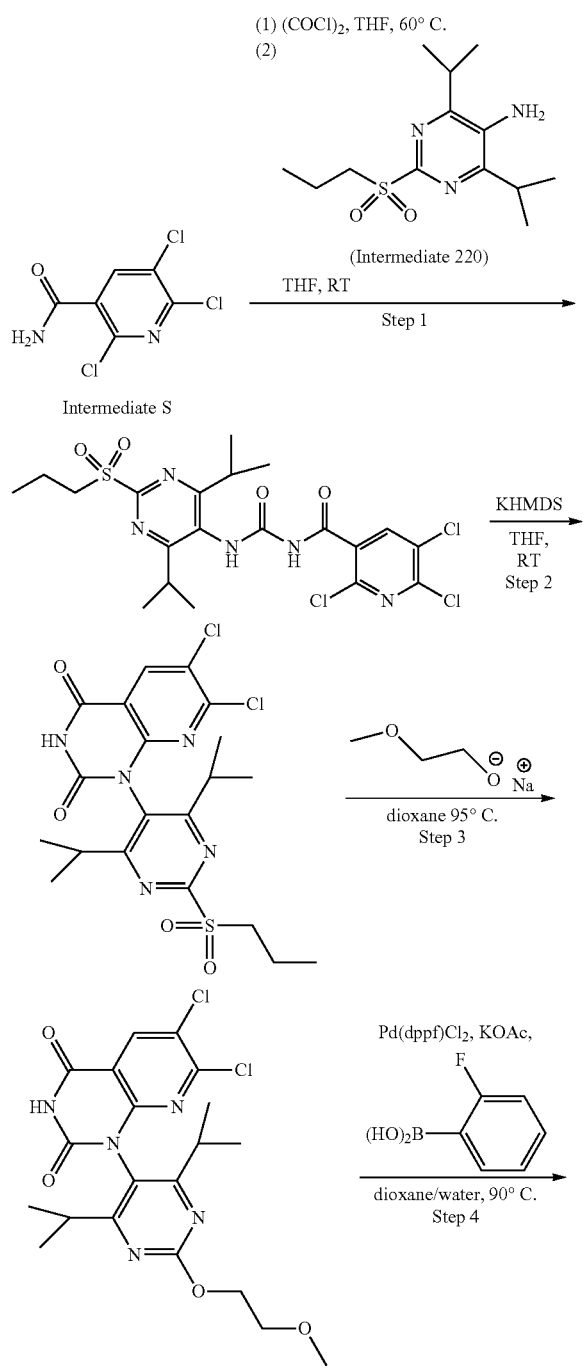

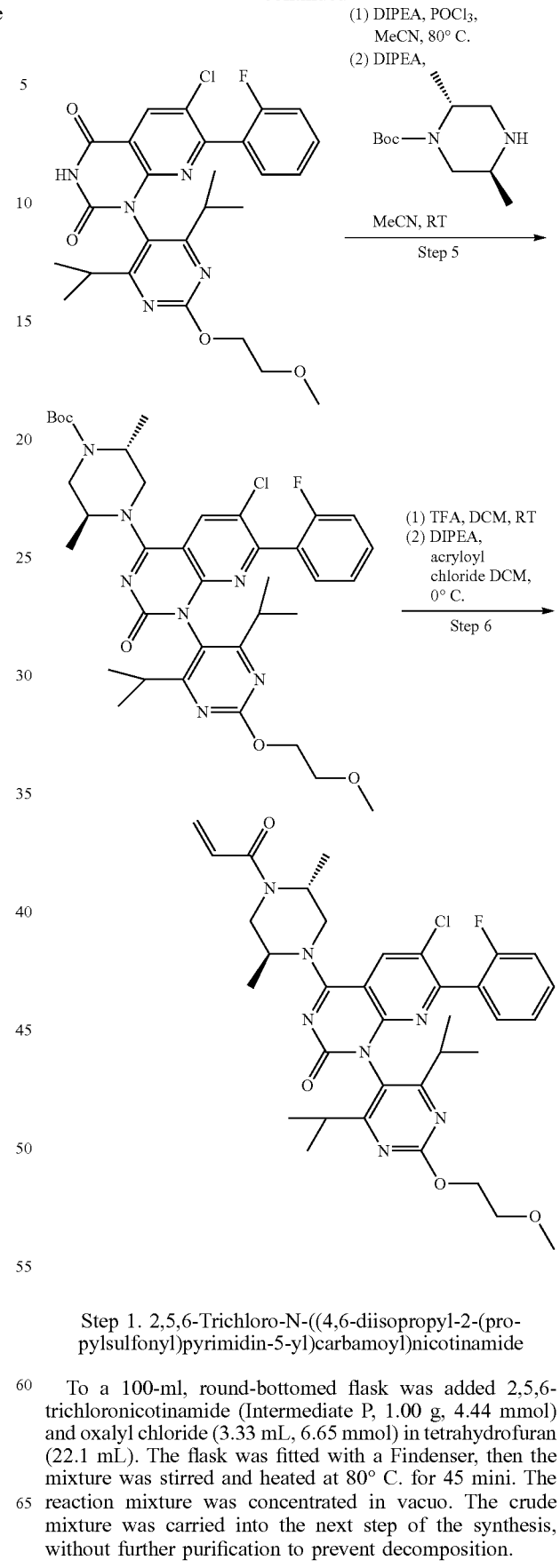

Step 1. 2,5,6-Trichloro-N-((4,6-diisopropyl-2-(propylsulfonyl)pyrimidin-5-yl)carbamoyl)nicotinamide To a 100-ml, round-bottomed flask was added 2,5,6-trichloronicotinamide (Intermediate P, 1.00 g, 4.44 mmol) and oxalyl chloride (3.33 mL, 6.65 mmol) in tetrahydrofuran (22.1 mL). The flask was fitted with a Findenser, then the mixture was stirred and heated at 80° C. for 45 mini. The reaction mixture was concentrated in vacuo. The crude mixture was carried into the next step of the synthesis, without further purification to prevent decomposition.

To a 150-mL round-bottomed flask was added (2,5,6-trichloronicotinoyl)carbamoyl isocyanate (crude material from previous step) in tetrahydrofuran (22.1 mL). The reaction mixture was cooled to −10° C. with a dilute acetone/dry ice bath, then a solution of 4,6-diisopropyl-2-(propylsulfonyl)pyrimidin-5-amine (Intermediate 220, 1.32 g, 4.66 mmol) in THF (5 mL) was added to the reaction mixture. The mixture was allowed to stir under an inert (N2) atmosphere for 1 h. The reaction mixture was concentrated in vacuo. The crude material was triturated from DCM and heptane and the solids were collected by filtration. The solids were washed with heptane. This afforded 2,5,6-trichloro-N-((4,6-diisopropyl-2-(propylsulfonyl)pyrimidin-5-yl)carbamoyl)nicotinamide (2.30 g, 4.28 mmol, 97% yield) as light-yellow solid. $^1$H NMR (400 MHz, DMSO-d$_6$) δ 11.52 (s, 1H) 9.88 (br s, 1H) 8.69 (s, 1H) 5.75 (s, 2H) 3.60-3.66 (m, 2H) 1.68-1.80 (m, 2H) 1.21 (d, J=6.84 Hz, 12H) 1.00-1.05 (m, 3H). m/z (ESI, +ve ion): 536.0 (M+H)$^+$.

Step 2. 6,7-Dichloro-1-(4,6-diisopropyl-2-(propylsulfonyl)pyrimidin-5-yl)pyrido[2,3-d]pyrimidine-2,4(1H,3H)-dione To a 250-mL round-bottomed flask was added 2,5,6-trichloro-N-((4,6-diisopropyl-2-(propylsulfonyl)pyrimidin-5-yl)carbamoyl)nicotinamide (2.30 g, 4.28 mmol) in tetrahydrofuran (48.3 mL). The reaction mixture was cooled to 0° C. in a wet ice/water bath. Then potassium bis(trimethylsilyl)amide, 1M solution in tetrahydrofuran (5.36 mL, 5.36 mmol) was added via an addition funnel, dropwise to the reaction mixture over 5 min. The ice bath was removed and the reaction mixture was allowed to slowly warm to ambient temperature, while stirred under an inert (N$_2$) atmosphere for 1 h. More KHMDS (0.5 eq; 2 mL) was added dropwise to the reaction mixture. The reaction mixture was quenched with sat. aq. NH$_4$Cl (50 mL), then the mixture was diluted with 3:1 EtOAc/MeOH and brine solution. The layers were separated and the aqueous layer was extracted with EtOAc. The combined organic extracts were dried over MgSO$_4$, filtered and concentrated in vacuo. The residue was diluted with DCM (50 mL), then agitated 5 min. The mixture was filtered and the filtrate was collected, then concentrated in vacuo. This afforded 6,7-dichloro-1-(4,6-diisopropyl-2-(propylsulfonyl)pyrimidin-5-yl)pyrido[2,3-d]pyrimidine-2,4(1H,3H)-dione (1.82 g, 3.65 mmol, 85% yield) as a tan solid. $^1$H NMR (400 MHz, DMSO-d$_6$) δ 12.32-12.59 (m, 1H) 8.50-8.81 (m, 1H) 3.67-3.74 (m, 2H) 3.13 (dt, J=13.22, 6.56 Hz, 2H) 1.78-1.87 (m, 2H) 1.23-1.24 (m, 3H) 1.11-1.14 (m, 6H) 1.03 (s, 6H). m/z (ESI, +ve ion): 500.0 (M+H)$^+$.

Step 3. 6,7-Dichloro-1-(4,6-diisopropyl-2-(2-methoxyethoxy)pyrimidin-5-yl)pyrido[2,3-d]pyrimidine-2,4(1H,3H)-dione To a 100-mL round-bottomed flask was added 6,7-dichloro-1-(4,6-diisopropyl-2-(propylsulfonyl)pyrimidin-5-yl)pyrido[2,3-d]pyrimidine-2,4(1H,3H)-dione (0.45 g, 0.89 mmol) and sodium methoxyethoxide (0.44 g, 4.50 mmol) in 1,4-dioxane (4.0 mL). The reaction mixture was stirred and heated at 95° C. for 16 h. The flask was removed from the heat bath and the reaction mixture was allowed to cool to ambient temperature. The reaction mixture was concentrated in vacuo. The residue was diluted with DCM and filtered through a fine-fritted funnel and the filtrate (desired material) was collected. The crude material was absorbed onto a plug of silica gel and purified by chromatography through a Interchim (25 micron) silica-gel column (40 grams), eluting with a gradient of 0-45% EtOAc/heptane, to afford 6,7-dichloro-1-(4,6-diisopropyl-2-(2-methoxyethoxy)pyrimidin-5-yl)pyrido[2,3-d]pyrimidine-2,4(1H,3H)-dione (0.12 g, 0.26 mmol, 29.9% yield) as white solid. 1H NMR (400 MHz, DMSO-d6) δ 12.29 (s, 1H) 8.59 (s, 1H) 4.45-4.55 (m, 2H) 3.71-3.77 (m, 2H) 3.33-3.35 (m, 3H) 2.81-2.92 (m, 2H) 1.07 (d, J=6.63 Hz, 6H) 0.97 (d, J=6.63 Hz, 6H). m/z (ESI, +ve ion): 468.0 (M+H)$^+$.

Step 4. 6-Chloro-1-(4,6-diisopropyl-2-(2-methoxyethoxy)pyrimidin-5-yl)-7-(2-fluorophenyl)pyrido[2,3-d]pyrimidine-2,4(1H,3H)-dione To a 100-mL round-bottomed flask was added 6,7-dichloro-1-(4,6-diisopropyl-2-(2-methoxyethoxy)pyrimidin-5-yl)pyrido[2,3-d]pyrimidine-2,4(1H,3H)-dione (0.24 g, 0.51 mmol) and potassium acetate (0.15 g, 1.53 mmol) in 1,4-dioxane (3.31 mL). The reaction mixture was deoxygenated by bubbling (N$_2$) gas into the mixture for 5 min. Then (1,1'-bis(diphenylphosphino) ferrocene) dichloropalladium (0.03 g, 0.05 mmol) was added to the reaction mixture. The reaction mixture was stirred and heated at 95° C. for 10 min. Then 2-fluorophenylboronic acid (0.08 g, 0.61 mmol), followed by water (0.05 mL) was added to the reaction mixture. The overall mixture was allowed to stir at 95° C. for 2 h. The reaction mixture was diluted with sat. aq. NH$_4$Cl and EtOAc. The layers were separated and the aqueous layer was extracted with EtOAc. The combined organic extracts were dried over MgSO$_4$, filtered and concentrated in vacuo. The crude material was absorbed onto a plug of silica gel and purified by chromatography through a Interchim (25 micron) silica-gel column (40 grams), eluting with a gradient of 0-10% MeOH/DCM, to afford 6-chloro-1-(4,6-diisopropyl-2-(2-methoxyethoxy)pyrimidin-5-yl)-7-(2-fluorophenyl)pyrido[2,3-d]pyrimidine-2,4(1H,3H)-dione (0.22 g, 0.42 mmol, 83% yield) as tan solid. $^1$H NMR (400 MHz, DMSO-d$_6$) δ 12.24 (br s, 1H) 8.57 (s, 1H) 7.47-7.55 (m, 1H) 7.25-7.35 (m, 2H) 7.17-7.23 (m, 1H) 4.39-4.49 (m, 2H) 3.63-3.73 (m, 2H) 3.29-3.30 (m, 3H) 2.80-2.94 (m, 2H) 1.08 (s, 6H) 0.91 (d, J=6.63 Hz, 6H). m/z (ESI, +ve ion): 528.0 (M+H)$^+$.

Step 5. tert-Butyl (2R,5S)-4-(6-chloro-1-(4,6-diisopropyl-2-(2-methoxyethoxy)pyrimidin-5-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added 6-chloro-1-(4,6-diisopropyl-2-(2-methoxyethoxy)pyrimidin-5-yl)-7-(2-fluorophenyl)pyrido[2,3-d]pyrimidine-2,4(1H,3H)-dione (0.22 g, 0.41 mmol) and N,N'-diisopropylethylamine (0.09 mL, 0.54 mmol) in acetonitrile (2.08 mL). Then phosphorous oxychloride (0.04 mL, 0.50 mmol) was added slowly to the reaction mixture. The flask was fitted with a Findenser, then the mixture was stirred and heated at 80° C., while under an inert (N2) atmosphere for 45 min. The reaction mixture was removed from the heat bath and allowed to cool to ambient temperature.

The reaction mixture was cooled to 0° C. with a wet ice/water bath, while stirred. Then DIPEA (0.5 mL) was added slowly to the reaction mixture. Then a mixture of (2R,5S)-1-Boc-2,5-dimethylpiperazine (0.11 g, 0.52 mmol) in MeCN (1 mL) was added slowly to the reaction mixture. The ice bath was removed and the overall mixture was allowed to slowly warm to ambient temperature over 1 h. Another aliquot of DIPEA (0.6 mL) and (2R,5S)-1-Boc-2,5-dimethylpiperazine (0.11 g, 0.52 mmol) in MeCN (2 mL)

was added to the mixture, then allowed the mixture to stir an additional 10 min. The mixture was diluted with EtOAc and sat. aq. NH₄C then the layers were separated. The aqueous layer was extracted with EtOAc. The combined organic extracts were dried over MgSO4, filtered and concentrated in vacuo. The crude material was absorbed onto a plug of silica gel and purified by chromatography through a Interchim (25 micron) silica-gel column (40 grams), eluting with a gradient of 0-5% MeOH/DCM, to afford tert-butyl (2R,5S)-4-(6-chloro-1-(4,6-diisopropyl-2-(2-methoxyethoxy) pyrimidin-5-yl)-7-(2-fluorophenyl)-2-oxo-1,2-dihydropyrido[2,3-d]pyrimidin-4-yl)-2,5-dimethylpiperazine-1-carboxylate (0.24 g, 0.33 mmol, 80% yield) as tan solid. ¹H NMR (400 MHz, DMSO-d₆) δ 8.44 (s, 1H) 7.48-7.56 (m, 1H) 7.31 (br d, J=7.88 Hz, 2H) 7.17-7.25 (m, 1H) 4.82 (br s, 1H) 4.34-4.49 (m, 2H) 4.15 (br d, J=13.48 Hz, 1H) 3.86 (br s, 1H) 3.50-3.75 (m, 5H) 2.91-3.07 (m, 2H) 1.44-1.47 (m, 6H) 1.39 (s, 9H) 1.32-1.36 (m, 2H) 1.15-1.20 (m, 3H) 1.04-1.12 (m, 10H). m/z (ESI, +ve ion): 724.1 (M+H)⁺.

Step 6. 4-((2S,5R)-4-Acryloyl-2,5-dimethylpiperazin-1-yl)-6-chloro-1-(4,6-diisopropyl-2-(2-methoxyethoxy)pyrimidin-5-yl)-7-(2-fluorophenyl) pyrido[2,3-d]pyrimidin-2(1H)-one To a 100-mL round-bottomed flask was added tert-butyl (2R,5S)-4-(6-chloro-1-(4,6-diisopropyl-2-(2-methoxyethoxy)pyrimidin-5-yl)-7-(2-fluorophenyl)-2-oxo-1,2-dihydropyrido[2,3-d]pyrimidin-4-yl)-2,5-dimethylpiperazine-1-carboxylate (0.24 g, 0.33 mmol) and trifluoroacetic acid (0.24 mL, 3.31 mmol) in 1,2-dichloroethane (3.92 mL). The reaction mixture was stirred and heated at 70° C. for 2 h, while under an inert (N₂) atmosphere. The reaction mixture was concentrated in vacuo. This material was carried directly into the next step of the synthesis, without further purification The previous residue was diluted with DCM (4 mL), then the reaction mixture was cooled to 0° C. with a wet ice bath. Then N,N'-diisopropylethylamine (0.69 mL, 3.98 mmol) was added to the reaction mixture and allowed the mixture to stir 2 min. Then acryloyl chloride (0.02 mL, 0.3 mmol was added to the mixture dropwise. The mixture was diluted with DCM and sat. aq. NaHCO₃, then the layers were separated. The aqueous layer was extracted with DCM. The combined organic extracts were dried over MgSO₄, filtered and concentrated in vacuo. The crude material was absorbed onto a plug of silica gel and purified by chromatography through a Interchim (25 micron) silica-gel column (40 grams), eluting with a gradient of 0-4% MeOH/CHCl₃. This afforded 4-((2S,5R)-4-acryloyl-2,5-dimethylpiperazin-1-yl)-6-chloro-1-(4,6-diisopropyl-2-(2-methoxyethoxy)pyrimidin-5-yl)-7-(2-fluorophenyl)pyrido[2,3-d]pyrimidin-2 (1H)-one (0.07 g, 0.10 mmol, 32.0% yield) as white solid. ¹H NMR (400 MHz, DMSO-d₆) δ 8.48 (d, J=4.35 Hz, 1H) 7.50-7.57 (m, 1H) 7.20-7.36 (m, 3H) 6.84 (td, J=17.10, 10.57 Hz, 1H) 6.20 (dd, J=16.59, 1.87 Hz, 1H) 5.73-5.79 (m, 1H) 4.74-4.95 (m, 2H) 4.38-4.55 (m, 3H) 4.12-4.28 (m, 1H) 3.80-3.95 (m, 2H) 3.66-3.71 (m, 2H) 3.29-3.31 (m, 3H) 2.55-2.70 (m, 2H) 1.31-1.39 (m, 3H) 1.26 (br d, J=6.63 Hz, 1H) 1.19 (d, J=6.63 Hz, 2H) 1.06 (dd, J=6.63, 3.52 Hz, 6H) 0.92 (br d, J=6.63 Hz, 6H). m/z (ESI, +ve ion): 678.4 (M+H)⁺.

Example 157

4-((2S,5R)-4-Acryloyl-2,5-dimethylpiperazin-1-yl)-6-chloro-1-(2-(2-(dimethylamino)ethoxy)-4,6-diisopropylpyrimidin-5-yl)-7-(2-fluorophenyl)pyrido[2,3-d]pyrimidin-2(1H)-one

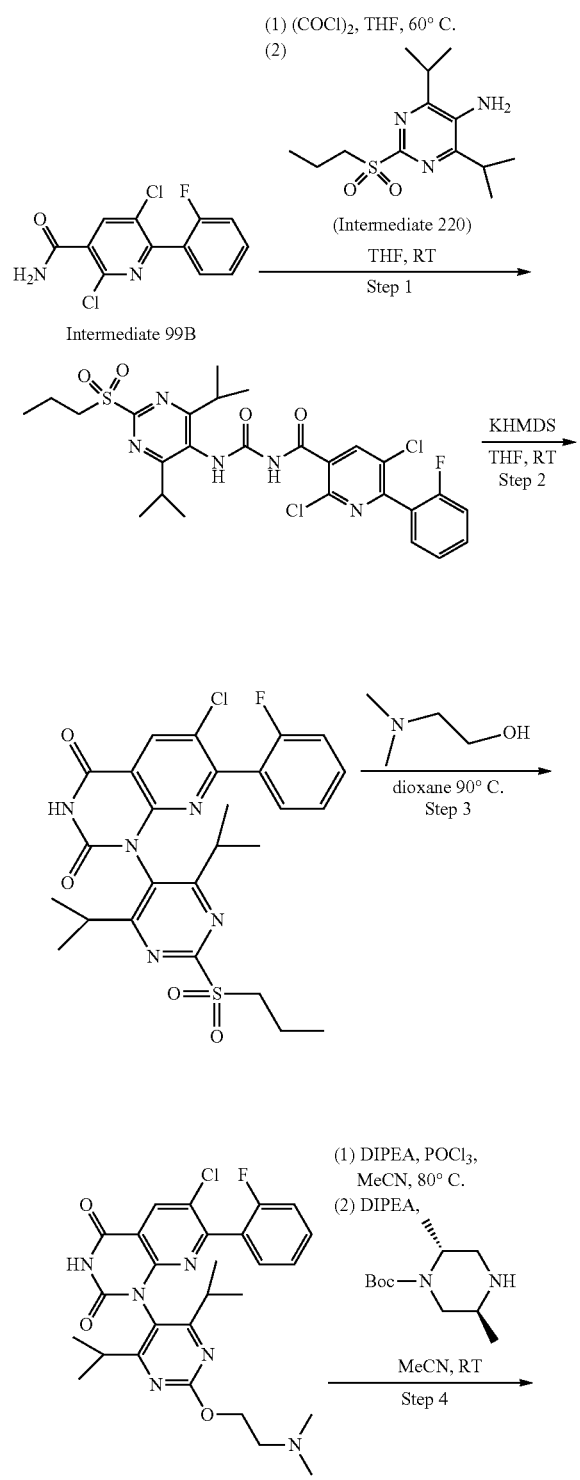

-continued

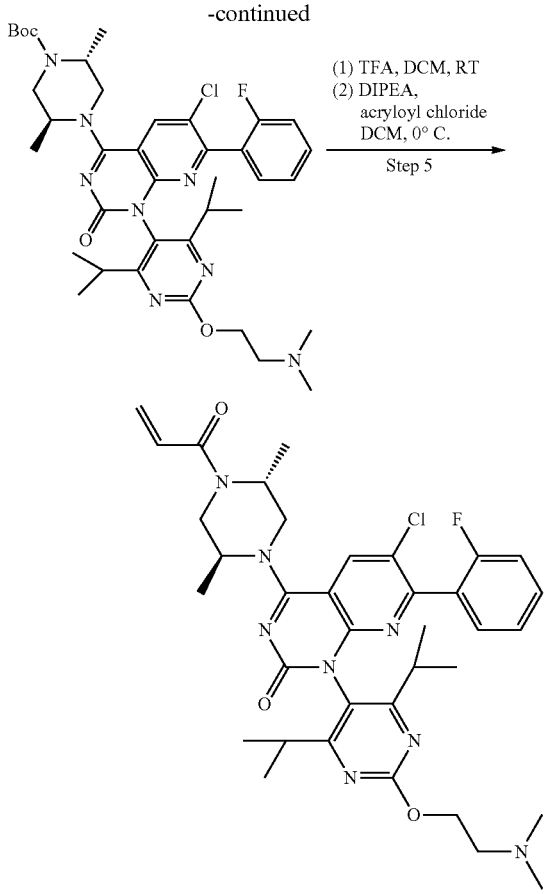

(1) TFA, DCM, RT
(2) DIPEA,
acryloyl chloride
DCM, 0° C.
Step 5

Step 1. 2,5-Dichloro-N-((4,6-diisopropyl-2-(propylsulfonyl)pyrimidin-5-yl)carbamoyl)-6-(2-fluorophenyl)nicotinamide To a 100-mL round-bottomed flask was added 2,5-dichloro-6-(2-fluorophenyl)nicotinamiide (Intermediate 99B, 1.00 g, 3.30 mmol) and oxalyl chloride (2.47 mL, 4.95 mmol) in tetrahydrofuran (16.49 mL). The flask was fitted with a Findenser. and mixture was stirred and heated at 80° C. for 45 min. The reaction mixture was concentrated in vacuo. The crude mixture was carried into the next step of the synthesis, without further purification to prevent decomposition.

To a 100-mL round-bottomed flask was added (2,5-dichloro-6-(2-fluorophenyl)nicotinoyl)carbamoyl isocyanate (crude material from previous step) in tetrahydrofuran (16.55 mL). The reaction mixture was cooled to −10° C. with a dilute acetone/dry ice bath, then a solution of 4,6-diisopropyl-2-(propylsulfonyl)pyrimidin-5-amine (Intermediate 220, 0.98 g, 3.46 mmol) in THF (3 mL) was added to the reaction mixture. The reaction mixture was allowed to stir under an inert (N2) atmosphere for 1 h. The reaction mixture was concentrated in vacuo. The crude material was triturated from EtOAc and heptane, then the solids were collected by filtration. The solids were washed with heptane. This afforded 2,5-dichloro-N-((4,6-diisopropyl-2-(propylsulfonyl)pyrimidin-5-yl)carbamoyl)-6-(2-fluorophenyl)nicotinamide (1.705 g, 2.86 mmol, 87% yield) as light-yellow solid. $^1$H NMR (400 MHz, DMSO-$d_6$) δ 11.56 (br s, 1H) 9.94 (br s, 1H) 8.64 (br s, 1H) 7.62 (s, 1H) 7.57 (br s, 1H) 7.40 (br s, 2H) 3.57-3.80 (m, 3H) 1.79 (br s, 2H) 1.22 (br s, 12H) 1.03 (br s, 4H). m/z (ESI, +ve ion): 596.0 (M+H)$^+$.

Step 2. 6-Chloro-1-(4,6-diisopropyl-2-(propylsulfonyl)pyrimidin-5-yl)-7-(2-fluorophenyl)pyrido[2,3-d]pyrimidine-2,4(1H,3H)-dione To a 150-mL round-bottomed flask was added 2,5-dichloro-N-((4,6-diisopropyl-2-(propylsulfonyl)pyrimidin-5-yl)carbamoyl)-6-(2-fluorophenyl)nicotinamide (1.48 g, 2.48 mmol) in tetrahydrofuran (12.44 mL). Then potassium bis(trimethylsilyl)amide, 1M solution in tetrahydrofuran (3.11 mL, 3.10 mmol) was added via an addition funnel dropwise to the reaction mixture over 5 min. The reaction mixture was allowed to stir under an inert (N2) atmosphere for 1 h. More KHMDS (0.5 eq; 2 mL) was added dropwise to the reaction mixture. The reaction mixture was quenched with sat. aq. NH$_4$Cl (50 mL), then the mixture was diluted with 3:1 EtOAc/MeOH and brine solution. The layers were separated and the aqueous layer was extracted with EtOAc. The combined organic extracts were dried over MgSO$_4$, filtered and concentrated in vacuo. This afforded 6-chloro-1-(4,6-diisopropyl-2-(propylsulfonyl)pyrimidin-5-yl)-7-(2-fluorophenyl)pyrido[2,3-d]pyrimidine-2,4(1H,3H)-dione (1.34 g, 2.39 mmol, 97% yield) as light-yellow solid. $^1$H NMR (400 MHz, DMSO-$d_6$) δ 8.60-8.64 (m, 1H) 7.48-7.54 (m, 1H) 7.23-7.33 (m, 3H) 7.15-7.21 (m, 1H) 3.61-3.67 (m, 2H) 3.13-3.19 (m, 2H) 1.66-1.74 (m, 2H) 1.21-1.23 (m, 3H) 1.13 (d, J=6.63 Hz, 6H) 0.96 (d, J=6.63 Hz, 6H). m/z (ESI, +ve ion): 560.0 (M+H)$^+$.

Step 3. 6-Chloro-1-(2-(2-(dimethylamino)ethoxy)-4,6-diisopropylpyrimidin-5-yl)-7-(2-fluorophenyl)pyrido[2,3-d]pyrimidine-2,4(1H,3H)-dione A resealable vial was charged with 6-chloro-1-(4,6-diisopropyl-2-(propylsulfonyl)pyrimidin-5-yl)-7-(2-fluorophenyl)pyrido[2,3-d]pyrimidine-2,4(1H,3H)-dione (0.53 g, 0.94 mmol) and N,N'-dimethylethanolamine (1.91 mL, 18.93 mmol) in 1,4-dioxane (9.46 mL). The vial was sealed, then the reaction mixture was stirred and heated at 90° C. for 16 h. The reaction mixture was concentrated in vacuo. The crude material was absorbed onto a plug of silica gel and purified by chromatography through a Interchim (25 micron) silica-gel column (80 grams), eluting with a gradient of 0-20% MeOH/DCM, to afford 6-chloro-1-(2-(2-(dimethylamino)ethoxy)-4,6-diisopropylpyrimidin-5-yl)-7-(2-fluorophenyl)pyrido[2,3-d]pyrimidine-2,4(1H,3H)-dione (0.255 g, 0.471 mmol, 49.8% yield) as light-yellow solid. $^1$H NMR (400 MHz, DMSO-$d_6$) δ 12.03-12.41 (m, 1H) 8.57 (s, 1H) 7.48-7.55 (m, 1H) 7.26-7.35 (m, 2H) 7.17-7.23 (m, 1H) 4.39 (t, J=5.91 Hz, 2H) 2.88 (quin, J=6.63 Hz, 2H) 2.64 (br t, J=5.80 Hz, 2H) 2.22 (s, 6H) 1.07 (d, J=6.63 Hz, 6H) 0.91 (d, J=6.63 Hz, 6H). m/z (ESI, +ve ion): 541.1 (M+H)$^+$.

Step 4. tert-Butyl (2R,5)-4-(6-chloro-1-(2-(2-(dimethylamino)ethoxy)-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added 6-chloro-1-(2-(2-(dimethylamino)ethoxy)-4,6-diisopropylpyrimidin-5-yl)-7-(2-fluorophenyl)pyrido[2,3-d]pyrimidine-2,4(1H,3H)-dione (0.22 g, 0.40 mmol) and N,N'-diisopropylethylamine (0.18 mL, 1.05 mmol) in acetonitrile (4.07 mL). Then phosphorous oxychloride (0.04 mL, 0.48 mmol) was added to the reaction mixture, then the mixture was heated and stirred at 80° C. for 15 min, while under an inert (N₂) atmosphere. The reaction mixture was removed from the heat bath and allowed to cool to rt.

The previous reaction mixture was cooled to 0° C. with a wet ice/water bath. Then DIPEA (2 mL) was added dropwise to the reaction mixture. Then a solution of (2R,5S)-tert-butyl 2,5-dimethylpiperazine-1-carboxylate (0.13 g, 0.61 mmol) in MeCN (1 mL) was added dropwise to the reaction mixture. The ice bath was removed and the mixture was allowed to warm to rt over 20 min. More DIPEA (2 mL) and (2R,5S)-tert-butyl 2,5-dimethylpiperazine-1-carboxylate (0.13 g, 0.61 mmol) was added to the reaction mixture and stirred an additional 10 min. The reaction mixture was diluted with EtOAc and sat. aq. NH₄Cl. The aqueous layer was extracted with EtOAc. The combined organic extracts were dried over MgSO4, filtered and concentrated in vacuo. The crude material was absorbed onto a plug of silica gel and purified by chromatography through a Interchim (25 micron) silica-gel column (80 grams), eluting with a gradient of 0-25% 2M NH3.MeOH in CH2CL2, to afford tert-butyl (2R,5S)-4-(6-chloro-1-(2-(2-(dimethylamino)ethoxy)-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate as tan solid. The crude material (0.450 grams) was carried into the next step of the synthesis, without further purification. m/z (ESI, +ve ion): 737.2 (M+H)⁺.

Step 5. 4-((2S,5R)-4-Acryloyl-2,5-dimethylpiperazin-1-yl)-6-chloro-1-(2-(2-(dimethylamino)ethoxy)-4,6-diisopropylpyrimidin-5-yl)-7-(2-fluorophenyl) pyrido[2,3-d]pyrimidin-2(1H)-one To a 100-mL round-bottomed flask was added tert-butyl (2R,5S)-4-(6-chloro-1-(2-(2-(dimethylamino)ethoxy)-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.30 g, 0.40 mmol) and trifluoroacetic acid (0.30 mL, 4.07 mmol) in 1,2-dichloroethane (4.07 mL). The reaction mixture was stirred and heated at 60° C. for 2 h, while under an inert (N₂) atmosphere. The reaction mixture was concentrated in vacuo. This material was carried directly into the next step of the synthesis, without further purification.

The previous residue was diluted with DCM (4 mL), the reaction mixture was cooled to 0° C. with a wet ice bath. Then N,N'-diisopropylethylamine (0.85 mL, 4.88 mmol) was added to the reaction mixture and allowed the mixture to stir 2 min. Then acryloyl chloride (1.1M in THF) (0.37 mL, 0.40 mmol) was added to the mixture dropwise. The reaction mixture was diluted with DCM and sat. aq. NaHCO₃, then the layers were separated. The aqueous layer was extracted with DCM. The combined organic extracts were dried over MgSO₄, filtered and concentrated in vacuo. The crude material was absorbed onto a plug of silica gel and purified by chromatography through a Interchim (25 micron) silica-gel column (40 grams), eluting with a gradient of 0-25% MeOH/DCM. This afforded 4-((2S,5R)-4-acryloyl-2,5-dimethylpiperazin-1-yl)-6-chloro-1-(2-(2-(dimethylamino)ethoxy)-4,6-diisopropylpyrimidin-5-yl)-7-(2-fluorophenyl)pyrido[2,3-d]pyrimidin-2(1H)-one (0.110 g, 0.159 mmol, 39.1% yield) as tan solid. ¹H NMR (400 MHz, DMSO-d₆) δ 8.48 (br d, J=4.35 Hz, 1H) 7.48-7.58 (m, 1H) 7.20-7.36 (m, 3H) 6.76-6.91 (m, 1H) 6.16-6.23 (m, 1H) 5.71-5.80 (m, 1H) 4.81-4.93 (m, 1H) 4.57-4.63 (m, 2H) 4.42-4.53 (m, 1H) 4.13-4.24 (m, 1H) 3.79-3.94 (m, 2H) 3.39-3.45 (m, 2H) 2.77 (s, 6H) 2.61-2.73 (m, 2H) 1.34 (br t, J=5.70 Hz, 3H) 1.23-1.23 (m, 2H) 1.16-1.20 (m, 2H) 1.07 (dd, J=6.53, 4.25 Hz, 6H) 0.93 (dd, J=6.53, 3.63 Hz, 6H). m/z (ESI, +ve ion): 691.3 (M+H)⁺.

Example 158

4-((2S,5R)-4-Acryloyl-2,5-dimethylpiperazin-1-yl)-6-chloro-1-(4,6-diisopropyl-2-(propylsulfonyl)pyrimidin-5-yl)-7-(2-fluorophenyl)pyrido[2,3-d]pyrimidin-2(1H)-one

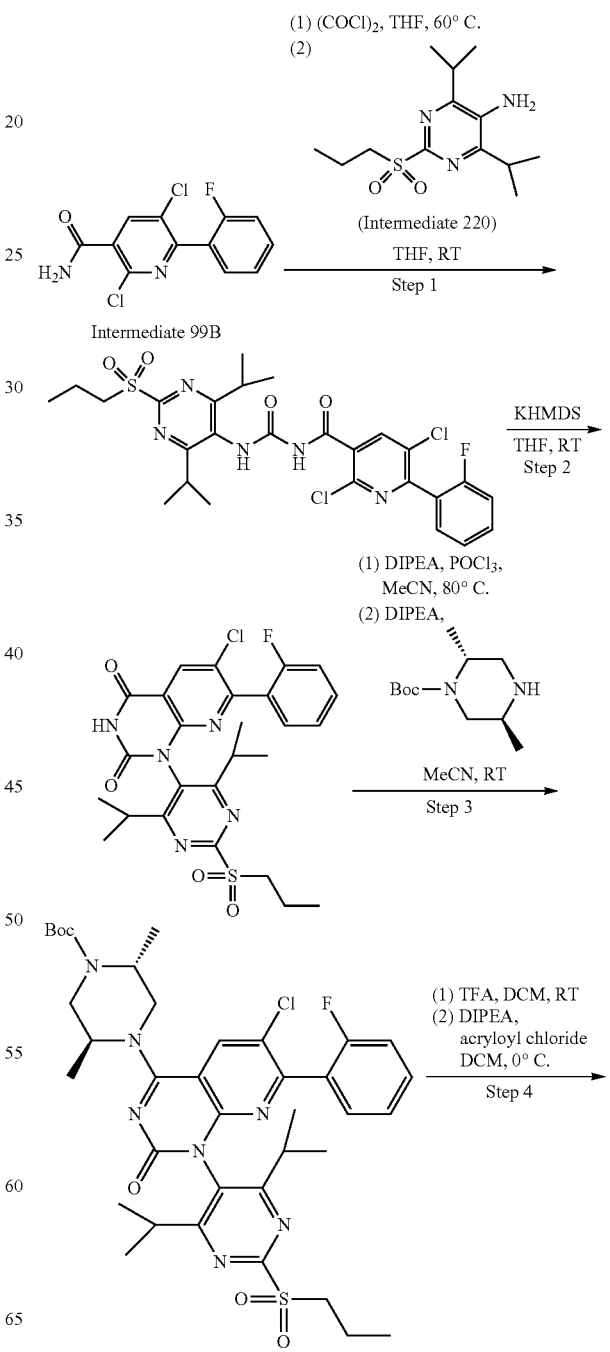

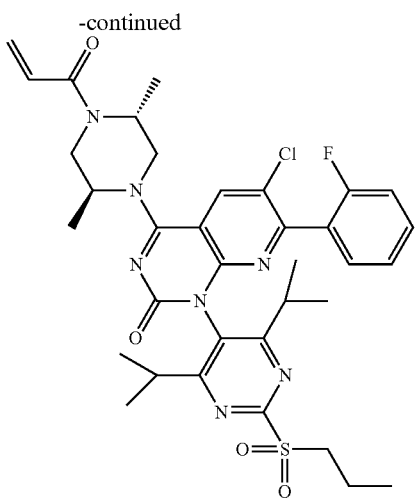

Step 1. 2,5-Dichloro-N-((4,6-diisopropyl-2-(propylsulfonyl)pyrimidin-5-yl)carbamoyl)-6-(2-fluorophenyl)nicotinamide To a 100-mL round-bottomed flask was added 2,5-dichloro-6-(2-fluorophenyl)nicotinamide (Intermediate 99B, 1.00 g, 3.30 mmol) and oxalyl chloride (2.47 mL, 4.95 mmol) in tetrahydrofuran (16.49 mL). The flask was fitted with a Findenser, and mixture was stirred and heated at 80° C. for 45 min. The reaction mixture was concentrated in vacuo. The crude mixture was carried into the next step of the synthesis, without further purification to prevent decomposition.

To a 100-mL round-bottomed flask was added (2,5-dichloro-6-(2-fluorophenyl)nicotinoyl)carbamoyl isocyanate (crude material from previous step) in tetrahydrofuran (16.49 mL). The reaction mixture was cooled to −10° C. with a dilute acetone/dry ice bath, then a solution of 4,6-diisopropyl-2-(propylsulfonyl)pyrimidin-5-amine (Intermediate 220, 0.98 g, 3.46 mmol) in THF (3 mL) was added to the reaction mixture. The reaction mixture was allowed to stir under an inert ($N_2$) atmosphere for 1 h. The reaction mixture was concentrated in vacuo. The crude material was triturated from EtOAc and heptane, then the solids were collected by filtration. The solids were washed with heptane. This afforded 2,5-dichloro-N-((4,6-diisopropyl-2-(propylsulfonyl)pyrimidin-5-yl)carbamoyl)-6-(2-fluorophenyl)nicotinamide (1.70 g, 2.86 mmol, 87% yield) as light-yellow solid. $^1$H NMR (400 MHz, DMSO-$d_6$) δ 11.56 (br s, 1H) 9.94 (br s, 1H) 8.64 (br s, 1H) 7.62 (s, 1H) 7.57 (br s, 1H) 7.40 (br s, 2H) 3.57-3.80 (m, 3H) 1.79 (br s, 2H) 1.22 (br s, 12H) 1.03 (br s, 4H). m/z (ESI, +ve ion): 596.0 (M+H)$^+$.

Step 2. 6-Chloro-1-(4,6-diisopropyl-2-(propylsulfonyl)pyrimidin-5-yl)-7-(2-fluorophenyl)pyrido[2,3-d]pyrimidine-2,4(1H,3H)-dione To a 150-mL round-bottomed flask was added 2,5-dichloro-N-((4,6-diisopropyl-2-(propylsulfonyl)pyrimidin-5-yl)carbamoyl)-6-(2-fluorophenyl)nicotinamide (1.48 g, 2.48 mmol) in tetrahydrofuran (12.41 mL). Then potassium bis(trimethylsilyl)amide, 1M solution in tetrahydrofuran (3.10 mL, 3.10 mmol) was added via an addition funnel dropwise to the reaction mixture over 5 min. The reaction mixture was allowed to stir under an inert ($N_2$) atmosphere for 1 h. More KHMDS (0.5 eq; 2 mL) was added dropwise to the reaction mixture. The reaction mixture was quenched with sat. aq. $NH_4Cl$ (50 mL), then the mixture was diluted with 3:1 EtOAc/MeOH and brine solution. The layers were separated and the aqueous layer was extracted with EtOAc. The combined organic extracts were dried over $MgSO_4$, filtered and concentrated in vacuo. This afforded 6-chloro-1-(4,6-diisopropyl-2-(propylsulfonyl)pyrimidin-5-yl)-7-(2-fluorophenyl)pyrido[2,3-d]pyrimidine-2,4(1H,3H)-dione (1.34 g, 2.39 mmol, 97% yield) as light-yellow solid. $^1$H NMR (400 MHz, DMSO-$d_6$) δ 8.60-8.64 (m, 1H) 7.48-7.54 (m, 1H) 7.23-7.33 (m, 3H) 7.15-7.21 (m, 1H) 3.61-3.67 (m, 2H) 3.13-3.19 (m, 2H) 1.66-1.74 (m, 2H) 1.21-1.23 (m, 3H) 1.13 (d, J=6.63 Hz, 6H) 0.96 (d, J=6.63 Hz, 6H). m/z (ESI, +ve ion): 560.0 (M+H)$^+$.

Step 3. tert-Butyl (2R,5S)-4-(6-chloro-1-(4,6-diisopropyl-2-(propylsulfonyl)pyrimidin-5-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added 6-chloro-1-(4,6-diisopropyl-2-(propylsulfonyl)pyrimidin-5-yl)-7-(2-fluorophenyl)pyrido[2,3-d]pyrimidine-2,4(1H,3H)-dione (0.35 g, 0.62 mmol) and N,N'-diisopropylethylamine (0.14 mL, 0.81 mmol) in acetonitrile (3.12 mL). Then phosphorous oxychloride (0.07 mL, 0.75 mmol) was added slowly to the reaction mixture. The flask was fitted with a Findenser, then the mixture was stirred and heated at 80° C. while under an inert (N2) atmosphere for 45 min. Another aliquot of N,N'-diisopropylethylamine (0.14 mL, 0.81 mmol) and phosphorous oxychloride (0.07 mL, 0.75 mmol) was added to the reaction mixture, then allowed the mixture to stir an additional 10 min. The reaction mixture was removed from the heat bath and allowed to cool to ambient temperature.

The previous reaction mixture was cooled to 0° C. with a wet ice/water bath, while stirred. Then DIPEA (2 mL) was added slowly to the mixture. Then a mixture of (2R,5S)-1-Boc-2,5-dimethylpiperazine (0.33 g, 0.78 mmol) in MeCN (1 mL) was added slowly to the reaction mixture. The ice bath was removed and the overall mixture was allowed to slowly warm to ambient temperature over 10 min. The mixture was diluted with EtOAc and sat. aq. $NH_4Cl$, then the layers were separated. The aqueous layer was extracted with EtOAc. The combined organic extracts were dried over MgSO4, filtered and concentrated in vacuo. The crude material was absorbed onto a plug of silica gel and purified by chromatography through a Interchim (25 micron) silica-gel column (40 grams), eluting with a gradient of 0-8% MeOH/DCM, to afford tert-butyl (2R,5S)-4-(6-chloro-1-(4,6-diisopropyl-2-(propylsulfonyl)pyrimidin-5-yl)-7-(2-fluorophenyl)-2-oxo-1,2-dihydropyrido[2,3-d]pyrimidin-4-yl)-2,5-dimethylpiperazine-1-carboxylate (0.42 g, 0.55 mmol, 89% yield) as tan solid. m/z (ESI, +ve ion): 756.0 (M+H)$^+$.

Step 4. 4-((2S,5R)-4-Acryloyl-2,5-dimethylpiperazin-1-yl)-6-chloro-1-(4,6-diisopropyl-2-(propylsulfonyl)pyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(4,6-diisopropyl-2-(propylsulfonyl)pyrimidin-5-yl)-7-(2-fluorophenyl)-2-oxo-1,2-dihydropyrido[2,3-d]pyrimidin-4-yl)-2,5-dimethylpiperazine-1-carboxylate (0.20 g, 0.26 mmol) and trifluoroacetic acid (0.19 mL, 2.64 mmol) in 1,2-dichloroethane (2.03 mL). The reaction mixture was stirred and heated at 60° C. for 2 h, while under an inert ($N_2$) atmosphere. The reaction mixture was concentrated in vacuo. This material was carried directly into the next step of the synthesis, without further purification.

The previous residue was diluted with DCM (4 mL), then the reaction mixture was cooled to 0° C. with a wet ice bath. Then N,N'-diisopropylethylamine (0.55 mL, 3.17 mmol) was added to the reaction mixture and allowed the mixture to stir 2 min. Then acryloyl chloride (0.02 mL, 0.26 mmol) was added to the mixture dropwise. The mixture was diluted with DCM and sat. aq. NaHCO$_3$, then the layers were separated. The aqueous layer was extracted with DCM. The combined organic extracts were dried over MgSO$_4$, filtered and concentrated in vacuo. The crude material was absorbed onto a plug of silica gel and purified by chromatography through a Interchim (15 micron) silica-gel column (25 grams), eluting with a gradient of 0-100/o % EtOAc/heptane. This afforded 4-((2S,5R)-4-acryloyl-2,5-dimethylpiperazin-1-yl)-6-chloro-1-(4,6-diisopropyl-2-(propylsulfonyl)pyrimidin-5-yl)-7-(2-fluorophenyl)pyrido[2,3-d]pyrimidin-2(1H)-one (0.023 g, 0.032 mmol, 12.25% yield) as light-yellow solid. $^1$H NMR (400 MHz, DMSO-d$_6$) δ 8.51 (d, J=7.46 Hz, 1H) 7.48-7.55 (m, 1H) 7.17-7.34 (m, 3H) 6.84 (ddd, J=19.95, 16.84, 10.47 Hz, 1H) 6.19 (br d, J=16.79 Hz, 1H) 5.73-5.79 (m, 1H) 4.76-4.98 (m, 2H) 4.14-4.34 (m, 2H) 3.80-3.94 (m, 2H) 3.60-3.66 (m, 2H) 2.79-2.96 (m, 2H) 1.71 (sxt, J=7.51 Hz, 2H) 1.33-1.40 (m, 3H) 1.18-1.29 (m, 3H) 1.10-1.14 (m, 6H) 0.90-1.00 (m, 9H). m/z (ESI, +ve ion): 710.0 (M+H)$^+$.

Example 159

4-((2S,5R)-4-Acryloyl-2,5-dimethylpiperazin-1-yl)-6-chloro-1-(4,6-diisopropyl-2-vinylpyrimidin-5-yl)-7-(2-fluorophenyl)pyrido[2,3-d]pyrimidin-2(1H)-one

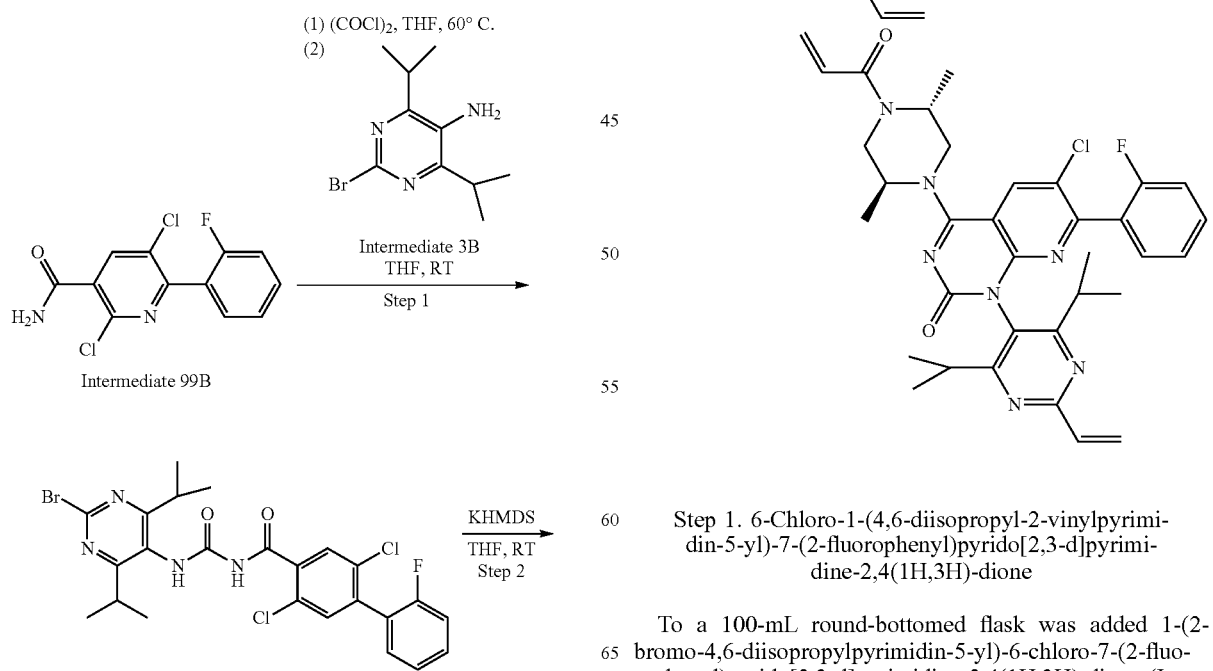

Step 1. 6-Chloro-1-(4,6-diisopropyl-2-vinylpyrimidin-5-yl)-7-(2-fluorophenyl)pyrido[2,3-d]pyrimidine-2,4(1H,3H)-dione To a 100-mL round-bottomed flask was added 1-(2-bromo-4,6-diisopropylpyrimidin-5-yl)-6-chloro-7-(2-fluorophenyl)pyrido[2,3-d]pyrimidine-2,4(1H,3H)-dione (Intermediate 231, 0.17 g, 0.31 mmol), sodium carbonate (0.10 g, 0.95 mmol) and vinylboronic acid pinacol ester (0.10 mL, 0.63 mmol) in 1,4-dioxane (2.32 mL)-water (0.55 mL) (4:1). The reaction mixture was deoxygenated by bubbling argong (gas) into the mixture for 5 min. Then (1,1'-bis(diphenylphosphino) ferrocene) dichloropalladium (0.02 g, 0.03 mmol) was added to the reaction mixture. The reaction mixture was stirred and heated at 90° C., while under an inert (N2) atmosphere for 16 h. The reaction mixture was allowed to cool to t, then the mixture was diluted was EtOAc and sat. aq. NH$_4$Cl. The layers were separated and the aqueous layer was extracted with EtOAc. The combined organic extracts were dried over MgSO$_4$, filtered and concentrated in vacuo. The crude material was absorbed onto a plug of silica gel and purified by chromatography through a Interchim (25 micron) silica-gel column (25 grams), eluting with a gradient of 0-50% EtOAc/heptane, to afford 6-chloro-1-(4,6-diisopropyl-2-vinylpyrimidin-5-yl)-7-(2-fluorophenyl)pyrido[2,3-d]pyrimidine-2,4(1H,3H)-dione (0.10 g, 0.21 mmol, 68.6% yield) as white solid. $^1$H NMR (400 MHz, DMSO-d$_6$) δ 12.28 (s, 1H) 8.59 (s, 1H) 7.47-7.53 (m, 1H) 7.25-7.33 (m, 2H) 7.18 (td, J=7.36, 1.66 Hz, 1H) 6.80 (dd, J=17.21, 10.37 Hz, 1H) 6.57 (dd, J=17.21, 2.07 Hz, 1H) 5.72-5.78 (m, 1H) 2.90-3.01 (m, 2H) 1.10 (d, J=6.63 Hz, 6H) 0.94 (d, J=6.63 Hz, 6H). m/z (ESI, +ve ion): 480.0 (M+H)$^+$.

Step 2. tert-Butyl (2R,5S)-4-(6-chloro-1-(4,6-diisopropyl-2-vinylpyrimidin-5-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added 6-chloro-1-(4,6-diisopropyl-2-vinylpyrimidin-5-yl)-7-(2-fluorophenyl)pyrido[2,3-d]pyrimidine-2,4(1H,3H)-dione (0.10 g, 0.20 mmol) and N,N-diisopropylethylamine (0.04 mL, 0.27 mmol) in acetonitrile (2.08 mL). Then phosphorous oxychloride (0.02 mL, 0.25 mmol) was added to the reaction mixture, then the mixture was heated and stirred at 80° C. for 30 min, while under an inert (N$_2$) atmosphere. The reaction mixture was removed from the heat bath and allowed to cool to rt.

The reaction mixture was cooled to 0° C. with a wet ice/water bath. Then DIPEA (0.7 mL) was added dropwise to the reaction mixture. Then a solution of (2R,5S)-1-Boc-2,5-dimethylpiperazine (0.067 g, 0.313 mmol) in MeCN (1 mL) was added dropwise to the reaction mixture. The ice bath was removed and the mixture was allowed to warm to rt. More DIPEA (0.7 mL) and (2R,5S)-1-Boc-2,5-dimethylpiperazine (0.067 g, 0.313 mmol) was added to the reaction mixture and stirred an additional 10 min. The reaction mixture was diluted with EtOAc and sat. aq. NH$_4$Cl. The aqueous layer was extracted with EtOAc. The combined organic extracts were dried over MgSO4, filtered and concentrated in vacuo. The crude material was absorbed onto a plug of silica gel and purified by chromatography through a Interchim (25 micron) silica-gel column (25 grams), eluting with a gradient of 0-50% EtOAc in CH2CL2, to provide tert-butyl (2R,5S)-4-(6-chloro-1-(4,6-diisopropyl-2-vinylpyrimidin-5-yl)-7-(2-fluorophenyl)-2-oxo-1,2-dihydropyrido[2,3-d]pyrimidin-4-yl)-2,5-dimethylpiperazine-1-carboxylate (0.132 g, 0.195 mmol, 94% yield) as light-yellow solid. m/z (ESI, +ve ion): 676.2 (M+H)$^+$.

Step 3. 4-((2S,5R)-4-Acryloyl-2,5-dimethylpiperazin-1-yl)-6-chloro-1-(4,6-diisopropyl-2-vinylpyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(4,6-diisopropyl-2-vinylpyrimidin-5-yl)-7-(2-fluorophenyl)-2-oxo-1,2-dihydropyrido[2,3-d]pyrimidin-4-yl)-2,5-dimethylpiperazine-1-carboxylate (0.13 g, 0.19 mmol) and trifluoroacetic acid (0.14 mL, 1.92 mmol) in 1,2-dichloroethane (1.92 mL). The reaction mixture was stirred and heated at 60° C. for 2 h, while under an inert (N$_2$) atmosphere. The reaction mixture was concentrated in vacuo. This material was carried directly into the next step of the synthesis, without further purification.

The previous residue was diluted with DCM (4 mL), then the reaction mixture was cooled to 0° C. with a wet ice bath. Then N,N'-diisopropylethylamine (0.40 mL, 2.30 mmol) was added to the reaction mixture and allowed the mixture to stir 2 min. Then acryloyl chloride (0.01 mL, 0.19 mmol) was added to the mixture dropwise. The mixture was diluted with DCM and sat. aq. NaHCO$_3$, then the layers were separated. The aqueous layer was extracted with DCM. The combined organic extracts were dried over MgSO$_4$, filtered and concentrated in vacuo. The crude material was absorbed onto a plug of silica gel and purified by chromatography through a Interchim (15 micron) silica-gel column (25 grams), eluting with a gradient of 0-100% EtOAc/DCM. This afforded 4-((2S,5R)-4-acryloyl-2,5-dimethylpiperazin-1-yl)-6-chloro-1-(4,6-diisopropyl-2-vinylpyrimidin-5-yl)-7-(2-fluorophenyl)pyrido[2,3-d]pyrimidin-2(1H)-one (0.082 g, 0.130 mmol, 67.7% yield) as white solid. $^1$H NMR (400 MHz, DMSO-d$_6$) δ 8.50 (d, J=4.77 Hz, 1H) 7.49-7.55 (m, 1H) 7.19-7.35 (m, 3H) 6.76-6.90 (m, 2H) 6.56 (dd, J=17.31, 1.97 Hz, 1H) 6.20 (dd, J=16.69, 1.97 Hz, 1H) 5.72-5.79 (m, 2H) 4.73-4.99 (m, 2H) 4.21 (q, J=14.31 Hz, 1H) 3.81-3.95 (m, 2H) 2.64-2.78 (m, 2H) 1.36 (t, J=5.60 Hz, 3H) 1.27 (br d, J=6.63 Hz, 2H) 1.20 (d, J=6.84 Hz, 2H) 1.10 (dd, J=6.63, 3.11 Hz, 6H) 0.95 (br d, J=6.63 Hz, 6H). m/z (ESI, +ve ion): 630.2 (M+H)$^+$.

Example 160

4-((2S,5R)-4-Acryloyl-2,5-dimethylpiperazin-1-yl)-6-chloro-1-(2-((dimethylamino)methyl)-4,6-diisopropylpyrimidin-5-yl)-7-(2-fluorophenyl)pyrido[2,3-d]pyrimidin-2(1H)-one

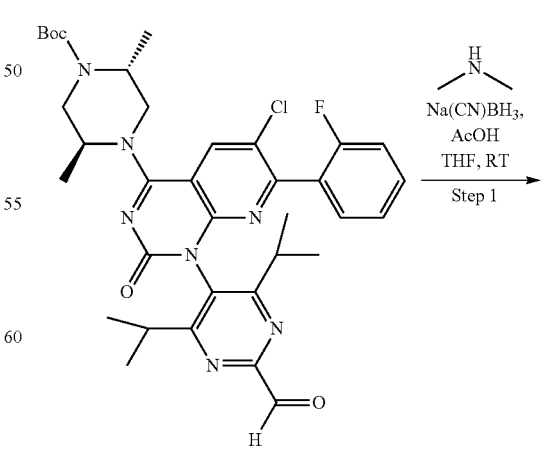

Intermediate 235

-continued

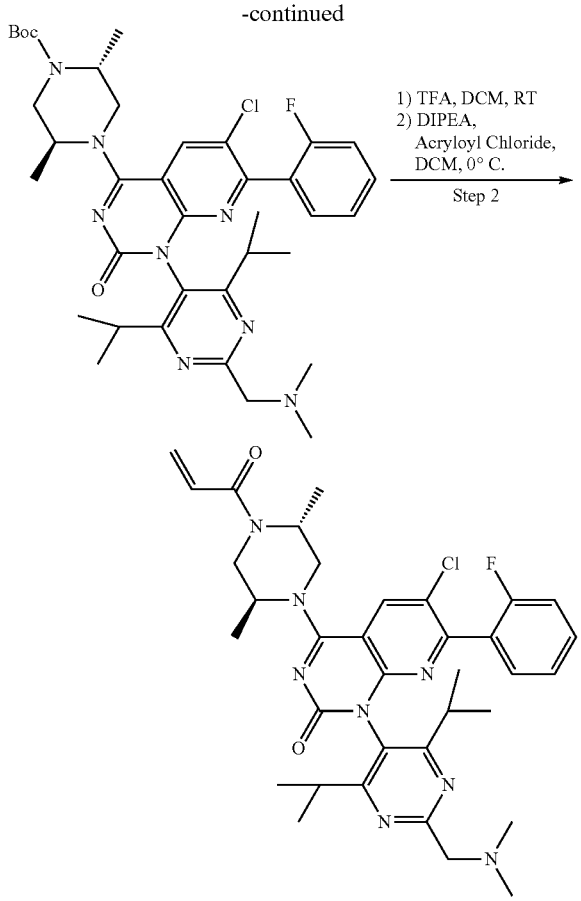

Step 1. tert-Butyl (2R,5S)-4-(6-chloro-1-(2-((dimethylamino)methyl)-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(3-chloro-2-(2-fluorophenyl)-8-(2-formyl-4,6-diisopropylpyrimidin-5-yl)-7-oxo-7,8-dihydro-1,6-naphthyridin-5-yl)-2,5-dimethylpiperazine-1-carboxylate (Intermediate 235, 0.16 g, 0.24 mmol) and dimethylamine (2.0M in THF) (0.18 mL, 0.36 mmol) in tetrahydrofuran (2.43 mL). Then glacial acetic acid (1.2 μL, 0.024 mmol), followed by sodium cyanoborohydride (0.03 mL, 0.73 mmol) was added to the reaction mixture. The overall reaction mixture was allowed to stir at rt, while under an inert (N?) atmosphere for 30 min. The reaction mixture was quenched with MeOH (0.5 mL), then allowed the mixture to stir 5 min. Then the mixture was diluted with EtOAc and sat. aq. NaHCO₃. The layers were separated and the aqueous layer was extracted with EtOAc. The combined organic extracts were dried over MgSO₄, filtered and concentrated in vacuo. The crude material (0.195 grams) was carried into the next step of the synthesis, without further purification. m/z (ESI, +ve ion)⁺: 707.2 (M+H)⁺.

Step 2. 4-((2S,5R)-4-Acryloyl-2,5-dimethylpiperazin-1-yl)-6-chloro-1-(2-((dimethylamino)methyl)-4,6-diisopropylpyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(2-((dimethylamino)methyl)-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.17 g, 0.24 mmol) and trifluoroacetic acid (0.17 mL, 2.40 mmol) in 1,2-dichloroethane (2.40 mL). The reaction mixture was stirred and heated at 60° C. for 20 min. while under an inert (N₂) atmosphere. The reaction mixture was concentrated in vacuo. This material was carried directly into the next step of the synthesis, without further purification.

The previous residue was diluted with DCM (4 mL), then the reaction mixture was cooled to 0° C. with a wet ice bath. Then N,N'-diisopropylethylamine (0.50 mL, 2.88 mmol) was added to the reaction mixture and allowed the mixture to stir 2 min. Then acryloyl chloride (1.1M in THF) (0.21 mL, 0.24 mmol) was added to the reaction mixture. The mixture was diluted with DCM and sat. aq. NaHCO₃, then the layers were separated. The aqueous layer was extracted with DCM. The combined organic extracts were dried over MgSO₄, filtered and concentrated in vacuo. The crude material was absorbed onto a plug of silica gel and purified by chromatography through a Interchim (15 micron) silica-gel column (40 grams), eluting with a gradient of 0-25% 2M NH3 in MeOH/DCM. This afforded 4-((2S,5R)-4-acryloyl-2,5-dimethylpiperazin-1-yl)-6-chloro-1-(2-((dimethylamino)methyl)-4,6-diisopropylpyrimidin-5-yl)-7-(2-fluorophenyl)pyrido[2,3-d]pyrimidin-2(1H)-one (0.083 g, 0.126 mmol, 52.2% yield) as white solid. ¹H NMR (400 MHz, DMSO-d₆) δ 8.49 (d, J=4.98 Hz, 1H) 7.52 (q, J=7.12 Hz, 1H) 7.18-7.34 (m, 3H) 6.84 (td, J=17.41, 10.37 Hz, 1H) 6.20 (br d, J=17.62 Hz, 1H) 5.76 (br d, J=10.37 Hz, 1H) 4.76-4.97 (m, 2H) 4.46-4.58 (m, 1H) 4.04-4.28 (m, 2H) 3.98 (br s, 2H) 3.69-3.95 (m, 2H) 3.15-3.21 (m, 2H) 2.66-2.80 (m, 2H) 1.35 (br t, J=5.39 Hz, 3H) 1.15-1.29 (m, 6H) 1.09 (dd, J=6.53, 2.80 Hz, 6H) 0.95 (br d, J=6.22 Hz, 6H). m/z (ESI, +ve ion): 661.1 (M+H)⁺.

Example 161

1-[2-(Azetidin-1-ylmethyl)-4,6-diisopropyl-pyrimidin-5-yl]-6-chloro-4-[(2S,5R)-2,5-dimethyl-4-prop-2-enoyl-piperazin-1-yl]-7-(2-fluorophenyl)pyrido[2,3-d]pyrimidin-2-one

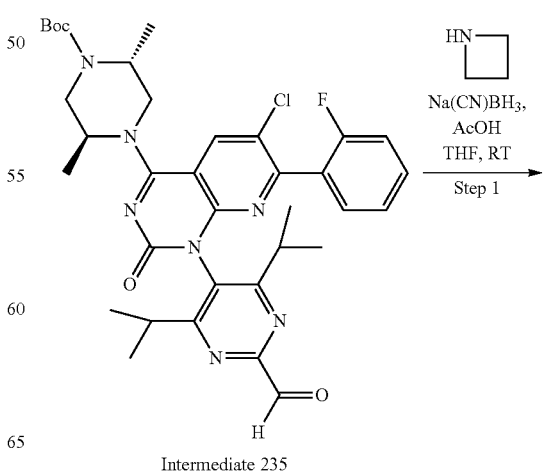

Intermediate 235

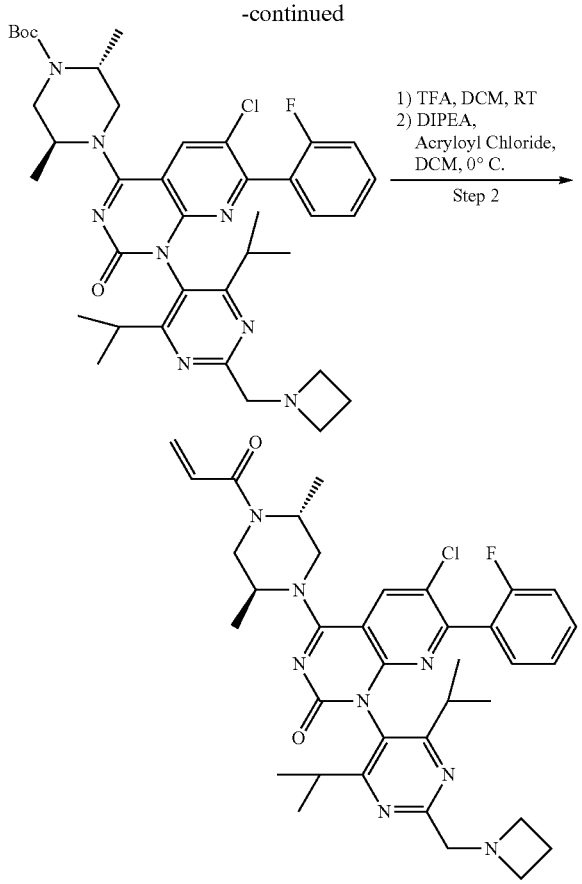

1) TFA, DCM, RT
2) DIPEA, Acryloyl Chloride, DCM, 0° C.

Step 2

Step 1. tert-Butyl (2R,5S)-4-(1-(2-(azetidin-1-ylmethyl)-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(3-chloro-2-(2-fluorophenyl)-8-(2-formyl-4,6-diisopropylpyrimidin-5-yl)-7-oxo-7,8-dihydro-1,6-naphthyridin-5-yl)-2,5-dimethylpiperazine-1-carboxylate (Intermediate 235, 0.200 g, 0.295 mmol) and azetidine (0.02 mL, 0.443 mmol) in tetrahydrofuran (2.95 mL). Then glacial acetic acid (1.7 µl, 0.03 mmol), followed by sodium cyanoborohydride (0.056 g, 0.886 mmol) was added to the reaction mixture. The overall reaction mixture was allowed to stir at it, while under an inert (N2) atmosphere for 30 min. The reaction mixture was quenched with MeOH (0.5 mL) and allowed the mixture to stir 5 min. Then the mixture was diluted with EtOAc and sat. aq. NaHCO₃. The layers were separated and the aqueous layer was extracted with EtOAc. The combined organic extracts were dried over MgSO₄, filtered and concentrated in vacuo. The crude material (0.212 grams) was carried into the next step of the synthesis, without further purification. m/z (ESI, +ve ion): 719.3 (M+H)⁺.

Step 2. 4-((2S,5R)-4-Acryloyl-2,5-dimethylpiperazin-1-yl)-1-(2-(azetidin-1-ylmethyl)-4,6-diisopropylpyrimidin-5-yl)-6-chloro-7-(2-fluorophenyl)pyrido[2,3-d]pyrimidin-2(1H)-one To a 100-mL round-bottomed flask was added tert-butyl (2R,5S)-4-(1-(2-(azetidin-1-ylmethyl)-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.18 g, 0.25 mmol) and trifluoroacetic acid (0.18 mL, 2.5 mmol) in 1,2-dichloroethane (2.4 mL). The reaction mixture was stirred and heated at 60° C. for 20 min, while under an inert (N₂) atmosphere. The reaction mixture was concentrated in vacuo. This material was carried directly into the next step of the synthesis, without further purification.

The previous residue was diluted with DCM (4 mL), then the reaction mixture was cooled to 0° C. with a wet ice bath. Then N,N'-diisopropylethylamine (0.5 mL, 3.0 mmol) was added to the reaction mixture and allowed the mixture to stir 2 min. Then acryloyl chloride (1.1M in THF) (0.2 mL, 0.25 mmol) was added to the mixture dropwise. The reaction mixture was diluted with DCM and sat. aq. NaHCO₃, then the layers were separated. The aqueous layer was extracted with DCM. The combined organic extracts were dried over MgSO₄, filtered and concentrated in vacuo. The crude material was absorbed onto a plug of silica gel and purified by chromatography through a Interchim (15 micron) silica-gel column (40 grams), eluting with a gradient of 0-25% 2M NH3-MeOH/DCM, This afforded 4-((2S,5R)-4-acryloyl-2,5-dimethylpiperazin-1-yl)-1-(2-(azetidin-1-ylmethyl)-4,6-diisopropylpyrimidin-5-yl)-6-chloro-7-(2-fluorophenyl)pyrido[2,3-d]pyrimidin-2(1H)-one (0.008 g, 0.012 mmol, 4.75% yield) as white solid. ¹H NMR (400 MHz, DMSO-d₆) δ 8.49 (d, J=4.77 Hz, 1H) 7.49-7.61 (m, 1H) 7.32 (s, 1H) 7.26-7.30 (m, 1H) 7.21 (br d, J=7.67 Hz, 1H) 6.74-6.94 (m, 1H) 6.16-6.23 (m, 1H) 5.67-5.81 (m, 1H) 4.76-4.94 (m, 1H) 4.41-4.55 (m, 1H) 4.12-4.28 (m, 1H) 3.87 (br s, 2H) 3.62-3.74 (m, 2H) 3.45-3.55 (m, 1H) 2.68 (br s, 4H) 2.32-2.48 (m, 1H) 1.79-2.05 (m, 2H) 1.35 (br t, J=5.80 Hz, 2H) 1.26 (br d, J=7.26 Hz, 1H) 1.19 (br d, J=7.46 Hz, 2H) 1.02-1.13 (m, 6H) 0.99 (s, 1H) 0.93 (br dd, J=6.43, 3.32 Hz, 7H). m/z (ESI, +ve ion): 673.3 (M+H)⁺.

Example 162

6-Chloro-1-[4,6-diisopropyl-2-(morpholinomethyl)pyrimidin-5-yl]-4-[(2S,5R)-2,5-dimethyl-4-prop-2-enoyl-piperazin-1-yl]-7-(2-fluorophenyl)pyrido[2,3-d]pyrimidin-2-one Na(CN)BH₃, AcOH
THF, RT Step 1

Intermediate 235

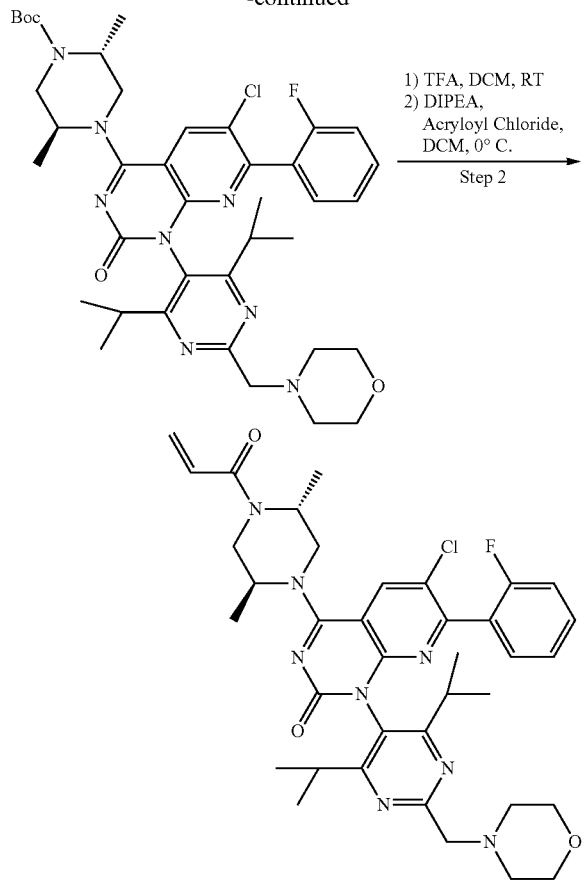

Step 1. tert-Butyl (2R,5S)-4-(6-chloro-1-(4,6-diisopropyl-2-(morpholinomethyl)pyrimidin-5-yl)-7-(2-fluorophenyl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(3-chloro-2-(2-fluorophenyl)-8-(2-formyl-4,6-diisopropylpyrimidin-5-yl)-7-oxo-7,8-dihydro-1,6-naphthyridin-5-yl)-2,5-dimethylpiperazine-1-carboxylate (Intermediate 235, 0.21 g, 0.29 mmol) and morpholine (0.03 mL, 0.44 mmol) in tetrahydrofuran (2.95 mL). Then glacial acetic acid (1.7 µl, 0.03 mmol), followed by sodium cyanoborohydride (0.056 g, 0.88 mmol) was added to the reaction mixture. The overall reaction mixture was allowed to stir at rt, while under an inert (N2) atmosphere for 30 min. The reaction mixture was quenched with MeOH (0.5 mL) and allowed the mixture to stir 5 min. Then the mixture was diluted with EtOAc and sat. aq. NaHCO₃. The layers were separated and the aqueous layer was extracted with EtOAc. The combined organic extracts were dried over MgSO₄, filtered and concentrated in vacuo. The crude material (0.263 grams) was carried into the next step of the synthesis, without further purification. m/z (ESI, +ve ion): 749.3 (M+H)⁺.

Step 2. 4-((2S,5R)-4-Acryloyl-2,5-dimethylpiperazin-1-yl)-6-chloro-1-(4,6-diisopropyl-2-(morpholinomethyl)pyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(4,6-diisopropyl-2-(morpholinomethyl)pyrimidin-5-yl)-7-(2-fluorophenyl)-2-oxo-1,2-dihydropyrido[2,3-d]pyrimidin-4-yl)-2,5-dimethylpiperazine-1-carboxylate (0.220 g, 0.294 mmol) and trifluoroacetic acid (0.2 mL, 2.94 mmol) in 1,2-dichloroethane (2.4 mL). The reaction mixture was stirred and heated at 60° C. for 20 min, while under an inert (N₂) atmosphere. The reaction mixture was concentrated in vacuo. This material was carried directly into the next step of the synthesis, without further purification.

The previous residue was diluted with DCM (4 mL), then the reaction mixture was cooled to 0° C. with a wet ice bath. Then N,N'-diisopropylethylamine (0.61 mL, 3.52 mmol) was added to the reaction mixture and allowed the mixture to stir 2 min. Then acryloyl chloride (1.1M in THF) (0.26 mL, 0.294 mmol) was added to the mixture dropwise. The mixture was diluted with DCM and sat. aq. NaHCO₃, then the layers were separated. The aqueous layer was extracted with DCM. The combined organic extracts were dried over MgSO₄, filtered and concentrated in vacuo. The crude material was absorbed onto a plug of silica gel and purified by chromatography through a Interchim (15 micron) silica-gel column (40 grams), eluting with a gradient of 0-25% 2M NH3-MeOH/DCM. This afforded 4-((2S,5R)-4-acryloyl-2,5-dimethylpiperazin-1-yl)-6-chloro-1-(4,6-diisopropyl-2-(morpholinomethyl)pyrimidin-5-yl)-7-(2-fluorophenyl)pyrido[2,3-d]pyrimidin-2(1H)-one (0.085 g, 0.121 mmol, 41.2% yield) as white solid. ¹H NMR (500 MHz, DMSO-d₆) δ 8.48 (d, J=6.62 Hz, 1H) 7.52 (q, J=7.14 Hz, 1H) 7.24-7.34 (m, 2H) 7.16-7.21 (m, 1H) 6.79-6.90 (m, 1H) 6.16-6.22 (m, 1H) 5.73-5.78 (m, 1H) 4.83-4.93 (m, 1H) 4.14-4.26 (m, 1H) 3.86-3.94 (m, 1H) 3.74 (s, 2H) 3.54-3.59 (m, 4H) 3.17 (d, J=5.32 Hz, 2H) 2.61-2.75 (m, 2H) 2.52-2.60 (m, 4H) 1.31-1.37 (m, 3H) 1.21-1.28 (m, 2H) 1.18 (d, J=6.75 Hz, 2H) 1.03-1.11 (m, 6H) 0.92 (br d, J=6.49 Hz, 6H). m/z (ESI, +ve ion): 703.1 (M+H)⁺.

Example 163

6-Chloro-1-[4,6-diisopropyl-2-(pyrrolidin-1-ylmethyl)pyrimidin-5-yl]-4-[(2S,5R)-2,5-dimethyl-4-prop-2-enoyl-piperazin-1-yl]-7-(2-fluorophenyl)pyrido[2,3-d]pyrimidin-2-one

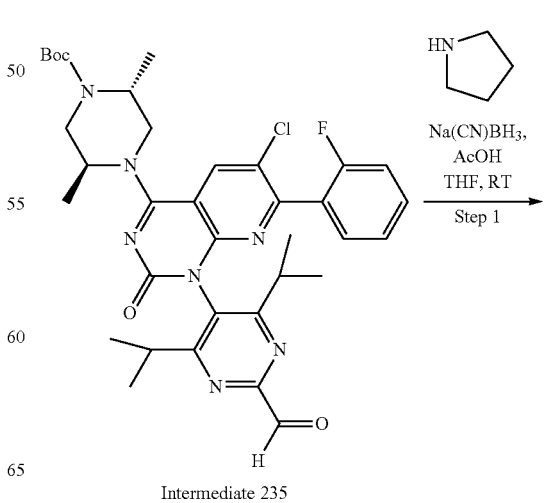

Intermediate 235

-continued

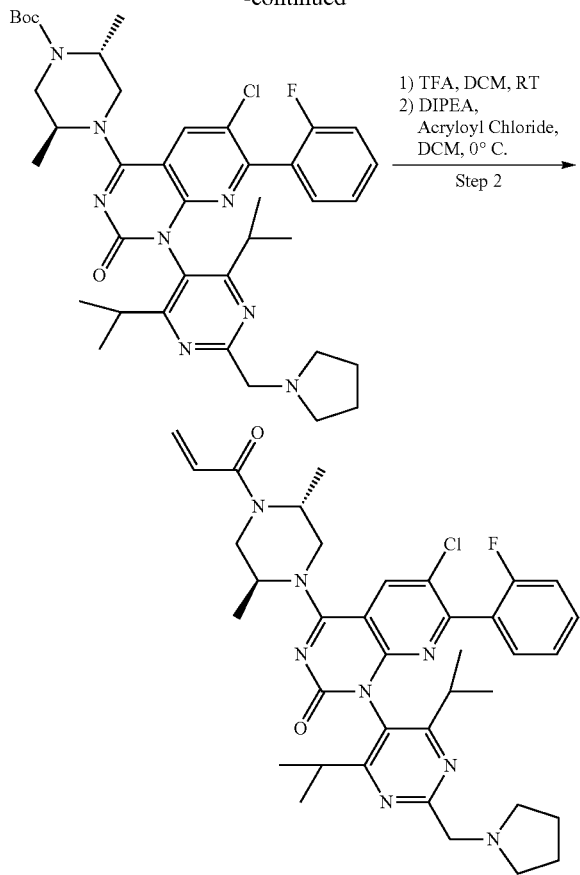

Step 1. tert-Butyl (2R,5S)-4-(6-chloro-1-(4,6-diisopropyl-2-(pyrrolidin-1-ylmethyl)pyrimidin-5-yl)-7-(2-fluorophenyl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(3-chloro-2-(2-fluorophenyl)-8-(2-formyl-4,6-diisopropylpyrimidin-5-yl)-7-oxo-7,8-dihydro-1,6-naphthyridin-5-yl)-2,5-dimethylpiperazine-1-carboxylate (Intermediate 235, 0.200 g, 0.295 mmol) and pyrrolidine (0.03 mL, 0.443 mmol) in tetrahydrofuran (2.95 mL). Then glacial acetic acid (1.7 µl, 0.030 mmol), followed by sodium cyanoborohydride (0.056 g, 0.886 mmol) was added to the reaction mixture. The overall reaction mixture was allowed to stir at it, while under an inert (N₂) atmosphere for 30 min. The reaction mixture was quenched with MeOH (0.5 mL) and allowed the mixture to stir 5 min. Then the mixture was diluted with EtOAc and sat. aq. NaHCO₃. The layers were separated and the aqueous layer was extracted with EtOAc. The combined organic extracts were dried over MgSO₄, filtered and concentrated in vacuo. The crude material (0.238 grams) was carried into the next step of the synthesis, without further purification. m/z (ESI, +ve ion): 733.3 (M+H)⁺.

Step 2. 4-((2S,5R)-4-Acryloyl-2,5-dimethylpiperazin-1-yl)-6-chloro-1-(4,6-diisopropyl-2-(pyrrolidin-1-ylmethyl)pyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(4,6-diisopropyl-2-(pyrrolidin-1-ylmethyl)pyrimidin-5-yl)-7-(2-fluorophenyl)-2-oxo-1,2-dihydropyrido[2,3-d]pyrimidin-4-yl)-2,5-dimethylpiperazine-1-carboxylate (0.190 g, 0.259 mmol) and trifluoroacetic acid (0.19 mL, 2.59 mmol) in 1,2-dichloroethane (2.40 mL). The reaction mixture was stirred and heated at 60° C. for 20 min, while under an inert (N₂) atmosphere. The reaction mixture was concentrated in vacuo. This material was carried directly into the next step of the synthesis, without further purification.

The previous residue was diluted with DCM (4 mL), then the reaction mixture was cooled to 0° C. with a wet ice bath. Then N,N'-diisopropylethylamine (0.54 mL, 3.11 mmol) was added to the reaction mixture and stirred 2 min. Then acryloyl chloride (1.1M in THF) (0.23 mL, 0.259 mmol) was added to the mixture dropwise. The mixture was diluted with DCM and sat. aq. NaHCO₃, then the layers were separated. The aqueous layer was extracted with DCM. The combined organic extracts were dried over MgSO₄, filtered and concentrated in vacuo. The crude material was absorbed onto a plug of silica gel and purified by chromatography through a Interchim (15 micron) silica-gel column (40 grams), eluting with a gradient of 0-25% 2M NH3-MeOH/DCM. This afforded 4-((2S,5R)-4-acryloyl-2,5-dimethylpiperazin-1-yl)-6-chloro-1-(4,6-diisopropyl-2-(pyrrolidin-1-ylmethyl)pyrimidin-5-yl)-7-(2-fluorophenyl)pyrido[2,3-d]pyrimidin-2(1H)-one (0.060 g, 0.087 mmol, 33.7% yield) as light-yellow solid. ¹H NMR (500 MHz, DMSO-d₆) δ 8.48 (d, J=6.49 Hz, 1H) 7.44-7.55 (m, 1H) 7.24-7.34 (m, 2H) 7.18 (td. J=7.46, 1.69 Hz, 1H) 6.79-6.89 (m, 1H) 6.19 (dt, J=16.64, 2.12 Hz, 1H) 5.76 (ddd, J=10.35, 6.07, 2.27 Hz, 1H) 4.83-4.93 (m, 1H) 4.78 (br s, 1H) 4.10-4.25 (m, 1H) 3.78-3.91 (m, 4H) 2.59-2.74 (m, 6H) 1.61-1.69 (m, 4H) 1.30-1.38 (m, 3H) 1.21-1.29 (m, 2H) 1.18 (d, J=6.75 Hz, 2H) 1.02-1.11 (m, 6H) 0.89-0.96 (m, 6H). m/z (ESI, +ve ion): 687.4 (M+H)⁺.

Example 164-1 (Peak 1)

6-Chloro-1-(6-cyclopropyl-2-isopropyl-4-methyl-3-pyridyl)-4-[(2S,5R)-2,5-dimethyl-4-prop-2-enoyl-piperazin-1-yl]-7-(2-fluorophenyl)pyrido[2,3-d]pyrimidin-2-one

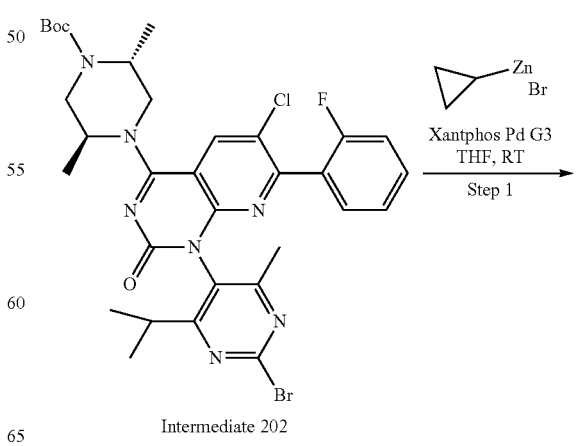

Intermediate 202

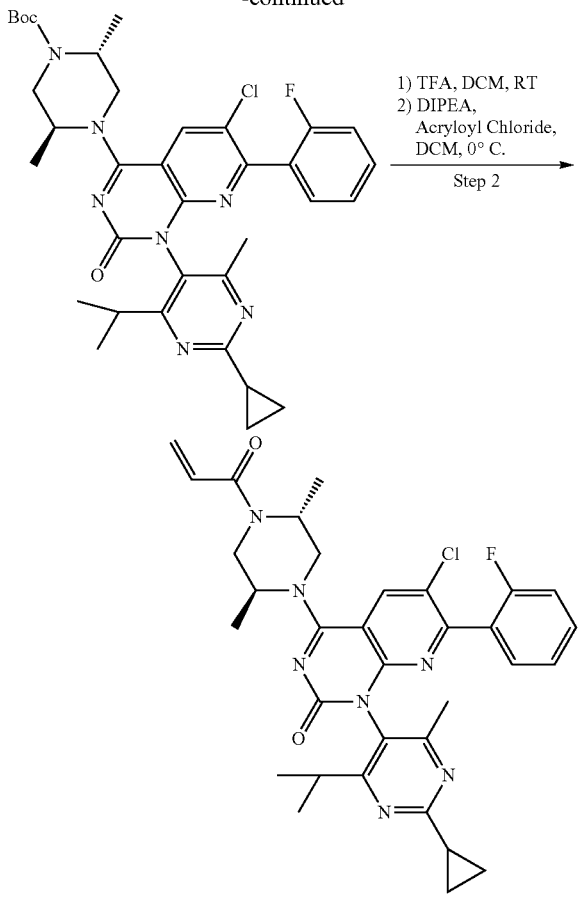

Step 1. tert-Butyl (2R,5S)-4-(6-chloro-1-(6-cyclopropyl-2-isopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(1-(6-bromo-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.275 g, 0.393 mmol, Intermediate 202) in tetrahydrofuran (2.86 mL). The reaction mixture was degassed by bubbling argon (gas) into the mixture for 5 min. Then Cyclopropylzinc bromide (0.5M in THF) (1.37 mL, 0.687 mmol) and xantphos pd g3 (0.011 g, 0.012 mmol) was added to the reaction mixture. The overall reaction mixture was allowed to stir under an inert ($N_2$) atmosphere at rt for 30 min. The reaction mixture was quenched with sat. aq. $NH_4Cl$ and the mixture was diluted with EtOAc. The layers were separated and the aqueous layer was extracted with EtOAc. The combined organic extracts were dried over $MgSO_4$, filtered and concentrated in vacuo. The crude material was absorbed onto a plug of silica gel and purified by chromatography through a Interchim (25 micron) silica-gel column (25 grams), eluting with a gradient of 0-40% EtOAc in CH2CL2, to provide tert-butyl (2R,5S)-4-(6-chloro-1-(6-cyclopropyl-2-isopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate (0.235 g, 0.355 mmol, 90% yield) as tan solid. $^1$H NMR (400 MHz, DMSO-$d_6$) δ 8.42 (d, J=6.22 Hz, 1H) 7.48-7.56 (m, 1H) 7.20-7.35 (m, 3H) 7.04 (d, J=5.80 Hz, 1H) 4.81 (br s, 1H) 4.36 (br s, 1H) 4.00-4.16 (m, 1H) 3.85 (br s, 1H) 3.69 (br d, J=13.48 Hz, 1H) 3.43-3.59 (m, 1H) 2.54-2.64 (m, 1H) 1.99-2.05 (m, 1H) 1.87 (d, J=12.44 Hz, 3H) 1.44 (s, 9H) 1.30-1.38 (m, 3H) 1.11-1.20 (m, 4H) 0.86-1.02 (m, 9H). m/z (ESI, +ve ion): 661.2 (M+H)$^+$.

Step 2. 4-((2S,5R)-4-Acryloyl-2,5-dimethylpiperazin-1-yl)-6-chloro-1-(6-cyclopropyl-2-isopropyl-4-methylpyridin-3-yl)-7-(2-fluorophenyl)pyrido[2,3-d]pyrimidin-2(1H)-one To a 100-mL round-bottomed flask was added tert-butyl (2R,5S)-4-(6-chloro-1-(6-cyclopropyl-2-isopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate (0.230 g, 0.348 mmol) and trifluoroacetic acid (0.25 mL, 3.48 mmol) in 1,2-dichloroethane (3.48 mL). The reaction mixture was stirred and heated at 60° C. for 30 min, while under an inert ($N_2$) atmosphere. The reaction mixture was concentrated in vacuo. This material was carried directly into the next step of the synthesis, without further purification.

The previous residue was diluted with 1,2-dichloroethane (3.48 mL), then the reaction mixture was cooled to 0° C. with a wet ice bath. Then n,n'-diisopropylethylamine (0.72 mL, 4.17 mmol) was added to the reaction mixture and stirred 2 min. Then acryloyl chloride (0.31 mL, 0.348 mmol) was added to the mixture dropwise and stirred under an inert (N2) atmosphere for 10 min. The mixture was diluted with EtOAc and sat. aq. $NaHCO_3$, then the layers were separated. The aqueous layer was extracted with EtOAc, then the combined organic extracts were dried over $MgSO_4$, filtered and concentrated in vacuo. The crude material was absorbed onto a plug of silica gel and purified by chromatography through a Interchim (15 micron) silica-gel column (40 grams), eluting with a gradient of 0-5% MeOH/DCM. The racemic mixture of atropisomers were separated by SFC; (Column: IC, 5 μm, 21×250 mm, F=80 mL/min, 40% MeOH/60% Carbon dioxide) This afforded Peak 1: 4-((2S,5R)-4-acryloyl-2,5-dimethylpiperazin-1-yl)-6-chloro-1-(6-cyclopropyl-2-isopropyl-4-methylpyridin-3-yl)-7-(2-fluorophenyl)pyrido[2,3-d]pyrimidin-2(1H)-one (0.060 g, 0.098 mmol, 28.0% yield) as off-white solid. $^1$H NMR (400 MHz, DMSO-$d_6$) δ 8.44 (d, J=3.11 Hz, 1H) 7.49-7.56 (m, 1H) 7.21-7.35 (m, 3H) 7.04 (s, 1H) 6.83 (td, J=16.90, 10.57 Hz, 1H) 6.19 (dd, J=16.59, 2.07 Hz, 1H) 5.72-5.78 (m, 1H) 4.84 (br s, 1H) 4.77 (br s, 1H) 4.10-4.20 (m, 1H) 3.79-3.92 (m, 2H) 3.45-3.53 (m, 1H) 2.55-2.65 (m, 1H) 1.90-2.05 (m, 1H) 1.87 (s, 3H) 1.29-1.36 (m, 3H) 1.24 (br d, J=6.63 Hz, 1H) 1.17 (d, J=6.63 Hz, 2H) 0.98-1.03 (m, 3H) 0.91 (br d, J=6.63 Hz, 7H). m/z (ESI, +ve ion): 615.2 (M+H)$^+$.

Example 164-2 (Peak 2)

The racemic mixture of atropisomers were separated by SFC; (Column: IC, 5 μm, 21×250 mm, F=80 mL/min, 40% MeOH/60% Carbon dioxide) This afforded Peak 2: 4-((2S,5R)-4-acryloyl-2,5-dimethylpiperazin-1-yl)-6-chloro-1-(6-cyclopropyl-2-isopropyl-4-methylpyridin-3-yl)-7-(2-fluorophenyl)pyrido[2,3-d]pyrimidin-2(1H)-one (0.055 g, 0.089 mmol, 25.7% yield) as off-white solid.

Example 165-1 (Peak 1)

4-((2S,5R)-4-Acryloyl-2,5-dimethylpiperazin-1-yl)-6-chloro-7-(2-fluorophenyl)-1-(2-isopropyl-4,6-dimethylpyridin-3-yl)pyrido[2,3-d]pyrimidin-2(1H)-one

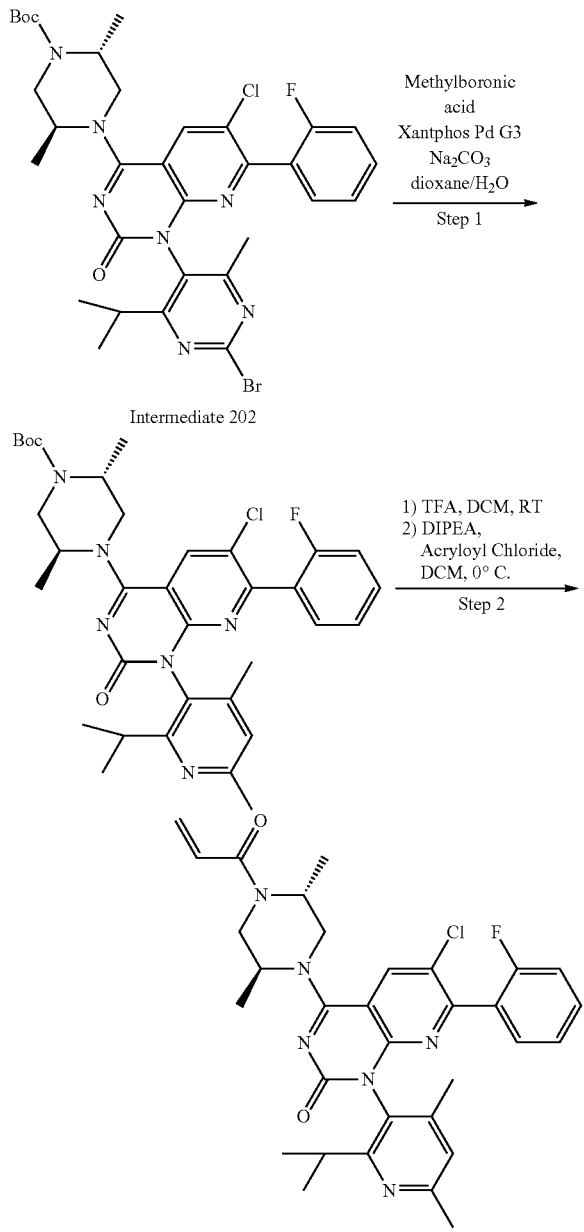

Step 1. tert-Butyl (2R,5S)-4-(6-chloro-7-(2-fluorophenyl)-1-(2-isopropyl-4,6-dimethylpyridin-3-yl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(1-(6-bromo-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.250 g, 0.357 mmol, Intermediate 202) and sodium carbonate (0.114 g, 1.071 mmol) in 1,4-dioxane (1.0 mL). The reaction mixture was degassed by bubbling argon (gas) into the mixture for 5 min. Then xantphos pd g3 (0.034 g, 0.036 mmol), water (0.2 mL) and methylboronic acid (1.069 g, 17.86 mmol) was added to the reaction mixture. The overall reaction mixture was stirred and heated at 100° C. for 2 h. The reaction mixture was cooled to rt, then the mixture was diluted with sat. aq. NaHCO₃ and EtOAc. The layers were separated and the aqueous layer was extracted with EtOAc. The combined organic extracts were dried over MgSO₄, filtered and concentrated in vacuo. The crude material was absorbed onto a plug of silica gel and purified by chromatography through a Interchim (25 micron) silica-gel column (25 grams), eluting with a gradient of 0-100% EtOAc in CH2CL2, to provide tert-butyl (2R,5S)-4-(6-chloro-7-(2-fluorophenyl)-1-(2-isopropyl-4,6-dimethylpyridin-3-yl)-2-oxo-1,2-dihydropyrido[2,3-d]pyrimidin-4-yl)-2,5-dimethylpiperazine-1-carboxylate (0.100 g, 0.157 mmol, 44.1% yield) as light-yellow solid. m/z (ESI, +ve ion): 635.2 (M+H)⁺.

Step 2. 4-((2S,5R)-4-Acryloyl-2,5-dimethylpiperazin-1-yl)-6-chloro-7-(2-fluorophenyl)-1-(2-isopropyl-4,6-dimethylpyridin-3-yl)pyrido[2,3-d]pyrimidin-2(1H)-one To a 100-mL round-bottomed flask was added tert-butyl (2R,5S)-4-(6-chloro-7-(2-fluorophenyl)-1-(2-isopropyl-4,6-dimethylpyridin-3-yl)-2-oxo-1,2-dihydropyrido[2,3-d]pyrimidin-4-yl)-2,5-dimethylpiperazine-1-carboxylate (0.100 g, 0.157 mmol) and trifluoroacetic acid (0.1 mL, 1.574 mmol) in 1,2-dichloroethane (1.5 mL). The reaction mixture was stirred and heated at 60° C. for 30 min, while under an inert (N₂) atmosphere. The reaction mixture was concentrated in vacuo. This material was carried directly into the next step of the synthesis, without further purification.

The previous residue was diluted with 1,2-dichloroethane (1.5 mL), then cooled the reaction mixture to 0° C. with a wet ice bath. Then n,n'-diisopropylethylamine (0.3 mL, 1.889 mmol) was added to the reaction mixture and stirred 2 min. Then acryloyl chloride (0.14 mL, 0.157 mmol) was added to the mixture dropwise and stirred under an inert (N2) atmosphere for 10 min. The mixture was diluted with EtOAc and sat. aq. NaHCO₃, then the layers were separated. The aqueous layer was extracted with EtOAc, then the combined organic extracts were dried over MgSO₄, filtered and concentrated in vacuo. The crude material was absorbed onto a plug of silica gel and purified by chromatography through a Interchim (15 micron) silica-gel column (40 grams), eluting with a gradient of 0-5% MeOH/DCM. The racemic mixture was separated by SFC; (Column, IA, 5 μm, 21×250 mm. F=80 mL/min, 15% Isopropanol/85% Carbon dioxide) This afforded the separated Atropisomers, as Peak 1 (M) 4-((2S,5R)-4-acryloyl-2,5-dimethylpiperazin-1-yl)-6-chloro-7-(2-fluorophenyl)-1-(2-isopropyl-4,6-dimethylpyridin-3-yl)pyrido[2,3-d]pyrimidin-2(1H)-one (0.030 g, 0.051 mmol, 32.3% yield) as white solid. ¹H NMR (400 MHz, DMSO-d₆) δ 8.38 (d, J=3.11 Hz, 1H) 7.42-7.48 (m, 1H) 7.14-7.27 (m, 3H) 6.96 (s, 1H) 6.76 (td, J=16.79, 10.37 Hz, 1H) 6.12 (dd, J=16.69, 1.76 Hz, 1H) 5.65-5.71 (m, 1H) 4.78 (br s, 1H) 4.70 (br s, 1H) 4.03-4.14 (m, 1H) 3.73-3.87 (m, 2H) 2.55-2.62 (m, 1H) 2.32-2.38 (m, 3H) 1.81 (s, 3H) 1.26 (t, J=6.63 Hz, 3H) 1.18 (br d, J=6.63 Hz, 2H) 1.11 (br d, J=6.84 Hz, 2H) 0.98 (d, J=6.63 Hz, 3H) 0.88 (d, J=6.63 Hz, 3H). m/z (ESI, +ve ion): 589.1 (M+H)⁺.

Example 165-2 (Peak 2)

The racemic mixture was separated by SFC; (Column, IA, 5 μm, 21×250 mm, F=80 mL/min, 15% Isopropanol/85%

Carbon dioxide) This afforded Peak 2 (P) 4-((2S,5R)-4-acryloyl-2,5-dimethylpiperazin-1-yl)-6-chloro-7-(2-fluorophenyl)-1-(2-isopropyl-4,6-dimethylpyridin-3-yl)pyrido[2,3-d]pyrimidin-2(1H)-one (0.035 g, 0.059 mmol, 37.7% yield) as white solid. $^1$H NMR (400 MHz, DMSO-d$_6$) δ 8.47 (s, 1H) 7.48-7.56 (m, 1H) 7.22-7.34 (m, 3H) 7.04 (s, 1H) 6.83 (ddd, J=16.59, 13.89, 10.57 Hz, 1H) 6.19 (dd, J=16.69, 2.18 Hz, 1H) 5.71-5.78 (m, 1H) 4.86 (br s, 1H) 4.76 (br s, 1H) 4.08-4.20 (m, 1H) 3.79-3.96 (m, 2H) 2.61-2.70 (m, 1H) 2.39-2.45 (m, 3H) 1.91 (s, 3H) 1.33 (br t, J=6.32 Hz, 3H) 1.23 (br d, J=6.43 Hz, 2H) 1.16 (br d, J=6.84 Hz, 2H) 1.04 (d, J=6.63 Hz, 3H) 0.92 (d, J=6.63 Hz, 3H). m/z (ESI, +ve ion): 589.1 (M+H)$^+$.

Example 166-1 (Peak 1)

6-Chloro-4-[(2S,5R)-2,5-dimethyl-4-prop-2-enoyl-piperazin-1-yl]-1-(6-ethyl-2-isopropyl-4-methyl-3-pyridyl)-7-(2-fluorophenyl)pyrido[2,3-d]pyrimidin-2-one

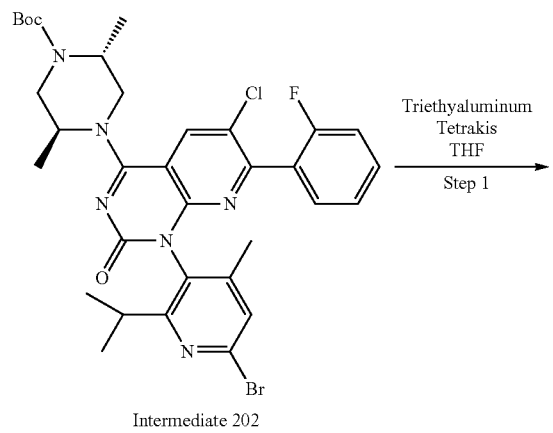

Intermediate 202

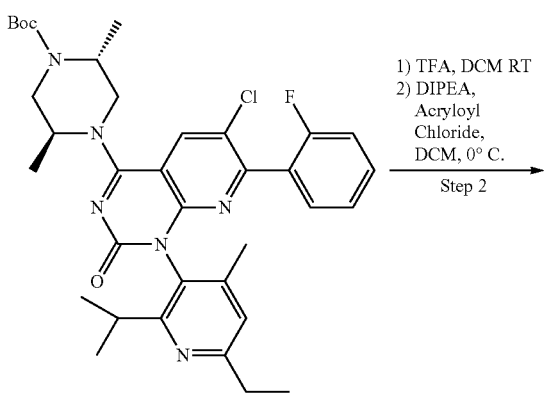

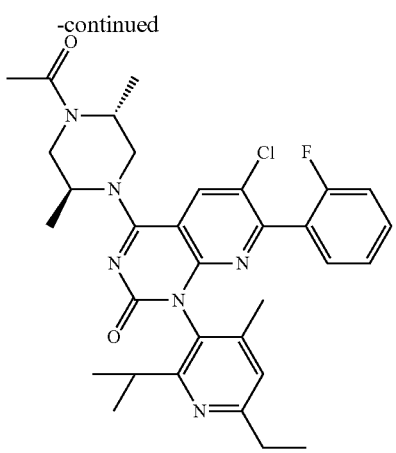

Step 1. tert-Butyl (2R,5S)-4-(6-chloro-1-(6-ethyl-2-isopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added tert-butyl (2R,5S)-4-(1-(6-bromo-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.230 g, 0.329 mmol, Intermediate 202) in tetrahydrofuran (1.6 mL). The reaction mixture was degassed by bubbling argon (gas) into the mixture for 5 min. Then triethylaluminum (1.0M in THF) (0.8 mL, 0.821 mmol) and tetrakis (0.038 g, 0.033 mmol) was added to the reaction mixture. The mixture was stirred and heated at 60° C. for 16 h, while under an inert (N$_2$) atmosphere. The reaction was quench with sat. aq. NaHCO$_3$ and diluted with mixture with EtOAc and brine. The layers were separated and the aqueous layer was extracted with EtOAc. The combined organic extracts were dried over MgSO$_4$, filtered and concentrated in vacuo. The crude material (0.250 g) was carried into the next step of the synthesis, without further purification. m/z (ESI, +ve ion): 649.3 (M+H)$^+$.

Step 2. 4-((2S,5R)-4-Acryloyl-2,5-dimethylpiperazin-1-yl)-6-chloro-1-(6-ethyl-2-isopropyl-4-methylpyridin-3-yl)-7-(2-fluorophenyl)pyrido[2,3-d]pyrimidin-2(1H)-one To a 100-mL round-bottomed flask was added tert-butyl (2R,5S)-4-(6-chloro-1-(6-ethyl-2-isopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate (0.213 g, 0.328 mmol) and trifluoroacetic acid (0.2 mL, 3.28 mmol) in 1,2-dichloroethane (1.5 mL). The reaction mixture was stirred and heated at 60° C. for 30 min, while under an inert (N2) atmosphere. The reaction mixture was concentrated in vacuo. This material was carried directly into the next step of the synthesis, without further purification.

The previous residue was diluted with 1,2-dichloroethane (1.5 mL), then the reaction mixture was cooled to 0° C. with a wet ice bath. Then n,n'-diisopropylethylamine (0.6 mL, 3.94 mmol) was added to the reaction mixture and stirred 2 min. Then acryloyl chloride (0.29 mL, 0.328 mmol) was added to the mixture dropwise and stirred under an inert (N$_2$) atmosphere for 10 min. The mixture was diluted with EtOAc and sat. aq. NaHCO$_3$, then the layers were separated. The aqueous layer was extracted with EtOAc, then the combined organic extracts were dried over MgSO₄, filtered and concentrated in vacuo. The crude material was absorbed onto a plug of silica gel and purified by chromatography through an Interchim (15 micron) silica-gel column (40 grams), eluting with a gradient of 0-5% MeOH/DCM. The racemates were separated by SFC; (Column, IA, 5 µm, 21×250 mm, F=80 mL/min, 15% MeOH/85: Carbon dioxide). This afforded the separated Atropisomers as Peak 1: 4-((2S,5R)-4-acryloyl-2,5-dimethylpiperazin-1-yl)-6-chloro-1-(6-ethyl-2-isopropyl-4-methylpyridin-3-yl)-7-(2-fluorophenyl)pyrido[2,3-d]pyrimidin-2(1H)-one (0.040 g, 0.066 mmol, 20.21% yield) as off-white solid. ¹H NMR (400 MHz, DMSO-d₆) δ 8.46 (d, J=2.90 Hz, 1H) 7.47-7.57 (m, 1H) 7.20-7.35 (m, 3H) 7.05 (s, 1H) 6.78-6.90 (m, 1H) 6.20 (dd, J=16.59, 1.87 Hz, 1H) 5.72-5.79 (m, 1H) 4.86 (br s, 1H) 4.77 (br s, 1H) 4.10-4.22 (m, 1H) 3.80-3.95 (m, 2H) 3.50 (br d, J=10.37 Hz, 1H) 2.55-2.75 (m, 3H) 1.90 (s, 3H) 1.34 (br t, J=6.74 Hz, 3H) 1.16-1.29 (m, 6H) 1.06 (d, J=6.63 Hz, 3H) 0.97 (d, J=6.63 Hz, 3H). m/z (ESI, +ve ion): 603.2 (M+H)⁺.

Example 166-2 (Peak 2)

The racemates were separated by SFC; (Column, IA, 5 µm, 21×250 mm, F=80 mL/min, 15% MeOH/85: Carbon dioxide). This afforded the separated Atropisomers as Peak 2: 4-((2S,5R)-4-acryloyl-2,5-dimethylpiperazin-1-yl)-6-chloro-1-(6-ethyl-2-isopropyl-4-methylpyridin-3-yl)-7-(2-fluorophenyl)pyrido[2,3-d]pyrimidin-2(1H)-one (0.030 g, 0.050 mmol, 15.16% yield) as off-white solid. ¹H NMR (400 MHz, DMSO-d₆) δ 8.48 (s, 1H) 7.49-7.56 (m, 1H) 7.22-7.35 (m, 3H) 7.06 (s, 1H) 6.78-6.89 (m, 1H) 6.20 (dd, J=16.59, 2.07 Hz, 1H) 5.73-5.79 (m, 1H) 4.87 (br s, 1H) 4.76 (br s, 1H) 4.14 (br d, J=13.06 Hz, 1H) 3.81-3.96 (m, 2H) 3.40-3.53 (m, 1H) 2.62-2.74 (m, 3H) 1.89-1.97 (m, 3H) 1.34 (br t, J=6.22 Hz, 3H) 1.16-1.27 (m, 6H) 1.05 (d, J=6.84 Hz, 3H) 0.94 (d, J=6.63 Hz, 3H). m/z (ESI, +ve ion): 603.2 (M+H)⁺.

Example 167

6-Chloro-1-(4,6-diisopropyl-2-methyl-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one

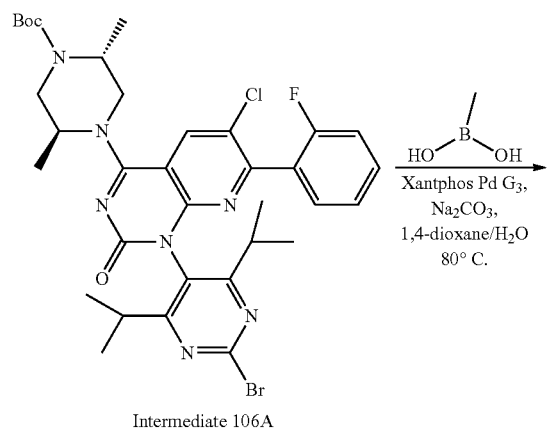

Intermediate 106A

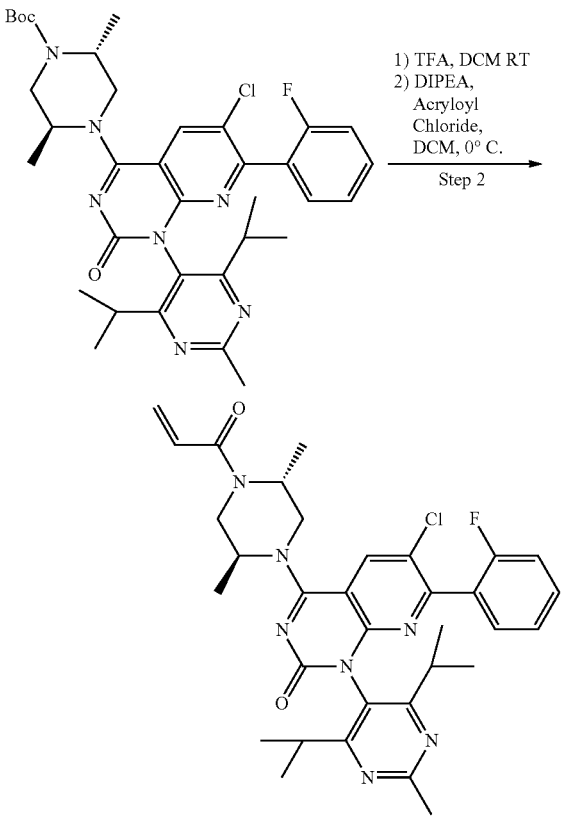

Step 1: tert-Butylbutyl (2R,5S)-4-(6-chloro-1-(4,6-diisopropyl-2-methylpyrimidin-5-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.300 g, 0.411 mmol, Intermediate 232) and sodium carbonate (0.131 g, 1.234 mmol) in 1,4-dioxane (1.6 mL). The reaction mixture was degassed by bubbling argon (gas) into the mixture for 5 min. Then xantphos pd g3 (0.020 g, 0.021 mmol), water (0.4 mL) and methylboronic acid (1.2 mL, 20.57 mmol) was added into the reaction mixture. The overall reaction mixture was stirred and heated at 80° C. for 8 h. The reaction mixture was cooled to rt, then the mixture was diluted with sat. aq. NaHCO₃ and EtOAc. The layers were separated and the aqueous layer was extracted with EtOAc. The combined organic extracts were dried over MgSO₄, filtered and concentrated in vacuo. The crude material was absorbed onto a plug of silica gel and purified by chromatography through a Interchim (25 micron) silica-gel column (25 grams), eluting with a gradient of 0-50% EtOAc in CH2CL2, to provide tert-butyl (2R,5S)-4-(6-chloro-1-(4,6-diisopropyl-2-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.207 g, 0.312 mmol, 76% yield) as light-yellow solid. m/z (ESI, +ve ion): 664.2 (M+H)⁺.

Step 2. 4-((2S,5R)-4-Acryloyl-2,5-dimethylpiperazin-1-yl)-6-chloro-1-(4,6-diisopropyl-2-methylpyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(4,6-diisopropyl-2-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.200 g, 0.301 mmol) and trifluoroacetic acid (0.2 mL, 3.01 mmol) in 1,2-dichloroethane (3.0 mL). The reaction mixture was stirred and heated at 60° C. for 30 min, while under an inert ($N_2$) atmosphere. The reaction mixture was concentrated in vacuo. This material was carried directly into the next step of the synthesis, without further purification.

The previous residue was diluted with 1,2-dichloroethane (3.0 mL), then the reaction mixture was cooled to 0° C. with a wet ice bath. Then n,n'-diisopropylethylamine (0.6 mL, 3.61 mmol) was added into the reaction mixture and stirred 2 min. Then acryloyl chloride (0.2 mL, 0.301 mmol) was added into the mixture dropwise and stirred under an inert ($N_2$) atmosphere for 10 min. The mixture was diluted with EtOAc and sat. aq. $NaHCO_3$, then the layers were separated. The aqueous layer was extracted with EtOAc, then the combined organic extracts were dried over $MgSO_4$, filtered and concentrated in vacuo. The crude material was absorbed onto a plug of silica gel and purified by chromatography through a Interchim (15 micron) silica-gel column (25 grams), eluting with a gradient of 0-8% MeOH/DCM. This afforded 4-((2S,5R)-4-acryloyl-2,5-dimethylpiperazin-1-yl)-6-chloro-1-(4,6-diisopropyl-2-methylpyrimidin-5-yl)-7-(2-fluorophenyl)pyrido[2,3-d]pyrimidin-2(1H)-one (0.130 g, 0.210 mmol, 69.8% yield) as off-white solid. $^1$H NMR (400 MHz, DMSO-$d_6$) δ 8.42 (d, J=4.15 Hz, 1H) 7.41-7.49 (m, 1H) 7.19-7.29 (m, 2H) 7.10-7.17 (n, 1H) 6.77 (td, J=17.00, 10.57 Hz, 1H) 6.13 (dd, J=16.69, 1.97 Hz, 1H) 5.65-5.73 (m, 1H) 4.76-4.87 (m, 1H) 4.71 (br s, 1H) 4.03-4.22 (m, 1H) 3.65-3.87 (m, 2H) 2.50-2.69 (m, 5H) 1.16-1.38 (i, 5H) 1.12 (br d, J=6.84 Hz, 2H) 1.00 (br d, J=3.73 Hz, 3H) 0.99 (br d, J=3.73 Hz, 3H) 0.82-0.90 (m, 6H). m/z (ESI, +ve ion): 618.0 (M+H)$^+$.

Example 168

6-Chloro-1-(2-cyclopropyl-4,6-diisopropyl-pyrimidin-5-yl)-4-[(2S,5R)-2,5-dimethyl-4-prop-2-enoyl-piperazin-1-yl]-7-(2-fluorophenyl)pyrido[2,3-d]pyrimidin-2-one

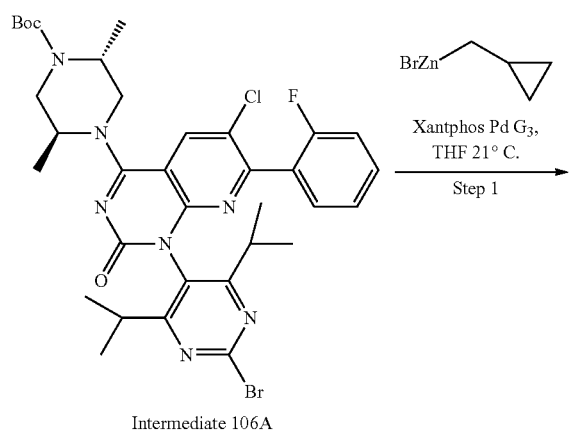

Intermediate 106A

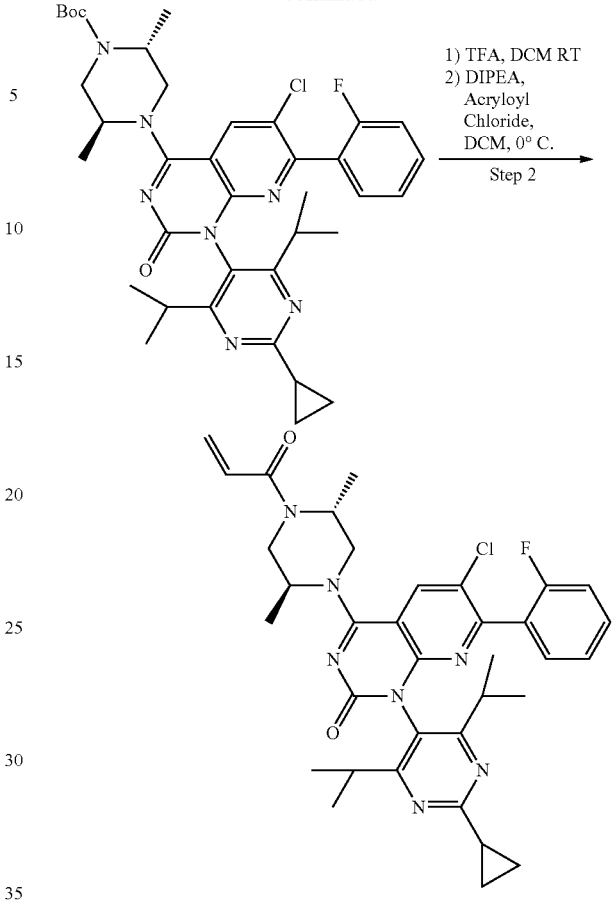

Step 1. tert-Butyl (2R,5S)-4-(6-chloro-1-(2-cyclopropyl-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.300 g, 0.411 mmol, Intermediate 232) in tetrahydrofuran (4.1 mL). The reaction mixture was degassed by bubbling argon (gas) into the mixture for 5 min. Then cyclopropylzinc bromide (0.5M in THF) (1.4 mL, 0.720 mmol) and xantphos pd g3 (0.012 g, 0.012 mmol) was added into the reaction mixture. The overall reaction mixture was allowed to stir under an inert ($N_2$) atmosphere at rt for 30 min. The reaction mixture was quenched with sat. aq. $NH_4Cl$ and diluted the mixture with EtOAc. The layers were separated and the aqueous layer was extracted with EtOAc. The combined organic extracts were dried over $MgSO_4$, filtered and concentrated in vacuo. The crude material was absorbed onto a plug of silica gel and purified by chromatography through a Interchim (25 micron) silica-gel column (25 grams), eluting with a gradient of 0-40% EtOAc in CH2CL2, to provide tert-butyl (2R,5S)-4-(6-chloro-1-(2-cyclopropyl-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.275 g, 0.398 mmol, 97% yield) as tan solid. m/z (ESI, +ve ion): 690.2 (M+H)$^+$.

Step 2. 4-((2S,5R)-4-Acryloyl-2,5-dimethylpiperazin-1-yl)-6-chloro-1-(2-cyclopropyl-4,6-diisopropylpyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(2-cyclopropyl-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.265 g, 0.384 mmol) and trifluoroacetic acid (0.2 mL, 3.84 mmol) in 1,2-dichloroethane (3.8 mL). The reaction mixture was stirred and heated at 60° C. for 30 min, while under an inert (N₂) atmosphere. The reaction mixture was concentrated in vacuo. This material was carried directly into the next step of the synthesis, without further purification.

The previous residue was diluted with 1,2-dichloroethane (3.8 mL), then the reaction mixture was cooled to 0° C. with a wet ice bath. Then n,n'-diisopropylethylamine (0.8 mL, 4.61 mmol) was added into the reaction mixture and stirred 2 min. Then acryloyl chloride (0.3 mL, 0.384 mmol) was added into the mixture dropwise and stirred under an inert (N₂) atmosphere for 10 min. The mixture was diluted with EtOAc and sat. aq. NaHCO₃, then the layers were separated. The aqueous layer was extracted with EtOAc, then the combined organic extracts were dried over MgSO₄, filtered and concentrated in vacuo. The crude material was absorbed onto a plug of silica gel and purified by chromatography through a Interchim (15 micron) silica-gel column (40 grams), eluting with a gradient of 0-8% MeOH/DCM. This afforded 4-((2S,5R)-4-acryloyl-2,5-dimethylpiperazin-1-yl)-6-chloro-1-(2-cyclopropyl-4,6-diisopropylpyrimidin-5-yl)-7-(2-fluorophenyl)pyrido[2,3-d]pyrimidin-2(1H)-one (0.180 g, 0.279 mmol, 72.8% yield) as off-white solid. $^1$H NMR (400 MHz, DMSO-$d_6$) δ 8.41 (d, J=3.94 Hz, 1H) 7.39-7.54 (m, 1H) 7.19-7.34 (m, 2H) 7.10-7.19 (m, 1H) 6.77 (td, J=16.90, 10.57 Hz, 1H) 6.13 (dd, J=16.59, 2.07 Hz, 1H) 5.64-5.73 (m, 1H) 4.75-4.87 (m, 1H) 4.71 (br s, 1H) 4.01-4.22 (m, 1H) 3.70-3.92 (m, 2H) 2.47-2.63 (m, 2H) 2.04-2.13 (m, 1H) 1.07-1.33 (m, 7H) 0.90-1.02 (m, 10H) 0.85 (dd, J=6.53, 3.01 Hz, 6H). m/z (ESI, +ve ion): 644.2 (M+H)⁺.

Example 169

6-Chloro-4-[(2S,5R)-2,5-dimethyl-4-prop-2-enoyl-piperazin-1-yl]-1-(2-ethyl-4,6-diisopropyl-pyrimidin-5-yl)-7-(2-fluorophenyl)pyrido[2,3-d]pyrimidin-2-one

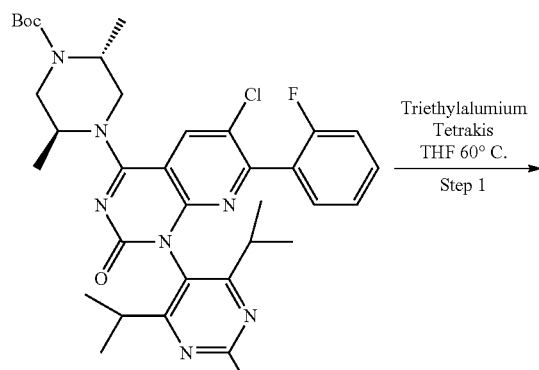

Intermediate 106A

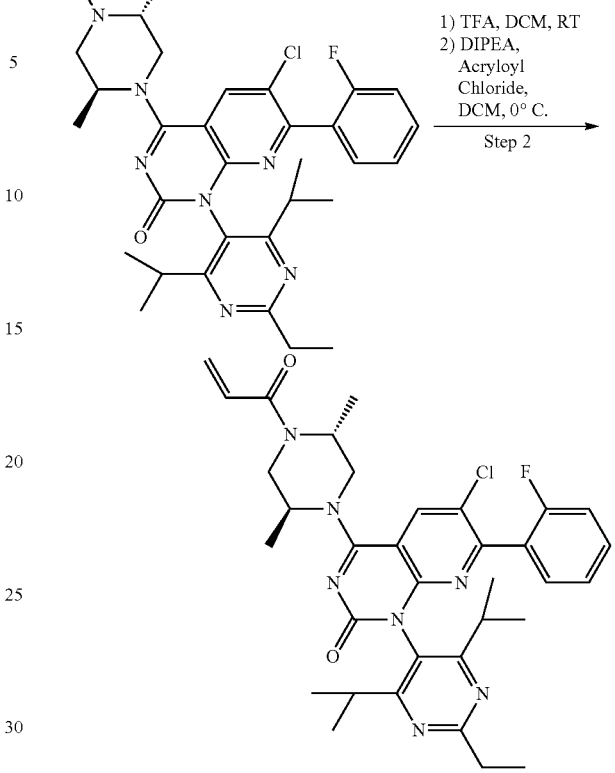

Step 1. tert-Butyl (2R,5S)-4-(6-chloro-1-(2-ethyl-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.200 g, 0.274 mmol, Intermediate 232) in tetrahydrofuran (1.6 mL). The reaction mixture was degassed by bubbling argon (gas) into the mixture for 5 min. Then triethylaluminum (1.0M in THF) (0.6 mL, 0.686 mmol) and tetrakis (0.032 g, 0.027 mmol) was added into the reaction mixture. The mixture was stirred and heated at 60° C. for 16 h, while under an inert (N2) atmosphere. The reaction was quench with sat. aq. NaHCO₃ and diluted with mixture with EtOAc and brine. The layers were separated and the aqueous layer was extracted with EtOAc. The combined organic extracts were dried over MgSO₄, filtered and concentrated in vacuo. The crude material was carried into the next step of the synthesis, without further purification. m/z (ESI, +ve ion): 678.2 (M+H)⁺.

Step 2. 4-((2S,5R)-4-Acryloyl-2,5-dimethylpiperazin-1-yl)-6-chloro-1-(2-ethyl-4,6-diisopropylpyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(2-ethyl-4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.036 g, 0.053 mmol) and trifluoroacetic acid (0.1 mL, 0.531 mmol) in 1,2-dichloroethane (1.5 mL). The reaction mixture was stirred and heated at 60° C. for 30 min, while under an inert (N2) atmosphere. The reaction mixture was concentrated in vacuo. This material was carried directly into the next step of the synthesis, without further purification.

The previous residue was diluted with 1,2-dichloroethane (0.5 mL), then the reaction mixture was cooled to 0° C. with a wet ice bath. Then n,n'-diisopropylethylamine (0.1 mL, 0.637 mmol) was added into the reaction mixture and stirred 2 min. Then acryloyl chloride (0.1 mL, 0.053 mmol) was added into the mixture dropwise and stirred under an inert (N2) atmosphere for 10 min. The mixture was diluted with EtOAc and sat. aq. NaHCO₃, then the layers were separated. The aqueous layer was extracted with EtOAc, then the combined organic extracts were dried over MgSO4, filtered and concentrated in vacuo. The crude material was absorbed onto a plug of silica gel and purified by chromatography through a Interchim (15 micron) silica-gel column (40 grams), eluting with a gradient of 0-8% MeOH/DCM. This afforded 4-((2S,5R)-4-acryloyl-2,5-dimethylpiperazin-1-yl)-6-chloro-1-(2-ethyl-4,6-diisopropylpyrimidin-5-yl)-7-(2-fluorophenyl)pyrido[2,3-d]pyrimidin-2(1H)-one (0.033 g, 0.052 mmol, 98% yield) as off-white solid. 1H NMR (400 MHz, DMSO-d6) δ 8.48 (d, J=4.15 Hz, 1H) 7.49-7.55 (m, 1H) 7.26-7.34 (m, 2H) 7.20 (td, J=7.36, 1.66 Hz, 1H) 6.77-6.89 (m, 1H) 6.19 (dd, J=16.59, 2.28 Hz, 1H) 5.73-5.78 (m, 1H) 4.87 (br s, 1H) 4.78 (br s, 1H) 4.10-4.25 (m, 1H) 3.79-3.95 (m, 2H) 2.87 (q, J=7.67 Hz, 2H) 2.61-2.73 (m, 2H) 1.34 (t, J=5.91 Hz, 3H) 1.26-1.30 (m, 4H) 1.24 (br d, J=3.32 Hz, 3H) 1.07 (dd, J=6.74, 3.84 Hz, 6H) 0.93 (dd, J=6.63, 3.32 Hz, 6H). m/z (ESI, +ve ion): 632.2 (M+H)⁺.

Example 170

6-Chloro-1-[4,6-diisopropyl-2-[(4-methylpiperazin-1-yl)methyl]pyrimidin-5-yl]-4-[(2S,5R)-2,5-dimethyl-4-prop-2-enoyl-piperazin-1-yl]-7-(2-fluorophenyl)pyrido[2,3-d]pyrimidin-2-one

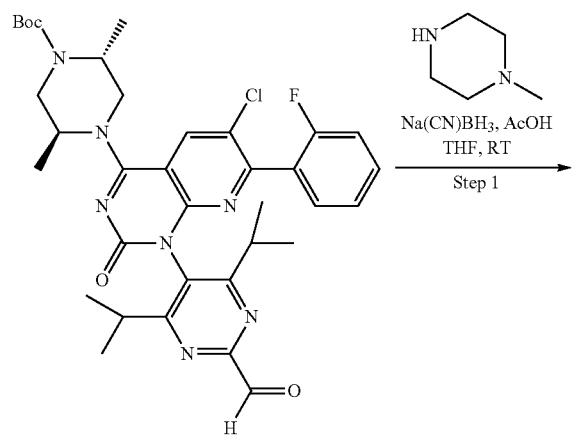

Intermediate 235

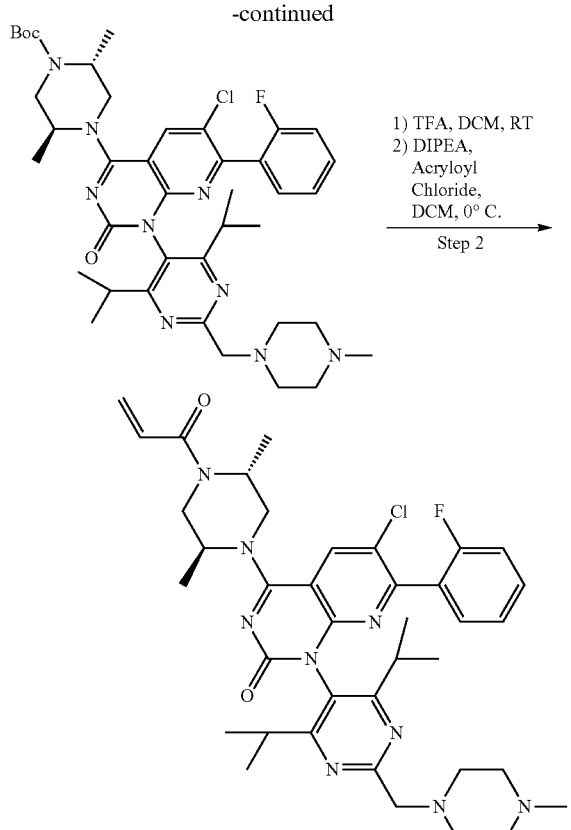

Step 1. tert-Butyl (2R,5S)-4-(6-chloro-1-(4,6-diisopropyl-2-((4-methylpiperazin-1-yl)methyl)pyrimidin-5-yl)-7-(2-fluorophenyl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(3-chloro-2-(2-fluorophenyl)-8-(2-formyl-4,6-diisopropylpyrimidin-5-yl)-7-oxo-7,8-dihydro-1,6-naphthyridin-5-yl)-2,5-dimethylpiperazine-1-carboxylate (Intermediate 235, 0.265 g, 0.391 mmol) and 1-methylpiperazine (0.1 mL, 0.587 mmol) in tetrahydrofuran (3.9 mL). Then glacial acetic acid (2.3 μl, 0.039 mmol), followed by sodium cyanoborohydride (0.074 g, 1.174 mmol) was added into the reaction mixture. The overall reaction mixture was allowed to stir at rt, while under an inert (N2) atmosphere for 30 min. The reaction mixture was quenched with MeOH (1 mL) and allowed the mixture to stir 5 min. Then the mixture was diluted with EtOAc and sat. aq. NaHCO₃. The layers were separated and the aqueous layer was extracted with EtOAc. The combined organic extracts were dried over MgSO₄, filtered and concentrated in vacuo. The crude material (0.250 g) was carried into the next step of the synthesis, without further purification. m/z (ESI, +ve ion): 762.2 (M+H)⁺.

Step 2. 4-((2S,5R)-4-Acryloyl-2,5-dimethylpiperazin-1-yl)-6-chloro-1-(4,6-diisopropyl-2-((4-methylpiperazin-1-yl)methyl)pyrimidin-5-yl)-7-(2-fluorophenyl)pyrido[2,3-d]pyrimidin-2(1H)-one To a 100-mL round-bottomed flask was added tert-butyl (2R,5S)-4-(6-chloro-1-(4,6-diisopropyl-2-((4-methylpiperazin-1-yl)methyl)pyrimidin-5-yl)-7-(2-fluorophenyl)-2-oxo-1,2-dihydropyrido[2,3-d]pyrimidin-4-yl)-2,5-dimethylpiperazine-1-carboxylate (0.250 g, 0.328 mmol) and trifluoroacetic acid (0.2 mL, 3.28 mmol) in 1,2-dichloroethane (1.5 mL). The reaction mixture was stirred and heated at 60° C. for 30 min, while under an inert (N2) atmosphere. The reaction mixture was concentrated in vacuo. This material was carried directly into the next step of the synthesis, without further purification.

The previous residue was diluted with 1,2-dichloroethane (1.5 mL), then the reaction mixture was cooled to 0° C. with a wet ice bath. Then n,n'-diisopropylethylamine (0.6 mL, 3.94 mmol) was added into the reaction mixture and stirred 2 min. Then acryloyl chloride (0.2 mL, 0.328 mmol) was added into the mixture dropwise and stirred under an inert (N$_2$) atmosphere for 10 min. The mixture was diluted with EtOAc and sat. aq. NaHCO$_3$, then the layers were separated. The aqueous layer was extracted with EtOAc, then the combined organic extracts were dried over MgSO$_4$, filtered and concentrated in vacuo. The crude material was absorbed onto a plug of silica gel and purified by chromatography through a Interchim (15 micron) silica-gel column (25 grams), eluting with a gradient of 0-5% MeOH/DCM. This afforded 4-((2S,5R)-4-acryloyl-2,5-dimethylpiperazin-1-yl)-6-chloro-1-(4,6-diisopropyl-2-((4-methylpiperazin-1-yl)methyl)pyrimidin-5-yl)-7-(2-fluorophenyl)pyrido[2,3-d]pyrimidin-2(1H)-one (0.050 g, 0.070 mmol, 21.29% yield) as white solid. $^1$H NMR (400 MHz, DMSO-d$_6$) δ 8.48 (d, J=4.77 Hz, 1H) 7.48-7.55 (m, 1H) 7.16-7.33 (m, 3H) 6.84 (td, J=17.31, 10.78 Hz, 1H) 6.19 (br d, J=16.59 Hz, 1H) 5.75 (br d, J=10.16 Hz, 1H) 4.88 (br s, 1H) 4.78 (br s, 1H) 4.43-4.54 (m, 1H) 4.13-4.26 (m, 1H) 3.79-3.93 (m, 2H) 3.70-3.76 (m, 2H) 3.39-3.55 (m, 1H) 2.53-2.78 (m, 6H) 2.28-2.37 (m, 3H) 2.15 (s, 3H) 1.34 (br t, J=5.49 Hz, 3 H) 1.26 (br d, J=6.43 Hz, 1H) 1.19 (br d, J=6.63 Hz, 2H) 1.02-1.10 (m, 6H) 0.92 (br d, J=6.63 Hz, 6H). m/z (ESI, +ve ion): 716.3 (M+H)$^+$.

Example 171

6-Chloro-4-[(2S,5R)-2,5-dimethyl-4-prop-2-enoyl-piperazin-1-yl]-7-(2-fluorophenyl)-1-[2-(3-furyl)-4,6-diisopropyl-pyrimidin-5-yl]pyrido[2,3-d]pyrimidin-2-one

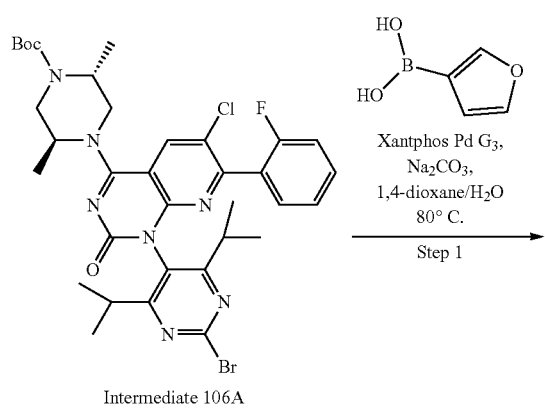

Intermediate 106A

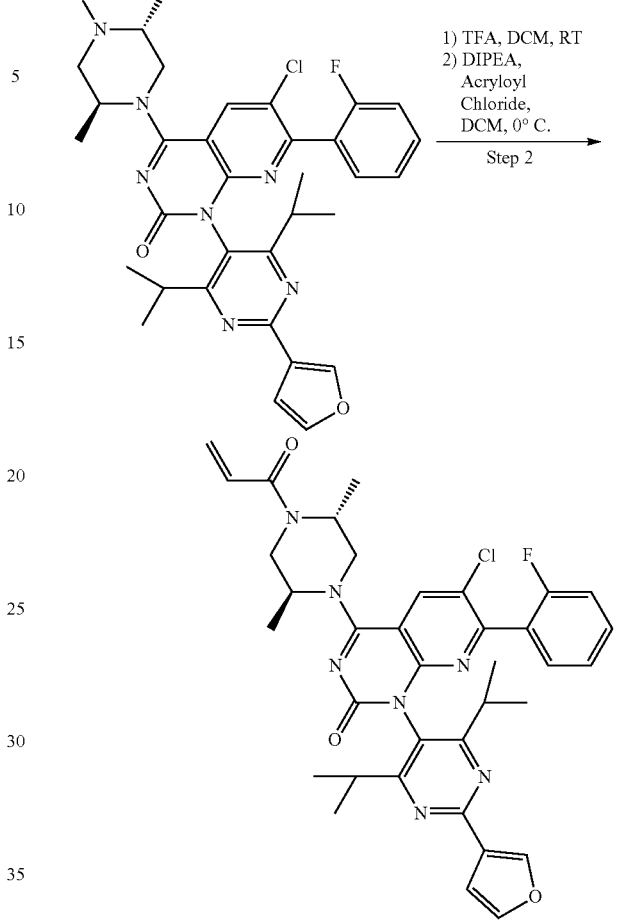

Step 1. tert-Butyl (2R,5S)-4-(6-chloro-7-(2-fluorophenyl)-1-(2-(furan-3-yl)-4,6-diisopropylpyrimidin-5-yl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (Intermediate 232, 0.080 g, 0.110 mmol) and sodium carbonate (0.035 g, 0.329 mmol) in 1,4-dioxane (2.4 mL). The reaction mixture was degassed by bubbling argon (gas) into the mixture for 5 min. Then xantphos pd g3 (5.20 mg, 5.49 mmol), water (0.6 mL) and 3-furanboronic acid (0.1 mL, 0.274 mmol) was added into the reaction mixture. The overall reaction mixture was stirred and heated at 80° C. for 16h. The reaction mixture was cooled to rt, then the mixture was diluted with sat. aq. NaHCO$_3$ and EtOAc. The layers were separated and the aqueous layer was extracted with EtOAc. The combined organic extracts were dried over MgSO$_4$, filtered and concentrated in vacuo. The crude material was absorbed onto a plug of silica gel and purified by chromatography through a Interchim (15 micron) silica-gel column (15 grams), eluting with a gradient of 0-25% EtOAc in CH2CL2, to provide tert-butyl (2R,5S)-4-(6-chloro-7-(2-fluorophenyl)-1-(2-(furan-3-yl)-4,6-diisopropylpyrimidin-5-yl)-2-oxo-1,2-dihydropyrido[2,3-d]pyrimidin- 4-yl)-2,5-dimethylpiperazine-1-carboxylate (0.070 g, 0.098 mmol, 89% yield) as tan solid. m/z (ESI, +ve ion): 716.2 (M+H)+.

Step 2. 4-((2S,5R)-4-Acryloyl-2,5-dimethylpiperazin-1-yl)-6-chloro-7-(2-fluorophenyl)-1-(2-(furan-3-yl)-4,6-diisopropylpyrimidin-5-yl)pyrido[2,3-d]pyrimidin-2(1H)-one To a 100-mL round-bottomed flask was added tert-butyl (2R,5S)-4-(6-chloro-7-(2-fluorophenyl)-1-(2-(furan-3-yl)-4,6-diisopropylpyrimidin-5-yl)-2-oxo-1,2-dihydropyrido[2,3-d]pyrimidin-4-yl)-2,5-dimethylpiperazine-1-carboxylate (0.070 g, 0.098 mmol) and trifluoroacetic acid (0.1 mL, 0.977 mmol) in 1,2-dichloroethane (1.7 mL). The reaction mixture was stirred and heated at 60° C. for 20 min, while under an inert (N₂) atmosphere. The reaction mixture was concentrated in vacuo. This material was carried directly into the next step of the synthesis, without further purification.

The previous residue was diluted with DCM (4 mL), then the reaction mixture was cooled to 0° C. with a wet ice bath. Then n,n'-diisopropylethylamine (0.2 mL, 1.173 mmol) was added into the reaction mixture and allowed the mixture to stir 2 min. Then acryloyl chloride (7.9 μl, 0.098 mmol) was added into the mixture dropwise over 2 min. The mixture was diluted with DCM and sat. aq. NaHCO₃, then the layers were separated. The aqueous layer was extracted with DCM. The combined organic extracts were dried over MgSO₄, filtered and concentrated in vacuo. The crude material was absorbed onto a plug of silica gel and purified by chromatography through a Interchim (15 micron) silica-gel column (25 grams), eluting with a gradient of 0-65% EtOAc/DCM. This afforded 4-((2S,5R)-4-acryloyl-2,5-dimethylpiperazin-1-yl)-6-chloro-7-(2-fluorophenyl)-1-(2-(furan-3-yl)-4,6-diisopropylpyrimidin-5-yl)pyrido[2,3-d]pyrimidin-2(1H)-one (0.010 g, 0.015 mmol, 15.27% yield) as white solid. ¹H NMR (500 MHz, DMSO-d₆) δ 8.49 (d, J=6.36 Hz, 1H) 8.39 (d, J=0.78 Hz, 1H) 7.79 (t, J=1.69 Hz, 1H) 7.46-7.53 (m, 1H) 7.19-7.33 (m, 3H) 7.02 (d, J=1.17 Hz, 1H) 6.79-6.90 (m, 1H) 6.17-6.22 (m, 1H) 5.73-5.78 (m, 1H) 4.84-4.94 (m, 1H) 4.14-4.26 (m, 1H) 3.81-3.95 (m, 2H) 2.65-2.77 (m, 2H) 2.54 (s, 2H) 1.30-1.40 (m, 3H) 1.16-1.28 (m, 3H) 1.12 (br d, J=4.02 Hz, 3H) 1.11 (br d, J=4.15 Hz, 3H) 0.94-1.01 (m, 6H). m/z (ESI, +ve ion): 670.2 (M+H)+.

Example 172

6-Chloro-1-(4,6-diisopropylpyrimidin-5-yl)-4-[(2S,5R)-2,5-dimethyl-4-prop-2-enoyl-piperazin-1-yl]-7-[2-(trifluoromethyl)phenyl]pyrido[2,3-d]pyrimidin-2-one

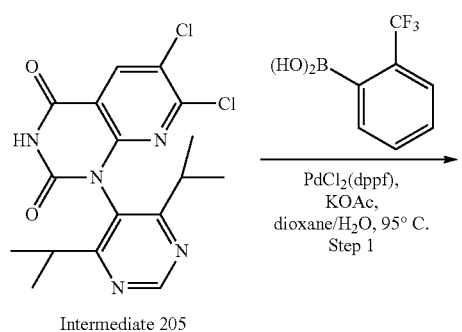

Intermediate 205

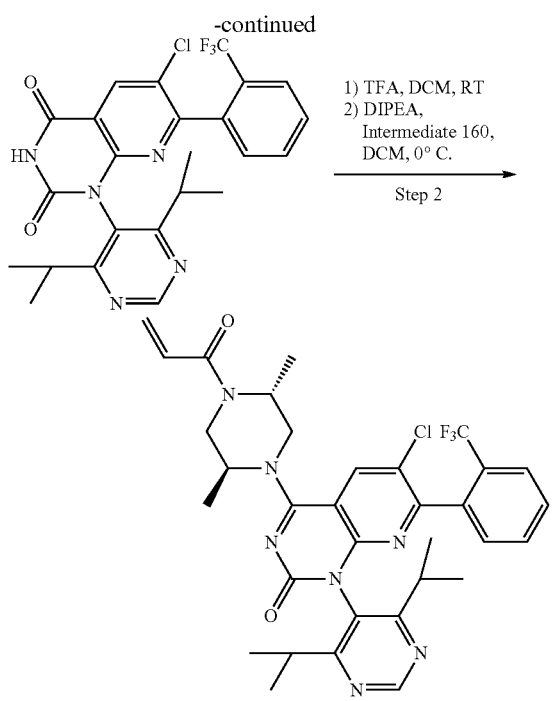

Step 1. 6-Chloro-1-(4,6-diisopropylpyrimidin-5-yl)-7-(2-(trifluoromethyl)phenyl)pyrido[2,3-d]pyrimidine-2,4(1H,3H)-dione To a 100-mL round-bottomed flask was added 6,7-dichloro-1-(4,6-diisopropylpyrimidin-5-yl)pyrido[2,3-d]pyrimidine-2,4(1H,3H)-dione (0.300 g, 0.761 mmol, Intermediate 205) and potassium acetate (0.224 g, 2.283 mmol) in 1,4-dioxane (3.8 mL). The reaction mixture was deoxygenated by bubbling (N₂) gas into the mixture 5 min. Then (1,1'-bis(diphenylphosphino) ferrocene) dichloropalladium (0.056 g, 0.076 mmol) was added into the reaction mixture. The reaction mixture was stirred and heated at 80° C. for 10 min. Then a solution of (2-(trifluoromethyl)phenyl)boronic acid (0.217 g, 1.141 mmol) in 1,4-dioxane (1 mL) was added into the mixture, followed by water (0.1 mL). The resulting reaction mixture was heated and stirred at 95° C. for 16 h. The reaction mixture was allowed to cool to ambient temperature, then the reaction mixture was diluted with sat. aq. NH₄Cl and EtOAc. The aqueous layer was extracted with EtOAc and brine. The combined organic extracts were dried over MgSO₄, filtered and concentrated in vacuo. The crude material was absorbed onto a plug of silica gel and purified by chromatography through a Redi-Sep pre-packed silica gel column (40 g), eluting with a gradient of 0-30% EtOAc in CH2CL2, to provide 6-chloro-1-(4,6-diisopropylpyrimidin-5-yl)-7-(2-(trifluoromethyl)phenyl)pyrido[2,3-d]pyrimidine-2,4(1H,3H)-dione (0.163 g, 0.323 mmol, 42.5% yield) as white solid. m/z (ESI, +ve ion): 504.1 (M+H)+.

Step 2. 4-((2S,5R)-4-Acryloyl-2,5-dimethylpiperazin-1-yl)-6-chloro-1-(4,6-diisopropylpyrimidin-5-yl)-7-(2-(trifluoromethyl)phenyl)pyrido[2,3-d]pyrimidin-2(1H)-one To a 100-mL round-bottomed flask was added 6-chloro-1-(4,6-diisopropylpyrimidin-5-yl)-7-(2-(trifluoromethyl)phenyl)pyrido[2,3-d]pyrimidine-2,4(1H,3H)-dione (0.150 g, 0.298 mmol) and n,n-diisopropylethylamine (0.1 mL, 0.387 mmol) in acetonitrile (1.4 mL). Then phosphorous oxychloride (0.1 mL, 0.357 mmol) was added into the reaction mixture, then the mixture was heated and stirred at 80° C. for 30 min, while under an inert (N₂) atmosphere. Another aliquot of n,n-diisopropylethylamine (0.1 mL, 0.387 mmol) and phosphorous oxychloride (0.1 mL, 0.357 mmol) was added into the mixture, then allowed the mixture to stir an additional 10 min. The reaction mixture was removed from the heat bath and allowed to cool to rt.

The reaction mixture was cooled to 0° C. with a wet ice/water bath. Then DIPEA (3 mL) was added dropwise into the reaction mixture. Then a solution of 1-((2R,5S)-2,5-dimethylpiperazin-1-yl)prop-2-en-1-one (0.233 g, 0.595 mmol, Intermediate 160) in MeCN (10 mL) was added dropwise into the reaction mixture. The ice bath was removed and the mixture was allowed to warm to rt over 20 min. More DIPEA (3 mL) and 1-((2R,5S)-2,5-dimethylpiperazin-1-yl)prop-2-en-1-one (0.233 g, 0.595 mmol, Intermediate 160) was added into the reaction mixture and stirred an additional 10 min. The reaction mixture was diluted with EtOAc and sat. aq. NH₄Cl. The aqueous layer was extracted with EtOAc. The combined organic extracts were dried over MgSO4, filtered and concentrated in vacuo. The crude material was absorbed onto a plug of silica gel and purified by chromatography through a Interchim (25 micron) silica-gel column (80 grams), eluting with a gradient of 0-80% EtOAc in CH2CL2, to provide 4-((2S,5R)-4-acryloyl-2,5-dimethylpiperazin-1-yl)-6-chloro-1-(4,6-diisopropylpyrimidin-5-yl)-7-(2-(trifluoromethyl)phenyl)pyrido[2,3-d]pyrimidin-2(1H)-one (0.020 g, 0.031 mmol, 10.27% yield) as white solid. ¹H NMR (500 MHz, DMSO-d₆) δ 9.02 (s, 1H) 8.60 (br s, 1H) 7.81 (d, J=7.78 Hz, 1H) 7.77 (t, J=7.56 Hz, 1H) 7.66-7.71 (m, 1H) 7.35 (br s, 1H) 6.82 (br dd, J=16.67, 10.45 Hz, 1H) 6.19 (dd, J=16.67, 2.27 Hz, 1H) 5.74-5.78 (m, 1H) 4.64-5.02 (m, 2H) 4.09 (br d, J=5.32 Hz, 1H) 4.04 (br s, 1H) 3.88 (br s, 2H) 2.64-2.83 (m, 2H) 1.30-1.38 (m, 3H) 1.21-1.30 (m, 2H) 1.19 (br s, 1H) 1.07 (br s, 6H) 0.92 (br s, 6H). m/z (ESI, +ve ion): 654.2 (M+H)⁺.

Example 173-1 (Peak 1)

6-Chloro-4-[(2S,5R)-2,5-dimethyl-4-prop-2-enoyl-piperazin-1-yl]-7-(2-fluorophenyl)-1-(6-isopropenyl-2-isopropyl-4-methyl-3-pyridyl)pyrido[2,3-d]pyrimidin-2-one

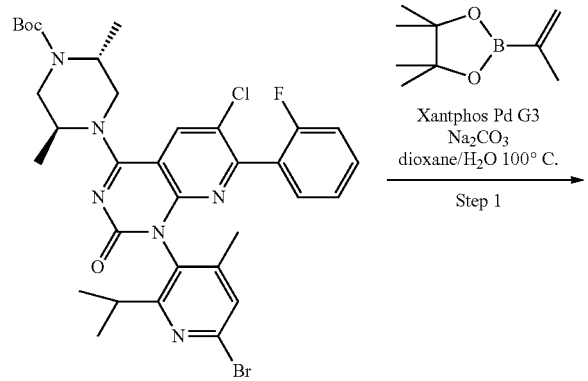

Intermediate 202

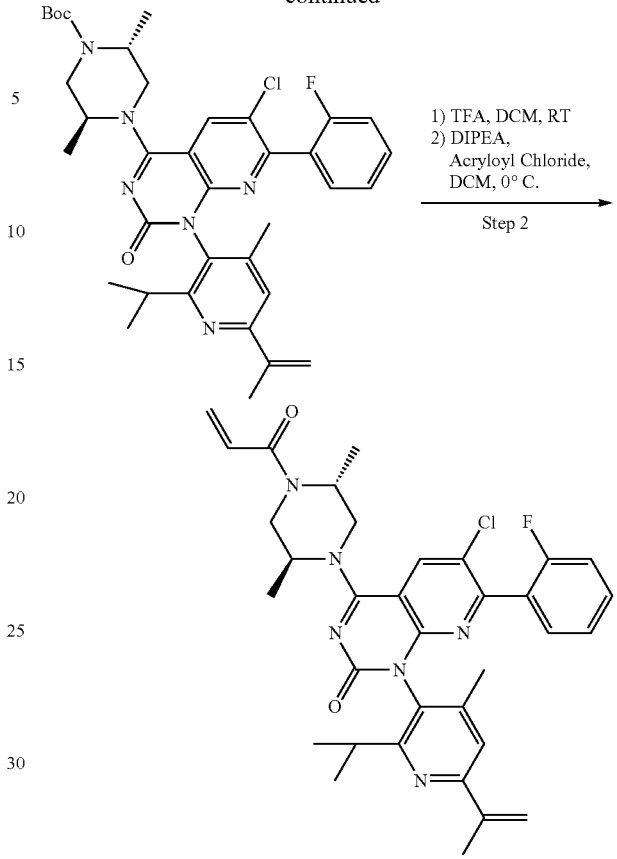

Step 1. tert-Butyl (2R,5S)-4-(6-chloro-7-(2-fluorophenyl)-1-(2-isopropyl-4-methyl-6-(prop-1-en-2-yl)pyridin-3-yl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(1-(6-bromo-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.420 g, 0.600 mmol, Intermediate 202) and sodium carbonate (0.191 g, 1.800 mmol) in 1,4-dioxane (2.4 mL). The reaction mixture was degassed by bubbling argon (gas) into the mixture for 5 min. Then xantphos pd g3 (0.028 g, 0.030 mmol), water (0.6 mL) and 2-isopropenyl boronic acid pinacol ester (0.2 mL, 1.500 mmol) was added into the reaction mixture. The overall reaction mixture was stirred and heated at 100° C. for 16 h. The reaction mixture was cooled to rt, then the mixture was diluted with sat. aq. NaHCO₃ and EtOAc. The layers were separated and the aqueous layer was extracted with EtOAc. The combined organic extracts were dried over MgSO₄, filtered and concentrated in vacuo. The crude material was absorbed onto a plug of silica gel and purified by chromatography through a Interchim (25 micron) silica-gel column (40 grams), eluting with a gradient of 0-20% EtOAc in CH2CL2, to provide tert-butyl (2R,5S)-4-(6-chloro-7-(2-fluorophenyl)-1-(2-isopropyl-4-methyl-6-(prop-1-en-2-yl)pyridin-3-yl)-2-oxo-1,2-dihydropyrido[2,3-d]pyrimidin-4-yl)-2,5-dimethylpiperazine-1-carboxylate (0.200 g, 0.302 mmol, 50.4% yield) as white solid. m/z (ESI, +ve ion): 661.3 (M+H)⁺.

Step 2. 4-((2S,5R)-4-Acryloyl-2,5-dimethylpiper-azin-1-yl)-6-chloro-7-(2-fluorophenyl)-1-(2-isopropyl-4-methyl-6-(prop-1-en-2-yl)pyridin-3-yl)pyrido[2,3-d]pyrimidin-2(1H)-one To a 100-mL round-bottomed flask was added tert-butyl (2R,5S)-4-(6-chloro-7-(2-fluorophenyl)-1-(2-isopropyl-4-methyl-6-(prop-1-en-2-yl)pyridin-3-yl)-2-oxo-1,2-dihydropyrido[2,3-d]pyrimidin-4-yl)-2,5-dimethylpiperazine-1-carboxylate (0.200 g, 0.302 mmol) and trifluoroacetic acid (0.2 mL, 3.02 mmol) in 1,2-dichloroethane (3.0 mL). The reaction mixture was stirred and heated at 60° C. for 30 min. while under an inert (N2) atmosphere. The reaction mixture was concentrated in vacuo. This material was carried directly into the next step of the synthesis, without further purification.

The previous residue was diluted with 1,2-dichloroethane (3.0 mL), then the reaction mixture was cooled to 0° C. with a wet ice bath. Then n,n'-diisopropylethylamine (0.6 mL, 3.63 mmol) was added into the reaction mixture and stirred 2 min. Then acryloyl chloride (0.2 mL, 0.302 mmol) was added into the mixture dropwise and stirred under an inert ($N_2$) atmosphere for 10 min. The mixture was diluted with EtOAc and sat. aq. $NaHCO_3$, then the layers were separated. The aqueous layer was extracted with EtOAc, then the combined organic extracts were dried over $MgSO_4$, filtered and concentrated in vacuo. The crude material was absorbed onto a plug of silica gel and purified by chromatography through a Interchim (15 micron) silica-gel column (40 grams), eluting with a gradient of 0-6% MeOH/DCM. The racemic mixture was separated by SFC, (Column, IC, 5 µm, 21×250 mm, F=80 mL/min, 30% Isopropanol/70% Carbon dioxide). This afforded the separated Atropisomers, which were arbitrarily assigned as (Peak 1) 4-((2S,5R)-4-acryloyl-2,5-dimethylpiperazin-1-yl)-6-chloro-7-(2-fluorophenyl)-1-(2-isopropyl-4-methyl-6-(prop-1-en-2-yl)pyridin-3-yl)pyrido[2,3-d]pyrimidin-2(1H)-one (0.060 g, 0.098 mmol, 32.2% yield) as white solid. $^1$H NMR (400 MHz, DMSO-$d_6$) δ 8.47 (d, J=3.52 Hz, 1H) 7.46-7.56 (m, 1H) 7.43 (s, 1H) 7.22-7.35 (m, 3H) 6.84 (td, J=16.74, 10.47 Hz, 1H) 6.20 (dd, J=16.79, 1.87 Hz, 1H) 5.97 (s, 1H) 5.73-5.79 (m, 1H) 5.30 (s, 1H) 4.86 (br s, 1H) 4.78 (br s, 1H) 4.12-4.23 (m, 1H) 3.80-4.00 (m, 2H) 2.66-2.75 (m, 1H) 2.15 (s, 3H) 1.95 (s, 3H) 1.32-1.39 (m, 3H) 1.24-1.28 (m, 2H) 1.17-1.21 (m, 2H) 1.09 (d, J=6.84 Hz, 3H) 0.99 (d, J=6.63 Hz, 3H). m/z (ESI, +ve ion): 615.2 (M+H)$^+$.

Example 173-2 (Peak 2)

The racemic mixture from example 173-1 was separated by SFC; (Column, IC, 5 µm, 21×250 mm, F=80 mL/min, 30% Isopropanol/70% Carbon dioxide). This afforded the separated Atropisomers, which were arbitrarily assigned as (Peak 2) 1H NMR (500 MHz, DMSO-d6) δ 8.48 (d, J=3.76 Hz, 1H) 7.49-7.54 (m, 1H) 7.44 (s, 1H) 7.23-7.33 (m, 3H) 6.83 (td, J=17.06, 10.51 Hz, 1H) 6.19 (br d, J=16.74 Hz, 1H) 5.96 (s, 1H) 5.73-5.78 (m, 1H) 5.29 (s, 1H) 4.83-4.91 (m, 1H) 4.76 (br s, 1H) 4.10-4.21 (m, 2H) 3.80-3.97 (m, 2H) 2.64-2.71 (m, 1H) 2.14 (s, 3H) 1.97 (s, 3H) 1.30-1.37 (m, 3H) 1.24 (d, J=6.49 Hz, 1H) 1.16 (d, J=6.75 Hz, 2H) 1.07 (d, J=6.75 Hz, 3H) 0.95 (d, J=6.75 Hz, 3H). m/z (ESI, +ve ion): 615.4 (M+H)$^+$.

Example 174

6-Chloro-1-(4,6-diisopropylpyrimidin-5-yl)-4-[(2S,5R)-2,5-dimethyl-4-prop-2-enoyl-piperazin-1-yl]-7-(5-hydroxy-2-methyl-phenyl)pyrido[2,3-d]pyrimidin-2-one

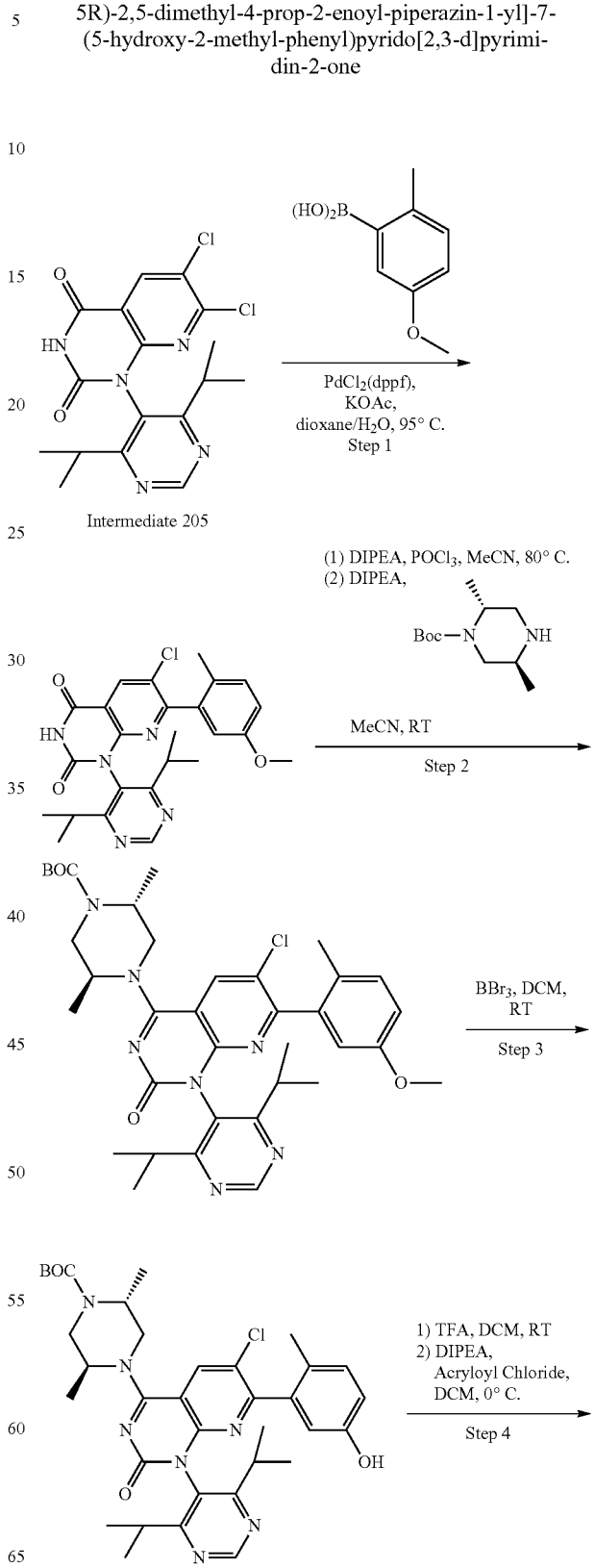

-continued

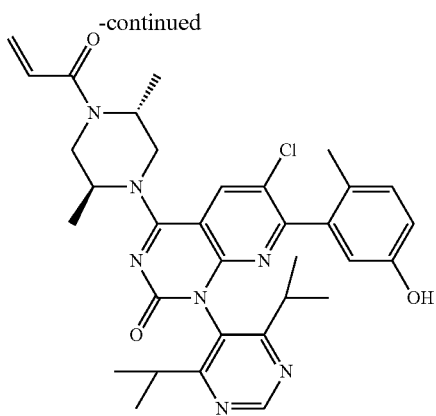

Step 1. 6-Chloro-1-(4,6-diisopropylpyrimidin-5-yl)-7-(5-methoxy-2-methylphenyl)pyrido[2,3-d]pyrimidine-2,4(1H,3H)-dione To a 100-mL round-bottomed flask was added 6,7-dichloro-1-(4,6-diisopropylpyrimidin-5-yl)pyrido[2,3-d]pyrimidine-2,4(1H,3H)-dione (0.400 g, 1.015 mmol, Intermediate 205) and potassium acetate (0.299 g, 3.04 mmol) in 1,4-dioxane (7.6 mL). The reaction mixture was deoxygenated by bubbling ($N_2$) gas into the mixture 5 min. Then PdCl2(dppf) (0.074 g, 0.101 mmol) was added into the reaction mixture. The mixture was stirred and heated at 105° C. for 10 min. Then a solution of (5-methoxy-2-methylphenyl)boronic acid (0.3 mL, 2.029 mmol) in 1,4-dioxane (1 mL) was added into the mixture, followed by water (1.9 mL). The resulting reaction mixture was heated and stirred at 105° C. for 3 h. The reaction mixture was allowed to cool to ambient temperature, then diluted the mixture with sat. aq. $NH_4Cl$ and EtOAc. The aqueous layer was extracted with EtOAc and brine. The combined organic extracts were dried over $MgSO_4$, filtered and concentrated in vacuo. The crude material was absorbed onto a plug of silica gel and purified by chromatography through a Redi-Sep pre-packed silica gel column (40 g), eluting with a gradient of 0-20% EtOAc in CH2CL2, to provide 6-chloro-1-(4,6-diisopropylpyrimidin-5-yl)-7-(5-methoxy-2-methylphenyl)pyrido[2,3-d]pyrimidine-2,4(1H,3H)-dione (0.450 g, 0.938 mmol, 92% yield) as tan solid. $^1$H NMR (400 MHz, DMSO-$d_6$) δ 12.28 (s, 1H) 9.07 (s, 1H) 8.57 (s, 1H) 7.16 (d, J=8.50 Hz, 1H) 6.85-6.93 (m, 1H) 6.51 (d, J=2.70 Hz, 1H) 3.63-3.67 (m, 3H) 2.98 (quin, J=6.63 Hz, 2H) 1.85 (s, 3H) 1.09 (d, J=6.63 Hz, 6H) 0.95 (d, J=6.63 Hz, 6H). m/z (ESI, +ve ion): 480.1 (M+H)$^+$.

Step 2. 4-((2S,5R)-4-((l1-Boraneyl)carbonyl)-2,5-dimethylpiperazin-1-yl)-6-chloro-1-(4,6-diisopropylpyrimidin-5-yl)-7-(5-methoxy-2-methylphenyl)pyrido[2,3-d]pyrimidin-2(1H)-one To a 100-mL round-bottomed flask was added 6-chloro-1-(4,6-diisopropylpyrimidin-5-yl)-7-(5-methoxy-2-methylphenyl)pyrido[2,3-d]pyrimidine-2,4(1H,3H)-dione (0.450 g, 0.938 mmol) and n,n-diisopropylethylamine (0.2 mL, 1.219 mmol) in acetonitrile (6.2 mL). Then phosphorous oxychloride (0.1 mL, 1.125 mmol) was added into the reaction mixture, then the mixture was heated and stirred at 80° C. for 30 min, while under an inert ($N_2$) atmosphere. The reaction mixture was removed from the heat bath and allowed to cool to rt.

The reaction mixture was cooled to 0° C. with a wet ice/water bath. Then DIPEA (2.5 mL) was added dropwise into the reaction mixture. Then a solution of (2r,5s)-1-boc-2,5-dimethylpiperazine (0.301 g, 1.406 mmol) in MeCN (4 mL) was added dropwise into the reaction mixture. The ice bath was removed and the mixture was allowed to warm to rt. The reaction mixture was diluted with DCM and sat. aq. $NH_4Cl$. The aqueous layer was extracted with DCM. The combined organic extracts were dried over $MgSO_4$, filtered and concentrated in vacuo. The crude material was absorbed onto a plug of silica gel and purified by chromatography through a Interchim (25 micron) silica-gel column (120 grams). eluting with a gradient of 0-10% MeOH in CH2CL2, to provide tert-butyl (2R,5S)-4-(6-chloro-1-(4,6-diisopropylpyrimidin-5-yl)-7-(5-methoxy-2-methylphenyl)-2-oxo-1,2-dihydropyrido[2,3-d]pyrimidin-4-yl)-2,5-dimethylpiperazine-1-carboxylate (0.600 g, 0.887 mmol, 95% yield) as tan solid. m/z (ESI, +ve ion): 676.3 (M+H)$^+$.

Step 3. tert-Butyl (2R,5S)-4-(6-chloro-1-(4,6-diisopropylpyrimidin-5-yl)-7-(5-hydroxy-2-methylphenyl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(6-chloro-1-(4,6-diisopropylpyrimidin-5-yl)-7-(5-methoxy-2-methylphenyl)-2-oxo-1,2-dihydropyrido[2,3-d]pyrimidin-4-yl)-2,5-dimethylpiperazine-1-carboxylate (0.600 g, 0.887 mmol) in 1,2-dichloroethane (17.7 mL). Then boron tribromide (1.0M in DCM) (4.4 mL, 4.44 mmol) was added dropwise into the reaction mixture, while the mixture was under an inert ($N_2$) atmosphere. The resulting reaction mixture was allowed to stir 30 min. The reaction mixture was quenched with the addition of MeOH (3 mL) and allowed the mixture to stir 10 min. Then the reaction mixture was diluted with DCM and sat. aq. $NaHCO_3$. The aqueous layer was extracted with DCM and the combined organic extracts were dried over MgSO4, filtered and concentrated in vacuo. This afforded tert-butyl (2R,5S)-4-(6-chloro-1-(4,6-diisopropylpyrimidin-5-yl)-7-(5-hydroxy-2-methylphenyl)-2-oxo-1,2-dihydropyrido[2,3-d]pyrimidin-4-yl)-2,5-dimethylpiperazine-1-carboxylate as tan solid. The crude mixture (0.499 grams) was carried into the next step of the synthesis, without further purification. m/z (ESI, +ve ion): 562.2 (M-BOC+H)$^+$.

Step 4. 4-((2S,5R)-4-Acryloyl-2,5-dimethylpiperazin-1-yl)-6-chloro-1-(4,6-diisopropylpyrimidin-5-yl)-7-(5-hydroxy-2-methylphenyl)pyrido[2,3-d]pyrimidin-2(1H)-one To a 100-mL round-bottomed flask was added 6-chloro-1-(4,6-diisopropylpyrimidin-5-yl)-4-((2S,5R)-2,5-dimethylpiperazin-1-yl)-7-(5-hydroxy-2-methylphenyl)pyrido[2,3-d]pyrimidin-2(1H)-one (0.499 g, 0.888 mmol) and n,n'-diisopropylethylamine (0.2 mL, 1.332 mmol) in 1,2-dichloroethane (4.4 mL). Then acryloyl chloride (1.1M in DCM) (0.8 mL, 0.888 mmol) was added slowly into the reaction mixture. The overall reaction mixture was allowed to stir under an inert ($N_2$) atmosphere 10 min. The reaction mixture was quenched with sat. aq. $NH_4Cl$, then diluted the mixture with DCM and water. The layers were separated and the aqueous layer was extracted with DCM. The combined organic extracts were dried over $MgSO_4$, filtered and concentrated in vacuo. The crude material was absorbed onto a plug of silica gel and purified by chromatography through a Redi-Sep pre-packed silica gel column (80 g), eluting with a gradient of 0-8% MeOH/DCM, to provide 4-((2S,5R)-4-acryloyl-2,5-dimethylpiperazin-1-yl)-6-chloro-1-(4,6-diisopropylpyrimidin-5-yl)-7-(5-hydroxy-2-methylphenyl)pyrido[2,3-d]pyrimidin-2(1H)-one (0.175 g, 0.284 mmol, 32.0% yield) as off-white solid. $^1$H NMR (400 MHz, DMSO-d6) δ 9.40 (s, 1H) 9.04 (s, 1H) 8.45 (d, J=3.32 Hz, 1H) 7.02 (d, J=8.29 Hz, 1H) 6.84 (td, J=16.64, 10.68 Hz, 1H) 6.70 (dd, J=8.29, 2.49 Hz, 1H) 6.40 (d, J=2.49 Hz, 1H) 6.19 (dd, J=16.59, 2.07 Hz, 1H) 5.75 (br dd, J=10.68, 3.42 Hz, 1H) 4.87 (br s, 1H) 4.13-4.25 (m, 1H) 3.79-3.94 (m, 2H) 3.16-3.18 (m, 1H) 2.63-2.79 (m, 2H) 1.82 (s, 3H) 1.34 (br t, J=5.80 Hz, 3H) 1.25 (br d, J=6.63 Hz, 2H) 1.18 (br d, J=6.63 Hz, 2H) 1.08 (dd, J=6.32, 4.66 Hz, 6H) 0.95 (br t, J=5.70 Hz, 6H). m/z (ESI, +ve ion): 616.2 (M+H)$^+$.

Example 175-1 (Peak 1)

1-[6-(Azetidin-1-yl)-2-isopropyl-4-methyl-3-pyridyl]-6-chloro-4-[(2S,5R)-2,5-dimethyl-4-prop-2-enoyl-piperazin-1-yl]-7-(2-fluorophenyl)pyrido[2,3-d]pyrimidin-2-one

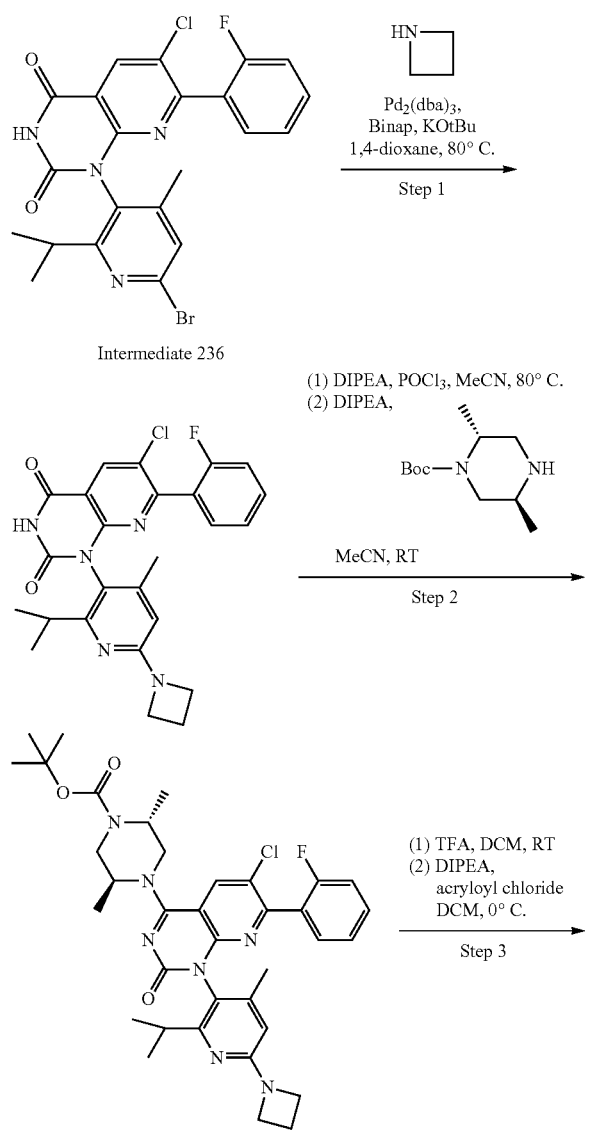

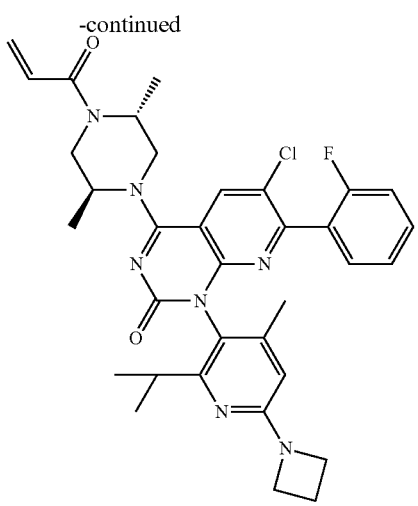

Step 1. 1-(6-(Azetidin-1-yl)-2-isopropyl-4-methylpyridin-3-yl)-6-chloro-7-(2-fluorophenyl)pyrido[2,3-d]pyrimidine-2,4(1H,3H)-dione To a 50-mL round-bottomed flask was added 1-(6-bromo-2-isopropyl-4-methylpyridin-3-yl)-6-chloro-7-(2-fluorophenyl)pyrido[2,3-d]pyrimidine-2,4(1H,3H)-dione (0.350 g, 0.695 mmol, Intermediate 236) and azetidine (0.3 mL, 6.95 mmol) in 1,4-dioxane (2.8 mL). The reaction mixture was stirred and heated at 70° C. while under an inert (N$_2$) atmosphere overnight. The mixture was allowed to cool to ambient temperature, then diluted the mixture with EtOAc and water. The aqueous layer was extracted with EtOAc (3×) and the combined organic extracts were dried over MgSO4, filtered and concentrated in vacuo. The crude material was absorbed onto a plug of silica gel and purified by chromatography through a Redi-Sep pre-packed silica gel column (40 g), eluting with a gradient of 0-10% EtOAc in CH2CL2, to provide 1-(6-(azetidin-1-yl)-2-isopropyl-4-methylpyridin-3-yl)-6-chloro-7-(2-fluorophenyl)pyrido[2,3-d]pyrimidine-2,4(1H,3H)-dione (0.240 g, 0.500 mmol, 72.0% yield) as yellow solid. $^1$H NMR (400 MHz, DMSO-d$_6$) δ 12.12 (s, 1H) 8.53 (s, 1H) 7.43-7.56 (m, 1H) 7.19-7.38 (m, 3H) 6.10 (s, 1H) 3.85-4.04 (m, 4H) 2.68-2.74 (m, 1H) 2.23-2.32 (m, 2H) 1.88 (s, 3H) 1.03 (d, J=6.84 Hz, 3H) 0.88 (d, J=6.63 Hz, 3H). m/z (ESI, +ve ion): 480.0 (M+H)$^+$.

Step 2. tert-Butyl (2R,5S)-4-(1-(6-(azetidin-1-yl)-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added 1-(6-(azetidin-1-yl)-2-isopropyl-4-methylpyridin-3-yl)-6-chloro-7-(2-fluorophenyl)pyrido[2,3-d]pyrimidine-2,4(1H,3H)-dione (0.480 g, 1.000 mmol) and n,n-diisopropylethylamine (0.2 ml, 1.300 mmol) in acetonitrile (6.6 ml). Then phosphorous oxychloride (0.1 ml, 1.200 mmol) was added into the reaction mixture, then the mixture was heated and stirred at 80° C. for 30 min, while under an inert (N2) atmosphere. The reaction mixture was removed from the heat bath and allowed to cool to it.

The reaction mixture was cooled to 0° C. with a wet ice/water bath. Then DIPEA (2.5 mL) was added dropwise into the reaction mixture. Then a solution of (2r,5s)-1-boc- 2,5-dimethylpiperazine (0.322 g, 1.500 mmol) in MeCN (4 mL) was added dropwise into the reaction mixture. The ice bath was removed and the mixture was allowed to warm to rt. The reaction mixture was diluted with DCM and sat. aq. NH₄Cl. The aqueous layer was extracted with DCM. The combined organic extracts were dried over MgSO₄, filtered and concentrated in vacuo. The crude material was absorbed onto a plug of silica gel and purified by chromatography through a Interchim (25 micron) silica-gel column (120 grams), eluting with a gradient of 0-30% EtOAc in CH₂CL₂, to provide tert-butyl (2R,5S)-4-(1-(6-(azetidin-1-yl)-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.385 g, 0.569 mmol, 56.9% yield) as yellow solid. m/z (ESI, +ve ion): 676.2 (M+H)⁺.

Step 3. 4-((2S,5R)-4-Acryloyl-2,5-dimethylpiperazin-1-yl)-1-(6-(azetidin-1-yl)-2-isopropyl-4-methylpyridin-3-yl)-6-chloro-7-(2-fluorophenyl)pyrido[2,3-d]pyrimidin-2(1H)-one To a 100-mL round-bottomed flask was added tert-butyl (2R,5S)-4-(1-(6-(azetidin-1-yl)-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.381 g, 0.563 mmol) and trifluoroacetic acid (0.4 mL, 5.63 mmol) in 1,2-dichloroethane (3.0 mL). The reaction mixture was stirred and heated at 60° C. for 30 min. while under an inert (N2) atmosphere. The reaction mixture was concentrated in vacuo. This material was carried directly into the next step of the synthesis, without further purification.

The previous residue was diluted with 1,2-dichloroethane (3.0 mL), then the reaction mixture was cooled to 0° C. with a wet ice bath. Then n,n'-diisopropylethylamine (1.1 mL, 6.76 mmol) was added into the reaction mixture and stirred 2 min. Then acryloyl chloride (0.5 mL, 0.563 mmol) was added into the mixture dropwise and stirred under an inert (N2) atmosphere for 10 min. The mixture was diluted with EtOAc and sat. aq. NaHCO₃, then the layers were separated. The aqueous layer was extracted with EtOAc, then the combined organic extracts were dried over MgSO₄, filtered and concentrated in vacuo. The crude material was absorbed onto a plug of silica gel and purified by chromatography through a Interchim (15 micron) silica-gel column (40 grams), eluting with a gradient of 0-6% MeOH/DCM. The racemates were separated by SFC; (Column, ID, 5 μm, 21×250 mm, F=60 mL/min, 40% EtOH/60%: Carbon dioxide). This afforded the separated Atropisomers as Peak 1: 4-((2S,5R)-4-acryloyl-2,5-dimethylpiperazin-1-yl)-1-(6-(azetidin-1-yl)-2-isopropyl-4-methylpyridin-3-yl)-6-chloro-7-(2-fluorophenyl)pyrido[2,3-d]pyrimidin-2(1H)-one (0.118 g, 0.187 mmol, 33.2% yield) as light-yellow solid. ¹H NMR (400 MHz, DMSO-d₆) δ 8.44 (s, 1H) 7.43-7.60 (m, 1H) 7.23-7.38 (m, 3H) 6.82 (dt J=16.53, 11.32 Hz, 1H) 6.11-6.22 (m, 2H) 5.75 (dt, J=12.75, 2.23 Hz, 1H) 4.84 (br s, 1H) 4.41-4.65 (m, 1H) 4.11 (br t. J=13.16 Hz, 2H) 3.90-3.94 (m, 4H) 3.79-3.87 (m, 1H) 2.28 (quin, J=7.31 Hz, 2H) 1.77-1.86 (m, 3H) 1.31 (br t, J=7.05 Hz, 3H) 1.22 (br d, J=6.63 Hz, 2H) 1.10-1.15 (m, 3H) 1.00 (d, J=6.63 Hz, 3H) 0.87 (d, J=6.63 Hz, 3H). m/z (ESI, +ve ion): 630.2 (M+H)⁺.

Example 175-2 (Peak 2)

The racemates were separated by SFC; (Column, ID, 5 μm, 21×250 mm, F=60 mL/min, 40% EtOH/60%: Carbon dioxide). This afforded the separated Atropisomers as Peak 2: 4-((2S,5R)-4-acryloyl-2,5-dimethylpiperazin-1-yl)-1-(6-(azetidin-1-yl)-2-isopropyl-4-methylpyridin-3-yl)-6-chloro-7-(2-fluorophenyl)pyrido[2,3-d]pyrimidin-2(1H)-one (0.120 g, 0.190 mmol, 33.8% yield) as light-yellow solid. ¹H NMR (400 MHz, DMSO-d₆) δ 8.42 (s, 1H) 7.43-7.61 (m, 1H) 7.20-7.39 (m, 3H) 6.83 (td, J=16.27, 10.57 Hz, 1H) 6.19 (br d, J=16.38 Hz, 1H) 6.11 (s, 1H) 5.74 (br d, J=9.95 Hz, 1H) 4.82 (br s, 1H) 4.54-4.67 (m, 1H) 4.12 (br t, J=12.96 Hz, 2H) 3.89-3.95 (m, 4H) 3.85 (br s, 1H) 2.28 (quin, J=7.20 Hz, 2H) 1.79 (s, 3H) 1.31 (br t, J=7.05 Hz, 3H) 1.24 (br d, J=6.01 Hz, 2H) 1.10-1.15 (m, 3H) 0.99-1.03 (m, 3H) 0.90 (br d, J=6.43 Hz, 3H). m/z (ESI, +ve ion): 630.2 (M+H)⁺.

Example 176-1 (Peak 1)

6-Chloro-1-(2,6-diisopropyl-4-methyl-3-pyridyl)-4-[(2S,5R)-2,5-dimethyl-4-prop-2-enoyl-piperazin-1-yl]-7-(2-fluorophenyl)pyrido[2,3-d]pyrimidin-2-one

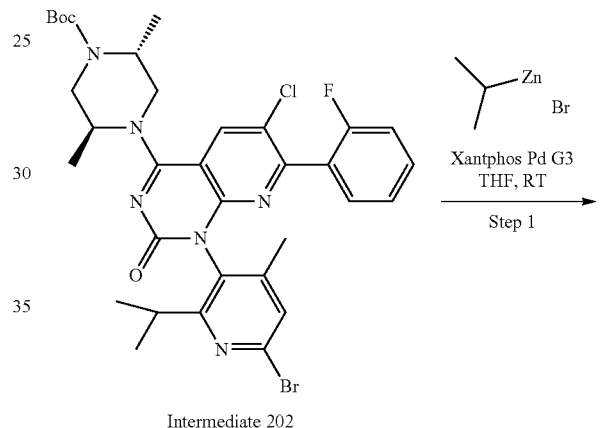

Intermediate 202

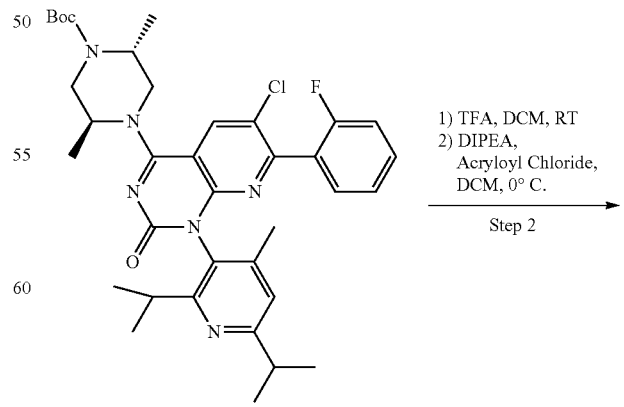

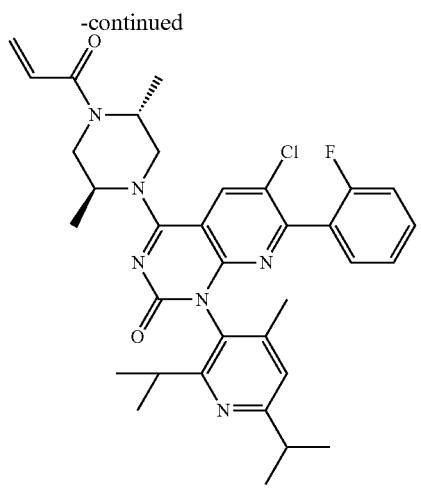

Step 1. tert-Butyl (2R,5S)-4-(6-chloro-1-(2,6-diisopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(1-(6-bromo-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.400 g, 0.571 mmol, Intermediate 202) in tetrahydrofuran (2.8 mL). The reaction mixture was degassed by bubbling argon (gas) into the mixture for 5 min. Then 2-propylzinc bromide (1.0M in THF) (3.0 mL, 3.03 mmol) and xantphos pd g3 (0.016 g, 0.017 mmol) was added into the reaction mixture. The overall reaction mixture was allowed to stir under an inert (N2) atmosphere at rt for 16 h. The reaction mixture was quenched with sat. aq. NH$_4$Cl and diluted the mixture with EtOAc. The layers were separated and the aqueous layer was extracted with EtOAc. The combined organic extracts were dried over MgSO$_4$, filtered and concentrated in vacuo. The crude material was absorbed onto a plug of silica gel and purified by chromatography through a Interchim (25 micron) silica-gel column (25 grams), eluting with a gradient of 0-40% EtOAc in CH2CL2, to provide tert-butyl (2R,5S)-4-(6-chloro-1-(2,6-diisopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate (0.253 g, 0.381 mmol, 66.8% yield) as tan solid. m/z (ESI, +ve ion): 663.2 (M+H)$^+$.

Step 2. 4-((2S,5R)-4-Acryloyl-2,5-dimethylpiperazin-1-yl)-6-chloro-1-(2,6-diisopropyl-4-methylpyridin-3-yl)-7-(2-fluorophenyl)pyrido[2,3-d]pyrimidin-2(1H)-one To a 100-mL round-bottomed flask was added tert-butyl (2R,5S)-4-(6-chloro-1-(2,6-diisopropyl-4-methylpyridin-3-yl)-7-(2-fluorophenyl)-2-oxo-1,2-dihydropyrido[2,3-d]pyrimidin-4-yl)-2,5-dimethylpiperazine-1-carboxylate (0.253 g, 0.381 mmol) and trifluoroacetic acid (0.2 mL, 3.81 mmol) in 1,2-dichloroethane (3.8 mL). The reaction mixture was stirred and heated at 60° C. for 30 min, while under an inert (N$_2$) atmosphere. The reaction mixture was concentrated in vacuo. This material was carried directly into the next step of the synthesis, without further purification.

The previous residue was diluted with 1,2-dichloroethane (3.8 mL), then the reaction mixture was cooled to 0° C. with a wet ice bath. Then n,n'-diisopropylethylamine (0.8 mL, 4.58 mmol) was added into the reaction mixture and stirred 2 min. Then acryloyl chloride (0.3 mL, 0.381 mmol) was added into the mixture dropwise and stirred under an inert (N$_2$) atmosphere for 10 min. The mixture was diluted with EtOAc and sat. aq. NaHCO$_3$, then the layers were separated. The aqueous layer was extracted with EtOAc, then the combined organic extracts were dried over MgSO$_4$, filtered and concentrated in vacuo. The crude material was absorbed onto a plug of silica gel and purified by chromatography through a Interchim (15 micron) silica-gel column (40 grams), eluting with a gradient of 0-6% MeOH/DCM. The racemates were separated by SFC, (Column, Chiralpak AD-H, 5 μm, 2×25 cm, F=80 mL/min, 25% Isopropanol/75%: Carbon dioxide). This afforded the separated Atropisomers as Peak 1: 4-((2S,5R)-4-acryloyl-2,5-dimethylpiperazin-1-yl)-6-chloro-1-(2,6-diisopropyl-4-methylpyridin-3-yl)-7-(2-fluorophenyl)pyrido[2,3-d]pyrimidin-2(1H)-one (0.070 g, 0.113 mmol, 29.7% yield) as white solid. $^1$H NMR (400 MHz, DMSO-d$_6$) δ 8.46 (d, 0.1-2.90 Hz, 1H) 7.48-7.55 (m, 1H) 7.20-7.34 (m, 3H) 7.05 (s, 1H) 6.83 (td, J=16.74, 10.47 Hz, 1H) 6.19 (dd, J=16.69, 2.18 Hz, 1H) 5.72-5.78 (m, 1H) 4.85 (br s, 1H) 4.77 (br s, 1H) 4.42-4.52 (m, 1H) 4.09-4.19 (m, 1H) 3.80-3.93 (m, 2H) 2.96 (quin, J=6.89 Hz, 1H) 2.61-2.69 (m, 1H) 1.91 (s, 3H) 1.33 (t, J=6.95 Hz, 3H) 1.15-1.28 (m, 9H) 1.06 (d, J=6.63 Hz, 3H) 0.97 (d, J=6.63 Hz, 3H). m/z (ESI, +ve ion): 617.2 (M+H)$^+$.

Example 176-2 (Peak 2)

The racemates were separated by SFC; (Column, Chiralpak AD-H, 5 μm, 2×25 cm, F=80 mL/min, 25% Isopropanol/75%: Carbon dioxide). This afforded the separated Atropisomers as Peak 2: 4-((2S,5R)-4-acryloyl-2,5-dimethylpiperazin-1-yl)-6-chloro-1-(2,6-diisopropyl-4-methylpyridin-3-yl)-7-(2-fluorophenyl)pyrido[2,3-d]pyrimidin-2(1H)-one (0.054 g, 0.087 mmol, 22.94% yield) as white solid. $^1$H NMR (400 MHz, DMSO-d$_6$) δ ppm 8.42-8.50 (m, 1H) 7.46-7.56 (m, 1H) 7.20-7.35 (m, 3H) 7.06 (s, 1H) 6.77-6.89 (m, 1H) 6.19 (dd, J=16.69, 2.18 Hz, 1H) 5.71-5.79 (m, 1H) 4.86 (br s, 1H) 4.76 (br s, 1H) 4.43-4.52 (m, 1H) 4.08-4.21 (m, 1H) 3.75-3.96 (m, 2H) 2.96 (spt, J=6.91 Hz, 1H) 2.61-2.68 (m, 1H) 1.93 (s, 3H) 1.33 (br t, J=6.22 Hz, 3H) 1.24 (dd, J=6.84, 1.04 Hz, 7H) 1.16 (br d, J=6.63 Hz, 2H) 1.02-1.08 (m, 3H) 0.94 (d, J=6.84 Hz, 3H). m/z (ESI, +ve ion): 617.2 (M+H)$^+$.

Example 177-1 (Peak 1)

6-Chloro-4-[(2S,5R)-2,5dimethyl-4-prop-2-enoyl-piperazin-1-yl]-7-(2-fluorophenyl)-1-(2-isopropyl-4-methyl-6-vinyl-3-pyridyl)pyrido[2,3-d]pyrimidin-2-one

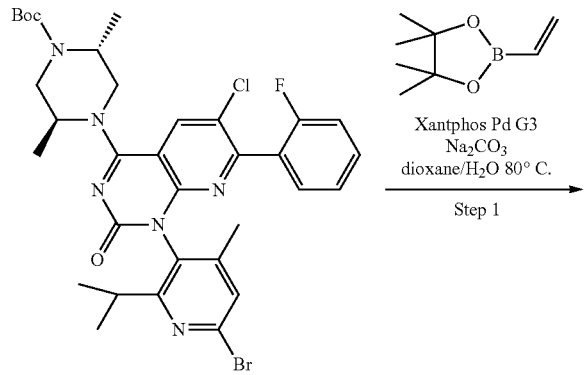

Intermediate 202

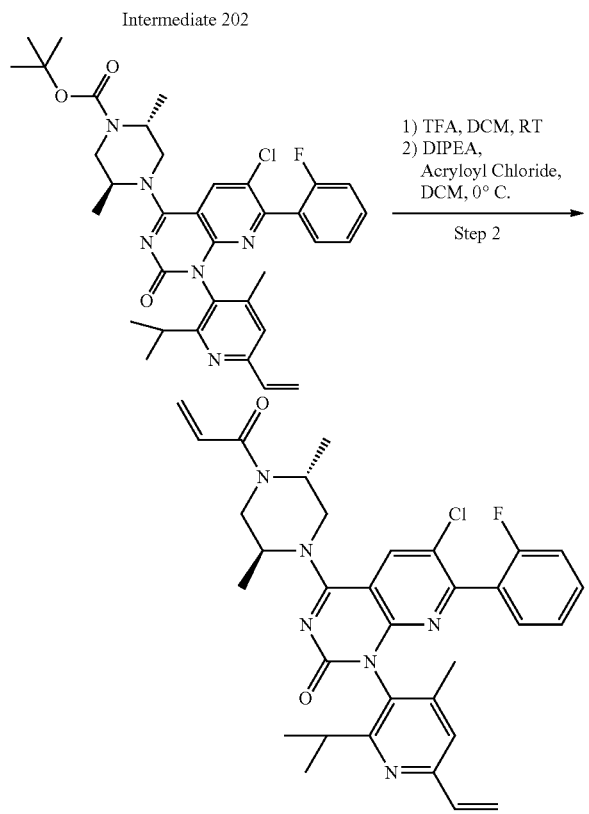

Step 1. tert-Butyl (2R,5S)-4-(6-chloro-7-(2-fluorophenyl)-1-(2-isopropyl-4-methyl-6-vinylpyridin-3-yl)-2-oxo-1,2-dihydropyrido[2,3-d]pyrimidin-4-yl)-2,5-dimethylpiperazine-1-carboxylate To a 50-mL round-bottomed flask was added tert-butyl (2R,5S)-4-(1-(6-bromo-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.420 g, 0.600 mmol, Intermediate 202) and sodium carbonate (0.191 g, 1.800 mmol) in 1,4-dioxane (2.4 mL). The reaction mixture was degassed by bubbling argon (gas) into the mixture for 5 min. Then xantphos pd g3 (0.028 g, 0.030 mmol), water (0.6 mL) and vinylboronic acid pinacol ester (0.2 mL, 1.500 mmol) was added into the reaction mixture. The overall reaction mixture was stirred and heated at 100° C. for 16 h. The reaction mixture was cooled to rt, then the mixture was diluted with sat. aq. NaHCO$_3$ and EtOAc. The layers were separated and the aqueous layer was extracted with EtOAc. The combined organic extracts were dried over MgSO$_4$, filtered and concentrated in vacuo. The crude material was absorbed onto a plug of silica gel and purified by chromatography through a Interchim (25 micron) silica-gel column (25 grams), eluting with a gradient of 0-30% EtOAc in CH2CL2, to provide tert-butyl (2R,5S)-4-(6-chloro-7-(2-fluorophenyl)-1-(2-isopropyl-4-methyl-6-vinylpyridin-3-yl)-2-oxo-1,2-dihydropyrido[2,3-d]pyrimidin-4-yl)-2,5-dimethylpiperazine-1-carboxylate (0.290 g, 0.448 mmol, 74.7% yield) as tan solid. m/z (ESI, +ve ion): 647.2 (M+H)$^+$.

Step 2. 4-((2S,5R)-4-Acryloyl-2,5-dimethylpiperazin-1-yl)-6-chloro-7-(2-fluorophenyl)-1-(2-isopropyl-4-methyl-6-vinylpyridin-3-yl)pyrido[2,3-d]pyrimidin-2(1H)-one To a 100-mL round-bottomed flask was added tert-butyl (2R,5S)-4-(6-chloro-7-(2-fluorophenyl)-1-(2-isopropyl-4-methyl-6-vinylpyridin-3-yl)-2-oxo-1,2-dihydropyrido[2,3-d]pyrimidin-4-yl)-2,5-dimethylpiperazine-1-carboxylate (0.290 g, 0.448 mmol) and trifluoroacetic acid (0.3 mL, 4.48 mmol) in 1,2-dichloroethane (2.0 mL). The reaction mixture was stirred and heated at 60° C. for 10 min, while under an inert (N$_2$) atmosphere. The reaction mixture was concentrated in vacuo. This material was carried directly into the next step of the synthesis, without further purification.

The previous residue was diluted with 1,2-dichloroethane (2.2 mL), then the reaction mixture was cooled to 0° C. with a wet ice bath. Then n,n'-diisopropylethylamine (0.9 mL, 5.38 mmol) was added into the reaction mixture and stirred 2 min. Then acryloyl chloride (0.4 mL, 0.448 mmol) was added into the mixture dropwise and stirred under an inert (N$_2$) atmosphere for 10 min. The mixture was diluted with EtOAc and sat. aq. NaHCO$_3$, then the layers were separated. The aqueous layer was extracted with EtOAc, then the combined organic extracts were dried over MgSO$_4$, filtered and concentrated in vacuo. The crude material was absorbed onto a plug of silica gel and purified by chromatography through a Interchim (15 micron) silica-gel column (40 grams), eluting with a gradient of 0-6% MeOH/DCM. The racemates were separated by SFC; (Column, AD, 5 µm, 20×250 mm, F=70 mL/min, 20% Isopropanol/80%: Carbon dioxide). This afforded the separated Atropisomers as Peak 1: 4-((2S,5R)-4-acryloyl-2,5-dimethylpiperazin-1-yl)-6-chloro-7-(2-fluorophenyl)-1-(2-isopropyl-4-methyl-6-vinylpyridin-3-yl)pyrido[2,3-d]pyrimidin-2(1H)-one (0.050 g, 0.083 mmol, 18.56% yield) as white solid. $^1$H NMR (400 MHz, DMSO-d$_6$) δ 8.47 (d, J=3.73 Hz, 1H) 7.49-7.55 (m, 1H) 7.22-7.34 (m, 4H) 6.73-6.90 (m, 2H) 6.17-6.27 (m, 2H) 5.73-5.79 (m, 1H) 5.46 (d, J=11.40 Hz, 1H) 4.87 (br s, 1H) 4.78 (br s, 1H) 4.13-4.22 (m, 1H) 3.81-3.93 (m, 2H) 2.66-2.75 (m, 1H) 1.94 (s, 3H) 1.34 (t, J=6.53 Hz, 3H) 1.26 (br d, J=6.63 Hz, 2H) 1.19 (br d, J=6.63 Hz, 2H) 1.08 (d, J=6.63 Hz, 3H) 0.98 (d, J=6.63 Hz, 3H). m/z (ESI, +ve ion): 601.2 (M+H)$^+$.

Example 177-2 (Peak 2)

The racemates were separated by SFC; (Column, AD, 5 µm, 20×250 mm, F=70 mL/min, 20% Isopropanol/80%:

Carbon dioxide). This afforded the separated Atropisomers as Peak 2: 4-((2S,5R)-4-acryloyl-2,5-dimethylpiperazin-1-yl)-6-chloro-7-(2-fluorophenyl)-1-(2-isopropyl-4-methyl-6-vinylpyridin-3-yl)pyrido[2,3-d]pyrimidin-2(1H)-one (0.060 g, 0.100 mmol, 22.28% yield) as white solid. $^1$H NMR (500 MHz, DMSO-$d_6$) δ ppm 8.48 (d, J=3.89 Hz, 1H) 7.49-7.54 (m, 1H) 7.23-7.33 (m, 4H) 6.73-6.88 (m, 2H) 6.21 (t, J=18.13 Hz, 2H) 5.73-5.78 (m, 1H) 5.44-5.48 (m, 1H) 4.82-4.91 (m, 1H) 4.76 (br s, 1H) 4.11-4.21 (m, 1H) 3.80-3.96 (m, 2H) 3.41-3.58 (m, 1H) 2.64-2.70 (m, 1H) 1.95 (s, 3H) 1.30-1.37 (m, 3H) 1.24 (d, J=6.75 Hz, 1H) 1.16 (d, J=6.75 Hz, 2H) 1.06 (d, J=6.75 Hz, 3H) 0.95 (d, J=6.75 Hz, 3H). m/z (ESI, +ve ion): 601.2 (M+H)$^+$.

Example 178

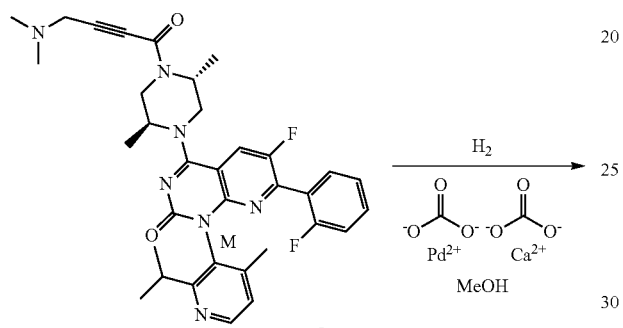

4-((2S,5R)-4-((Z)-4-(Dimethylamino)but-2-enoyl)-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one 4-((2S,5R)-4-(4-(Dimethylamino)but-2-ynoyl)-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one (Example 119-2, 64 mg, 0.10 mmol) in methanol (1.7 mL) was treated with Lindlar catalyst (5.6 mg, 0.021 mmol) and purged with hydrogen 4×30 psi and then allowed to stir under 30 psi hydrogen overnight. Added more Lindlar catalyst (5.6 mg, 0.021 mmol) and stirred under 35 psi for 24 h to get full conversion. The reaction mixture was filtered through a plug of celite, washed with MeOH, and concentrated to dryness on the rotavap. Purification of the crude by chromatography on silica gel using an ISCO Combiflash RF (12 g RediSep Gold column, using a gradient of 0-100% 3:1 EtOAc/EtOH in heptane, then switch to 20% MeOH in DCM, afforded 4-((2S,5R)-4-((Z)-4-(dimethylamino)but-2-enoyl)-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one (5.5 mg, 8.9 μmol, 8.6% yield) as off-white solid. m/z (ESI, +ve ion): 616.4 (M+H)$^+$. $^1$H NMR (400 MHz, CHLOROFORM-d) δ 8.52 (d, J=4.77 Hz, 1H), 7.82 (dd, J=4.46, 9.02 Hz, 1H), 7.39-7.49 (m, 1H), 7.27-7.29 (m, 1H), 7.05-7.22 (m, 3H), 4.75-5.20 (m, 2H), 4.23-4.46 (m, 1H), 4.18 (br d, J=14.31 Hz, 1H), 4.06 (br d, J=14.10 Hz, 1H), 3.83-3.99 (m, 2H), 3.74 (s, 1H), 3.50 (d, J=3.11 Hz, 2H), 2.64-2.75 (m, 1H), 2.36-2.37 (d, J=4.0 Hz, 6H), 1.48 (d, J=6.63 Hz, 3H), 1.43 (dd, J=1.45, 6.84 Hz, 3H), 1.31 (d, J=6.84 Hz, 3H), 1.24 (d, 0.1-6.84 Hz, 3H), 1.08 (dd, J=2.07, 6.63 Hz, 3H). $^{19}$F NMR (376 MHz, CHLOROFORM-d) δ −112.45 (dd, J=19.07, 41.61 Hz, 1F), −126.70 (dd, J=28.61, 41.62 Hz, 1F).

Example 179

4-((2S,5R)-4-Acryloyl-2,5-dimethylpiperazin-1-yl)-6-chloro-7-(2-fluorophenyl)-1-(5-isopropyl-2,3-dimethylpyridin-4-yl)pyrido[2,3-d]pyrimidin-2(1H)-one

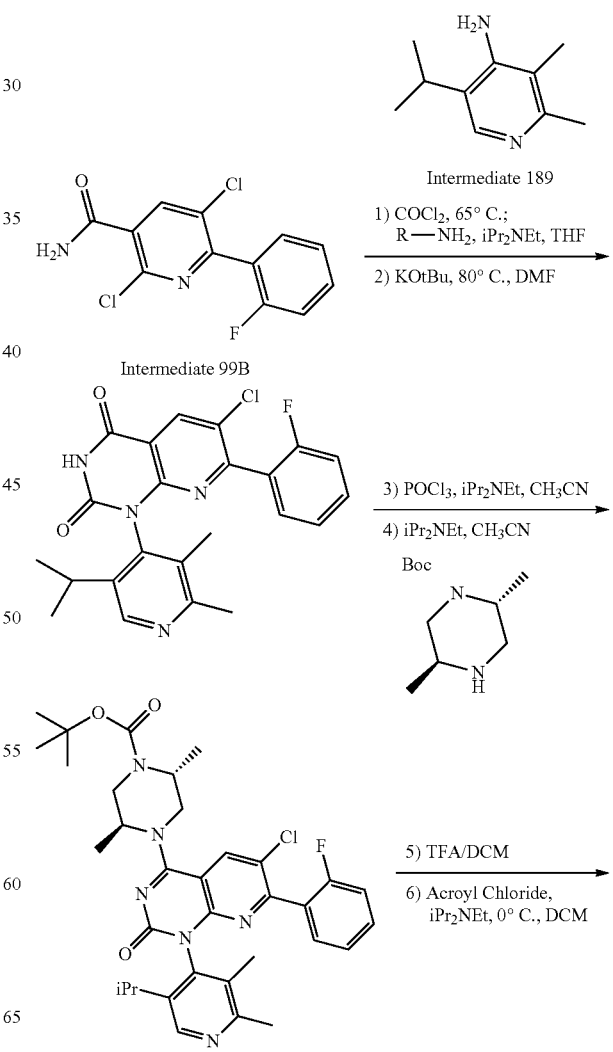

Steps 1&2. 6-Chloro-7-(2-fluorophenyl)-1-(5-isopropyl-2,3-dimethylpyridin-4-yl)pyrido[2,3-d]pyrimidine-2,4(1H,3H)-dione

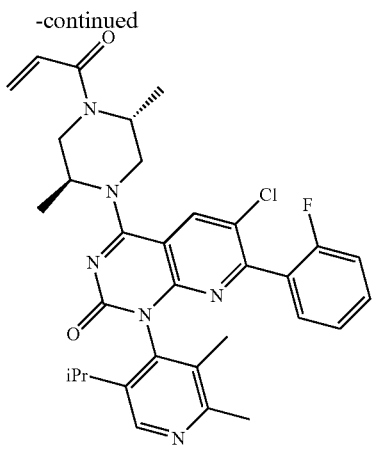

A 50-mL round-bottomed flask was charged with 2,5-dichloro-6-(2-fluorophenyl)nicotinamide (Intermediate 99B, 0.45 g, 1.58 mmol) and tetrahydrofuran (5 ml). Oxalyl dichloride (0.95 ml, 1.9 mmol) was added and the mixture was stirred at 65° C. for 1 h. 5-Isopropyl-2,3-dimethylpyridin-4-amine (Intermediate 189, 0.28 g, 1.7 mmol) dissolved in 2 mL of THF was then added, followed by N,N-diisopropylethylamine (0.69 ml, 3.9 mmol). The reaction mixture was stirred at rt for 30 mins and then heated at 65° C. for 30 min. The reaction mixture was partitioned between water (30 mL) and EtOAc (50 mL). The aqueous phase was extracted with EtOAc (50 mL). The combined organic phases were dried and concentrated to give a tan solid.

To the residue 2,5-dichloro-6-(2-fluorophenyl)-N-((5-isopropyl-2,3-dimethylpyridin-4-yl)carbamoyl)nicotinamide (0.73 g, 1.54 mmol, 97% yield) dissolved in THF (10 mL) was added sodium tert-butoxide (0.30 g, 3.2 mmol). The resulting suspension was stirred for 5 h then diluted with water and extracted with EtOAc (2×). The combined organic phases were dried (Na$_2$SO$_4$), concentrated and the residue purified by chromatography on silica gel eluting with EtOAc in heptane (30%-50%) to afford 6-chloro-7-(2-fluorophenyl)-1-(5-isopropyl-2,3-dimethylpyridin-4-yl)pyrido[2,3-d]pyrimidine-2,4(1H,3H)-dione (0.16 g, 0.36 mmol, 23% yield) as white solid. m/z (ESI, +ve ion): 439.1 (M+H)$^+$.

Steps 3&4. tert-Butyl (2R,5S)-4-(6-chloro-7-(2-fluorophenyl)-1-(5-isopropyl-2,3-dimethylpyridin-4-yl)-2-oxo-1,2-dihydropyrido[2,3-d]pyrimidin-4-yl)-2,5-dimethylpiperazine-1-carboxylate Phosphoryl trichloride (40 ul, 0.43 mmol) was added dropwise to a solution of 6-chloro-7-(2-fluorophenyl)-1-(5-isopropyl-2,3-dimethylpyridin-4-yl)pyrido[2,3-d]pyrimidine-2,4(1H,3H)-dione (0.16 g, 0.36 mmol) and N-ethyl-N-isopropylpropan-2-amine (0.087 ml, 0.50 mmol) in CH$_3$CN (1.2 mL) under N$_2$. This mixture was then heated to 80° C. for 1 h. Added more POCl$_3$ (10 uL, 0.1 mmol, 0.3 eq) and stirred at 80° C. for another hour. The reaction mixture was cooled to 0° C. and N-ethyl-N-isopropylpropan-2-amine (0.17 ml, 1.0 mmol) was added followed by tert-butyl (2R,5S)-2,5-dimethylpiperazine-1-carboxylate (Astatech, 0.084 g, 0.39 mmol). This mixture was stirred at rt over 30 min. and then was poured into cold saturated NaHCO$_3$ solution and stirred vigorously for 10 min. The mixture was extracted with EtOAc, the combined organics were dried over Na$_2$SO$_4$, filtered, concentrated and purified by chromatography on silica gel using 0-40% 3:1 EtOAc/EtOH in heptane to afford tert-butyl (2R,5S)-4-(6-chloro-7-(2-fluorophenyl)-1-(5-isopropyl-2,3-dimethylpyridin-4-yl)-2-oxo-1,2-dihydropyrido[2,3-d]pyrimidin-4-yl)-2,5-dimethylpiperazine-1-carboxylate (0.125 g, 0.197 mmol, 55.0% yield) as light-yellow solid. m/z (ESI, +ve ion): 635.2 (M+H)$^+$.

Step 5&6. 6-Chloro-4-[(2S,5R)-2,5-dimethyl-4-prop-2-enoyl-piperazin-1-yl]-7-(2-fluorophenyl)-1-(5-isopropyl-2,3-dimethyl-4-pyridyl)pyrido[2,3-d]pyrimidin-2-one To tert-butyl (2R,5S)-4-(6-chloro-7-(2-fluorophenyl)-1-(5-isopropyl-2,3-dimethylpyridin-4-yl)-2-oxo-1,2-dihydropyrido[2,3-d]pyrimidin-4-yl)-2,5-dimethylpiperazine-1-carboxylate (125 mg, 0.197 mmol) dissolved in dichloromethane (1 ml) was added trifluoroacetic acid (0.33 ml, 4.4 mmol). The reaction mixture was stirred at RT for 1 h then concentrated in vacuo and the residue was re-dissolved in dichloromethane (1 mL) and 1,1'-dimethyltriethylamine (0.10 ml, 0.59 mmol) was added followed by dropwise addition of acryloyl chloride (0.018 ml, 0.22 mmol) at 0° C. The reaction was stirred at 0° C. for 30 min. The reaction mixture was purified by chromatography on silica gel using a RediSep Gold (24 g Gold) column. eluting with a gradient of 0% to 50% 3:1 EtOAc/EtOH in hetane, to give 4-((2S,5R)-4-acryloyl-2,5-dimethylpiperazin-1-yl)-6-chloro-7-(2-fluorophenyl)-1-(5-isopropyl-2,3-dimethylpyridin-4-yl)pyrido[2,3-d]pyrimidin-2(1H)-one (54 mg, 0.046 mmol, 46% yield) as white solid. m/z (ESI, +ve ion): 589.1 (M+H)$^+$.

Example 179-1

SFC conditions: Sample from above was purified via preparative SFC using an (R,R) Whelk-01 (250×21 mm, 5u) column, a mobile phase of 30% MeOH/CO$_2$ at 100 bar and at a flowrate of 80 g/min to generate 18 mg of peak 1 with an ee of >99% (chemical purity 99.74%) and 9 mg of peak 2 with an ee of 99.34% (chemical purity 99.61%).

6-Chloro-4-[(2S,5R)-2,5-dimethyl-4-prop-2-enoyl-piperazin-1-yl]-7-(2-fluorophenyl)-1-(5-isopropyl-2,3-dimethyl-4-pyridyl)pyrido[2,3-d]pyrimidin-2-one (3380251, M isomer). $^1$H NMR (400 MHz, CHLOROFORM-d) δ 8.42 (s, 1H), 8.10 (s, 1H), 7.36-7.49 (m, 1H), 7.07-7.19 (m, 3H), 6.51-6.73 (m, 1H), 6.40 (br t, J=14.82 Hz, 1H), 5.75-5.87 (m, 1H), 4.87-5.24 (m, 2H), 4.22-4.54 (m, 1H), 3.80-4.10 (m, 2H), 3.72 (br d, J=13.89 Hz, 1H), 3.45-3.77 (m, 1H), 3.43-3.56 (m, 1H), 2.52 (s, 3H), 1.89-1.99 (m, 3H), 1.40-1.48 (m, 3H), 1.32 (br d, J=6.84 Hz, 3H), 1.22 (d, J=6.84 Hz, 3H), 1.08 (d, J=6.84 Hz, 3H). $^{19}$F NMR (376 MHz, CHLOROFORM-d) δ 112.70-112.47 (m, 1F). m/z (ESI, +ve ion): 589.1 (M+H)$^+$.

Example 179-2

6-Chloro-4-[(2S,5R)-2,5-dimethyl-4-prop-2-enoyl-piperazin-1-yl]-7-(2-fluorophenyl)-1-(5-isopropyl-2,3-dimethyl-4-pyridyl)pyrido[2,3-d]pyrimidin-2-one (3380252, P Isomer)

$^1$H NMR (400 MHz, CHLOROFORM-d) δ 8.40 (s, 1H), 8.04-8.13 (m, 1H), 7.37-7.47 (m, 1H), 7.05-7.20 (m, 3H), 6.48-6.73 (m, 1H), 6.40 (br t, J=15.03 Hz, 1H), 5.73-5.88 (m, 1H), 4.84-5.26 (m, 2H), 4.21-4.56 (m, 1H), 3.40-4.11 (m, 3H), 2.53 (s, 3H), 1.88-1.98 (m, 3H), 1.38-1.50 (m, 3H), 1.30 (br d, J=6.84 Hz, 3H), 1.21 (d, J=6.84 Hz, 3H), 1.04 (d, J=6.84 Hz, 3H). $^{19}$F NMR (376 MHz, CHLOROFORM-d) δ -112.75--112.67 (m, 1F). m/z (ESI, +ve ion): 589.1 (M+H)$^{+}$.

Example 180

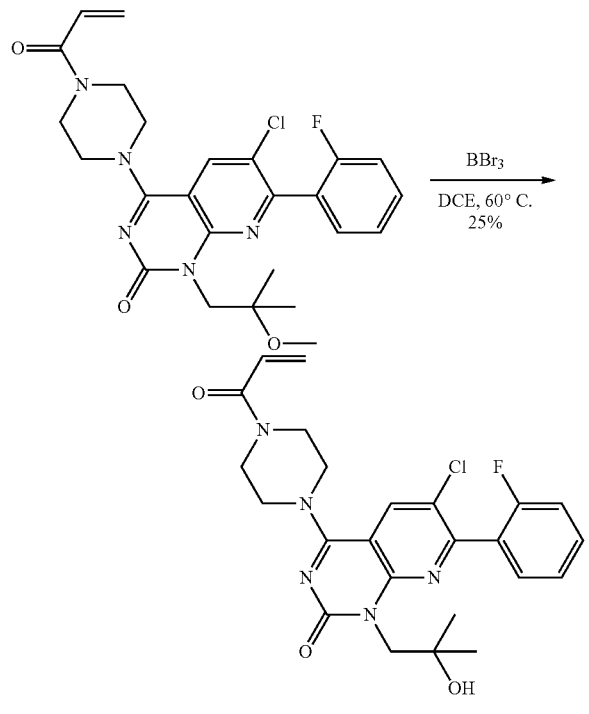

4-(4-Acryloylpiperazin-1-yl)-6-chloro-7-(2-fluorophenyl)-1-(2-hydroxy-2-methylpropyl)pyrido[2,3-d]pyrimidin-2(1H)-one To a solution of 4-(4-acryloylpiperazin-1-yl)-6-chloro-7-(2-fluorophenyl)-1-(2-methoxy-2-methylpropyl)pyrido[2,3-d]pyrimidin-2(1H)-one (24 mg, 0.048 mmol) in 1,1-dichloroethane (240 μl) was added boron tribromide, 1.0m solution in methylene chloride (53 μl, 0.053 mmol) at 0° C. The reaction mixture was stirred at 0° C. for 15 min (no change), then heated to 60° C. and stirred for 5 h. The crude product was purified by ISCO chromatography through a Redi-Sep pre-packed silica gel column (column size: 24 g, flow rate: 20 mL/min, eluent: 0-80% 3:1 EtOAc/EtOH in heptane for 35 min) to give 4-(4-acryloylpiperazin-1-yl)-6-chloro-7-(2-fluorophenyl)-1-(2-hydroxy-2-methylpropyl)pyrido[2,3-d]pyrimidin-2(1H)-one (5.8 mg, 0.012 mmol, 25% yield) as off-white solid. m/z (ESI, +ve ion): 486.2 (M+H)$^{+}$. $^{1}$H NMR (400 MHz, CHLOROFORM-d) δ 8.07 (s, 1H), 7.43-7.56 (m, 2H), 7.26-7.35 (m, 2H), 6.57 (dd, J=10.57, 16.59 Hz, 1H), 6.36 (dd, J=1.66, 16.79 Hz, 1H), 5.77 (dd, J=1.87, 10.57 Hz, 1H), 4.51 (s, 2H), 3.92-3.98 (m, 4H), 3.59-3.70 (m, 1H), 3.02-3.12 (m, 1H), 1.40 (d, J=6.84 Hz, 6H), 1.24 (s, 6H). $^{19}$F NMR (376 MHz, CHLOROFORM-d) δ -112.83 (s, 1F).

Example 181

1-(4-(3-Chloro-2-(2-fluorophenyl)-8-(2-isopropylphenyl)-7-(morpholinomethyl)-1,6-naphthyridin-5-yl)piperazin-1-yl)prop-2-en-1-one

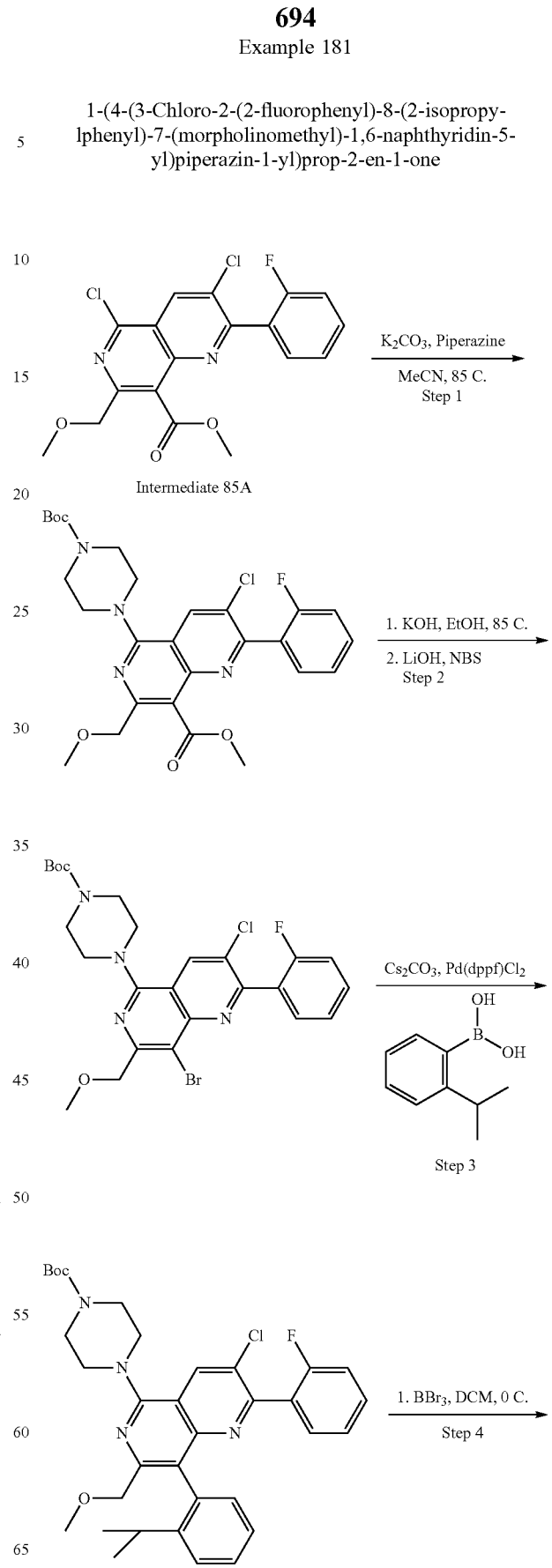

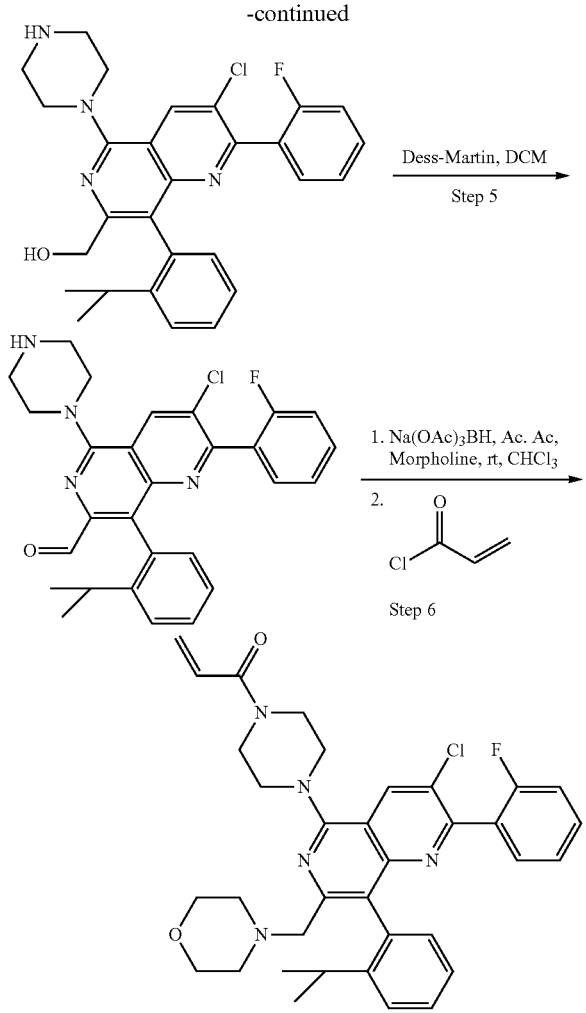

Step 1. Methyl 5-(4-(tert-butoxycarbonyl)piperazin-1-yl)-3-chloro-2-(2-fluorophenyl)-7-(methoxymethyl)-1,6-naphthyridine-8-carboxylate A mixture of methyl 3,5-dichloro-2-(2-fluorophenyl)-7-(methoxymethyl)-1,6-naphthyridine-8-carboxylate (1.50 g, 3.80 mmol, Intermediate 85A), tert-butyl piperazine-1-carboxylate (2.83 g, 15.18 mmol, Aldrich), potassium carbonate (10.49 g, 76 mmol, Aldrich) and sodium sulfate (10.78 g, 76 mmol) in $CH_3CN$ (30 mL) was heated at 85 C for 2 h. The reaction went to completion, brought to rt, washed with water and extracted with EtOAc. The combined organics were dried over $Na_2SO_4$, filtered, concentrated and purified by chromatography on silica gel using 0-50% EtOAc in heptane to afford methyl 5-(4-(tert-butoxycarbonyl)piperazin-1-yl)-3-chloro-2-(2-fluorophenyl)-7-(methoxymethyl)-1,6-naphthyridine-8-carboxylate (1.09 g, 2.000 mmol, 52.7% yield) as a yellow solid. m/z (ESI, +ve ion): 545.2 $(M+H)^+$.

Step 2. tert-Butyl 4-(8-bromo-3-chloro-2-(2-fluorophenyl)-7-(methoxymethyl)-1,6-naphthyridin-5-yl)piperazine-1-carboxylate To a solution of methyl 5-(4-(tert-butoxycarbonyl)piperazin-1-yl)-3-chloro-2-(2-fluorophenyl)-7-(methoxymethyl)-1,6-naphthyridine-8-carboxylate (1.09 g, 2.000 mmol) in EtOH (15 mL) was added KOH (2.469 g, 44.0 mmol, Aldrich) and the resulting mixture was heated at 85 C for 20 min. The reaction went to completion and concentrated to afford 5-(4-(tert-butoxycarbonyl)piperazin-1-yl)-3-chloro-2-(2-fluorophenyl)-7-(methoxymethyl)-1,6-naphthyridine-8-carboxylic acid to be used as is. m/z (ESI, +ve ion): 531.2 $(M+H)^+$.

To 5-(4-(tert-butoxycarbonyl)piperazin-1-yl)-3-chloro-2-(2-fluorophenyl)-7-(methoxymethyl)-1,6-naphthyridine-8-carboxylic acid was added $CH_3CH$ (30 mL) and water (15 mL) followed by the addition of LiOH (6.56 g, 274 mmol, Aldrich) and NBS (7.12 g, 40.0 mmol, Aldrich) at rt and the resulting mixture was stirred for 7 min. The reaction went to completion, washed with sat. $NaHCO_3$ and extracted with DCM. The combined organics were dried over $Na_2SO_4$, filtered, concentrated and purified by chromatography on silica gel using 0-50% EtOAc in heptane to afford tert-butyl 4-(8-bromo-3-chloro-2-(2-fluorophenyl)-7-(methoxymethyl)-1,6-naphthyridin-5-yl)piperazine-1-carboxylate (1.0 g, 1.767 mmol, 88% yield) as a yellow solid. m/z (ESI, +ve ion): 567.2 $(M+H)^+$.

Step 3. tert-Butyl 4-(3-chloro-2-(2-fluorophenyl)-8-(2-isopropylphenyl)-7-(methoxymethyl)-1,6-naphthyridin-5-yl)piperazine-1-carboxylate A mixture of tert-butyl 4-(8-bromo-3-chloro-2-(2-fluorophenyl)-7-(methoxymethyl)-1,6-naphthyridin-5-yl)piperazine-1-carboxylate (1.0 g, 1.767 mmol), cesium carbonate (2.303 g, 7.07 mmol, Aldrich), (1,1'-bis(diphenylphosphino)ferrocene) dichloropalladium (0.078 ml, 0.106 mmol, Aldrich) and [2-(1-methylethyl)phenyl]-boronic acid (0.870 ml, 5.30 mmol, Combi-Blocks) was purged with N2 followed by the addition of 1,4-dioxane/water (4/0.4 mL) and the resulting mixture was heated at 85 C for 1 h. The reaction went to completion, brought to rt, washed with sat. $NaHCO_3$ and extracted with EtOAC. The combined organics were purified on silica gel using 0-50% EtOAc in heptane to afford tert-butyl 4-(3-chloro-2-(2-fluorophenyl)-8-(2-isopropylphenyl)-7-(methoxymethyl)-1,6-naphthyridin-5-yl)piperazine-1-carboxylate (0.701 g, 1.158 mmol, 65.5% yield) as a yellow-greenish oil. m/z (ESI, +ve ion): 604.6 $(M+H)^+$.

Step 4. (3-Chloro-2-(2-fluorophenyl)-8-(2-isopropylphenyl)-5-(piperazin-1-yl)-1,6-naphthyridin-7-yl)methanol To a solution of tert-butyl 4-(3-chloro-2-(2-fluorophenyl)-8-(2-isopropylphenyl)-7-(methoxymethyl)-1,6-naphthyridin-5-yl)piperazine-1-carboxylate (0.701 g, 1.158 mmol) in DCM (20 mL) at 0 C was added bbr3 (5.79 ml, 5.79 mmol, Aldrich) dropwise. After complete addition, the ice bath was removed and the resulting suspension was stirred at rt for 2 h. The reaction was brought to 0 C, carefully basified with sat. $NaHCO_3$ and extracted with DCM. The combined organics were purified on silica gel using 0-10% MeOH in DCM to afford (3-chloro-2-(2-fluorophenyl)-8-(2-isopropylphenyl)-5-(piperazin-1-yl)-1,6-naphthyridin-7-yl)methanol (0.23 g, 0.468 mmol, 40.4% yield) as a yellow solid. m/z (ESI, +ve ion): 490.6 (M+H)⁺.

Step 5. 3-Chloro-2-(2-fluorophenyl)-8-(2-isopropylphenyl)-5-(piperazin-1-yl)-1,6-naphthyridine-7-carbaldehyde To a suspension of (3-chloro-2-(2-fluorophenyl)-8-(2-isopropylphenyl)-5-(piperazin-1-yl)-1,6-naphthyridin-7-yl) methanol (0.23 g, 0.468 mmol, 40.4% yield) in DCM (20 mL) was added Dess-martinperiodinane (0.737 g, 1.738 mmol, Aldrich) and the resulting mixture was stirred at rt for 2 h. The reaction went to completion, washed with sat. NaHCO₃, extracted with DCM and concentrated to afford 3-chloro-2-(2-fluorophenyl)-8-(2-isopropylphenyl)-5-(piperazin-1-yl)-1,6-naphthyridine-7-carbaldehyde as a yellow solid to be used as is. m/z (ESI, +ve ion): 488.6 (M+H)⁺.

Step 6. 1-(4-(3-Chloro-2-(2-fluorophenyl)-8-(2-isopropylphenyl)-7-(morpholinomethyl)-1,6-naphthyridin-5-yl)piperazin-1-yl)prop-2-en-1-one To a solution of 3-chloro-2-(2-fluorophenyl)-8-(2-isopropylphenyl)-5-(piperazin-1-yl)-1,6-naphthyridine-7-carbaldehyde (0.22 g, 0.450 mmol) in chloroform (15 mL) were added morpholine (0.078 ml, 0.900 mmol, Aldrich) and acetic acid (0.026 ml, 0.450 mmol, Aldrich) and the resulting mixture was stirred at rt for 10 min then sodium triacetoxyborohydride (0.381 g, 1.800 mmol, Aldrich) was added and the stirring continued for 1 h more. The reaction went to completion, brought to 0 C and carefully basified with sat. NaHCO₃. The mixture % as extracted with DCM, dried over Na₂SO₄, filtered and concentrated and purified by chromatography to afford 4-((3-chloro-2-(2-fluorophenyl)-8-(2-isopropylphenyl)-5-(piperazin-1-yl)-1,6-naphthyridin-7-yl)methyl)morpholine (0.050 g, 0.089 mmol, 19.84% yield) as a light solid. m/z (ESI, +ve ion): 560 (M+H)⁺.

4-((3-chloro-2-(2-fluorophenyl)-8-(2-isopropylphenyl)-5-(piperazin-1-yl)-1,6-naphthyridin-7-yl)methyl)morpholine (0.050 g, 0.089 mmol, 19.84% yield) was dissolved in DCM (5 mL) followed by the addition of acryloyl chloride (8.94 µl, 0.110 mmol, Aldrich) and the resulting mixture was stirred at rt for 30 min. The reaction went to completion, washed with sat. NaHCO₃, extracted with DCM and purified by chromatography on silica gel using 0-10% MeOH in DCM to afford 1-(4-(3-chloro-2-(2-fluorophenyl)-8-(2-isopropylphenyl)-7-(morpholinomethyl)-1,6-naphthyridin-5-yl)piperazin-1-yl)prop-2-en-1-one (0.039 g, 0.064 mmol, 14.11% yield) as a yellow solid. m/z (ESI, +ve ion): 613.6 (M+H)⁺. ¹H NMR (CHLOROFORM-d) δ: 8.38-8.45 (m, 1H), 7.31-7.47 (m, 4H), 7.01-7.19 (m, 4H), 6.62-6.76 (m, 1H), 6.33-6.44 (m, 1H), 5.72-5.83 (m, 1H), 3.84-4.08 (m, 7H), 3.62-3.74 (m, 4H), 3.50-3.60 (m, 3H), 3.38-3.47 (m, 1H), 2.38-2.66 (m, 4H), 1.04-1.12 (m, 3H), 0.93-0.99 (m, 3H).

Example 182

4-((2S,5R)-4-Acryloyl-2,5-dimethylpiperazin-1-yl)-1-(6-(azetidin-1-yl)-2,4-diisopropylpyridin-3-yl)-6-chloro-7-(2-fluorophenyl)pyrido[2,3-d]pyrimidin-2(1H)-one

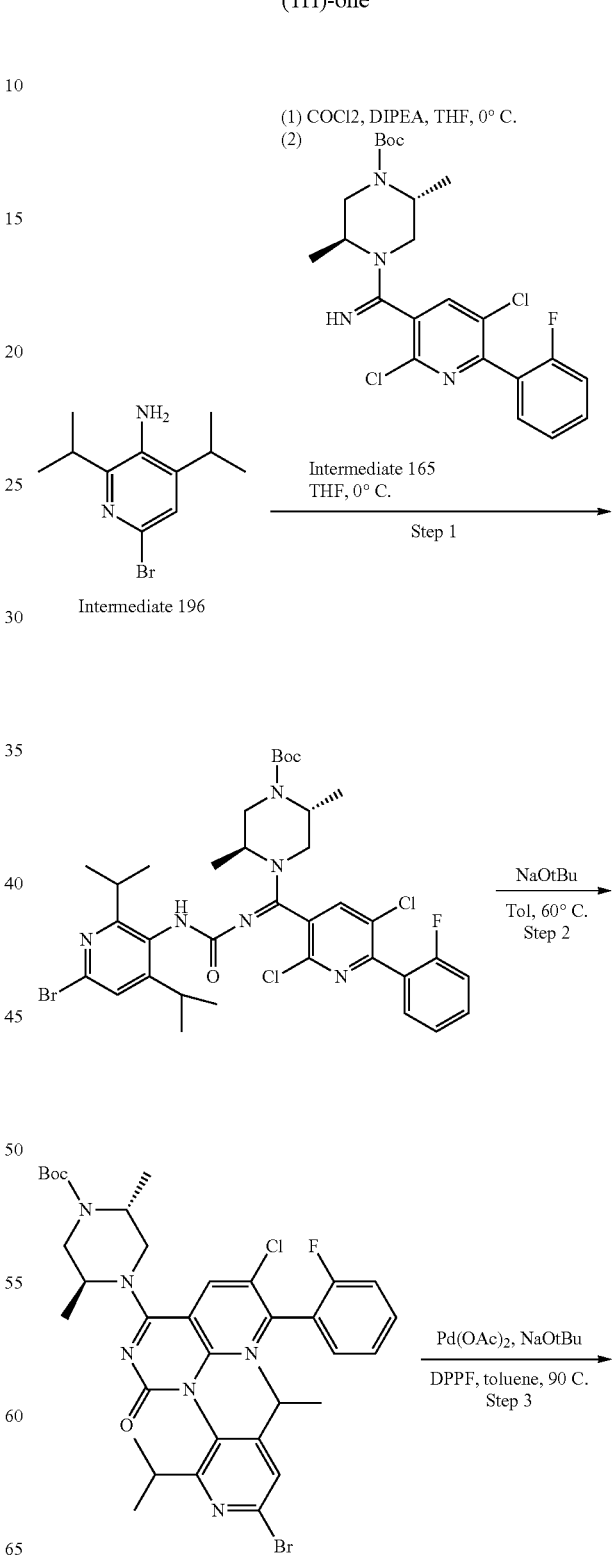

-continued

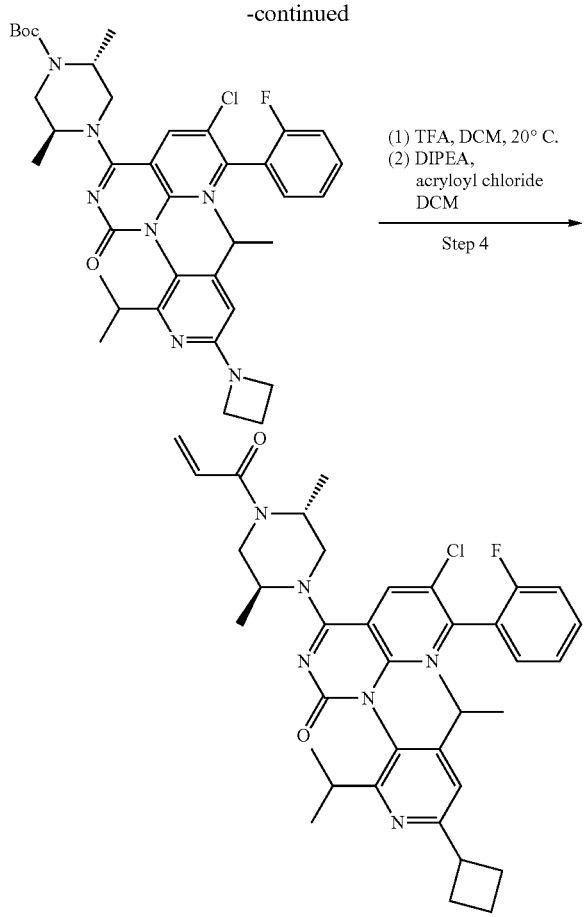

(1) TFA, DCM, 20° C.
(2) DIPEA, acryloyl chloride DCM
Step 4

Step 1. tert-Butyl (2R,5S)-4-((((6-bromo-2,4-diisopropylpyridin-3-yl)carbamoyl)imino)(2,5-dichloro-6-(2-fluorophenyl)pyridin-3-yl)methyl)-2,5-dimethylpiperazine-1-carboxylate To a solution of 6-bromo-2,4-diisopropylpyridin-3-amine (0.217 g, 0.844 mmol, Intermediate 196) and DIEA (0.309 ml, 1.772 mmol, Aldrich) in THF (10 mL) at rt was added dropwise phosgene solution, 15% in toluene (0.662 ml, 0.928 mmol, Aldrich) and the mixture was stirred at rt for 10 min then the mixture was brought to 0 C and solid tert-butyl (2R,5S)-4-((2,5-dichloro-6-(2-fluorophenyl)pyridin-3-yl)(imino)methyl)-2,5-dimethylpiperazine-1-carboxylate (0.487 g, 1.013 mmol, Intermediate 165) was added in three portions. The ice-bath was removed and after stirring for 15 min at rt tert-butyl (2R,5S)-4-((((6-bromo-2,4-diisopropylpyridin-3-yl)carbamoyl)imino)(2,5-dichloro-6-(2-fluorophenyl)pyridin-3-yl)methyl)-2,5-dimethylpiperazine-1-carboxylate was observed. m/z (ESI, +ve ion): 764.4 (M+H)$^+$.

Step 2. tert-Butyl (2R,5S)-4-(1-(6-bromo-2,4-diisopropylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate Then sodium tert-butoxide (0.243 g, 2.53 mmol, Aldrich) was added and the resulting mixture was stirred at rt for 20 min. The reaction went to completion, washed with water, extracted with EtOAc and purified by chromatography on silica gel using 0-40% EtOAc in heptane to afford tert-butyl (2R,5S)-4-(1-(6-bromo-2,4-diisopropylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.213 g, 0.293 mmol, 34.7% yield) as a light yellow solid. m/z (ESI, +ve ion): 728.4 (M+H)$^+$.

Step 3. tert-Butyl (2R,5S)-4-(1-(6-(azetidin-1-yl)-2,4-diisopropylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate A mixture of tert-butyl (2R,5)-4-(1-(6-bromo-2,4-diisopropylpyridin-3-yl)-6-chloro-7-(2-fluorophenyl)-2 oxo-1,2-dihydropyrido[2,3-d]pyrimidin-4-yl)-2,5-dimethylpiperazine-1-carboxylate (0.085 g, 0.117 mmol), 1,1'-bis(diphenylphosphino)ferrocene (5.18 mg, 9.34 µmol, Strem), palladium (ii) acetate (1.048 mg, 4.67 µmol, Strem) and sodium tert-butoxide (0.017 g, 0.175 mmol, Aldrich) was purged with N$_2$ followed by the addition of azetidine (7.33 µl, 0.128 mmol, Combi-Blocks) and toluene (4 mL). The resulting mixture was heated at 90 C for 17 h. The starting material was consumed and desired mass was observed with other peaks. The reaction was brought to it, quenched with sat. NaHCO$_3$ and extracted with EtOAc. The combined organics were purified by HPLC to afford tert-butyl (2R, 5S)-4-(1-(6-(azetidin-1-yl)-2,4-diisopropylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.035 g, 0.050 mmol, 42.6% yield) as a light yellow solid. m/z (ESI, +ve ion): 703.4 (M+H)$^+$.

Step 4. 4-((2S,5R)-4-Acryloyl-2,5-dimethylpiperazin-1-yl)-1-(6-(azetidin-1-yl)-2,4-diisopropylpyridin-3-yl)-6-chloro-7-(2-fluorophenyl)pyrido[2,3-d]pyrimidin-2(1H)-one To a solution of tert-butyl (2R,5S)-4-(1-(6-(azetidin-1-yl)-2,4-diisopropylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (0.035 g, 0.050 mmol) in DCM (3 mL) was added tfa (2.0 mL, 26.0 mmol) and the resulting mixture was stirred at rt for 30 min. The reaction went to completion, concentrated and used as is in the next step. 1-(6-(azetidin-1-yl)-2,4-diisopropylpyridin-3-yl)-6-chloro-4-((2S,5R)-2,5-dimethylpiperazin-1-yl)-7-(2-fluorophenyl)pyrido[2,3-d]pyrimidin-2(1H)-one. m/z (ESI, +ve ion): 603.4 (M+H)$^+$.

1-(6-(azetidin-1-yl)-2,4-diisopropylpyridin-3-yl)-6-chloro-4-((2S,5R)-2,5-dimethylpiperazin-1-yl)-7-(2-fluorophenyl)pyrido[2,3-d]pyrimidin-2(l1H)-one was dissolved in DCM (3 mL) then acryloyl chloride (4.04 µl, 0.050 mmol, Aldrich) was added at it. The reaction was stirred at rt for 15 min, washed with sat. NaHCO$_3$ and extracted with DCM. The combined organics were purified by chromatography on silica gel using 0-5% MeOH in DCM to afford 4-((2S,5R)-4-acryloyl-2,5-dimethylpiperazin-1-yl)-1-(6-(azetidin-1-yl)-2,4-diisopropylpyridin-3-yl)-6-chlor-7-(2-fluorophenyl)pyrido[2,3-d]pyrimidin-2(1H)-one as a light yellow solid. m/z (ESI, +ve ion): 657.4 (M+H)$^+$. $^1$H NMR (400 MHz, DMSO-d$_6$) δ 7.94-8.04 (m, 1H), 7.69-7.78 (m, 1H), 7.38-7.48 (m, 1H), 7.20-7.28 (m, 2H), 7.11-7.19 (m, 1H), 6.97-7.11 (m, 1H), 6.16 (br d, J=16.8 Hz, 1H), 5.71-5.75 (m, 1H), 4.64-5.00 (m, 1H), 4.17-4.38 (m, 1H), 3.79-3.93 (m, 1H), 3.57-3.75 (m, 2H), 3.40-3.55 (m, 1H), 3.14-3.28 (m, 2H), 2.96-3.15 (m, 2H), 1.24 (br dd, J=10.9, 6.7 Hz, 6H), 1.16 (br s, 5H), 1.02-1.11 (m, 4H), 0.89-1.00 (m, 7H).

The racemic mixture was separated under the following conditions: SFC. IE (5 um, 21×250 mm two in series, total 50 cm) F=65 ml, 35%; ethanol, 65% carbon dioxide, Back pressure=90 bar.

Example 182-1

4-((2S,5R)-4-Acryloyl-2,5-dimethylpiperazin-1-yl)-1-(6-(azetidin-1-yl)-2,4-diisopropylpyridin-3-yl)-6-chloro-7-(2-fluorophenyl)pyrido[2,3-d]pyrimidin-2(1H)-one m/z (ESI, +ve ion): 657.6 (M+H)$^+$
$^1$H NMR (400 MHz, DMSO-$d_6$) δ 8.44 (s, 1H), 7.48-7.58 (m, 1H), 7.26-7.38 (m, 2H), 7.16-7.24 (m, 1H), 6.75-6.90 (m, 1H), 6.19 (dd, J=16.6, 2.3 Hz, 1H), 6.10 (s, 1H), 5.71-5.80 (m, 1H), 4.72-4.94 (m, 2H), 4.50 (br d, J=2.7 Hz, 1H), 4.08-4.19 (m, 1H), 3.89-3.99 (m, 4H), 3.83-3.88 (m, 1H), 2.26-2.33 (m, 2H), 1.29-1.36 (m, 3H), 1.22-1.27 (m, 4H), 1.00-1.07 (m, 7H), 0.88 (dd, J=6.4, 4.8 Hz, 7H).

Example 182-2

4-((2S,5R)-4-Acryloyl-2,5-dimethylpiperazin-1-yl)-1-(6-(azetidin-1-yl)-2,4-diisopropylpyridin-3-yl)-6-chloro-7-(2-fluorophenyl)pyrido[2,3-d]pyrimidin-2(1H)-one m/z (ESI, +ve ion): 657.6 (M+H)$^+$
$^1$H NMR (400 MHz, DMSO-$d_6$) δ 8.45 (s, 1H), 7.49-7.57 (m, 1H), 7.28-7.38 (m, 2H), 7.17-7.25 (m, 1H), 6.76-6.92 (m, 1H), 6.19 (dd, J=16.7, 2.2 Hz, 1H), 6.11 (s, 1H), 5.72-5.79 (m, 1H), 4.70-4.91 (m, 2H), 4.41-4.51 (m, 1H), 4.08-4.18 (m, 1H), 3.89-3.99 (m, 4H), 3.82-3.88 (m, 1H), 2.24-2.32 (m, 2H), 1.28-1.35 (m, 3H), 1.25 (s, 4H), 0.99-1.07 (m, 7H), 0.91 (d, J=6.8 Hz, 3H), 0.86 (br d, J=6.6 Hz, 4H).

Example 183-1

(S)-4-(4-Acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one
(First Eluting Compound)

Example 183-2

(S)-4-(4-Acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one
(Second Eluting Compound)

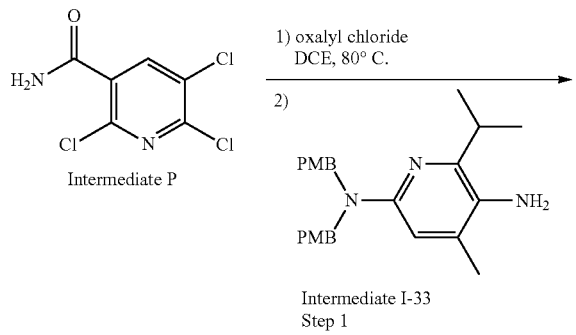

Intermediate I-33
Step 1

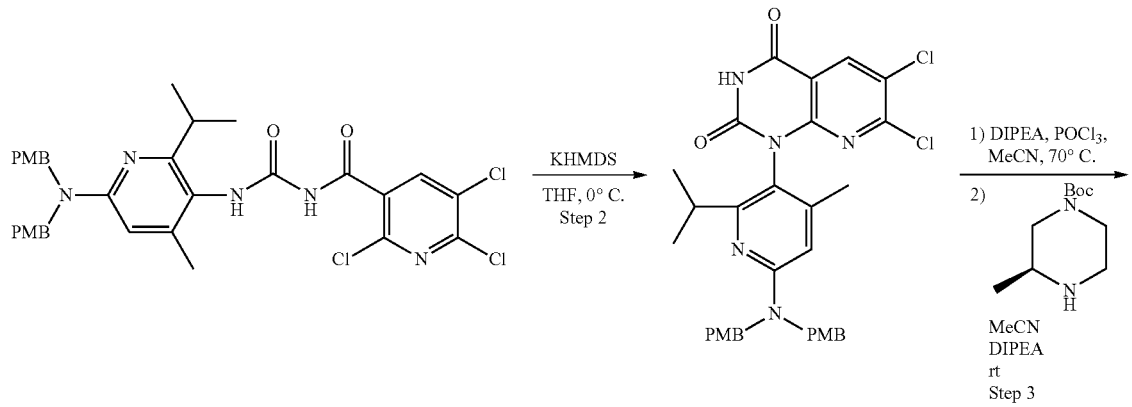

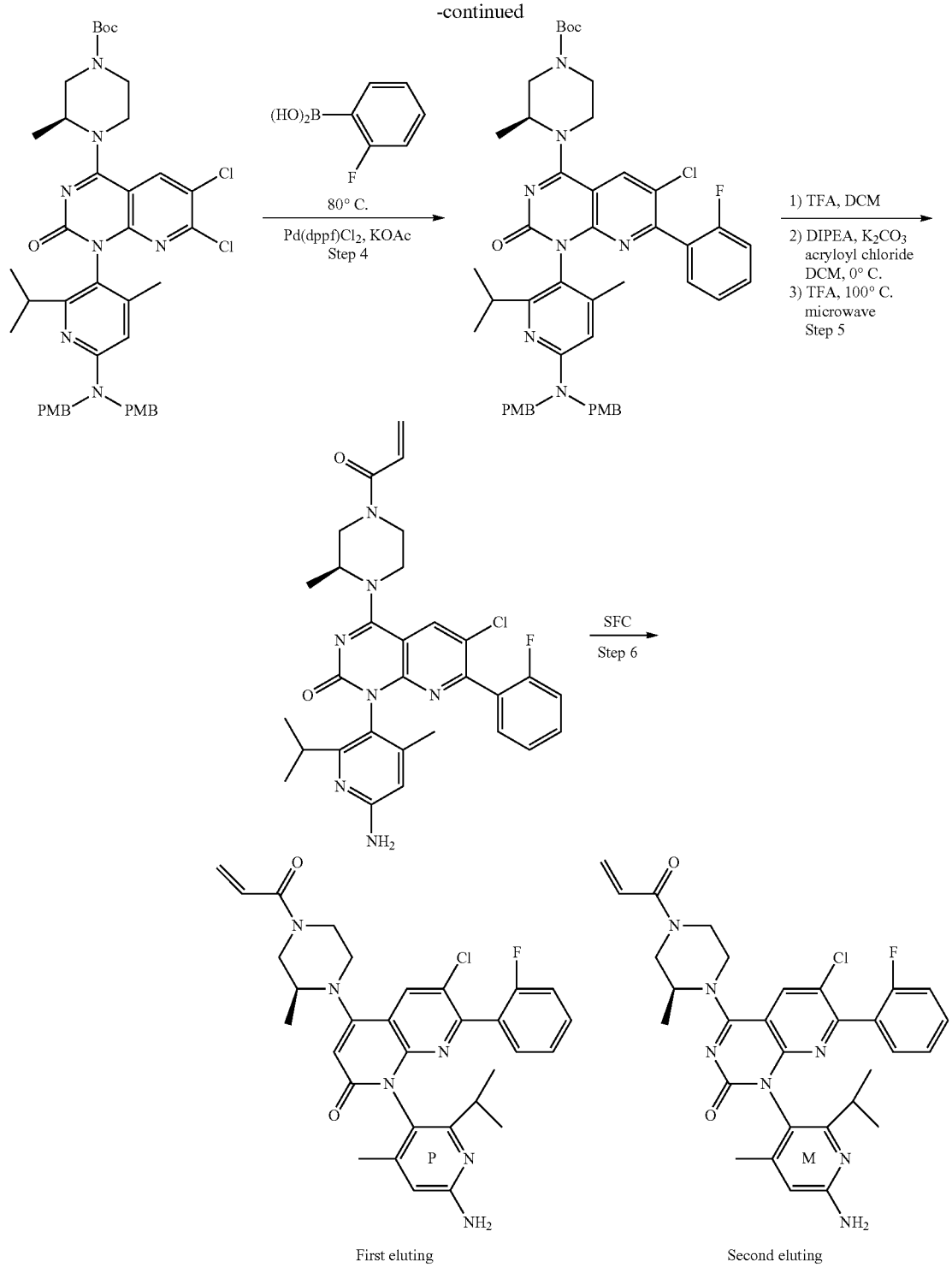

Step 1: N-((6-(Bis(4-methoxybenzyl)amino)-2-isopropyl-4-methylpyridin-3-yl)carbamoyl)-2,5,6-trichloronicotinamide To a solution of 2,5,6-trichloronicotinamide (187 mg, 0.831 mmol, intermediate P) in 1,2-dichloroethane (10 mL) under $N_2$ was added oxalyl chloride, 2.0 M solution in methylene chloride (0.457 mL, 0.914 mmol). The resulting mixture was then stirred at 80° C. for 1 hour. Then, the mixture was cooled to room temperature and a solution of 6-isopropyl-N2,N2-bis(4-methoxybenzyl)-4-methylpyridine-2,5-diamine (337 rag, 0.831 mmol, intermediate I-33) in MeCN (5 mL) was added. The resulting mixture was then stirred at room temperature for 1 hour. Then, the mixture was quenched with saturated $NH_4Cl$ (5 mL) and was then diluted with saturated $NaHCO_3$ (25 mL). The mixture was then extracted with EtOAc (2×100 mL). The combined organic extracts were then dried over $MgSO_4$ and concentrated under reduced pressure. Chromatographic purification of the residue (silica gel, 0%-100% EtOAc:EtOH (3:1)/heptane) provided N-((6-(bis(4-methoxybenzyl)amino)-2-isopropyl-4-methylpyridin-3-yl)carbamoyl)-2,5,6-trichloronicotinamide as a yellow solid which was used in the next step without purification requirement. m/z (ESI, +ve ion) 656.0 (M+H)$^+$.

Step 2: 1-(6-(Bis(4-methoxybenzyl)amino)-2-isopropyl-4-methylpyridin-3-yl)-6,7-dichloropyrido[2,3-d]pyrimidine-2,4(1H,3H)-dione To a solution of N-((6-(bis(4-methoxybenzyl)amino)-2-isopropyl-4-methylpyridin-3-yl)carbamoyl)-2,5,6-trichloronicotinamide (546 mg, 0.831 mmol) in tetrahydrofuran (15 mL) at 0° C. under N2 was added potassium bis(trimethylsilyl)amide, 1M solution in tetrahydrofuran (1.66 mL 1.66 mmol) dropwise. After addition, the mixture was then stirred at 0° C. for 30 mins. Then, the mixture was quenched with saturated NH$_4$Cl (5 mL) and was then diluted with saturated NaHCO$_3$ (16 mL). The mixture was then extracted with EtOAc (2×100 mL). The combined organic extracts were then dried over MgSO$_4$ and concentrated under reduced pressure. Chromatographic purification of the residue (silica gel, 0%-100% EtOAc:EtOH (3:1)/heptane) provided 1-(6-(bis(4-methoxybenzyl)amino)-2-isopropyl-4-methylpyridin-3-yl)-6,7-dichloropyrido[2,3-d]pyrimidine-2,4(1H,3H)-dione (476 mg, 0.767 mmol, 92% yield) as a yellow solid. m/z (ESI, +ve ion) 620.0 (M+H)

Step 3: tert-Butyl (S)-4-(1-(6-(bis(4-methoxybenzyl)amino)-2-isopropyl-4-methylpyridin-3-yl)-6,7-dichloro-2-oxo-1,2-dihydropyrido[2,3-d]pyrimidin-4-yl)-3-methylpiperazine-1-carboxylate To a solution of 1-(6-(bis(4-methoxybenzyl)amino)-2-isopropyl-4-methylpyridin-3-yl)-6,7-dichloropyrido[2,3-d]pyrimidine-2,4(1H,3H)-dione (471 mg, 0.759 mmol) in acetonitrile (8 mL) was added 1,1'-dimethyltriethylamine (0.464 mL, 2.66 mmol) and phosphorus oxide chloride (0.177 mL, 1.90 mmol). The resulting mixture was then stirred at 70° C. under N$_2$ for 30 mins. Then, the mixture was cooled to room temperature and a solution of (3s)-1-(tert-butoxycarbonyl)-3-methylpiperazine (0.304 mL, 1.52 mmol. Ark Pharm, Inc., Arlington Heights, Ill., USA) and 1,1'-dimethyltriethylamine (0.464 mL, 2.66 mmol) in MeCN (4 mL) was added. The resulting mixture was then stirred at room temperature under N$_2$ for 30 mins. The mixture was then diluted with water (20 mL) and was then extracted with EtOAc (2×50 mL). The combined organic extracts were then dried over MgSO$_4$ and concentrated under reduced pressure. Chromatographic purification of the residue (silica gel, 0%-80% EtOAc:EtOH (3:1)/heptane) provided tert-butyl (S)-4-(1-(6-(bis(4-methoxybenzyl)amino)-2-isopropyl-4-methylpyridin-3-yl)-6,7-dichloro-2-oxo-1,2-dihydropyrido[2,3-d]pyrimidin-4-yl)-3-methylpiperazine-1-carboxylate as a yellow solid which was used in the next step without purification requirement. m/z (ESI, +ve ion) 746.0 (M+H)$^+$.

Step 4: tert-Butyl (S)-4-(1-(6-(bis(4-methoxybenzyl)amino)-2-isopropyl-4-methylpyridin-3-yl)-6-chloro-7-(2-fluorophenyl)-2-oxo-1,2-dihydropyrido[2,3-d]pyrimidin-4-yl)-3-methylpiperazine-1-carboxylate To a solution of tert-butyl (S)-4-(1-(6-(bis(4-methoxybenzyl)amino)-2-isopropyl-4-methylpyridin-3-yl)-6,7-dichloro-2-oxo-1,2-dihydropyrido[2,3-d]pyrimidin-4-yl)-3-methylpiperazine-1-carboxylate (609 mg, 0.759 mmol) in 1,4-dioxane (7 mL) was added (2-fluorophenyl)boranediol (0.212 mL, 1.52 mmol, Combi-Blocks Inc., San Diego, Calif., USA), (1,1'-bis(diphenylphosphino) ferrocene) dichloropalladium (0.056 mL, 0.076 mmol), and potassium acetate (0.237 mL, 3.79 mmol). The resulting mixture was then stirred at 80° C. under N2 for 1 hour. Then, the mixture was diluted with saturated NaHCO$_3$ (10 mL) and was then extracted with EtOAc (2×50 mL). The combined organic extracts were then dried over MgSO$_4$ and concentrated under reduced pressure. Chromatographic purification of the residue (silica gel, 0%-100% EtOAc:EtOH (3:1)/heptane) provided tert-butyl (S)-4-(1-(6-(bis(4-methoxybenzyl)amino)-2-isopropyl-4-methylpyridin-3-y)-6-chloro-7-(2-fluorophenyl)-2-oxo-1,2-dihydropyrido[2,3-d]pyrimidin-4-yl)-3-methylpiperazine-1-carboxylate (654 mg, 0.758 mmol, 100% yield) as a yellow solid. m/z (ESI, +ve ion) 862.2 (M+H)$^+$.

Step 5: (S)-4-(4-Acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one Step 5-1: (S)-1-(6-(Bis(4-methoxybenzyl)amino)-2-isopropyl-4-methylpyridin-3-yl)-6-chloro-7-(2-fluorophenyl)-4-(2-methylpiperazin-1-yl)pyrido[2,3-d]pyrimidin-2(1H)-one trifluoracetic acid To a solution of tert-butyl (S)-4-(1-(6-(bis(4-methoxybenzyl)amino)-2-isopropyl-4-methylpyridin-3-yl)-6-chloro-7-(2-fluorophenyl)-2-oxo-1,2-dihydropyrido[2,3-d]pyrimidin-4-yl)-3-methylpiperazine-1-carboxylate (654 mg, 0.758 mmol) in dichloromethane (5 mL) was added trifluoroacetic acid (1.130 mL, 15.17 mmol). The resulting mixture was then stirred at room temperature for 1 hour. Then, the mixture was concentrated and dried in vacuo provided (S)-1-(6-(bis(4-methoxybenzyl)amino)-2-isopropyl-4-methylpyridin-3-yl)-6-chloro-7-(2-fluorophenyl)-4-(2-methylpiperazin-1-yl)pyrido[2,3-d]pyrimidin-2(1H)-one trifluoroacetic acid which was used in the next step without purification requirement. m/z (ESI, +ve ion) 762.2 (M+H)$^+$.

Step 5-2: (S)-4-(4-Acryloyl-2-methylpiperazin-1-yl)-1-(6-(bis(4-methoxybenzyl)amino)-2-isopropyl-4-methylpyridin-3-yl)-6-chloro-7-(2-fluorophenyl) pyrido[2,3-d]pyrimidin-2(1H)-one To a solution of (S)-1-(6-(bis(4-methoxybenzyl)amino)-2-isopropyl-4-methylpyridin-3-yl)-6-chloro-7-(2-fluorophenyl)-4-(2-methylpiperazin-1-yl)pyrido[2,3-d]pyrimidin-2(1H)-one trifluoroacetic acid in dichloromethane (7 mL) at 0° C. under N2 was added potassium carbonate (0.230 mL, 3.79 mmol), 1,1'-dimethyltriethylamine (1.986 mL, 11.37 mmol), and a solution of 2-propenoyl chloride (0.062 mL, 0.758 mmol) in DCM (0.3 mL). The resulting mixture was then stirred at 0° C. for 15 mins. The mixture was then quenched with saturated NaHCO$_3$ (10 mL) and was then extracted with EtOAc (2×30 mL). The combined organic extracts were then dried over MgSO$_4$ and concentrated under reduced pressure. Chromatographic purification of the residue (silica gel, 0%-100% EtOAc:EtOH (3:1)/heptane) provided (S)-4-(4-acryloyl-2-methylpiperazin-1-yl)-1-(6-(bis(4-methoxybenzyl)amino)-2-isopropyl-4-methylpyridin-3-yl)-6-chloro-7-(2-fluorophenyl)pyrido[2,3-d]pyrimidin-2(1H)-one which was used in the next step without purification requirement. m/z (ESI, +ve ion) 816.5 (M+H)⁺.

Step 5-3: (S)-4-(4-Acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one A solution of (S)-4-(4-acryloyl-2-methylpiperazin-1-yl)-1-(6-(bis(4-methoxybenzyl)amino)-2-isopropyl-4-methylpyridin-3-yl)-6-chloro-7-(2-fluorophenyl)pyrido[2,3-d]pyrimidin-2(1H)-one (568 mg, 0.696 mmol) in trifluoroacetic acid (3.6 mL, 48.7 mmol) was subjected to a microwave irradiation at 100° C. for 10 mins. Then, the mixture was concentrated under reduced pressure. Then, the residue was dissolved in DCM (20 mL) and saturated NaHCO₃ (50 mL) was added slowly at 0° C. After addition, the mixture was then stirred at room temperature for 5 mins. The organic layer was collected, dried over MgSO₄, and concentrated under reduced pressure. Chromatographic purification of the residue (silica gel, 0%-10% NH₃ 2M in MeOH/DCM) provided (S)-4-(4-acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one (165 mg, 0.143 mmol, 41.2% yield) as a yellow solid. m/z (ESI, +ve ion) 576.0 (M+H)⁺. ¹H NMR (DMSO-d6) δ: 8.40 (br s, 1H), 7.48-7.60 (m, 1H), 7.22-7.36 (m, 3H), 6.78-6.93 (m, 1H), 6.15-6.25 (m, 2H), 5.70-5.84 (m, 3H), 4.79-5.03 (m, 1H), 4.22-4.49 (m, 2H), 3.96-4.19 (m, 1H), 3.40-3.83 (m, 2H), 3.01-3.29 (m, 2H), 1.73 (s, 3H), 1.29-1.35 (m, 3H), 0.99 (d, J=6.8 Hz, 3H), 0.86-0.89 (m, 3H).

Step 6: (S)-4-(4-Acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one (First Eluting Atropisomer, 3371969) and (S)-4-(4-acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one (Second Eluting Atropisomer)

An atropisomeric mixture of (S)-4-(4-acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one (155 mg) was separated by preparative Thar 200 SFC method, column: AS (150×30 mm, 5u), mobile phase: 80:20 (A:B) with A: Liquid CO2 and B: methanol(NH3), flow rate: 180 g/min; column/oven temp.: ambient temperature provided (S)-4-(4-acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one (61 mgs, first eluting atropisomer, 3371969) as a yellow solid. m/z (ESI, +ve ion) 576.0 (M+H)⁺. ¹H NMR (DMSO-d6) δ: 8.41 (br d, J=3.7 Hz, 1H), 7.48-7.58 (m, 1H), 7.21-7.36 (m, 3H), 6.78-6.94 (m, 1H), 6.16-6.25 (m, 2H), 5.76-5.80 (m, 2H), 5.73-5.76 (m, 1H), 4.83-5.00 (m, 1H), 4.21-4.49 (m, 2H), 3.97-4.19 (m, 1H), 3.38-3.83 (m, 2H), 3.00-3.30 (m, 2H), 1.72 (s, 3H), 1.31 (d, J=6.6 Hz, 3H), 0.99 (d, J=6.6 Hz, 3H), 0.87 (d, J=6.6 Hz, 3H). ¹⁹F NMR (DMSO-d6) δ: −114.13 (s, 1F) and (S)-4-(4-acryloyl-2-methylpiperazin-1-yl)-1-(6-amino-2-isopropyl-4-methylpyridin-3-yl)-6-chloro-7-(2-fluorophenyl)pyrido[2,3-d]pyrimidin-2(1H)-one (63 mgs, second eluting atropisomer, 3371970) as a yellow solid. m/z (ESI, +ve ion) 576.0 (M+H)⁺. ¹H NMR (DMSO-d6) δ: 8.39 (br d, J=4.8 Hz, 1H), 7.48-7.58 (m, 1H), 7.22-7.36 (m, 3H), 6.77-6.93 (m, 1H), 6.15-6.26 (m, 2H), 5.76-5.79 (m, 2H), 5.74-5.76 (m, 1H), 4.89 (br s, 1H), 4.21-4.45 (m, 2H), 3.96-4.19 (m, 1H), 3.40-3.81 (m, 2H), 2.99-3.30 (m, 2H), 1.73 (s, 3H), 1.32 (d, J=6.6 Hz, 3H), 0.99 (d, J=6.6 Hz, 3H), 0.87 (d, J=6.6 Hz, 31). ¹⁹F NMR (DMSO-d6) δ: −114.09 (s, 1F)

Example 184

4-((2S,5R)-4-Acryloyl-2,5-dimethylpiperazin-1-yl)-7-(2-amino-6-fluorophenyl)-1-(4-((dimethylamino)methyl)-2-isopropyl-6-methylphenyl)-6-fluoropyrido[2,3-d]pyrimidin-2(1H)-one

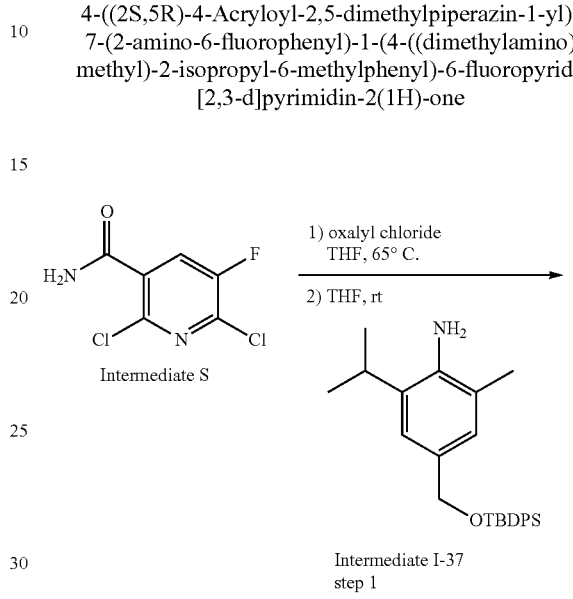

Intermediate S

Intermediate I-37
step 1

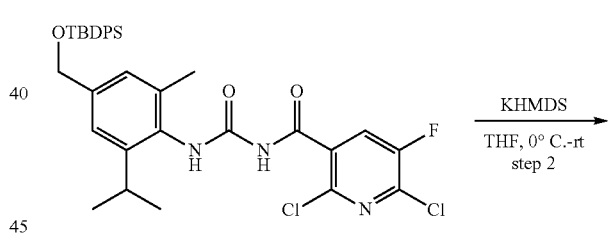

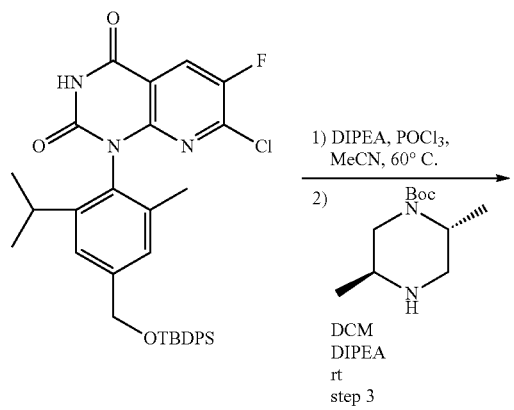

709
-continued

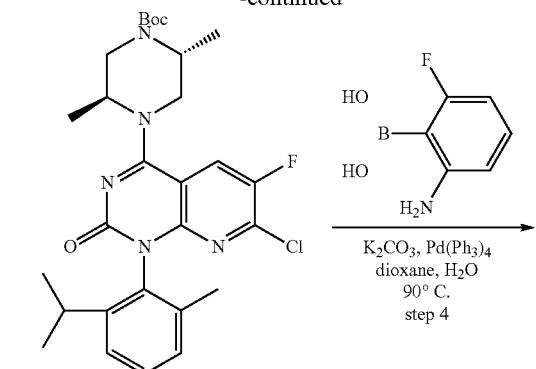

710
-continued

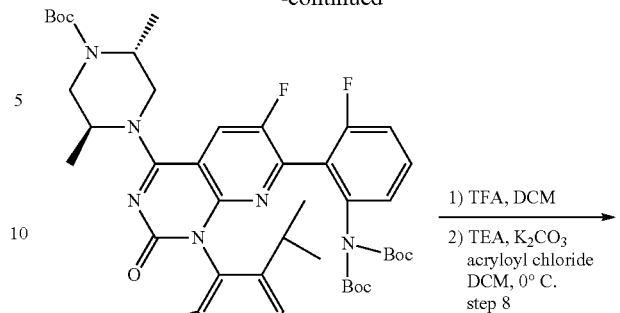

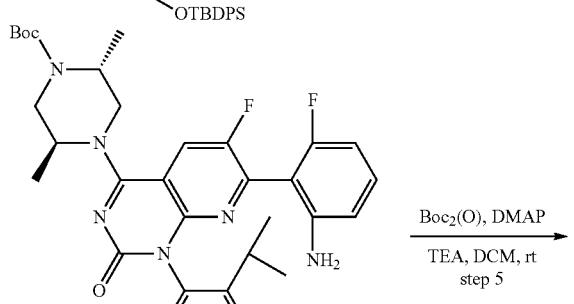

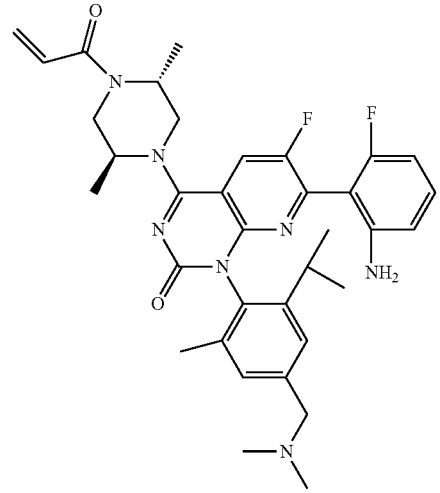

Mixture of atropisomers (M/P)

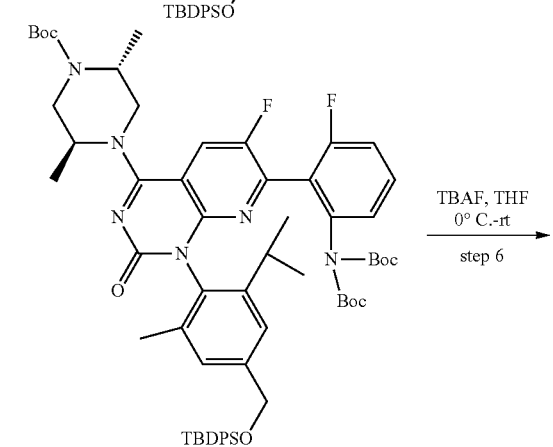

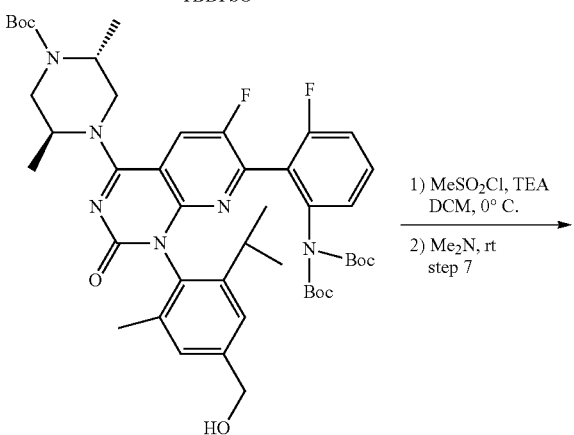

Step 1: N-((4-(((tert-Butyldiphenylsilyl)oxy)methyl)-2-isopropyl-6-methylphenyl)carbamoyl)-2,6-dichloro-5-fluoronicotinamide To a solution of 2,6-dichloro-5-fluoronicotinamide (998 mg, 4.78 mmol, intermediate S) in tetrahydrofuran (15 mL) was added oxalyl chloride, 2.0M in DCM (2.45 mL, 4.89 mmol) dropwise. The resulting mixture was then stirred at 65° C. under $N_2$ for 3 hours. Then, the mixture was cooled to room temperature and was then concentrated under reduced pressure to afford a light-yellow syrup which was redissolved in tetrahydrofuran (15 mL). Then, 4-(((tert-butyldiphenylsilyl)oxy)methyl)-2-isopropyl-6-methylaniline (2.12 g, 5.08 mmol, intermediate 1-37) in tetrahydrofuran (15 mL) was added to the solution. The resulting mixture was then stirred at room temperature for 30 min. Then, the mixture was concentrated under reduced pressure provided N-((4-(((tert-butyldiphenylsilyl)oxy)methyl)-2-isopropyl-6-methylphenyl)carbamoyl)-2,6-dichloro-5-fluoronicotinamide which was used in the next step without purification requirement. m/z (ESI, +ve ion) 652.2 (M+H)$^+$.

Step 2: 1-(4-(((tert-Butyldiphenylsilyl)oxy)methyl)-2-isopropyl-6-methylphenyl)-7-chloro-6-fluoropyrido[2,3-d]pyrimidine-2,4(1H,3H)-dione To a stirred solution of crude N-((4-(((tert-butyldiphenylsilyl)oxy)methyl)-2-isopropyl-6-methylphenyl)carbamoyl)-2,6-dichloro-5-fluoronicotinamide (2.9 g, 4.44 mmol) in tetrahydrofuran (16.0 mL) at 0° C. was added potassium bis(trimethylsilyl)amide (8.89 mL, 8.89 mmol). After the mixture was stirred at room temperature for 2 hours, an additional potassium bis(trimethylsilyl)amide (1.0 mL, 1.0 mmol) was added. After 30 mins, an additional potassium bis(trimethylsilyl)amide (1.0 mL, 1.0 mmol) was added. The resulting mixture was then stirred at room temperature for 15 min. The reaction was quenched by saturated $NH_4Cl$ (75 mL) and diluted with EtOAc (50 mL). The mixture was then extracted with EtOAc (1×30 mL). The organic layer was collected, dried over $MgSO_4$, and concentrated under reduced pressure. Chromatographic purification of the residue (silica gel, 0%-40% EtOAc/heptane) provided 1-(4-(((tert-butyldiphenylsilyl)oxy)methyl)-2-isopropyl-6-methylphenyl)-7-chloro-6-fluoropyrido[2,3-d]pyrimidine-2,4(1H,3H)-dione (2.365 g, 3.84 mmol, 86% yield) as a light-yellow solid. m/z (ESI, +ve ion) 616.0 $(M+H)^+$. $^1H$ NMR (400 MHz, DMSO-d6) δ 0.96 (d, J=6.8 Hz, 3H), 1.05 (d, J=6.8 Hz, 3H), 1.08 (s, 9H), 1.96 (s, 3H), 2.67 (sept, J=6.8 Hz, 1H), 4.84 (s, 2H), 7.12 (s, 1H), 7.34 (s, 1H), 7.40-7.53 (m, 6H), 7.69 (dd, J=6.2, 1.2 Hz, 4H), 8.46 (d, J=7.5 Hz, 1H), 12.18 (br s, 1H).

Step 3: tert-Butyl (2R,5S)-4-(1-(4-(((tert-butyldiphenylsilyl)oxy)methyl)-2-isopropyl-6-methylphenyl)-7-chloro-6-fluor-2-oxo-1,2-dihydropyrido[2,3-d]pyrimidin-4-yl)-2,5-dimethylpiperazine-1-carboxylate To a solution of 1-(4-(((tert-butyldiphenylsilyl)oxy)methyl)-2-isopropyl-6-methylphenyl)-7-chloro-6-fluoropyrido[2,3-d]pyrimidine-2,4(1H,3H)-dione (2.37 g, 3.84 mmol) in acetonitrile (20 mL) under $N_2$ was DIPEA (1.00 mL, 5.76 mmol) and $POCl_3$ (0.537 mL, 5.76 mmol) at room temperature. The resulting mixture was then stirred at 60° C. for 1 hour 20 mins. The mixture was then cooled to room temperature and was concentrated under reduced pressure. The crude mixture was then dissolved in dichloromethane (20 mL) and was cooled to 0° C. Then, DIPEA (3.34 mL, 19.19 mmol) was added, followed by tert-butyl (2R,5S)-2,5-dimethylpiperazine-1-carboxylate (1.65 g, 7.68 mmol, eNovation Chemicals LLC, Bridgewater, N.J., USA). The resulting mixture was then stirred at room temperature for 2.5 hours. Then, the mixture was diluted with water (150 mL) and EtOAc (50 mL). The mixture was then extracted with EtOAc (2×30 mL). The combined organic extracts were then dried over $MgSO_4$ and concentrated under reduced pressure. Chromatographic purification of the residue (silica gel, 0%-50% EtOAc/heptane) provided tert-butyl (2R,5S)-4-(1-(4-(((tert-butyldiphenylsilyl)oxy)methyl)-2-isopropyl-6-methylphenyl)-7-chloro-6-fluoro-2-oxo-1,2-dihydropyrido[2,3-d]pyrimidin-4-yl)-2,5-dimethylpiperazine-1-carboxylate (2.78 g, 3.42 mmol, 89% yield) as a tan foam. m/z (ESI, +ve ion) 812.1 $(M+H)^+$. $^1H$ NMR (400 MHz, DMSO-d6) δ 0.96 (dd, J=13.5, 6.8 Hz, 3H), 1.02 (dd, J=6.8, 3.4 Hz, 3H), 1.08 (s, 9H), 1.10-1.13 (m, 2H), 1.28 (br dd, J=10.2, 6.6 Hz, 1H), 1.44 (s, 9H), 1.87 (s, 3H), 2.34-2.47 (m, 1H), 3.42-3.59 (m, 1H), 3.62-3.71 (m, 1H), 3.76-3.88 (m, 1H), 3.89-4.09 (m, 1H), 4.13-4.25 (m, 1H), 4.26-4.39 (m, 1H), 4.74-4.80 (m, 1H), 4.83 (s, 2H), 7.11 (br d, J=6.4 Hz, 1H), 7.31 (br d, J=10.0 Hz, 1H), 7.42-7.54 (m, 6H), 7.65-7.75 (m, 4H), 8.35 (dd, J=12.9, 8.3 Hz, 1H).

Step 4: tert-Butyl (2R,5S)-4-(7-(2-amino-6-fluorophenyl)-1-(4-(((tert-butyldiphenylsilyl)oxy)methyl)-2-isopropyl-6-methylphenyl)-6-fluoro-2-oxo-1,2-dihydropyrido[2,3-d]pyrimidin-4-yl)-2,5-dimethylpiperazine-1-carboxylate A solution of tert-butyl (2R,5S)-4-(1-(4-(((tert-butyldiphenylsilyl)oxy)methyl)-2-isopropyl-6-methylphenyl)-7-chloro-6-fluoro-2-oxo-1,2-dihydropyrido[2,3-d]pyrimidin-4-yl)-2,5-dimethylpiperazine-1-carboxylate (450 mg, 0.554 mmol), (2-amino-6-fluorophenyl)boronic acid (129 mg, 0.831 mmol, Aces Pharma. Princeton, N.J., USA), potassium carbonate (383 mg, 2.77 mmol), tetrakis(triphenylphosphine)palladium(0) (64.0 mg, 0.055 mmol) in dioxane (4.4 mL) and water (1.1 mL) was deoxygenated by bubbling nitrogen gas through the solvents for 10 mins. Then, the mixture was stirred at 90° C. overnight. Then, the mixture was cooled to room temperature and was concentrated under reduced pressure. Chromatographic purification of the residue (silica gel, 0%-100% EtOAc/heptane) provided tert-butyl (2R,5S)-4-(7-(2-amino-6-fluorophenyl)-1-(4-(((tert-butyldiphenylsilyl)oxy)methyl)-2-isopropyl-6-methylphenyl)-6-fluoro-2-oxo-1,2-dihydropyrido[2,3-d]pyrimidin-4-yl)-2,5-dimethylpiperazine-1-carboxylate (513.4 mg, 0.579 mmol, 94% yield) as a goldenrod-colored. m/z (ESI, +ve ion) 887.1 $(M+H)^+$.

Step 5: 2-Methyl-2-propanyl (2R,53)-4-(7-(2-(bis(((2-methyl-2-propanyl)oxy)carbonyl)amino)-6-fluorophenyl)-6-fluoro-1-(2-methyl-4-((((2-methyl-2-propanyl)(diphenyl)silyl)oxy)methyl)-6-(2-propanyl)phenyl)-2-oxo-1,2-dihydropyrido[2,3-d]pyrimidin-4-yl)-2,5-dimethyl-1-piperazinecarboxylate To a solution of tert-butyl (2R,5S)-4-(7-(2-amino-6-fluorophenyl)-1-(4-(((tert-butyldiphenylsilyl)oxy)methyl)-2-isopropyl-6-methylphenyl)-6-fluoro-2-oxo-1,2-dihydropyrido[2,3-d]pyrimidin-4-yl)-2,5-dimethylpiperazine-1-carboxylate (490 mg, 0.552 mmol) in dichloromethane (4 mL) was added di-tert-butyl dicarbonate (241 mg, 1.11 mmol), 4-dimethylaminopyridine (135 mg, 1.11 mmol), and triethylamine (0.155 mL, 1.11 mmol). The resulting mixture was then stirred at room temperature for 4.5 hours. Then, the mixture was concentrated under reduced pressure. Chromatographic purification of the residue (silica gel, 0%-100% EtOAc/heptane) provided 2-methyl-2-propanyl (2R,5S)-4-(7-(2-(bis(((2-methyl-2-propanyl)oxy)carbonyl)amino)-6-fluorophenyl)-6-fluoro-1-(2-methyl-4-((((2-methyl-2-propanyl)(diphenyl)silyl)oxy)methyl)-6-(2-propanyl)phenyl)-2-oxo-1,2-dihydropyrido[2,3-d]pyrimidin-4-yl)-2,5-dimethyl-1-piperazinecarboxylate (470 mg, 0.432 mmol, 78% yield) as a yellow solid. m/z (ESI, +ve ion) 1087.2 (M+H).

Step 6: 2-Methyl-2-propanyl (2R,5S)-4-(7-(2-(bis(((2-methyl-2-propanyl)oxy)carbonyl)amino)-6-fluorophenyl)-6-fluoro-1-(4-(hydroxymethyl)-2-methyl-6-(2-propanyl)phenyl)-2-oxo-1,2-dihydropyrido[2,3-d]pyrimidin-4-yl)-2,5-dimethyl-1-piperazinecarboxylate To a solution of 2-methyl-2-propanyl (2R,5S)-4-(7-(2-(bis(((2-methyl-2-propanyl)oxy)carbonyl)amino)-6-fluorophenyl)-6-fluoro-1-(2-methyl-4-((((2-methyl-2-propanyl)

(diphenyl)silyl)oxy)methyl)-6-(2-propanyl)phenyl)-2-oxo-1,2-dihydropyrido[2,3-d]pyrimidin-4-yl)-2,5-dimethyl-1-piperazinecarboxylate (465 mg, 0.428 mmol) in tetrahydrofuran (3.5 mL) at 0° C. was added tetra-n-butylammonium fluoride 1M in THF (0.428 mL, 0.428 mmol). The resulting mixture was then stirred at room temperature for 4.5 hours and was then concentrated under reduced pressure. Chromatographic purification of the residue (silica gel, 0%-100% EtOAc/heptane) provided 2-methyl-2-propanyl (2R,5S)-4-(7-(2-(bis(((2-methyl-2-propanyl)oxy)carbonyl)amino)-6-fluorophenyl)-6-fluoro-1-(4-(hydroxymethyl)-2-methyl-6-(2-propanyl)phenyl)-2-oxo-1,2-dihydropyrido[2,3-d]pyrimidin-4-yl)-2,5-dimethyl-1-piperazinecarboxylate (125 mg, 0.147 mmol, 34% yield) as a yellow solid. m/z (ESI, +ve ion) 749.2 (M+H)+.

Step 7: 2-Methyl-2-propanyl (2R,5S)-4-(7-(2-(bis(((2-methyl-2-propanyl)oxy)carbonyl)amino)-6-fluorophenyl)-1-(4-((dimethylamino)methyl)-2-methyl-6-(2-propanyl)phenyl)-6-fluoro-2-oxo-1,2-dihydropyrido[2,3-d]pyrimidin-4-yl)-2,5-dimethyl-1-piperazinecarboxylate To a solution of 2-methyl-2-propanyl (2R,5S)-4-(7-(2-(bis(((2-methyl-2-propanyl)oxy)carbonyl)amino)-6-fluorophenyl)-6-fluoro-1-(4-(hydroxymethyl)-2-methyl-6-(2-propanyl)phenyl)-2-oxo-1,2-dihydropyrido[2,3-d]pyrimidin-4-yl)-2,5-dimethyl-1-piperazinecarboxylate (125 mg, 0.147 mmol) in dichloromethane (1.5 mL) at 0° C. under $N_2$ was added triethylamine (0.062 mL, 0.442 mmol) followed by a solution of methanesulfonyl chloride (0.011 mL, 0.147 mmol) in DCM (0.2 mL). The resulting mixture was then stirred at 0° C. for 1 hour. Then, dimethylamine (2M in THF) (0.736 mL, 1.47 mmol) and triethylamine (0.062 mL, 0.442 mmol) were added. The mixture was stirred at room temperature for 30 mins. Then, the mixture was diluted with saturated $NaHCO_3$ (5 mL) and was then extracted with EtOAc (2×20 mL). Chromatographic purification of the residue (silica gel, 0%-20% NH3 2M in MeOH/DCM) provided 2-methyl-2-propanyl (2R,5S)-4-(7-(2-(bis(((2-methyl-2-propanyl)oxy)carbonyl)amino)-6-fluorophenyl)-1-(4-((dimethylamino)methyl)-2-methyl-6-(2-propanyl)phenyl)-6-fluoro-2-oxo-1,2-dihydropyrido[2,3-d]pyrimidin-4-yl)-2,5-dimethyl-1-piperazinecarboxylate (98 mg, 0.112 mmol, 76% yield) as a yellow solid. m/z (ESI, +ve ion) 876.2 (M+H).

Step 8: 4-((2S,5R)-4-Acryloyl-2,5-dimethylpiperazin-1-yl)-7-(2-amino-6-fluorophenyl)-1-(4-((dimethylamino)methyl)-2-isopropyl-6-methylphenyl)-6-fluoropyrido[2,3-d]pyrimidin-2(1H)-one trifluoroacetic acid To a solution of 2-methyl-2-propanyl (2R,5S)-4-(7-(2-(bis(((2-methyl-2-propanyl)oxy)carbonyl)amino)-6-fluorophenyl)-1-(4-((dimethylamino)methyl)-2-methyl-6-(2-propanyl)phenyl)-6-fluoro-2-oxo-1,2-dihydropyrido[2,3-d]pyrimidin-4-yl)-2,5-dimethyl-1-piperazinecarboxylate (98 mg, 0.112 mmol) in dichloromethane (1.0 mL) was added trifluoroacetic acid (0.167 mL, 2.237 mmol). The resulting mixture was then stirred at room temperature for 40 mins. Then, the mixture was concentrated and dried in vacuo. Then, the residue was dissolved in DCM (20 mL) and saturated $NaHCO_3$ (40 mL) was added. The mixture was then stirred at room temperature for 15 mins. The organic layer was then collected and aqueous layer was extracted with EtOAc (2×20 mL). The combined organic extracts were then dried over $MgSO_4$, concentrated, and dried in vacuo. The residue was then dissolved in dichloromethane (1 mL). The mixture was then cooled to 0° C. under $N_2$ and triethylamine (0.015 mL, 0.106 mmol) was added followed by a solution of acryloyl chloride (8.6 µl, 0.106 mmol) in DCM (0.2 mL) dropwise. After stirring at 0° C. for 5 mins, triethylamine (0.075 mL) and potassium carbonate (0.032 mL, 0.530 mmol) were added. The mixture was then stirred for 25 mins. The mixture was then quenched with saturated $NaHCO_3$ (5 mL) and was extracted with EtOAc (3×15 mL). The combined organic extracts were then dried over $MgSO_4$ and concentrated. Chromatographic purification of the residue (silica gel, 0%-20% $NH_3$ 2M in MeOH/DCM) then by purified via preparative HPLC (Phenomenex Gemini C18 column, 150×30 mm, 10u, 110 A, 10-100% 0.1% TFA in MeCN/$H_2O$) provided 4-((2S,5R)-4-acryloyl-2,5-dimethylpiperazin-1-yl)-7-(2-amino-6-fluorophenyl)-1-(4-((dimethylamino)methyl)-2-isopropyl-6-methylphenyl)-6-fluoropyrido[2,3-d]pyrimidin-2(1H)-one (2.3 mg, 1.83 µmol, 1.7% yield), TFA salt as a yellow solid. m/z (ESI, +ve ion) 630.2 (M+H). $^{19}$F NMR (METHANOL-d4) δ: −76.95 (s, 1F), −128.59 (dd, J=32.5, 4.8 Hz, 1F), −130.14 (br d, J=32.1 Hz, 1F). $^1$H NMR (400 MHz, METHANOL-d4) δ 8.17-8.25 (m, 1H), 7.31-7.36 (m, 1H), 7.21-7.25 (m, 1H), 6.75-6.92 (m, 3H), 6.57 (td, J=2.67, 5.65 Hz, 1H), 6.30 (ddd, J=1.76, 6.69, 16.64 Hz, 1H), 5.83 (ddd, J=1.76, 6.17, 10.52 Hz, 1H), 4.87-5.15 (m, 2H), 4.19-4.59 (m, 2H), 3.89-4.11 (m, 2H), 3.83 (br s, 2H), 2.58-2.66 (m, 1H), 2.42-2.58 (m, 6H), 1.99-2.04 (m, 3H), 1.45-1.51 (m, 3H), 1.19 (dd, J=2.49, 6.84 Hz, 3H), 0.99-1.06 (m, 3H), 0.91 (br t, J=6.74 Hz, 3H).

Example 185

1-((2R,5S)-4-(6-Chloro-7-(2-fluorophenyl)-2-imino-1-(2-isopropylphenyl)-1,2-dihydropyrido[2,3-d]pyrimidin-4-yl)-2,5-dimethylpiperazin-1-yl)prop-2-en-1-one

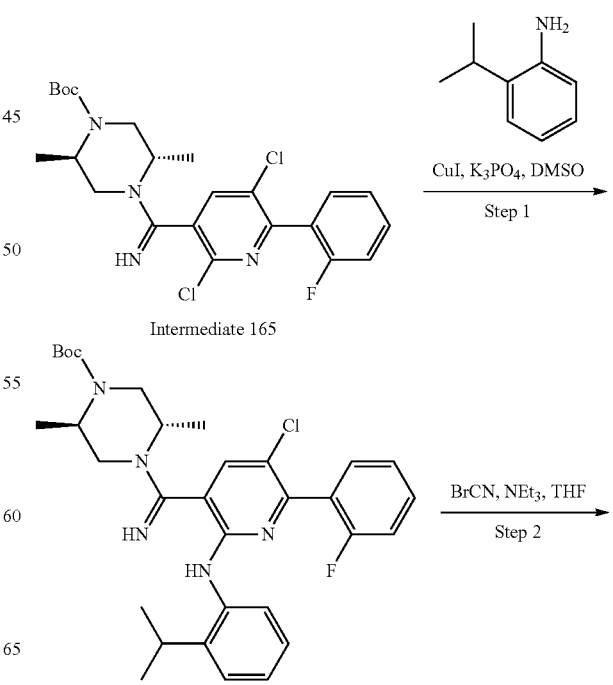

715
-continued

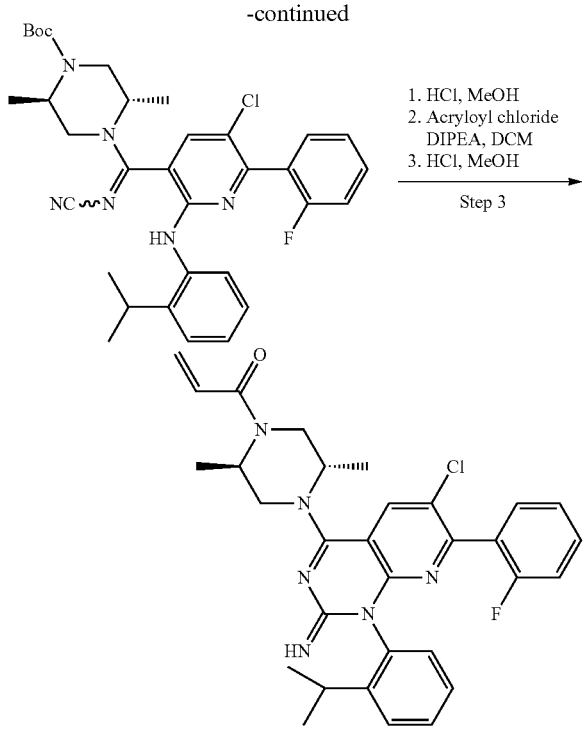

Step 1: tert-Butyl (2R,5S)-4-((5-chloro-6-(2-fluorophenyl)-2-((2-isopropylphenyl)amino)pyridin-3-yl)(imino)methyl)-2,5-dimethylpiperazine-1-carboxylate A vial was charged with tert-butyl (2R,5S)-4-((2,5-dichloro-6-(2-fluorophenyl)pyridin-3-yl)(imino)methyl)-2,5-dimethylpiperazine-1-carboxylate (Intermediate 165, 1 g, 2.1 mmol), copper(I) iodide (40 mg, 0.2 mmol), and potassium phosphate (1.1 g, 5.2 mmol). The vial was evacuated and backfilled with nitrogen. DMSO (4 ml) were added to the reaction mixture, followed by addition of 2-(methylethyl)phenylamine (365 μl, 2.7 mmol) added. The reaction mixture was heated to 80° C. After 1 hour, the reaction mixture was diluted with water and extracted with EtOAc. The organic phase was washed with 1M LiCl solution and dried over MgSO$_4$. The filtrate was concentrated in vacuo to give the crude material. Purification by preparative SFC (Chiralcel IC column (5 μm, 21×250 mm). F=80 mL, (20% MeOH with 0.2% NEt$_3$)/80% CO$_2$) afforded tert-butyl (2R,5S)-4-((5-chloro-6-(2-fluorophenyl)-2-((2-isopropylphenyl)amino)pyridin-3-yl)(imino)methyl)-2,5-dimethylpiperazine-1-carboxylate. m/z (ESI, +ve ion): 580.0 (M+H)$^+$.

Step 2: tert-Butyl (2R,5S)-4-((5-chloro-6-(2-fluorophenyl)-2-((2-isopropylphenyl)amino)pyridin-3-yl)cyanoimino)methyl)-2,5-dimethylpiperazine-1-carboxylate Triethylamine (0.2 mL, 1.5 mmol) and cyanogen bromide (3 M in DCM; 0.29 mL, 0.86 mmol) were added to a solution of tert-butyl (2R,5S)-4-((5-chloro-6-(2-fluorophenyl)-2-((2-isopropylphenyl)amino)pyridin-3-yl)(imino)methyl)-2,5-dimethylpiperazine-1-carboxylate (50 mg, 0.086 mmol) in tetrahydrofuran (1.5 mL). The reaction mixture was allowed to stir overnight. The reaction mixture was filtered and the filtrate was washed with aqueous saturated NaHCO$_3$ solution, dried over MgSO$_4$ and concentrated under reduced pressure. The crude product was taken onto the next step without further purification. m/z (ESI, +ve ion): 604.6 (M)$^+$.

Step 3: 1-((2R,5S)-4-(6-Chloro-7-(2-fluorophenyl)-2-imino-1-(2-isopropylphenyl)-1,2-dihydropyrido[2,3-d]pyrimidin-4-yl)-2,5-dimethylpiperazin-1-yl)prop-2-en-1-one Hydrochloric acid (5N, 0.13 mL, 0.66 mmol) was added to a solution of tert-butyl (2R,5S)-4-((5-chloro-6-(2-fluorophenyl)-2-((2-isopropylphenyl)amino)pyridin-3-yl)(cyanoimino)methyl)-2,5-dimethylpiperazine-1-carboxylate (40 mg, 0.066 mmol) in MeOH (1 mL). The reaction mixture was stirred for 10 min at it and then heated to 72° C. for one hour. The reaction mixture was cooled to t, neutralized with aqueous saturated NaHCO$_3$ solution and extracted with EtOAc. The organic extract was washed with brine and dried over MgSO$_4$. The solution was filtered and concentrated in vacuo to give the crude material. Residual solvents were removed from the crude residue by azeotropic distillation with toluene (3 mL). The residue was dissolved in DCM (2 mL) and the solution was cooled to 10° C. 1,1'-Dimethyltriethylamine (0.023 mL, 0.13 mmol) added, followed by solution of 2-propenoyl chloride (1.1 M in DCM; 0.06 mL, 0.066 mmol). After 5 min, the reaction mixture was concentrated under reduced pressure. The residue was dissolved in MeOH (1 mL) and treated with hydrochloric acid (5N, 0.3 mL). The reaction mixture was heated to 72° C. for 30 min and then neutralized with aqueous saturated NaHCO$_3$ solution (5 mL). The reaction mixture was extracted with EtOAc and washed with brine. The organic phase was separated and dried over MgSO$_4$. The solvent was removed under reduced pressure and the crude material was absorbed onto silica gel. Purification by silica gel chromatography (eluent: 10-100% of EtOAc/heptane, followed by 100% (3:1 EtOH in EtOAc), followed by 100% (20% (2 M NH3/MeOH) in DCM)) provided 1-((2R,5S)-4-(6-chloro-7-(2-fluorophenyl)-2-imino-1-(2-isopropylphenyl)-1,2-dihydropyrido[2,3-d]pyrimidin-4-yl)-2,5-dimethylpiperazin-1-yl)prop-2-en-1-one (10 mg, 9 μmol, 13% yield). m/z (ESI, +ve ion): 559.3 (M+H)$^+$. $^1$H NMR (400 MHz, DMSO-d6) δ 0.94-1.01 (m, 3H) 1.14-1.17 (m, 3H) 1.22-1.31 (m, 3H) 1.47 (br s, 3H) 2.52-2.66 (m, 1H) 3.38-4.29 (m, 4H) 4.52-5.16 (m, 2H) 5.78 (br d, J=10.37 Hz, 1H) 6.21 (dt, J=16.64, 2.15 Hz, 1H) 6.65-6.98 (m, 1H) 7.14-7.64 (m, 8H) 8.43-8.69 (m, 1H) 9.04 (br s, 1H)

Example 186

4-((2S,5R)-4-Acryloyl-2,5-dimethylpiperazin-1-yl)-6-chloro-7-(2-fluorophenyl)-1-(2-isopropylphenyl)pyrido[2,3-d]pyrimidin-2(1H)-one

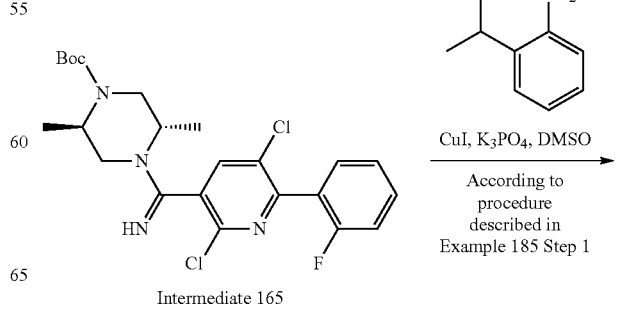

Intermediate 165

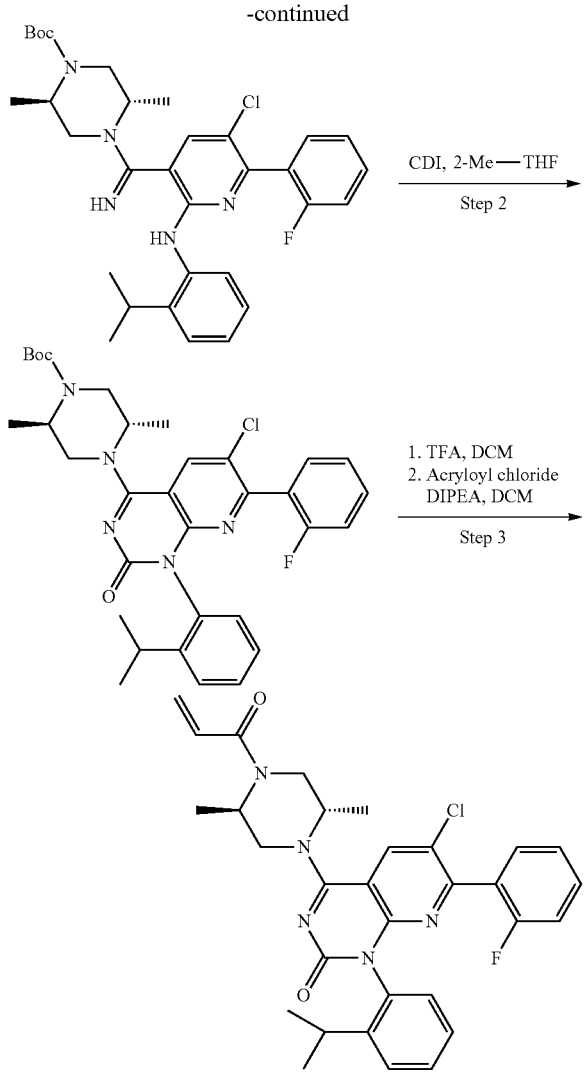

Step 1: tert-Butyl (2R,5S)-4-((5-chloro-6-(2-fluorophenyl)-2-((2-isopropylphenyl)amino)pyridin-3-yl)(imino)methyl)-2,5-dimethylpiperazine-1-carboxylate The synthesis of the title compound is described in Step 1 of Example 185.

Step 2: tert-Butyl (2R,5r)-4-(6-chloro-7-(2-fluorophenyl)-1-(2-isopropylphenyl)-2-oxo-1,2-dihydropyrido[2,3-d]pyrimidin-4-yl)-2,5-dimethylpiperazine-1-carboxylate A solution of tert-butyl (2R,5S)-4-((5-chloro-6-(2-fluorophenyl)-2-((2-isopropylphenyl)amino)pyridin-3-yl)(imino)methyl)-2,5-dimethylpiperazine-1-carboxylate (0.065 g, 0.11 mmol) and 1,1'-carbonyldiimidazole (0.036 g, 0.22 mmol, Acros Organics) in 2-Me-tetrahydrofuran (1 mL) was heated to 100° C. for 12 h. The reaction mixture was cooled to rt and absorbed onto a pad of silica gel. Purification by silica gel chromatography (eluent: 10-100% of EtOAc/heptane) afforded tert-butyl (2R,5S)-4-(6-chloro-7-(2-fluorophenyl)-1-(2-isopropylphenyl)-2-oxo-1,2-dihydropyrido[2,3-d]pyrimidin-4-yl)-2,5-dimethylpiperazine-1-carboxylate (25 mg, 0.04 mmol, 36% yield). m/z (ESI, +ve ion): 605.6 (M+H)+.

Step 3: 4-((2S,5R)-4-Acryloyl-2,5-dimethylpiperazin-1-yl)-6-chloro-7-(2-fluorophenyl)-1-(2-isopropylphenyl)pyrido[2,3-d]pyrimidin-2(1H)-one TFA (0.1 mL) was added to a solution of tert-butyl (2R,5S)-4-(6-chloro-7-(2-fluorophenyl)-1-(2-isopropylphenyl)-2-oxo-1,2-dihydropyrido[2,3-d]pyrimidin-4-yl)-2,5-dimethylpiperazine-1-carboxylate in (1 mL) at rt. After 1 h, the reaction mixture was concentrated under reduced pressure and residual solvents were removed from the crude residue by azeotropic distillation with toluene (2 mL). The crude material was dissolved in DCM (2 mL) and the solution was cooled to 10° C., followed by the addition of 1,1'-dimethyltriethylamine (0.02 mL, 0.1 mmol) and 2-propenoyl chloride (1.1 M in DCM; 0.067 mL, 0.074 mmol). After 10 min, the reaction mixture was diluted with DCM and treated with aqueous saturated NaHCO3 (5 mL) and brine. The organic phase was separated, dried over MgSO4 and filtered. The crude material was absorbed onto silica gel and purified by siliga gel chromatography (eluent: 10-100% EtOAc/heptane) to afford 4-((2S,5R)-4-acryloyl-2,5-dimethylpiperazin-1-yl)-6-chloro-7-(2-fluorophenyl)-1-(2-isopropylphenyl)pyrido[2,3-d]pyrimidin-2(1H)-one (10 mg, 0.018 mmol, 36% yield). m/z (ESI, +ve ion): 560.2 (M+H)+. $^1$H NMR (400 MHz, DMSO-d6) δ 0.92-1.01 (m, 3H) 1.07 (d, J=6.84 Hz, 3H) 1.17-1.37 (m, 6H) 2.53-2.61 (m, 1H) 3.39-4.27 (m, 4H) 4.42-4.95 (m, 2H) 5.69-5.80 (m, 1H) 6.19 (br d, J=16.79 Hz, 1H) 6.73-6.92 (m, 1H) 7.14 (d, J=7.67 Hz, 1H) 7.18-7.37 (m, 5H) 7.38-7.44 (m, 1H) 7.46-7.55 (m, 1H) 8.35-8.47 (m, 1H)

Example 187

N-[5-[6-Chloro-4-[(2S,5R)-2,5-dimethyl-4-prop-2-enoyl-piperazin-1-yl]-7-(2-fluorophenyl)-2-oxo-pyrido[2,3-d]pyrimidin-1-yl]-4,6-diisopropyl-pyrimidin-2-yl]-N-methyl-acetamide

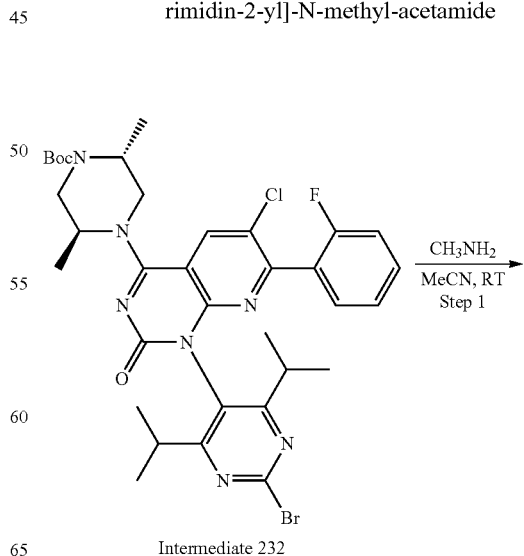

Intermediate 232

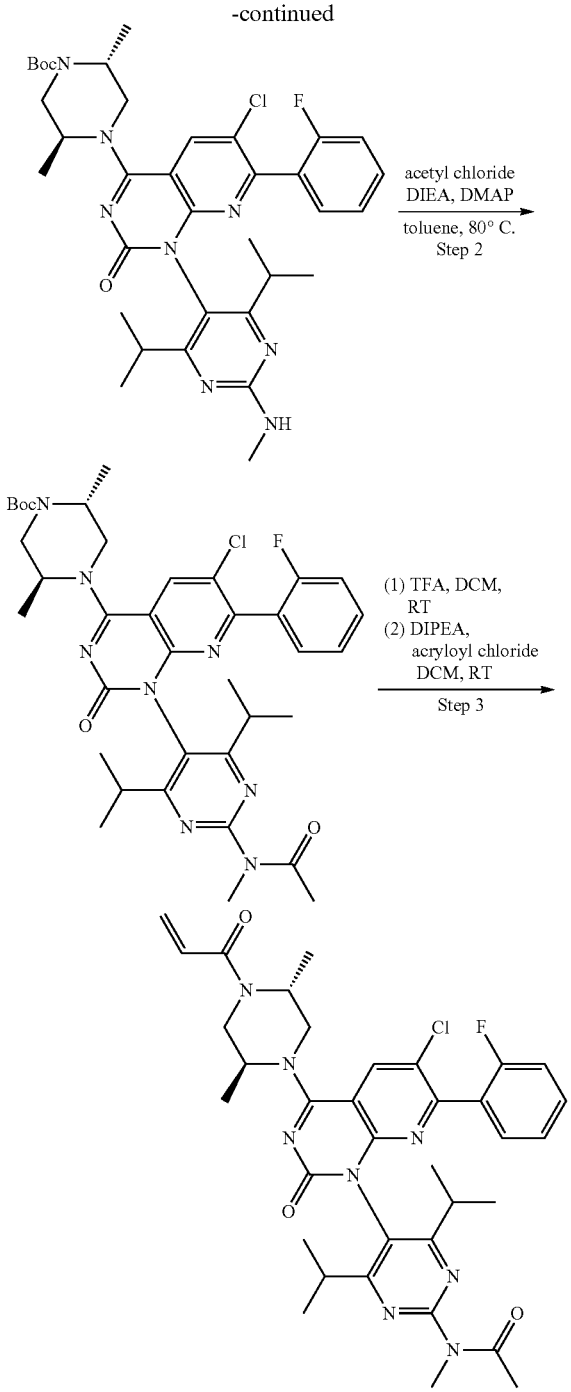

Step 1: tert-Butyl (2R,S)-4-(6-chloro-1-(4,6-diisopropyl-2-(methylamino)pyrimidin-5-yl)-7-(2-fluorophenyl)-2-oxo-1,2-dihydropyrido[2,3-d]pyrimidin-4-yl)-2,5-dimethylpiperazine-1-carboxylate Methylamine (2.0 M in tetrahydrofuran, 0.312 mL, 0.624 mmol) was added to a stirred solution of tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (91 mg, 0.125 mmol, Intermediate 232) in acetonitrile (0.5 mL). The reaction mixture was stirred at room temperature for 9 h. The reaction mixture was concentrated in vacuo. The crude product was purified by silica gel chromatography (eluent 0-50% [(3:1) EtOAc/EtOH]/heptane) to provide tert-butyl (2R,5S)-4-(6-chloro-1-(4,6-diisopropyl-2-(methylamino)pyrimidin-5-yl)-7-(2-fluorophenyl)-2-oxo-1,2-dihydropyrido[2,3-d]pyrimidin-4-yl)-2,5-dimethylpiperazine-1-carboxylate as a yellow solid (45 mg, 0.066 mmol, 53.1% yield). $^1$H NMR (400 MHz, CHLOROFORM-d) δ 8.13 (1H, s) 7.45-7.52 (1H, m) 7.21-7.29 (2H, m) 7.14-7.20 (1H, m) 3.53-5.12 (7H, m) 3.05 (3H, d, J=4.98 Hz) 2.49-2.61 (2H, m) 1.57 (9H, s) 1.44-1.54 (3H, m) 1.30-1.36 (3H, m) 1.21 (3H, dd, J=6.34, 4.25 Hz) 1.01 (6H, br t, J=7.26 Hz). m/z (ESI, +ve ion): 679.1 (M+H)$^+$.

Step 2: tert-Butyl (2R,5S)-4-(6-chloro-1-(4,6-diisopropyl-2-(N-methylacetamido)pyrimidin-5-yl)-7-(2-fluorophenyl)-2-oxo-1,2-dihydropyrido[2,3-d]pyrimidin-4-yl)-2,5-dimethylpiperazine-1-carboxylate tert-Butyl (2R,5S)-4-(6-chloro-1-(4,6-diisopropyl-2-(methylamino)pyrimidin-5-yl)-7-(2-fluorophenyl)-2-oxo-1,2-dihydropyrido[2,3-d]pyrimidin-4-yl)-2,5-dimethylpiperazine-1-carboxylate (154 mg, 0.227 mmol), N,N-diisopropylethylamine (0.198 mL, 1.134 mmol), and 4-(N,N-dimethylamino)-pyridine (1.385 mg, 0.011 mmol) were mixed in toluene (1 mL) in a sealed vial. Acetyl chloride (0.036 mL, 0.453 mmol) was added, and the reaction mixture was stirred at 80° C. for 18 h. The reaction mixture was diluted with EtOAc (60 mL) and washed with saturated aqueous NH$_4$Cl (40 mL). The organic layer was separated, washed with brine (40 mL), dried over MgSO$_4$, filtered, and concentrated in vacuo. The crude product was purified by silica gel chromatography (eluent 0-50% [(3:1) EtOAc/EtOH]/heptane) to provide tert-butyl (2R,5S)-4-(6-chloro-1-(4,6-diisopropyl-2-(N-methylacetamido)pyrimidin-5-yl)-7-(2-fluorophenyl)-2-oxo-1,2-dihydropyrido[2,3-d]pyrimidin-4-yl)-2,5-dimethylpiperazine-1-carboxylate as a yellow solid (135 mg, 0.187 mmol, 83% yield). $^1$H NMR (400 MHz, CHLOROFORM-d) δ 8.19 (1H, s) 7.47-7.54 (1H, m) 7.15-7.29 (3H, m) 3.59 (3H. s) 3.55-5.12 (6H, m) 2.73 (2H, dq, J=13.01, 6.58 Hz) 2.62 (3H, s) 1.59 (9H, s) 1.49-1.57 (3H, m) 1.32-1.39 (3H, m) 1.27 (6H, dd, J=6.63, 2.49 Hz) 1.07 (6H, t, J=6.84 Hz). m/z (ESI, +ve ion): 721.3 (M+H)$^+$.

Step 3: N-(5-(4-((2S,5R)-4-Acryloyl-2,5-dimethylpiperazin-1-yl)-6-chloro-7-(2-fluorophenyl)-2-oxopyrido[2,3-d]pyrimidin-1(2H)-yl)-4,6-diisopropylpyrimidin-2-yl)-N-methylacetamide Trifluoroacetic acid (0.5 mL, 6.71 mmol) was added to a stirred solution of tert-butyl (2R,5S)-4-(6-chloro-1-(4,6-diisopropyl-2-(N-methylacetamido)pyrimidin-5-yl)-7-(2-fluorophenyl)-2-oxo-1,2-dihydropyrido[2,3-d]pyrimidin-4-yl)-2,5-dimethylpiperazine-1-carboxylate (135 mg, 0.187 mmol) in dichloromethane (1 mL). The reaction mixture was stirred at room temperature for 20 min. The reaction mixture was concentrated in vacuo to give crude N-(5-(6-chloro-4-((2S,5R)-2,5-dimethylpiperazin-1-yl)-7-(2-fluorophenyl)-2-oxopyrido[2,3-d]pyrimidin-1(2H)-yl)-4,6-diisopropylpyrimidin-2-yl)-N-methylacetamide that was used without purification assuming 100% yield.

Acryloyl chloride (1.1 M in DCM, 0.204 mL, 0.224 mmol) was added to a stirred mixture of the crude N-(5-(6-chloro-4-((2S,5R)-2,5-dimethylpiperazin-1-yl)-7-(2-fluorophenyl)-2-oxopyrido[2,3-d]pyrimidin-1(2H)-yl)-4,6-diisopropylpyrimidin-2-yl)-N-methylacetamide (116 mg, 0.187 mmol) and N,N-diisopropylethylamine (0.163 mL, 0.934 mmol) in dichloromethane (1 mL). The reaction mixture was stirred at room temperature for 45 min. The reaction mixture was diluted with DCM (50 mL) and washed with saturated aqueous NH$_4$Cl (30 mL). The organic layer was separated, dried over MgSO$_4$, filtered, and concentrated in vacuo. The crude product was purified by silica gel chromatography (eluent 0-100% EtOAc/heptane) to provide N-(5-(4-((2S,5R)-4-acryloyl-2,5-dimethylpiperazin-1-yl)-6-chloro-7-(2-fluorophenyl)-2-oxopyrido[2,3-d]pyrimidin-1(2H)-yl)-4,6-diisopropylpyrimidin-2-yl)-N-methylacetamide as a light yellow solid (95 mg, 0.141 mmol, 75% yield). $^1$H NMR (400 MHz, CHLOROFORM-d) δ 8.19 (1H, s) 7.47-7.55 (1H, m) 7.16-7.28 (3H, m) 6.59-6.76 (1H, m) 6.42-6.52 (1H, m) 5.84-5.91 (1H, m) 3.59 (3H, s) 3.52-5.26 (6H, m) 2.65-2.78 (2H, m) 2.61 (3H s) 1.47-1.58 (4H, m) 1.37-1.42 (2H, m) 1.27 (6H, dd, J=6.63, 2.28 Hz) 1.03-1.11 (6H, m). m/z (ESI, +ve ion): 675.3 (M+H)$^+$.

Example 188

N-[5-[6-Chloro-4-[(2S,5R)-2,5-dimethyl-4-prop-2-enoyl-piperazin-1-yl]-7-(2-fluorophenyl)-2-oxo-pyrido[2,3-d]pyrimidin-1-yl]-4,6-diisopropyl-pyrimidin-2-yl]acetamide

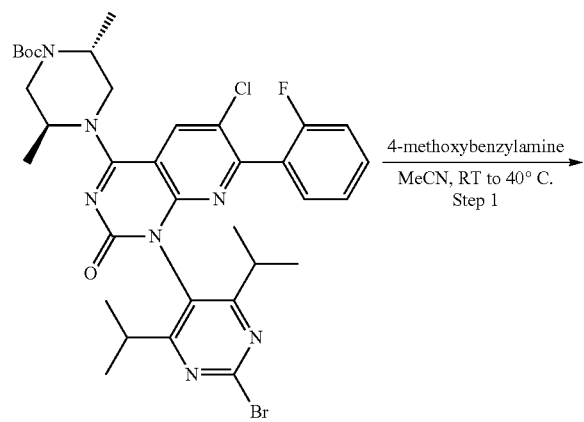

Intermediate 232

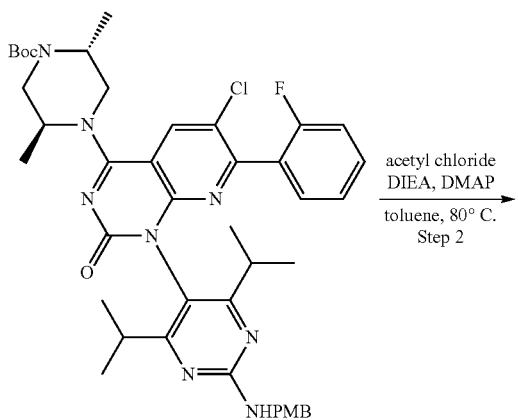

NHPMB

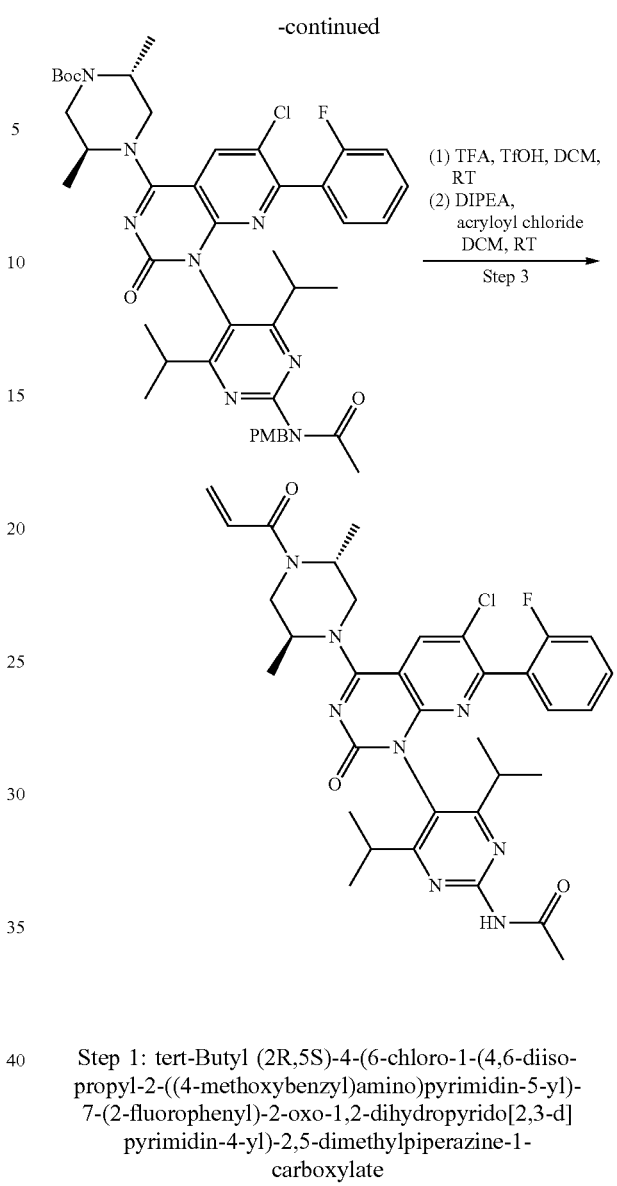

Step 1: tert-Butyl (2R,5S)-4-(6-chloro-1-(4,6-diisopropyl-2-((4-methoxybenzyl)amino)pyrimidin-5-yl)-7-(2-fluorophenyl)-2-oxo-1,2-dihydropyrido[2,3-d]pyrimidin-4-yl)-2,5-dimethylpiperazine-1-carboxylate 4-Methoxybenzylamine (0.283 mL, 2.147 mmol) was added to a stirred solution of tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (313 mg, 0.429 mmol, Intermediate 232) in acetonitrile (1.5 mL). The reaction mixture was stirred at room temperature for 20 h before being warmed to 40° C. and stirred for another 7 h. The reaction mixture was concentrated in vacuo. The crude product was purified by silica gel chromatography (eluent 0-50% [(3:1) EtOAc/EtOH]/heptane) to provide tert-butyl (2R,5S)-4-(6-chloro-1-(4,6-diisopropyl-2-((4-methoxybenzyl)amino)pyrimidin-5-yl)-7-(2-fluorophenyl)-2-oxo-1,2-dihydropyrido[2,3-d]pyrimidin-4-yl)-2,5-dimethylpiperazine-1-carboxylate as a light yellow solid (179 mg, 0.228 mmol, 53.1% yield). $^1$H NMR (400 MHz, CHLOROFORM-d) δ 8.05 (1H, m) 7.25-7.45 (3H, m) 7.04-7.19 (3H, m) 6.79-6.93 (2H, m) 3.76 (3H, s) 3.43-5.31 (8H, m) 2.40-2.57 (2H, m) 1.48 (9H, s) 1.37-1.44 (3H, m) 1.18-1.27 (3H, m) 1.07-1.17 (6H, m) 0.88-0.99 (6H, m). m/z (ESI, +ve ion): 785.2 (M+H)$^+$.

Step 2: tert-Butyl (2R,5S)-4-(6-chloro-1-(4,6-diisopropyl-2-(N-(4-methoxybenzyl)acetamido)pyrimidin-5-yl)-7-(2-fluorophenyl)-2-oxo-1,2-dihydropyrido[2,3-d]pyrimidin-4-yl)-2,5-dimethylpiperazine-1-carboxylate tert-Butyl (2R,5S)-4-(6-chloro-1-(4,6-diisopropyl-2-((4-methoxybenzyl)amino)pyrimidin-5-yl)-7-(2-fluorophenyl)-2-oxo-12-dihydropyrido[2,3-d]pyrimidin-4-yl)-2,5dimethylpiperazine-1-carboxylate (169 mg, 0.215 mmol), N,N-diisopropylethylamine (0.188 mL, 1.076 mmol), and 4-(N,N-dimethylamino)-pyridine (2 mg, 0.016 mmol) were mixed in toluene (1 mL) in a sealed vial. Acetyl chloride (0.034 mL, 0.430 mmol) was added, and the reaction mixture was stirred at 80° C. for 16 h. The reaction mixture was diluted with EtOAc (50 mL) and washed with saturated aqueous NH₄Cl (40 mL). The organic layer was separated, washed with brine (40 mL), dried over MgSO₄, filtered, and concentrated in vacuo. The crude product was purified by silica gel chromatography (eluent 0-70% EtOAc/heptane) to provide tert-butyl (2R,5S)-4-(6-chloro-1-(4,6-diisopropyl-2-(N-(4-methoxybenzyl)acetamido)pyrimidin-5-yl)-7-(2-fluorophenyl)-2-oxo-1,2-dihydropyrido[2,3-d]pyrimidin-4-yl)-2,5-dimethylpiperazine-1-carboxylate as a light yellow solid (108 mg, 0.131 mmol, 60.7% yield). $^1$H NMR (400 MHz, CHLOROFORM-d) δ 8.08 (1H, s) 7.36-7.44 (1H, m) 7.33 (2H, d, J=8.71 Hz) 7.05-7.15 (3H, m) 6.69-6.73 (2H, m) 5.22 (2H, s) 3.72 (3H, s) 3.35-5.01 (6H, m) 2.55-2.67 (2H, m) 2.51 (3H, s) 1.48 (9H, s) 1.38-1.46 (3H, m) 1.20-1.28 (3H, m) 1.15 (6H, dd, J=6.63, 2.70 Hz) 0.93 (6H, J=7.26 Hz). m/z (ESI, +ve ion): 827.3 (M+H)⁺.

Step 3: N-(5-(4-((2S,5R)-4-Acryloyl-2,5-dimethylpiperazin-1-yl)-6-chloro-7-(2-fluorophenyl)-2-oxopyrido[2,3-d]pyrimidin-1(2H)-yl)-4,6-diisopropylpyrimidin-2-yl)acetamide Trifluoroacetic acid (0.5 mL, 6.71 mmol) and trifluoromethane sulfonic acid (0.05 mL, 0.563 mmol) were added to a stirred solution of tert-butyl (2R,5S)-4-(6-chloro-1-(4,6-diisopropyl-2-(N-(4-methoxybenzyl)acetamido)pyrimidin-5-yl)-7-(2-fluorophenyl)-2-oxo-1,2-dihydropyrido[2,3-d]pyrimidin-4-yl)-2,5-dimethylpiperazine-1-carboxylate (100 mg, 0.121 mmol) in dichloromethane (0.5 mL). The reaction mixture was stirred at room temperature for 7 h. The reaction mixture was diluted with DCM (40 mL) and washed with saturated aqueous NaHCO₃ (25 mL). The organic layer was separated, dried over MgSO₄, filtered, and concentrated in vacuo to give crude N-(5-(6-chloro-4-((2S,5R)-2,5-dimethylpiperazin-1-yl)-7-(2-fluorophenyl)-2-oxopyrido[2,3-d]pyrimidin-(2H)-yl)-4,6-diisopropylpyrimidin-2-yl)acetamide that was used without purification assuming 100% yield.

Acryloyl chloride (1.1 M in DCM, 0.131 mL, 0.144 mmol) was added to a stirred solution of the crude N-(5-(6-chloro-4-((2S,5R)-2,5-dimethylpiperazin-1-yl)-7-(2-fluorophenyl)-2-oxopyrido[2,3-d]pyrimidin-1(2H)-yl)-4,6-diisopropylpyrimidin-2-yl)acetamide (73 mg, 0.120 mmol) in dichloromethane (0.5 mL). The reaction mixture was stirred at room temperature for 2 h. The reaction mixture was concentrated in vacuo. The crude product was purified by silica gel chromatography (eluent 0-50% [(3:1) EtOAc/EtOH]/heptane) to provide N-(5-(4-((2S,5R)-4-acryloyl-2,5-dimethylpiperazin-1-yl)-6-chloro-7-(2-fluorophenyl)-2-oxopyrido[2,3-d]pyrimidin-1(2H)-yl)-4,6-diisopropylpyrimidin-2-yl)acetamide as a white solid (20 mg, 0.030 mmol, 25.2% yield). $^1$H NMR (400 MHz, CHLOROFORM-d) δ 8.17 (1H, s) 7.97 (1H, s) 7.46-7.53 (1H, m) 7.14-7.28 (3H, m) 6.57-6.74 (1H, m) 6.40-6.50 (1H, m) 5.82-5.89 (1H, m) 3.50-5.24 (6H, m) 2.59-2.73 (5H, m) 1.45-1.56 (4H, m) 1.38 (2H, br d, J=6.84 Hz) 1.23 (6H, dd, J=6.63, 2.70 Hz) 0.99-1.07 (6H, m). m/z (ESI, +ve ion): 661.2 (M+H)⁺.

Example 189

4-((2S,5R)-4-Acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one

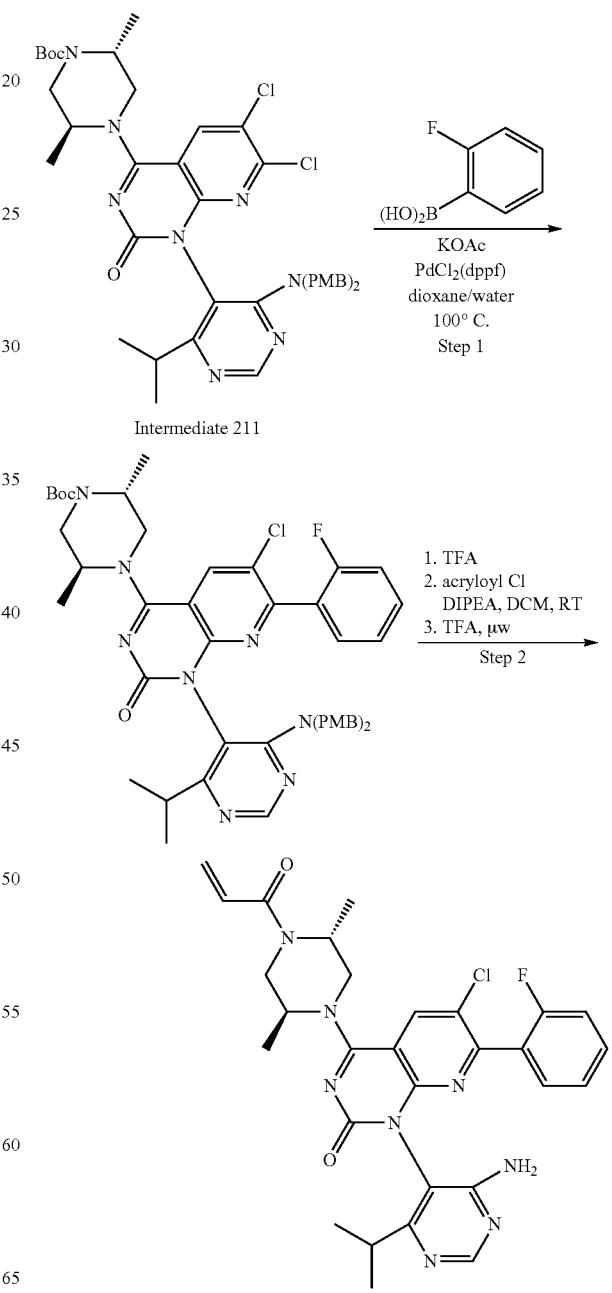

Step 1: tert-Butyl (2R,5S)-4-(1-(4-(bis(4-methoxybenzyl)amino)-6-isopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate A mixture of tert-butyl (2R,5S)-4-(1-(4-(bis(4-methoxybenzyl)amino)-6-isopropylpyrimidin-5-yl)-6,7-dichloro-2-oxo-1,2-dihydropyrido[2,3-d]pyrimidin-4-yl)-2,5-dimethylpiperazine-1-carboxylate (0.228 g, 0.284 mmol, Intermediate 211), (2-fluorophenyl)boronic acid (0.060 g, 0.43 mmol; Combi-Blocks, Inc., San Diego, Calif.), PdCl$_2$(dppf) (0.021 g, 0.028 mmol), and potassium acetate (0.084 g, 0.85 mmol) in 1,4-dioxane (2.6 mL)/water (0.26 mL) was sparged with nitrogen then stirred at 100° C. for 1 h. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-60% [(3:1) EtOAc/EtOH]/heptane) to give tert-butyl (2R,5S)-4-(1-(4-(bis(4-methoxybenzyl)amino)-6-isopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (252 mg, 0.292 mmol, >99% yield) as a brown solid. MS (ESI, +ve) m/z: 863.1 (M+1)$^+$.

Step 2: 4-((2S,5R)-4-Acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one A solution of tert-butyl (2R,5S)-4-(1-(4-(bis(4-methoxybenzyl)amino)-6-isopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.252 g, 0.292 mmol) in 2,2,2-trifluoroacetic acid (3.33 g, 29.2 mmol) was stirred at RT for 15 min. The reaction mixture was concentrated.

A yellow solution of the resulting oil, acryloyl chloride (0.5 M in DCM, 0.700 mL, 0.350 mmol), and DIPEA (0.153 mL, 0.876 mmol) in dichloromethane (1.5 mL) was stirred at RT for 15 min. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo.

A solution of the resulting oil in 2,2,2-trifluoroacetic acid (3.33 g, 29.2 mmol) was heated in the microwave at 100° C. for 5 min, 120° C. for 10 min, then 100° C. for 30 min. The reaction mixture was concentrated. The crude product in DCM was loaded onto the column and was purified via automated flash chromatography (silica gel, 0-100% [(3:1) EtOAc/EtOH]/heptane then 0-5% [2 M ammonia in MeOH]/DCM) to give 4-((2S,5R)-4-acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one (11 mg, 0.019 mmol, 7% yield) as an off-white solid. $^1$H NMR (400 MHz, CDCl$_3$) 8.54 (s, 1H) 8.08-8.13 (m, 1H) 7.41-7.48 (m, 1H) 7.23-7.30 (m, 1H) 7.16-7.22 (m, 1H) 7.08-7.16 (m, 1H) 6.50-6.71 (m, 1H) 6.33-6.46 (m, 1H) 5.75-5.85 (m, 1H) 4.89-5.19 (m, 2H) 4.79-4.88 (m, 2H) 4.28-4.53 (m, 1H) 3.38-4.01 (m, 3H) 2.48-2.65 (m, 1H) 1.30-1.52 (m, 6H) 1.15-1.20 (m, 3H) 0.99-1.05 (m, 3H). $^{19}$F NMR (377 MHz, CDCl$_3$) δ −112.26-−112.15 (m, 1F). MS (ESI, +ve) m/z: 576.8 (M+1)$^+$.

Example 189-1

4-((2S,5R)-4-Acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one, Single Isomer

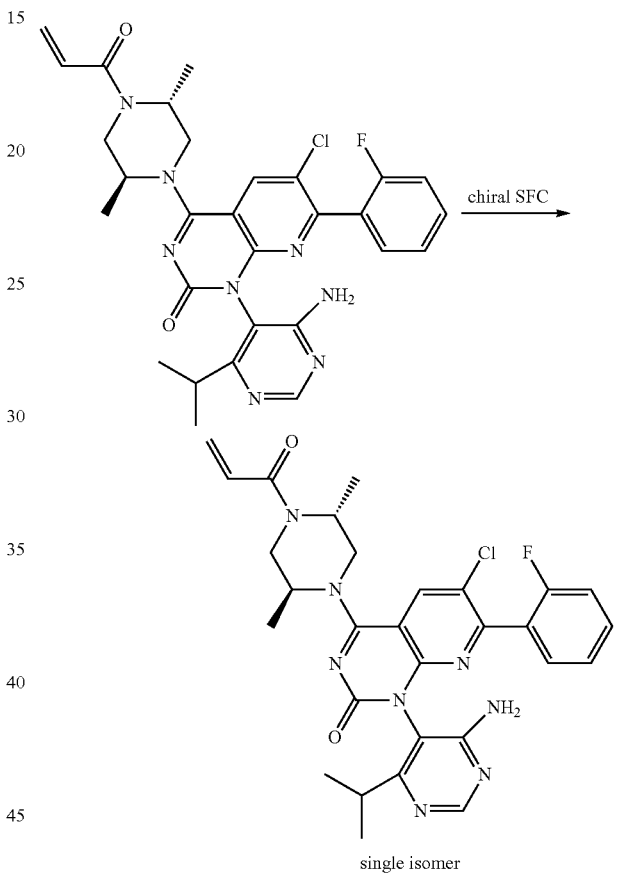

single isomer

Atropisomers of 4-((2S,5R)-4-acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one (139 mg, 0.241 mmol) were separated by chiral SFC: ID 250×21 mm, 5 μm, 45% MeOH/CO$_2$, 70 g/min, 204 bar. This gave 4-((2S,5R)-4-acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one (58 mg, 0.10 mmol, 42% yield) (first eluting isomer) as a yellow solid. $^1$H NMR (400 MHz, CDCl$_3$) 8.57 (s, 1H) 8.11 (s, 1H) 7.40-7.50 (m, 1H) 7.23-7.29 (m, 1H) 7.08-7.21 (m, 2H) 6.50-6.69 (m, 1H) 6.34-6.45 (m, 1H) 5.76-5.85 (m, 1H) 4.90-5.21 (m, 1H) 4.74 (s, 2H) 3.39-4.56 (m, 5H) 2.49-2.63 (m, 1H) 1.33-1.52 (m, 6H) 1.19 (d, J=6.6 Hz, 3H) 1.03 (br d, J=6.4 Hz, 3H). $^{19}$F NMR (377 MHz, CDCl$_3$) δ −112.21-−112.13 (m, 1F). MS (ESI, +ve) m/z: 577.1 (M+1)$^+$.

Example 189-2

4-((2S,5R)-4-Acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one, Single Isomer

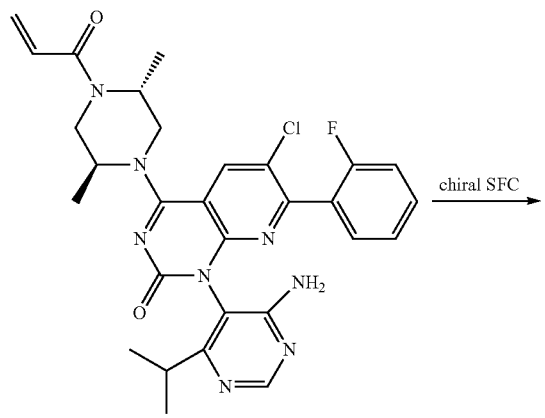

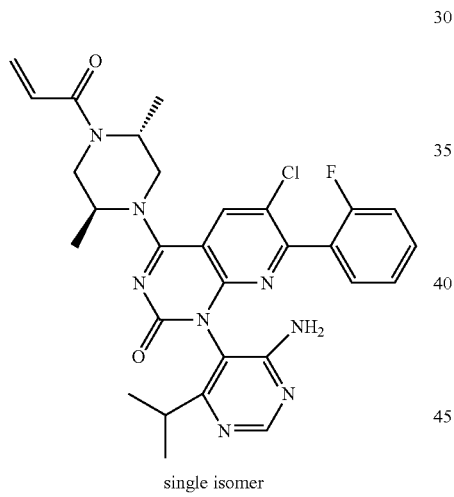

single isomer

Atropisomers of 4-((2S,5R)-4-acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one (139 mg, 0.241 mmol) were separated by chiral SFC: ID 250×21 mm, 5 μm, 45% MeOH/CO$_2$, 70 g/min, 204 bar. This gave 4-((2S,5R)-4-acryloyl-2,5-dimethylpiperazin-1-yl)-1-(4-amino-6-isopropylpyrimidin-5-yl)-6-chloro-7-(2-fluorophenyl)pyrido[2,3-d]pyrimidin-2(1H)-one (58 mg, 0.10 mmol, 42% yield) (second eluting isomer) as a yellow solid. $^1$H NMR (400 MHz, CDCl$_3$) δ 8.56 (s, 1H) 8.08-8.12 (m, 1H) 7.41-7.49 (m, 1H) 7.24-7.30 (m, 1H) 7.17-7.22 (m, 1H) 7.10-7.16 (m, 1H) 6.51-6.70 (m, 1H) 6.35-6.45 (m, 1H) 5.77-5.85 (m, 1H) 4.87-5.20 (m, 1H) 4.76 (br s, 2H) 3.39-4.51 (m, 5H) 2.50-2.66 (m, 1H) 1.30-1.51 (m, 6H) 1.18 (d, J=6.6 Hz, 3H) 1.01 (d, J=6.8 Hz, 3H). $^{19}$F NMR (377 MHz, CDCl$_3$) δ -112.22--112.11 (m, 1F). MS (ESI, +ve) m/z: 577.1 (M+1)$^+$.

Example 190

4-((2S,5R)-4-Acryloyl-2,5-dimethylpiperazin-1-yl)-1-(4-amino-6-isopropylpyrimidin-5-yl)-6-chloro-7-(2-fluoro-6-hydroxyphenyl)pyrido[2,3-d]pyrimidin-2(1H)-one

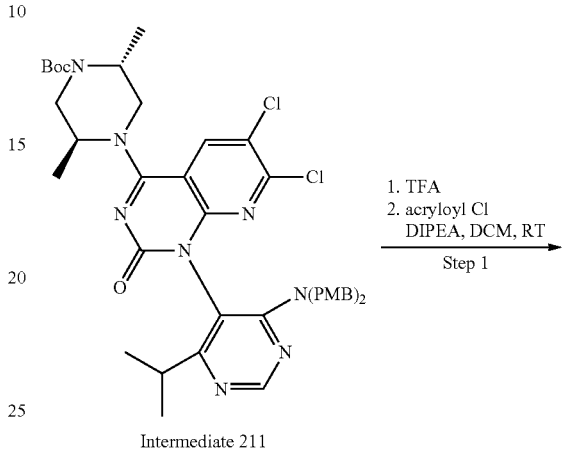

Intermediate 211

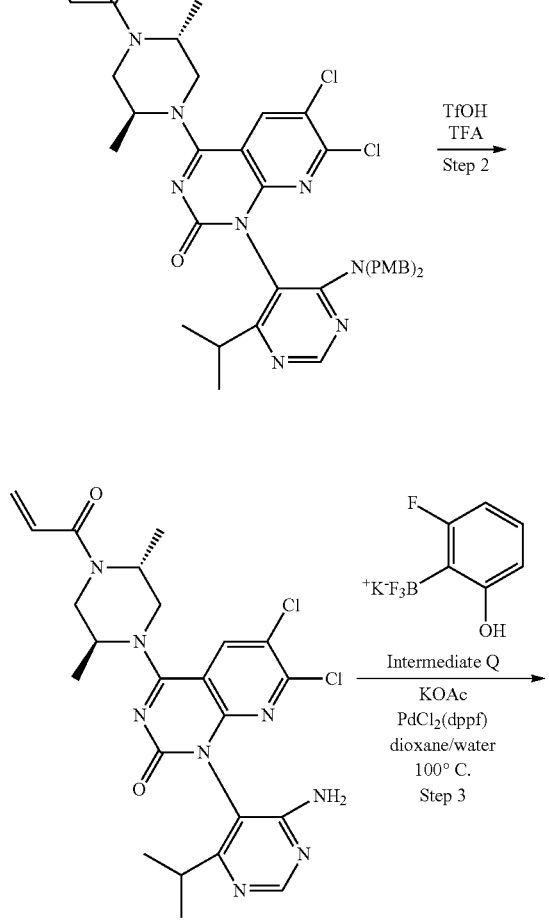

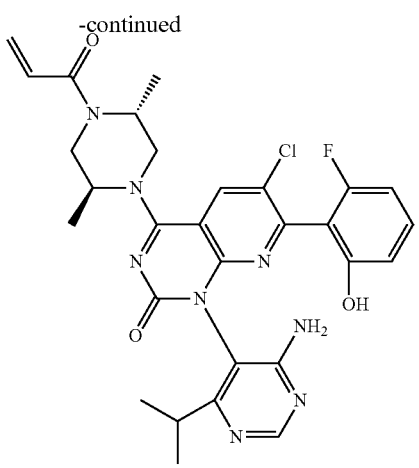

Step 1: 4-((2S,5R)-4-Acryloyl-2,5-dimethylpiperazin-1-yl)-1-(4-(bis(4-methoxybenzyl)amino)-6-isopropylpyrimidin-5-yl)-6,7-dichloropyrido[2,3-d]pyrimidin-2(1H)-one A solution of tert-butyl (2R,5S)-4-(1-(4-(bis(4-methoxybenzyl)amino)-6-isopropylpyrimidin-5-yl)-6,7-dichloro-2-oxo-1,2-dihydropyrido[2,3-d]pyrimidin-4-yl)-2,5-dimethylpiperazine-1-carboxylate (0.194 g, 0.241 mmol, Intermediate 211) and 2,2,2-trifluoroacetic acid (2.75 g, 24.1 mmol) in dichloromethane (1.2 mL) was stirred at RT for 15 min. The reaction mixture was concentrated.

A yellow solution of the resulting oil, acryloyl chloride (0.5 M in DCM, 0.579 mL, 0.290 mmol), and DIPEA (0.126 mL, 0.724 mmol) in dichloromethane (1.2 mL) was stirred at RT for 30 min. The reaction mixture was diluted with EtOAc (100 mL), added to a separatory funnel, and washed with saturated, aqueous sodium bicarbonate (2×75 mL), the organic layer was separated, dried over anhydrous $Na_2SO_4$, and concentrated in vacuo to give 4-((2S,5R)-4-acryloyl-2,5-dimethylpiperazin-1-yl)-1-(4-(bis(4-methoxybenzyl)amino)-6-isopropylpyrimidin-5-yl)-6,7-dichloropyrido[2,3-d]pyrimidin-2(1H)-one (0.171 g, 0.226 mmol). MS (ESI, +ve) m/z: 756.7 (M+1)$^+$.

Step 2: 4-((2S,5R)-4-Acryloyl-2,5-dimethylpiperazin-1-yl)-1-(4-amino-6-isopropylpyrimidin-5-yl)-6,7-dichloropyrido[2,3-d]pyrimidin-2(1H)-one A solution of 4-((2S,5R)-4-acryloyl-2,5-dimethylpiperazin-1-yl)-1-(4-(bis(4-methoxybenzyl)amino)-6-isopropylpyrimidin-5-yl)-6,7-dichloropyrido[2,3-d]pyrimidin-2(1H)-one (0.171 g, 0.226 mmol) and trifluoromethane sulfonic acid (0.020 mL, 0.226 mmol) in 2,2,2-trifluoroacetic acid (1.8 mL, 22.6 mmol) was stirred at RT for 30 min, 50° C. for 30 min, then 80° C. for 5 min. The reaction mixture was diluted with EtOAc (100 mL), added to a separatory funnel, and washed with saturated, aqueous sodium bicarbonate (2×75 mL); the organic layer was separated, dried over anhydrous $Na_2SO_4$, and concentrated in vacuo to give 4-((2S,5R)-4-acryloyl-2,5-dimethylpiperazin-1-yl)-1-(4-amino-6-isopropylpyrimidin-5-yl)-6,7-dichloropyrido[2,3-]pyrimidin-2(1H)-one (0.100 g, 0.193 mmol). MS (ESI, +ve) m/z: 516.8 (M+1)$^+$.

Step 3: 4-((2S,5R)-4-Acryloyl-2,5-dimethylpiperazin-1-yl)-1-(4-amino-6-isopropylpyrimidin-5-yl)-6-chloro-7-(2-fluoro-6-hydroxyphenyl)pyrido[2,3-d]pyrimidin-2(1H)-one A mixture of 4-((2S,5R)-4-acryloyl-2,5-dimethylpiperazin-1-yl)-1-(4-amino-6-isopropylpyrimidin-5-yl)-6,7-dichloropyrido[2,3-d]pyrimidin-2(1H)-one (0.100 g, 0.193 mmol), potassium F-phenol-trifluoroborate (0.063 g, 0.29 mmol, Intermediate Q), $PdCl_2$(dppf) (0.014 g, 0.019 mmol), and potassium acetate (0.057 g, 0.58 mmol) in 1,4-dioxane (1.8 mL)/water (0.18 mL) was sparged with nitrogen then stirred at 100° C. for 1.5 h. The reaction mixture was diluted with EtOAc (100 mL), added to a separatory funnel, and washed with saturated, aqueous sodium bicarbonate (2×75 mL); the organic layer was separated, dried over anhydrous $Na_2SO_4$, and concentrated in vacuo. The crude product was adsorbed onto silica and was purified via automated flash chromatography (silica gel, 0-100% [(3:1) EtOAc/EtOH]/heptane: elutes slowly) to give 4-((2S,5R)-4-acryloyl-2,5-dimethylpiperazin-1-yl)-1-(4-amino-6-isopropylpyrimidin-5-yl)-6-chloro-7-(2-fluoro-6-hydroxyphenyl)pyrido[2,3-d]pyrimidin-2(1H)-one (36 mg, 0.061 mmol, 31% yield) as a light brown solid. $^1$H NMR (400 MHz, $CDCl_3$) δ 8.47-8.53 (m, 1H) 8.10-8.20 (m, 1H) 7.35-7.63 (m, 1H) 7.21-7.31 (m, 1H) 6.73-6.79 (m, 1H) 6.47-6.72 (m, 2H) 6.31-6.44 (m, 1H) 5.75-5.87 (m, 1H) 4.79-5.23 (m, 4H) 4.18-4.68 (m, 2H) 3.75-4.04 (m, 2H) 2.58-2.72 (m, 1H) 1.33-1.49 (m, 6H) 1.21-1.25 (m, 3H) 1.19 (d, J=6.6 Hz, 3H). $^{19}$F NMR (377 MHz, $CDCl_3$) δ -111.92 (br s, 1F). MS (ESI, +ve) m/z: 592.8 (M+1)$^+$.

Example 191-1

4-((2S,5R)-4-Acryloyl-2,5-dimethylpiperazin-1-yl)-6-chloro-1-(2-chloro-4-isopropyl-6-methylpyrimidin-5-yl)-7-(2-fluorophenyl)pyrido[2,3-d]pyrimidin-2(1H)-one, Single Isomer

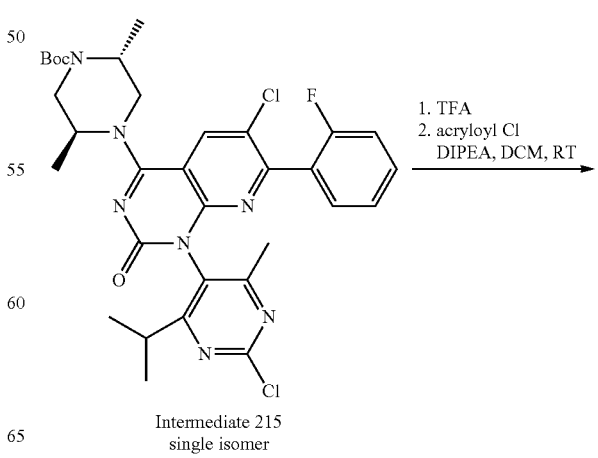

Intermediate 215
single isomer

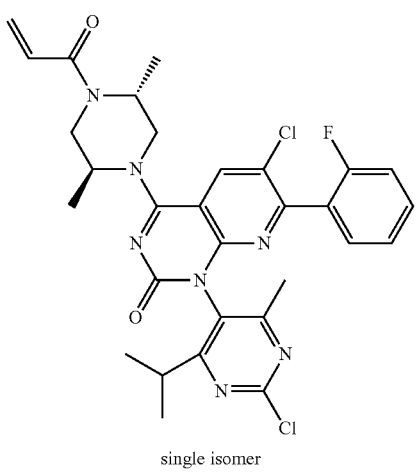

single isomer

A solution of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.048 g, 0.073 mmol, Intermediate 215) in 2,2,2-trifluoroacetic acid (0.560 mL, 7.31 mmol) was stirred at RT for 10 min. The reaction mixture was concentrated.

A solution of the resulting oil. acryloyl chloride (0.5 M in DCM, 0.175 mL, 0.088 mmol), and DIPEA (0.051 mL, 0.292 mmol) in dichloromethane (0.7 mL) was stirred at RT for 10 min. The reaction mixture was diluted with EtOAc (100 mL), added to a separatory funnel, and washed with saturated, aqueous sodium bicarbonate (2×75 mL); the organic layer was separated, dried over anhydrous Na₂SO₄, and concentrated in vacuo. The crude product was adsorbed onto silica and was purified via automated flash chromatography (silica gel, 0-50% [(3:1) EtOAc/EtOH]/heptane) to give 4-((2S,5R)-4-acryloyl-2,5-dimethylpiperazin-1-yl)-6-chloro-1-(2-chloro-4-isopropyl-6-methylpyrimidin-5-yl)-7-(2-fluorophenyl)pyrido[2,3-d]pyrimidin-2(1H)-one (42 mg, 0.069 mmol, 94% yield) as a light yellow solid. $^1$H NMR (400 MHz, CDCl₃) δ 8.13 (s, 1H) 7.42-7.50 (m, 1H) 7.17-7.24 (m, 2H) 7.09-7.17 (m, 1H) 6.51-6.71 (m, 1H) 6.36-6.45 (m, 1H) 5.75-5.85 (m, 1H) 3.43-5.24 (m, 6H) 2.63-2.77 (m, 1H) 2.20-2.27 (m, 3H) 1.29-1.53 (m, 6H) 1.22 (d, J=6.8 Hz, 3H) 1.04 (d, J=6.6 Hz, 3H). $^{19}$F NMR (377 MHz, CDCl₃) δ 112.95—112.86 (m, 1F). MS (ESI, +ve) m/z: 610.0 (M+1)⁺.

Example 191-2

4-((2S,5R)-4-Acryloyl-2,5-dimethylpiperazin-1-yl)-6-chloro-1-(2-chloro-4-isopropyl-6-methylpyrimidin-5-yl)-7-(2-fluorophenyl)pyrido[2,3-d]pyrimidin-2(1H)-one, Single Isomer

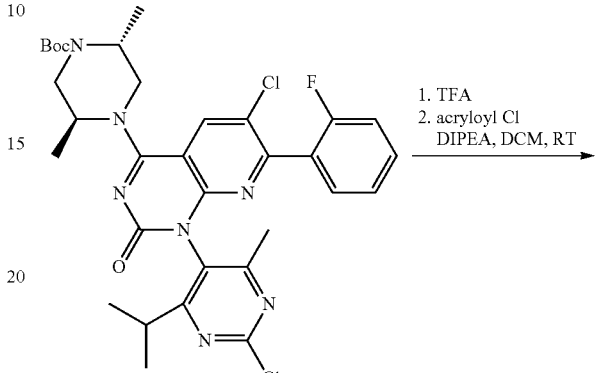

Intermediate 204
single isomer

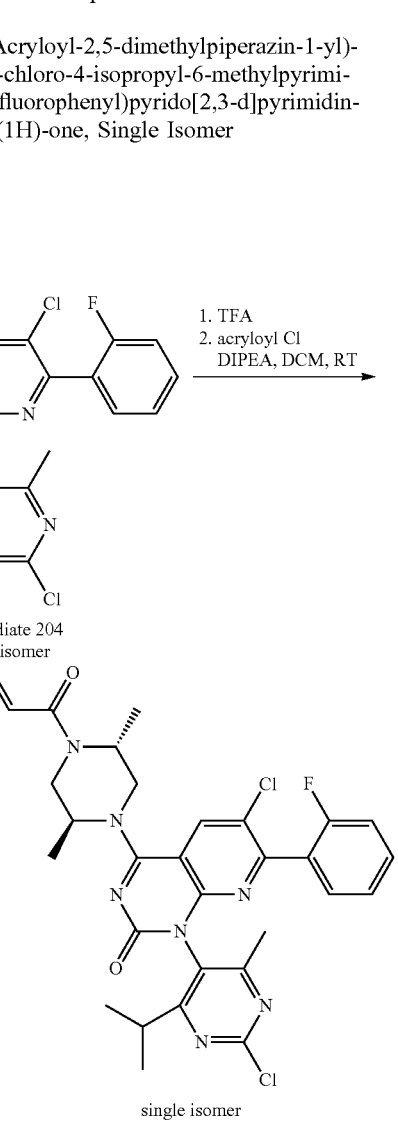

single isomer

A solution of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.103 g, 0.157 mmol, Intermediate 204) in 2,2,2-trifluoroacetic acid (1.20 mL, 15.7 mmol) was stirred at RT for 10 min. The reaction mixture was concentrated.

A solution of the resulting oil, acryloyl chloride (0.5 M in DCM, 0.345 mL, 0.173 mmol), and DIPEA (0.082 mL, 0.471 mmol) in dichloromethane (0.8 mL) was stirred at RT for 15 min. The reaction mixture was diluted with EtOAc (100 mL), added to a separatory funnel, and washed with saturated, aqueous sodium bicarbonate (2×100 mL); the organic layer was separated, dried over anhydrous Na₂SO₄, and concentrated in vacuo. The crude product was adsorbed onto silica and was purified via automated flash chromatography (silica gel, 0-60% [(3:1) EtOAc/EtOH]/heptane) to give 4-((2S,5R)-4-acryloyl-2,5-dimethylpiperazin-1-yl)-6-c-chloro-1-(2-chloro-4-isopropyl-6-methylpyrimidin-5-yl)-7-(2-fluorophenyl)pyrido[2,3-d]pyrimidin-2(1H)-one (47 mg, 0.077 mmol, 49% yield) as an off-white solid. $^1$H NMR (400 MHz, CDCl₃) δ 8.13 (s, 1H) 7.42-7.50 (m, 1H)

7.17-7.24 (m, 2H) 7.10-7.17 (m, 1H) 6.51-6.70 (m, 1H) 6.41 (br t, J=14.7 Hz, 1H) 5.77-5.85 (m, 1H) 3.42-5.19 (m, 6H) 2.63-2.75 (m, 1H) 2.19-2.25 (m, 3H) 1.31-1.51 (m, 6H) 1.23 (d, J=6.8 Hz, 3H) 1.07 (br d, J=6.6 Hz, 3H). $^{19}$F NMR (377 MHz, CDCl$_3$) δ −112.96−−112.83 (m, 1F). MS (ESI, +ve) m/z: 610.1 (M+1)$^+$.

Example 192

4-((2S,5R)-4-Acryloyl-2,5-dimethylpiperazin-1-yl)-7-(2-amino-6-fluorophenyl)-1-(4-amino-6-isopropylpyrimidin-5-yl)-6-chloropyrido[2,3-d]pyrimidin-2(1H)-one

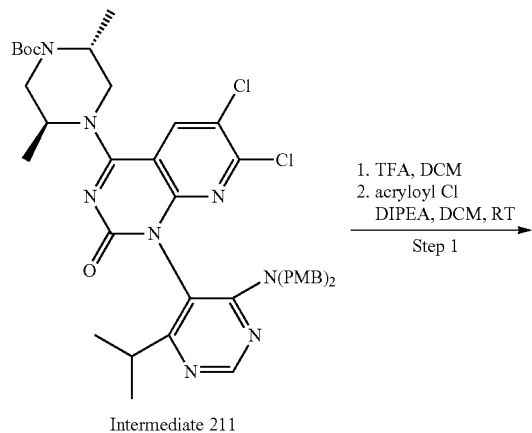

Intermediate 211

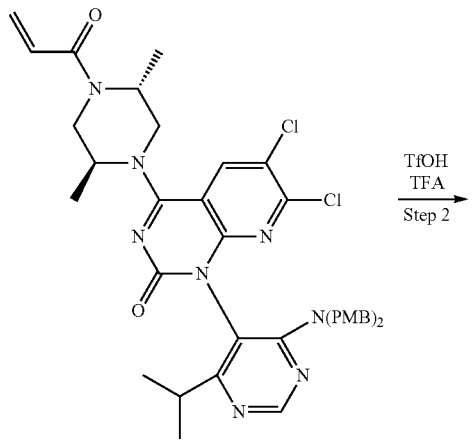

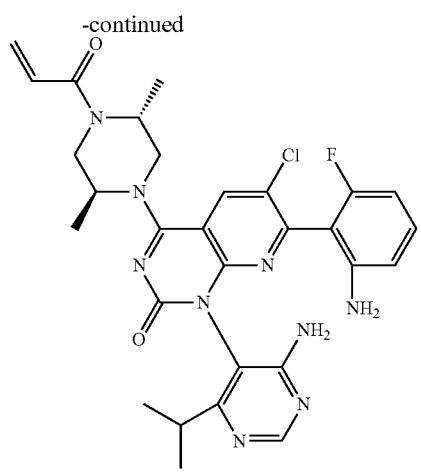

Step 1: 4-((2S,5R)-4-Acryloyl-2,5-dimethylpiperazin-1-yl)-1-(4-(bis(4-methoxybenzyl)amino)-6-isopropylpyrimidin-5-yl)-6,7-dichloropyrido[2,3-d]pyrimidin-2(1H)-one A solution of tert-butyl (2R,5S)-4-(1-(4-(bis(4-methoxybenzyl)amino)-6-isopropylpyrimidin-5-yl)-6,7-dichloro-2-oxo-1,2-dihydropyrido[2,3-d]pyrimidin-4-yl)-2,5-dimethylpiperazine-1-carboxylate (0.723 g, 0.899 mmol, Intermediate 211) and 2,2,2-trifluoroacetic acid (10 g, 90 mmol) in dichloromethane (5 mL) was stirred at RT for 15 min. The reaction mixture was concentrated.

A yellow solution of the resulting oil, acryloyl chloride (0.5 M in DCM, 2.16 mL, 1.08 mmol), and DIPEA (0.470 mL, 2.70 mmol) in dichloromethane (5 mL) was stirred at RT for 30 min. The reaction mixture was diluted with EtOAc (100 mL), added to a separatory funnel, and washed with saturated, aqueous sodium bicarbonate (2×75 mL), the organic layer was separated, dried over anhydrous Na$_2$SO$_4$, and concentrated in vacuo to give 4-((2S,5R)-4-acryloyl-2,5-dimethylpiperazin-1-yl)-1-(4-(bis(4-methoxybenzyl)amino)-6-isopropylpyrimidin-5-yl)-6,7-dichloropyrido[2,3-d]pyrimidin-2(1H)-one. MS (ESI, +ve) m/z: 756.8 (M+1)$^+$.

Step 2: 4-((2S,5R)-4-Acryloyl-2,5-dimethylpiperazin-1-yl)-1-(4-amino-6-isopropylpyrimidin-5-yl)-6,7-dichloropyrido[2,3-d]pyrimidin-2(1H)-one A solution of 4-((2S,5R)-4-acryloyl-2,5-dimethylpiperazin-1-yl)-1-(4-(bis(4-methoxybenzyl)amino)-6-isopropylpyrimidin-5-yl)-6,7-dichloropyrido[2,3-d]pyrimidin-2(1H)-one (0.682 g, 0.900 mmol) and trifluoromethane sulfonic acid (0.400 mL, 4.50 mmol) in 2,2,2-trifluoroacetic acid (6.9 mL, 90 mmol) was stirred at RT for 1 h. The reaction mixture was concentrated, diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo to give 4-((2S,5R)-4-acryloyl-2,5-dimethylpiperazin-1-yl)-1-(4-amino-6-isopropylpyrimidin-5-yl)-6,7-dichloropyrido[2,3-d]pyrimidin-2(1H)-one (0.500 g, 0.966 mmol, >99% yield) as a light yellow solid. MS (ESI, +ve) m/z: 516.8 (M+1)$^+$.

Step 3: 4-((2S,5R)-4-Acryloyl-2,5-dimethylpiperazin-1-yl)-7-(2-amino-6-fluorophenyl)-1-(4-amino-6-isopropylpyrimidin-5-yl)-6-chloropyrido[2,3-d]pyrimidin-2(1H)-one A mixture of 4-((2S,5R)-4-acryloyl-2,5-dimethylpiperazin-1-yl)-1-(4-amino-6-isopropylpyrimidin-5-yl)-6,7-dichloropyrido[2,3-d]pyrimidin-2(1H)-one (0.055 g, 0.11 mmol), (2-amino-6-fluorophenyl)boronic acid pinacol ester (0.038 mL, 0.16 mmol, CombiPhos Catalysts, Inc., Trenton, N.J.), PdCl$_2$(dppf) (8 mg, 11 μmol), and potassium acetate (0.031 g, 0.32 mmol) in 1,4-dioxane (1 mL)/water (0.1 mL) was sparged with nitrogen then stirred at 100° C. for 1.5 h. The reaction mixture was diluted with EtOAc (100 mL), added to a separatory funnel, and washed with saturated, aqueous sodium bicarbonate (2×75 mL), the organic layer was separated, dried over anhydrous Na$_2$SO$_4$, and concentrated in vacuo. The crude product was adsorbed onto silica and was purified via automated flash chromatography (silica gel, 0-10% [2 M ammonia in MeOH]/DCM then 0-100% [(3:1) EtOAc/EtOH]/heptane) to give 4-((2S,5R)-4-acryloyl-2,5-dimethylpiperazin-1-yl)-7-(2-amino-6-fluorophenyl)-1-(4-amino-6-isopropylpyrimidin-5-yl)-6-chloropyrido[2,3-d]pyrimidin-2(1H)-one (3 mg, 5.1 μmol, 5% yield) as a yellow film. $^1$H NMR (400 MHz, CDCl$_3$) δ 8.54-8.61 (m, 1H) 8.13-8.22 (m, 1H) 7.11-7.19 (m, 1H) 6.35-6.72 (m, 4H) 5.77-5.86 (m, 1H) 4.80-5.23 (m, 2H) 4.67-4.79 (m, 2H) 4.17-4.57 (m, 3H) 3.78-4.07 (m, 1H) 3.74 (s, 1H) 2.50-2.79 (m, 1H) 1.38-1.53 (m, 6H) 1.20 (d, J=6.6 Hz, 3H) 0.97-1.06 (m, 3H). $^{19}$F NMR (377 MHz, CDCl$_3$) δ −111.95 (br d, J=23.4 Hz, 1F). MS (ESI, +ve) m/z: 591.8 (M+1)$^+$.

Example 193

4-((2S,5R)-4-Acryloyl-2,5-dimethylpiperazin-1-yl)-6-chloro-7-(2-fluorophenyl)-1-(4-isopropyl-2,6-dimethylpyrimidin-5-yl)pyrido[2,3-d]pyrimidin-2(1H)-one, Single Isomer

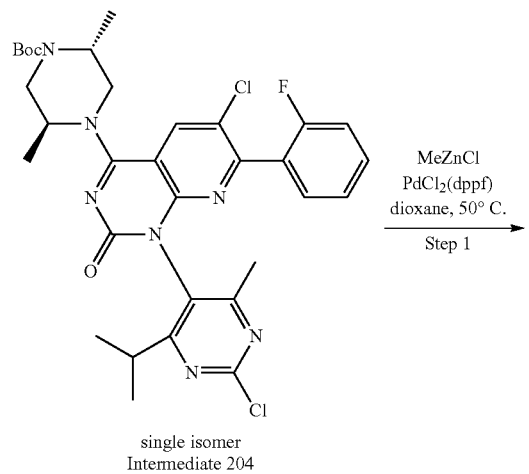

single isomer
Intermediate 204

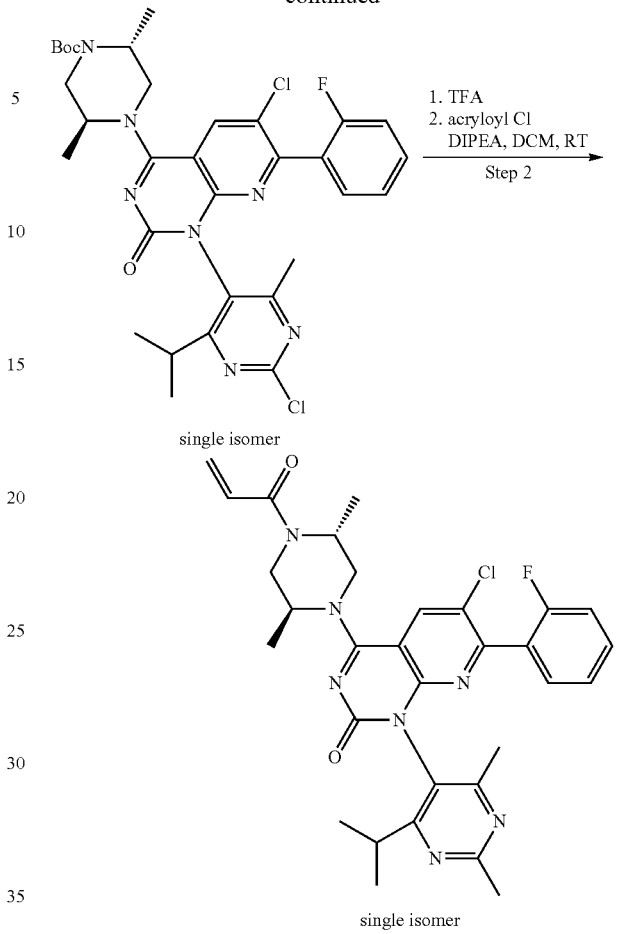

Step 1: tert-Butyl (2R,5S)-4-(6-chloro-7-(2-fluorophenyl)-1-(4-isopropyl-2,6-dimethylpyrimidin-5-yl)-2-oxo-1,2-dihydropyrido[2,3-d]pyrimidin-4-yl)-2,5-dimethylpiperazine-1-carboxylate A mixture of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.103 g, 0.157 mmol, Intermediate 204), methylzinc chloride (2 M in THF, 0.094 mL, 0.188 mmol; Sigma-Aldrich, St. Louis, Mo.), and [1,1'-bis(diphenylphosphino)ferrocene]palladium(II) chloride (6 mg, 8 μmol) in 1,4-dioxane (0.8 mL) was sparged with nitrogen then stirred at 50° C. for 16 h. The reaction mixture was diluted with EtOAc (100 mL), added to a separatory funnel, and washed with saturated, aqueous ammonium chloride (2×75 mL); the organic layer was separated, dried over anhydrous Na$_2$SO$_4$, and concentrated in vacuo. The crude product was adsorbed onto silica and was purified via automated flash chromatography (silica gel, 0-50% [(3:1) EtOAc/EtOH]/heptane) to give tert-butyl (2R,5S)-4-(6-chloro-7-(2-fluorophenyl)-1-(4-isopropyl-2,6-dimethylpyrimidin-5-yl)-2-oxo-1,2-dihydropyrido[2,3-d]pyrimidin-4-yl)-2,5-dimethylpiperazine-1-carboxylate (41 mg, 0.064 mmol, 41% yield). $^1$H NMR (400 MHz, CDCl$_3$) δ 8.11 (s, 1H) 7.39-7.47 (m, 1H) 7.15-7.23 (m, 2H) 7.09-7.14 (m, 1H) 3.41-5.10 (m, 6H) 2.70 (s, 3H) 2.18 (s, 3H) 1.51 (s, 9H) 1.45 (br s, 3H) 1.29 (d, J=6.8 Hz, 3H) 1.21 (d, J=6.8 Hz, 3H) 1.05 (d, J=6.8 Hz, 3H). $^{19}$F NMR (377 MHz, CDCl$_3$) δ −112.70 (br s, 1F). MS (ESI, +ve) m/z: 636.2 (M+1)$^+$.

Step 2: 4-((2S,5R)-4-Acryloyl-2,5-dimethylpiperazin-1-yl)-6-chloro-7-(2-fluorophenyl)-1-(4-isopropyl-2,6-dimethylpyrimidin-5-yl)pyrido[2,3-d]pyrimidin-2(1H)-one A solution of tert-butyl (2R,5S)-4-(6-chloro-7-(2-fluorophenyl)-1-(4-isopropyl-2,6-dimethylpyrimidin-5-yl)-2-oxo-1,2-dihydropyrido[2,3-d]pyrimidin-4-yl)-2,5-dimethylpiperazine-1-carboxylate (0.041 g, 0.064 mmol) in 2,2,2-trifluoroacetic acid (0.49 mL, 6.4 mmol) was stirred at RT for 10 min. The reaction mixture was concentrated.

A solution of the resulting oil, acryloyl chloride (0.5 M in DCM, 0.14 mL, 0.071 mmol), and DIPEA (0.034 mL, 0.19 mmol) in dichloromethane (0.3 mL) was stirred at RT for 15 min. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$. and concentrated in vacuo. The crude product was adsorbed onto silica and was purified via automated flash chromatography (silica gel, 0-80% [(3:1) EtOAc/EtOH]/heptane) to give 4-((2S,5R)-4-acryloyl-2,5-dimethylpiperazin-1-yl)-6-chloro-7-(2-fluorophenyl)-1-(4-isopropyl-2,6-dimethylpyrimidin-5-yl)pyrido[2,3-d]pyrimidin-2(1H)-one (50 mg, 0.085 mmol, >99% yield) as an off-white solid. $^1$H NMR (400 MHz, CDCl$_3$) δ 8.11 (s, 1H) 7.40-7.48 (m, 1H) 7.15-7.23 (m, 2H) 7.12 (t, J=9.1 Hz, 1H) 6.51-6.70 (m, 1H) 6.33-6.45 (m, 1H) 5.76-5.84 (m, 1H) 3.44-5.19 (m, 6H) 2.70 (s, 3H) 2.61-2.69 (m, 1H) 2.19 (s, 3H) 1.30-1.51 (m, 6H) 1.27 (d, J=6.8 Hz, 3H) 1.05 (d, J=6.6 Hz, 3H). $^{19}$F NMR (377 MHz, CDCl$_3$) δ 112.73−−112.64 (m, 1F). MS (ESI, +ve) m/z: 590.2 (M+1)$^+$.

Example 194

4-((2S,5R)-4-Acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one

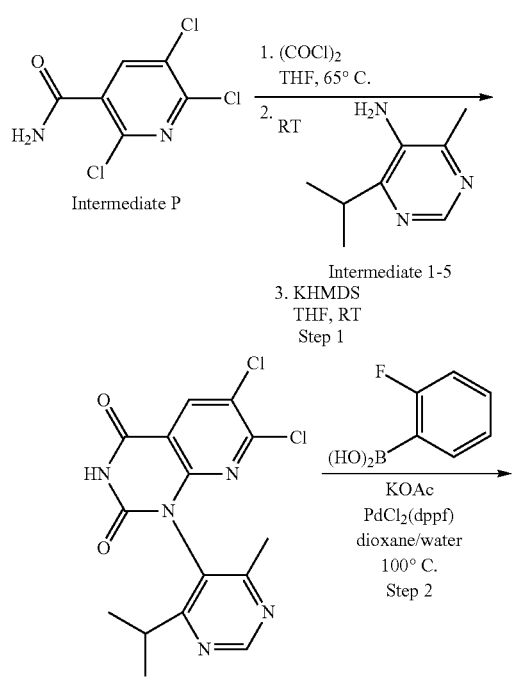

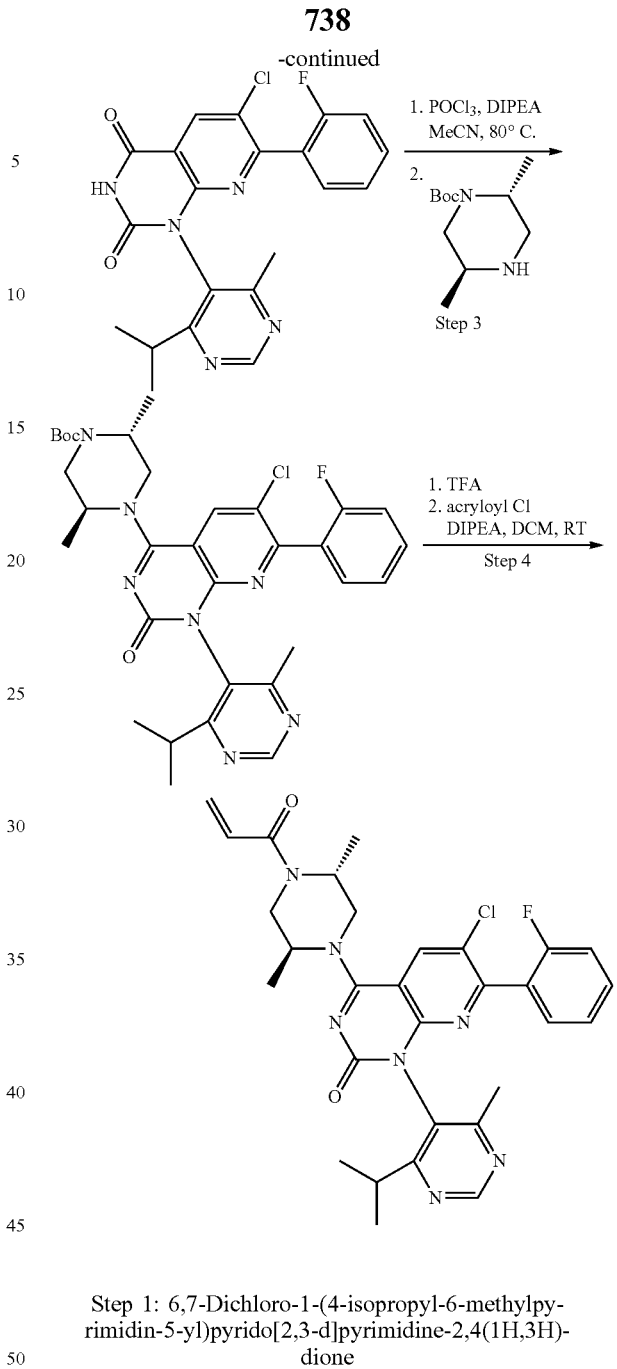

Step 1: 6,7-Dichloro-1-(4-isopropyl-6-methylpyrimidin-5-yl)pyrido[2,3-d]pyrimidine-2,4(1H,3H)-dione To a solution of 2,5,6-trichloronicotinamide (2.43 g, 10.8 mmol; Intermediate P) in THF (20 mL) was added oxalyl chloride (5.38 mL, 10.8 mmol), and the resulting mixture was stirred at 65° C. under a reflux condenser and drying tube for 2 h.

The reaction mixture was concentrated, dissolved in THF (20 mL), and cooled to 0° C.; a solution of 4-isopropyl-6-methylpyrimidin-5-amine (1.48 g, 9.79 mmol; Intermediate 1-5) in THF (10 mL) was added, and the resulting mixture was stirred at 0° C. for 1 h. The reaction was diluted with EtOAc, quenched with brine and saturated aqueous NH$_4$Cl, extracted with EtOAc, and concentrated in vacuo. The crude product was purified via automated flash chromatography (silica gel, 0-5% MeOH/DCM) to give 2,5,6-trichloro-N-((4-isopropyl-6-methylpyrimidin-5-yl)carbamoyl)nicotinamide (3.24 g, 8.05 mmol, 82% yield) as a brown solid.

To a solution of 2,5,6-trichloro-N-((4-isopropyl-6-methylpyrimidin-5-yl)carbamoyl)nicotinamide (3.24 g, 7.95 mmol) in THF (40 mL) in a water-bath was added dropwise potassium bis(trimethylsilyl)amide (1 M in THF, 14.3 mL, 14.3 mmol). The mixture was stirred for 10 min; the water bath was removed, and the reaction mixture was stirred at RT for 30 min. The reaction mixture was quenched with saturated aqueous NH$_4$Cl and was extracted with EtOAc. The combined organics were dried over Na$_2$SO$_4$, filtered, and concentrated in vacuo. The product was azeotropically dried to give 6,7-dichloro-1-(4-isopropyl-6-methylpyrimidin-5-yl)pyrido[2,3-d]pyrimidine-2,4(1H,3H)-dione. $^1$H NMR (DMSO-d$_6$) δ 12.20-12.47 (m, 1H), 8.90-9.18 (m, 1H), 8.46-8.67 (m, 1H), 2.82-3.09 (m, 1H), 2.19-2.28 (m, 3H), 1.06-1.10 (m, 3H), 0.98-1.04 (m, 3H). MS (ESI, +ve) m/z: 366.0 (M+1)$^+$.

Step 2: 6-Chloro-7-(2-fluorophenyl)-1-(4-isopropyl-6-methylpyrimidin-5-yl)pyrido[2,3-d]pyrimidine-2,4(1H,3H)-dione A mixture of 6,7-dichloro-1-(4-isopropyl-6-methylpyrimidin-5-yl)pyrido[2,3-d]pyrimidine-2,4(1H,3H)-dione (0.350 g, 0.956 mmol), (2-fluorophenyl)boronic acid (0.201 g, 1.43 mmol; Combi-Blocks, Inc., San Diego, Calif.), PdCl$_2$(dppf) (0.070 g, 0.096 mmol), and potassium acetate (0.281 g, 2.87 mmol) in 1,4-dioxane (8.7 mL)/water (0.87 mL) was sparged with nitrogen then stirred at 100° C. for 16 h. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-80% EtOAc/heptane) to give 6-chloro-7-(2-fluorophenyl)-1-(4-isopropyl-6-methylpyrimidin-5-yl)pyrido[2,3-d]pyrimidine-2,4(1H,3H)-dione (200 mg, 0.470 mmol, 49% yield) as an amber oil. MS (ESI, +ve) m/z: 425.9 (M+1)$^+$.

Step 3: tert-Butyl (2R,5S)-4-(6-chloro-7-(2-fluorophenyl)-1-(4-isopropyl-6-methylpyrimidin-5-yl)-2-oxo-1,2-dihydropyrido[2,3-d]pyrimidin-4-yl)-2,5-dimethylpiperazine-1-carboxylate A solution of 6-chloro-7-(2-fluorophenyl)-1-(4-isopropyl-6-methylpyrimidin-5-yl)pyrido[2,3-d]pyrimidine-2,4(1H,3H)-dione (0.200 g, 0.470 mmol), phosphoryl trichloride (0.053 mL, 0.56 mmol), and DIPEA (0.491 mL, 2.82 mmol) in acetonitrile (1.2 mL) was stirred at 80° C. for 30 min. The reaction mixture was removed from the heating block, and a solution of tert-butyl (2R,5S)-2,5-dimethylpiperazine-1-carboxylate (0.151 g, 0.704 mmol; eNovation Chemicals LLC, Bridgewater, N.J.) in acetonitrile (1.2 mL) was added; the reaction mixture was stirred at RT for 1 h. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was loaded onto the column and was purified via automated flash chromatography (silica gel, 0-70% [(3:1) EtOAc/EtOH]/heptane) to give tert-butyl (2R,5S)-4-(6-chloro-7-(2-fluorophenyl)-1-(4-isopropyl-6-methylpyrimidin-5-yl)-2-oxo-1,2-dihydropyrido[2,3-d]pyrimidin-4-yl)-2,5-dimethylpiperazine-1-carboxylate (112 mg, 0.180 mmol, 38% yield) as an amber oil. $^1$H NMR (400 MHz, CDCl$_3$) δ 9.03 (s, 1H) 8.12 (s, 1H) 7.39-7.47 (m, 1H) 7.14-7.20 (m, 2H) 7.07-7.14 (m, 1H) 4.81-5.05 (m, 1H) 4.31-4.81 (m, 1H) 3.78-4.23 (m, 3H) 3.44-3.66 (m, 1H) 2.68-2.80 (m, 1H) 2.25 (d, J=5.8 Hz, 3H) 1.52 (s, 9H) 1.29 (d, J=6.8 Hz, 3H) 1.21-1.28 (m, 6H) 1.06 (dd, J=11.8, 6.6 Hz, 3H). $^{19}$F NMR (376 MHz, CDCl$_3$) δ −112.68 (br d, J=5.2 Hz, 1F). MS (ESI, +ve) m/z: 621.8 (M+1)$^+$.

Step 4: 4-((2S,5R)-4-Acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one A solution of tert-butyl (2R,5S)-4-(6-chloro-7-(2-fluorophenyl)-1-(4-isopropyl-6-methylpyrimidin-5-yl)-2-oxo-1,2-dihydropyrido[2,3-d]pyrimidin-4-yl)-2,5-dimethylpiperazine-1-carboxylate (0.112 g, 0.180 mmol) in 2,2,2-trifluoroacetic acid (1.38 mL, 18.0 mmol) was stirred at RT for 30 min. The reaction mixture was concentrated in vacuo.

A solution of the resulting oil, acryloyl chloride (0.5 M in DCM, 0.360 mL, 0.180 mmol), and DIPEA (0.125 mL, 0.720 mmol) in dichloromethane (0.9 mL) was stirred at RT for 1 h. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-100% [(3:1) EtOAc/EtOH]/heptane) to give 4-((2S,5R)-4-acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one (97 mg, 0.17 mmol, 94% yield) as a yellow solid. $^1$H NMR (400 MHz, CDCl$_3$) δ 9.03 (s, 1H) 8.13 (s, 1H) 7.39-7.48 (m, 1H) 7.07-7.21 (m, 3H) 6.50-6.71 (m, 1H) 6.41 (br t, J=14.8 Hz, 1H) 5.76-5.86 (m, 1H) 4.33-5.22 (m, 3H) 3.45-4.08 (m, 3H) 2.65-2.81 (m, 1H) 2.21-2.28 (m, 3H) 1.31-1.48 (m, 6H) 1.23 (dd, J=6.8, 3.5 Hz, 3H) 1.02-1.09 (m, 3H). $^{19}$F NMR (376 MHz, CDCl$_3$) δ −112.71--112.60 (m, 1F). MS (ESI, +ve) m/z: 575.8 (M+1)$^+$.

Example 194-1

4-((2S,5R)-4-Acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one, Single Isomer

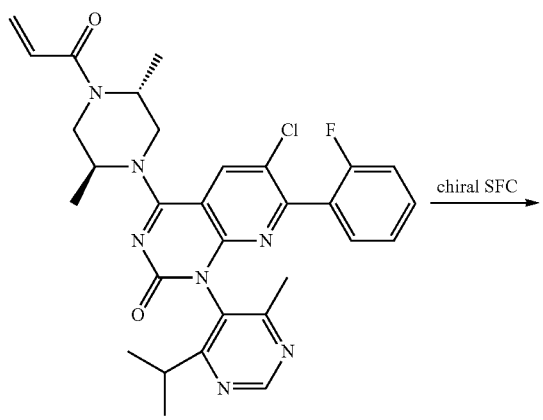

chiral SFC

741

-continued

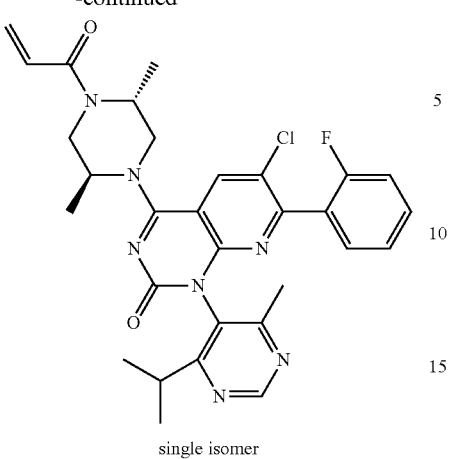

single isomer

742

-continued

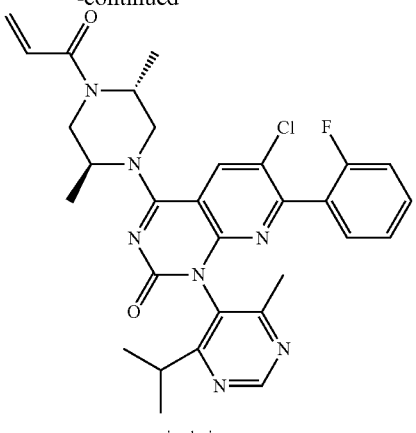

single isomer

Atropisomers of 4-((2S,5R)-4-acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one (97 mg, 0.168 mmol) were separated by chiral SFC: Chirakpak IC, ID 250×2 mm, 5 μm, 45% methanol/CO$_2$, 70 mL/min, 220 nm, 185 bar. This gave 4-((2S,5R)-4-acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one (31 mg, 0.054 mmol, 32% yield, first eluting isomer) as a light yellow solid. $^1$H NMR (400 MHz, CDCl$_3$) δ 9.03 (s, 1H) 8.13 (s, 1H) 7.40-7.48 (m, 1H) 7.15-7.21 (m, 2H) 7.07-7.15 (m, 1H) 6.52-6.71 (m, 1H) 6.34-6.46 (m, 1H) 5.76-5.86 (m, 1H) 5.02-5.20 (m, 1H) 4.31-4.53 (m, 1H) 4.00-4.13 (m, 1H) 3.45-4.00 (m, 3H) 2.66-2.80 (m, 1H) 2.21-2.27 (m, 3H) 1.31-1.52 (m, 6H) 1.24 (d, J=6.6 Hz, 3H) 1.07 (d, J=6.6 Hz, 3H), $^{19}$F NMR (377 MHz, CDCl$_3$) δ −112.71−−112.58 (m, 1F). MS (ESI, +ve) m/z: 575.9 (M+1)$^+$.

Example 194-2

4-((2S,5R)-4-Acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one, Single Isomer Atropisomers of 4-((2S,5R)-4-acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one (97 mg, 0.168 mmol) were separated by chiral SFC: Chirakpak IC, ID 250×2 mm, 5 μm, 45% methanol/CO$_2$, 70 mL/min, 220 nm, 185 bar. This gave 4-((2S,5R)-4-acryloyl-2,5-dimethylpiperazin-1-yl)-6-chloro-7-(2-fluorophenyl)-1-(4-isopropyl-6-methylpyrimidin-5-yl)pyrido[2,3-d]pyrimidin-2(1H)-one (10 mg, 0.017 mmol, 10% yield; second eluting isomer) as a light yellow solid. $^1$H NMR (400 MHz, CDCl$_3$) δ 9.11 (s, 1H) 8.19 (s, 1H) 7.45-7.54 (m, 1H) 7.22-7.28 (m, 2H) 7.14-7.22 (m, 1H) 6.57-6.80 (m, 1H) 6.40-6.54 (m, 1H) 5.80-5.93 (m, 1H) 5.11-5.29 (m, 1H) 4.40-4.62 (m, 1H) 3.50-4.20 (m, 4H) 2.75-2.87 (m, 1H) 2.26-2.36 (m, 3H) 1.38-1.60 (m, 7H) 1.30 (d, J=6.8 Hz, 3H) 1.12 (d, J=6.6 Hz, 3H). $^{19}$F NMR (376 MHz, CDCl$_3$) δ −112.70−−112.61 (m, 1F). MS (ESI, +ve) m/z: 575.9 (M+1)$^+$.

Example 195

4-((2S,5R)-4-Acryloyl-2,5-dimethylpiperazin-1-yl)-7-(2-fluorophenyl)-1-(4-isopropyl-2,6-dimethylpyrimidin-5-yl)-6-methylpyrido[2,3-d]pyrimidin-2(1H)-one, Single Isomer

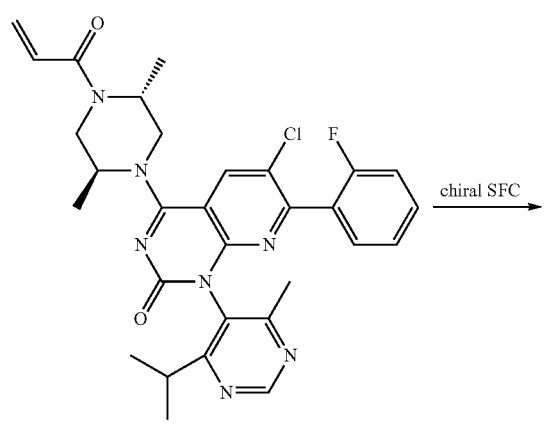

chiral SFC →

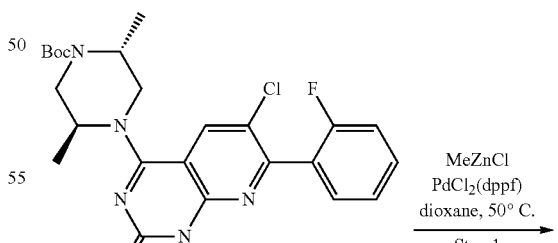

single isomer
Intermediate 204

MeZnCl
PdCl$_2$(dppf)
dioxane, 50° C.

Step 1

743

-continued

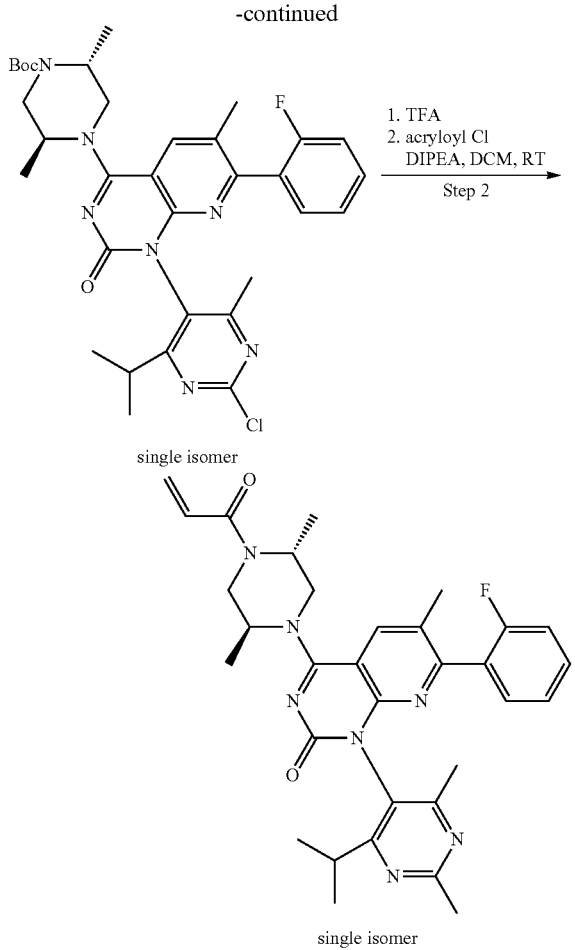

single isomer single isomer

Step 1: tert-Butyl (2R,5S)-4-(7-(2-fluorophenyl)-1-(4-isopropyl-2,6-dimethylpyrimidin-5-yl)-6-methyl-2-oxo-1,2-dihydropyrido[2,3-d]pyrimidin-4-yl)-2,5-dimethylpiperazine-1-carboxylate A mixture of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.103 g, 0.157 mmol; Intermediate 204), methylzinc chloride (2 M in THF, 0.094 mL, 0.188 mmol; Sigma-Aldrich, St. Louis, Mo.), and [1,1'-bis(diphenylphosphino)ferrocene]palladium(II) chloride (6 mg, 8 µmol) in 1,4-dioxane (0.8 mL) was sparged with nitrogen then stirred at 50° C. for 16 h. The reaction mixture was diluted with EtOAc (100 mL), added to a separatory funnel, and washed with saturated, aqueous ammonium chloride (2×75 mL); the organic layer was separated, dried over anhydrous $Na_2SO_4$, and concentrated in vacuo. The crude product was adsorbed onto silica and was purified via automated flash chromatography (silica gel, 0-50% [(3:1) EtOAc/EtOH]/heptane) to give tert-butyl (2R, 5S)-4-(7-(2-fluorophenyl)-1-(4-isopropyl-2,6-dimethylpyrimidin-5-yl)-6-methyl-2-oxo-1,2-dihydropyrido[2,3-d]pyrimidin-4-yl)-2,5-dimethylpiperazine-1-carboxylate (30 mg, 0.049 mmol, 31% yield). $^1$H NMR (400 MHz, $CDCl_3$) δ 7.92 (s, 1H) 7.36-7.44 (m, 1H) 7.06-7.21 (m, 3H) 3.47-5.05 (m, 6H) 2.75 (s, 3H) 2.28 (d, J=1.5 Hz, 3H) 2.24 (s, 3H) 1.51 (s, 9H) 1.44 (br s, 3H) 1.28 (d, J=6.8 Hz, 3H) 1.22 (d, J=6.8

744

Hz, 3H) 1.05 (d, J=6.8 Hz, 3H). $^{19}$F NMR (377 MHz, $CDCl_3$) δ −114.75 (br s, 1F). MS (ESI, +ve) m/z: 616.3 $(M+1)^+$.

Step 2: 4-((2S,5R)-4-Acryloyl-2,5-dimethylpiperazin-1-yl)-7-(2-fluorophenyl)-1-(4-isopropyl-2,6-dimethylpyrimidin-5-yl)-6-methylpyrido[2,3-d]pyrimidin-2(1H)-one A solution of tert-butyl (2R,5S)-4-(7-(2-fluorophenyl)-1-(4-isopropyl-2,6-dimethylpyrimidin-5-yl)-6-methyl-2-oxo-1,2-dihydropyrido[2,3-d]pyrimidin-4-yl)-2,5-dimethylpiperazine-1-carboxylate (0.030 g, 0.049 mmol) in 2,2,2-trifluoroacetic acid (0.37 mL, 4.9 mmol) was stirred at RT for 10 min. The reaction mixture was concentrated.

A solution of the resulting oil, acryloyl chloride (0.5 M in DCM, 0.11 mL, 0.054 mmol), and DIPEA (0.025 mL, 0.15 mmol) in dichloromethane (0.24 mL) was stirred at RT for 15 min. The reaction mixture was diluted with EtOAc (100 mL), added to a separatory funnel, and washed with saturated, aqueous sodium bicarbonate ($2^y$ 75 mL); the organic layer was separated, dried over anhydrous $Na_2SO_4$, and concentrated in vacuo. The crude product was adsorbed onto silica and was purified via automated flash chromatography (silica gel, 0-80% [(3:1) EtOAc/EtOH]/heptane) to give 4-((2S,5R)-4-acryloyl-2,5-dimethylpiperazin-1-yl)-7-(2-fluorophenyl)-1-(4-isopropyl-2,6-dimethylpyrimidin-5-yl)-6-methylpyrido[2,3-d]pyrimidin-2(1H)-one (10 mg, 0.018 mmol, 36% yield) as an off-white solid. $^1$H NMR (400 MHz, $CDCl_3$) δ 7.86-7.94 (m, 1H) 7.36-7.44 (m, 1H) 7.07-7.21 (m, 3H) 6.51-6.72 (m, 1H) 6.33-6.47 (m, 1H) 5.74-5.84 (m, 1H) 3.46-5.24 (m, 6H) 2.70 (s, 3H) 2.64-2.69 (m, 1H) 2.29 (br s, 3H) 2.14-2.22 (m, 3H) 1.27-1.48 (m, 6H) 1.21 (d, J=6.8 Hz, 3H) 1.04 (br d, =6.6 Hz, 3H). $^{19}$F NMR (377 MHz, $CDCl_3$) δ 114.83−−114.51 (m, 1F). MS (ESI, +ve) m/z: 570.2 $(M+1)^+$.

Example 196

4-((2S,5R)-4-Acryloyl-2,5-dimethylpiperazin-1-yl)-6-chloro-1-(2-(dimethylamino)-4-isopropyl-6-methylpyrimidin-5-yl)-7-(2-fluorophenyl)pyrido[2,3-d]pyrimidin-2(1H)-one, Single Isomer

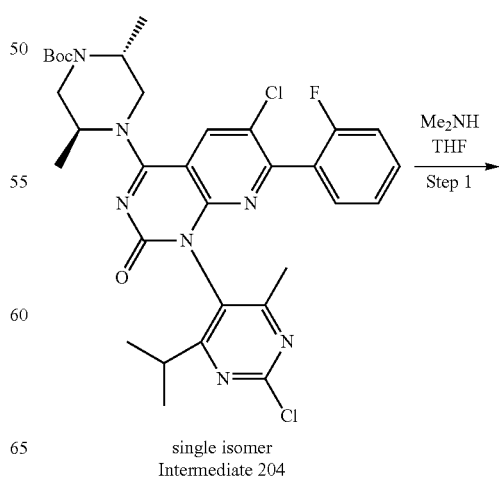

single isomer
Intermediate 204

-continued

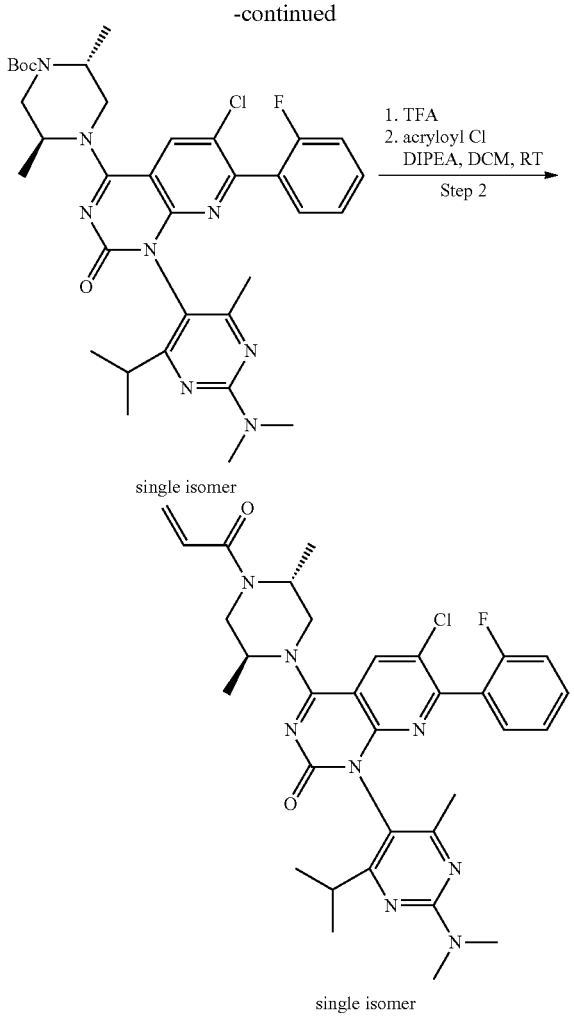

Step 1: tert-Butyl (2R,5)-4-(6-chloro-1-(2-(dimethylamino)-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate A solution of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.103 g, 0.157 mmol; Intermediate 204) and dimethylamine (2 M in THF, 1.18 mL, 2.35 mmol; Sigma-Aldrich, St. Louis, Mo.) was stirred at 50° C. for 4 h. The reaction mixture was diluted with EtOAc (100 mL), added to a separatory funnel, and washed with saturated, aqueous ammonium chloride (2×75 mL); the organic layer was separated, dried over anhydrous Na$_2$SO$_4$, and concentrated in vacuo. The crude product was adsorbed onto silica and was purified via automated flash chromatography (silica gel, 0-50% [(3:1) EtOAc/EtOH]/heptane) to give tert-butyl (2R,5S)-4-(6-chloro-1-(2-(dimethylamino)-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (101 mg, 0.152 mmol, 97% yield) as a yellow oil. $^1$H NMR (400 MHz, CDCl$_3$) δ 8.06 (s, 1H) 7.39-7.47 (m, 1H) 7.15-7.25 (m, 2H) 7.12 (t, J=9.1 Hz, 1H) 3.46-5.03 (m, 6H) 2.46-2.57 (m, 1H) 2.03 (s, 3H) 1.51 (s, 9H) 1.43 (br s, 3H) 1.23-1.33 (m, 9H) 1.17 (d, J 6.6 Hz, 3H) 1.00 (d, J=6.6 Hz, 3H). $^{19}$F NMR (377 MHz, CDCl$_3$) δ −112.86 (br s, 1F). MS (ESI, +ve) m/z: 665.2 (M+1)$^+$.

Step 2: 4-((2S,5R)-4-Acryloyl-2,5-dimethylpiperazin-1-yl)-6-chloro-1-(2-(dimethylamino)-4-isopropyl-6-methylpyrimidin-5-yl)-7-(2-fluorophenyl)pyrido[2,3-d]pyrimidin-2(1H)-one A solution of tert-butyl (2R,5S)-4-(6-chloro-1-(2-(dimethylamino)-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.101 g, 0.152 mmol) in 2,2,2-trifluoroacetic acid (1.16 mL, 15.2 mmol) was stirred at RT for 10 min. The reaction mixture was concentrated.

A solution of the resulting oil, acryloyl chloride (0.5 M in DCM, 0.33 mL, 0.17 mmol), and DIPEA (0.079 mL, 0.46 mmol) in dichloromethane (0.8 mL) was stirred at RT for 15 min. The reaction mixture was diluted with EtOAc (100 mL), added to a separatory funnel, and washed with saturated, aqueous sodium bicarbonate (2×75 mL); the organic layer was separated. dried over anhydrous Na$_2$SO$_4$, and concentrated in vacuo. The crude product was adsorbed onto silica and was purified via automated flash chromatography (silica gel, 0-80% [(3:1) EtOAc/EtOH]/heptane) to give 4-((2S,5R)-4-acryloyl-2,5-dimethylpiperazin-1-yl)-6-chloro-1-(2-(dimethylamino)-4-isopropyl-6-methylpyrimidin-5-yl)-7-(2-fluorophenyl)pyrido[2,3-d]pyrimidin-2(1H)-one (97 mg, 0.157 mmol, >99% yield) as a yellow solid. $^1$H NMR (400 MHz, CDCl$_3$) δ 8.07 (s, 1H) 7.40-7.48 (m, 1H) 7.16-7.26 (m, 2H) 7.12 (t, J=9.1 Hz, 1H) 6.50-6.71 (m, 1H) 6.39 (br t, J=15.2 Hz, 1H) 5.74-5.86 (m, 1H) 3.45-5.20 (m, 6H) 3.19 (s, 6H) 2.43-2.55 (m, 1H) 1.99-2.06 (m, 3H) 1.29-1.46 (m, 6H) 1.17 (d, J=6.8 Hz, 3H) 1.00 (d, J=6.6 Hz, 3H). $^{19}$F NMR (377 MHz, CDCl$_3$) δ 112.90-−112.77 (m, 1F). MS (ESI, +ve) m/z: 619.3 (M+1)$^+$.

Example 197-1

4-((2S,5R)-4-Acryloyl-2,5-dimethylpiperazin-1-yl)-1-(2-bromo-4-isopropyl-6-methylpyrimidin-5-yl)-6-chloro-7-(2-fluorophenyl)pyrido[2,3-d]pyrimidin-2(1H)-one, Single Isomer

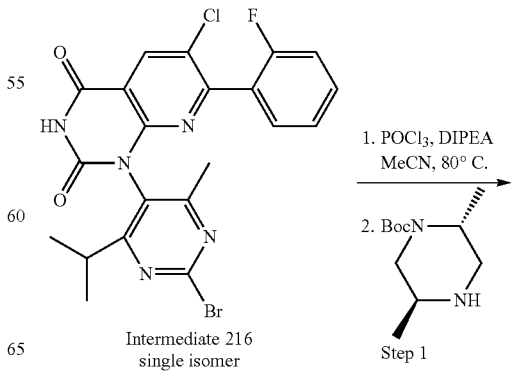

-continued

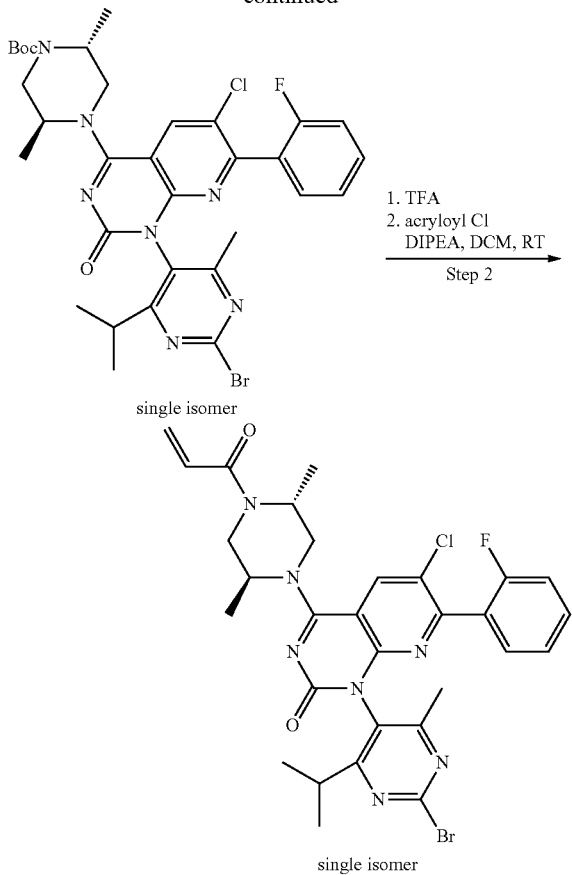

Step 1: tert-Butyl (2R,5S)-4-(1-(2-bromo-4-isopropyl-6-methylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate A solution of 1-(2-bromo-4-isopropyl-6-methylpyrimidin-5-yl)-6-chloro-7-(2-fluorophenyl)pyrido[2,3-d]pyrimidine-2,4(1H,3H)-dione (0.556 g, 1.10 mmol; Intermediate 216), phosphoryl trichloride (0.123 mL, 1.32 mmol), DIPEA (0.768 mL, 4.41 mmol) in acetonitrile (5.5 mL) was stirred at 80° C. for 30 min.

The solution was cooled in an ice bath, then tert-butyl (2R,5S)-2,5-dimethylpiperazine-1-carboxylate (0.236 g, 1.102 mmol; eNovation Chemicals LLC, Bridgewater, N.J.) was added, and the dark red solution was stirred at RT for 5 min. The reaction mixture was diluted with EtOAc (150 mL), added to a separatory funnel, and washed with saturated, aqueous sodium bicarbonate (2×100 mL); the organic layer was separated, dried over anhydrous $Na_2SO_4$, and concentrated in vacuo. The crude product was adsorbed onto silica and was purified via automated flash chromatography (silica gel, 0-80% EtOAc/heptane) to give tert-butyl (2R,5S)-4-(1-(2-bromo-4-isopropyl-6-methylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (423 mg, 0.603 mmol, 55% yield) as a light yellow solid. $^1H$ NMR (400 MHz, CDCl) δ 8.12 (s, 1H) 7.43-7.50 (m, 1H) 7.17-7.24 (m, 2H) 7.10-7.17 (m, 1H) 3.43-5.04 (m, 6H) 2.61-2.74 (m, 1H) 2.23 (s, 3H) 1.51 (s, 9H) 1.41-1.50 (m, 3H) 1.26-1.28 (m, 3H) 1.22 (d, J=6.8 Hz, 3H) 1.03 (d, J=6.6 Hz, 3H). $^{19}F$ NMR (377 MHz, CDCl$_3$) δ −112.94 (br s, 1F). MS (ESI, +ve) m/z: 702.0 (M+1)$^+$.

Step 2: 4-((2S,5R)-4-Acryloyl-2,5-dimethylpiperazin-1-yl)-1-(2-bromo-4-isopropyl-6-methylpyrimidin-5-yl)-6-chloro-7-(2-fluorophenyl)pyrido[2,3-d]pyrimidin-2(1H)-one A solution of tert-butyl (2R,5S)-4-(1-(2-bromo-4-isopropyl-6-methylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.101 g, 0.144 mmol) in 2,2,2-trifluoroacetic acid (1.10 mL, 14.4 mmol) was stirred at RT for 10 min. The reaction mixture was concentrated.

A solution of the resulting oil, acryloyl chloride (0.5 M in DCM, 0.317 mL, 0.158 mmol), and DIPEA (0.075 mL, 0.43 mmol) in dichloromethane (0.72 mL) was stirred at RT for 15 min. The reaction mixture was diluted with EtOAc (100 mL), added to a separatory funnel, and washed with saturated, aqueous sodium bicarbonate (2×75 mL); the organic layer was separated, dried over anhydrous $Na_2SO_4$, and concentrated in vacuo. The crude product was adsorbed onto silica and was purified via automated flash chromatography (silica gel, 0-80% [(3:1) EtOAc/EtOH]/heptane) to give 4-((2S,5R)-4-acryloyl-2,5-dimethylpiperazin-1-yl)-1-(2-bromo-4-isopropyl-6-methylpyrimidin-5-yl)-6-chloro-7-(2-fluorophenyl)pyrido[2,3-d]pyrimidin-2(1H)-one (72 mg, 0.11 mmol, 76% yield) as a light yellow solid. $^1H$ NMR (400 MHz, CDCl$_3$) δ 8.12 (s, 1H) 7.42-7.52 (m, 1H) 7.17-7.24 (m, 2H) 7.10-7.17 (m, 1H) 6.48-6.69 (m, 1H) 6.41 (br t, J=15.1 Hz, 1H) 5.77-5.85 (m, 1H) 3.41-5.18 (m, 6H) 2.60-2.75 (m, 1H) 2.19-2.26 (m, 3H) 1.30-1.52 (m, 6H) 1.22 (d, J=6.6 Hz, 3H) 1.04 (d, J=6.8 Hz, 3H). $^{19}F$ NMR (377 MHz, CDCl$_3$) δ 112.97−−112.88 (m, 1F). MS (ESI, +ve) m/z: 656.0 (M+1)$^+$.

Example 197-2

4-((2S,5R)-4-Acryloyl-2,5-dimethylpiperazin-1-yl)-1-(2-bromo-4-isopropyl-6-methylpyrimidin-5-yl)-6-chloro-7-(2-fluorophenyl)pyrido[2,3-d]pyrimidin-2(1H)-one, Single Isomer

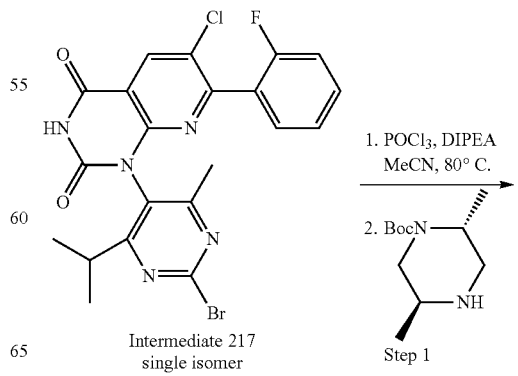

Intermediate 217
single isomer

Step 1

749

-continued

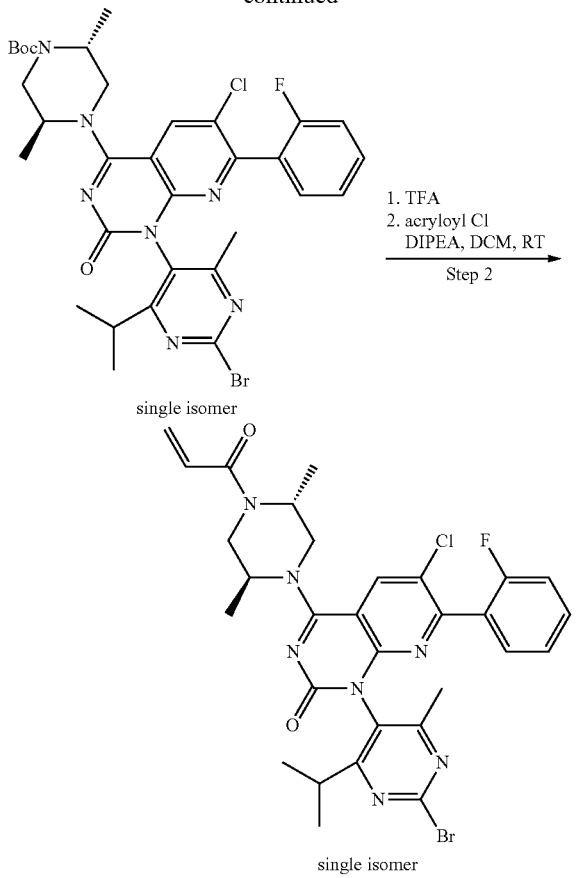

Step 1: tert-Butyl (2R,5S)-4-(1-(2-bromo-4-isopropyl-6-methylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate A solution of 1-(2-bromo-4-isopropyl-6-methylpyrimidin-5-yl)-6-chloro-7-(2-fluorophenyl)pyrido[2,3-d]pyrimidine-2,4(1H,3H)-dione (0.525 g, 1.04 mmol; Intermediate 217). phosphoryl trichloride (0.116 mL, 1.25 mmol), and DIPEA (0.725 mL, 4.16 mmol) in acetonitrile (5.2 mL) was stirred at 80° C. for 30 min.

The solution was cooled in an ice bath, then tert-butyl (2R,5S)-2,5-dimethylpiperazine-1-carboxylate (0.223 g, 1.040 mmol; eNovation Chemicals LLC, Bridgewater, N.J.) was added, and the dark red solution was stirred at RT for 5 min. The reaction mixture was diluted with EtOAc (150 mL), added to a separatory funnel, and washed with saturated, aqueous sodium bicarbonate (2×100 mL); the organic layer was separated, dried over anhydrous Na$_2$SO$_4$, and concentrated in vacuo. The crude product was adsorbed onto silica and was purified via automated flash chromatography (silica gel, 0-70% EtOAc/heptane) to give tert-butyl (2R,5S)-4-(1-(2-bromo-4-isopropyl-6-methylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (317 mg, 0.452 mmol, 44% yield). $^1$H NMR (400 MHz, CDCl$_3$) δ 8.13 (s, 1H) 7.43-7.51 (m, 1H) 7.18-7.24 (m, 2H) 7.11-7.18 (m, 1H) 3.42-5.05 (m, 6H) 2.68 (quin, J=6.8 Hz, 1H) 2.22 (s, 3H) 1.52 (s, 9H) 1.43-1.50 (m, 3H) 1.29 (d, J=6.6 Hz, 3H) 1.24 (d, J=6.6 Hz, 3H) 1.07 (d, J=6.8 Hz, 3H). $^{19}$F NMR (377 MHz, CDCl$_3$) δ −112.93 (br s, 1F). MS (ESI, +ve) m/z: 702.0 (M+1)$^+$.

750

Step 2: 4-((2S,5R)-4-Acryloyl-2,5-dimethylpiperazin-1-yl)-1-(2-bromo-4-isopropyl-6-methylpyrimidin-5-yl)-6-chloro-7-(2-fluorophenyl)pyrido[2,3-d]pyrimidin-2(1H)-one A solution of tert-butyl (2R,5S)-4-(1-(2-bromo-4-isopropyl-6-methylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.043 g, 0.061 mmol) in 2,2,2-trifluoroacetic acid (0.47 mL, 6.1 mmol) was stirred at RT for 10 min. The reaction mixture was concentrated.

A solution of the resulting oil, acryloyl chloride (0.5 M in DCM, 0.14 mL, 0.067 mmol), and DIPEA (0.032 mL, 0.18 mmol) in dichloromethane (0.31 mL) was stirred at RT for 15 min. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-80% [(3:1) EtOAc/EtOH]/heptane) to give 4-((2S,5R)-4-acryloyl-2,5-dimethylpiperazin-1-yl)-1-(2-bromo-4-isopropyl-6-methylpyrimidin-5-yl)-6-chloro-7-(2-fluorophenyl)pyrido[2,3-d]pyrimidin-2(1H)-one (30 mg, 0.046 mmol, 75% yield) as a light yellow solid. $^1$H NMR (400 MHz, CDCl$_3$) δ 8.13 (s, 1H) 7.42-7.51 (m, 1H) 7.17-7.24 (m, 2H) 7.09-7.17 (m, 1H) 6.50-6.69 (m, 1H) 6.40 (br t, J=15.3 Hz, 1H) 5.76-5.86 (m, 1H) 4.33-5.22 (m, 3H) 3.43-4.09 (m, 3H) 2.60-2.74 (m, 1H) 2.16-2.26 (m, 3H) 1.30-1.52 (m, 6H) 1.23 (d, J=6.8 Hz, 3H) 1.06 (br d, J=6.4 Hz, 3H). $^{19}$F NMR (377 MHz, CDCl$_3$) δ −112.94--112.86 (m, 1F). MS (ESI, +ve) m/z: 656.0 (M+1)$^+$.

Example 198

4-((2S,5R)-4-Acryloyl-2,5-dimethylpiperazin-1-yl)-6-chloro-1-(2-cyclopropyl-4-isopropyl-6-methylpyrimidin-5-yl)-7-(2-fluorophenyl)pyrido[2,3-d]pyrimidin-2(1H)-one, Single Isomer

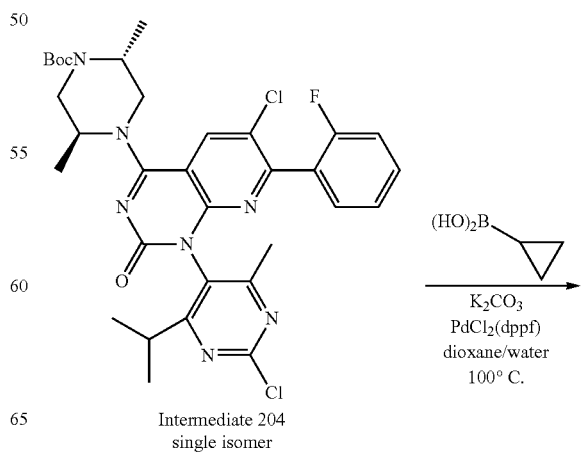

Intermediate 204
single isomer

-continued

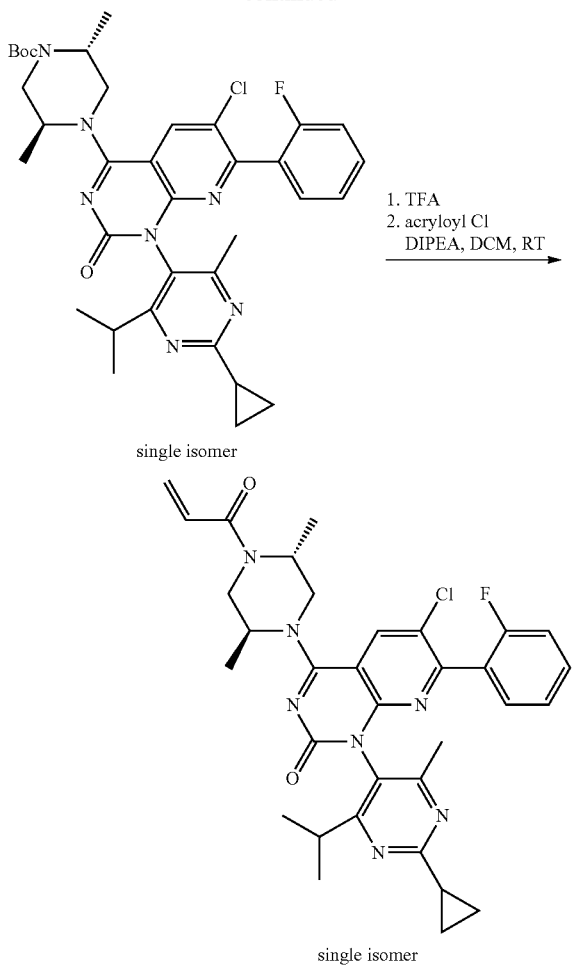

single isomer single isomer

Step 1: tert-Butyl (2R,5S)-4-(6-chloro-1-(2-cyclo-propyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate A mixture of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.102 g, 0.155 mmol; Intermediate 204), cyclopropylboronic acid (0.040 g, 0.47 mmol; Oakwood Chemical, Estill, S.C.), PdCl$_2$(dppf) (0.011 g, 0.016 mmol), and potassium carbonate 2 M aq.; 0.233 mL, 0.466 mmol) in 1,4-dioxane (0.4 mL) was stirred at 100° C. for 1 h. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-70% [(3:1) EtOAc/EtOH]/heptane) to give tert-butyl (2R,5S)-4-(6-chloro-1-(2-cyclopropyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (56 mg, 0.085 mmol, 54% yield) as an amber oil. MS (ESI, +ve) m/z: 662.2 (M+1)$^+$.

Step 2: 4-((2S,5R)-4-Acryloyl-2,5-dimethylpiperazin-1-yl)-6-chloro-1-(2-cyclopropyl-4-isopropyl-6-methylpyrimidin-5-yl)-7-(2-fluorophenyl)pyrido[2,3-d]pyrimidin-2(1H)-one A solution of tert-butyl (2R,5S)-4-(6-chloro-1-(2-cyclopropyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.058 g, 0.088 mmol) and 2,2,2-trifluoroacetic acid (0.67 mL, 8.8 mmol) in DCM (2 mL) was stirred at RT for 15 min. The reaction mixture was concentrated.

A solution of the resulting oil, acryloyl chloride (0.5 M in DCM, 0.210 mL, 0.105 mmol), and DIPEA (0.061 mL, 0.350 mmol) in dichloromethane (0.876 mL) was stirred at RT for 30 min. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 40-70% [(3:1) EtOAc/EtOH]/heptane then isocratic 60% [(3:1) EtOAc/EtOH]/heptane) to give 4-((2S,5R)-4-acryloyl-2,5-dimethylpiperazin-1-yl)-6-chloro-1-(2-cyclopropyl-4-isopropyl-6-methylpyrimidin-5-yl)-7-(2-fluorophenyl)pyrido[2,3-d]pyrimidin-2(1H)-one (40 mg, 0.065 mmol, 74% yield) as an off-white solid. $^1$H NMR (400 MHz, CDCl$_3$) δ 8.10 (s, 1H) 7.41-7.49 (m, 1H) 7.15-7.22 (m, 2H) 7.08-7.15 (m, 1H) 6.51-6.71 (m, 1H) 6.40 (br t, J=14.8 Hz, 1H) 5.74-5.85 (m, 1H) 3.44-5.20 (m, 6H) 2.54-2.67 (m, 1H) 2.17-2.25 (m, 1H) 2.16 (s, 3H) 1.30-1.48 (m, 6H) 1.12-1.20 (m, 5H) 0.98-1.05 (m, 5H). $^{19}$F NMR (377 MHz, CDCl$_3$) δ −112.77−−112.69 (m, 1F). MS (ESI, +ve) m/z: 616.1 (M+1)$^+$.

Example 199

4-((2S,5R)-4-Acryloyl-2,5-dimethylpiperazin-1-yl)-6-chloro-1-(2-ethyl-4-isopropyl-6-methylpyrimidin-5-yl)-7-(2-fluorophenyl)pyrido[2,3-d]pyrimidin-2(1H)-one, Single Isomer

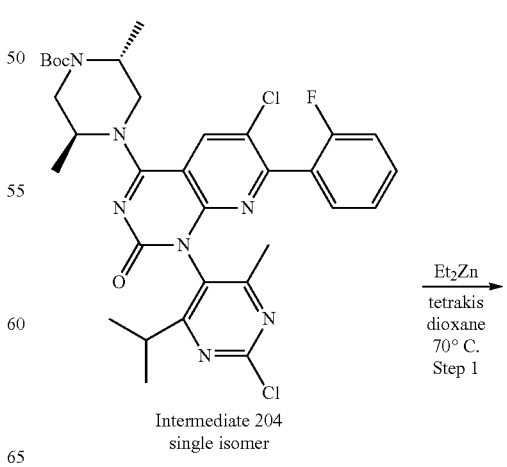

Intermediate 204
single isomer

Et$_2$Zn
tetrakis
dioxane
70° C.
Step 1

753
-continued

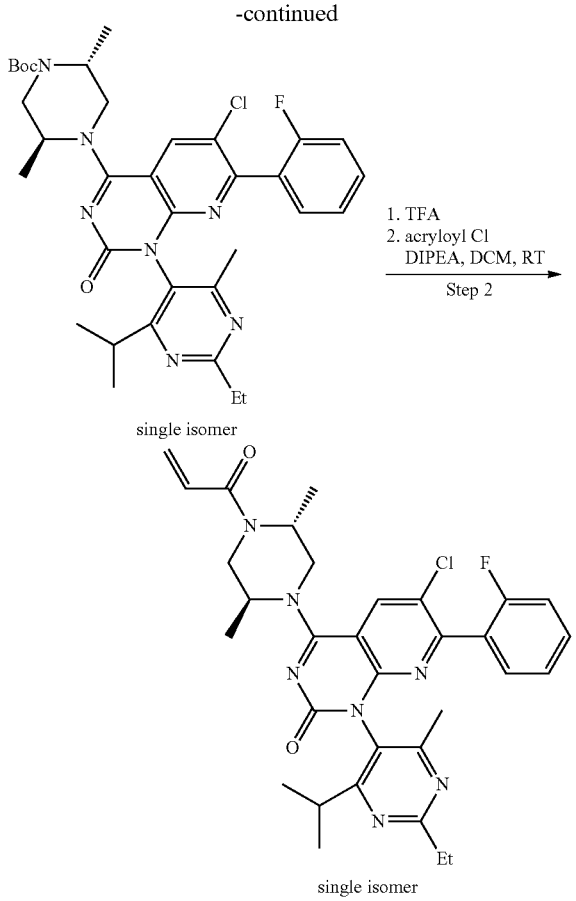

Step 1: tert-Butyl (2R,5S)-4-(6-chloro-1-(2-ethyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate A mixture of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.100 g, 0.152 mmol; Intermediate 204), diethyl zinc (1 M in hexanes. 0.305 mL, 0.305 mmol; Sigma-Aldrich, St. Louis, Mo.), and tetrakis (0.018 g, 0.015 mmol) in 1,4-dioxane (0.8 mL) was sparged with nitrogen then stirred at 70° C. for 18 h. The reaction mixture was diluted with EtOAc (100 mL), added to a separatory funnel, and washed with saturated, aqueous ammonium chloride (2×75 mL); the organic layer was separated, dried over anhydrous Na$_2$SO$_4$. and concentrated in vacuo. The crude product was adsorbed onto silica and was purified via automated flash chromatography (silica gel, 0-100% EtOAc/heptane) to give tert-butyl (2R,5S)-4-(6-chloro-1-(2-ethyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (50 mg, 0.077 mmol, 51% yield) as an amber oil. $^1$H NMR (400 MHz, CDCl$_3$) δ 8.10 (s, 1H) 7.39-7.47 (m, 1H) 7.14-7.22 (m, 2H) 7.07-7.14 (m, 1H) 3.46-5.06 (m, 6H) 2.94 (q, J=7.6 Hz, 2H) 2.60-2.74 (m, 1H) 2.19 (s, 3H) 1.51 (s, 9H) 1.36 (t, J=7.6 Hz, 3H) 1.23-1.31 (m, 6 H) 1.21 (d, J=6.6 Hz, 3H) 1.05 (d, J=6.6 Hz, 3H). $^{19}$F NMR (377 MHz, CDCl$_3$) δ −112.55 (br s, 1F). MS (ESI, +ve) m/z: 650.2 (M+1)$^+$.

Step 2: 4-((2S,5R)-4-Acryloyl-2,5-dimethylpiperazin-1-yl)-6-chloro-1-(2-ethyl-4-isopropyl-6-methylpyrimidin-5-yl)-7-(2-fluorophenyl)pyrido[2,3-d]pyrimidin-2(1H)-one A solution of tert-butyl (2R,5S)-4-(6-chloro-1-(2-ethyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.050 g, 0.077 mmol) in 2,2,2-trifluoroacetic acid (0.59 mL, 7.7 mmol) was stirred at RT for 10 min. The reaction mixture was concentrated.

A solution of the resulting oil, acryloyl chloride (0.5 in DCM, 0.17 mL, 0.085 mmol), and DIPEA (0.040 mL, 0.23 mmol) in dichloromethane (0.4 mL) was stirred at RT for 15 min. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-90% [(3:1) EtOAc/EtOH]/heptane) to give 4-((2S,5R)-4-acryloyl-2,5-dimethylpiperazin-1-yl)-6-chloro-1-(2-ethyl-4-isopropyl-6-methylpyrimidin-5-yl)-7-(2-fluorophenyl)pyrido[2,3-d]pyrimidin-2(1H)-one (51 mg, 0.084 mmol, >99% yield) as an off-white solid. $^1$H NMR (400 MHz, CDCl$_3$) δ 8.11 (s, 1H) 7.38-7.49 (m, 1H) 7.15-7.23 (m, 2H) 7.07-7.15 (m, 1H) 6.50-6.71 (m, 1H) 6.40 (br t, J=14.9 Hz, 1H) 5.75-5.86 (m, 1H) 3.44-5.23 (m, 6H) 2.95 (q. J=7.7 Hz, 2H) 2.60-2.72 (m, 1H) 2.20 (s, 3H) 1.37 (t, J=7.7 Hz, 3H) 1.30-1.50 (m, 6H) 1.22 (d, J=6.8 Hz, 3H) 1.05 (d, J=6.6 Hz, 3H). $^{19}$F NMR (377 MHz, CDCl$_3$) δ 112.57−−112.48 (m, 1F). MS (ESI, +ve) m/z: 604.3 (M+1)$^+$.

Example 200

4-((2S,5R)-4-Acryloyl-2,5-dimethylpiperazin-1-yl)-6-chloro-1-(2-fluoro-4isopropyl-6-methylpyrimidin-5-yl)-7-(2-fluorophenyl)pyrido[2,3-d]pyrimidin-2(1H)-one, Single Isomer

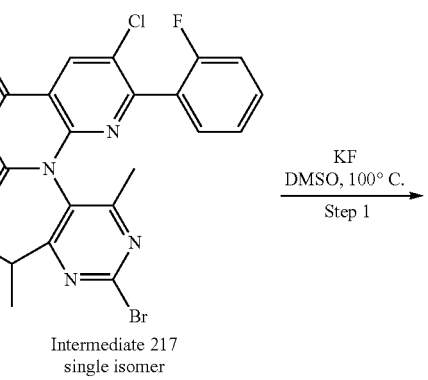

Intermediate 217
single isomer

KF
DMSO, 100° C.
Step 1

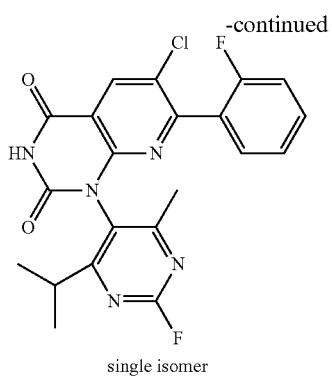

1. POCl₃, DIPEA
   MeCN, 80° C.
2. 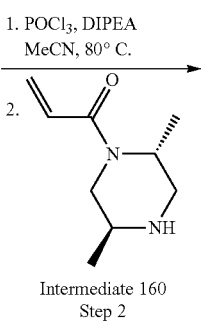

Intermediate 160
Step 2

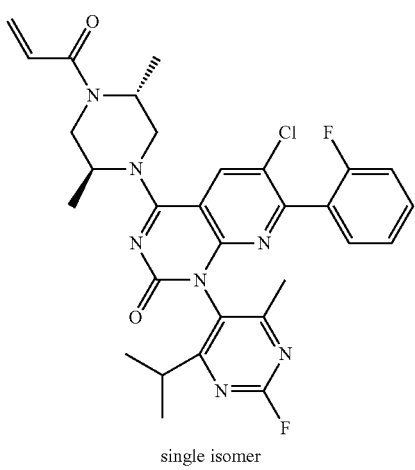

single isomer

Step 1: 6-Chloro-1-(2-fluoro-4-isopropyl-6-methylpyrimidin-5-yl)-7-(2-fluorophenyl)pyrido[2,3-d]pyrimidine-2,4(1H,3H)-dione A solution of 1-(2-bromo-4-isopropyl-6-methylpyrimidin-5-yl)-6-chloro-7-(2-fluorophenyl)pyrido[2,3-d]pyrimidine-2,4(1H,3H)-dione (0.080 g, 0.16 mmol; Intermediate 217) and potassium fluoride, anhydrous (0.046 g, 0.79 mmol) in dimethyl sulfoxide (0.8 mL) was stirred in the microwave at 170° C. for 2 h. The reaction mixture was diluted with EtOAc (100 mL), added to a separatory funnel, and washed with saturated, aqueous sodium bicarbonate (2×75 mL); the organic layer was separated, dried over anhydrous Na₂SO₄, and concentrated in vacuo. The crude product was adsorbed onto silica and was purified via automated flash chromatography (silica gel, 0-60% EtOAc/heptane) to give 6-chloro-1-(2-fluoro-4-isopropyl-6-methylpyrimidin-5-yl)-7-(2-fluorophenyl)pyrido[2,3-d]pyrimidine-2,4(1H,3H)-dione (125 mg, 0.282 mmol) as a white solid. ¹H NMR (400 MHz, CDCl₃) δ 8.73 (br s, 1H) 8.62 (s, 1H) 7.42-7.50 (m, 1H) 7.09-7.24 (m, 3H) 2.73-2.86 (m, 1H) 2.31 (s, 3H) 1.24 (d, J=6.8 Hz, 3H) 1.08 (d, J=6.6 Hz, 3H).

¹⁹F NMR (376 MHz, CDCl₃) δ 45.06 (s, 1F) −113.22 (s, 1F). MS (ESI, +ve) m/z: 444.0 (M+1)⁺.

Step 2: 4-((2S,5R)-4-Acryloyl-2,5-dimethylpiperazin-1-yl)-6-chloro-1-(2-fluoro-4-isopropyl-6-methylpyrimidin-5-yl)-7-(2-fluorophenyl)pyrido[2,3-d]pyrimidin-2(1H)-one A solution of 6-chloro-1-(2-fluoro-4-isopropyl-6-methylpyrimidin-5-yl)-7-(2-fluorophenyl)pyrido[2,3-d]pyrimidine-2,4(1H,3H)-dione (0.095 g, 0.21 mmol), phosphoryl trichloride (0.024 mL, 0.26 mmol), and DIPEA (0.097 mL, 1.1 mmol) in acetonitrile (1.1 mL) was stirred at 80° C. for 30 min.

The reaction mixture was removed from the heating block, and 1-((2R,5S)-2,5-dimethylpiperazin-1-yl)prop-2-en-1-one, TFA salt (0.265 g, 0.428 mmol; Intermediate 160) was added to the reaction mixture; this was stirred at RT for 10 min. The reaction mixture was diluted with EtOAc (100 mL), added to a separatory funnel, and washed with saturated, aqueous sodium bicarbonate (2×75 mL); the organic layer was separated, dried over anhydrous Na₂SO₄, and concentrated in vacuo. The crude product was adsorbed onto silica and was purified via automated flash chromatography (silica gel, 0-90% [(3:1) EtOAc/EtOH]/heptane then 30-50% [(3:1) EtOAc/EtOH]/heptane) to give 4-((2S,5R)-4-acryloyl-2,5-dimethylpiperazin-1-yl)-6-chloro-1-(2-fluoro-4-isopropyl-6-methylpyrimidin-5-yl)-7-(2-fluorophenyl)pyrido[2,3-d]pyrimidin-2(1H)-one (22 mg, 0.037 mmol, 17% yield) as a yellow solid. ¹H NMR (400 MHz, CDCl₃) δ 8.13 (s, 1H) 7.42-7.50 (m, 1H) 7.17-7.23 (m, 2H) 7.09-7.17 (m, 1H) 6.50-6.71 (m, 1H) 6.35-6.47 (m, 1H) 5.75-5.88 (m, 1H) 3.43-5.21 (m, 6H) 2.63-2.77 (m, 1H) 2.20-2.25 (m, 3H) 1.32-1.51 (m, 6H) 1.19-1.25 (m, 3H) 1.02-1.08 (m, 3H). ¹⁹F NMR (376 MHz, CDCl₃) δ −46.32-−46.38 (m, 1F) −112.78-112.87 (m, 1F). MS (ESI, +ve) m/z: 594.0 (M+1)⁺.

Example 201

4-((2S,5R)-4-Acryloyl-2,5-dimethylpiperazin-1-yl)-6-chloro-7-(2-fluorophenyl)-1-(4-isopropyl-6-methyl-2-(prop-1-en-2-yl)pyrimidin-5-yl)pyrido[2,3-d]pyrimidin-2(1H)-one, Single Isomer

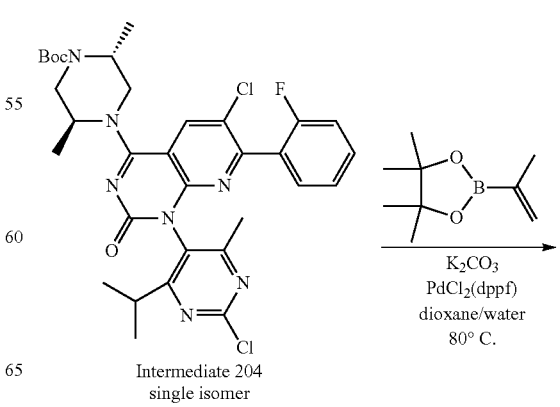

Intermediate 204
single isomer

K₂CO₃
PdCl₂(dppf)
dioxane/water
80° C.

-continued

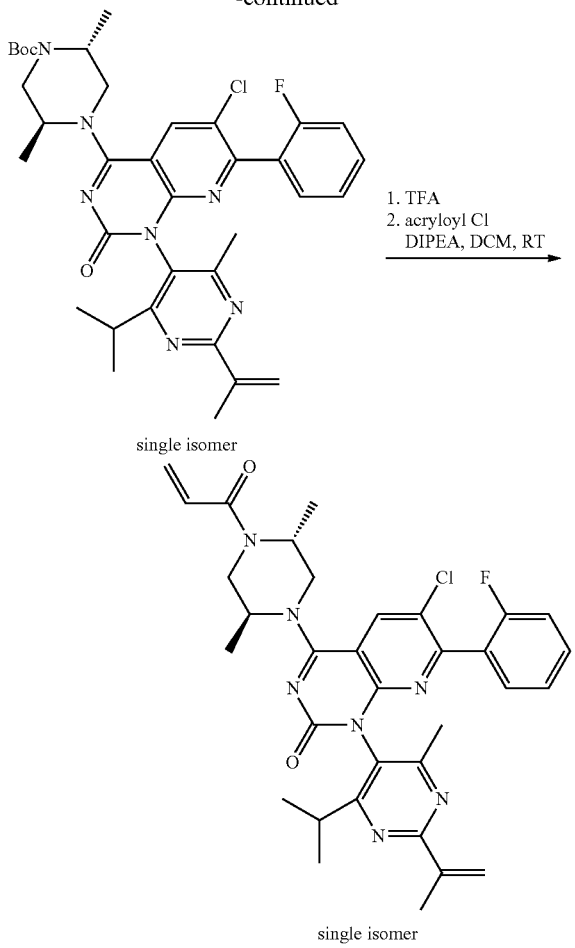

single isomer

1. TFA
2. acryloyl Cl
DIPEA, DCM, RT single isomer

Step 1: tert-Butyl (2R,5S)-4-(6-chloro-7-(2-fluorophenyl)-1-(4-isopropyl-6-methyl-2-(prop-1-en-2-yl)pyrimidin-5-yl)-2-oxo-1,2-dihydropyrido[2,3-d]pyrimidin-4-yl)-2,5-dimethylpiperazine-1-carboxylate A solution of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.309 g, 0.471 mmol; Intermediate 204), 4,4,5,5-tetramethyl-2-(prop-1-en-2-yl)-1,3,2-dioxaborolane (0.133 mL, 0.706 mmol; Combi-Blocks, Inc., San Diego, Calif.), PdCl$_2$(dppf) (0.034 g, 0.047 mmol), and sodium carbonate (2 M, aq., 0.706 mL, 1.41 mmol) in 1,4-dioxane (2.4 mL) was sparged in nitrogen then was stirred at 80° C. for 2 h. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-60% EtOH/[heptane/EtOAc (2:1)]) to give tert-butyl (2R,5S)-4-(6-chloro-7-(2-fluorophenyl)-1-(4-isopropyl-6-methyl-2-(prop-1-en-2-yl)pyrimidin-5-yl)-2-oxo-1,2-dihydropyrido[2,3-d]pyrimidin-4-yl)-2,5-dimethylpiperazine-1-carboxylate (336 mg, 0.507 mmol, >99% yield) as an amber oil. $^1$H NMR (400 MHz, CDCl$_3$) δ 8.11 (s, 1H) 7.37-7.46 (m, 1H) 7.14-7.21 (m, 2H) 7.11 (t, J=9.2 Hz, 1H) 6.43-6.45 (m, 1H) 5.47-5.49 (m, 1H) 3.46-5.07 (m, 6H) 2.68 (spt. J=6.7 Hz, 1H) 2.24 (s, 3H) 2.22 (s, 3H) 1.51 (s, 9H) 1.25-1.27 (m, 6H) 1.20-1.23 (m, 3H) 1.06 (d, J=6.8 Hz, 3H). $^{19}$F NMR (377 MHz, CDCl$_3$) δ –112.81 (br s, 1F). MS (ESI, +ve) m/z: 662.2 (M+1)$^+$.

Step 2: 4-((2S,5R)-4-Acryloyl-2,5-dimethylpiperazin-1-yl)-6-chloro-7-(2-fluorophenyl)-1-(4-isopropyl-6-methyl-2-(prop-1-en-2-yl)pyrimidin-5-yl)pyrido[2,3-d]pyrimidin-2(1H)-one A solution of tert-butyl (2R,5S)-4-(6-chloro-7-(2-fluorophenyl)-1-(4-isopropyl-6-methyl-2-(prop-1-en-2-yl)pyrimidin-5-yl)-2-oxo-1,2-dihydropyrido[2,3-d]pyrimidin-4-yl)-2,5-dimethylpiperazine-1-carboxylate (0.100 g, 0.151 mmol) in 2,2,2-trifluoroacetic acid (1.16 mL, 15.1 mmol) was stirred at RT for 15 min. The reaction mixture was concentrated.

A solution of the resulting oil, acryloyl chloride (0.5 M in DCM, 0.362 mL, 0.181 mmol), and DIPEA (0.105 mL, 0.604 mmol) in dichloromethane (1.5 mL) was stirred at RT for 30 min. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-90% [(3:1) EtOAc/EtOH]/heptane) to give 4-((2S,5R)-4-acryloyl-2,5-dimethylpiperazin-1-yl)-6-chloro-7-(2-fluorophenyl)-1-(4-isopropyl-6-methyl-2-(prop-1-en-2-yl)pyrimidin-5-yl)pyrido[2,3-d]pyrimidin-2(1H)-one (66 mg, 0.11 mmol, 71% yield) as a light yellow solid. $^1$H NMR (400 MHz, CDCl$_3$) δ 8.11 (s, 1H) 7.37-7.48 (m, 1H) 7.14-7.22 (m, 2H) 7.05-7.14 (m, 1H) 6.50-6.71 (m, 1H) 6.31-6.47 (m, 2H) 5.75-5.86 (m, 1H) 5.47-5.50 (m, 1H) 4.17-5.22 (m, 3H) 3.44-4.08 (m, 3H) 2.63-2.74 (m, 1H) 2.25 (s, 3H) 2.22 (s, 3H) 1.31-1.50 (m, 6H) 1.23 (d, J=6.6 Hz, 3H) 1.06 (d, J=6.6 Hz, 3H). $^{19}$F NMR (377 MHz, CDCl$_3$) δ –112.88--112.71 (m, 1F). MS (ESI, +ve) m/z: 616.1 (M+1)$^+$.

Example 202

4-((2S,5R)-4-Acryloyl-2,5-dimethylpiperazin-1-yl)-6-chloro-7-(2-fluorophenyl)-1-(4-isopropyl-6-methyl-2-vinylpyrimidin-5-yl)pyrido[2,3-d]pyrimidin-2(1H)-one, Single Isomer

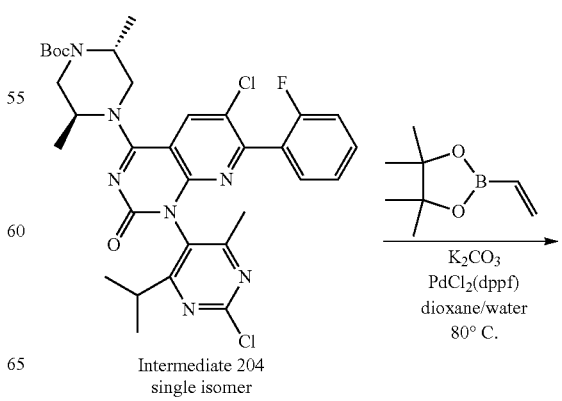

Intermediate 204
single isomer

K$_2$CO$_3$
PdCl$_2$(dppf)
dioxane/water
80° C.

-continued

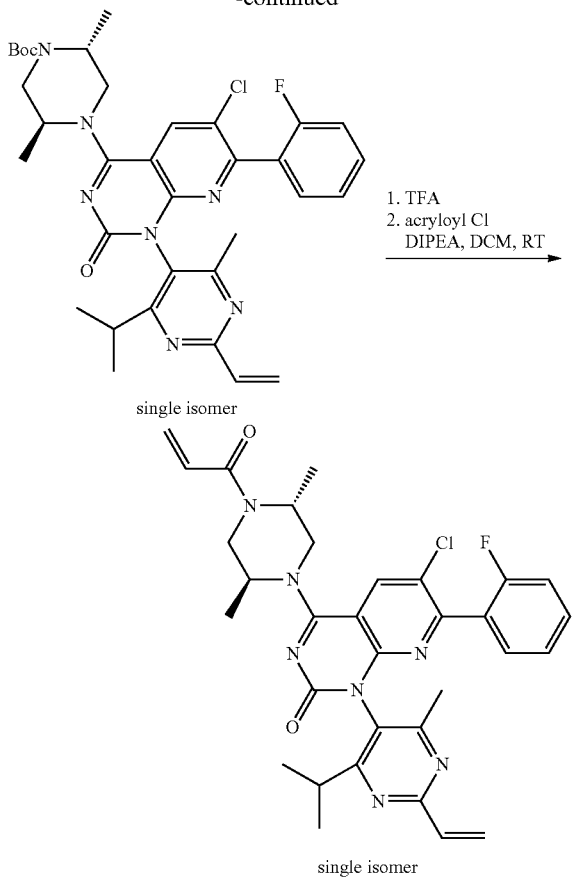

single isomer

1. TFA
2. acryloyl Cl
DIPEA, DCM, RT single isomer

Step 1: tert-Butyl (2R,5S)-4-(6-chloro-7-(2-fluorophenyl)-1-(4-isopropyl-6-methyl-2-vinylpyrimidin-5-yl)-2-oxo-1,2-dihydropyrido[2,3-d]pyrimidin-4-yl)-2,5-dimethylpiperazine-1-carboxylate A solution of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.170 g, 0.259 mmol; Intermediate 204), 4,4,5,5-tetramethyl-2-vinyl-1,3,2-dioxaborolane (0.060 g, 0.39 mmol; AstaTech, Inc., Bristol, Pa.), PdCl$_2$(dppf) (0.019 g, 0.026 mmol), and sodium carbonate (2 M aq., 0.388 mL, 0.777 mmol) in 1,4-dioxane (1.3 mL) was sparged in nitrogen then was stirred at 80° C. for 1 h then at 100° C. for 1 h. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-50% EtOH/[heptane/EtOAc (2:1)]) to give tert-butyl (2R,5S)-4-(6-chloro-7-(2-fluorophenyl)-1-(4-isopropyl-6-methyl-2-vinylpyrimidin-5-yl)-2-oxo-1,2-dihydropyrido[2,3-d]pyrimidin-4-yl)-2,5-dimethylpiperazine-1-carboxylate (0.131 g, 0.202 mmol, 78% yield as a light yellow solid. $^1$H NMR (400 MHz, CDCl$_3$) δ 8.11 (s, 1H) 7.38-7.46 (m, 1H) 7.13-7.21 (m, 2H) 7.06-7.13 (m, 1H) 6.81-6.92 (m, 1H) 6.64 (dd, J=17.2, 2.1 Hz, 1H) 5.64-5.71 (m, 1H) 3.46-5.05 (m, 6H) 2.70 (spt, J=6.6 Hz, 1H) 2.22 (s, 3H) 1.51 (s, 9H) 1.42-1.49 (m, 3H) 1.29 (d, J=6.8 Hz, 3H) 1.21-1.24 (m, 3H) 1.07 (d, J=6.6 Hz, 3H). $^{19}$F NMR (377 MHz, CDCl$_3$) δ −112.80 (br s, 1F). MS (ESI, +ve) m/z: 648.2 (M+1)$^+$.

Step 2: 4-((2S,5R)-4-Acryloyl-2,5-dimethylpiperazin-1-yl)-6-chloro-7-(2-fluorophenyl)-1-(4-isopropyl-6-methyl-2-vinylpyrimidin-5-yl)pyrido[2,3-d]pyrimidin-2(1H)-one A solution of tert-butyl (2R,5S)-4-(6-chloro-7-(2-fluorophenyl)-1-(4-isopropyl-6-methyl-2-vinylpyrimidin-5-yl)-2-oxo-1,2-dihydropyrido[2,3-d]pyrimidin-4-yl)-2,5-dimethylpiperazine-1-carboxylate (0.131 g, 0.202 mmol) and 2,2,2-trifluoroacetic acid (1.55 mL, 20.2 mmol) in DCM (2 mL) was stirred at RT for 15 min. The reaction mixture was concentrated.

A solution of the resulting oil, acryloyl chloride (0.5 M in DCM, 0.485 mL, 0.243 mmol), and DIPEA (0.141 mL, 0.808 mmol) in dichloromethane (2.0 mL) was stirred at RT for 30 min. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-80% [(3:1) EtOAc/EtOH]/heptane) to give 4-((2S,5R)-4-acryloyl-2,5-dimethylpiperazin-1-yl)-6-chloro-7-(2-fluorophenyl)-1-(4-isopropyl-6-methyl-2-vinylpyrimidin-5-yl)pyrido[2,3-d]pyrimidin-2(1H)-one (97 mg, 0.16 mmol, 80% yield) as a light yellow solid. $^1$H NMR (400 MHz, CDCl$_3$) δ 8.12 (s, 1H) 7.38-7.47 (m, 1H) 7.14-7.22 (m, 2H) 7.07-7.14 (m, 1H) 6.81-6.91 (m, 1H) 6.51-6.70 (m, 2H) 6.40 (br t, J=14.7 Hz, 1H) 5.76-5.85 (m, 1H) 5.66-5.72 (m, 1H) 4.29-5.21 (m, 3H) 3.45-4.08 (m, 3H) 2.63-2.76 (m, 1H) 2.22 (s, 3H) 1.29-1.51 (m, 6H) 1.23 (d, J=6.6 Hz, 3H) 1.07 (br d, J=6.6 Hz, 3H). $^{19}$F NMR (377 MHz, CDCl$_3$) δ −112.83-−112.69 (m, 1F). MS (ESI, +ve) m/z: 602.2 (M+1)$^+$.

Example 203

4-((2S,5R)-4-Acryloyl-2,5-dimethylpiperazin-1-yl)-6-chloro-1-(2,4-diisopropyl-6-methylpyrimidin-5-yl)-7-(2-fluorophenyl)pyrido[2,3-d]pyrimidin-2(1H)-one, Single Isomer

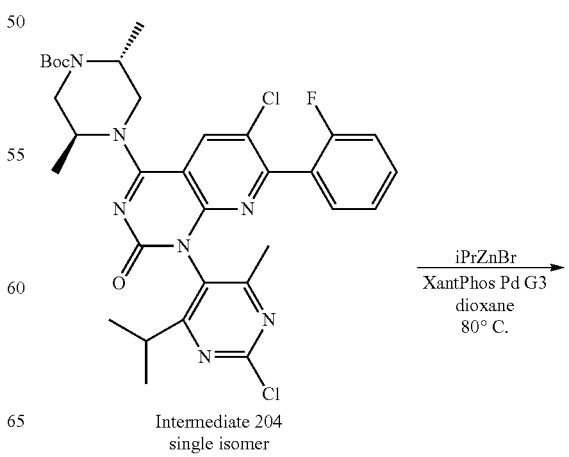

Intermediate 204
single isomer iPrZnBr
XantPhos Pd G3
dioxane
80° C.

-continued

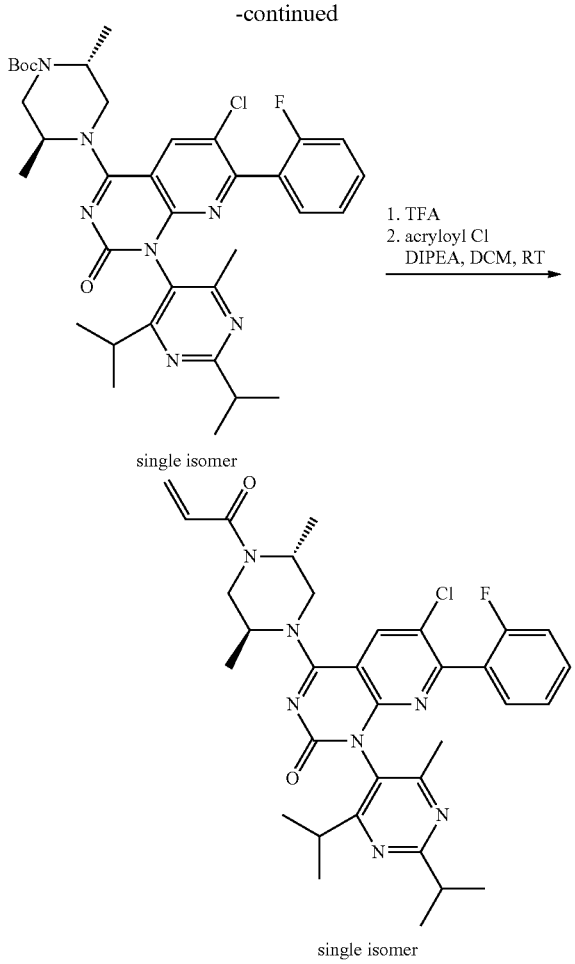

single isomer

1. TFA
2. acryloyl Cl
DIPEA, DCM, RT single isomer

Step 1: tert-Butyl (2R,5S)-4-(6-chloro-1-(2,4-diisopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate A solution of ter-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.166 g, 0.253 mmol; Intermediate 204). isopropylzinc bromide (0.5 M in THF, 0.607 mL, 0.303 mmol; Sigma-Aldrich, St. Louis, Mo.), and XantPhos Pd G3 (0.013 g, 0.013 mmol) in 1,4-dioxane (1.3 mL) was sparged in nitrogen then was stirred at 50° C. for 1 h. More isopropylzinc bromide (0.5 M in THF, 0.607 mL, 0.303 mmol) was added, and the reaction mixture was then stirred at 80° C. for 2 h. The reaction mixture was diluted with EtOAc (100 mL), added to a separatory funnel, and washed with saturated, aqueous sodium bicarbonate (2×75 mL); the organic layer was separated, dried over anhydrous $Na_2SO_4$, and concentrated in vacuo. The crude product was adsorbed onto silica and was purified via automated flash chromatography (silica gel, 0-50% EtOH/[heptane/EtOAc (2:1)]) to give impure tert-butyl (2R,5S)-4-(6-chloro-1-(2,4-diisopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (70 mg, 0.11 mmol, 42% yield) as an off-white solid. MS (ESI, +ve) m/z: 664.3 (M+1)$^+$.

Step 2: 4-((2S,5R)-4-Acryloyl-2,5-dimethylpiperazin-1-yl)-6-chloro-1-(2,4-diisopropyl-6-methylpyrimidin-5-yl)-7-(2-fluorophenyl)pyrido[2,3-d]pyrimidin-2(1H)-one A solution of tert-butyl (2R,5S)-4-(6-chloro-1-(2,4-diisopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.070 g, 0.11 mmol) and 2,2,2-trifluoroacetic acid (0.81 mL, 11 mmol) in DCM (2 mL) was stirred at RT for 15 min. The reaction mixture was concentrated.

A solution of the resulting oil, acryloyl chloride (0.5 M in DCM, 0.25 mL, 0.13 mmol), and DIPEA (0.073 mL, 0.42 mmol) in dichloromethane (1.1 mL) was stirred at RT for 30 min. The reaction mixture was diluted with EtOAc (100 mL), added to a separatory funnel, and washed with saturated, aqueous sodium bicarbonate (2×75 mL); the organic layer was separated. dried over anhydrous $Na_2SO_4$. and concentrated in vacuo. The crude product in methanol was purified via preparative HPLC (Phenomenex Kinetex EVO $C_{18}$ column, 150×21.2 mm, Axia packed, 5 μm; 50-70% 0.1% TFA in MeCN/$H_2O$, 35 mL/min, 13 min); the pure fractions were diluted with EtOAc (75 mL), added to a separatory funnel, and washed with saturated, aqueous sodium bicarbonate (2×50 mL); the organic layer was separated, dried over anhydrous $Na_2SO_4$, and concentrated in vacuo to give 4-((2S,5R)-4-acryloyl-2,5-dimethylpiperazin-1-yl)-6-chloro-1-(2,4-diisopropyl-6-methylpyrimidin-5-yl)-7-(2-fluorophenyl)pyrido[2,3-d]pyrimidin-2(1H)-one (23 mg, 0.037 mmol, 35% yield) as an off-white solid. $^1$H NMR (400 MHz, $CDCl_3$) δ 8.10 (s, 1H) 7.39-7.47 (m, 1H) 7.14-7.22 (m, 2H) 7.07-7.14 (m, 1H) 6.52-6.70 (m, 1H) 6.40 (br t, J=14.9 Hz, 1H) 5.75-5.85 (m, 1H) 4.25-5.25 (m, 3H) 3.39-4.08 (m, 3H) 3.09-3.21 (m, 1H) 2.58-2.71 (m, 1H) 2.19 (s, 3H) 1.31-1.49 (m, 12H) 1.21 (d, J=6.6 Hz, 3H) 1.04 (d, J=6.6 Hz, 3H). $^{19}$F NMR (377 MHz, $CDCl_3$) δ 112.30-- 112.15 (m, 1F). MS (ESI, +ve) m/z: 618.0 (M+1)$^+$.

Example 204

4-((2S,5R)-4-Acryloyl-2,5-dimethylpiperazin-1-yl)-6-chloro-1-(2-ethynyl-4-isopropyl-6-methylpyrimidin-5-yl)-7-(2-fluorophenyl)pyrido[2,3-d]pyrimidin-2(1H)-one, Single Isomer

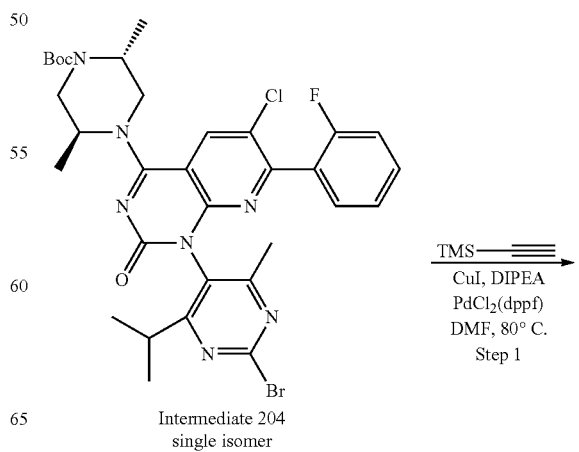

Intermediate 204
single isomer

TMS≡≡≡
CuI, DIPEA
PdCl$_2$(dppf)
DMF, 80° C.
Step 1

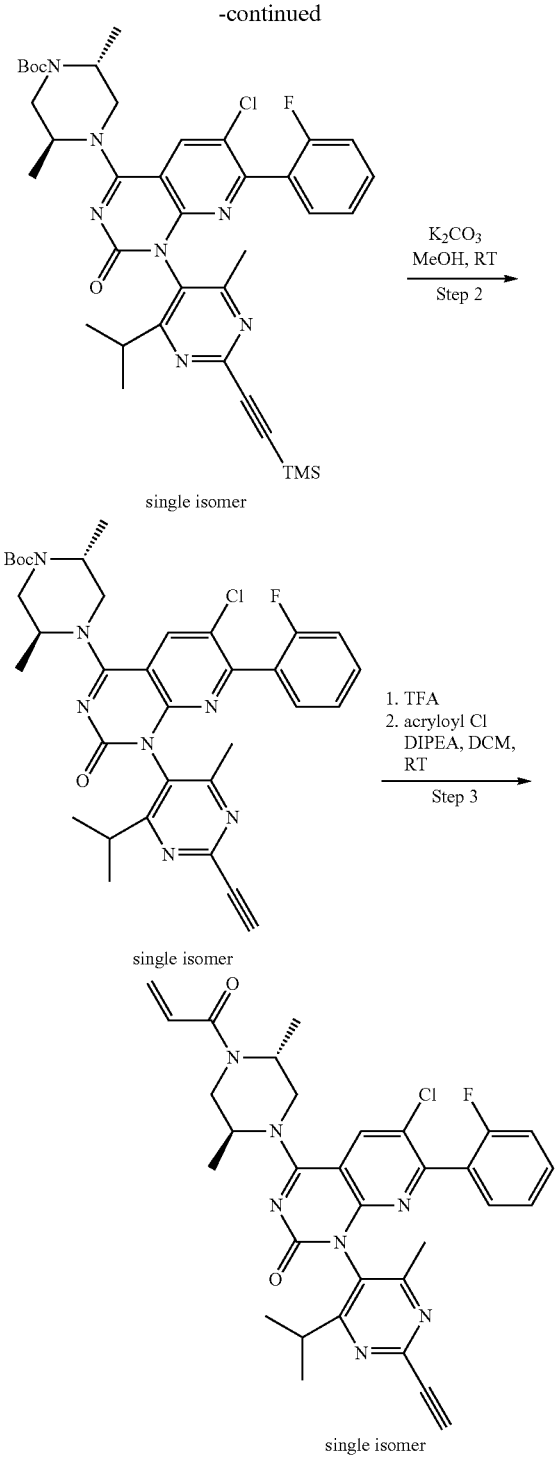

Step 1: tert-Butyl (2R,5S)-4-(6-chloro-7-(2-fluorophenyl)-1-(4-isopropyl-6-methyl-2-((trimethylsilyl)ethynyl)pyrimidin-5-yl)-2-oxo-1,2-dihydropyrido[2,3-d]pyrimidin-4-yl)-2,5-dimethylpiperazine-1-carboxylate A solution of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.233 g, 0.355 mmol; Intermediate 204), ethynyltrimethylsilane (0.098 mL, 0.71 mmol; Matrix Scientific, Columbia, S.C.), DIPEA (0.248 mL, 1.42 mmol), copper(I) iodide (14 mg, 0.071 mmol), and PdCl$_2$(dppf) (0.026 g, 0.035 mmol) in DMF (3.6 mL) was sparged with nitrogen then was stirred at 80° C. for 3 h. The reaction mixture was diluted with EtOAc (100 mL), added to a separatory funnel, and washed with saturated, aqueous sodium bicarbonate (2×100 mL); the organic layer was separated, dried over anhydrous Na$_2$SO$_4$, and concentrated in vacuo. The crude product was adsorbed onto silica and was purified via automated flash chromatography (silica gel, 0-50% [(3:1) EtOAc/EtOH]/heptane) to give tert-butyl (2R,5S)-4-(6-chloro-7-(2-fluorophenyl)-1-(4-isopropyl-6-methyl-2-((trimethylsilyl)ethynyl)pyrimidin-5-yl)-2-oxo-1,2-dihydropyrido[2,3-d]pyrimidin-4-yl)-2,5-dimethylpiperazine-1-carboxylate (188 mg, 0.262 mmol, 74% yield) as an amber oil. $^1$H NMR (400 MHz, CDCl$_3$) δ 8.08-8.13 (m, 1H) 7.40-7.49 (m, 1H) 7.15-7.22 (m, 2H) 7.08-7.15 (m, 1H) 3.43-5.05 (m, 6H) 2.65-2.77 (m, 1H) 2.22 (s, 3H) 1.51 (s, 9H) 1.26-1.30 (m, 6H) 1.23 (d, J=6.8 Hz, 3H) 1.07 (d, J=6.8 Hz, 3H) 0.29 (s, 8H). $^{19}$F NMR (377 MHz, CDCl$_3$) δ −112.89 (s, 1F). MS (ESI, +ve) m/z: 718.1 (M+1)$^+$.

Step 2: tert-Butyl (2R,5S)-4-(6-chloro-1-(2-ethynyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate A solution of tert-butyl (2R,5S)-4-(6-chloro-7-(2-fluorophenyl)-1-(4-isopropyl-6-methyl-2-((trimethylsilyl)ethynyl)pyrimidin-5-yl)-2-oxo-1,2-dihydropyrido[2,3-d]pyrimidin-4-yl)-2,5-dimethylpiperazine-1-carboxylate (0.188 g, 0.262 mmol) and potassium carbonate (7 mg, 0.05 mmol) in methanol (3 mL) was stirred at 22° C. for 3 h. The reaction mixture was diluted with EtOAc (100 mL), added to a separatory funnel, and washed with saturated, aqueous sodium bicarbonate (2×100 mL); the organic layer was separated, dried over anhydrous Na$_2$SO$_4$, and concentrated in vacuo. The crude product was adsorbed onto silica and was purified via automated flash chromatography (silica gel, 0-50% [(3:1) EtOAc/EtOH]/heptane) to give tert-butyl (2R,5S)-4-(6-chloro-1-(2-ethynyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (82 mg, 0.13 mmol, 49% yield) as an amber oil. $^1$H NMR (400 MHz, CDCl$_3$) δ 8.12 (s, 1H) 7.39-7.49 (m, 1H) 7.08-7.21 (m, 3H) 4.91-5.06 (m, 1H) 4.36-4.65 (m, 1H) 4.05-4.23 (m, 1H) 3.77-3.98 (m, 2H) 3.44-3.64 (m, 1H) 3.09 (s, 1H) 2.66-2.77 (m, 1H) 2.23 (s, 3H) 1.51 (s, 9H) 1.20-1.32 (m, 9H) 1.07 (d, J=6.6 Hz, 3H). $^{19}$F NMR (377 MHz, CDCl$_3$) δ −112.79 (br s, 1F). MS (ESI, +ve) m/z: 646.1 (M+1)$^+$.

Step 3: 4-((2S,5R)-4-Acryloyl-2,5-dimethylpiperazin-1-yl)-6-chloro-1-(2-ethynyl-4-isopropyl-6-methylpyrimidin-5-yl)-7-(2-fluorophenyl)pyrido[2,3-d]pyrimidin-2(1H)-one A solution of tert-butyl (2R,5S)-4-(6-chloro-1-(2-ethynyl-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (0.082 g, 0.13 mmol) and 2,2,2-trifluoroacetic acid (0.97 mL, 13 mmol) in DCM (2 mL) was stirred at RT for 15 min. The reaction mixture was concentrated.

A solution of the resulting oil, acryloyl chloride (0.5 M in DCM, 0.31 mL, 0.15 mmol), and DIPEA (0.088 mL, 0.51 mmol) in dichloromethane (1.3 mL) was stirred at RT for 30 min. The reaction mixture was diluted with EtOAc (100 mL), added to a separatory funnel, and washed with saturated, aqueous sodium bicarbonate (2×75 mL); the organic layer was separated, dried over anhydrous Na$_2$SO$_4$. and concentrated in vacuo. The crude product was adsorbed onto silica and was purified via automated flash chromatography (silica gel, 0-80% [(3:1) EtOAc/EtOH]/heptane) to give 4-((2S,5R)-4-acryloyl-2,5-dimethylpiperazin-1-yl)-6-chloro-1-(2-ethynyl-4-isopropyl-6-methylpyrimidin-5-yl)-7-(2-fluorophenyl)pyrido[2,3-d]pyrimidin-2(1H)-one (59 mg, 0.098 mmol, 77% yield) as an off-white solid. $^1$H NMR (400 MHz, CDCl$_3$) δ 8.13 (s, 1H) 7.40-7.49 (m, 1H) 7.08-7.23 (m, 3H) 6.51-6.70 (m, 1H) 6.40 (br t, J=14.7 Hz, 1H) 5.76-5.86 (m, 1H) 4.33-5.21 (m, 3H) 3.44-4.07 (m, 3H) 3.10 (s, 1H) 2.65-2.78 (m, 1H) 2.21-2.26 (m, 3H) 1.29-1.51 (m, 6H) 1.24 (d, J=6.6 Hz, 3H) 1.07 (br d, J=6.6 Hz, 3H). $^{19}$F NMR (377 MHz, CDCl$_3$) δ −112.92−−112.59 (m, 1F). MS (ESI, +ve) m/z: 600.0 (M+1)$^+$.

Example 205

4-((2S,5R)-4-Acryloyl-2,5-dimethylpiperazin-1-yl)-6-chloro-1-(3,5-diisopropylpyridazin-4-yl)-7-(2-fluorophenyl)pyrido[2,3-d]pyrimidin-2(1H)-one

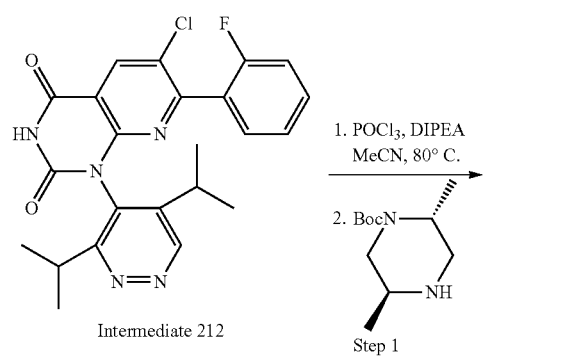

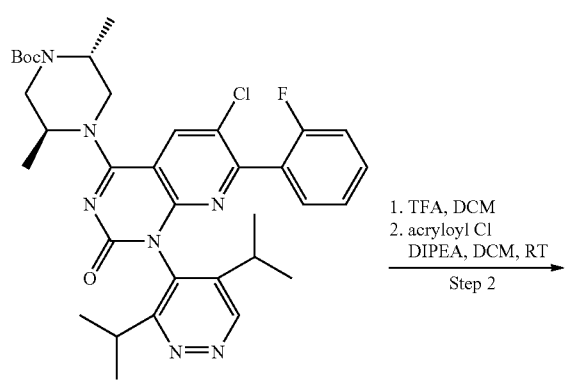

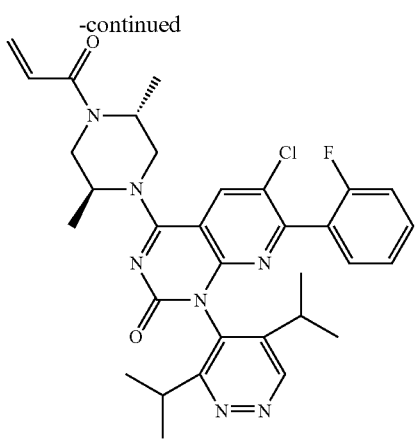

Step 1: tert-Butyl (2S,5R)-4-(6-chloro-1-(3,5-diisopropylpyridazin-4-yl)-7-(2-fluorophenyl)-2-oxo-1,2-dihydropyrido[2,3-d]pyrimidin-4-yl)-2,5-dimethylpiperazine-1-carboxylate A solution of 6-chloro-1-(3,5-diisopropylpyridazin-4-yl)-7-(2-fluorophenyl)pyrido[2,3-d]pyrimidine-2,4(1H,3H)-dione (0.439 g, 0.967 mmol, Intermediate 212), phosphoryl trichloride (0.108 mL, 1.16 mmol), and DIPEA (0.168 mL, 0.967 mmol) in acetonitrile (5 mL) was stirred under an air condensor and drying tube at 80° C. for 30 min. The reaction mixture was cooled to RT, and tert-butyl (2S,5R)-2,5-dimethylpiperazine-1-carboxylate (0.207 g, 0.967 mmol; eNovation Chemicals LLC, Bridgewater, N.J.) was added; the solution was stirred a RT for 30 min. The reaction mixture was diluted with EtOAc (200 mL), added to a separatory funnel, and washed with saturated, aqueous sodium bicarbonate (2×100 mL); the organic layer was separated, dried over anhydrous Na$_2$SO$_4$, and concentrated in vacuo. The crude product was adsorbed onto silica and was purified via automated flash chromatography (silica gel. 0-100% EtOAc/heptane) to give tert-butyl (2S,5R)-4-(6-chloro-1-(3,5-diisopropylpyridazin-4-yl)-7-(2-fluorophenyl)-2-oxo-1,2-dihydropyrido[2,3-d]pyrimidin-4-yl)-2,5-dimethylpiperazine-1-carboxylate (258 mg, 0.397 mmol, 41% yield) as a yellow solid. $^1$H NMR (400 MHz, CDCl$_3$) δ 9.11 (d, J=2.3 Hz, 1H) 8.13 (d, J=1.9 Hz, 1H) 7.38-7.47 (m, 1H) 7.05-7.18 (m, 3H) 4.16-5.08 (m, 3H) 3.76-4.08 (m, 2H) 3.45-3.65 (m, 1H) 2.70-2.82 (m, 1H) 2.58-2.70 (m, 1H) 1.52 (s, 9H) 1.24-1.37 (m, 12H) 1.17 (dd, J=9.1, 6.8 Hz, 3H) 1.04 (dd, J=6.7, 4.7 Hz, 3H). $^{19}$F NMR (377 MHz, CDCl$_3$) δ −113.34−−113.24 (m, 1F). MS (ESI, +ve) m/z: 650.2 (M+1)$^+$.

Step 2: 4-((2S,5R)-4-Acryloyl-2,5-dimethylpiperazin-1-yl)-6-chloro-1-(3,5-diisopropylpyridazin-4-yl)-7-(2-fluorophenyl)pyrido[2,3-d]pyrimidin-2(1H)-one A solution of tert-butyl (2S,5R)-4-(6-chloro-1-(3,5-diisopropylpyridazin-4-yl)-7-(2-fluorophenyl)-2-oxo-1,2-dihydropyrido[2,3-d]pyrimidin-4-yl)-2,5-dimethylpiperazine-1-carboxylate (0.258 g, 0.397 mmol) and 2,2,2-trifluoroacetic acid (3.04 mL, 39.7 mmol) in DCM (2 mL) was stirred at RT for 15 min. The reaction mixture was concentrated.

A solution of the resulting oil, acryloyl chloride (0.5 M in DCM, 0.952 mL, 0.476 mmol), and DIPEA (0.276 mL, 1.59 mmol) in dichloromethane (4 mL) was stirred at RT for 10 min. The reaction mixture was diluted with EtOAc (100 mL), added to a separatory funnel, and washed with saturated, aqueous sodium bicarbonate (2×75 mL), the organic layer was separated, dried over anhydrous Na₂SO₄, and concentrated in vacuo. The crude product was adsorbed onto silica and was purified via automated flash chromatography (silica gel, 0-100% [(3:1) EtOAc/EtOH]/heptane) to give 4-((2S,5R)-4-acryloyl-2,5-dimethylpiperazin-1-yl)-6-chloro-1-(3,5-diisopropylpyridazin-4-yl)-7-(2-fluorophenyl)pyrido[2,3-d]pyrimidin-2(1H)-one (145 mg, 0.240 mmol, 61% yield) as an amber oil. $^1$H NMR (400 MHz, CDCl₃) δ 9.11-9.13 (m, 1H) 8.14 (s, 1H) 7.38-7.47 (m, 1H) 7.06-7.19 (m, 3H) 6.52-6.70 (m, 1H) 6.41 (br t, J=14.9 Hz, 1H) 5.77-5.85 (m, 1H) 3.80-5.21 (m, 6H) 2.70-2.85 (m, 1H) 2.55-2.70 (m, 1H) 1.23-1.53 (m, 15H) 1.14-1.21 (m, 3H). $^{19}$F NMR (377 MHz, CDCl₃) δ -113.43--113.09 (m, 1F). MS (ESI, +ve) m/z: 604.1 (M+1)⁺.

Example 205-1

4-((2S,5R)-4-Acryloyl-2,5-dimethylpiperazin-1-yl)-6-chloro-1-(3,5-diisopropylpyridazin-4-yl)-7-(2-fluorophenyl)pyrido[2,3-d]pyrimidin-2(1H)-one, Single Isomer

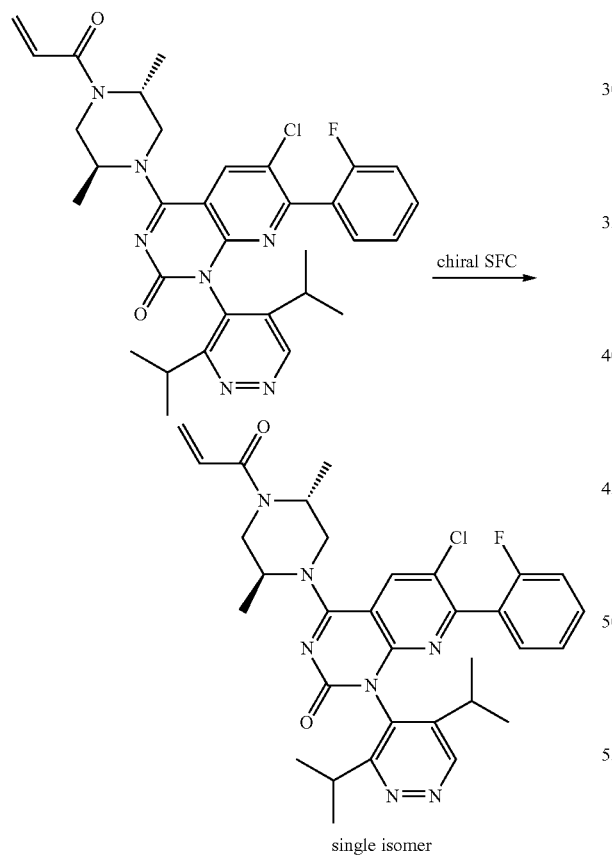

single isomer

Atropisomers of 4-((2S,5R)-4-acryloyl-2,5-dimethylpiperazin-1-yl)-6-chloro-1-(3,5-diisopropylpyridazin-4-yl)-7-(2-fluorophenyl)pyrido[2,3-d]pyrimidin-2(11H)-one (0.145 g, 0.240 mmol) were separated by chiral SFC: Chirakpak IC, ID 150×30 mm, 5 μm, 60% methanol/CO₂, 80 mL/min. This gave 4-((2S,5R)-4-acryloyl-2,5-dimethylpiperazin-1-yl)-6-chloro-1-(3,5-diisopropylpyridazin-4-yl)-7-(2-fluorophenyl)pyrido[2,3-d]pyrimidin-2(1H)-one (42.0 mg, 0.070 mmol, 29% yield; first eluting isomer) as an off-white solid. $^1$H NMR (400 MHz, CDCl₃) δ 9.12 (s, 1H) 8.13 (s, 1H) 7.38-7.47 (m, 1H) 7.06-7.19 (m, 3H) 6.50-6.70 (m, 1H) 6.41 (br t, J=15.2 Hz, 1H) 5.77-5.88 (m, 1H) 4.91-5.23 (m, 2H) 4.33-4.51 (m, 1H) 3.68-4.11 (m, 3H) 2.70-2.84 (m, 1H) 2.56-2.70 (m, 1H) 1.40-1.52 (m, 5H) 1.30-1.38 (m, 4H) 1.26 (d, J=7.0 Hz, 3H) 1.16 (br d, J=6.8 Hz, 3H) 1.02-1.07 (m, 3H). $^{19}$F NMR (376 MHz, CDCl₃) δ -113.28 (s, 1F). MS (ESI, +ve) m/z: 604.1 (M+1).

Example 205-2

4-((2S,5R)-4-Acryloyl-2,5-dimethylpiperazin-1-yl)-6-chloro-1-(3,5-diisopropylpyridazin-4-yl)-7-(2-fluorophenyl)pyrido[2,3-d]pyrimidin-2(1H)-one, Single Isomer

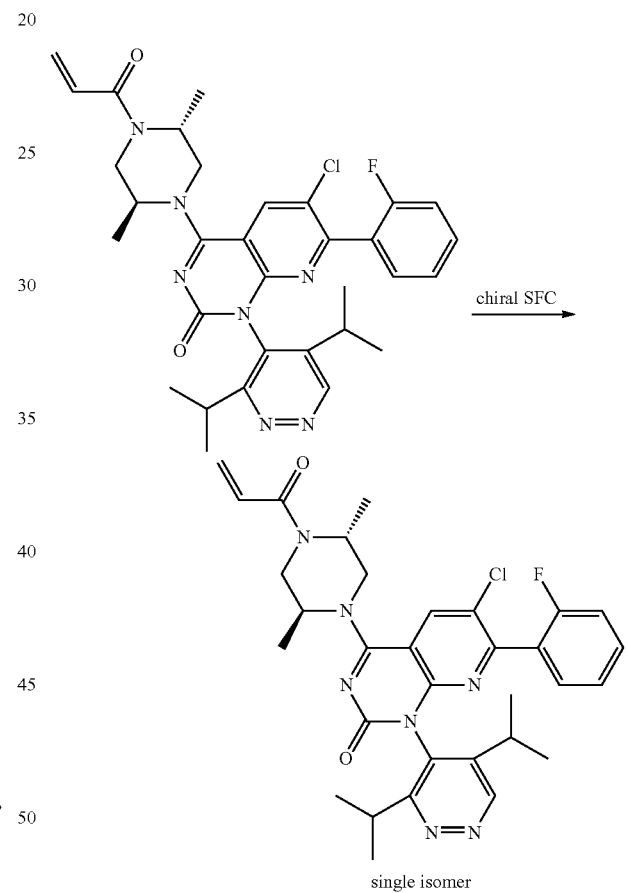

single isomer

Atropisomers of 4-((2S,5R)-4-acryloyl-2,5-dimethylpiperazin-1-yl)-6-chloro-1-(3,5-diisopropylpyridazin-4-yl)-7-(2-fluorophenyl)pyrido[2,3-d]pyrimidin-2(1H)-one (0.145 g, 0.240 mmol) were separated by chiral SFC: Chirakpak IC, ID 150×30 mm, 5 μm, 60% methanol/CO₂, 80 mL/min. This gave 4-((2S,5R)-4-acryloyl-2,5-dimethylpiperazin-1-yl)-6-chloro-1-(3,5-diisopropylpyridazin-4-yl)-7-(2-fluorophenyl)pyrido[2,3-d]pyrimidin-2(1H)-one (43 mg, 0.071 mmol, 30% yield; second eluting isomer) as an off-white solid. $^1$H NMR (400 MHz, CDCl₃) δ 9.12 (s, 1H) 8.14 (s, 1H) 7.38-7.49 (m, 1H) 7.05-7.19 (m, 3H) 6.51-6.70 (m, 1H) 6.41 (br t, J=14.7 Hz, 1H) 5.75-5.86 (m, 1H) 4.91-5.22 (m, 2H) 4.37-4.52 (m, 1H) 3.69-4.14 (m, 3H) 2.69-2.83 (m, 1H)

2.57-2.69 (m, 1H) 1.41-1.54 (m, 5H) 1.30-1.37 (m, 4H) 1.22-1.28 (m, 3H) 1.14-1.20 (m, 3H) 1.00-1.08 (m, 3H). $^{19}$F NMR (376 MHz, CDCl$_3$) δ −113.30−−113.20 (m, 1F). MS (ESI, +ve) m/z: 604.1 (M+1).

Examples 206-1 & 206-2

4-(cis-4-Acryloyl-3,5-dimethylpiperazin-1-yl)-6-chloro-1-(3,5-diisopropylpyridazin-4-yl)-7-(2-fluorophenyl)pyrido[2,3-d]pyrimidin-2(1H)-one, Single Isomers

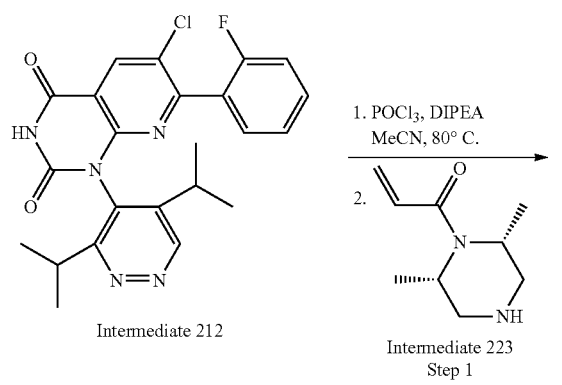

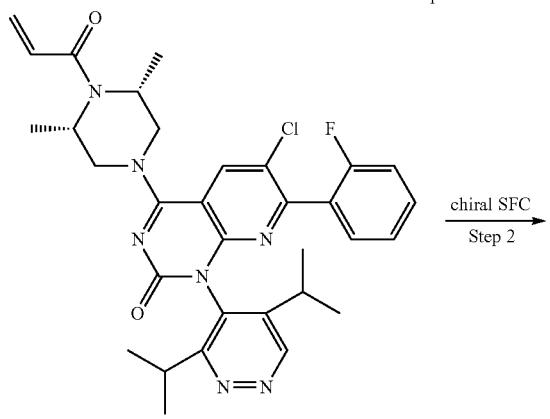

single isomer

Step 1: 4-(cis-4-Acryloyl-3,5-dimethylpiperazin-1-yl)-6-chloro-1-(3,5-diisopropylpyridazin-4-yl)-7-(2-fluorophenyl)pyrido[2,3-d]pyrimidin-2(1H)-one A solution of 6-chloro-1-(3,5-diisopropylpyridazin-4-yl)-7-(2-fluorophenyl)pyrido[2,3-d]pyrimidine-2,4(1H,3H)-dione (0.439 g, 0.967 mmol; Intermediate 212), phosphoryl trichloride (0.108 mL, 1.16 mmol), and DIPEA (0.168 mL, 0.967 mmol) in acetonitrile (5 mL) was stirred under an air condenser and drying tube at 80° C. for 30 min. The reaction mixture was cooled to RT and 1-(cis-2,6-dimethylpiperazin-1-yl)prop-2-en-1-one (0.644 g, 0.967 mmol; Intermediate 223) was added; the solution was stirred a RT for 30 min. The reaction mixture was diluted with EtOAc (200 mL), added to a separatory funnel, and washed with saturated, aqueous sodium bicarbonate (2×100 mL); the organic layer was separated, dried over anhydrous Na$_2$SO$_4$, and concentrated in vacuo. The crude product was adsorbed onto silica and was purified via automated flash chromatography (silica gel, 20-100% [(3:1) EtOAc/EtOH]/heptane) to give 4-(cis-4-acryloyl-3,5-dimethylpiperazin-1-yl)-6-chloro-1-(3,5-diisopropylpyridazin-4-yl)-7-(2-fluorophenyl)pyrido[2,3-d]pyrimidin-2(1)-one (120 mg, 0.199 mmol, 21% yield). MS (ESI, +ve) m/z: 604.1 (M+1)$^+$.

Step 2: 4-(cis-4-Acryloyl-3,5-dimethylpiperazin-1-yl)-6-chloro-1-(3,5-diisopropylpyridazin-4-yl)-7-(2-fluorophenyl)pyrido[2,3-d]pyrimidin-2(1H)-one, Single Isomers Atropisomers of 4-(cis-4-acryloyl-3,5-dimethylpiperazin-1-yl)-6-chloro-1-(3,5-diisopropylpyridazin-4-yl)-7-(2-fluorophenyl)pyrido[2,3-d]pyrimidin-2(1H)-one (0.120 g, 0.199 mmol) were separated by chiral SFC: Welko SS, ID 250×21 mm, 5 µm, 35% methanol/CO$_2$, 80 mL/min. 90 bar. This gave 4-(cis-4-acryloyl-3,5-dimethylpiperazin-1-yl)-6-chloro-1-(3,5-diisopropylpyridazin-4-yl)-7-(2-fluorophenyl)pyrido[2,3-d]pyrimidin-2(1H)-one (30 mg, 0.050 mmol, 25% yield; first eluting isomer) [$^1$H NMR (400 MHz, CDCl$_3$) δ 9.12 (s, 1H) 8.35 (s, 1H) 7.38-7.48 (m, 1H) 7.06-7.19 (m, 3H) 6.64 (dd, J=16.7, 10.5 Hz, 1H) 6.44 (dd, J=16.7, 2.0 Hz, 1H) 5.76-5.85 (m, 1H) 4.60-4.83 (m, 2H) 4.34 (br d, J=12.9 Hz, 2H) 3.69 (dd, J=13.5, 5.0 Hz, 2H) 2.71-2.83 (m, 1H) 2.58-2.71 (m, 1H) 1.59 (d, J=1.9 Hz, 3H) 1.57 (d, J=1.9 Hz, 3H) 1.35 (d, J=6.8 Hz, 3H) 1.26 (d, J=6.8 Hz, 3H) 1.17 (d, J=6.8 Hz, 3H) 1.04 (d, J=7.0 Hz, 3H). $^{19}$F NMR (377 MHz, CDCl$_3$) δ −113.33 (s, 1F). MS (ESI, +ve) m/z: 604.1 (M+1)$^+$] as a dark yellow solid and 4-(cis-4-acryloyl-3,5-dimethylpiperazin-1-yl)-6-chloro-1-(3,5-diisopropylpyridazin-4-yl)-7-(2-fluorophenyl)pyrido[2,3-d]pyrimidin-2(1H)-one (30 mg, 0.050 mmol, 25% yield; second eluting isomer) [$^1$H NMR (400 MHz, CDCl$_3$) δ 9.12 (s, 1H) 8.35 (s, 1H) 7.39-7.47 (m, 1H) 7.05-7.19 (m, 3H) 6.64 (dd, J=16.7, 10.5 Hz, 1H) 6.44 (dd, J=16.7, 2.0 Hz, 1H) 5.78-5.84 (m, 1H) 4.65-4.83 (m, 2H) 4.34 (br d, J=13.7 Hz, 2H) 3.69 (dd, J=13.4, 4.9 Hz, 2H) 2.71-2.81 (m, 1H) 2.58-2.69 (m, 1H) 1.59 (d, J=1.9 Hz, 3H) 1.57 (d, J=1.9 Hz 3H) 1.35 (d, J=6.8 Hz, 3H) 1.26 (d, J=6.8 Hz, 3H) 1.17 (d, J=6.8 Hz, 3H) 1.04 (d, J=7.0 Hz, 3H). $^{19}$F NMR (377 MHz, CDCl$_3$) δ −113.33 (s, 1F). MS (ESI, +ve) m/z: 604.1 (M+1)$^+$] as a dark yellow solid.

Example 207

(M)-6-Chloro-4-[(2S,5R)-2,5-dimethyl-4-prop-2-enoyl-piperazin-1-yl]-1-(2-isopropyl-4-methyl-3-pyridyl)-7-[norcaran-1-yl]pyrido[2,3-d]pyrimidin-2-one

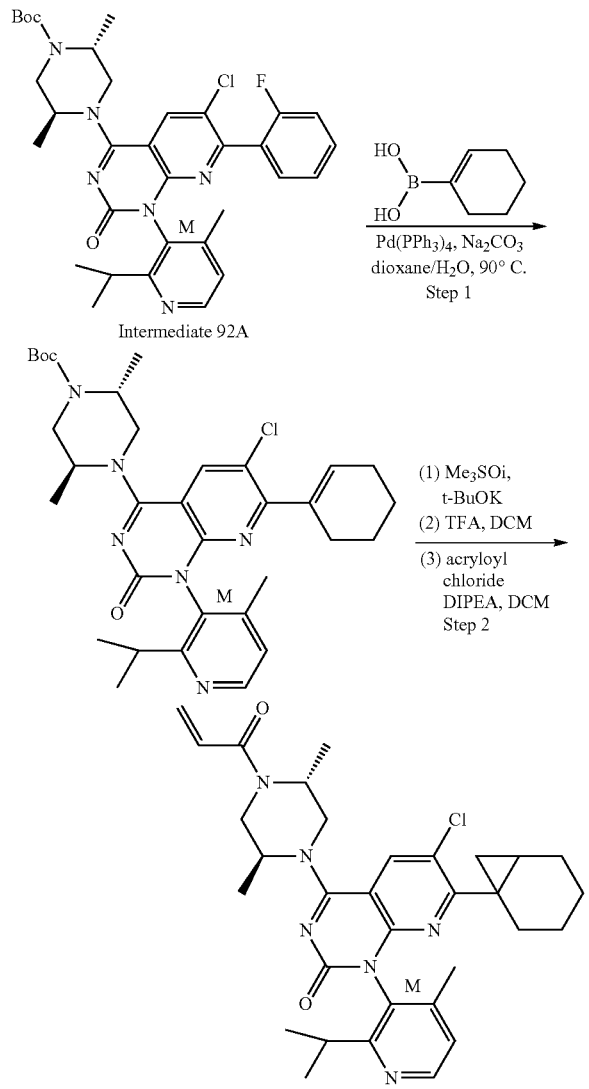

Step 1: (M)-tert-Butyl (2R,5S)-4-(6-chloro-7-(cyclohex-1-en-1-yl)-1-(2-isopropyl-4-methylpyridin-3-yl)-2-oxo-1,2-dihydropyrido[2,3-d]pyrimidin-4-yl)-2,5-dimethylpiperazine-1-carboxylate A yellow heterogeneous mixture of tert-butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 92A, 0.50 g, 0.89 mmol), cyclohexen-1-ylboronic acid (0.17 g, 1.34 mmol), sodium carbonate, anhydrous, powder (0.28 g, 2.67 mmol), and tetrakis(triphenylphosphine) palladium(0) (0.10 g, 0.09 mmol) in 1,4-dioxane (3.0 mL) and water (1.5 mL) was stirred and heated at 90° C. for 3.5 h. The reaction mixture was allowed to cool to room temperature and evaporated to dryness. The resulting crude product was purified by silica gel chromatography (eluent: 0-100% of EtOAc/heptane) to provide tert-butyl (2R,5S)-4-(6-chloro-7-(cyclohex-1-en-1-yl)-1-(2-isopropyl-4-methylpyridin-3-yl)-2-oxo-1,2-dihydropyrido[2,3-d]pyrimidin-4-yl)-2,5-dimethylpiperazine-1-carboxylate (0.26 g, 0.43 mmol, 48.8% yield) as white syrupy solid. $^1$H NMR (400 MHz, DMSO-$d_6$) δ 8.44-8.48 (m, 1H), 8.27 (s, 1H), 7.22-7.25 (m, 1H), 6.33 (t, J=3.7 Hz, 1H), 4.78 (br s, 1H), 4.18-4.41 (m, 1H), 3.36-4.09 (m, 4H), 2.55-2.68 (m, 1H), 2.14 (br d, J=1.9 Hz, 2H), 2.05 (br s, 1H), 1.96 (br d, J=2.1 Hz, 1H), 1.85-1.91 (m, 3H), 1.47-1.56 (m, 4H), 1.44 (s, 9H), 1.31 (d, J=6.4 Hz, 3H), 1.13 (br d, J=6.4 Hz, 3H), 1.05 (d, J=6.6 Hz, 3H), 0.94-0.99 (m, 3H). m/z (ESI, +ve ion): 607.3 (M+H)$^+$.

Step 2: (M)-6-Chloro-4-[(2S,5R)-2,5-dimethyl-4-prop-2-enoyl-piperazin-1-yl]-1-(2-isopropyl-4-methyl-3-pyridyl)-7-[norcaran-1-yl]pyrido[2,3-d]pyrimidin-2-one To a stirred yellow clear solution of trimethylsulfoxonium iodide (0.11 g, 0.51 mmol) in dimethyl sulfoxide (1 mL) was added potassium tert-butoxide solution (1 M in THF, 0.51 mL, 0.51 mmol) and the resulting colorless clear mixture was stirred at room temperature. After 40 minutes, to the above colorless clear mixture was added a solution of tert-butyl (2R,5S)-4-(6-chloro-7-(cyclohex-1-en-1-yl)-1-(2-isopropyl-4-methylpyridin-3-yl)-2-oxo-1,2-dihydropyrido[2,3-d]pyrimidin-4-yl)-2,5-dimethylpiperazine-1-carboxylate (0.26 g, 0.43 mmol) in tetrahydrofuran (2 mL) and the resulting red clear mixture was stirred at room temperature. After 21.5 hours, the reaction mixture was quenched with sat'd NH4Cl (50 mL) and extracted with EtOAc (2 t 50 mL). The combined organic extracts were dried over MgSO4. The solution was filtered and concentrated in vacuo to give the crude material as a yellow syrup. The resulting crude product was purified by silica gel chromatography (eluent: 0-100% of EtOAc-EtOH (3:1)/heptane) to provide tert-butyl (2R,5S)-4-(7-(bicyclo[4.1.0]heptan-1-yl)-6-chloro-1-(2-isopropyl-4-methylpyridin-3-yl)-2-oxo-1,2-dihydropyrido[2,3-d]pyrimidin-4-yl)-2,5-dimethylpiperazine-1-carboxylate (0.06 g, 0.10 mmol, 23.70% yield) as white syrupy solid, which was including triphenylphosphine oxdie and byproducts. m/z (ESI, +ve ion): 621.3 (M+H)$^+$. The material was used in the next step without further purification.

To a colorless clear solution of tert-butyl (2R,5S)-4-(7-(bicyclo[4.1.0]heptan-1-yl)-6-chloro-1-(2-isopropyl-4-methylpyridin-3-yl)-2-oxo-1,2-dihydropyrido[2,3-d]pyrimidin-4-yl)-2,5-dimethylpiperazine-1-carboxylate (0.06 g, 0.10 mmol) in dichloromethane (2.0 mL) was added trifluoroacetic acid (2.0 mL) and the resulting yellow clear mixture was stirred at room temperature. After 20 minutes, the mixture was concentrated in vacuo to give 7-(bicyclo[4.1.0]heptan-1-yl)-6-chloro-4-((2S,5R)-2,5-dimethylpiperazin-1-yl)-1-(2-isopropyl-4-methylpyridin-3-yl)pyrido[2,3-d]pyrimidin-2(1H)-one as yellow syrup. m/z (ESI, +ve ion): 521.2 (M+H)$^+$.

The above yellow syrup was dissolved in dichloromethane (2.0 mL) at 0° C. and treated with DIPEA (0.25 mL, 1.46 mmol), followed by acryloyl chloride (9.49 µl, 0.12 mmol) dropwise. The resulting mixture was stirred at 0° C. for 10 minutes and diluted with EtOAc (50 mL) and sat'd NH4Cl (50 mL). The aqueous layer was extracted with EtOAc (2×50 mL). The combined organic extracts were washed with satd NaHCO$_3$ (1×50 mL) and dried over Na2SO4. The solution was filtered and concentrated in vacuo to give the crude material as a yellow syrup. The resulting crude product was purified by silica gel chromatography (eluent: 0-100% of EtOAc-EtOH (3:1)/heptane) to provide a light-yellow syrupy solid. The above solid was further purified by reverse-phase preparative HPLC (using a Phenimenex Gemini column, 5 μm, C18, 110 Å, AXIA, 150×30 mm, 0.1% TFA in CH$_3$CN/H2O, gradient 10% to 90% over 15 min). The pure fractions were combined, neutralized with sat'd NaHCO$_3$ (50 mL), and extracted with DCM (2×50 mL). The combined organic extracts were dried over Na2SO4. The solution was filtered and concentrated in vacuo to give (M)-6-chloro-4-[(2S,5R)-2,5-dimethyl-4-prop-2-enoyl-piperazin-1-yl]-1-(2-isopropyl-4-methyl-3-pyridyl)-7-[norcaran-1-yl]pyrido[2,3-d]pyrimidin-2-one (0.01 g, 7.65 μmol. 15.7% yield) as yellow solid: $^1$H NMR (400 MHz, DMSO-d$_6$) δ 8.47 (d, J=4.8 Hz, 1H), 8.22-8.29 (m, 1H), 7.22-7.27 (m, 1H), 6.75-6.89 (m, 1H), 6.18 (dd, J=16.7, 2.2 Hz, 1H), 5.70-5.77 (m, 1H), 4.39-4.88 (m, 2H), 3.44-4.17 (m, 4H), 2.57-2.65 (m, 1H), 2.18 (t, J=7.4 Hz, 1H), 1.83-1.93 (m, 4H), 1.70-1.81 (m, 2H), 1.57-1.66 (m, 1H), 1.44-1.51 (m, 1H), 1.28 (br dd, J=9.5, 2.7 Hz, 5H), 1.10-1.20 (m, 4H), 1.06 (dd, J=12.2, 6.8 Hz, 3H), 0.95 (br dd, J=17.8, 6.6 Hz, 3H), 0.70-0.77 (m, 1H), 0.52 (t, J=5.4 Hz, 1H). m/z (ESI, +ve ion): 574.6 (M+H)$^+$.

Example 208

4-((2S,5R)-4-Acryloyl-2,5-dimethylpiperazin-1-yl)-6-chloro-7-(2-fluorophenyl)-1-(2-isopropyl-4-(methylsulfonyl)phenyl)pyrido[2,3-d]pyrimidin-2(1H)-one

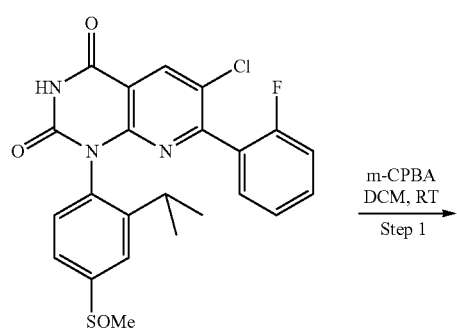

Method 103 using intermediate 173

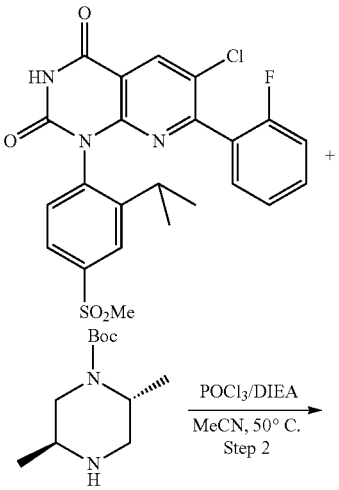

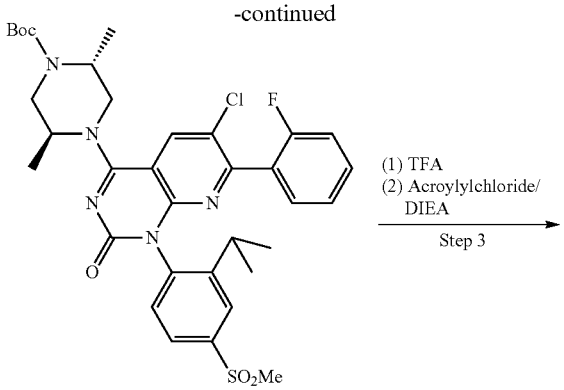

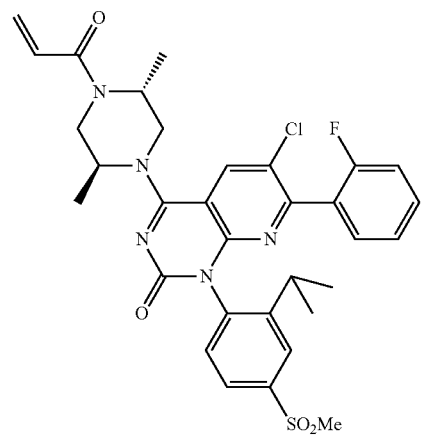

Example 208

Step 1: 6-Chloro-7-(2-fluorophenyl)-1-(2-isopropyl-4-(methylsulfonyl)phenyl)pyrido[2,3-d]pyrimidine-2,4(1H,3H)-dione To a stirring solution of 6-chloro-7-(2-fluorophenyl)-1-(2-isopropyl-6-(methylsulfinyl)phenyl)pyrido[2,3-d]pyrimidine-2,4(1H,3H)-dione (700 mg, 1.483 mmol, Method 103 using Intermediate 173) in DCM (12 mL) was added m-chloroperoxybenzoic acid (77 wt %, 512 mg, 2.22 mmol) at 20° C. After 15 min, the reaction was then washed with sat. NaHCO$_3$ (2 mL), dried over MgSO4, then purified by silica gel chromatography (4 g) eluting product with a gradient of 15>40% EtOAc/EtOH (3:1 blend)/heptane to afford 6-chloro-7-(2-fluorophenyl)-1-(2-isopropyl-4-(methylsulfonyl)phenyl)pyrido[2,3-d]pyrimidine-2,4(1H,3H)-dione as white solid. $^1$H NMR (400 MHz, CDCl$_3$) δ 8.58 (s, 1H), 8.57 (br s, 1H), 8.01 (d, J=2.28 Hz, 1H), 7.85 (dd, J=1.87, 8.29 Hz, 1H), 7.39-7.46 (m, 1H), 7.36 (d, J=8.29 Hz, 1H), 7.06-7.19 (m, 3H), 3.09-3.11 (m, 3H), 2.81 (spt, J=41.90 Hz, 1H), 1.24 (d, J=6.84 Hz, 3H), 1.09 (d, J=6.84 Hz, 3H). m/z (ESI, +ve ion): 488.0 (M+H)$^3$.

Step 2: tert-Butyl (2R,5S)-4-(6-chloro-7-(2-fluorophenyl)-1-(2-isopropyl-4-(methylsulfonyl)phenyl)-2-oxo-1,2-dihydropyrido[2,3-d]pyrimidin-4-yl)-2,5-dimethylpiperazine-1-carboxylate To a stirring solution of 6-chloro-7-(2-fluorophenyl)-1-(2-isopropyl-4-(methylsulfonyl)phenyl)pyrido[2,3-d]pyrimidine-2,4(1H,3H)-dione (660 mg, 1.353 mmol) in MeCN (6 mL) at 20° C. was added DIEA (354 µl, 2.029 mmol) followed by phosphorus(V) oxide chloride (189 µl, 2.029 mmol). After 45 min, the reaction was concentrated under reduced pressure, then azeotroped once with dry toluene (10 mL). The residue was dissolved in THF (6 mL), chilled to 0° C., DIEA added (1 mL) followed by (2R,5S)-tert-butyl 2,5-dimethylpiperazine-1-carboxylate (435 µl, 2.029 mmol). After 10 min, the reaction was partitioned between EtOAc (30 mL) and sat. NaHCO₃ (15 mL). The organic was dried over MgSO4, concentrated under reduced pressure, then purified via silica gel chromatography (40 g) eluting product with a gradient of 5>50% EtOAc/EtOH (3:1 blend) to afford tert-butyl (2R,5S)-4-(6-chloro-7-(2-fluorophenyl)-1-(2-isopropyl-4-(methylsulfonyl)phenyl)-2-oxo-1,2-dihydropyrido[2,3-d]pyrimidin-4-yl)-2,5-dimethylpiperazine-1-carboxylate as white solid. m/z (ESI, +ve ion): 684.0 (M+H)⁺.

Step 3: 4-((2S,5R)-4-Acryloyl-2,5-dimethylpiperazin-1-yl)-6-chloro-7-(2-fluorophenyl)-1-(2-isopropyl-4-(methylsulfonyl)phenyl)pyrido[2,3-d]pyrimidin-2(1H)-one (Example 208)

A solution of tert-butyl (2R,5S)-4-(6-chloro-7-(2-fluorophenyl)-1-(2-isopropyl-4-(methylsulfonyl)phenyl)-2-oxo-1,2-dihydropyrido[2,3-d]pyrimidin-4-yl)-2,5-dimethylpiperazine-1-carboxylate (400 mg, 0.585 mmol) was stirred in TFA for 10 min at RT. The reaction was concentrated under reduced pressure and azeotroped once with dry toluene (10 mL). The residue was then dissolved in DCM (5 mL), chilled to 0° C. under nitrogen, and DIEA (1 mL) added. To the reaction was added a solution of 2-propenoyl chloride (52.2 µl, 0.643 mmol) in DCM (1 mL). After 5 min, the reaction was partitioned between DCM (5 mL) and sat. NaHCO₃ (10 mL). The aqueous was further extracted with DCM (2 mL). The combined organics were then dried over MgSO4, concentrated under reduced pressure, then purified via silica gel chromatography (40 g) eluting products with a gradient of 5>80% EtOAc/EtOH (3:1 blend) to afford 4-((2S,5R)-4-acryloyl-2,5-dimethylpiperazin-1-yl)-6-chloro-7-(2-fluorophenyl)-1-(2-isopropyl-4-(methylsulfonyl)phenyl)pyrido[2,3-d]pyrimidin-2(1H)-one (Example 208) as white solid. ¹H NMR (400 MHz, CDCl3) δ 8.10 (s, 1H), 7.96-8.01 (m, 1H), 7.80-7.88 (m, 1H), 7.38-7.47 (m, 1H), 7.30-7.37 (m, 1H), 7.07-7.20 (m, 3H), 6.50-6.70 (m, 1H), 6.33-6.46 (m, 1H), 5.75-5.84 (m, 1H), 4.86-5.25 (m, 2H), 4.26-4.53 (m, 1H), 3.36-4.06 (m, 3H), 3.08-3.12 (m, 3H), 2.61-2.80 (m, 1H), 1.30-1.54 (m, 6H), 1.20-1.29 (m, 6H). m/z (ESI, +ve ion): 638.2 (M+H)⁺.

Example 208-1

4-((2S,5R)-4-Acryloyl-2,5-dimethylpiperazin-1-yl)-6-chloro-7-(2-fluorophenyl)-1-(2-isopropyl-6-(methylsulfonyl)phenyl)pyrido[2,3-d]pyrimidin-2(1H)-one, Single Isomer

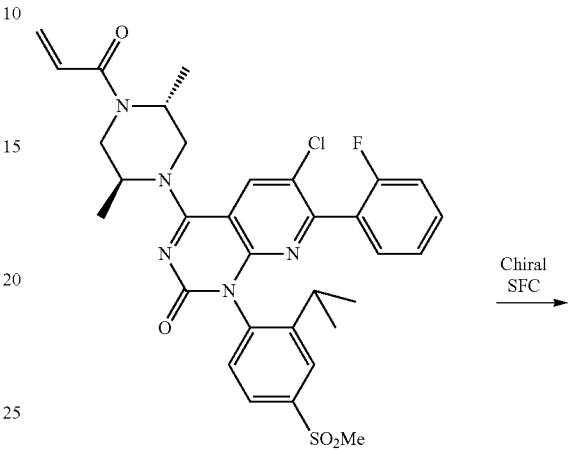

Atropisomers of 4-((2S,5R)-4-acryloyl-2,5-dimethylpiperazin-1-yl)-6-chloro-7-(2-fluorophenyl)-1-(2-isopropyl-6-(methylsulfonyl)phenyl)pyrido[2,3-d]pyrimidin-2(1H)-one (Example 208, 200 mg, 0.157 mmol) were separated by chiral SFC: ID 150×21 mm, 5 µm, 60% MeOH/CO₂, 80 g/min, 102 bar. This gave 4-((2S,5R)-4-acryloyl-2,5-dimethylpiperazin-1-yl)-6-chloro-7-(2-fluorophenyl)-1-(2-isopropyl-6-(methylsulfonyl)phenyl)pyrido[2,3-d]pyrimidin-2(1H)-one (Example 208-1), first eluting isomer, as white fluffy solid from lyophilization. ¹H NMR (400 MHz, DMSO-d₆) δ 8.43 (d, J=6.84 Hz, 1H), 7.94 (d, J=1.87 Hz, 1H), 7.84 (dd, J=1.87, 8.29 Hz, 1H), 7.48-7.56 (m, 2H), 7.21-7.34 (m, 3H), 6.77-6.92 (m, 1H), 6.20 (d, J=15.76 Hz, 1H), 5.72-5.80 (m, 1H), 4.44-4.92 (m, 2H), 3.73-4.31 (m, 4H), 3.31 (s, 3H), 2.64-2.77 (m, 1H). 1.36 (d, J=6.43 Hz, 3H), 1.24 (dd, J=6.63, 26.54 Hz, 3H), 1.14 (d, J=6.84 Hz, 3H), 1.04 (d, J=6.84 Hz, 3H). ¹⁹F NMR (376 MHz, DMSO-d₆) δ -113.55 (s, 1F), -113.57 (s, 1F). MS (ESI, +ve) m/z: 638.2 (M+1)⁺.

Example 208-2

4-((2S,5R)-4-Acryloyl-2,5-dimethylpiperazin-1-yl)-6-chloro-7-(2-fluorophenyl)-1-(2-isopropyl-6-(methylsulfonyl)phenyl)pyrido[2,3-d]pyrimidin-2(1H)-one, Single Isomer

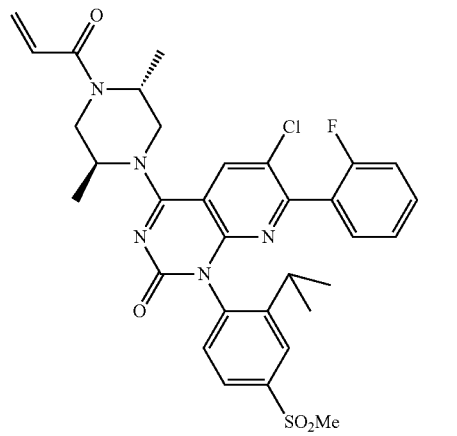

Example 208

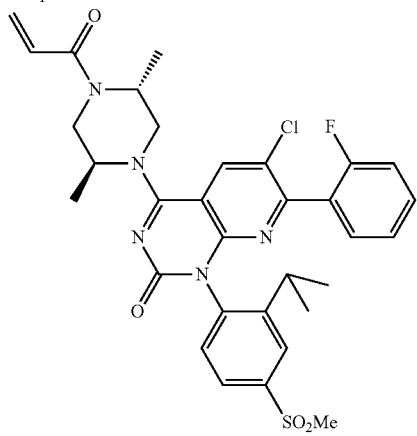

Single Isomer

Example 209-1 and Example 209-2

4-((2S,5R)-4-Acryloyl-2,5-dimethylpiperazin-1-yl)-6-chloro-7-(2-fluorophenyl)-1-(2-isopropyl-6-(methylsulfinyl)phenyl)pyrido[2,3-d]pyrimidin-2(1H)-one, 2 Single Isomers

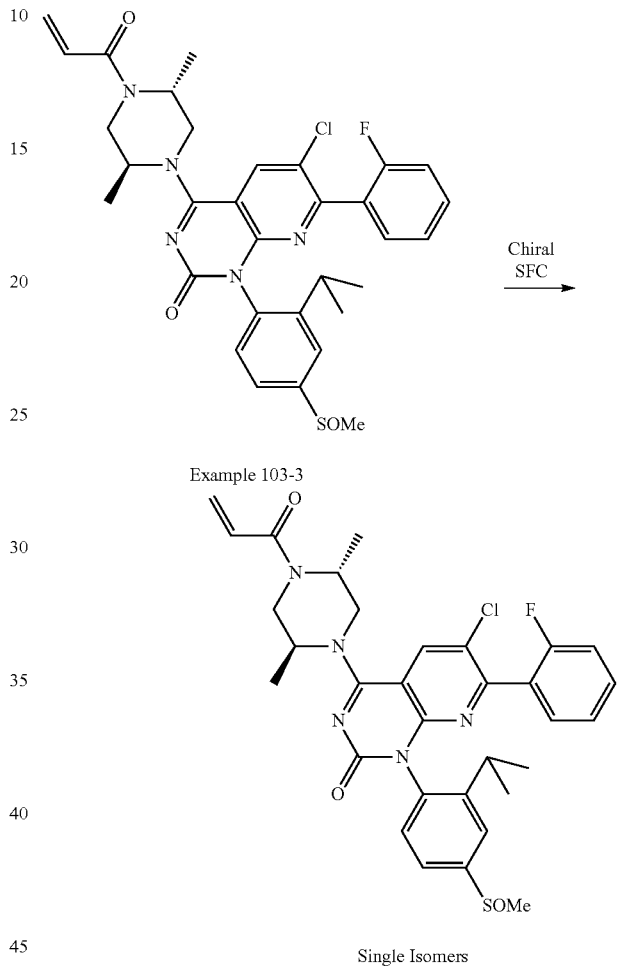

Atropisomers of 4-((2S,5R)-4-acryloyl-2,5-dimethylpiperazin-1-yl)-6-chloro-7-(2-fluorophenyl)-1-(2-isopropyl-6-(methylsulfonyl)phenyl)pyrido[2,3-d]pyrimidin-2(1H)-one (Example 208, 200 mg, 0.157 mmol) were separated by chiral SFC: ID 150×21 mm, 5 μm, 60% MeOH/CO$_2$, 80 g/min, 102 bar. This gave 4-((2S,5R)-4-acryloyl-2,5-dimethylpiperazin-1-yl)-6-chloro-7-(2-fluorophenyl)-1-(2-isopropyl-6-(methylsulfonyl)phenyl)pyrido[2,3-d]pyrimidin-2(1H)-one (Example 208-2), second eluting isomer, as a white fluffy solid from lyophilization. $^1$H NMR (400 MHz, DMSO-d$_6$) δ 8.47 (d, J=1.66 Hz, 1H), 7.94 (d, J=1.66 Hz, 1H), 7.82 (dd, J=2.28, 8.29 Hz, 1H), 7.46-7.54 (m, 2H), 7.18-7.34 (m, 3H), 6.75-6.92 (m, 1H), 6.19 (d, J=15.34 Hz, 1H), 5.71-5.79 (m, 1H), 4.44-4.96 (m, 2H), 3.46-4.22 (m, 4H), 3.30 (s, 3H), 2.58-2.77 (m, 1H), 1.32 (t, J=14.30 Hz, 3H), 1.23 (dd, J=7.05, 26.95 Hz, 3H), 1.12 (d, J=6.84 Hz, 3H), 1.04 (d, J=6.63 Hz, 3H). $^{19}$F NMR (376 MHz, DMSO-d$_6$) δ −113.74 (s, 1F), −113.75 (s, 1F). MS (ESI, +ve) m/z: 638.2 (M+1)$^+$.

Atropisomers of 4-((2S,5R)-4-acryloyl-2,5-dimethylpiperazin-1-yl)-6-chloro-7-(2-fluorophenyl)-1-(2-isopropyl-6-(methylsulfinyl)phenyl)pyrido[2,3-d]pyrimidin-2(1H)-one (Example 103-3) were separated by chiral SFC: Step 1 chiral SFC AD-H, 30×250 mm, 5 μm, 20% IPA/CO$_2$, 150 g/min, 178 bar. Step 2: chiral SFC Welko (R,R) 21×250 mm, 5 μm, 60% MeOH/CO$_2$, 64 bar. This gave 4-((2S,5R)-4-acryloyl-2,5-dimethylpiperazin-1-yl)-6-chloro-7-(2-fluorophenyl)-1-(2-isopropyl-6-(methylsulfinyl)phenyl)pyrido[2,3-d]pyrimidin-2(1H)-one (Example 209-1), single isomer, this was the first eluting peak of step 2, and was isolated as a white fluffy solid from lyophilization. $^1$H NMR (400 MHz, CDCl$_3$) δ 8.01-8.18 (m, 1H), 7.61-7.68 (m, 1H), 7.58-7.61 (m, 1H), 7.29-7.48 (m, 2H), 7.13-7.20 (m, 2H), 7.09 (t, J=18.50 Hz, 1H), 6.50-6.72 (m, 1H), 6.39 (t, J=30.30 Hz, 1H), 5.80 (dd, J=8.09, 16.59 Hz, 1H), 4.42-5.27 (m, 2H), 3.42-4.42 (m, 4H), 2.75-2.82 (m, 3H), 2.60-2.72 (m, 1H), 1.19-1.45 (m, 9H), 1.01-1.10 (m, 3H). $^{19}$F NMR (376 MHz, CDCl$_3$) δ 112.42 (s, 1F), −112.45 (s, 1F). MS (ESI, +ve) m/z: 622.3 (M+1)$^+$. The separation also provided 4-((2S, 5R)-4-acryloyl-2,5-dimethylpiperazin-1-yl)-6-chloro-7-(2-fluorophenyl)-1-(2-isopropyl-6-(methylsulfinyl)phenyl)pyrido[2,3-d]pyrimidin-2(1H)-one (Example 209-2), single isomer, this was the second eluting peak of step 2, and isolated as white fluffy solid from lyophilization. $^1$H NMR (400 MHz, CDCl$_3$) δ 8.09 (br s, 1H), 7.54-7.90 (m, 2H), 7.30-7.48 (m, 2H), 7.14-7.20 (m, 2H), 7.10 (t, J=18.00 Hz, 1H), 6.49-6.71 (m, 1H), 6.33-6.47 (m, 1H), 5.72-5.89 (m, 1H), 3.35-5.21 (m, 6H), 2.78 (s, 3H), 2.63-2.75 (m, 1H), 1.17-1.48 (m, 9H), 1.01-1.09 (m, 3H). $^{19}$F NMR (376 MHz, CDCl$_3$) δ −112.34 (s, 1F), −112.35 (s, 1F), −112.39 (s, 1F). MS (ESI, +ve) m/z: 622.2 (M+1)$^+$.

Example 209-3

4-((2S,5R)-4-Acryloyl-2,5-dimethylpiperazin-1-yl)-6-chloro-7-(2-fluorophenyl)-1-(2-isopropyl-6-(methylsulfinyl)phenyl)pyrido[2,3-d]pyrimidin-2(1H)-one, Single Isomer nyl)phenyl)pyrido[2,3-d]pyrimidin-2(1H)-one (Example 209-3), single isomer, this was the third eluting peak (peak 1 and peak 2 overlap), and was isolated as a white fluffy solid from lyophilization. $^1$H NMR (400 MHz, CDCl$_3$) δ 8.08 (s, 1H), 7.88 (d, J=1.87 Hz, 1H), 7.38-7.47 (m, 1H), 7.35 (dd, J=1.87, 7.88 Hz, 1H), 7.21-7.25 (m, 1H), 7.13-7.18 (m, 2H), 7.09 (t, J=18.70 Hz, 1H), 6.51-6.70 (m, 1H), 6.40 (t, J=30.10 Hz, 1H), 5.80 (dd, J=8.09, 17.83 Hz, 1H), 3.44-5.26 (m, 6H), 2.78 (s, 3H), 2.59-2.71 (m, 1H), 1.30-1.48 (m, 6H), 1.25 (d, J=6.63 Hz, 3H), 1.07 (d, J=6.63 Hz, 3H) [33H]. $^{19}$F NMR (376 MHz, CDCl$_3$) δ −112.37 (s, 1F), −112.41 (s, 1F), −112.43 (s, 1F). MS (ESI, +ve) m/z: 622.3 (M+1)$^+$.

Example 209-4

4-((2S,5R)-4-Acryloyl-2,5-dimethylpiperazin-1-yl)-6-chloro-7-(2-fluorophenyl)-1-(2-isopropyl-6-(methylsulfinyl)phenyl)pyrido[2,3-d]pyrimidin-2(1H)-one, Single Isomer

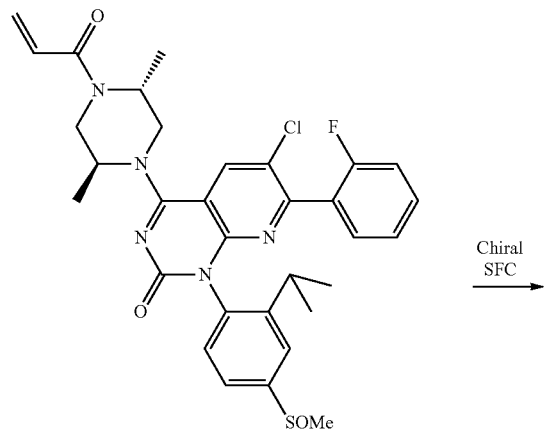

Example 103-3

Chiral SFC →

Single Isomer

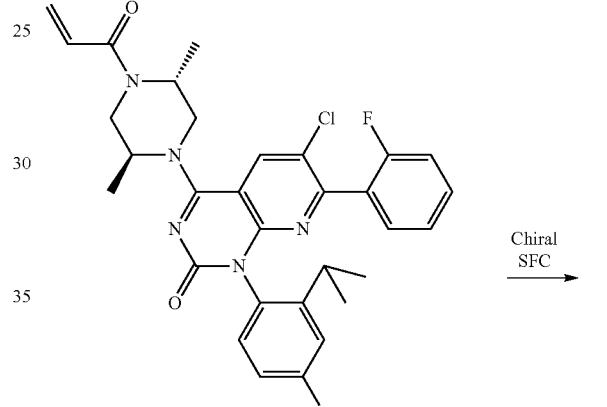

Example 103-3

Chiral SFC →

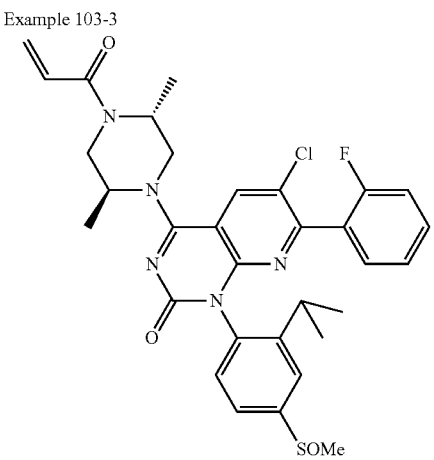

Single Isomer

Atropisomers of 4-((2S,5R)-4-acryloyl-2,5-dimethylpiperazin-1-yl)-6-chloro-7-(2-fluorophenyl)-1-(2-isopropyl-6-(methylsulfinyl)phenyl)pyrido[2,3-d]pyrimidin-2(1H)-one (Example 103-3) were separated by chiral SFC: AD-H, 30×250 mm, 5 μm, 20% IPA/CO$_2$, 150 g/min, 178 bar. This gave 4-((2S,5R)-4-acryloyl-2,5-dimethylpiperazin-1-yl)-6-chloro-7-(2-fluorophenyl)-1-(2-isopropyl-6-(methylsulfi- Atropisomers of 4-((2S,5R)-4-acryloyl-2,5-dimethylpiperazin-1-yl)-6-chloro-7-(2-fluorophenyl)-1-(2-isopropyl-6-(methylsulfinyl)phenyl)pyrido[2,3-d]pyrimidin-2(1H)-one (Example 103-3) were separated by chiral SFC: AD-H, 30×250 mm, 5 μm, 20% IPA/CO$_2$, 150 g/min, 178 bar. This gave 4-((2S,5R)-4-acryloyl-2,5-dimethylpiperazin-1-yl)-6- chloro-7-(2-fluorophenyl)-1-(2-isopropyl-6-(methylsulfinyl)phenyl)pyrido[2,3-d]pyrimidin-2(1H)-one (Example 209-4), single isomer. This was the forth eluting peak (peak 1 and peak 2 overlap), and was isolated as a white fluffy solid from lyophilization. ¹H NMR (400 MHz, CDCl₃) δ 8.09 (s, 1H), 7.86 (s, 1H), 7.33-7.47 (m, 2H), 7.21-7.25 (m, 1H), 7.14-7.19 (m, 2H), 7.10 (t, J=18.70 Hz, 1H), 6.49-6.74 (m, 1H), 6.40 (t, J=32.30 Hz, 1H), 5.80 (t, J=17.60 Hz, 1H), 3.38-5.19 (m, 6H), 2.78 (s, 3H), 2.71 (br s, 1H), 1.18-1.54 (m, 9H), 1.05 (d, J=7.46 Hz, 3H) [33H]. ¹⁹F NMR (376 MHz, CDCl₃) δ -112.34 (s, 1F), -112.39 (s, 1F). MS (ESI, +ve) m/z: 622.3 (M+1)⁺.

Example 210

4-((2S,5R)-4-Acryloyl-2,5-dimethylpiperazin-1-yl)-6-chloro-1-(2-isopropyl-4-methylpyridin-3-yl)-7-(2-(methylsulfonyl)phenyl)pyrido[2,3-d]pyrimidin-2(1H)-one

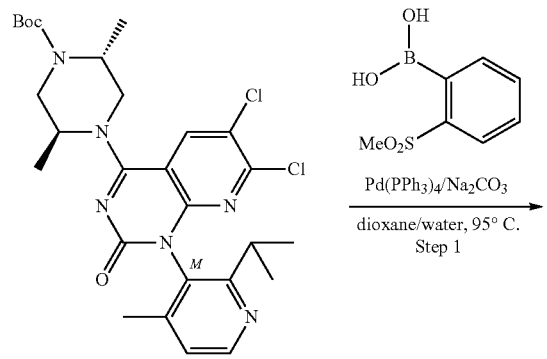

Intermediate 92A

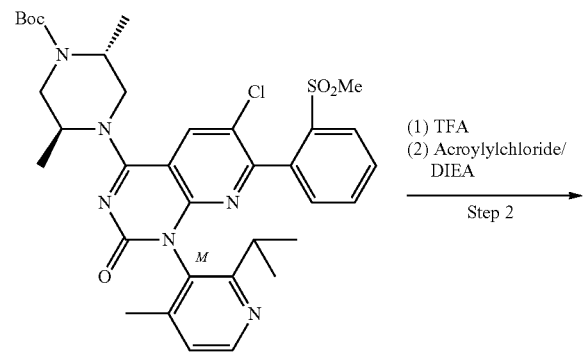

(1) TFA
(2) Acroylylchloride/DIEA

Step 2

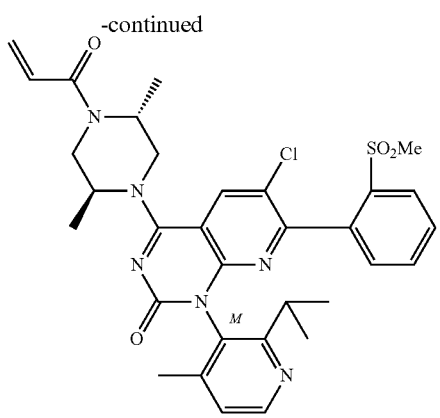

Example 210

Step 1: tert-Butyl (2R,5S)-4-(6-chloro-1-(2-isopropyl-4-methylpyridin-3-yl)-7-(2-(methylsulfonyl)phenyl)-2-oxo-1,2-dihydropyrido[2,3-d]pyrimidin-4-yl)-2,5-dimethylpiperazine-1-carboxylate A suspension of tert-butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (250 mg, 0.445 mmol, Intermediate 92A), 2-(methylsulfonyl)phenyl)boronic acid (Sigma-Aldrich, St. Louis, Mo., USA, 134 mg, 0.668 mmol), tetrakis(triphenylphosphine)palladium(0) (51.5 mg, 0.045 mmol), sodium carbonate (142 mg, 1.336 mmol) in 1,4-dioxane (2 mL) and water (1 mL) was sparged with argon for 1 min then heated to 95° C. for 40 min. The reaction was then extracted with EtOAc (20 mL), dried over MgSO₄, concentrated under reduced pressure, then purified by silica gel chromatography (24 g) eluting products with a gradient of 5>60% EtOAc/EtOH (3:1 blend)/heptane to give tert-butyl (2R,5S)-4-(6-chloro-1-(2-isopropyl-4-methylpyridin-3-yl)-7-(2-(methylsulfonyl)phenyl)-2-oxo-1,2-dihydropyrido[2,3-d]pyrimidin-4-yl)-2,5-dimethylpiperazine-1-carboxylate as colorless solid. m/z (ESI, +ve ion): 681.2 (M+H)⁺.

Step 2: 4-((2S,5R)-4-Acryloyl-2,5-dimethylpiperazin-1-yl)-6-chloro-1-(2-isopropyl-4-methylpyridin-3-yl)-7-(2-(methylsulfonyl)phenyl)pyrido[2,3-d]pyrimidin-2(1H)-one (Example 210)

A solution of tert-butyl (2R,S)-4-(6-chloro-1-(2-isopropyl-4-methylpyridin-3-yl)-7-(2-(methylsulfonyl)phenyl)-2-oxo-1,2-dihydropyrido[2,3-d]pyrimidin-4-yl)-2,5-dimethylpiperazine-1-carboxylate (135 mg, 0.198 mmol) was stirred in TFA (2 mL) for 15 min at 20° C. The reaction was then concentrated under reduced pressure, and the residue was dissolved in DCM (5 mL) with DIEA (0.25 mL) added. The solution was chilled to 0° C. and acryloyl chloride (19.3 μl, 0.238 mmol) added. The cooling bath was removed and the solution stirred at 20° C. for 1 hr. The reaction was then washed with sat. NaHCO₃ (5 mL). The organic was dried over MgSO₄, concentrated under reduced pressure, then purified by silica gel chromatography (4 g) eluting products with a gradient of 15>100% EtOAc/EtOH (3:1 blend)/heptane to afford 4-((2S,5R)-4-acryloyl-2,5-dimethylpiperazin-1-yl)-6-chloro-1-(2-isopropyl-4-methylpyridin-3-yl)-7-(2-(methylsulfonyl)phenyl)pyrido[2,3-d]pyrimidin-2(1H)-one (Example 210) as white solid. ¹H NMR (400 MHz, CDCl3) δ 8.45 (d, J=4.77 Hz, 1H), 8.14 (s, 1H), 8.01-8.07 (m, 1H), 7.60-7.73 (m, 2H), 7.20-7.51 (m, 1H), 7.04 (d, J=4.98 Hz, 1H), 6.31-6.71 (m, 2H), 5.75-5.86 (m, 1H), 3.51-5.23 (m, 6H), 2.57-2.72 (m, 1H), 2.47-2.54 (m, 3H), 1.90-2.17 (m, 3H), 0.92-1.55 (m, 12H). m/z (ESI, +ve ion): 635.2 (M+H)$^+$.

Example 211-1

(M)-4-((2S,5R)-4-Acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one

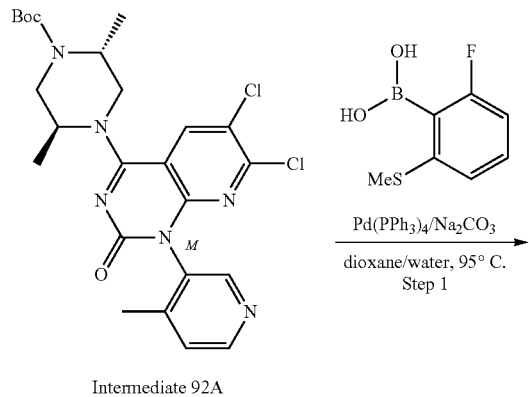

Intermediate 92A

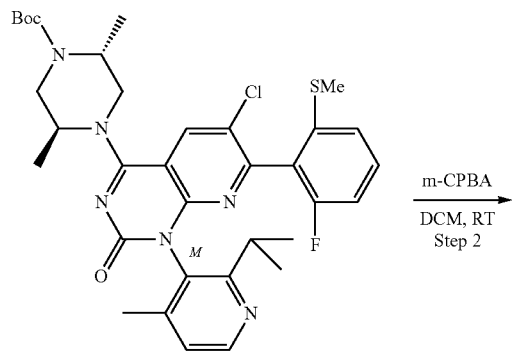

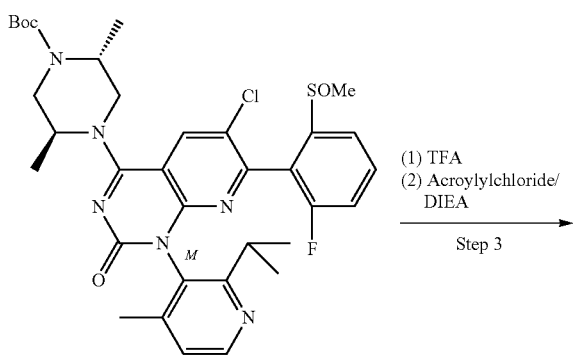

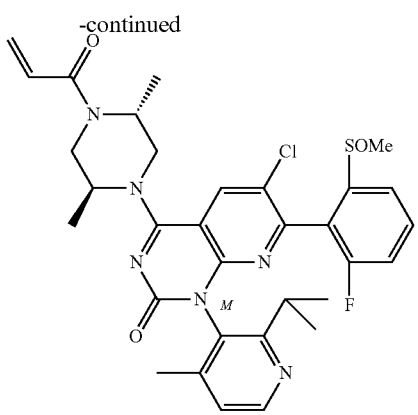

Example 211-1

Step 1: tert-Butyl (2R,5S)-4-(6-chloro-7-(2-fluoro-6-(methylthio)phenyl)-1-(2-isopropyl-4-methylpyridin-3-yl)-2-oxo-1,2-dihydropyrido[2,3-d]pyrimidin-4-y)-2,5-dimethylpiperazine-1-carboxylate A suspension of tert-butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (350 mg, 0.623 mmol, Intermediate 92A), (2-fluoro-6-(methylthio)phenyl)boronic acid (Aurum Pharmatech LLC, Franklin Park, N.J., USA, 128 mg, 0.686 mmol), tetrakis(triphenylphosphine)palladium(0) (72.0 mg, 0.062 mmol), sodium carbonate (198 mg, 1.87 mmol) in 1,4-dioxane (4 mL) and water (2 mL) was sparged with argon for 1 min then heated to 95° C. for 60 min. The reaction was then extracted with EtOAc (20 mL). dried over MgSO$_4$, concentrated under reduced pressure, then purified by silica gel chromatography (24 g) eluting products with a gradient of 5>60% EtOAc/EtOH (3:1 blend)/heptane to give tert-butyl (2R,5S)-4-(6-chloro-7-(2-fluoro-6-(methylthiophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate as white solid. $^1$H NMR (400 MHz, CDCl$_3$) δ 8.47 (d, J=3.73 Hz, 1H), 8.15 (d, J=1.87 Hz, 1H), 7.30-7.39 (m, 1H), 7.04-7.11 (m, 2H), 6.90 (q, J=24.70 Hz, 1H), 4.16-5.05 (m, 3H), 3.44-3.96 (m, 4H), 2.63-2.92 (m, 1H), 2.32 (d, J=14.51 Hz, 3H), 2.02 (d, J=35.66 Hz, 3H), 1.51 (s, 9H), 1.28-1.50 (m, 8H), 1.01-1.16 (m, 3H). $^{19}$F NMR (376 MHz, CDCl$_3$) δ 114.43 (s, 1F), −115.25 (s, 1F). m/z (ESI, +ve ion): 667.3 (M+H)$^+$.

Step 2: tert-Butyl (2R,5S)-4-(6-chloro-7-(2-fluoro-6-(methylsulfinyl)phenyl)-1-(2-isopropyl-4-methylpyridin-3-yl)-2-oxo-1,2-dihydropyrido[2,3-d]pyrimidin-4-y)-2,5-dimethylpiperazine-1-carboxylate To a stirring solution of tert-butyl (2R,5S)-4-(6-chloro-7-(2-fluoro-6-(methylthio)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (210 mg, 0.315 mmol) in DCM (5 mL) at 20° C. was added dropwise a solution of m-chloroperoxobenzoic acid (77 wt %, 78 mg, 0.346 mmol) in DCM (1 mL). The reaction was then washed with 5% Na2CO3 (5 mL). The aqueous was then further extracted with DCM. The combined organics were then dried over MgSO$_4$, concentrated under reduced pressure, then purified by silica gel chromatography (12 g) eluting products with a gradient of 15>70% EtOAc/EtOH (3:1 blend)/heptane to afford tert-butyl (2R,5S)-4-(6-chloro-7-(2-fluoro-6-(methylsulfinyl)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate as colorless film. m/z (ESI, +ve ion): 683.0 (M+H)+.

Step 3: 4-((2S,5R)-4-Acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one (Example 211-1)

A solution of tert-butyl (2R,5S)-4-(6-chloro-7-(2-fluoro-6-(methylsulfinyl)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (170 mg, 0.249 mmol) in TFA was stirred for 15 min at 20° C. The reaction was then concentrated under reduced pressure, and the residue was dissolved in DCM (5 mL), DIEA (1 mL) followed by the addition of acryloyl chloride (30.3 µl, 0.373 mmol) at 20° C. The solution was stirred at RT for 1 hr, then washed with sat. Na$_2$CO$_3$ (5 mL). The separated aqueous was further extracted with DCM (10 mL). The organic was dried over MgSO$_4$, concentrated under reduced pressure, then purified by silica gel chromatography (4 g) eluting products with a gradient of 15>100% EtOAc/EtOH (3:1 blend)/heptane to afford (M)-4-((2S,5R)-4-acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one (Example 211-1) as white solid. $^1$H NMR (400 MHz, CDCl$_3$) δ 8.47-8.61 (m, 1H), 8.11-8.23 (m, 1H), 7.46-7.95 (m, 2H), 7.28-7.32 (m, 1H), 7.06-7.20 (m, 1H), 6.33-6.69 (m, 2H), 5.75-5.98 (m, 1H), 3.67-5.19 (m, 6H), 2.50-2.96 (m, 1H), 1.90-2.19 (m, 6H), 1.13-1.47 (m, 12H). $^{19}$F NMR (376 MHz, CDCl$_3$) δ –112.28 (d, J=13.88 Hz, 1F), –112.63 (d, J=20.81 Hz, 1F). m/z (ESI, +ve ion): 637.1 (M+H)+.

Example 211-2

(M)-4-((2S,5R)-4-Acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one, Single Isomer

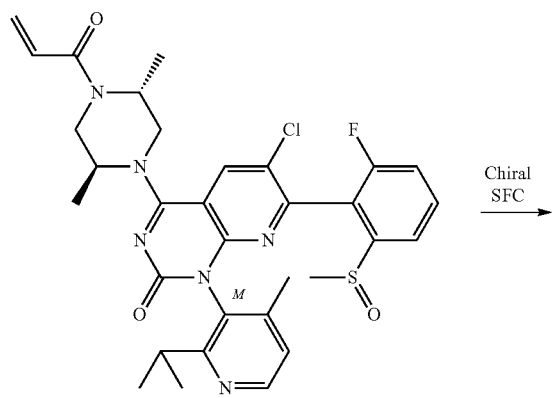

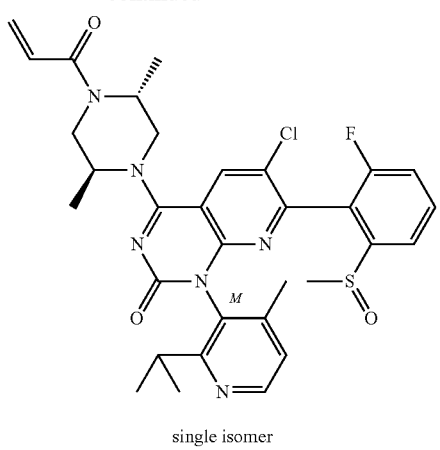

single isomer

Atropisomers of (M)-4-((2S,5R)-4-acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one (Example 211-1) were separated by chiral SFC: OD, 21×150 mm, 5 µm, 15% EtOH/CO$_2$, 80 g/min, 102 bar. This gave (M)-4-((2S,5R)-4-acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one (Example 211-2), single isomer, first eluting peak. and isolated as white fluffy powder from lyophilization. $^1$H NMR (600 MHz, CDCl3) δ 8.48 (d, J=5.20 Hz, 1H), 8.18 (s, 1H), 7.91 (d, J=7.94 Hz, 1H), 7.67-7.73 (m, 1H), 7.29 (t, J=16.70 Hz, 1H), 7.13 (br s, 1H), 6.53-6.69 (m, 1H), 6.37-6.45 (m, 1H), 5.78-5.85 (m, 1H), 3.48-5.18 (m, 6H), 2.55-2.65 (m, 1H), 2.10-2.15 (m, 6H), 1.13-1.53 (m, 12H). m/z (ESI, +ve ion): 637.3 (M+H)+.

Example 211-3

(M)-4-((2S,5R)-4-Acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one, Single Isomer

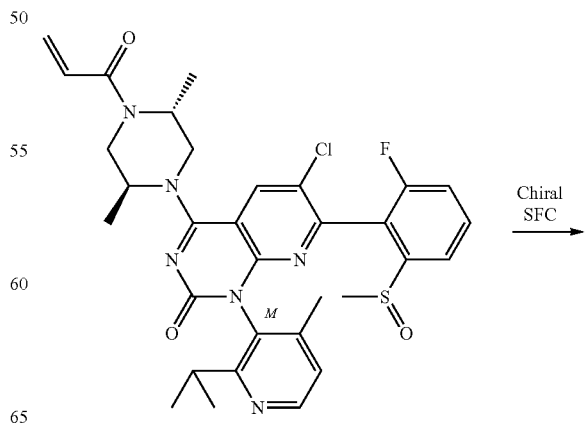

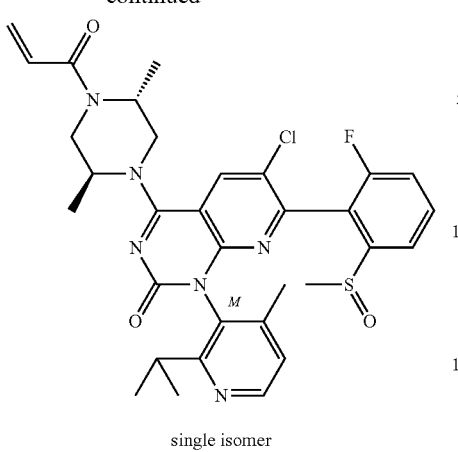

single isomer

Atropisomers of (M)-4-((2S,5R)-4-acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one (Example 211-1) were separated by chiral SFC: OD, 21×150 mm, 5 μm, 15% EtOH/CO$_2$, 80 g/min, 102 bar. This gave (M)-4-((2S,5R)-4-acryloyl-2,5-dimethylpiperazin-1-yl)-6-chloro-7-(2-fluoro-6-(methylsulfinyl)phenyl)-1-(2-isopropyl-4-methylpyridin-3-yl)pyrido[2,3-d]pyrimidin-2(1H)-one (Example 211-3), single isomer, second eluting peak, and isolated as white fluffy powder from lyophilization. $^1$H NMR (600 MHz, CDCl3) δ 8.47 (d, J=4.65 Hz, 1H), 8.10-8.22 (m, 1H), 7.44-7.97 (m, 2H), 7.22-7.33 (m, 2H), 7.00-7.14 (m, 1H), 6.50-6.71 (m, 1H), 6.33-6.46 (m, 1H), 5.73-5.87 (m, 1H), 3.37-5.18 (m, 6H), 2.61-2.90 (m, 1H), 1.91-2.11 (m, 6H), 1.15-1.58 (m, 12H). m/z (ESI, +ve ion): 637.3 (M+H)$^+$.

Example 212-1

(M)-4-((2S,5R)-4-Acryloyl-2,5-dimethylpiperazin-1-yl)-6-chloro-1-(2-isopropyl-4-methylpyridin-3-yl)-7-(2-(methylsulfinyl)phenyl)pyrido[2,3-d]pyrimidin-2(1H)-one

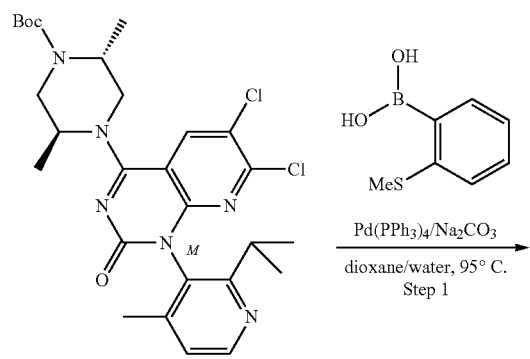

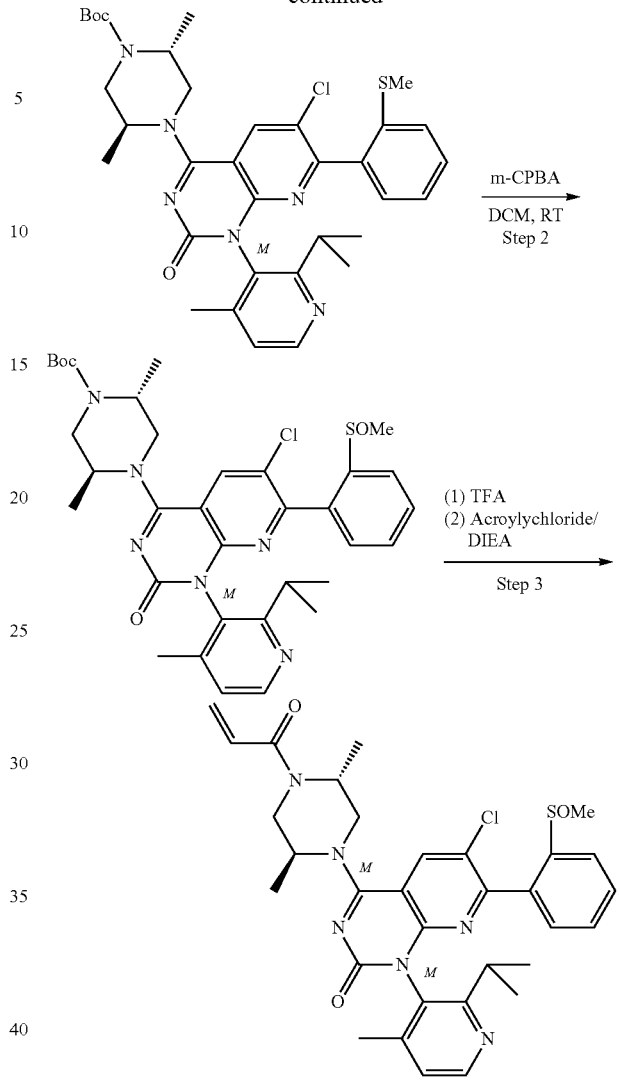

Example 212-1

Step 1: (M)-tert-Butyl (2R,5S)-4-(6-chloro-1-(2-isopropyl-4-methylpyridin-3-yl)-7-(2-(methylthio)phenyl)-2-oxo-1,2-dihydropyrido[2,3-d]pyrimidin-4-yl)-2,5-dimethylpiperazine-1-carboxylate A suspension of (M)-tert-butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 92A. 1.0 g, 1.78 mmol), 2-(methylthio)phenylboronic acid (Sigma-Aldrich Corp., St. Louis, Mo., USA, 0.449 g, 2.67 mmol), tetrakis(triphenylphosphine)palladium(0) (0.103 g, 0.089 mmol), sodium carbonate (0.224 ml, 5.34 mmol) in 1,4-dioxane (8 mL) and water (4 mL) was sparged with argon for 1 min then heated to 95° C. for 30 min. The reaction was then extracted with EtOAc (60 mL), dried over MgSO$_4$, concentrated under reduced pressure, then purified by silica gel chromatography (40 g) eluting products with a gradient of 5>60% EtOAc/EtOH (3:1 blend)/heptane to give tert-butyl (2R,5S)-4-(6-chloro-1-(2-isopropyl-4-methylpyridin-3-yl)-7-(2-(methylthio)phenyl)-2-oxo-1,2-dihydropyrido[2,3-d]pyrimidin-4- yl)-2,5-dimethylpiperazine-1-carboxylate as yellow tar. ¹H NMR (400 MHz, CDCl₃) δ 8.47 (br s, 1H), 8.12 (s, 1H), 7.31-7.73 (m, 3H), 7.19 (ddd, J=1.45, 7.46, 14.51 Hz, 1H), 7.03 (dd, J=0.83, 7.26 Hz, 1H), 3.42-5.02 (m, 6H), 2.66-2.86 (m, 1H), 2.28-2.32 (m, 3H), 2.01-2.10 (m, 3H), 1.49-1.55 (m, 9H), 1.43-1.49 (m, 3H), 1.21-1.35 (m, 6H), 0.99-1.15 (m, 3H). m/z (ESI, +ve ion): 649.1 (M+H)⁺.

Step 2: (M)-tert-Butyl (2R,5)-4-(6-chloro-1-(2-isopropyl-4-methylpyridin-3-yl)-7-(2-(methylsulfinyl)phenyl)-2-oxo-1,2-dihydropyrido[2,3-d]pyrimidin-4-yl)-2,5-dimethylpiperazine-1-carboxylate (Intermediate 212-1b)

To a stirring solution of (M)-tert-butyl (2R,5S)-4-(6-chloro-1-(2-isopropyl-4-methylpyridin-3-yl)-7-(2-(methylthio)phenyl)-2-oxo-1,2-dihydropyrido[2,3-d]pyrimidin-4-yl)-2,5-dimethylpiperazine-1-carboxylate (1.0 g, 1.54 mmol) in DCM (10 mL) at 20° C. was added dropwise a solution of m-chloroperoxobenzoic acid (77 wt %, 0.345 g, 1.54 mmol) in DCM (5 mL). After 5 min, the reaction was then washed with 5% Na2CO₃ (10 mL). The aqueous was then further extracted with DCM. The combined organics were then dried over MgSO₄, concentrated under reduced pressure, then purified by silica gel chromatography (40 g) eluting products with a gradient of 15>70% EtOAc/EtOH (3:1 blend)/heptane to give (M)-tert-butyl (2R,5S)-4-(6-chloro-1-(2-isopropyl-4-methylpyridin-3-yl)-7-(2-(methylsulfinyl)phenyl)-2-oxo-1,2-dihydropyrido[2,3-d]pyrimidin-4-yl)-2,5-dimethylpiperazine-1-carboxylate as colorless film. ¹H NMR (400 MHz, CDCl₃) δ 8.48 (d, J=4.56 Hz, 1H), 8.16-8.20 (m, 1H), 8.03-8.14 (m, 1H), 7.63-7.72 (m, 1H), 7.54 (dd, J=7.05, 15.13 Hz, 1H), 7.37-7.48 (m, 1H), 7.00-7.20 (m, 1H), 3.76-5.06 (m, 6H), 2.49-2.91 (m, 1H), 1.94-2.17 (m, 7H), 1.51-1.53 (m, 9H), 1.27-1.50 (m, 10H), 1.13-1.21 (m, 3H). m/z (ESI, +ve ion): 665.3 (M+H)⁺.

Step 3: (M)-4-((2S,5R)-4-Acryloyl-2,5-dimethylpiperazin-1-yl)-6-chloro-1-(2-isopropyl-4-methylpyridin-3-yl)-7-(2-(methylsulfinyl)phenyl)pyrido[2,3-d]pyrimidin-2(1H)-one (Example 212-1)

A solution of (M)-tert-butyl (2R,5S)-4-(6-chloro-1-(2-isopropyl-4-methylpyridin-3-yl)-7-(2-(methylsulfinyl)phenyl)-2-oxo-1,2-dihydropyrido[2,3-d]pyrimidin-4-yl)-2,5-dimethylpiperazine-1-carboxylate (0.65 g, 0.977 mmol) in TFA (2 mL) was stirred for 15 min at 20° C. The reaction was then concentrated under reduced pressure, and the residue was dissolved in DCM (5 mL) with DIEA (1 mL) added. The solution was chilled to 15° C. and acryloyl chloride (0.119 ml, 1.46 mmol) added. The cooling bath was removed and the solution stirred at 20° C. for 15 min. The reaction was then washed with sat. Na₂CO₃ (5 mL). The separated aqueous was further extracted with DCM (10 mL). The organic was dried over MgSO₄, concentrated under reduced pressure, then purified by silica gel chromatography (40 g) eluting products with a gradient of 15>100% EtOAc/EtOH (3:1 blend)/heptane to give as colorless film. The film was then dissolved in 1:1 MeCN/water (2 mL), frozen, then lyophilized to afford (M)-4-((2S,5R)-4-acryloyl-2,5-dimethylpiperazin-1-yl)-6-chloro-1-(2-isopropyl-4-methylpyridin-3-yl)-7-(2-(methylsulfinyl)phenyl)pyrido[2,3-d]pyrimidin-2(1H)-one (Example 212-1) as white fluffy solid. m/z (ESI, +ve ion): 619.3 (M+H)⁺.

Example 212-2

(M)-4-((2S,5R)-4-Acryloyl-2,5-dimethylpiperazin-1-yl)-6-chloro-1-(2-isopropyl-4-methylpyridin-3-yl)-7-(2-(methylsulfinyl)phenyl)pyrido[2,3-d]pyrimidin-2(1H)-one, Single Isomer

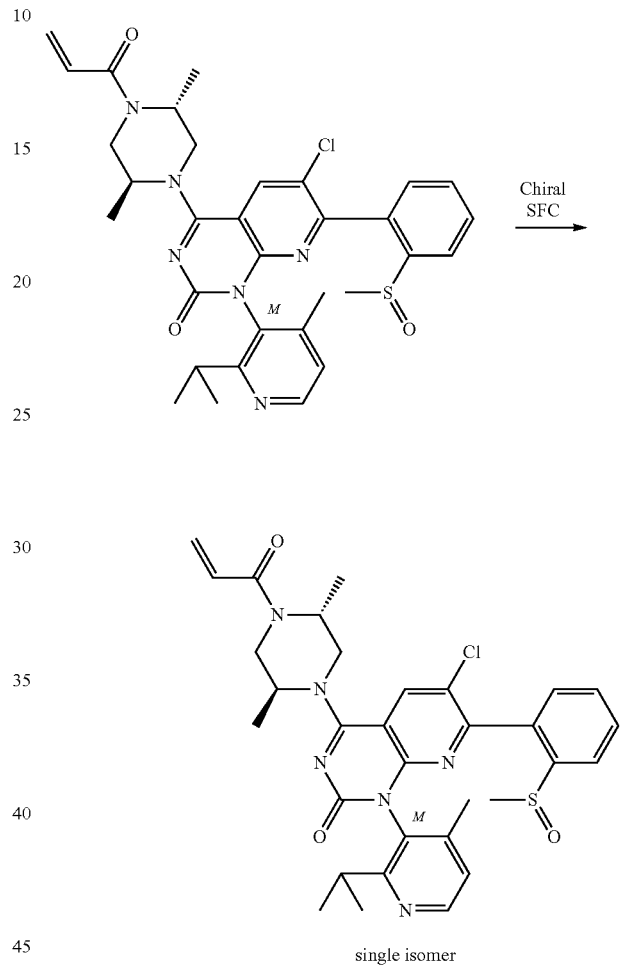

Atropisomers of (M)-4-((2S,5R)-4-acryloyl-2,5-dimethylpiperazin-1-yl)-6-chloro-1-(2-isopropyl-4-methylpyridin-3-yl)-7-(2-(methylsulfinyl)phenyl)pyrido[2,3-d]pyrimidin-2(1H)-one (Example 212-1) were separated by chiral SFC: OX, 21×250 mm, 5 μm, 45% MeOH/CO₂, 80 g/min, 102 bar. This gave (M)-4-((2S,5R)-4-acryloyl-2,5-dimethylpiperazin-1-yl)-6-chloro-1-(2-isopropyl-4-methylpyridin-3-yl)-7-(2-(methylsulfinyl)phenyl)pyrido[2,3-d]pyrimidin-2(1H)-one (Example 212-2), first eluting peak, isolated as a white fluffy powder from lyophilization. ¹H NMR (400 MHz, DMSO-d₆) δ 8.53 (d, J=3.11 Hz, 1H), 8.39 (d, J=4.98 Hz, 1H), 8.00 (d, J=7.88 Hz, 1H), 7.71-7.79 (m, 1H), 7.61-7.68 (m, 1H), 7.47 (d, J=7.67 Hz, 1H), 7.26 (d, J=4.98 Hz, 1H), 6.77-6.92 (m, 1H), 6.20 (dd, J=1.87, 16.59 Hz, 1H), 5.72-5.81 (m, 1H), 4.82-4.98 (m, 1H), 4.41-4.81 (m, 1H), 3.48-4.27 (m, 4H), 2.59-2.71 (m, 1H), 2.07 (s, 3H), 2.01 (s, 3H), 1.35 (t, J=12.20 Hz, 3H), 1.22 (dd, J=6.43, 27.78 Hz, 3H), 1.02 (d, J=6.63 Hz, 3H), 0.83 (d, J=5.60 Hz, 3H). m/z (ESI, +ve ion): 619.1 (M+H)⁺.

Example 212-3

(M)-4-((2S,5R)-4-Acryloyl-2,5-dimethylpiperazin-1-yl)-6-chloro-1-(2-isopropyl-4-methylpyridin-3-yl)-7-(2-(methylsulfinyl)phenyl)pyrido[2,3-d]pyrimidin-2(1H)-one, Single Isomer

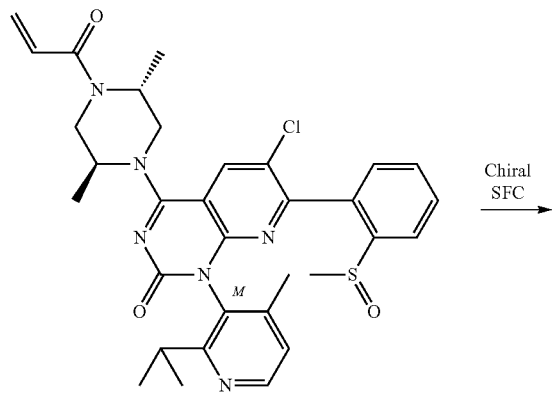

single isomer

Atropisomers of (M)-4-((2S,5R)-4-acryloyl-2,5-dimethylpiperazin-1-yl)-6-chloro-1-(2-isopropyl-4-methylpyridin-3-yl)-7-(2-(methylsulfinyl)phenyl)pyrido[2,3-d]pyrimidin-2(1H)-one (Example 212-1) were separated by chiral SFC: OX, 21×250 mm, 5 μm, 45% MeOH/CO$_2$, 80 g/min, 102 bar. This gave (M)-6-chloro-4-[(2S,5R)-2,5-dimethyl-4-prop-2-enoyl-piperazin-1-yl]-1-(2-isopropyl-4-methyl-3-pyridyl)-7-(2-methylsulfinyl)phenyl]pyrido[2,3-d]pyrimidin-2-one (Example 212-3), second eluting peak, isolated as white fluffy powder from lyophilization. $^1$H NMR (400 MHz, DMSO-d6) δ 8.46 (d, J=7.88 Hz, 1H), 8.41 (d, J=3.94 Hz, 1H), 7.97 (d, J=8.29 Hz, 1H), 7.71-7.78 (m, 1H), 7.61-7.68 (m, 1H), 7.47 (d, J=7.26 Hz, 1H), 7.22 (t, J=9.30 Hz, 1H), 6.76-6.93 (m, 1H), 6.22 (dd, J=1.87, 16.59 Hz, 1H), 5.72-5.82 (m, 1H), 3.72-4.96 (m, 6H), 2.75-2.88 (m, 1H), 2.07 (s, 3H), 1.91 (s, 3H), 1.35-1.42 (m, 3H), 1.26 (dd, J=6.43, 23.84 Hz, 3H), 1.10 (d, 0.1-6.63 Hz, 3H), 1.03 (dd, J=2.07, 6.43 Hz, 3H). m/z (ESI, +ve ion): 619.1 (M+H)$^+$.

Example 213

4-((2S,5R)-4-Acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one

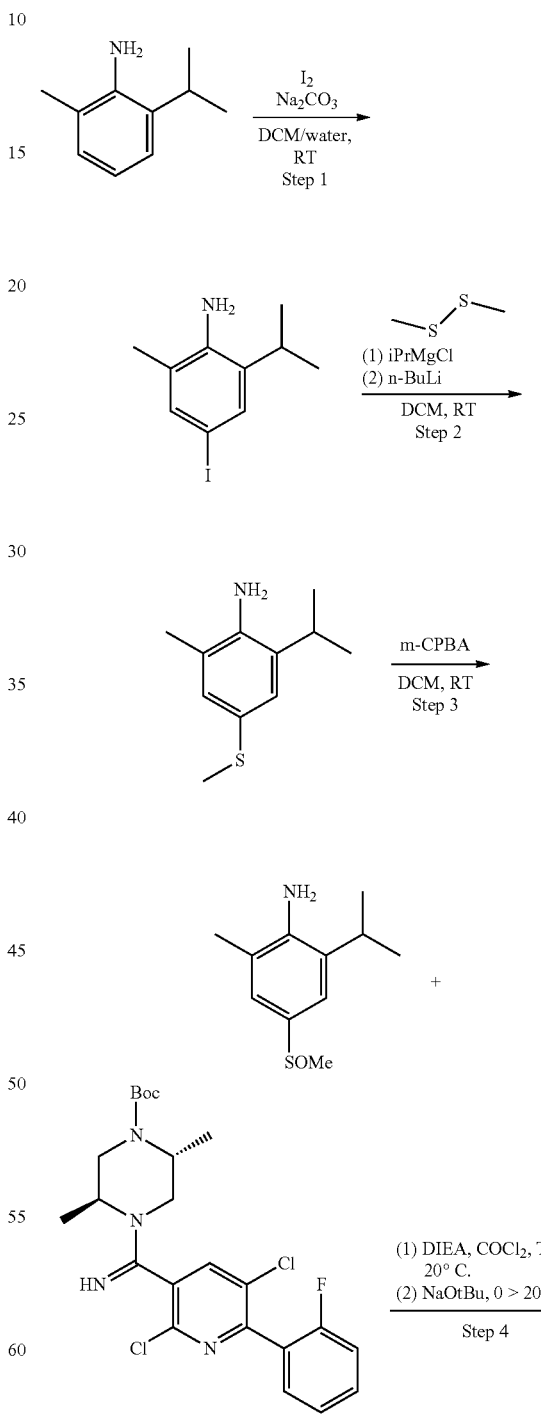

Intermediate 165

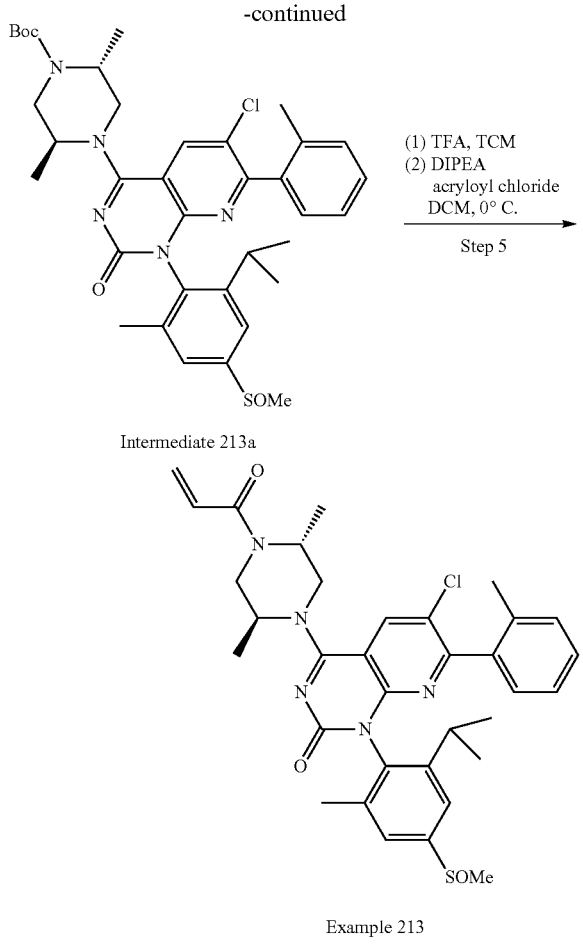

Intermediate 213a

Example 213

Step 1: 4-Iodo-2-isopropyl-6-methylaniline

To a biphasic solution of 2-isopropyl-6-methylaniline (Enamine, Monmouth Jct., N.J., USA, 2.6 g, 17.42 mmol) and sodium bicarbonate, powder (2.93 g, 34.8 mmol) in DCM (20 mL) and water (20 mL) at 20° C. was added iodine (4.42 g, 17.4 mmol). After 10 min. the organic was pushed through a plug of silica (40 g) eluting products with 20% EtOH/EtOAc (1:3 blend)/heptane to afford 4-iodo-2-isopropyl-6-methylaniline (4.26 g, 15.5 mmol, 89% yield) as an amber oil. $^1$H NMR (400 MHz, CDCl$_3$) δ 7.28 (d, J=1.66 Hz, 1H), 7.24 (d, J=1.87 Hz, 1H), 3.40-3.99 (bs, 2H), 2.83 (spt. J=40.80 Hz, 1H), 2.13 (s, 3H), 1.24 (d, J=6.84 Hz, 6H). m/z (ESI, +ve ion): 276.1 (M+H)$^+$.

Step 2: 2-Isopropyl-6-methyl-4-(methylthio)aniline

To a stirring solution of 4-iodo-2-isopropyl-6-methylaniline (4.2 g, 15.3 mmol) in THF (15 mL) at 0° C. under nitrogen was added isopropylmagnesium chloride, 2.0 M in THF (16.0 ml, 32.1 mmol) dropwise at a rate not to exceed an internal temp of 10° C. The solution was stirred for 5 min, cooled to −70° C., then n-butyllithium, 2.5 M in hexanes (10.7 ml, 26.7 mmol) added dropwise at a rate not to exceed an internal temp of −60° C. The solution was stirred for 10 min, then dimethyl disulfide (2.77 ml, 30.5 mmol) added. The cooling bath was removed and reaction quenched with sat. NH$_4$Cl (20 mL) at −20° C. The suspension was then partitioned between EtOAc (120 mL) and water (20 mL). The organic was further extracted with EtOAc (20 mL). The combined organics were then dried over MgSO4, filtered, then concentrated under reduced pressure to afford 2-isopropyl-6-methyl-4-(methylthio)aniline (3.6 g) as tan oil. m/z (ESI, +ve ion): 196.3 (M+H)$^+$.

Step 3: 2-Isopropyl-6-methyl-4-(methylsulfinyl)aniline

To a stirring solution of crude (50%) 2-isopropyl-6-methyl-4-(methylthio)aniline (3.6 g, 18.4 mmol) in DCM (30 mL) at 20° C. was added m-chloroperoxybenzoic acid (77 wt %, 2.06 g, 9.22 mmol). After 5 min, the reaction was washed with 0.5 M NaOH (20 mL), and the organic directly purified by silica gel chromatography (40 g) eluting products with a gradient of 0>50% EtOAc/EtOH (3:1 blend)/heptane to give 2-isopropyl-6-methyl-4-(methylsulfinyl)aniline (1.0 g, 4.73 mmol, 25.7% yield) as tan oil. $^1$H NMR (400 MHz, CDCl$_3$) δ 7.33 (d, J=1.66 Hz, 1H), 7.25 (d, J=1.45 Hz, 1H), 3.95 (br s, 2H), 2.85-2.98 (m, 1H), 2.69 (s, 3H), 2.23 (s, 3H), 1.27-1.31 (m, 6H). m/z (ESI, +ve ion): 212.3 (M+H)$^+$.

Step 4: tert-Butyl (2R,5S)-4-(6-chloro-7-(2-fluorophenyl)-1-(2-isopropyl-6-methyl-4-(methylsulfinyl)phenyl)-2-oxo-1,2-dihydropyrido[2,3-d]pyrimidin-4-yl)-2,5-dimethylpiperazine-1-carboxylate (Intermediate 213a)

To a diluted solution of phosgene solution, 15% in toluene (3.34 ml, 4.67 mmol) in THF (10 mL) at 0° C. was added a second solution of tert-butyl (2R,5S)-4-((2,5-dichloro-6-(2-fluorophenyl)pyridin-3-yl)(imino)methyl)-2,5-dimethylpiperazine-1-carboxylate (Intermediate 165, 1.5 g, 3.12 mmol) and DIEA (2.17 ml, 12.5 mmol) in THF (12 mL). After 5 min, a solution of 2-isopropyl-6-methyl-4-(methylsulfinyl)aniline (0.988 g, 4.67 mmol) in THF (8 mL) was added. The reaction was then partitioned between EtOAc (80 mL) and sat. NaHCO$_3$ (20 mL). The organic was washed with sat. NaCl (10 mL), dried over MgSO$_4$, then concentrated under reduced pressure. The residue was then dissolved in toluene (15 mL). The solution was chilled to 10° C. under nitrogen and then sodium tert-butoxide (0.374 g, 3.89 mmol) added. After 20 min, the reaction was then partitioned between EtOAc (60 mL) and sat. NaHCO$_3$ (20 mL). The organic was washed with sat. NaCl (10 mL), dried over MgSO$_4$, concentrated under reduced pressure, then purified by silica gel chromatography (40 g) eluting products with a gradient of 0>70% EtOAc/EtOH (3:1 blend)/heptane to afford tert-butyl (2R,5S)-4-(6-chloro-7-(2-fluorophenyl)-1-(2-isopropyl-6-methyl-4-(methylsulfinyl)phenyl)-2-oxo-1,2-dihydropyrido[2,3-d]pyrimidin-4-yl)-2,5-dimethylpiperazine-1-carboxylate (Intermediate 213a) as yellow foam. $^1$H NMR (400 MHz, CDCl$_3$) δ 8.10 (s, 1H), 7.48-7.69 (m, 1H), 7.06-7.46 (m, 5H), 4.23-5.08 (m, 2H), 3.43-4.07 (m, 4H), 2.77 (s, 3H), 2.53-2.69 (m, 1H), 2.05-2.10 (m, 3H), 1.50-1.55 (m, 9H), 1.40-1.49 (m, 3H), 0.98-1.27 (m, 9H). $^{19}$F NMR (376 MHz, CDCl$_3$) δ −112.48 (s, 1F), −112.57 (s, 1F), −112.62 (s, 1F). m/z (ESI, +ve ion): 682.1 (M+H)$^+$.

Step 5: 4-((2S,5R)-4-Acryloyl-2,5-dimethylpiperazin-1-yl)-6-chloro-7-(2-fluorophenyl)-1-(2-isopropyl-6-methyl-4-(methylsulfinyl)phenyl)pyrido[2,3-d]pyrimidin-2(1H)-one (Example 213)

A solution of tert-butyl (2R,5S)-4-(6-chloro-7-(2-fluorophenyl)-1-(2-isopropyl-6-methyl-4-(methylsulfinyl)phenyl)-2-oxo-1,2-dihydropyrido[2,3-d]pyrimidin-4-yl)-2,5-dimethylpiperazine-1-carboxylate (Intermediate 213a, 390 mg, 0.572 mmol) in TFA (2 mL) was stirred for 15 min at 20° C. The reaction was then concentrated under reduced pressure, and the residue was dissolved in DCM (5 mL) with DIEA (1 mL) added. To the solution was added acryloyl chloride (69.7 µl, 0.857 mmol). After 15 min, the reaction was then washed with sat. Na$_2$CO$_3$ (5 mL). The separated aqueous was further extracted with DCM (10 mL). The combined organics were then dried over MgSO$_4$, concentrated under reduced pressure, then purified by silica gel chromatography (40 g) eluting products with a gradient of 15>100% EtOAc/EtOH (3:1 blend)/heptane to afford 4-((2S,5R)-4-acryloyl-2,5-dimethylpiperazin-1-yl)-6-chloro-7-(2-fluorophenyl)-1-(2-isopropyl-6-methyl-4-(methylsulfinyl)phenyl)pyrido[2,3-d]pyrimidin-2(1H)-one (Example 213) as tan foam. m/z (ESI, +ve ion): 636.1 (M+H)$^+$.

Example 213-1

4-((2S,5R)-4-Acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one, Single Isomer 70 g/min, 164 bar. This gave 4-((2S,5R)-4-acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one, single isomer (Example 213-1), the first eluting peak, isolated as a white fluffy powder from lyophilization. $^1$H NMR (400 MHz, CDCl3) δ 8.49 (s, 1H), 8.11 (d, J=5.60 Hz, 1H), 7.51-7.56 (m, 1H), 7.35-7.46 (m, 2H), 7.06-7.19 (m, 3H), 6.50-6.72 (m, 1H), 6.40 (t, J=31.50 Hz, 1H), 5.80 (dd, J=8.09, 17.42 Hz, 1H), 3.41-5.23 (m, 6H), 2.77 (s, 3H), 2.64 (spt, J=42.70 Hz, 1H), 2.05-2.11 (m, 3H), 0.98-1.50 (m, 12H). $^{19}$F NMR (376 MHz, CDCl3) δ −112.53 (s, 1F), −112.56 (s, 1F), −112.58 (s, 1F). m/z (ESI, +ve ion): 636.2 (M+H)$^+$.

Example 213-2

4-((2S,5R)-4-Acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one, Single Isomer, Single Isomer

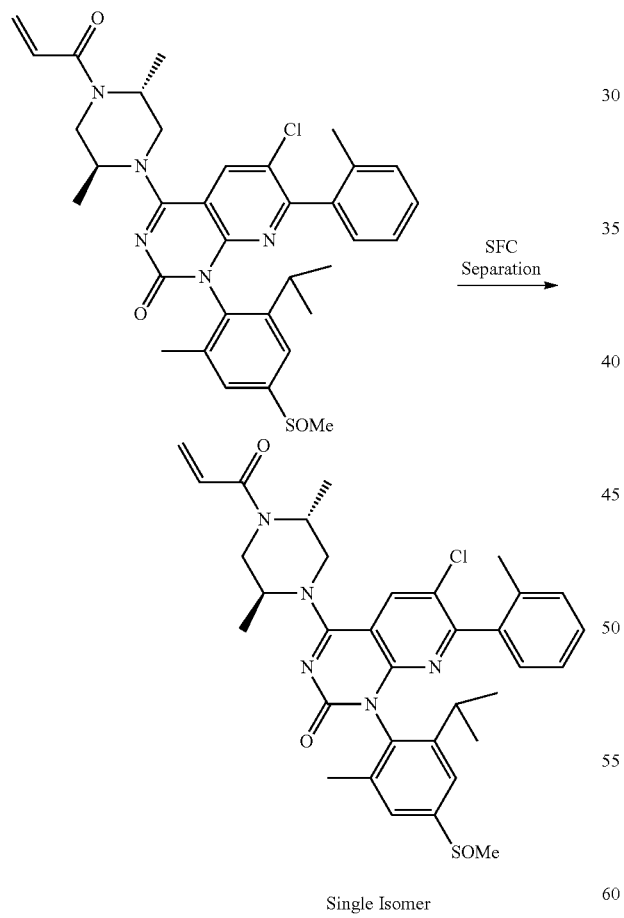

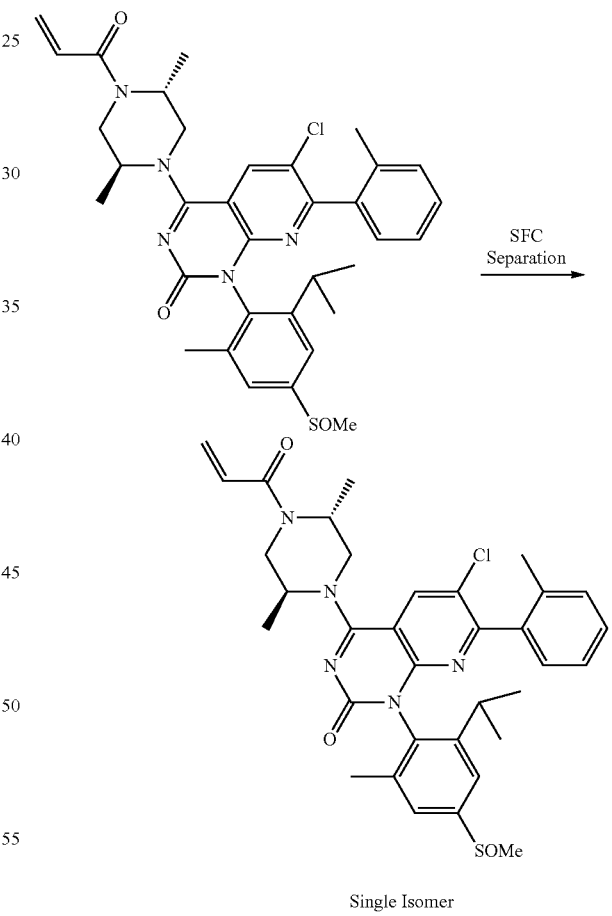

Atropisomers of 4-((2S,5R)-4-acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one (Example 213) were separated by were separated by chiral Whelk O1(S,S), 20×250 mm, 5 µm, 35% MeOH/CO$_2$, Atropisomers 4-((2S,5R)-4-acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one (Example 213) were separated by chiral SFC Whelk O1(S,S), 20×250 mm, 5 µm, 35% MeOH/CO$_2$, 70 g/min, 164 bar. This gave 4-((2S,5R)-4-acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)- one (Example 213-2). single isomer, the second eluting peak, and isolated as white fluffy powder from lyophilization. $^1$H NMR (400 MHz, CDCl3) δ 8.10 (s, 1H), 7.67 (s, 1H), 7.37-7.47 (m, 1H), 7.05-7.24 (m, 4H), 6.50-6.70 (m, 1H), 6.39 (t, J=30.70 Hz, 1H), 5.80 (t, J=18.50 Hz, 1H), 3.45-5.20 (m, 6H), 2.77 (s, 3H), 2.54-2.68 (m, 1H), 2.03-2.07 (m, 3H), 1.01-1.49 (m, 12H). $^{19}$F NMR (376 MHz, CDCl3) δ −112.43 (s, 1F), −112.49 (s, 1F). m/z (ESI, +ve ion): 636.2 (M+H)$^+$.

Example 213-3

4-((2S,5R)-4-Acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one, Single Isomer

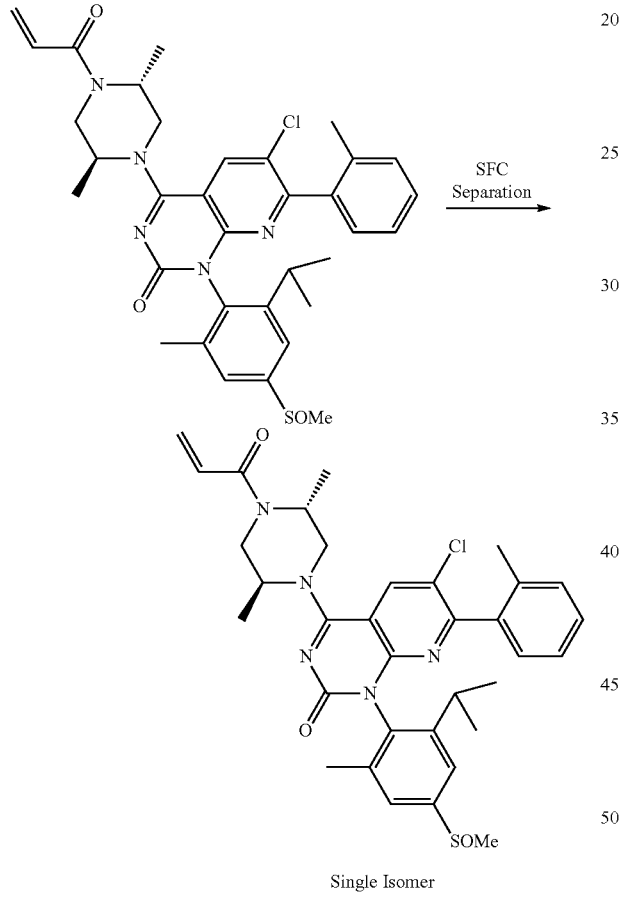

Single Isomer

Atropisomers of 4-((2S,5R)-4-acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one (Example 213) were separated by chiral SFC Step 1: Whelk O1(S,S), 20×250 mm, 5 μm, 35% MeOH/CO$_2$, 70 g/min, 164 bar. Peaks 3 and 4 co-eluted and were then further purified by Step 2: Whelk O1(R,R), 20×250 mm, 5 μm, 30% MeOH/CO$_2$. 70 g/min, 196 bar. This gave 4-((2S,5R)-4-acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one (Example 213-3), single isomer, the first eluting peak from step 2. isolated as a white fluffy powder from lyophilization. $^1$H NMR (400 MHz, CDCl3) δ 8.10 (s, 1H), 7.49-7.69 (m, 1H), 7.36-7.46 (m, 2H), 7.05-7.17 (m, 3H), 6.49-6.71 (m, 1H), 6.39 (t, J=31.10 Hz, 1H), 5.80 (t, J=17.40 Hz, 1H), 3.47-5.22 (m, 6H), 2.77 (s, 3H), 2.54-2.66 (m, 1H), 2.02-2.12 (m, 3H), 1.03-1.47 (m, 12H). $^{19}$F NMR (376 MHz, CDCl3) δ −112.43 (s, 1F), −112.49 (s, 1F), −112.52 (s, 1F), −112.55 (s, 1F), −112.57 (s, 1F). m/z (ESI, +ve ion): 636.2 (M+H)$^+$.

Example 213-4

4-((2S,5R)-4-Acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one, Single Isomer, Single Isomer

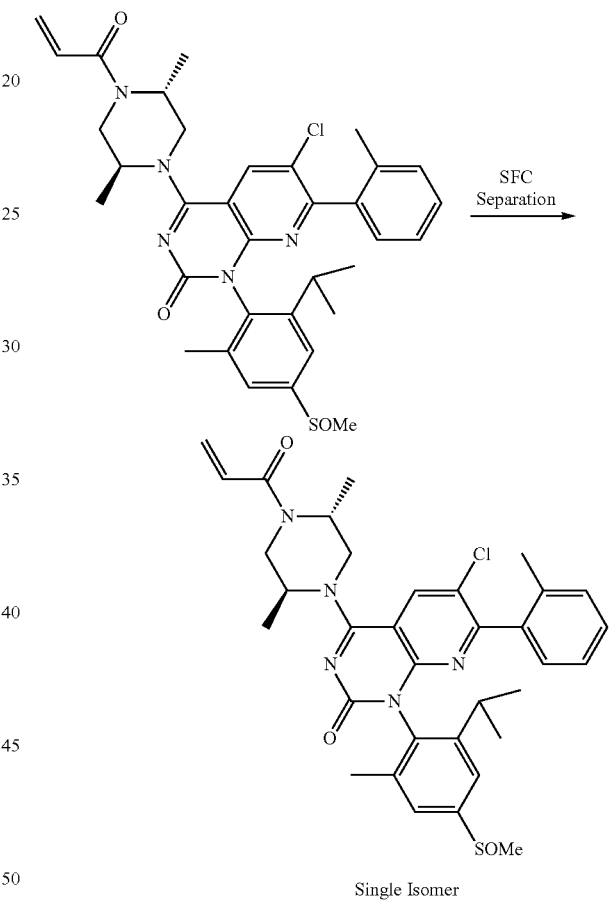

Single Isomer

Atropisomers of 4-((2S,5R)-4-acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one (Example 213) were separated by chiral SFC Step 1: Whelk O1(S,S), 20×250 mm, 5 μm, 35% MeOH/CO$_2$, 70 g/min, 164 bar. Peaks 3 and 4 co-eluted and were then further purified by Step 2: Whelk O1(R,R), 20×250 mm, 5 μm, 30% MeOH/CO$_2$, 70 g/min, 196 bar. This gave 4-((2S,5R)-4-acryloyl-2,5-dimethylpiperazin-1-yl)-6-chloro-1-(2-isopropyl-6-methyl-4-(methylsulfinyl)phenyl)-7-(o-tolyl)pyrido[2,3-d]pyrimidin-2(1H)-one (Example 213-4), single isomer, the second eluting peak from step 2, isolated as white fluffy powder from lyophilization. $^1$H NMR (400 MHz, CDCl3) δ 8.09 (d, J=4.98 Hz, 1H), 7.63-7.68 (m, 1H), 7.38-7.47 (m, 1H), 6.99-7.26 (m, 4H), 6.51-6.70 (m, 1H), 6.39 (t, J=31.30 Hz, 1H), 5.81 (dd, J=7.26, 16.79 Hz, 1H), 3.43-5.18 (m, 6H), 2.77 (s, 3H), 2.59-2.71 (m, 1H), 2.05 (s, 3H), 0.99-1.48 (m, 12H). $^{19}$F NMR (376 MHz, CDCl3) δ −112.54 (s, 1F). m/z (ESI, +ve ion): 636.2 (M+H)$^+$.

Example 214

(M)-4-((2S,5R)-4-Acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one

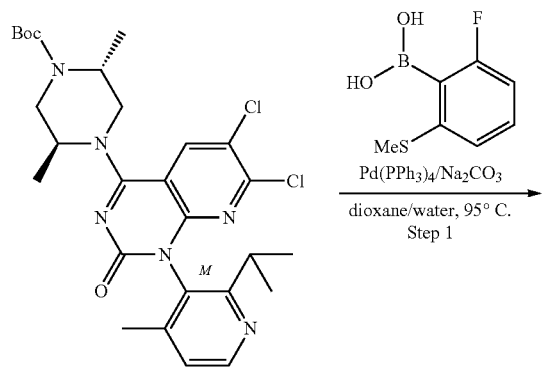

Intermediate 92A

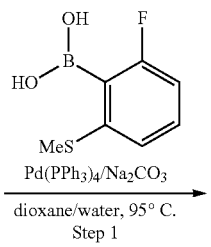

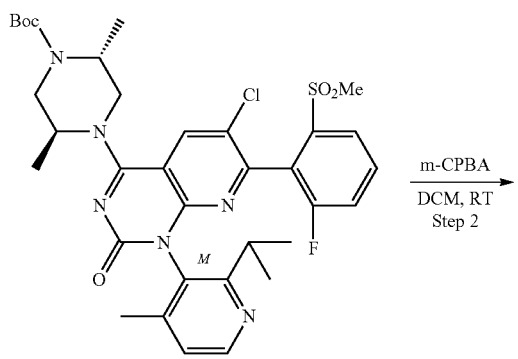

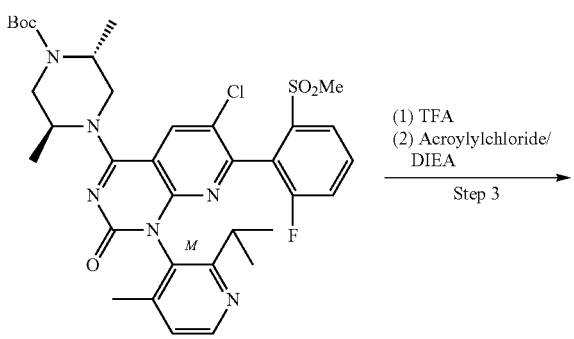

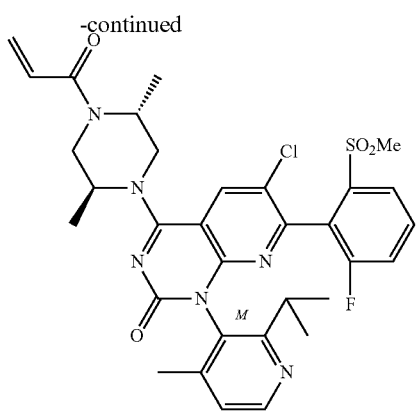

Example 214

Step 1: (M)-tert-Butyl (2R,5S)-4-(6-chloro-7-(2-fluoro-6-(methylthio)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate A suspension of (M)-tert-butyl (2R,5S)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 92A, 2.0 g, 3.56 mmol), 2-fluoro-6-(methylthio)phenyl)boronic acid (0.861 g, 4.63 mmol, Aurum Pharmatech LLC, Franklin Park, N.J., USA, 128 mg, 0.686 mmol), tetrakis(triphenylphosphine)palladium(0) (0.206 g, 0.178 mmol). sodium carbonate (1.133 g, 10.69 mmol) in 1,4-dioxane (20 mL) and water (10 mL) was sparged with argon for 1 min then heated to 95° C. for 60 min. The reaction was then extracted with EtOAc (150 mL), dried over MgSO$_4$, concentrated under reduced pressure, then purified by silica gel chromatography (80 g) eluting products with a gradient of 10>60% EtOAc/EtOH (3:1 blend)/heptane to give (M)-tert-butyl (2R,5S)-4-(6-chloro-7-(2-fluoro-6-(methylthio)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate as white foam. $^1$H NMR (400 MHz, CDCl3) δ 8.46 (d, J=4.56 Hz, 1H), 8.15 (d, J=1.66 Hz, 1H), 7.30-7.38 (m, 1H), 7.02-7.10 (m. 2H), 6.86-6.95 (m, 1H), 3.41-5.03 (m, 6H), 2.64-2.92 (m, 1H), 2.28-2.37 (m, 3H), 1.93-2.08 (m, 3H), 1.50-1.52 (m, 9H), 1.42-1.49 (m, 3H), 1.20-1.40 (m, 6H), 1.00-1.14 (m, 3H). $^{19}$F NMR (376 MHz, CDCl3) δ −114.43 (s, 1F), −115.22 (s, 1F). m/z (ESI, +ve ion): 667.3 (M+H)$^+$.

Step 2: (M)-tert-Butyl (2R,5S)-4-(6-chloro-7-(2-fluoro-6-(methylsulfonyl)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate To a stirring solution of (M)-tert-butyl (2R,5S)-4-(6-chloro-7-(2-fluoro-6-(methylthio)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (850 mg, 1.27 mmol) in DCM (8 mL) at 20° C. was added m-chloroperoxybenzoic acid (600 mg, 2.68 mmol) (2×300 mg portions). After 20 min, the reaction was then extracted with sat. Na$_2$CO$_3$ (5 mL). The organic was dried over MgSO$_4$, concentrated under reduced pressure, then purified by silica gel chromatography (40 g) eluting products with a gradient of 10>60% EtOAc/EtOH (3:1 blend)/heptane to afford (M)-tert-butyl (2R,5S)-4-(6-chloro-7-(2-fluoro-6-(methylsulfonyl)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate as white foam. m/z (ESI, +ve ion): 699.2 (M+H)+.

Step 3: (M)-4-((2S,5R)-4-Acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one (Example 214)

A solution of (M)-tert-butyl (2R,5S)-4-(6-chloro-7-(2-fluoro-6-(methylsulfonyl)phenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (370 mg, 0.529 mmol) in TFA (4 mL) was stirred for 15 min at 20° C. The reaction was then concentrated under reduced pressure, and the residue was dissolved in DCM (5 mL) with DIEA (462 µl, 2.65 mmol) added. The solution was chilled to 15° C. and acryloyl chloride (64.5 µl, 0.794 mmol) added. After 20 min, the reaction was then washed with sat. Na₂CO₃ (5 mL). The separated aqueous was further extracted with DCM (10 mL). The organic was dried over MgSO₄, concentrated under reduced pressure, then purified by silica gel chromatography (24 g) eluting products with a gradient of 15>100% EtOAc/EtOH (3:1 blend)/heptane to give (M)-4-((2S,5R)-4-acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one (Example 214) as colorless foam. ¹H NMR (400 MHz, CDCl3) δ 8.43-8.51 (m, 1H), 8.12-8.18 (m, 1H), 7.82-7.90 (m, 1H), 7.62-7.71 (m, 1H), 7.45 (t, J=17.20 Hz, 1H), 7.02-7.12 (m, 1H), 6.51-6.70 (m, 1H), 6.33-6.46 (m, 1H), 5.75-5.85 (m, 1H), 4.17-5.21 (m, 3H), 3.51-3.99 (m, 3H), 2.61-3.00 (m, 1H), 2.57 (s, 3H), 1.93-2.15 (m, 3H), 1.42-1.49 (m, 3H), 0.99-1.32 (m, 9H). ¹⁹F NMR (376 MHz, CDCl3) δ -111.28 (s, 1F), -111.31 (s, 1F). m/z (ESI, +ve ion): 653.3 (M+H)+.

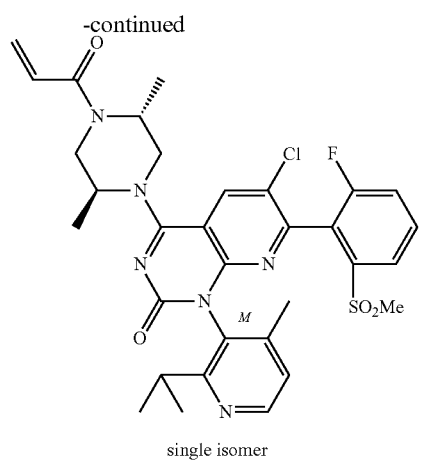

single isomer

Atropisomers of (M)-4-((2S,5R)-4-acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one (Example 214) were separated by chiral SFC Step 1: OX, 21×250 mm, 5 µm, 30% MeOH/CO₂, 80 g/min, 185 bar. (M)-4-((2S,5R)-4-acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one (Example 214-1) was the first eluting peak, and isolated as a white fluffy solid from lyophilization. ¹H NMR (400 MHz, CDCl3) δ 8.46 (d, J=4.98 Hz, 1H), 8.14 (s, 1H), 7.86 (d, J=8.29 Hz, 1H), 7.61-7.69 (m, 1H), 7.44 (dd, J=8.71, 17.00 Hz, 1H), 7.04 (d, J=4.77 Hz, 1H), 6.49-6.68 (m, 1H), 6.39 (t, J=29.40 Hz, 1H), 5.75-5.84 (m, 1H), 4.17-5.24 (m, 3H), 4.00-4.06 (m, 1H), 3.88-3.99 (m, 1H), 3.50-3.78 (m, 1H), 2.60-2.74 (m, 1H), 2.56 (s, 3H), 2.11 (s, 3H), 1.45 (t, J=13.70 Hz, 3H), 1.34 (dd, J=6.63, 34.83 Hz, 3H), 1.19 (d, J=6.84 Hz, 3H), 0.99 (d, J=6.43 Hz, 3H). ¹⁹F NMR (376 MHz, CDCl3) δ -111.29 (d, J=10.41 Hz, 1F). m/z (ESI, +ve ion): 653.0 (M+H)+.

Example 214-1

(M)-4-((2S,5R)-4-Acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one, Single Isomer Example 214-2

(M)-4-((2S,5R)-4-Acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one, Single Isomer

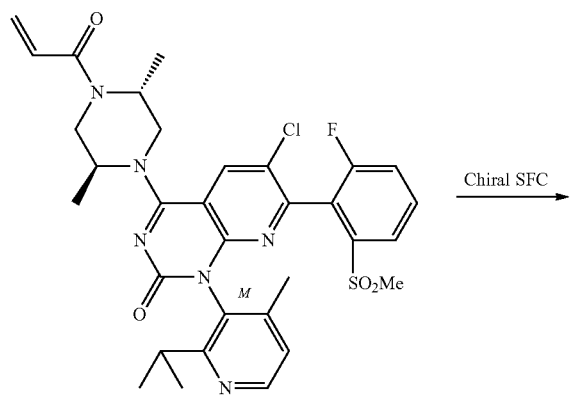

Chiral SFC →

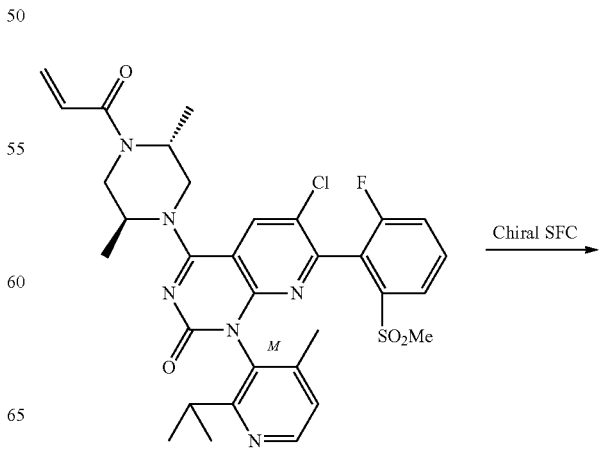

Chiral SFC →

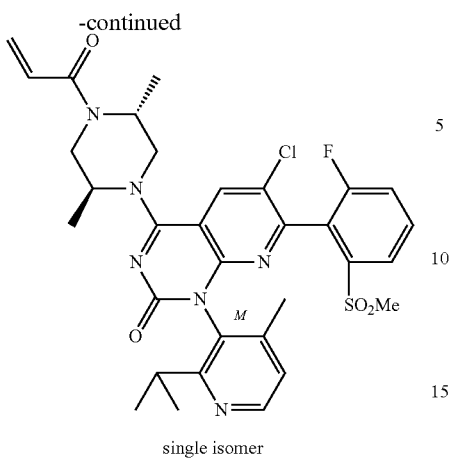

single isomer

Atropisomers of (M)-4-((2S,5R)-4-acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one (Example 214) were separated by chiral SFC Step 1: OX, 21×250 mm, 5 μm, 30% MeOH/CO$_2$, 80 g/min, 185 bar. (M)-4-((2S,5R)-4-acryloyl-2,5-dimethylpiperazin-1-yl)-6-chloro-7-(2-fluoro-6-(methylsulfonyl)phenyl)-1-(2-isopropyl-4-methylpyridin-3-yl)pyrido[2,3-d]pyrimidin-2(1H)-one (Example 214-2) was the second eluting peak, and isolated as a white fluffy solid from lyophilization. $^1$H NMR (400 MHz, CDCl3) δ 8.45 (d, J=4.35 Hz, 1H), 8.16 (d, J=9.74 Hz, 1H), 7.87 (d, J=8.09 Hz, 1H), 7.63-7.71 (m, 1H), 7.45 (t, J=17.60 Hz, 1H), 7.07 (d, J=3.32 Hz, 1H), 6.51-6.73 (m, 1H), 6.40 (t, J=29.00 Hz, 1H), 5.80 (t, J=19.90 Hz, 1H), 3.29-5.20 (m, 6H), 2.92 (spt, J=39.40 Hz, 1H), 2.57 (s, 3H), 1.96 (s, 3H), 1.43-1.62 (m, 6H), 1.26 (br d, J=6.01 Hz, 3H), 1.19 (d, J=6.22 Hz, 3H). $^{19}$F NMR (376 MHz, CDCl3) δ −111.73 (br d, J=13.01 Hz, 1F). m/z (ESI, +ve ion): 653.0 (M+H)$^+$.

Example 215

4-((2S,5R)-4-Acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2(1H)-one

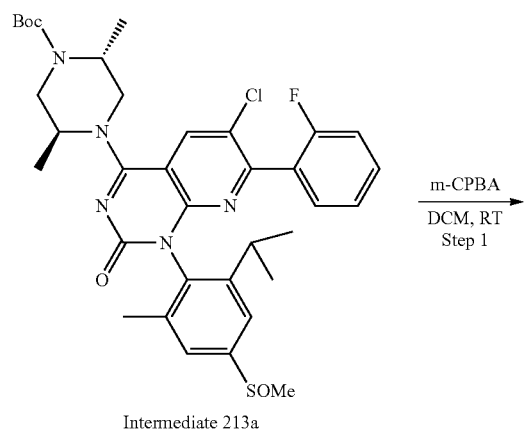

Intermediate 213a

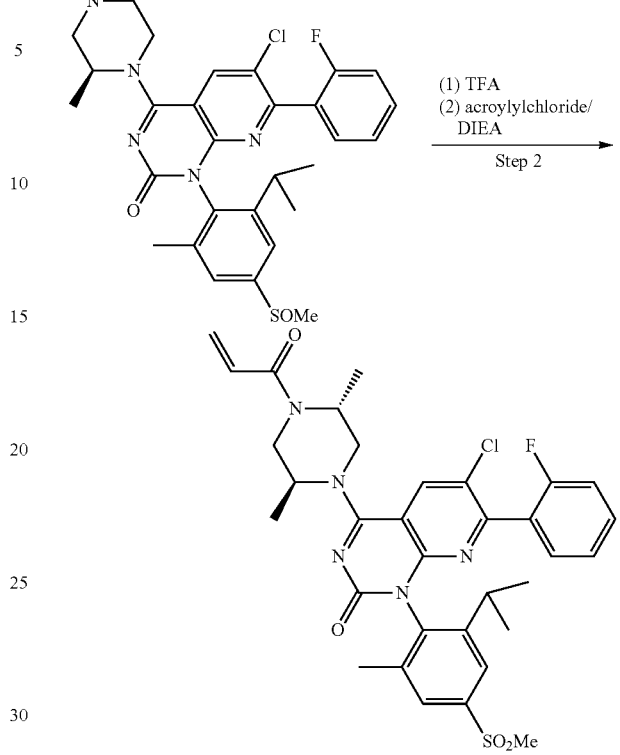

Example 215

Step 1: tert-Butyl (2R,5S)-4-(6-chloro-7-(2-fluorophenyl)-1-(2-isopropyl-6-methyl-4-(methylsulfonyl)phenyl)-2-oxo-1,2-dihydropyrido[2,3-d]pyrimidin-4-yl)-2,5-dimethylpiperazine-1-carboxylate To a stirring solution of tert-butyl (2R,5S)-4-(6-chloro-7-(2-fluorophenyl)-1-(2-isopropyl-6-methyl-4-(methylsulfinyl)phenyl)-2-oxo-1,2-dihydropyrido[2,3-d]pyrimidin-4-yl)-2,5-dimethylpiperazine-1-carboxylate (Intermediate 213a, 310 mg, 0.454 mmol) in DCM (3 mL) at 0° C. was added m-chloroperoxybenzoic acid (77 wt %, 107 mg, 0.477 mmol) in DCM. After 1 hr, the reaction was then washed with 5% Na2CO3 (1 mL), brine (1 mL), dried over MgSO4, filtered, then concentrated to dryness under reduced pressure to afford tert-butyl (2R,5S)-4-(6-chloro-7-(2-fluorophenyl)-1-(2-isopropyl-6-methyl-4-(methylsulfonyl)phenyl)-2-oxo-1,2-dihydropyrido[2,3-d]pyrimidin-4-yl)-2,5-dimethylpiperazine-1-carboxylate as white solid. m/z (ESI, +ve ion): 698.0 (M+H)$^+$.

Step 2: 4-((2S,5R)-4-Acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2(1H)-one (Example 215)

A solution of tert-butyl (2R,5S)-4-(6-chloro-7-(2-fluorophenyl)-1-(2-isopropyl-6-methyl-4-(methylsulfonyl)phenyl)-2-oxo-1,2-dihydropyrido[2,3-d]pyrimidin-4-yl)-2,5-dimethylpiperazine-1-carboxylate (320 mg, 0.458 mmol) in TFA (2 mL) was stirred for 15 min at 20° C. The reaction was then concentrated under reduced pressure, and the residue was dissolved in DCM (3 mL), DIEA (200 μl, 1.146 mmol)) followed by the addition of acryloyl chloride (48.4 µl, 0.596 mmol) at 20° C. The solution was stirred at 20° C. for 1 hr. The reaction was then partitioned between EtOAc (10 mL) and sat. NaHCO$_3$ (3 mL). The separated aqueous was further extracted with EtOAc (3 mL). The organic was dried over MgSO$_4$, concentrated under reduced pressure, then purified by silica gel chromatography (4 g) eluting products with a gradient of 15>80% EtOAc/EtOH (3:1 blend)/heptane to afford 4-((2S,5R)-4-acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2(1H)-one (Example 215) as white solid. $^1$H NMR (400 MHz, CDCl$_3$) δ 8.09-8.13 (m, 1H), 7.66-7.85 (m, 2H), 7.37-7.48 (m, 1H), 7.06-7.21 (m, 3H), 6.50-6.70 (m, 1H), 6.34-6.46 (m, 1H), 5.76-5.85 (m, 1H), 4.19-5.23 (m, 3H), 3.44-4.08 (m, 3H), 3.09 (s, 3H), 2.56-2.73 (m, 1H), 2.06-2.13 (m, 3H), 0.99-1.53 (m, 12H). m/z (ESI, +ve ion): 652.1 (M+H)$^+$.

Example 215-1

4-((2S,5R)-4-Acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2(1H)-one, Single Isomer (1H)-one (Example 215) were separated by chiral SFC Step 1: OX-H, 21×250 mm, 5 µm, 45% MeOH/CO$_2$, 80 g/min, 120 bar. This gave 4-((2S,5R)-4-Acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2(1H)-one (Example 215-1), single isomer, was the first eluting peak, and isolated as a white fluffy solid from lyophilization. $^1$H NMR (400 MHz, DMSO-d$_6$) δ 8.49 (d, J=3.32 Hz, 1H), 7.74-7.78 (m, 2H), 7.47-7.56 (m, 1H), 7.21-7.35 (m, 3H), 6.76-6.91 (m, 1H), 6.20 (dd, J=2.07, 16.17 Hz, 1H), 5.72-5.80 (m, 1H), 4.36-4.97 (m, 2H), 3.48-4.25 (m, 4H), 3.29 (s, 3H), 2.59-2.70 (m, 1H), 2.04 (s, 3H), 1.35 (dd, J=6.01, 12.02 Hz, 3H), 1.21 (dd, J=6.22, 29.23 Hz, 3H), 1.10 (d, J=7.26 Hz, 3H), 0.99 (d, J=6.63 Hz, 3H). $^{19}$F NMR (376 MHz, DMSO-d$_6$) δ −113.97 (s, 1F), −113.98 (s, 1F). m/z (ESI, +ve ion): 652.1 (M+H)$^+$.

Example 215-2

4-((2S,5R)-4-Acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2(1H)-one, Single Isomer

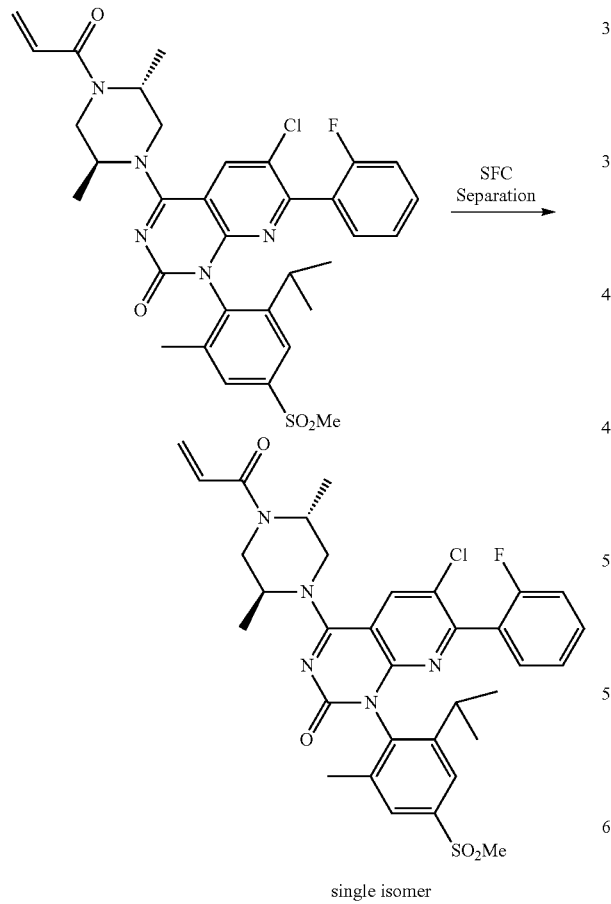

single isomer

Atropisomers of 4-((2S,5R)-4-acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2

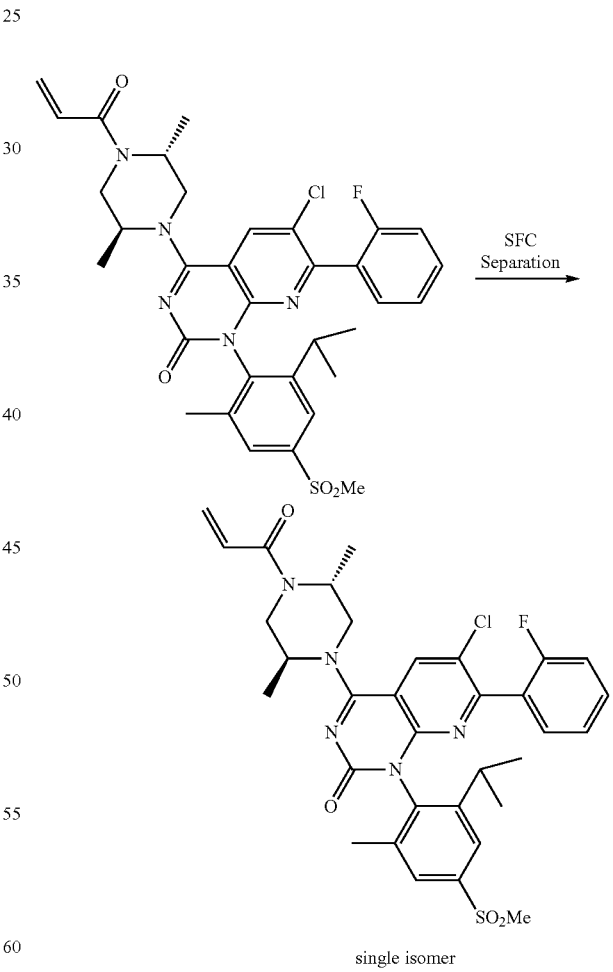

single isomer

Atropisomers of 4-((2S,5R)-4-acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2 (1H)-one (Example 215) were separated by chiral SFC Step 1: OX-H, 21×250 mm, 5 µm, 45% MeOH/CO$_2$, 80 g/min.

120 bar. This gave 4-((2S,5R)-4-acryloyl-2,5-dimethylpiperazin-1-yl)-6-chloro-7-(2-fluorophenyl)-1-(2-isopropyl-6-methyl-4-(methylsulfonyl)phenyl)pyrido[2,3-d]pyrimidin-2(1H)-one (Example 215-2), single isomer, was the second eluting peak, and isolated as a white fluffy solid from lyophilization. $^1$H NMR (400 MHz, DMSO-$d_6$) δ 8.49 (d, J=4.15 Hz, 1H), 7.76 (d, J=5.39 Hz, 2H), 7.47-7.56 (m, 1H), 7.17-7.36 (m, 3H), 6.76-6.94 (m, 1H), 6.22 (d, J=17.00 Hz, 1H), 5.69-5.80 (m, 1H), 4.40-4.98 (m, 2H), 3.46-4.27 (m, 4H), 3.29 (s, 3H), 2.60-2.73 (m, 1H), 2.02 (s, 3H), 1.34 (dd, J=6.63, 13.06 Hz, 3H), 1.21 (dd, J=6.63, 29.02 Hz, 3H), 1.11 (d, J=6.84 Hz, 3H), 1.02 (d, J=6.43 Hz, 3H). $^{19}$F NMR (376 MHz, DMSO-$d_6$) δ 113.88 (s, 1F). −113.88 (s, 1F). m/z (ESI, +ve ion): 652.1 (M+H)$^+$.

Example 217

5-((2S,5R)-4-Acryloyl-2,5-dimethylpiperazin-1-yl)-7-chloro-8-(2-fluorophenyl)-1-neopentyl-1,2-dihydro-3H-pyrido[2,3-e][1,4]diazepin-3-one

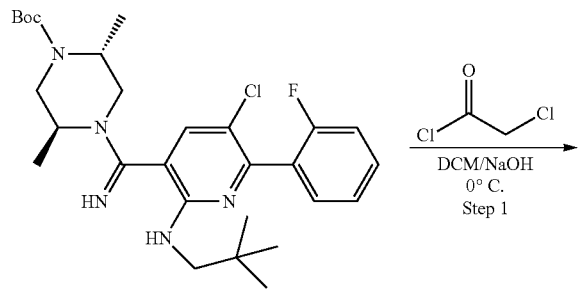

Example 150, Step 1

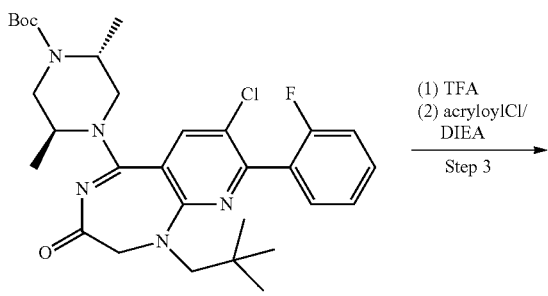

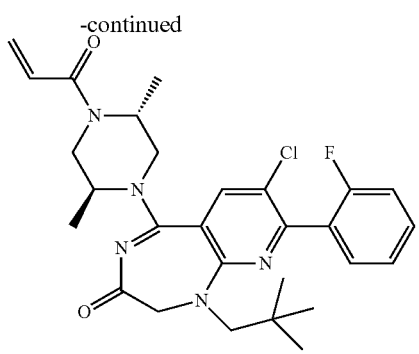

Example 217

Step 1: tert-Butyl (2R,5S)-4-((5-chloro-6-(2-fluorophenyl)-2-(neopentylamino)pyridin-3-yl)((2-chloroacetyl)imino)methyl)-2,5-dimethylpiperazine-1-carboxylate (Intermediate 217a)

To a stirring biphasic solution of tert-butyl (2R,5S)-4-((5-chloro-6-(2-fluorophenyl)-2-(neopentylamino)pyridin-3-yl)imino)methyl)-2,5-dimethylpiperazine-1-carboxylate (Example 150, Step 1: 650 mg, 1.22 mmol) in DCM (5 mL) and 1 M sodium hydroxide (195 µl, 1.95 mmol) at 0° C. was added a solution of 2-chloroacetyl chloride (107 µl, 1.34 mmol) in DCM (1 mL). After 10 min, the aqueous phase was discarded and the organic was washed with sat. NaCl (5 mL). The organic was then purified by silica gel chromatography (24 g) eluting products with a gradient of 0>30% EtOAc/heptane to afford tert-butyl (2R,5S)-4-((5-chloro-6-(2-fluorophenyl)-2-(neopentylamino)pyridin-3-yl)((2-chloroacetyl)imino)methyl)-2,5-dimethylpiperazine-1-carboxylate as a white foam. m/z (ESI, +ve ion): 608.3 (M+H)$^+$.

Step 2: tert-Butyl (2R,5S)-4-(7-chloro-8-(2-fluorophenyl)-1-neopentyl-3-oxo-2,3-dihydro-1H-pyrido[2,3-e][1,4]diazepin-5-yl)-2,5-dimethylpiperazine-1-carboxylate To a stirring solution of tert-butyl (2R,5S)-4-((5-chloro-6-(2-fluorophenyl)-2-(neopentylamino)pyridin-3-yl((2-chloroacetyl)imino)methyl)-2,5-dimethylpiperazine-1-carboxylate (230 mg, 0.378 mmol) in THF (3 mL) at 0° C. under nitrogen was added sodium hydride, 60% dispersion in mineral oil (60.5 mg, 1.51 mmol). After 10 min, the cooling bath was removed and the suspension was stirred for 2 hrs at 20° C. The reaction was chilled to 0° C., then carefully quenched with sat. NH4Cl (1 mL). The reaction was then partitioned between EtOAc (20 mL) and water (2 mL). The organic was washed with sat. NaCl (2 mL), dried over MgSO4, and then purified by silica gel chromatography (12 g) eluting products with EtOAc/EtOH (3:1 blend)/heptanes to afford tert-butyl (2R,5S)-4-(7-chloro-8-(2-fluorophenyl)-1-neopentyl-3-oxo-2,3-dihydro-1H-pyrido[2,3-e][1,4]diazepin-5-yl)-2,5-dimethylpiperazine-1-carboxylate as colorless film. $^1$H NMR (400 MHz, CDCl$_3$) δ 7.41-7.52 (m, 3H), 7.27-7.30 (m, 1H), 7.18 (dd, J=9.12, 18.24 Hz, 1H), 2.90-5.08 (m, 10H), 1.48 (s, 9H), 1.20-1.42 (m, 6H), 0.87 (br s, 9H). m/z (ESI, +ve ion): 572.3 (M+H)$^+$.

Step 3: 5-((2S,5R)-4-Acryloyl-2,5-dimethylpiperazin-1-yl)-7-chloro-8-(2-fluorophenyl)-1-neopentyl-1,2-dihydro-3H-pyrido[2,3-e][1,4]diazepin-3-one (Example 217)

A solution of tert-butyl (2R,5S)-4-(7-chloro-8-(2-fluorophenyl)-1-neopentyl-3-oxo-2,3-dihydro-1H-pyrido[2,3-e]

[1,4]diazepin-5-yl)-2,5-dimethylpiperazine-1-carboxylate (60 mg, 0.105 mmol) in TFA (2 mL) was stirred for 15 min at RT. The solvent was then removed under reduced pressure, and the resulting residue was then partitioned between EtOAc (20 mL) and 5% Na2CO3 (5 mL). The organic was then washed with sat. NaCl (2 mL), dried over MgSO4, then concentrated under reduced pressure. The residue was then dissolved in DCM (4 mL) and DIPEA (55.0 µl, 0.315 mmol) was added. The stirring solution was then chilled to 0° C. under nitrogen and a second solution of acryloyl chloride (9.41 µl, 0.115 mmol) in DCM (1 mL) was added dropwise. The cooling bath was removed, stirred for 10 min, then the reaction was washed with sat. NaHCO$_3$ (2 mL). The separated organic was then directly purified by silica gel chromatography (4 g) eluting products with a gradient of 10>50% EtOAc/EtOH (3:1 blend)/heptane to afford a light yellow foam. The material was then dissolved in 1:1 MeCN/water (2 mL), frozen, and lyophilized to afford 5-((2S,5R)-4-acryloyl-2,5-dimethylpiperazin-1-yl)-7-chloro-8-(2-fluorophenyl)-1-neopentyl-1,2-dihydro-3H-pyrido[2,3-e][1,4]diazepin-3-one (Example 217) as light yellow fluffy powder. $^1$H NMR (400 MHz, DMSO-d$_6$) δ 8.00 (br s, 1H), 7.48-7.62 (m, 2H), 7.34-7.41 (m, 2H), 6.67-6.89 (m, 1H). 6.12-6.20 (m, 1H), 5.73 (br d, J=10.37 Hz, 1H), 3.21-4.90 (m, 10H), 1.04-1.49 (m, 6H), 0.84 (br s, 9H). $^{19}$F NMR (376 MHz, DMSO-d$_6$) δ −114.06 (s, 1F). m/z (ESI, +ve ion): 526.3 (M+H)$^+$.

Example 218

5-((2S,5R)-4-Acryloyl-2,5-dimethylpiperazin-1-yl)-7-chloro-8-(2-fluorophenyl)-1-(2-isopropyl-4-methylpyridin-3-yl)-1,2-dihydro-3H-pyrido[2,3-e][1,4]diazepin-3-one

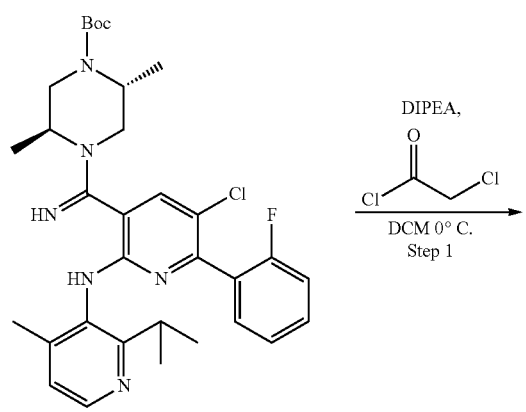

Intermediate 237

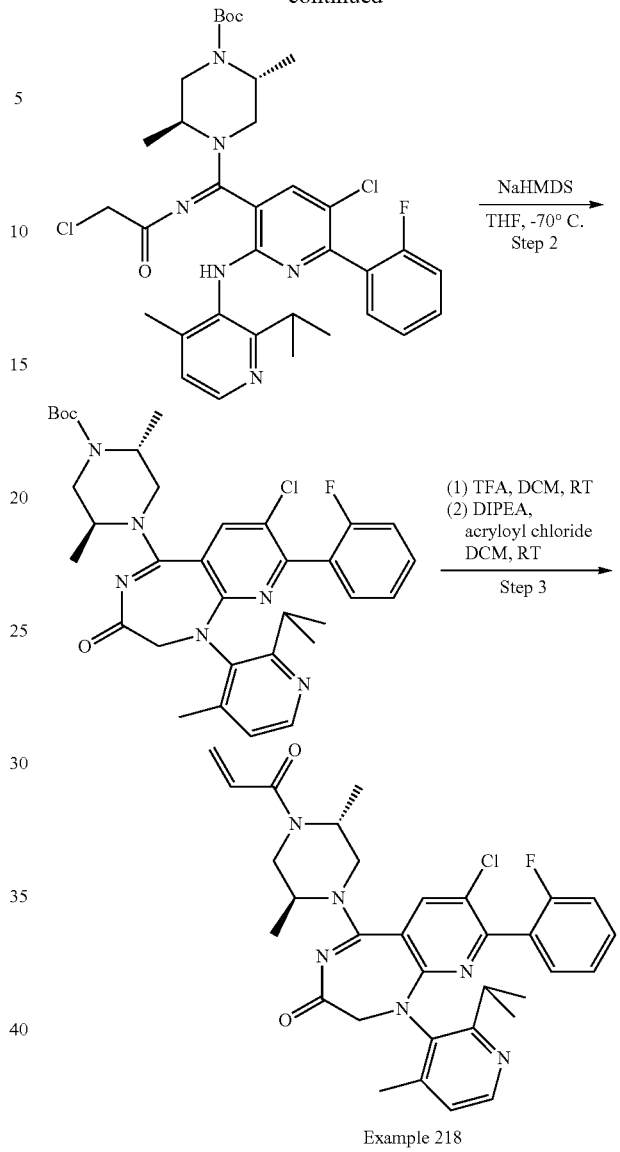

Example 218

Step 1: tert-Butyl (2R,5S)-4-((5-chloro-6-(2-fluorophenyl)-2-((2-isopropyl-4-methylpyridin-3-yl)amino)pyridin-3-yl)((2-chloroacetyl)imino)methyl)-2,5-dimethylpiperazine-1-carboxylate To a stirring solution of tert-butyl (2R,5S)-4-((5-chloro-6-(2-fluorophenyl)-2-((2-isopropyl-4-methylpyridin-3-yl)amino)pyridin-3-yl)(imino)methyl)-2,5-dimethylpiperazine-1-carboxylate (Intermediate 237) (0.5 g, 0.840 mmol) and DIPEA (0.161 ml, 0.924 mmol) in DCM (10 mL) at 0° C. under argon was added a second solution of chloroacetyl chloride (0.053 ml, 0.672 mmol) in DCM (0.5 mL). After 5 min, the reaction was then directly purified by silica gel chromatography (12 g) eluting products with a gradient of 10>40% EtOAc/heptane to afford tert-butyl (2R,5S)-4-((5-chloro-6-(2-fluorophenyl)-2-((2-isopropyl-4-methylpyridin-3-yl)amino)pyridin-3-yl)((2-chloroacetyl)imino)methyl)-2,5-dimethylpiperazine-1-carboxylate as white solid. m/z (ESI, +ve ion): 671.3 (M+H)$^+$.

Step 2: tert-Butyl (2R,5S)-4-(7-chloro-8-(2-fluorophenyl)-1-(2-isopropyl-4-methylpyridin-3-yl)-3-oxo-2,3-dihydro-1H-pyrido[2,3-e][1,4]diazepin-5-yl)-2,5-dimethylpiperazine-1-carboxylate To a stirring solution of tert-butyl (2R,5S)-4-((5-chloro-6-(2-fluorophenyl)-2-((2-isopropyl-4-methylpyridin-3-yl)amino)pyridin-3-yl)((2-chloroacetyl)imino)methyl)-2,5-dimethylpiperazine-1-carboxylate (225 mg, 0.335 mmol) in THF (5 mL) at −70° C. under argon was added sodium bis(trimethylsilyl)amide, 1 M in THF (670 µl, 0.670 mmol). After 5 min, the reaction was then quenched with sat. NH4Cl (0.5 mL). The reaction was then partitioned between EtOAc (10 mL) and water (1 mL). The organic was washed with sat. NaCl (1 mL), dried over MgSO₄, concentrated under reduced pressure, then purified by silica gel chromatography (12 g) eluting products with a gradient of 10>60% EtOAc/EtOH (3:1 blend)/heptane to afford tert-butyl (2R,5S)-4-(7-chloro-8-(2-fluorophenyl)-1-(2-isopropyl-4-methylpyridin-3-yl)-3-oxo-2,3-dihydro-1H-pyrido[2,3-e][1,4]diazepin-5-yl)-2,5-dimethylpiperazine-1-carboxylate as yellow fim. m/z (ESI, +ve ion): 635.3 (M+H)⁺.

Step 3: 5-((2S,5R)-4-Acryloyl-2,5-dimethylpiperazin-1-yl)-7-chloro-8-(2-fluorophenyl)-1-(2-isopropyl-4-methylpyridin-3-yl)-1,2-dihydro-3H-pyrido[2,3-e][1,4]diazepin-3-one (Example 218)

A solution of tert-butyl (2R,5S)-4-(7-chloro-8-(2-fluorophenyl)-1-(2-isopropyl-4-methylpyridin-3-yl)-3-oxo-2,3-dihydro-1H-pyrido[2,3-e][1,4]diazepin-5-yl)-2,5-dimethylpiperazine-1-carboxylate (65 mg, 0.102 mmol) in TFA was stirred for 5 min at RT. The solvent was then removed under reduced pressure, and the residue was partitioned between EtOAc (10 mL) and 5% Na₂CO₃ (5 mL). The organic was washed with sat. NaCl (1 mL), dried over MgSO₄, then concentrated under reduced pressure. The resulting residue was then dissolved in DCM (2 mL), DIEA (17.9 µl, 0.102 mmol) added. chilled to 0° C. under nitrogen, and a second solution of acryloyl chloride (8.31 µl, 0.102 mmol) in DCM (0.5 mL) was added dropwise. After 5 min, the reaction was then directly purified by silica gel chromatography (4 g) eluting products with a gradient of 10>70% EtOAc/EtOH (3:1 blend)/heptane to afford a yellow oil. The oil was then suspended in MeCN/water (1:1; 1.5 mL), frozen, and lyophilized to afford 5-((2S,5R)-4-acryloyl-2,5-dimethylpiperazin-1-yl)-7-chloro-8-(2-fluorophenyl)-1-(2-isopropyl-4-methylpyridin-3-yl)-1,2-dihydro-3H-pyrido[2,3-e][1,4]diazepin-3-one (Example 218) as an off white fluffy powder. m/z (ESI, +ve ion): 589.3 (M+H)⁺. ¹H NMR (400 MHz, DMSO-d₆) δ 8.29 (d, J=4.77 Hz, 1H), 8.03 (br s, 1H), 7.34-7.48 (m, 1H), 7.04-7.27 (m, 4H), 6.73-6.89 (m, 1H), 6.17 (br d, J=16.79 Hz, 1H), 5.70-5.77 (m, 1H), 3.32-4.93 (m, 8H), 2.82-3.19 (m, 1H), 2.08 (br d, J=6.22 Hz, 3H), 1.09-1.36 (m, 9H), 0.84-0.92 (m, 3H).

Example 219

5-((2S,5R)-4-Acryloyl-2,5-dimethylpiperazin-1-yl)-7-chloro-8-(2-fluorophenyl)-1-(2-isopropyl-4-methylpyridin-3-yl)-1,3-dihydro-2H-pyrido[2,3-e][1,4]diazepin-2-one

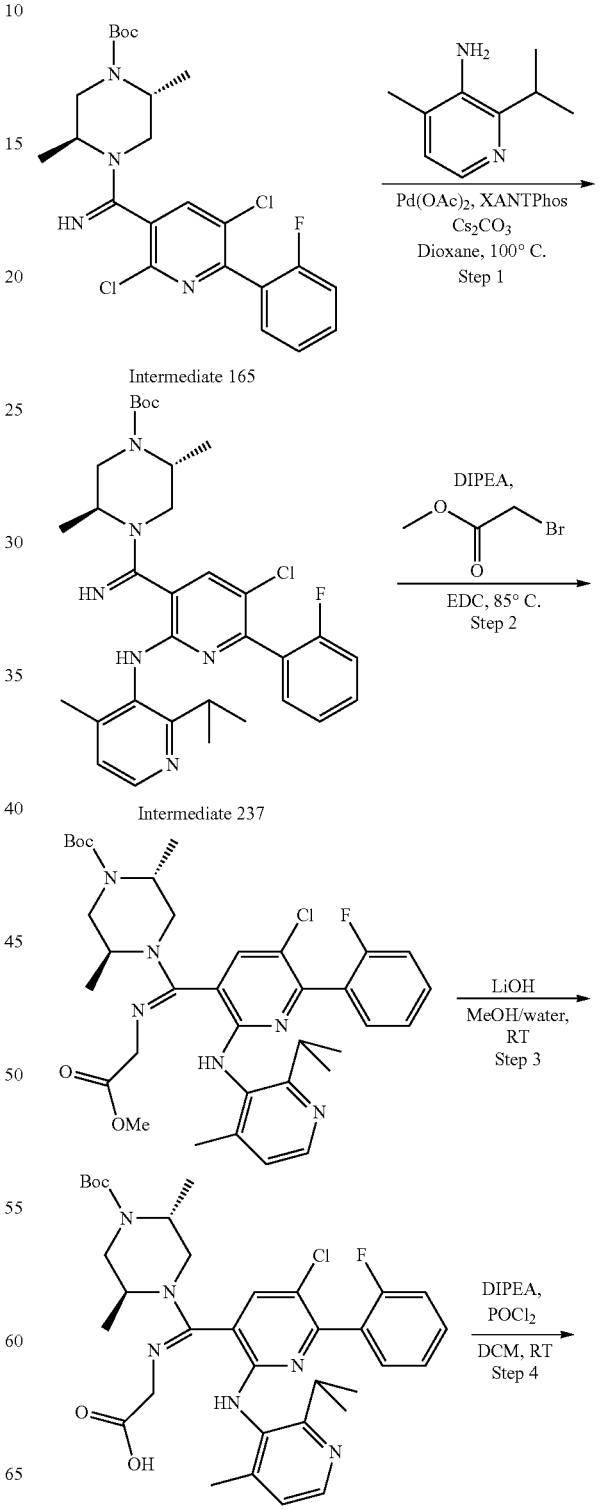

-continued

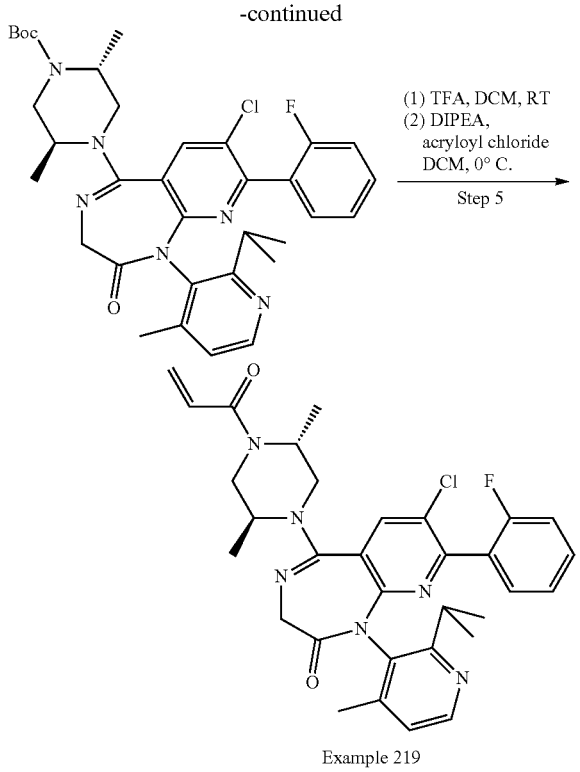

Example 219

Step 1: tert-Butyl (2R,5)-4-((5-chloro-6-(2-fluoro-phenyl)-2-((2-isopropyl-4-methylpyridin-3-yl)amino)pyridin-3-yl)(imino)methyl)-2,5-dimethylpiperazine-1-carboxylate (Intermediate 237)

A 500 mL round bottom flask was flushed with argon then charged with diacetoxypalladium (1.68 g, 7.48 mmol), (9,9-dimethyl-9H-xanthene-4,5-diyl)bis(diphenylphosphane) (6.49 g, 11.2 mmol), cesium carbonate (12.2 g, 37.4 mmol), and 1,4-dioxane (60 mL). The suspension was then sparged with nitrogen for 2 min, stirred for 10 min at 20° C., then tert-butyl (2R,5S)-4-((2,5-dichloro-6-(2-fluorophenyl)pyridin-3-yl)(imino)methyl)-2,5-dimethylpiperazine-1-carboxylate (Intermediate 165, 6.0 g, 12.5 mmol) and 2-isopropyl-4-methylpyridin-3-amine (Intermediate R, 2.34 g, 15.6 mmol) were added. The suspension was then heated to 100° C. After 45 min, the reaction was partitioned between EtOAc (200 mL) and water (100 mL). The organic was then dried over MgSO$_4$, and concentrated under reduced pressure. The resulting residue was dissolved in EtOAc (150 mL). and SiliaMetS® Thiol by Silicycle (40 g, 1.3 mmol/g). The slurry was stirred for 90 min at RT. The solvent was removed under reduced pressure, and then purified by silica gel chromatography (4 g) eluting products with a gradient of 10>50% EtOAc/EtOH (3:1 blend)/heptane to afford tert-butyl (2R,5S)-4-((5-chloro-6-(2-fluorophenyl)-2-((2-isopropyl-4-methylpyridin-3-yl)amino)pyridin-3-yl)(imino)methyl)-2,5-dimethylpiperazine-1-carboxylate (Intermediate 237) as brown foam. m/z (ESI, +ve ion): 595.4 (M+H)$^+$.

Step 2: tert-Butyl (2R,5S)-4-((E)-(5-chloro-6-(2-fluorophenyl)-2-((2-isopropyl-4-methylpyridin-3-yl)amino)pyridin-3-yl)((2-methoxy-2-oxoethyl)imino)methyl)-2,5-dimethylpiperazine-1-carboxylate To a stirring solution of tert-butyl (2R,5S)-4-((5-chloro-6-(2-fluorophenyl)-2-((2-isopropyl-4-methylpyridin-3-yl)amino)pyridin-3-yl)(imino)methyl)-2,5-dimethylpiperazine-1-carboxylate (Intermediate 237, 400 mg, 0.672 mmol) and DIPEA (235 µl, 1.34 mmol) in 1,2-dichloroethane (8 mL) was added methyl bromoacetate (623 µl, 6.72 mmol). The solution was stirred at 85° C. in a 20 mL reaction vessel equipped with a pressure relief cap for 16 hrs. The reaction was then directly purified by silica gel chromatography (12 g) eluting products with a gradient of 0>50% EtOAc/EtOH (3:1 blend)/heptane to afford tert-butyl (2R,5S)-4-((E)-(5-chloro-6-(2-fluorophenyl)-2-((2-isopropyl-4-methylpyridin-3-yl)amino)pyridin-3-yl)((2-methoxy-2-oxoethyl)imino)methyl)-2,5-dimethylpiperazine-1-carboxylate as a white solid. m/z (ESI, +ve ion): 667.3 (M+H)$^+$.

Step 3: 2-(((E)-((2S,5R)-4-(tert-Butoxycarbonyl)-2,5-dimethylpiperazin-1-yl)(5-chloro-6-(2-fluorophenyl)-2-((2-isopropyl-4-methylpyridin-3-yl)amino)pyridin-3-yl)methylene)amino)acetic acid A suspension of tert-butyl (2R,5S)-4-((E)-(5-chloro-6-(2-fluorophenyl)-2-((2-isopropyl-4-methylpyridin-3-yl)amino)pyridin-3-yl)((2-methoxy-2-oxoethyl)imino)methyl)-2,5-dimethylpiperazine-1-carboxylate (125 mg, 0.187 mmol) and lithium hydroxide, monohydrate (9.83 mg, 0.234 mmol) in THF (1 mL). MeOH (0.5 mL), water (0.5 mL) was stirred for 18 hrs at RT. The reaction was then partitioned between DCM (20 ml) and sat. NaHCO$_3$ (10 mL). The aqueous was then further extracted with DCM (5 mL). The combined organics were washed with sat. NaCl (5 mL), dried over MgSO$_4$, filtered, then concentrated under reduced pressure to afford as yellow solid. This material was then further purified by silica gel chromatography (4 g) eluting products with 100% EtOAc/EtOH (3:1 blend) to afford 2-(((E)-((2S,5R)-4-(tert-butoxycarbonyl)-2,5-dimethylpiperazin-1-yl)(5-chloro-6-(2-fluorophenyl)-2-((2-isopropyl-4-methylpyridin-3-yl)amino)pyridin-3-yl)methylene)amino)acetic acid as white solid. m/z (ESI, +ve ion): 653.3 (M+H)$^+$.

Step 4: tert-Butyl (2R,5S)-4-(7-chloro-8-(2-fluorophenyl)-1-(2-isopropyl-4-methylpyridin-3-yl)-2-oxo-2,3-dihydro-1H-pyrido[2,3-e][1,4]diazepin-5-yl)-2,5-dimethylpiperazine-1-carboxylate To a stirring solution of 2-(((E)-((2S,5R)-4-(tert-butoxycarbonyl)-2,5-dimethylpiperazin-1-yl)(5-chloro-6-(2-fluorophenyl)-2-((2-isopropyl-4-methylpyridin-3-yl)amino)pyridin-3-yl)methylene)amino)acetic acid (45 mg, 0.069 mmol) and DIEA (15.0 µl, 0.086 mmol in DCM (2 mL) at 0° C. under nitrogen was added phosphorus oxychloride (6.42 µl, 0.069 mmol). After 10 min, the reaction was then partitioned between EtOAc (10 mL) and sat. NaHCO$_3$ (5 mL). The organic was further washed with sat. NaCl (2 mL), then dried over MgSO$_4$. The organic layer was then concentrated under reduced pressure, and purified by silica gel chromatography (4 g) eluting the product with a gradient of 10>50% EtOAc/EtOH (3:1 blend)/heptane to afford tert-butyl (2R,5S)-4-(7-chloro-8-(2-fluorophenyl)-1-(2-isopropyl-4-methylpyridin-3-yl)-2-oxo-2,3-dihydro-1H-pyrido[2,3-e][1,4]diazepin-5-yl)-2,5-dimethylpiperazine-1-carboxylate as colorless film. m/z (ESI, +ve ion): 635.3 (M+H)$^+$.

Step 5: 5-((2S,5R)-4-Acryloyl-2,5-dimethylpiperazin-1-yl)-7-chloro-8-(2-fluorophenyl)-1-(2-isopropyl-4-methylpyridin-3-yl)-1,3-dihydro-2H-pyrido[2,3-e][1,4]diazepin-2-one (Example 219)

A solution of tert-butyl (2R,5S)-4-(7-chloro-8-(2-fluorophenyl)-1-(2-isopropyl-4-methylpyridin-3-yl)-2-oxo-2,3-dihydro-1H-pyrido[2,3-e][1,4]diazepin-5-yl)-2,5-dimethylpiperazine-1-carboxylate (6 mg, 9.45 µmol) in TFA (1 mL) was stirred for 15 min at RT. The solvent was then removed under reduced pressure, and the residue was azeotropted with tolune (2×5 mL). The residue was then dissolved in DCM (1 mL), DIEA (16.5 µL, 0.094 mmol) added, and chilled to 0° C. under an atmosphere of argon. To this was added a second solution of acryloyl chloride (0.767 µl, 9.45 µmol) in DCM (0.5 mL). The reaction was then directly purified by silica gel chromatography (4 g) eluting the products with a gradient of 10>60% EtOAc/EtOH (3:1 blend)/heptane to afford 5-((2S,5R)-4-acryloyl-2,5-dimethylpiperazin-1-yl)-7-chloro-8-(2-fluorophenyl)-1-(2-isopropyl-4-methylpyridin-3-yl)-1,3-dihydro-2H-pyrido[2,3-e][1,4]diazepin-2-one (Example 219) as a colorless film. m/z (ESI, +ve ion): 589.1 (M+H)$^+$. $^1$H NMR (400 MHz, CDCl3) δ 8.41-8.64 (m, 1H), 7.96-8.09 (m, 1H), 7.37-7.48 (m, 1H), 7.07-7.23 (m, 4H), 6.27-6.75 (m, 2H), 5.76 (br d, J=10.37 Hz, 1H), 4.17-5.12 (m, 3H), 2.50-3.99 (m, 6H), 1.91-2.35 (m, 3H), 1.47-1.61 (m, 3H), 1.08-1.46 (m, 6H), 0.81-0.95 (m, 3H). $^{19}$F NMR (376 MHz, CDCl3) δ −112.62 (s, 1F).

Example 220

5-((2S,5R)-4-Acryloyl-2,5-dimethylpiperazin-1-yl)-7-chloro-8-(2-fluorophenyl)-1-neopentyl-1,3-dihydro-2H-pyrido[2,3-e][1,4]diazepin-2-one

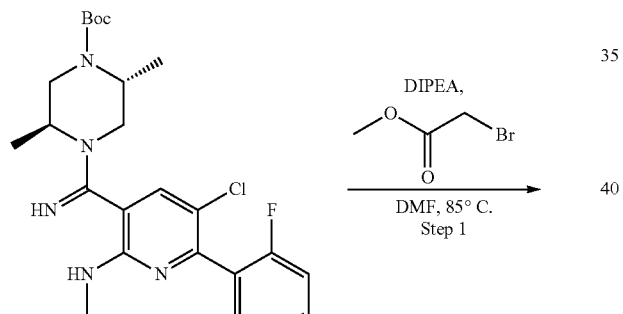

Example 190, Step 1

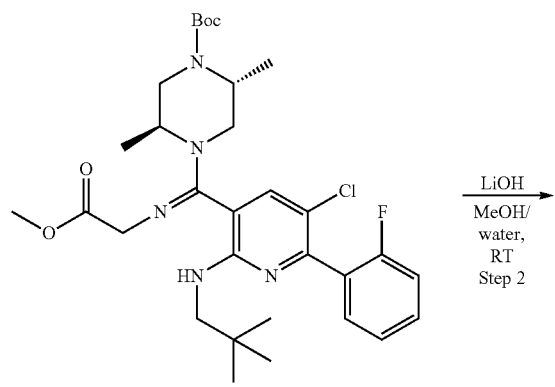

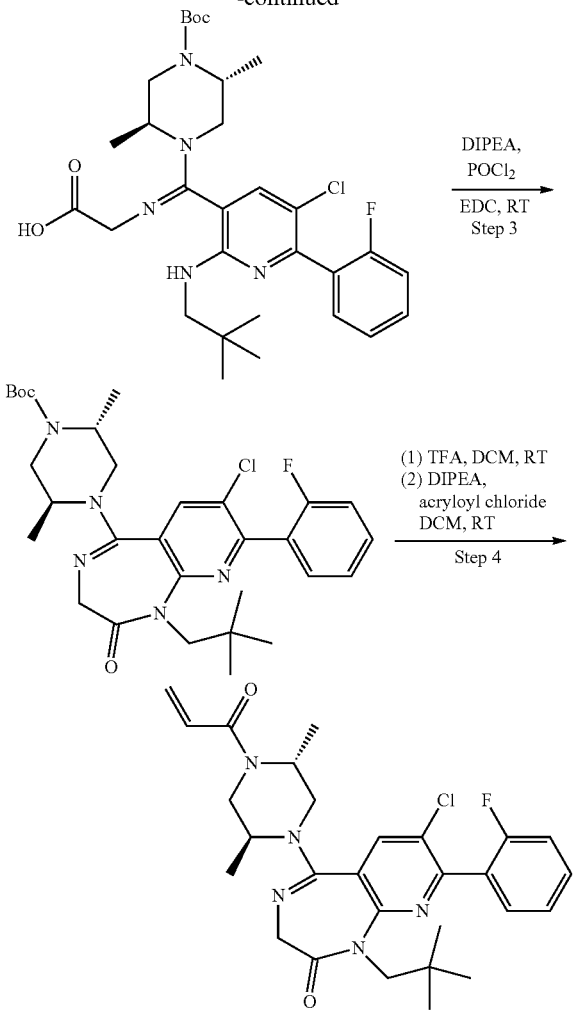

Example 220

Step 1: tert-Butyl (2R,5S)-4-((5-chloro-6-(2-fluorophenyl)-2-(neopentylamino)pyridin-3-yl)((2-methoxy-2-oxoethyl)imino)methyl)-2,5-dimethylpiperazine-1-carboxylate A solution of tert-butyl (2R,5S)-4-((5-chloro-6-(2-fluorophenyl)-2-(neopentylamino)pyridin-3-yl)(imino)methyl)-2,5-dimethylpiperazine-1-carboxylate (Example 150, Step 1, 400 mg, 0.752 mmol), methyl bromoacetate (348 µl, 3.76 mmol), DIPEA (197 µl, 1.13 mmol) in DMF (3 mL) was heated to 85° C. for 16 hrs. The reaction mixture was then partitioned between EtOAc (20 mL) and sat. NaHCO$_3$ (20 mL). The organic was then further washed with water (10 mL) and sat. NaCl (5 mL), then dried over MgSO$_4$. The organic layer was concentrated under reduced pressure, and then purified by silica gel chromatography (24 g) eluting the product with a gradient of 10>50% EtOAc/EtOH (3:1 blend)/heptane to afford tert-butyl (2R,5S)-4-((5-chloro-6-(2-fluorophenyl)-2-(neopentylamino)pyridin-3-yl)((2-methoxy-2-oxoethyl)imino)methyl)-2,5-dimethylpiperazine-1-carboxylate as white solid, m/z (ESI, +ve ion): 604.4 (M+H)$^+$.

Step 2: 2-((((2S,5R)-4-(tert-Butoxycarbonyl)-2,5-dimethylpiperazin-1-yl)(5-chloro-6-(2-fluorophenyl)-2-(neopentylamino)pyridin-3-yl)methylene)amino)acetic acid A suspension of tert-butyl (2R,5S)-4-((5-chloro-6-(2-fluorophenyl)-2-(neopentylamino)pyridin-3-yl)((2-methoxy-2-oxoethyl)imino)methyl)-2,5-dimethylpiperazine-1-carboxylate (310 mg, 0.513 mmol) and lithium hydroxide, monohydrate (23.7 mg, 0.564 mmol) in MeOH (5 mL) and water (1 mL) was stirred at RT for 3 days. The reaction mixture was then partitioned between DCM (20 ml) and sat. NaHCO$_3$ (10 mL). The aqueous layer was further extracted with DCM (5 mL). The combined organics were washed with sat. NaCl (5 mL), dried over MgSO4, filtered, and then concentrated under reduced pressure to afford 2-((((2S,5R)-4-(tert-butoxycarbonyl)-2,5-dimethylpiperazin-1-yl)(5-chloro-6-(2-fluorophenyl)-2-(neopentylamino)pyridin-3-yl)methylene)amino)acetic acid as white solid. m/z (ESI, +ve ion): 590.4 (M+H)$^+$.

Step 3: tert-Butyl (2R,5S)-4-(7-chloro-8-(2-fluorophenyl)-1-neopentyl-2-oxo-2,3-dihydro-1H-pyrido[2,3-e][1,4]diazepin-5-yl)-2,5-dimethylpiperazine-1-carboxylate To a stirring solution of 2-((((2S,5R)-4-(tert-butoxycarbonyl)-2,5-dimethylpiperazin-1-yl)(5-chloro-6-(2-fluorophenyl)-2-(neopentylamino)pyridin-3-yl)methylene)amino)acetic acid (300 mg, 0.508 mmol) in 1,2-dichloroethane (3 mL) at RT was added DIPEA (266 µl, 1.53 mmol) followed by phosphorus oxychloride (95 µl, 1.02 mmol). After 15 min, the reaction was then partitioned between EtOAc (20 mL) and sat. NaHCO$_3$ (20 mL). The organic was then washed with sat. NaCl (5 mL). dried over MgSO$_4$, concentrated under reduced pressure, and then purified by silica gel chromatography (12 g) eluting products with a gradient of 10>40% EtOAc/EtOH (3:1 blend)/heptane to afford tert-butyl (2R,5S)-4-(7-chloro-8-(2-fluorophenyl)-1-neopentyl-2-oxo-2,3-dihydro-1H-pyrido[2,3-e][1,4]diazepin-5-yl)-2, 5-dimethylpiperazine-1-carboxylate as white solid. m/z (ESI, +ve ion): 572.2 (M+H)$^+$.

Step 4: tert-Butyl (2R,5S)-4-(7-chloro-8-(2-fluorophenyl)-1-neopentyl-2-oxo-2,3-dihydro-1H-pyrido[2,3-e][1,4]diazepin-5-yl)-2,5-dimethylpiperazine-1-carboxylate (Example 220)

A solution of tert-butyl (2R,5S)-4-(7-chloro-8-(2-fluorophenyl)-1-neopentyl-2-oxo-2,3-dihydro-1H-pyrido[2,3-e][1,4]diazepin-5-yl)-2,5-dimethylpiperazine-1-carboxylate (40 mg, 0.070 mmol) in TFA (1 ml) was stirred for 15 min at RT. The solvent was then removed under reduced pressure, and the residue was azeotropted with toluene (2×5 mL). The resulting residue was then dissolved in DCM (1 mL), DIPEA (12.2 µl, 0.070 mmol) added, and the solution was then chilled to 0° C. under an atmosphere of argon. To this solution was added a second solution of acryloyl chloride (5.68 µl, 0.070 mmol) in DCM (0.5 mL). After 5 min, the reaction was then directly purified by silica gel chromatography (4 g) eluting products with a gradient of 10>60% EtOAc/EtOH (3:1 blend)/heptane to afford the product as colorless film. The film was then suspended in MeCN/water (1:1:2 mL), frozen, then lyophilized to afford tert-butyl (2R,5S)-4-(7-chloro-8-(2-fluorophenyl)-1-neopentyl-2-oxo-2,3-dihydro-1H-pyrido[2,3-e][1,4]diazepin-5-yl)-2,5-dimethylpiperazine-1-carboxylate (Example 2201) as a white fluffy powder. m/z (ESI, +ve ion): 526.6 (M+H)$^+$. $^1$H NMR (400 MHz, CDCl$_3$) δ 7.85-7.98 (m, 1H), 7.43-7.54 (m, 2H), 7.27-7.35 (m, 1H), 7.21 (t, J=18.00 Hz, 1H), 6.45-6.69 (m, 1H), 6.28-6.40 (m, 1H), 5.69-5.79 (m, 1H), 3.02-5.05 (m, 10H), 1.36-1.55 (m, 3H), 0.93-1.26 (m, 3H), 0.72-0.78 (m, 9H). $^{19}$F NMR (376 MHz, CDCl$_3$) δ −113.20 (s, 1F), −113.23 (s, 1F), −113.30 (s, 1F).

Example 221

4-(4-Acryloylpiperazin-1-yl)-6-chloro-7-(2-fluorophenyl)-1-(2-isopropyl-4-methylpyridin-3-yl)-2-oxo-1,2-dihydro-1,8-naphthyridine-3-carboxamide

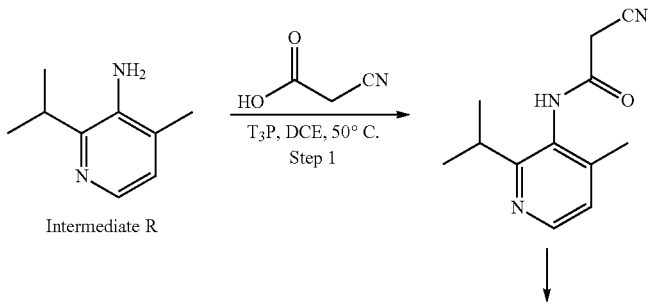

Intermediate R

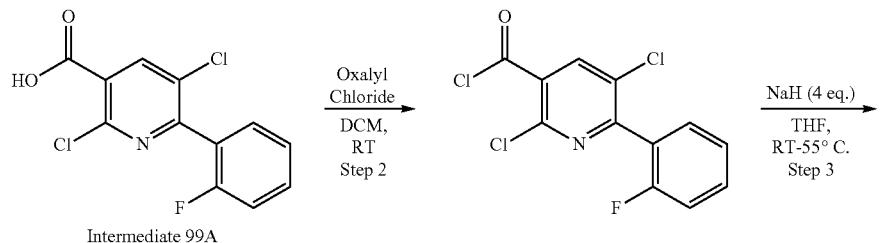

Intermediate 99A

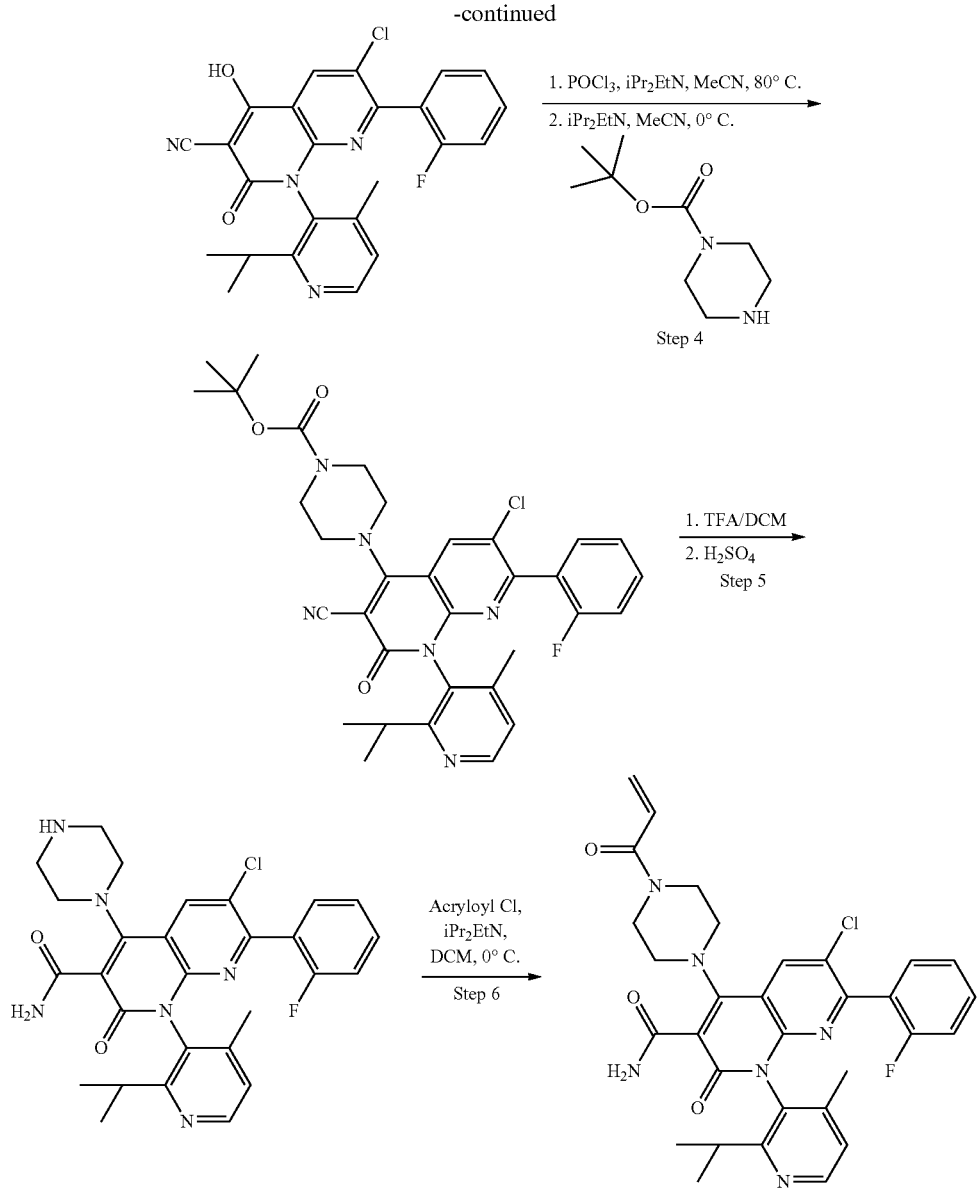

Step 1: 2-Cyano-N-(2-isopropyl-4-methylpyridin-3-yl)acetamide

To a solution of 2-isopropyl-4-methylpyridin-3-amine (4.18 g, 27.8 mmol, Intermediate R) and cyano acetic acid (3.31 g, 39 mmol, Sigma-Aldrich, St. Louis, Mo.) in DCE (25 mL) was added 1-propanephosphonic acid cyclic anhydride, 50 wt. % solution in ethyl acetate (25.1 mL, 36 mmol, Sigma-Aldrich, St. Louis, Mo.) and iPr$_2$EtN (9.72 mL, 57 mmol). The mixture was heated to 50° C. for 30 min. The mixture was cooled to rt, added 30 mL ethyl acetate and 30 mL of satd. NaHCO$_3$ and stirred for 5 min. The organic layer was separated, washed with brine (20 mL), dried over Na$_2$SO$_4$, filtered, and concentrated in vacuo. The yellow solid obtained was triturated in heptane:EtOAc (5:1) (20 mL), filtered off, and dried under vacuum. 2-Cyano-N-(2-isopropyl-4-methylpyridin-3-yl)acetamide was obtained as a light yellow solid. m/z (ESI, +ve) 218.0 (M+H)$^+$.

Step 2: 2,5-Dichloro-6-(2-fluorophenyl)nicotinoyl chloride

To a solution of 2,5-dichloro-6-(2-fluorophenyl)nicotinic acid (7.1 g, 25 mmol, Intermediate 99A) in DCM (50 mL) was added oxalyl chloride. 2.0 M solution in methylene chloride (15.4 mL, 31 mmol, Sigma-Aldrich, St. Louis, Mo.), followed by several drops of DMF. The mixture was stirred at RT for 45 min, evaporated, dried in vacuo to provide 2,5-dichloro-6-(2-fluorophenyl)nicotinoyl chloride, that was carried forward into the next step.

Step 3: 6-Chloro-7-(2-fluorophenyl)-4-hydroxy-1-(2-isopropyl-4-methylpyridin-3-yl)-2-oxo-1,2-dihydro-1,8-naphthyridine-3-carbonitrile To a 250-mL round-bottomed flask was added 2-cyano-N-(2-isopropyl-4-methylpyridin-3-yl)acetamide (4.97 g, 22.9 mmol) in THF (30 mL). The reaction mixture was cooled to 0° C. and slowly added sodium hydride (3.66 g, 91 mmol, 60%, Sigma-Aldrich, St. Louis, Mo.) portion wise. The mixture was then stirred at rt for 20 min and cooled to 0° C. and slowly added 2,5-dichloro-6-(2-fluorophenyl) nicotinoyl chloride (7.31 g, 24.0 mmol) in THF (20 mL). After stirring at rt for 10 min, the mixture was heated in 55° C. for 1 h. The reaction mixture was allowed to cool to rt and quenched with saturated aqueous NH$_4$Cl (10 mL) and extracted with EtOAc (10 mL). The organic layer was separated, washed with brine (5 mL), dried over Na$_2$SO$_4$, filtered, and concentrated in vacuo. The orange solid obtained was triturated in heptane:EtOAc (5:1) (10 mL), filtered off, and dried under vacuum. 6-Chloro-7-(2-fluorophenyl)-4-hydroxy-1-(2-isopropyl-4-methylpyridin-3-yl)-2-oxo-1,2-dihydro-1,8-naphthyridine-3-carbonitrile was obtained as an orange solid. m/z (ESI, +ve) 448.9 (M+H)$^+$.

Step 4: tert-Butyl 4-(6-chloro-3-cyano-7-(2-fluorophenyl)-1-(2-isopropyl-4-methylpyridin-3-yl)-2-oxo-1,2-dihydro-1,8-naphthyridin-4-yl)piperazine-1-carboxylate To a solution of 6-chloro-7-(2-fluorophenyl)-4-hydroxy-1-(2-isopropyl-4-methylpyridin-3-yl)-2-oxo-1,2-dihydro-1,8-naphthyridine-3-carbonitrile (7.71 g, 17.2 mmol) and IPr2EtN (9 mL. 51.5 mmol) in ACN (40 mL) at 0° C. was added phosphorus oxychloride (2.1 mL, 22.3 mmol, Sigma-Aldrich, St. Louis, Mo.), and the resulting solution was stirred at 80° C. for 30 min. The reaction mixture was cooled down to 0° C. and iPr$_2$EtN (9 mL, 51.5 mmol) was added followed by tert-butyl piperazine-1-carboxylate (4.80 g, 25.8 mmol, Sigma-Aldrich, St. Louis, Mo.) in ACN (6 mL). After stirring at rt for 20 min, satd NaHCO$_3$ (10 mL) and EtOAc (O1 mL) were added. The organic layer was taken, washed with water, dried over Na$_2$SO$_4$, filtered, and concentrated in vacuo. Chromatographic purification of the residue (silica gel, 0-25% EtOAc:EtOH (3:1) in heptane) provided tert-butyl 4-(6-chloro-3-cyano-7-(2-fluorophenyl)-1-(2-isopropyl-4-methylpyridin-3-yl)-2-oxo-1,2-dihydro-1,8-naphthyridin-4-yl)piperazine-1-carboxylate as a light orange solid: m/z (ESI, +ve) 617.0 (M+H)$^+$.

Step 5: 6-Chloro-7-(2-fluorophenyl)-1-(2-isopropyl-4-methylpyridin-3-yl)-2-oxo-4-(piperazin-1-yl)-1,2-dihydro-1,8-naphthyridine-3-carboxamide To a 50-mL round-bottomed flask was added tert-butyl 4-(6-chloro-3-cyano-7-(2-fluorophenyl)-1-(2-isopropyl-4-methylpyridin-3-yl)-2-oxo-1,2-dihydro-1,8-naphthyridin-4-yl)piperazine-1-carboxylate (133 mg, 0.22 mmol), DCM (2 mL), and trifluoroacetic acid (1 mL). The reaction mixture was stirred at rt for 30 min and the solvent was removed under vacuum. The orange residue obtained was suspended in H$_2$SO$_4$ 95% (1 mL) and heated at 70° C. for 16 h. The reaction mixture was allowed to cool to rt and slowly poured over ice water. The solution was neutralized with NaOH (2 N) and extracted with EtOAc. The organic layer was taken, washed with water, dried over Na$_2$SO$_4$, filtered, and concentrated in vacuo. 6-Chloro-7-(2-fluorophenyl)-1-(2-isopropyl-4-methylpyridin-3-yl)-2-oxo-4-(piperazin-1-yl)-1,2-dihydro-1,8-naphthyridine-3-carboxamide was obtained as a light yellow solid. m/z (ESI, +ve) 535.1 (M+H)$^+$.

Step 6: 4-(4-Acryloylpiperazin-1-yl)-6-chloro-7-(2-fluorophenyl)-1-(2-isopropyl-4-methylpyridin-3-yl)-2-oxo-1,2-dihydro-1,8-naphthyridine-3-carboxamide To a 50-mL round bottomed flask was added 6-chloro-7-(2-fluorophenyl)-1-(2-isopropyl-4-methylpyridin-3-yl)-2-oxo-4-(piperazin-1-yl)-1,2-dihydro-1,8-naphthyridine-3-carboxamide (110 mg, 0.21 mmol), DCM (5 mL) and iPr$_2$EtN (0.14 mL, 0.82 mmol). The reaction mixture was cooled to 0° C. and acryloyl chloride (0.45 mL, 0.23 mmol, 0.5 M in DCM) was added. The reaction mixture was stirred at 0° C. for 60 min and quenched with saturated aqueous NaHCO$_3$ (5 mL) and extracted with EtOAc (10 mL). The organic layer was separated, washed with brine (5 mL), dried over Na$_2$SO$_4$, filtered, and concentrated in vacuo. Chromatographic purification of the residue (silica gel, 0-60% EtOAc:EtOH (3:1) in heptane) provided 4-(4-acryloylpiperazin-1-yl)-6-chloro-7-(2-fluorophenyl)-1-(2-isopropyl-4-methylpyridin-3-yl)-2-oxo-1,2-dihydro-1,8-naphthyridine-3-carboxamide as a light yellow solid. $^1$H NMR (400 MHz, DMSO-d$_6$) δ 8.43 (s, 1H), 8.41 (d, J=4.77 Hz, 1H), 7.87 (s, 1H), 7.66 (s, 1H), 7.44-7.56 (m, 1H), 7.17-7.33 (m, 4H), 6.90 (dd, J=16.59, 10.37 Hz, 1H), 6.18 (dd, J=16.59, 2.49 Hz, 1H), 5.71-5.80 (m, 1H), 3.86 (br s, 4H), 3.25-3.30 (m, 4H), 2.64 (quin, J=6.84 Hz, 1H), 1.90 (s, 3H), 1.07 (d, J=6.63 Hz, 3H), 0.91 (d, J=6.63 Hz, 3H); m/z (ESI, +ve) 589.0 (M+H)$^+$.

Example 222

(M)-4-(5-Acryloyl-2,5-diazabicyclo[4.1.0]heptan-2-yl)-6-chloro-7-(2-fluorophenyl)-1-(2-isopropyl-4-methylpyridin-3-yl)pyrido[2,3-d]pyrimidin-2(1H)-one (Examples 222, 222-1, and 222-2)

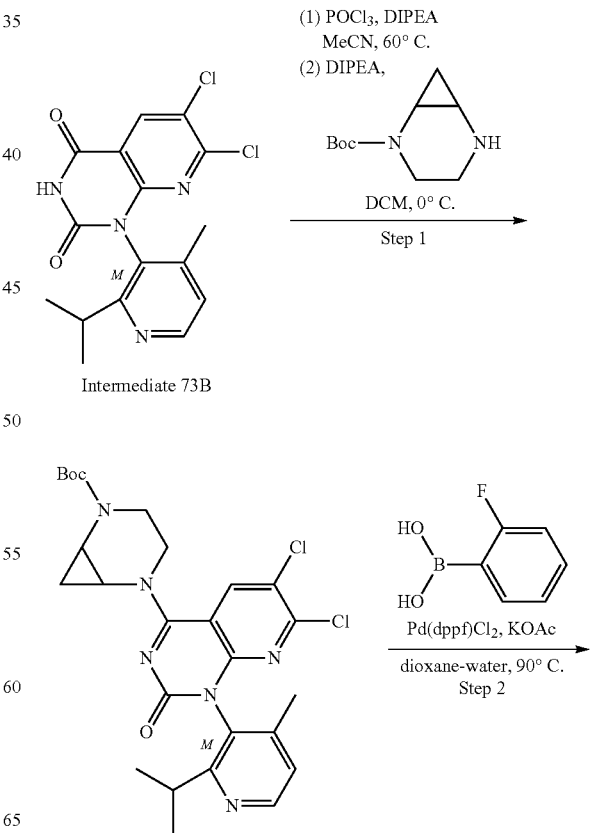

-continued

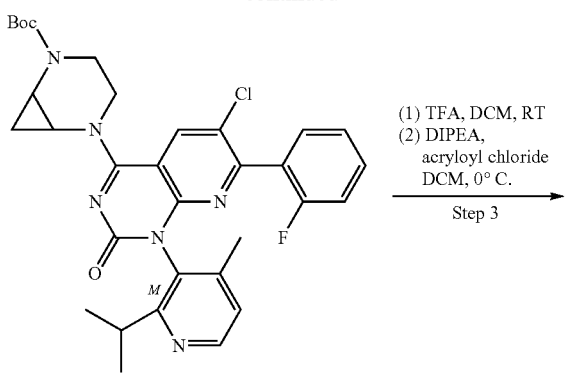

(1) TFA, DCM, RT
(2) DIPEA,
  acryloyl chloride
  DCM, 0° C.

Step 3

-continued

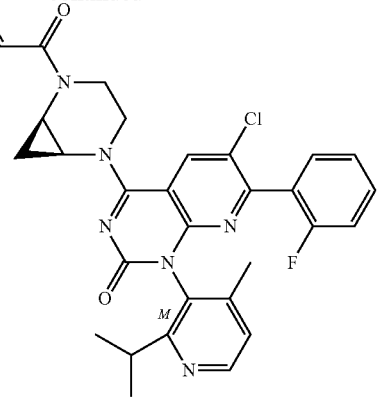

Example 222-2
2nd-eluting isomer

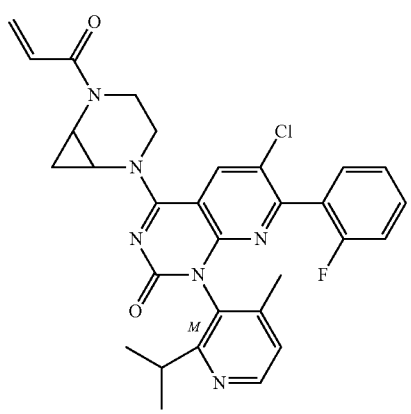

Example 222

Chiral
Separation
Step 4

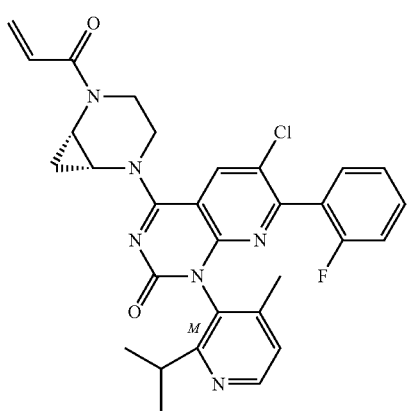

Example 222-1
1st-eluting isomer

Step 1: (M)-tert-Butyl 5-(6,7-dichloro-1-(2-isopropyl-4-methylpyridin-3-yl)-2-oxo-1,2-dihydropyrido[2,3-d]pyrimidin-4-yl)-2,5-diazabicyclo[4.1.0]heptane-2-carboxylate DIPEA (0.19 mL, 1.1 mmol) and POCl₃ (0.10 mL, 1.11 mmol) were sequentially added to a room temperature solution of (M)-6,7-dichloro-1-(2-isopropyl-4-methylpyridin-3-yl)pyrido[2,3-d]pyrimidine-2,4(1H,3H)-dione (Intermediate 73B, 270 mg, 0.74 mmol) in acetonitrile (3.5 mL). The homogenous bright-yellow solution was heated at 60° C. After 2 h, the reaction mixture was concentrated under reduced pressure and azeotropically dried with heptane. The resulting dark-orange residue was dissolved in DCM (2.0 mL) and cooled to 0° C. DIPEA (0.65 mL, 3.7 mmol) was added, followed by a solution of tert-butyl 2,5-diazabicyclo[4.1.0]heptane-2-carboxylate (Aurum Pharmatech LLC, Franklin Park, N.J., USA, 250 mg, 1.3 mmol) in DCM (1.5 mL). After 18 h, the reaction was diluted with EtOAc (70 mL) and water (70 mL). The layers were partitioned and the aqueous phase was extracted with EtOAc (2×30 mL). The combined organic extracts were dried over anhydrous magnesium sulfate, filtered, and concentrated to afford an orange oil which was purified by silica gel chromatography (eluent: 0-50% (3:1 EtOAc-EtOH)/heptane) to afford (M)-tert-butyl 5-(6,7-dichloro-1-(2-isopropyl-4-methylpyridin-3-yl)-2-oxo-1,2-dihydropyrido[2,3-d]pyrimidin-4-yl)-2,5-diazabicyclo[4.1.0]heptane-2-carboxylate (390 mg, 0.72 mmol, 97% yield) as a bright yellow-orange solid.

Step 2: (M)-tert-Butyl 5-(6-chloro-7-(2-fluorophenyl)-1-(2-isopropyl-4-methylpyridin-3-yl)-2-oxo-1,2-dihydropyrido[2,3-d]pyrimidin-4-yl)-2,5-diazabicyclo[4.1.0]heptane-2-carboxylate A biphasic mixture of (M)-tert-butyl 5-(6,7-dichloro-1-(2-isopropyl-4-methylpyridin-3-yl)-2-oxo-1,2-dihydropyrido[2,3-d]pyrimidin-4-yl)-2,5-diazabicyclo[4.1.0]heptane-2-carboxylate (390 mg, 0.72 mmol), 2-fluorophenylboronic acid (0.15 mg, 1.1 mmol, Combi-Blocks Inc., San Diego, Calif., USA), Pd(dppf)Cl₂ (53 mg, 0.072 mmol), and potassium acetate (0.23 mg, 3.6 mmol) in 1,4-dioxane (4.2 mL)/water (0.10 mL) was deoxygenated with bubbling nitrogen gas for 10 min, then heated at 90° C. overnight. The reaction mixture was filtered through Celite and diluted with EtOAc (100 mL). The organic phase was sequentially washed with saturated aqueous ammonium chloride (100 mL), water (100 mL), and brine (100 mL), then dried over anhydrous magnesium sulfate, filtered, and concentrated to afford crude (M)-tert-butyl 5-(6-chloro-7-(2-fluorophenyl)-1-(2-isopropyl-4-methylpyridin-3-yl)-2-oxo-1,2-dihydropyrido[2,3-d]pyrimidin-4-yl)-2,5-diazabicyclo[4.1.0]heptane-2-carboxylate as a brown foam which was carried forward in the next step without purification, assuming theoretical yield.

Step 3: (M)-4-(5-Acryloyl-2,5-diazabicyclo[4.1.0]heptan-2-yl)-6-chloro-7-(2-fluorophenyl)-1-(2-isopropyl-4-methylpyridin-3-yl)pyrido[2,3-d]pyrimidin-2(1H)-one (Example 222)

A solution of (M)-tert-butyl 5-(6-chloro-7-(2-fluorophenyl)-1-(2-isopropyl-4-methylpyridin-3-yl)-2-oxo-1,2-dihydropyrido[2,3-d]pyrimidin-4-yl)-2,5-diazabicyclo[4.1.0]heptane-2-carboxylate (440 mg, 0.72 mmol) in DCM (4.0 mL) was treated with trifluoroacetic acid (2.0 mL, 26 mmol). After 15 min, the mixture was concentrated in vacuo, then the crude intermediate was redissolved in DCM (8.0 mL) and cooled to 0° C. Sequentially, DIPEA (1.4 mL, 8.0 mmol) and acryloyl chloride solution (0.26 M in DCM, 3.0 mL, 0.77 mmol) were added and the mixture was allowed to warm to ambient temperature. After 45 min, the reaction was quenched with sat. aq. sodium bicarbonate (15 mL) and diluted with DCM (15 mL). The layers were partitioned and then the aqueous layer was extracted with DCM (2×40 mL). The combined organic extracts were dried over anhydrous magnesium sulfate, filtered, and concentrated to afford a dark orange-brown residue which was purified by silica gel chromatography (eluent: 0-100% (3:1 EtOAc-EtOH)/heptane) to afford (M)-4-(5-acryloyl-2,5-diazabicyclo[4.1.0]heptan-2-yl)-6-chloro-7-(2-fluorophenyl)-1-(2-isopropyl-4-methylpyridin-3-yl)pyrido[2,3-d]pyrimidin-2(1H)-one (Example 222, 360 mg, 0.64 mmol, 88% yield) as a mixture of piperazine diastereomers. $^1$H NMR (400 MHz, DMSO-$d_6$) δ 0.91 (t, J=5.8 Hz, 3H), 1.06 (d, J=6.6 Hz, 3H), 1.45-1.54 (m, 1H), 1.85-2.00 (m, 3H), 2.62 (sept, J=6.6 Hz, 0.5H), 2.79 (sept, J=6.6 Hz, 0.5H), 3.35-4.08 (m, 6H), 4.56-4.81 (m, 1H), 5.75-5.83 (m, 1H), 6.16-6.32 (m, 1H), 6.96 (ddd, J=16.9, 10.4, 3.8 Hz, 1H), 7.15-7.36 (m, 4H), 7.46-7.56 (m, 1H), 8.38 (dd, J=4.8, 1.2 Hz, 1H), 9.09 (s, 1H); $^{19}$F{$^1$H} NMR (376 MHz, DMSO-$d_6$) δ 114.20 (s, 1F), −114.18 (s, 1F); LRMS: (ESI, +ve ion) m/z 559.1 (M+H)$^+$.

Step 4: (M)-4-((1R,6S)-5-Acryloyl-2,5-diazabicyclo[4.1.0]heptan-2-yl)-6-chloro-7-(2-fluorophenyl)-1-(2-isopropyl-4-methylpyridin-3-yl)pyrido[2,3-d]pyrimidin-2(1H)-one (Example 222-1) and (M)-4-((1S,6R)-5-acryloyl-2,5-diazabicyclo[4.1.0]heptan-2-yl)-6-chloro-7-(2-fluorophenyl)-1-(2-isopropyl-4-methylpyridin-3-yl)pyrido[2,3-d]pyrimidin-2(1H)-one (Example 222-2)

(M)-4-(5-Acryloyl-2,5-diazabicyclo[4.1.0]heptan-2-yl)-6-chloro-7-(2-fluorophenyl)-1-(2-isopropyl-4-methylpyridin-3-yl)pyrido[2,3-d]pyrimidin-2(1H)-one (350 mg, 0.62 mmol) was dissolved in MeOH (4.0 mL) and DCM (1.0 mL) and purified by preparative SFC (Chiralcel ID column (5 um, 21×250 mm), F=80 mL, 50% MeOH/50% CO$_2$) to afford (M)-4-((1R,6S)-5-acryloyl-2,5-diazabicyclo[4.1.0]heptan-2-yl)-6-chloro-7-(2-fluorophenyl)-1-(2-isopropyl-4-methylpyridin-3-yl)pyrido[2,3-d]pyrimidin-2(1H)-one (Example 222-1, 150 mg, 0.26 mmol) as a tan solid (1$^{st}$-eluting isomer) and (M)-4-((1S,6R)-5-acryloyl-2,5-diazabicyclo[4.1.0]heptan-2-yl)-6-chloro-7-(2-fluorophenyl)-1-(2-isopropyl-4-methylpyridin-3-yl)pyrido[2,3-d]pyrimidin-2(1H)-one (Example 222-2, 130 mg, 0.24 mmol) as a tan solid (2$^{nd}$-eluting isomer). Example 222-1: $^1$H NMR (400 MHz, DMSO-$d_6$) δ 0.92 (d, J=6.6 Hz, 3H), 1.06 (d, J=6.6 Hz, 3H), 1.10-1.17 (m, 1H), 1.50 (q, J=6.4 Hz, 1H), 1.85-1.91 (m, 3H), 2.71-2.87 (m, 1H), 3.44-4.81 (m, 6H), 5.76-5.84 (m, 1H), 6.19-6.30 (m, 1H), 6.96 (dd, J=16.8, 10.4 Hz, 1H), 7.14-7.34 (m, 4H), 7.47-7.55 (m, 1H), 8.38 (d, J=5.0 Hz, 1H), 9.09 (s, 1H); $^{19}$F{$^1$H} NMR (376 MHz, DMSO-$d_6$) δ 114.17 (s, 1F); LRMS: (ESI, +ve ion) m/z 559.1 (M+H)$^+$. Example 222-2: $^1$H NMR (400 MHz, DMSO-$d_6$) δ 0.91 (d, J=6.8 Hz, 3H), 1.06 (d, J=6.8 Hz, 3H), 1.08-1.12 (m, 1H), 1.50 (q, J=6.4 Hz, 1H), 1.92-2.02 (m, 3H), 2.62 (sept, J=6.6 Hz, 1H), 3.43-4.78 (m, 6H) 5.76-5.83 (m, 1H), 6.16-6.29 (m, 1H), 6.95 (dd, J=16.8, 10.4 Hz, 1H), 7.13-7.35 (m, 4H), 7.46-7.55 (m, 1H), 8.37 (d, J=4.8 Hz, 1H), 9.09 (s, 1H); $^{19}$F{$^1$H} NMR (376 MHz, DMSO-$d_6$) δ −114.11 (s, 1F); LRMS: (ESI, +ve ion) m/z 559.3 (M+H)$^+$.

Example 223

(M)-4-((2S,5R)-4-Acryloyl-2,5-dimethylpiperazin-1-yl)-6-chloro-7-(2-fluoro-5-(methylsulfonyl)phenyl)-1-(2-isopropyl-4-methylpyridin-3-yl)pyrido[2,3-d]pyrimidin-2(1H)-one (Example 223)

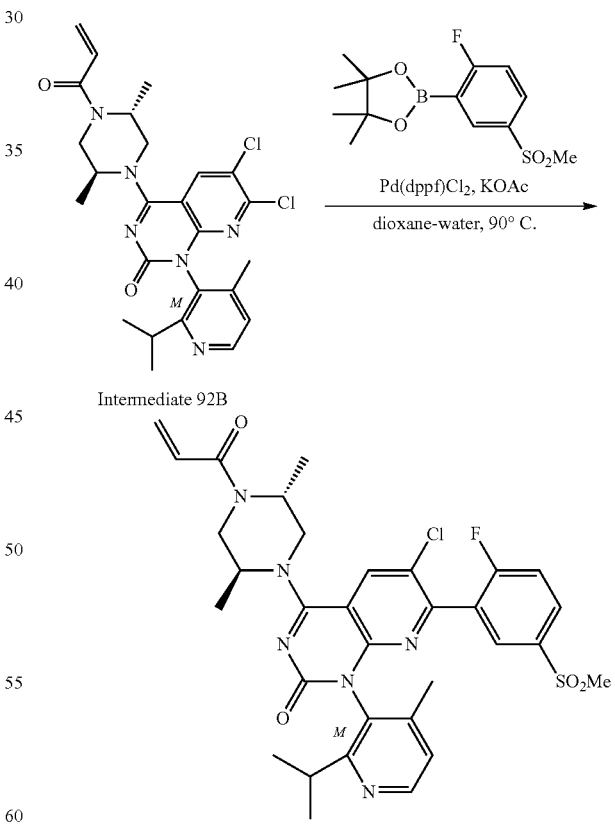

Intermediate 92B

Example 223

A biphasic mixture of (M)-4-((2S,5R)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate 92B, 220 mg, 0.43 mmol), 2-(2-fluoro-5-

(methylsulfonyl)phenyl)-4,4,5,5-tetramethyl-1,3,2-dioxaborolane (Aurum Pharmatech LLC, Franklin Park, N.J., USA, 220 mg, 0.73 mmol), Pd(dppf)Cl$_2$ (31 mg, 0.043 mmol), and potassium acetate (210 mg, 2.1 mmol) in 1,4-dioxane (2.2 mL)/water (200 µL) was deoxygenated with bubbling nitrogen gas for 10 min, then heated at 90° C. overnight. The reaction mixture was filtered through Celite using EtOAc (100 mL). The organic phase was sequentially washed with 50% saturated aqueous ammonium chloride (2×100 mL) and brine (100 mL), then dried over anhydrous magnesium sulfate. filtered, and concentrated to afford a gold-orange oil which was purified by silica gel chromatography (eluent: 10-100% 3:1 EtOAc-EtOH/heptane) to afford (M)-4-((2S,5R)-4-acryloyl-2,5-dimethylpiperazin-1-yl)-6-chloro-7-(2-fluoro-5-(methylsulfonyl)phenyl)-1-(2-isopropyl-4-methylpyridin-3-yl)pyrido[2,3-d]pyrimidin-2(1H)-one (Example 223, 210 mg, 0.32 mmol, 75% yield) as an orange solid. $^1$H NMR (400 MHz, DMSO-d$_6$) δ 1.00 (br d, J=6.6 Hz, 3H), 1.07 (d, J=6.6 Hz, 3H), 1.13-1.28 (m, 3H), 1.34 (br t, J=6.6 Hz, 3H), 1.94 (s, 3H), 2.68-2.76 (m, 1H), 3.21 (s, 3H), 3.46-4.97 (m, 6H), 5.75 (s, 1H), 6.19 (br d, J=17.2 Hz, 1H), 6.84 (td, J=16.5, 10.6 Hz, 1H), 7.19 (d, J=4.8 Hz, 1H), 7.65 (t, J=9.1 Hz, 1H), 7.84 (br d, J=4.6 Hz, 1H), 8.04-8.18 (m, 1H), 8.40 (d, J=4.8 Hz, 1H), 8.52 (d, J=2.9 Hz, 1H); $^{19}$F{$^1$H} NMR (376 MHz, DMSO-d$_6$) δ −106.12−−106.13 (m, 1F); LRMS: (ESI, +ve ion) m/z 652.4 (M+H)$^+$.

Example 224

4-((3R,5S)-4-Acryloyl-3,5-dimethylpiperazin-1-yl)-6-chloro-7-(2-fluorophenyl)-1-(2-isopropyl-4-methylpyridin-3-yl)pteridin-2(1H)-one (Examples 224, 224-1, and 224-2)

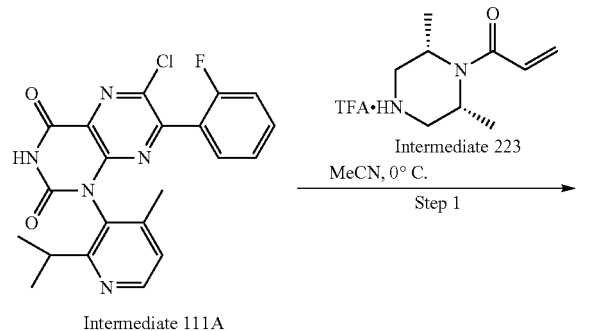

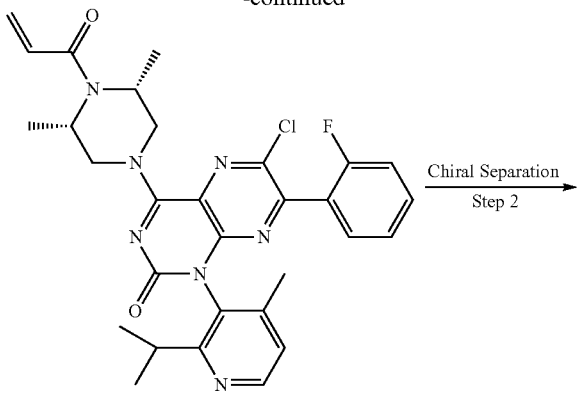

Example 224

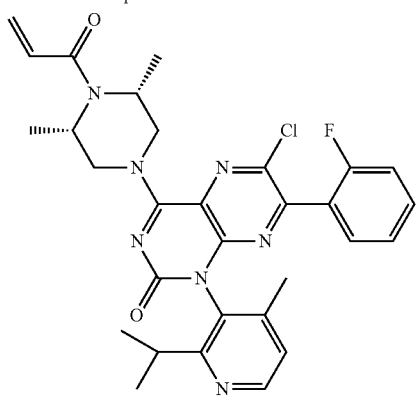

Example 224-1
1$^{st}$- eluting isomer

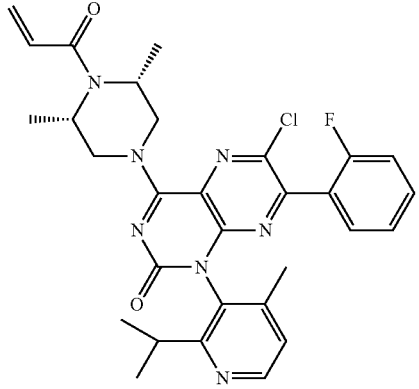

Example 224-2
2$^{nd}$- eluting isomer

Step 1: 4-((3R,5S)-4-Acryloyl-3,5-dimethylpiperazin-1-yl)-6-chloro-7-(2-fluorophenyl)-1-(2-isopropyl-4-methylpyridin-3-yl)pteridin-2(1H)-one (Example 224)

A room-temperature mixture of 6-chloro-7-(2-fluorophenyl)-1-(2-isopropyl-4-methylpyridin-3-yl)pteridine-2,4(1H,3H)-dione (Intermediate 111A, 260 mg, 0.62 mmol) and DIPEA (0.18 mL, 1.1 mmol) in acetonitrile (5.0 mL) was treated with phosphorus oxychloride (0.058 mL, 0.63 mmol). The resulting homogenous brown mixture was heated at 80° C. for 3 h. The reaction mixture was concentrated in vacuo and the resulting brown residue was dissolved in acetonitrile (4.0 mL) and cooled to 0° C. in an ice-water bath. DIPEA (1.1 mL, 6.2 mmol) was added, followed by drop-wise addition of a suspension of 1-((2R,6S)-2,6-dimethylpiperazin-1-yl)prop-2-en-1-one 2,2,2-trifluoroacetate (Intermediate 223, 240 mg, 0.85 mmol) in acetonitrile (2.0 mL). After 1 h, the reaction mixture was diluted with EtOAc (30 mL) and washed with 50% saturated aqueous ammonium chloride (100 mL). The layers were partitioned and the aqueous phase was extracted with EtOAc (2×30 mL). The combined organic extracts were dried over anhydrous magnesium sulfate, filtered, and concentrated to afford a red-brown residue which was purified by silica gel chromatography (eluent: 0-100% 3:1 EtOAc-EtOH/heptane) to afford 4-((3R,5S)-4-acryloyl-3,5-dimethylpiperazin-1-yl)-6-chloro-7-(2-fluorophenyl)-1-(2-isopropyl-4-methylpyridin-3-yl)pteridin-2(1H)-one (Example 224, 190 mg, 0.32 mmol, 52% yield) as a rust-colored solid (mixture of atropisomers). $^1$H NMR (400 MHz, DMSO-$d_6$) δ 0.82-0.89 (m, 3H), 0.96 (br d, J=6.4 Hz, 3H), 1.07 (d, J=6.6 Hz, 3H), 1.25 (br s, 3H), 1.99 (d, J=2.7 Hz, 3H), 2.77-2.95 (m, 1H), 3.34-3.90 (m, 2H), 4.46-5.25 (m, 3H), 5.32-5.68 (m, 1H), 5.71-5.81 (m, 1H), 6.21 (dd, J=16.5, 2.4 Hz, 1H), 6.87 (dd, J=16.7, 10.5 Hz, 1H), 7.20 (d, J=4.8 Hz, 1H), 7.27-7.42 (m, 3H), 7.50-7.64 (m, 1H), 8.41 (d, J=4.8 Hz, 1H); $^{19}$F{$^1$H} NMR (376 MHz, DMSO-$d_6$) δ −113.7 (s, 1F); LRMS: (ESI, +ve ion) 576.2 m/z (M+H)$^+$.

Step 2: Chiral Separation of 4-((3R,5S)-4-acryloyl-3,5-dimethylpiperazin-1-yl)-6-chloro-7-(2-fluorophenyl)-1-(2-isopropyl-4-methylpyridin-3-yl)pteridin-2(1H)-one (Examples 224-1 and 224-2)

4-((3R,5S)-4-Acryloyl-3,5-dimethylpiperazin-1-yl)-6-chloro-7-(2-fluorophenyl)-1-(2-isopropyl-4-methylpyridin-3-yl)pteridin-2(1H)-one (Example 224, 170 mg, 0.29 mmol) was dissolved in MeOH (8.0 mL) and DCM (2.0 mL) and purified by preparative SFC (Chiralcel AS-H column (5 um, 21×250 mm), F=80 mL, 15% iPrOH/85% CO$_2$) to afford 4-((3R,5S)-4-acryloyl-3,5-dimethylpiperazin-1-yl)-6-chloro-7-(2-fluorophenyl)-1-(2-isopropyl-4-methylpyridin-3-yl)pteridin-2(1H)-one (Example 224-1, 50 mg, 0.089 mmol, 61% yield) as an orange solid (single isomer, 1$^{st}$-eluting isomer) and 4-((3R,5S)-4-acryloyl-3,5-dimethylpiperazin-1-yl)-6-chloro-7-(2-fluorophenyl)-1-(2-isopropyl-4-methylpyridin-3-yl)pteridin-2(1H)-one (53 mg, 0.093 mmol, 64% yield) as an orange solid (single isomer, 2$^{nd}$-eluting isomer). Example 224-1: $^1$H NMR (400 MHz, DMSO-$d_6$) δ 0.96 (br d, J=6.4 Hz, 3H), 1.07 (d, J=6.6 Hz, 3H), 1.37 (br s, 6H), 1.99 (s, 3H), 2.86 (sept, J=6.6 Hz, 1H), 3.31-5.71 (m, 6H), 5.73-5.85 (m, 1H), 6.21 (dd, J=16.5, 2.4 Hz, 1H), 6.87 (dd, J=16.6, 10.4 Hz, 1H), 7.20 (d, J=4.8 Hz, 1H), 7.27-7.42 (m, 3H), 7.51-7.66 (m, 1H), 8.41 (d, J=5.0 Hz, 1H); $^{19}$F{$^1$H} NMR (376 MHz, DMSO-$d_6$) δ −113.68 (s, 1F); LRMS: (ESI, +ve ion) 576.2 m/z (M+H)$^+$. Example 224-2: $^1$H NMR (400 MHz, DMSO-d6) δ 0.96 (br d, J=6.4 Hz, 3H), 1.07 (d, J=6.8 Hz, 3H), 1.37 (br s, 6H), 1.99 (s, 3H), 2.86 (sept J=6.6 Hz, 1H), 3.38-3.72 (m, 2H), 4.59-4.79 (m, 2H), 4.85-5.15 (m, 1H), 5.43-5.68 (m, 1H). 5.70-5.80 (m, 1H), 6.21 (dd, J=16.5, 2.4 Hz, 1H), 6.87 (dd, J=16.7, 10.5 Hz, 1H), 7.20 (d, J=5.0 Hz, 1H), 7.26-7.42 (m, 3H), 7.51-7.61 (m, 1H), 8.41 (d, J=4.8 Hz, 1H); $^{19}$F{$^1$H} NMR (376 MHz, DMSO-$d_6$) δ −113.68 (s, 1F); LRMS: (ESI, +ve ion) 576.2 m/z (M+H)$^+$.

Example 225

4-((2S,5R)-4-Acryloyl-2,5-dimethylpiperazin-1-yl)-7-(2-fluorophenyl)-1-(2-isopropyl-4-methylpyridin-3-yl)-6-methylpteridin-2(1H)-one (Examples 225, 225-1, and 225-2)

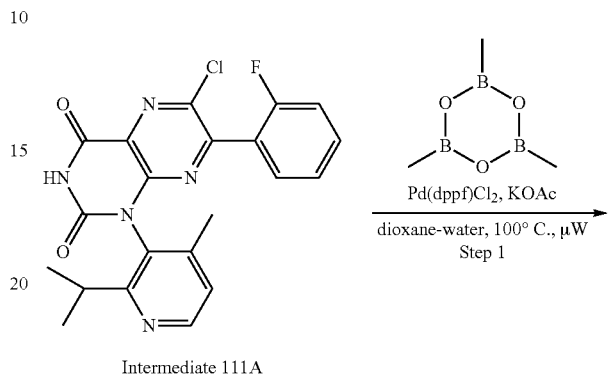

Intermediate 111A

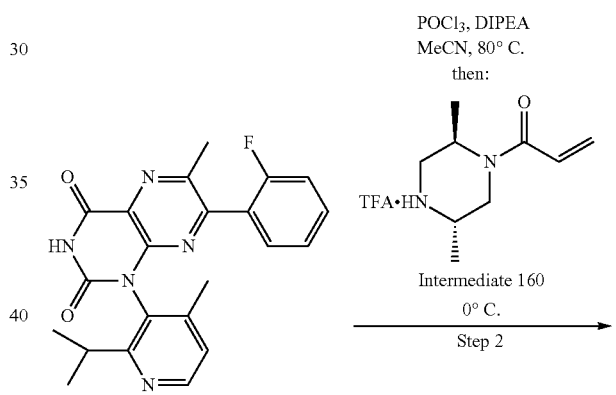

Intermediate 160

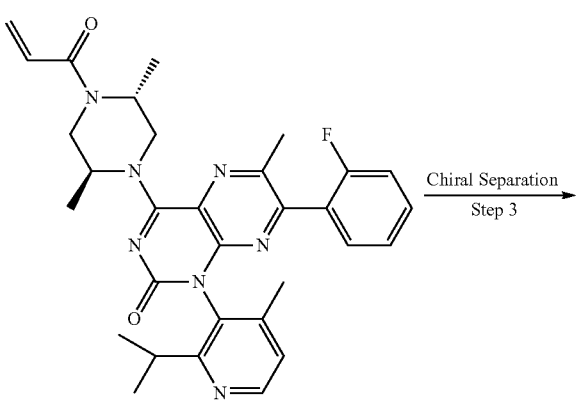

Example 225

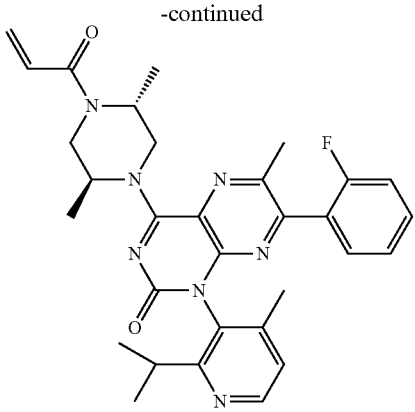

Example 225-1
1st - eluting isomer

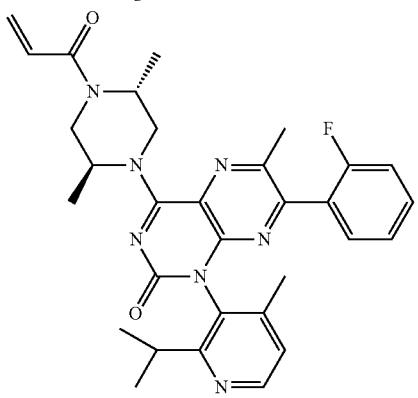

Example 225-2
2nd - eluting isomer

Step 1: 7-(2-Fluorophenyl)-1-(2-isopropyl-4-methylpyridin-3-yl)-6-methylpteridine-2,4(1H,3H)-dione A nitrogen-sparged mixture of 6-chloro-7-(2-fluorophenyl)-1-(2-isopropyl-4-methylpyridin-3-yl)pteridine-2,4(1H,3H)-dione (Intermediate 111A, 500 mg, 1.2 mmol), trimethylboroxine (0.33 mL, 2.3 mmol), potassium carbonate (330 mg, 2.3 mmol), and Pd(dppf)Cl$_2$ (86 mg, 0.12 mmol) in 1,4-dioxane (5.0 mL)/water (0.50 mL) was heated in a Biotage Initiator+ microwave at 100° C. for 1.5 h. The reaction mixture was diluted with water (50 mL) and extracted with EtOAc (2×50 mL). Sat. aq. sodium bicarbonate (30 mL) was added to the aqueous phase which was further extracted with EtOAc (2×50 mL). The combined organic extracts were dried over anhydrous magnesium sulfate, filtered, and concentrated in vacuo to give crude 7-(2-fluorophenyl)-1-(2-isopropyl-4-methylpyridin-3-yl)-6-methylpteridine-2,4(1H,3H)-dione as a burgundy-colored foam which was carried forward in the next step without purification, assuming theoretical yield.

Step 2: 4-((2S,5R)-4-Acryloyl-2,5-dimethylpiperazin-1-yl)-7-(2-fluorophenyl)-1-(2-isopropyl-4-methylpyridin-3-yl)-6-methylpteridin-2(1H)-one A room-temperature mixture of crude 7-(2-fluorophenyl)-1-(2-isopropyl-4-methylpyridin-3-yl)-6-methylpteridine-2,4(1H,3H)-dione (480 mg, 1.2 mmol) and DIPEA (0.41 mL, 2.3 mmol) in acetonitrile (7.8 mL) was treated with phosphorus oxychloride (0.22 mL, 2.3 mmol). The resulting homogenous brown mixture was heated at 80° C. for 2 h, then additional phosphorus oxychloride (0.10 mL, 1.1 mmol) was added and the dark brown mixture heated at 80° C. for 2 h, after which time the reaction mixture was cooled to 0° C. 1-((2R,5S)-2,5-dimethylpiperazin-1-yl)prop-2-en-1-one 2,2,2-trifluoroacetate (Intermediate 160, 2.1 g, 2.9 mmol) was added as a solution in acetonitrile (5.0 mL) and the reaction mixture stirred slowly warming to room temp overnight. The reaction mixture was diluted with EtOAc (30 mL) and washed with 50%, saturated aqueous ammonium chloride (100 mL). The layers were partitioned and the aqueous phase was washed with EtOAc (2×30 mL). The combined organic extracts were dried over anhydrous magnesium sulfate, filtered, and concentrated to afford a red-brown residue that was purified by silica gel chromatography (eluent: 0-100% 3:1 EtOAc-EtOH/heptane) and preparative SFC (Step I, Princeton DEAP (5 um, 21×250 mm), F=80 mL, 15% MeOH/85% CO$_2$, back pressure=90 bars, 1.0 mL injection; Step II, Welko RR (5 um, 21×250 mm), F=80 mL, 35% MeOH/65% CO$_2$, back pressure=90 bars, 1.0 mL injection) to afford 4-((2S,5R)-4-acryloyl-2,5-dimethylpiperazin-1-yl)-7-(2-fluorophenyl)-1-(2-isopropyl-4-methylpyridin-3-yl)-6-methylpteridin-2(1H)-one (Example 225, 130 mg, 0.23 mmol) as a mixture of atropisomers. $^1$H NMR (400 MHz, DMSO-d$_6$) δ 0.87-0.99 (m, 3H), 1.08 (br d, J=6.6 Hz, 3H), 1.16-1.50 (m, 6H), 1.95 (br d, J=17.6 Hz, 3H), 2.45 (s, 3H), 3.65-3.84 (m, 1H), 3.95 (br d, J=13.3 Hz, 1H), 4.28 (br d, J=13.3 Hz, 1H), 4.52-4.63 (m, 1H), 4.77-4.98 (m, 1H), 5.15-5.38 (m, 1H), 5.75 (dt, J=10.3, 2.6 Hz, 1H), 5.85-6.04 (m, 1H), 6.19 (br d, J=17.4 Hz, 1H), 6.78-6.97 (m, 1H), 7.15-7.23 (m, 1H), 7.24-7.39 (m, 3H), 7.48-7.59 (m, 1H), 8.40 (d, J=4.8 Hz, 1H); $^{19}$F{$^1$H} NMR (376 MHz, DMSO-d$_6$) δ −115.43--115.26 (m, 1F); LRMS: (ESI, +ve ion) 555.6 m/z (M+H)$^+$.

Step 3: Chiral separation of 4-((2S,5R)-4acryloyl-2,5-dimethylpiperazin-1-yl)-7-(22-fluorophenyl)-1-(2-isopropyl-4-methylpyridin-3-yl)-6-methylpteridin-2(1H)-one (Examples 225-1 and 225-2)

4-((2S,5R)-4-Acryloyl-2,5-dimethylpiperazin-1-yl)-7-(2-fluorophenyl)-1-(2-isopropyl-4-methylpyridin-3-yl)-6-methylpteridin-2(1H)-one (Example 225, 120 mg, 0.22 mmol) was dissolved in 1:1 DCM-MeOH (25 mL) and purified by preparative SFC (Chiralcel AD-H (5 um, 21×250 mm), F=80 mL, 20% iPrOH/80% CO$_2$, back pressure=90 bars, 2.0 mL injections) to afford 4-((2S,5R)-4-acryloyl-2,5-dimethylpiperazin-1-yl)-7-(2-fluorophenyl)-1-(2-isopropyl-4-methylpyridin-3-yl)-6-methylpteridin-2(1H)-one (Example 225-1, 42 mg, 0.076 mmol, 73% yield) as a yellow-tan solid (single isomer, 1$^{st}$-eluting peak) and 4-((2S,5R)-4-acryloyl-2,5-dimethylpiperazin-1-yl)-7-(2-fluorophenyl)-1-(2-isopropyl-4-methylpyridin-3-yl)-6-methylpteridin-2(1H)-one (Example 225-2, 42 mg, 0.076 mmol, 73% yield) as a yellow-tan solid (single isomer, 2$^{nd}$-eluting peak). Example 225-1: $^1$H NMR (400 MHz, DMSO-d$_6$) δ 0.95 (d, J=6.6 Hz, 3H), 1.00-1.12 (m, 3H), 1.18-1.51 (m, 6H), 1.97 (br s, 3H), 2.45 (s, 3H), 2.64-2.75 (m, 1H), 3.31-3.56 (m, 1H), 3.67-3.83 (m, 1H), 3.95 (br d, J=13.5 Hz, 0.5H), 4.24-4.33 (m, 0.5H), 4.59 (br s, 0.5H), 4.79-4.96 (m, 1H), 5.16-5.38 (m, 0.5H), 5.69-5.80 (m, 1H), 5.84-6.04 (m, 0.5H), 6.19 (br d, J=16.8 Hz, 1.5H), 6.76-6.98 (m, 1H), 7.19 (d, J=4.8 Hz, 1H), 7.25-7.39 (m, 3H), 7.50-7.58 (m, 1H), 8.40 (d, J=5.0 Hz, 1H); $^{19}$F{$^1$H} NMR (376 MHz, DMSO-d$_6$) δ 115.32--115.26 (m, 1F); LRMS: (ESI, +ve ion) 556.3 m/z (M+H)+. Example 225-2: 1H NMR (400 MHz, DMSO-d6) δ 0.93 (br d, J=6.2 Hz, 3H), 1.08 (d, J=6.8 Hz, 3H), 1.20-1.50 (m, 6H), 1.93 (br s, 3H), 2.45 (s, 3H), 2.77-2.86 (m, 1H), 3.31-3.55 (m, 1H), 3.64-3.83 (m, 1H), 3.95 (br d, J=14.3 Hz, 0.5H), 4.20-4.35 (m, 0.5H), 4.58 (br s, 0.5H), 4.75-4.95 (m, 1H), 5.15-5.37 (m, 0.5H), 5.69-5.80 (m, 1H), 5.86-6.04 (m, 0.5H), 6.19 (br d, J=16.8 Hz, 1.5H), 6.77-6.97 (m, 1H), 7.20 (d, J=5.0 Hz, 1H), 7.27-7.38 (m, 3H), 7.49-7.58 (m, 1H), 8.40 (d, J=4.8 Hz, 1H); 19F{1H} NMR (376 MHz, DMSO-d6) δ −115.42−−115.36 (m, 1F); LRMS: (ESI, +ve ion) 556.3 m/z (M+H)+.

Example 226

(M)-6-Chloro-4-[(2S,5R)-2,5-dimethyl-4-prop-2-enoyl-piperazin-1-yl]-7-(5-ethynyl-2-fluoro-phenyl)-1-(2-isopropyl-4-methyl-3-pyridyl)pyrido[2,3-d]pyrimidin-2-one

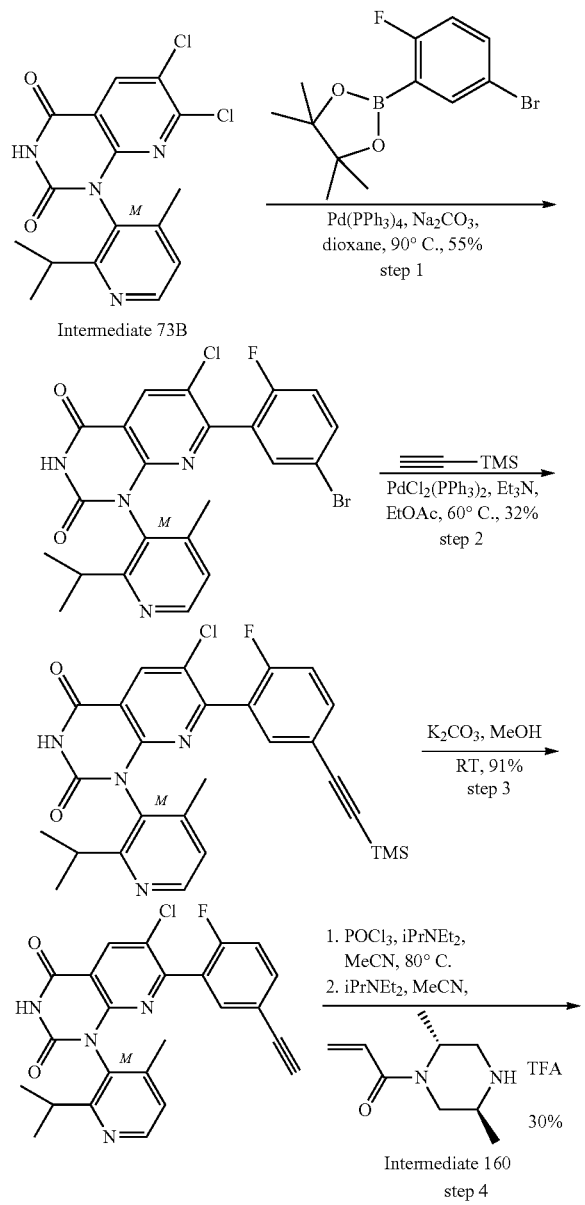

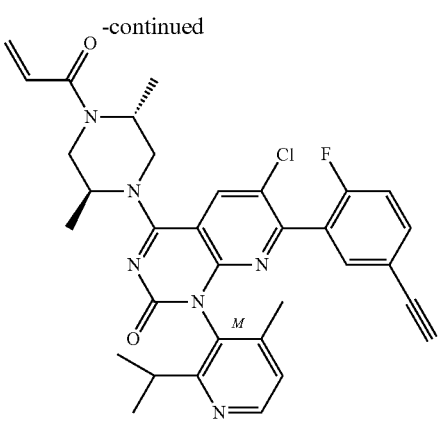

Step 1: (M)-7-(5-Bromo-2-fluorophenyl)-6-chloro-1-(2-isopropyl-4-methylpyridin-3-yl)pyrido[2,3-d]pyrimidine-2,4(1H,3H)-dione A mixture of (M)-6,7-dichloro-1-(2-isopropyl-4-methylpyridin-3-yl)pyrido[2,3-d]pyrimidine-2,4(1H,3H)-dione (Intermediate 73B, 300 mg, 0.82 mmol), tetrakis(triphenylphosphine)palladium (285 mg, 0.25 mmol), 2-(5-bromo-2-fluorophenyl)-4,4,5,5-tetramethyl-1,3,2-dioxaborolane (494 mg, 1.64 mmol) and sodium carbonate (435 mg, 4.11 mmol) in 1,4-dioxane (3 mL)/water (1.5 mL) was stirred at 90° C. for 1 h. The reaction mixture was diluted with EtOAc (10 mL)/water (10 mL). The aqueous was added sat'd sodium chloride (5 mL) and extracted with EtOAc (10 mL×2). The combined organic extracts were dried over MgSO4. The solution was filtered and concentrated in vacuo to give the crude material. The crude material brown oil was purified by silica gel chromatography (eluent: 0-50% of EtOAc/heptane) to provide (M)-7-(5-bromo-2-fluorophenyl)-6-chloro-1-(2-isopropyl-4-methylpyridin-3-yl)pyrido[2,3-d]pyrimidine-2,4(1H,3H)-dione (229 mg, 0.45 mmol, 55.3% yield) as a light yellow foam. 1H NMR (400 MHz, DMSO-d6) δ 12.25 (br s, 1H), 8.59 (s, 1H), 8.44 (d, J=4.8 Hz, 1H), 7.70 (ddd, J=8.8, 4.6, 2.6 Hz, 1H), 7.43 (dd, J=6.2, 2.5 Hz, 1H), 7.32 (t, J=9.2 Hz, 1H), 7.22 (d, J=5.0 Hz, 1H), 2.91 (quin, J=6.6 Hz, 1H), 2.03 (s, 3H), 1.04-1.12 (m, 3H), 0.97 (d, J=6.6 Hz, 3H). 19F NMR (376 MHz, DMSO-d6) δ −116.25 (s, 1F). m/z (ESI, +ve ion): 442.2 (M+H)+.

Step 2: (M)-6-Chloro-7-(2-fluoro-5-((trimethylsilyl)ethynyl)phenyl)-1-(2-isopropyl-4-methylpyridin-3-yl)pyrido[2,3-d]pyrimidine-2,4(1H,3H)-dione A mixture of (M)-7-(5-bromo-2-fluorophenyl)-6-chloro-1-(2-isopropyl-4-methylpyridin-3-yl)pyrido[2,3-d]pyrimidine-2,4(1H,3H)-dione (182 mg, 0.36 mmol), (trimethylsilyl)acetylene (0.7 mL, 0.47 mmol), triethylamine, anhydrous (0.6 mL, 4.27 mmol), copper(i) iodide (21 mg, 0.11 mmol) and trans-dichlorobis(triphenyl-phosphine)palladium (ii) (76 mg, 0.11 mmol) in ethyl acetate (1.0 mL) was stirred at 50° C. for 18 h. The reaction mixture was concentrated in vacuo and purified by silica gel chromatography (eluent: 0-50% of EtOAc/heptane) to provide (M)-6-chloro-7-(2-fluoro-5-((trimethylsilyl)ethynyl)phenyl)-1-(2-isopropyl-4-methylpyridin-3-yl)pyrido[2,3-d]pyrimidine-2,4(1H,3H)-dione (60 mg, 0.12 mmol, 31.9% yield) as a light yellow foam. m/z (ESI, +ve ion): 521.2 (M+H)+.

Step 3: (M)-6-Chloro-7-(2,2-dimethyl-1-piperidyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one A mixture of (M)-6-chloro-7-(2-fluoro-5-((trimethylsilyl) ethynyl)phenyl)-1-(2-isopropyl-4-methylpyridin-3-yl) pyrido[2,3-d]pyrimidine-2,4(1H,3H)-dione (60 mg, 0.12 mmol) and potassium carbonate (32 mg, 0.23 mmol) in methanol (1 mL) was stirred at 25° C. for 30 min. The reaction mixture was diluted with satd NH₄Cl (3 mL) and extracted with EtOAc (2×10 mL). The combined organic extracts were dried over MgSO₄. The solution was filtered and concentrated in vacuo to give (M)-6-chloro-7-(5-ethynyl-2-fluorophenyl)-1-(2-isopropyl-4-methylpyridin-3-yl) pyrido[2,3-d]pyrimidine-2,4(1H,3H)-dione (47 mg, 0.11 mmol, 91% yield) as a brown foam. m/z (ESI, +ve ion): 449.0 (M+H)⁺.

Step 4: (M)-6-Chloro-4-[(2S,5R)-2,5-dimethyl-4-prop-2-enoyl-piperazin-1-yl]-7-(5-ethynyl-2-fluoro-phenyl)-1-(2-isopropyl-4-methyl-3-pyridyl)pyrido[2,3-d]pyrimidin-2-one A mixture of (M)-6-chloro-7-(5-ethyl-2-fluorophenyl)-1-(2-isopropyl-4-methylpyridin-3-yl)pyrido[2,3-d]pyrimidine-2,4(1H,3H)-dione (47 mg, 0.11 mmol) and n,n'-diisopropylethylamine (0.1 mL, 0.52 mmol) in acetonitrile (1 mL) was treated with phosphorous oxychloride (0.03 mL, 0.31 mmol) at room temperature. The mixture was stirred at 80° C. for 1 h. The reaction mixture was evaporated to dryness to give (M)-4,6-dichloro-7-(5-ethynyl-2-fluorophenyl)-1-(2-isopropyl-4-methylpyridin-3-yl)pyrido[2,3-d]pyrimidin-2(1H)-one as a brown solid. m/z (ESI, +ve ion): 467.0 (M+H)⁺. The resulting brown solid was used in next step without purification.

To the mixture of (M)-4,6-dichloro-7-(5-ethynyl-2-fluorophenyl)-1-(2-isopropyl-4-methylpyridin-3-yl)pyrido[2,3-d]pyrimidin-2(1H)-one and DIPEA (0.1 mL, 0.52 mmol) in acetonitrile (1 mL) was added a mixture of 1-((2R,5S)-2,5-dimethylpiperazin-1-yl)prop-2-en-1-one TFA salt (148 mg, 0.524 mmol) and DIPEA (0.1 mL, 0.52 mmol) in acetonitrile (0.5 mL) and stirred at rt for 5 min. The resulting mixture was evaporated to dryness. The resulting crude product was purified by silica gel chromatography (eluent: 0-100% of MeOH-EtOAc (5:95)/heptane) to provide (M)-6-Chloro-4-[(2S,5R)-2,5-dimethyl-4-prop-2-enoyl-piperazin-1-yl]-7-(5-ethynyl-2-fluoro-phenyl)-1-(2-isopropyl-4-methyl-3-pyridyl)pyrido[2,3-d]pyrimidin-2-one (19 mg, 30% yield) as an yellow solid. ¹H NMR (400 MHz, DMSO-d₆) δ 8.50 (d, J=2.7 Hz, 1H), 8.43 (d, J=4.8 Hz, 1H), 7.64 (ddd, J=8.7, 4.9, 2.2 Hz, 1H), 7.31-7.42 (m, 2H), 7.24 (d, J=5.0 Hz, 1H), 6.75-6.95 (m, 1H), 6.20 (dd, J=16.7, 2.4 Hz, 1H), 5.69-5.85 (m, 1H), 4.83-4.95 (m, 1H), 4.40-4.81 (m, 1H), 4.25 (s, 1H), 3.79-4.22 (m, 4H), 2.69-2.83 (m, 1H), 1.96 (s, 3H), 1.30-1.38 (m, 3H), 1.14-1.28 (m, 4H), 1.08 (d, J=6.6 Hz, 3H), 1.00 (d, J=6.6 Hz, 3H). ¹⁹F NMR (376 MHz, DMSO-d₆) δ −111.42 (s, 1F). m/z (ESI, +ve ion): 599.2 (M+H)⁺.

Example 227

(M)-6-Chloro-7-(2,2-dimethyl-1-piperidyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one

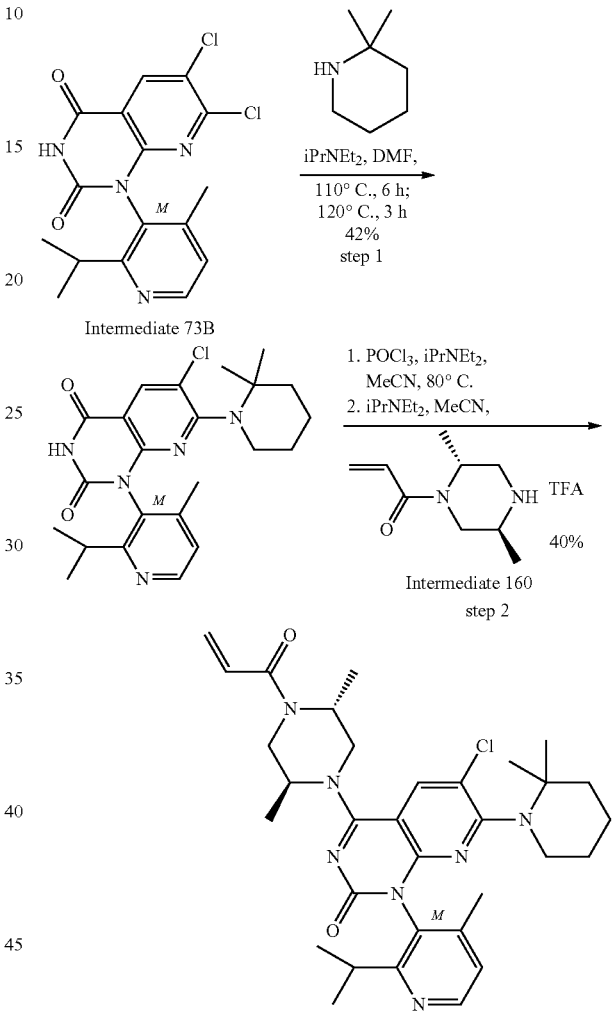

Step 1: (A)-6-Chloro-7-(2,2-dimethylpiperidin-1-yl)-1-(2-isopropyl-4-methylpyridin-3-yl)pyrido[2,3-d]pyrimidine-2,4(1H,3H)-dione A glass microwave reaction vessel was charged with 2,2-dimethylpiperidine (511 mg, 4.52 mmol). 6,7-dichloro-1-(2-isopropyl-4-methylpyridin-3-yl)pyrido[2,3-d]pyrimidine-2,4(1H,3H)-dione (Intermediate 73B, 550 mg, 1.51 mmol) and DIPEA (1.3 mL, 7.53 mmol) in DMF (1.0 mL). The reaction mixture was stirred and heated in an Initiator microwave reactor (Personal Chemistry, Biotage AB, Inc., Upssala, Sweden) at 110° C. for 6 h and then 120° C. for 3 h. The reaction mixture was diluted with water (5 mL) and extracted with EtOAc (3×5 mL). The organic extracts were combined and dried over MgSO₄. The solution was filtered and concentrated in vacuo to give the crude material as a brown solid. The crude material brown solid was purified by silica gel chromatography (eluent: 0-50% of EtOAc/heptane) to provide (M)-6-chloro-7-(2,2-dimethylpiperidin-1-yl)-1-(2-isopropyl-4-methylpyridin-3-yl)pyrido[2,3-d]pyrimidine-2,4(1H,3H)-dione (276 mg, 0.624 mmol, 41.5% yield) as a light yellow solid. $^1$H NMR (400 MHz, DMSO-d$_6$) δ 11.90 (s, 1H), 8.49 (d, J=4.8 Hz, 1H), 8.18 (s, 1H), 7.28 (d, J=4.8 Hz, 1H), 3.10-3.23 (m, 1H), 2.91-3.02 (m, 1H), 2.74-2.86 (m, 1H), 2.02 (s, 3H), 1.43-1.61 (m, 4H), 1.31 (br t, J=4.8 Hz, 2H), 1.08 (d, J=6.6 Hz, 3H), 1.03 (d, J=6.6 Hz, 3H), 0.81 (s, 3H), 0.69 (s, 3H). m/z (ESI, +ve ion): 442.2 (M+H)$^+$.

Step 2: (M)-6-Chloro-7-(2,2-dimethyl-1-piperidyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one A mixture of (M)-6-chloro-7-(2,2-dimethylpiperidin-1-yl)-1-(2-isopropyl-4-methylpyridin-3-yl)pyrido[2,3-d]pyrimidine-2,4(1H,3H)-dione (252 mg, 0.570 mmol) and DIPEA (0.5 mL, 2.85 mmol) in acetonitrile (2.0 mL) was treated with phosphorous oxychloride (0.2 mL, 1.71 mmol) at room temperature. The mixture was stirred at 80° C. for 1 h. The reaction mixture was evaporated to dryness to give (M)-4,6-dichloro-7-(2,2-dimethylpiperidin-1-yl)-1-(2-isopropyl-4-methylpyridin-3-yl)pyrido[2,3-d]pyrimidin-2 (1H)-one as a brown solid. m/z (ESI, +ve ion): 460.2 (M+H)$^+$. The resulting brown solid was used in next step without purification.

The mixture of (M)-4,6-dichloro-7-(2,2-dimethylpiperidin-1-yl)-1-(2-isopropyl-4-methylpyridin-3-yl)pyrido[2,3-d]pyrimidin-2(1H)-one and DIPEA (0.5 mL, 2.85 mmol) in acetonitrile (2.0 mL) was added a solution of 1-((2R,5S)-2,5-dimethylpiperazin-1-yl)prop-2-en-1-one TFA salt (483 mg, 1.71 mmol) and DIPEA (0.5 mL, 2.85 mmol) in MeCN (1.0 mL) and stirred at rt for 5 min. The resulting mixture was diluted with water (5 mL) and extracted with EtOAc (3×10 mL). The organic extracts were combined and dried over MgSO$_4$. The solution was filtered and concentrated in vacuo to give the crude material as a brown solid. The crude material brown solid which was absorbed onto a plug of silica gel and purified by silica gel chromatography (eluent: 0-100% of MeOH-EtOAc (5:95)/heptane) to provide (M)-6-chloro-7-(2,2-dimethyl-1-piperidyl)-4-[(2S,5R)-2,5-dimethyl-4-prop-2-enoyl-piperazin-1-yl]-1-(2-isopropyl-4-methyl-3-pyridyl)pyrido[2,3-d]pyrimidin-2-one (134 mg, 0.23 mmol, 39.7% yield) as a light yellow solid. $^1$H NMR (400 MHz, DMSO-d$_6$) δ 8.49 (br t, J=5.3 Hz, 1H), 7.85-8.17 (m, 1H), 7.32 (br s, 1H), 6.67-6.93 (m, 1H), 6.17 (br d, J=16.6 Hz, 1H), 5.73 (br d, J=8.1 Hz, 1H), 4.36-4.95 (m, 3H), 3.67-4.17 (m, 4H), 2.80-3.45 (m, 2H), 2.60-2.77 (m, 1H), 1.94 (br d, J=7.7 Hz, 3H), 1.47-1.67 (m, 6H), 1.19-1.34 (m, 6H), 1.12 (tt, J=12.4, 6.3 Hz, 6H), 1.01 (br d, J=6.4 Hz, 3H), 0.70-0.84 (m, 2H). m/z (ESI, +ve ion): 592.2 (M+H)$^+$.

Example 228

4-((S)-4-Acryloyl-2-methylpiperazin-1-yl)-6-chloro-1-(2-isopropyl-4-methylpyridin-3-yl)-7-(5-methyl-2-oxoindolin-4-yl)pyrido[2,3-d]pyrimidin-2(1H)-one

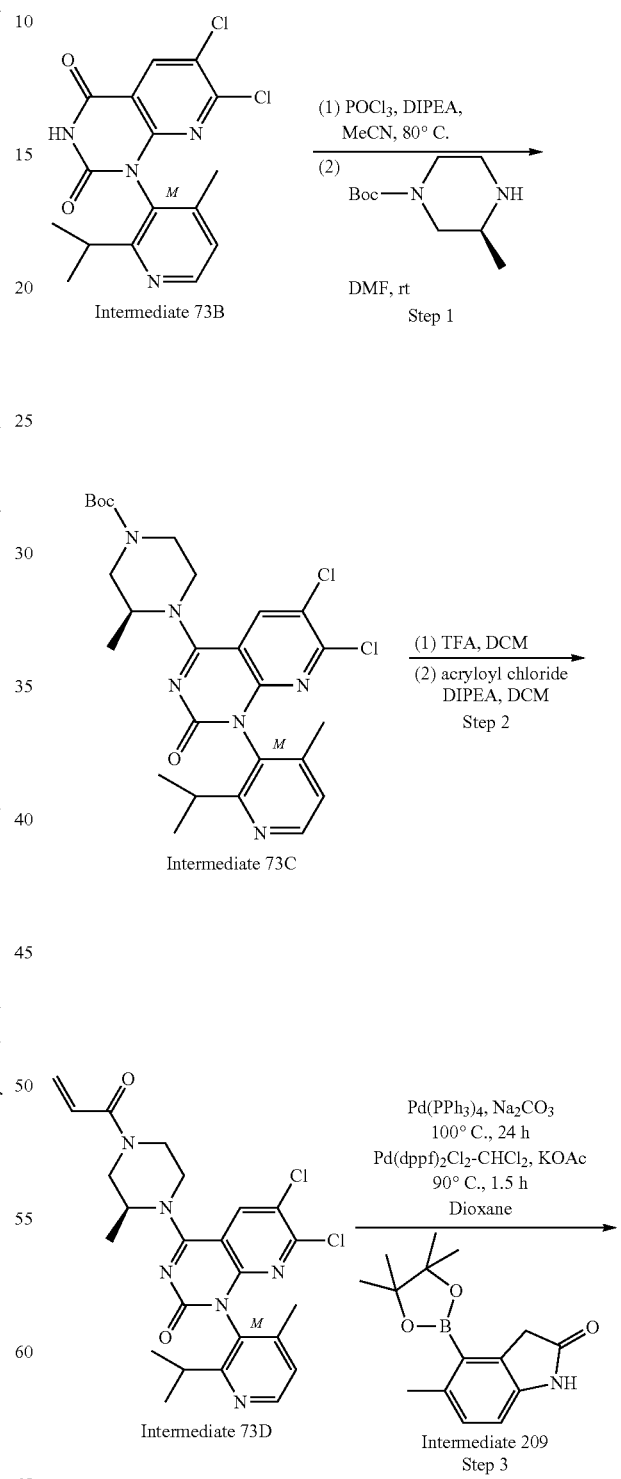

-continued

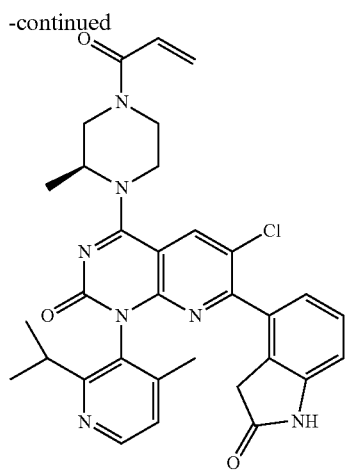

Step 1: (M)-tert-Butyl (S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate A 250-mL round-bottomed flask was charged with (M)-6,7-dichloro-1-(2-isopropyl-4-methylpyridin-3-yl)pyrido[2,3-d]pyrimidine-2,4(1H,3H)-dione (Intermediate 73B, 5.9 g, 16 mmol) and DIPEA (4.2 mL, 24 mmol) in acetonitrile (65 mL) followed by phosphorous oxychloride (1.8 mL, 19.2 mmol). The mixture was stirred at 80° C. for 1 h. The reaction mixture was concentrated in vacuo to give a brown solid. The crude solid was used in the next step without purification. m/z (ESI, +ve ion): 383.0 (M+H)$^+$.

The above crude solid and DIPEA (4.2 mL, 24 mmol) in DMF (50 mL) was treated with (3S)-1-(tert-butoxycarbonyl)-3-methylpiperazine (4.81 g, 24 mmol, Ark Pharm, Inc.) and stirred at rt for 30 min. The resulting mixture was added to ice water (100 mL) and stirred for 15 min. The resulting precipitate was collected by filtration, washed with water, and dried to give (M)-tert-butyl (S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 73C, 7.71 g, 14.1 mmol, 88% yield). $^1$H NMR (400 MHz, DMSO-d$_6$) δ ppm 8.39-8.54 (m, 2H), 7.25 (d, J=5.0 Hz, 1H), 4.87 (br d, J=1.0 Hz, 1H), 4.15 (br d, J=13.3 Hz, 1H), 3.95 (br dd, J=5.9, 4.0 Hz, 1H), 3.83 (br d, J=13.3 Hz, 1H), 3.71 (br t, J=11.0 Hz, 1H), 2.96-3.27 (m, 2H), 2.57-2.64 (m, 1H), 1.94 (s, 3H), 1.45 (s, 9H), 1.32 (d, J=6.6 Hz, 3H), 1.06 (d, J=6.8 Hz, 3H), 1.01 (d, J=6.6 Hz, 3H). m/z (ESI, +ve ion): 547.3 (M+H)$^+$.

Step 2: (M,S)-4-(4-Acryloyl-2-methylpiperazin-1-yl)-6,7-dichloro-1-(2-isopropyl-4-methylpyridin-3-yl)pyrido[2,3-d]pyrimidin-2(1H)-one To a solution of (M)-tert-butyl (S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 73C, 2.71 g, 4.95 mmol) in DCM (25 mL) was treated with TFA (10 mL, 134 mmol) at rt and stirred for 20 min. The reaction was concentrated in vacuo to afford (M,S)-6,7-dichloro-1-(2-isopropyl-4-methylpyridin-3-yl)-4-(2-methylpiperazin-1-yl)pyrido[2,3-d]pyrimidin-2(1H)-one as a brown solid. m/z (ESI, +ve ion): 447.2 (M+H)$^+$.

A mixture of (M,S)-6,7-dichloro-1-(2-isopropyl-4-methylpyridin-3-yl)-4-(2-methylpiperazin-1-yl)pyrido[2,3-d]pyrimidin-2(1H)-one and DIPEA (4.3 mL, 24.8 mmol) in DCM (25 mL) was treated with acryloyl chloride (0.36 mL, 4.5 mmol) at 0° C. and stirred for 20 min. The reaction mixture was concentrated in vacuo. The crude product was purified by silica gel chromatography (eluent: 0-60% EtOAc-EtOH(3:1)/heptane) to provide pure (M,S)-4-(4-acryloyl-2-methylpiperazin-1-yl)-6,7-dichloro-1-(2-isopropyl-4-methylpyridin-3-yl)pyrido[2,3-d]pyrimidin-2(1H)-one (Intermediate 73D; 2.28 g, 4.55 mmol, 92% yield) as a light-yellow foam. $^1$H NMR (400 MHz, DMSO-d$_6$) δ ppm 8.50 (d, J=4.8 Hz, 2H), 7.30 (d, J=4.8 Hz, 1H), 6.77-6.94 (m, 1H), 6.20 (br d, J=16.0 Hz, 1H), 5.76 (dd, J=10.5, 2.4 Hz, 1H), 4.92 (br s, 1H), 3.96-4.44 (m, 3H), 3.54-3.85 (m, 2H), 3.00-3.24 (m, 1H), 2.59-2.70 (m, 1H), 1.97 (s, 3H), 1.30 (br d, J=6.6 Hz, 3H), 1.07 (d, J=6.6 Hz, 3H), 1.02 (d, J=6.6 Hz, 3H). m/z (ESI, +ve ion): 501.2 (M+H)$^+$.

Step 3: 4-((S)-4-Acryloyl-2-methylpiperazin-1-yl)-6-chloro-1-(2-isopropyl-4-methylpyridin-3-yl)-7-(5-methyl-2-oxoindolin-4-yl)pyrido[2,3-d]pyrimidin-2(1H)-one To a pressure vial was charged (S)-4-(4-acryloyl-2-methylpiperazin-1-yl)-6,7-dichloro-1-(2-isopropyl-4-methylpyridin-3-yl)pyrido[2,3-d]pyrimidin-2(11H)-one (Intermediate 73D, 0.2 g, 0.399 mmol), 5-methyl-4-(4,4,5,5-tetramethyl-1,3,2-dioxaborolan-2-yl)indolin-2-one (Intermediate 209, 0.163 g, 0.598 mmol), tetrakis(triphenylphosphine)palladium(0) (0.046 g, 0.040 mmol). sodium carbonate (0.127 g, 1.20 mmol), and 1,4-dioxane (5 mL). The vial was purged with N$_2$ for 3 min. sealed and then heated at 100° C. for 24 h. LCMS showed mostly SM. To the reaction mixture was added potassium acetate (0.117 g, 1.20 mmol), Pd(dppf)Cl$_2$ CH$_2$Cl$_2$ adduct (0.033 g, 0.040 mmol) and water (0.3 mL). The reaction was heated at 90° C. for 1.5 h. The reaction mixture was partitioned between EtOAc and water. The separated organic layer was washed with brine, dried over Na$_2$SO$_4$ and then filtered. The filtrate was concentrated and purified by silica gel chromatography (0-90% EtOAc/heptane) to afford 4-((S)-4-acryloyl-2-methylpiperazin-1-yl)-6-chloro-1-(2-isopropyl-4-methylpyridin-3-yl)-7-(5-methyl-2-oxoindolin-4-yl)pyrido[2,3-d]pyrimidin-2(1H)-one (0.042 g, 0.069 mmol, 17.2% yield) as light brown solid. $^1$H NMR (CHLOROFORM-d) δ: 8.47 (d, J=4.8 Hz, 1H), 8.14 (s, 1H), 7.70 (br s, 1H), 7.03-7.13 (m, 2H), 6.79 (d, J=7.9 Hz, 1H), 6.62 (br s, 1H), 6.38-6.46 (m, 1H), 5.80-5.85 (m, 1H), 4.32-5.14 (m, 3H), 3.54-4.10 (m, 3H), 3.09-3.39 (m, 1H), 2.88-3.06 (m, 2H), 2.70-2.84 (m, 1H), 2.00 (s, 6H), 1.53 (br d, J=0.8 Hz, 3H), 1.22 (d, J=6.8 Hz, 3H), 1.03 (br d, J=6.6 Hz, 3H). m/z (ESI, +ve ion): 612.0 (M+H)$^+$.

Example 229

4-((2S,5R)-4-Acryloyl-2,5-dimethylpiperazin-1-yl)-1-(2-amino-4,6-diisopropylpyrimidin-5-yl)-6-chloro-7-(2-fluorophenyl)pyrido[2,3-d]pyrimidin-2(1H)-one

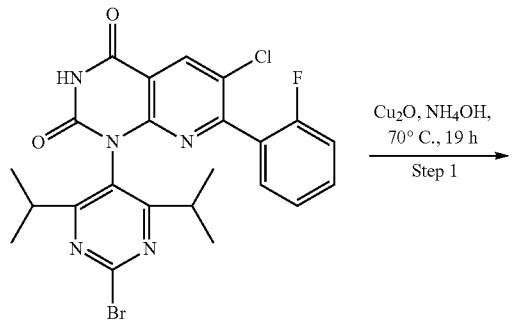

Intermediate 231

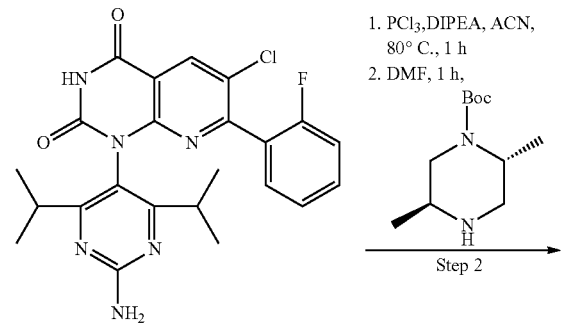

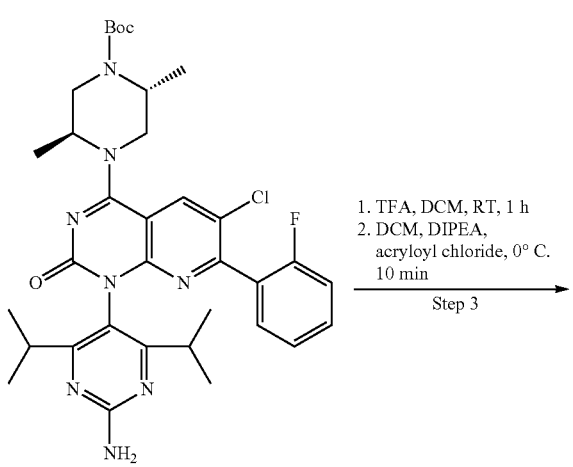

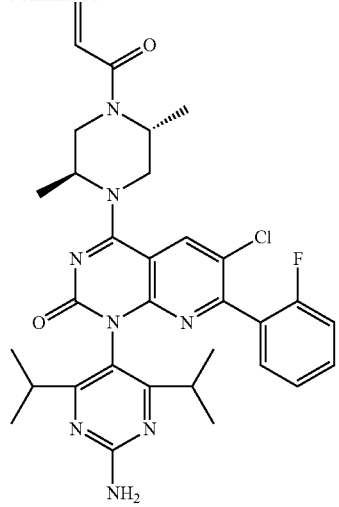

Step 1. 1-(2-Amino-4,6-diisopropylpyrimidin-5-yl)-6-chloro-7-(2-fluorophenyl)pyrido[2,3-d]pyrimidine-2,4(1H,3H)-dione To a pressure vial was charged 1-(2-bromo-4,6-diisopropylpyrimidin-5-yl)-6-chloro-7-(2-fluorophenyl)pyrido[2,3-d]pyrimidine-2,4(1H,3H)-dione (Intermediate 231, 0.28 g, 0.53 mmol), copper (I) oxide (3.76 mg, 0.158 mmol), ammonium hydroxide solution, 28.0-30%, $NH_3$ basis (3.57 ml, 26.3 mmol) and methanol (3.5 mL). The vial was sealed and heated at 70° C. for 19 h. The product mixture was concentrated to dryness. The resulted solid residue was dissolved in EtOAc and partitioned with saturated $NH_4Cl$. The separated organic layer was washed with water and brine, dried over $Na_2SO_4$ and then filtered. The filtrate was concentrated and purified by silica gel chromatography to afford 1-(2-amino-4,6-diisopropylpyrimidin-5-yl)-6-chloro-7-(2-fluorophenyl)pyrido[2,3-d]pyrimidine-2,4(1H,3H)-dione (0.164 g, 0.350 mmol, 66% yield) as a white solid. $^1H$ NMR (400 MHz, DMSO-$d_6$) δ 0.86 (d, J=6.63 Hz, 6H) 1.02 (d, J=6.63 Hz, 6H) 2.68 (quin, J=6.69 Hz, 2H) 6.58 (s, 2H) 7.21 (td, J=7.52, 1.55 Hz, 1H) 7.28-7.35 (m, 2H) 7.48-7.56 (m, 1H) 8.54 (s, 1H) 12.15 (s, 1H).

Step 2. tert-Butyl (2R,5S)-4-(1-(2-amino-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate To a mixture of 1-(2-amino-4,6-diisopropylpyrimidin-5-yl)-6-chloro-7-(2-fluorophenyl)pyrido[2,3-d]pyrimidine-2,4(1H,3H)-dione (0.100 g, 0.213 mmol) and N-ethyl-N-isopropylpropan-2-amine (0.111 ml, 0.640 mmol) in acetonitrile (5 ml) was added phosphoryl trichloride (0.040 ml, 0.427 mmol) at RT and the reaction was heated at 80° C. for 30 min. Additional phosphoryl trichloride (0.040 ml, 0.427 mmol) was added and heated for an additional 30 min. The mixture was concentrated to give the crude 1-(2-amino-4,6-diisopropylpyrimidin-5-yl)-4,6-dichloro-7-(2-fluorophenyl)pyrido[2,3-d]pyrimidin-2(1H)-one as brown oil which was used in the next step without purification.

Crude 1-(2-amino-4,6-diisopropylpyrimidin-5-yl)-4,6-dichloro-7-(2-fluorophenyl)pyrido[2,3-d]pyrimidin-2(1H)-one was dissolved in DMF (2 mL). To this solution was added N-ethyl-N-isopropylpropan-2-amine (0.111 ml, 0.640 mmol) followed by (2R,5S)-tert-butyl 2,5-dimethylpiperazine-1-carboxylate (0.050 ml, 0.235 mmol, eNovation Chemicals, LLC). The mixture was stirred at RT for 1 h. Water was added to quench the reaction, and the resulting suspension was filtered. The recovered solid was purified by silica gel chromatography (0-100% (3:1 EtOAc:EtOH)/heptane) to afford tert-butyl (2R,5S)-4-(1-(2-amino-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.05 g, 0.075 mmol, 35% yield) as light yellow solid. m/z (ESI, +ve ion): 665.2 (M+H)+.

Step 3. 4-((2S,5R)-4-Acryloyl-2,5-dimethylpiperazin-1-yl)-1-(2-amino-4,6-diisopropylpyrimidin-5-yl)-6-chloro-7-(2-fluorophenyl)pyrido[2,3-d]pyrimidin-2(1H)-one To a solution of tert-butyl (2R,5S)-4-(1-(2-amino-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (0.050 g, 0.075 mmol) in DCM (3 mL) was added TFA (0.5 mL, 6.49 mmol). The mixture was stirred at RT for 30 min. The mixture was concentrated to afford 1-(2-amino-4,6-diisopropylpyrimidin-5-yl)-6-chloro-4-((2S5R)-2,5-dimethylpiperazin-1-yl)-7-(2-fluorophenyl)pyrido[2,3-d]pyrimidin-2(1H)-one as light yellow oil that was used without purification.
Crude 1-(2-amino-4,6-diisopropylpyrimidin-5-yl)-6-chloro-4-((2S,5R)-2,5-dimethylpiperazin-1-yl)-7-(2-fluorophenyl)pyrido[2,3-d]pyrimidin-2(1H)-one was dissolved in DCM (3 mL) and cooled with an ice bath. To this solution was added diisopropylethylamine (0.10 mL, 0.57 mmol) followed by acryloyl chloride. 0.258 M in DCM (0.262 mL, 0.068 mmol). The reaction was stirred at 0° C. for 10 min, then concentrated to remove the solvent. The residue was purified by silica gel chromatography (0-60% (3:1 EtOAc:EtOH)/heptane) to afford 4-((2S,5R)-4-acryloyl-2,5-dimethylpiperazin-1-yl)-1-(2-amino-4,6-diisopropylpyrimidin-5-yl)-6-chloro-7-(2-fluorophenyl)pyrido[2,3-d]pyrimidin-2(1H)-one (0.024 g, 0.039 mmol, 52% yield) as an off-white solid. $^1$H NMR (400 MHz, DMSO-$d_6$) δ 0.86 (dd, J=6.84, 3.11 Hz, 6H) 1.00 (dd, J=6.63, 4.35 Hz, 6H) 1.25 (br s, 3H) 1.32 (t, J=6.84 Hz, 3H) 2.40-2.48 (m, 2H) 3.31-3.53 (m, 1H) 3.81-3.92 (m, 2H) 4.10-4.19 (m, 1H) 4.43-4.93 (m, 2H) 5.71-5.80 (m, 1H) 6.18 (dd, J=16.69, 2.18 Hz, 1H) 6.50 (s, 2H) 6.83 (td, J=16.17, 10.57 Hz, 1H) 7.21-7.27 (m, 1H) 7.28-7.36 (m, 2H) 7.50-7.57 (m, 1H) 8.44 (s, 1H). m/z (ESI, +ve ion): 618.6 (M+H)+.

Section 3—Synthesis of Intermediates

Intermediate I-5

4-Isopropyl-6-methylpyrimidin-5-amine

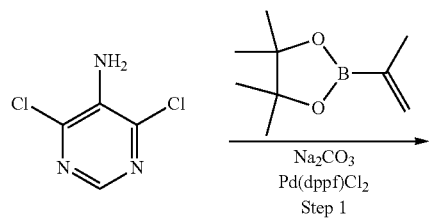

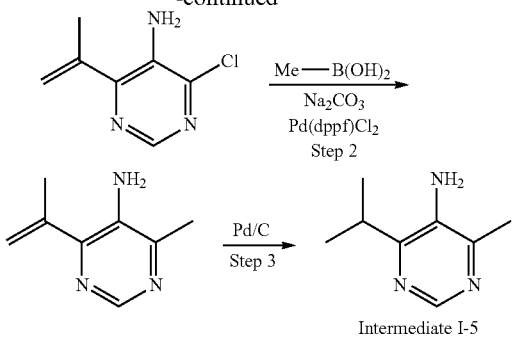

Step 1: 4-Chloro-6-(prop-1-en-2-yl)pyrimidin-5-amine

A mixture of 4,6-dichloro-5-aminopyrimidine (5.00 g, 30.5 mmol). 2-isopropenylboronic acid, pincol ester (6.15 g, 36.6 mmol, Combi-Blocks, San Diego, Calif.), Pd(dppf)Cl$_2$ (2.23 g, 3.05 mmol), and sodium carbonate (9.69 g, 91 mmol) in a mixture of 1,4-dioxane (40 mL) and water (10 mL) was sparged with N$_2$ then heated at 95° C. for 2 h. The mixture was cooled to rt, satd. aq. NaHCO$_3$ was added, and the resulting mixture was extracted with EtOAc. The combined extracts were concentrated in vacuo, and the residue was purified by silica gel chromatography (eluent: 0-40% EtOAc/heptane) to provide 4-chloro-6-(prop-1-en-2-yl)pyrimidin-5-amine (1.24 g, 7.31 mmol, 24% yield) as a yellow oil. m/z (ESI, +ve ion): 170.0 (M+H)+.

Step 2: 4-Methyl-6-(prop-1-en-2-yl)pyrimidin-5-amine

A mixture of 4-chloro-6-(prop-1-en-2-yl)pyrimidin-5-amine (2.0 g, 11.79 mmol), methylboronic acid (3.53 g, 59.0 mmol, Combi-Blocks, San Diego, Calif.), Pd(dppf)Cl$_2$ (0.863 g, 1.179 mmol) and sodium carbonate (6.25 g, 59.0 mmol) in 1,4-dioxane (40 mL) and water (10 mL) was sparged with N$_2$, then heated at 95° C. for 17 h. The mixture was then cooled to rt. diluted with satd. aq. NaHCO$_3$, and extracted with EtOAc. The combined extracts were concentrated in vacuo, and the residue was purified by silica gel chromatography (eluent: 0-5% MeOH/DCM) to provide 4-methyl-6-(prop-1-en-2-yl)pyrimidin-5-amine (1.3 g, 8.71 mmol, 73.9% yield). m/z (ESI, +ve ion): 150.2 (M+H)+.

Step 3: 4-Isopropyl-6-methylpyrimidin-5-amine (Intermediate I-5)

Palladium 10 wt. % on activated carbon (0.522 g, 0.491 mmol) was added to a solution of 4-methyl-6-(prop-1-en-2-yl)pyrimidin-5-amine (1.464 g, 9.81 mmol) in EtOH (30 mL), and the resulting suspension was stirred under hydrogen gas (30 psi) for 1.5 h. The resulting mixture was subsequently filtered through Celite, and the filtrate was concentrated in vacuo to provide 4-isopropyl-6-methylpyrimidin-5-amine (Intermediate I-5, 1.48 g, 9.79 mmol, 100% yield) as a brown oil. $^1$H NMR (400 MHz, DMSO-d6) δ: 7.96-8.30 (m, 1H), 4.94-5.11 (m, 2H), 3.12-3.27 (m, 1H), 2.22-2.31 (m, 3H), 1.13-1.16 (m, 6H). m/z (ESI, +ve ion): 152.2 (M+H)+.

Intermediate I-33

6-Isopropyl-$N^2,N^2$-bis(4-methoxybenzyl)-4-methylpyridine-2,5-diamine

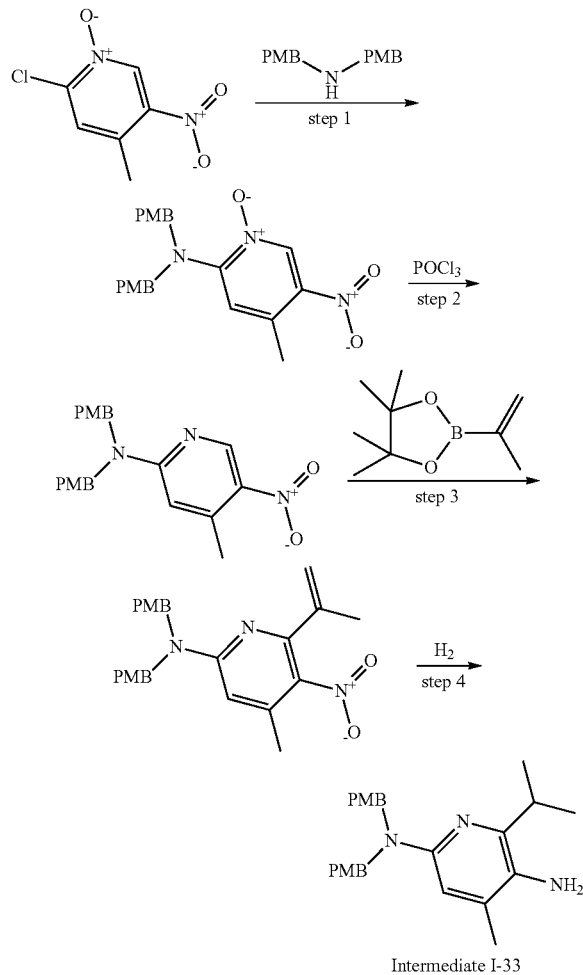

PMB = p-methoxybenzyl

Step 1: 2-(Bis(4-methoxybenzyl)amino)-4-methyl-5-nitropyridine 1-oxide

A mixture of 2-chloro-4-methyl-5-nitropyridine 1-oxide (2.3 g, 12.20 mmol; product of step 2 in preparation of Intermediate I-32), bis(4-methoxybenzyl)-amine (3.45 g, 13.42 mmol), and sodium carbonate (anhydrous, powder; 2.6 g, 24.39 mmol) in toluene (70 mL) was stirred at 70° C. for 16 h. Additional sodium carbonate (anhydrous, powder, 2.6 g, 24.39 mmol) and bis(4-methoxybenzyl)-amine (3.45 g, 13.42 mmol) were added, and the resulting mixture was stirred at 90° C. for 2 h. The reaction mixture was then filtered, and the filter cake washed with DCM (3×100 mL). The combined filtrates were concentrated in vacuo and the residue chromatographically purified (silica gel, 0%-10% MeOH/DCM) to provide 2-(bis(4-methoxybenzyl)amino)-4-methyl-5-nitropyridine 1-oxide (2.75 g, 6.72 mmol, 55% yield) as a brown solid. $^1$H NMR (CDCl$_3$) δ: 9.11 (s, 1H), 7.26 (d, J=8.7 Hz, 4H), 6.92 (d, J=8.7 Hz, 4H), 6.60 (s, 1H), 4.77 (s, 4H), 3.87 (s, 6H), 2.59 (s, 3H). m/z (ESI, +ve ion): 410.0 (M+H)$^+$.

Step 2: 6-Chloro-N,N-bis(4-methoxybenzyl)-4-methyl-5-nitropyridin-2-amine

Phosphorus oxychloride (12.29 ml, 132 mmol) was added, dropwise, to a solution of 2-(bis(4-methoxybenzyl) amino)-4-methyl-5-nitropyridine 1-oxide (2.7 g, 6.59 mmol) in N,N'-diisopropylethylamine (27.6 mL, 158 mmol) at 0° C., and the resulting mixture was heated to 70° C. and stirred for 10 mins. The reaction mixture was then concentrated in vacuo and the residue diluted with ice water (20 mL) and EtOAc (100 mL). The resulting mixture was stirred as saturated aq. NaHCO$_3$ (50 mL) was slowly added until a pH of 10-11 was achieved. The resulting mixture was then stirred at room temperature for 30 mins before the organic layer was separated, dried over MgSO4, and concentrated in vacuo. Chromatographic purification of the residue (silica gel, 0%-100% EtOAc/heptane) provided 6-chloro-N,N-bis (4-methoxybenzyl)-4-methyl-5-nitropyridin-2-amine (1.62 g, 3.77 mmol, 57% yield) as a yellow solid. $^1$H NMR (METHANOL-d4) δ: 7.15 (br d, J=8.7 Hz, 4H), 6.87 (d, J=8.7 Hz, 4H), 6.44 (s, 1H), 4.72 (s, 4H), 3.77 (s, 6H), 2.21 (s, 3H). m/z (ESI, +ve ion): 427.9 (M+H)$^+$.

Step 3: N,N-Bis(4-Methoxybenzyl)-4-methyl-5-nitro-6-(prop-1-en-2-yl)pyridin-2-amine A mixture of 6-chloro-N,N-bis(4-methoxybenzyl)-4-methyl-5-nitropyridin-2-amine (1.59 g, 3.72 mmol), 2-isopropenylboronic acid, pincol ester (1.873 g, 11.15 mmol), cesium carbonate (3.63 g, 11.15 mmol), and trans-dichlorobis(triphenyl-phosphine)palladium (II) (0.261 g, 0.372 mmol) in 1,2-dimethoxyethane (20 mL) and water (4.00 mL) was sparged with N2(g) for 5 min and then stirred at 80° C. for 3 h. Additional 2-isopropenylboronic acid, pincol ester (1.873 g, 11.15 mmol), cesium carbonate (3.63 g, 11.2 mmol), and trans-dichlorobis(triphenyl-phosphine)palladium (11) (0.261 g, 0.372 mmol) were then added, and the resulting mixture was stirred at 80° C. for 1 hour. After cooling to rt. saturated aq. NaHCO$_3$ (30 mL) was added, and the resulting mixture was extracted with EtOAc (2×120 mL). The combined extracts were dried over MgSO$_4$ and concentrated in vacuo. Chromatographic purification of the residue (silica gel, 0%-100% EtOAc:EtOH (3:1)/heptane) provided N,N-bis(4-methoxybenzyl)-4-methyl-5-nitro-6-(prop-1-en-2-yl)pyridin-2-amine (1.00 g, 2.31 mmol, 62% yield) as a yellow solid. m/z (ESI, +ve ion): 434.0 (M+H)$^+$.

Step 4: 6-Isopropyl-$N^2,N^2$-bis(4-methoxybenzyl)-4-methylpyridine-2,5-diamine (Intermediate I-33)

A mixture of N,N-bis(4-methoxybenzyl)-4-methyl-5-nitro-6-(prop-1-en-2-yl)pyridin-2-amine (1.00 g, 2.31 mmol) and palladium, 10 wt. % on activated carbon (0.1 g) in ethanol (15 mL) and ethyl acetate (15 mL) was then stirred under H$_{2(g)}$ (40 psi) at rt for 1.5 hours, then under H$_{2(g)}$ (30 psi) at rt for 16 hours. The mixture was subsequently filtered through Celite (washing with EtOAc (2×100 mL)), and the combined filtrates were concentrated in vacuo. Chromatographic purification of the residue (silica gel, 0%-10% ammonia in MeOH 2M/heptane) provided 6-isopropyl-N2, $N^2$-bis(4-methoxybenzyl)-4-methylpyridine-2,5-diamine (Intermediate I-33, 340 mg, 0.838 mmol, 36% yield) as a yellow oil. $^1$H NMR (CDCl$_3$) δ: 7.26 (br d, J=7.3 Hz, 4H), 6.90 (br d, J=7.9 Hz, 4H), 6.13-6.26 (m, 1H), 4.56-4.83 (m, 4H), 3.87 (s, 8H), 3.02-3.19 (m, 1H), 2.17 (br d, J=10.4 Hz, 3H), 1.34 (br d, J=5.6 Hz, 6H). m/z (ESI, +ve ion): 406.1 $(M+H)^+$.

Intermediate I-36

4,6-Diisopropyl-2-methoxypyrimidin-5-amine

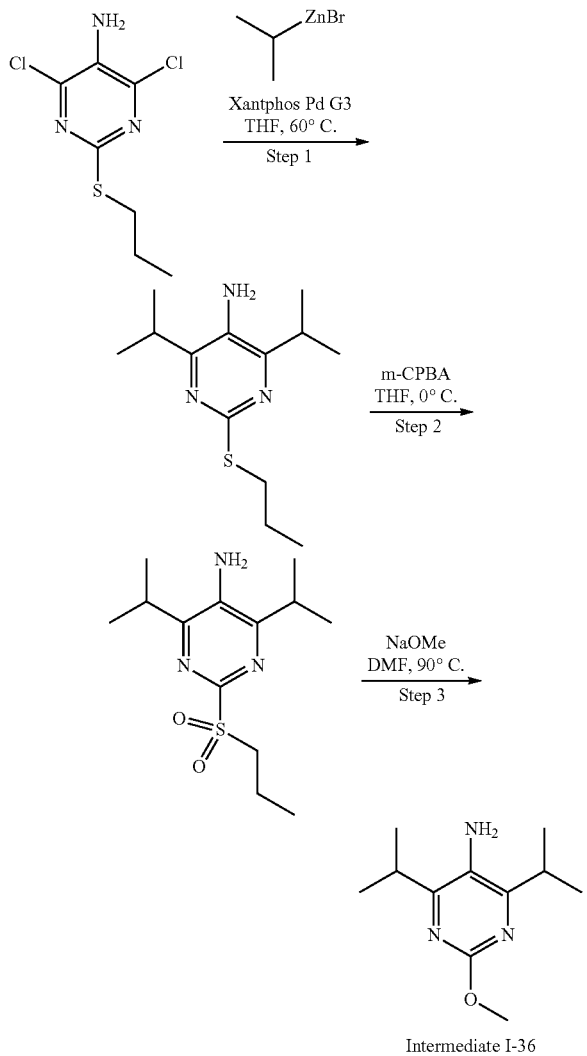

Intermediate I-36

Step 1:
4,6-Diisopropyl-2-(propylthio)pyrimidin-5-amine

A mixture of 4,6-dichloro-2-(propylthio)pyrimidin-5-amine (2.45 g, 10.29 mmol) and tetrahydrofuran (20.6 mL) was spared with argon gas for 5 min, then 2-propylzinc bromide (0.5 M in THF, 61.7 mL, 30.9 mmol) and Xantphos Pd G3 (Sigma-Aldrich, St. Louis, Mo.; 0.293 g, 0.309 mmol) were sequentially added. The resulting mixture was heated to 60° C. and stirred for 2 h, then cooled to rt. Sat. aq. NH₄Cl (30 mL) was added, and the resulting mixture was stirred for 10 min, then diluted with EtOAc and brine (10 mL). The organic layer was separated, and the aqueous layer was extracted with EtOAc. The combined organic extracts were dried over MgSO₄, filtered, and concentrated in vacuo. Chromatographic purification of the residue (silica gel, 0-30% EtOAc/heptane) provided 4,6-diisopropyl-2-(propylthio)pyrimidin-5-amine (1.75 g, 6.91 mmol, 67% yield) as a tan oil. ¹H NMR (400 MHz, DMSO-d₆) δ 4.80 (s, 2H) 3.13-3.25 (m, 2H) 2.91-3.05 (m, 2H) 1.66 (sxt, J=7.26 Hz, 2H) 1.12 (d, J=6.63 Hz, 12H) 0.96 (t, J=7.36 Hz, 3H). m/z (ESI, +ve ion): 254.1 $(M+H)^+$.

Step 2: 4,6-Diisopropyl-2-(propylsulfonyl)pyrimidin-5-amine

A mixture of 4,6-diisopropyl-2-(propylthio)pyrimidin-5-amine (1.56 g, 6.16 mmol) and 3-chloroperoxybenzoic acid (3.45 g, 15.4 mmol) in THF (30.8 mL) was stirred at rt for 45 min, then cooled to 0° C. Sat. aq. NaHCO₃ was added slowly (3×10 mL portions) over 20 min. The resulting mixture was diluted with 4:1 EtOAc/MeOH and brine (20 mL), and the organic layer was separated. The aqueous layer was extracted with EtOAc, and the combined organic extracts were then dried over MgSO₄, filtered, and concentrated in vacuo. The residue was diluted with DMF (20 mL) and agitated by sonication to provide a homogeneous mixture. The mixture was slowly poured into water (100 mL), and the precipitated solid was collected by filtration, then washed with water and dried in a reduced-pressure oven at 45° C. overnight to afforded 4,6-diisopropyl-2-(propylsulfonyl)pyrimidin-5-amine (1.65 g, 5.76 mmol, 94% yield) as tan solid.

¹H NMR (400 MHz, DMSO-d₆) δ 6.08 (br s, 2H) 3.48-3.68 (m, 3H) 1.79 (br s, 2H) 1.29 (br s, 12H) 1.07 (br s, 4H). m/z (ESI, +ve ion): 286.2 $(M+H)^+$.

Step 3:
4,6-Diisopropyl-2-methoxypyrimidin-5-amine
(Intermediate I-36)

A mixture of 4,6-diisopropyl-2-(propylsulfonyl)pyrimidin-5-amine (0.300 g, 1.05 mmol) and sodium methoxide (0.5 M in MeOH, 3.4 mL, 1.68 mmol) in N, N-dimethylformamide (3.5 mL) was stirred in a sealed vial at 90° C. for 16 h. Additional sodium methoxide (0.5 M in MeOH, 3.4 mL, 1.68 mmol) was subsequently added, and the resulting mixture was stirred at 90° C. for an additional 16 h. After cooling, the reaction mixture was partitioned between EtOAc and sat. aq. NH₄Cl. The organic layer was separated, and the aqueous layer was extracted with EtOAc. The combined organic extracts were then dried over MgSO₄, filtered, and concentrated in vacuo. The residue was triturated with EtOAc and heptane, and the collected solids were washed with heptane and dried to provide 4,6-diisopropyl-2-methoxypyrimidin-5-amine (Intermediate I-36, 0.095 g, 0.454 mmol, 43% yield) as tan oil. m/z (ESI, +ve ion): 210.2 $(M+H)^+$.

Intermediate I-37

4-(((tert-Butyldiphenylsilyl)oxy)methyl)-2-isopropyl-6-methylaniline

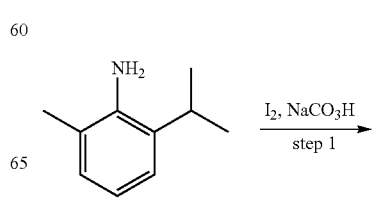

-continued

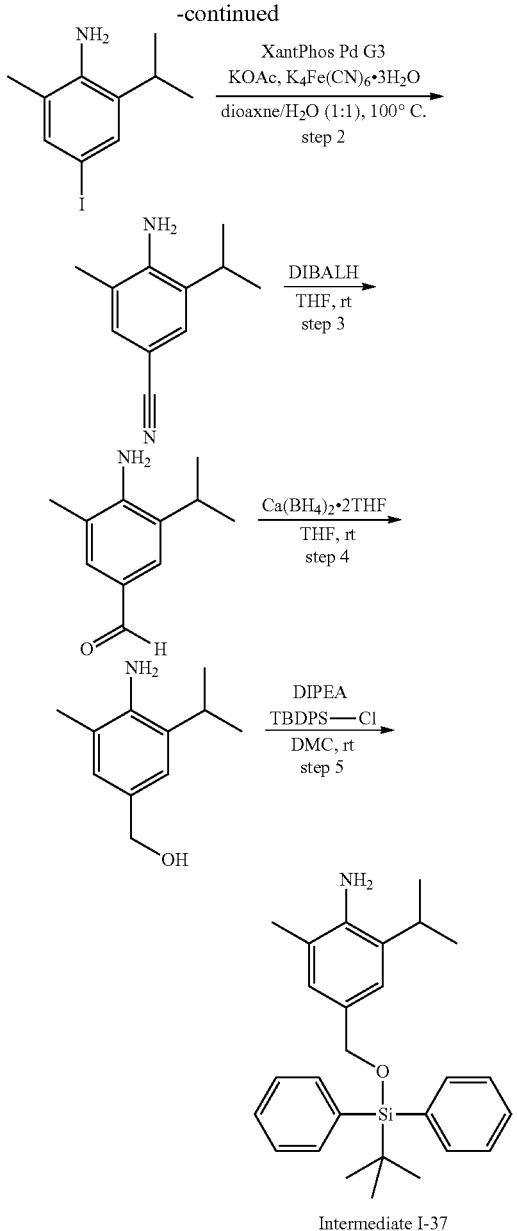

Intermediate I-37

Step 1: 4-Iodo-2-isopropyl-6-methylaniline

To a suspension of 2-isopropyl-6-methylaniline (3.2 mL, 20 mmol, Advanced Chemblocks Inc., Burlingame, Calif., USA). and sodium bicarbonate (3.4 g, 40 mmol) in DCM (20 mL) and water (20 mL) was added iodine (5.4 g, 21 mmol) in three portions. After 90 min, the 1 N sodium thiosulfate (30 mL) was added, and the resulting mixture was partitioned between DCM (30 mL) and water (10 mL). The organic layer was separated, and the aqueous layer was extracted with DCM (100 mL). The combined organic layers were then sequentially washed with brine (300 mL), dried over magnesium sulfate, filtered, and concentrated in vacuo. Chromatographic purification of the residue (silica gel, eluent: 0-30% EtOAc in heptanes) afforded 4-iodo-2-isopropyl-6-methylaniline as a red-purple oil. $^1$H NMR (400 MHz, DMSO-$d_6$) δ 1.11 (d, J=6.8 Hz, 6H), 2.04 (s, 3H), 2.97 (sept, J=6.8 Hz, 1H), 4.73 (s, 2H), 7.08-7.10 (s, 1H), 7.10-7.13 (m, 1H); m/z (ESI, +ve ion) 275.9 (M+H)$^+$.

Step 2: 4-Amino-3-isopropyl-5-methylbenzonitrile

A nitrogen-sparged suspension of 4-iodo-2-isopropyl-6-methylaniline (2.2 g, 7.9 mmol), XantPhos Pd G3 (170 mg, 0.20 mmol), potassium acetate (580 mg, 5.9 mmol), and potassium hexacyanoferrate(II) trihydrate (5.0 g, 12 mmol) in 1,4-dioxane (20 mL) and water (20 mL) was vigorously stirred at 100° C. for 4 h. The reaction mixture was then partitioned between water (200 mL) and EtOAc (150 mL). The organic layer was separated, and the aqueous layer was extracted with EtOAc (2×70 mL). The combined organic extracts were then dried over magnesium sulfate, filtered, and concentrated in vacuo. Chromatographic purification of the residue (silica gel, eluent: 0-40% EtOAc in heptanes) afforded 4-amino-3-isopropyl-5-methylbenzonitrile as an amber oil. $^1$H NMR (400 MHz, DMSO-$d_6$) δ 1.09-1.18 (m, 6H), 2.08 (s, 3H), 3.02 (sept, J=6.6 Hz, 1H), 5.59 (br s, 2H), 7.20 (br s, 1H), 7.22 (br s, 1H); m/z (ESI, +ve ion) 175.1 (M+H)$^+$.

Step 3: 4-Amino-3-isopropyl-5-methylbenzaldehyde

Diisobutylaluminum hydride (1 M in toluene, 17 mL, 17 mmol) was added. dropwise, to a room temperature solution of 4-amino-3-isopropyl-5-methylbenzonitrile (1.2 g, 6.9 mmol) in THF (34 mL). After 20 min, the reaction mixture was cooled to 0° C. and 1 M aq. Rochelle salt (35 mL) was added. The resulting mixture was stirred for 45 min. and the organic layer was then separated. The aqueous layer was extracted with EtOAc (1×70 mL). and the combined organic extracts were then sequentially washed with brine (300 mL), dried over magnesium sulfate, filtered through Celite®, and concentrated in vacuo. Chromatographic purification of the residue (silica gel, eluent: 0-15% EtOAc in heptanes) afforded 4-amino-3-isopropyl-5-methylbenzaldehyde as a thick yellow oil. $^1$H NMR (400 MHz, DMSO-$d_6$) δ 1.17 (d, J=6.6 Hz, 6H), 2.14 (s, 3H), 3.06 (spt, J=6.6 Hz, 1H), 5.75 (s, 2H), 7.35 (s, 1H), 7.44 (s, 1H), 9.59 (s, 1H); m/z (ESI, +ve ion) 178.1 (M+H)$^+$.

Step 4: (4-Amino-3-isopropyl-5-methylphenyl)methanol

Calcium borohydride bis(tetrahydrofuran) (1.8 g, 8.2 mmol) was added to a stirred solution of 4-amino-3-isopropyl-5-methylbenzaldehyde (970 mg, 5.5 mmol) in THF (8 mL), and the resulting mixture was stirred at rt for 2 h. Saturated aqueous NH4Cl (30 mL) was then slowly added, and the resulting mixture was extracted with (3×20 mL). The combined organic extracts were washed with brine, dried over sodium sulfate, filtered, and concentrated in vacuo to give crude (4-amino-3-isopropyl-5-methylphenyl)methanol, which was used without purification. m/z (ESI, +ve ion) 180.2 (M+H)$^+$.

Step 5: 4-(((tert-Butyldiphenylsilyl)oxy)methyl)-2-isopropyl-6-methylaniline (Intermediate I-37)

DIPEA (1.4 mL, 8.2 mmol) and tert-butyl(chloro)diphenylsilane (1.7 mL, 6.6 mmol) were sequentially added to a solution of (4-amino-3-isopropyl-5-methylphenyl)methanol (710 mg, 4.0 mmol) in DCM (10 mL), and the resulting mixture was stirred at room temperature for 4 h. The reaction mixture was then concentrated in vacuo and the residue chromatographically purified (silica gel, eluent: 0-40% EtOAc in heptanes) to provide 4-(((tert-butyldiphenylsilyl)oxy)methyl)-2-isopropyl-6-methylaniline (Intermediate I-37). m/z (ESI, +ve ion) 418.1 (M+H)+.

Intermediate I-38

2-Bromo-4,6-diisopropylpyrimidin-5-amine

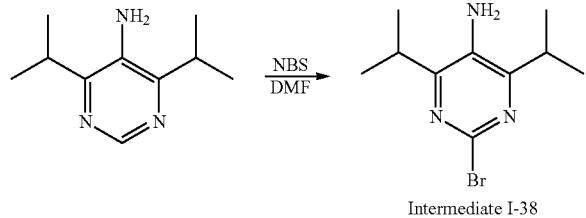

Intermediate I-38

A mixture of 4,6-diisopropylpyrimidin-5-amine (1 g, 5.58 mmol, Intermediate U), 1-bromopyrrolidine-2,5-dione (1.191 g, 6.69 mmol), and DMF (5 mL) was heated at 70° C. in a sealed pressure vial for 4 h, then cooled to rt and diluted with water. The resulting mixture was extracted with EtOAc, and the combined extracts were washed with brine, dried over Na$_2$SO$_4$, filtered, and concentrated in vacuo. Chromatographic purification of the residue (silica gel, 0-40% EtOAc/heptane) furnished 2-bromo-4,6-diisopropylpyrimidin-5-amine (Intermediate I-38) as brown oil. $^1$H NMR (400 MHz, DMSO-d$_6$) δ 1.12 (d, J=6.63 Hz, 12H) 3.12-3.27 (m, 2H) 5.27 (s, 2H). m/z (ESI, +ve ion): 258.0/260.0 (M+H)+

Intermediate I-40

2-(((tert-Butyldiphenylsilyl)oxy)methyl)-6-isopropylaniline

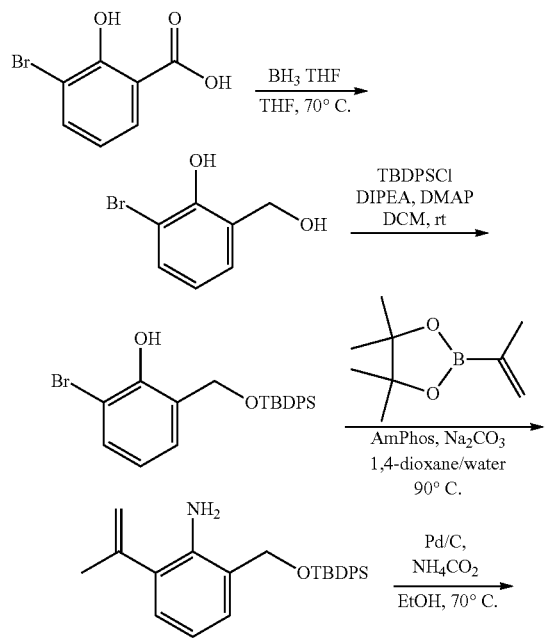

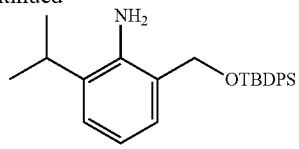

Intermediate I-40

Step 1: (2-Amino-3-bromophenyl)methanol

Borane tetrahydrofuran complex (1.0 M solution in THF, 23.4 mL, 23.4 mmol) was added, dropwise over 20 min, to a mixture of 2-amino-3-bromobenzoic acid (2.02 g, 9.34 mmol, Sigma-Aldrich. St. Louis, Mo., USA) and THF (30 mL) at 0° C. The resulting mixture was allowed to warm to rt and stir for 30 min before being stirred at 70° C. for 20 h. The reaction mixture was subsequently cooled to 0° C., and MeOH (~5 mL) and ice-water (30 mL) were sequentially added. The aqueous layer was saturated with solid NaCl, and the resulting mixture was extracted with EtOAc (2×40 mL). The combined extracts were dried over sodium sulfate, filtered and concentrated in vacuo. Chromatographic purification of the residue (silica gel, 10-50% EtOAc in heptane) furnished (2-amino-3-bromophenyl)methanol as a white solid (1.83 g, 9.04 mmol, 97% yield). m/z (ESI, +ve ion): 184.0 (M+H)+.

Step 2: 2-Bromo-6-(((tert-butyldiphenylsilyl)oxy)methyl)aniline tert-Butyldiphenylsilyl chloride (2.0 mL, 7.66 mmol, Sigma-Aldrich) was added to a mixture of (2-amino-3-bromophenyl)methanol (1.19 g, 5.89 mmol), DIPEA (3.6 mL, 20.6 mmol), DMAP (0.035 g, 0.28 mmol), and DCM (20 mL). The resulting mixture was stirred at rt for 24 h, then concentrated in vacuo. Chromatographic purification of the residues (silica gel, 0-50% EtOAc in heptane) provided 2-bromo-6-(((tert-butyldiphenylsilyl)oxy)methyl)aniline (2.42 g, 5.50 mmol, 93% yield) as a clear oil. m/z (ESI, +ve ion): 462.2 (M+Na)+.

Step 3: 2-(((tert-Butyldiphenylsilyl)oxy)methyl)-6-(prop-1-en-2-yl)aniline

A mixture of 2-bromo-6-(((tert-butyldiphenylsilyl)oxy)methyl)aniline (2.22 g, 5.04 mmol), (4,4,5,5-tetramethyl-1,3,2-dioxaborolan-2-yl)isopropene (1.23 mL, 6.55 mmol, Combi-Blocks, Inc.), bis-(di-tert-butyl(4-dimethylaminophenyl)phosphine)dichloropalladium(II) (0.432 g, 0.610 mmol, Sigma-Aldrich), sodium carbonate (2 M aq solution; 6.30 mL, 12.60 mmol). and 1,4-dioxane (25 mL) was sparged with Art) for 5 min, then stirred at 90° C. for 3 h. After cooling to rt, water (30 mL) was added, and the resulting mixture was extracted with EtOAc (2×30 mL). The combined extracts were dried over sodium sulfate, filtered, and concentrated in vacuo. Chromatographic purification of the residue (silica gel, 0-20% EtOAc in heptane) gave 2-(((tert-butyldiphenylsilyl)oxy)methyl)-6-(prop-1-en-2-yl)aniline (1.80 g, 4.49 mmol, 89% yield) as a blue-green tinged oil.

Step 4: 2-(((tert-Butyldiphenylsilyl)oxy)methyl)-6-isopropylaniline (Intermediate I-40)

A mixture of 2-(((tert-butyldiphenylsilyl)oxy)methyl)-6-(prop-1-en-2-yl)aniline (1.80 g, 4.48 mmol), palladium, 10 wt. % (dry basis) on activated carbon (wet, Degussa type E101 NE/W; 0.477 g, 0.224 mmol), ammonium formate (2.83 g, 44.8 mmol), and EtOH (20 mL) was stirred at 70° C. for 30 min. The mixture was then cooled to rt and filtered through a pad of diatomaceous earth. The filtrate was concentrated in vacuo, and the residue was partitioned between EtOAc (30 mL) and water (30 mL). The organic layer was separated and sequentially washed with water (10 mL), dried over sodium sulfate, filtered, and concentrated in vacuo to afford 2-(((tert-butyldiphenylsilyl)oxy)methyl)-6-isopropylaniline (Intermediate I-40, 1.73 g, 4.29 mmol, 96% yield) as clear paste. $^1$H NMR (400 MHz, CDCl$_3$) δ 7.71 (4H, dd, J=7.9, 1.5 Hz), 7.37-7.46 (6H, m), 7.13 (1H, dd, J=7.7, 1.2 Hz), 6.74-6.79 (1H, m), 6.66-6.72 (1H, m), 4.75 (2H, s), 4.42 (2H, br d, J=1.5 Hz), 2.98 (1H, dt, J=13.5, 6.8 Hz), 1.31 (6H, d, J=6.6 Hz), 1.07 (9H, s). m/z (ESI, +ve ion): 426.2 (M+Na).

Example 50, Step 3

3,6-Dichloro-5-(2-fluorophenyl)pyrazine-2-carboxamide

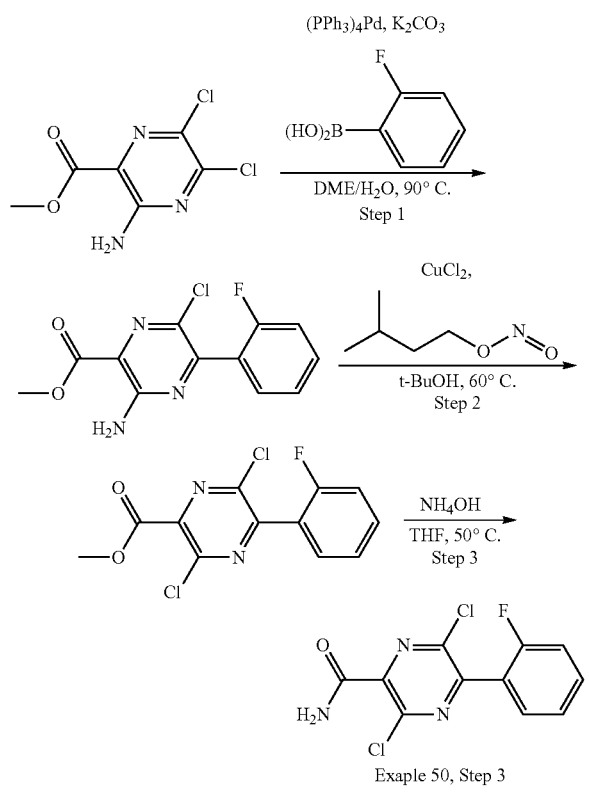

Exaple 50, Step 3

Step 1: Methyl 3-amino-6-chloro-5-(2-fluorophenyl)pyrazine-2-carboxylate

A mixture of methyl 3-amino-5,6-dichloropyrazine-2-carboxylate (10.0 g, 45 mmol, Ark Pharm, Inc., Arlington Heights, Ill.), (2-fluorophenyl)boronic acid (6.93 g, 49.5 mmol, Combi-Blocks, San Diego, Calif., USA) and potassium carbonate (13.1 g, 95 mmol) in a 10:1 mixture of DME/water (220 mL) was degassed with nitrogen for 5 min and then tetrakis(triphenylphosphine)palladium(0) (1.04 g, 0.90 mmol) was added. The reaction mixture was stirred at 90° C. for 16 h, then was allowed to cool to room temperature and partitioned between EtOAc (200 mL) and 1 N HCl (200 mL). The organic layer was dried over anhydrous sodium sulfate and concentrated to provide methyl 3-amino-6-chloro-5-(2-fluorophenyl)pyrazine-2-carboxylate. m/z (ESI, +ve): 282.1 (M+H)$^+$.

Step 2: Methyl 3,6-dichloro-5-(2-fluorophenyl)pyrazine-2-carboxylate

To a solution of methyl 3-amino-6-chloro-5-(2-fluorophenyl)pyrazine-2-carboxylate (22.0 g, 78 mmol) in t-BuOH (220 mL) was added isoamyl nitrite (15.8 mL, 117 mmol) and copper chloride (12.6 g, 94 mmol). The resulting mixture was stirred at 60° C. for 16 h and then was partitioned between water (1 L) and EtOAc (2 L). The organic layer was dried over anhydrous sodium sulfate and concentrated. The residue was purified by silica gel chromatography (eluent: 0-5% EtOAc/hexane) to provide methyl 3,6-dichloro-5-(2-fluorophenyl)pyrazine-2-carboxylate, m/z (ESI, +ve ion): 300.9 (M+H)$^+$.

Step 3: 3,6-Dichloro-5-(2-fluorophenyl)pyrazine-2-carboxamide

To a solution of methyl 3,6-dichloro-5-(2-fluorophenyl)pyrazine-2-carboxylate (13.5 g, 44.8 mmol) in THF (150 mL) was added ammonium hydroxide solution (30%, 150 mL, 44.8 mmol). The resulting mixture was heated at 50° C. for 4 h, then was allowed to cool to room temperature and partitioned between water and EtOAc (500 mL). The organic layer was dried over anhydrous sodium sulfate and concentrated. The residue was purified by silica gel chromatography (eluent: 0-30% EtOAc/hexanes) to provide 3,6-dichloro-5-(2-fluorophenyl)pyrazine-2-carboxamide (Example 50, Step 3). $^1$H NMR (400 MHz, DMSO-d$_6$) δ 8.32 (br s, 1H), 8.16 (br s, 1H), 7.64-7.77 (m, 2H), 7.41-7.47 (m, 2H). m/z (ESI, +ve): 286.0 (M+H)$^+$.

Intermediate P 2,5,6-Trichloronicotinamide

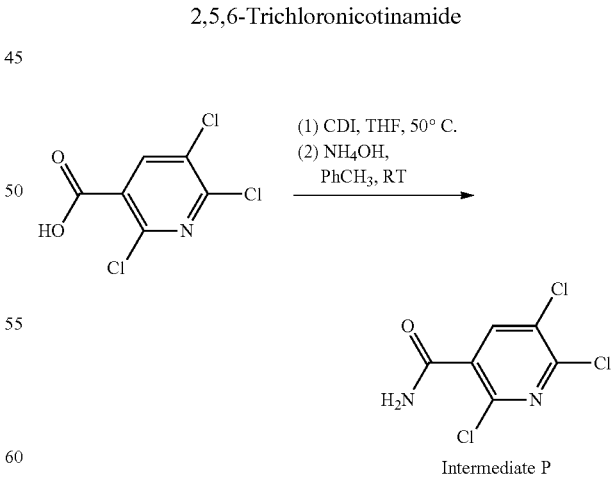

Intermediate P 1,1'-Carbonyldiimidazole (40 g, 247 mmol) was added in portions to 2,5,6-trichloronicotinic acid (50.7 g, 224 mmol, Combi-Blocks, San Diego, Calif., USA) in THF (400 mL), allowing gas evolution to cease between additions. The resulting mixture was stirred for 5 min and then was degassed with house vacuum and flushed with nitrogen (×2). The resulting mixture was heated to 50° C. for 60 min, then diluted with toluene (100 mL) and concentrated to half volume. The resulting mixture was cooled to 0° C. and ammonium hydroxide (60 mL, 437 mmol) was added slowly via syringe. The reaction was stirred for 10 min at room temperature, diluted with EtOAc (200 mL) and washed with water (3×100 mL). The organic layer was dried over anhydrous sodium sulfate and concentrated. The residue was suspended in 9:1 heptane/EtOAc (300 mL) and filtered. The filtered solids were collected and the remaining mother liquor was partially evaporated to half volume, cooled to 0° C., and filtered. The two crops of filtered solids were combined to provide 2,5,6-trichloronicotinamide (Intermediate P, 46.2 g, 92% yield).

Intermediate Q (2-Fluoro-6-hydroxyphenyl)potassium trifluoroborate

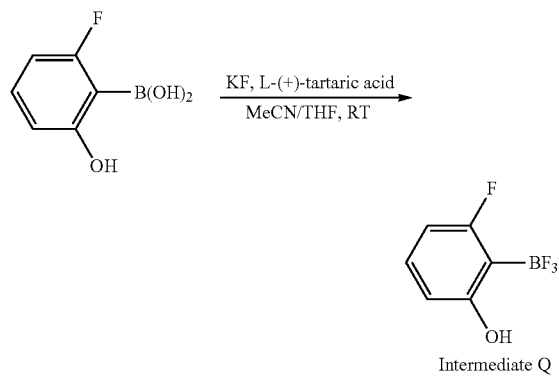

Intermediate Q

A solution of potassium fluoride (44.7 g, 770 mmol) in water (75 mL) was added to a suspension of (2-fluoro-6-hydroxyphenyl)boronic acid (30 g, 192 mmol, Combi-Blocks, San Diego, Calif., USA) in acetonitrile (750 mL). The mixture was stirred for 2 min and then a solution of L-(+)-tartaric acid (72.2 g, 481 mmol) in THF (375 mL) was added over a 10 min period via addition funnel. The mixture was stirred vigorously with a mechanical stirrer for 1 h, and then the resulting suspension was filtered, and the filtered solids were washed with a small amount of THF. The solids were discarded and the filtrate was partially concentrated until solids started to precipitate out of solution. The mixture was then cooled to −20° C. and stirred for 16 h. The reaction was slowly warmed and 2-propanol (20 mL) was added. The resulting suspension was filtered and the filtered solids were washed with 2-propanol to provide 27.5 g of solid. The filtrate was again partially concentrated until a suspension formed and then was cooled to −20° C. and stirred for an additional 20 min. The resulting suspension was diluted with 2-propanol and filtered, and the filtered solids were washed with 2-propanol. The two batches of solids were combined to provide 2-fluoro-6-hydroxyphenyl)potassium trifluoroborate (Intermediate Q, 37.9 g, 90% yield). $^1$H NMR (400 MHz, DMSO-d$_6$) δ 8.07 (q, J=14.7 Hz, 1H) 6.93 (q, J=7.5 Hz, 1H) 6.30-6.38 (m, 2H).

Intermediate R

2-Isopropyl-4-methylpyridin-3-amine

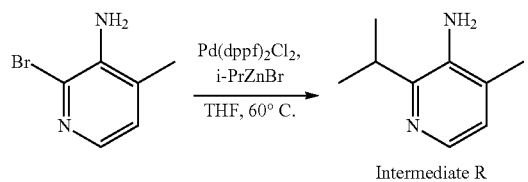

Intermediate R

To a slurry of 3-amino-2-bromo-4-picoline (360 mg, 1.9 mmol, Combi-Blocks. San Diego, Calif., USA) in THF (4 mL) was added [1,1'-bis(diphenylphosphino)ferrocene]dichloropalladium(II), complex with dichloromethane (79 mg, 0.10 mmol). The resulting slurry was deoxygenated with argon for 2 min and then 2-propylzinc bromide (0.5 M solution in THF, 5.40 mL, 2.7 mmol) was added. The resulting solution was heated at 60° C. for 17 h, then the heating was stopped and the reaction was allowed to cool to room temperature. The reaction mixture was quenched with water (10 mL) and 1 N NaOH solution (20 mL) and then was extracted with EtOAc (2×). The combined organic layers were dried over anhydrous sodium sulfate and concentrated. The residue was purified by silica gel chromatography (eluent: 0-15% MeOH/DCM) to provide 2-isopropyl-4-methylpyridin-3-amine (Intermediate R, 284 mg, 98% yield). $^1$H NMR (400 MHz, DMSO-d6) S 7.66 (d, J=4.6 Hz, 1H), 6.78 (d, J=4.8 Hz, 1H), 4.72 (br s, 2H), 3.14-3.25 (m, 1H), 2.08 (s, 3H), 1.14 (d, J=6.8 Hz, 6H). m/z (ESI, +ve ion): 151.1 (M+H)$^+$.

Intermediate U 4,6-Diisopropylpyrimidin-5-amine

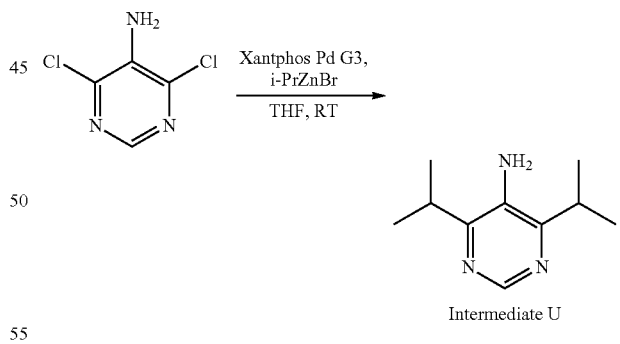

Intermediate U

A solution of 4,6-dichloro-5-aminopyrimidine (3.00 g, 18.29 mmol, Combi-Blocks Inc., San Diego, Calif., USA) in THF (18 mL) was deoxygenated by bubbling argon into the mixture for 5 min. 2-Isopropylzinc bromide (0.5 M solution in THF. 91.0 mL, 45.5 mmol) was added via syringe followed by XantPhos Pd G3 (434 mg, 0.46 mmol, Sigma-Aldrich, St. Louis, Mo., USA). The resulting mixture was stirred at room temperature for 16 h and then was filtered through a pad of Celite. The filter cake was rinsed with EtOAc, and the filtrate was collected and concentrated to afford 4,6-diisopropylpyrimidin-5-amine (Intermediate U, 3.45 g). This material was used without further purification in the following step. m/z (ESI, +ve ion): 180.2 (M+H)+.

Intermediates 61A and 61B 6,7-Dichloro-1-(2-isopropylphenyl)pyrido[2,3-d]pyrimidine-2,4(1H,3H)-dione and (S)-tert-Butyl 4-(6,7-dichloro-1-(2-isopropylphenyl)-2-oxo-1,2-dihydropyrido[2,3-d]pyrimidin-4-yl)-3-methylpiperazine-1-carboxylate

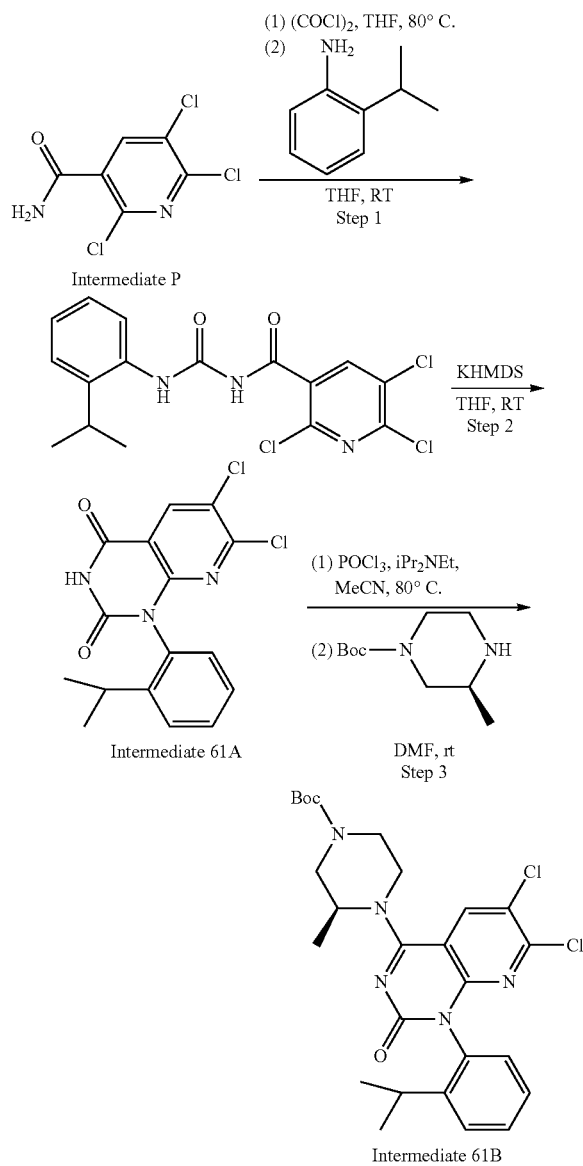

Intermediate 61B

Step 1: 2,5,6-Trichloro-N-((2-isopropylphenyl)carbamoyl)nicotinamide

A suspension mixture of 2,5,6-trichloronicotinamide (Intermediate P, 6.7 g, 29.7 mmol) in 1,2-dichloroethane (100 mL) was treated with oxalyl chloride (3.0 mL, 35.7 mmol) at rt. The resulting reaction mixture was stirred at 80° C. for 30 min then the white suspension was evaporated to give a slurry. The slurry was treated with acetonitrile (100 mL) and then with 2-isopropylaniline (4.6 mL, 32.7 mmol, Sigma-Aldrich Corporation, St. Louis, Mo., USA) at rt. The mixture was stirred for 15 min and the white solid was collected by filtration, washed with acetonitrile and dried to give pure 2,5,6-trichloro-N-((2-isopropylphenyl)carbamoyl)nicotinamide (8.55 g, 22.1 mmol, 74.4% yield) as a white solid. m/z (ESI, +ve ion): 386.0 (M+H)+.

Step 2: 6,7-Dichloro-1-(2-isopropylphenyl)pyrido[2,3-d]pyrimidine-2,4(1H,3H)-dione (Intermediate 61A)

A mixture of 2,5,6-trichloro-N-((2-isopropylphenyl)carbamoyl)nicotinamide (8.55 g, 22.1 mmol) in THF (74 mL) at 0° C. was treated with KHDMS (1M solution in THF, 44.3 mL, 44.3 mmol). The mixture was stirred at 0° C. for 10 min and at rt for 30 min. The reaction mixture was quenched with satd. ammonium chloride (100 mL) and extracted with EtOAc (200 mL). The organic layer was separated, washed with brine (150 mL), dried over $Na_2SO_4$, filtered, and concentrated in vacuo. The resulting crude product was sonicated in MeOH (20 mL), filtered, and washed with MeOH and dried to give pure 6,7-dichloro-1-(2-isopropylphenyl)pyrido[2,3-d]pyrimidine-2,4(1H,3H)-dione (Intermediate 61A, 7.17 g, 20.5 mmol, 92% yield) as a tan solid. $^1$H NMR (400 MHz, DMSO-$d_6$) δ 12.10 (s, 1H), 8.52 (s, 1H), 7.38-7.60 (m, 2H), 7.12-7.38 (m, 2H), 2.74 (dt, J=13.5, 6.8 Hz, 1H), 1.08 (d, J=6.8 Hz, 3H), 1.03 (d, J=6.8 Hz, 3H).). m/z (ESI, +ve ion): 350.0 (M+H)+.

Step 3: (S)-tert-Butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B)

To a mixture of 6,7-dichloro-1-(2-isopropylphenyl)pyrido[2,3-d]pyrimidine-2,4(1H,3H)-dione (Intermediate 61A, 1.03 g, 2.94 mmol) and DIPEA (1.5 mL, 8.82 mmol) in acetonitrile (19.6 mL) was added phosphorus oxychloride (1.4 mL, 8.82 mmol) at rt and heated at 80° C. for 30 min. The mixture was concentrated in vacuo to give the crude 4,6,7-trichloro-1-(2-isopropylphenyl)pyrido[2,3-d]pyrimidin-2(1H)-one as a brown solid. m/z (ESI, +ve ion): 368.0 (M+H)+. The crude material was used in next step without purification.

To a mixture of the above 4,6,7-trichloro-1-(2-isopropylphenyl)pyrido[2,3-d]pyrimidin-2(1H)-one (1.08 g, 2.94 mmol) and DIPEA (1.5 mL, 8.82 mmol) in DMF (14.7 mL) was added (S)-4-N-Boc-2-methyl piperazine (0.88 g, 4.41 mmol) and stirred at rt for 10 min. Ice water (10 mL) was added and stirred for 15 min. The resulting precipitate was collected by filtration, washed with water, and dried to give (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 1.52 g, 2.85 mmol, 97% yield) as a yellow solid. m/z (ESI, +ve ion): 532.0 (M+H)+.

Intermediates S and 72A 2,6-Dichloro-5-fluoronicotinamide and 7-chloro-6-fluoro-1-(2-isopropyl-4-methylpyridin-3-yl)pyrido[2,3-d]pyrimidine-2,4(1H,3H)-dione

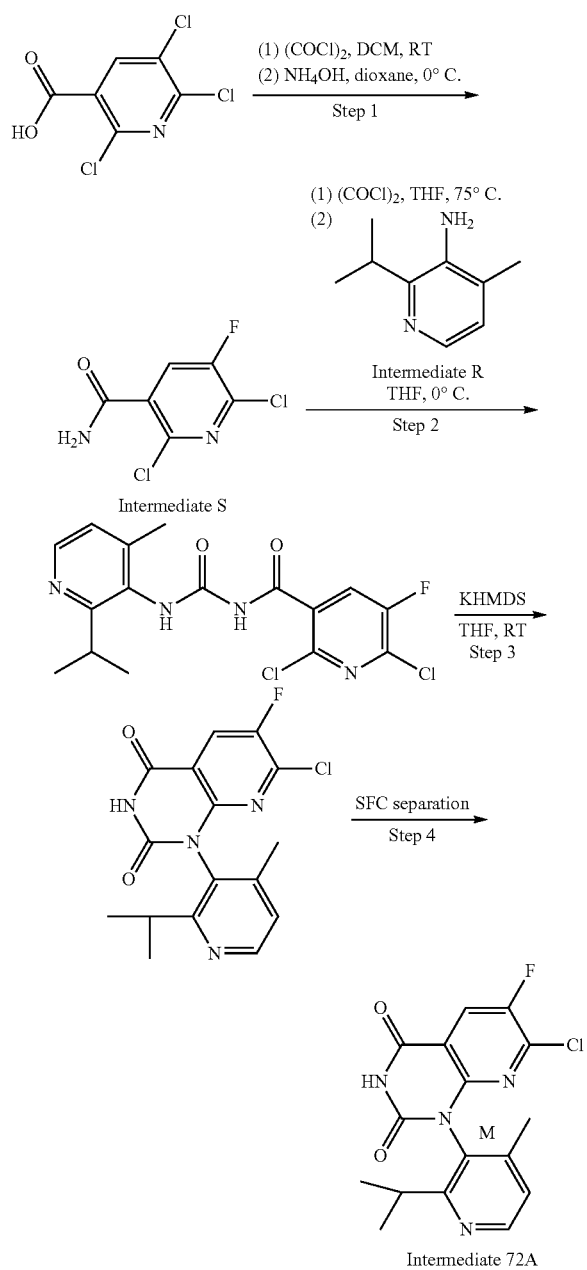

Intermediate S

Intermediate 72A

Step 1: 2,6-Dichloro-5-fluoronicotinamide (Intermediate S)

To a mixture of 2,6-dichloro-5-fluoro-nicotinic acid (4.0 g, 19.1 mmol, AstaTech Inc., Bristol, Pa.) in dichloromethane (48 mL) was added oxalyl chloride (2M solution in DCM. 11.9 mL, 23.8 mmol), followed by a catalytic amount of DMF (0.05 mL). The reaction was stirred at room temperature overnight and then was concentrated. The residue was dissolved in 1,4-dioxane (48 mL) and cooled to 0° C. Ammonium hydroxide solution (28.0-30% NH3 basis. 3.6 mL. 28.6 mmol) was added slowly via syringe. The resulting mixture was stirred at 0° C. for 30 min and then was concentrated. The residue was diluted with a 1:1 mixture of EtOAc/heptane and agitated for 5 min, then was filtered. The filtered solids were discarded, and the remaining mother liquor was partially concentrated to half volume and filtered. The filtered solids were washed with heptane and dried in a reduced-pressure oven (45° C.) overnight to provide 2,6-dichloro-5-fluoronicotinamide (Intermediate S, 2.00 g, 50% yield). $^{1}$H NMR (400 MHz, DMSO-d$_6$) δ 8.23 (d, J=7.9 Hz, 1H) 8.09 (br s, 1H) 7.93 (br s, 1H). m/z (ESI, +ve ion): 210.9 (M+H)$^{+}$.

Step 2: 2,6-Dichloro-5-fluoro-N-((2-isopropyl-4-methylpyridin-3-yl)carbamoyl)nicotinamide To an ice-cooled slurry of 2,6-dichloro-5-fluoronicotinamide (Intermediate S, 5.0 g, 23.9 mmol) in THF (20 mL) was added oxalyl chloride (2 M solution in DCM, 14.4 mL, 28.8 mmol) slowly via syringe. The resulting mixture was heated at 75° C. for 1 h, then heating was stopped, and the reaction was concentrated to half volume. After cooling to 0° C., THF (20 mL) was added, followed by a solution of 2-isopropyl-4-methylpyridin-3-amine (Intermediate R, 3.59 g, 23.92 mmol) in THF (10 mL), dropwise via cannula. The resulting mixture was stirred at 0° C. for 1 h and then was quenched with a 1:1 mixture of brine and saturated aqueous ammonium chloride. The mixture was extracted with EtOAc (3×) and the combined organic layers were dried over anhydrous sodium sulfate and concentrated to provide 2,6-dichloro-5-fluoro-N-((2-isopropyl-4-methylpyridin-3-yl)carbamoyl)nicotinamide (9.2 g, 100% yield). This material was used without further purification in the following step. m/z (ESI, +ve ion): 385.1 (M+H)$^{+}$.

Step 3: 7-Chloro-6-fluoro-1-(2-isopropyl-4-methylpyridin-3-yl)pyrido[2,3-d]pyrimidine-2,4(1H,3H)-dione To an ice-cooled solution of 2,6-dichloro-5-fluoro-N-((2-isopropyl-4-methylpyridin-3-yl)carbamoyl)nicotinamide (9.2 g, 24.0 mmol) in THF (40 mL) was added KHMDS (1 M solution in THF, 50.2 mL, 50.2 mmol) slowly via syringe. The ice bath was removed and the resulting mixture was stirred for 40 min at room temperature. The reaction was quenched with saturated aqueous ammonium chloride and extracted with EtOAc (3×). The combined organic layers were dried over anhydrous sodium sulfate and concentrated. The residue was purified by silica gel chromatography (eluent: 0-50% 3:1 EtOAc-EtOH/heptane) to provide 7-chloro-6-fluoro-1-(2-isopropyl-4-methylpyridin-3-yl)pyrido[2,3-d]pyrimidine-2,4(1H,3H)-dione (5.0 g, 60% yield). $^{1}$H NMR (400 MHz, DMSO-d6) δ 12.27 (br s, 1H), 8.48-8.55 (m, 2H), 7.29 (d, J=4.8 Hz, 1H), 2.87 (quin, J=6.6 Hz, 1H), 1.99-2.06 (m, 3H), 1.09 (d, J=6.6 Hz, 3H), 1.01 (d, J=6.6 Hz, 3H). $^{19}$F NMR (376 MHz, DMSO-d$_6$) δ: −126.90 (s, 1F). m/z (ESI, +ve ion): 349.1 (M+H)$^{+}$.

Step 4: 7-Chloro-6-fluoro-1-(2-isopropyl-4-methylpyridin-3-yl)pyrido[2,3-d]pyrimidine-2,4(1H,3H)-dione (Intermediate 72A)

A mixture of atropisomers 7-chloro-6-fluoro-1-(2-isopropyl-4-methylpyridin-3-yl)pyrido[2,3-d]pyrimidine-2,4(1H,3H)-dione (Example 41, Step 3, 648 g) was purified by SFC (AD, 150×50 mm, 5 μm, 50% MeOH/CO$_2$, 180 g/min, 102 bar) to obtain two peaks: Peak 1 (P isomer, 230.6 g, >99% ee) and Peak 2 (M isomer, 227.8 g, 97.1% ee, Intermediate 72A).

Intermediates 73A and 73B (P)- and (M)-6,7-Dichloro-1-(2-isopropyl-4-methylpyridin-3-yl)pyrido[2,3-d]pyrimidine-2,4(1H,3H)-dione

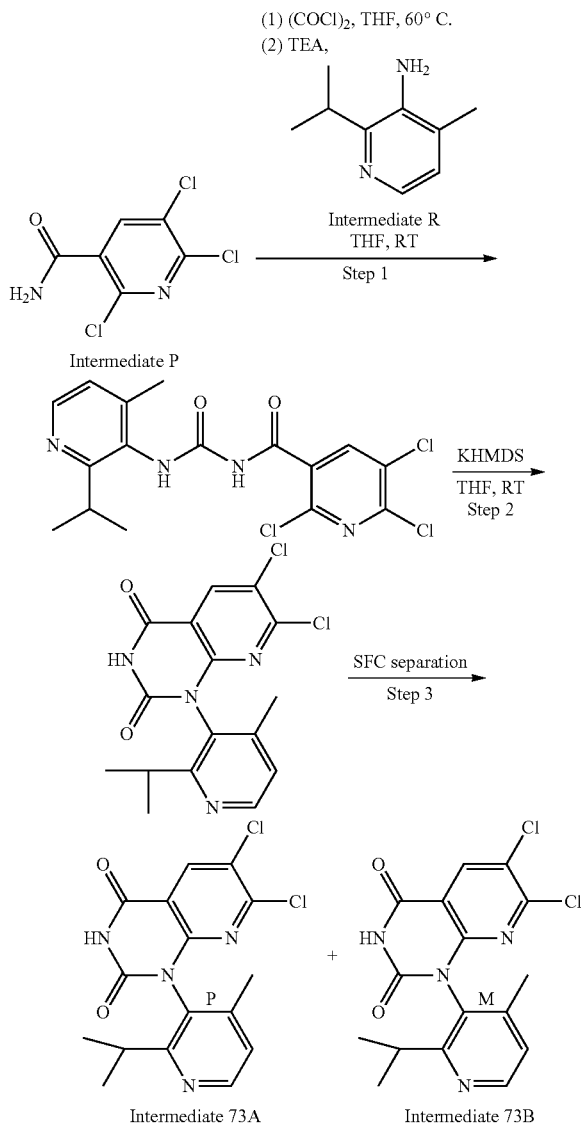

Step 1: 2-Isopropyl-4-methylpyridin-3-amine (Intermediate R)

To a slurry of 3-amino-2-bromo-4-picoline (360 mg, 1.9 mmol, Combi-Blocks, San Diego, Calif. USA) in THF (4 mL) was added [1,1'-bis(diphenylphosphino)ferrocene]dichloropalladium(II), complex with dichloromethane (79 mg, 0.10 mmol). The resulting slurry was deoxygenated with argon for 2 min and then 2-propylzinc bromide (0.5 M solution in THF, 5.40 mL, 2.7 mmol) was added. The resulting solution was heated at 60° C. for 17 h, then the heating was stopped and the reaction was allowed to cool to room temperature. The reaction mixture was quenched with water (10 mL) and 1 N NaOH solution (20 mL) and then was extracted with EtOAc (2×). The combined organic layers were dried over anhydrous sodium sulfate and concentrated. The residue was purified by silica gel chromatography (eluent: 0-15% MeOH/DCM) to provide 2-isopropyl-4-methylpyridin-3-amine (284 mg, 98% yield). $^1$H NMR (400 MHz, DMSO-d$_6$) δ 7.66 (d, J=4.6 Hz, 1H), 6.78 (d, J=4.8 Hz, 1H), 4.72 (br s, 2H), 3.14-3.25 (m, 1H), 2.08 (s, 3H), 1.14 (d, J=6.8 Hz, 6H). m/z (ESI, +ve ion): 151.1 (M+H)$^+$.

Step 2: 2,5,6-Trichloro-N-((2-isopropyl-4-methylpyridin-3-yl)carbamoyl)nicotinamide To a −78° C. slurry of 2,5,6-trichloronicotinamide (Intermediate P, 3.10 g, 13.8 mmol) in THF (46 mL) was added oxalyl chloride (2 M solution in DCM, 7.4 mL, 14.7 mmol) slowly via syringe. The resulting slurry was heated at 60° C. for 3.5 h, then heating was stopped and the reaction was cooled to −78° C. Triethylamine (6.0 mL, 42.6 mmol) was added followed by a solution of 2-isopropyl-4-methylpyridin-3-amine (Intermediate R, 2.12 g, 14.1 mmol) via cannula. The resulting slurry was warmed to room temperature and stirred for 1 h, then was partitioned between water (120 mL) and EtOAc (175 mL). The organic layer was dried over anhydrous sodium sulfate and concentrated. The residue was suspended in 9:1 heptane/EtOAc and filtered. The filtered solids were collected to provide 2,5,6-trichloro-N-((2-isopropyl-4-methylpyridin-3-yl)carbamoyl)nicotinamide (4.71 g, 85% yield). $^1$H NMR (400 MHz, DMSO-d$_6$) δ 11.31 (s, 1H), 9.54 (s, 1H), 8.66 (s, 1H), 8.34 (d, J=4.8 Hz, 1H), 7.16 (d, J=5.0 Hz, 1H), 3.24-3.33 (m, 1H), 2.22 (s, 3H), 1.17 (d, J=6.6 Hz, 6H). m/z (ESI, +ve ion): 400.9 (M+H)$^+$.

Step 3: 6,7-Dichloro-1-(2-isopropyl-4-methylpyridin-3-yl)pyrido[2,3-d]pyrimidine-2,4(1H,3H)-dione A mixture of atropisomers 6,7-dichloro-1-(2-isopropyl-4-methylpyridin-3-yl)pyrido[2,3-d]pyrimidine-2,4(1H,3H)-dione (55.1 g) was purified by SFC (AD, 250×50 mm, 5 μm, 50% MeOH/CO2, 180 g/min, 102 bar) to obtain two peaks: Peak 1 (Intermediate 73A, (P)-isomer, 22.1 g, >99% ee) and Peak 2 ((M)-isomer, 23.2 g, >99% ee). Peak 2 was the desired material (Intermediate 73B).

Intermediate 76A (M)-6-Chloro-7-(2-fluorophenyl)-4-hydroxy-1-(2-isopropyl-4-methylpyridin-3-yl)pyrido[2,3-d]pyrimidin-2(1H)-one

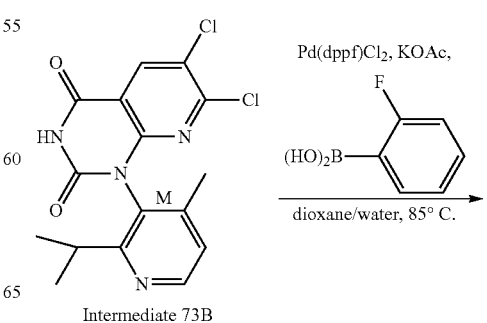

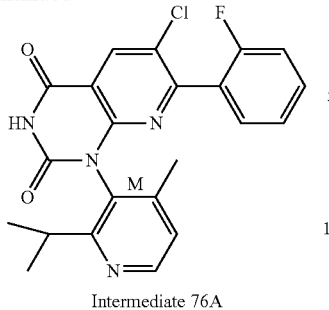

Intermediate 76A

A mixture of (M)-6,7-dichloro-1-(2-isopropyl-4-methylpyridin-3-yl)pyrido[2,3-d]pyrimidine-2,4(1H,3H)-dione (Intermediate 73B, 4.38 g, 12 mmol), 2-fluorophenylboronic acid (2.35 g, 16.8 mmol), (1,1'-bis(diphenylphosphino) ferrocene) dichloropalladium (0.351 g, 0.48 mmol), potassium acetate (5.1 g, 52.0 mmol) in 1,4-dioxane (30 mL) and water (1 mL) was stirred and heated at 85° C. for 15 h. The mixture was cooled to rt and diluted with EtOAc and water. The organic layer was washed with brine, dried over $Na_2SO_4$, filtered, and concentrated in vacuo. The residue was purified by silica gel chromatography (eluent: 0-40% EtOAc/heptane) to provide (M)-6-chloro-7-(2-fluorophenyl)-1-(2-isopropyl-4-methylpyridin-3-yl)pyrido[2,3-d]pyrimidine-2,4 (1H,3H)-dione (Intermediate 76A) as white solids. m/z (ESI, +ve ion): 424.9 $(M+H)^+$.

Intermediate 85A

Methyl 3,5-dichloro-2-(2-fluorophenyl)-7-(methoxymethyl)-1,6-naphthyridine-8-carboxylate

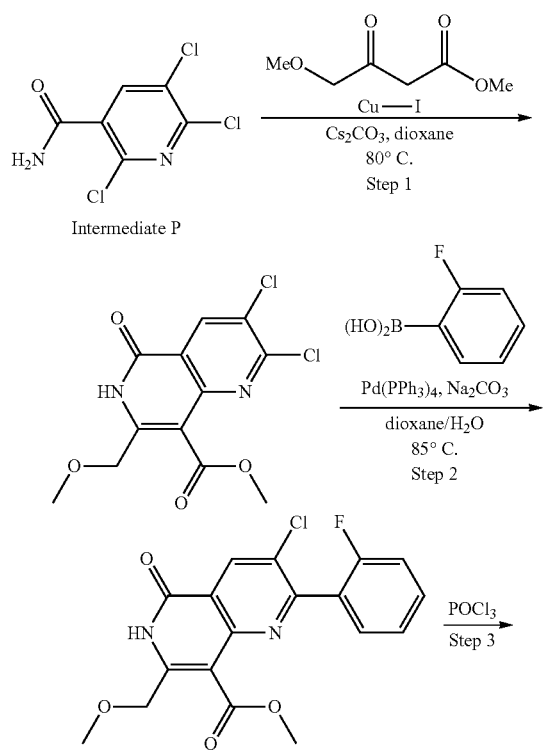

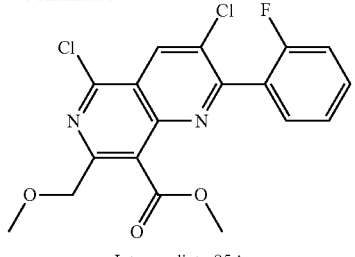

Intermediate 85A

Step 1: Methyl 2,3-dichloro-7-(methoxymethyl)-5-oxo-5,6-dihydro-1,6-naphthyridine-8-carboxylate A mixture of 2,5,6-trichloronicotinamide (Intermediate P, 5.0 g, 22 mmol), 4-methoxy-3-oxo-butanoic acid methyl ester (4.86 mL, 33.3 mmol), copper(I) iodide (0.42 g, 2.22 mmol) and cesium carbonate (14.45 g, 44.4 mmol) was purged with N2 followed by the addition of 1,4-dioxane (110 mL) and the reaction mixture was heated at 80° C. under nitrogen for 16 h. The mixture was quenched with 9:1 sat. $NH_4Cl/NH_4OH$ and extracted with EtOAc. The combined organics were concentrated to give methyl 2,3-dichloro-7-(methoxymethyl)-5-oxo-5,6-dihydro-1,6-naphthyridine-8-carboxylate (4.0 g, 12.6 mmol, 56.9% yield). m/z (ESI, +ve ion): 317.0 $(M+H)^+$. The crude material was used as is in the subsequent step. 13

Step 2: Methyl 3-chloro-2-(2-fluorophenyl)-7-(methoxymethyl)-5-oxo-5,6-dihydro-1,6-naphthyridine-8-carboxylate A mixture of methyl 2,3-dichloro-7-(methoxymethyl)-5-oxo-5,6-dihydro-1,6-naphthyridine-8-carboxylate (4.0 g, 12.6 mmol). (2-fluorophenyl)boronic acid (2.29 g, 16.4 mmol, Combi-Blocks Inc.), palladium tetrakis (1.46 g, 1.26 mmol) and sodium carbonate (4.01 g, 37.8 mmol) in 1,4-dioxane/water (30/7.5 mL) was heated at 85° C. for 45 min. The reaction was quenched with saturated $NaHCO_3$ and extracted with EtOAc. The crude product was purified by silica gel chromatography (eluent: 0-50% EtOAc:EtOH (3:1)/heptane) to provide methyl 3-chloro-2-(2-fluorophenyl)-7-(methoxymethyl)-5-oxo-5,6-dihydro-1,6-naphthyridine-8-carboxylate (4.0 g, 10.6 mmol, 84% yield) as a yellow solid. m/z (ESI, +ve ion): 377.0 $(M+H)^+$.

Step 3: Methyl 3,5-dichloro-2-(2-fluorophenyl)-7-(methoxymethyl)-1,6-naphthyridine-8-carboxylate (Intermediate 85A)

A solution of methyl 3-chloro-2-(2-fluorophenyl)-7-(methoxymethyl)-5-oxo-5,6-dihydro-1,6-naphthyridine-8-carboxylate (0.30 g, 0.80 mmol) and phosphoryl trichloride (5.0 mL, 54 mmol) was heated at 90° C. for 1 h. The reaction was concentrated in vacuo and the residue was diluted with EtOAc, washed with sat. $NaHCO_3$ and brine. The combined organics were concentrated to afford methyl 3,5-dichloro-2-(2-fluorophenyl)-7-(methoxymethyl)-1,6-naphthyridine-8-carboxylate (Intermediate 85A, 0.3 g, 0.759 mmol, 95% yield) as a brown solid. m/z (ESI, +ve ion): 395.0 $(M+H)^+$.

Intermediate 92B

4-((2S,5R,M)-4-Acryloyl-2,5-dimethylpiperazin-1-yl)-6,7-dichloro-1-(2-isopropyl-4-methylpyridin-3-yl)pyrido[2,3-d]pyrimidin-2(1H)-one

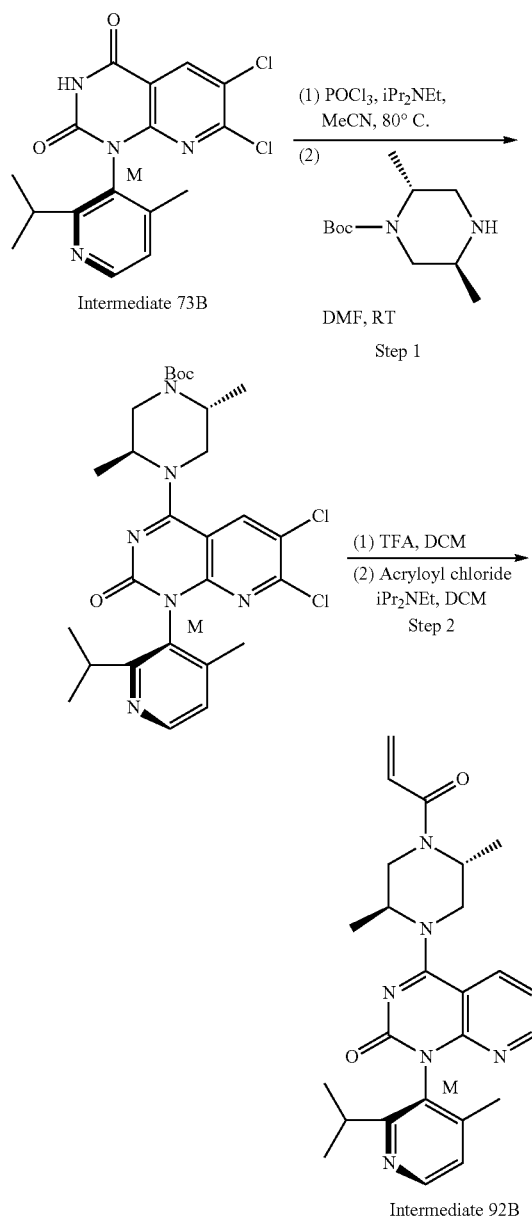

Intermediate 92B

Step 1: (2R,5S,M)-tert-Butyl 4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate A 250-mL round-bottomed flask was charged with (M)-6,7-dichloro-1-(2-isopropyl-4-methylpyridin-3-yl)pyrido[2,3-d]pyrimidine-2,4(1H,3H)-dione (Intermediate 73B, 6.65 g, 18.2 mmol) and DIPEA (4.8 mL, 27.3 mmol) in acetonitrile (91 mL) followed by phosphorous oxychloride (2.6 mL, 27.3 mmol). The resulting mixture was stirred at 80° C. for 30 min and then concentrated in vacuo to give (M)-4,6,7-trichloro-1-(2-isopropyl-4-methylpyridin-3-yl)pyrido[2,3-d]pyrimidin-2(1H)-one as a brown solid. The crude brown solid was used in next step without purification. m/z (ESI, +ve): 383.0 (M+H)$^+$.

To a mixture of crude (M)-4,6,7-trichloro-1-(2-isopropyl-4-methylpyridin-3-yl)pyrido[2,3-d]pyrimidin-2(1H)-one and DIPEA (4.8 mL, 27.3 mmol) in DMF (50 mL) was added (2R. 5S)-1-Boc-2,5-dimethylpiperazine (4.29 g, 20.03 mmol. AstaTech Inc., Bristol, Pa.) and the mixture was stirred at rt for 15 min. The mixture was added to ice water (80 mL) and stirred for 15 min. The resulting precipitate was collected by filtration, washed with water, and dried to give tert-butyl (2R,5S,M)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (4.70 g, 8.37 mmol, 46.0% yield) as a yellow solid. The filtrate was extracted with EtOAc (2×100 mL). The combined organic extracts were dried over MgSO$_4$. The solution was filtered and concentrated in vacuo to give additional title compound (5.51 g, 9.81 mmol, 53.9% yield) as a yellow solid. $^1$H NMR (400 MHz, DMSO-d$_6$) δ 8.59 (br d, J=4.8 Hz, 1H), 8.54 (s, 1H), 7.40 (br d, J=2.7 Hz, 1H), 4.87 (br s, 1H), 4.23-4.44 (m, 1H), 4.01-4.09 (m, 1H), 3.95 (br s, 1H), 3.73 (br dd, J=13.7, 2.5 Hz, 1H), 3.46-3.65 (m, 1H), 2.67-2.76 (m, 1H), 2.04 (s, 3H), 1.45-1.57 (m, 9H), 1.36 (d, J=6.6 Hz, 3H), 1.08-1.18 (m, 9H). m/z (ESI, +ve): 561.2 (M+H)$^+$.

Step 2: 4-((2S,5R,M)-4-Acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate 92B)

To a solution of tert-butyl (2R,5S,M)-4-(6,7-dichloro-1-(2-isopropyl-4-methylpyridin-3-yl)-2-oxo-, 2-dihydropyrido[2,3-d]pyrimidin-4-yl)-2,5-dimethylpiperazine-1-carboxylate (5.51 g, 9.81 mmol) in DCM (20 mL) was added trifluoroacetic acid (10 mL, 134 mmol) at rt and the mixture was stirred for 1 h. After the reaction was complete, the mixture was concentrated in vacuo to afford (M)-6,7-dichloro-4-((2S,5R)-2,5-dimethylpiperazin-1-yl)-1-(2-isopropyl-4-methylpyridin-3-yl)pyrido[2,3-d]pyrimidin-2(1H)-one, m/z (ESI, +ve): 461.2 (M+H)$^+$.

To the above (M)-6,7-dichloro-4-((2S,5R)-2,5-dimethylpiperazin-1-yl)-1-(2-isopropyl-4-methylpyridin-3-yl)pyrido[2,3-d]pyrimidin-2(1H)-one and N,N-diisopropylethylamine (8.6 mL, 49.1 mmol) in DCM (20 mL) was added acryloyl chloride (0.8 mL, 9.81 mmol) at 0° C. and the mixture was stirred for 1 h. The reaction mixture was diluted with DCM (50 mL) and washed with sat. ammonium chloride solution (50 mL). To the aqueous was added sat'd sodium chloride (25 mL) and the mixture was extracted with DCM (50 mL×2). The organic extracts were combined and dried over MgSO$_4$. The solution was filtered and concentrated in vacuo to give a brown oil. The crude brown oil was adsorbed onto a plug of silica gel and purified by silica gel chromatography (eluent: 0-10% of MeOH/DCM) to give (M)-4-((2S. 5R)-4-acryloyl-2,5-dimethylpiperazin-1-yl)-6,7-dichloro-(2-isopropyl-4-methylpyridin-3-yl)pyrido[2,3-d]pyrimidin-2(1H)-one (Intermediate 92B, 4.66 g, 9.04 mmol, 92% yield) as a light yellow foam. $^1$H NMR (400 MHz, DMSO-d$_6$) δ 8.46-8.54 (m, 2H), 7.30 (d, J=5.0 Hz, 1H), 6.82 (ddd, J=16.5, 14.0, 10.5 Hz, 1H), 6.18 (dd, J=16.7, 2.2 Hz, 1H). 5.74 (dt, J=10.4, 2.7 Hz, 1H), 4.78-4.91 (m, 1H), 4.39-4.75 (m, 1H), 3.97-4.16 (m, 1H). 3.94 (br s, 1H), 3.83 (br d, J=3.9 Hz, 1H), 3.49 (br dd, J=13.9, 3.7 Hz, 1H), 2.59-2.70 (m, 1 H), 1.97 (s, 3H), 1.25-1.32 (m, 3H), 1.09-1.20 (m, 3H), 1.05 (dd, J=11.4, 6.6 Hz, 6H). m/z (ESI, +ve): 515.2 (M+H)+.

Intermediate 94B (M)-4-((2S,5R)-4-Acryloyl-2,5-dimethylpiperazin-1-yl)-7-chloro-6-fluoro-1-(2-isopropyl-4-methylpyridin-3-yl)pyrido[2,3-d]pyrimidin-2(1H)-one

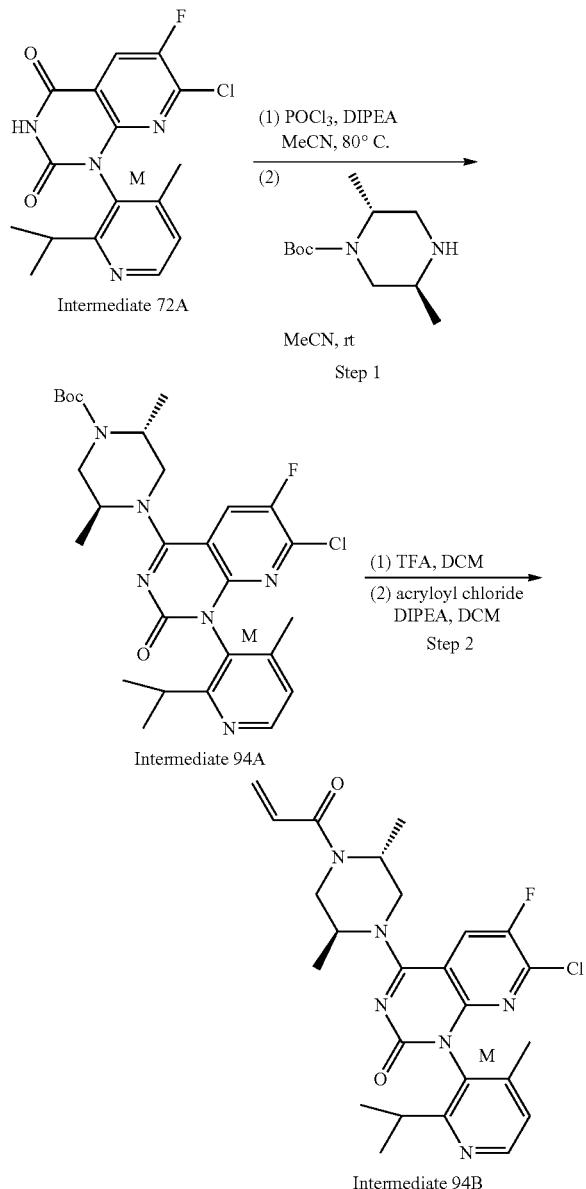

Step 1: (M)-tert-Butyl (2R,5S)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate A solution of (M)-7-chloro-6-fluoro-1-(2-isopropyl-4-methylpyridin-3-yl)pyrido[2,3-d]pyrimidine-2,4(1H,3H)-dione (Intermediate 72A; 3.35 g, 9.61 mmol), phosphorous oxychloride (1.07 mL, 11.53 mmol), and DIPEA (5.02 mL, 28.8 mmol) in acetonitrile (24 mL) was stirred at 80° C. for 30 min. The reaction mixture was cooled to rt and added (2R,5S)-tert-butyl 2,5-dimethylpiperazine-1-carboxylate (2.26 g, 10.6 mmol). The reaction mixture was stirred at it for 15 min. The reaction mixture was diluted with EtOAc (200 mL), washed with satd. NaHCO₃ (3×75 mL), dried over Na₂SO₄, filtered, and concentrated in vacuo. The crude product was purified by silica gel chromatography (eluent: 0-100% EtOAc/heptane) to provide (M)-tert-butyl (2R,5S)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 94A; 2.2 g, 4.04 mmol, 42.0% yield) as yellow-orange solid. ¹H NMR (400 MHz, CHLOROFORM-d) δ 8.57 (d, J=5.0 Hz, 1H), 7.79 (br d, J=7.5 Hz, 1H), 7.13-7.16 (m, 1H), 4.80-5.04 (m, 1H), 4.32-4.64 (m, 1H), 3.73-4.08 (m, 3H), 3.43-3.66 (m, 1H), 2.58 (dt, J=13.4, 6.6 Hz, 1H), 2.04 (s, 3H), 1.59 (s, 9H), 1.39-1.48 (m, 3H), 1.11-1.25 (m, 9H). ¹⁹F NMR (377 MHz, CHLOROFORM-d) δ −126.30 (br s, 1F) −126.34 (br s, 1F). m/z (ESI, +ve ion): 544.8 (M+H)+.

Step 2: (M)-4-((2S,5R)-4-Acryloyl-2,5-dimethylpiperazin-1-yl)-7-chloro-6-fluoro-1-(2-isopropyl-4-methylpyridin-3-yl)pyrido[2,3-d]pyrimidin-2(1H)-one A mixture of (M)-tert-butyl (2R,5S)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 94A; 8.16 g, 14.97 mmol) in DCM (30 mL) and TFA (30 mL) was stirred at rt for 30 min. The reaction mixture was concentrated in vacuo to provide (M)-7-chloro-4-((2S,5R)-2,5-dimethylpiperazin-1-yl)-6-fluoro-1-(2-isopropyl-4-methylpyridin-3-yl)pyrido[2,3-d]pyrimidin-2(1H)-one. The crude product was used in next step without purification. m/z (ESI, +ve ion) 445.1 (M+H)+.

A mixture of (M) 7-chloro-4-((2S,5R)-2,5-dimethylpiperazin-1-yl)-6-fluoro-1-(2-isopropyl-4-methylpyridin-3-yl)pyrido[2,3-d]pyrimidin-2(1H)-one and DIPEA (13.1 mL, 74.9 mmol) in DCM (20 mL) was cooled to 0° C. To the cooled mixture was added acryloyl chloride (1.22 mL, 14.97 mmol) and stirred for 1 h. The reaction mixture was quenched with satd. NH₄Cl (50 mL), extracted with DCM (2×50 mL)), dried over MgSO4, filtered, and concentrated in vacuo. The crude product was purified by silica gel chromatography (eluent: 0-100% EtOAc-MeOH (9:1)/heptane) to provide (M)-4-((2S,5R)-4-acryloyl-2,5-dimethylpiperazin-1-yl)-7-chloro-6-fluoro-1-(2-isopropyl-4-methylpyridin-3-yl)pyrido[2,3-d]pyrimidin-2(1H)-one (Intermediate 94B; 5.62 g, 11.3 mmol, 75% yield) as light-yellow foam. ¹H NMR (400 MHz, DMSO-d₆) δ 8.53 (d, J=5.0 Hz, 1H), 8.44 (d, J=8.5 Hz, 1H), 7.35 (br d, J=3.7 Hz, 1H), 6.83 (td, J=16.9, 10.6 Hz, 1H), 6.18 (dd, J=16.6, 2.3 Hz, 1H), 5.69-5.80 (m, 1H), 4.65-4.92 (m, 2H), 3.79-4.15 (m, 3H), 3.07-3.69 (m, 1H), 2.60-2.72 (m, 1H), 1.98 (s, 3H), 1.20-1.33 (m, 6H), 1.06 (dd, J=13.1, 6.8 Hz, 6H). m/z (ESI, +ve ion): 499.2 (M+H)+.

Intermediate 99 A and B

2,5-Dichloro-6-(2-fluorophenyl)nicotinamide

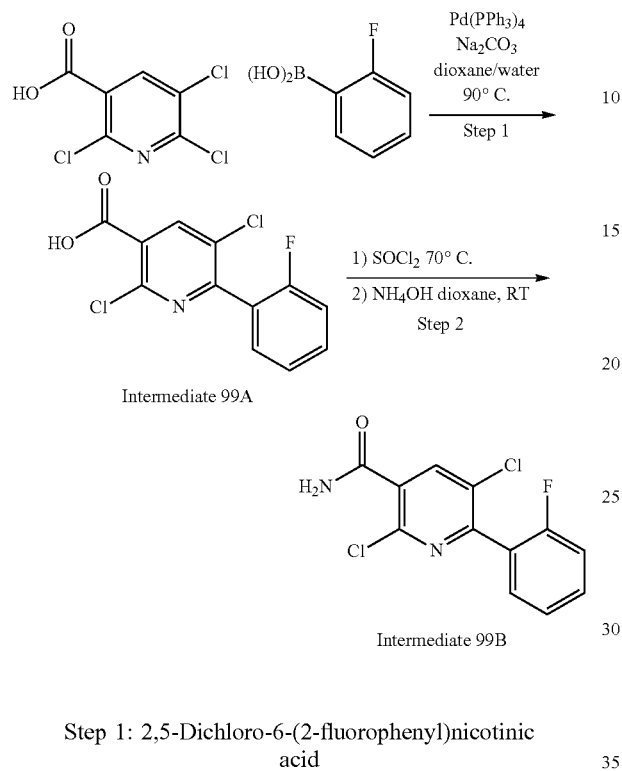

Intermediate 99A

Intermediate 99B

Step 1: 2,5-Dichloro-6-(2-fluorophenyl)nicotinic acid

A mixture of 2,5,6-trichloronicotinic acid (1.03 g, 4.54 mmol, Combi-Blocks, San Diego, Calif.), palladium tetrakis (0.131 g, 0.114 mmol), (2-fluorophenyl)boronic acid (0.699 g, 5.0 mmol, TCI America, Portland, Oreg.). and sodium carbonate (2M in water, 6.82 mL, 13.6 mmol) in 1,4-dioxane (11 mL) was sparged with nitrogen and heated to 80° C. for 1 h followed by 90° C. for 5 h. The reaction mixture was diluted with EtOAc (150 mL), washed with 1 N aqueous citric acid (2×100 mL); the organic layer was separated, dried over anhydrous $Na_2SO_4$, and concentrated in vacuo to give 2,5-dichloro-6-(2-fluorophenyl)nicotinic acid (Intermediate 99A, 1.27 g, 4.43 mmol, 97% yield) as an amber oil. m/z (ESI, +ve ion): 285.8 $(M+H)^+$.

Step 2: 2,5-Dichloro-6-(2-fluorophenyl)nicotinamide

A solution of 2,5-dichloro-6-(2-fluorophenyl)nicotinic acid (Intermediate 99A, 1.27 g, 4.43 mmol) in sulfurous dichloride (13 mL, 177 mmol) was stirred at 70° C. for 30 min. The reaction mixture was concentrated in vacuo to give a dark brown oil. The oil was dissolved in 1,4-dioxane (8.9 mL) and treated with ammonium hydroxide (30% aq., 3.5 mL, 89 mmol) and the mixture was stirred at rt for 5 min. The reaction mixture was diluted with EtOAc (150 mL), added to a separatory funnel, and washed with saturated, aqueous sodium bicarbonate (3×100 mL); the organic layer was separated, dried over anhydrous $Na_2SO_4$, and concentrated in vacuo. The crude product was purified by silica gel chromatography (eluent: 0-80% EtOAc/heptane) to provide crude product as an off-white solid. The solid was stirred in EtOH (8 mL) at it for 15 min and filtered to give 2,5-dichloro-6-(2-fluorophenyl)nicotinamide (Intermediate 99B, 0.449 g, 1.58 mmol, 36% yield) as a white solid. m/z (ESI, +ve ion): 284.8 $(M+H)^+$.

Intermediate 106A

7-Bromo-6-chloro-1-(2-isopropyl-6-methylphenyl)quinazoline-2,4(1H,3H)-dione

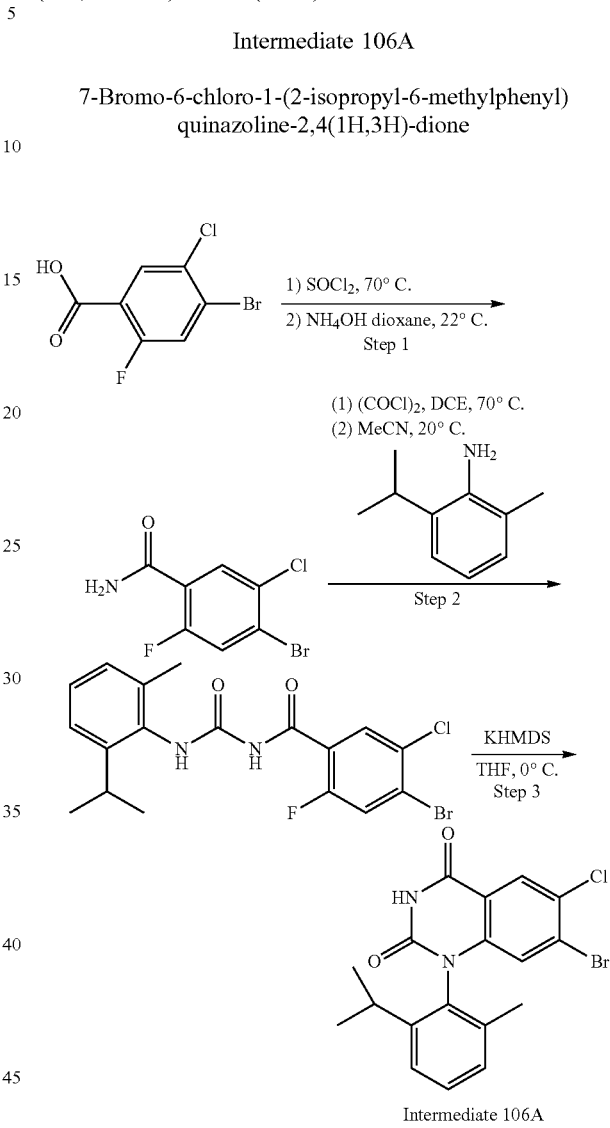

Intermediate 106A

Step 1: 4-Bromo-5-chloro-2-fluorobenzamide

A mixture of 4-bromo-5-chloro-2-fluorobenzoic acid (Oxchem Corp., Wood Dale, Ill., USA; 23.3 g, 92 mmol) in thionyl chloride (67 mL, 0.92 mol) was stirred at 70° C. for 1 h. The reaction mixture was then concentrated in vacuo, and the residue was taken up in 1,4-dioxane (200 mL), treated with ammonium hydroxide (30% aqueous, 82 mL, 0.64 mol), and stirred at it for 15 min. The reaction mixture was concentrated in vacuo to give 4-bromo-5-chloro-2-fluorobenzamide: m/z (ESI, +ve ion): 251.8 $(M+H)^+$.

Step 2: 4-Bromo-5-chloro-2-fluoro-N-((2-isopropyl-6-methylphenyl)carbamoyl) benzamide Oxalyl chloride (2 M in DCM, 8.9 mL, 17.8 mmol) was added over a 2 min period to a suspension of 4-bromo-5-chloro-2-fluorobenzamide (3.0 g, 11.9 mmol) in 1,2-dichloroethane (30 mL) under nitrogen atmosphere. The suspension was stirred at rt for 5 min and then heated to 70° C. for 75 min. The reaction mixture was concentrated in vacuo to afford a white solid. This solid was suspended in acetonitrile (15 mL), and a solution of 2-(1-methylethyl)-6-methylaniline (2.13 g, 14.3 mmol, Advanced Chemblocks Inc., Burlingame, Calif.) in acetonitrile (5 mL) was added dropwise at rt. The precipitate was filtered off, washed with heptane, and dried under reduced pressure to give 4-bromo-5-chloro-2-fluoro-N-((2-isopropyl-6-methylphenyl)carbamoyl)benzamide. m/z (ESI, +ve ion): 427.0 and 428.9 (M+H)$^+$.

Step 3: 7-Bromo-6-chloro-1-(2-isopropyl-6-methylphenyl)quinazoline-2,4(1H,3H)-dione (Intermediate 106A)

KHMDS (1 M in THF, 20.6 mL, 20.6 mmol) was added portion-wise over a period of 10 min to a suspension of 4-bromo-5-chloro-2-fluoro-N-((2-isopropyl-6-methylphenyl)carbamoyl)benzamide (4.4 g, 10.3 mmol) in THF (30 mL) cooled to 0° C. under nitrogen atmosphere. The reaction mixture was allowed to warm to it and stirred for 18 h. The reaction mixture was then partitioned between EtOAc (100 mL) and satd. NaHCO$_3$ (50 mL). The organic layer was washed with brine (20 mL), dried over MgSO$_4$. and concentrated in vacuo to give 7-bromo-6-chloro-1-(2-isopropyl-6-methylphenyl)quinazoline-2,4(1H,3H)-dione (Intermediate 106A). m/z (ESI, +ve ion): 407.0 and 409.0 (M+H)$^+$.

Intermediate 111A

6-Chloro-7-(2-fluorophenyl)-1-(2-isopropyl-4-methylpyridin-3-yl)pteridine-2,4(1H,3H)-dione

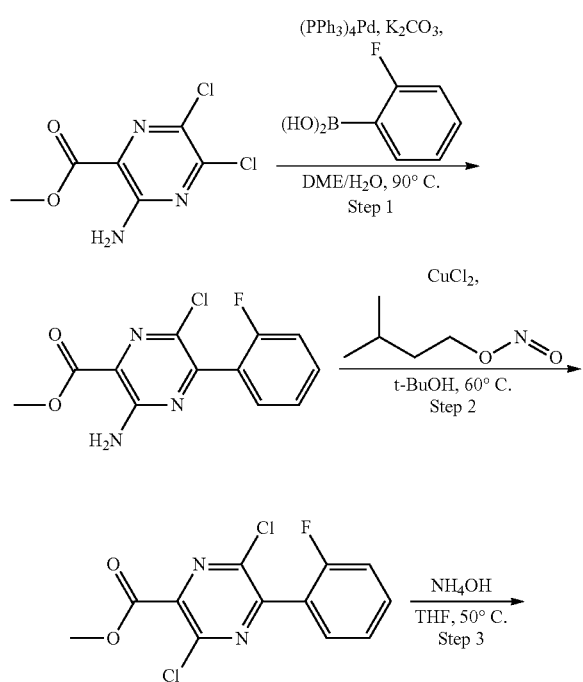

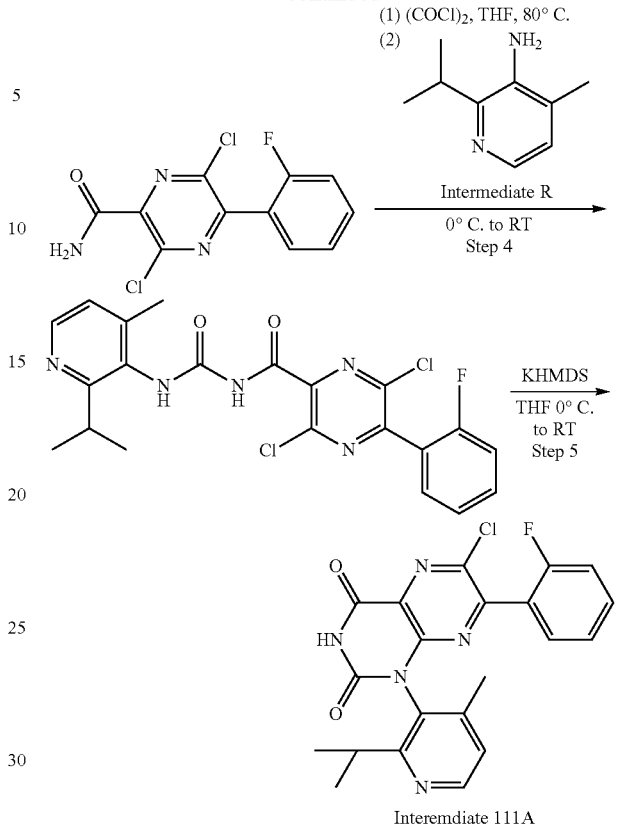

Interemdiate 111A

Step 1: Methyl 3-amino-6-chloro-5-(2-fluorophenyl)pyrazine-2-carboxylate

A mixture of methyl 3-amino-5,6-dichloropyrazine-2-carboxylate (10.0 g, 45 mmol, Ark Pharm, Inc., Arlington Heights, Ill.), (2-fluorophenyl)boronic acid (6.93 g, 49.5 mmol. Combi-Blocks, San Diego, Calif., USA) and potassium carbonate (13.1 g, 95 mmol) in a 10:1 mixture of DME/water (220 mL) was degassed with nitrogen for 5 min and then tetrakis(triphenylphosphine)palladium(0) (1.04 g, 0.90 mmol) was added. The reaction mixture was stirred at 90° C. for 16 h, then was allowed to cool to room temperature and partitioned between EtOAc (200 mL) and 1 N HCl (200 mL). The organic layer was dried over anhydrous sodium sulfate and concentrated to provide methyl 3-amino-6-chloro-5-(2-fluorophenyl)pyrazine-2-carboxylate. m/z (ESI, +ve): 282.1 (M+H)$^+$.

Step 2: Methyl 3,6-dichloro-5-(2-fluorophenyl)pyrazine-2-carboxylate

To a solution of methyl 3-amino-6-chloro-5-(2-fluorophenyl)pyrazine-2-carboxylate (22.0 g, 78 mmol) in t-BuOH (220 mL) was added isoamyl nitrite (15.8 mL, 117 mmol) and copper chloride (12.6 g, 94 mmol). The resulting mixture was stirred at 60° C. for 16 h and then was partitioned between water (1 L) and EtOAc (2 L). The organic layer was dried over anhydrous sodium sulfate and concentrated. The residue was purified by silica gel chromatography (eluent: 0-5% EtOAc/hexane) to provide methyl 3,6-dichloro-5-(2-fluorophenyl)pyrazine-2-carboxylate. m/z (ESI, +ve ion): 300.9 (M+H)$^+$.

Step 3: 3,6-Dichloro-5-(2-fluorophenyl)pyrazine-2-carboxamide

To a solution of methyl 3,6-dichloro-5-(2-fluorophenyl)pyrazine-2-carboxylate (13.5 g, 44.8 mmol) in THF (150 mL) was added ammonium hydroxide solution (30%, 150 mL, 44.8 mmol). The resulting mixture was heated at 50° C. for 4 h, then was allowed to cool to room temperature and partitioned between water and EtOAc (500 mL). The organic layer was dried over anhydrous sodium sulfate and concentrated. The residue was purified by silica gel chromatography (eluent: 0-30% EtOAc/hexanes) to provide 3,6-dichloro-5-(2-fluorophenyl)pyrazine-2-carboxamide. $^1$H NMR (400 MHz, DMSO-$d_6$) δ 8.32 (br s, 1H), 8.16 (br s, 1H), 7.64-7.77 (m, 2H), 7.41-7.47 (m, 2H). m/z (ESI, +ve): 286.0 (M+H)$^+$.

Step 4: 3,6-Dichloro-5-(2-fluorophenyl)-N-((2-isopropyl-4-methylpyridin-3-yl)carbamoyl)pyrazine-2-carboxamide A mixture of 3,6-dichloro-5-(2-fluorophenyl)pyrazine-2-carboxamide (Example 50, Step 3, 1.45 g, 5.06 mmol) and oxalyl chloride (2 M in DCM, 2.8 mL, 5.6 mmol) in THF (25 mL) was heated to 80° C. for 2 h. The reaction mixture was then cooled to 0° C. and 2-isopropyl-4-methylpyridin-3-amine (Intermediate R, 0.8 g, 5.34 mmol) was added. The cold bath was removed and stirring was continued at rt for 45 min. The reaction mixture was concentrated in vacuo, the residue was taken up in EtOAc, and sonicated. The precipitate was filtered off and dried to give 3,6-dichloro-5-(2-fluorophenyl)-N-((2-isopropyl-4-methylpyridin-3-yl)carbamoyl)pyrazine-2-carboxamide as a light yellow solid. m/z (ESI, +ve ion): 461.8 and 463.8 (M+H)$^+$.

Step 5: 6-Chloro-7-(2-fluorophenyl)-1-(2-isopropyl-4-methylpyridin-3-yl)pteridine-2,4(1H,3H)-dione (Intermediate 111A)

KHMDS (1 M in THF, 5.3 mL, 5.3 mmol) was added to a solution of 3,6-dichloro-5-(2-fluorophenyl)-N-((2-isopropyl-4-methylpyridin-3-yl)carbamoyl)pyrazine-2-carboxamide (1.22 g, 2.64 mmol) in THF (15 mL) at 0° C. The reaction mixture was allowed to warm to rt over a period of 1 h. The reaction mixture was then diluted with EtOAc and washed with said. ammonium chloride. The organic layer was dried over Na$_2$SO$_4$, and concentrated in vacuo. The crude product was purified by silica gel chromatography (eluent: 0-50% EtOAc/heptane) to provide 6-chloro-7-(2-fluorophenyl)-1-(2-isopropyl-4-methylpyridin-3-yl)pteridine-2,4(1H,3H)-dione (Intermediate 111A) as a light yellow solid: H NMR (400 MHz, DMSO-$d_6$) δ 12.40 (s, 1H), 8.44 (br d, J=4.6 Hz, 1H), 7.52-7.62 (m, 1H), 7.28-7.39 (m, 3H), 7.21 (br d, J=4.6 Hz, 1H), 3.03 (dt, J=12.7, 6.4 Hz, 1H), 2.07 (s, 3H), 1.07 (br d, J=6.6 Hz, 3H), 0.95 (br d, J=6.4 Hz, 3H). m/z (ESI, +ve) 425.9 and 427.9 (M+H)$^+$.

Intermediate 160

1-((2R,5S)-2,5-Dimethylpiperazin-1-yl)prop-2-en-1-one 2,2,2-trifluoroacetate

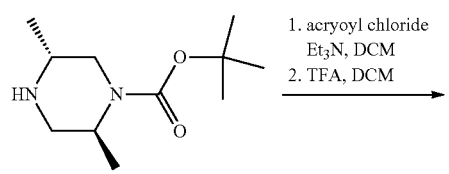

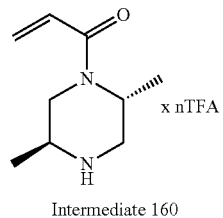

Intermediate 160

To a solution of (2S,5R)-1-Boc-2,5-dimethylpiperazine (3.5 g, 16.3 mmol, Astatech) in dichloromethane (35 ml), anhydrous triethylamine (4.59 ml, 32.7 mmol) was added and the mixture was cooled to 0° C. in ice-water bath. Acryloyl chloride (1.46 ml, 18.0 mmol) was added dropwise over ~5 min at which point the reaction mixture became yellow and viscous and formation of a white precipitate was observed. Water (10 ml) was added and the mixture was removed from the ice bath and was allowed to stir for 10 min. The organic layer was separated, quickly washed with 2N HCl (40 ml), water and brine, filtered through pad of MgSO4 and concentrated to afford crude tert-butyl (2S,5R)-4-acryloyl-2,5-dimethylpiperazine-1-carboxylate (4.4 g) as yellow oil. This material was redissolved in DCM (40 ml) and TFA (12.6 ml, 163 mmol) was added and the mixture was stirred at rt for 4 h at which point complete deprotection was observed. The mixture was concentrated under reduced pressure and dried under vacuum to afford 1-((2R,5S)-2,5-dimethylpiperazin-1-yl)prop-2-en-1-one 2,2,2-trifluoroacetate (Intermediate 160, ~9 g) as an oil. Analysis by qNMR using benzyl benzoate as internal standard showed 40.2 wt % purity. The material was used without further purification. $^1$H NMR (400 MHz, DMSO-$d_6$) δ 9.03 (br s, 1H), 8.95 (br s, 1H), 6.77 (dd, J=10.6, 16.8 Hz, 1H), 6.16 (dd, J=2.3, 16.8 Hz, 1H), 5.74 (dd, J=2.3, 10.6 Hz, 1H), 4.69-4.56 (m, 1H), 4.09-3.94 (m, 1H), 3.70-3.57 (m, 1H), 3.45-3.19 (m, 2H), 2.98-3.09 (m, 1H), 1.25 (d, J=6.8 Hz, 3H), 1.20 (d, J=6.8 Hz, 3H). m/z (ESI, +ve ion): 169.3 (M+H)$^+$.

Intermediate 161

1,4-Diisopropyl-1H-pyrazol-5-amine

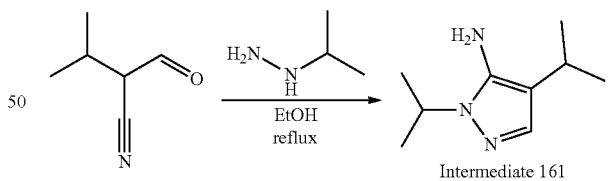

Intermediate 161

To a mixture of 2-formyl-3-methylbutanenitrile (1.5 ml, 13.5 mmol)<autotext key="18F898A2" name="[Reactants]" index="1" field="Reactants" type="field" length="53"/> in EtOH (45 mL)<autotext key="18F898A3" name="[Solvents]" index="1" field="Solvents" type="field" length="17"/> was added isopropylhydrazine (1.0 g, 13.5 mmol, Matrix Scientific)<autotext key="18F898A4" name="[Reactants]" index="2" field="Reactants" type="field" length="40"/> and the mixture <autotext key=" " name="124102-8-02" type="SampleID" length="11"/> was stirred and heated at 85° C. for 21 h. The mixture was concentrated in vacuo. The residue was treated with <autotext key="18F898A9"

satd NaHCO₃ (50 mL), extracted with EtOAc (2×50 mL), dried over Na₂SO₄, filtered and concentrated in vacuo. The crude material was purified by silica gel chromatography (eluent: 0-50% EtOAc/heptane) to provide 1,4-diisopropyl-1H-pyrazol-5-amine (Intermediate 161, 1.04 g, 6.21 mmol, 46.0% yield) as light-yellow syrupy solid. $^1$H NMR (400 MHz, DMSO-$d_6$) δ 6.95 (s, 1H), 4.65 (s, 2H), 4.37 (spt, J=6.5 Hz, 1H), 2.68 (spt, J=6.8 Hz, 1H), 1.25 (d, J=6.6 Hz, 6H), 1.08 (d, J=6.8 Hz, 6H). m/z (ESI, +ve ion): 168.2 (M+H)⁺.

Intermediate 162

3,5-Diisopropylpyridin-4-amine

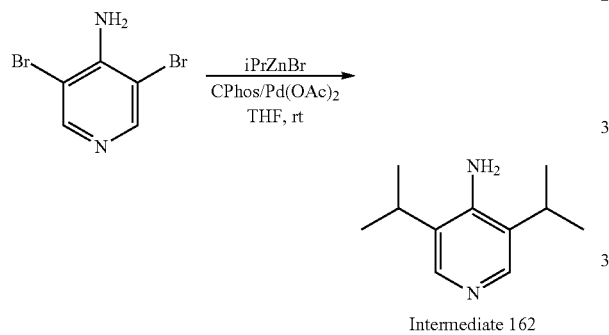

Intermediate 162

To a mixture of 3,5-dibromo-4-amino-pyridine (5.0 g, 19.9 mmol, AstaTech, Inc.), Cphos (0.868 g, 1.989 mmol), palladium acetate (0.223 g, 0.994 mmol), and THF (40 mL) was added 2-propylzinc bromide (1 M in THF) (80 mL, 80 mmol, Rieke Metals, Inc.) dropwise and the mixture was stirred at rt for 2 h. The reaction mixture was quenched with 5 N NaOH (100 mL), extracted with EtOAc (2×50 mL), dried over Na2SO4, filtered and concentrated in vacuo. The crude material was purified by silica gel chromatography (eluent 0-30% DCM-MeOH (4:1)/DCM) to provide 3,5-diisopropylpyridin-4-amine (Intermediate 162, 1.4 g, 7.8 mmol, 39.4% yield) as orange syrup. $^1$H NMR (400 MHz, DMSO-$d_6$) δ 7.88 (s, 2H), 5.47-5.60 (m, 2H), 3.00 (spt, J=6.8 Hz, 2H), 1.17 (d, J=6.8 Hz, 12H). m/z (ESI, +ve ion): 179.1 (M+H)⁺.

Intermediate 163

2-Isopropyl-N⁴,N⁴-dimethylpyridine-3,4-diamine

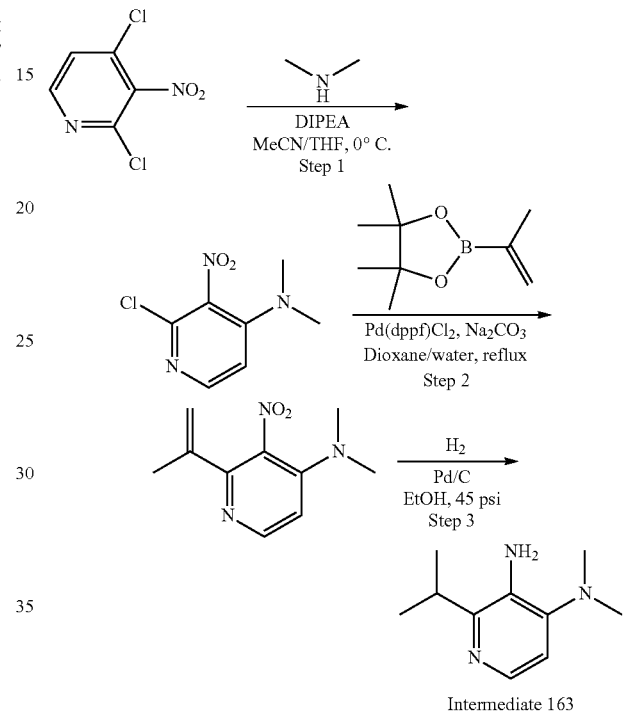

Intermediate 163

Step 1:
2-Chloro-N,N-dimethyl-3-nitropyridin-4-amine

To a stirring solution of 2,4-dichloro-3-nitropyridine (Ark Pharm, Inc., Arlington Heights, Ill., 4.9 g, 25.4 mmol) in MeCN (20 mL) and triethylamine (3.93 ml, 27.9 mmol) at 0° C. under nitrogen was added dimethylamine. 2 M in THF (12.70 ml, 25.4 mmol) dropwise at a rate not to exceed an internal temp of 10° C. After addition the ice bath was removed and the suspension stirred for 10 min reaching 20° C. The reaction was then partitioned between EtOAc (100 mL) and sat. NaCl (25 mL). The organic was dried over MgSO4, filtered, and concentrated under reduced pressure. The resulting solid was dissolved in DCM, dry silica added (30 g), then concentrated under reduced pressure. The products were then separated by silica gel chromatography (120 g) eluting products with a gradient of 15>60% EtOAc/heptane to afford 2-chloro-N,N-dimethyl-3-nitropyridin-4-amine as yellow solid. $^1$H NMR (400 MHz, CDCl₃) δ 8.02 (d, J=6.01 Hz, 1H), 6.66 (d, J=6.22 Hz, 1H), 3.03 (s, 6H). m/z (ESI, +ve ion): 202.1 (M+H)⁺.

Step 2: N,N-Dimethyl-3-nitro-2-(prop-1-en-2-yl)pyridin-4-amine

A suspension of 2-chloro-N,N-dimethyl-3-nitropyridin-4-amine (3.7 g, 18.35 mmol) in 1,4-dioxane (30 mL) and water (15 mL) was sparged with argon for 5 min followed by the addition of (4,4,5,5-tetramethyl-1,3,2-dioxaborolan-2-yl) isopropene (7.71 g, 45.9 mmol), (1,1'-bis(diphenylphosphino) ferrocene) dichloropalladium (0.336 g, 0.459 mmol), and sodium carbonate (5.84 g, 55.1 mmol). After 5 min of additional argon sparging, the suspension was heated to reflux. After 2 hrs, the reaction was then partitioned between EtOAc (100 mL), sat. NaHCO$_3$ (30 mL), and water (30 mL). The organic was then dried over MgSO$_4$, concentrated under reduced pressure, then purified by silica gel chromatography (80 g) eluting products with a gradient of 10>30% EtOAc/heptane to afford N,N-dimethyl-3-nitro-2-(prop-1-en-2-yl) pyridin-4-amine as yellow solid. $^1$H NMR (400 MHz, CDCl$_3$) δ 8.23 (d, F=6.01 Hz, 1H), 6.64 (d, J=6.01 Hz, 1H), 5.18-5.22 (m, 1H), 5.02 (s, 1H), 2.99 (s, 6H), 2.15 (s, 3H). m/z (ESI, +ve ion): 208.3 (M+H)$^+$.

Step 3: 2-isopropyl-N$^4$,N$^4$-dimethylpyridine-3,4-diamine (Intermediate 163)

A hydrogenation apparatus was set up with 250 mL glass cylinder, which was flushed with N$_2$, and then charged with palladium 10 wt. % on activated carbon (0.976 g, 0.917 mmol). A solution of N,N-dimethyl-3-nitro-2-(prop-1-en-2-yl)pyridin-4-amine (3.8 g, 18.34 mmol) in ethanol (40 mL) was then transferred into the glass cylinder. The cylinder was sealed, purged with H$_2$, and then vented—this procedure was repeated twice. Hydrogen was then charged into the cylinder to 45 psi. The reaction mixture was stirred under H2 for 3 hr. The reaction was then filtered through a bed of Celite, concentrated under reduced pressure, then purified by silica gel chromatography (80 g) eluting products with a gradient of 10>30% Solvent A: EtOAc/EtOH (3:1 blend with 4% by volume of 2 M NH3 in MeOH)/Solvent B: heptane to afford 2-isopropyl-N$^4$,N$^4$-dimethylpyridine-3,4-diamine (Intermediate 163) as colorless oil. $^1$H NMR (400 MHz, CDCl$_3$) δ 8.00 (d, J=5.18 Hz, 1H), 6.74 (d, J=5.39 Hz, 1H), 3.82 (br s, 2H), 3.04 (td, J=6.82, 13.53 Hz, 1H), 2.70 (s, 6H), 1.31 (d, J=6.84 Hz, 6H). m/z (ESI, +ve ion): 180.2 (M+H)$^+$.

Intermediate 164

N$^4$,N$^4$-Diethyl-2-isopropylpyridine-3,4-diamine

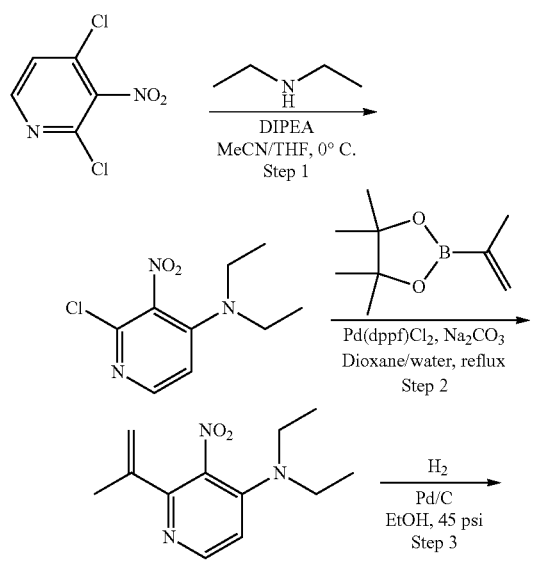

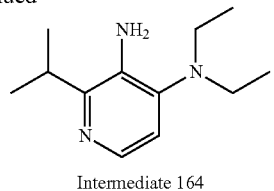

Intermediate 164

Step 1:
2-Chloro-N,N-diethyl-3-nitropyridin-4-amine

To a stirring solution of 2,4-dichloro-3-nitropyridine (4.0 g, 20.73 mmol) in MeCN (16 mL, 4:1) and triethylamine (2.91 ml, 20.7 mmol) at 0° C. under nitrogen was added diethylamine (2.37 ml, 22.8 mmol) in THF (10 mL) dropwise. After the addition was complete, the ice bath was removed and the suspension was stirred for 3 hrs. The reaction was then partitioned between EtOAc (100 mL) and sat. NaCl (25 mL). The organic was dried over MgSO4, filtered, and concentrated under reduced pressure, then purified by silica gel chromatography (120 g) eluting products with a gradient of 15>60% EtOAc/heptane to afford 2-chloro-N,N-diethyl-3-nitropyridin-4-amine as yellow solid. $^1$H NMR (400 MHz, CDCl$_3$) δ 8.00 (d, J=6.01 Hz, 1H), 6.69 (d, J=6.22 Hz, 1H), 3.31 (q, J=7.12 Hz, 4H), 1.20 (t, J=7.05 Hz, 6H). m/z (ESI, +ve ion): 230.2 (M+H)$^+$.

Step 2: N,N-Diethyl-3-nitro-2-(prop-1-en-2-yl)pyridin-4-amine

A suspension of 2-chloro-N,N-diethyl-3-nitropyridin-4-amine (2.2 g, 9.58 mmol) in 1,4-dioxane (20 mL) and water (10 mL) was sparged with argon for 5 min followed by the addition of (4,4,5,5-tetramethyl-1,3,2-dioxaborolan-2-yl) isopropene (3.22 g, 19.2 mmol), (1,1'-bis(diphenylphosphino) ferrocene) dichloropalladium (0.175 g, 0.239 mmol), and sodium carbonate (3.05 g, 28.7 mmol). After 5 min of additional sparging, the suspension was heated to reflux for 2 hrs. The reaction was then partitioned between EtOAc (60 mL) and sat. NaHCO3 (20 mL). The organic was then dried over MgSO4, concentrated under reduced pressure, then purified by silica gel chromatography (40 g) eluting products with a gradient of 10>60% EtOAc/heptane to afford N,N-diethyl-3-nitro-2-(prop-1-en-2-yl)pyridin-4-amine as yellow oil. $^1$H NMR (400 MHz, CDCl$_3$) δ 8.23 (d, J=6.22 Hz, 1H), 6.70 (d, J=6.01 Hz, 1H), 5.21 (s, 1H), 5.04 (s, 1H), 3.27 (q, J=7.05 Hz, 4H), 2.14 (s, 3H), 1.17 (dd, J=6.63, 13.68 Hz, 6H). m/z (ESI, +ve ion): 236.2 (M+H)$^+$.

Step 3: N$^4$,N$^4$-Diethyl-2-isopropylpyridine-3,4-diamine (Intermediate 164)

A hydrogenation apparatus was set up with a 250 mL glass cylinder, was sparged with N$_2$, and was then filled with palladium 10 wt. % on activated carbon (0.249 g, 0.234 mmol). A solution of N,N-diethyl-3-nitro-2-(prop-1-en-2-yl) pyridin-4-amine (2.2 g, 9.35 mmol) in ethanol (40 mL) was then transferred into the glass cylinder. The cylinder was sealed, purged with H$_2$, and then vented—this procedure was repeated twice. Hydrogen was then charged into the cylinder to 45 psi. The reaction mixture was started stirring under H2 for 6 hrs. The reaction was then filtered through a bed of Celite, and the filtrated concentrated under reduced pressure to afford N$^4$,N$^4$-diethyl-2-isopropylpyridine-3,4- diamine (Intermediate 164) as amber oil. ¹H NMR (400 MHz, CDCl₃) δ 7.98 (d, J=5.18 Hz, 1H), 6.76 (d, J=5.18 Hz, 1H), 3.92 (br s, 2H), 2.93-3.09 (m, 5H), 1.31 (d, J=6.84 Hz, 6H), 1.01 (t, J=7.05 Hz, 6H). m/z (ESI, +ve ion): 208.3 (M+H)⁺.

Intermediate 165 tert-Butyl (2R,5S)-4-((2,5-dichloro-6-(2-fluorophenyl)pyridin-3-yl)(imino)methyl)-2,5-dimethylpiperazine-1-carboxylate

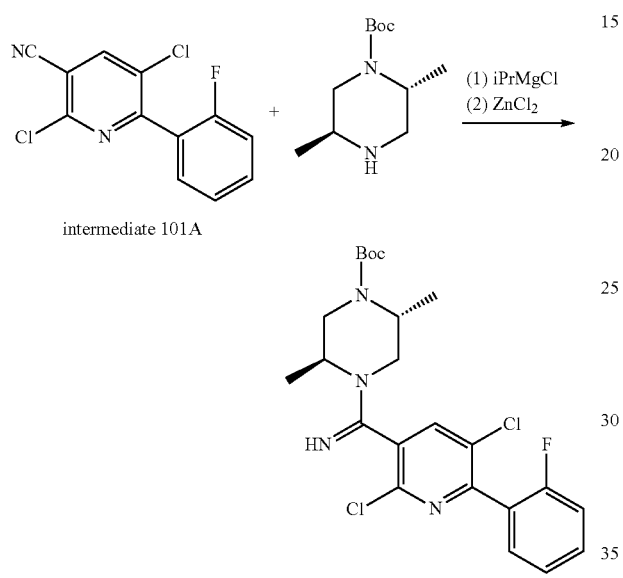

intermediate 101A

A 3 neck flask equipped with overhead stirrer, thermocouple, and nitrogen inlet was charged with tert-butyl (2R,5S)-2,5-dimethylpiperazine-1-carboxylate (Astatech, Bristol, Pa., USA, 78 g, 365 mmol) and THF (400 mL). The resulting solution was degassed and purged with argon then cooled to 0° C. Isopropylmagnesium chloride (183 mL, 365 mmol) (2M in THF) was added dropwise via an addition funnel to the solution. The mixture was stirred for 1 hr at 0° C. Zinc chloride (192 mL, 365 mmol) (1.9M in 2-Me THF) was added dropwise via an addition funnel. The mixture was warmed to RT and stirred for 12 hours. In a separate flask was dissolved 2,5-dichloro-6-(2-fluorophenyl)nicotinonitrile (Intermediate 101A, 65 g, 243 mmol) in THF (400 mL). The orange solution was added to the reaction flask dropwise via an addition funnel. The mixture was stirred overnight at RT. The hazy reaction mixture was cooled to 0° C. Ten volumes of ethyl acetate and 10 volumes of 15 wt % NH₄Cl (aq) were added. The biphasic mixture was stirred for 1 hour and the aqueous layer was separated. The organic layer was washed with 15 wt % sat. NaCl. The organic layer was concentrated to a dark orange oil. Isopropanol was added and evaporated several times. Eight volumes of 1:1 isopropanol/water was added to the crude oil. The resulting solids were filtered through a glass frit. The filter cake was washed with 25% IPA/water solution. The solid was dried under vacuum with nitrogen sweep to afford tert-butyl (2R,5S)-4-((2,5-dichloro-6-(2-fluorophenyl)pyridin-3-yl)(imino)methyl)-2,5-dimethylpiperazine-1-carboxylate (Intermediate 165). ¹H NMR (500 MHz, DMSO-d₆) δ 8.03-8.19 (m, 1H), 7.57-7.63 (m, 1H), 7.36-7.56 (m, 4H), 4.18 (br s, 1H), 3.62 (br s, 1H), 3.39 (br d, J=13.75 Hz, 1H), 3.32 (s, 2H), 3.02-3.23 (m, 1H), 1.35-1.45 (m, 9H), 1.09-1.21 (m, 4H), 1.05 (br dd, J=12.52, 6.16 Hz, 2H). m/z (ESI, +ve ion): 481.2 (M+H)⁺.

Intermediate 168 tert-Butyl (2R,5S)-4-((2,5-dichloro-6-(o-tolyl)pyridin-3-yl)(imino)methyl)-2,5-dimethylpiperazine-1-carboxylate

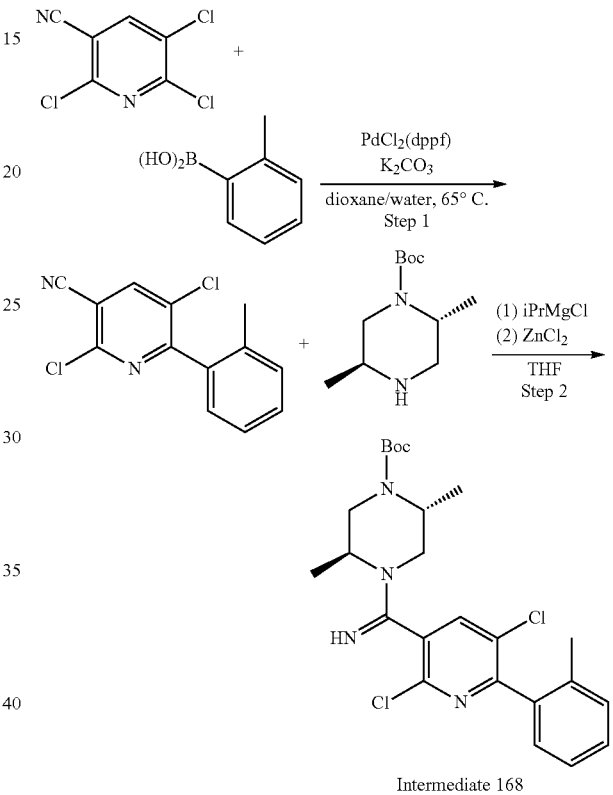

Intermediate 168

Step 1: 2,5-Dichloro-6-(o-tolyl)nicotinonitrile

A 3 neck flask equipped with an overhead stirrer, thermocouple, condensor and nitrogen inlet was charged with 2,5,6-trichloronicotinonitrile (Syngene, 70 g, 337 mmol), o-tolylboronic acid (Combi-Blocks, San Diego, Calif., USA, 48.2 g, 354 mmol). K₂CO₃ (140 g, 1012 mmol) and PdCl₂(dppf) (12.35 g, 16.87 mmol). Nitrogen sparged 1,4-dioxane (700 mL) was added to the flask followed by nitrogen sparged water (233 mL). The reaction flask was purged with argon, stirred for 10 min, and then warmed to 65° C. for 1 hour. The reaction was cooled to RT and stirred overnight. The aqueous layer was separated from the reaction mixture. The organic layer was diluted with ethyl acetate and water. The aqueous layer was separated. The organic layer was washed with brine. The organic layer was dried over sodium sulfate and concentrated to dryness. The residue was taken up in neat DCM and filtered through a silica gel pad washing with DCM. The filtrate was concentrated to a reddish oil under reduced pressure. The oil was dissolved in 500 mL isopropanol. The resulting red solution was charged with crystalline seed and the slurry was stirred for 4 hours at RT. The slurry was filtered, washed with minimal cold IPA, then dried under vacuum with nitrogen sweep to afford 2,5-dichloro-6-(o-tolyl)nicotinonitrile as an off white solid. $^1$H NMR (500 MHz, DMSO-d6) δ 8.92 (s, 1H), 7.27-7.44 (m, 4H), 2.11 (s, 3H). m/z (ESI, +ve ion): 263.2 (M+H)$^+$.

Step 2: tert-Butyl (2R,5S)-4-((2,5-dichloro-6-(o-tolyl)pyridin-3-yl)(imino)methyl)-2,5-dimethylpiperazine-1-carboxylate (Intermediate 168)

A 3 L (3 neck) round bottom flask equipped with an overhead stirrer, thermocouple, and nitrogen inlet was charged with tert-butyl (2R,5S)-2,5-dimethylpiperazine-1-carboxylate (Astatech, Bristol, Pa., USA, 57.2 g, 267 mmol) and THF (300 mL). The resulting solution was degassed, purged with argon, then cooled to 0° C. To the solution was charged isopropylmagnesium chloride (133 mL, 267 mmol) (2M in THF) dropwise via addition funnel and the mixture was stirred for 1 hr at 0° C. Zinc chloride (140 mL, 267 mmol) (1.9M in THF) was added dropwise via addition funnel. The reaction was then allowed to warm to RT and stir overnight. A solution of 2,5-dichloro-6-(o-tolyl)nicotinonitrile (46.8 g, 178 mmol) in THF (300 mL) was charged to reaction flask dropwise via addition funnel. The reaction was then stirred overnight at RT. The reaction was then quenched into a stirring biphasic mixture of 15 wt % NH$_4$Cl (500 mL) and 500 mL EtOAc. The mixture was stirred for 10 min and the aqueous layer was separated. The organic layer was washed with 15 wt % sat. NaCl. The organic layer was concentrated to orange oil under reduced pressure. A 3 neck flask equipped with overhead stirrer, thermocouple and nitrogen inlet was charged with fine filter frit and vacuum port. The crude oil was dissolved in 3 volumes of IPA (250 mL), and then filtered to remove inorganic salts. The orange solution was seeded with a crystal and stirred for 18 hrs at RT. The solids were isolated by filtration, and washed with cold IPA. The solids were then further purified by a plug of silica gel and washing with 100% EtOH/EtOAc (3:1 blend) to afford tert-butyl (2R,5S)-4-((2,5-dichloro-6-(o-tolyl)pyridin-3-yl)imino)methyl)-2,5-dimethylpiperazine-1-carboxylate (Intermediate 168) as a white solid. m/z (ESI, +ve ion): 477.2 (M+H)$^+$.

Intermediate 170 tert-Butyl (2R,5S)-4-((2,5-dichloro-6-(2-isopropylphenyl)pyridin-3-yl)(imino)methyl)-2,5-dimethylpiperazine-1-carboxylate

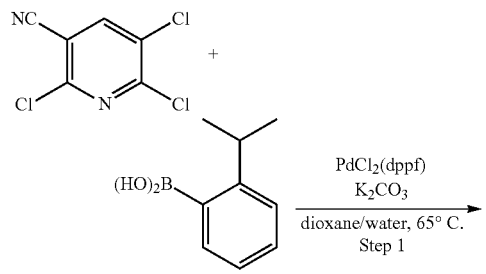

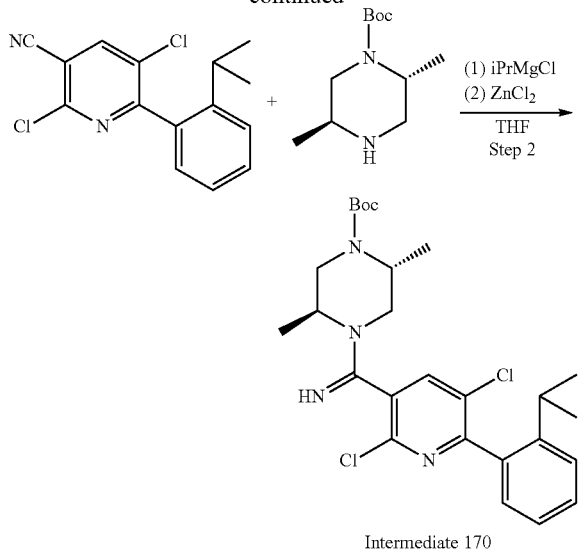

Intermediate 170

Step 1:
2,5-Dichloro-6-(2-isopropylphenyl)nicotinonitrile

To a 2-L three neck round bottom flask equipped with condenser with a nitrogen inlet, an overhead stirrer and thermocouple was added 2,5,6-trichloronicotinonitrile (90 g, 434 mmol), 2-(1-methylethyl)phenyl]-boronic acid (74.7 ml, 456 mmol), potassium carbonate (180 g, 1302 mmol), and (1,1'-bis(diphenylphosphino) ferrocene) dichloropalladium (15.80 g, 21.69 mmol). The flask was purged and filled with argon 3 times. Water (300 ml) and 1,4-dioxane (900 ml) were added by canulation. The reaction was heated to 65° C. and stirred for 1.5 hrs. The reaction was then diluted with water and extracted three times with ethyl acetate. The organics were dried over sodium sulfate and concentrated under reduced pressure. The dried organics were dissolved in DCM and filtered through sand and silica gel. The filtrate was evaporated. The residue was taken up in isopropanol (600 mL). The resulting solid product was then isolated by filtration to afford 2,5-dichloro-6-(2-isopropylphenyl)nicotinonitrile as white solid. $^1$H NMR (500 MHz, DMSO-d6) δ 8.91 (s, 1H), 7.47-7.52 (m, 2H), 7.29-7.35 (m, 1H), 7.21 (d, J=7.40 Hz, 1H), 2.54-2.62 (m, 1H), 1.11 (br d, J=6.75 Hz, 6H). m/z (ESI, +ve ion): 291.2 (M+H)$^+$.

Step 2: tert-Butyl (2R,5S)-4-((2,5-dichloro-6-(2-isopropylphenyl)pyridin-3-yl)(imino)methyl)-2,5-dimethylpiperazine-1-carboxylate A 3 neck flask equipped with overhead stirrer, thermocouple and nitrogen inlet was charged with tert-butyl (2R,5S)-2,5-dimethylpiperazine-1-carboxylate (Astatech, Bristol, Pa., USA, 44.2 g, 206 mmol) and THF (250 mL). The resulting solution was degassed and purged with argon and cooled to 0° C. Isopropylmagnesium chloride (103 mL, 206 mmol) (2M in THF) was added dropwise via addition funnel into the solution. The mixture was stirred for 1 hr at 0° C. Zinc chloride (108 mL, 206 mmol) (1.9M in 2-Me THF) was added dropwise via addition funnel. The mixture was allowed to warm to RT and was stirred for 12 hours. In a separate flask was dissolved 2,5-dichloro-6-(2-isopropylphenyl)nicotinonitrile (40 g, 137 mmol) in THF (250 mL).

The mixture was added to the reaction flask dropwise via addition funnel. The mixture was stirred at RT for 18 hrs. The hazy reaction mixture was cooled to 0° C. and charged with 10 volumes of ethyl acetate and 10 volumes of 15 wt % NH₄Cl (aq). The biphasic mixture was stirred for 1 hour and the aqueous layer was separated. The organics were washed with 15 wt % brine. The organics were concentrated to a dark orange oil. Isopropanol was added and evaporated several times. Eight volumes of 1:1 isopropanol/water were added to the crude oil. The resulting solid was isolated by filtration to afford tert-butyl (2R,5S)-4-((2,5-dichloro-6-(2-isopropylphenyl)pyridin-3-yl)(imino)methyl)-2,5-dimethylpiperazine-1-carboxylate (Intermediate 170) as an off white solid. m/z (ESI, +ve ion): 505.2 (M+H)⁺.

Intermediate 175 tert-Butyl (2R,5S)-4-(6-chloro-1-(4-chloro-6-isopropylpyrimidin-5-yl)-7-(2-fluorophenyl)-2-oxo-1,2-dihydropyrido[2,3-d]pyrimidin-4-y)-2,5-dimethylpiperazine-1-carboxylate Step 1-2: tert-Butyl (2R,5S)-4-(6-chloro-1-(4-chloro-6-isopropylpyrimidin-5-yl)-7-(2-fluorophenyl)-2-oxo-1,2-dihydropyrido[2,3-d]pyrimidin-4-yl)-2,5-dimethylpiperazine-1-carboxylate Synthesized analogous to Steps 1 and 2 in Method 102 using Intermediate 177 in Step 1 and performing Step 2 in toluene. ¹H NMR (400 MHz, CHLOROFORM-d) δ 8.93 (1H, s) 8.12 (1H, s) 7.40-7.48 (1H, m) 7.09-7.25 (3H, m) 3.46-5.07 (6H, m) 2.85-2.94 (1H, m) 1.51 (9H, s) 1.42-1.50 (3H, m) 1.23-1.32 (6H, m) 1.06-1.13 (3H, m). m/z (ESI, +ve ion): 642.2 (M+H)⁺.

Intermediate 176 tert-Butyl (2R,5S)-4-(6-chloro-1-(4-chloro-6-isopropylpyrimidin-5-yl)-2-oxo-7-(o-tolyl)-1,2-dihydropyrido[2,3-d]pyrimidin-4-yl)-2,5-dimethylpiperazine-1-carboxylate

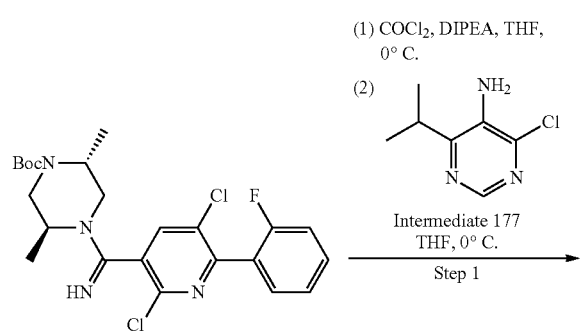
Intermediate 165

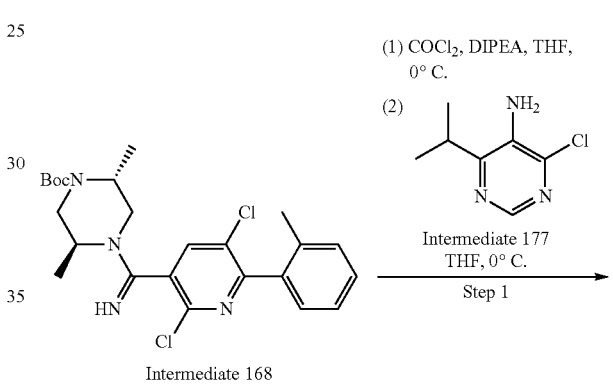
Intermediate 168

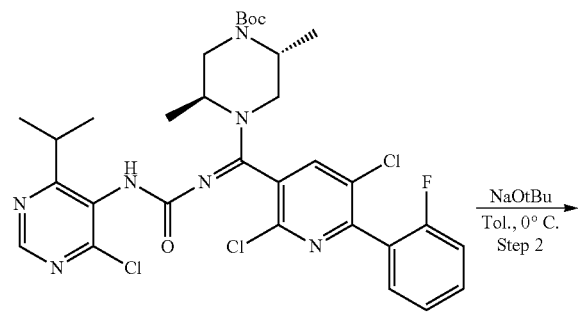

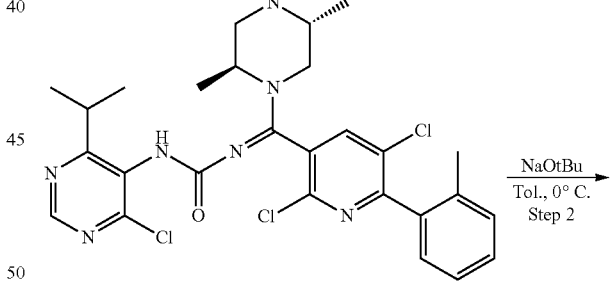

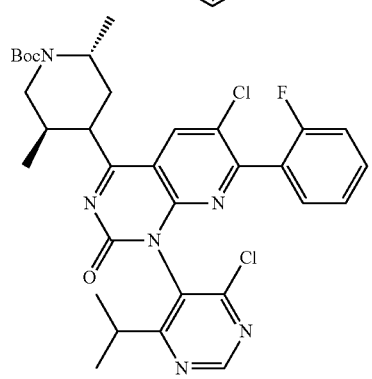

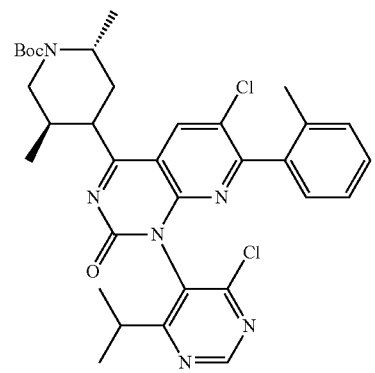

Steps 1-2: tert-Butyl (2R,5S)-4-(6-chloro-1-(4-chloro-6-isopropylpyrimidin-5-yl)-2-oxo-7-(o-tolyl)-1,2-dihydropyrido[2,3-d]pyrimidin-4-yl)-2,5-dimethylpiperazine-1-carboxylate Synthesized analogous to Steps 1 and 2 in Method 102 using Intermediate 168 and Intermediate 177 in Step 1 and performing Step 2 in toluene. $^1$H NMR (400 MHz, CHLOROFORM-d) δ 8.87 (1H, s) 8.11 (1H, s) 7.26-7.31 (1H, m) 7.15-7.21 (2H, m) 7.03-7.08 (1H, m) 3.43-5.04 (6H, m) 2.82-2.91 (1H, m) 2.00-2.04 (3H, m) 1.49 (9H, s) 1.41-1.51 (3H, m) 1.21-1.31 (6H, m) 1.00-1.05 (3H, m). m/z (ESI, +ve ion): 638.2 (M+H)$^+$.

Intermediate 177

4-Chloro-6-isopropylpyrimidin-5-amine

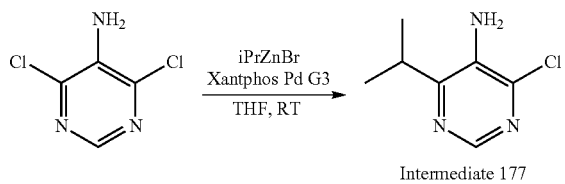

Intermediate 177

4-Chloro-6-isopropylpyrimidin-5-amine

2-Propylzinc bromide (1.0 M in THF, 13.42 ml, 13.42 mmol) was added to a flask charged with 4,6-dichloro-5-aminopyrimidine (2.00 g, 12.20 mmol) and Xantphos Pd G3 (0.578 g, 0.610 mmol) under an argon atmosphere. The reaction mixture was stirred at room temperature for 4 h. The reaction mixture was diluted with EtOAc (125 mL) and quenched with saturated aqueous NH$_4$Cl (75 mL). The organic layer was separated, washed with saturated aqueous sodium chloride (75 mL), dried over MgSO$_4$, filtered, and concentrated in vacuo. The crude product was purified by silica gel chromatography (eluent 0-30% EtOAc/heptane) to provide 4-chloro-6-isopropylpyrimidin-5-amine as a yellow solid (Intermediate 177, 1.18 g, 6.88 mmol, 56.4% yield). $^1$H NMR (400 MHz, CHLOROFORM-d) δ 8.39 (1H, s) 4.09 (2H, br s) 3.02 (1H, spt, J=6.74 Hz) 1.31 (6H, d, J=6.84 Hz). m/z (ESI, +ve ion): 172.1 (M+H)$^+$.

Intermediate 185 tert-Butyl (2R,5S)-4-(6-fluoro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate

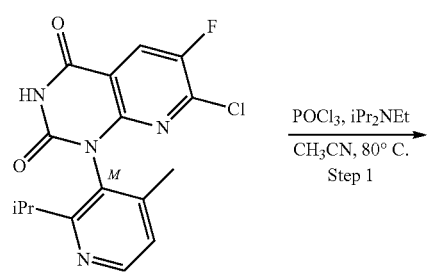

Intermediate 72A

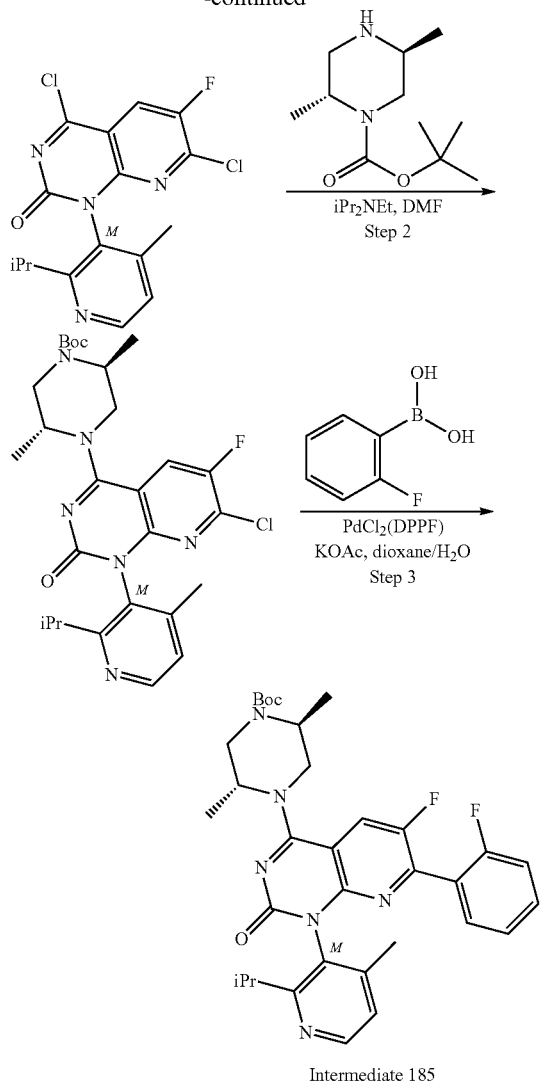

Intermediate 185

Step 1. 4,7-Dichloro-6-fluoro-1-(2-isopropyl-4-methylpyridin-3-yl)pyrido[2,3-d]pyrimidin-2(1H)-one To a RBF was added 7-chloro-6-fluoro-1-(2-isopropyl-4-methylpyridin-3-yl)pyrido[2,3-d]pyrimidine-2,4(1H,3H)-dione (4.81 g, 13.8 mmol, Intermediate 72A), toluene (55 ml), and hunig's base (4.8 ml, 27.6 mmol). To this was added phosphorous oxychloride (2.57 ml, 27.6 mmol) dropwise at rt and the reaction was stirred for 50 minutes at 50° C. at which point LC/MS showed near complete consumption of SM and desired product. The reaction was concentrated under reduced pressure and used directly in the next step.

Step 2. tert-Butyl (2R,5)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate To a flask charged with 4,7-dichloro-6-fluoro-1-(2-isopropyl-4-methylpyridin-3-yl)pyrido[2,3-d]pyrimidin-2

(1H)-one (5.2 g, 14.2 mmol) was added DMF (118 ml) followed by (2R,5S)-tert-butyl 2,5-dimethylpiperazine-1-carboxylate (4.55 ml, 21.2 mmol). To the solution was added hunig's base (12.4 ml, 70.8 mmol) dropwise, with stirring. Upon complete addition, the reaction was quenched by the slow addition of water then further diluted with water and EtOAc before transferring to a separated funnel. The phases were mixed and the organic layer was separated. The organic phase was washed with 1M LiCl and brine then dried over magnesium sulfate. The material was purified via ISCO (120 g, dry load, 0-80% 3:1 EtOAc/EtOH in heptane) to afford tert-butyl (2R,5S)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (6.87 g, 12.60 mmol, 89% yield). m/z (ESI, +ve ion): 545.2 (M+H)$^+$.

Step 3. tert-Butyl (2R,5S)-4-(6-fluoro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate A resealable vial was charged with potassium acetate (0.35 g, 3.6 mmol), tert-butyl (2R,5S)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (0.39 g, 0.72 mmol) and dichloro[1,1'-bis(diphenylphosphino)ferrocene]palladium (ii) dichloromethane adduct (0.052 g, 0.072 mmol). The vial was sealed and evacuated/backfilled with Nitrogen. Dioxane (4.5 ml) was added followed by water (0.2 ml). The cap was replaced and the reaction was heated to 90° C. for 2 minutes and (2-fluorophenyl)boronic acid (0.2 g, 1.43 mmol) were added and the reaction was stirred at 90° C. for 2 hours. The reaction was poured into a separated funnel containing water and EtOAc. The phases were mixed and the organic phase was separated, washed with brine, dried over magnesium sulfate and concentrated under reduced pressure. The crude residue was purified via ISCO (40 g, 0-60% 3:1 EtOAc/EtOH in heptane) to afford tert-butyl (2R,5S)-4-(6-fluoro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate 185, 0.262 g, 0.433 mmol, 60.6% yield) as off-white solid. m/z (ESI, +ve ion): 605.3 (M+H)$^+$.

Intermediate 186

4-(Dimethylamino)but-2-ynoic acid

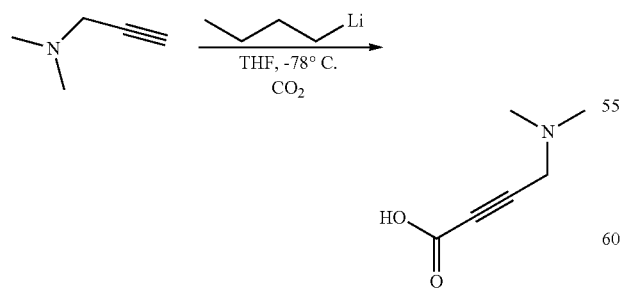

To a solution of 1-dimethylamino-2-propyne (3.0 g, 36.1 mmol) in THF (30 mL) cooled in a −78° C. bath was slowly added butyl lithium, 2.5 M in hexanes (14.4 mL, 36.1 mmol) dropwise. The solution was stirred at −78° C. for 1 h. The reaction mixture was then quenched with crushed dry ice (carbon dioxide (1.59 g, 36.1 mmol) and the reaction mixture was removed from the ice bath and allowed to warm to r.t. The reaction mixture was concentrated to dryness. treated with water (50 mL), extracted with EtOAc (30 mL) and the aqueous was again concentrated on the rotovap. The crude residue was taken up in MeOH and filtered and the concentrated residue was dried on the lyophilizer overnight affording 4-(dimethylamino)but-2-ynoic acid (5.67 g, 44.6 mmol, 123% yield, 75% pure) as a light yellow solid. $^1$H NMR (400 MHz, DMSO-d$_6$) δ 3.15 (2H, s), 2.15 (6H, s). m/z (ESI, +ve ion): 128.1 (M+H)$^+$.

Intermediate 187

6-((Dimethylamino)methyl)-2-isopropyl-4-methylpyridin-3-amine

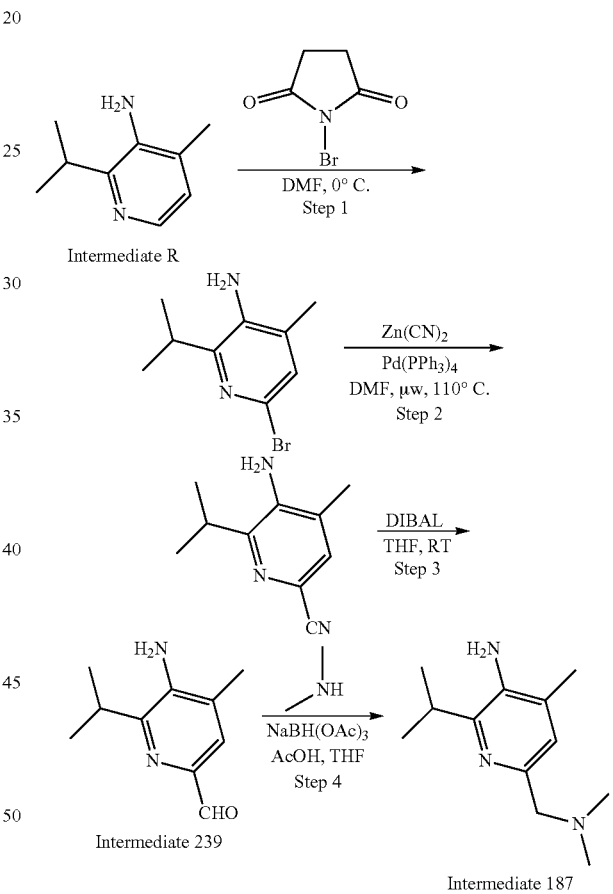

Step 1.
6-Bromo-2-isopropyl-4-methylpyridin-3-amine

To 2-isopropyl-4-methylpyridin-3-amine (Intermediate R, 4 g, 26.6 mmol) dissolved in N,N-dimethylformamide (81 ml) at 0° C. was added bromosuccinimide (4.98 g, 28.0 mmol) in one portion. The reaction mixture was stirred at 0° C. for 1 h. Water was added to the resulting reaction mixture to stop the reaction. The aqueous layer was extracted with ethyl acetate (2×). The organic layer was dried over anhydrous sodium sulfate, filtered and concentrated. The crude material was purified by chromatography through an ISCO 24 Gold column, eluting with a gradient of 0% to 25% 3:1 EtOAc/EtOH in heptane, to provide 6-bromo-2-isopropyl-4-methylpyridin-3-amine (5 g, 21.82 mmol, 82% yield) as orange oil. $^1$H NMR (400 MHz, CHLOROFORM-d) δ 7.00 (s, 1H), 3.58 (br s, 2H), 2.96 (td, J=6.74, 13.48 Hz, 1H), 2.13 (s, 3H), 1.28 (d J=6.63 Hz, 6H). m/z (ESI, +ve ion): 228.9 (M+H)$^+$.

Step 2.
5-Amino-6-isopropyl-4-methylpicolinonitrile

A 5 mL microwave vial containing was charged with a magnetic stir bar, 6-bromo-2-isopropyl-4-methylpyridin-3-amine (1.16 g, 5.06 mmol), tetrakis(triphenylphosphine)palladium(0) (0.585 g, 0.506 mmol), dicyanozinc (0.832 g, 7.09 mmol). The vial was evacuated and flushed with nitrogen. N,N-dimethylformamide (13 ml) was added the reaction mixture was stirred and heated in a Emrys Optmizer microwave reactor (Personal Chemistry, Biotage AB, Inc., Upssala, Sweden) at 110° C. for 30 min. The reaction mixture was partitioned between EtOAc and brine. The layers were separated and the aqueous layer was further extracted with EtOAc (2×). The combined organic extracts were dried over sodium sulfate, filtered, and concentrated. The crude material was purified on a 40 g HP-GOLD column eluting with a gradient of 0-30% 3:1 EtOAc/EtOH in heptane over 30 min. to afford 5-amino-6-isopropyl-4-methylpicolinonitrile as a dark-red oil. m/z (ESI, +ve ion): 176.1 (M+H)$^+$.

Step 3.
5-Amino-6-isopropyl-4-methylpicolinaldehyde (Intermediate 239)

A nitrogen-flushed 100 mL round-bottomed flask containing 5-amino-6-isopropyl-4-methylpicolinonitrile (1 g, 5.7 mmol) was charged with a magnetic stir bar and tetrahydrofuran (19 mL). diisobutylaluminium hydride (45.7 ml, 45.7 mmol) was added dropwise at room temp and the resulting orange solution stirred for 30 min. The reaction mixture was then cooled to 0° C. in an ice-water bath and quenched by adding 1 M Rochelle salt (40 mL) dropwise to the reaction mixture (hydrogen gas was generated) and diluted with EtOAc (100 mL). The resulting biphasic mixture was stirred for 15 min at room temp and was then filtered through a glass frit and washed with EtOAc. The filtrate was transferred to a separatory funnel and the layers were partitioned. The aqueous phase was extracted with EtOAc (2×70 mL) and the combined organic extracts were dried over anhydrous sodium sulfate, filtered, and concentrated. The crude material was dissolved in DCM and then purified on a 40 g HP-GOLD column eluting with a gradient of 0-40% 3:1 EtOAc/EtOH in heptane over 30 min, to afford 5-amino-6-isopropyl-4-methylpicolinaldehyde (Intermediate 239 0.18 g, 1.0 mmol, 18% yield) as a thick yellow oil which was carried forward in the next step without further purification. m/z (ESI, +ve ion): 179.1 (M+H)$^+$.

Step 4. 6-((Dimethylamino)methyl)-2-isopropyl-4-methylpyridin-3-amine

A nitrogen-purged 100 mL round-bottomed flask containing 5-amino-6-isopropyl-4-methylpicolinaldehyde (Intermediate 239, 180 mg, 1.0 mmol) and a magnetic stir bar was charged with tetrahydrofuran (5 mL), dimethylamine solution 2.0m in THF (0.56 mL, 1.1 mmol), acetic acid, glacial (0.058 mL, 1.0 mmol), and sodium triacetoxyborohydride (428 mg, 2.02 mmol). The resulting cloudy mixture was stirred at RT for 2 h then quenched by adding water (~20 mL) and saturated aqueous sodium bicarbonate (~20 mL) and the mixture was diluted with EtOAc (~50 mL). The biphasic mixture was transferred to a separatory funnel and the layers were partitioned. The aqueous phase was extracted with EtOAc until the desired mass was no longer detected in the aqueous phase. The combined organic extracts were dried over magnesium sulfate, filtered, and concentrated to afford crude 6-((dimethylamino)methyl)-2-isopropyl-4-methylpyridin-3-amine (Intermediate 187) as a light-yellow oil $^1$H NMR (400 MHz, CHLOROFORM-d) δ 6.92 (s, 1H), 3.53 (br s, 2H), 3.46 (s, 2H), 2.96-3.10 (m, 1H), 2.27 (s, 6H), 2.16 (s, 3H), 1.29 (d, J=6.63 Hz, 6H). m/z (ESI, +ve ion): 208.3 (M+H)$^+$.

Intermediate 188

2-Isopropyl-4-methyl-6-(pyrrolidin-1-ylmethyl)pyridin-3-amine

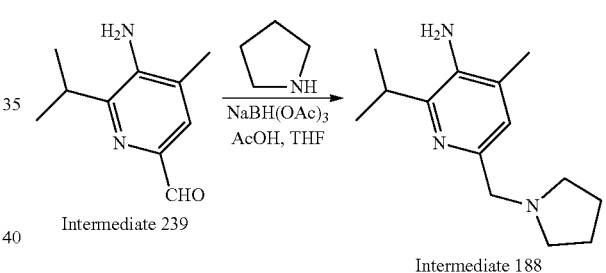

A nitrogen-purged 50 mL round-bottomed flask containing 5-amino-6-isopropyl-4-methylpicolinaldehyde (Intermediate 239, 265 mg, 1.49 mmol) and a magnetic stir bar was charged with tetrahydrofuran (5 mL), pyrrolidine (137 µl, 1.64 mmol), acetic acid, glacial (85 µl, 1.49 mmol). and sodium triacetoxyborohydride (630 mg, 2.97 mmol). The resulting cloudy mixture was stirred at RT for 18 h. The reaction was quenched by adding water (~10 mL) and saturated aqueous sodium bicarbonate (~10 mL) and the mixture was diluted with EtOAc (~40 mL). The biphasic mixture was transferred to a separatory funnel and the layers were partitioned. The aqueous phase was extracted with EtOAc until the desired mass was no longer detected in the aqueous phase. The combined organic extracts were dried over magnesium sulfate, filtered, and concentrated to afford crude 2-isopropyl-4-methyl-6-(pyrrolidin-1-ylmethyl)pyridin-3-amine as a light-yellow oil (Intermediate 188). $^1$H NMR (400 MHz, CHLOROFORM-d) δ 6.93 (s, 1H), 3.66 (s, 2H), 3.52 (br s, 2H), 2.93-3.11 (m, 1H), 2.60 (br s, 4H), 2.15 (s, 3H), 1.78 (td, J=3.32, 6.63 Hz, 4H), 1.29 (d, J=6.84 Hz, 6H). m/z (ESI, +ve ion): 234.2 (M+H)$^+$.

Intermediate 189

5-Isopropyl-2,3-dimethylpyridin-4-amine

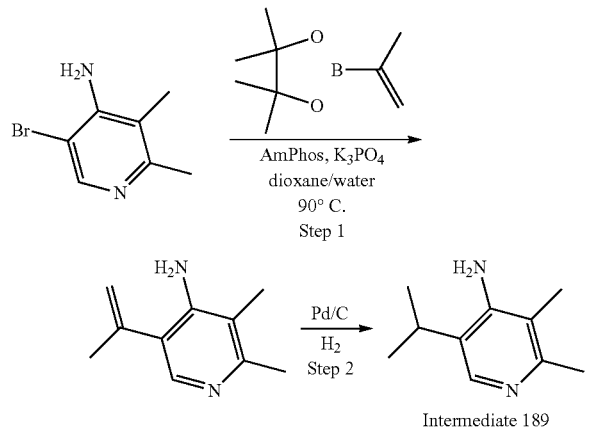

Intermediate 189

Step 1. 2,3-Dimethyl-5-(prop-1-en-2-yl)pyridin-4-amine

To a RBF was added 5-bromo-2,3-dimethylpyridin-4-amine (ACES Pharma, 1.05 g, 5.22 mmol), 4,4,5,5-tetramethyl-2-(prop-1-en-2-yl)-1,3,2-dioxaborolane (0.965 g, 5.74 mmol) and AmPhos (0.074 g, 0.10 mmol). The flask was evacuated under vacuum and then nitrogen was flushed through it for 1 min. 1,4-dioxane (17 mL) and aqueous potassium phosphate (3.33 g, 15.7 mmol in 6 mL of water) was added and the reaction was warmed to 90° C. for 3 h. Added more AmPhos (100 mg, 0.25 eq) and stirred at 90° C. for another 16 h. The mixture was partitioned between EtOAc and brine. The aqueous layer was back extracted with EtOAc (3×) and the combined organics was dried (Na2SO4) and concentrated. The crude was purified by chromatography through a Biotage 40 g ultra column, eluting with a gradient of 0% to 50/o EtOAc in heptane, to provide 2,3-dimethyl-5-(prop-1-en-2-yl)pyridin-4-amine (0.27 g, 1.6 mmol, 32% yield) as light-green oil. m/z (ESI, +ve ion): 163.2 (M+H)$^+$.

Step 2. 5-Isopropyl-2,3-dimethylpyridin-4-amine

A mixture of 2,3-dimethyl-5-(prop-1-en-2-yl)pyridin-4-amine (0.27 g, 1.6 mmol) in ethanol (5.5 mL) under nitrogen was treated with palladium 10 wt. % on activated carbon (0.089 g, 0.083 mmol) in a 75-mL glass reaction vessel, the solution was purged 5×40 psi with hydrogen and allowed to stir under an atmosphere of hydrogen at ca. 30-40 psi for 3 h. The reaction mixture was filtered through a pad of celite, washed with EtOH and concentrated to dryness affording 5-isopropyl-2,3-dimethylpyridin-4-amine (Intermediate 189, 0.29 g, 1.7 mmol, 104% yield) as orange viscous oil. m/z (ESI, +ve ion): 165.2 (M+H)$^+$.

Intermediate 190

4-Chloro-2-isopropylpyridin-3-amine

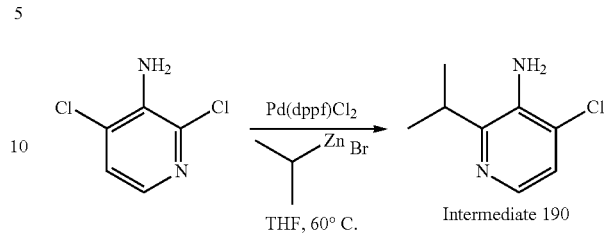

A mixture of 2,4-dichloro-3-aminopyridine (5.00 ml, 30.7 mmol, Combi-Blocks) and 1,1'-bis(diphenylphosphino)ferrocene-palladium dichloride (2.244 g, 3.07 mmol) was purged with N2 followed by the addition of THF (100 mL) and 2-propylzinc bromide (46.0 ml, 46.0 mmol). The resulting mixture was heated at 60° C. After 2 h the reaction went to completion. The reaction was brought to rt. washed with sat. NaHCO3 and extracted with EtOAc. The combined organics were purified by chromatography on silica gel using 0-30% EtOAc in heptane to afford 4-chloro-2-isopropylpyridin-3-amine (Intermediate 190, 3.45 g, 20.22 mmol, 65.9% yield) as a light yellow oil. $^1$H NMR (400 MHz, CHLOROFORM-d) δ 7.92 (d, J=5.2 Hz, 1H), 7.07 (d, J=5.4 Hz, 1H), 4.09 (br s, 2H), 2.86-3.22 (m, 1H), 1.32 (d, J=6.6 Hz, 6H). m/z (ESI, +ve ion): 170 (M+H)$^+$.

Intermediates 240 and 191

6,7-Dichloro-1-(4-chloro-2-isopropylpyridin-3-yl)pyrido[2,3-d]pyrimidine-2,4(1H,3H)-dione 6-Chloro-1-(4-chloro-2-isopropylpyridin-3-yl)-7-methoxypyrido[2,3-d]pyrimidine-2,4(1H,3H)-dione

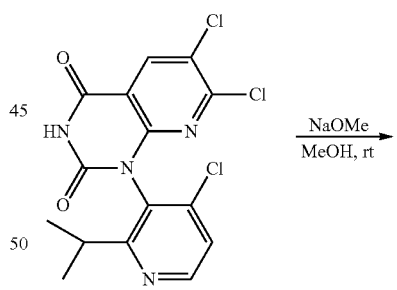

Intermediate 240

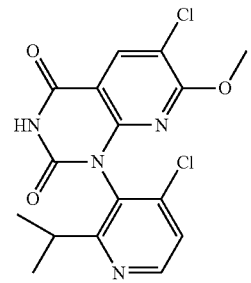

Intermediate 191

To a solution of 6,7-dichloro-1-(4-chloro-2-isopropylpyridin-3-yl)pyrido[2,3-d]pyrimidine-2,4(1H,3H)-dione (0.500 g, 1.297 mmol, Intermediate 240) in dry MeOH (15 mL) at rt was added sodium methoxide (0.700 g, 12.97 mmol) and the resulting mixture was heated at 50 C for 2 h. The reaction went to completion and concentrated. The white residue was washed with water and extracted with EtOAc. The combined organics were dried over $Na_2SO_4$, filtered and concentrated to afford 6-chloro-1-(4-chloro-2-isopropylpyridin-3-yl)-7-methoxypyrido[2,3-d]pyrimidine-2,4(1H,3H)-dione, Intermediate 191. $^1$H NMR (400 MHz, CHLOROFORM-d) δ 8.58 (d, J=5.2 Hz, 1H), 8.36 (s, 1H), 7.34 (d, J=5.2 Hz, 1H), 3.61 (s, 3H), 2.88 (br d, J=6.6 Hz, 1H), 1.22 (br d, J=6.6 Hz, 3H), 1.20-1.21 (m, 1H), 1.13 (br d, J=6.6 Hz, 3H). m/z (ESI, +ve ion): 380.6 (M+H)$^+$.

Intermediate 192

Dimethyl(2-(4,4,5,5-tetramethyl-1,3,2-dioxaborolan-2-yl)phenyl)phosphine oxide

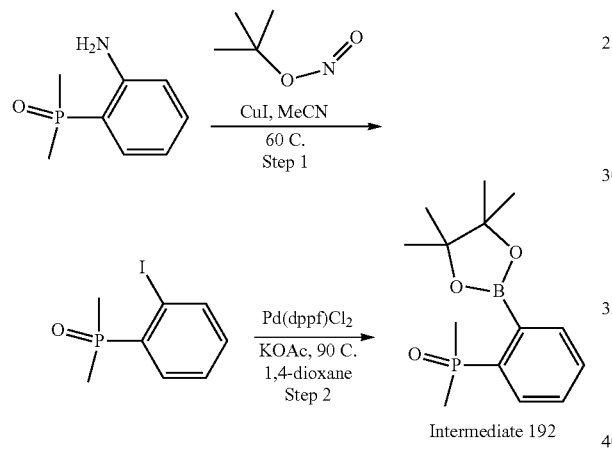

Intermediate 192

Step 1. (2-Iodophenyl)dimethylphosphine oxide

A mixture of (2-aminophenyl)dimethylphosphine oxide (1.500 ml, 8.87 mmol, AstaTech, Inc.), copper(i) iodide (0.602 ml, 17.73 mmol) and 1,1-dimethylethylnitrite (1.829 ml, 17.73 mmol) in MeCN (25 mL) was heated at 60 C overnight. The reaction went to completion, poured into water and extracted with EtOAc. The combined organics were dried over $Na_2SO_4$, filtered, concentrated and purified by chromatography on silica gel using 0-50% EtOAc in heptane to afford (2-iodophenyl)dimethylphosphine oxide (0.88 g, 3.14 mmol, 35.4% yield) as brown solid. m/z (ESI, +ve ion): 280.8 (M+H)$^+$.

Step 2

A mixture of (2-iodophenyl)dimethylphosphine oxide (0.88 g, 3.14 mmol), bis(pinacolato)diboron (1.037 g, 4.09 mmol), (1,1'-bis(diphenylphosphino) ferrocene) dichloropalladium (0.115 ml, 0.157 mmol) and potassium acetate (0.617 g, 6.28 mmol) was purged with N2 followed by the addition of 1,4-dioxane and the resulting mixture was heated at 90 C for 6 h. The reaction was washed with sat. NaHCO$_3$, extracted with EtOAc, DCM and purified by chromatography on silica gel using 0-10% MeOH in DCM to afford a brown oil as dimethyl(2-(4,4,5,5-tetramethyl-1,3,2-dioxaborolan-2-yl)phenyl)phosphine oxide (Intermediate 192, 0.15 g, 0.536 mmol, 17.04% yield). 1H NMR (400 MHz, CHLOROFORM-d) δ 7.92-8.03 (m, 1H), 7.51 (br d, J=6.6 Hz, 3H), 1.82-1.93 (m, 6H), 1.39 (s, 12H). m/z (ESI, +ve ion): 380.6 (M+H)$^+$.

Intermediate 193

2,6-Diisopropylaniline

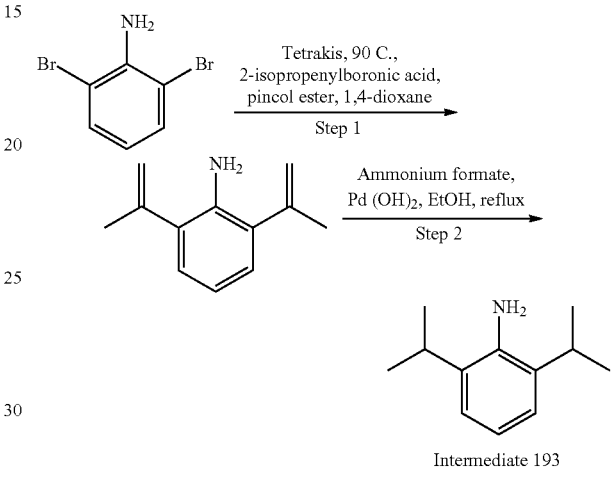

Intermediate 193

Step 1. 2,6-Di(prop-1-en-2-yl)aniline

A mixture of 2,6-dibromoaniline (5.00 ml, 19.93 mmol, Ark Pharma),2-isopropenylboronic acid, pincol ester (8.37 g, 49.8 mmol, Combi-Blocks), sodium carbonate (12.67 g, 120 mmol) and tetrakis (2.303 g, 1.993 mmol) in 1,4-dioxane/water (24/6 mL) was heated at 90 C for 24 h. The reaction went to completion, quenched with sat. NaHCO$_3$ and extracted with EtOAc. The combined organics were purified by chromatography on silica gel using 0-50% EtOAc in heptane to afford 2,6-di(prop-1-en-2-yl)aniline (1.31 g, 7.56 mmol, 37.9% yield) as a greenish oil with another impurity. m/z (ESI, +ve ion): 174 (M+H)$^+$.

Step 2. 2,6-Diisopropylaniline

A mixture of 2,6-di(prop-1-en-2-yl)aniline (1.31 g, 7.56 mmol), ammonium formate (15.02 ml, 302 mmol) and palladium hydroxide carbon (2.65 ml, 3.78 mmol) was purged with N2, followed by the addition of EtOH (30 mL). The resulting mixture was heated to reflux for 1 h. The reaction went to completion and filtered through celite. The filtrate was washed with sat. NaHCO$_3$, water, brine, dried over $Na_2SO_4$, and concentrated. The crude product was chomatographed on silica gel using 0-70% EtOAc in heptane to afford 2,6-diisopropylaniline (Intermediate 193) as a brown oil. 1H NMR (400 MHz, CHLOROFORM-d) δ 7.04 (d, J=7.7 Hz, 2H), 6.77-6.86 (m, 1H), 2.88-3.01 (m, 2H), 1.27 (d, J=6.8 Hz, 12H). NH2 not observed. m/z (ESI, +ve ion): 178 (M+H)$^+$.

Intermediate 194

2,4-Diisopropylpyridin-3-amine

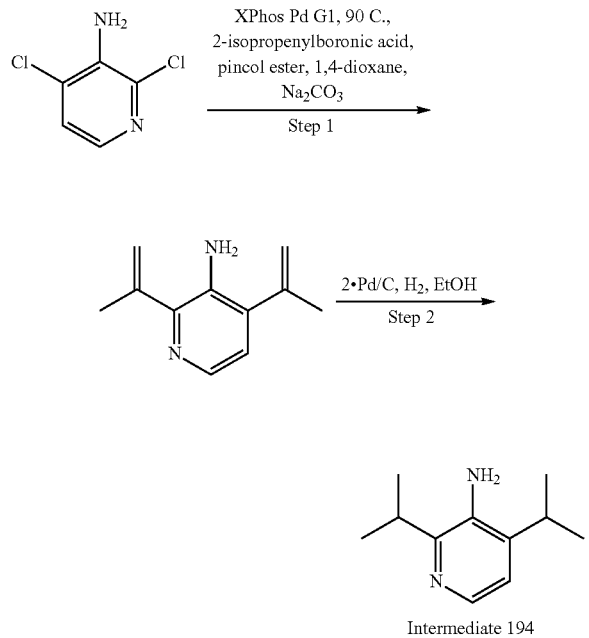

Intermediate 194

Step 1. 2,4-Di(prop-1-en-2-yl)pyridin-3-amine

A mixture of 2,4-dichloro-3-aminopyridine (4.40 ml, 27.0 mmol, Combi-Blocks), 4,4,5,5-tetramethyl-2-(prop-1-en-2-yl)-1,3,2-dioxaborolane (10.89 g, 64.8 mmol, Combi-Blocks), sodium carbonate (14.30 g, 135 mmol) and chloro(2-dicyclohexylphosphino-2',4',6'-tri-i-propyl-1,1'-biphenyl)[2-(2-aminoethyl)phenyl] palladium(ii) methyl-t-butylether adduct (2.232 ml, 2.70 mmol) in 1,4-dioxane/water (100/25 mL) was heated at 90 C for 6 h. The reaction went to completion, quenched with sat. NaHCO$_3$ and extracted with EtOAc. The combined organics were purified by chromatography on silica gel using 0-80 EtOAc in heptane to afford 2,4-di(prop-1-en-2-yl)pyridin-3-amine (4.5 g, 25.8 mmol, 96% yield) as a yellow oil. m/z (ESI, +ve ion): 175 (M+H)$^+$.

Step 2. 2,4-Diisopropylpyridin-3-amine

Through a mixture of 2,4-di(prop-1-en-2-yl)pyridin-3-amine (4.5 g, 25.8 mmol) and palladium 10 wt. % on activated carbon (0.229 ml, 2.58 mmol) in EtOH (100 mL) was bubbled H$_2$ through a hydrogenation kit at 30 psi for 1 h. The reaction went to completion, filtered through celite and concentrated to afford 2,4-diisopropylpyridin-3-amine (Intermediate 194, 4.0 g, 22.44 mmol, 87% yield) as a bright yellow oil. 1H NMR (400 MHz, CHLOROFORM-d) δ 8.05 (d, J=5.2 Hz, 1H), 6.96 (br d, J=5.0 Hz, 1H), 3.72 (br d, J=7.0 Hz, 2H), 3.09 (s, 1H), 2.71-2.96 (m, 1H), 1.35 (d, J=6.8 Hz, 6H), 1.27 (d, J=6.8 Hz, 6H). m/z (ESI, +ve ion): 179 (M+H)$^+$.

Intermediate 195

6,7-Dichloro-1-(2,4-diisopropylpyridin-3-yl)pyrido[2,3-d]pyrimidine-2,4(1H,3H)-dione

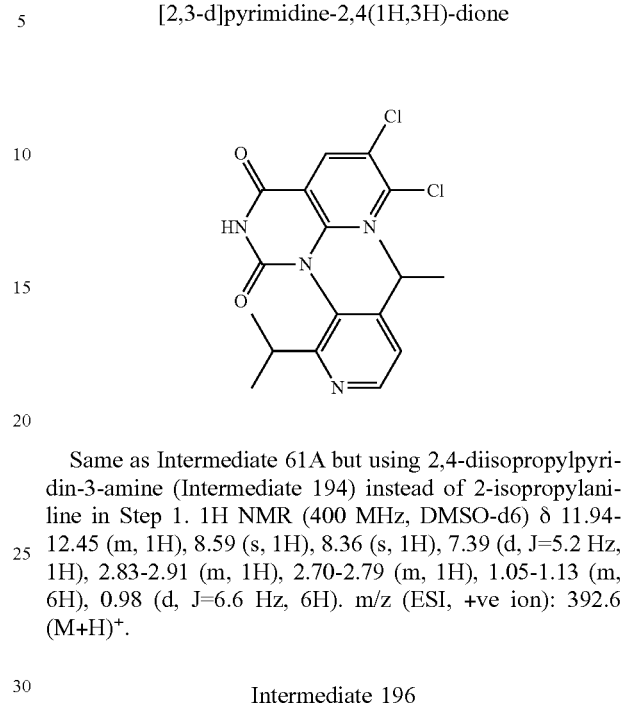

Same as Intermediate 61A but using 2,4-diisopropylpyridin-3-amine (Intermediate 194) instead of 2-isopropylaniline in Step 1. 1H NMR (400 MHz, DMSO-d6) δ 11.94-12.45 (m, 1H), 8.59 (s, 1H), 8.36 (s, 1H), 7.39 (d, J=5.2 Hz, 1H), 2.83-2.91 (m, 1H), 2.70-2.79 (m, 1H), 1.05-1.13 (m, 6H), 0.98 (d, J=6.6 Hz, 6H). m/z (ESI, +ve ion): 392.6 (M+H)$^+$.

Intermediate 196

6-Bromo-2,4-diisopropylpyridin-3-amine

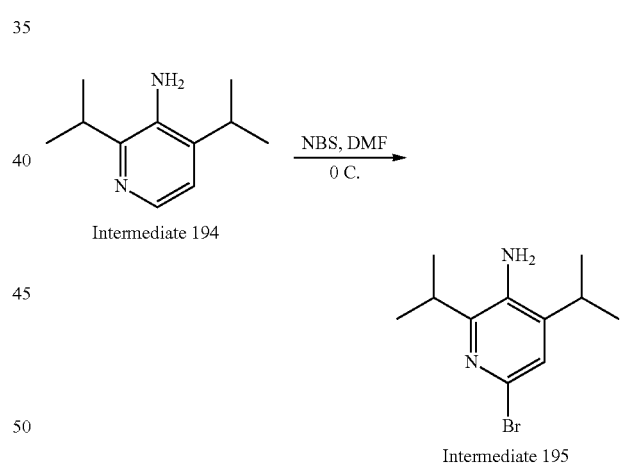

To a solution of 2,4-diisopropylpyridin-3-amine (0.500 g, 2.80 mmol, Intermediate 194) in DMF (10 mL) at 0 C was added NBS (0.499 g, 2.80 mmol) in one portion and the resulting mixture was stirred at this temperature for 30 min. The reaction went to completion. The mixture was washed with water (60 mL), extracted with EtOAc. The combined organics were dried over Na$_2$SO$_4$, filtered, concentrated and purified by chromatography on silica gel using 0-40% EtOAc in heptane to afford 6-bromo-2,4-diisopropylpyridin-3-amine (Intermediate 195, 0.31 g, 1.205 mmol, 43.0% yield) as an orange oil. 1H NMR (400 MHz, CHLOROFORM-d) δ 7.04 (s, 1H), 2.93-3.09 (m, 1H), 2.71-2.90 (m, 1H), 1.29 (d, J=6.6 Hz, 6H), 1.25 (d, J=6.8 Hz, 6H). NH2 not observed. m/z (ESI, +ve ion): 258.8 (M+H)$^+$.

Intermediate 197

4-Ethyl-2-isopropylpyridin-3-amine

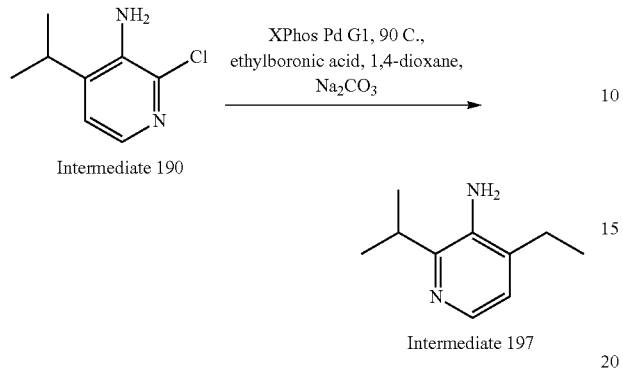

A mixture of 4-chloro-2-isopropylpyridin-3-amine (0.800 g, 4.69 mmol, Intermediate 190), ethylboronic acid (0.416 g, 5.63 mmol, FSSI), sodium carbonate (2.484 g, 23.44 mmol) and chloro(2-dicyclohexylphosphino-2',4',6'-tri-i-propyl-1,1'-biphenyl)[2-(2-aminoethyl)phenyl] palladium(ii) methyl-t-butylether adduct (0.388 ml, 0.469 mmol) in 1,4-dioxane/water (100/25 mL) was heated at 90 C for 17 h. The reaction was quenched with sat. NaHCO$_3$ and extracted with EtOAc. The combined organics were purified by chromatography on silica gel using 0-80 EtOAc in heptane to afford 4-ethyl-2-isopropylpyridin-3-amine (Intermediate 197, 0.093 g, 0.566 mmol, 12.08% yield) as a green oil. 1H NMR (400 MHz, DMSO-d6) δ 7.71 (d, J=4.6 Hz, 1H), 6.79 (d, J=4.8 Hz, 1H), 4.73 (s, 2H), 2.43-2.49 (m, 3H), 1.15 (d, J=6.8 Hz, 9H). m/z (ESI, +ve ion): 165.2 (M+H)$^+$.

Intermediate 198

4-Cyclopropyl-2-isopropylpyridin-3-amine

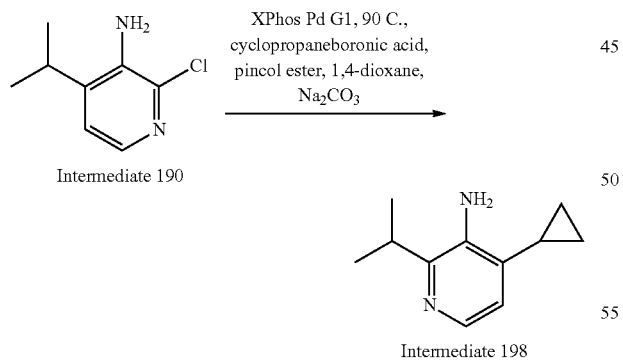

A mixture of 4-chloro-2-isopropylpyridin-3-amine (0.900 g, 5.27 mmol, Intermediate 190), cyclopropaneboronic acid (0.680 ml, 7.91 mmol, Small Molecules, Inc.), sodium carbonate (2.236 g, 21.10 mmol) and chloro(2-dicyclohexylphosphino-2',4',6'-tri-i-propyl-1,1'-biphenyl)[2-(2-aminoethyl)phenyl] palladium(ii) methyl-t-butylether adduct (0.436 ml, 0.527 mmol) in 1,4-dioxane/water (100/25 mL) was heated at 90 C for 24 h. The reaction was washed with sat. NaHCO$_3$, extracted with EtOAc and purified by chromatography on silica gel using 0-5% MeOH in DCM to afford 4-cyclopropyl-2-isopropylpyridin-3-amine (Intermediate 198, 0.74 g, 4.20 mmol, 80% yield) as a yellow oil. $^1$H NMR (400 MHz, CHLOROFORM-d) δ 7.97 (d, J=5.0 Hz, 1H), 6.77 (d, J=4.8 Hz, 1H), 3.94 (br s, 2H), 1.63-1.70 (m, 1H), 1.37-1.43 (m, 1H), 1.32 (d, J=6.8 Hz, 6H), 0.98 (dd, J=8.4, 1.8 Hz, 2H), 0.64 (dd, J=5.4, 1.5 Hz, 2H). m/z (ESI, +ve ion): 177 (M+H)$^+$.

Intermediate 199

6-Chloro-1-(4-cyclopropyl-2-isopropylpyridin-3-yl)-7-(o-tolyl)pyrido[2,3-d]pyrimidine-2,4(1H,3H)-dione

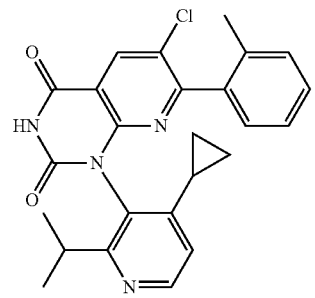 [SMILES: Cc1ccccc1-c1nc2c(cc1Cl)c(=O)[nH]c(=O)n2-c1c(C2CC2)ccnc1C(C)C]

Same as Example 153 up to step 3 but using 4-cyclopropyl-2-isopropylpyridin-3-amine (Intermediate 198) in Step 1 and o-tolylboronic acid is Step 3. $^1$H NMR (400 MHz, DMSO-d6) δ 12.22 (br s, 1H), 8.56 (s, 1H), 8.38 (d, J=5.0 Hz, 1H), 7.31 (s, 1H), 7.21-7.27 (m, 2H), 7.06 (d, J=7.5 Hz, 1H), 6.81 (d, J=5.2 Hz, 1H), 2.85-3.01 (m, 1H), 1.94 (s, 3H), 1.64-1.77 (m, 1H), 1.10 (d, J=6.6 Hz, 3H), 0.93 (d, J=6.6 Hz, 3H), 0.84-0.90 (m, 2H), 0.70-0.79 (m, 2H). m/z (ESI, +ve ion): 447.2 (M+H)$^+$.

Intermediate 200

6-Chloro-1-(2,4-diisopropylpyridin-3-yl)-7-(o-tolyl)pyrido[2,3-d]pyrimidine-2,4(1H,3H)-dione

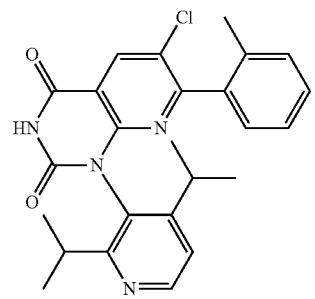 [SMILES: Cc1ccccc1-c1nc2c(cc1Cl)c(=O)[nH]c(=O)n2-c1c(C(C)C)ccnc1C(C)C]

Same as Example 153 up to step 3 using 2,4-di(prop-1-en-2-yl)pyridin-3-amine (Intermediate 194) in Step 1 and o-tolylboronic acid is Step 3. $^1$H NMR (400 MHz, DMSO-d6) δ 12.09-12.37 (m, 1H), 8.56 (s, 1H), 8.48 (d, J=5.2 Hz, 1H), 7.17-7.34 (m, 4H), 6.98 (d, J=7.3 Hz, 1H), 2.88 (quin, J=6.6 Hz, 1H), 2.71-2.81 (m, 1H), 1.92 (s, 3H), 1.09 (d, J=6.6 Hz, 6H), 0.94 (d, J=6.6 Hz, 6H). m/z (ESI, +ve ion): 448.6 (M+H)$^+$.

Intermediate 201

6-bromo-2-isopropyl-4-methylpyridin-3-amine

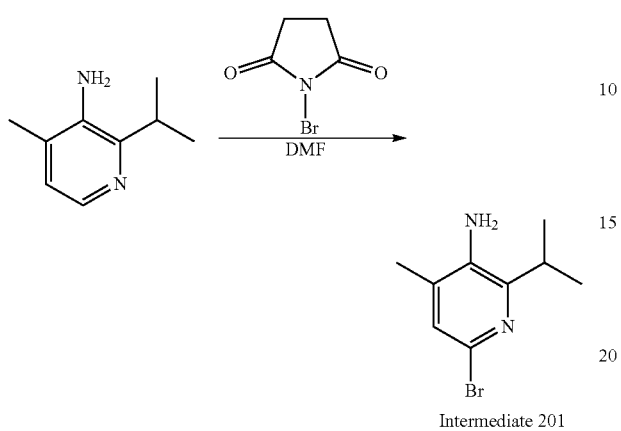

Intermediate 201

To a 150-mL round-bottomed flask was added 2-isopropyl-4-methylpyridin-3-amine (3.00 g, 19.97 mmol) and n-bromosuccinimide (4.44 g, 24.96 mmol) in N, N-dimethylformamide (24.96 mL). The reaction mixture was stirred and heated at 60° C. for 1.5 h, while under an inert atmosphere. The reaction mixture was poured into water (50 mL), then agitated (sonicator) 5 min. The mixture was diluted with EtOAc and the layers were separated. The aqueous layer was extracted with EtOAc and water. The combined organics were washed with sat. aq. NaHCO$_3$. The organics were collected, dried over MgSO$_4$, filtered and concentrated in vacuo, to afford 6-bromo-2-isopropyl-4-methylpyridin-3-amine (Intermediate 201, 3.27 g, 14.30 mmol, 72% Yield) as tan oil. m/z (ESI, +ve ion): 230.1 (M+H)$^+$. *(Note: The crude oil was carried into the next step of the synthesis, without further purification).

Intermediate 202 tert-Butyl (2R,5S)-4-(1-(6-bromo-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate

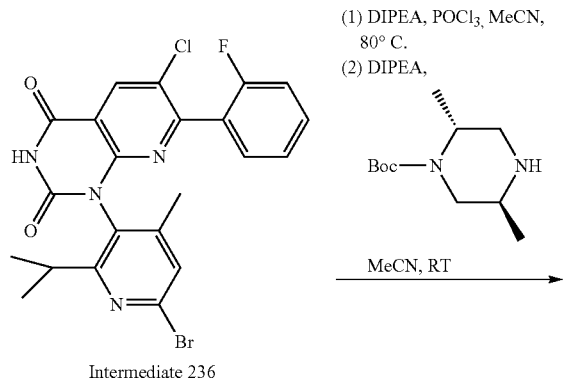

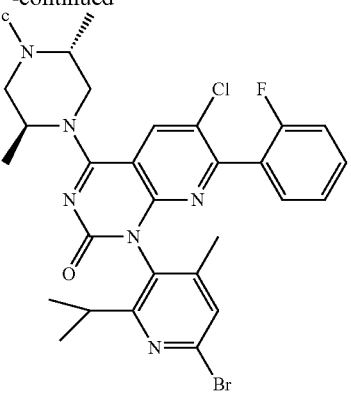

To a 250-mL round-bottomed flask was added 1-(6-bromo-2-isopropyl-4-methylpyridin-3-yl)-6-chloro-7-(2-fluorophenyl)pyrido[2,3-d]pyrimidine-2,4(1H,3H)-dione (2.00 g, 3.97 mmol) and N,N-diisopropylethylamine (0.90 mL, 5.16 mmol) in acetonitrile (19.85 mL). Then phosphorous oxychloride (0.44 mL, 4.76 mmol) was added to the reaction mixture, then the mixture was heated and stirred at 80° C. for 30 min, while under an inert (N$_2$) atmosphere. The reaction mixture was removed from the heat bath and allowed to cool to rt.

The reaction mixture was cooled to 0° C. with a wet ice/water bath. Then DIPEA (10 mL) was added dropwise to the reaction mixture. Then a solution of (2r,5s)-1-boc-2,5-dimethylpiperazine (1.27 g, 5.96 mmol) in MeCN (4 mL) was added dropwise to the reaction mixture. The ice bath was removed and the mixture was allowed to warm to rt. More DIPEA (2 mL) and (2r,5s)-1-boc-2,5-dimethylpiperazine (1.27 g, 5.96 mmol) was added to the reaction mixture and stirred an additional 10 min. The reaction mixture was diluted with EtOAc and sat. aq. NH$_4$Cl. The aqueous layer was extracted with EtOAc. The combined organic extracts were dried over MgSO$_4$, filtered and concentrated in vacuo. The crude material was absorbed onto a plug of silica gel and purified by chromatography through a Interchim (25 micron) silica-gel column (120 grams), eluting with a gradient of 0-50% EtOAc in CH2CL2, to afford tert-butyl (2R,5S)-4-(1-(6-bromo-2-isopropyl-4-methylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (1.16 g, 1.66 mmol, 41.9% yield, Intermediate 202) as tan solid. $^1$H NMR (400 MHz, DMSO-d$_6$) δ 8.44 (d, J=4.98 Hz, 1H) 7.48-7.56 (m, 2H) 7.23-7.36 (m, 3H) 4.83 (br s, 1H) 4.37 (br s, 1H) 4.14 (br d, J=13.48 Hz, 1H) 3.86 (br s, 1H) 3.71 (br d, J=13.89 Hz, 1H) 2.61-2.73 (m, 1H) 1.89-1.99 (m, 3H) 1.45 (s, 9H) 1.35 (d, J=6.63 Hz, 3H) 1.10-1.24 (m, 4H) 1.04 (dd, J=6.74, 2.80 Hz, 3H) 0.93 (dd, J=8.50, 6.84 Hz, 3H). m/z: (ESI, +ve ion): 699.0 (M+H)$^+$.

Intermediate 205

6,7-Dichloro-1-(4,6-diisopropylpyrimidin-5-yl)pyrido[2,3-d]pyrimidine-2,4(1H,3H)-dione

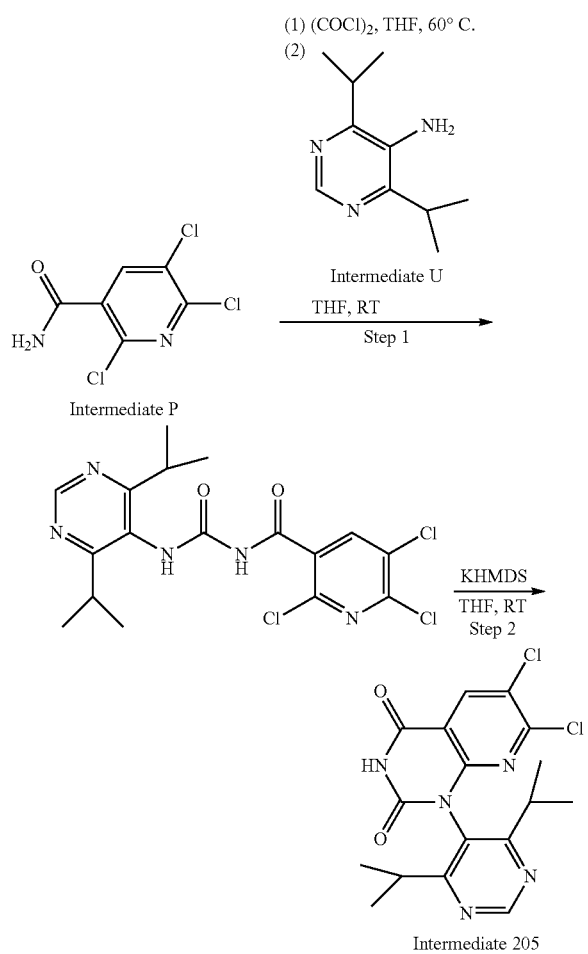

Intermediate 205

Step 1. 2,5,6-Trichloro-N-((4,6-diisopropylpyrimidin-5-yl)carbamoyl)nicotinamide To a 250-mL round-bottomed flask was added 2,5,6-trichloronicotinamide (Intermediate P, 4.450 g, 19.74 mmol) and oxalyl chloride (14.80 mL, 29.6 mmol) in tetrahydrofuran (39.5 mL). The flask was fitted with a Findenser, and the mixture was stirred and heated at 80° C. for 1 h. The reaction mixture was concentrated in vacuo. The crude mixture was carried into the next step of the synthesis, without further purification to prevent decomposition.

To a 250-mL round-bottomed flask was added (2,5,6-trichloronicotinoyl)carbamoyl isocyanate (crude material from previous step) in tetrahydrofuran (39.5 mL). Then a solution of 4,6-diisopropylpyrimidin-5-amine (Intermediate U, 3.72 g, 20.72 mmol) in THF (10 mL) was added dropwise into the reaction mixture. The mixture was allowed to stir under an inert (N2) atmosphere for 1.5 h. The reaction mixture was diluted with DCM (50 mL) and heptane (200 mL), then allowed the mixture to stir 30 min. The mixture was filtered and the filtrate (desired material) was collected, then concentrated in vacuo. The residue was triturated from a small amount of EtOAc (20 mL) and heptane (200 mL). The precipitate was collected by filtration and the solids were washed with heptane, to afford 2,5,6-trichloro-N-((4,6-diisopropylpyrimidin-5-yl)carbamoyl)nicotinamide (6.310 g, 14.65 mmol, 74.2% yield) as light-yellow solid. $^1$H NMR (400 MHz, DMSO-$d_6$) δ 11.35-11.49 (m, 1H) 9.60-9.87 (m, 1H) 8.91-9.13 (m, 1H) 8.56-8.78 (m, 1H) 3.23-3.30 (m, 2H) 1.17 (d, J=6.84 Hz, 12H). m/z (ESI, +ve ion): 430.1 (M+H)+.

Step 2. 6,7-Dichloro-1-(4,6-diisopropylpyrimidin-5-yl)pyrido[2,3-d]pyrimidine-2,4(1H,3H)-dione (Intermediate 205)

To a 250-mL round-bottomed flask was added 2,5,6-trichloro-N-((4,6-diisopropylpyrimidin-5-yl)carbamoyl)nicotinamide (3.125 g, 7.26 mmol) in tetrahydrofuran (36.3 mL). The reaction mixture was cooled to 0° C. in a wet ice/water bath. Then potassium bis(trimethylsilyl)amide, 1M solution in tetrahydrofuran (9.07 mL, 9.07 mmol) was added via an addition funnel dropwise into the reaction mixture over 5 min. The ice bath was removed and the reaction mixture was allowed to slowly warm to ambient temperature, while stirred under an inert (N2) atmosphere for 1 h. More KHMDS (0.5 eq; 6 mL) was added dropwise into the reaction mixture, until SM was mostly consumed *(Note: While adding reagent, carefully monitor reaction as side-product will form if too much KHMDS is added at this step) The reaction mixture was quenched with sat. aq. NH$_4$Cl (50 mL), then the mixture was diluted with 3:1 EtOAc/MeOH and brine solution. The layers were separated and the aqueous layer was extracted with EtOAc. The combined organic extracts were dried over MgSO$_4$, filtered and concentrated in vacuo. This afforded 6,7-dichloro-1-(4,6-diisopropylpyrimidin-5-yl)pyrido[2,3-d]pyrimidine-2,4(1H,3H)-dione (2.326 g, 5.90 mmol, 81% yield, Intermediate 205) as a light-yellow solid. $^1$H NMR (400 MHz, DMSO-$d_6$) δ 12.33 (br s, 1H) 9.18 (s, 1H) 8.60 (s, 1H) 2.95 (spt J=6.60 Hz, 2H) 1.09 (d, J=6.63 Hz, 6H) 0.99 (d, J=6.63 Hz, 6H). m/z (ESI, +ve ion): 394.1 (M+H)+.

Intermediate 206

(S)-4-(4-Acryloyl-2-methylpiperazin-1-yl)-6-chloro-7-(2-fluorophenyl)-1-(2-(hydroxymethyl)-6-isopropylphenyl)pyrido[2,3-d]pyrimidin-2(1H)-one, First Eluting Isomer

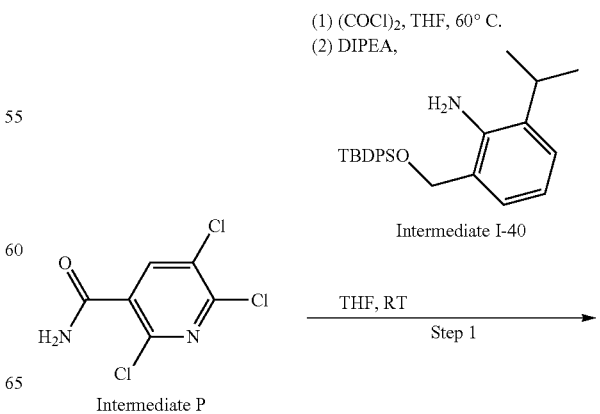

903
-continued

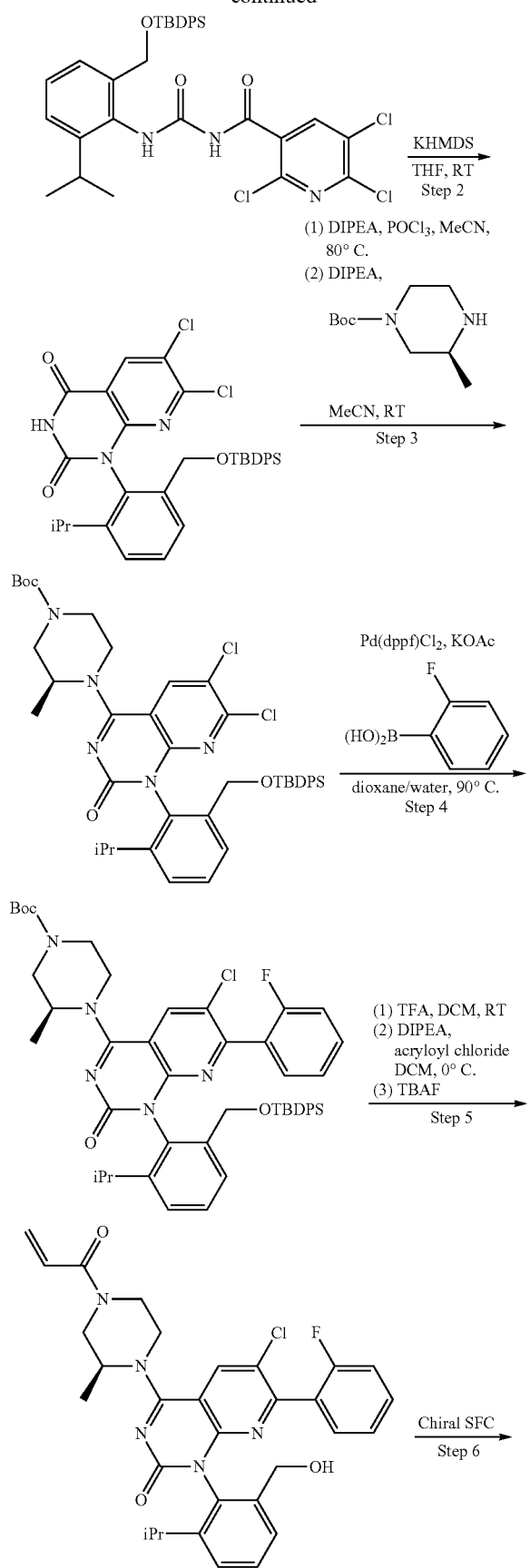

904
-continued

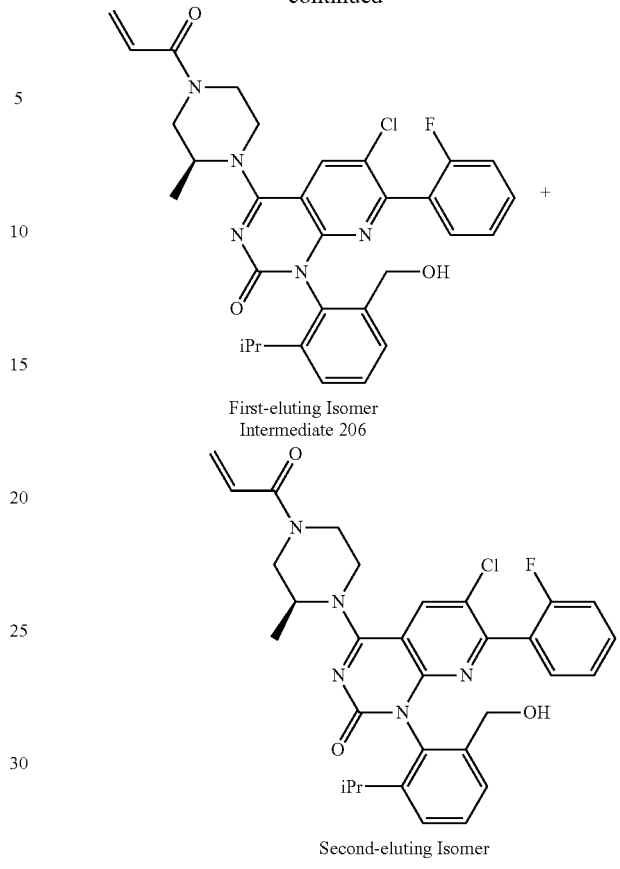

First-eluting Isomer
Intermediate 206

Second-eluting Isomer

Step 1: N-((2-(((tert-Butyldiphenylsilyl)oxy)methyl)-6-isopropylphenyl)carbamoyl)-2,5,6-trichloronicotinamide To a mixture of 2,5,6-trichloronicotinamide (Intermediate P, 0.70 g, 3.12 mmol) in THF (22 mL) was added oxalyl chloride, 2 M solution in DCM (1.71 mL, 3.43 mmol) at rt. The resulting yellow heterogeneous mixture was stirred and heated at 70° C. After 50 min, the mixture was concentrated and the residue redissolved in THF (8 mL). 2-(((tert-Butyldiphenylsilyl)oxy)methyl)-6-isopropylaniline (Intermediate I-40, 1.31 g, 3.25 mmol) was added as a solution in THF (7 mL), and the mixture was stirred at rt for 20 min. The mixture was evaporated and the residue was purified by chromatography on silica gel (0-40$ ethyl acetate in heptane) to give N-((2-(((tert-butyldiphenylsilyl)oxy)methyl)-6-isopropylphenyl)carbamoyl)-2,5,6-trichloronicotinamide (1.88 g, 2.88 mmol, 98% yield) as a white solid $^1$H NMR (400 MHz, DMSO-d6) δ 11.19 (1H, br s). 9.19-9.59 (1H, m), 8.50 (1H, s), 7.60-7.65 (4H, m), 7.41-7.48 (6H, m), 7.36-7.40 (2H, m), 7.29-7.33 (1H, m), 4.75 (2H, s), 3.07-3.16 (1H, m), 1.17 (6H, d, J=6.8 Hz), 1.03 (9H, s). m/z (ESI, +ve ion): 678.2 (M+Na)$^+$.

Step 2: 1-(2-(((tert-Butyldiphenylsilyl)oxy)methyl)-6-isopropylphenyl)-6,7-dichloropyrido[2,3-d]pyrimidine-2,4(1H,3H)-dione To a cooled mixture of N-((2-(((tert-butyldiphenyl silyl)oxy)methyl)-6-isopropylphenyl)carbamoyl)-2,5,6-trichloronicotinamide (1.88 g, 2.87 mmol) in THF (15 mL) at 0° C.

was added dropwise KHMDS, 1 M solution in THF (5.74 mL, 5.74 mmol) and the mixture was stirred at rt. After 40 min the mixture was cooled to 0° C. and KHMDS, 1 M solution in THF (1.0 mL, 1.0 mmol) was added. The mixture was stirred at rt 10 min and then quenched with half-satd. ammonium chloride (30 mL) and extracted with EtOAc (2×20 mL). The organic phase was washed with water (30 mL) and dried by passage through a Chem Elut extraction cartridge (10 mL, 1219-8007) eluting with ethyl acetate (2×10 mL). The filtrate was evaporated and the reside was purified by silica gel chromatography (0-40% ethyl acetate in heptane) to provide 1-(2-(((tert-butyldiphenylsilyl)oxy)methyl)-6-isopropylphenyl)-6,7-dichloropyrido[2,3-d]pyrimidine-2,4(1H,3H)-dione (1.15 g, 65% yield). $^1$H NMR (400 MHz, CHLOROFORM-d) δ 8.35 (s, 1H), 7.48-7.56 (m, 5H), 7.36-7.47 (m, 5H), 7.29-7.35 (m, 4H), 4.42-4.52 (m, 2H), 2.50-2.60 (m, 1H), 1.18 (d, J=6.84 Hz, 3H), 1.10 (d, J=6.84 Hz, 3H), 0.94 (s, 9H). m/z (ESI, +ve ion): 640.2 (M+Na)$^+$.

Step 3: tert-Butyl (S)-4-(1-(2-(((tert-butyldiphenylsilyl)oxy)methyl)-6-isopropylphenyl)-6,7-dichloro-2-oxo-1,2-dihydropyrido[2,3-d]pyrimidin-4-yl)-3-methylpiperazine-1-carboxylate A solution of 1-(2-(((tert-butyldiphenylsilyl)oxy)methyl)-6-isopropylphenyl)-6,7-dichloropyrido[2,3-d]pyrimidine-2,4(1H,3H)-dione (0.509 g, 0.823 mmol), DIPEA (0.187 mL, 1.07 mmol), and phosphoryl trichloride (0.092 ml, 0.987 mmol) in acetonitrile (5 ml) was stirred at 80° C. for 0.5 h. The reaction mixture cooled to rt, DIPEA (0.43 mL, 2.47 mmol) and tert-butyl (S)-3-methylpiperazine-1-carboxylate (0.181 g, 0.905 mmol) were added and the reaction was stirred at rt for 10 min. The mixture was poured into cold, satd. NaHCO$_3$ (20 mL) and stirred vigorously for 10 min. The mixture was partitioned between EtOAc (100 mL), and satd. NaHCO$_3$ (75 mL), the organic layer was washed with satd. NaHCO$_3$ (75 mL). The organic extract was dried by passage through a Chem Elut extraction cartridge (10 mL, 1219-8007) eluting with ethyl acetate (2×10 mL). The filtrate was evaporated and the reside was purified by silica gel chromatography (10-60% ethyl acetate in heptane) to provide tert-butyl (S)-4-(1-(2-(((tert-butyldiphenylsilyl)oxy)methyl)-6-isopropylphenyl)-6,7-dichloro-2-oxo-1,2-dihydropyrido[2,3-d]pyrimidin-4-yl)-3-methylpiperazine-1-carboxylate (0.584 g, 0.729 mmol, 89% yield). $^1$H NMR (400 MHz, CHLOROFORM-d) δ 7.84 (s, 1H), 7.52-7.56 (m, 2H), 7.45-7.51 (m, 3H), 7.28-7.44 (m, 7H), 4.63-5.03 (m, 1H), 4.45-4.57 (m, 2H), 3.73-4.36 (m, 4H), 3.40-3.71 (m, 1H), 2.72-3.32 (m, 2H), 2.40 (dt, J=2.90, 6.84 Hz, 1H), 1.51 (d, J=1.45 Hz, 9H), 1.31 (br d, J=6.63 Hz, 3H), 1.17 (dd, J=2.07, 6.63 Hz, 3H), 1.11 (dd, J=2.90, 6.84 Hz, 3H), 0.89 (s, 9H). m/z (ESI, +ve ion): 800.2 (M+H)$^+$.

Step 4: tert-Butyl (S)-4-(1-(2-(((tert-butyldiphenylsilyl)oxy)methyl)-6-isopropylphenyl)-6-chloro-7-(2-fluorophenyl)-2-oxo-1,2-dihydropyrido[2,3-d]pyrimidin-4-yl)-3-methylpiperazine-1-carboxylate A mixture of tert-butyl (S)-4-(1-(2-(((tert-butyldiphenylsilyl)oxy)methyl)-6-isopropylphenyl)-6,7-dichloro-2-oxo-1,2-dihydropyrido[2,3-d]pyrimidin-4-yl)-3-methylpiperazine-1-carboxylate (0.57 g, 0.712 mmol), 2-fluorophenyl boronic acid (Comi-Blocks, Inc., 119 mg, 0.852 mmol), Pd(dppf)Cl$_2$ (0.037 g, 0.050 mmol) and potassium acetate (0.358 g, 3.64 mmol) was purged with argon followed by the addition of 1,4-dioxane (7.5 mL) and a drop of water. The mixture was heated at 90° C. for 2 h. Fluorophenyl boronic acid (Comi-Blocks, Inc., 76.4 mg) and Pd(dppf)Cl$_2$ (29.9 mg) was added and the reaction was continued overnight. The mixture was cooled and fluorophenyl boronic acid (Comi-Blocks, Inc., 49.8 mg), Pd(dppf)Cl$_2$ (13.7 mg) and potassium acetate (98.8 mg) was added, the mixture was degassed by bubbling argon, a drop of water was added and the mixture was heated to 90 C for one hour. The mixture was cooled and filtered through diaomaceous earth. The filtrate was dried by passage though a ChemElute extraction cartridge (5 mL, 1219-0006) eluting with ethyl acetate. The solvent was evaporated and the residue was purified by chromatography on silica gel (20-80% ethyl acetate in heptane to provide tert-butyl (S)-4-(1-(2-(((tert-butyldiphenylsilyl)oxy)methyl)-6-isopropylphenyl)-6-chloro-7-(2-fluorophenyl)-2-oxo-12-dihydropyrido[2,3-d]pyrimidin-4-yl)-3-methylpiperazine-1-carboxylate as a light yellow foam (0.38 g, 0.44 mmol, 61% yield). $^1$H NMR (400 MHz, CHLOROFORM-d) δ 7.93 (d, J=2.28 Hz, 1H), 7.51-7.56 (m, 2H), 7.45-7.50 (m, 3H), 7.38-7.43 (m, 2H), 7.28-7.37 (m, 4H), 7.23-7.26 (m, 1H), 7.16-7.22 (m, 2H), 7.04-7.11 (m, 3H), 4.64-4.99 (m, 1H), 4.54-4.60 (m, 1H), 4.39-4.45 (m, 1H), 3.77-4.37 (m, 4H), 3.44-3.73 (m, 1H), 3.08-3.34 (m, 1H), 2.47-2.57 (m, 1H), 1.52 (s, 9H), 1.37 (d, J=6.84 Hz, 3H), 1.18 (br d, J=6.84 Hz, 3H), 1.01 (dd, J=2.90, 6.84 Hz, 3H), 0.91 (s, 9H). m/z (ESI, +ve ion): 860.4 (M+H)$^+$.

Step 5: (S)-4-(4-Acryloyl-2-methylpiperazin-1-yl)-6-chloro-7-(2-fluorophenyl)-1-(2-(hydroxymethyl)-6-isopropylphenyl)pyrido[2,3-d]pyrimidin-2(1H)-one A 250-mL round-bottomed flask was charged with tert-butyl (S)-4-(1-(2-(((tert-butyldiphenylsilyl)oxy)methyl)-6-isopropylphenyl)-6-chloro-7-(2-fluorophenyl)-2-oxo-1,2-dihydropyrido[2,3-d]pyrimidin-4-yl)-3-methylpiperazine-1-carboxylate (0.376 g, 0.437 mmol) and DCM (3 mL). TFA (1.5 mL, 19.5 mmol) was added and the mixture was stirred at rt for 25 min. The mixture was concentrated and redissolved in DCM (4 mL). The mixture was cooled in an ice water bath. DIPEA (0.382 mL, 2.19 mmol) was added followed by acryloyl chloride (1.78 mL, 0.437 mmol). The mixture was stirred at 0° C. for 10 min. The mixture was concentrated and the crude product was purified by chromatography on silica gel (EtOAc in heptanes 30%-100%) to afford 0.251 g of off-white foam.

The material was dissolved in THF (3 mL) and tetrabutylammonium fluoride (0.481 mL, 0.481 mmol) was added. The mixture was stirred at rt for 3 h. The mixture was concentrated and the crude product was purified by chromatography on silica gel (3:1 EtOAc/EtOH in heptanes 30%-100%) to provide (S)-4-(4-acryloyl-2-methylpiperazin-1-yl)-6-chloro-7-(2-fluorophenyl)-1-(2-(hydroxymethyl)-6-isopropylphenyl)pyrido[2,3-d]pyrimidin-2(1H)-one as an off-white solid (0.0102 g, 0.018 mmol, 4%). $^1$H NMR (400 MHz, CHLOROFORM-d) δ 8.10 (1H, s), 7.35-7.45 (4H, m), 7.05-7.19 (3H, m), 6.53-6.73 (1H, m), 6.37-6.47 (1H, m), 5.82 (1H, d, J=10.4 Hz), 4.54-5.22 (2H, m), 4.37-4.53 (1H, m), 4.36 (2H, br s), 3.87 (1H, br s), 3.63 (1H, br s), 2.98-3.37 (1H, m), 2.54 (1H, br s). 2.11-2.46 (1H, m), 1.65 (3H, br s), 1.22-1.28 (1H, m), 1.18 (3H, d, J=6.8 Hz), 0.96-1.03 (3H, m). m/z (ESI, +ve ion): 576.2 (M+H)$^+$.

Step 6: (S)-4-(4-Acryloyl-2-methylpiperazin-1-yl)-6-chloro-7-(2-fluorophenyl)-1-(2-(hydroxymethyl)-6-isopropylphenyl)pyrido[2,3-d]pyrimidin-2(1H)-one, first eluting isomer (Intermediate 206)

The mixture was purified by SFC (Chiralpak IE (150×20 mm, 5 µm), 50% MeOH/CO$_2$, 60 mL/min, 165 bar), to provide (S)-4-(4-Acryloyl-2-methylpiperazin-1-yl)-6-chloro-7-(2-fluorophenyl)-1-(2-(hydroxymethyl)-6-isopropylphenyl)pyrido[2,3-d]pyrimidin-2(1H)-one (Intermediate 206, as the first-eluting isomer. $^1$H NMR (400 MHz, METHANOL-$d_4$) δ 8.43 (br d, J=4.56 Hz, 1H), 7.34-7.50 (m, 4H), 7.10-7.25 (m, 3H), 6.84 (dt, J=10.68, 16.53 Hz, 1H), 6.32 (br d, J=16.59 Hz, 1H), 5.83 (dd, J=1.87, 10.57 Hz, 1H), 5.05 (br s, 1H), 4.42-4.62 (m, 2H), 4.34-4.41 (m, 1H), 4.24-4.30 (m, 1H), 4.04-4.23 (m, 1H), 3.58-3.90 (m, 2H), 3.33-3.43 (m, 1H), 3.17-3.29 (m, 1H), 2.51-2.66 (m, 1H), 1.49 (br d, J=6.63 Hz, 3H), 1.15 (d, J=6.84 Hz, 3H), 1.00 (d, J=6.84 Hz, 3H). m/z (ESI, +ve ion): 576.2 (M+H)$^+$. The second eluting isomer was also characterized. $^1$H NMR (400 MHz, METHANOL-$d_4$) δ 8.43 (br d, J=4.35 Hz, 1H), 7.34-7.50 (m, 4H), 7.10-7.26 (m, 3H), 6.77-6.92 (m, 1H), 6.31 (br dd, J=3.01, 16.90 Hz, 1H), 5.83 (dd, J=1.87, 10.57 Hz, 1H), 5.09 (br s 1H), 4.55 (br d, J=5.81 Hz, 1H), 4.45 (br d, J=4.56 Hz, 1H), 4.34-4.41 (m, 1H), 4.23-4.32 (m, 1H), 4.03-4.21 (m, 1H), 3.82-3.95 (m, 1H), 3.55-3.79 (m, 1H), 3.34-3.44 (m, 1H), 3.16-3.28 (m, 1H), 2.51-2.66 (m, 1H), 1.48 (br d, J=6.43 Hz, 3H), 1.16 (d, J=6.84 Hz, 3H), 1.00 (d, J=6.84 Hz, 3H). m/z (ESI, +ve ion): 576.2 (M+H)$^+$.

Intermediate 207

4-(((tert-Butyldiphenylsilyl)oxy)methyl)-2-isopropylpyridin-3-amine

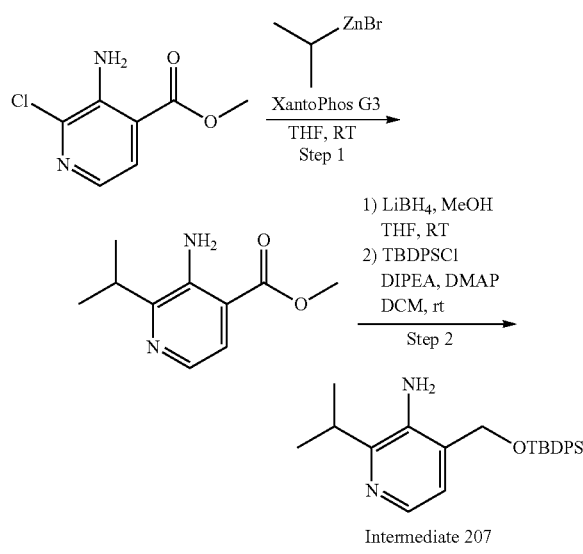

Step 1. Methyl 3-amino-2-isopropylisonicotinate

A 250-mL round-bottomed flask was charged with 3-amino-2-chloro-4-(methoxycarbonyl)pyridine (3.09 g, 16.6 mmol, Combi-Block, Inc.), methanesulfonato[9,9-dimethyl-4,5-bis(diphenylphosphino)xanthene][2'-amino-1,1'-biphenyl]palladium(ii) dichloromethane adduct (Xantophos G3) (0.862 g, 0.835 mmol,) and THF (50 mL) under argon. 2-Propylzinc bromide (0.5 M in THF, 43.1 mL, 21.5 mmol, Aldrich) was added slowly via addition funnel. The addition funnel was swapped with a Findensor condenser and the mixture was stirred at 50° C. for 20 min. The mixture was cooled to rt then placed in an ice water bath. Water (~80 mL) and EtOAc (~50 mL) were added and the mixture was filtered through fine frit glass filter funnel (eluent:EtOAc) to remove insoluble emulsions. The phases were separated and the aqueous phase was extracted with EtOAc (2×50 mL). The combined organic phases were dried over sodium sulfate, filtered and concentrated. A chromatographic purification (silica gel, 5-60% EtOAc/heptane) obtained methyl 3-amino-2-isopropylisonicotinate (2.31 g, 11.9 mmol, 72% yield) as a yellow oil. $^1$H NMR (400 MHz, CHLOROFORM-d) δ 7.94 (1H, d, J=5.2 Hz), 7.50 (1H, d, J=5.2 Hz), 5.87 (2H, br s), 3.91 (3H, s), 3.08 (1H, dt, J=13.5, 6.7 Hz), 1.32 (6H, d, J=6.8 Hz). m/z (ESI, +ve ion): 195.2 [M+H].

Step 2. 4-(((tert-Butyldiphenylsilyl)oxy)methyl)-2-isopropylpyridin-3-amine

A 100-mL round-bottomed flask was charged with methyl 3-amino-2-isopropylisonicotinate (2.20 g, 11.3 mmol) and THF (20 mL). Lithium borohydride (2 M in THF, 8.49 mL, 17.0 mmol, Aldrich) was added dropwise. The mixture was stirred at rt for 15 min. Then methanol (3.67 mL, 91 mmol) was added slowly and the mixture was stirred at rt for 18 h. Saturated NH$_4$Cl (~20 mL) was added slowly. The aqueous phase was extracted with EtOAc (2×20 mL). The combined organic phases were dried over Na$_2$SO$_4$, filtered and concentrated. This material was dissolved in DCM (20 mL). Benzene, 1,1'-[chloro(1,1-dimethylethyl)silylene]bis- (3.83 mL, 14.7 mmol), DIPEA (6.92 mL, 39.6 mmol) and DMAP (0.0707 g, 0.579 mmol) were added and the mixture was stirred at rt for 20 h. The mixture was washed with water. The organic phase was dried over sodium sulfate, filtered and concentrated in vacuo. A chromatographic purification (silica gel, 0-40% EtOAc/heptane) afforded 4-(((tert-butyldiphenylsilyl)oxy)methyl)-2-isopropylpyridin-3-amine (Intermediate 207, 1.31 g, 3.25 mmol, 29% yield). $^1$H NMR (400 MHz, CHLOROFORM-d) δ 7.97 (1H, d, J=4.8 Hz), 7.68 (4H, dd, J=8.1, 1.5 Hz), 7.37-7.43 (6H, m), 6.73 (1H, d, J=4.8 Hz), 4.68 (2H, s), 4.19 (2H, br s). 3.04-3.14 (1H, m), 1.34 (6H, d, J=6.6 Hz), 1.07 (9H, s). m/z (ESI, +ve ion): 405.2 [M+H].

Intermediate 208

4-(((tert-Butyldiphenylsilyl)oxy)methyl)-6-isopropylpyrimidin-5-amine

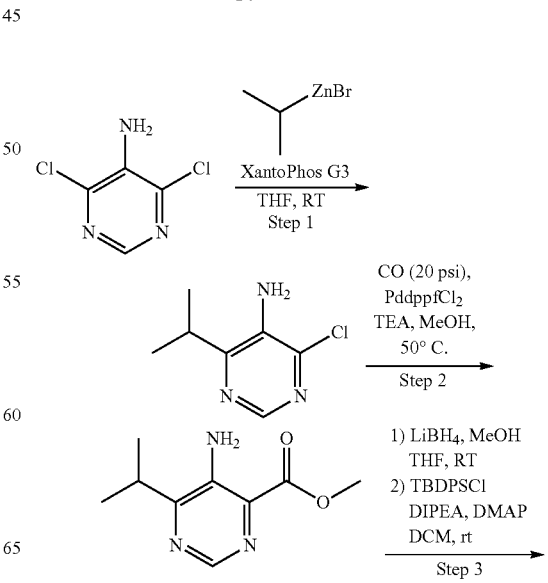

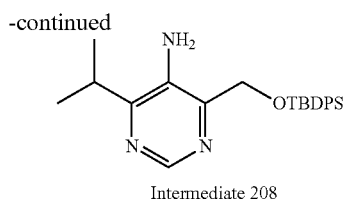

Intermediate 208

Step 1. 4-Chloro-6-isopropylpyrimidin-5-amine

A 250-mL round-bottomed flask was charged with 4,6-dichloro-5-aminopyrimidine (3.01 ml, 18.4 mmol) and THF (20 mL). XantPhos Pd G3 (0.957 g, 0.926 mmol) was added and 2-propylzinc bromide (1.0 M in THF, 19.3 ml, 19.3 mmol, Tieki Metal) was added dropwise via addition funnel. The mixture was stirred at rt for 20 h. Additional 2-propylzinc bromide (10 mL) was added slowly and the mixture was stirred at rt for 3 h. The reaction mixture was diluted with EtOAc (150 mL), added to a separatory funnel, and washed with saturated, aqueous ammonium chloride (3×75 mL). The organic layer was separated, dried over anhydrous $Na_2SO_4$, and concentrated in vacuo. A chromatographic purification (silica gel, 0-40% EtOAc/heptane) afforded 4-chloro-6-isopropylpyrimidin-5-amine (0.912 g, 5.31 mmol, 29% yield) as a yellow solid. $^1$H NMR (400 MHz, CHLOROFORM-d) δ 8.39 (1H, s), 4.10 (2H, br s), 3.02 (1H, spt, J=6.7 Hz), 1.31 (6H, d, J=6.8 Hz). m/z (ESI, +ve ion): 172.1 [M+1].

Step 2. Methyl 5-amino-6-isopropylpyrimidine-4-carboxylate

4-Chloro-6-isopropylpyrimidin-5-amine (0.75 g, 4.4 mmol), TEA (1.83 mL, 13.1 mmol), PddppfCl$_2$ (0.327 g, 0.447 mmol, Strem) were suspended in MeOH (15 mL). The suspension was divided into 4 reaction glass tube and stirred at 50° C. under 20 psi CO for 18 h using Endeavor reactor (Biotage). The reaction mixture was combined and concentrated. A chromatographic purification (silica gel, 20-80% EtOAc/heptane) afforded methyl 5-amino-6-isopropylpyrimidine-4-carboxylate (0.871, g 4.46 mmol, 100% yield) as light yellow solid. $^1$H NMR (400 MHz, CHLOROFORM-d) δ 8.64 (1H, s), 5.87 (2H, br s), 4.00 (3H, s), 3.10 (1H, dt, J=13.4, 6.7 Hz), 1.34 (6H, d, J=6.8 Hz). m/z (ESI, +ve ion): 196.1 [M+H].

Step 3. 4-(((tert-Butyldiphenylsilyl)oxy)methyl)-6-isopropylpyrimidin-5-amine To a stirred solution of methyl 5-amino-6-isopropylpyrimidine-4-carboxylate (0.870 g, 4.46 mmol) in THF (10 mL) was added a solution of lithium borohydride (2 M in THF, 3.34 mL, 6.68 mmol, Aldrich) dropwise. After the addition was completed, the reaction mixture was stirred for 15 min. Then methanol (1.44 mL, 35.7 mmol) was added slowly. The reaction mixture was then stirred at RT for 18 h. 10 mL of saturated NH$_4$Cl was added slowly. The aqueous phase was extracted with EtOAc (3×10 mL). The combined organic phases were dried over Na$_2$SO$_4$, filtered and concentrated. This material was dissolved into DCM (10 mL). tert-butylchlorodiphenylsilane (1.51 mL, 5.79 mmol), DIPEA (2.72 mL, 15.6 mmol) and DMAP (0.031 g, 0.25 mmol) were added and the mixture was stirred at rt for 20 h. The reaction mixture was washed with water and dried over Na$_2$SO$_4$, filtered and concentrated. A chromatographic puridication (silica gel, 0-40% EtOAc/heptane) afforded 4-(((tert-butyldiphenylsilyl)oxy)methyl)-6-isopropylpyrimidin-5-amine (Intermediate 208, 1.12 g, 2.76 mmol, 62% yield) as a clear oil. $^1$H NMR (400 MHz, CHLOROFORM-d) δ 8.47 (1H, s), 7.64-7.69 (4H, m), 7.42-7.47 (2H, m), 7.36-7.41 (4H, m), 4.91 (2H, s), 4.55 (2H, br s), 3.06 (1H, quin, J=6.7 Hz), 1.32 (6H, d, J=6.8 Hz), 1.09 (9H, s). m/z (ESI, +ve ion): 406.1 [M+H].

Intermediate 209

5-Methyl-4-(4,4,5,5-tetramethyl-1,3,2-dioxaborolan-2-yl)indolin-2-one

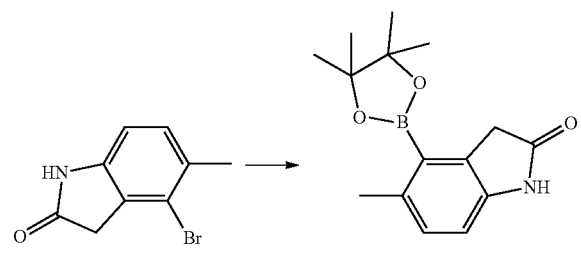 [SMILES: Cc1ccc2c(c1Br)CC(=O)N2 ; Cc1ccc2c(c1B1OC(C)(C)C(C)(C)O1)CC(=O)N2]

To a pressure vial was added 4-bromo-5-methylindolin-2-one (0.5 g, 2.21 mmol, ChemShuttle, Hayward, Calif.), bis(pinacolato)diboron (1.12 g, 4.42 mmol, Matrix Scientific, Columbia, S.C.), [1,1'-bis(diphenylphosphino)ferrocene]-dichloropalladium(ii), complex with dichloromethane (0.181 g, 0.221 mmol, Sigma-Aldrich, St. Louis, Mo.), potassium acetate (0.651 g, 6.64 mmol) and 1,4-dioxane (10 mL). The vial was purged with N$_2$ for 3 min, sealed and then heated at 100° C. for 18 h. LCMS showed convesion of the starting material was complete. The reaction mixture was partitioned between EtOAc and water. The separated organic layer was washed with brine, dried over Na2SO4 and then filtered. The filtrate was concentrated and purified by silica gel chromatography (0-40% (3:1 EtOAc:EtOH)/heptane) to afford 5-methyl-4-(4,4,5,5-tetramethyl-1,3,2-dioxaborolan-2-yl)indolin-2-one (Intermediate 209, 0.365 g, 1.336 mmol, 60.4% yield) as an off-white solid. 1H NMR (400 MHz, DMSO-d$_6$) δ 1.36 (s, 12H) 2.41 (s, 3H) 3.51 (s, 2H) 6.80 (d, J=7.67 Hz, 1H) 7.02 (d, J=7.88 Hz, 1H) 10.26 (s, 1H), m/z (ESI, +ve ion): 274.1 (M+H)$^+$.

Intermediate 210

3-Amino-4-isopropyl-N,N-dimethylpicolinamide

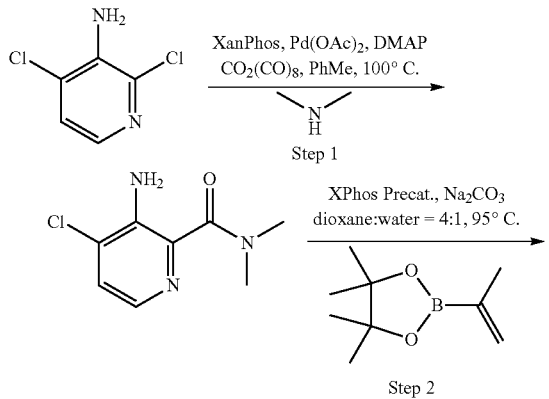

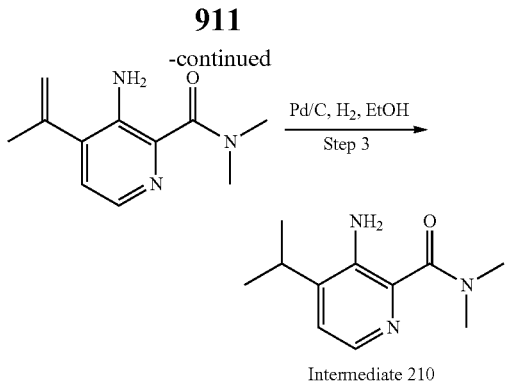

Intermediate 210

Step 1:
3-Amino-4-chloro-N,N-dimethylpicolinamide

To a 20 mL microwave vial was added palladium (II) acetate (0.070 g, 0.312 mmol, Strem Chemicals, Newburyport Mass.), 9,9-dimethyl-4,5-bis(bis[3,5-dimethyl-4-methoxyphenyl]phosphino)xanthene (0.355 g, 0.613 mmol, Strem Chemicals. Newburyport, Mass.) and 4-(dimethylamino) pyridine (1.5 g, 12.3 mmol, Aldrich. St. Louis, Mo.). The vial was purged with Ar followed by adding 2,4-dichloro-3-aminopyridine (1.0 g, 6.13 mmol, Combi-Blocks, San Diego, Calif.) in toluene (10 mL) and dimethylamine solution, 2 M in THF (6.13 mL, 12.3 mmol, Aldrich, St. Louis, Mo.). The vial was capped and underwent microwave heating at 100° C. for 30 min. The reaction was partitioned between EtOAc (60 mL) and water (30 mL). The aqueous layer was extracted with EtOAc (50 mL). The combined organic layers were dried over MgSO$_4$, filtered, and concentrated. The crude product was purified by silica gel chromatography (eluent: 5-40% acetone/heptane) to provide 3-amino-4-chloro-N,N-dimethylpicolinamide as a light brown oil (0.620 g). $^1$H NMR (400 MHz, CHLOROFORM-d) δ 7.86 (d, J=4.98 Hz, 1H), 7.23 (d, J=4.98 Hz, 1H), 5.20 (br s, 2H), 3.14 (s, 3H), 3.13 (s, 3H). m/z (ESI) M+H: 200.2.

Step 2: 3-Amino-N,N-dimethyl-4-(prop-1-en-2-yl)picolinamide

To a 150 mL round bottom flask was added 3-amino-4-chloro-N,N-dimethylpicolinamide (1.2 g, 6.01 mmol), chloro(2-dicyclohexylphosphino-2',4',6'-tri-i-propyl-1,1'-biphenyl)[2-(2-aminoethyl)phenyl] palladium(II) methyl-t-butylether adduct (0.350 g, 0.423 mmol, Strem Chemicals, Newburyport, Mass.), sodium carbonate (1.6 g, 15.1 mmol, Aldrich, St. Louis, Mo.), 1,4-dioxane (40 mL), water (10 mL), and 2-isopropenylboronic acid, pincol ester (4.04 g, 24.04 mmol, Aurum Pharmatech, Franklin Park, N.J.). The resulting mixture was heated at 95° C. under N$_2$ for 2 h. The reaction was cooled to rt and partitioned between EtOAc (60 mL) and water (20 mL). The aqueous layer was extracted with EtOAc (30 mL). The combined organic layers were dried over MgSO$_4$, filtered, and concentrated. The crude product was purified by silica gel chromatography (eluent: 5-40% acetone/heptane) to provide 3-amino-N,N-dimethyl-4-(prop-1-en-2-yl)picolinamide as a light brown oil (1.2 g). $^1$H NMR (400 MHz, CHLOROFORM-d) δ 7.93 (d, J=4.77 Hz, 1H), 6.95 (d, J=4.77 Hz, 1H), 5.40 (t, J=1.45 Hz, 1H), 5.15 (s, 1H), 4.88 (br s, 2H), 3.14 (d, J=4.35 Hz, 6H), 2.07 (s, 3H). m/z (ESI) M+H: 206.2

Step 3: 3-Amino-4-isopropyl-N,N-dimethylpicolinamide

A 250 mL hydrogenation apparatus was pre-treated with N$_2$. Palladium 10 wt. % on activated carbon (0.311 g, 0.292 mmol, Aldrich, St. Louis, Mo.) was added. A solution of 3-amino-N,N-dimethyl-4-(prop-1-en-2-yl)picolinamide (1.2 g, 5.85 mmol) in ethanol (50 mL) was then added. The cylinder was sealed, purged with H$_2$ then vented and this procedure was repeated. Fresh H2 was then introduced to 30 psi. The reaction mixture was stirred under H2 for 2 h. Reaction mixture was filtered through a plug of celite, and rinsed with MeOH. The resulting filtrate was concentrated to provide 3-amino-4-isopropyl-N,N-dimethylpicolinamide as brown solid (1.16 g, Intermediate 210). $^1$H NMR (400 MHz, CHLOROFORM-d) δ 7.96 (d, J=4.98 Hz, 1H), 7.06 (d, J=4.98 Hz, 1H), 4.73 (br s, 2H), 3.12 (br d, J=18.24 Hz, 6H), 2.90 (s, 1H), 1.28 (d, J=6.84 Hz, 6H). m/z (ESI) M+H: 208.3.

Intermediate 211 tert-Butyl (2R,5S)-4-(1-(4-(bis(4-methoxybenzyl)amino)-6-isopropylpyrimidin-5-yl)-6,7-dichloro-2-oxo-1,2-dihydropyrido[2,3-d]pyrimidin-4-yl)-2,5-dimethylpiperazine-1-carboxylate

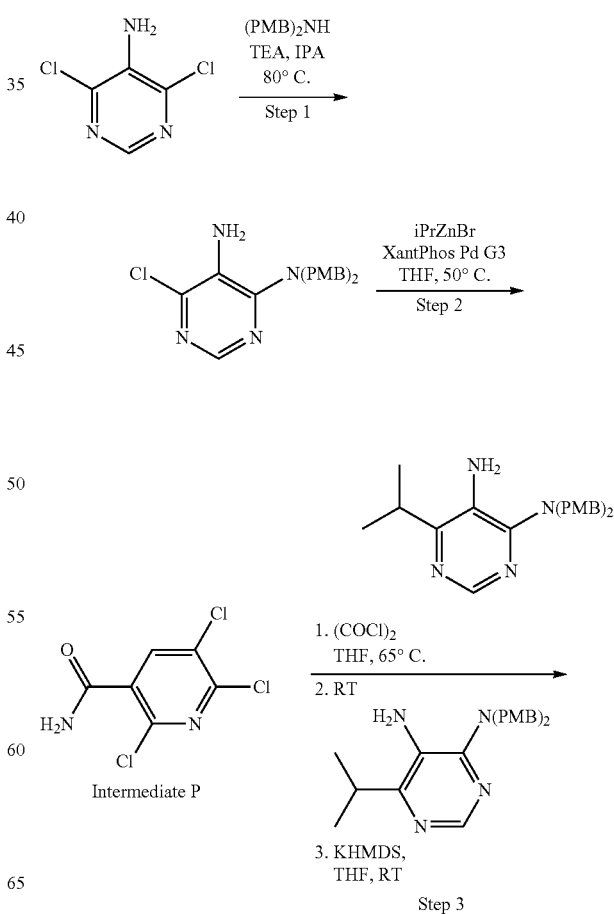

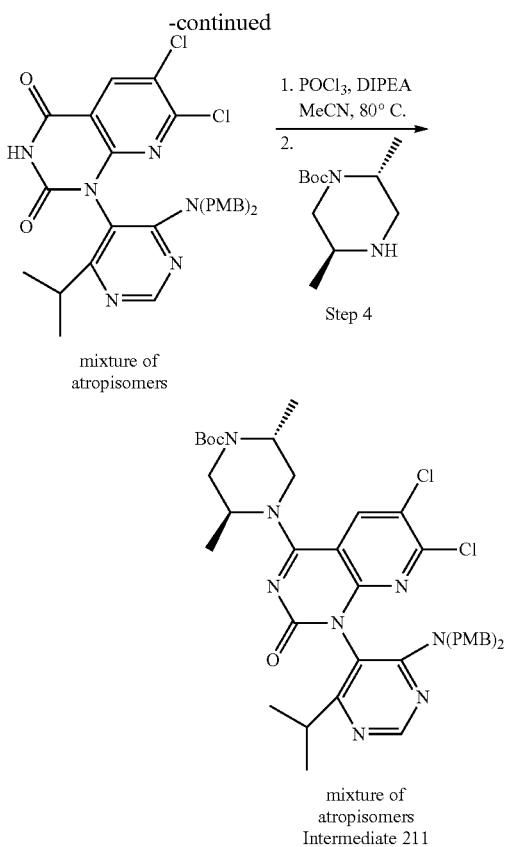

Step 1: 6-Chloro-N⁴,N⁴-bis(4-methoxybenzyl)pyrimidine-4,5-diamine

An amber solution of 4,6-dichloropyrimidin-5-amine (1.7 g, 10.4 mmol; CombiBlocks, Inc., San Diego, Calif.), bis(4-methoxybenzyl)amine (2.67 g, 10.4 mmol; Sigma-Aldrich, St. Louis, Mo.), and Et$_3$N (2.89 mL, 20.7 mmol) in isopropanol (10 mL) was stirred in the microwave at 120° C. for 1 h then at 160° C. for 1 h. The reaction mixture was diluted with EtOAc (200 mL), added to a separatory funnel, and washed with water (3×75 mL); the organic layer was separated, dried over anhydrous Na$_2$SO$_4$, and concentrated in vacuo. The crude product was adsorbed onto silica and was purified via automated flash chromatography (silica gel, 0-50% EtOAc/heptane) to give 6-chloro-N⁴,N⁴-bis(4-methoxybenzyl)pyrimidine-4,5-diamine (2.11 g, 5.48 mmol, 53% yield) as an amber oil. ¹H NMR (400 MHz, CDCl$_3$) δ 8.12 (s, 1H) 7.14 (br d, J=8.1 Hz, 4H) 6.85 (br d, J=8.5 Hz, 4H) 4.47 (br s, 4H) 3.91 (br s, 2H) 3.80 (s, 6H). MS (ESI, +ve) m/z: 385.0 (M+1)⁺.

Step 2: 6-Isopropyl-N⁴,N⁴-bis(4-methoxybenzyl)pyrimidine-4,5-diamine

A solution of 6-chloro-N⁴,N⁴-bis(4-methoxybenzyl)pyrimidine-4,5-diamine (2.11 g, 5.48 mmol), isopropylzinc bromide in THF (11.5 mL, 5.75 mmol), and XantPhos Pd G3 (0.283 g, 0.274 mmol) in 1,4-dioxane (5 mL) was stirred at RT for 2 h. More isopropylzinc bromide in THF (11.5 mL, 5.75 mmol) was added, and the reddish solution was stirred at 50° C. for 16 h. The reaction mixture was diluted with EtOAc (150 mL), added to a separatory funnel, and washed with saturated, aqueous ammonium chloride (2×100 mL); the organic layer was separated, dried over anhydrous Na$_2$SO$_4$, and concentrated in vacuo. The crude product was adsorbed onto silica and was purified via automated flash chromatography (silica gel, 0-80% EtOAc/heptane) to give 6-isopropyl-N⁴,N⁴-bis(4-methoxybenzyl)pyrimidine-4,5-diamine (1.24 g, 3.15 mmol, 58% yield) as a brown oil. ¹H NMR (400 MHz, CDCl$_3$) δ 8.39 (s, 1H) 7.13 (d, J=8.5 Hz, 4H) 6.82 (d, J=8.7 Hz, 4H) 4.32 (s, 4H) 3.79 (s, 6H) 3.67 (s, 2H) 3.01 (spt, J=6.7 Hz, 1H) 1.30 (d, J=6.8 Hz, 6H). MS (ESI, +ve) m/z: 393.0 (M+1)⁺.

Step 3: [1-(4-(bis(4-Methoxybenzyl)amino)-6-isopropylpyrimidin-5-yl)-6,7-dichloropyrido[2,3-d]pyrimidine-2,4(1H,3H)-dione Oxalyl chloride (2 M in DCM. 1.73 mL, 3.46 mmol) was added to a mixture of 2,5,6-trichloronicotinamide (0.710 g, 3.15 mmol, Intermediate P) in tetrahydrofuran (16 mL); the mixture was stirred at 65° C. for 30 min. The reaction mixture was poured into a flask containing 6-isopropyl-N4,N4-bis(4-methoxybenzyl)pyrimidine-4,5-diamine (1.236 g, 3.15 mmol), and the reaction mixture was stirred at RT for 15 min. The reaction mixture was diluted with EtOAc (150 mL), added to a separatory funnel, and washed with saturated, aqueous sodium bicarbonate (2×100 mL); the organic layer was separated, dried over anhydrous Na$_2$SO$_4$, and concentrated in vacuo to give N-((4-(bis(4-methoxybenzyl)amino)-6-isopropylpyrimidin-5-yl)carbamoyl)-2,5,6-trichloronicotinamide (2.30 g, 3.57 mmol, >99% yield) as an amber foam. MS (ESI, +ve) m/z: 642.7/644.8 (M+1)⁺.

A solution of N-((4-(bis(4-methoxybenzyl)amino)-6-isopropylpyrimidin-5-yl)carbamoyl)-2,5,6-trichloronicotinamide (2.03 g, 3.15 mmol) and potassium bis(trimethylsilyl)amide (1 M in THF, 6.30 mL, 6.30 mmol) in tetrahydrofuran (16 mL) was stirred at RT for 2 min. The reaction mixture was diluted with EtOAc (100 mL), added to a separatory funnel, and washed with saturated, aqueous ammonium chloride (2×75 mL); the organic layer was separated, dried over anhydrous Na$_2$SO$_4$, and concentrated in vacuo. The crude product was adsorbed onto silica and was purified via automated flash chromatography (silica gel, 0-70% EtOAc/heptane) to give 1-(4-(bis(4-methoxybenzyl)amino)-6-isopropylpyrimidin-5-yl)-6,7-dichloropyrido[2,3-d]pyrimidine-2,4(1H,3H)-dione (1.22 g, 2.00 mmol, 64% yield) as a light yellow amorphous solid and a mixture of atopisomers (first eluting product with desired mass). ¹H NMR (400 MHz, CDCl$_3$) δ 8.76 (s, 1H) 8.16 (br. s., 1H) 8.13 (s, 1H) 6.93-6.97 (m, 4H) 6.69-6.74 (m, 4H) 4.83 (d, J=16.8 Hz, 2H) 4.46 (d, J=16.8 Hz, 2H) 3.76 (s, 6H) 2.35-2.47 (m, 1H) 1.18 (d, J=6.6 Hz, 3H) 0.99 (d, J=6.6 Hz. 3H). MS (ESI, +ve) m/z: 606.8 (M+1)⁺.

Step 4: tert-Butyl (2R,5S)-4-(~(4-(bis(4-methoxybenzyl)amino)-6-isopropylpyrimidin-5-yl)-6,7-dichloro-2-oxo-1,2-dihydropyrido[2,3-d]pyrimidin-4-yl)-2,5-dimethylpiperazine-1-carboxylate A solution of 1-(4-(bis(4-methoxybenzyl)amino)-6-isopropylpyrimidin-5-yl)-6,7-dichloropyrido[2,3-d]pyrimidine-2,4(1H,3H)-dione (1.22 g, 2.00 mmol), phosphoryl trichloride (0.224 mL, 2.40 mmol), and DIPEA (1.05 mL, 6.01 mmol) in acetonitrile (5 mL) was stirred at 80° C. for 30 min. The reaction mixture was removed from the reaction block, and a solution of tert-butyl (2R,5S)-2,5-dimethylpiperazine-1-carboxylate (0.515 g, 2.40 mmol; eNovation Chemicals LLC, Bridgewater, N.J.) in acetonitrile (5 mL)

was added; the reaction mixture was stirred at RT for 1 h. The reaction mixture was diluted with EtOAc (100 mL), added to a separatory funnel, and washed with saturated, aqueous sodium bicarbonate (2×75 mL); the organic layer was separated, dried over anhydrous Na₂SO₄, and concentrated in vacuo. The crude product was loaded onto the column and was purified via automated flash chromatography (silica gel, 0-90% [(3:1) EtOAc/EtOH]/heptane) to give tert-butyl (2R,5S)-4-(1-(4-(bis(4-methoxybenzyl)amino)-6-isopropylpyrimidin-5-yl)-6,7-dichloro-2-oxo-1,2-dihydro-pyrido[2,3-d]pyrimidin-4-yl)-2,5-dimethylpiperazine-1-carboxylate (Intermediate 211, 1.15 g, 1.43 mmol, 71% yield) as a yellow solid and a mixture of atropisomers. ¹H NMR (400 MHz, CDCl₃) δ 8.72 (s, 1H) 7.61-7.71 (m, 1H) 6.94 (t, J=8.4 Hz, 4H) 6.62-6.73 (m, 4H) 5.05 (br d, J=16.8 Hz, 1H) 4.88 (br d, J=16.6 Hz, 1H) 4.47-4.69 (m, 1H) 4.30 (dd, J=16.5, 12.1 Hz, 2H) 3.75 (s, 3H) 3.74 (s, 3H) 3.25-3.94 (m, 5H) 2.25-2.42 (m, 1H) 1.50 (s, 9H) 1.26 (t, J=7.2 Hz, 3H) 1.16-1.24 (m, 6H) 0.85-1.00 (m, 3H). MS (ESI, +ve) m/z: 802.7 (M+1)⁺.

Intermediate 212

6-Chloro-1-(3,5-diisopropylpyridazin-4-yl)-7-(2-fluorophenyl)pyrido[2,3-d]pyrimidine-2,4(1H,3H)-dione

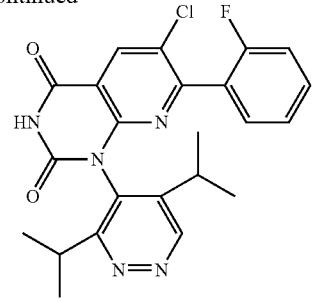

mixture of atropisomers
Intermediate 212

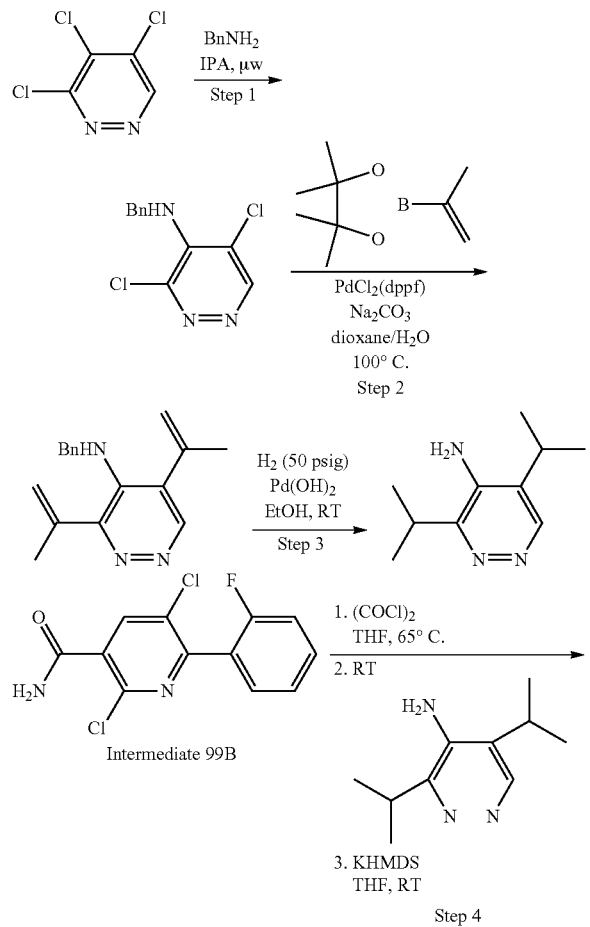

Step 1: N-Benzyl-3,5-dichloropyridazin-4-amine

A solution of 3,4,5-trichloropyridazine (2.04 g, 11.1 mmol; CombiBlocks, Inc., San Diego, Calif.) and benzylamine (3.65 mL, 33.4 mmol; Sigma-Aldrich, St. Louis, Mo.) in isopropanol (10 mL) was heated in the microwave at 120° C. for 20 min when a solid had formed (run four times) and two isomers with product mass were observed. The four reaction mixtures were cooled to RT, suspended in heptane, and filtered to give an off-white solid (mostly the undesired isomer). The solute was concentrated to give a reddish oil; the resulting oil (in DCM/MeOH) was loaded onto the column and was purified via automated flash chromatography (silica gel. 0-40% EtOAc/heptane) to give N-benzyl-3,5-dichloropyridazin-4-amine (3.92 g, 15.4 mmol, 35% yield) as a reddish oil which became a yellowish waxy solid overnight. ¹H NMR (400 MHz, CDCl₃) δ 8.63 (s, 1H) 7.29-7.43 (m, 5H) 5.22-5.29 (m, 1H) 4.93 (d, J=6.0 Hz, 2H). MS (ESI, +ve) m/z: 254.0 (M+1)⁺.

Step 2: N-Benzyl-3,5-di(prop-1-en-2-yl)pyridazin-4-amine

A mixture (separated into 4 equal reactions, ~1 g each) of N-benzyl-3,5-dichloropyridazin-4-amine (3.92 g, 15.4 mmol), 4,4,5,5-tetramethyl-2-(prop-1-en-2-yl)-1,3,2-dioxaborolane (11.6 mL, 61.8 mmol), PdCl2(dppf) (0.791 g, 1.081 mmol), and sodium carbonate (2 M aq., 30.9 mL, 61.8 mmol) in 1,4-dioxane (39 mL) was sparged with nitrogen then was heated in the microwave at 160° C. for 1 h. Each reaction mixture was diluted with EtOAc (150 mL), added to a separatory funnel, and washed with saturated, aqueous sodium bicarbonate (2×100 mL); the organic layer was separated, dried over anhydrous Na₂SO₄. The combined crude products were adsorbed onto silica and were purified via automated flash chromatography (silica gel, 0-80% [(3:1) EtOAc/EtOH]/heptane) to give N-benzyl-3,5-di(prop-1-en-2-yl)pyridazin-4-amine (2.24 g, 8.44 mmol, 54.7% yield) as a brown oil. ¹H NMR (400 MHz, CDCl₃) δ 8.46 (s, 1H) 7.27-7.37 (m, 3H) 7.11-7.19 (m, 2H) 5.51 (t, J=1.6 Hz, 1H) 5.35 (t, J=1.6 Hz, 1H) 5.23 (s, 1H) 5.15 (s, 1H) 4.90 (br t, J=5.6 Hz 1H) 4.39 (d, J=6.2 Hz, 2H) 2.16 (s, 3H) 2.05 (s, 3H). MS (ESI, +ve) m/z: 266.1 (M+1)⁺.

Step 3: 3,5-Diisopropylpyridazin-4-amine

Palladium hydroxide on carbon, wet (1.19 g, 0.844 mmol) was added to a solution of N-benzyl-3,5-di(prop-1-en-2-yl)pyridazin-4-amine (2.24 g, 8.44 mmol) in ethanol (42 mL)

in a hydrogenation vial at RT under a blanket of nitrogen. The reaction mixture was stirred at RT under hydrogen (50 psig) for 3 h (pressure (c 27 psig). The reaction mixture was stirred again at RT under hydrogen (50 psig) for 2.5 d (pressure @ 30 psig). The mixture was filtered through a pad of Celite, covered with sand, washed with MeOH (2×100 mL), and concentrated to give an off-white solid.

Palladium hydroxide on carbon, wet (1.19 g, 0.844 mmol) was added to a solution of the off-white solid in EtOH (42 mL) and was stirred under hydrogen (42 psig) at RT for 20 h (pressure @ 36 psig). The reaction mixture was charged with more palladium hydroxide on carbon, wet (1.185 g, 0.844 mmol) and was stirred under hydrogen (50 psig) for 5 d (pressure (@ 42 psig). The mixture was filtered through a pad of Celite, covered with sand, washed with MeOH (3×100 mL), and concentrated to give 3,5-diisopropylpyridazin-4-amine (1.407 g, 7.85 mmol, 93% yield) as an off-white solid. The crude product in DCM/MeOH was loaded onto the column and was purified via automated flash chromatography (silica gel. 0-100% MeOH/DCM) to give 3,5-diisopropylpyridazin-4-amine (0.923 g, 5.15 mmol, 61% yield) as a light yellow waxy solid. The solid was dissolved in THF (5 mL) and concentrated (2×) to remove any excess methanol. $^1$H NMR (400 MHz, CDCl$_3$) δ 8.62 (s, 1H) 4.25 (br s, 2H) 3.08 (spt, J=6.8 Hz, 1H) 2.85 (spt, J=6.9 Hz, 1H) 1.42 (d, J=6.8 Hz, 6H) 1.30 (d, J=6.8 Hz, 6H).

Step 4: 6-Chloro-1-(3,5-diisopropylpyridazin-4-yl)-7-(2-fluorophenyl)pyrido[2,3-d]pyrimidine-2,4(1H,3H)-dione A solution of 2,5-dichloro-6-(2-fluorophenyl)nicotinamide (1.07 g, 3.75 mmol, Intermediate 99B) and oxalyl chloride (2 M in DCM, 2.07 mL, 4.13 mmol) in tetrahydrofuran (13 mL) was stirred at 65° C. for 1 h. The reaction mixture was removed from the heating block, and 3,5-diisopropylpyridazin-4-amine (0.673 g, 3.75 mmol) in THF (10 mL) was added; the solution became a white slurry, then DIEA (1.31 mL, 7.51 mmol) was added; the reaction mixture was stirred at RT for 5 min. The reaction mixture was diluted with EtOAc (150 mL), added to a separatory funnel, and washed with saturated, aqueous sodium bicarbonate (2×75 mL); the organic layer was separated, dried over anhydrous Na$_2$SO$_4$, and concentrated in vacuo. The crude product was adsorbed onto silica and was purified via automated flash chromatography (silica gel, 0-100% EtOAc/heptane) to give 2,5-dichloro-N-((3,5-diisopropylpyridazin-4-yl)carbamoyl)-6-(2-fluorophenyl)nicotinamide (1.09 g, 2.21 mmol, 59% yield) as a colorless oil. MS (ESI, +ve) m/z: 490.0 (M+1)$^+$.

A solution of 2,5-dichloro-N-((3,5-diisopropylpyridazin-4-yl)carbamoyl)-6-(2-fluorophenyl)nicotinamide (0.985 g, 2.01 mmol) and potassium bis(trimethylsilyl)amide (1 M in THF, 4.02 mL, 4.02 mmol) in tetrahydrofuran (10 mL) (light yellow solid formed) was stirred at 0° C. for 5 min then was allowed to warm to RT and stir for 15 min. The reaction mixture was diluted with EtOAc (200 mL), added to a separatory funnel, and washed with saturated, aqueous ammonium chloride (2×100 mL); the organic layer was separated, dried over anhydrous Na$_2$SO$_4$, and concentrated in vacuo. The crude product was adsorbed onto silica and was purified via automated flash chromatography (silica gel, 0-80% [(3:1) EtOAc/EtOH]/heptane) to give impure 6-chloro-1-(3,5-diisopropylpyridazin-4-yl)-7-(2-fluorophenyl)pyrido[2,3-d]pyrimidine-2,4(1H,3H)-dione (Intermediate 212, 878 mg, 1.93 mmol, 96% yield) as a colorless oil. MS (ESI, +ve) m/z: 454.1 (M+1)$^+$.

Intermediate 213

1-((1R,5S)-3,8-Diazabicyclo[3.2.1]octan-8-yl)prop-2-en-1-one

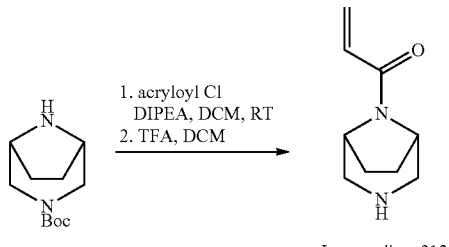

Intermediate 213

1-((1R,5S)-3,8-Diazabicyclo[3.2.1]octan-8-yl)prop-2-en-1-one

A solution of 3-Boc-3,8-diazabicyclo[3.2.1]octane (0.50 g, 2.36 mmol; CombiBlocks, Inc., San Diego, Calif.), acryloyl chloride (0.5 M in DCM, 5.65 mL, 2.83 mmol), and DIEA (1.23 mL, 7.07 mmol) in dichloromethane (24 mL) was stirred at RT for 30 min. The reaction mixture was washed with saturated, aqueous sodium bicarbonate (75 mL); the organic layer was separated, dried over anhydrous Na$_2$SO$_4$, and concentrated in vacuo. The crude product was adsorbed onto silica and was purified via automated flash chromatography (silica gel, 0-100% EtOAc/heptane) to give tert-butyl (1R,5S)-8-acryloyl-3,8-diazabicyclo[3.2.1]octane-3-carboxylate (535 mg, 2.01 mmol, 85% yield) as a light yellow oil. $^1$H NMR (400 MHz, CDCl$_3$) δ 6.43-6.52 (m, 1H) 6.36-6.42 (m, 1H) 5.73 (dd, J=10.0, 2.5 Hz, 1H) 4.69-4.83 (m, 1H) 4.27 (br d, J=16.0 Hz, 1H) 3.68-4.03 (m, 2H) 2.84-3.21 (m, 2H) 1.71-2.01 (m, 4H) 1.46 (s, 9H). MS (ESI, +ve) m/z: 289.0 (M+Na)$^+$.

A solution of tert-butyl (1R,5S)-8-acrloyl-3,8-diazabicyclo[3.2.1]octane-3-carboxylate (535 mg, 2.01 mmol) and TFA (2.72 mL, 35.3 mmol) in dichloromethane (24 mL) was stirred at RT for 15 min. The reaction mixture was concentrated to give 1-((1R,5S)-3,8-diazabicyclo[3.2.1]octan-8-yl) prop-2-en-1-one 2,2,2-trifluoroacetate (Intermediate 213, 0.921 g, 3.29 mmol, >99% yield) as an amber oil which was used as is. $^1$H NMR (400 MHz, CDCl$_3$) δ 8.57-9.12 (m, 2H) 6.48 (s, 1H) 6.46 (d, J=4.1 Hz, 1H) 5.92-5.97 (m, 1H) 4.98 (br s, 1H) 4.55 (br s, 1H) 3.17-3.55 (m, 4H) 2.13-2.47 (m, 4H). MS (ESI, +ve) m/z: 167.0 (M+1)$^+$.

Intermediate 214

1-(3,9-Diazabicyclo[3.3.1]nonan-3-yl)prop-2-en-1-one

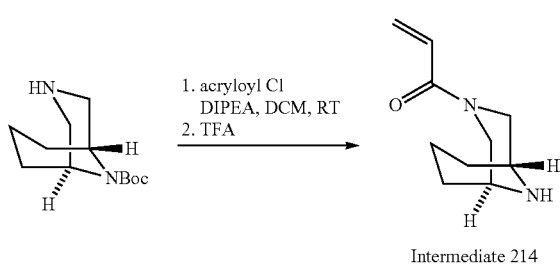 [SMILES: CC(C)(C)OC(=O)N1[C@@H]2CCC[C@H]1CNC2 ; C=CC(=O)N1C[C@H]2CCC[C@@H](C1)N2]

Intermediate 214

1-(3,9-Diazabicyclo[3.3.1]nonan-3-yl)prop-2-en-1-one

A solution of tert-butyl 3,9-diazabicyclo[3.3.1]nonane-9-carboxylate (0.581 g, 2.57 mmol; Enamine LLC, Monmouth Jct., N.J.), acryloyl chloride (0.250 mL, 3.08 mmol), and DIPEA (1.34 mL, 7.70 mmol) in dichloromethane (13 mL) was stirred at RT for 30 min. The reaction mixture was diluted with EtOAc (100 mL), added to a separatory funnel, and washed with saturated, aqueous sodium bicarbonate (2×75 mL); the organic layer was separated, dried over anhydrous $Na_2SO_4$, and concentrated in vacuo. The crude product was adsorbed onto silica and was purified via automated flash chromatography (silica gel, 0-90% EtOAc/heptane) to give tert-butyl 3-acryloyl-3,9-diazabicyclo[3.3.3]nonane-9-carboxylate (587 mg, 2.09 mmol, 82% yield) as a colorless oil. $^1$H NMR (400 MHz, $CDCl_3$) δ 6.50-6.62 (m, 1H) 6.30 (dd, J=16.8, 1.9 Hz, 1H) 5.71 (dd, J=10.6, 1.9 Hz, 1H) 4.57-4.65 (m, 1H) 4.29 (br s, 1H) 4.17 (br s, 1H) 3.88-3.96 (m, 1H) 3.39-3.48 (m, 1H) 2.92-3.06 (m, 1H) 1.66-1.99 (m, 5H) 1.49-1.56 (m, 1H) 1.48 (s, 9H). MS (ESI, +ve) m/z: 303.0 (M+Na)$^+$.

A solution of the resulting oil in 2,2,2-trifluoroacetic acid (29.3 g, 257 mmol) was stirred at RT for 15 min. The reaction mixture was concentrated to give 1-(3,9-diazabicyclo[3.3.1]nonan-3-yl)prop-2-en-1-one 2,2,2-trifluoroacetate (Intermediate 214, 818 mg, 2.78 mmol, >99% yield) as a colorless oil which was used as is. MS (ESI, +ve) m/z: 181.1 (M+1).

Intermediates 204 & 215 tert-Butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (Two Atropisomers)

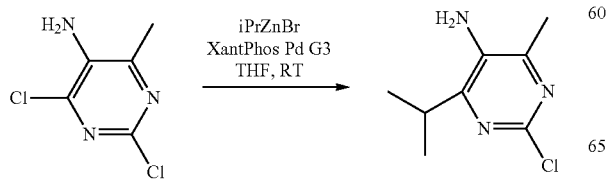

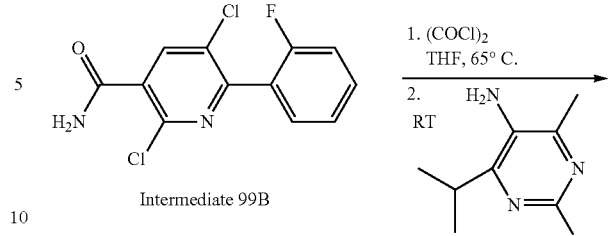

Intermediate 99B

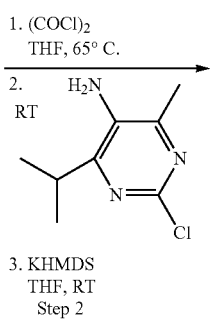

3. KHMDS
THF, RT
Step 2

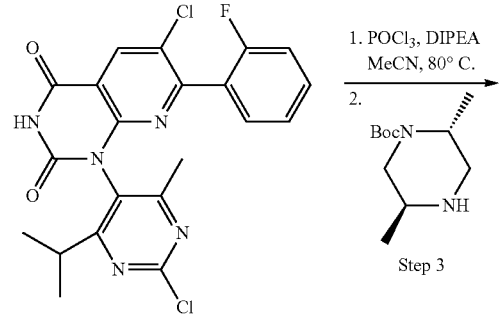

1. POCl$_3$, DIPEA
MeCN, 80° C.

2.

Step 3

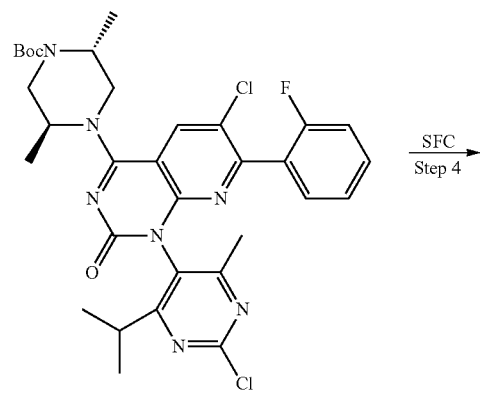

SFC
Step 4

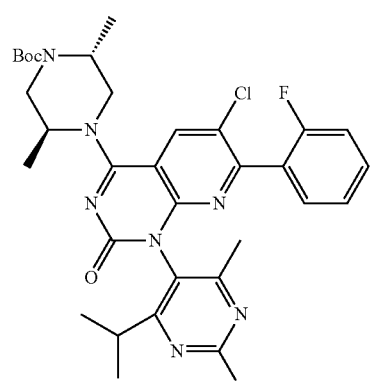

Intermediate 204
first eluting atropisomer

-continued

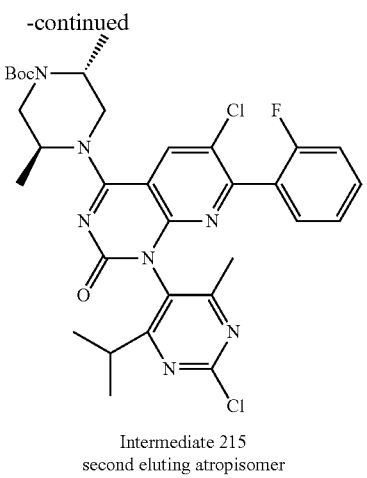

Intermediate 215
second eluting atropisomer

Step 1: 2-Chloro-4-isopropyl-6-methylpyrimidin-5-amine

To a 1-L three-necked RBF was added 2,4-dichloro-6-methylpyrimidin-5-amine (16.1 g, 90 mmol; CombiBlocks, Inc., San Diego, Calif.) and [(4,5-bis(diphenylphosphino)-9,9-dimethylxanthene)-2-(2'-amino-1,1'-biphenyl)]palladium(II) methanesulfonate (4.28 g, 4.51 mmol) in tetrahydrofuran (180 mL) under argon. 2-Propylzinc bromide (0.5 M in tetrahydrofuran. 198 mL, 99 mmol; Sigma-Aldrich, St. Louis, Mo.) was added over 5 min (no exotherm observed). The reaction mixture was then stirred at 23° C. for 90 min. To the reaction mixture was added ice (~15 g) and Celite (~50 g) with stirring, and the mixture was filtered through a fine fritted glass filter funnel (eluent: EtOAc) to remove insoluble emulsions. The combined organic phases were dried over sodium sulfate, filtered, and concentrated in vacuo. The crude product was adsorbed onto silica and was purified via automated flash chromatography (silica gel, 0-70% EtOAc/heptane) to give 2-chloro-4-isopropyl-6-methylpyrimidin-5-amine (8.83 g, 47.6 mmol, 53% yield) as yellow oil. $^1$H NMR (400 MHz, DMSO-$d_6$) δ 1.12 (d, J=6.63 Hz, 6H) 2.27 (s, 3H) 3.20 (spt, J=6.70 Hz, 1H) 5.25 (s, 2H). MS (ESI, +ve) m/z: 186.0 (M+1)$^+$.

Step 2: 6-Chloro-1-(2-chloro-4-isopropyl-6-methylpyrimidin-5-yl)-7-(2-fluorophenyl)pyrido[2,3-d]pyrimidine-2,4(1H,3H)-dione A solution of 2,5-dichloro-6-(2-fluorophenyl)nicotinamide (9.41 g, 33.0 mmol, Intermediate 99B) and oxalyl chloride (2 M in DCM, 18.2 mL, 36.3 mmol) in tetrahydrofuran (100 mL) was stirred under an air condensor and drying tube at 65° C. for 1 h. The solution was cooled to RT; 2-chloro-4-isopropyl-6-methylpyrimidin-5-amine (6.13 g, 33.0 mmol) in THF (5 mL) at RT was added, and the yellow solution was stirred at RT for 30 min. The reaction mixture was concentrated, diluted with EtOAc (150 mL), added to a separatory funnel, and washed with saturated, aqueous sodium bicarbonate (3×100 mL); the organic layer was separated, dried over anhydrous Na$_2$SO$_4$, and concentrated in vacuo to give impure product. The crude product in DCM was loaded onto the column and was purified via automated flash chromatography (silica gel, 0-40% EtOAc/heptane) to give 2,5-dichloro-N-((2-chloro-4-isopropyl-6-methylpyrimidin-5-yl)carbamoyl)-6-(2-fluorophenyl)nicotinamide (12.2 g, 24.6 mmol, 75% yield) as a white solid. MS (ESI, +ve) m/z: 496.0/497.9 (M+1)$^+$.

A solution of 2,5-dichloro-N-((2-chloro-4-isopropyl-6-methylpyrimidin-5-yl)carbamoyl)-6-(2-fluorophenyl)nicotinamide (12.2 g, 24.6 mmol) and potassium bis(trimethylsilyl)amide (1 M in THF, 49.2 mL, 49.2 mmol) in tetrahydrofuran (100 mL) was stirred at 0° C. for 20 min. The reaction mixture was diluted with EtOAc (150 mL), added to a separatory funnel, and washed with saturated, aqueous ammonium chloride (2×100 mL); the organic layer was separated, dried over anhydrous Na$_2$SO$_4$, and concentrated in vacuo. The crude product was adsorbed onto silica and was purified via automated flash chromatography (silica gel, 0-50% EtOAc/heptane) to give 6-chloro-1-(2-chloro-4-isopropyl-6-methylpyrimidin-5-yl)-7-(2-fluorophenyl)pyrido[2,3-d]pyrimidine-2,4(1H,3H)-dione (3.18 g, 6.91 mmol, 28% yield) as an off-white solid and slightly impure 6-chloro-1-(2-chloro-4-isopropyl-6-methylpyrimidin-5-yl)-7-(2-fluorophenyl)pyrido[2,3-d]pyrimidine-2,4(1H,3H)-dione (5.89 g, 12.8 mmol, 52% yield) as a light yellow solid. $^1$H NMR (400 MHz, CDCl$_3$) δ 9.21 (br s, 1H) 8.63 (s, 1H) 7.42-7.52 (m, 1H) 7.08-7.24 (m, 3H) 2.78 (spt, J=6.7 Hz, 1H) 2.30 (s, 3H) 1.24 (d, J=6.6 Hz, 3H) 1.09 (d, J=6.6 Hz, 3H). $^{19}$F NMR (377 MHz, CDCl$_3$) δ 113.25 (s, 1F). MS (ESI, +ve) m/z: 460.0 (M+1)$^+$.

Step 3: tert-Butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate A solution of 6-chloro-1-(2-chloro-4-isopropyl-6-methylpyrimidin-5-yl)-7-(2-fluorophenyl)pyrido[2,3-d]pyrimidine-2,4(1H,3H)-dione (5.89 g, 12.8 mmol), phosphoryl trichloride (1.43 mL, 15.4 mmol), and DIPEA (8.92 mL, 51.2 mmol) in acetonitrile (64 mL) was stirred at 80° C. for 30 min.

The solution was cooled in an ice bath, then tert-butyl (2R,5S)-2,5-dimethylpiperazine-1-carboxylate (2.74 g, 12.80 mmol, AstaTech, Inc., Bristol, Pa.) was added, and the dark red solution was stirred at RT for 5 min. The reaction mixture was diluted with EtOAc (150 mL), added to a separatory funnel, and washed with saturated, aqueous sodium bicarbonate (2×100 mL); the organic layer was separated, dried over anhydrous Na$_2$SO$_4$, and concentrated in vacuo. The crude product was adsorbed onto silica and was purified via automated flash chromatography (silica gel, 0-80% EtOAc/heptane) to give tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (6.13 g, 9.34 mmol, 73% yield) as an amber foam and a mixture of atropisomers. MS (ESI, +ve) m/z: 656.0 (M+1)$^+$.

Step 4: tert-Butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (Separated Atropisomers)

Atropisomers of tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (6.13 g, 9.34 mmol) were separated via chiral SFC (IC, 21×250 mm, 5 μm, 40% MeOH/CO$_2$, 80 mL/min); this gave tert-butyl (2R,5S)-4-(6-chloro-1-(2-chloro-4-isopropyl-6-methylpyrimidin-5-yl)-7-

(2-fluorophenyl)-2-oxo-1,2-dihydropyrido[2,3-d]pyrimidin-4-yl)-2,5-dimethylpiperazine-1-carboxylate (first eluting isomer, 2.70 g, 4.12 mmol, 44% yield, Intermediate 204) [¹H NMR (400 MHz, CDCl₃) δ 8.13 (s, 1H) 7.41-7.49 (m, 1H) 7.16-7.24 (m, 2H) 7.09-7.16 (m, 1H) 3.45-5.07 (m, 6H) 2.62-2.77 (m, 1H) 2.22 (s, 3H) 1.51 (s, 9H) 1.43-1.49 (m, 3H) 1.29 (d, J=6.8 Hz, 3H) 1.23 (d, J=6.8 Hz, 3H) 1.07 (d, J=6.6 Hz, 3H). ¹⁹F NMR (377 MHz, CDCl₃) δ -112.91 (br s, 1F). MS (ESI, +ve) m/z: 656.0 (M+1)⁺.] as a yellow solid and tert-butyl (2R,5S)-4-(6-chloro-1-(2-chloro-4-isopropyl-6-methylpyrimidin-5-yl)-7-(2-fluorophenyl)-2-oxo-1,2-dihydropyrido[2,3-d]pyrimidin-4-yl)-2,5-dimethylpiperazine-1-carboxylate (second eluting isomer, 3.54 g, 5.39 mmol, 58% yield, Intermediate 215) [¹H NMR (400 MHz, CDCl₃) δ 8.13 (s, 1H) 7.42-7.49 (m, 1H) 7.17-7.24 (m, 2H) 7.10-7.17 (m, 1H) 3.41-5.07 (m, 6H) 2.70 (quin, J=6.6 Hz, 1H) 2.24 (s, 3H) 1.51 (s, 9H) 1.43-1.50 (m, 3H) 1.28 (d, J=6.8 Hz, 3H) 1.22 (d, J=6.8 Hz, 3H) 1.04 (d, J=6.8 Hz, 3H). ¹⁹F NMR (377 MHz, CDCl₃) δ -112.93 (br s, 1F). MS (ESI, +ve) m/z: 656.0 (M+1)⁺.].

Intermediates 216 & 217

1-(2-Bromo-4-isopropyl-6-methylpyrimidin-5-yl)-6-chloro-7-(2-fluorophenyl)pyrido[2,3-d]pyrimidine-2,4(1H,3H)-dione (Two Atropisomers)

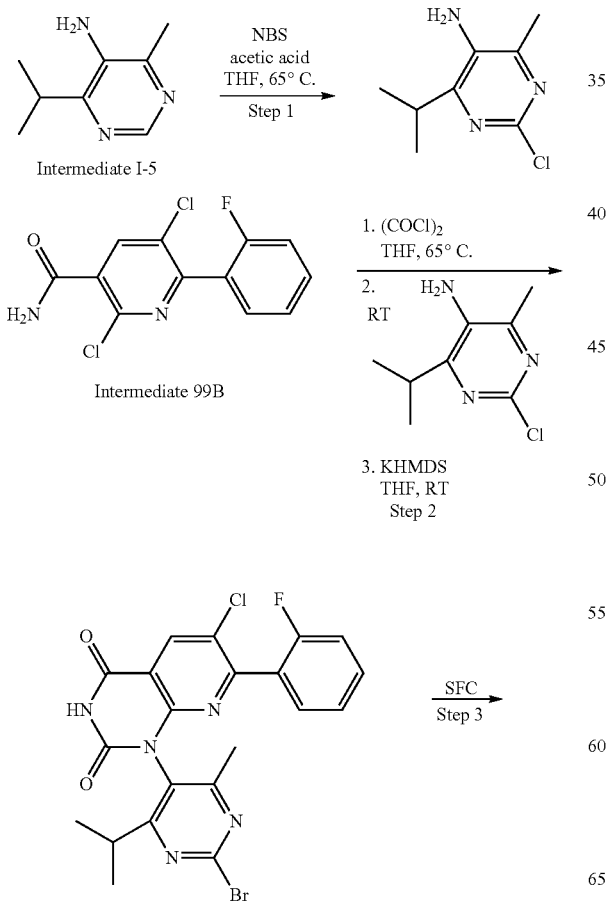

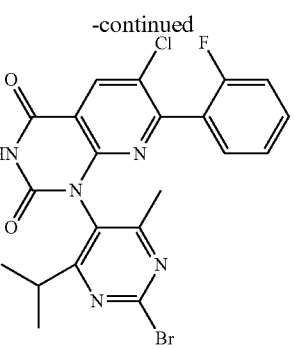

Intermediate 216
first eluting
atropisomer

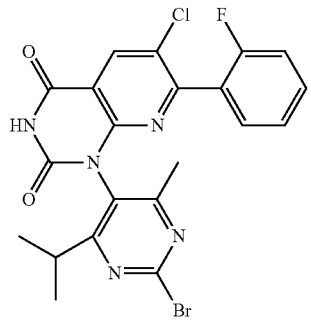

Intermediate 217
second eluting
atropisomer

Step 1:
2-Bromo-4-isopropyl-6-methylpyrimidin-5-amine

A solution of 4-isopropyl-6-methylpyrimidin-5-amine (2.01 g, 13.3 mmol, Intermediate I-5), acetic acid (0.076 mL, 1.33 mmol), and NBS (3.55 g, 20.0 mmol) in tetrahydrofuran (67 mL) was stirred at 65° C. for 15 min. The reaction mixture was diluted with EtOAc (300 mL), added to a separatory funnel, and washed with saturated, aqueous sodium bicarbonate (3×100 mL); the organic layer was separated, dried over anhydrous Na₂SO₄, and concentrated in vacuo. The crude product in DCM was loaded onto the column and was purified via automated flash chromatography (silica gel, 0-50% EtOAc/heptane) to give 2-bromo-4-isopropyl-6-methylpyrimidin-5-amine (2.07 g, 9.01 mmol, 68% yield) as an amber oil. ¹H NMR (400 MHz, CDCl₃) δ 3.59 (br s, 2H) 2.94 (spt, J=6.8 Hz, 1H) 2.38 (s, 3H) 1.28 (d, J=6.6 Hz, 6H). MS (ESI, +ve) m/z: 230.0/232.1 (M+1)⁺.

Step 2: 1-(2-Bromo-4-isopropyl-6-methylpyrimidin-5-yl)-6-chloro-7-(2-fluorophenyl)pyrido[2,3-d]pyrimidine-2,4(1H,3H)-dione A solution of 2,5-dichloro-6-(2-fluorophenyl)nicotinamide (2.57 g, 9.01 mmol, Intermediate 99B) and oxalyl chloride (2 M in DCM, 4.95 mL, 9.91 mmol) in tetrahydrofuran (45 mL) was stirred under an air condenser and drying tube at 65° C. for 45 min; more oxalyl chloride (2 M in DCM, 4 mL, 8 mmol) was then added, and the reaction mixture was stirred for 15 min. The solution was concentrated, dissolved in tetrahydrofuran (45 mL), and cooled in an ice bath; the solution was added to 2-bromo-4-isopropyl-6-methylpyrimidin-5-amine (2.07 g, 9.01 mmol) in THF (5 mL) at RT; the yellow solution was stirred at RT for 5 min. The reaction mixture was concentrated, diluted with EtOAc (150 mL), added to a separatory funnel, and washed with saturated, aqueous sodium bicarbonate (3×100 mL); the organic layer was separated, dried over anhydrous Na$_2$SO$_4$, and concentrated in vacuo to give impure product as an amber oil. The crude product in DCM was loaded onto the column and was purified via automated flash chromatography (silica gel, 0-50% EtOAc/heptane) to give N-((2-bromo-4-isopropyl-6-methylpyrimidin-5-yl)carbamoyl)-2,5-dichloro-6-(2-fluorophenyl)nicotinamide (3.42 g, 6.32 mmol, 70% yield) as a light yellow foam. MS (ESI, +ve) m/z: 541.8 (M+1)$^+$.

A solution of N-((2-bromo-4-isopropyl-6-methylpyrimidin-5-yl)carbamoyl)-2,5-dichloro-6-(2-fluorophenyl)nicotinamide (3.42 g, 6.32 mmol) and potassium bis(trimethylsilyl)amide (1 M in THF, 12.6 mL, 12.6 mmol) in tetrahydrofuran (32 mL) was stirred at 0° C. for 10 min. The reaction mixture was diluted with EtOAc (150 mL), added to a separatory funnel, and washed with saturated, aqueous ammonium chloride (2×100 mL); the organic layer was separated, dried over anhydrous Na$_2$SO$_4$, and concentrated in vacuo. The crude product was adsorbed onto silica and was purified via automated flash chromatography (silica gel, 0-50% EtOAc/heptane) to give 1-(2-bromo-4-isopropyl-6-methylpyrimidin-5-yl)-6-chloro-7-(2-fluorophenyl)pyrido[2,3-d]pyrimidine-2,4(1H,3H)-dione (1.95 g, 3.86 mmol, 61% yield) as a light yellow solid. MS (ESI, +ve) m/z: 505.9 (M+1)$^+$.

Step 3: 1-(2-Bromo-4-isopropyl-6-methylpyrimidin-5-yl)-6-chloro-7-(2-fluorophenyl)pyrido[2,3-d]pyrimidine-2,4(1H,3H)-dione (Separated Atropisomers)

Atropisomers of 1-(2-bromo-4-isopropyl-6-methylpyrimidin-5-yl)-6-chloro-7-(2-fluorophenyl)pyrido[2,3-d]pyrimidine-2,4(1H,3H)-dione (1.95 g, 3.86 mmol) were separated via SFC (OD 250×21 mm, 5 μm, 20% MeOH/CO$_2$, 80 g/min, 102 bar). This gave 1-(2-bromo-4-isopropyl-6-methylpyrimidin-5-yl)-6-chloro-7-(2-fluorophenyl)pyrido[2,3-d]pyrimidine-2,4(1H,3H)-dione (first eluting isomer, 556 mg, 1.10 mmol, 29% yield, Intermediate 216) [$^1$H NMR (400 MHz, CDCl$_3$) δ 8.62 (s, 1H) 7.42-7.50 (m, 1H) 7.10-7.24 (m, 3H) 2.75 (spt, J=6.7 Hz, 1H) 2.28 (s, 3H) 1.23 (d, J=6.6 Hz, 3H) 1.07 (d, J=6.6 Hz, 3H). $^{19}$F NMR (377 MHz, CDCl$_3$) δ -113.27 (s, 1F). MS (ESI, +ve) m/z: 506.0 (M+1)$^+$.] as a beige solid and 1-(2-bromo-4-isopropyl-6-methylpyrimidin-5-yl)-6-chloro-7-(2-fluorophenyl)pyrido[2,3-d]pyrimidine-2,4(1H,3H)-dione (second eluting isomer, 511 mg, 1.01 mmol, 26% yield, Intermediate 217) [$^1$H NMR (400 MHz, CDCl$_3$) δ 8.61 (s, 1H) 7.42-7.50 (m, 1H) 7.10-7.24 (m, 3H) 2.75 (spt, J=6.7 Hz, 1H) 2.28 (s, 3H) 1.23 (d, J=6.8 Hz, 3H) 1.07 (d, J=6.6 Hz, 3H). $^{19}$F NMR (377 MHz, CDCl$_3$) δ -113.27 (s, 1F). MS (ESI, +ve) m/z: 506.0 (M+1)$^+$.] as a beige solid.

Intermediate 218

Rac-2-(4-Acryloylpiperazin-2-yl)acetonitrile

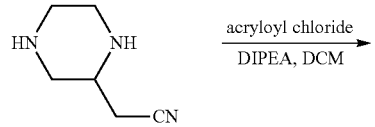

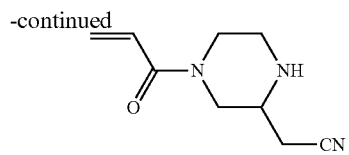

A white suspension solution of 2-(piperazin-2-yl)acetonitrile dihydrochloride (287 mg, 1.45 mmol. Enamine Ltd.) in DCM (7 mL) was treated with n,n'-diisopropylethylamine (0.5 mL, 2.90 mmol) at room temperature. The resulting clear solution was cooled to 0° C. and then treated with acryloyl chloride (1.1 M in DCM, 1.3 mL, 1.45 mmol) and stirred for 5 min. The reaction mixture was evaporated to dryness to provide a mixture of the desired 2-(4-acryloylpiperazin-2-yl)acetonitrile and undesired 2-(1,4-diacryloylpiperazin-2-yl)acetonitrile as 1:1 ratio. The crude material was used in next step without purification.

Intermediate 219

5-Amino-4,6-diisopropylpyrimidine-2-carbonitrile

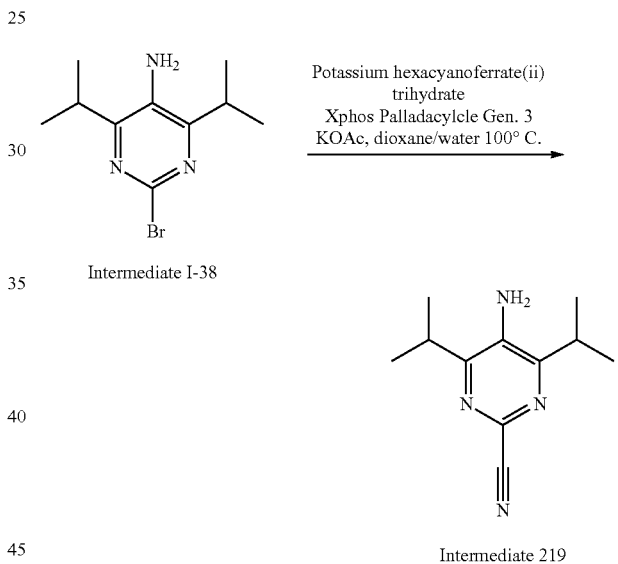

To a 100-mL round-bottomed flask was added 2-bromo-4,6-diisopropylpyrimidin-5-amine (0.500 g, 1.937 mmol, Intermediate I-38), potassium hexacyanoferrate(ii) trihydrate (3.27 g, 7.75 mmol, Sigma-Aldrich, St. Louis, Mo., USA), water (6.46 mL) and potassium acetate (0.570 g, 5.81 mmol) in 1,4-dioxane (6.46 mL). The reaction mixture was deoxygenated by bubbling Argon gas into the mixture for 5 min. Then methanesulfonato(2-dicyclohexylphosphino-2',4',6'-tri-i-propyl-1,1'-biphenyl)(2'-amino-1,1'-biphenyl-2-yl)palladium(ii) (0.164 g, 0.194 mmol, Strem Chemicals, Inc., Newburyport, Mass., USA) was added to the reaction mixture. The mixture was heated and stirred at 100° C. for 1 h, while under an inert (N$_2$) atmosphere. The flask was removed from the heat bath and allowed the reaction mixture to cool to ambient temperature. The mixture was diluted with sat. aq. NaHCO$_3$ and EtOAc. The layers were separated and the aqueous layer was extracted with EtOAc. The combined organic extracts were dried over MgSO4, filtered and concentrated in vacuo. The crude material was triturated from EtOAc and heptane. The precipitate was collected by filtration and the solids were washed with heptane. This afforded 5-amino-4,6-diisopropylpyrimidine-2-carbonitrile (0.210 g, 1.028 mmol, 53.1% yield, Intermediate 219) as tan solid. $^1$H NMR (400 MHz, DMSO-d$_6$) δ 6.18 (s, 2H) 3.21-3.29 (m, 2H) 1.15 (d, J=6.63 Hz, 12H). m/z (ESI, +ve ion): 205.3 (M+H)$^+$.

Intermediate 220

4,6-Diisopropyl-2-(propylsulfonyl)pyrimidin-5-amine

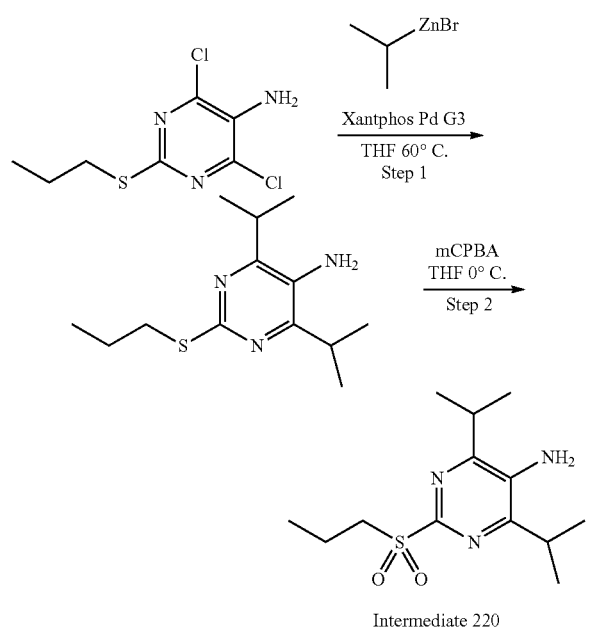

Intermediate 220

Step 1.
4,6-Diisopropyl-2-(propylthio)pyrimidin-5-amine

To a 250-mL round-bottomed flask was added 4,6-dichloro-2-(propylthio)pyrimidin-5-amine (8.00 g, 33.6 mmol, Synthonix, Wake Forest, N.C., USA) in tetrahydrofuran (67.2 mL). The mixture was deoxygenated by bubbling Argon (gas) into the mixture 5 min. Then 2-propylzinc bromide (0.5M in THF) (94 mL, 94 mmol), followed by xantphos pd g3 (0.956 g, 1.008 mmol) was added to the reaction mixture. The reaction mixture was heated to 60° C. and allowed the mixture to stir under an inert (N2) atmosphere for 2 h. The reaction mixture was quenched with sat. aq. NH4Cl (50 mL) and allowed the mixture to stir 10 min. The mixture was diluted with EtOAc and Brine solution (50 mL). The layers were separated and aqueous layer was extracted with EtOAc. The combined organic extracts were dried over MgSO4, filtered and concentrated in vacuo. The crude material was absorbed onto a plug of silica gel and purified by chromatography through a Interchim (25 micron) silica-gel column (220 grams), eluting with a gradient of 0-30% EtOAc/heptane, to provide 4,6-diisopropyl-2-(propylthio)pyrimidin-5-amine (6.148 g, 24.26 mmol, 72.2% yield) as tan oil. 1H NMR (400 MHz, DMSO-d6) δ 4.80 (s, 2H) 3.13-3.25 (m, 2H) 2.91-3.05 (m, 2H) 1.66 (sxt, J=7.26 Hz, 2H) 1.12 (d, J=6.63 Hz, 12H) 0.96 (t, J=7.36 Hz, 3H). m/z (ESI, +ve ion): 254.1 (M+H)$^+$.

Step 2. 4,6-Diisopropyl-2-(propylsulfonyl)pyrimidin-5-amine

To a 150-mL round-bottomed flask was added 4,6-diisopropyl-2-(propylthio)pyrimidin-5-amine (1.560 g. 6.16 mmol) and 3-chloroperoxybenzoic acid (3.45 g, 15.39 mmol, Sigma-Aldrich, St. Louis, Mo., USA) in tetrahydrofuran (30.8 mL). The reaction mixture was allowed to stir under an inert (N2) atmosphere for 45 min. The reaction mixture was cooled to 0° C. with a wet ice/water bath. Then sat. aq. NaHCO$_3$ was added slowly (3×10 mL portions) over 20 min. The mixture was diluted with 4:1 EtOAc/MeOH and brine solution (20 mL). The aqueous layer was extracted with EtOAc and the organic extracts were combined, dried over MgSO4, filtered and concentrated in vacuo. The crude material (3.118 grams) was diluted with DMF (20 mL), then agitated with sonicator until mixture became homogeneous. The mixture was slowly poured into water (100 mL) and the precipitate was collected by filtration. The solids were washed with water and allowed to dry in a reduced-pressure oven (45° C.) overnight. This afforded 4,6-diisopropyl-2-(propylsulfonyl)pyrimidin-5-amine (1.645 g, 5.76 mmol, 94% yield, Intermediate 220) as tan solid. 1H NMR (400 MHz, DMSO-d6) δ 6.08 (br s, 2H) 3.48-3.68 (m, 3H) 1.79 (br s, 2H) 1.29 (br s, 12H) 1.07 (br s, 4H). m/z (ESI, +ve ion): 286.3 (M+H)+.

Intermediate 221

(4-Amino-3-isopropyl-5-methylphenyl)dimethylphosphine oxide

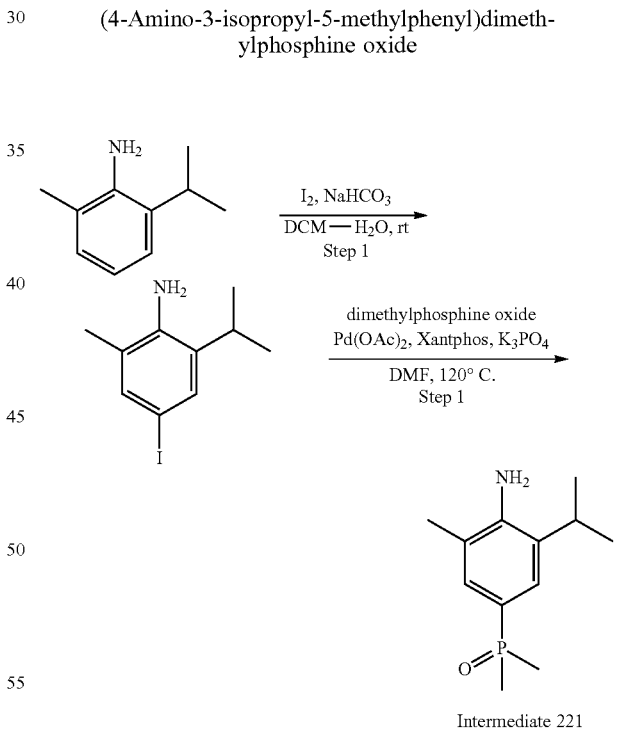

Intermediate 221

Step 1: 4-Iodo-2-isopropyl-6-methylaniline

Iodine (9.3 g, 37 mmol) was slowly added to a biphasic mixture of 2-(1-methylethyl)-6-methylaniline (Advanced ChemBlocks Inc., Burlingame, Calif., USA, 5.5 mL, 35 mmol) and sodium bicarbonate (5.9 g, 70 mmol) in DCM-water (1:1, 70 mL) at room temperature. After 1 h, the reaction was quenched by adding 1 N aqueous sodium thiosulfate (100 mL). Additional DCM (70 mL) was added and the biphasic mixture stirred vigorously for 30 min at room temperature. The layers were partitioned and the aqueous layer was washed with DCM (1×100 mL). The combined organic extracts were dried over anhydrous magnesium sulfate, filtered, and concentrated in vacuo to afford crude 4-iodo-2-isopropyl-6-methylaniline (9.4 g, 98% yield) as a dark purple oil that was carried forward in the next step without purification. LRMS: (ESI, +ve ion) m/z 275.9 (M+H)$^+$.

Step 2: (4-Amino-3-isopropyl-5-methylphenyl)dimethylphosphine oxide (Intermediate 221)

A nitrogen-sparged mixture of 4-iodo-2-isopropyl-6-methylaniline (500 mg, 1.8 mmol), dimethylphosphine oxide (170 mg, 2.2 mmol), potassium phosphate, tribasic (420 mg, 2.0 mmol), palladium(II) acetate (20 mg, 0.091 mmol), and Xantphos (53 mg, 0.091 mmol) in DMF (3.2 mL) was stirred 120° C. for 18 h. The reaction mixture was filtered through a pad of Celite and rinsed with EtOAc. The filtrate was concentrated in vacuo and then redissolved in DCM (50 mL). The solution was washed with 1 M LiCl (2×50 mL) and the aqueous layer was back-extracted with EtOAc (1×50 mL). The combined organic extracts were dried over anhydrous magnesium sulfate, filtered, and concentrated to afford (4-amino-3-isopropyl-5-methylphenyl)dimethylphosphine oxide (Intermediate 221, 440 mg, 100% yield) as a thick red-brown oil. $^1$H NMR (400 MHz, DMSO-d$_6$) δ 1.16 (d, J=6.6 Hz, 6H), 1.52 (d, J=13.1 Hz, 6H), 2.11 (s, 3H), 3.04 (sept, J=6.6 Hz, 1H), 5.07 (s, 2H), 7.14 (d, J=11.4 Hz, 1H), 7.23 (d, J=12.1 Hz, 1H), $^{31}$P{$^1$H} NMR (162 MHz, DMSO-d$_6$) δ 31.71 (s, 1P); LRMS: (ESI, +ve ion) m/z 226.1 (M+H)$^+$.

Intermediate 222

3-Isopropyl-5-methylpyridin-4-amine

Diego, Calif., USA. 6.8 mL, 36 mmol) in dioxane-water (2:1, 90 mL) was heated at 90° C. for 15 h. EtOAc (100 mL) and water (100 mL) were added and the layers were partitioned. The aqueous layer was washed with EtOAc (2×50 mL). The combined organic extracts were sequentially washed with 25% saturated sodium bicarbonate (100 mL) and water (100 mL), then treated with 1 N HCl (2×150 mL). The combined acidic aqueous washes were collected and the organic phase was discarded. The aqueous was treated with 5 N NaOH (200 mL) and extracted with EtOAc (2×100 mL). The combined organic extracts were dried over anhydrous sodium sulfate, filtered, and then concentrated in vacuo to give 3-methyl-5-(prop-1-en-2-yl)pyridin-4-amine (3.7 g, 92% yield) as a purple-brown oil which was carried forward in the next step without purification. $^1$H NMR (400 MHz, DMSO-d$_6$) δ 2.00 (s, 3H), 2.03 (s, 3H), 4.97-4.99 (m, 1H), 5.25-5.29 (m, 1H), 5.33 (br s, 2H), 7.77 (s, 1H), 7.83 (s, 1H); LRMS: (ESI, +ve ion) m/z 149.0 (M+H)$^+$.

Step 2: 3-Isopropyl-5-methylpyridin-4-amine (Intermediate 222)

Crude 3-methyl-5-(prop-1-en-2-yl)pyridin-4-amine (3.7 g, 25 mmol) was dissolved in ethanol (60 mL) and then palladium 10 wt. % on activated carbon (11 g, 5.0 mmol) and ammonium formate (17 g, 270 mmol) were added. The resulting black solution was heated at 80° C. for 9 h, then filtered through a pad of Celite using EtOAc. The filtrate was concentrated to ~50 mL in vacuo and then 5 N sodium hydroxide (100 mL), water (200 mL), and MTBE (150 mL) were added and the phases mixed and separated. The aqueous layer was extracted with additional MTBE (3×100 mL) and the organic layers were combined, dried over anhydrous magnesium sulfate, and concentrated in vacuo to give 3-isopropyl-5-methylpyridin-4-amine (Intermediate 222, 3.7 g, 100% yield) as a clear oil that later solidified to an opaque off-white wax. $^1$H NMR (400 MHz, DMSO-d$_6$) δ 1.17 (d, J=6.8 Hz, 6H), 2.01 (s, 3H), 2.95-3.06 (m, 1H), 5.43 (br s, 2H), 7.78 (s, 1H), 7.88 (s, 1H); LRMS: (ESI, +ve ion) m/z 151.1 (M+H)$^+$.

Intermediate 223

1-(cis-2,6-Dimethylpiperazin-1-yl)prop-2-en-1-one 2,2,2-trifluoroacetate

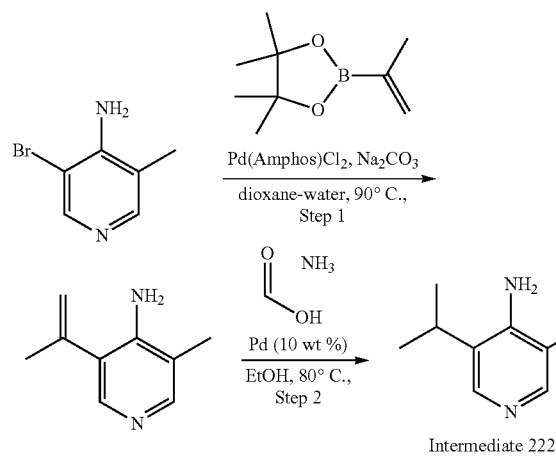

Step 1: 3-Methyl-5-(prop-1-en-2-yl)pyridin-4-amine

A nitrogen-sparged mixture of sodium carbonate (7.7 g, 72 mmol), Pd(Amphos)Cl$_2$ (0.64 g, 0.90 mmol), 3-bromo-5-methyl-4(1H)-pyridinimine (5.1 g, 27 mmol), and 2-isopropenylboronic acid, pincol ester (Combi-Blocks Inc., San

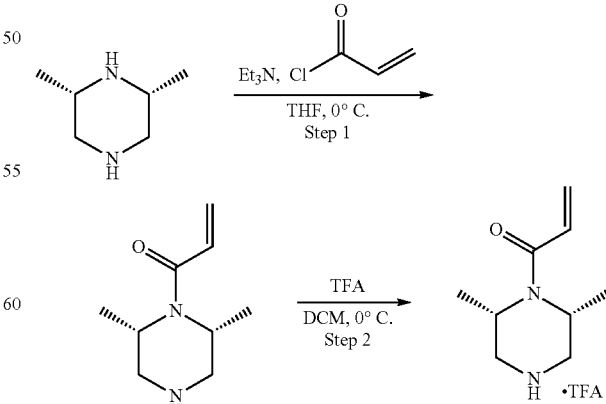

Intermediate 223

Step 1: tert-Butyl 4-acryloyl-cis-3,5-dimethylpiperazine-1-carboxylate

To a solution of tert-butyl cis-3,5-dimethylpiperazine-1-carboxylate (Combi-Blocks Inc., San Diego, Calif., USA, 130 g, 580 mmol, 1.0 equiv) and triethylamine (100 mL, 700 mmol, 1.2 equiv) in tetrahydrofuran (1250 mL, 10 mL/g) was added acryloyl chloride (56 mL, 700 mmol, 1.2 equiv) at 0° C. The reaction mixture was stirred for 1 h at 0° C. The reaction mixture was diluted with ethyl acetate (2.0 L) and washed with water (2×500 mL). The organic layer was washed with 1 N aqueous HCl (500 mL), saturated NaHCO$_3$ (500 mL), and brine (500 mL). The organic layer was dried over sodium sulfate, filtered, and concentrated in vacuo. The crude material was adsorbed to a plug of silica gel and purified by silica gel column chromatography (30-40% EtOAc/hexane) to provide the title compound as off-white solid (140 g, 91%). MS (ESI, +ve ion) m/z: 269.0 [M+1]; $^1$H NMR (400 MHz, DMSO-d$_6$) δ 6.78-6.72 (ddd, J=16.7, 10.4, 1.5 Hz, 1H), 6.15-6.11 (dt, J=16.6, 1.9 Hz, 1H), 5.70-5.67 (dt, J=10.6, 1.9 Hz, 1H), 4.35-4.25 (m, 2H), 3.82 (d, J=12.5 Hz, 2H), 3.01-2.95 (m, 2H), 1.43-1.42 (d, J=1.6 Hz, 9H), 1.19-1.14 (m, 6H).

Step 2: 1-(cis-2,6-Dimethylpiperazin-1-yl)prop-2-en-1-one 2,2,2-trifluoroacetate (Intermediate 223)

To a solution of tert-butyl 4-acryloyl-cis-3,5-dimethylpiperazine-1-carboxylate (140 g, 530 mmol, 1.0 equiv) in dichloromethane (1.4 L, 10 mug) was added trifluoroacetic acid (510 mL, 6900 mmol, 13 equiv) at 0° C. The reaction mixture was stirred for 1 h at 0° C. and concentrated in vacuo. The crude material was stirred with diethyl ether (1.0 L) for 30 min at room temperature. The precipitated solid was filtered and washed with n-hexane (500 mL) and dried to afford 1-(cis-2,6-dimethylpiperazin-1-yl)prop-2-en-1-one 2,2,2-trifluoroacetate (Intermediate 223, 140 g, 96%) as off-white solid. MS (ESI, +ve ion) m/z: 169.0 [M+1]; $^1$H NMR (400 MHz, DMSO-d$_6$) δ 9.59 (br, 1H), 9.17 (br, 1H), 6.82-6.75 (ddt, J=17.0, 10.8, 2.1 Hz, 1H), 6.21-6.16 (dq, J=16.5, 2.3 Hz, 1H), 5.77-5.74 (dq, J=10.6, 2.8, 2.4 Hz, 1H), 4.60 (t, J=6.9 Hz, 2H), 3.40-3.38 (dd, J=13.4, 5.7 Hz, 2H), 3.14-3.11 (dd, J=13.2, 5.5 Hz, 2H), 1.31-1.29 (m, 6H).

Intermediate 224

6-Chloro-1-(4-chloro-2-isopropylpyridin-3-yl)-7-(2-fluorophenyl)pyrido[2,3-d]pyrimidine-2,4(1H,3H)-dione

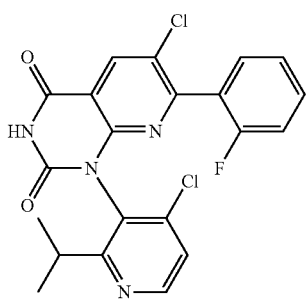 [SMILES: CC(C)c1nccc(Cl)c1-n1c(=O)[nH]c(=O)c2cc(Cl)c(-c3ccccc3F)nc21]

Same as Example 153 up tp Step 3 using 4-chloro-2-isopropylpyridin-3-amine (Intermediate 19o) in Step 1 and (2-fluorophenyl) boronic acid in Step 3. $^1$H NMR (DMSO-d$_4$) δ: 12.20-12.54 (m, 1H), 8.60-8.62 (m, 1H), 8.57-8.59 (m, 1H), 7.56-7.60 (m, 1H), 7.49-7.56 (m, 1H), 7.26-7.35 (m, 2H), 7.19-7.26 (m, 1H), 3.07-3.16 (m, 1H), 1.10-1.14 (m, 3H), 0.99-1.03 (m, 3H). MS (ESI, +ve) m/z: 444.6 (M+1)$^+$.

Intermediate 225

6,7-Dichloro-1-(4-(dimethylamino)-2-isopropylpyridin-3-yl)pyrido[2,3-d]pyrimidine-2,4(1H,3H)-dione

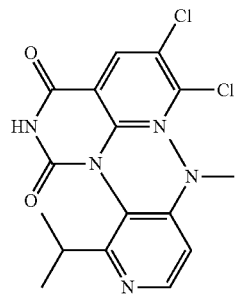 [SMILES: CC(C)c1nccc(N(C)C)c1-n1c(=O)[nH]c(=O)c2cc(Cl)c(Cl)nc21]

Same as Intermediate 61A using 2-isopropyl,N$^4$,N$^4$-dimethylpyridine-3,4-diamine (Intermediate 163) instead of 2-isopropylaniline in Step 1. $^1$H NMR (400 MHz, DMSO-d$_6$) δ 12.32 (br s, 1H), 8.59 (s, 1H), 8.28 (d, J=5.8 Hz, 1H), 6.77 (d, J=5.8 Hz, 1H), 2.69 (s, 7H), 1.05 (d, J=6.6 Hz, 3H), 0.95 (d, J=6.6 Hz, 3H). MS (ESI, +ve) m/z: 393.6 (M+1)$^+$.

Intermediate 226

4-((2S,5R)-4-Acryloyl-2,5-dimethylpiperazin-1-yl)-6,7-dichloro-1-(4-(dimethylamino)-2-isopropylpyridin-3-yl)pyrido[2,3-d]pyrimidin-2(1H)-one

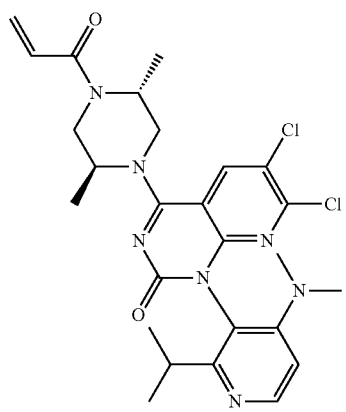 [SMILES: C=CC(=O)N1C[C@H](C)N(c2nc(=O)n(-c3c(N(C)C)ccnc3C(C)C)c3nc(Cl)c(Cl)cc23)C[C@H]1C]

Same as Intermediate 92B using 2-isopropyl, N$^4$,N$^4$-dimethylpyridine-3,4-diamine (Intermediate 163). 1H NMR (400 MHz, DMSO-d6) δ 8.54 (s, 1H), 8.42 (d, J=9.3 Hz, 1H), 8.25 (dd, J=9.7, 5.8 Hz, 1H), 6.75 (br d, J=5.8 Hz, 1H), 6.18 (dd, J=16.8, 2.3 Hz, 1H), 5.72-5.78 (m, 1H), 4.60-4.96 (m, 2H), 4.33-4.52 (m, 1H), 3.92-4.25 (m, 2H), 3.83 (br s, 2H), 2.68 (br d, J=6.0 Hz, 6H), 1.34 (br d, J=6.4 Hz, 3H), 1.23-1.30 (m, 3H), 1.11 (br d, J=6.6 Hz, 3H), 1.01-1.05 (m, 3H). MS (ESI, +ve) m/z: 543.6 (M+1)$^+$.

Intermediate 227

6,7-Dichloro-1-(2-(dimethylphosphoryl)phenyl)pyrido[2,3-d]pyrimidine-2,4(1H,3H)-dione

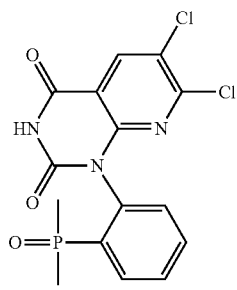 [SMILES: CP(C)(=O)c1ccccc1-n1c(=O)[nH]c(=O)c2cc(Cl)c(Cl)nc21]

Same as Intermediate 61A using (2-aminophenyl)dimethylphosphine oxide (AstaTech, Inc.) instead of 2-isopropylaniline. $^1$H NMR (400 MHz, DMSO-$d_6$) δ ppm 11.78-12.20 (m, 1H), 8.53 (s, 1H), 7.82-7.90 (m, 1H), 7.70-7.77 (m, 1H), 7.60-7.67 (m, 1H), 7.46 (dd, J=7.9, 2.9 Hz, 1H), 1.60 (d, J=13.5 Hz, 3H), 1.53 (d, J=13.5 Hz, 3H). MS (ESI, +ve) m/z: 384 (M+1)$^+$.

Intermediate 228 tert-Butyl (2R,5S)-4-(1-(6-bromo-2,4-diisopropylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate

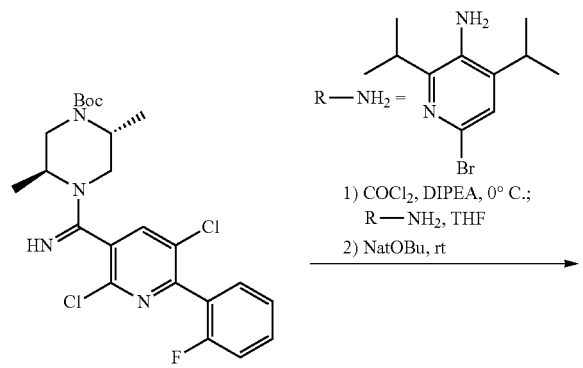

Intermediate 165

1) COCl$_2$, DIPEA, 0° C.;
   R—NH$_2$, THF
2) NaOtBu, rt

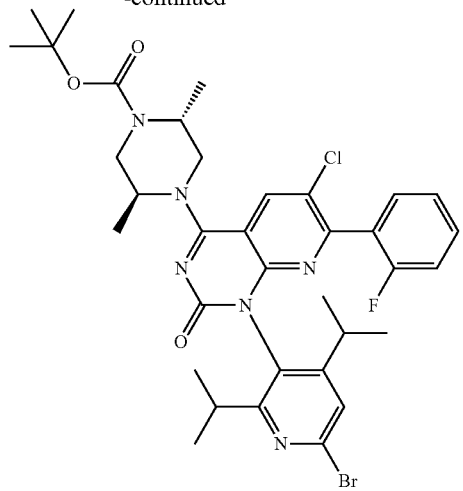

Intermediate 228

To a solution of 6-bromo-2,4-diisopropylpyridin-3-amine (0.217 g, 0.844 mmol. Intermediate 196)and DIPEA (0.309 ml, 1.772 mmol) in THF (10 mL) at rt was added dropwise phosgene solution, 15% in toluene (0.662 ml, 0.928 mmol) and the resulting mixture was stirred at rt for 10 min then the mixture was brought to 0 C and solid tert-butyl (2R,5S)-4-((2,5-dichloro-6-(2-fluorophenyl)pyridin-3-yl(imino)methyl)-2,5-dimethylpiperazine-1-carboxylate (Intermediate 165, 0.487 g, 1.013 mmol) was added in three portions. The ice-bath was removed and after stirring for 15 min at rt tert-butyl (2R,5S)-4-((((6-bromo-2,4-diisopropylpyridin-3-yl)carbamoyl)imino)(2,5-dichloro-6-(2-fluorophenyl)pyridin-3-yl)methyl)-2,5-dimethylpiperazine-1-carboxylate was observed then sodium tert-butoxide (0.243 g, 2.53 mmol) was added and the resulting mixture was stirred at rt for 20 min. The reaction went to completion, washed with water, extracted with EtOAc and purified by chromatography on silica gel using 0-40% EtOAc in heptane to afford tert-butyl (2R,5S)-4-(1-(6-bromo-2,4-diisopropylpyridin-3-yl)-6-chloro-7-(2-fluorophenyl)-2-oxo-1,2-dihydropyrido[2,3-d]pyrimidin-4-yl)-2,5-dimethylpiperazine-1-carboxylate (Intermediate 228, 0.213 g, 0.293 mmol, 34.7% yield) as a light yellow solid. $^1$H NMR (400 MHz, DMSO-$d_6$) δ 8.46 (s, 1H), 7.52 (d, J=4.4 Hz, 2H), 7.27-7.37 (m, 2H), 7.16-7.24 (m, 1H), 4.79-4.89 (m, 1H), 4.23-4.43 (m, 1H), 4.16 (br d, J=13.5 Hz, 1H), 3.78-3.92 (m, 1H), 3.66-3.76 (m, 1H), 1.46 (s, 9H), 1.35 (br d, J=6.8 Hz, 2H), 1.26 (br s, 4H), 1.15-1.21 (m, 3H), 1.02-1.09 (m, 6H), 0.87-0.96 (m, 6H). MS (ESI, +ve) m/z: 728.4 (M+1)$^+$.

Intermediate 229

6-Chloro-1-(4-ethyl-2-isopropylpyridin-3-yl)-7-(2-fluorophenyl)pyrido[2,3-d]pyrimidine-2,4(1H,3H)-dione

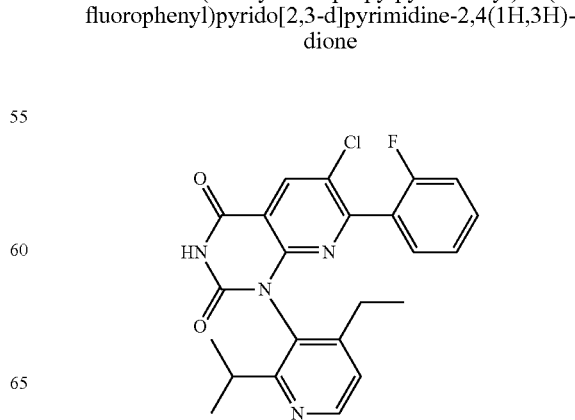

Same as Example 153 up to Step 3 using Intermediate 197 in Step 1 and (2-fluorophenyl) boronic acid in Step 3. $^1$H NMR (400 MHz, DMSO-d$_6$) δ 12.03-12.45 (m, 1H), 8.56 (s, 1H), 8.48 (d, J=5.0 Hz, 1H), 7.21-7.33 (m, 4H), 7.16-7.21 (m, 1H), 2.89 (quin, J=6.5 Hz, 1H), 2.35-2.44 (m, 2H), 1.09 (d, J=6.8 Hz, 3H), 1.00 (t, J=7.6 Hz, 3H), 0.95 (d, J=6.6 Hz, 3H). MS (ESI, +ve) m/z: 439.1 (M+1)$^+$.

Intermediate 233

4-((2S,5R,M)-4-Acryloyl-2,5-dimethylpiperazin-1-yl)-7-(2-amino-6-fluorophenyl)-6-chloro-1-(2-isopropyl-4-methylpyridin-3-yl)pyrido[2,3-d]pyrimidin-2(1H)-one

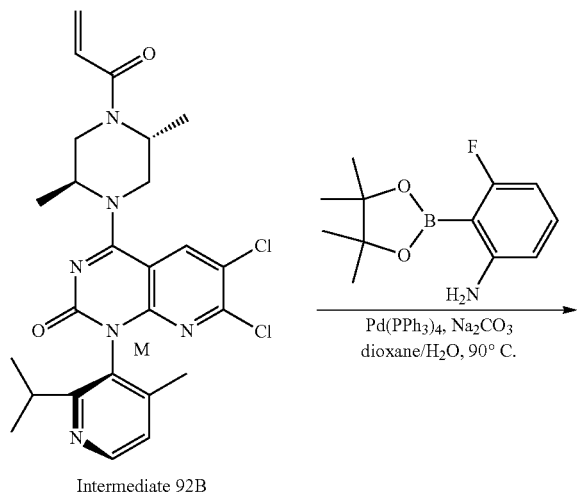

Intermediate 92B

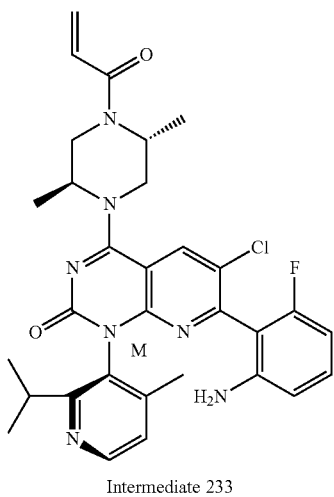

Intermediate 233

A mixture of 4-((2S,5R,M)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate 92B, 3.07 g, 5.96 mmol), tetrakis(triphenylphosphine)palladium (0.34 g, 0.30 mmol), (2-amino-6-fluorophenyl)boronic acid pinacol ester (1.55 g, 6.55 mmol, CombiPhos, Trenton, N.J.) and sodium carbonate, anhydrous, powder (3.16 g, 29.8 mmol) in 1,4-dioxane (20 mL)/water (10 mL) was stirred at 90° C. for 40 min. To the resulting mixture was added water (25 mL) and the mixture was extracted with EtOAc (2×50 mL). The organic extracts were combined and dried over MgSO$_4$. The solution was filtered and concentrated in vacuo to give the crude product as a yellow solid. The resulting crude product was adsorbed onto a plug of silica gel and purified by silica gel chromatography (eluent: 0-10% EtOAc (with 10% MeOH)/heptane) to give 4-((2S,5R,M)-4-acryloyl-2,5-dimethylpiperazin-1-yl)-7-(2-amino-6-fluorophenyl)-6-chloro-1-(2-isopropyl-4-methylpyridin-3-yl)pyrido[2,3-d]pyrimidin-2(1H)-one (Intermediate 233, 1.83 g, 3.09 mmol, 52.0% yield) as a yellow solid. $^1$H NMR (400 MHz, DMSO-d$_6$) δ 8.43 (s, 1H), 8.39 (d, J=4.8 Hz, 1H), 7.19 (d, J=4.8 Hz, 1H), 7.00-7.11 (m, 1H), 6.82 (br dd, J=16.6, 10.6 Hz, 1H), 6.45 (d, J=8.3 Hz, 1H), 6.27-6.35 (m, 1H), 6.19 (dd, J=16.6, 2.3 Hz, 1H), 5.76 (ddd, J=10.1, 5.5, 2.2 Hz, 1H), 5.07-5.19 (m, 2H), 4.45-4.90 (m, 2H), 3.47-4.24 (m, 4H), 2.60-2.88 (m, 1H), 1.85-1.99 (m, 3H), 1.30-1.39 (m, 3H), 1.16-1.29 (m, 3H), 1.03-1.11 (m, 3H), 0.87-1.03 (m, 3H). $^{19}$F NMR (376 MHz, DMSO-d$_6$) δ -116.01--115.34 (m, 1F). m/z (ESI, +ve): 590.2 (M+H)$^+$.

Intermediate 234

5-Amino-6-isopropyl-3-methylpyrimidin-4(3H)-one

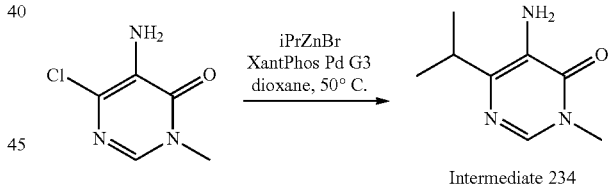

Intermediate 234

A solution of 5-amino-6-chloro-3-methyl-3,4-dihydropyrimidin-4-one (0.414 g, 2.59 mmol; Enamine LLC, Monmouth Jct., N.J.), XantPhos Pd G3 (0.268 g, 0.259 mmol), and isopropylzinc bromide (0.5 M in THF, 5.71 mL, 2.85 mmol) in 1,4-dioxane (3 mL) was stirred at 50° C. for 30 min. The reaction mixture was diluted with EtOAc (100 mL), added to a separatory funnel, and washed with saturated, aqueous ammonium chloride (2×75 mL); the organic layer was separated, dried over anhydrous Na$_2$SO$_4$, and concentrated in vacuo. The crude product was adsorbed onto silica and was purified via automated flash chromatography (silica gel, 0-90% [(3:1) EtOAc/EtOH]/heptane) to give 5-amino-6-isopropyl-3-methylpyrimidin-4(3H)-one (34 mg, 0.20 mmol, 8% yield, Intermediate 234) as a light brown film. $^1$H NMR (400 MHz, CDCl$_3$) δ 7.67 (s, 1H) 3.94 (br s, 2H) 3.52 (s, 3H) 2.85 (spt. J=6.8 Hz, 1H) 1.22 (d, J=6.8 Hz, 6H). MS (ESI, +ve) m/z: 168.1 (M+1)$^+$.

Intermediate 235 tert-Butyl (2R,5)-4-(6-chloro-7-(2-fluorophenyl)-1-(2-formyl-4,6-diisopropylpyrimidin-5-yl)-2-oxo-1,2-dihydropyrido[2,3-d]pyrimidin-4-yl)-2,5-dimethylpiperazine-1-carboxylate

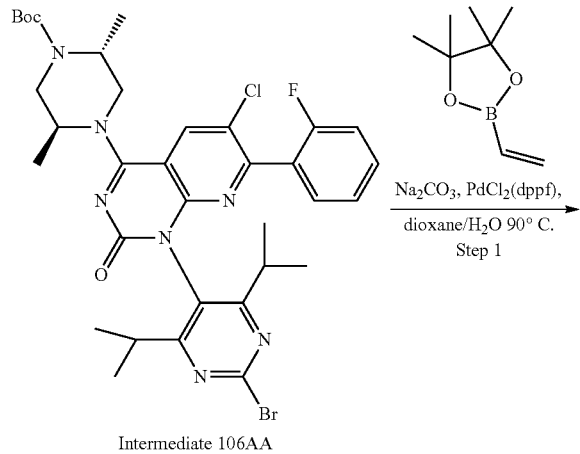

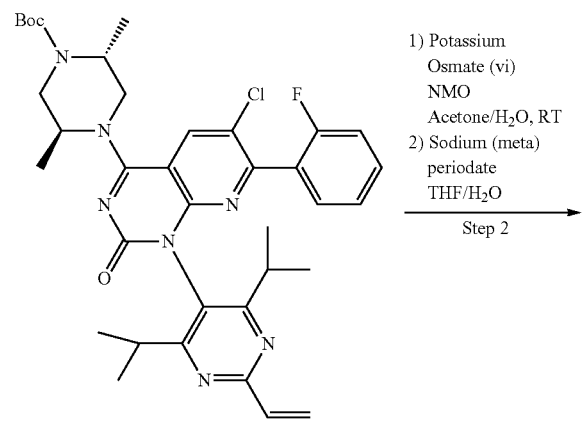

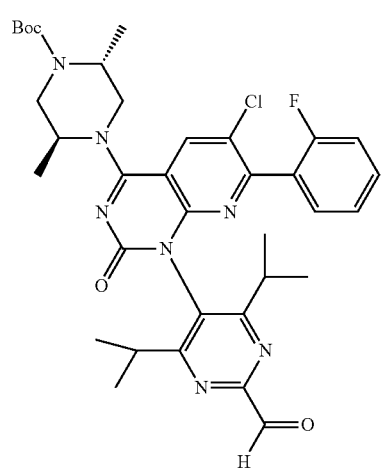

Intermediate 235

Step 1. tert-Butyl (2R,5S)-4-(6-chloro-1-(4,6-diisopropyl-2-vinylpyrimidin-5-yl)-7-(2-fluorophenyl)-2-oxo-1,2-dihydropyrido[2,3-d]pyrimidin-4-yl)-2,5-dimethylpiperazine-1-carboxylate To a 250-mL round-bottomed flask was added tert-butyl (2R,5S)-4-(1-(2-bromo-4,6-diisopropylpyrimidin-5-yl)-6-chloro-7-(2-fluorophenyl)-2-oxo-1,2-dihydropyrido[2,3-d]pyrimidin-4-yl)-2,5-dimethylpiperazine-1-carboxylate (Intermediate 232, 2.352 g, 3.23 mmol), sodium carbonate (1.026 g, 9.68 mmol) and vinylboronic acid pinacol ester (1.09 mL, 6.45 mmol) in 1,4-dioxane (25.8 mL)-water (6.45 mL) (4:1). The reaction mixture was deoxygenated by bubbling argong (gas) into the mixture for 5 min. Then (1,1'-bis(diphenylphosphino) ferrocene) dichloropalladium (0.236 g, 0.323 mmol) was added to the reaction mixture. The reaction mixture was stirred and heated at 90° C., while under an inert ($N_2$) atmosphere for 16 h. The reaction mixture was allowed to cool to rt, then the mixture was diluted was EtOAc and sat. aq. $NaHCO_3$. The layers were separated and the aqueous layer was extracted with EtOAc. The combined organic extracts were dried over $MgSO_4$, filtered and concentrated in vacuo. The crude material was absorbed onto a plug of silica gel and purified by chromatography through a Interchim (25 micron) silica-gel column (200 grams), eluting with a gradient of 0-70% EtOAc/DCM, to provide tert-butyl (2R,5S)-4-(6-chloro-1-(4,6-diisopropyl-2-vinylpyrimidin-5-yl)-7-(2-fluorophenyl)-2-oxo-1,2-dihydropyrido[2,3-d]pyrimidin-4-yl)-2,5-dimethylpiperazine-1-carboxylate (1.579 g, 2.335 mmol, 72.4% yield) as tan solid. $^1$H NMR (400 MHz, DMSO-$d_6$) δ 8.46 (s, 1H) 7.48-7.54 (m, 1H) 7.18-7.34 (m, 3H) 6.79 (dd, J=17.21, 10.37 Hz, 1H) 6.55 (dd, J=17.21, 2.07 Hz, 1H) 5.71-5.76 (m, 1H) 4.85 (br s, 1H) 4.26-4.42 (m, 1H) 4.17 (br d, J=14.31 Hz, 1H) 3.81-3.92 (m, 1H) 3.71 (br d, J=12.65 Hz, 1H) 3.44-3.61 (m, 1H) 2.62-2.76 (m, 2H) 1.45 (s, 9H) 1.36 (d, J=6.63 Hz, 3H) 1.16-1.20 (m, 3H) 1.07-1.11 (m, 6H) 0.91-0.97 (m, 6H). m/z (ESI, +ve ion): 676.2 (M+H)$^+$.

Step 2. tert-Butyl (2R,5S)-4-(6-chloro-7-(2-fluorophenyl)-1-(2-formyl-4,6-diisopropylpyrimidin-5-yl)-2-oxo-1,2-dihydropyrido[2,3-d]pyrimidin-4-yl)-2,5-dimethylpiperazine-1-carboxylate To a 100-mL round-bottomed flask was added tert-butyl (2R,5S)-4-(6-chloro-1-(4,6-diisopropyl-2-vinylpyrimidin-5-yl)-7-(2-fluorophenyl)-2-oxo-1,2-dihydropyrido[2,3-d]pyrimidin-4-yl)-2,5-dimethylpiperazine-1-carboxylate (0.300 g, 0.444 mmol) in acetone (3.70 mL)-water (0.74 mL) (5:1). To this solution was added potassium osmate(vi) (0.016 g, 0.044 mmol) and solid 4-methylmorpholine 4-oxide (0.182 g, 1.553 mmol). The overall reaction mixture was allowed to stir under an inert ($N_2$) atmosphere, while at rt for 15 min. The reaction mixture was quenched with solid sodium sulfite (40 mg) and allowed the mixture to stir 5 min. The reaction mixture was partially concentrated (to remove acetone) in vacuo. The mixture was diluted with EtOAc and brine soln. The layers were separated and the aqueous layer was extracted with EtOAc. The organics were combined, dried over $MgSO_4$, filtered and concentrated in vacuo. The crude residue (0.362 grams) was carried immediately into the next step of the synthesis, without further purification.

The crude diol was diluted with THF (15 mL) then sodium (meta)periodate (0.190 g, 0.887 mmol), followed by water (0.1 mL) was added to the mixture. The resulting reaction mixture was allowed to stir under an inert (N2) atmosphere for 2 h. The reaction mixture was diluted with a mixture of EtOAc/heptane (1:1) (40 mL). The mixture was agitated with sonicator 1 min. The mixture was filtered and the filtrate was collected, then the mixture was diluted with sat. aq. NaHCO₃ (40 mL. The layers were separated and the aqueous layer was extracted with EtOAc (3×). The combined organic extracts were dried over MgSO₄, filtered and concentrated in vacuo. This afforded tert-butyl (2R,5S)-4-(3-chloro-2-(2-fluorophenyl)-8-(2-formyl-4,6-diisopropylpyrimidin-5-yl)-7-oxo-7,8-dihydro-1,6-naphthyridin-5-yl)-2,5-dimethylpiperazine-1-carboxylate (0.190 g, 0.281 mmol, 63.2% yield, Intermediate 235) as a light-yellow solid. This material was carried into the next step of the synthesis, without further purification. ¹H NMR (400 MHz, DMSO-d₆) δ 9.99 (s, 1H) 8.55 (s, 1H) 7.50-7.62 (m, 1H) 7.21-7.40 (m, 3H) 4.92 (br s, 1H) 4.32-4.51 (m, 1H) 4.27 (br d, J=13.48 Hz, 1H) 3.85-3.99 (m, 1H) 3.78 (br d, J=13.06 Hz, 1H) 3.48-3.67 (m, 1H) 2.73-2.98 (m, 2H) 1.51 (s, 9H) 1.41-1.45 (m, 3H) 1.23-1.27 (m, 3H) 1.15-1.21 (m, 6H) 1.00-1.08 (m, 6H). m/z (ESI, +ve ion): 678.1 (M+H)⁺.

Intermediate 236

1-(6-Bromo-2-isopropyl-4-methylpyridin-3-yl)-6-chloro-7-(2-fluorophenyl)pyrido[2,3-d]pyrimidine-2,4(1H,3H)-dione

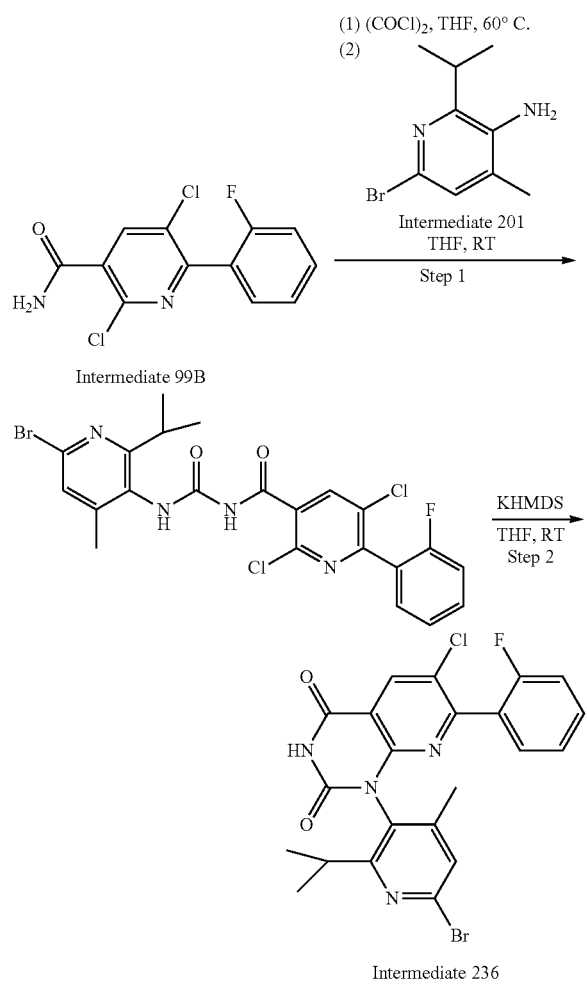

Intermediate 236

Step 1. N-((6-Bromo-2-isopropyl-4-methylpyridin-3-yl)carbamoyl)-2,5-dichloro-6-(2-fluorophenyl)nicotinamide To a 250-mL round-bottomed flask was added 2,5-dichloro-6-(2-fluorophenyl)nicotinamide (Intermediate 99B. 6.00 g, 19.78 mmol) and oxalyl chloride (14.8 mL, 29.7 mmol) in tetrahydrofuran (39.6 mL). The flask was fitted with a Findenser, and the reaction mixture was stirred and heated at 80° C. for 45 min. The reaction mixture was concentrated in vacuo. The crude mixture was carried into the next step of the synthesis, without further purification to prevent decomposition.

To a 150-mL round-bottomed flask was added (2,5-dichloro-6-(2-fluorophenyl)nicotinoyl)carbamoyl isocyanate (crude material from previous step) in tetrahydrofuran (39.6 mL). The reaction mixture was cooled to −10° C. with a dilute acetone/dry ice bath, then a solution of 6-bromo-2-isopropyl-4-methylpyridin-3-amine (5.21 g, 22.75 mmol, Intermediate 201) in THF (3 mL) was added into the reaction mixture. The mixture was allowed to stir under an inert (N2) atmosphere for 1 h. The reaction mixture was concentrated in vacuo. The crude material was triturated from EtOAc and heptane, then the solids were collected by filtration. The solids were washed with heptane. This afforded N-((6-bromo-2-isopropyl-4-methylpyridin-3-yl)carbamoyl)-2,5-dichloro-6-(2-fluorophenyl)nicotinamide (6.880 g, 12.74 mmol, 64.4% yield) as tan solid. m/z (ESI, +ve ion): 539.0 (M+H)⁺.

Step 2. 1-(6-Bromo-2-isopropyl-4-methylpyridin-3-yl)-6-chloro-7-(2-fluorophenyl)pyrido[2,3-d]pyrimidine-2,4(1H,3H)-dione To a 250-mL round-bottomed flask was added N-((6-bromo-2-isopropyl-4-methylpyridin-3-yl)carbamoyl)-2,5-dichloro-6-(2-fluorophenyl)nicotinamide (5.00 g, 9.26 mmol) in tetrahydrofuran (63.3 mL). Then potassium bis(trimethylsilyl)amide, 1m solution in tetrahydrofuran (11.5 mL, 11.57 mmol) was added via an addition funnel dropwise into the reaction mixture over 5 min. The reaction mixture was allowed to stir under an inert (N2) atmosphere for 3 h. More KHMDS (0.5 eq; 8 mL) was added dropwise into the reaction mixture. The reaction mixture was quenched with sat. aq. NH₄Cl (50 mL), then diluted the mixture with 3:1 EtOAc/MeOH and brine solution. The layers were separated and the aqueous layer was extracted with EtOAc. The combined organic extracts were dried over MgSO₄, filtered and concentrated in vacuo. The crude material was absorbed onto a plug of silica gel and purified by chromatography through a ISCO (300 gram column), eluting with a gradient of 0-20% EtOAc in CH₂CL₂, to provide 1-(6-bromo-2-isopropyl-4-methylpyridin-3-yl)-6-chloro-7-(2-fluorophenyl)pyrido[2,3-d]pyrimidine-2,4(1H,3H)-dione (2.05 g, 4.07 mmol, Intermediate 236) as light-yellow solid. m/z (ESI, +ve ion): 503.0 (M+H)⁺.

Intermediate 240

6,7-dichloro-1-(4-chloro-2-isopropylpyridin-3-yl)pyrido[2,3-d]pyrimidine-2,4(1H,3H)-dione

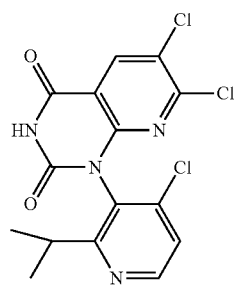 [SMILES: CC(C)c1nccc(Cl)c1-n1c(=O)[nH]c(=O)c2cc(Cl)c(Cl)nc21]

Intermediate 240 was made same as Intermediate 61A but using Intermediate 190 instead of 2-isopropylaniline. $^1$H NMR (DMSO-d6) δ: 12.34-12.56 (m, 1H), 8.66-8.70 (m, 1H), 8.61-8.64 (m, 1H), 7.62-7.68 (m, 1H), 1.10-1.15 (m, 3H), 1.05-1.09 (m, 3H). m/z (ESI, +ve ion): 385 (M+H)$^+$.

Biological Analysis

Section 4—Biochemical and Cellular Activity of Compounds

For compounds in the "Biological Data" table below, the following assay conditions were employed:
Coupled Nucleotide Exchange Assay:

Purified GDP-bound KRAS protein (aa 1-169), containing both G12C and C118A amino acid substitutions and an N-terminal His-tag, was pre-incubated in assay buffer (25 mM HEPES pH 7.4, 10 mM MgCl$_2$, and 0.01% Triton X-100) with a compound dose-response titration for either 5 min or 2 hours (see Table 15). Following compound pre-incubation, purified SOS protein (aa 564-1049) and GTP (Roche 10106399001) were added to the assay wells and incubated for an additional 30 min (for 5 min compound pre-incubation) or 1 hour (for 2 hour compound pre-incubation). To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 10 minutes. The assay plates were then read on a PerkinElmer EnVision Multilabel Reader, using AlphaScreen® technology, and data were analyzed using a 4-parameter logistic model to calculate IC$_{50}$ values.
Phospho-ERK1/2 MSD Assay:

MIA PaCa-2 (ATCC® CRL-1420™) and A549 (ATCC® CCL-185™) cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, MIA PaCa-2 or A549 cells were seeded in 96-well cell culture plates at a density of 25,000 cells/well and incubated at 37° C., 5% CO2. A compound dose-response titration was diluted in growth media, added to appropriate wells of a cell culture plate, and then incubated at 37° C., 5% CO2 for 2 or 4 hours (see Table 15). Following compound treatment, cells were stimulated with 10 ng/mL EGF (Roche 11376454001) for 10 min, washed with ice-cold Dulbecco's phosphate-buffered saline, no Ca2+ or Mg2+ (ThermoFisher Scientific 14190144), and then lysed in RIPA buffer (50 mM Tris-HCl pH 7.5, 1% Igepal, 0.5% sodium deoxycholate, 150 mM NaCl. and 0.5% sodium dodecyl sulfate) containing protease inhibitors (Roche 4693132001) and phosphatase inhibitors (Roche 4906837001). Phosphorylation of ERK1/2 in compound-treated lysates was assayed using Phospho-ERK1/2 Whole Cell Lysate kits (Meso Scale Discovery K151DWD) according to the manufacturer's protocol. Assay plates were read on a Meso Scale Discovery Sector Imager 6000, and data were analyzed using a 4-parameter logistic model to calculate IC50 values.

| Biological Data | | | |
|---|---|---|---|
| Ex.# | Coupled exchange IC50 (5 min; μM) | p-ERK IC$_{50}$ (2 h, MiaPaCa-2; μM) | p-ERK IC$_{50}$ (2 h, A549; μM) |
| 55-50 | 0.09 | 0.023 | >7.5 |
| 55-51 | 0.19 | 0.079 | >7.5 |
| 55-51-1 | 0.298 | 0.157 | >7.5 |
| 55-51-2 | 0.07 | 0.037 | >7.5 |
| 55-52 | 10.215 | 10 | >7.5 |
| 55-53 | 0.356 | — | — |
| 55-54 | 0.032 | 0.016 | >7.5 |
| 55-55 | 3.14 | — | — |
| 55-56 | 0.023 | 0.01 | >7.5 |
| 55-57 | 0.168 | 0.177 | >7.5 |
| 55-58 | 0.052 | 0.056 | >7.5 |
| 55-58-1 | 0.03 | 0.107 | >7.5 |
| 55-58-2 | 0.092 | 0.101 | >7.5 |
| 55-59 | 174 | 10 | >7.5 |
| 55-60 | 7.85 | 7.77 | >7.5 |
| 69-10 | 11 | — | — |
| 69-11 | 1.14 | — | — |
| 69-12 | 2.88 | — | — |
| 72-20 | 0.382 | 0.223 | >7.5 |
| 72-21 | 0.468 | 0.306 | >7.5 |
| 72-22 | 0.408 | — | — |
| 72-23 | 0.647 | — | — |
| 79-10 | 2.78 | — | — |
| 79-11 | 26.7 | — | — |
| 79-12 | 5.46 | — | — |
| 80-10 | 0.077 | 0.063 | >7.5 |
| 80-10-1 | 2.04 | — | — |
| 80-10-2 | 0.053 | 0.04 | >7.5 |
| 80-11 | 0.078 | 0.222 | >7.5 |
| 80-12 | 0.064 | 0.074 | >7.5 |
| 80-13 | 0.043 | 0.053 | >7.5 |
| 80-14-1 | 1.26 | — | — |
| 80-14-2 | 0.061 | 0.031 | >7.5 |
| 80-16-1 | 0.061 | 0.041 | >7.5 |
| 80-16-2 | 0.903 | — | — |
| 80-18-1 | 1.39 | — | — |
| 80-18-2 | 0.11 | 0.044 | >7.5 |
| 80-20 | 0.763 | 0.735 | >7.5 |
| 80-20-1 | 13.9 | — | — |
| 80-20-2 | 0.368 | 0.295 | >7.5 |
| 80-21 | 0.25 | 0.138 | >7.5 |
| 80-21-1 | 0.949 | — | — |
| 80-21-2 | 0.061 | 0.072 | >7.5 |
| 92-1 | 0.016 | 0.014 | >7.5 |
| 92-2 | 0.024 | 0.035 | >7.5 |
| 92-3 | 0.095 | 0.094 | >7.5 |
| 92-4 | 0.044 | 0.042 | >7.5 |
| 92-5 | 0.094 | 0.119 | >7.5 |
| 92-6 | 0.174 | 0.237 | >7.5 |
| 92-7 | 0.031 | 0.259 | >7.5 |
| 92-8 | 0.985 | — | — |
| 92-9 | 8.53 | — | — |
| 92-10 | 0.059 | 0.367 | >7.5 |
| 92-11 | 0.086 | 0.262 | >7.5 |
| 92-12 | 0.019 | 0.022 | >7.5 |
| 92-13 | 0.201 | 0.251 | >7.5 |
| 92-14 | 0.121 | 0.074 | >7.5 |
| 92-15 | 0.094 | 0.125 | >7.5 |

-continued

| Ex.# | Biological Data | | |
|---|---|---|---|
| | Coupled exchange IC50 (5 min; μM) | p-ERK IC$_{50}$ (2 h, MiaPaCa-2; μM) | p-ERK IC$_{50}$ (2 h, A549; μM) |
| 92-16 | 0.043 | 0.015 | >7.5 |
| 92-17 | 0.042 | 0.018 | >7.5 |
| 92-18 | 0.085 | 0.17 | >7.5 |
| 92-19 | 0.044 | 0.027 | >7.5 |
| 92-20 | 0.403 | — | — |
| 92-21 | 0.051 | 0.637 | >7.5 |
| 92-22 | 2.94 | — | — |
| 92-23 | 0.038 | 0.036 | >7.5 |
| 92-24 | 0.019 | 0.116 | >7.5 |
| 92-25 | 0.04 | 0.016 | >7.5 |
| 92-26 | 0.101 | 0.023 | >7.5 |
| 92-27 | 0.149 | 0.735 | >7.5 |
| 92-28 | 0.123 | 0.11 | >7.5 |
| 92-29 | 0.139 | 10 | >7.5 |
| 92-30 | 0.479 | — | — |
| 92-31 | 0.014 | 0.022 | >7.5 |
| 92-32 | 0.075 | 0.129 | >7.5 |
| 92-33 | 0.113 | 0.216 | >7.5 |
| 92-34 | 0.054 | 0.06 | >7.5 |
| 92-35 | 0.758 | — | — |
| 92-36 | 0.275 | 0.133 | 1.87 |
| 92-37 | 0.048 | 0.06 | >7.5 |
| 92-38 | 0.042 | 0.042 | >7.5 |
| 92-39 | 0.032 | 0.145 | >7.5 |
| 92-40 | 0.244 | 0.14 | >7.5 |
| 92-41 | 0.117 | 0.075 | 3.75 |
| 92-42 | 0.117 | 0.08 | >7.5 |
| 92-43 | 0.054 | 0.076 | >7.5 |
| 92-44 | 0.04 | 0.098 | >7.5 |
| 92-45 | 0.025 | 0.023 | >7.5 |
| 92-46 | 0.023 | 0.032 | >7.5 |
| 92-47 | 0.057 | 0.049 | >7.5 |
| 92-48 | 0.247 | 0.365 | >7.5 |
| 92-49 | 0.123 | 0.328 | >7.5 |
| 92-50 | 1.1 | — | — |
| 92-51 | 0.033 | 0.03 | >7.5 |
| 92-52 | 0.161 | 0.196 | >7.5 |
| 92-53 | 0.135 | 0.309 | >7.5 |
| 92-54 | 0.169 | 0.217 | >7.5 |
| 92-55 | 0.021 | 0.018 | >7.5 |
| 92-56 | 0.591 | — | — |
| 92-57 | 0.126 | 0.126 | >7.5 |
| 92-58 | 0.074 | 0.023 | >7.5 |
| 92-59 | 0.028 | 0.034 | >7.5 |
| 92-60 | 0.02 | 0.018 | >7.5 |
| 92-61 | 0.008 | 0.027 | >7.5 |
| 92-62 | 0.01 | 0.075 | >7.5 |
| 92-63 | 0.039 | 0.052 | >7.5 |
| 92-64 | 0.039 | 0.044 | >7.5 |
| 92-65 | 0.066 | 0.046 | >7.5 |
| 92-66 | 0.034 | 0.033 | >7.5 |
| 92-67 | 0.13 | 0.062 | >7.5 |
| 92-68 | 3.31 | — | — |
| 92-69 | 1.36 | — | — |
| 92-70 | 0.6 | — | — |
| 92-71 | 1.36 | — | — |
| 92-72 | 8.87 | — | — |
| 93-1 | 0.055 | 0.097 | >7.5 |
| 93-2 | 0.305 | 0.558 | >7.5 |
| 94-1 | 0.077 | 0.107 | >7.5 |
| 94-2 | 0.322 | 0.204 | >7.5 |
| 94-3 | 0.684 | — | — |
| 94-4 | 0.222 | 0.218 | >7.5 |
| 94-5 | 0.708 | 0.265 | >7.5 |
| 94-6 | 0.468 | — | — |
| 94-7 | 0.976 | — | — |
| 94-8 | 0.255 | 0.131 | >7.5 |
| 94-9 | 0.469 | — | — |
| 94-10 | 0.137 | 0.079 | >7.5 |
| 94-11 | 0.844 | — | — |
| 94-12 | 0.184 | 0.128 | >7.5 |
| 94-13 | 0.387 | — | — |
| 94-14 | 38.2 | — | — |
| 94-15 | 0.963 | — | — |
| 94-16 | 73.7 | — | — |
| 94-17 | 0.39 | — | — |
| 94-18 | 0.749 | — | — |
| 94-19 | 0.067 | 0.518 | >7.5 |
| 94-20 | 0.452 | — | — |
| 94-21 | 32.4 | — | — |
| 95-1 | 0.053 | 0.318 | >7.5 |
| 95-2 | 1.04 | — | — |
| 95-3 | 0.631 | — | — |
| 95-4 | 0.571 | — | — |
| 95-5 | 0.304 | 0.611 | >7.5 |
| 95-6 | 0.823 | — | — |
| 95-7 | 34 | — | — |
| 96-1 | 0.345 | — | — |
| 96-2 | 1.22 | — | — |
| 100-1 | 0.084 | 0.123 | >7.5 |
| 100-1-1 | 0.061 | 0.091 | >7.5 |
| 100-1-2 | 0.062 | 0.098 | >7.5 |
| 100-2 | 0.324 | 0.298 | >7.5 |
| 100-3 | 0.763 | — | — |
| 100-4 | 0.006 | 0.106 | >7.5 |
| 100-5 | 58.3 | — | — |
| 100-6 | 250 | — | — |
| 100-7 | 5.097 | — | — |
| 100-8 | 0.05 | 0.042 | >7.5 |
| 100-9 | 1.15 | — | — |
| 101-1 | 0.134 | 0.116 | >7.5 |
| 101-2 | 0.16 | 0.116 | >7.5 |
| 101-3 | 0.195 | 0.208 | >7.5 |
| 102-1 | 0.071 | 0.395 | 5.245 |
| 102-2 | 1.23 | — | — |
| 102-3 | 0.037 | 0.032 | >7.5 |
| 102-4 | 0.079 | 0.262 | 4.73 |
| 102-5 | 0.071 | 0.084 | >7.5 |
| 102-5-1 | 0.031 | 0.058 | >7.5 |
| 102-5-2 | 0.173 | 0.873 | >7.5 |
| 102-6 | 0.066 | 0.063 | >7.5 |
| 102-6-1 | 0.094 | 0.056 | >7.5 |
| 102-6-2 | 0.726 | — | — |
| 102-7 | 0.376 | — | — |
| 102-7-1 | 0.181 | 1.063 | >7.5 |
| 102-7-2 | 5.28 | — | — |
| 102-8 | 184 | — | — |
| 103-1 | 0.105 | 0.107 | >7.5 |
| 103-1-1 | 1.26 | — | — |
| 103-1-2 | 0.053 | 0.039 | >7.5 |
| 103-2 | 0.084 | 0.04 | >7.5 |
| 103-3 | 0.677 | 0.143 | >7.5 |
| 103-4 | 0.057 | 0.062 | >7.5 |
| 103-5 | 0.2 | 0.507 | >7.5 |
| 103-6 | 0.08 | 0.474 | >7.5 |
| 103-6-1 | 1.15 | — | — |
| 103-6-2 | 0.112 | 0.26 | 5.19 |
| 103-7 | 0.143 | 0.128 | 3.75 |
| 103-7-1 | 0.653 | — | — |
| 103-7-2 | 0.088 | 0.052 | >7.5 |
| 106-1 | 0.08 | 0.096 | 4.545 |
| 106-2 | 1.01 | 5.31 | >7.5 |
| 106-3 | 8.34 | 10 | >7.5 |
| 106-4 | 5.04 | 2.45 | >7.5 |
| 106-5 | 6.13 | 1.46 | >7.5 |
| 106-6 | 0.322 | — | — |
| 106-6-1 | 3.67 | — | — |
| 106-6-2 | 0.059 | 0.301 | >7.5 |
| 106-7 | 0.301 | — | — |
| 106-7-1 | 1.98 | — | — |
| 106-7-2 | 0.129 | 0.271 | >7.5 |
| 106-8 | 3.35 | 1.88 | >7.5 |
| 106-9 | 3.7 | 2.24 | >7.5 |
| 106-10 | 12.1 | — | — |

-continued

Biological Data

| Ex.# | Coupled exchange IC50 (5 min; μM) | p-ERK IC$_{50}$ (2 h, MiaPaCa-2; μM) | p-ERK IC$_{50}$ (2 h, A549; μM) |
|---|---|---|---|
| 107-1 | 0.026 | 0.064 | 5.57 |
| 107-2 | 0.098 | 0.299 | 1.25 |
| 107-3 | 0.114 | 0.144 | 3.735 |
| 107-4 | 0.051 | 0.085 | >7.5 |
| 107-5 | 0.103 | 0.3 | 3.255 |
| 108-1 | 0.009 | 0.039 | >7.5 |
| 108-1-1 | 0.006 | 0.021 | >7.5 |
| 108-1-2 | 0.008 | 0.054 | >7.5 |
| 108-2 | 0.049 | 0.032 | >7.5 |
| 108-2-1 | 0.035 | 0.046 | >7.5 |
| 108-2-2 | 0.181 | 0.148 | >7.5 |
| 109-1 | 0.194 | 0.052 | >7.5 |
| 109-1-1 | 0.06 | 0.045 | >7.5 |
| 109-1-2 | 0.209 | 0.08 | >7.5 |
| 109-2 | 0.107 | 0.098 | >7.5 |
| 109-2-1 | 0.059 | 0.065 | >7.5 |
| 109-2-2 | 0.226 | — | — |
| 110-1 | 0.57 | 1.12 | >7.5 |
| 110-2 | 13.4 | — | — |
| 119-1 | 24 | — | — |
| 119-2 | 0.33 | — | — |
| 121-1 | 0.195 | 0.086 | >7.5 |
| 121-2 | 0.096 | 0.081 | >7.5 |
| 121-3 | 0.066 | 0.027 | >7.5 |
| 121-4 | 1.48 | — | — |
| 122-1 | 0.455 | — | — |
| 122-2 | 0.357 | 1.21 | — |
| 122-2-1 | 17.3 | — | — |
| 122-2-2 | 0.088 | 0.63 | >7.5 |
| 122-3 | 0.503 | — | — |
| 122-3-1 | 6.82 | — | — |
| 122-3-2 | 0.179 | 0.145 | >7.5 |
| 123-1 | 1.25 | — | — |
| 123-2 | 0.4 | 0.26 | >7.5 |
| 123-3 | 14 | — | — |
| 123-4 | 1 | — | — |
| 123-5 | 7.53 | 10 | — |
| 123-6 | 0.231 | 0.133 | >7.5 |
| 124-1 | 0.027 | 0.024 | >7.5 |
| 124-2 | 0.033 | 0.032 | >7.5 |
| 124-3 | 0.028 | 0.032 | >7.5 |
| 124-4 | 0.022 | 0.016 | >7.5 |
| 124-5 | 0.439 | — | — |
| 124-6 | 0.037 | 0.062 | >7.5 |
| 124-7 | 0.109 | 0.093 | >7.5 |
| 124-8 | 0.034 | 0.24 | 6.355 |
| 124-9 | 0.122 | 0.169 | >7.5 |
| 124-10 | 0.046 | 0.049 | >7.5 |
| 124-11 | 0.075 | 0.098 | >7.5 |
| 124-12 | 0.313 | 0.231 | >7.5 |
| 124-13 | 0.068 | 0.094 | >7.5 |
| 124-14-1 | 22.2 | — | — |
| 124-14-2 | 59.5 | — | — |
| 124-16-1 | 1.12 | — | — |
| 124-16-2 | 7.37 | — | — |
| 125-1 | 0.028 | 0.055 | >7.5 |
| 125-2 | 0.042 | 0.038 | >7.5 |
| 125-3 | 0.04 | 0.041 | >7.5 |
| 125-4 | 0.038 | 0.023 | >7.5 |
| 125-5 | 0.46 | — | — |
| 125-6 | 0.038 | 0.105 | >7.5 |
| 125-7 | 0.085 | 0.137 | >7.5 |
| 125-8 | 0.113 | 0.137 | 5.05 |
| 125-9 | 0.035 | 0.048 | >7.5 |
| 125-10 | 0.032 | 0.068 | >7.5 |
| 125-11 | 0.091 | 0.187 | >7.5 |
| 129-1 | 0.054 | 0.124 | >7.5 |
| 129-2 | 0.065 | 0.027 | >7.5 |
| 129-3 | 0.352 | — | — |
| 129-4 | 0.053 | 0.058 | >7.5 |
| 129-5 | 0.19 | 0.087 | >7.5 |
| 129-6 | 0.06 | 0.058 | >7.5 |
| 129-7 | 0.064 | 0.025 | >7.5 |
| 129-8 | 0.056 | 0.023 | >7.5 |
| 129-9 | 0.008 | 0.048 | >7.5 |
| 129-10 | 0.041 | 0.049 | >7.5 |
| 129-11 | 0.152 | 0.247 | >7.5 |
| 129-12 | 0.167 | 0.39 | >7.5 |
| 129-13 | 0.067 | 0.054 | >7.5 |
| 132-1 | 0.053 | 0.46 | >7.5 |
| 132-2 | 0.57 | — | — |
| 141-1 | 0.268 | — | — |
| 141-2 | 0.279 | — | — |
| 141-3 | 0.197 | 0.331 | >7.5 |
| 144-1 | 0.166 | 0.23 | >7.5 |
| 144-2 | 24.9 | — | — |
| 144-2-1 | 63.7 | — | — |
| 144-2-2 | 9.13 | 3.1 | 4 |
| 144-3 | 0.166 | 2.41 | >7.5 |
| 145-1 | 2.07 | 10 | 5.75 |
| 145-1-1 | 1.71 | 1.3 | 5.53 |
| 145-1-2 | 1.15 | 1.05 | 3.94 |
| 145-2 | 0.344 | 1.68 | >7.5 |
| 145-2-1 | 0.294 | 0.356 | >7.5 |
| 145-2-2 | 0.238 | 0.213 | >7.5 |
| 145-3 | 3.82 | 10 | 4.41 |
| 146-1 | 12.8 | — | — |
| 146-1-1 | 9.43 | — | — |
| 146-1-2 | 53.8 | — | — |
| 146-2 | 0.028 | 0.038 | 6.51 |
| 146-2-1 | 0.025 | 0.024 | — |
| 146-2-2 | 0.061 | 0.096 | 5.475 |
| 146-3 | 7.03 | 4.26 | >7.5 |
| 146-3-1 | 204 | — | — |
| 146-3-2 | 4.4 | 1.05 | >7.5 |
| 146-3-3 | 57.3 | — | — |
| 146-3-4 | 7.96 | 1.26 | >7.5 |
| 146-4 | 8.13 | 4.19 | >7.5 |
| 150 | 0.313 | — | — |
| 151 | 0.348 | — | — |
| 152 | 132 | — | — |
| 153 | 0.38 | 0.264 | >7.5 |
| 154 | 0.062 | 0.049 | 6.96 |
| 155 | 0.104 | 0.063 | 2.59 |
| 156 | 0.369 | 0.148 | >7.5 |
| 157 | 0.064 | 0.07 | >7.5 |
| 158 | 0.189 | 0.191 | 3.835 |
| 159 | 0.046 | 0.119 | 3.035 |
| 160 | 0.081 | 0.058 | >7.5 |
| 161 | 0.294 | 0.061 | >7.5 |
| 162 | 0.133 | 0.078 | >7.5 |
| 163 | 0.127 | 0.055 | >7.5 |
| 164-1 | 0.066 | 0.198 | 6.05 |
| 164-2 | 3.44 | — | — |
| 165-1 | 0.073 | 0.049 | >7.5 |
| 165-2 | 1.61 | — | — |
| 166-1 | 0.049 | 0.118 | >7.5 |
| 166-2 | 1.032 | — | — |
| 167 | 0.052 | 0.083 | >7.5 |
| 168 | 0.096 | 0.198 | 4.345 |
| 169 | 0.55 | — | — |
| 170 | 0.064 | 0.077 | >7.5 |
| 171 | 0.206 | — | — |
| 172 | 0.08 | 0.099 | >7.5 |
| 173-1 | 0.128 | 0.229 | 5.97 |
| 173-2 | 5.25 | — | — |
| 174 | 0.069 | 0.082 | >7.5 |
| 175-1 | 1.16 | — | — |
| 175-2 | 0.071 | 0.171 | >7.5 |
| 176-1 | 0.131 | 0.347 | 5.755 |
| 176-2 | 2.43 | — | — |
| 177-1 | 0.031 | 0.063 | 3.34 |
| 177-2 | 1.26 | — | — |
| 178 | 3.77 | — | — |

Biological Data

| Ex.# | Coupled exchange IC50 (5 min; μM) | p-ERK IC$_{50}$ (2 h, MiaPaCa-2; μM) | p-ERK IC$_{50}$ (2 h, A549; μM) |
|---|---|---|---|
| 179-1 | 0.048 | 0.049 | >7.5 |
| 179-2 | 2.42 | — | — |
| 179 | 0.069 | 0.069 | >7.5 |
| 180 | 85.1 | 10 | — |
| 181 | 4.53 | 10 | >7.5 |
| 182-1 | 0.14 | 0.319 | 6.62 |
| 182-2 | 0.187 | 0.365 | 5.62 |
| 182 | 8.794 | 0.239 | 3.52 |
| 183-1 | 0.61 | — | — |
| 183-2 | 0.058 | 0.043 | >7.5 |
| 184 | 2.81 | — | — |
| 185 | 0.055 | 0.08 | >7.5 |
| 186 | 0.093 | 0.199 | >7.5 |
| 187 | 0.09 | 0.081 | 0.317 |
| 188 | 0.038 | 0.04 | 4.975 |
| 189-1 | 0.036 | 0.072 | >7.5 |
| 189-2 | 14.7 | — | — |
| 189 | 0.158 | 0.209 | >7.5 |
| 190 | 0.126 | 1.705 | >7.5 |
| 191-1 | 2.99 | — | — |
| 191-2 | 0.079 | 0.079 | >7.5 |
| 192 | 0.029 | 0.161 | >7.5 |
| 193 | 0.056 | 0.055 | >7.5 |
| 194-1 | 0.067 | 0.033 | >7.5 |
| 194-2 | 1.45 | — | — |
| 194 | 0.186 | 0.048 | >7.5 |
| 195 | 0.488 | — | — |
| 196 | 0.048 | 0.097 | >7.5 |
| 197-1 | 1.59 | — | — |
| 197-2 | 0.01 | 0.091 | >7.5 |
| 198 | 0.075 | 0.136 | 5.96 |
| 199 | 0.132 | 0.087 | >7.5 |
| 200 | 0.03 | 0.094 | >7.5 |
| 201 | 0.075 | 0.205 | 5.05 |
| 202 | 0.071 | 0.075 | >7.5 |
| 203 | 0.223 | 0.243 | >7.5 |
| 204 | 0.066 | 0.091 | 3.01 |
| 205-1 | 0.098 | 0.07 | >7.5 |
| 205-2 | 0.078 | 0.091 | >7.5 |
| 205 | 0.08 | 0.095 | >7.5 |
| 206-1 | 0.143 | 0.1 | >7.5 |
| 206-2 | 0.098 | 0.139 | >7.5 |
| 207 | 0.932 | — | — |
| 208-1 | 2.56 | — | — |
| 208-2 | 0.117 | 0.106 | >7.5 |
| 208 | 0.231 | 0.14 | >7.5 |
| 209-1 | 0.088 | 0.116 | >7.5 |
| 209-2 | 1.34 | — | — |
| 209-3 | 0.115 | 0.107 | >7.5 |
| 210 | 0.049 | 0.039 | >7.5 |
| 211-1 | 0.113 | 0.128 | >7.5 |
| 211-2 | 0.05 | 0.106 | >7.5 |
| 211-3 | 0.084 | 0.253 | >7.5 |
| 212-1 | 0.256 | 0.705 | >7.5 |
| 212-2 | 0.104 | 0.237 | >7.5 |
| 212-3 | 0.703 | — | — |
| 213-1 | 1.5 | — | — |
| 213-2 | 0.072 | 0.069 | >7.5 |
| 213-3 | 0.066 | 0.074 | >7.5 |
| 213-4 | 1.51 | — | — |
| 213 | 0.182 | 0.104 | >7.5 |
| 214-1 | 0.025 | 0.03 | >7.5 |
| 214-2 | 2.84 | — | — |
| 214 | 0.02 | 0.025 | >7.5 |
| 215-1 | 3.79 | — | — |
| 215-2 | 0.055 | 0.086 | >7.5 |
| 215 | 0.076 | 0.275 | — |
| 216 | 2.01 | — | — |
| 217 | 1.56 | 0.972 | >7.5 |
| 218 | 0.094 | 0.035 | >7.5 |
| 219 | 250 | — | — |
| 220 | 250 | — | — |
| 221 | 1.26 | — | — |
| 222-1 | 0.95 | — | — |
| 222-2 | 0.014 | 0.048 | 2.52 |
| 222 | 0.705 | 0.057 | 2.71 |
| 223 | 0.18 | 0.659 | >7.5 |
| 224-1 | 23.3 | — | — |
| 224-2 | 1.29 | — | — |
| 224 | 7.62 | — | — |
| 225-1 | 7.62 | — | — |
| 225-2 | 0.501 | — | — |
| 225 | 4.43 | — | — |
| 226 | 0.04 | 0.063 | >7.5 |
| 227 | 3.57 | — | — |
| 228 | 0.769 | — | — |
| 229 | 0.071 | 0.032 | >7.5 |

(—) denotes not tested

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. A compound selected from the group consisting of:

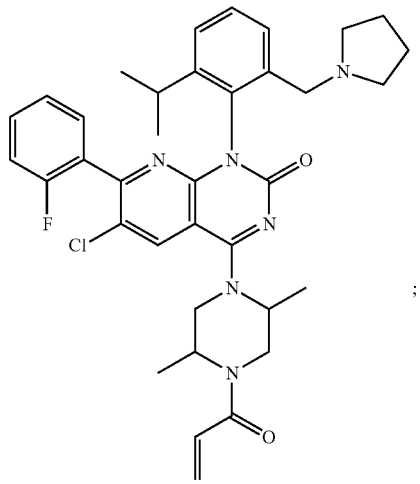

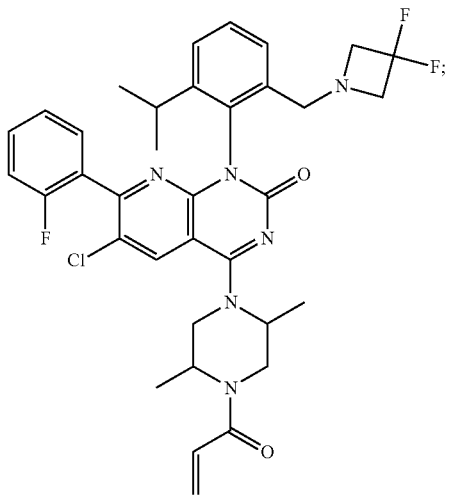

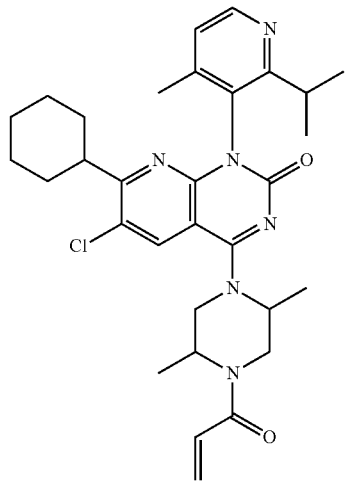

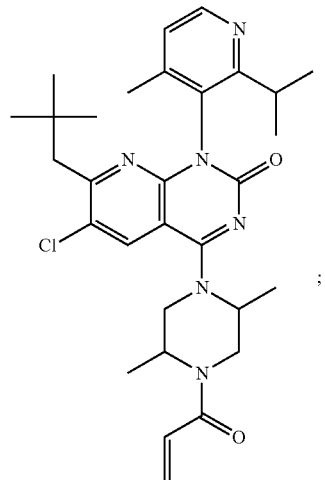

963
-continued
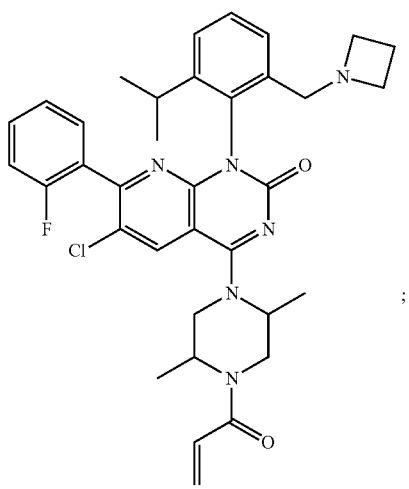
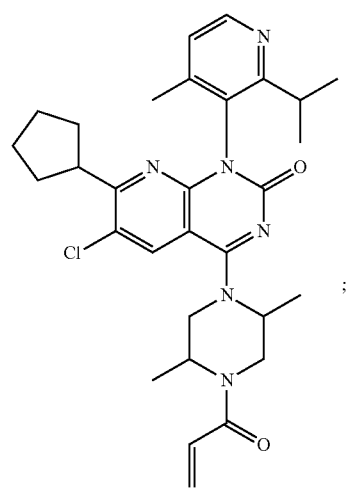
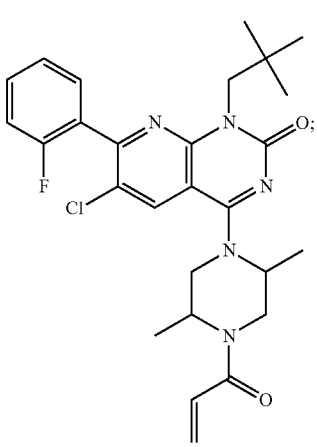
964
-continued
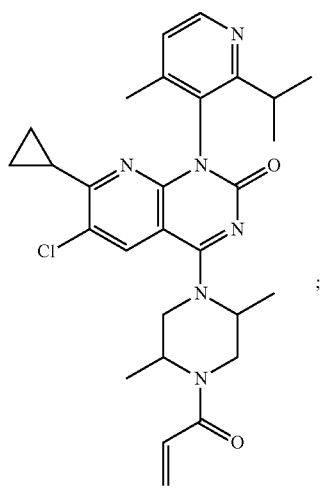
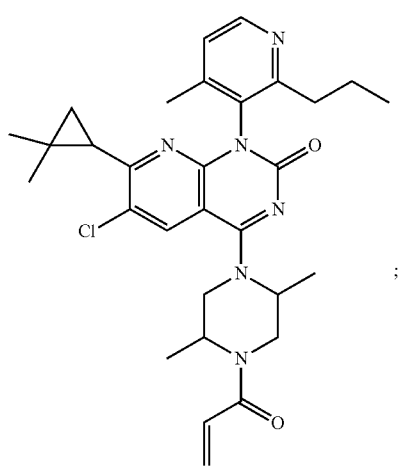
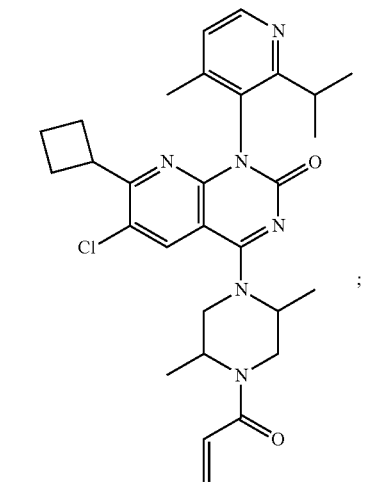

965
-continued
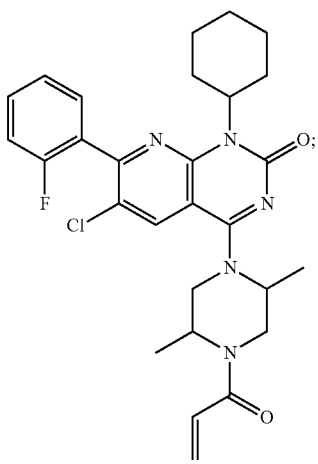
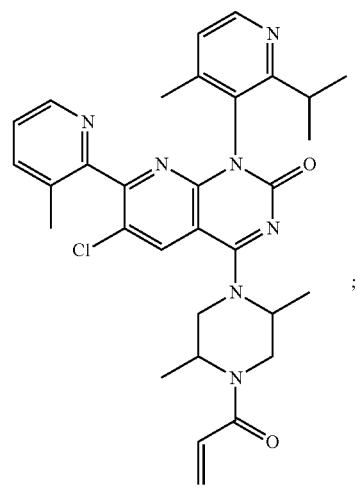
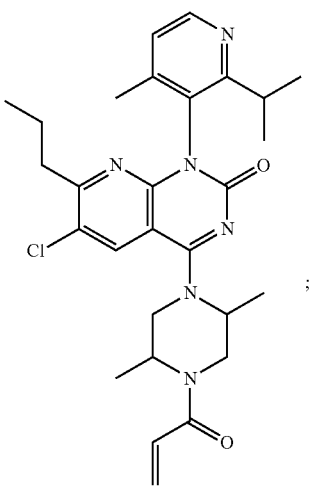
966
-continued
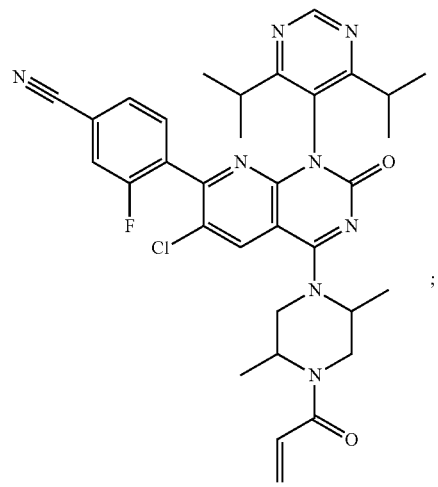
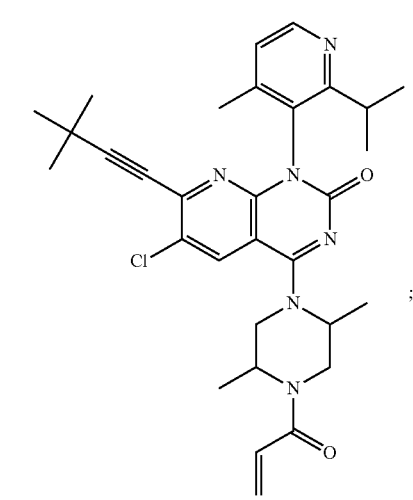
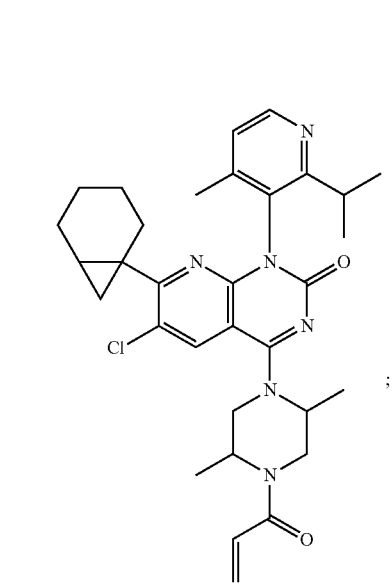

967
-continued
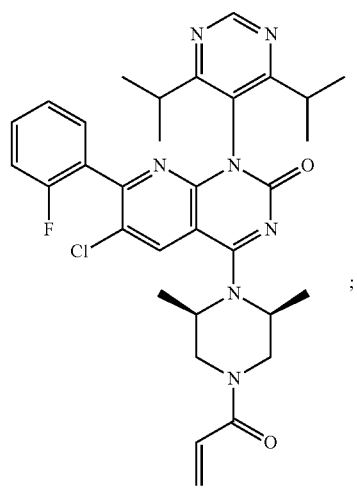
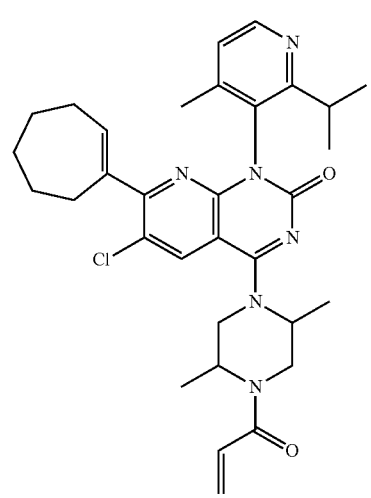
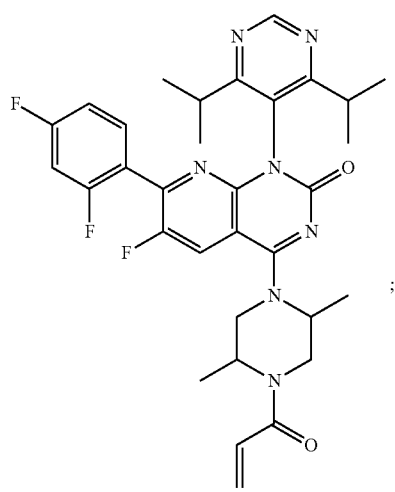
968
-continued
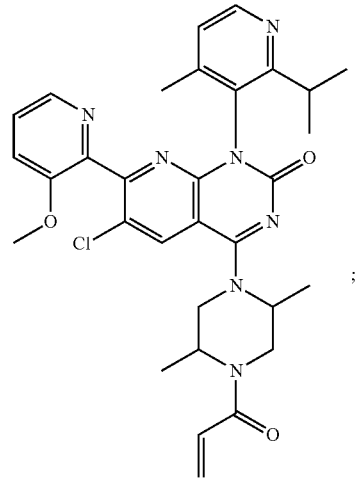
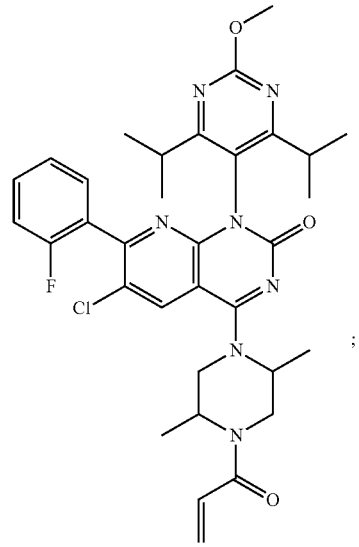
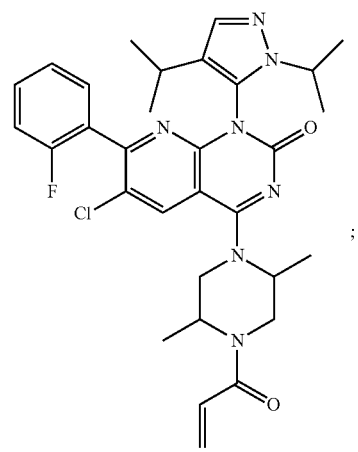

969
-continued
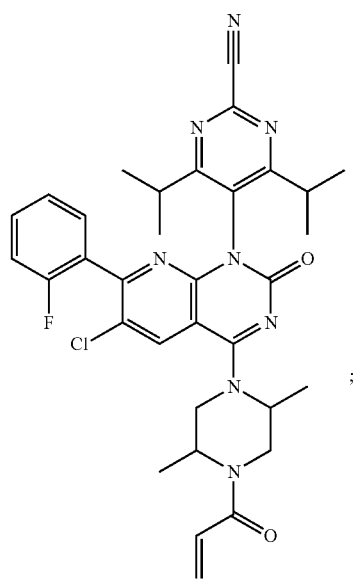
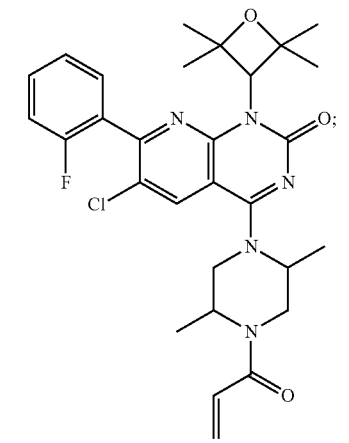
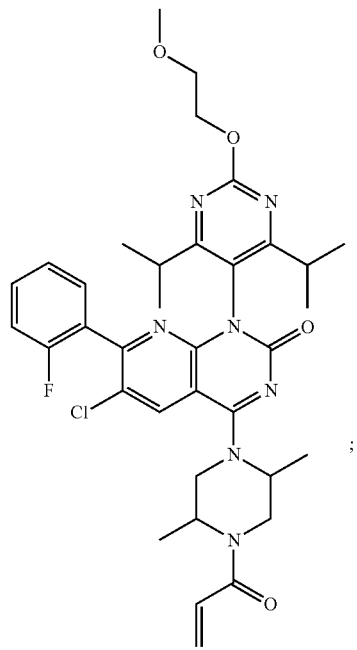
970
-continued
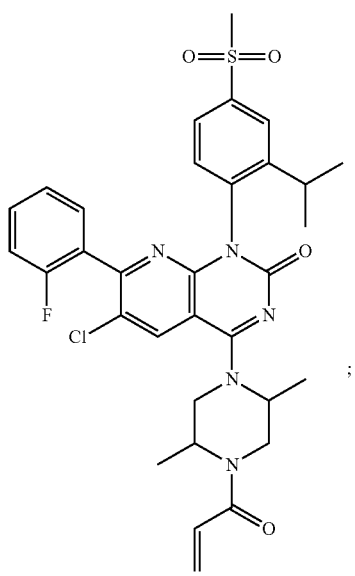
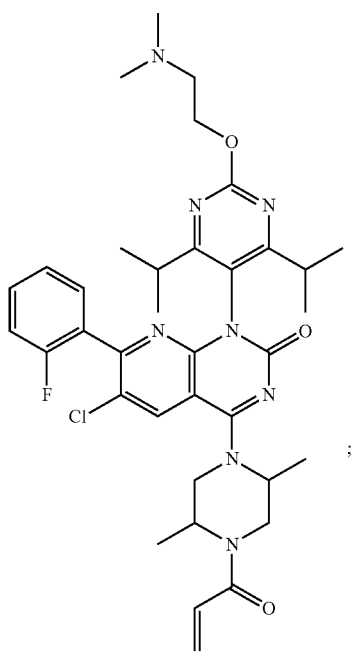

971
-continued
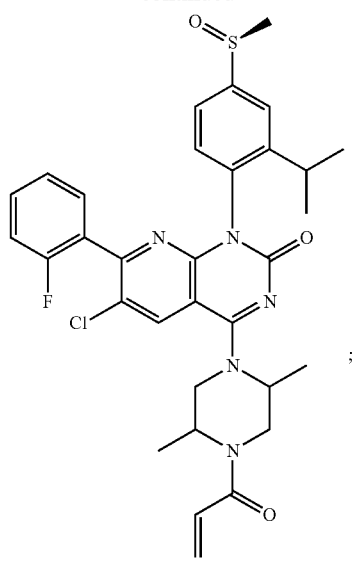
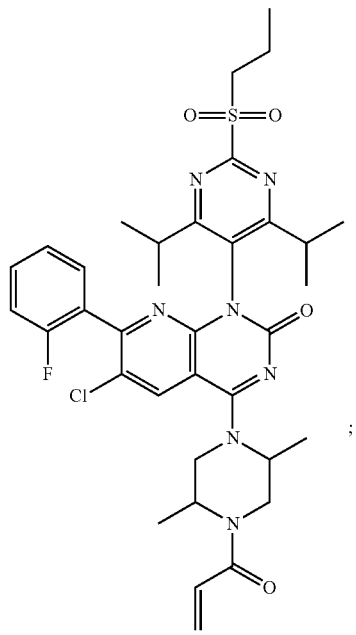
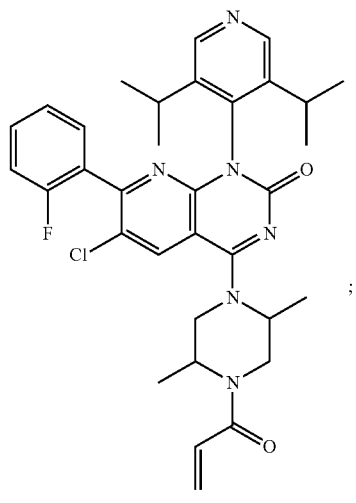
972
-continued
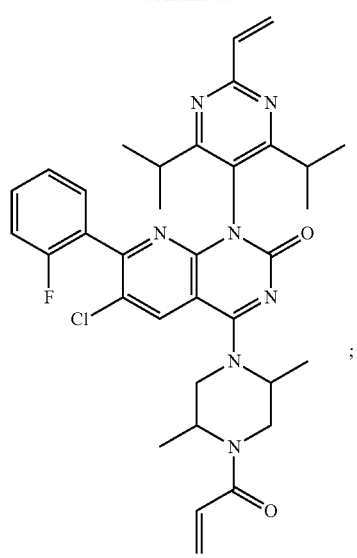
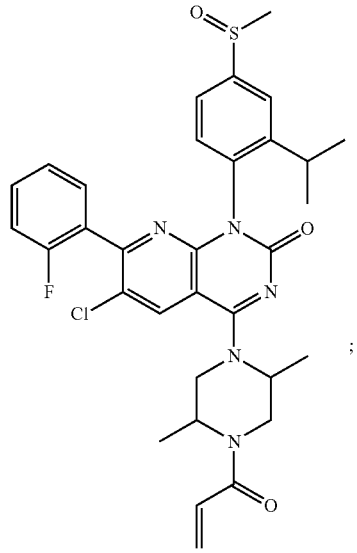
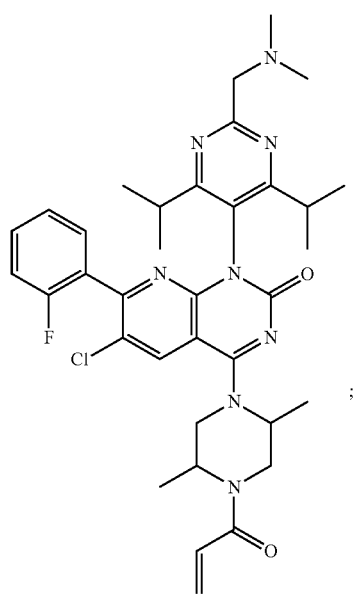

973
-continued
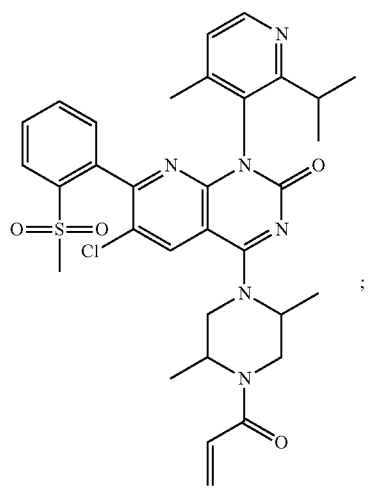
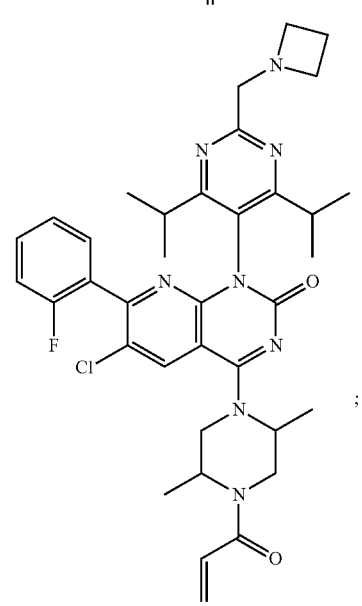
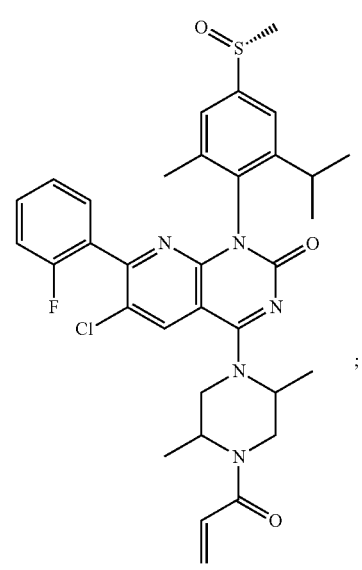
974
-continued
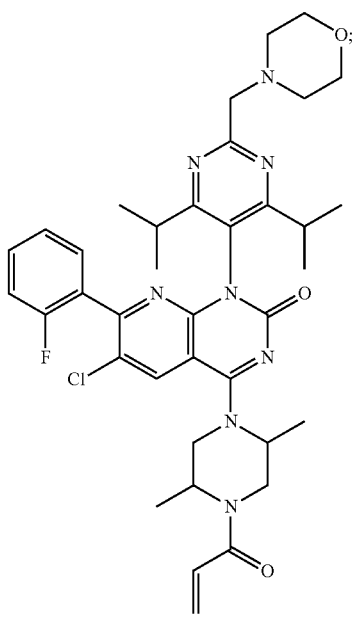
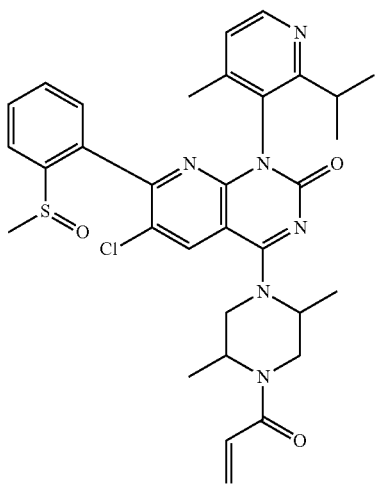
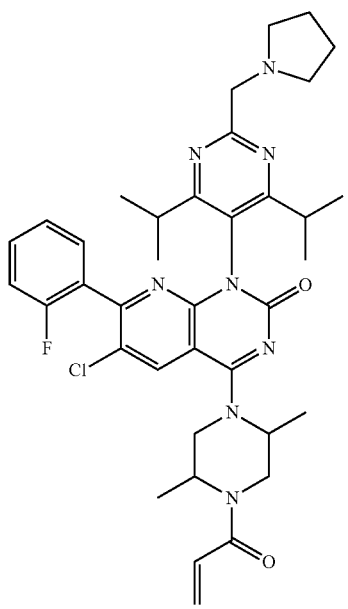

975
-continued
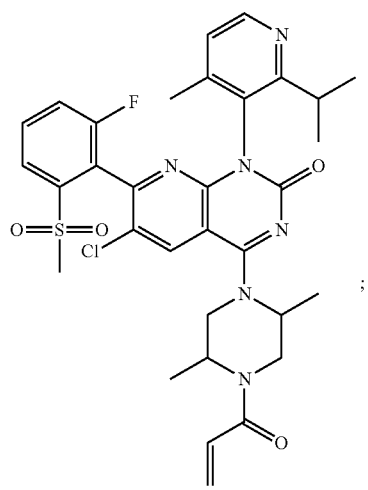
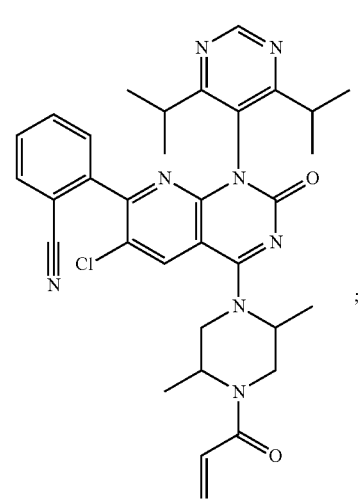
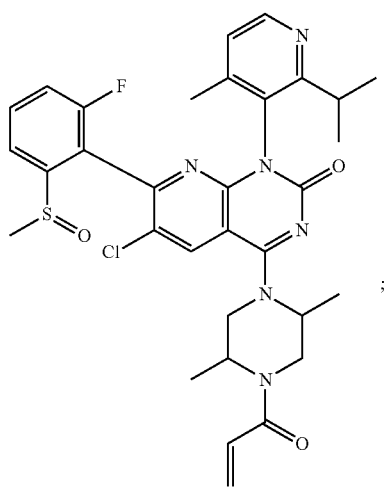
976
-continued
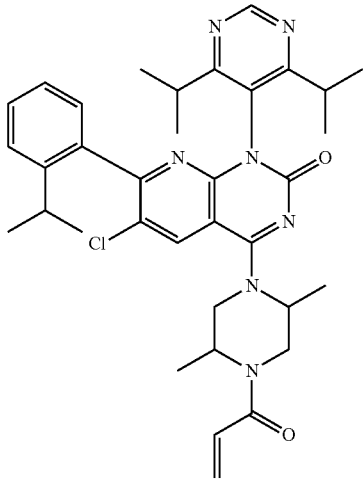
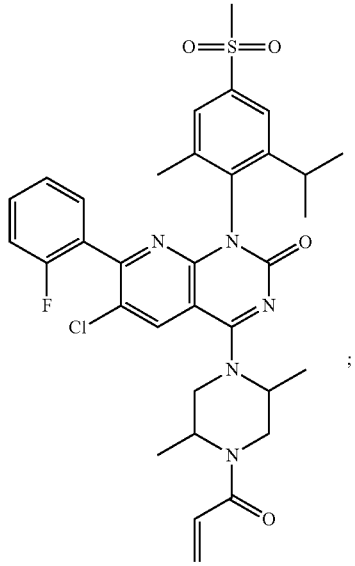
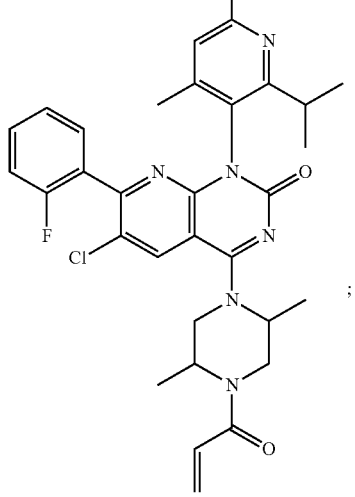

977
-continued
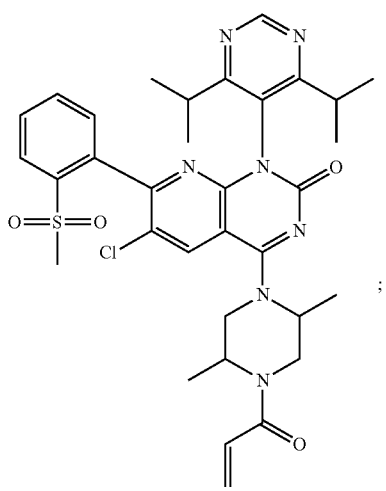
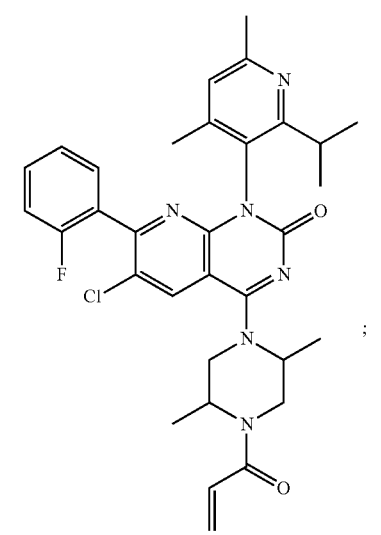
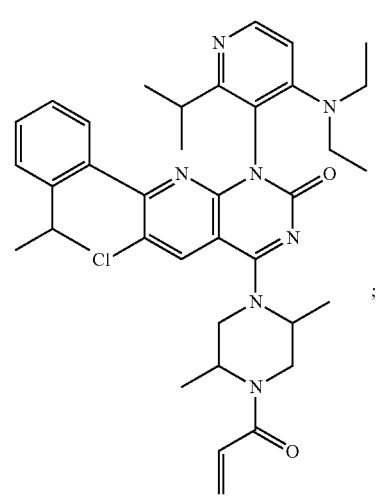
978
-continued
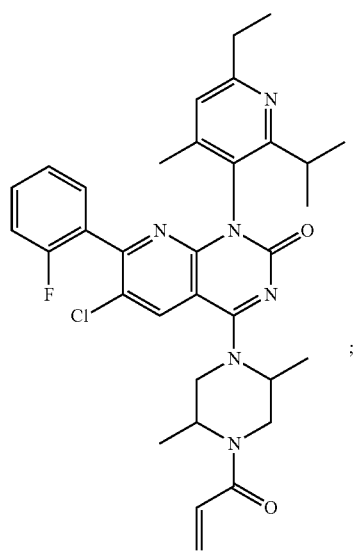
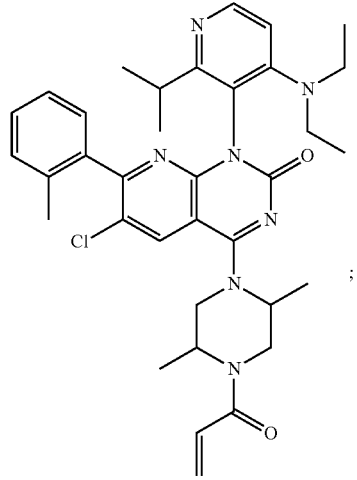
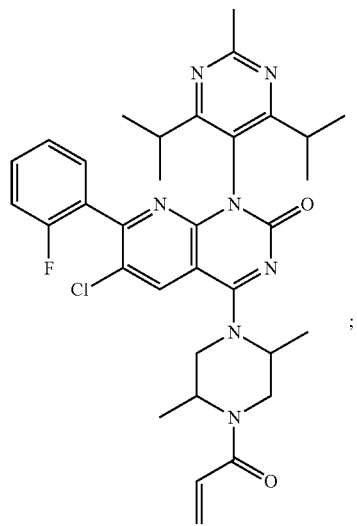

979
-continued
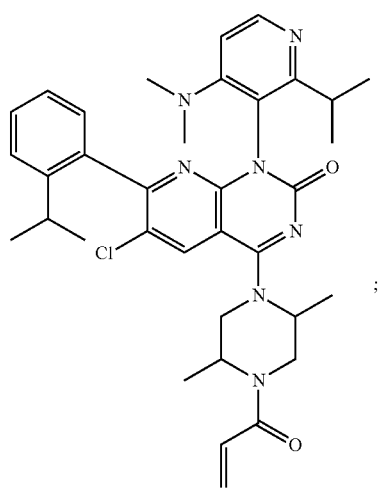
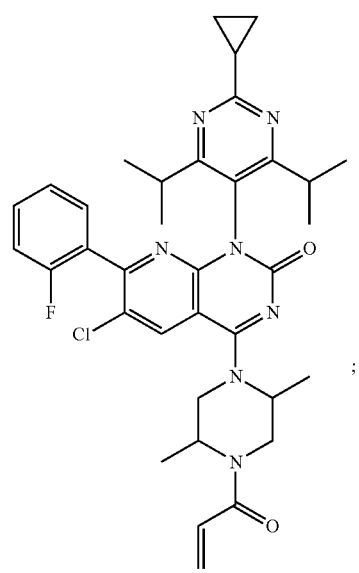
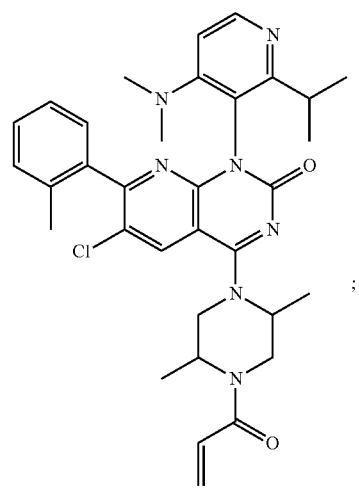
980
-continued
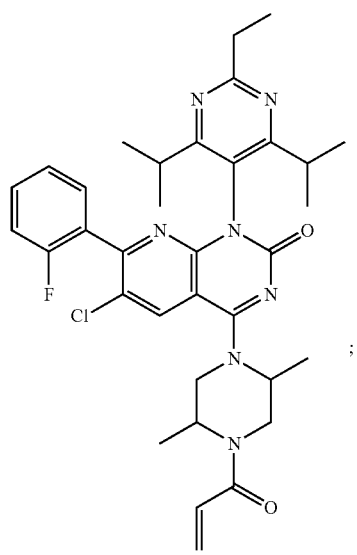
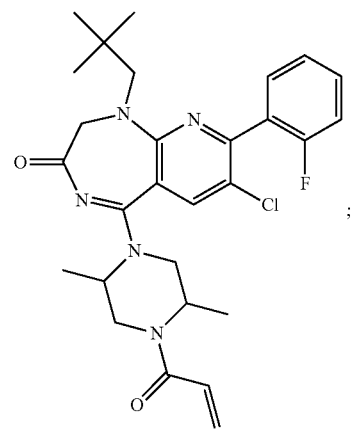
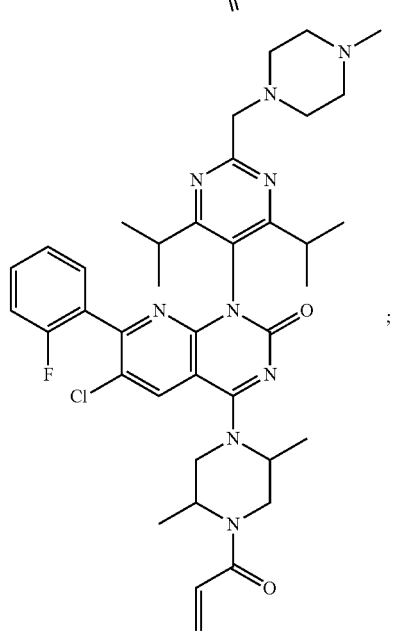

981
-continued
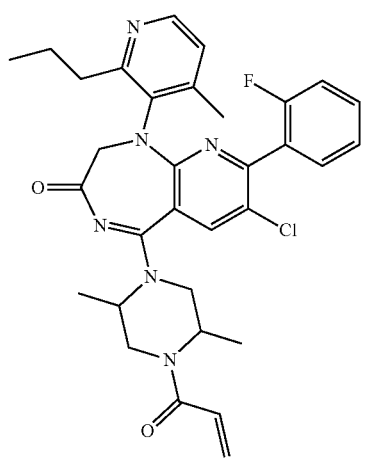
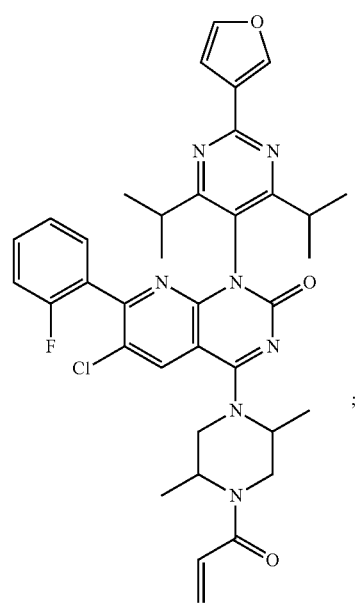
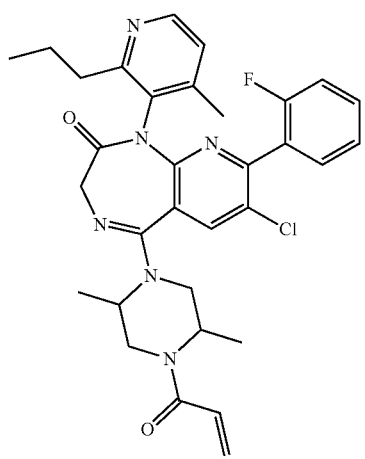
982
-continued
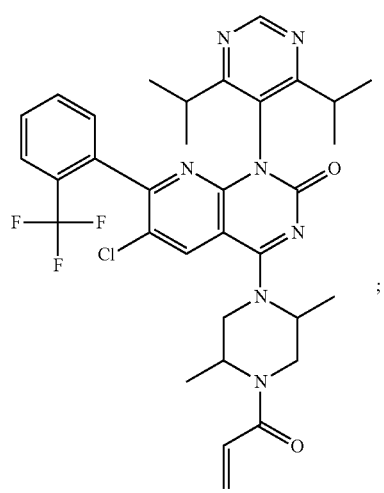
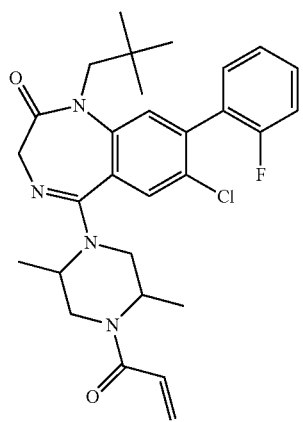
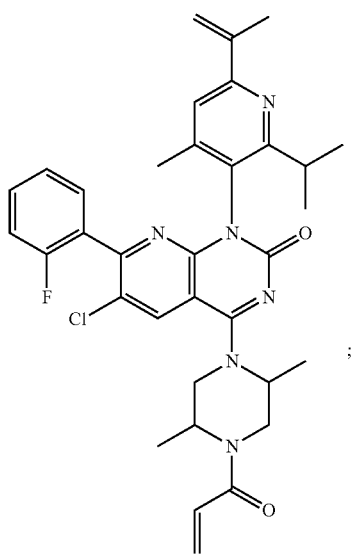

983
-continued
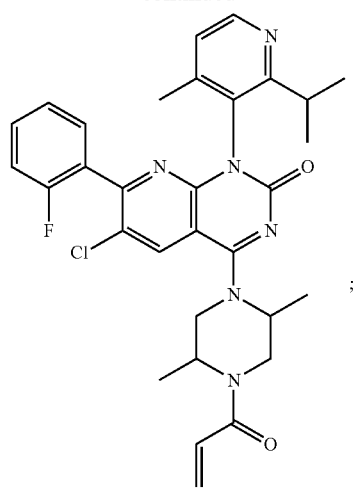
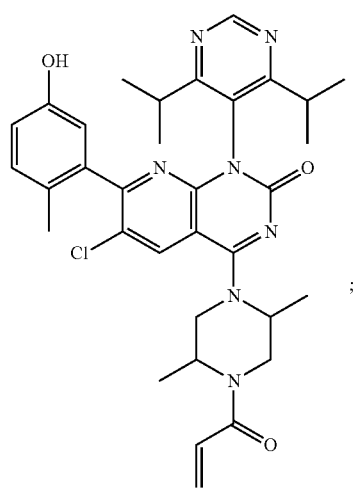
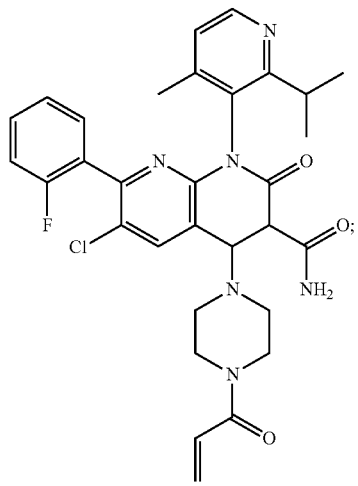
984
-continued
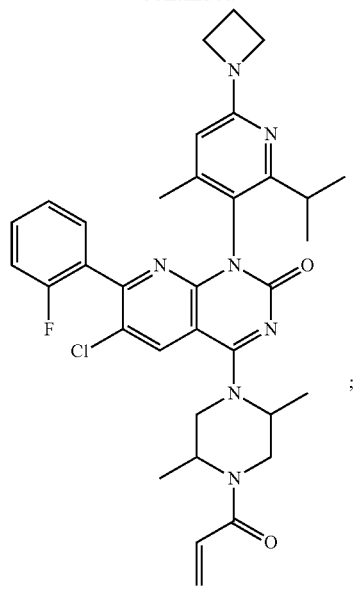
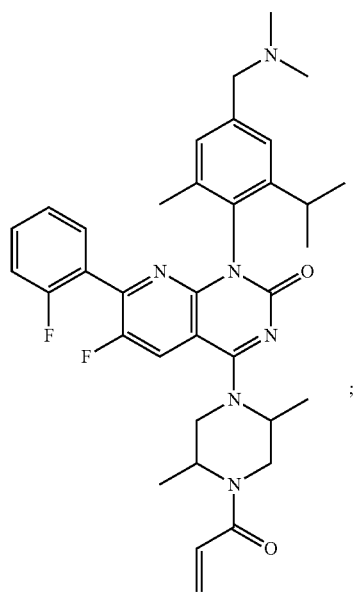
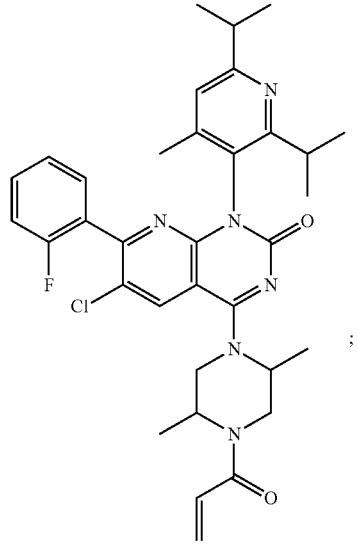

985
-continued
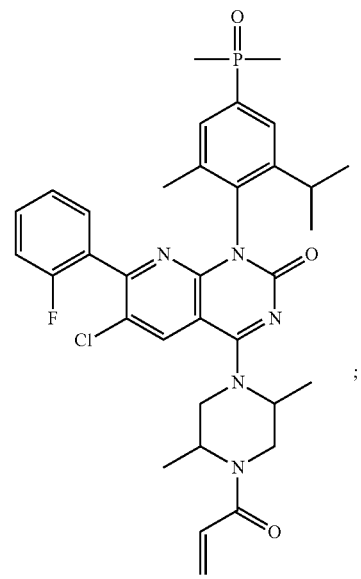
;
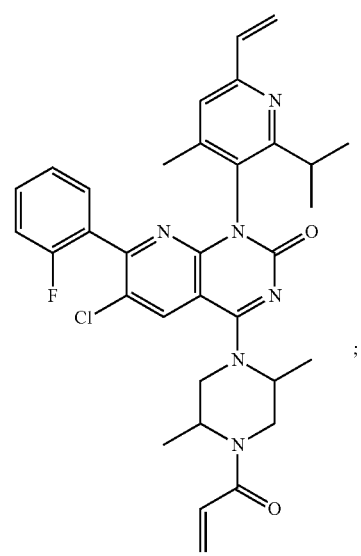 [SMILES: C=CC(=O)N1CC(C)N(c2nc(=O)n(-c3c(C)cc(C=C)nc3C(C)C)c3nc(-c4ccccc4F)c(Cl)cc23)CC1C]
;
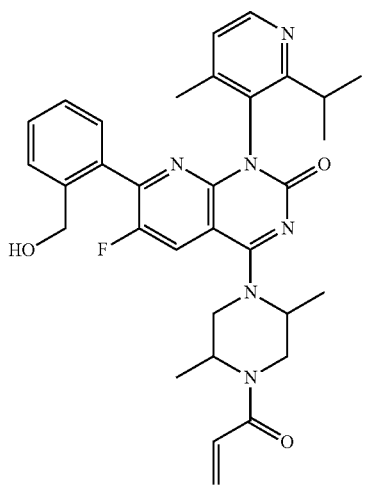
;
986
-continued
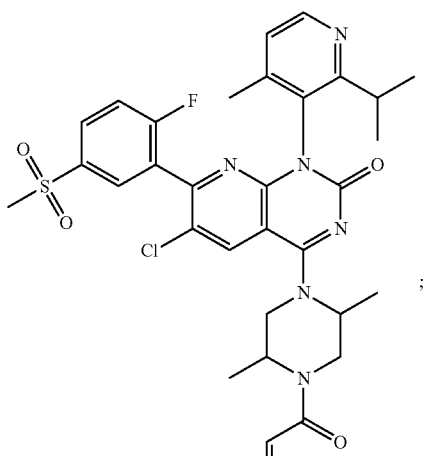
;
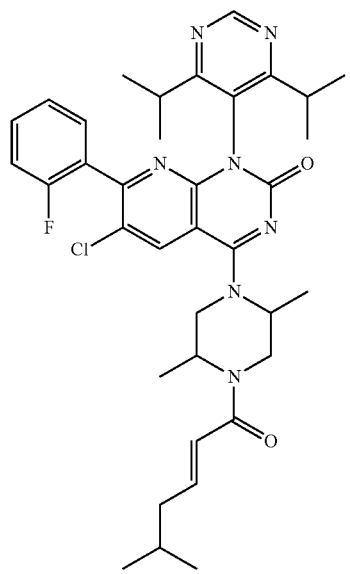
;
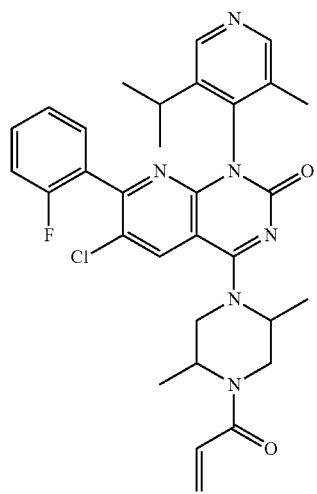
;

987
-continued
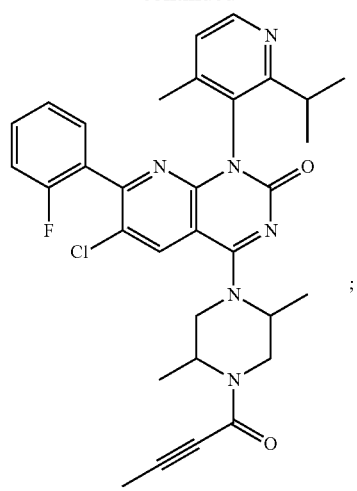
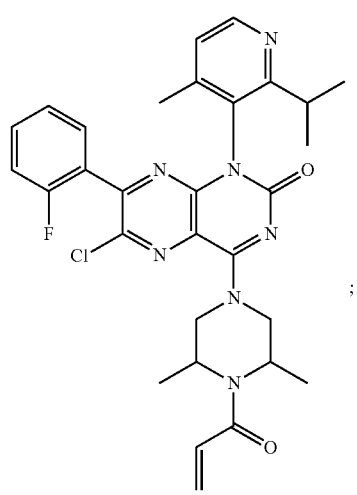
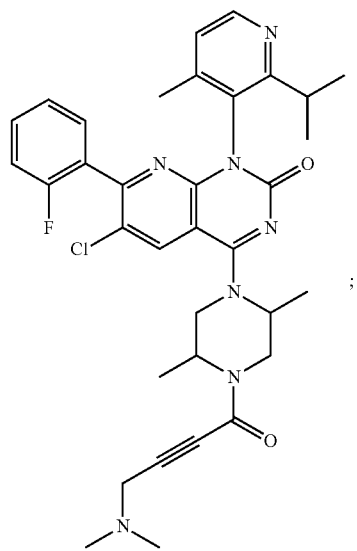
988
-continued
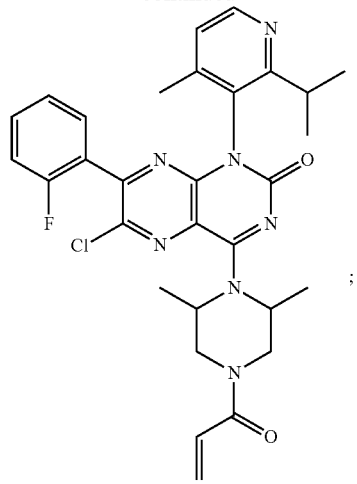
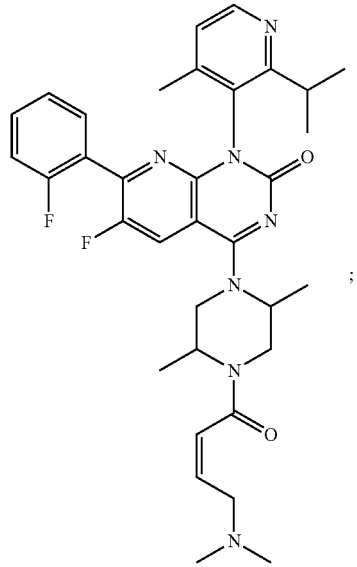
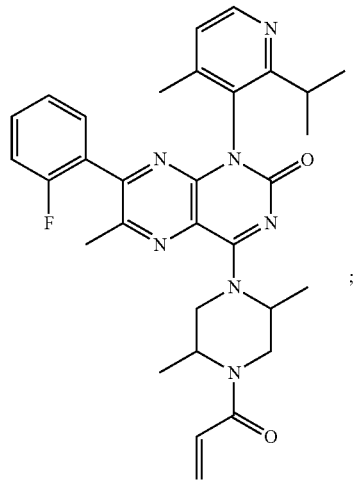

989
-continued
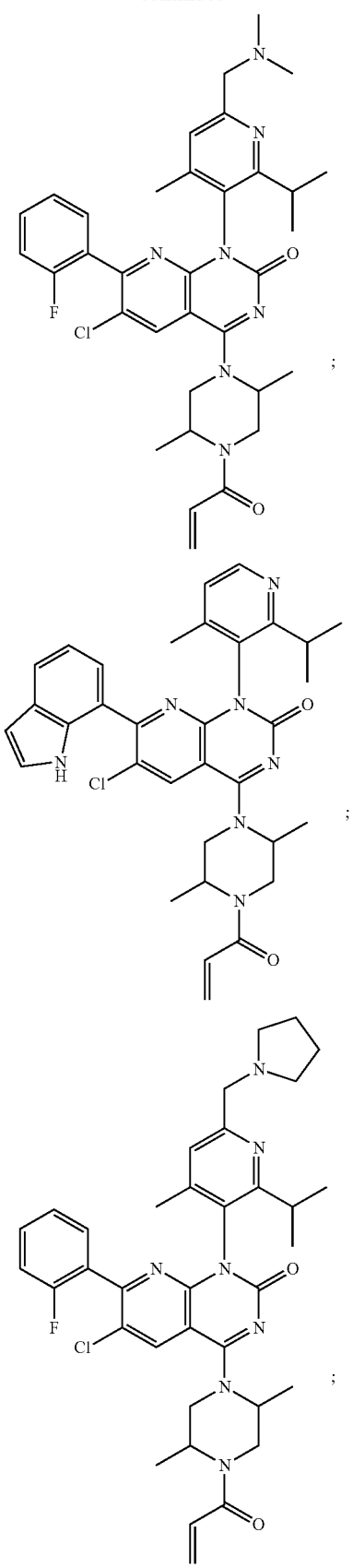
990
-continued
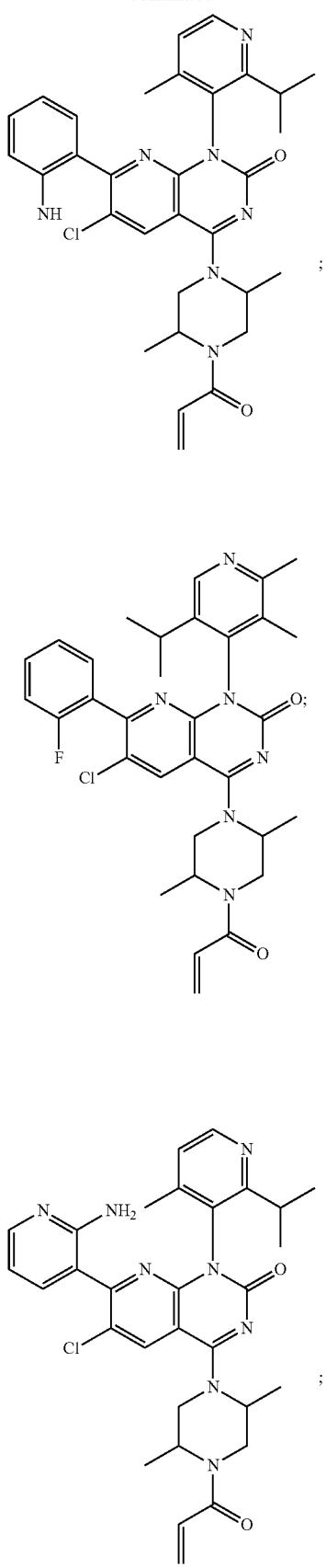

991
-continued
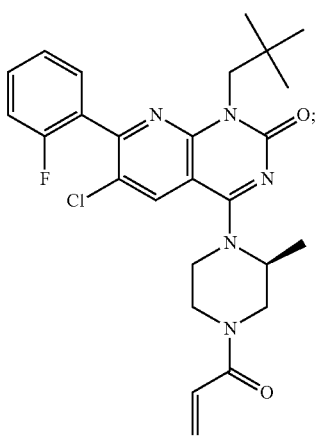
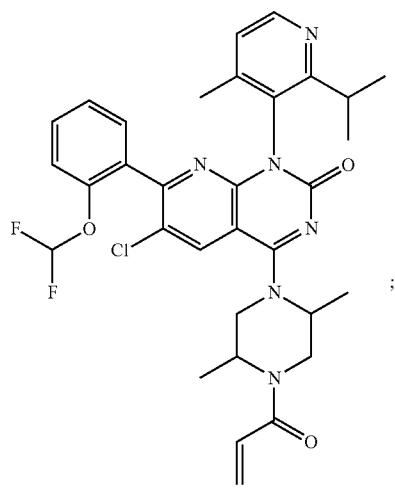
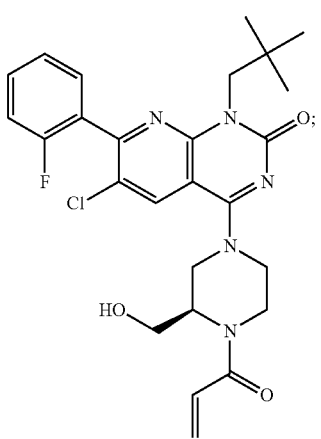
992
-continued
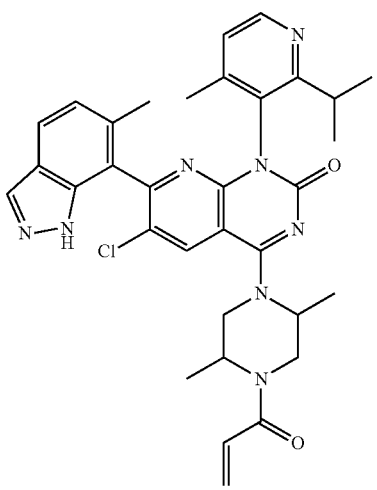
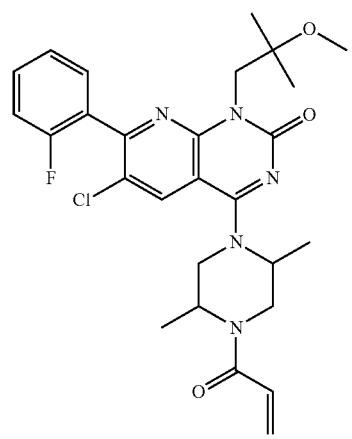
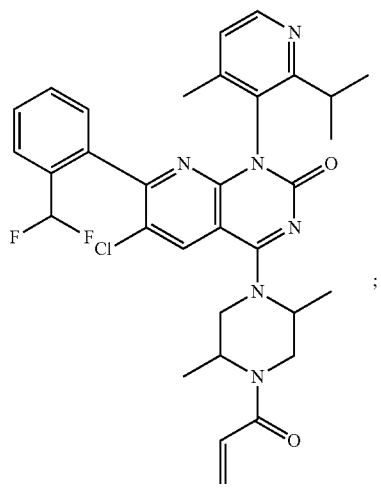

993
-continued
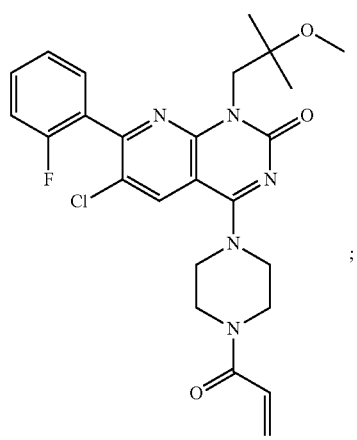
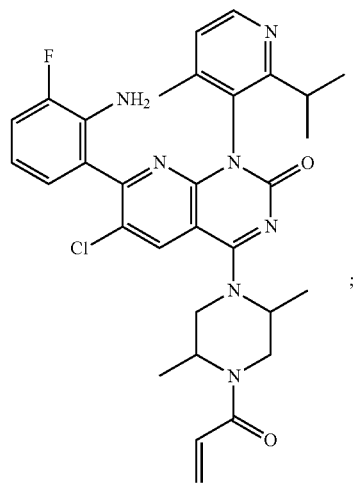
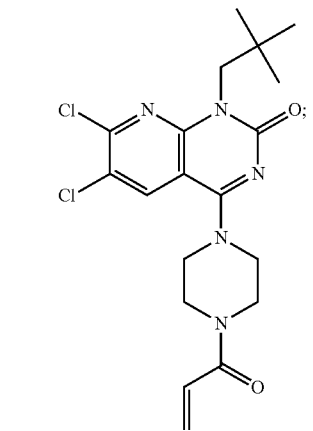
994
-continued
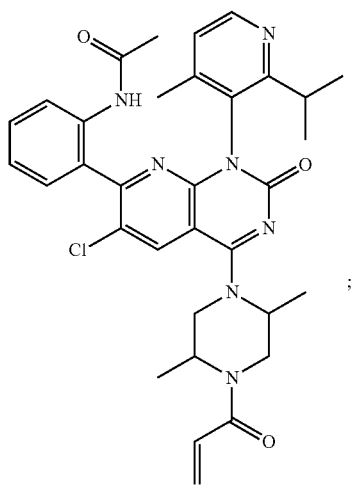
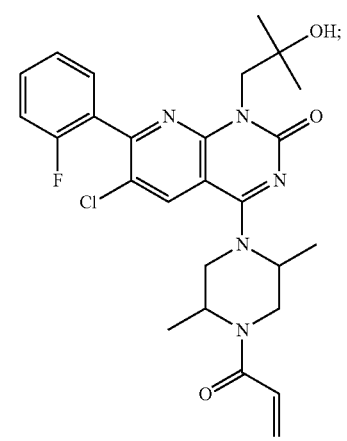
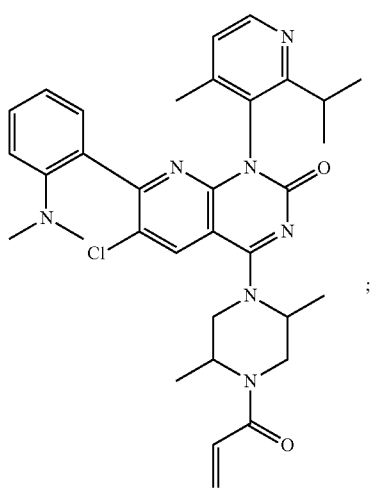

995
-continued
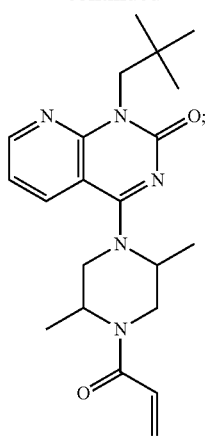
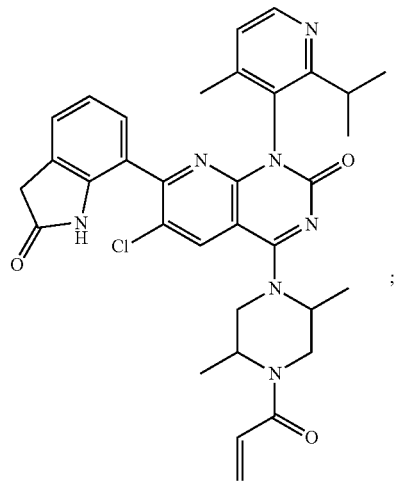
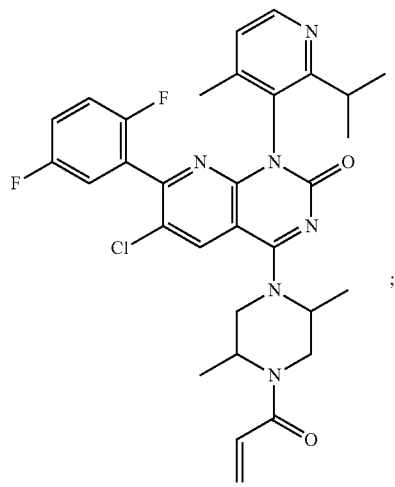
996
-continued
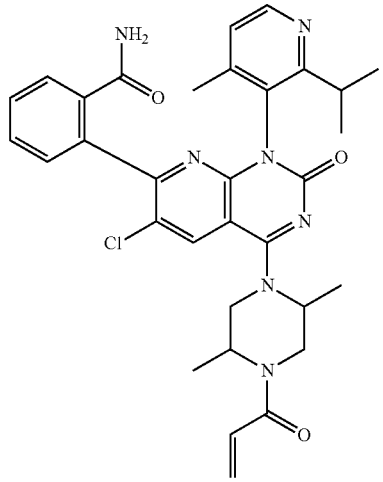
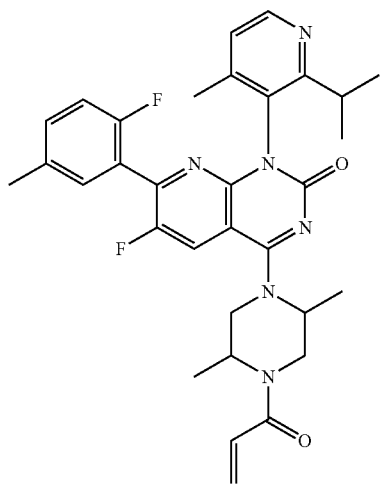
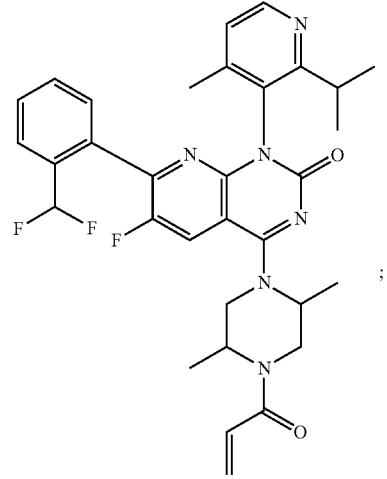

997
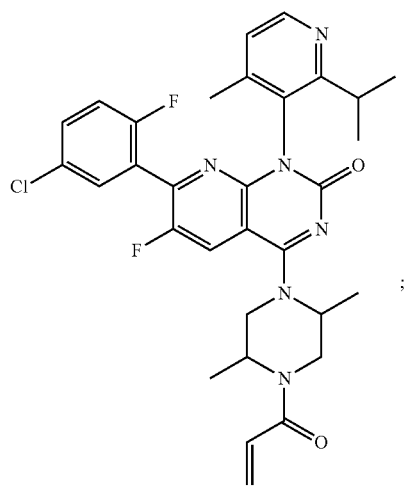
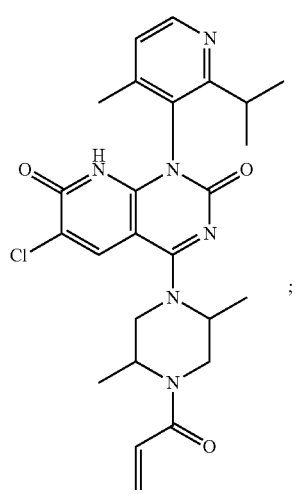
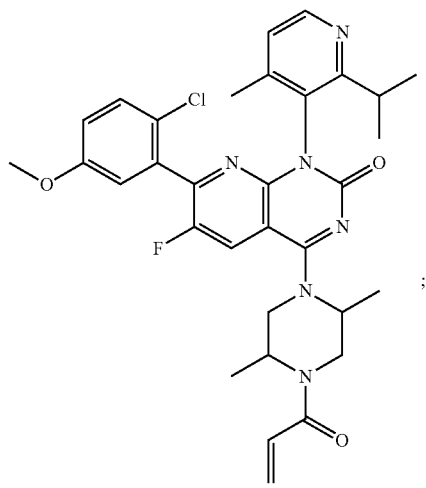
998
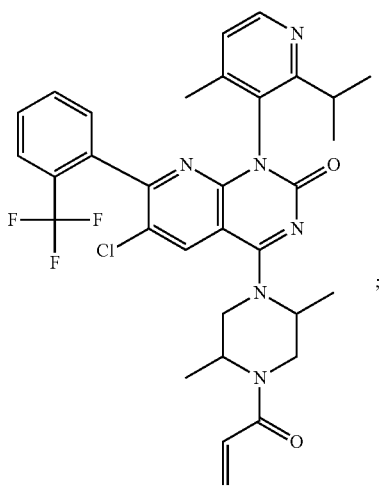
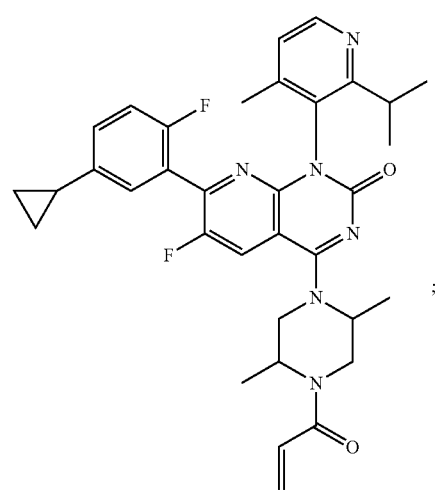
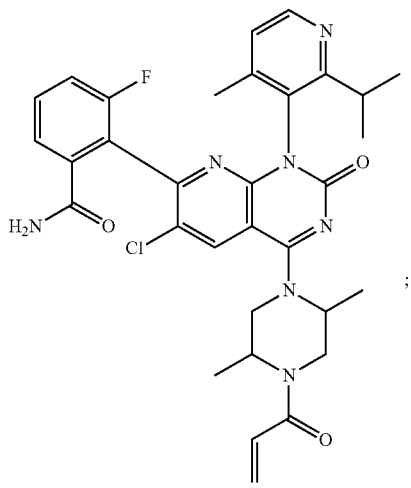

999
-continued
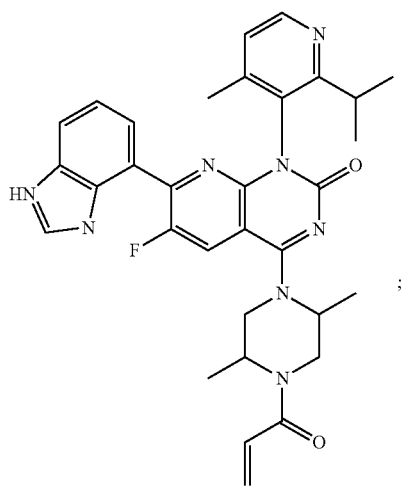 [SMILES: C=CC(=O)N1CC(C)N(c2nc(=O)n(-c3c(C)ccnc3C(C)C)c3nc(-c4cccc5nc[nH]c45)c(F)cc23)CC1C]
;
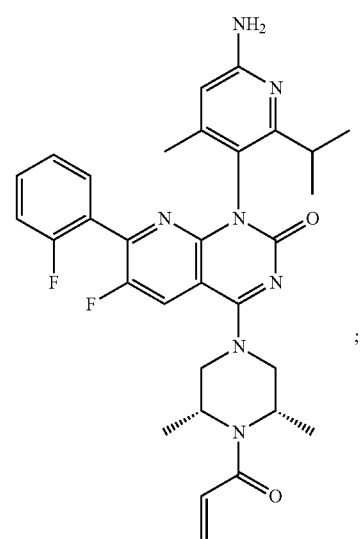
;
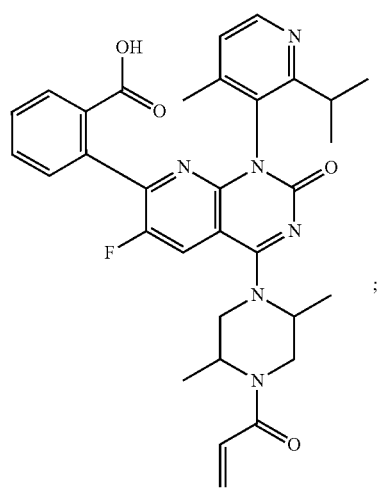
;
1000
-continued
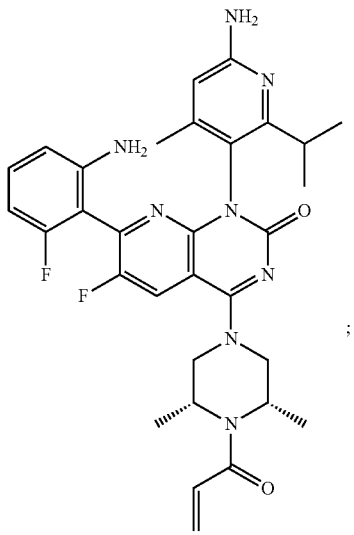
;
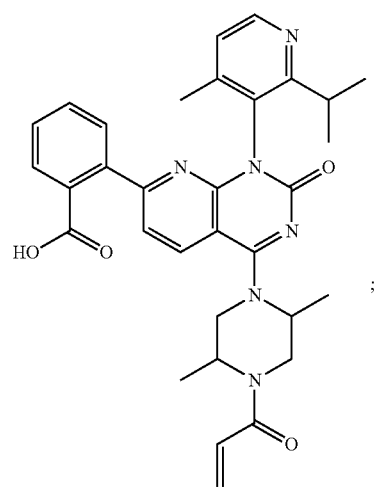
;
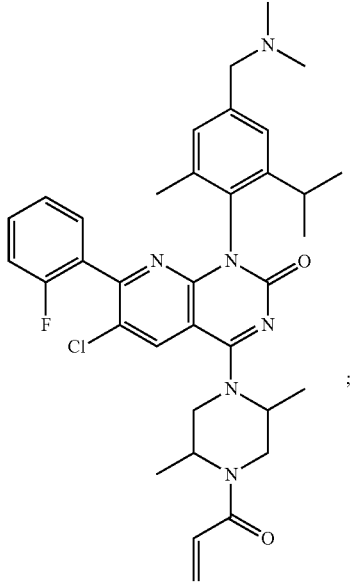
;

1001
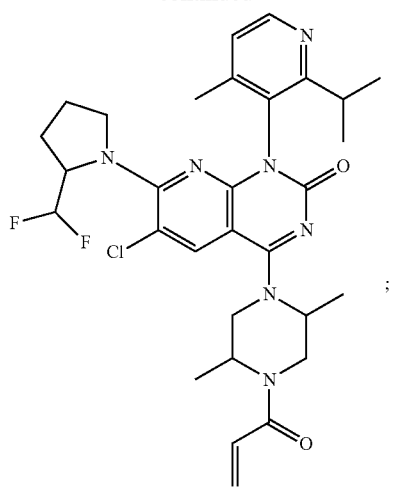
;
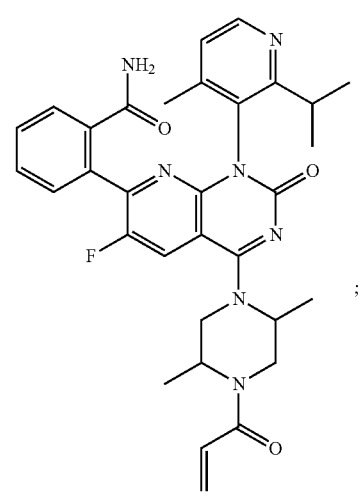 [SMILES: C=CC(=O)N1CC(C)N(c2nc(=O)n(-c3c(C)ccnc3C(C)C)c3nc(-c4ccccc4C(N)=O)c(F)cc23)CC1C]
;
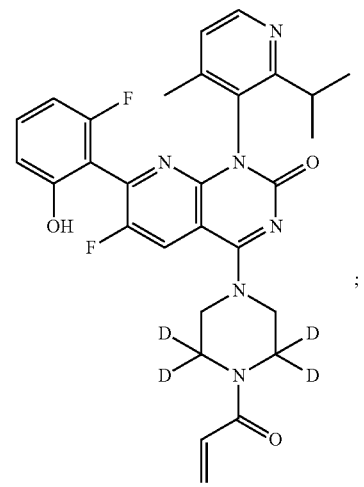
;
1002
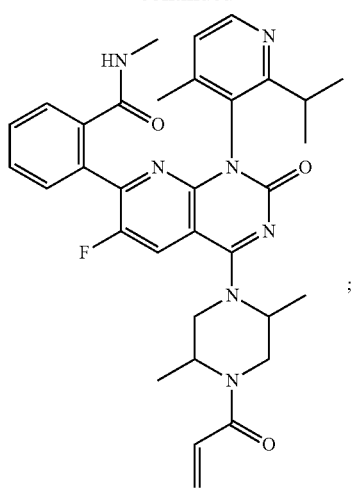
;
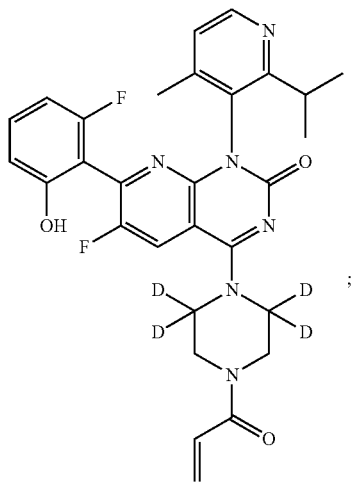
;
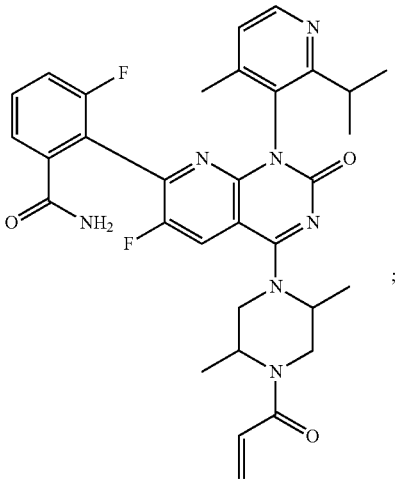
;

1003
-continued
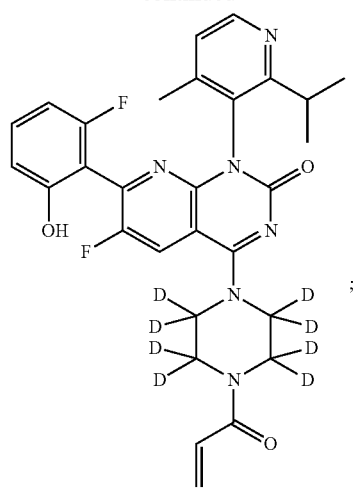
1004
-continued
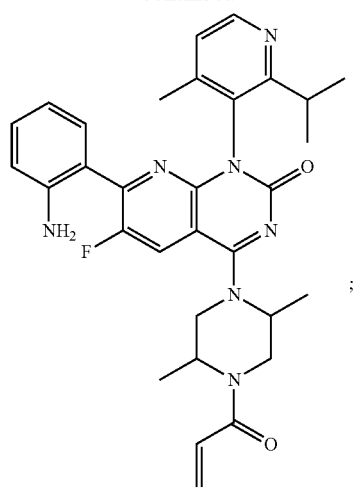
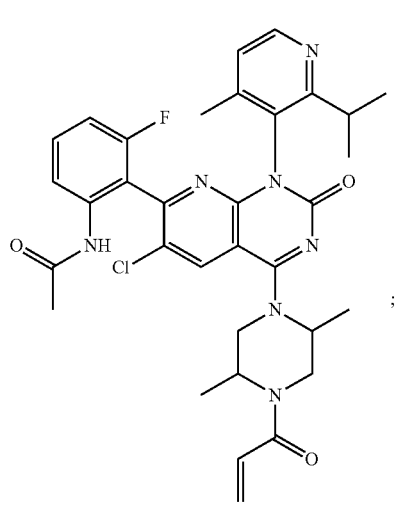
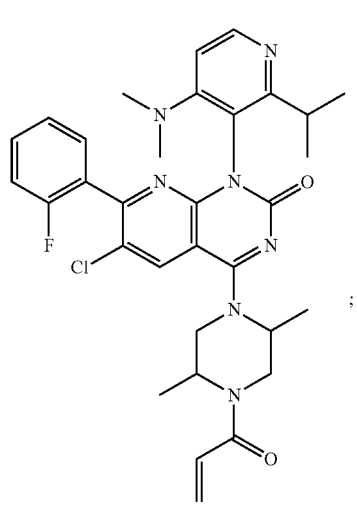
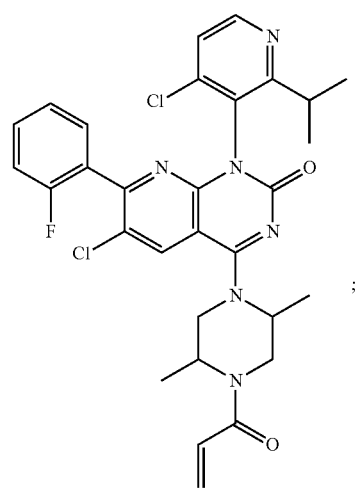
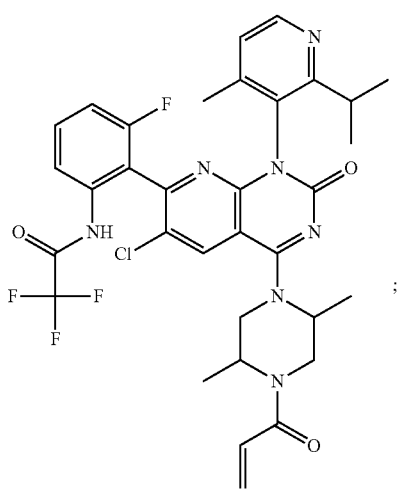

1005
-continued
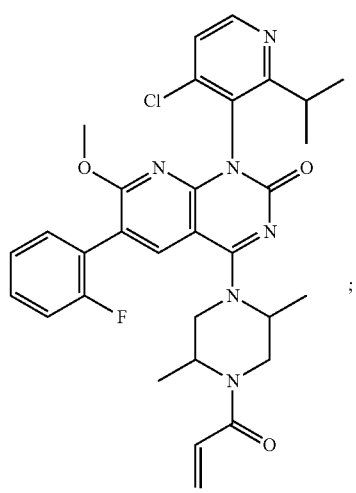
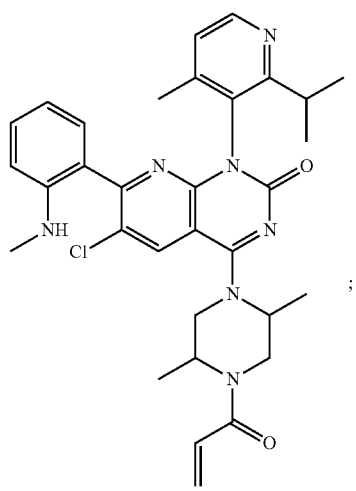
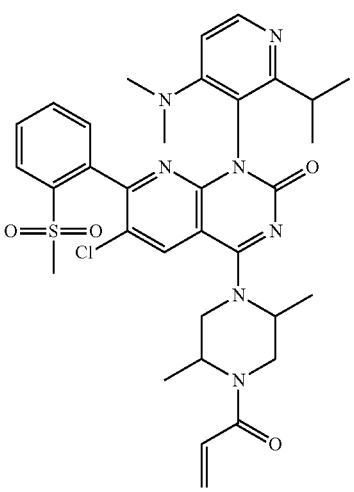
1006
-continued
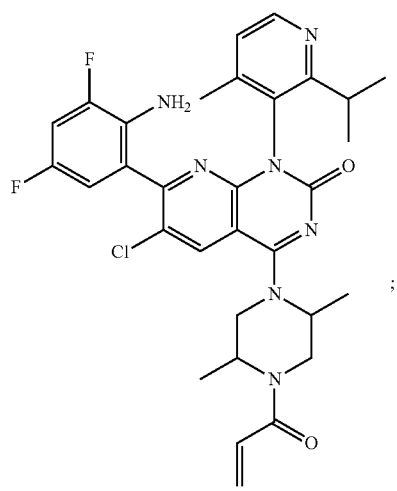
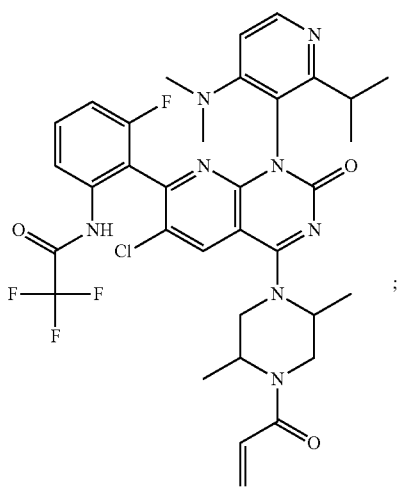
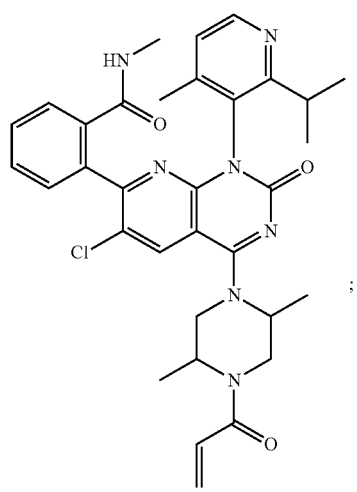

1007
-continued
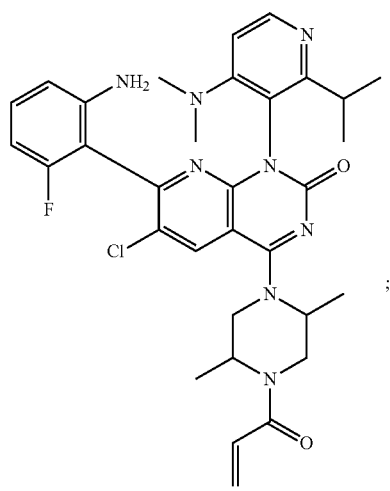
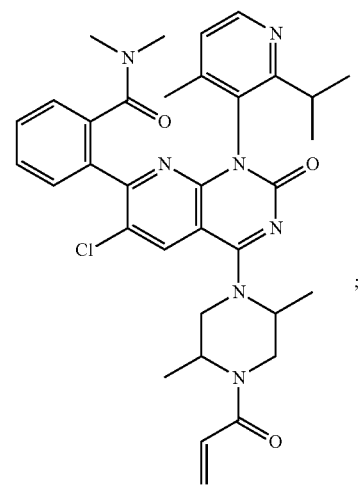
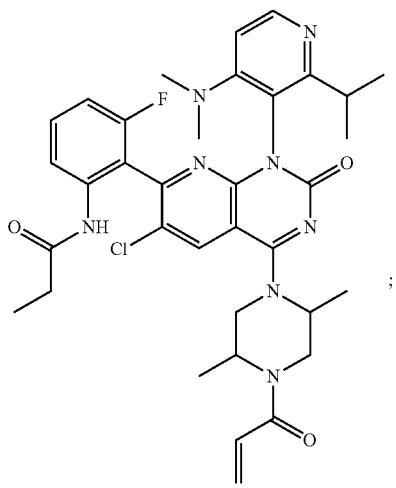
1008
-continued
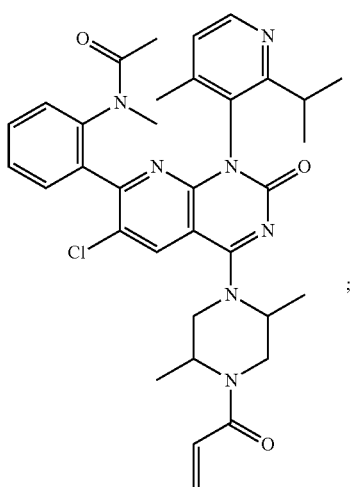
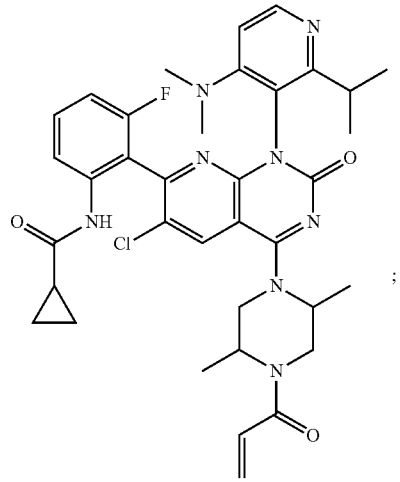
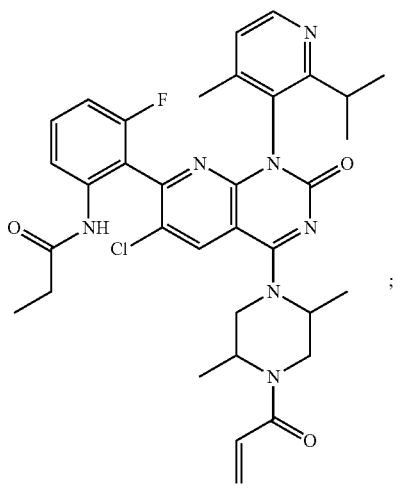

1009
-continued
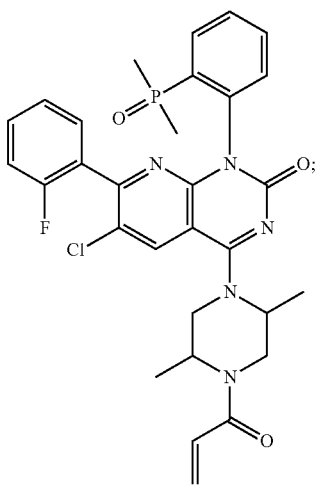
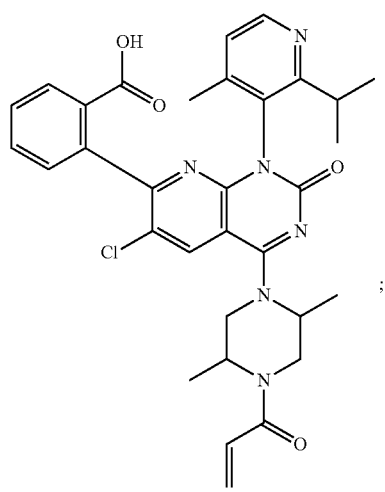
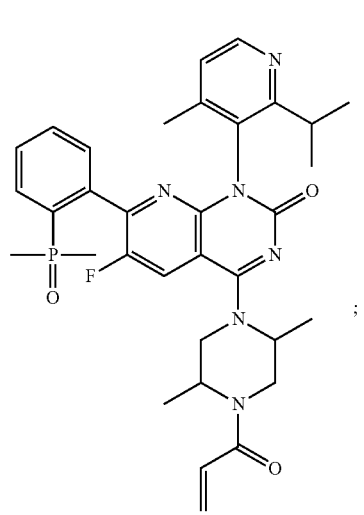
1010
-continued
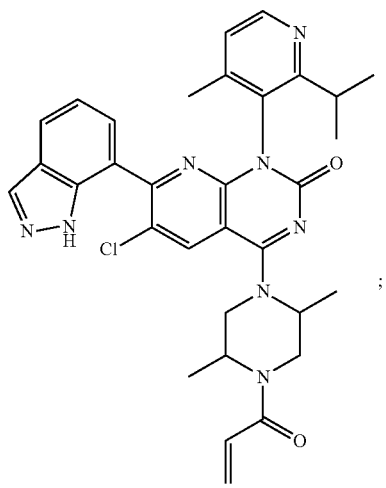
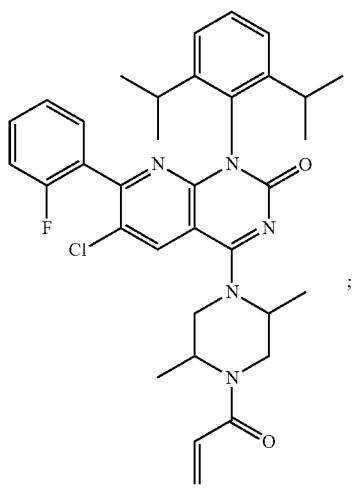
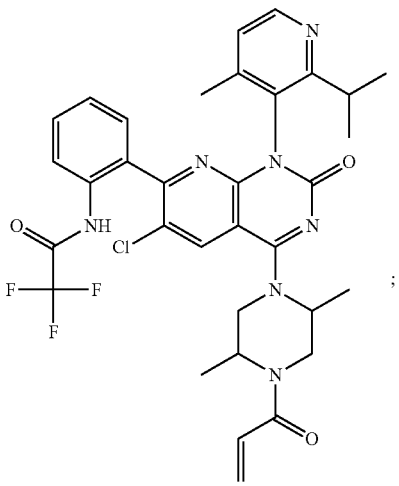

1011
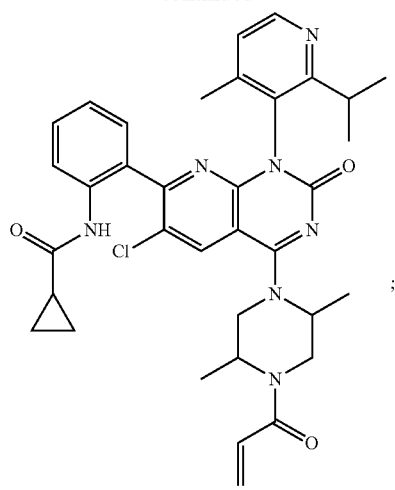 [SMILES: C=CC(=O)N1CC(C)N(c2nc(=O)n(-c3c(C)ccnc3C(C)C)c3nc(-c4ccccc4NC(=O)C4CC4)c(Cl)cc23)CC1C]
;
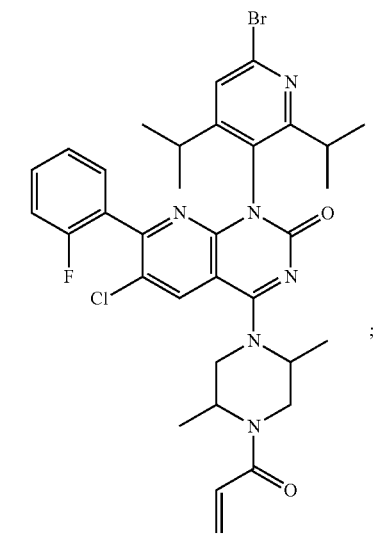
;
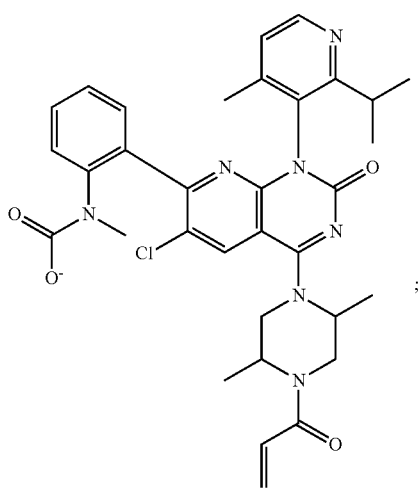
;
1012
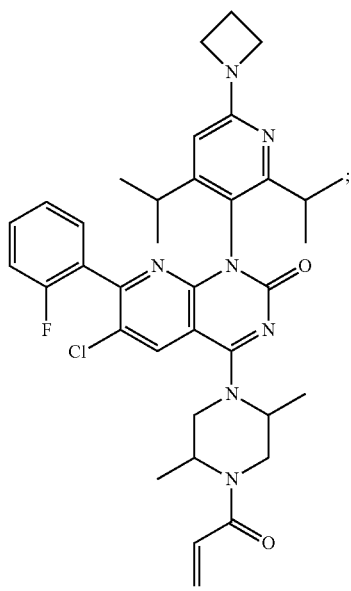
;
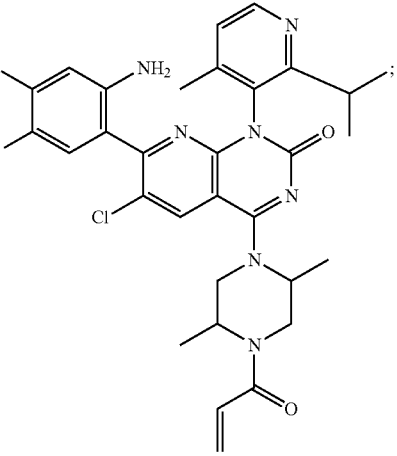
;
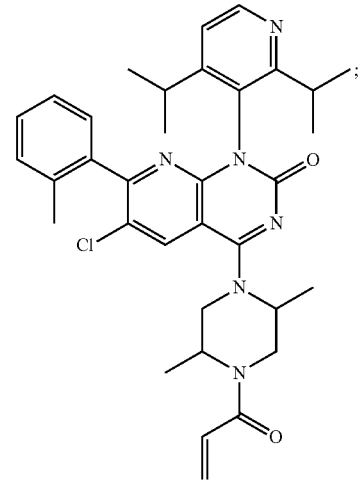

1013
-continued
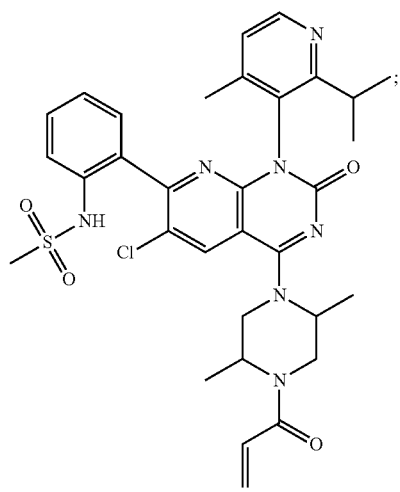
1014
-continued
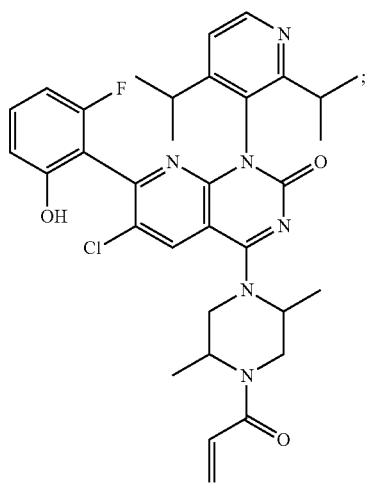
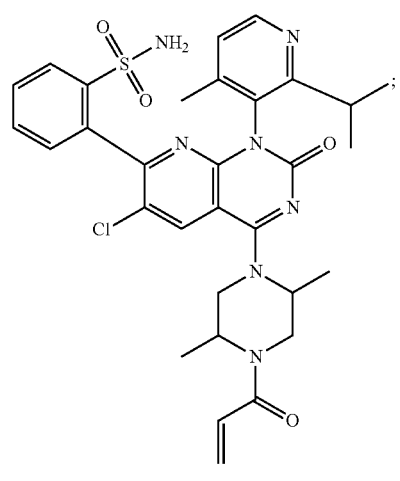
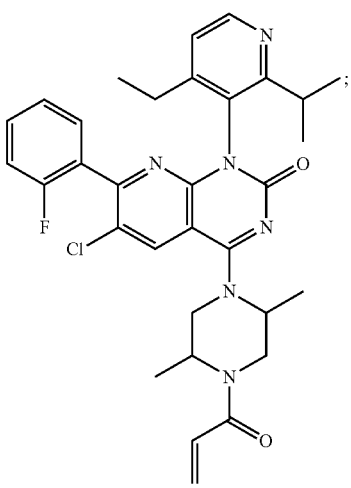

1015
-continued
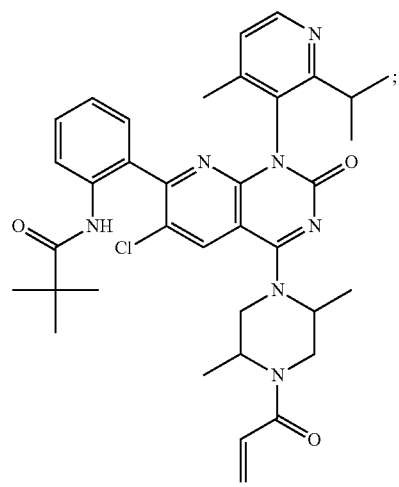
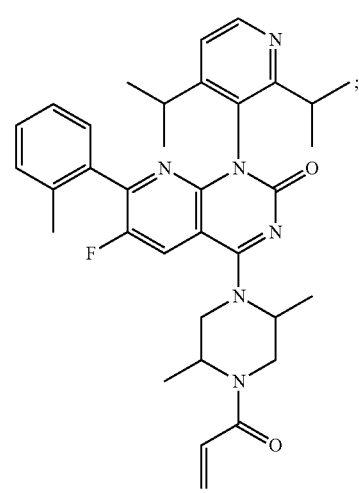
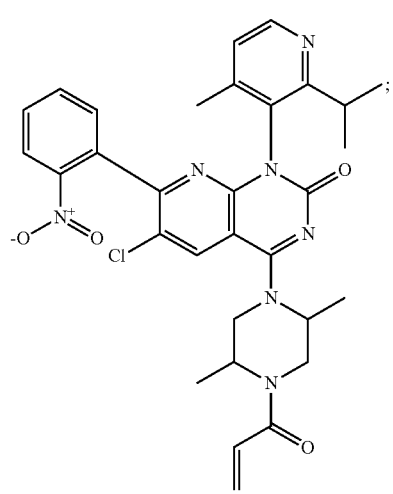
1016
-continued
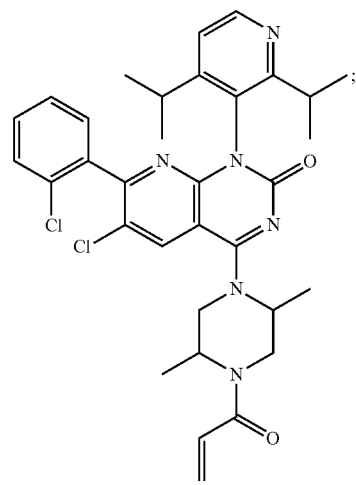
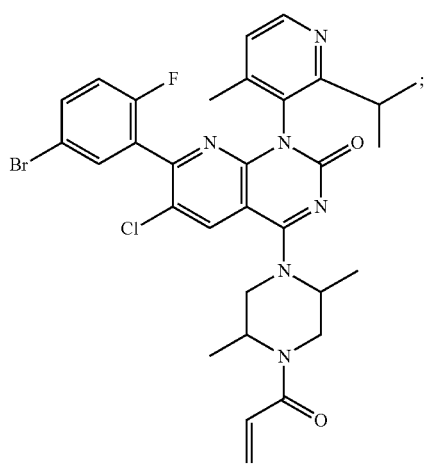
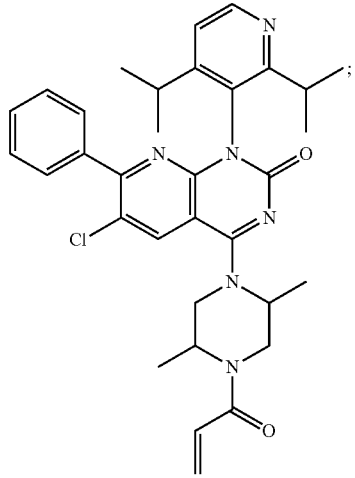

1017
-continued
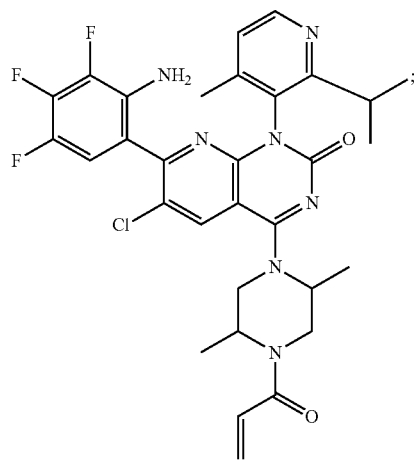
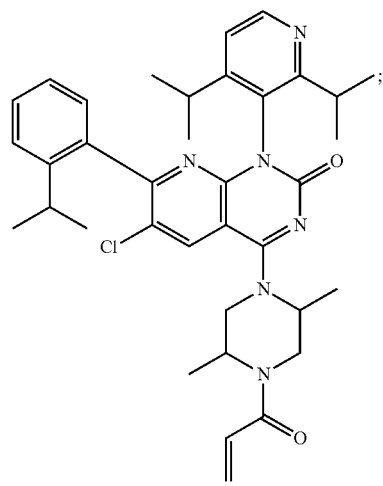
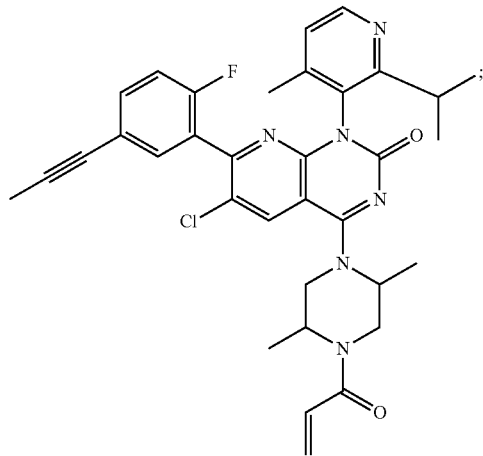
1018
-continued
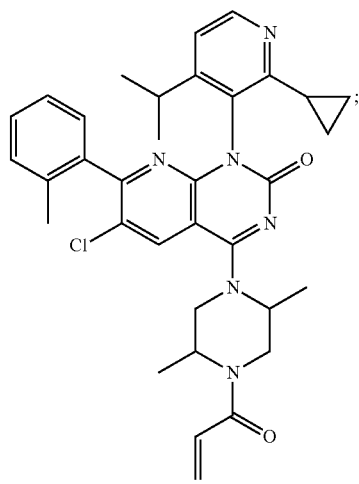
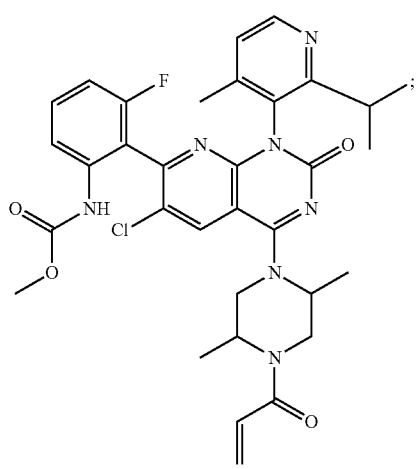
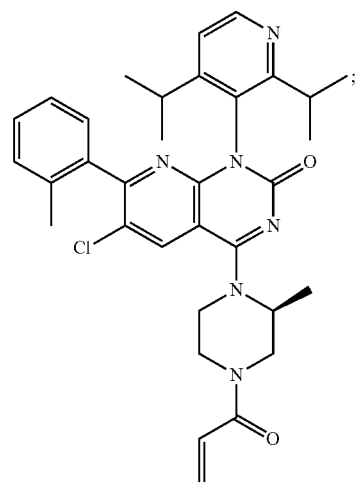

-continued
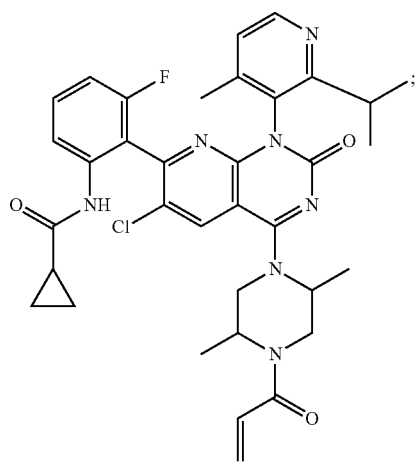
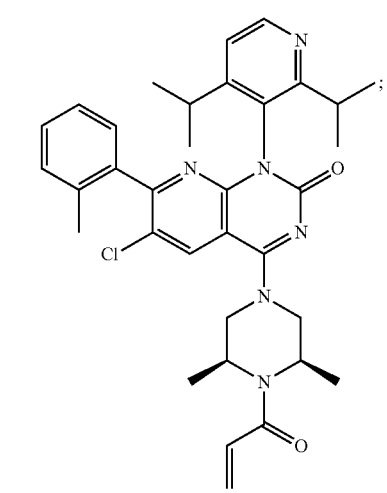
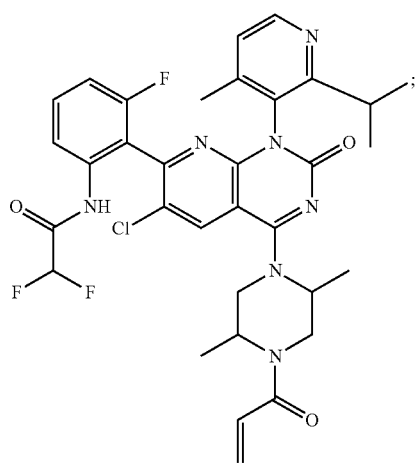
-continued
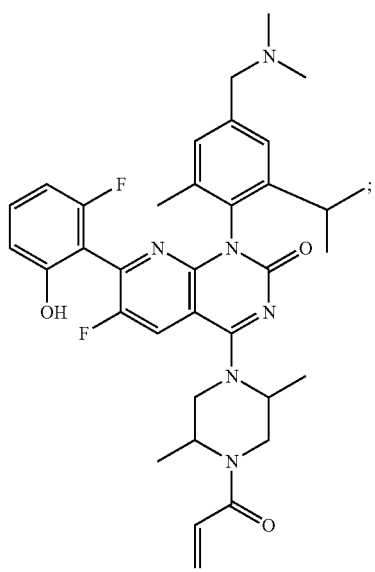
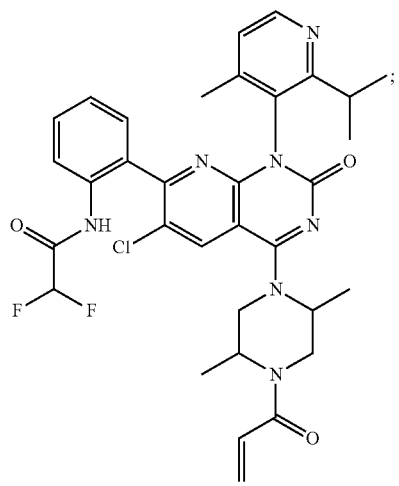
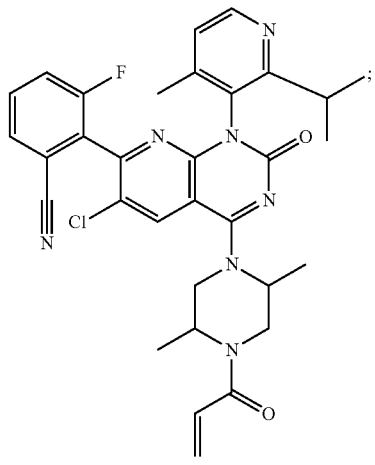

1021
-continued
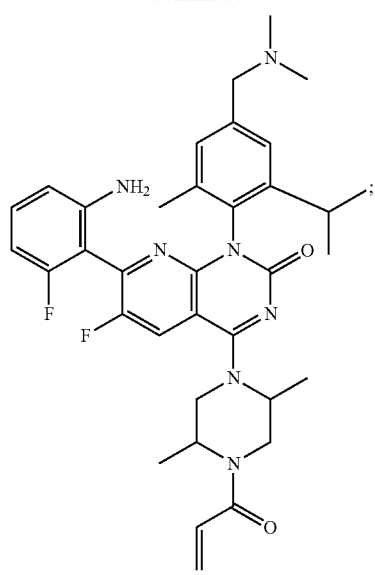
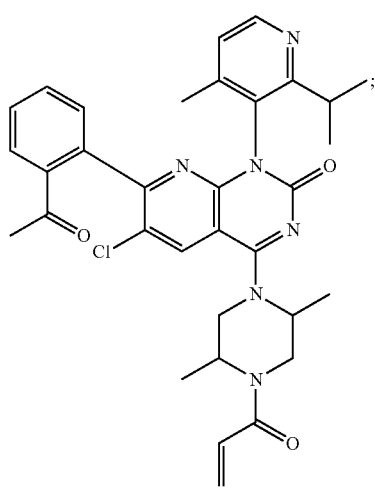
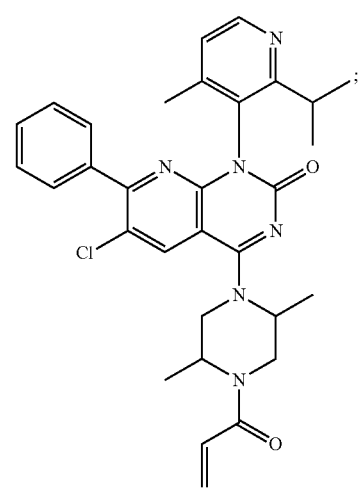
1022
-continued
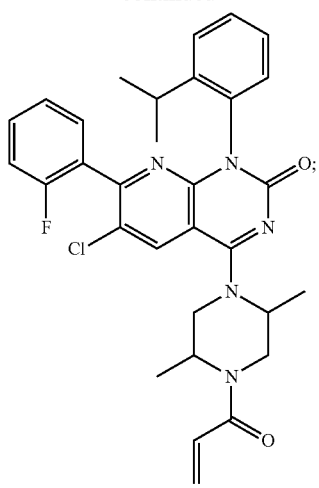
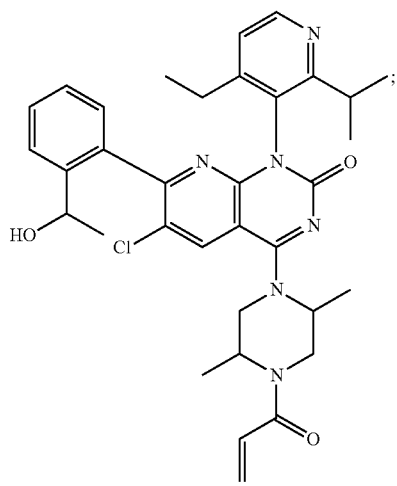
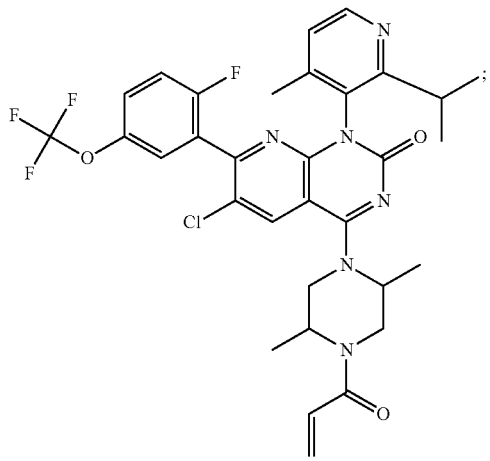

1023
-continued
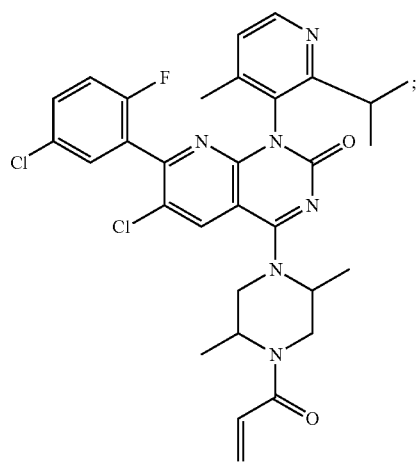
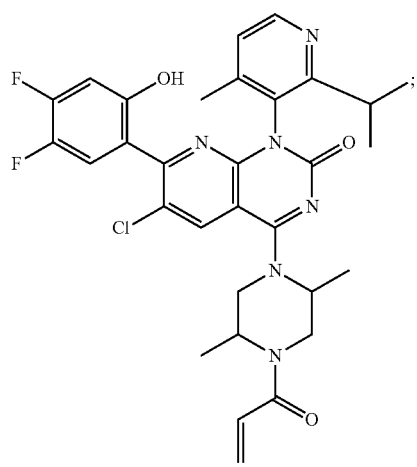
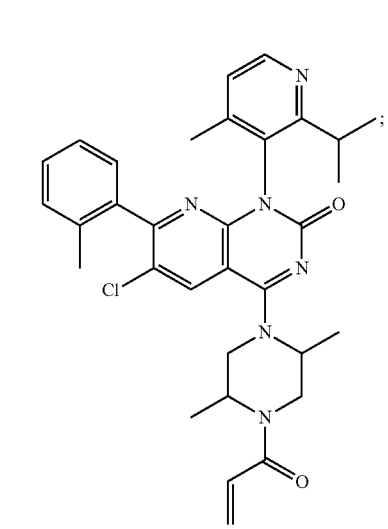
1024
-continued
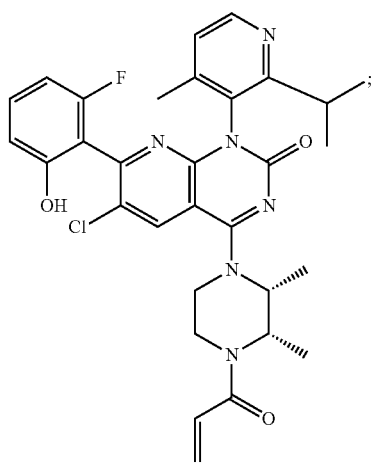
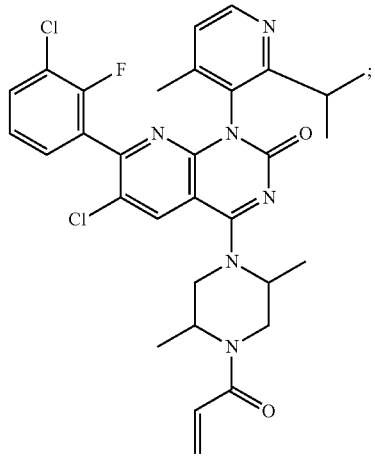
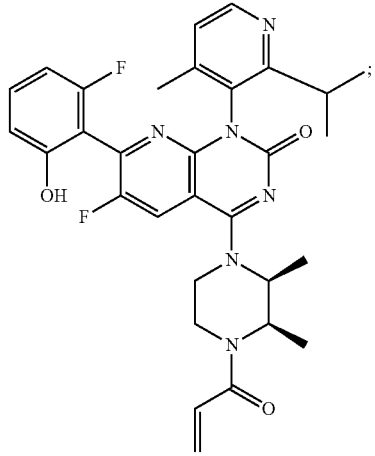

1025
-continued
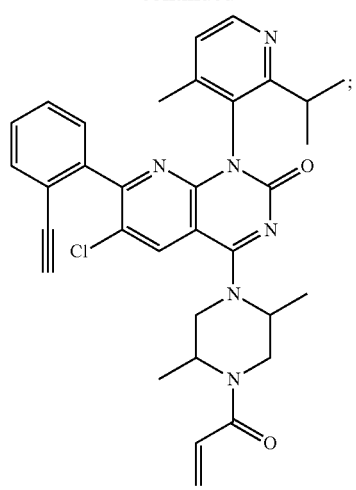
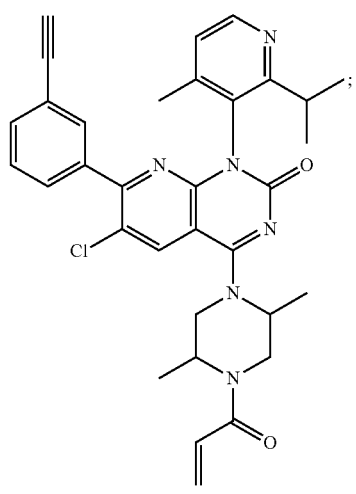
1026
-continued
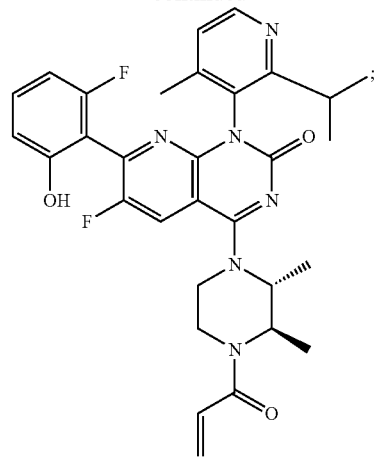
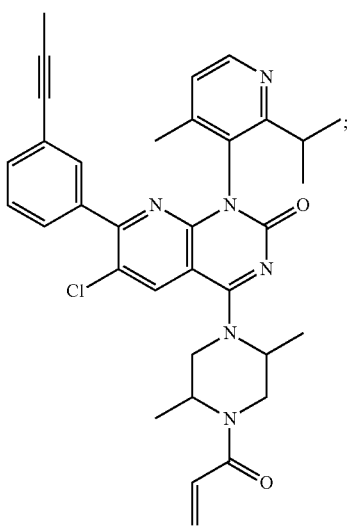
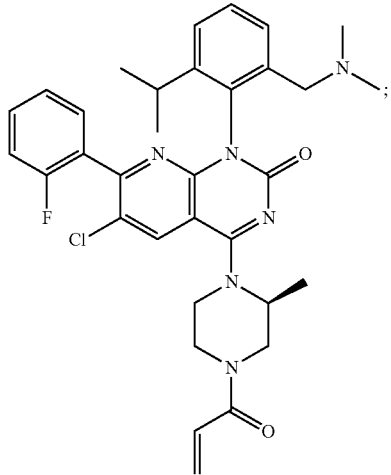

1027
-continued
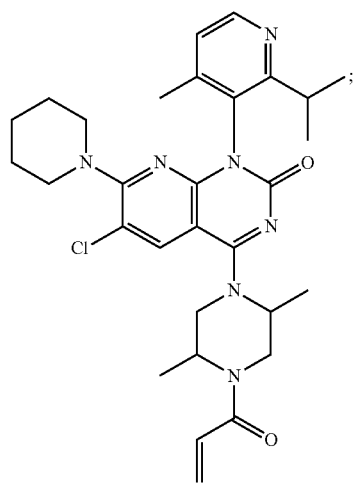
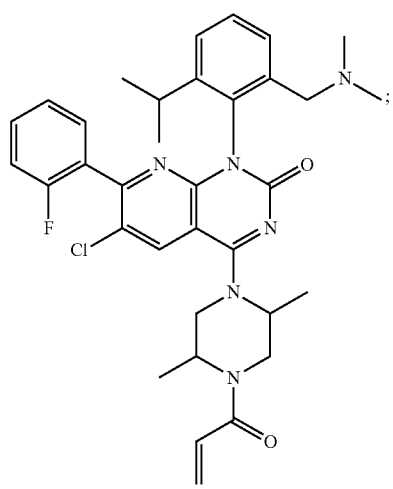
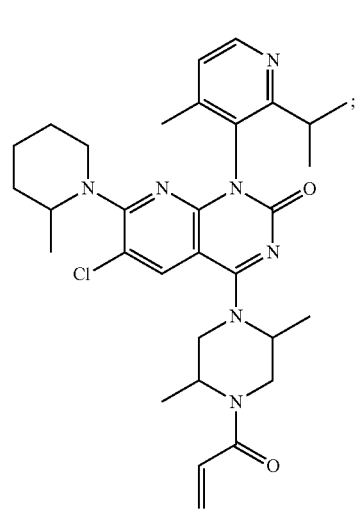
1028
-continued
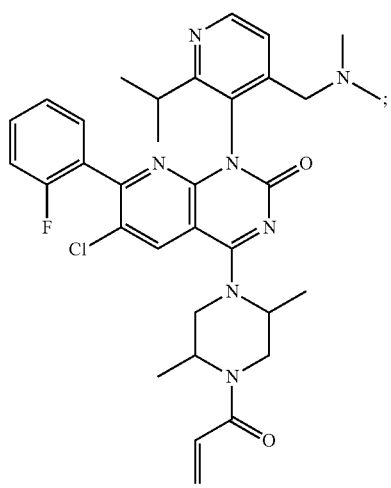
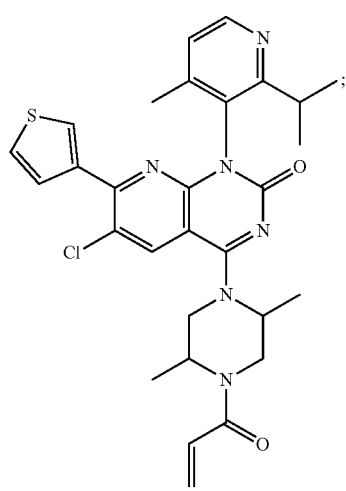
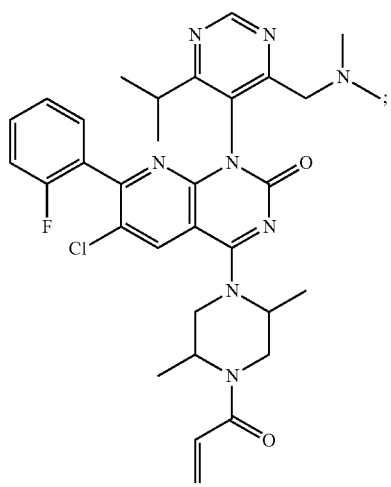

1029
-continued
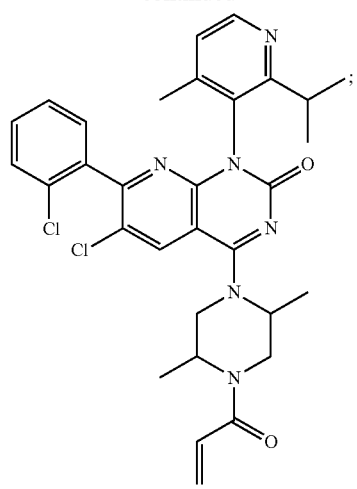
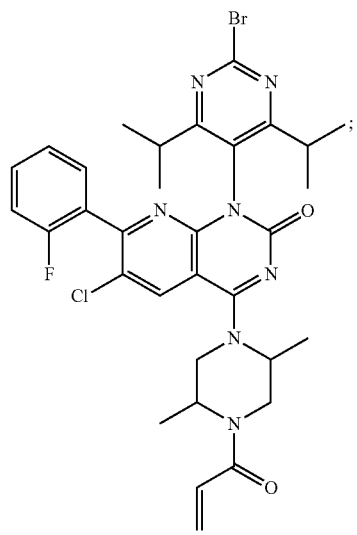
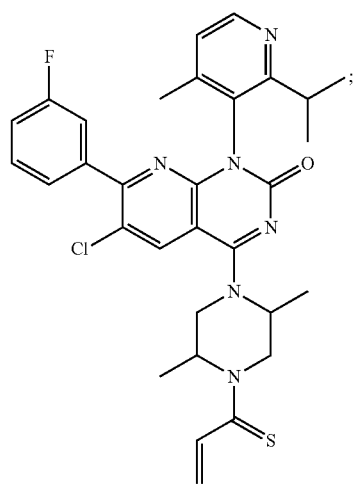
1030
-continued
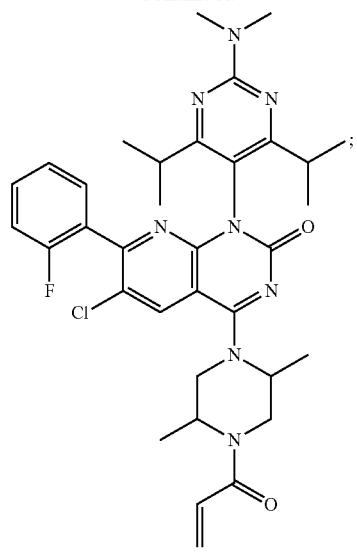
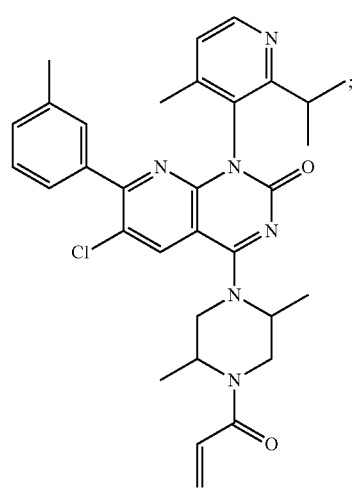
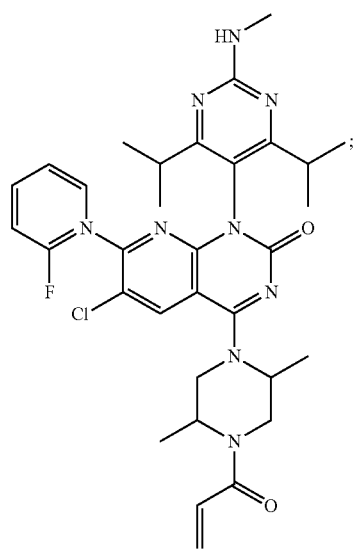

1031
-continued
1032
-continued
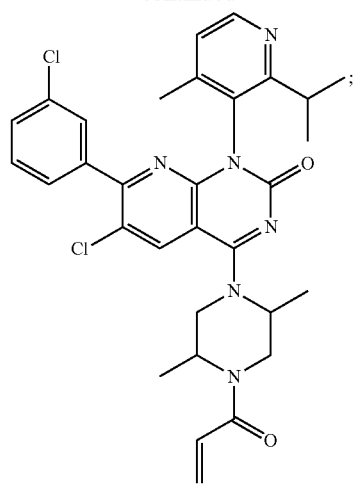
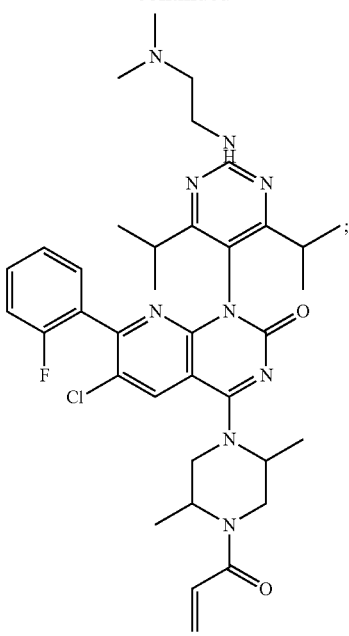
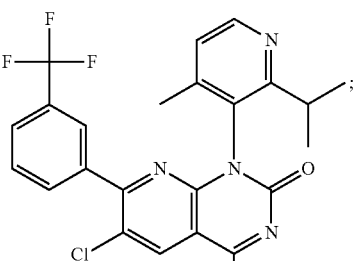
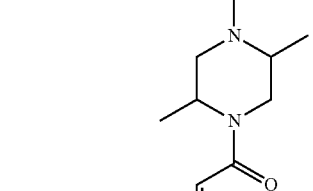
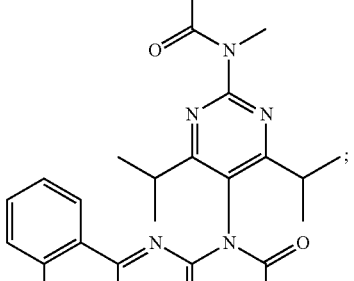
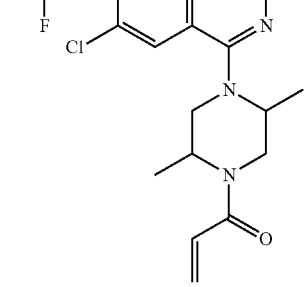

1033
-continued
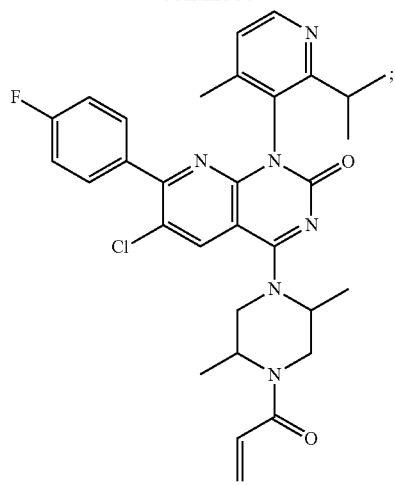
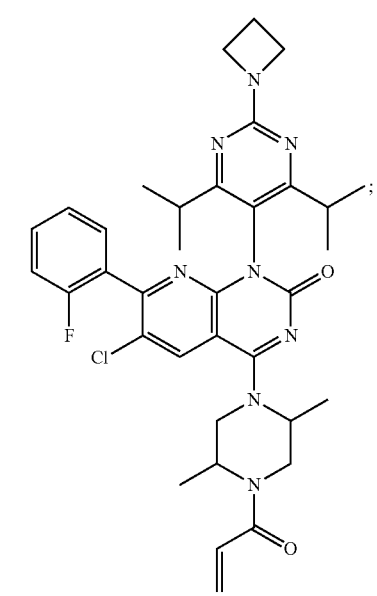
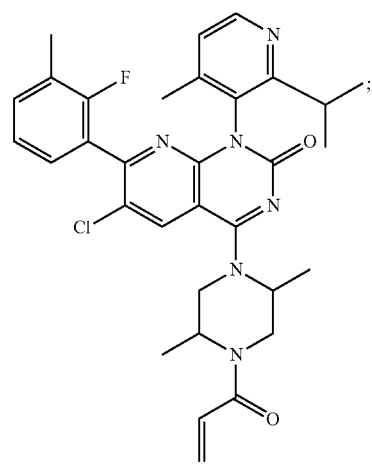
1034
-continued
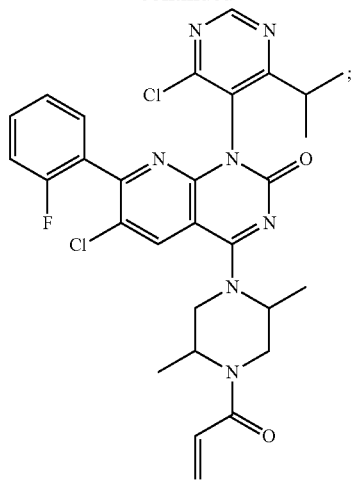
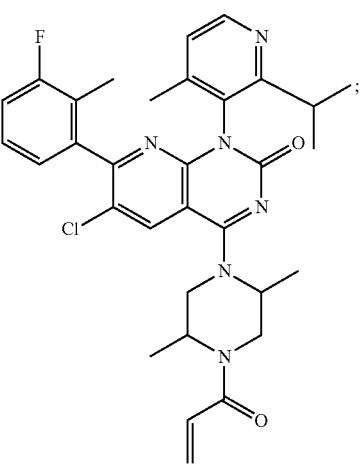
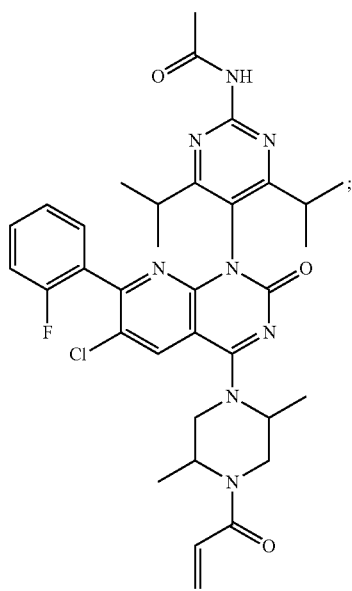

1035
-continued
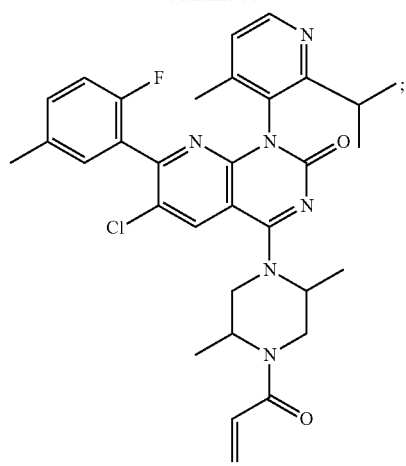
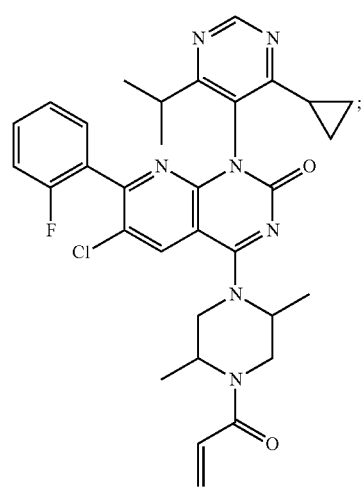
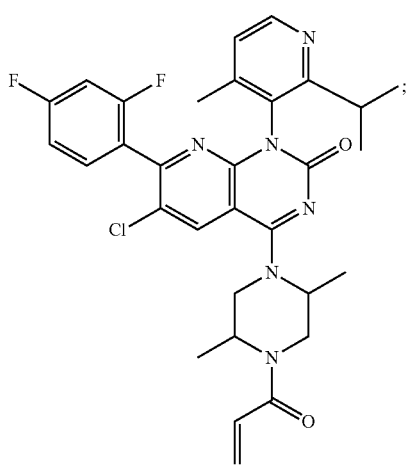
1036
-continued
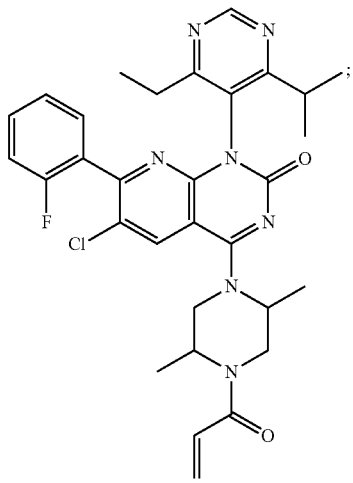
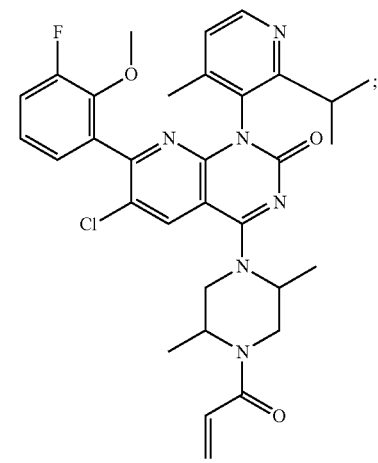
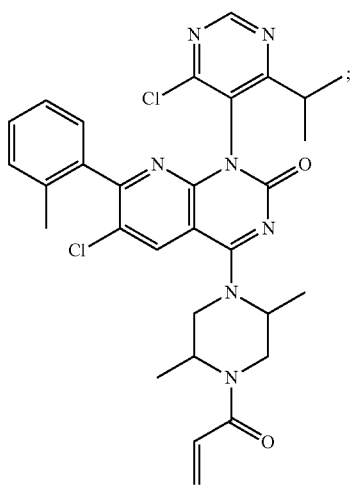

1037
-continued
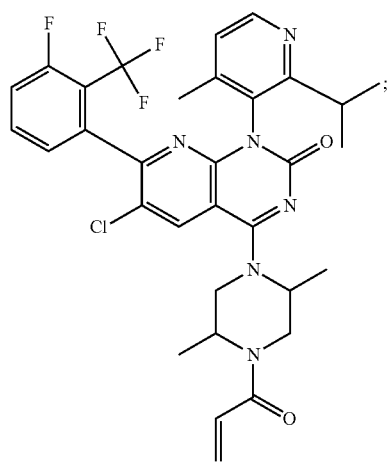
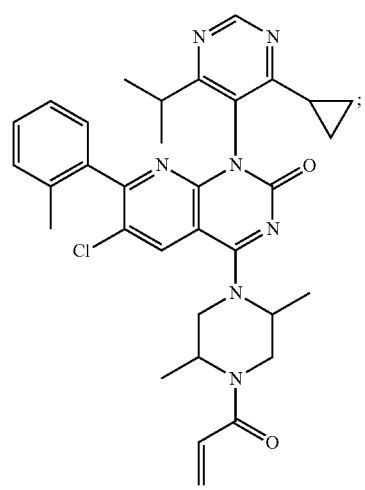
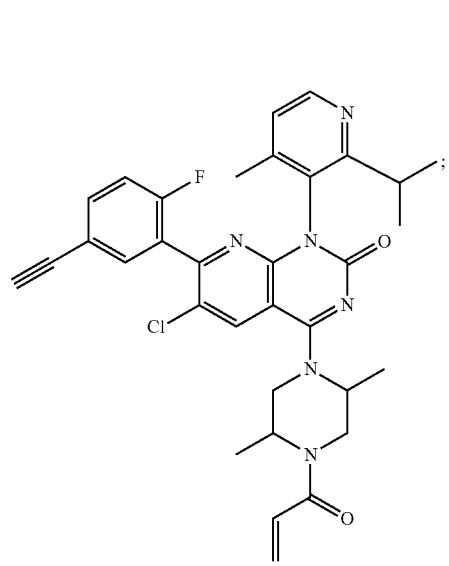
1038
-continued
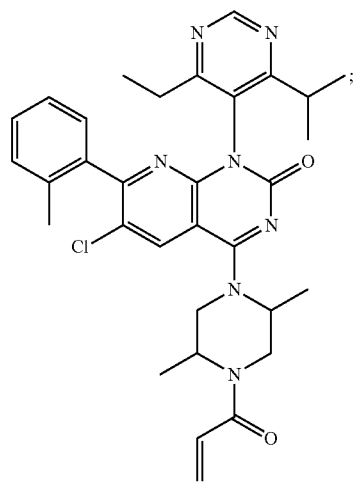
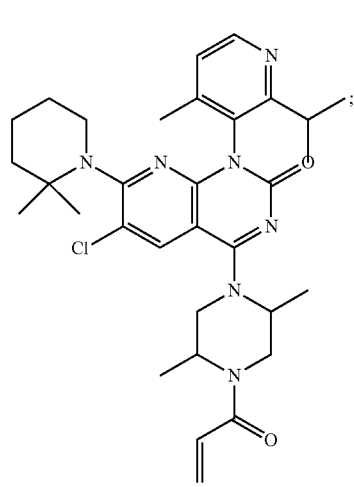
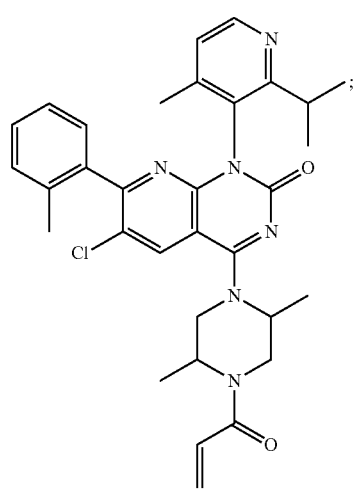

1039
-continued
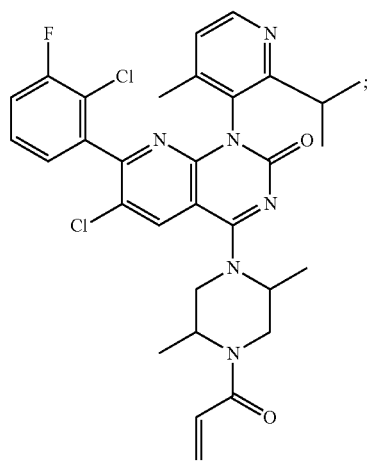
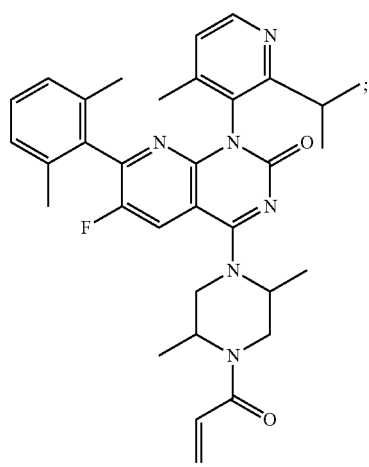
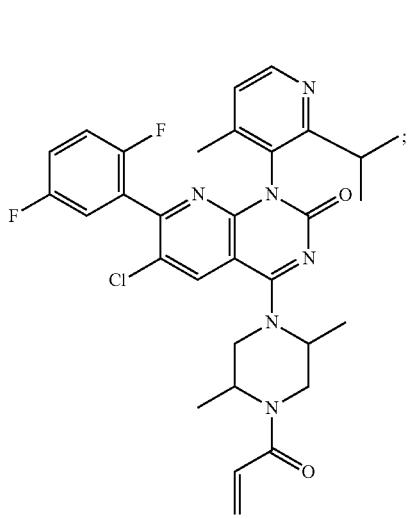
1040
-continued
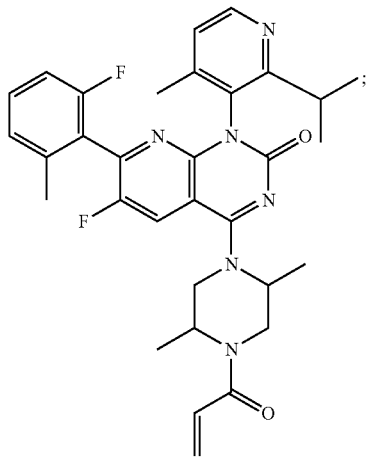
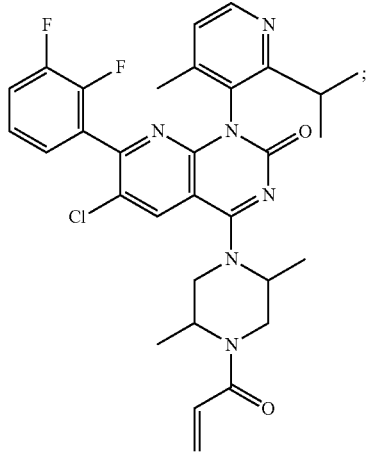
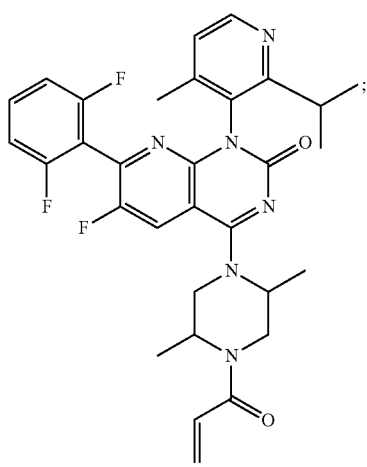

1041
-continued
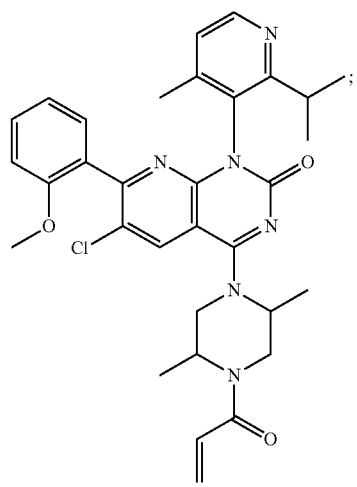
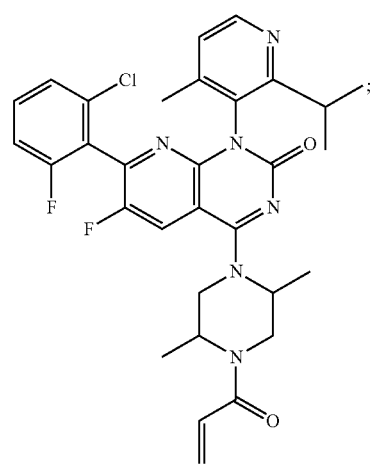
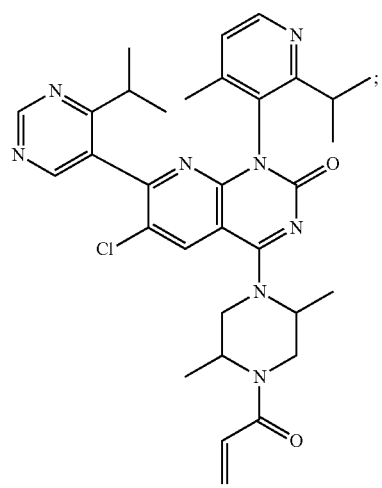
1042
-continued
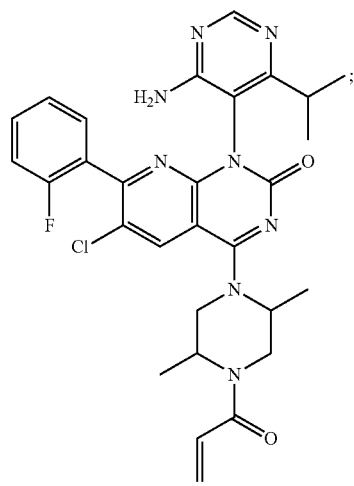
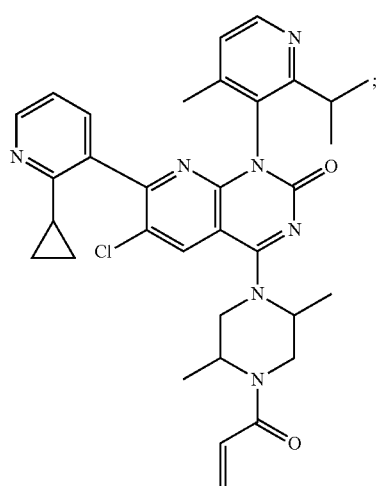
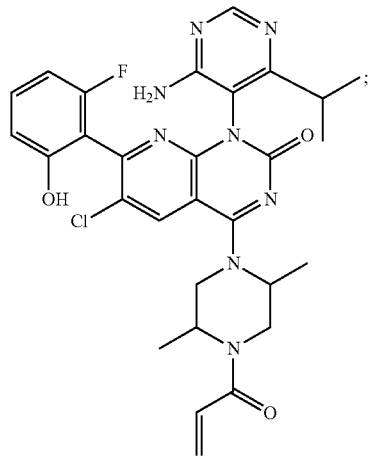

1043
-continued
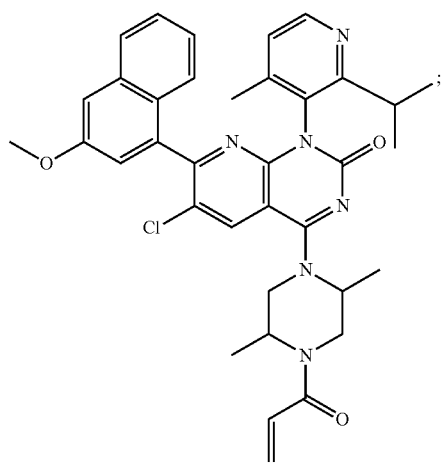
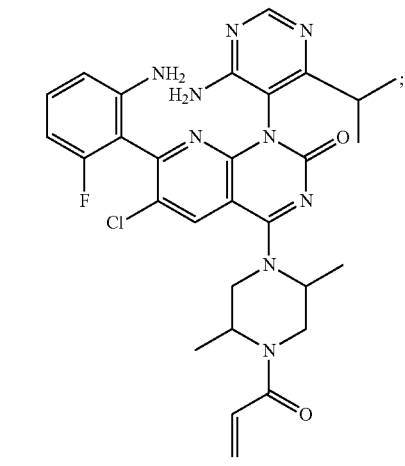
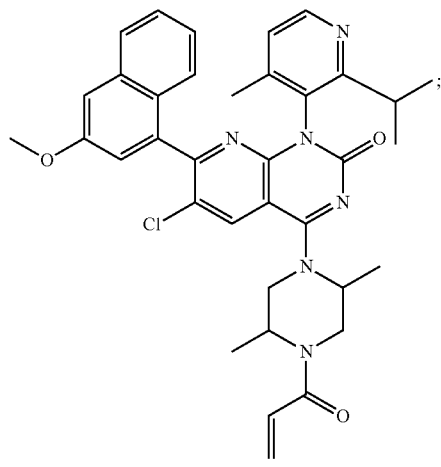
1044
-continued
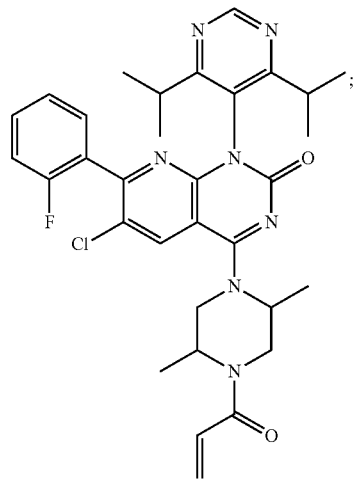
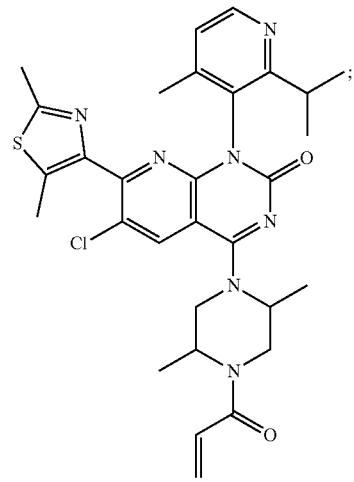
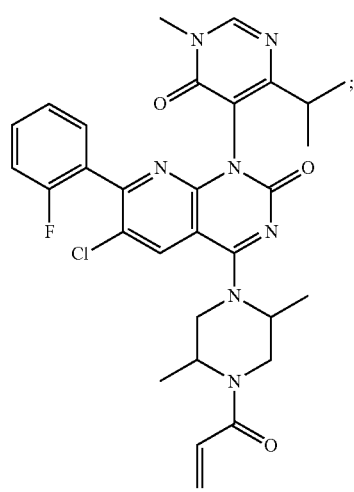

1045
-continued
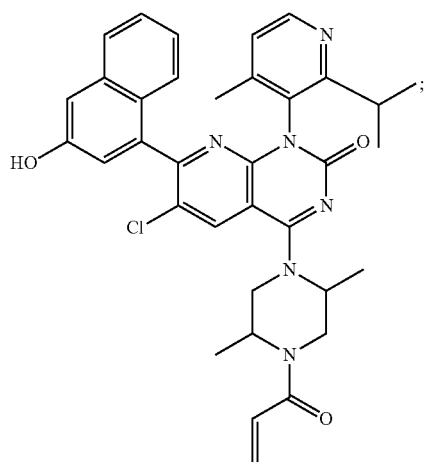
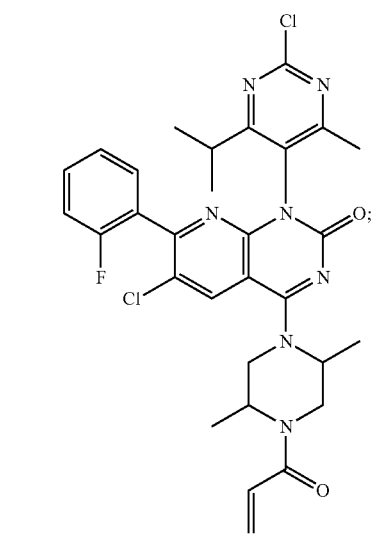
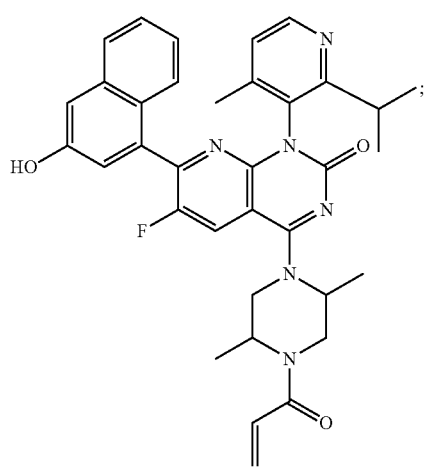
1046
-continued
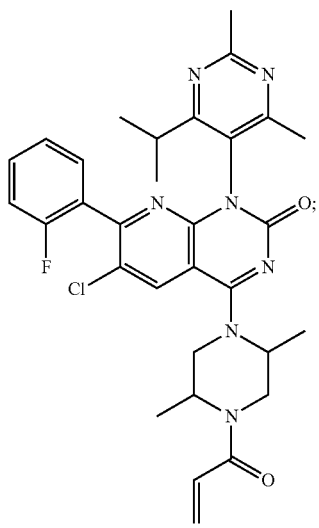
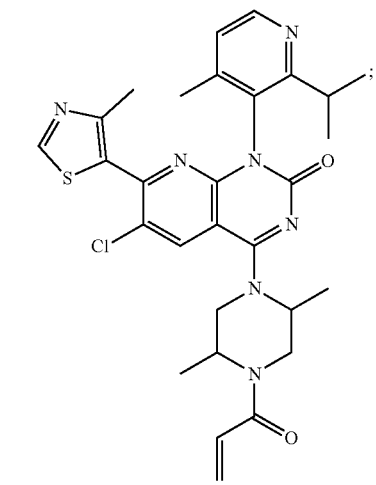
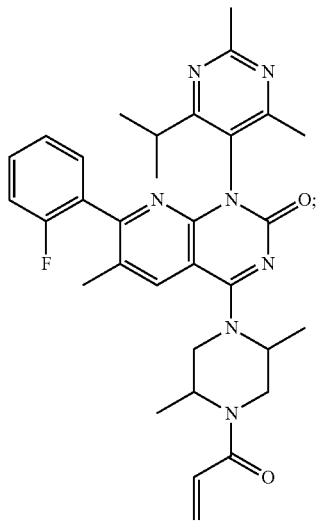

1047
-continued
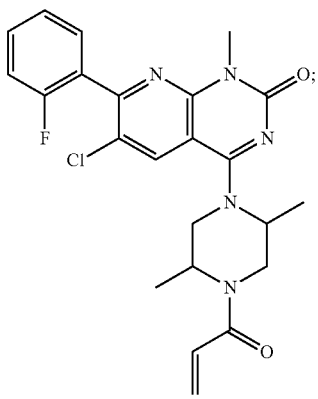
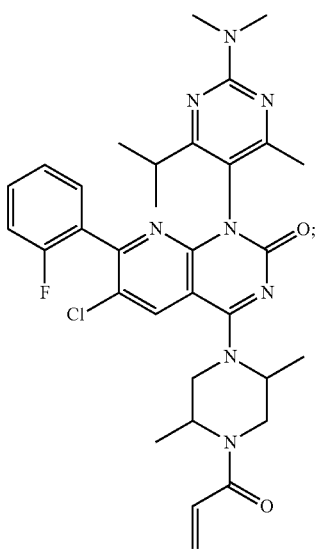
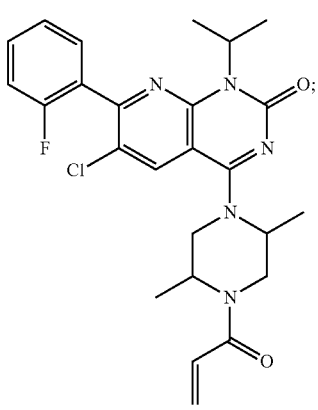
1048
-continued
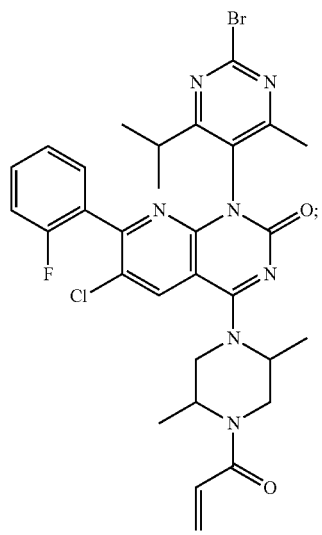
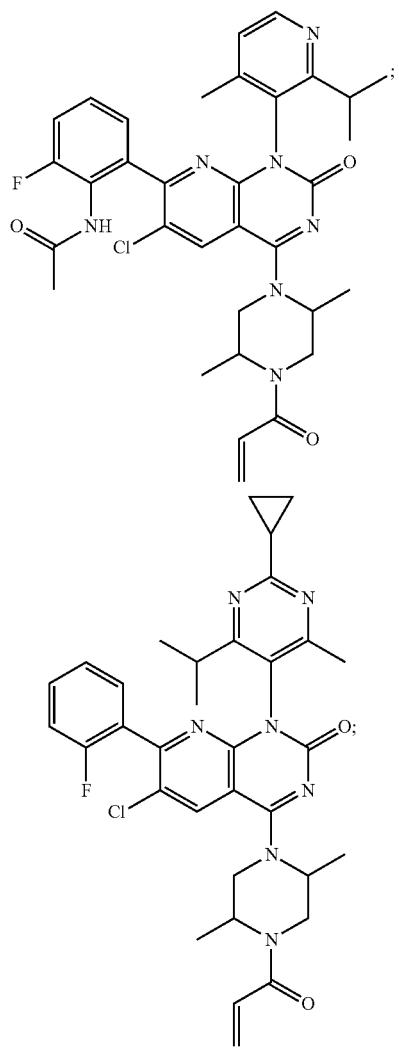

1049
-continued
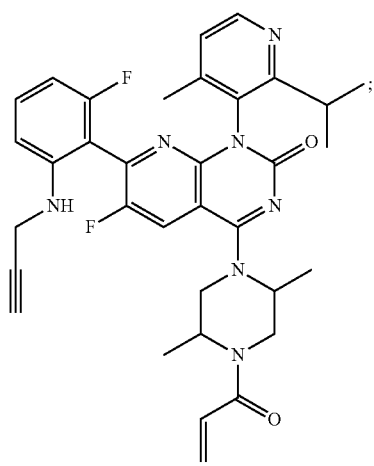
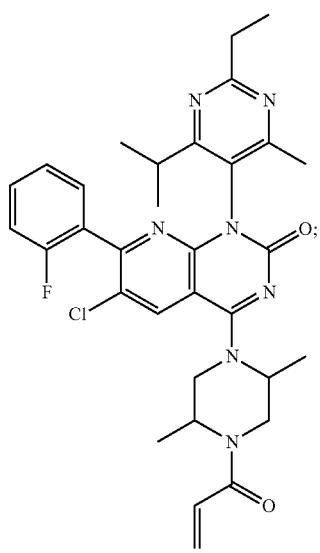
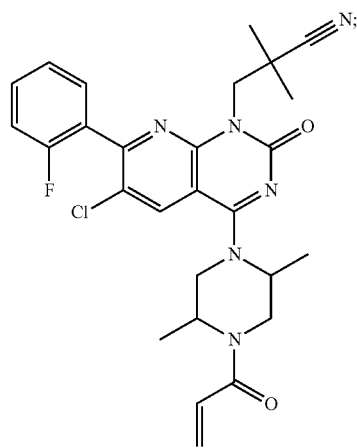
1050
-continued
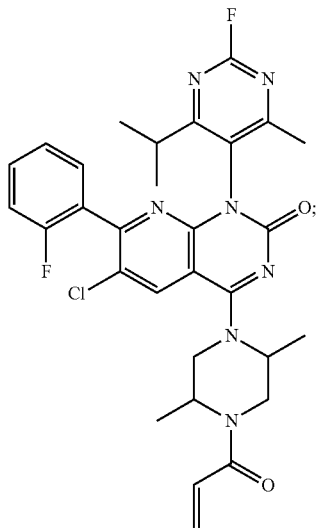
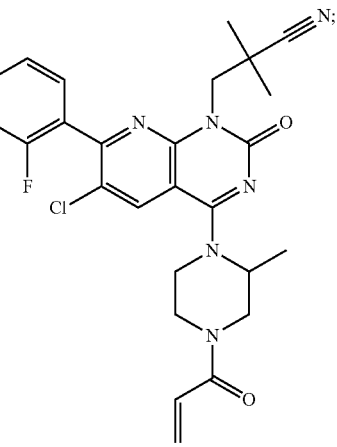
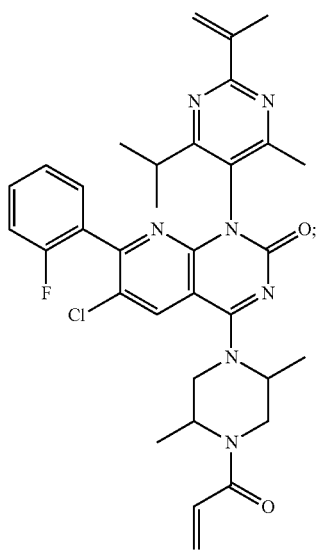

1051
-continued
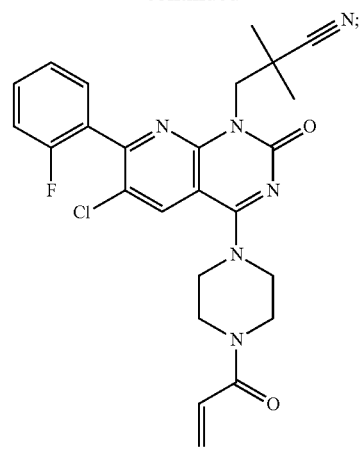
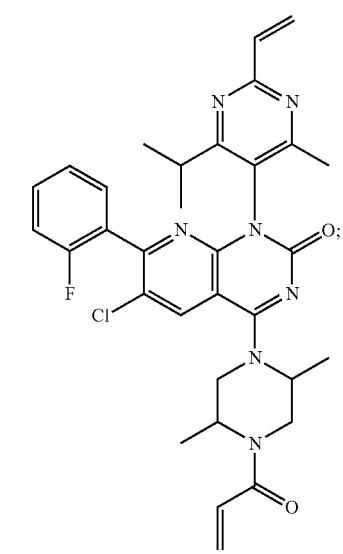
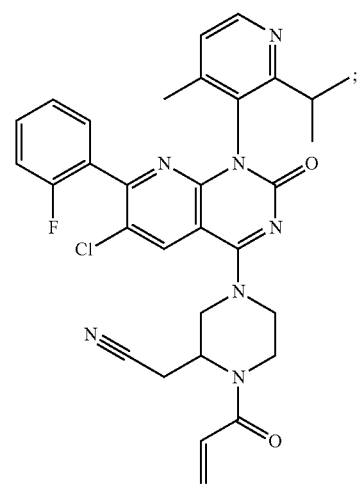
1052
-continued
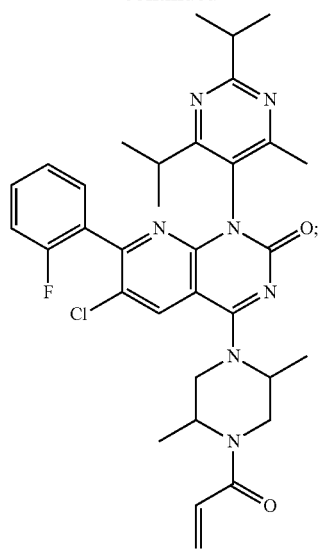
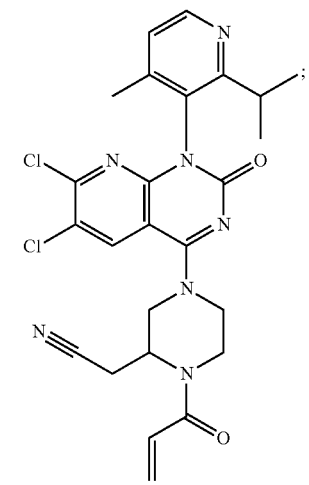
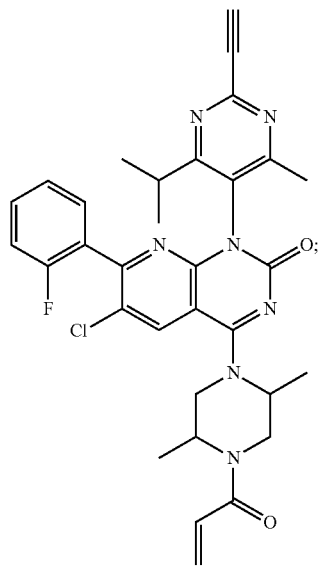

1053
-continued
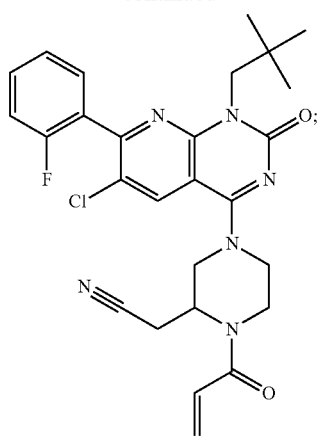
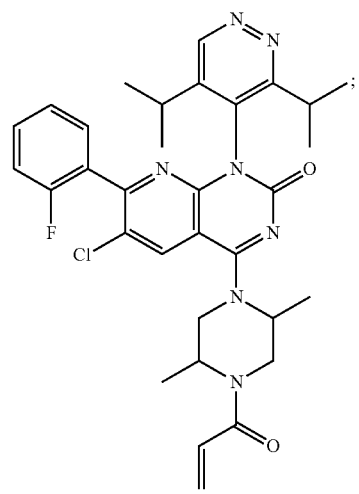
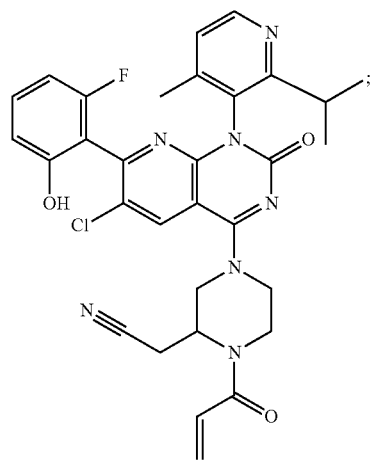
1054
-continued
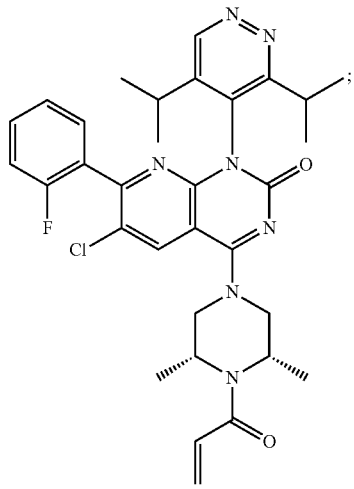
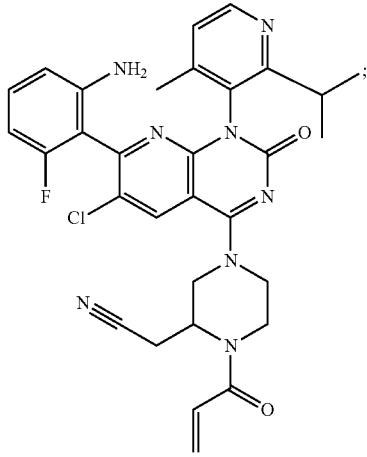
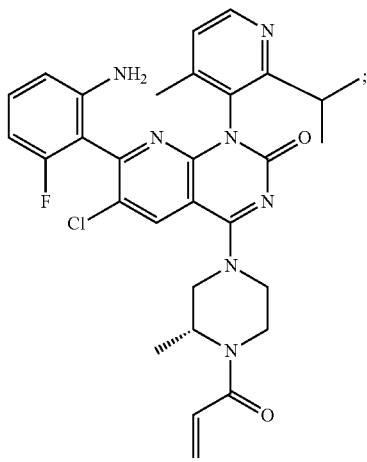

1055
-continued
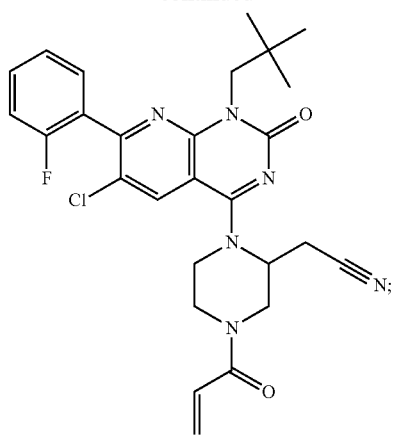
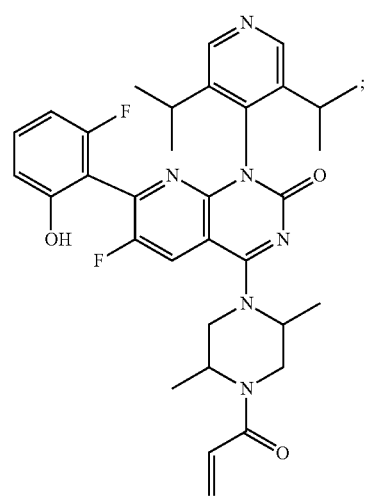
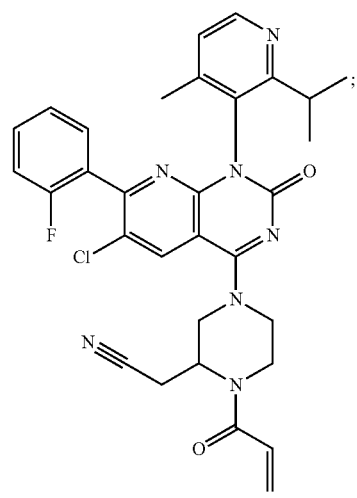
1056
-continued
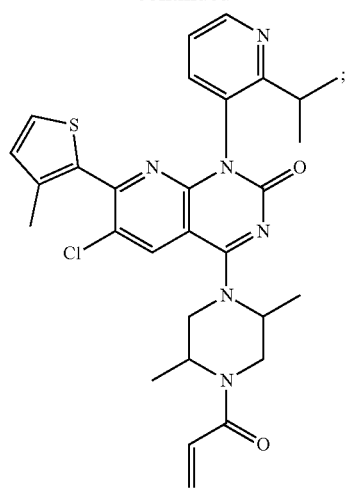
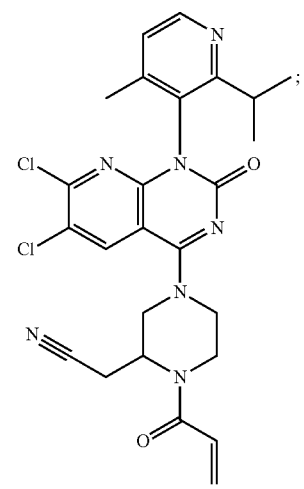
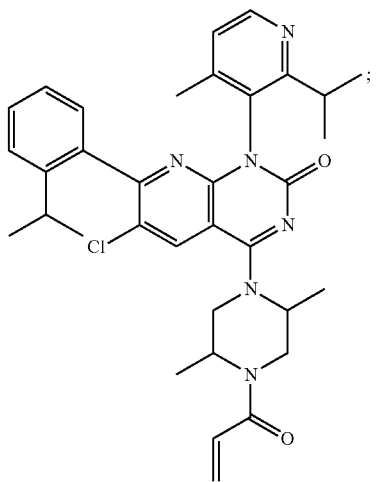

1057
-continued
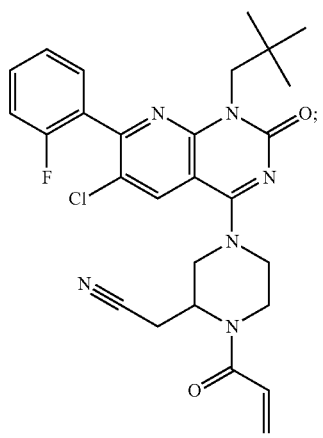
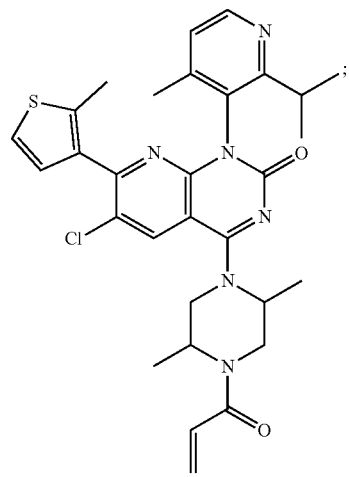
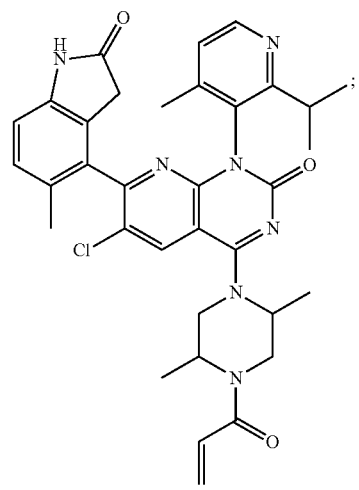
1058
-continued
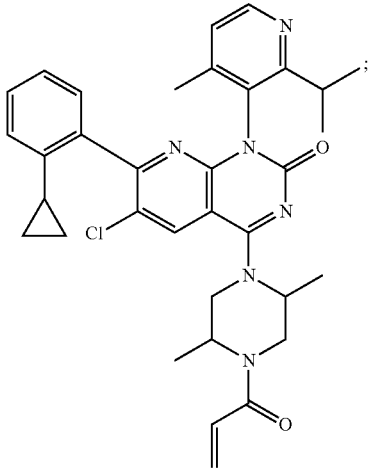
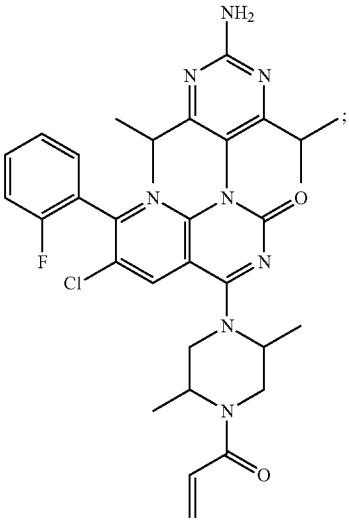
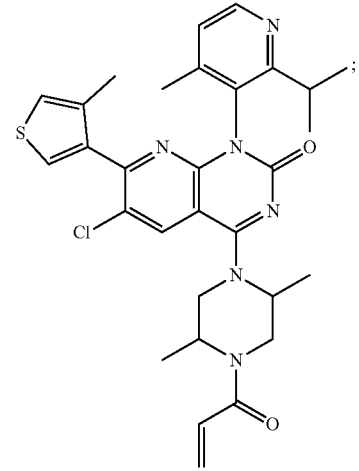

1059
-continued
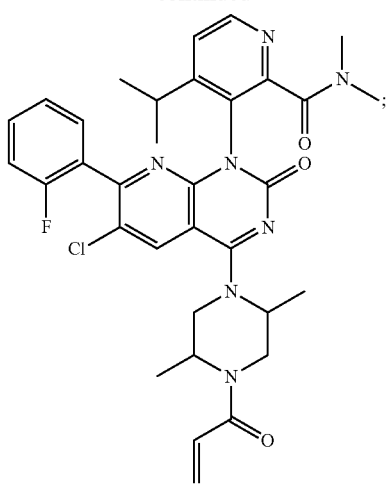
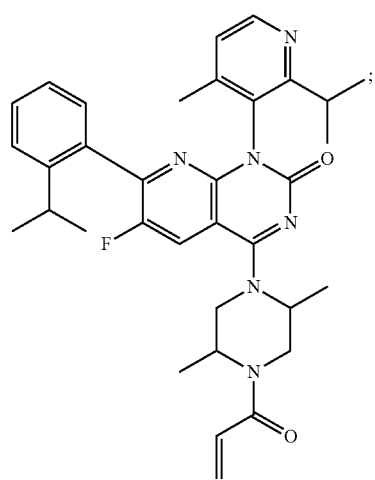
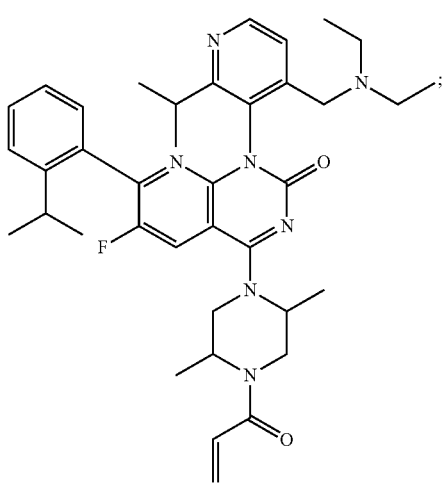
1060
-continued
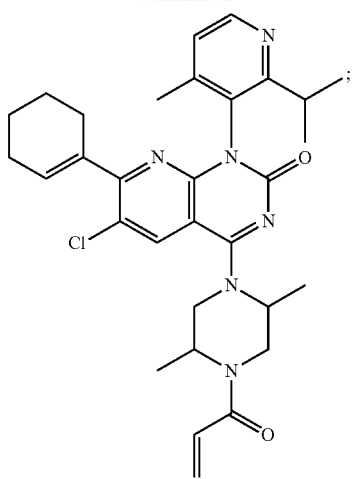
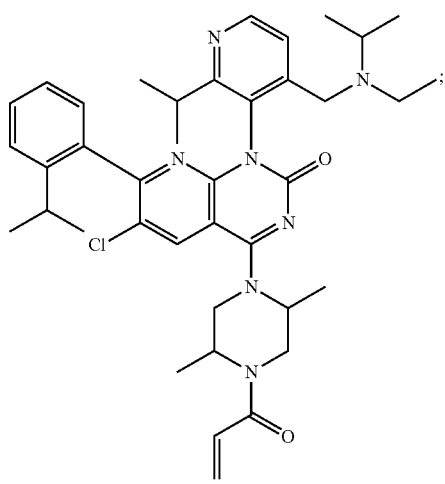
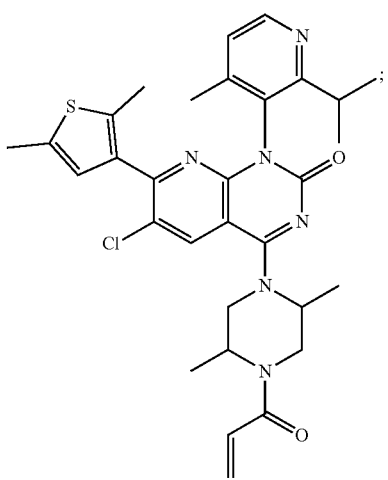

1061
-continued
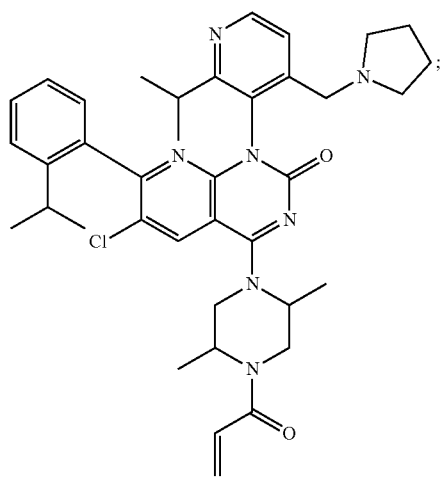
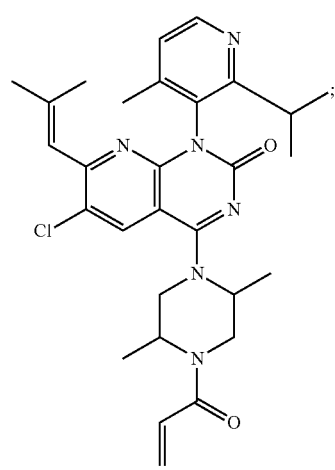
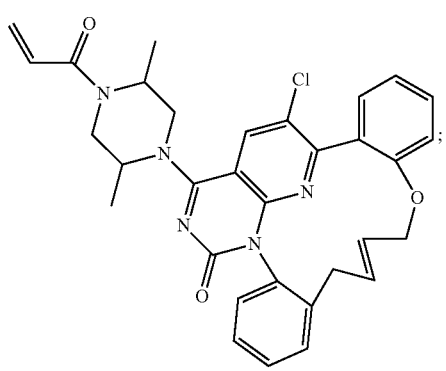
1062
-continued
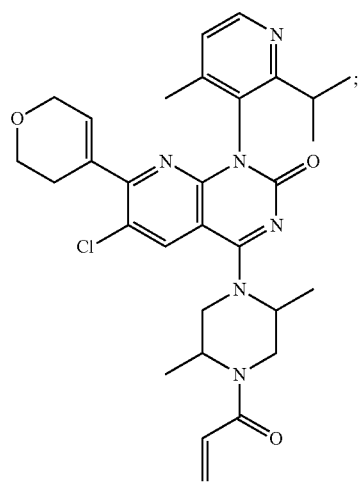
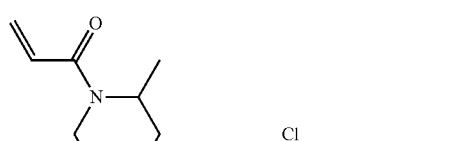
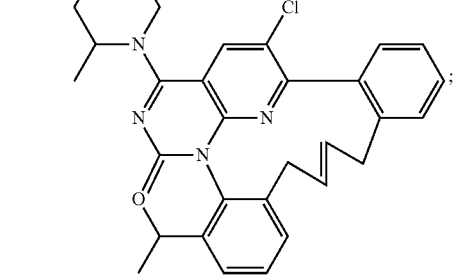
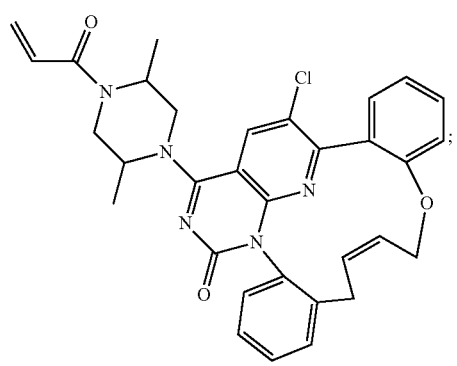

1063
-continued

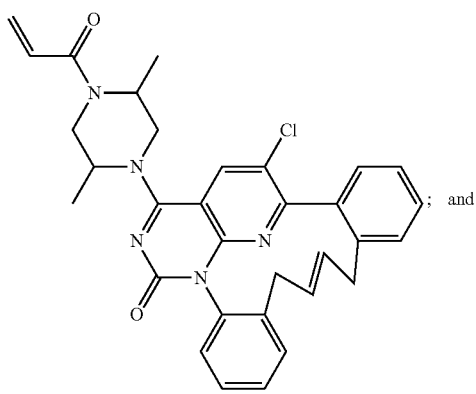
; and

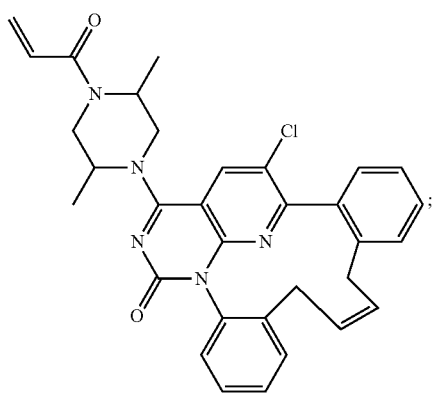 [SMILES: C=CC(=O)N1CC(C)N(c2nc(=O)n3c4nc(c(Cl)cc24)-c2ccccc2C/C=C\Cc2ccccc2-3)CC1C]
;

or a stereoisomer thereof, or a pharmaceutically acceptable salt of said compound or said stereoisomer.

2. A pharmaceutical composition comprising the compound of claim 1, or a stereoisomer thereof, or a pharmaceutically acceptable salt of said compound or said stereoisomer, and a pharmaceutically acceptable excipient.

3. A compound selected from the group consisting of:

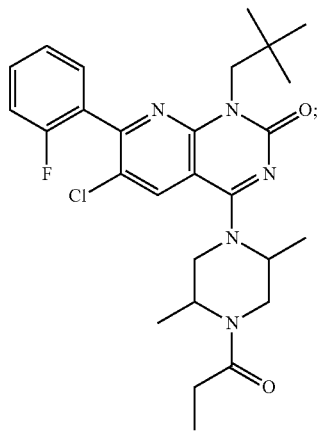

1064
-continued

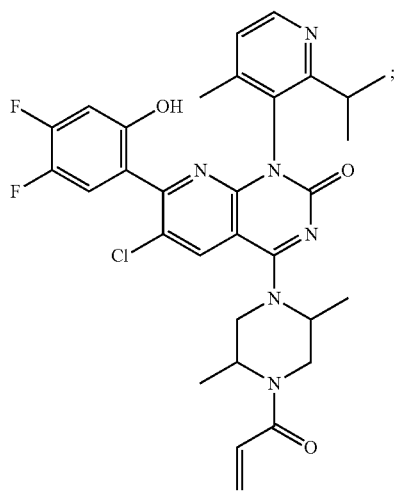
;

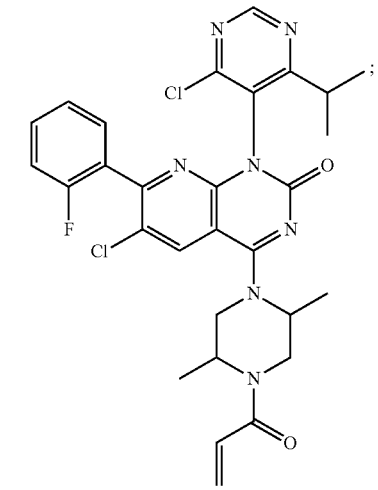
;

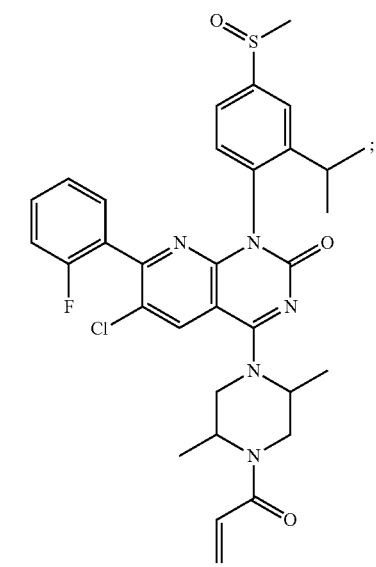

1065
-continued
1066
-continued
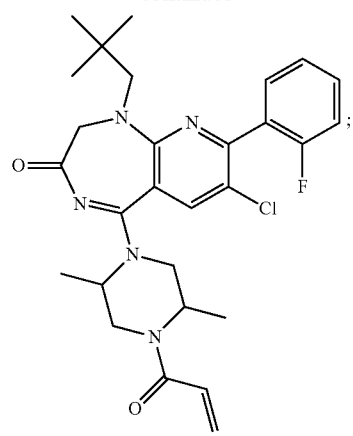
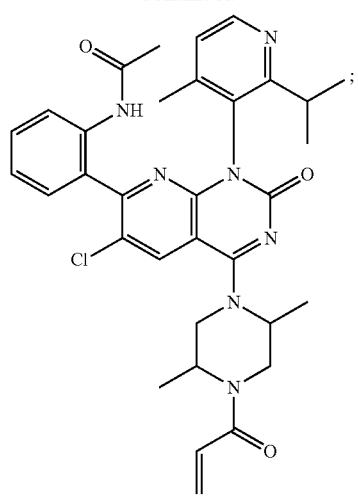
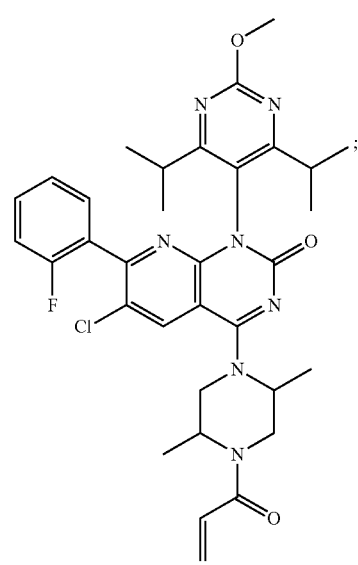
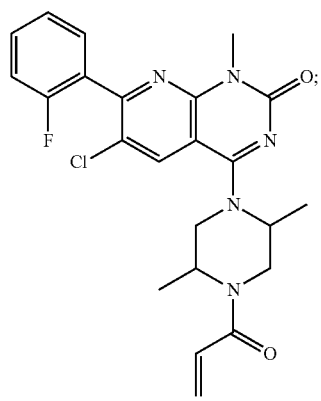
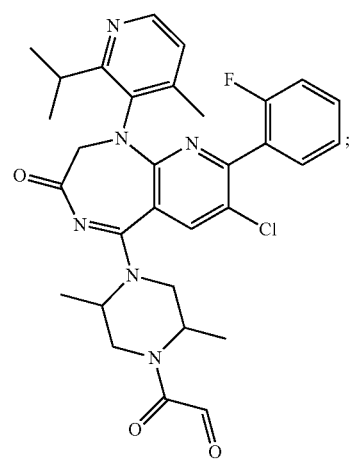
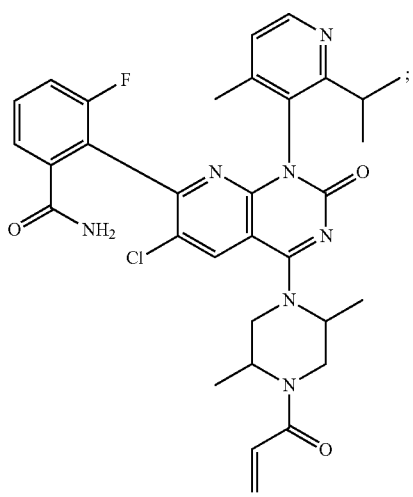

1067
-continued
1068
-continued
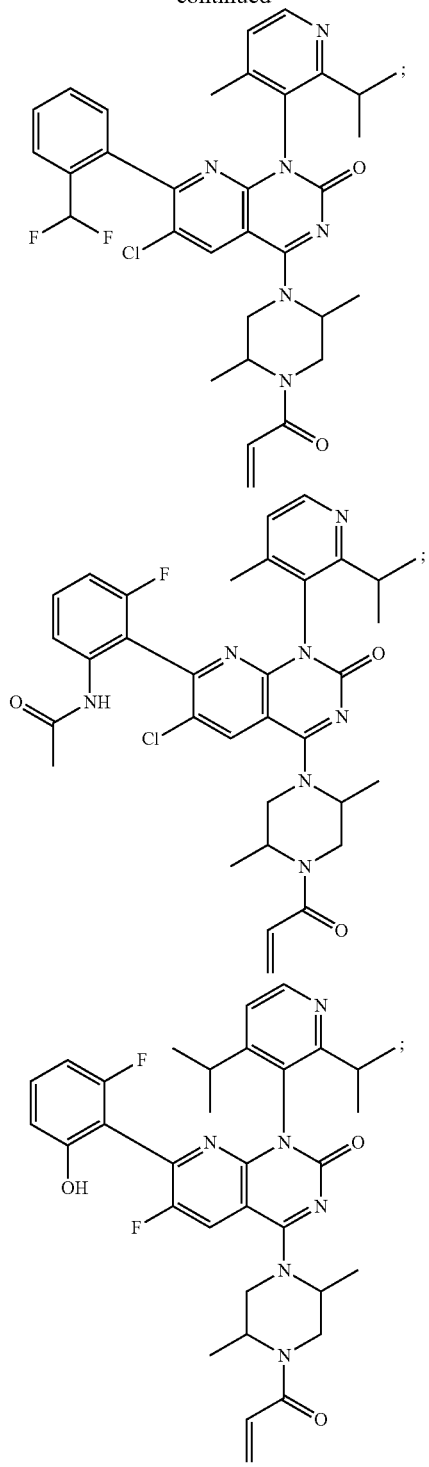
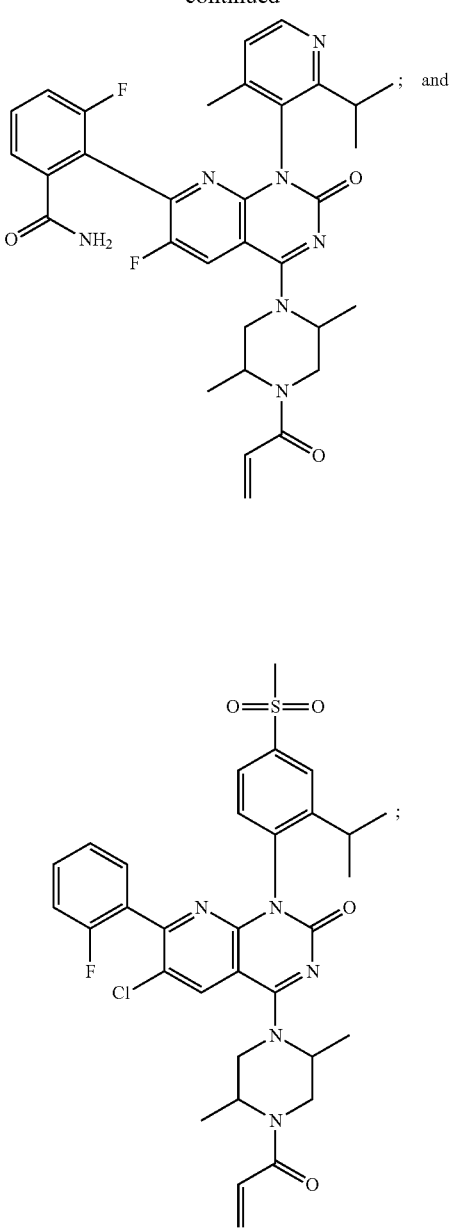
or a stereoisomer thereof, or a pharmaceutically acceptable salt of said compound or said stereoisomer.
4. A pharmaceutical composition comprising the compound of claim 3, or a stereoisomer thereof, or a pharmaceutically acceptable salt of said compound or said stereoisomer, and a pharmaceutically acceptable excipient.
* * * * *

SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Ser Tyr Asp Met Ser
1               5

<210> SEQ ID NO 2
<211> LENGTH: 16

```
<212> TYPE: PRT
<213> ORGANISM: Artificial Sequence
<220> FEATURE:
<223> OTHER INFORMATION: Synthetic peptide

<400> SEQUENCE: 2

Leu Ile Ser Gly Gly Gly Ser Gln Thr Tyr Tyr Ala Glu Ser Val Lys
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Pro Ser Gly His Tyr Phe Tyr Ala Met Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Arg Ala Ser Gln Gly Ile Ser Asn Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Gln Gln Ala Glu Ser Phe Pro His Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic peptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
```

```
                35                  40                  45
Ser Leu Ile Ser Gly Gly Ser Gln Thr Tyr Tyr Ala Glu Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Phe Cys
                 85                  90                  95
Ala Ser Pro Ser Gly His Tyr Phe Tyr Ala Met Asp Val Trp Gly Gln
                100                 105                 110
Gly Thr Thr Val Thr Val Ser Ser
                115                 120

<210> SEQ ID NO 8
<211> LENGTH: 107
<212> TYPE: PRT
<213> ORGANISM: Artificial Sequence
<220> FEATURE:
<223> OTHER INFORMATION: Synthetic peptide

<400> SEQUENCE: 8

Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Ser Asn Trp
                20                  25                  30
Leu Ala Trp Tyr Gln Gln Lys Pro Gly Lys Ala Pro Lys Leu Leu Ile
                35                  40                  45
Phe Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Glu Ser Phe Pro His
                 85                  90                  95
Thr Phe Gly Gly Gly Thr Lys Val Glu Ile Lys
                100                 105

<210> SEQ ID NO 9
<211> LENGTH: 472
<212> TYPE: PRT
<213> ORGANISM: Artificial Sequence
<220> FEATURE:
<223> OTHER INFORMATION: Synthetic peptide

<400> SEQUENCE: 9

Met Asp Met Arg Val Pro Ala Gln Leu Leu Gly Leu Leu Leu Leu Trp
 1               5                  10                  15
Leu Arg Gly Ala Arg Cys Glu Val Gln Leu Leu Glu Ser Gly Gly Gly
                20                  25                  30
Leu Val Gln Pro Gly Gly Ser Leu Arg Leu Ser Cys Ala Ala Ser Gly
                35                  40                  45
Phe Thr Phe Ser Ser Tyr Asp Met Ser Trp Val Arg Gln Ala Pro Gly
 50                  55                  60
Lys Gly Leu Glu Trp Val Ser Leu Ile Ser Gly Gly Ser Gln Thr
 65                  70                  75                  80
Tyr Tyr Ala Glu Ser Val Lys Gly Arg Phe Thr Ile Ser Arg Asp Asn
                 85                  90                  95
Ser Lys Asn Thr Leu Tyr Leu Gln Met Asn Ser Leu Arg Ala Glu Asp
                100                 105                 110
```

```
Thr Ala Val Tyr Phe Cys Ala Ser Pro Ser Gly His Tyr Phe Tyr Ala
            115                 120                 125

Met Asp Val Trp Gly Gln Gly Thr Thr Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Cys Glu Glu Gln
305                 310                 315                 320

Tyr Gly Ser Thr Tyr Arg Cys Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 10
<211> LENGTH: 236
<212> TYPE: PRT
<213> ORGANISM: Artificial Sequence
<220> FEATURE:
<223> OTHER INFORMATION: Synthetic peptide

<400> SEQUENCE: 10
```

```
Met Asp Met Arg Val Pro Ala Gln Leu Leu Gly Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
            35                  40                  45

Gln Gly Ile Ser Asn Trp Leu Ala Trp Tyr Gln Gln Lys Pro Gly Lys
    50                  55                  60

Ala Pro Lys Leu Leu Ile Phe Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Ala Glu Ser Phe Pro His Thr Phe Gly Gly Gly Thr Lys Val Glu Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 11
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 11
agctatgaca tgagc                                                    15

<210> SEQ ID NO 12
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 12
cttattagtg gtggtggtag tcaaacatac tacgcagaat ccgtgaaggg c             51

<210> SEQ ID NO 13
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 13
```

```
cccagtggcc actacttcta cgctatggac gtc                                  33

<210> SEQ ID NO 14
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 14
cgggcgagtc agggtattag caactggtta gcc                                  33

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 15
gctgcatcca gtttgcaaag t                                               21

<210> SEQ ID NO 16
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 16
caacaggctg aaagtttccc tcacact                                         27

<210> SEQ ID NO 17
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 17
gaggtgcagc tgttggagtc tgggggaggc ttggtacagc ctgggggtc cctgagactc      60 tcctgtgcag cctctggatt cacctttagc agctatgaca tgagctgggt ccgccaggct     120
ccagggaagg gctggaatg gtctcactt attagtggtg gtggtagtca aacatactac       180
gcagaatccg tgaagggccg gttcaccatc tccagagaca attccaagaa cacgctgtat     240
ctgcaaatga acagcctgag agccgaggac acggccgtat attctgtgc gtccccagt      300 ggccactact tctacgctat ggacgtctgg ggccaaggga ccacggtcac cgtctcctca    360

<210> SEQ ID NO 18
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 18
gacatccaga tgacccagtc tccatcttcc gtgtctgcat ctgttggaga cagagtcacc     60
atcacttgtc gggcgagtca gggtattagc aactggttag cctggtatca gcagaaacca    120
gggaaagccc ctaagctcct gatctttgct gcatccagtt tgcaaagtgg ggtcccatca    180
aggttcagcg gcagtggatc tgggacagat ttcaccctca ccatcagcag cctgcagcct    240
gaagattttg caacttacta ttgtcaacag gctgaaagtt tccctcacac tttcggcgga   300
```

| gggaccaagg tggagatcaa a | 321 |

<210> SEQ ID NO 19
<211> LENGTH: 1416
<212> TYPE: DNA
<213> ORGANISM: Artificial Sequence
<220> FEATURE:
<223> OTHER INFORMATION: Synthetic polynucleotide

<400> SEQUENCE: 19

| atggacatga gggtgcccgc tcagctcctg gggctcctgc tgctgtggct gagaggtgcg | 60 |
| cgctgtgagg tgcagctgtt ggagtctggg ggaggcttgg tacagcctgg ggggtccctg | 120 |
| agactctcct gtgcagcctc tggattcacc tttagcagct atgacatgag ctgggtccgc | 180 |
| caggctccag ggaaggggct ggaatgggtc tcacttatta gtggtggtgg tagtcaaaca | 240 |
| tactacgcag aatccgtgaa gggccggttc accatctcca gagacaattc caagaacacg | 300 |
| ctgtatctgc aaatgaacag cctgagagcc gaggacacgg ccgtatattt ctgtgcgtcc | 360 |
| cccagtggcc actacttcta cgctatggac gtctggggcc aagggaccac ggtcaccgtc | 420 |
| tcctcagcct ccaccaaggg cccatcggtc ttccccctgg cacccctcct caagagcacc | 480 |
| tctgggggca cagcggccct gggctgcctg gtcaaggact acttccccga accggtgacg | 540 |
| gtgtcgtgga actcaggcgc cctgaccagc ggcgtgcaca ccttcccggc tgtcctacag | 600 |
| tcctcaggac tctactccct cagcagcgtg gtgaccgtgc cctccagcag cttgggcacc | 660 |
| cagacctaca tctgcaacgt gaatcacaag cccagcaaca ccaaggtgga caagaaagtt | 720 |
| gagcccaaat cttgtgacaa aactcacaca tgcccaccgt gcccagcacc tgaactcctg | 780 |
| gggggaccgt cagtcttcct cttccccccca aaacccaagg acaccctcat gatctcccgg | 840 |
| acccctgagg tcacatgcgt ggtggtggac gtgagccacg aagaccctga ggtcaagttc | 900 |
| aactggtacg tggacggcgt ggaggtgcat aatgccaaga caaagccgtg cgaggagcag | 960 |
| tacggcagca cgtaccgttg cgtcagcgtc ctcaccgtcc tgcaccagga ctggctgaat | 1020 |
| ggcaaggagt acaagtgcaa ggtgtccaac aaagccctcc cagcccccat cgagaaaacc | 1080 |
| atctccaaag ccaaagggca gccccgagaa ccacaggtgt acaccctgcc cccatcccgg | 1140 |
| gaggagatga ccaagaacca ggtcagcctg acctgcctgg tcaaaggctt ctatcccagc | 1200 |
| gacatcgccg tggagtggga gagcaatggg cagccggaga caactacaa gaccacgcct | 1260 |
| cccgtgctgg actccgacgg ctccttcttc ctctatagca agctcaccgt ggacaagagc | 1320 |
| aggtggcagc aggggaacgt cttctcatgc tccgtgatgc atgaggctct gcacaaccac | 1380 |
| tacacgcaga agagcctctc cctgtctccg ggtaaa | 1416 |

<210> SEQ ID NO 20
<211> LENGTH: 708
<212> TYPE: DNA
<213> ORGANISM: Artificial Sequence
<220> FEATURE:
<223> OTHER INFORMATION: Synthetic polynucleotide

<400> SEQUENCE: 20

| atggacatga gggtgcccgc tcagctcctg gggctcctgc tgctgtggct gagaggtgcg | 60 |
| cgctgtgaca tccagatgac ccagtctcca tcttccgtgt ctgcatctgt tggagacaga | 120 |
| gtcaccatca cttgtcgggc gagtcagggt attagcaact ggttagcctg gtatcagcag | 180 |
| aaaccaggga aagcccctaa gctcctgatc tttgctgcat ccagtttgca aagtggggtc | 240 |

-continued

| | | | | |
|---|---|---|---|---|
| ccatcaaggt | tcagcggcag | tggatctggg | acagatttca | ccctcaccat cagcagcctg | 300 |
| cagcctgaag | attttgcaac | ttactattgt | caacaggctg | aaagtttccc tcacactttc | 360 |
| ggcggaggga | ccaaggtgga | gatcaaacga | acggtggctg | caccatctgt cttcatcttc | 420 |
| ccgccatctg | atgagcagtt | gaaatctgga | actgcctctg | ttgtgtgcct gctgaataac | 480 |
| ttctatccca | gagaggccaa | agtacagtgg | aaggtggata | acgccctcca atcgggtaac | 540 |
| tcccaggaga | gtgtcacaga | gcaggacagc | aaggacagca | cctacagcct cagcagcacc | 600 |
| ctgacgctga | gcaaagcaga | ctacgagaaa | cacaaagtct | acgcctgcga agtcacccat | 660 |
| cagggcctga | gctcgcccgt | cacaaagagc | ttcaacaggg | gagagtgt | 708 |